United States Patent
Darst et al.

(12) 
(10) Patent No.: US 6,225,076 B1
(45) Date of Patent: May 1, 2001

(54) CRYSTAL OF BACTERIAL CORE RNA POLYMERASE AND METHODS OF USE THEREOF

(75) Inventors: Seth A. Darst, New York, NY (US); Gongyi Zhang, Denver, CO (US); Elizabeth Campbell, New York, NY (US); Leonid Minakin, Piscataway; Konstantin Severinov, New Brunswick, both of NJ (US)

(73) Assignees: The Rockefeller University, New York, NY (US); Rutgers, the State University of New Jersey, Piscataway, NJ (US)

( * ) Notice: Subject to any disclaimer, the term of this patent is extended or adjusted under 35 U.S.C. 154(b) by 0 days.

(21) Appl. No.: 09/396,651

(22) Filed: Sep. 15, 1999

(51) Int. Cl.⁷ .................................................. C12Q 1/48
(52) U.S. Cl. ............................................. 435/15; 702/19
(58) Field of Search .................................. 435/15; 702/19

(56) References Cited

PUBLICATIONS

Archambault and Friesen, *Microbiological Reviews*, 57:703–724 (1993).
Adams et al., *Proc. Natl. Acad. Sci. USA*, 94:5018–5023 (1997).
Borukhov et al., *J. Biol. Chem.*, 266:23921–23926 (1991).
Carson, *J. Appl. Crystallogr.*, 24:958–961 (1991).
Cheetham et al, *Nature*, 399:80–83 (1999).
Conaway and Conaway, *Science*, 248:1550–1553 (1990).
Darst et al., *Nature*, 340:730–732 (1989).
Darst et al., *Cell*, 66:121–128 (1991).
Darst et al., *J. Structural Biol.*, 124:115–122 (1998).
Darst et al., *Cold Spring Harbor Symp. Quant. Biol.*, 63:269–276 (1998).
Degryse et al. *Arch. Microbiol.*, 117:189–196 (1978).
Doublie, *Methods Enzymol.*, 276:523–530 (1997).
Erie et al., *Annual Review of Biophysics & Biomolecular Structure*, 21:379–415 (1992).
Furey and Swaminathan, *Methods Enzymol.*, 277:590–620 (1997).
Gentry and Burgess, *Biochemistry*, 32:11224–11227 (1993).
Gnatt et al., *J. Biol. Chem.* 272:30799–30805 (1997).
Gross et al., *Philosophical Transactions of the Royal Society of London—Series B:Biological Sciences*, 351:475–482 (1996).
Helmann and Chamberlin, *Annual. Reviews of Biochemistry*, 57:839–872 (1988).
Heyduk_et al., *Proc. Natl. Acad. Sci. USA*, 93:101612–10166 (1996).
Jin and Gross, *J. Mol. Biol.*, 202:45–58 (1988).
Jokerst et al., *Mol. Gen. Genet.*, 215:266–275 (1989).
Jones et al., *Acta Cryst*, A 47:110–119 (1991).
Markovtsov et al., *Proc. Natl. Acad. Sci. USA*, 93:3221–3226 (1996).
Mecsas et al., *J. Mol. Biol.*, 220:585–597 (1991).
Metzger et al, *EMBO J.*, 8;2745–2754 (1989).
Mustaev et al., *J. Biol. Chem.*, 266:23927–23931 (1991).
Mukherjee and Chatterji, *Eur. J. Biochem.*, 247: 884–889 (1997).
Mustaev et al. Proc. Natl. Acad. Sci. USA 91:12036–12040 (1994).
Mustaev_et al., *Proc. Natl. Acad. Sci. USA*, 94:6641–6645 (1997).
Nicholls et al., *Proteins Struct. Funct. Genet.*, 11:281–296 (1991).
Nudler et al., *Science*, 281:424–428 (1998).
Nudler et al. *Science*, 273211–217 (1996).
Nudler, *J. Mol. Biol.*, 288:1–12 (1999).
Nudler et al., *Cell*, 89:33–41 (1997).
Otwinowski, *Isomorphous Replacement and Anomalous Sacttering* (Eds. Wolf, Evans and Leslie) (Science and Engineering Research Council, Daresbury Laboratory, Daresbury, UK, 1991) pp. 80–86.
Polyakov et al., *Cell*, 83:365–373 (1995).
Rost and Sander, *J. Mol. Biol*, 232:584–599 (1993).
Sentenac et al., Yeast RNA Polymerase Subunits and Genes in *Transcriptional Regulation* (eds. McKnight, S. L. & Yamamoto, K. R.) 27–54 (Cold Spring Harbor Laboratory, Cold Spring Harbor, 1992) pp. 27–54.
Shickor et al., *EMBO J.*, 9:2215–2220 (1990).
Schultz et al., *EMBO J.*, 12:2601–2607 (1993).
Severinov et al. *Mol. Gen. Genet.*, 244:120–126 (1994).
Severinov et al., J. Biol. Chem. 267:12813–12819 (1992).
Severinov et al., *J. Biol. Chem.*, 268:14820–14825 (1993).
Severinov et al., *J. Biol. Chem.*, 270:29428–29432 (1995).
Sweetser et al., *Proc. Natl. Acad. Sci. USA*, 84:1192–1196 (1987).
von Hippel et al., *Annual Reviews of Biochemistry*, 53:389–446 (1984).
Wang et al., *J. Mol. Biol.*, 270:648–662: (1997).
Zakharova et al., *J. Bacteriol*, 181:3857–3859 (1999).
Zaychikov et al. *Science*, 273:107–109 (1996).
Zhang and Darst, *Science*, 281:262–266 (1998).

*Primary Examiner*—Ponnathapu Achutamurthy
(74) *Attorney, Agent, or Firm*—Klauber & Jackson

(57) ABSTRACT

A detailed three dimensional structure for a bacterial core RNA polymerase is provided. Crystals of the bacterial core RNA polymerase are also included in the invention. The present invention further provides procedures for identifying agents that can inhibit bacterial proliferation through the use of rational drug design predicated on the crystals and crystallographic data disclosed.

14 Claims, 10 Drawing Sheets

(9 of 10 Drawing Sheet(s) Filed in Color)

sequence homology sequence homology functional site mapping functional site mapping

CRYSTAL OF BACTERIAL CORE RNA POLYMERASE AND METHODS OF USE THEREOF

FIELD OF THE INVENTION

The present invention provides a crystal of a bacterial core RNA polymerase from *Thermus aquaticus*. The three-dimensional structural information is included in the invention. The present invention provides procedures for identifying agents that can inhibit bacterial cell growth through the use of rational drug design predicated on the crystallographic data.

BACKGROUND OF THE INVENTION

RNA in all cellular organisms is synthesized by a complex molecular machine, the DNA-dependent RNA polymerase (RNAP). In its simplest bacterial form, the enzyme comprises at least 4 subunits with a total molecular mass of around 400 kDa. The eukaryotic enzymes comprise upwards of a dozen subunits with a total molecular mass of around 500 kDa. The essential core component of the RNAP (subunit composition $\alpha_2\beta\beta'$) is evolutionarily conserved from bacteria to man [Archambault and Friesen, *Microbiological Reviews*, 57:703–724 (1993)]. Sequence homologies point to structural and functional homologies, making the simpler bacterial RNAPs excellent model systems for understanding the multisubunit cellular RNAPs in general.

The basic elements of the transcription cycle were elucidated through study of the prokaryotic system. In this cycle, the RNAP, along with other factors, locates specific sequences called promoters within the double-stranded DNA, forms the open complex by melting a portion of the DNA surrounding the transcription start site, initiates the synthesis of an RNA chain, and elongates the RNA chain completely processively while translocating itself and the melted transcription bubble along the DNA template. Finally it releases itself and the completed transcript from the DNA when a specific termination signal is encountered. The current view is that the transcribing RNAP contains sites for binding the DNA template as well as forming and maintaining the transcription bubble, binding the RNA transcript, and binding the incoming nucleotide-triphosphate substrate.

From the initial indications of DNA-dependent RNAP activity from a number of systems, [Weiss and Gladstone, *J. Am. Chem. Soc.*, 81:4118–4119 (1959)]; Hurwitz et al., *Biochem. Biophys. Res. Commun.*, 3:15 (1960); Stevens, *Biochem. Biophys. Res. Commun.*, 3:92 (1960); Huang et al., *Biochem. Biophys. Res. Commun.*, 3:689 (1960); and Weiss and Nakamoto, *J. Biol. Chem.*, 236:PC 19 (1961)], and the isolation of the RNAP enzyme from bacterial sources [Chamberlin and Berg, *Proc. Natl. Acad. Sci. USA*, 48:81–94 (1962)], a wealth of biochemical, biophysical, and genetic information has accumulated on RNAP and its complexes with nucleic acids and accessory factors. Nevertheless, the enzyme itself, in terms of its structure/function relationship, remains a black box. An essential step towards understanding the mechanism of transcription and its regulation is to determine three-dimensional structures of RNAP and its complexes with DNA, RNA, and regulatory factors [von Hippel et al., *Annual reviews of Biochemistry*, 53:389–446 (1984); Erie et al., *Annual Review of Biophysics & Biomolecular Structure*, 21:379–415 (1992); Sentenac et al., *Transcriptional Regulation* (eds. McKnight, S. L. & Yamamoto, K. R.) 27–54 (Cold Spring Harbor Laboratory, Cold Spring Harbor, 1992); Gross et al., *Philosophical Transactions of the Royal Society of London—Series B:Biological Sciences*, 351:475–482 (1996); and Nudler, *J. Mol. Biol.*, 288:1–12 (1999)].

The key feature of low-resolution structures of bacterial and eukaryotic RNAPs, provided by electron crystallography, is a thumblike projection surrounding a groove or channel that is an appropriate size for accommodating double-helical DNA [Darst et al., *Nature*, 340:730–732 (1989); Darst et al., *Cell*, 66:121–128 (1991); Schultz et al., *EMBO J.*, 12:2601–2607 (1993); Polyakov et al., *Cell*, 83:365–373 (1995); Darst et al., *J. Structural Biol.*, 124:115–122 (1998); and Darst et al., *Cold Spring Harbor Symp. Quant. Biol.*, 63:269–276 (1998)].

Bacterial infections remain among the most common and deadly causes of human disease. Infectious diseases are the third leading cause of death in the United States and the leading cause of death worldwide [Binder et al., *Science* 284:1311–1313 (1999)].

Although, there was initial optimism in the middle of this century that diseases caused by bacteria would be quickly eradicated, it has become evident that the so-called "miracle drugs" are not sufficient to accomplish this task. Indeed, antibiotic resistant pathogenic strains of bacteria have become common-place, and bacterial resistance to the new variations of these drugs appears to be outpacing the ability of scientists to develop effective chemical analogs of the existing drugs [See, Stuart B. Levy, The Challenge of Antibiotic Resistance, in *Scientific American*, 46–53 (March, 1998)]. Therefore, new approaches to drug development are necessary to combat the ever-increasing number of antibiotic-resistant pathogens.

Classical penicillin-type antibiotics effect a single class of proteins known as autolysins. Thus, the development of new drugs which effect an alternative bacterial target protein would be desirable. Such a target protein ideally would be indispensable for bacterial survival. A enzyme such as bacterial RNAP would thus be a prime candidate for such drug development.

Therefore, there is a need to develop methods for identifying drugs that interfere with bacterial RNAP. Unfortunately, such identification has heretofore relied on serendipity and/or systematic screening of large numbers of natural and synthetic compounds. One superior method for drug screening relies on structure based rational drug design. In such cases, a three dimensional structure of the protein or peptide is determined and potential agonists and/or antagonists are designed with the aid of computer modeling [Bugg et al., *Scientific American*, Dec.: 92–98 (1993); West et al., *TIPS*, 16:67–74 (1995); Dunbrack et al., *Folding & Design*, 2:27–42 (1997)].

Therefore, there is a need for obtaining a crystal of the bacterial RNAP that is amenable to high resolution X-ray crystallographic analysis. In addition, there is a need for determining the three-dimensional structure of the RNAP. Furthermore, there is a need for developing procedures of structure based rational drug design using such three-dimensional information. Finally, there is a need to employ such procedures to develop new anti-bacterial drugs.

The citation of any reference herein should not be construed as an admission that such reference is available as "Prior Art" to the instant application.

SUMMARY OF THE INVENTION

The present invention provides crystals of RNA polymerase. More particularly, the present invention provides crystals of the bacterial core RNA polymerase. In addition, the present invention also provides detailed three-dimensional structural data for the bacterial core RNA polymerase. The structural data obtained for the bacterial core RNA polymerase can be used for the rational design of drugs that inhibit bacterial cell proliferation. The present invention further provides methods of identifying and/or improving inhibitors of the bacterial core RNA polymerase which can be used in place of and/or in conjunction with other bacterial inhibitors including antibiotics.

One aspect of the present invention provides crystals of the bacterial core RNA polymerase that can effectively diffract X-rays for the determination of the atomic coordinates of the core RNA polymerase to a resolution of better than 5.0 Angstroms. In a preferred embodiment the crystal effectively diffracts X-rays for the determination of the atomic coordinates of the core RNA polymerase to a resolution of 3.5 Angstroms or better. In a particular embodiment the crystal effectively diffracts X-rays for the determination of the atomic coordinates of the core RNA polymerase to a resolution of 3.3 Angstroms or better.

In a particular embodiment the bacterial core RNA polymerase of the crystal is a thermophilic bacterial core RNA polymerase. In a preferred embodiment of this type the thermophilic bacterial core RNA polymerase is a Thermus aquaticus bacterial core RNA polymerase. Such a core RNA polymerase comprises a β' subunit, a β subunit, and a pair of α subunits. Preferably, the core RNA polymerase further comprises an ω subunit. In a particular embodiment the β' subunit has the amino acid sequence of SEQ ID NO:1. In another embodiment the β subunit has the amino acid sequence of SEQ ID NO:2. In still another embodiment an α subunit has the amino acid sequence of SEQ ID NO:3. In a preferred embodiment the core RNA polymerase is comprised of a β' subunit having the amino acid sequence of SEQ ID NO:1, a β subunit having the amino acid sequence of SEQ ID NO:2, and a pair of α subunits having the amino acid sequence of SEQ ID NO:3. More preferably, this core RNA polymerase further comprises an ω subunit.

A crystal of the present invention may take a variety of forms all of which are included in the present invention. In a preferred embodiment the crystal has a space group of $P4_12_12$ and a unit cell of dimensions of a=b=201 and c=294 Å.

The present invention provides an isolated bacterial β' subunit of an RNAP that has the amino acid sequence of SEQ ID NO:1. In a related embodiment the β' subunit has the amino acid sequence of SEQ ID NO:1 having one or more conservative amino acid substitutions. The present invention further provides an isolated bacterial β subunit of an RNAP that has the amino acid sequence of SEQ ID NO:2. In a related embodiment the β subunit has the amino acid sequence of SEQ ID NO:2 having one or more conservative amino acid substitutions. The present invention also provides an isolated bacterial a subunit of an RNAP that has the amino acid sequence of SEQ ID NO:3. In a related embodiment the α subunit has the amino acid sequence of SEQ ID NO:3 having one or more conservative amino acid substitutions. In addition, fragments of these subunits which retain their ability to form an active core RNA polymerase (i.e., that can transcribe a DNA template) are also part of the present invention.

The present invention also includes the isolated nucleic acids that encode the α, β, and β' subunits and the fragments of these subunits which retain their ability to form an active core RNA polymerase. In addition, the present invention also provides expression vectors which comprise a nucleic acid of the present invention operatively associated with an expression control sequence. The present invention further includes a cell transfected or transformed with an expression vector of the present invention. In one such embodiment the cell is a prokaryotic cell.

The present invention also includes methods of expressing the nucleic acids of the present invention comprising culturing a cell that expresses the β subunit or fragment of the present invention, for example, in an appropriate cell culture medium under conditions that provide for expression of the protein by the cell.

The present invention further includes methods of using the proteins of the present invention to grow a crystal of the core RNA polymerase. One such method comprises growing a core bacterial RNA polymerase crystal in a buffered solution containing 40–45% saturated ammonium sulfate. Preferably the crystal effectively diffracts X-rays for the determination of the atomic coordinates of the core RNA polymerase to a resolution of better than 5.0 Angstroms. In a preferred embodiment the crystal effectively diffracts X-rays for the determination of the atomic coordinates of the core RNA polymerase to a resolution of 3.5 Angstroms or better. In a particular embodiment the crystal effectively diffracts X-rays for the determination of the atomic coordinates of the core RNA polymerase to a resolution of 3.3 Angstroms or better.

In a particular embodiment the crystal is grown by vapor diffusion. In one such embodiment the crystal is grown by hanging-drop vapor diffusion. In another embodiment the crystal is grown by sitting-drop vapor diffusion. Standard micro and/or macro seeding may be used to obtain a crystal of X-ray quality, i.e. a crystal that will diffract to allow resolution better than 5.0 Angstroms.

Still another aspect of the present invention comprises a method of using a crystal of the present invention and/or a dataset comprising the three-dimensional coordinates obtained from the crystal in a drug screening assay.

In addition, the present invention provides three-dimensional coordinates for the core RNA polymerase. In a particular embodiment the coordinates are for the *Thermus aquaticus* core RNA polymerase as disclosed in Table 3 (in Appendix following the Sequence Listing). Thus the data set of Table 3 below, is part of the present invention. Furthermore, the data set of Table 3 below, in a computer readable form is also part of the present invention. In addition, methods of using such coordinates (including in computer readable form) in the drug assays and drug screens as exemplified herein, are also part of the present invention. In a particular embodiment of this type, the coordinates contained in the data set of Table 3 below, can be used to identify potential modulators of the core RNA polymerase. In a preferred embodiment, the modulator is designed to interfere with the bacterial RNAP, but not to interfere with the human RNAP.

Accordingly, the present invention provides methods of identifying an agent or drug that can be used to treat bacterial infections. One such embodiment comprises a method of identifying an agent for use as an inhibitor of bacterial RNA polymerase using a crystal of a core RNA polymerase (RNAP) and/or a dataset comprising the three-dimensional coordinates obtained from the crystal. In a particular embodiment the three-dimensional coordinates are determined for the *Thermus aquaticus* core RNA polymerase. Preferably the core RNAP effectively diffracts X-rays for the determination of the atomic coordinates to a resolution of, or better than 3.5 Angstroms. More preferably the core RNAP effectively diffracts X-rays for the determination of the atomic coordinates to a resolution of, or better than 3.3 Angstroms. Preferably the selection is performed in conjunction with computer modeling.

In one embodiment the potential agent is selected by performing rational drug design with the three-dimensional coordinates determined for the crystal. As noted above, preferably the selection is performed in conjunction with computer modeling. The potential agent is then contacted with the bacterial RNA polymerase and the activity of the bacterial RNA polymerase is determined (e.g., measured). A potential agent is identified as an agent that inhibits bacterial RNA polymerase when there is a decrease in the activity determined for the bacterial RNA polymerase.

In a preferred embodiment the method further comprises growing a supplemental crystal containing the core RNA polymerase formed in the presence of the potential agent. Preferably the supplemental crystal effectively diffracts X-rays for the determination of the atomic coordinates to a resolution of better than 5.0 Angstroms, more preferably to a resolution equal to or better than 3.5 Angstroms, and even more preferably to a resolution equal to or better than 3.3 Angstroms. The three-dimensional coordinates of the supplemental crystal are then determined with molecular replacement analysis and a second generation agent is selected by performing rational drug design with the three-dimensional coordinates determined for the supplemental crystal. Preferably the selection is performed in conjunction with computer modeling.

As should be readily apparent the three-dimensional structure of a supplemental crystal can be determined by molecular replacement analysis or multiwavelength anomalous dispersion or multiple isomorphous replacement. A candidate drug is then selected by performing rational drug design with the three-dimensional structure determined for the supplemental crystal, preferably in conjunction with computer modeling. The candidate drug can then be tested in a large number of drug screening assays using standard biochemical methodology exemplified herein.

The method can further comprise contacting the second generation agent with a eukaryotic RNA polymerase and determining (e.g., measuring) the activity of the eukaryotic RNA polymerase. A potential agent is then identified as an agent for use as an inhibitor of bacterial RNA polymerase when there is significantly less change (a factor of two or more) in the activity of the eukaryotic RNA polymerase relative to that observed for the bacterial RNA polymerase. Preferably no, or alternatively minimal change (i.e., less than 15%) in the activity of the eukaryotic RNA polymerase is determined.

The present invention further provides a method of identifying an agent that inhibits bacterial growth using the crystal of a core RNA polymerase (RNAP) or a dataset comprising the three-dimensional coordinates obtained from the crystal. In a particular embodiment the three-dimensional coordinates are determined for the *Thermus aquaticus* core RNA polymerase.

Preferably the core RNAP effectively diffracts X-rays for the determination of the atomic coordinates to a resolution of, or better than 3.5 Angstroms. More preferably the core RNAP effectively diffracts X-rays for the determination of the atomic coordinates to a resolution of, or better than 3.3 Angstroms. Preferably the selection is performed in conjunction with computer modeling.

In one embodiment the potential agent is selected by performing rational drug design with the three-dimensional coordinates determined for the crystal. As noted above, preferably the selection is performed in conjunction with computer modeling. The potential agent is contacted with and/or added to a bacterial culture and the growth of the bacterial culture is determined. A potential agent is identified as an agent that inhibits bacterial growth when there is a decrease in the growth of the bacterial culture. The method can further comprise growing a supplemental crystal containing the core RNA polymerase formed in the presence of the potential agent. Preferably the supplemental crystal effectively diffracts X-rays for the determination of the atomic coordinates to a resolution of better than 5.0 Angstroms, more preferably to a resolution equal to or better than 3.5 Angstroms, and even more preferably to a resolution equal to or better than 3.3 Angstroms. The three-dimensional coordinates of the supplemental crystal are then determined with molecular replacement analysis and a second generation agent is selected by performing rational drug design with the three-dimensional coordinates determined for the supplemental crystal. Preferably the selection is performed in conjunction with computer modeling. The candidate drug can then be tested in a large number of drug screening assays using standard biochemical methodology exemplified herein.

In a particular embodiment the second generation agent is contacted with a eukaryotic cell and the amount of proliferation of the eukaryotic cell is determined. A potential agent is identified as an agent for inhibiting bacterial growth when there is significantly less change (a factor of two or more) in the proliferation of the eukaryotic cell relative to that observed for the bacterial cell. Preferably no, or alternatively minimal change (i.e., less than 15%) in the proliferation of the eukaryotic cell is determined.

The present invention further provides a method of obtaining a crystal of a core bacterial RNA polymerase that comprises growing the core bacterial RNA polymerase crystal in a buffered solution containing 40–45% saturated ammonium sulfate. In one such embodiment the growing is performed by batch crystallization. In another embodiment the growing is performed by vapor diffusion. In yet another embodiment the growing is performed by microdialysis.

Computer analysis may be performed with one or more of the computer programs including: QUANTA, CHARMM, INSIGHT, SYBYL, MACROMODEL and ICM [Dunbrack et al., *Folding & Design*, 2:27–42 (1997)]. In a further embodiment of this aspect of the invention, an initial drug screening assay is performed using the three-dimensional structure so obtained, preferably along with a docking computer program. Such computer modeling can be performed with one or more Docking programs such as DOC, GRAM and AUTO DOCK [Dunbrack et al., *Folding & Design*, 2:27–42 (1997)].

It should be understood that in all of the drug screening assays provided herein, a number of iterative cycles of any or all of the steps may be performed to optimize the selection. For example, assays and drug screens that monitor the activity of the RNA polymerase in the presence and/or absence of a potential modulator (or potential drug) are also included in the present invention and can be employed as the sole assay or drug screen, or more preferably as a single step in a multi-step protocol for identifying modulators of bacterial proliferation and the like.

The present invention further provides the novel agents (modulators or drugs) that are identified by a method of the present invention, along with the method of using agents (modulators or drugs) identified by a method of the present invention, for inhibiting bacterial RNA polymerase and/or bacterial proliferation.

Accordingly, it is a principal object of the present invention to provide a crystal containing the core bacterial RNA polymerase.

It is a further object of the present invention to provide the three-dimensional coordinates of the *Thermus aquaticus* core RNA polymerase.

It is a further object of the present invention to provide methods for the rational design of drugs that inhibit bacterial RNA polymerase.

It is a further object of the present invention to provide methods of identifying drugs that can modulate bacterial proliferation.

It is a further object of the present invention to provide methods for the rational design of drugs that inhibit bacterial proliferation without negatively effecting human RNA polymerase.

It is a further object of the present invention to provide methods of identifying agents that can be used to treat bacterial infections in mammals and preferably in humans.

These and other aspects of the present invention will be better appreciated by reference to the following drawings and Detailed Description.

The file of this patent contains at least one drawing executed in color. Copies of this patent with color drawing(s) will be provided by the Patent and Trademark Office upon request and payment of the necessary fee.

BRIEF DESCRIPTION OF THE DRAWINGS

FIG. 2A is a thin slice from the MIR electron density map, after density modification (see Methods in the Example below), showing the region corresponding to the αNTD dimer. The α-carbon backbone of one αNTD monomer from the final, refined structure is shown in yellow, the other in green. At the upper right is a small portion of a symmetry-related molecule. At the bottom are some regions from other subunits of the RNAP. Shown in green are selenomethionine difference Fourier peaks contoured at 3σ. The corresponding methionine residues in the structure are labeled. FIG. 2A is a closeup view of the MIR electron density map, after density modification, in the region of the αNTD dimer interface, with the refined model superimposed.

FIG. 3A is a view roughly parallel with the main axis of the RNAP channel. FIG. 3B is the view of FIG. 3A rotated 90° clockwise about the vertical axis. FIG. 3C is the view of FIG. 3A rotated 180° about the vertical axis, giving a view down the opposite end of the main channel.

FIG. 4A is a stereo view showing the α-carbon backbone of β' (rose) and β (cyan) around the region of the active center $Mg^{2+}$ ion (magenta sphere). The sites of hydroxyl-radical cleavage of the β and β' polypeptides by $Fe^{2+}$ substituted in the active center $Mg^{2+}$ site [Zaychikov et al., *Science*, 273:107–109 (1996) and Mustaev et al., *Proc. Natl. Acad.*, 94:6641–6645 (1997)] are colored red and labeled according to the subunit and the conserved region. FIG.4B is a stereo RIBBONS diagram of the RNAP active center. The view is roughly the same as FIG. 3B. The RNAP subunits are color-coded as in FIG. 3 (β', rose; β, cyan; αI, yellow). The locations of some conserved regions of β and β' are labeled with white letters. The active center $Mg^{2+}$ is shown as a pink sphere. The side chains of the absolutely conserved -NADFDGD- motif (SEQ ID NO:4) from $β'_D$, responsible for chelating the active center $Mg^{2+}$ [Zaychikov et al., *Science*, 273:107–109 (1996)], are shown in red. The side chains shown in yellow are three residues from β that have been mapped to within a few Ångstroms of the initiating NTP substrate's α-phosphate (βK838, βH999, and βK1004). The magenta spheres denote the α-carbons of amino acid positions where substitutions give rise to rifampicin resistance ($Rif^r$). These residues line a small pocket on the roof of the main RNAP channel.

FIG.5A, left, is the same view as shown in FIG. 3B whereas FIG.5B, right, is a similar view as shown in FIG. 3C. The active site $Mg^{2+}$ is visible as a magenta sphere. In this view, one can view directly through the molecule down the axis of the secondary channel.

FIGS.6A–6D show the molecular surface representations of the 'open book' views of the inside of the RNAP channel. The top row (FIGS.6A and 6C) shows the inside, top surface of the channel (primarily β), the bottom row (FIGS.6B and 6D) shows the inside, bottom surface (primarily β'). Colored grey are the parts of the protein structure that have been sliced away (the grey surfaces of the top and bottom views do not match because the slicing and viewing angles are different to afford the best views of the structural features discussed). The active center $Mg^{2+}$ is visible as a magenta sphere. On the left, (FIGS.6A and 6B) the sequence homology is mapped onto the structure as in FIG. 5. On the right (FIGS.6C and 6D) various functional sites determined from DNA and RNA crosslinking experiments are mapped onto the structure. The color coding is as follows: red, absolutely conserved -NADFDGD- (SEQ ID NO:4) motif of $β'_D$; orange, crosslinks to various probes positioned at the 3'-end of the RNA transcript [Markovtsov et al., Proc. Natl. Acad. Sci USA, 93:3221–3226 (1996); and Nudler et al., Science, 20 281:424–428 (1998)]; yellow, crosslinks to various probes position at the 5'-end of the i-site NTP substrate [Zaychikov et al., Science, 273:107–109 (1996); Mustaev et al., J. Biol. Chem.., 266:23927–23931 (1991); and Severinov et al., J. Biol. Chem., 270:29428–29432 (1995)]; green, crosslinks from probes incorporated into specific positions of the template strand of the DNA [Nudler et al., Science, 273211–217 (1996)]; blue, a crosslink mapped from a probe incorporated at the −10 position of the RNA transcript [Nudler et al., Science, 281:424428 (1998)]. FIGS. 6E–6F shows a schematic model of the structure of a ternary transcription complex. FIG. 6E, top, is a view with the intact RNAP molecule whereas FIG. 6F bottom, is the same view but with parts of the RNAP cut away (shown in grey) to reveal the inner workings of the complex, which are labeled.

DETAILED DESCRIPTION OF THE INVENTION

Figure 1:
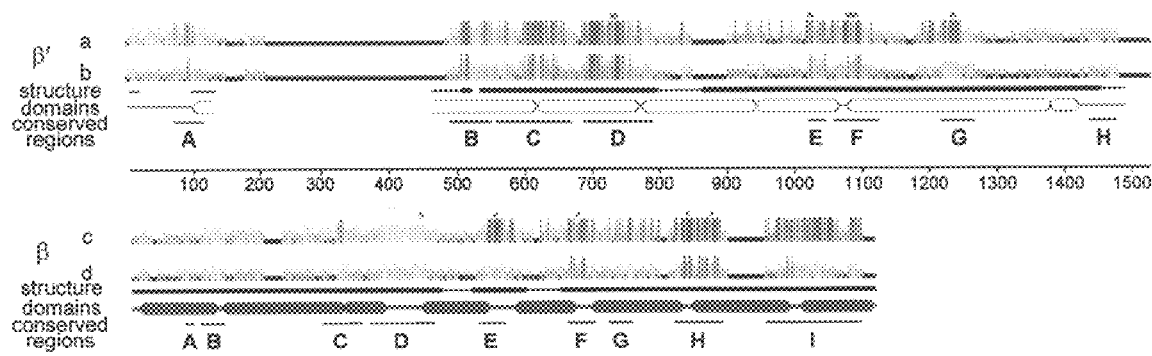
FIGS. 1A–1D show the sequence features of *T. aquaticus* β' (FIGS. 1A–1B) and β (FIGS. 1C–1D). The histograms represent the results of a sequence alignment of β' or β homologs from 50 prokaryotic and chloroplast RNAP sequences (FIGS. 1A, 1C) plus 26 eukaryotic and archaebacterial sequences (FIGS. 1B, 1D). 100% sequence homology among all the sequences is represented by a tall red bar, less than 20% is represented by a small blue bar, intermediate levels are represented by orange or light green bars. The numbered scale in the middle represents amino acid position. The first row underneath the histograms (labeled 'structure') depicts the modeled portion of the structure, with full modeled structure with sequence represented by a thick black line and poly Ala model represented by a thinner line. The next row underneath (labeled 'domains') depicts the domain architecture of the subunit. The next row (labeled 'conserved regions') denotes the most highly conserved regions among all the prokaryotic, chloroplast, archaebacterial, and eukaryotic sequences, as initially identified for β' by [Jokerst et al., *Mol. Gen. Genet.*, 215:266–275 (1989)] and for β by [Sweetser et al., *Proc. Natl. Acad. Sci. USA*, 84:1192–1196 (1987)] but with expanded conserved regions due to the larger number of aligned sequences. Above the histograms, yellow bars denote the positions of crosslinks to initiating nucleotide analogs [Zaychikov et al., *Science*, 273:107–109 (1996); Mustaev et al., *J. Biol. Chem.*, 266:23927–23931 (1991); and Severinov et al., *J. Biol. Chem.*, 270:29428–29432 (1995)], red bars denote the positions of cleavage sites by hydroxyl-radicals generated from the active center metal-chelation site [Zaychikov et al., *Science*, 273:107–109 (1996) and Mustaev et al., *Proc. Natl. Acad. Sci. USA*, 94:6641–6645 (1997)], and magenta bars represent the locations of mutations that confer rifampicin resistance [Jin and Gross, *J. Mol. Biol.*, 202:45–58 (1988) and Severinov et al., Mol. Gen. Genet., 244:120–126 (1994)].

The present invention provides crystals of a bacterial core RNA polymerase. The present invention further provides the structural coordinates for the core RNA polymerase and methods of using such structural coordinates in drug assays. More particularly, the present invention provides the structural coordinates for Thermus aquaticus core RNA polymerase (see Table 3 in Appendix following the Sequence Listing).

The X-ray crystal structure of Thermus aquaticus core RNA polymerase reveals a 'crab-claw' shaped molecule with a 27 Å wide internal channel. Located on the back wall of the channel is a $Mg^{2+}$ ion required for catalytic activity, which is chelated by an absolutely conserved motif from all bacterial and eukaryotic cellular RNA polymerases. The structure places key functional sites, defined by mutational and crosslinking analysis, on the inner walls of the channel in close proximity to the active center $Mg^{2+}$. Further out from the catalytic center, structural features are found that may be involved in maintaining the melted transcription bubble, clamping onto the RNA product and/or DNA template to assure processivity, and delivering nucleotide substrates to the active center.

The present invention further exploits the structural information disclosed herein and provides methods of identifying agents or drugs that can be used to control the proliferation of bacteria, e.g., for use as treatments for bacterial infections.

Therefore, if appearing herein, the following terms shall have the definitions set out below:

As used herein the term "core RNA polymerase" minimally comprises the subunit composition of $α_2ββ'$ which is evolutionarily conserved from bacteria to man.

The three-dimensional structure of the Thermus aquaticus core RNA polymerase is disclosed in the Example below and the structural coordinates are listed in Table 3 (in Appendix following the Sequence Listing).

As used herein an "active RNA polymerase" is an RNA polymerase that minimally contains a pair of α subunits, a β' subunit, and a β subunit; or fragments thereof, but still retains at least 25% of the activity of the core RNA polymerase made up of the full length α, β', and β subunits. Thus active RNA polymerases can comprise fragments of the α subunit and/or β' subunit and/or β subunit.

As used herein a "small organic molecule" is an organic compound [or organic compound complexed with an inorganic compound (e.g., metal)] that has a molecular weight of less than 3 Kd.

As used herein the term "about" means within 10 to 15%, preferably within 5 to 10%. For example an amino acid sequence that contains about 60 amino acid residues can contain between 51 to 69 amino acid residues, more preferably 57 to 63 amino acid residues.

Nucleic Acids Encoding Subunits of Bacterial RNA Polymerases

The present invention contemplates isolation of nucleic acids encoding a subunit of an RNA polymerase including a full length, i.e., naturally occurring form of the RNA polymerase from any prokaryotic source, preferably a thermophilic bacterial source. The present invention further provides for subsequent modification of the nucleic acid to generate a fragment or modification of the subunit that can still be used to form a core RNA polymerase that will crystallize.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment.

A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous DNA" refers to DNA not naturally located in the cell, or in a chromosomal site of the cell. Preferably, the heterologous DNA includes a gene foreign to the cell.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another embodiment the heterologous nucleotide can function as a means of detecting a nucleotide sequence of the present invention. A heterologous nucleotide sequence can comprise non-coding sequences including restriction sites, regulatory sites, promoters and the like.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminry screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which may then be trans-RNA spliced and translated into the protein encoded by the coding sequence.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program with the default parameters.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding an RNA polymerase, including genomic DNA or cDNA, can be isolated from any source, particularly from a thermophilic bacterial source. In view and in conjunction with the present teachings, methods well known in the art, as described above can be used for obtaining the genes encoding RNA polymerase from any source [see, e.g., Sambrook et al., 1989, supra].

Accordingly, any cell potentially can serve as the nucleic acid source for the molecular cloning of a gene encoding RNA polymerase. The DNA may be obtained by standard procedures known in the art from cloned DNA (e.g., a DNA "library"), and preferably is obtained from a cDNA library, by cDNA cloning, or by the cloning of genomic DNA, or fragments thereof, purified from the desired cell [See, for example, Sambrook et al., 1989, supra; Glover, D. M. (ed.), 1985, DNA Cloning: A Practical Approach, MRL Press, Ltd., Oxford, U.K. Vol. I, II]. Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The present invention also relates to cloning vectors containing genes encoding analogs and derivatives of RNA polymerase including and fragments of the various subunits, that can form active forms of RNA polymerase. Included are homologs of RNA polymerase and fragments thereof, from other species. Therefore the production and use of derivatives and analogs related to RNA polymerase are within the scope of the present invention.

RNA polymerase derivatives can be made by altering encoding nucleic acid sequences by substitutions, additions or deletions including to provide for functionally equivalent molecules. Preferably, derivatives are made that are capable of forming crystals of the RNA polymerase that effectively diffract X-rays for the determination of the atomic coordinates of the protein-ligand complex to a resolution of better than 5.0 Angstroms, preferably to a resolution equal to or better than 3.5 Angstroms.

Due to the degeneracy of nucleotide coding sequences, other DNA sequences which encode substantially the same amino acid sequence as a RNA polymerase gene may be used in the practice of the present invention. These include but are not limited to allelic genes, homologous genes from other species, and nucleotide sequences comprising all or portions of RNA polymerase genes which are altered by the substitution of different codons that encode the same amino acid residue within the sequence, thus producing a silent change. Likewise, the RNA polymerase derivatives of the invention include, but are not limited to, those containing, as a primary amino acid sequence, all or part of the amino acid sequence of a RNA polymerase including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding RNA polymerase derivatives and analogs of the invention can be produced by various methods known in the art. The manipulations which result in their production can occur at the gene or protein level. For example, the cloned RNA polymerase gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of RNA polymerase, care should be taken to ensure that the modified gene remains within the same translational reading frame as the RNA polymerase gene, uninterrupted by translational stop signals, in the gene region where the desired activity is encoded.

Additionally, the RNA polymerase-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity and crystallization properties of the mutated RNA polymerase gene product. Any technique for mutagenesis known in the art can be used, including but not limited to, in vitro site-directed mutagenesis (Hutchinson, C., et al., 1978, *J. Biol. Chem.* 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification*, H. Erlich, ed., Stockton Press, Chapter 6, pp. 61–70].

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of RNA Polymerase

The nucleotide sequence coding for RNA polymerase, a fragment of RNA polymerase or a derivative or analog thereof, including a functionally active derivative, such as a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a RNA polymerase of the invention or a fragment thereof is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding RNA polymerase and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant RNA polymerase protein of the invention, or RNA polymerase fragment, derivative, chimeric construct, or analog thereof, may be expressed chromosomally, after integration of the coding sequence by recombination. In this regard, any of a number of amplification systems may be used to achieve high levels of stable gene expression [See Sambrook et al., 1989, supra].

The cell containing the recombinant vector comprising the nucleic acid encoding RNA polymerase is cultured in an appropriate cell culture medium under conditions that provide for expression of RNA polymerase by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of RNA polymerase may be controlled by any promoter/enhancer element known in the art, but these regulatory elements must be functional in the host selected for expression. Promoters that may be used to control RNA polymerase gene expression are well known in the art including prokaryotic expression vectors such as the β-lactamase promoter [Villa-Kamaroff, et al., *Proc. Natl. Acad. Sci. U.S.A.*, 75:3727–3731 (1978)], or the tac promoter [DeBoer, et al., *Proc. Natl. Acad. Sci. U.S.A.*, 80:21–25 (1983)].

Expression vectors containing a nucleic acid encoding an RNA polymerase of the invention can be identified by a number of means including four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding RNA polymerase is inserted within the "selection marker" gene sequence of the vector, recombinants containing the RNA polymerase insert can be identified by the absence of the selection marker gene function. In the fourth approach, recombinant expression vectors can be identified by assaying for the activity, biochemical, or immunological characteristics of the RNA polymerase expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX [Smith et al., *Gene*, 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmnIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700(BamH1 and KpnI cloning site, in which the BamH1 recognition site begins with the 5 initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuI, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to express the bacterial RNA polymerase. For example, the non-fusion pYES2 vector (xbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.*, 267:963–967 (1992); Wu and Wu, *J. Biol. Chem.*, 263:14621–14624 (1988); Hartmut et al., Canadian Patent Application No. 2,012,311, filed Mar. 15, 1990).

Peptide Synthesis

Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield [*J. Am. Chem. Soc.*, 85:2149–2154 (1963)], or the base-labile $N^\alpha$-amino protected 9-fluorenylmethoxycarbonyl (Fmoc) amino acids first described by Carpino and Han [*J. Org. Chem.*, 37:3403–3409 (1972)]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, λ-turns, and cyclic peptides can be generated.

Isolation and Crystallization of the Bacterial RNA Polymerase

The present invention provides a core RNA polymerase that can be crystallized into a crystal that effectively diffracts X-rays for the determination of the atomic coordinates of the RNA polymerase to a resolution of better than 5.0 Angstroms and preferably to a resolution equal to or better than 3.5 Angstroms. The RNA polymerase can be expressed either as described below in the Example, or as described above. Of course, the specific core RNA polymerase provided herein serves only as example, since the crystallization process can tolerate a broad range of active RNA polymerases. Therefore, any person with skill in the art of protein crystallization having the present teachings and without undue experimentation could crystallize a large number of alternative forms of the RNA polymerase from a variety of RNA polymerase fragments, or alternatively using a full length RNA polymerase from a related source. As mentioned above, an RNA polymerase having conservative substitutions in its amino acid sequence are also included in the invention, including a selenomethionine substituted form, as exemplified below.

Crystals of the RNA polymerase of the present invention can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used.

Exemplified below is the hanging-drop vapor diffusion procedure. 10 μl of *T. aquaticus* core RNAP (17 mg/ml) was mixed with the same volume of a solution containing 40–45% saturated $(NH_4)_2SO_4$, 0.1 M Tris-HCl, pH 8.0, and 20 mM $MgCl_2$, and incubated as a hanging drop over the same solution. Crystals giew in 2–3 weeks to typical dimensions of 0.15 mm×0.15 mm×0.4 mm at room temperature. For cryo-crystallography, the crystals are pre-soaked in stabilization solution (same as the crystallization solution except with 50% saturated ammonium sulfate). The crystals are then soaked in stabilization solution containing 50% (g/v) sucrose for about 30 minutes before flash freezing. The frozen crystals diffract to 5.0 Å from an in-house X-ray generator. Spots can sometimes be observed, in one direction, to 2.7 Å resolution at synchrotron beamlines. Diffraction data was processed using DENZO and SCALEPACK [Otwinowski, *Isomorphous Replacement and Anomalous Scattering* (eds. Wolf, Evans and Leslie) Science and Engineering Research Council, Daresbury Laboratory, Daresbury, UK, (1991)].

Alternative methods may also be used. For example, crystals can be characterized by using X-rays produced in a conventional source (such as a sealed tube or a rotating anode) or using a synchrotron source. Methods of characterization include, but are not limited to, precision photography, oscillation photography and diffractometer data collection. Selenium-Methionine may be used as described in the Example below, or alternatively a mercury derivative data set (e.g., using PCMB) could be used in place of the Selenium-Methionine derivatization.

As detailed in the Example below, Selenomethionyl core RNAP was prepared and crystallized using the same procedures from *T. aquaticus* cells grown in minimal media (culture medium 162) [Degryse et al., *Arch. Microbiol.*, 117:189–196 (1978)]. Cells can be induced to incorporate selenomethionine by suppression of methionine biosynthesis [Doublie, *Methods Enzymol.*, 276:523–530 (1997)].

Structural determinations can be performed by calculating Patterson maps using PHASES [Furey and Swaminathan, *Methods Enzymol.*, 277:590–620 (1997)] for the ethyl-$HgCl_2$ and $Ta_6Br_{14}$ derivatives and using the Pb-derivative as native. In the Example below, strong peaks (6 to 8 σ) were observed on Harker sections for both derivatives at 6 Å resolution. As exemplified below, the location of a single binding site was derived manually and confirmed using HEAVY [Terwilliger et al., *Acta Cryst.*, A 43:34–38 (1987)] for each derivative, and cross-confirmed using difference Fourier techniques. Additional sites, as well as sites for all the other heavy-metal derivatives, can be obtained using difference Fourier techniques. The final phasing calculations can be performed using SHARP [LaFortelle et al., *Crystallographic Computing*, (Eds. Bourne and Watenpaugh) 1997)]. Due to large errors between groups of data from each synchrotron beamline, the four data sets from CHESS A1 (Tables 1A–1C) were initially refined with SHARP. Other groups of data were subsequently included but with the refined heavy-atom parameters for the previously refined data sets fixed for all subsequent refinements. After each trial refinement, density modification and phase extension from 4.5 to 3.2 Å resolution was performed using SOLOMON. In the Example below, data sets were discarded and the previous refinement was used unless the new maps were noticeably improved by visual inspection. Of the 40 total derivative data sets that were collected, the nine listed in Tables 1A–1C, below, were used for the final phase calculations.

Map interpretation and model building can be performed using O [Jones et al., *Acta Cryst,* A 47:110–119 (1991)]. In the Example below, model building started with the α subunits, the fold of which was immediately recognized from the previously solved *E. coli* αNTD [Zhang and Darst, *Science,* 281:262–266 (1998)]. Preliminary rounds of a refinement were performed by creating a solvent mask around the α model, cutting out the electron density map inside the volume of the α-mask, then back-transforming the resulting electron density map. The resulting structure factors were used for two rounds of refinement of the α structure. Subsequently, initial refinements of the entire RNAP model were performed by keeping the α coordinates fixed. Only in the last round of positional refinement was a refined along with the rest of the RNAP model (but with tight non-crystallographic restraints between the appropriate α domains). Refinement calculations were performed using CNS [Adams et al., *Proc. Natl. Acad Sci. USA,* 94:5018–5023 (1997)]. From an initial R-factor of 0.44 ($R_{free}$=0.45) in the Example below, the current R-factor is 0.35 ($R_{free}$=0.41) for data from 100–3.2 Å resolution and a 0 σ cutoff (with bulk solvent correction and group b-factor refinement), 33% for data from 8–3.3 ($R_{free}$=0.40). The $R_{free}$ was closely monitored during all refinement procedures.

Protein-structure Based Design of Inhibitors of Bacterial RNA Polymerase

Once the three-dimensional structure of a crystal comprising a RNA Polymerase is determined, (e.g., see the coordinates in Table 3 below, in Appendix following the Sequence Listing) a potential modulator of RNA Polymerase, can be examined through the use of computer modeling using a docking program such as GRAM, DOCK, or AUTODOCK [Dunbrack et al., *Folding & Design,* 2:27–42 (1997)], to identify potential modulators of the RNA Polymerase. This procedure can include computer fitting of potential modulators to the RNA Polymerase to ascertain how well the shape and the chemical structure of the potential modulator will bind to either the individual bound subunits or to the RNA Polymerase [Bugg et al., *Scientific American,* Dec.:92–98 (1993); West et al., *TIPS,* 16:67–74 (1995)]. Computer programs can also be employed to estimate the attraction, repulsion, and steric hindrance of the subunits with a modulator/inhibitor (e.g., the RNA Polymerase and a potential stabilizer).

Indeed, the present invention provides the shape of RNA polymerase which is reminiscent of a crab-claw, with an internal groove or channel running along the full-length (between the claws). The molecule is about 150 Å long (from the back to the tips of the claws), 115 Å tall, and 110 Å wide (along the direction of the channel). The channel has many internal features, but the overall width is about 27 Å. Thus the structural determination disclosed herein allows particular compounds to be selected on the basis of their binding to the channel, for example.

Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential sideeffects due to unwanted interactions with other proteins.

Initially compounds known to bind bacterial RNA polymerase, for example rifampicin which binds to the β subunit, can be systematically modified by computer modeling programs until one or more promising potential analogs are identified. In addition systematic modification of selected analogs can then be systematically modified by computer modeling programs until one or more potential analogs are identified. Such analysis has been shown to be effective in the development of HIV protease inhibitors [Lam et al., *Science* 263:380–384 (1994); Wlodawer et al., *Ann. Rev. Biochem.* 62:543–585 (1993); Appelt, *Perspectives in Drug Discovery and Design* 1:23–48 (1993); Erickson, *Perspectives in Drug Discovery and Design* 1:109–128 (1993)]. Alternatively a potential modulator could be obtained by initially screening a random peptide library produced by recombinant bacteriophage for example, [Scott and Smith, *Science,* 249:386–390 (1990); Cwirla et al., *Proc. Natl. Acad. Sci.,* 87:6378–6382 (1990); Devlin et al., *Science,* 249:404–406 (1990)]. A peptide selected in this manner would then be systematically modified by computer modeling programs as described above, and then treated analogously to a structural analog as described below.

Once a potential modulator/inhibitor is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential modulator may be synthesized de novo. As mentioned above, the de novo synthesis of one or even a relatively small group of specific compounds is reasonable in the art of drug design. The potential modulator can be placed into a standard binding assay with RNA polymerase or an active fragment thereof, for example. The subunit fragments can be synthesized by either standard peptide synthesis described above, or generated through recombinant DNA technology or classical proteolysis. Alternatively the corresponding full-length proteins may be used in these assays.

For example, the β subunit can be attached to a solid support. Methods for placing the β subunit on the solid support are well known in the art and include such things as linking biotin to the β subunit and linking avidin to the solid support. The solid support can be washed to remove unreacted species. A solution of a labeled potential modulator (e.g., an inhibitor) can be contacted with the solid support. The solid support is washed again to remove the potential modulator not bound to the support. The amount of labeled potential modulator remaining with the solid support and thereby bound to the β subunit can be determined. Alternatively, or in addition, the dissociation constant between the labeled potential modulator and the β subunit, for example can be determined. Suitable labels for either the bacterial RNA polymerase subunit or the potential modulator are exemplified herein. In a particular embodiment, isothermal calorimetry can be used to determine the stability of the bacterial RNA polymerase in the absence and presence of the potential modulator.

In another embodiment, a Biacore machine can be used to determine the binding constant of the bacterial RNA polymerase to a DNA template in the presence and absence of the potential modulator. Alternatively, one or more of the bacterial RNA polymerase subunits can be immobilized on a sensor chip. The remaining subunits can then be contacted with (e.g., flowed over) the sensor chip to form the bacterial RNA polymerase.

In this case the dissociation constant for the bacterial RNA polymerase can be determined by monitoring changes in the refractive index with respect to time as buffer is passed over the chip. [O'Shannessy et al. Anal. Biochem. 212:457–468 (1993); Schuster et al., Nature 365:343–347 (1993)]. Scatchard Plots, for example, can be used in the analysis of the response functions using different concentrations of a particular subunit. Flowing a potential modulator at various concentrations over the bacterial RNA polymerase and monitoring the response function (e.g., the change in the refractive index with respect to time) allows the bacterial RNA polymerase dissociation constant to be determined in the presence of the potential modulator and thereby indicates whether the potential modulator is either an inhibitor, or an agonist of the bacterial RNA polymerase complex.

In another aspect of the present invention a potential modulator is assayed for its ability to inhibit the bacterial RNA polymerase. A modulator that inhibits the RNA polymerase can then be selected. In a particular embodiment, the effect of a potential modulator on the catalytic activity of bacterial RNA polymerase is determined. The potential modulator is then be added to a bacterial culture to ascertain its effect on bacterial proliferation. A potential modulator that inhibits bacterial proliferation can then be selected.

In a particular embodiment, the effect of the potential modulator on the catalytic activity of the bacterial RNA polymerase is determined (either independently, or subsequent to a binding assay as exemplified above). In one such embodiment, the rate of the DNA-dependent RNA transcription is determined. For such assays a labeled nucleotide could be used. This assay can be performed using a real-time assay e.g., with a fluorescent analog of a nucleotide. Alternatively, the determination can include the withdrawal of aliquots from the incubation mixture at defined intervals and subsequent placing of the aliquots on nitrocellulose paper or on gels. In a particular embodiment the potential modulator is selected when it is an inhibitor of the bacterial RNA polymerase.

One assay for RNA polymerase activity is a modification of the method of Burgess et al. [*J. Biol. Chem.*, 244:6160 (1969)]

[See also http://www.worthington-biochem.com/manual/R/RNAP.html].

One unit incorporates one nanomole of UMP into acid insoluble products in 10 minutes at 37° C. under the assay conditions such as those listed below. The suggested reagents are:

(a) 0.04 M Tris-HCl, pH 7.9, containing 0.01 M $MgCl_2$, 0.15 M KCl, and 0.5 mg/ml BSA;

(b) Nucleoside triphosphates (NTP) : 0.15 mM each of ATP, CTP, GTP, UTP; spiked with $^3$H - UTP 75000–150000 cpms/0.1 ml;

(c) 0.15 mg/ml calf thymus DNA;

(d) 10% cold perchloric acid; and (e) 1% cold perchloric acid.

0.1–0.5 units of RNA polymerase in 5 ul–10 ul is used as the starting enzyme concentration.

The procedure is to add 0.1 ml Tris-HCl, 0.1 ml NTP and 0.1 ml DNA to a test tube for each sample or blank. At zero time enzyme (or buffer for blank) is added to each test tube, and the contents are then mixed and incubated at 37° C. for 10 minutes. 1 ml of 10% perchloric acid is added to the tubes to stop the reaction. The acid insoluble products can be collected by vacuum filtration through MILLIPORE filter discs having a pore size of 0.45 u–10 u (or equivalent). The filters are then washed four times with 1% cold perchloric acid using 1 ml–3 ml for each wash. These filters are then placed in scintillation vials. 2 mls of methyl cellosolve are added to the scintillation vials to dissolve the filters. When the filters are completely dissolved (after about five minutes) 10 mls of scintillation fluid are added and the vials are counted in a scintillation counter.

For calculation of units of RNA polymerase/mg of protein the following equation can be used:

$$\text{units/mg} = \frac{CPM_{test} - CPM_{blank}}{CPM_{total} \times \text{mg protein}_{in\,test}}$$

When suitable potential modulators are identified, a supplemental crystal can be grown which comprises the bacterial RNA polymerase and the potential modulator. Preferably the crystal effectively diffracts X-rays for the determination of the atomic coordinates of the protein-ligand complex to a resolution of better than 5.0 Angstroms, more preferably equal to or better than 3.5 Angstroms. The three-dimensional structure of the supplemental crystal is determined by Molecular Replacement Analysis. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR (see above), CNS, (Crystallography and NMR System, a next level of XPLOR), and AMORE [J. Navaza, *Acta Crystallographics ASO*, 157–163 (1994)]. Once the position and orientation are known an electron density map can be calculated using the search model to provide X-ray phases. Thereafter, the electron density is inspected for structural differences and the search model is modified to conform to the new structure. Using this approach, it will be possible to use the claimed crystal of the bacterial RNA polymerase to solve the three-dimensional structures of other bacterial core RNA polymerases having pre-ascertained amino acid sequences. Other computer programs that can be used to solve the structures of the bacterial RNA polymerase from other organisms include: QUANTA, CHARMM; INSIGHT; SYBYL; MACROMODE; and ICM.

A candidate drug can be selected by performing rational drug design with the three-dimensional structure determined for the supplemental crystal, preferably in conjunction with computer modeling discussed above. The candidate drug (e.g., a potential modulator of bacterial RNA polymerase) can then be assayed as exemplified above, or in situ. A candidate drug can be identified as a drug, for example, if it inhibits bacterial proliferation.

A potential inhibitor (e.g., a candidate drug) would be expected to interfere with bacterial growth. Therefore, an assay that can measure bacterial growth may be used to identify a candidate drug.

Methods of testing a potential bactericidal agent (e.g., the candidate drug) in an animal model are well known in the art, and can include standard bactericidal assays. The potential modulators can be administered by a variety of ways including topically, orally, subcutaneously, or intraperitoneally depending on the proposed use. Generally, at least two groups of animals are used in the assay, with at least one group being a control group which is administered the administration vehicle without the potential modulator.

For all of the drug screening assays described herein further refinements to the structure of the drug will generally be necessary and can be made by the successive iterations of any and/or all of the steps provided by the particular drug screening assay.

Labels

Suitable labels include enzymes, fluorophores e.g., fluorescein isothiocyanate (FITC), phycoerythrin (PE), Texas red (TR), rhodamine, free or chelated lanthanide series salts, especially $Eu^{3+}$, to name a few fluorophores and including fluorescent GTP and GDP analogs such as mantGTP and mantGDP, chromophores, radioisotopes, chelating agents, dyes, colloidal gold, latex particles, ligands (e.g., biotin), and chemiluminescent agents. When a control marker is employed, the same or different labels may be used for the test and control marker.

In the instance where a radioactive label, such as the isotopes $^3H$, $^{14}C$, $^{32}P$, 35S, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313, 734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017) Other direct labels include a radionucleotide, a luminescent moiety, or a fluorescent moiety including as a modified/fusion chimera of green fluorescent protein (as described in U.S. Pat. No. 5,625,048 filed Apr. 29, 1997, and WO 97/26333, published Jul. 24, 1997, the disclosures of each are hereby incorporated by reference herein in their entireties). In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70:419–439 (1980) and in U.S. Pat. No. 4,857,453. Suitable enzymes include, but are not limited to, alkaline phosphatase and horseradish peroxidase. Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^3H$]-amino acids (with the tritium substituted at non-labile positions).

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Crystal Structure o *Thermus aquaticus* Core RNA Polymerase at 3.3 Å Resolution

Introduction

To provide a more detailed framework to interpret the existing genetic, biochemical, and biophysical information, as well as to guide further studies aimed at understanding the transcription process and its regulation, the three-dimensional structure of a bacterial core RNAP by X-ray crystallography at 3.3 Å resolution has been determined as detailed below.

Methods

Purification and crystallization: The preparative procedure for *T. aquaticus* core RNAP is similar to the preparation of *E. coli* core RNAP [Polyakov et al., Cell, 83:365–373 (1995)]. Briefly, approximately 200 g wet cell paste is thawed and lysed using a continuous-flow French press. After a low-speed spin, the soluble fraction is precipitated with 0.6% Polymin-P. RNAP is eluted from the Polymin-P pellet with TGED buffer (10 mM Tris -HCl, pH 8, 5% glycerol, 1 mM EDTA, 1 mM DTT) plus 1 M NaCl, then precipitated by adding 33%(g/v) ammonium sulfate. The pellet is resuspended and loaded onto a 50 ml column of heparin-SEPHAROSE FF (Pharmacia) equilibrated with TGED buffer plus 0.2 M NaCl. The RNAP is eluted from the column with TGED buffer plus 0.6 M NaCl. The RNAP was again precipitated with ammonium sulfate, then resuspended and loaded on a SUPERDEX-200 gel filtration column equilibrated with TGED buffer plus 0.5 M NaCl. Fractions containing RNAP were pooled and loaded onto a MONO-Q (Pharmacia) ion-exchange column equilibrated with TGED buffer plus 0.1 M NaCl. The protein was eluted with a gradient from 0.1 to 0.5 M NaCl. The RNAP peak eluted at around 0.3 M NaCl. The RNAP was concentrated using a centrifugal filter, then loaded onto an SP SEPHAROSE (Pharmacia) column equilibrated in TGED buffer plus 0.1 M NaCl. After loading, the column was incubated at 4° C. for at least 10 hours, then pure RNAP was eluted with a 0.1 to 0.5 M NaCl gradient (core RNAP elutes at around 0.3 M NaCl). 200 g wet cell paste typically yielded 15 mg of core RNAP, which was more than 99% pure as judged from overloaded, Coomassie-stained SDS gels. This sample is ready for crystallization.

Crystals of *T. aquaticus* core RNAP were grown by vapor diffusion. 10 µl of *T. aquaticus* core RNAP (17 mg/ml) was mixed with the same volume of a solution containing 40–45% saturated $(NH_4)_2SO_4$, 0.1 M Tris-HCl, pH 8.0, and 20 mM $MgCl_2$, and incubated as a hanging drop over the same solution. Crystals grow in 2–3 weeks to typical dimensions of 0.15 mm×0.15 mm×0.4 mm at room temperature. For cryo-crystallography, the crystals are pre-soaked in stabilization solution (same as the crystallization solution except with 50% saturated ammonium sulfate). The crystals are then soaked in stabilization solution containing 50% (g/v) sucrose for about 30 minutes before flash freezing. The frozen crystals diffract to 5.0 Å from an in-house X-ray generator. Spots can sometimes be observed, in one direction, to 2.7 Å resolution at synchrotron beamlines. Diffraction data was processed using DENZO and SCALEPACK [Otwinowski, *Isomorphous Replacement and Anomalous Scattering* (eds. Wolf, Evans and Leslie) Science and Engineering Research Council, Daresbury Laboratory, Daresbury, UK, (1991)].

Selenomethionyl core RNAP was prepared and crystallized using the same procedures from *T. aquaticus* cells grown in minimal media (culture medium 162) [Degryse et al., *Arch. Microbiol.*, 117:189–196 (1978)]. Cells were induced to incorporate selenomethionine by suppression of methionine biosynthesis [Doublie, *Methods Enzymol.*, 276:523–530 (1997)].

Structure Determination: Patterson maps were calculated using PHASES [Furey and Swaminathan, *Methods Enzymol.*, 277:590–620 (1997)] for the ethyl-$HgCl_2$ and $Ta_6Br_{14}$ derivatives and using the Pb-derivative as native. Strong peaks (6 to 8 σ) were observed on Harker sections for both derivatives at 6 Å resolution. The location of a single binding site was derived manually and confirmed using HEAVY [Terwilliger et al., *Acta Cryst.*, A 43:34–38 (1987)] for each derivative, and cross-confirmed using difference Fourier techniques. Additional sites, as well as sites for all the other heavy-metal derivatives, were obtained using difference Fourier techniques. The final phasing calculations were performed using SHARP [LaFortelle et al., *Crystallographic Computing*, (Eds. Bourne and Watenpaugh) 1997)]. Due to large errors between groups of data from each synchrotron beamline, the four data sets from CHESS A1 (Tables 1A–1C) were initially refined with SHARP. Other groups of data were subsequently included but with the refined heavy-atom parameters for the previously refined data sets fixed for all subsequent refinements. After each trial refinement, density modification and phase extension from 4.5 to 3.2 Å resolution was performed using SOLOMON. Data sets were discarded and the previous refinement was used unless the new maps were noticeably improved by visual inspection. Of 40 total derivative data sets that were collected, the nine listed in Tables 1A–1C were used for the final phase calculations (see Tables 1A–1C, below).

Map interpretation and model building was done using O [Jones et al., *Acta Cryst*, A 47:110–119 (1991)]. Model building started with the α subunits, the fold of which was immediately recognized from the previously solved *E. coli* αNTD [Zhang and Darst, *Science*, 281:262–266 (1998)]. Preliminary rounds of α refinement were performed by creating a solvent mask around the α model, cutting out the electron density map inside the volume of the α-mask, then back-transforming the resulting electron density map. The resulting structure factors were used for two rounds of refinement of the α structure. Subsequently, initial refinements of the entire RNAP model were performed by keeping the α coordinates fixed. Only in the last round of positional refinement was α refined along with the rest of the RNAP model (but with tight non-crystallographic restraints between the appropriate α domains). Refinement calculations were performed using CNS [Adams et al., *Proc. Natl. Acad. Sci. USA*, 94:5018–5023 (1997)]. From an initial R-factor of 0.44 ($R_{free}$=0.45), the current R-factor is 0.35 ($R_{free}$=0.41) for data from 100–3.2 Å resolution and a 0 σ cutoff (with bulk solvent correction and group b-factor refinement), 33% for data from 8–3.3 ($R_{free}$=0.40). The $R_{free}$ was closely monitored during all refinement procedures.

Results

Purification, crystallization and structure determination: The core RNAP isolated from *Thermus aquaticus* (see Methods above) comprised four distinct polypeptides. The three largest polypeptides were cloned and sequenced, identifying them as β', β, and α (FIG. 1, Table 2). The fourth polypeptide (about 10.5 kDa) was tentatively identified as the ω subunit (see below). The isolated enzyme was active in a non-promoter specific transcription assay.

Tetragonal crystals, space group $P4_12_12$ (a=b=201, c=294 Å), were grown by vapor diffusion (see Methods, above). The crystals contained one 375.4 kDa core RNAP molecule per asymmetric unit, with a solvent content of 65%. Diffraction from the radiation-sensitive crystals was anisotropic, with reflections observed along the best and worst directions at 3.0 Å and 3.4 Å Bragg spacings, respectively. The structure was solved by the method of multiple isomorphous replacement (see Methods, and Tables 1A–1C).

TABLE 1A

Crystallographic data

| Data set | Resolution (Å) | $R_{merge}$[1] (%) (+/− ano) | No. of unique reflections (+/− ano) | Total observations[2] |
|---|---|---|---|---|
| TriMetPb[a] | 3.2 | 10.0/7.6 | 78640/122450 | 181691 |
| $HgCl_2$[a] | 3.2 | 6.2/5.5 | 70627/103250 | 245952 |
| EthylHgCl[a] | 3.2 | 7.5/5.7 | 77123/120759 | 188044 |
| $Ta_6Br_{14}$[a] | 3.7 | 7.7/5.8 | 47995/72245 | 107255 |
| Mersalyl[b] | 3.2 | 7.7/6.2 | 90039/169685 | 248398 |
| $KAu(CN)_2$[b] | 3.3 | 12.1/9.8 | 70851/104869 | 145942 |
| EMTS[b] | 3.2 | 11.3/8.7 | 77657/111598 | 140480 |
| $Ir_4$[c] | 3.0 | 9.5/8.0 | 866353/161702 | 308116 |
| $HgCl_2$[c] | 3.0 | 9.1/8.0 | 926452/15026 | 346661 |
| Se Me[ad] | 4.0 | 9.7 | 45071 | 133158 |

[1]$R_{merge} = \Sigma|Ij-<I>|/\Sigma Ij$, with or without Bijvoet pairs treated as equivalent.
[2]Total observations, the number of full and partial observations measured with non-negative intensity to the indicated resolution.
[a,b,c]Data sets were collected at [a]CHESS A1, F1, OR F2, [b]APS 14-BM-C, or [c]NSLS X25.
[d]SeMet data was not included in phase calculations.

TABLE 1B

Crystallographic data

| | Completeness[3] (%) (+/− ano) | Phasing Power[4] centric/acentric/ano | No. of sites |
|---|---|---|---|
| TriMetPb[a] | 82.5/67.4 | −/−/0.22 | 1 |
| $HgCl_2$[a] | 77.1/50.5 | 1.10/1.23/0.58 | 4 |
| EthylHgCl[a] | 78.5/64.5 | 1.10/1.45/0.48 | 3 |
| $Ta_6Br_{14}$[a] | 75.4/59.9 | 0.55/0.68/0.50 | 5 |
| Mersalyl[b] | 92.5/75.3 | 1.06/1.48/0.75 | 1 |
| $KAu(CN)_2$[b] | 79.8/62.1 | 0.39/0.44/0.12 | 1 |
| EMTS[b] | 79.4/59.8 | 1.22/1.64/0.81 | 5 |
| $Ir_4$[c] | 74.7/71.4 | 0.46/0.65/0.32 | 4 |
| $HgCl_2$[c] | 77.0/65.4 | 1.71/1.50/0.98 | 4 |
| Se Me[ad] | 80.1 | | 45 |

[3]Completeness, the percentage of possible unique reflections measured with $I/\delta(I) \geq 0$ to the indicated resolution.
[4]Phasing power and figure of merit are from SHARP [ref].
[a,b,c]Data sets were collected at [a]CHESS A1, F1, OR F2, [b]APS 14-BM-C, or [c]NSLS X25.
[d]SeMet data was not included in phase calculations.

TABLE 1C

Crystallographic data: Mean Figure of Merit[4]

| Resolution (Å) | No. of reflections | F.O.M. |
|---|---|---|
| 40.36 – 8.27 | 6070 | 0.756 |
| 5.91 | 10153 | 0.674 |
| 4.84 | 12928 | 0.543 |
| 4.20 | 15112 | 0.406 |
| 3.76 | 17054 | 0.278 |
| 3.44 | 18761 | 0.165 |
| 3.18 | 20004 | 0.085 |
| overall | 100082 | 0.341 |

[4]Phasing power and figure of merit are from SHARP [ref].

TABLE 2

Structural model

| Subunit | n[1] | $M_r$ (kDa) | Residues in sequence | model | regions modeled |
|---|---|---|---|---|---|
| β' | 1 | 170.7 | 1,525 | 1,077 | 4–22, 96–132, 462–523, 535–1493 (polyAla: 4–22, 96–132, 462–509, 797–869, 1451–1493) |
| β | 1 | 124.4 | 1,119 | 1,112 | 2–1113 (polyAla: 478–521, 599–652) |
| α | 2 | 34.9 | 313 | 226 | 6–231 |
| ω | 1 | 10.5 | 91 | 91 | 1–91 (polyAla: 1–91) |
| total | 5 | 375.4 | 3,361 | 2,732 | |

[1]Number of copies of the subunit in the RNAP assembly

Figure 2A:
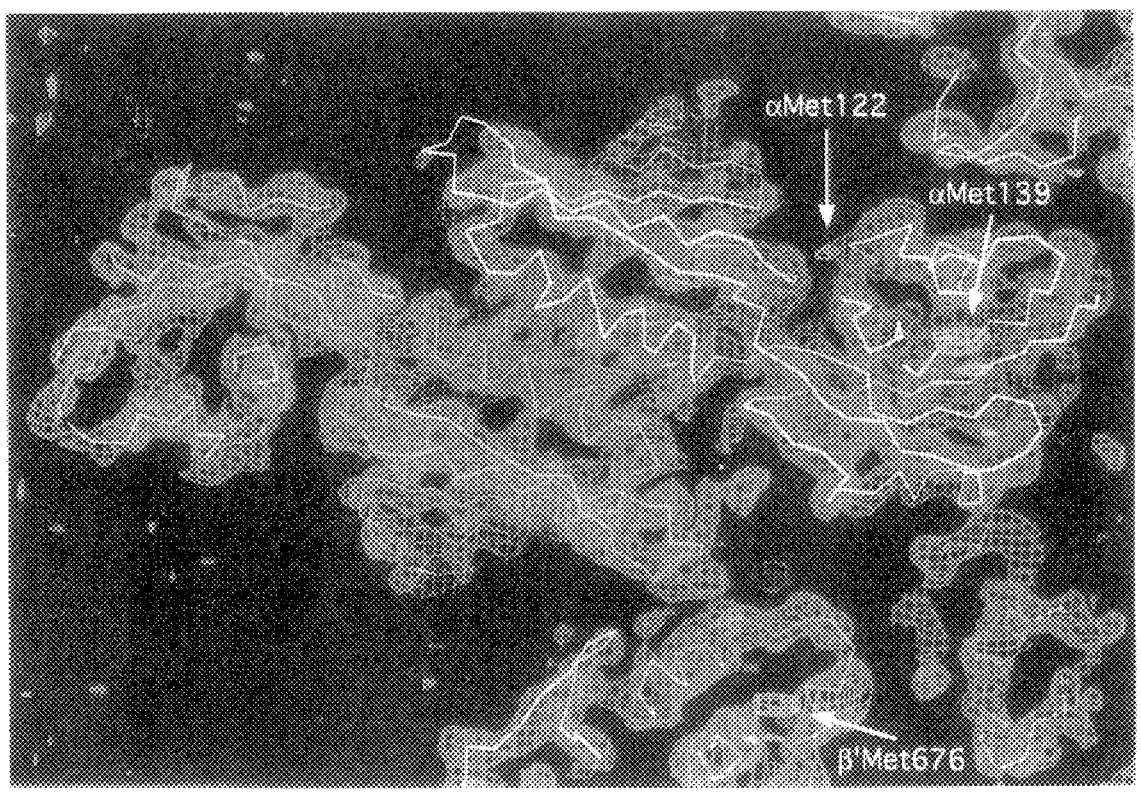
FIGS. 2A–2B show the experimental electron density maps.
Figure 2B:
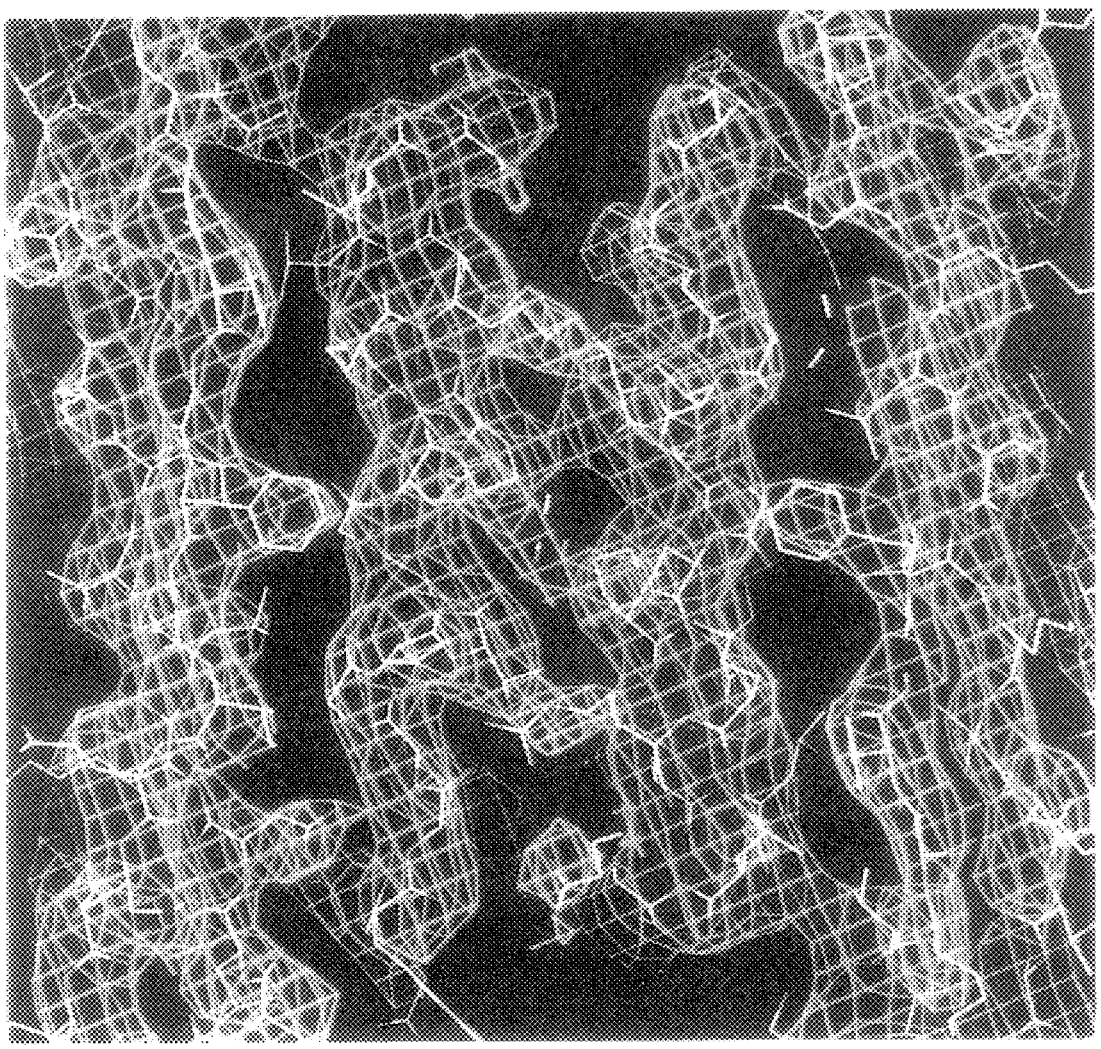

Modeling and refinement: The initial MIR map showed protein-solvent boundaries and contained some identifiable α-helices. Density modification resulted in a dramatically improved map (FIG. 2). The fold of the previously solved α-subunit N-terminal domain (NTD) dimer [Zhang and Darst, Science, 281:262–266 (1998)] was easily recognized, and the αNTD structure was modeled and refined as described in the Methods below (FIG. 2). Phase combination and multi-domain non-crystallographic symmetry averaging were then used to obtain a slightly improved map. This map was exceptionally clean, with secondary structural elements and well-connected main-chain density over most of the structure, allowing building of a poly-alanine model containing about 85% of the expected number of residues for β and β'. Side-chain density, while present in much of the map, was weak to non-existent in other regions. For this reason, selenomethionyl core RNAP was prepared and crystallized (see Methods, above). The resulting Fourier-difference peaks aided in the localization of methionine residues during modeling (FIG. 2a).

After positional refinement of an initial model, the resulting phase-combined maps revealed additional side-chain density, allowing adjustment of the model and assignment of additional sequence. The current model (Table 2) contains about 70% of the main-chain of β', the complete main-chain of β (except for a few residues at each terminus), the αNTD dimer, a 91 residue poly Ala model of ω, one $Mg^{2+}$-ion (chelated at the active center), and one $Zn^{2+}$-ion. Lacking electron density and presumably disordered in the crystal are both α C-terminal domains, as well as a 74 residue segment of β' that includes a $Zn^{2+}$-binding motif along with most of β' conserved region A ($β'_A$). The region of primarily helical, well-defined electron density assigned to ω was completely detached from any other density and was at odds with the secondary structure predicted for $β'_A$ (the only region not assigned that was large enough to account for the density), which was completely β-sheet [Rost and Sander, J. Mol. Biol, 232:584–599 (1993)]. Secondary structure predictions using the sequence of either E. coli or Deinococcus radiodurans (evolutionarily closely related to T. aquaticus) ω matched the structure of this portion almost to the residue, leading to its assignment as ω. A non-conserved sequence of 330 residues inserted between $β'_A$ and $β'_B$ is currently not modeled. Electron density for this domain is present but weak and generally not well connected. Several stretches of residues are modeled as poly Ala.

These include linker regions between $β'_D$ and $β'_E$, as well as between $β_{D-E}$ and $β_{E-F}$. The R-factor for the current model is 0.329 for data from 8–3.3 Å resolution ($R_{free}$= 0.399). With the exception of $β'_A$, which is disordered and not modeled, the conserved regions of the large subunits are generally well-defined. In addition, the structure of the αNTD dimer was easily built from the known structure with no ambiguities. Serving to limit the possibility of errors in the structure was the availability of selenomethionine difference peaks; within the modeled portion of the structure, there are 42 methionine residues, 38 of these correlate with selenomethionine peaks. Also, within the modeled portion of the structure, there are 9 cysteine residues, 7 of these are bound by various Hg-derivatives (Tables 1A–1C), the other two are buried and do not appear to be solvent-accessible. Furthermore, the binding site for a single-site Pb-derivative was interpreted to be the known site of $Mg^{2+}$-chelation in the enzyme active center by three Asp residues in the absolutely conserved -NADFDGD- motif (SEQ ID NO:4) of $β'_D$ [Zaychikov et al., 273:107–109 (1996)]. It was subsequently shown that Pb-ions bind to this site in the protein with a very high affinity.

Figure 4A:
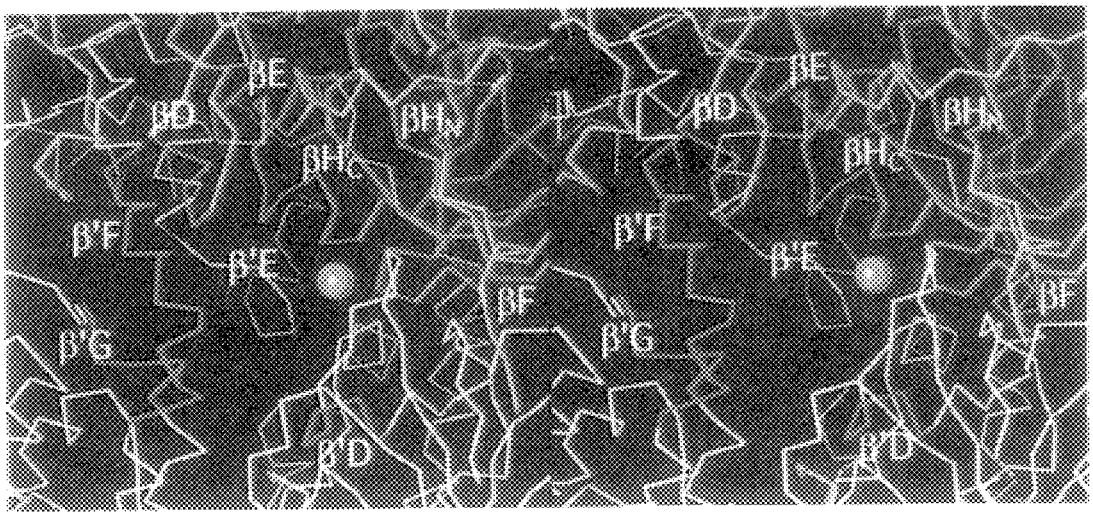
FIGS. 4A–4B show the active center of RNAP.
Figure 4B:
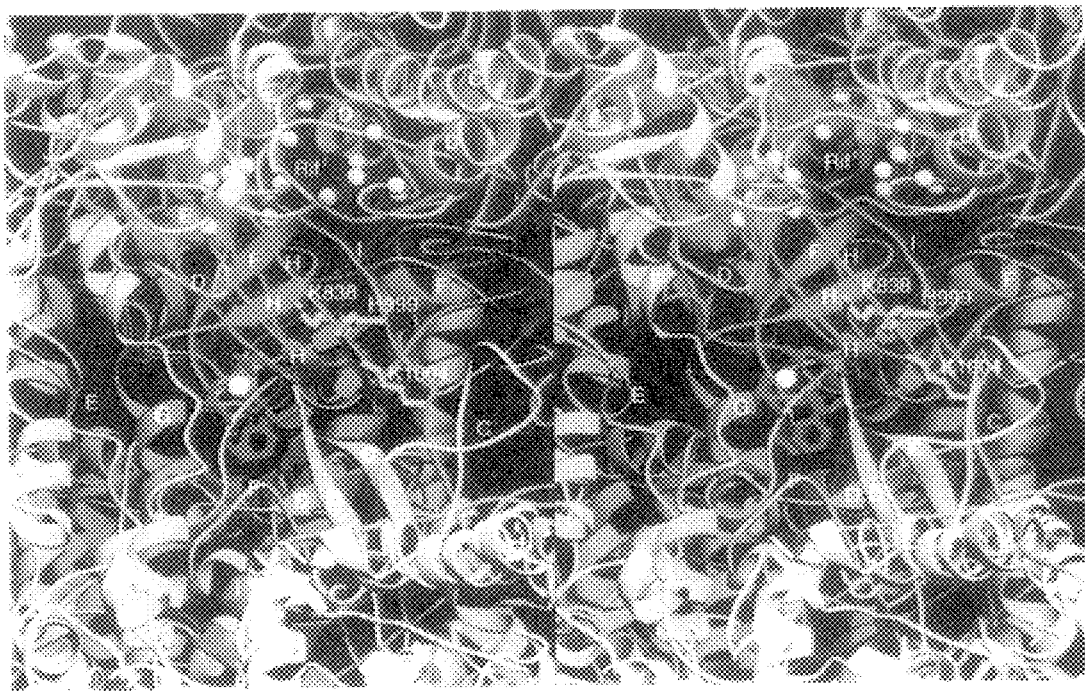

Further support for the structure comes from the fact that it explains a wide range of independent biochemical, biophysical, and genetic data available in the literature (which was not used to guide the model-building process). The available evidence supporting the model includes:

1) With only a few exceptions, the structure corresponds to the predicted secondary structure [Rost and Sander, J. Mol. Biol., 232:584–599 (1993)], which is expected to be accurate because of the large number of highly homologous sequences used in the prediction for β and β' (50 and 86, respectively);

2) Prokaryotic RNAPs are inhibited by the antibiotic rifampicin, which binds with high affinity to a genetically well-characterized site in β. Mutations conferring rifampicin resistance are scattered throughout β [Jin and Gross, J. Mol. Biol., 202:45–58 (1988) and Severinov et al., J. Biol. Chem.,, 268:14820–14825 (1993)] (FIG. 1) but these residues are clustered together in the structure (FIG. 4B);

3) Genetic and crosslinking studies have identified residues in widely separated regions of β that are directly involved in binding the initiating NTP substrate or are within a few Ångstroms of the site [Mustaev et al., J. Biol. Chem., 266:23927–23931 (1991) and Severinov et al., J. Biol. Chem., 270:29428–29432 (1995)] (FIG. 1) and these residues are clustered together in the structure (FIG. 4B);

4) A fusion between the C-terminus of β and the N-terminus of β' in *E. coli* shows no detectable defects in vivo or in vitro [Severinov et al., *J. Biol. Chem.*, In Press (1997)], and the fusion occurs naturally in some bacterial species [Zakharova et al., *J. Bacteriol*, 181:3857–3859 (1999)]. These two sites are immediately adjacent to one another in the structure (FIG. 3);

5) Known sites of protease sensitivity in intact RNAP [Borukhov et al., *J. Biol. Chem.*, 266:23921–23926 (1991) and Severinov et al., 267:12813–12819 (1992)] are exposed on the surface of the structure;

6) Mustaev et al.,[*Proc. Natl. Acad. Sci. USA*, 94:6641–6645 (1997)] used $Fe^{2+}$-generated hydroxyl-radical cleavage to identify 9 widely separated sites, five in β and four in β' (FIG. 1), that are all close to the active center $Mg^{2+}$. These sites are all less than 20 Å from the active center $Mg^{2+}$ in the structure (FIG. 4a);

7) Mustaev et al.,[*Proc. Natl. Acad. Sci. USA*, 91:12036–12040 (1994)] used chimeric rifampicin-ATP compounds to show that the rifampicin binding site and the initiating NTP substrate site (the i-site) are within 15 Å of each other, which is consistent with the structure (FIG. 4b).

Figure 5A:
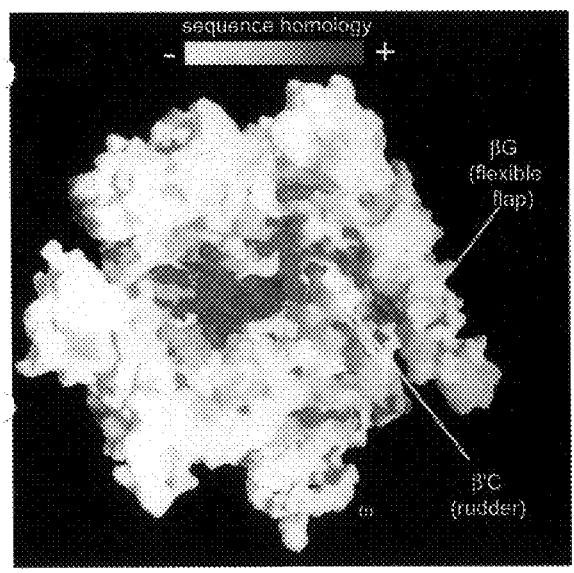
FIGS. 5A–5B depict the sequence homology in β and β' mapped onto the core RNAP structure. Shown are molecular surface representations of core RNAP. Color-coding is according to amino acid sequence homology within the β and β' subunits (the α and ω surfaces are not color-coded and are white), with low sequence homology shown as white, very high (100%) shown in red, with a gradient in between. Some structural features discussed in the text are labeled. The figure is displayed using the program GRASP [Nicholls et al., *Proteins Struct. Funct. Genet.*, 11:281–296 (1991)].
Figure 5B:
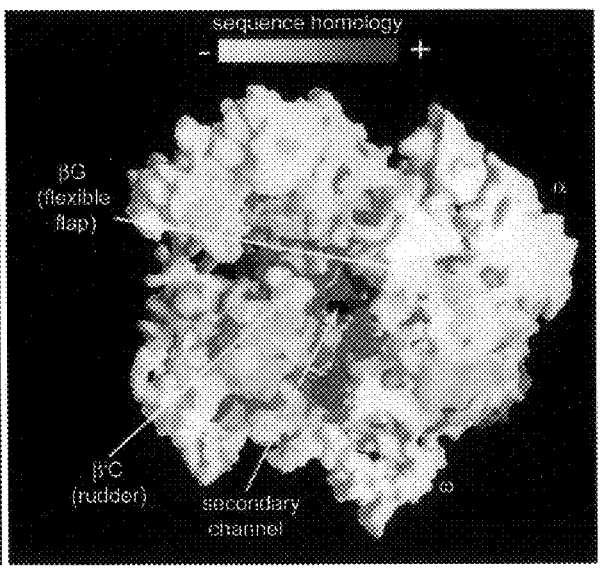

General architecture: The shape and size of the *T. aquaticus* core RNAP X-ray structure (FIG. 3, FIG. 5) corresponds extremely well with the low-resolution structure of *E. coli* core RNAP from cryo-electron microscopy [Darst et al., *J. Structural Biol.*, 124:115–122 (1998); and Darst et al., *Cold Spring Harbor Symp. Quant. Biol.*, 63:269–276 (1998)]. The shape is reminiscent of a crab-claw, with an internal groove or channel running along the full-length (between the claws). The molecule is about 150 Å long (from the back to the tips of the claws), 115 Å tall, and 110 Å wide (along the direction of the channel). The channel has many internal features, but the overall width is about 27 Å.

Subunit interactions: The RNAP subunits make extensive interfaces with each other. β and β' each contribute about 17% of their solvent-accessible surface [Lee and Richards, *J. Mol. Biol.*, 55:379–400 (1971)] to contacts with other subunits. Indicative of its presumed role in assembly, each αNTD monomer contributes about 24% of its solvent-accessible surface to intersubunit contacts. The structure supports the view that the αNTD dimer functions to aid the assembly of β and β' but does not participate directly in catalysis. In fact, no residues of the αNTD dimer have access to the internal channel of RNAP where catalysis takes place.

β regions F, G, H, and I contact the αNTD dimer almost exclusively through only one of the αNTD monomers (denoted αI; FIG. 3), with the primary interface being $β_H$, consistent with the findings of Wang et al. [*J. Mol. Biol.*, 270:648–662: (1997)]. β' regions C, D, G, and H contact exclusively the other α monomer (αII). The interactions that β and β' make with the αNTD dimer closely match the hydroxyl-radical protein footprinting data of Heyduk et al. [Proc. Natl. Acad. Sci. USA, 93:10162–10166 (1996)].

β and β' make extensive interactions with each other. A major interface between the two large subunits occurs at the base of the channel where the active center $Mg^{2+}$ is chelated (FIG. 3). Particularly critical are interactions between β regions H and I and β' region D, which position the -NADFDGD- motif of $β'_D$ for chelating the active site $Mg^{2+}$ (FIG. 4b).

Also of particular importance is $β_I$. An N-terminal part of $β_I$ (residues 974–979) makes contacts with α that are critical for the formation of the $α_2β$ assembly intermediate [Wang et al., *J. Mol. Biol.*, 270:648–662 (1997)]. The middle of $β_I$ (residues 998–1008) contacts β' regions C, G, and H along with $β_H$ and $β'_D$ to help form the catalytic center (FIG. 4b). Finally, the C-terminal part of $β_I$ (residues 1009–1099), which is required to recruit β' into the $α_2β$ assembly intermediate [Wang et al., *J. Mol. Biol.*, 270:648–662 (1997)], forms a separate domain from the rest of β but is almost completely surrounded by β' regions B, C, D, and H (FIG. 3). Overall, β regions A, B, and C are the only conserved regions of the two large subunits that do not make intersubunit contacts.

The ω subunit makes contacts only with β', consistent with the crosslinking results of Gentry and Burgess [Gentry and Burgess, *Biochemistry*, 32:11224–11227 (1993)]. The ω subunit completely wraps around the C-terminal tail of β' (FIG. 3), suggesting ω may play a chaperonin role in the final stages of RNAP assembly [Mukherjee and Chatterji, *Eur. J. Biochem.*, 247:884–889 (1997)].

Subunit structure: The structure of the αNTD dimer in the core RNAP is almost identical to the isolated αNTD structure [Zhang and Darst, *Science*, 281:262–266 (1998)] except for domain movements. In the RNAP structure, domain II of each αNTD monomer is rotated towards the RNAP. Domain II (along with domain I) of each αNTD monomer makes interactions with β (αI) or β' (αII), but the interactions between domain II of αI and β are much more extensive. In fact, domain II of αII makes contacts with a region of β' between regions D and E that shows little homology with eukaryotes. Thus, this interaction may not be critical for RNAP assembly.

As expected for such large proteins, both β and β' comprise a number of relatively distinct domains (FIG. 1). Two domains of β are unique in that they extend away from the main body of β' and do not interact with other β domains. One of these, the already mentioned C-terminal part of $β_I$, makes extensive interactions with β'. The second domain, which spans $β_F$ and $β_H$ and includes $β_G$, forms a flap-like domain that appears to be flexibly-connected to the rest of β (FIG. 3); the position of this domain in the crystal structure is fixed only by crystal contacts with symmetry-related RNAP molecules.

Figure 3A:
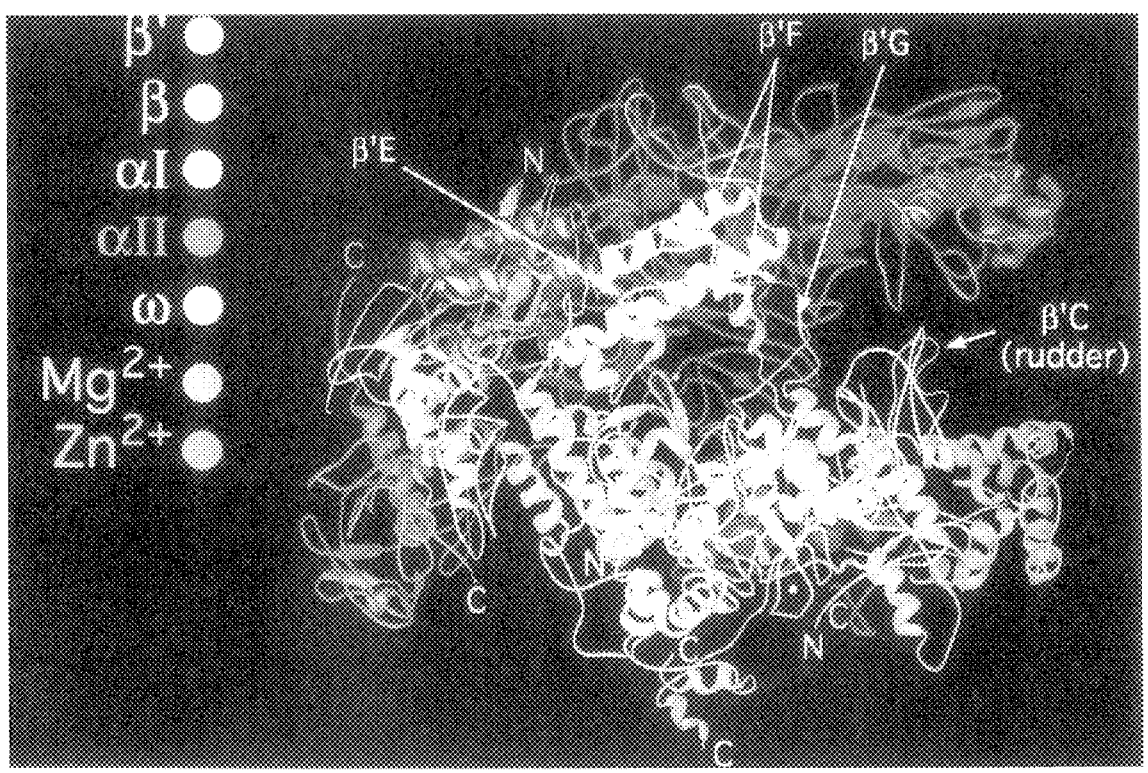
FIGS. 3A–3C depict the structure of the *T. aquaticus* core RNAP. RIBBONS [Carson, *J. Appl. Crystallogr.*, 24:958–961 (1991)] diagram of the three-dimensional structure of core RNAP. Various features discussed in the text are labeled. The break in the chain of β' due to the disordered region A is indicated by the red bullseyes.
Figure 3B:
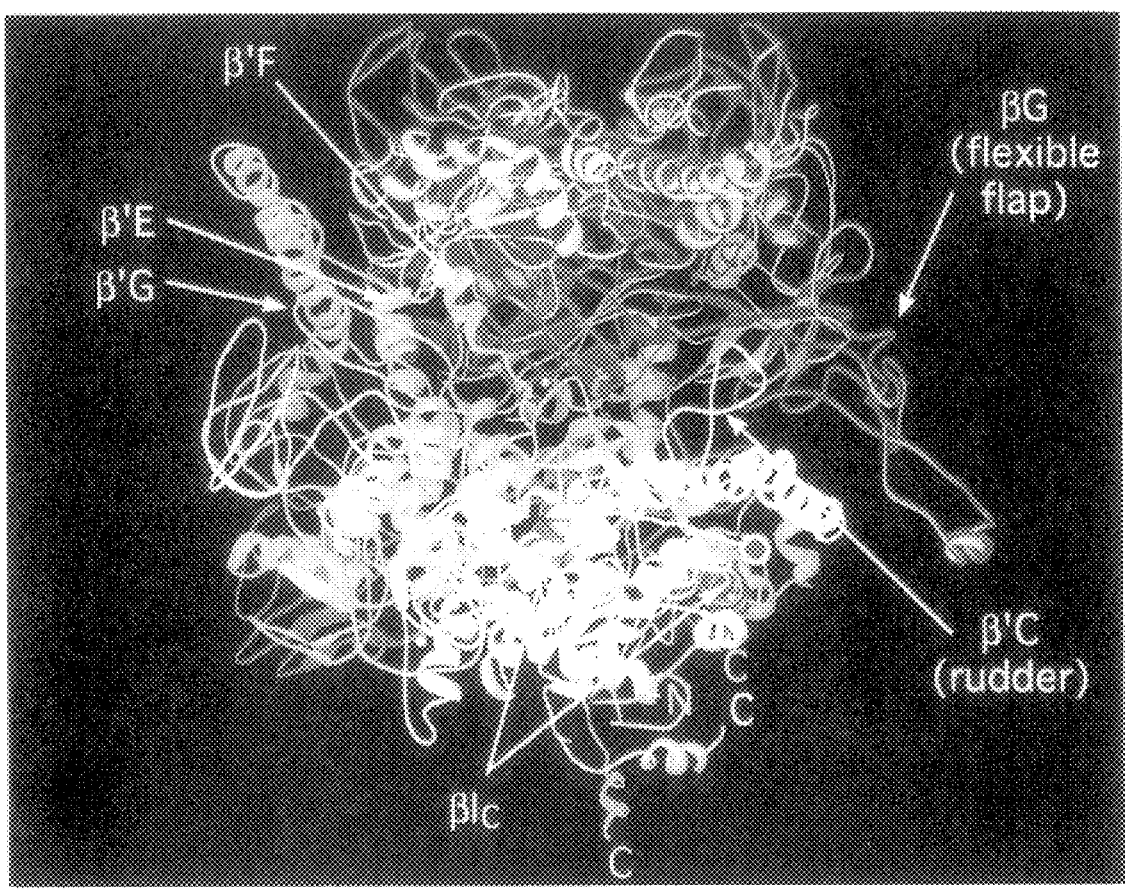
Figure 3C:
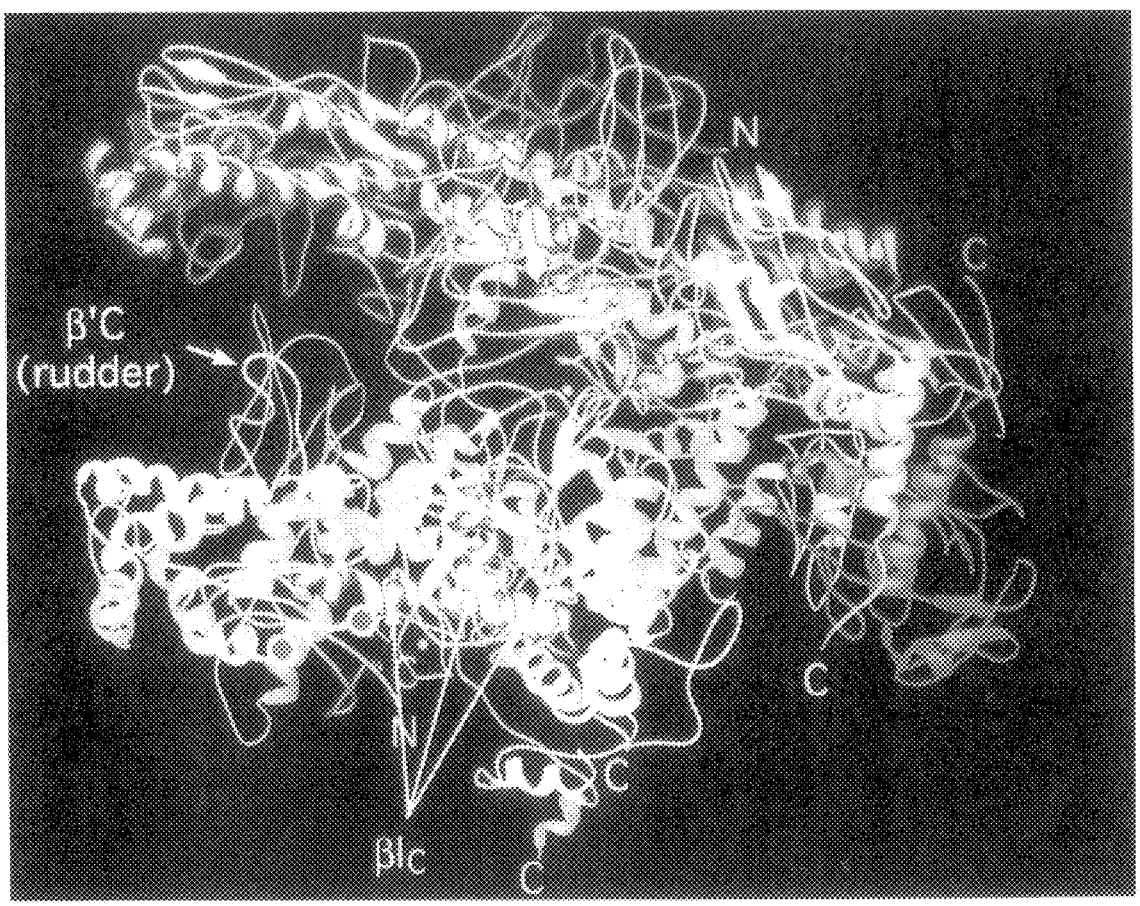

The overall topology of β' is circular in that the N- and C-termini are near each other (FIG. 3). A domain of β' that includes $β'_E$ extends up and interacts with β on the face of the RNAP molecule nearest the viewer in FIG. 3A. Region F of β' is most remarkable, it begins in the upper domain of β' where $β'_E$ ends, then forms a helical segment and loop that extends across the middle of the main channel (FIG. 3), then ends firmly anchored in the main body of β'. The active center $Mg^{2+}$ is positioned at the base of the main channel directly across from the $β'_F$ helix (FIGS. 6A–6D). The $β'_F$ helix conspires with $β'_G$, which forms a long loop that extends into the main channel, to form a wall-like structure that forks the main channel into two separate channels (FIGS. 6A–6D). The secondary channel thus formed is roughly 10–12 Å in diameter, which is not large enough to accommodate double-stranded nucleic acid (either DNA—DNA or DNA—RNA). Furthermore, examination of the structure suggests that threading of a single strand of DNA (such as in the melted region of the transcription bubble) through the secondary channel is unlikely. To achieve this without breaking a covalent bond in the DNA, the secondary channel would have to be opened by disrupting the extensive interactions between β' regions E and F with β at the N-terminal end of the $β'_F$ helix. Finally, coiled-coil like structure extends from the main channel (seen at the right in FIG. 3B) and supports another loop-like structure that protrudes upwards, forming a rudder-like feature comprising β' region C.

β' contains an unusual $Zn^{2+}$-binding motif (FIG. 3) comprising four Cysteine residues between regions F and G. Three of the Cys residues are arranged in a sequence reminiscent of a $Zn^{2+}$-binding motif (β'1195—$CX_6CX_2C$). The fourth Cys participating in the $Zn^{2+}$ chelation is β'Cys1113, eighty-two residues away, explaining why this was not identified as a $Zn^{2+}$-binding site from sequence analysis. The four Cys residues are absolutely conserved in prokaryotes (they correspond to positions 814, 888, 895, and 898 of E. coli β') but are not conserved in eukaryotes. This, along with its location on the bottom side of β' on the outside of the channel (FIG. 3), suggests it plays a critical structural role in the folding of β' that is performed by some other subunit of the eukaryotic enzymes.

Active center: As expected, the three Asp residues within the absolutely conserved -NADFDGD- motif (SEQ ID NO:4) of $β'_D$ chelate a $Mg^{2+}$-ion (FIG. 4). Substitution of these Asp residues by Ala gives rise to a dominant-lethal phenotype, which is explained by the in vitro ability of the mutant RNAP to occupy promoter sites on the DNA and form stable open complexes but that lack any detectable catalytic activity [Zaychikov et al., Science, 273:107–109 (1996)], identifying the chelated $Mg^{2+}$ as the catalytic center of the enzyme. The hydroxyl-radical cleavage experiment of [Mustaev et al., Proc. Natl. Acad. Sci. USA, 94:6641–6645 (1997)] identified 9 widely separated sites, five in β and four in β' (FIG. 1), that must be close to the active center $Mg^{2+}$. All of the mapped hydroxyl-radical cleavage sites converge near the active center $Mg^{2+}$ in the structure (FIG. 4a). One cleavage site (β'E in FIG. 4a) is 20 Å from the active center $Mg^{2+}$, the others are 12 Å or less, although some residues adjacent to the mapped regions (never more than 3 or 4 residues) are sometimes even closer to the active center $Mg^{2+}$ but were not mapped. Two additional protein fragments are within 12 Å of the active center $Mg^{2+}$. One is centered about βHis999 (within $β_I$, see FIG. 4b). This fragment would not have been mapped in the hydroxyl-radical cleavage experiment because it lies C-terminal of the site used to radioactively label the β subunit. A second region is centered about β' residue 632 (within $β'_C$). The hydroxyl-radical cleavage sites were mapped by analysis of the electrophoretic mobility of the protein cleavage products. Small errors in the analysis due to anomalous mobilities of the protein fragments could easily account for the small discrepancies with the structure noted above. Furthermore, the hydroxyl-radical cleavage experiment was done on a binary complex of RNAP holoenzyme with promoter DNA. Conformational changes of the RNAP around the active center, as well as protection of some protein fragments from hydroxyl-radical cleavage by the presence of the DNA or the a subunit, could also account for these discrepancies.

The high degree of sequence homology between the large RNAP subunits from prokaryotes to eukaryotes (FIG. 1) points to structural homologies, which are borne out by low-resolution structures from electron microscopy [Darst et al., Cell, 66:121–128 (1991); Darst et al., J. Structural Biol., 124:115–122 (1998); and Darst et al., Cold Spring Harbor Symp. Quant. Biol., 63:269–276 (1998)]. The multiple functions performed by the elongating RNAP, which result in the rapid, highly processive, and accurate synthesis of RNA complementary to the template strand of the DNA, likely leave little room for evolutionary variability in the region surrounding the active center. This is indeed the case (FIGS. 5 and 6), regions of very high sequence homology (approaching 100%) are concentrated around the active center $Mg^{2+}$ and radiate outward in all directions, dissipating at the outer portions of the molecule where species-specific regulatory interactions are likely to occur.

Substrate & inhibitor binding: The RNAP contains binding sites for two NTP substrates, the i-site, which will ultimately become the 5'-end of the RNA transcript, and the i+1 site (sometimes called the elongation site), which will extend the i-site nucleotide in the 3'-direction when phosphodiester bond formation takes place. Crosslinking experiments with initiating nucleotide analogs have identified three residues that are within Ångstroms of the α-phosphate of the initiating nucleotide occupying the i-site [Zaychikov et al., Science, 273:107–109 (1996) and Mustaev et al., J. Biol. Chem., 266:23927–23931 (1991)] (FIG. 1), βLys838 (within $β_H$), and βHis999 and βLys1004 (within $β_I$), corresponding to E. coli βLys1065, βHis1237, and βLys1242. These three residues are clustered together on the back wall of the RNAP channel, all no more than 11 Å from the active center $Mg^{2+}$ (FIG. 4b). Interestingly, these residues are very highly conserved (βLys838 is absolutely conserved) but cannot play a role in the RNAP catalytic activity since RNAP with crosslinked nucleotide adducts at these positions remains active for phosphodiester bond formation.

All of the amino acid substitutions that confer rifampicin resistance ($Rif^r$) to E. coli RNAP have been mapped to different regions of the β subunit (FIG. 1). These sites cluster around a pocket on the upper face of the main channel (FIGS. 4b and 6A–6F). The center of the pocket is roughly 20 Å (in a straight line) from the catalytic center $Mg^{2+}$. Consistent with the structure, initiating nucleotide analogs covalently attached to rifampicin by a 15 Å linker arm are active for phosphodiester bond formation [Mustaev et al., 91:12036–12040 (1994)]. A number of observations indicate the rif-site lies along the 5'-direction upstream from the active center, near the −2 to −3 position of the DNA template strand [Mustaev et al., 91:12036–12040 (1994)]. Consistent with this, a fourth site of crosslinking to the γ-phosphate of an initiating substrate analog (but not the α- or β-phosphate) has been mapped to a peptide fragment contained within one of the Rif regions [Severinov et al., 270:29428–29432 (1995)] (FIGS. 6A–6F). In the presence of rifampicin, RNAP forms the open complex on promoter DNA and initiates RNA synthesis, but elongation of the RNA product halts after only a few nucleotides. Elongating RNAP, however, is resistant to rifampicin. These properties have led to the idea that the presence of rifampicin inhibits RNA synthesis by blocking the path of the elongating RNA.

DNA & RNA interactions: To map the structural components of the RNAP involved in the formation of the template DNA and product RNA binding sites, a series of stalled elongation complexes were analyzed in which crosslinkable probes were incorporated into specific positions of the DNA or RNA [Markovtsov et al., Proc. Natl. Acad. Sci. USA, 93:3221–3226 (1996); Nudler et al., Science, 273:211–217 (1996); and (Nuder et al., Science, 281:424–428 (1998). The results of these studies are summarized in a recent review

[Nudler, *J. Mol. Biol.*, 288:1–12 (1999)] and mapped onto the structure in FIGS. 6A–6D. In these views, the RNAP molecule has been sliced in half down the middle of the channel, then the two halves have been splayed apart (like opening a book) to view the inner surfaces of the top and bottom walls of the channel. In these views, some of the structural features discussed earlier become very apparent. These include the wall formed by β' regions F and G that forks the main channel (causing the formation of the secondary channel), and the 'rudder' formed by β'$_C$, which extends up from the bottom surface of the channel. On the left side of FIG. 6, (FIGS. 6A and 6B) the sequence homology in β and β' is mapped onto the exposed surfaces. On the right side of FIG. 6, (FIGS. 6C and 6D) the crosslink mapping studies and other information are displayed. On the right, surrounding the active center Mg$^{2+}$ (magenta sphere) is the conserved -NADFDGD- motif (SEQ ID NO:4), shown in red. Crosslinks mapped to the α-phosphate of the initiating nucleotide occupying the i-site are shown in yellow (just visible near the active center Mg$^{2+}$ on the bottom view). Further in the 5' direction, the γ-phosphate of the initiating nucleotide crosslinks to a peptide fragment on the upper face of the channel (shown in yellow in the top view) which is coincident with the Rif site (shown in magenta in the top view). Alternatively, crosslinks from the 3'-end of the RNA transcript are mapped in orange.

Crosslinks from the downstream portion of the DNA template strand (from +3 to +15, with −1 denoting the 3'-end of the RNA transcript) map to the upper surface of the channel (shown in green in the top view), while crosslinks from probes incorporated further upstream on the template strand (from +12 to −4) map mainly to the bottom surface of the channel (shown in green in the bottom view). Finally, crosslinks from probes incorporated at the −10 position of the RNA transcript map to a region on the bottom surface of the channel near the 'rudder' (shown in blue in the bottom view).

Discussion

Figure 6A:
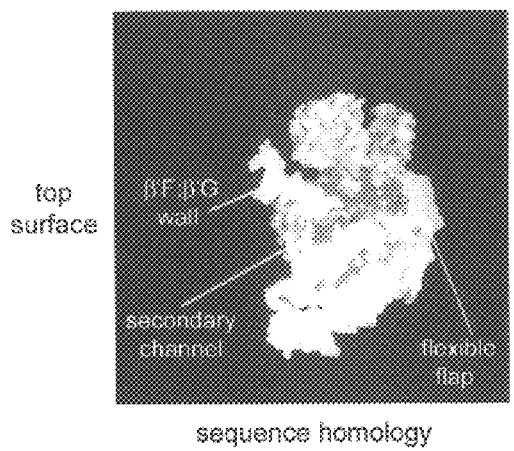
FIGS. 6A–6F show the RNAP structure/function relationship.
Figure 6B:
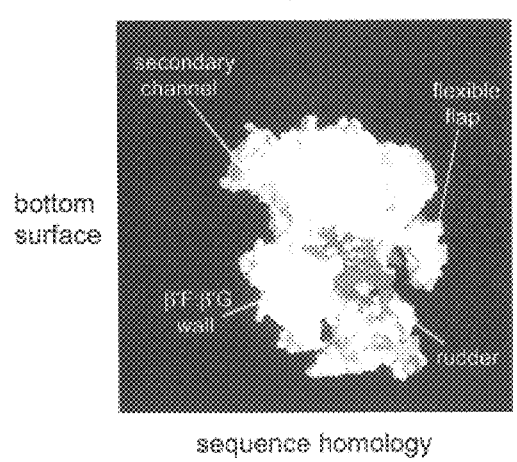
Figure 6C:
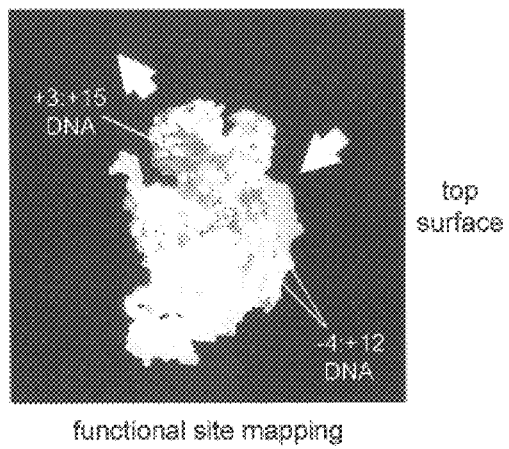
Figure 6D:
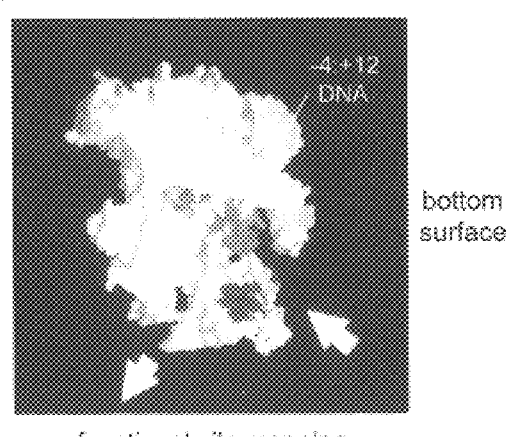
Figure 6E:
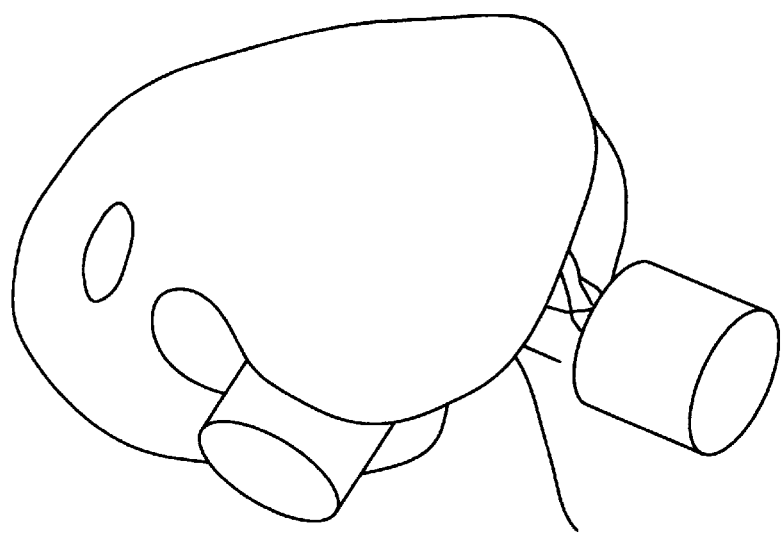
Figure 6F:
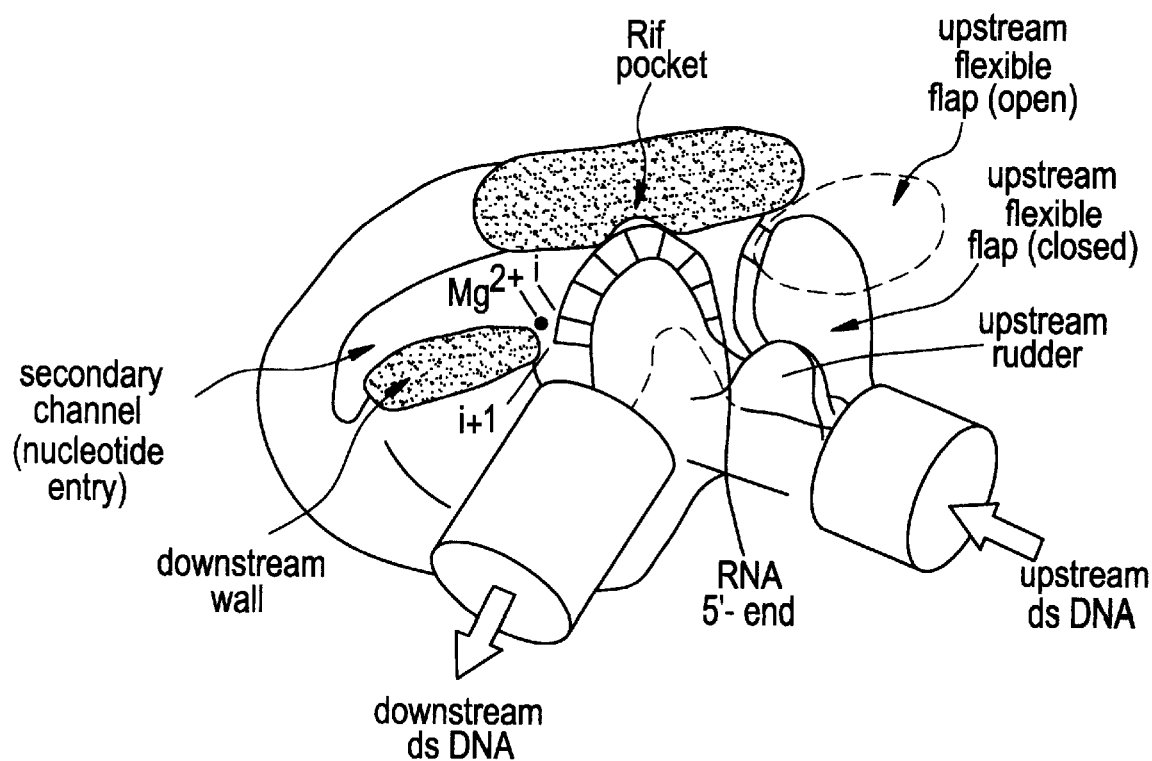

The features and dimensions of the core RNAP structure, along with the mapping results localizing relative positions of the nucleotide framework within the elongating RNAP, suggest a model for the transcription complex schematically illustrated in FIGS. 6E–6F. All of the results mapped onto the structure in FIGS. 6A–6D, including the relative orientations of 3' and 5' sites of the RNA transcript, as well as downstream and upstream positions of the DNA template, orient the RNAP with respect to the nucleotide framework as indicated by the arrows in FIGS. 6A–6D. These considerations place the wall that bifurcates the main channel in a downstream position, and the rudder and flexible flap upstream.

The 3'-proximal 8 to 9 nucleotides of the RNA transcript (positions −1 to −9) form an RNA-DNA hybrid with the DNA template strand [Nudler et al., *Cell*, 89:33–41 (1997)]. The crosslink from the −10 position of the RNA to a site near the upstream rudder places this protein feature near the upstream edge of the transcription bubble, where the DNA template strand is separated from the RNA transcript and re-anneals with the DNA non-template strand. This indirectly suggests that the upstream rudder may play a role in these processes. It is interesting to note that a β-hairpin loop in T7 RNAP, which is reminiscent of the upstream rudder, plays a direct role in forming the upstream edge of the transcription bubble in that system [Cheetham et al, *Nature*, 399:80–83 (1999)].

In the downstream direction, the two DNA strands re-anneal only 1 or two bases downstream of the RNA 3'-end, and about 9 bp of double-stranded DNA are bound in the RNAP and required for the stability of the elongation complex [Nudler et al., *Science*, 273:424–428 (1998)]. Moreover, both strands of the DNA in this downstream region are completely protected from hydroxyl-radical cleavage, suggesting enclosure in a protein tunnel [Polyakov et al., *Cell*, 83:365–373 (1995); Metzger et al, *EMBO J.*, 8:2745–2754 (1989); Schickor et al., *EMBO J.*, 9:2215–2220 (1990); and Mecsas et al, *J. Mol. Biol.*, 220:585–597 (1991)]. Assuming the DNA is B-form, then about 30 Å of double-stranded DNA need to be accommodated in the channel. The length of the RNAP channel from the bifurcation point at the β'$_F$ helix to the proposed exit point of the downstream DNA (the proposed upstream entry and downstream exit paths of the DNA are indicated by arrows in FIGS. 6A–6D) is approximately 30 Å and could thus account for these findings. The DNA in this region is enclosed between the walls of the channel, accounting for the hydroxyl-radical footprinting results.

In the disclosed model, the main chamber of the RNAP channel is occupied by 9 basepairs of double-stranded DNA, about 9 basepairs of the RNA-DNA hybrid, and the non-template strand of the DNA, which is in some unknown location. This appears to leave little room for the entry of the NTP substrates into the active center. Thus the secondary channel allows access of the NTP substrates to the active center of the RNAP.

It should be noted that this model depicts the structure of the ternary elongation complex, which is able to maintain the structure of the transcription bubble and RNA-DNA hybrid as it processively translocates along the DNA template in the downstream direction. However, the core RNAP is unable to initiate the formation of this structure from a double-stranded DNA template. This function requires additional protein factors, either the promoter-specificity σ subunit of prokaryotes [Helmann and Chamberlin, *Annual. Reviews of Biochemistry*, 57:839–872 (1988)], or a set of basal transcription factors for the eukaryotic enzymes [Conaway and Conaway, *Science*, 248:1550–1553 (1990)]. This model derived by the structure disclosed herein is consistent with the available evidence. Nevertheless, the present invention is not predicated on this particular model and indeed, other models consistent with the data disclosed herein could be constructed and used to carry out the methods of the present invention.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

SEQUENCE LISTING

<160> NUMBER OF SEQ ID NOS: 4

<210> SEQ ID NO 1
<211> LENGTH: 1525
<212> TYPE: PRT
<213> ORGANISM: Thermus aquaticus
<220> FEATURE:
<221> NAME/KEY: SITE
<222> LOCATION: (1247)
<223> OTHER INFORMATION: Any amino acid can be at this position

<400> SEQUENCE: 1

```
Met Lys Lys Glu Val Arg Lys Val Arg Ile Ala Leu Ala Ser Pro Glu
  1               5                  10                  15

Lys Ile Arg Ser Trp Ser Tyr Gly Glu Val Glu Lys Pro Glu Thr Ile
                 20                  25                  30

Asn Tyr Arg Thr Leu Lys Pro Glu Arg Asp Gly Leu Phe Asp Glu Arg
             35                  40                  45

Ile Phe Gly Pro Ile Lys Asp Tyr Glu Cys Ala Cys Gly Lys Tyr Lys
         50                  55                  60

Arg Gln Arg Phe Glu Gly Lys Val Cys Glu Arg Cys Gly Val Glu Val
 65                  70                  75                  80

Thr Arg Ser Ile Val Arg Arg Tyr Arg Met Gly His Ile Glu Leu Ala
                 85                  90                  95

Thr Pro Ala Ala His Ile Trp Phe Val Lys Asp Val Pro Ser Lys Ile
            100                 105                 110

Gly Thr Leu Leu Asp Leu Phe Ala Thr Glu Leu Glu Gln Val Leu Tyr
        115                 120                 125

Phe Asn Lys Tyr Ile Val Leu Asp Pro Lys Gly Ala Val Leu Asp Gly
130                 135                 140

Val Pro Val Glu Lys Arg Gln Leu Leu Thr Asp Glu Glu Tyr Arg Glu
145                 150                 155                 160

Leu Arg Tyr Gly Lys Gln Glu Thr Tyr Pro Leu Pro Ala Gly Val Asp
                165                 170                 175

Ala Leu Val Lys Asp Gly Glu Val Val Lys Gly Gln Glu Leu Ala
            180                 185                 190

Pro Gly Val Val Ser Arg Met Asp Gly Val Gly Ser Leu Pro Leu Pro
        195                 200                 205

Arg Arg Val Arg Val Asp Tyr Leu Arg Lys Glu Arg Ala Ala Leu Arg
210                 215                 220

Ile Pro Leu Ser Ala Trp Val Glu Lys Glu Pro Tyr Arg Pro Gly Glu
225                 230                 235                 240

Val Leu Ala Glu Leu Ser Glu Pro Tyr Leu Phe Arg Ala Glu Glu Ser
                245                 250                 255

Gly Val Val Glu Leu Lys Asp Leu Ala Glu Gly His Leu Ile Tyr Leu
            260                 265                 270

Arg Gln Glu Glu Val Val Ala Arg Tyr Phe Leu Pro Ala Gly Met
        275                 280                 285

Thr Pro Leu Val Val Glu Gly Glu Ile Val Glu Val Gly Gln Pro Leu
    290                 295                 300

Ala Glu Gly Lys Gly Leu Leu Arg Leu Pro Arg His Met Thr Ala Lys
305                 310                 315                 320

Glu Val Glu Ala Glu Glu Gly Asp Ser Val His Leu Thr Leu Phe
                325                 330                 335
```

-continued

```
Leu Glu Trp Thr Glu Pro Lys Asp Tyr Lys Val Ala Pro His Met Asn
            340                 345                 350

Val Ile Val Pro Glu Gly Ala Lys Val Gln Ala Gly Glu Lys Ile Val
            355                 360                 365

Ala Ala Ile Asp Pro Glu Glu Val Ile Ala Gln Ala Glu Gly Val
            370                 375             380

Val His Leu His Glu Pro Ala Ser Ile Leu Val Val Lys Ala Arg Val
385             390                 395                 400

Tyr Pro Phe Glu Asp Asp Val Glu Val Thr Thr Gly Asp Arg Val Ala
                405                 410                 415

Pro Gly Asp Val Leu Ala Asp Gly Lys Val Lys Ser Glu Ile Tyr
            420                 425             430

Gly Arg Val Glu Val Asp Leu Val Arg Asn Val Val Arg Val Val Glu
            435                 440                 445

Ser Tyr Asp Ile Asp Ala Arg Met Gly Ala Glu Ala Ile Gln Glu Leu
    450                 455                 460

Leu Lys Glu Leu Asp Leu Glu Lys Leu Glu Arg Glu Leu Leu Glu Glu
465             470                 475                 480

Met Lys His Pro Ser Arg Ala Arg Ala Lys Ala Arg Lys Arg Leu
            485                 490                 495

Glu Val Val Arg Ala Phe Leu Asp Ser Gly Asn Arg Pro Glu Trp Met
            500                 505                 510

Ile Leu Glu Ala Val Pro Val Leu Pro Pro Asp Leu Arg Pro Met Val
            515                 520                 525

Gln Val Asp Gly Gly Arg Phe Ala Thr Ser Asp Leu Asn Asp Leu Tyr
    530                 535                 540

Arg Arg Leu Ile Asn Arg Asn Asn Arg Leu Lys Lys Leu Leu Ala Gln
545                 550                 555                 560

Gly Ala Pro Glu Ile Ile Arg Asn Glu Lys Arg Met Leu Gln Glu
            565                 570                 575

Ala Val Asp Ala Val Ile Asp Asn Gly Arg Arg Gly Ser Pro Val Thr
                580                 585                 590

Asn Pro Gly Ser Glu Arg Pro Leu Arg Ser Leu Thr Asp Ile Leu Ser
            595                 600                 605

Gly Lys Gln Gly Arg Phe Arg Gln Asn Leu Leu Gly Lys Arg Val Asp
            610                 615                 620

Tyr Ser Gly Arg Ser Val Ile Val Val Gly Pro Gln Leu Lys Leu His
625                 630                 635                 640

Gln Cys Gly Leu Pro Lys Arg Met Ala Leu Glu Leu Phe Lys Pro Phe
            645                 650                 655

Leu Leu Lys Lys Met Glu Glu Lys Ala Phe Ala Pro Asn Val Lys Ala
            660                 665                 670

Ala Arg Arg Met Leu Glu Arg Gln Arg Asp Ile Lys Asp Glu Val Trp
            675                 680                 685

Asp Ala Leu Glu Glu Val Ile His Gly Lys Val Val Leu Leu Asn Arg
            690                 695                 700

Ala Pro Thr Leu His Arg Leu Gly Ile Gln Ala Phe Gln Pro Val Leu
705                 710                 715                 720

Val Glu Gly Gln Ser Ile Gln Leu His Pro Leu Val Cys Glu Ala Phe
                725                 730                 735

Asn Ala Asp Phe Asp Gly Asp Gln Met Ala Val His Val Pro Leu Ser
            740                 745                 750

Ser Phe Ala Gln Ala Glu Ala Arg Ile Gln Met Leu Ser Ala His Asn
```

-continued

```
                755                 760                 765
    Leu Leu Ser Pro Ala Ser Gly Glu Pro Leu Ala Lys Pro Ser Arg Asp
        770                 775                 780

Ile Ile Leu Gly Leu Tyr Tyr Ile Thr Gln Val Arg Lys Glu Lys Lys
    785                 790                 795                 800

Gly Ala Gly Met Ala Phe Ala Thr Pro Glu Glu Ala Leu Ala Ala Tyr
                    805                 810                 815

Glu Arg Gly Glu Val Ala Leu Asn Ala Pro Ile Val Val Ala Gly Arg
                820                 825                 830

Glu Thr Ser Val Gly Arg Leu Lys Phe Val Phe Ala Asn Pro Asp Glu
                835                 840                 845

Ala Leu Leu Ala Val Ala His Gly Leu Leu Asp Leu Gln Asp Val Val
        850                 855                 860

Thr Val Arg Tyr Leu Gly Arg Arg Leu Glu Thr Asn Pro Gly Arg Ile
    865                 870                 875                 880

Leu Phe Ala Arg Ile Val Gly Glu Ala Val Gly Asp Glu Lys Val Ala
                    885                 890                 895

Gln Glu Leu Ile Gln Met Asp Val Pro Gln Glu Lys Asn Ser Leu Lys
                900                 905                 910

Asp Leu Val Tyr Gln Ala Phe Leu Arg Leu Gly Met Glu Lys Thr Ala
                915                 920                 925

Arg Leu Leu Asp Ala Leu Lys Tyr Tyr Gly Phe Thr Leu Ser Thr Thr
        930                 935                 940

Ser Gly Ile Ile Thr Ile Gly Ile Asp Asp Ala Val Ile Pro Glu Glu
    945                 950                 955                 960

Lys Gln Arg Tyr Leu Glu Glu Ala Asp Arg Lys Leu Arg Gln Ile Glu
                    965                 970                 975

Gln Ala Tyr Glu Met Gly Phe Leu Thr Asp Arg Glu Arg Tyr Asp Gln
                980                 985                 990

Val Ile Gln Leu Trp Thr Glu Thr Thr Glu Lys Val Thr Gln Ala Val
                995                 1000                1005

Phe Asn Asn Phe Glu Glu Asn Tyr Pro Phe Asn Pro Leu Tyr Val Met
        1010                1015                1020

Ala Gln Ser Gly Ala Arg Gly Asn Pro Gln Gln Ile Arg Gln Leu Cys
    1025                1030                1035                1040

Gly Met Arg Gly Leu Met Gln Lys Pro Ser Gly Glu Thr Phe Glu Val
                    1045                1050                1055

Pro Val Arg Ser Ser Phe Arg Glu Gly Leu Thr Val Leu Glu Tyr Phe
                1060                1065                1070

Ile Ser Ser His Gly Ala Arg Lys Gly Gly Ala Asp Thr Ala Leu Arg
                1075                1080                1085

Thr Ala Asp Ser Gly Tyr Leu Thr Arg Lys Leu Val Asp Val Ala His
        1090                1095                1100

Glu Ile Val Val Arg Glu Ala Asp Cys Gly Thr Thr Lys Tyr Ile Ser
    1105                1110                1115                1120

Val Pro Leu Phe Gln Met Asp Glu Val Thr Arg Thr Leu Arg Leu Arg
                    1125                1130                1135

Lys Arg Ser Asp Ile Glu Ser Gly Leu Tyr Gly Arg Val Leu Ala Arg
                1140                1145                1150

Glu Val Glu Ala Leu Gly Arg Arg Leu Glu Glu Gly Arg Tyr Leu Ser
                1155                1160                1165

Leu Glu Asp Val His Phe Leu Ile Lys Ala Ala Glu Ala Gly Glu Val
        1170                1175                1180
```

Arg Glu Val Pro Val Arg Ser Pro Leu Thr Cys Gln Thr Arg Tyr Gly
1185                1190                1195                1200

Val Cys Gln Lys Cys Tyr Gly Tyr Asp Leu Ser Met Ala Arg Pro Val
            1205                1210                1215

Ser Ile Gly Glu Ala Val Gly Val Ala Ala Glu Ser Ile Gly Glu
        1220                1225                1230

Pro Gly Thr Gln Leu Thr Met Arg Thr Phe His Thr Gly Gly Xaa Ala
            1235                1240                1245

Val Gly Thr Asp Ile Thr Gln Gly Leu Pro Arg Val Ile Glu Leu Phe
        1250                1255                1260

Glu Ala Arg Arg Pro Lys Ala Lys Ala Val Ile Ser Glu Ile Asp Gly
1265                1270                1275                1280

Val Val Arg Ile Glu Glu Gly Glu Asp Arg Leu Ser Val Phe Val Glu
                1285                1290                1295

Ser Glu Gly Phe Ser Lys Glu Tyr Lys Leu Pro Lys Asp Ala Arg Leu
        1300                1305                1310

Leu Val Lys Asp Gly Asp Tyr Val Glu Ala Gly Gln Pro Leu Thr Arg
        1315                1320                1325

Gly Ala Ile Asp Pro His Gln Leu Leu Glu Ala Lys Gly Pro Glu Ala
        1330                1335                1340

Val Glu Arg Tyr Leu Val Asp Glu Ile Gln Lys Val Tyr Arg Ala Gln
1345                1350                1355                1360

Gly Val Lys Leu His Asp Lys His Ile Glu Ile Val Val Arg Gln Met
            1365                1370                1375

Leu Lys Tyr Val Glu Val Thr Asp Pro Gly Asp Ser Pro Leu Leu Glu
        1380                1385                1390

Gly Gln Val Leu Glu Lys Trp Asp Val Glu Ala Leu Asn Glu Arg Leu
        1395                1400                1405

Ile Ala Glu Gly Lys Val Pro Val Ala Trp Lys Pro Leu Leu Met Gly
            1410                1415                1420

Val Thr Lys Ser Ala Leu Ser Thr Lys Ser Trp Leu Ser Ala Ala Ser
1425                1430                1435                1440

Phe Gln Asn Thr Thr His Val Leu Thr Glu Ala Ala Ile Ala Gly Lys
                1445                1450                1455

Lys Asp Glu Leu Ile Gly Leu Lys Glu Asn Val Ile Leu Gly Arg Leu
            1460                1465                1470

Ile Pro Ala Gly Thr Gly Ser Asp Phe Val Arg Phe Thr Gln Val Val
            1475                1480                1485

Asp Gln Arg Thr Leu Lys Ala Ile Glu Glu Ala Arg Lys Glu Ala Val
        1490                1495                1500

Glu Ala Lys Glu Lys Glu Ala Pro Arg Arg Pro Val Arg Arg Glu Gln
1505                1510                1515                1520

Pro Gly Lys Gly Leu
            1525

<210> SEQ ID NO 2
<211> LENGTH: 1119
<212> TYPE: PRT
<213> ORGANISM: Thermus aquaticus
<220> FEATURE:
<221> NAME/KEY: SITE
<222> LOCATION: (695)..(696)
<223> OTHER INFORMATION: Any amino acids can be at these two positions.

<400> SEQUENCE: 2

-continued

```
Met Lys Ile Lys Arg Phe Gly Arg Ile Arg Glu Val Ile Pro Leu Pro
 1               5                  10                 15

Pro Leu Thr Glu Ile Gln Val Glu Ser Tyr Lys Lys Ala Leu Gln Ala
             20                 25                 30

Asp Val Pro Glu Lys Arg Glu Asn Val Gly Ile Gln Ala Ala Phe
         35                 40                 45

Lys Glu Thr Phe Pro Ile Glu Glu Gly Asp Lys Gly Lys Gly Gly Leu
 50                 55                 60

Val Leu Asp Phe Leu Glu Tyr Arg Ile Gly Asp Pro Pro Phe Ser Gln
 65             70                 75                 80

Asp Glu Cys Arg Glu Lys Asp Leu Thr Tyr Gln Ala Pro Leu Tyr Ala
             85                 90                 95

Arg Leu Gln Leu Ile His Lys Asp Thr Gly Leu Ile Lys Glu Asp Glu
             100                105                110

Val Phe Leu Gly His Leu Pro Leu Met Thr Glu Asp Gly Ser Phe Ile
             115                120                125

Ile Asn Gly Ala Asp Arg Val Ile Val Ser Gln Ile His Arg Ser Pro
 130                135                140

Gly Val Tyr Phe Thr Pro Asp Pro Ala Arg Pro Gly Arg Tyr Ile Ala
145                 150                155                160

Ser Ile Ile Pro Leu Pro Lys Arg Gly Pro Trp Ile Asp Leu Glu Val
             165                170                175

Glu Ala Ser Gly Val Val Thr Met Lys Val Asn Lys Arg Lys Phe Pro
             180                185                190

Leu Val Leu Leu Leu Arg Val Leu Gly Tyr Asp Gln Glu Thr Leu Val
             195                200                205

Arg Glu Leu Ser Ala Tyr Gly Asp Leu Val Gln Gly Leu Leu Asp Glu
             210                215                220

Ala Val Leu Ala Met Arg Pro Glu Glu Ala Met Val Arg Leu Phe Thr
225                 230                235                240

Leu Leu Arg Pro Gly Asp Pro Lys Lys Asp Lys Ala Leu Ala Tyr
             245                250                255

Leu Phe Gly Leu Leu Ala Asp Pro Lys Arg Tyr Asp Leu Gly Glu Ala
             260                265                270

Gly Arg Tyr Lys Ala Glu Glu Lys Leu Gly Val Gly Leu Ser Gly Arg
             275                280                285

Thr Leu Val Arg Phe Glu Asp Gly Glu Phe Lys Asp Glu Val Phe Leu
             290                295                300

Pro Thr Leu Arg Tyr Leu Phe Ala Leu Thr Ala Gly Val Pro Gly His
305                 310                315                320

Glu Val Asp Asp Ile Asp His Leu Gly Asn Arg Arg Ile Arg Thr Val
                 325                330                335

Gly Glu Leu Met Ala Asp Gln Phe Arg Val Gly Leu Ala Arg Leu Ala
             340                345                350

Arg Gly Val Arg Glu Arg Met Val Met Gly Ser Pro Asp Thr Leu Thr
             355                360                365

Pro Ala Lys Leu Val Asn Ser Arg Pro Leu Glu Ala Ala Leu Arg Glu
 370                375                380

Phe Phe Ser Arg Ser Gln Leu Ser Gln Phe Lys Asp Glu Thr Asn Pro
385                 390                395                400

Leu Ser Ser Leu Arg His Lys Arg Arg Ile Ser Ala Leu Gly Pro Gly
                 405                410                415

Gly Leu Thr Arg Glu Arg Ala Gly Phe Asp Val Arg Asp Val His Arg
```

```
                    420             425             430
Thr His Tyr Gly Arg Ile Cys Pro Val Glu Thr Pro Glu Gly Ala Asn
        435             440             445
Ile Gly Leu Ile Thr Ser Leu Ala Ala Tyr Ala Arg Val Asp Ala Leu
    450             455             460
Gly Phe Ile Arg Thr Pro Tyr Arg Arg Val Lys Asn Gly Val Val Thr
465             470              475             480
Glu Glu Val Val Tyr Met Thr Ala Ser Glu Glu Asp Arg Tyr Thr Ile
                485             490             495
Ala Gln Ala Asn Thr Pro Leu Glu Gly Asp Arg Ile Ala Thr Asp Arg
            500             505             510
Val Val Ala Arg Arg Gly Glu Pro Val Ile Val Ala Pro Glu Glu
        515             520             525
Val Glu Phe Met Asp Val Ser Pro Lys Gln Val Phe Ser Leu Asn Thr
    530             535             540
Asn Leu Ile Pro Phe Leu Glu His Asp Asp Ala Asn Arg Ala Leu Met
545             550             555             560
Gly Ser Asn Met Gln Thr Gln Ala Val Pro Leu Ile Arg Ala Gln Ala
                565             570             575
Pro Val Val Met Thr Gly Leu Glu Glu Arg Val Val Arg Asp Ser Leu
            580             585             590
Ala Ala Leu Tyr Ala Glu Glu Asp Gly Glu Val Val Lys Val Asp Gly
        595             600             605
Thr Arg Ile Ala Val Arg Tyr Glu Asp Gly Arg Leu Val Glu His Pro
    610             615             620
Leu Arg Arg Tyr Ala Arg Ser Asn Gln Gly Thr Ala Phe Asp Gln Arg
625             630             635             640
Pro Arg Val Arg Val Gly Gln Arg Val Lys Lys Gly Asp Leu Leu Ala
                645             650             655
Asp Gly Pro Ala Ser Glu Glu Gly Phe Leu Ala Leu Gly Gln Asn Val
            660             665             670
Leu Val Ala Ile Met Pro Phe Asp Gly Tyr Asn Phe Glu Asp Ala Ile
        675             680             685
Val Ile Ser Glu Glu Leu Xaa Xaa Arg Asp Phe Tyr Thr Ser Ile His
    690             695             700
Ile Glu Arg Tyr Glu Ile Glu Ala Arg Asp Thr Lys Leu Gly Pro Glu
705             710             715             720
Arg Ile Thr Arg Asp Ile Pro His Leu Ser Glu Ala Ala Leu Arg Asp
                725             730             735
Leu Asp Glu Glu Gly Ile Val Arg Ile Gly Ala Glu Val Lys Pro Gly
            740             745             750
Asp Ile Leu Val Gly Arg Thr Ser Phe Lys Gly Glu Gln Glu Pro Ser
        755             760             765
Pro Glu Glu Arg Leu Leu Arg Ser Ile Phe Gly Glu Lys Ala Arg Asp
    770             775             780
Val Lys Asp Thr Ser Leu Arg Val Pro Pro Gly Glu Gly Gly Ile Val
785             790             795             800
Val Gly Arg Leu Arg Leu Arg Arg Gly Asp Pro Gly Val Glu Leu Lys
                805             810             815
Pro Gly Val Arg Glu Val Val Arg Val Phe Val Ala Gln Lys Arg Lys
            820             825             830
Leu Gln Val Gly Asp Lys Leu Ala Asn Arg His Gly Asn Lys Gly Val
        835             840             845
```

-continued

```
Val Ala Lys Ile Leu Pro Val Glu Asp Met Pro His Leu Pro Asp Gly
        850                 855                 860

Thr Pro Val Asp Val Ile Leu Asn Pro Leu Gly Val Pro Ser Arg Met
865                 870                 875                 880

Asn Leu Gly Gln Ile Leu Glu Thr His Leu Gly Leu Ala Gly Tyr Phe
                885                 890                 895

Leu Gly Gln Arg Tyr Ile Ser Pro Val Phe Asp Gly Ala Thr Glu Pro
                900                 905                 910

Glu Ile Lys Glu Leu Leu Ala Glu Ala Phe Asn Leu Tyr Phe Gly Lys
            915                 920                 925

Arg Gln Gly Glu Gly Phe Gly Val Asp Lys Arg Glu Lys Glu Val Leu
        930                 935                 940

Ala Arg Ala Glu Lys Leu Gly Leu Val Ser Pro Gly Lys Ser Pro Glu
945                 950                 955                 960

Glu Gln Leu Lys Glu Leu Phe Asp Leu Gly Lys Val Val Leu Tyr Asp
                965                 970                 975

Gly Arg Thr Gly Glu Pro Phe Glu Gly Pro Ile Val Val Gly Gln Met
                980                 985                 990

Phe Ile Met Lys Leu Tyr His Met Val Glu Asp Lys Met His Ala Arg
            995                 1000                1005

Ser Thr Gly Pro Tyr Ser Leu Ile Thr Gln Gln Pro Leu Gly Gly Lys
        1010                1015                1020

Ala Gln Phe Gly Gly Gln Arg Phe Gly Glu Met Glu Val Trp Ala Leu
1025                1030                1035                1040

Glu Ala Tyr Gly Ala Ala His Thr Leu Gln Glu Met Leu Thr Ile Lys
                1045                1050                1055

Ser Asp Asp Ile Glu Gly Arg Asn Ala Ala Tyr Gln Ala Ile Ile Lys
                1060                1065                1070

Gly Glu Asp Val Pro Glu Pro Ser Val Pro Glu Ser Phe Arg Val Leu
            1075                1080                1085

Val Lys Glu Leu Gln Ala Leu Ala Leu Asp Val Gln Thr Leu Asp Glu
        1090                1095                1100

Lys Asp Asn Pro Val Asp Ile Phe Glu Gly Leu Ala Ser Lys Arg
1105                1110                1115

<210> SEQ ID NO 3
<211> LENGTH: 313
<212> TYPE: PRT
<213> ORGANISM: Thermus aquaticus

<400> SEQUENCE: 3

Met Leu Glu Ser Lys Leu Lys Ala Pro Val Phe Thr Ala Thr Thr Gln
1               5                   10                  15

Gly Asp His Tyr Gly Glu Phe Val Leu Glu Pro Leu Glu Arg Gly Phe
            20                  25                  30

Gly Val Thr Leu Gly Asn Pro Leu Arg Arg Ile Leu Leu Ser Ser Ile
        35                  40                  45

Pro Gly Thr Ala Val Thr Ser Val Tyr Ile Glu Asp Val Leu His Glu
    50                  55                  60

Phe Ser Thr Ile Pro Gly Val Lys Glu Asp Val Val Glu Ile Ile Leu
65                  70                  75                  80

Asn Leu Lys Glu Leu Val Val Arg Phe Leu Asp Pro Arg Trp Arg Thr
                85                  90                  95

Thr Leu Ile Leu Arg Ala Glu Gly Pro Lys Glu Val Arg Ala Val Asp
```

```
                    100                 105                 110
Phe Thr Pro Ser Ala Asp Val Glu Ile Met Asn Pro Asp Leu His Ile
        115                 120                 125
Ala Thr Leu Glu Glu Gly Gly Lys Leu Tyr Met Glu Val Arg Val Asp
130                 135                 140
Arg Gly Val Gly Tyr Val Pro Ala Glu Arg His Gly Ile Lys Asp Arg
145                 150                 155                 160
Ile Asn Ala Ile Pro Val Asp Ala Ile Phe Ser Pro Val Arg Arg Val
                165                 170                 175
Ala Phe Gln Val Glu Asp Thr Arg Leu Gly Gln Arg Thr Asp Leu Asp
        180                 185                 190
Lys Leu Thr Leu Arg Ile Trp Thr Asp Gly Ser Val Thr Pro Leu Glu
        195                 200                 205
Ala Leu Asn Gln Ala Val Ala Ile Leu Lys Glu His Leu Asn Tyr Phe
        210                 215                 220
Ala Asn Pro Glu Ala Ser Leu Leu Pro Thr Pro Glu Val Ser Lys Gly
225                 230                 235                 240
Glu Lys Arg Glu Ser Ala Glu Glu Asp Leu Asp Leu Pro Leu Glu Glu
                245                 250                 255
Leu Gly Leu Ser Thr Arg Val Leu His Ser Leu Lys Glu Glu Gly Ile
                260                 265                 270
Glu Ser Val Arg Ala Leu Leu Ala Leu Asn Leu Lys Asp Leu Arg Asn
        275                 280                 285
Ile Pro Gly Ile Gly Glu Arg Ser Leu Glu Glu Ile Arg Gln Ala Leu
        290                 295                 300
Ala Lys Lys Gly Phe Thr Leu Lys Glu
305                 310

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: natural
      part of bacterial proteins

<400> SEQUENCE: 4

Asn Ala Asp Phe Asp Gly Asp
1               5
```

Appendix

Table 3

```
REMARK coordinates from minimization refinement
REMARK refinement resolution: 100.0 - 3.2 A
REMARK starting r= 0.3631 free_r= 0.4208
REMARK final    r= 0.3466 free_r= 0.4154
REMARK rmsd bonds= 0.009443 rmsd angles= 1.93913
REMARK wa= 16.2281
REMARK target= mlf cycles= 1 steps= 250
REMARK sg= P4(1)2(1)2 a= 200.76 b= 200.76 c= 292.938 alpha= 90 beta= 90 gamma= 90
REMARK parameter file 1  : CNS_TOPPAR:protein_rep.param
REMARK parameter file 2  : CNS_TOPPAR:ion.param
REMARK molecular structure file: ../pdb/rnap_m3_gen.mtf
REMARK input coordinates: ../bgroup/bg1.pdb
REMARK reflection file= ../../fobs/scale_b25.cv
REMARK ncs= restrain  ncs file= ../ncs100.def
REMARK B-correction resolution: 8.0 - 3.2
REMARK initial B-factor correction applied to f_scale :
REMARK    B11=  0.112 B22=  0.112 B33= -0.224
REMARK    B12=  0.000 B13=  0.000 B23=  0.000
REMARK B-factor correction applied to coordinate array B:   0.067
REMARK bulk solvent: density level= 0.315481 e/A^3, B-factor= 300 A^2
REMARK reflections with |Fobs|/sigma_F < 0.0 rejected
REMARK reflections with |Fobs| > 10000 * rms(Fobs) rejected
REMARK theoretical total number of refl. in resol. range:    98907 ( 100.0 % )
REMARK number of unobserved reflections (no entry or |F|=0):  5201 (   5.3 % )
REMARK number of reflections rejected:                           0 (   0.0 % )
REMARK total number of reflections used:                     93706 (  94.7 % )
REMARK number of reflections in working set:                 88974 (  90.0 % )
REMARK number of reflections in test set:                     4732 (   4.8 % )
CRYST1  200.760  200.760  292.938  90.00  90.00  90.00 P 41 21 2
REMARK FILENAME="min1_100-3.2.pdb"
REMARK VERSION:0.4a
ATOM      1  CB  ALA A    6       1.632  67.447  73.985  1.00 51.08      A
ATOM      2  C   ALA A    6       1.498  65.047  73.318  1.00100.07      A
ATOM      3  O   ALA A    6       2.714  64.811  73.324  1.00100.07      A
ATOM      4  N   ALA A    6       1.065  65.705  75.679  1.00100.07      A
ATOM      5  CA  ALA A    6       0.907  66.105  74.245  1.00100.07      A
ATOM      6  N   ALA A    7       0.639  64.425  72.515  1.00 85.24      A
ATOM      7  CA  ALA A    7       1.075  63.413  71.564  1.00 85.24      A
ATOM      8  CB  ALA A    7       1.051  62.030  72.216  1.00 14.75      A
ATOM      9  C   ALA A    7       0.130  63.450  70.380  1.00 85.24      A
ATOM     10  O   ALA A    7      -0.677  64.368  70.252  1.00 85.24      A
ATOM     11  N   ALA A    8       0.242  62.448  69.519  1.00100.07      A
ATOM     12  CA  ALA A    8      -0.605  62.342  68.340  1.00100.07      A
ATOM     13  CB  ALA A    8      -1.848  61.513  68.673  1.00100.07      A
ATOM     14  C   ALA A    8      -1.025  63.704  67.786  1.00100.07      A
ATOM     15  O   ALA A    8      -2.031  64.276  68.207  1.00100.07      A
ATOM     16  N   PRO A    9      -0.248  64.248  66.841  1.00 56.97      A
ATOM     17  CD  PRO A    9       1.082  63.783  66.416  1.00100.07      A
ATOM     18  CA  PRO A    9      -0.561  65.545  66.236  1.00 56.97      A
ATOM     19  CB  PRO A    9       0.774  65.969  65.640  1.00100.07      A
ATOM     20  CG  PRO A    9       1.355  64.665  65.227  1.00100.07      A
ATOM     21  C   PRO A    9      -1.661  65.430  65.188  1.00 56.97      A
ATOM     22  O   PRO A    9      -2.702  64.838  65.445  1.00 56.97      A
ATOM     23  N   VAL A   10      -1.419  65.997  64.011  1.00 83.69      A
ATOM     24  CA  VAL A   10      -2.377  65.972  62.907  1.00 83.69      A
ATOM     25  CB  VAL A   10      -3.291  67.218  62.930  1.00 46.48      A
ATOM     26  CG1 VAL A   10      -4.123  67.287  61.657  1.00 46.48      A
ATOM     27  CG2 VAL A   10      -4.196  67.180  64.147  1.00 46.48      A
ATOM     28  C   VAL A   10      -1.555  66.004  61.625  1.00 83.69      A
ATOM     29  O   VAL A   10      -0.401  66.437  61.637  1.00 83.69      A
ATOM     30  N   PHE A   11      -2.129  65.546  60.519  1.00 35.63      A
ATOM     31  CA  PHE A   11      -1.393  65.576  59.273  1.00 35.63      A
ATOM     32  CB  PHE A   11      -0.988  64.172  58.831  1.00100.07      A
ATOM     33  CG  PHE A   11       0.221  64.162  57.943  1.00100.07      A
ATOM     34  CD1 PHE A   11       1.403  64.764  58.368  1.00100.07      A
ATOM     35  CD2 PHE A   11       0.178  63.597  56.674  1.00100.07      A
ATOM     36  CE1 PHE A   11       2.521  64.808  57.545  1.00100.07      A
ATOM     37  CE2 PHE A   11       1.297  63.635  55.838  1.00100.07      A
ATOM     38  CZ  PHE A   11       2.470  64.244  56.277  1.00100.07      A
ATOM     39  C   PHE A   11      -2.180  66.268  58.168  1.00 35.63      A
ATOM     40  O   PHE A   11      -2.207  65.819  57.012  1.00 35.63      A
ATOM     41  N   THR A   12      -2.821  67.371  58.546  1.00 60.55      A
ATOM     42  CA  THR A   12      -3.590  68.189  57.615  1.00 60.55      A
ATOM     43  CB  THR A   12      -3.781  69.612  58.175  1.00100.07      A
ATOM     44  OG1 THR A   12      -4.149  69.541  59.557  1.00100.07      A
ATOM     45  CG2 THR A   12      -4.858  70.350  57.402  1.00100.07      A
ATOM     46  C   THR A   12      -2.728  68.294  56.363  1.00 60.55      A
```

```
ATOM    47  O   THR A  12     -1.609  68.785  56.430  1.00 60.55      A
ATOM    48  N   ALA A  13     -3.227  67.855  55.218  1.00 47.73      A
ATOM    49  CA  ALA A  13     -2.390  67.910  54.029  1.00 47.73      A
ATOM    50  CB  ALA A  13     -1.906  66.489  53.705  1.00 36.60      A
ATOM    51  C   ALA A  13     -2.941  68.571  52.760  1.00 47.73      A
ATOM    52  O   ALA A  13     -2.799  68.003  51.683  1.00 47.73      A
ATOM    53  N   THR A  14     -3.530  69.764  52.861  1.00 59.31      A
ATOM    54  CA  THR A  14     -4.067  70.450  51.671  1.00 59.31      A
ATOM    55  CB  THR A  14     -4.181  72.005  51.888  1.00 61.51      A
ATOM    56  OG1 THR A  14     -5.094  72.296  52.959  1.00 61.51      A
ATOM    57  CG2 THR A  14     -4.686  72.684  50.617  1.00 61.51      A
ATOM    58  C   THR A  14     -3.168  70.184  50.447  1.00 59.31      A
ATOM    59  O   THR A  14     -2.124  70.818  50.290  1.00 59.31      A
ATOM    60  N   THR A  15     -3.586  69.255  49.582  1.00 99.60      A
ATOM    61  CA  THR A  15     -2.809  68.870  48.396  1.00 99.60      A
ATOM    62  CB  THR A  15     -3.093  67.393  47.999  1.00 63.08      A
ATOM    63  OG1 THR A  15     -2.281  67.041  46.875  1.00 63.08      A
ATOM    64  CG2 THR A  15     -4.566  67.188  47.645  1.00 63.08      A
ATOM    65  C   THR A  15     -2.928  69.749  47.139  1.00 99.60      A
ATOM    66  O   THR A  15     -2.776  70.970  47.200  1.00 99.60      A
ATOM    67  N   GLN A  16     -3.187  69.120  45.997  1.00 86.73      A
ATOM    68  CA  GLN A  16     -3.299  69.833  44.733  1.00 86.73      A
ATOM    69  CB  GLN A  16     -2.026  70.664  44.527  1.00 99.43      A
ATOM    70  CG  GLN A  16     -1.992  71.545  43.289  1.00 99.43      A
ATOM    71  CD  GLN A  16     -3.015  72.660  43.323  1.00 99.43      A
ATOM    72  OE1 GLN A  16     -3.247  73.270  44.366  1.00 99.43      A
ATOM    73  NE2 GLN A  16     -3.620  72.946  42.173  1.00 99.43      A
ATOM    74  C   GLN A  16     -3.471  68.828  43.580  1.00 86.73      A
ATOM    75  O   GLN A  16     -4.194  67.831  43.700  1.00 86.73      A
ATOM    76  N   GLY A  17     -2.807  69.100  42.462  1.00100.07      A
ATOM    77  CA  GLY A  17     -2.882  68.214  41.319  1.00100.07      A
ATOM    78  C   GLY A  17     -1.503  67.656  41.035  1.00100.07      A
ATOM    79  O   GLY A  17     -1.334  66.592  40.433  1.00100.07      A
ATOM    80  N   ASP A  18     -0.506  68.399  41.487  1.00 44.89      A
ATOM    81  CA  ASP A  18      0.888  68.039  41.305  1.00 44.89      A
ATOM    82  CB  ASP A  18      1.133  67.484  39.902  1.00100.07      A
ATOM    83  CG  ASP A  18      0.675  68.439  38.815  1.00100.07      A
ATOM    84  OD1 ASP A  18     -0.544  68.692  38.724  1.00100.07      A
ATOM    85  OD2 ASP A  18      1.532  68.945  38.054  1.00100.07      A
ATOM    86  C   ASP A  18      1.577  69.383  41.457  1.00 44.89      A
ATOM    87  O   ASP A  18      2.127  69.939  40.507  1.00 44.89      A
ATOM    88  N   HIS A  19      1.502  69.919  42.667  1.00 68.86      A
ATOM    89  CA  HIS A  19      2.119  71.197  42.969  1.00 68.86      A
ATOM    90  CB  HIS A  19      1.223  72.365  42.553  1.00 74.00      A
ATOM    91  CG  HIS A  19      0.752  72.307  41.141  1.00 74.00      A
ATOM    92  CD2 HIS A  19     -0.494  72.351  40.616  1.00 74.00      A
ATOM    93  ND1 HIS A  19      1.617  72.232  40.074  1.00 74.00      A
ATOM    94  CE1 HIS A  19      0.924  72.234  38.950  1.00 74.00      A
ATOM    95  NE2 HIS A  19     -0.360  72.307  39.252  1.00 74.00      A
ATOM    96  C   HIS A  19      2.316  71.310  44.460  1.00 68.86      A
ATOM    97  O   HIS A  19      2.633  70.332  45.121  1.00 68.86      A
ATOM    98  N   TYR A  20      2.085  72.516  44.976  1.00 99.95      A
ATOM    99  CA  TYR A  20      2.253  72.802  46.387  1.00 99.95      A
ATOM   100  CB  TYR A  20      1.078  73.590  46.935  1.00 74.92      A
ATOM   101  CG  TYR A  20      1.149  75.062  46.652  1.00 74.92      A
ATOM   102  CD1 TYR A  20      0.943  75.554  45.359  1.00 74.92      A
ATOM   103  CE1 TYR A  20      0.938  76.932  45.100  1.00 74.92      A
ATOM   104  CD2 TYR A  20      1.366  75.980  47.686  1.00 74.92      A
ATOM   105  CE2 TYR A  20      1.366  77.357  47.442  1.00 74.92      A
ATOM   106  CZ  TYR A  20      1.147  77.826  46.148  1.00 74.92      A
ATOM   107  OH  TYR A  20      1.103  79.180  45.901  1.00 74.92      A
ATOM   108  C   TYR A  20      2.419  71.555  47.216  1.00 99.95      A
ATOM   109  O   TYR A  20      3.529  71.051  47.384  1.00 99.95      A
ATOM   110  N   GLY A  21      1.315  71.037  47.726  1.00 45.46      A
ATOM   111  CA  GLY A  21      1.427  69.850  48.542  1.00 45.46      A
ATOM   112  C   GLY A  21      1.726  70.270  49.963  1.00 45.46      A
ATOM   113  O   GLY A  21      2.474  69.612  50.678  1.00 45.46      A
ATOM   114  N   GLU A  22      1.159  71.398  50.368  1.00 35.21      A
ATOM   115  CA  GLU A  22      1.366  71.868  51.722  1.00 35.21      A
ATOM   116  CB  GLU A  22      0.490  73.088  51.988  1.00 81.30      A
ATOM   117  CG  GLU A  22      0.755  74.249  51.052  1.00 81.30      A
ATOM   118  CD  GLU A  22     -0.177  75.412  51.313  1.00 81.30      A
ATOM   119  OE1 GLU A  22     -0.505  75.638  52.497  1.00 81.30      A
ATOM   120  OE2 GLU A  22     -0.572  76.106  50.348  1.00 81.30      A
ATOM   121  C   GLU A  22      0.996  70.726  52.675  1.00 35.21      A
ATOM   122  O   GLU A  22     -0.143  70.283  52.696  1.00 35.21      A
ATOM   123  N   PHE A  23      1.941  70.213  53.443  1.00 32.98      A
ATOM   124  CA  PHE A  23      1.585  69.147  54.359  1.00 32.98      A
ATOM   125  CB  PHE A  23      2.382  67.904  54.023  1.00 49.28      A
ATOM   126  CG  PHE A  23      2.300  67.536  52.591  1.00 49.28      A
ATOM   127  CD1 PHE A  23      1.085  67.579  51.927  1.00 49.28      A
ATOM   128  CD2 PHE A  23      3.426  67.159  51.887  1.00 49.28      A
ATOM   129  CE1 PHE A  23      0.989  67.251  50.559  1.00 49.28      A
ATOM   130  CE2 PHE A  23      3.347  66.826  50.517  1.00 49.28      A
```

```
ATOM    131  CZ   PHE A  23       2.125  66.873  49.855  1.00 49.28           A
ATOM    132  C    PHE A  23       1.849  69.610  55.775  1.00 32.98           A
ATOM    133  O    PHE A  23       2.958  70.018  56.105  1.00 32.98           A
ATOM    134  N    VAL A  24       0.828  69.552  56.621  1.00100.03           A
ATOM    135  CA   VAL A  24       0.982  70.049  57.979  1.00100.03           A
ATOM    136  CB   VAL A  24       0.010  71.190  58.264  1.00 18.08           A
ATOM    137  CG1  VAL A  24       0.513  71.953  59.436  1.00 18.08           A
ATOM    138  CG2  VAL A  24      -0.153  72.093  57.043  1.00 18.08           A
ATOM    139  C    VAL A  24       0.837  69.105  59.154  1.00100.03           A
ATOM    140  O    VAL A  24      -0.154  68.389  59.289  1.00100.03           A
ATOM    141  N    LEU A  25       1.835  69.141  60.024  1.00 70.43           A
ATOM    142  CA   LEU A  25       1.806  68.359  61.240  1.00 70.43           A
ATOM    143  CB   LEU A  25       3.193  68.286  61.851  1.00 75.51           A
ATOM    144  CG   LEU A  25       3.742  66.876  61.936  1.00 75.51           A
ATOM    145  CD1  LEU A  25       5.146  66.912  62.490  1.00 75.51           A
ATOM    146  CD2  LEU A  25       2.845  66.056  62.820  1.00 75.51           A
ATOM    147  C    LEU A  25       0.932  69.269  62.076  1.00 70.43           A
ATOM    148  O    LEU A  25      -0.045  69.820  61.566  1.00 70.43           A
ATOM    149  N    GLU A  26       1.281  69.459  63.343  1.00100.07           A
ATOM    150  CA   GLU A  26       0.486  70.341  64.188  1.00100.07           A
ATOM    151  CB   GLU A  26      -0.931  69.788  64.324  1.00 33.20           A
ATOM    152  CG   GLU A  26      -1.963  70.760  63.848  1.00 33.20           A
ATOM    153  CD   GLU A  26      -1.722  72.117  64.439  1.00 33.20           A
ATOM    154  OE1  GLU A  26      -1.411  72.153  65.653  1.00 33.20           A
ATOM    155  OE2  GLU A  26      -1.840  73.128  63.701  1.00 33.20           A
ATOM    156  C    GLU A  26       1.131  70.604  65.551  1.00100.07           A
ATOM    157  O    GLU A  26       2.210  71.194  65.606  1.00100.07           A
ATOM    158  N    PRO A  27       0.503  70.181  66.666  1.00 46.06           A
ATOM    159  CD   PRO A  27      -0.442  69.092  66.971  1.00 30.49           A
ATOM    160  CA   PRO A  27       1.258  70.517  67.871  1.00 46.06           A
ATOM    161  CB   PRO A  27       0.380  69.974  68.972  1.00 30.49           A
ATOM    162  CG   PRO A  27      -0.016  68.670  68.386  1.00 30.49           A
ATOM    163  C    PRO A  27       2.581  69.773  67.809  1.00 46.06           A
ATOM    164  O    PRO A  27       2.652  68.650  67.307  1.00 46.06           A
ATOM    165  N    LEU A  28       3.624  70.401  68.326  1.00100.07           A
ATOM    166  CA   LEU A  28       4.946  69.802  68.322  1.00100.07           A
ATOM    167  CB   LEU A  28       5.558  69.950  66.921  1.00 56.66           A
ATOM    168  CG   LEU A  28       4.960  69.040  65.843  1.00 56.66           A
ATOM    169  CD1  LEU A  28       5.190  69.595  64.443  1.00 56.66           A
ATOM    170  CD2  LEU A  28       5.575  67.660  66.011  1.00 56.66           A
ATOM    171  C    LEU A  28       5.761  70.556  69.364  1.00100.07           A
ATOM    172  O    LEU A  28       6.266  71.650  69.100  1.00100.07           A
ATOM    173  N    GLU A  29       5.866  69.966  70.552  1.00 99.76           A
ATOM    174  CA   GLU A  29       6.590  70.576  71.655  1.00 99.76           A
ATOM    175  CB   GLU A  29       6.947  69.505  72.693  1.00100.07           A
ATOM    176  CG   GLU A  29       5.680  68.888  73.315  1.00100.07           A
ATOM    177  CD   GLU A  29       5.952  67.897  74.434  1.00100.07           A
ATOM    178  OE1  GLU A  29       6.663  66.897  74.190  1.00100.07           A
ATOM    179  OE2  GLU A  29       5.441  68.118  75.556  1.00100.07           A
ATOM    180  C    GLU A  29       7.805  71.360  71.175  1.00 99.76           A
ATOM    181  O    GLU A  29       8.707  70.830  70.528  1.00 99.76           A
ATOM    182  N    ARG A  30       7.768  72.653  71.470  1.00 78.24           A
ATOM    183  CA   ARG A  30       8.799  73.609  71.102  1.00 78.24           A
ATOM    184  CB   ARG A  30       8.934  74.646  72.225  1.00100.07           A
ATOM    185  CG   ARG A  30       9.973  75.730  71.982  1.00100.07           A
ATOM    186  CD   ARG A  30       9.413  77.113  72.296  1.00100.07           A
ATOM    187  NE   ARG A  30      10.388  78.166  72.021  1.00100.07           A
ATOM    188  CZ   ARG A  30      10.064  79.418  71.722  1.00100.07           A
ATOM    189  NH1  ARG A  30       8.786  79.770  71.658  1.00100.07           A
ATOM    190  NH2  ARG A  30      11.016  80.311  71.481  1.00100.07           A
ATOM    191  C    ARG A  30      10.167  73.030  70.773  1.00 78.24           A
ATOM    192  O    ARG A  30      10.859  72.509  71.651  1.00 78.24           A
ATOM    193  N    GLY A  31      10.549  73.125  69.502  1.00 82.60           A
ATOM    194  CA   GLY A  31      11.854  72.646  69.095  1.00 82.60           A
ATOM    195  C    GLY A  31      11.892  71.458  68.174  1.00 82.60           A
ATOM    196  O    GLY A  31      12.842  70.682  68.217  1.00 82.60           A
ATOM    197  N    PHE A  32      10.870  71.301  67.346  1.00 70.02           A
ATOM    198  CA   PHE A  32      10.843  70.184  66.413  1.00 70.02           A
ATOM    199  CB   PHE A  32       9.910  69.080  66.905  1.00 38.84           A
ATOM    200  CG   PHE A  32      10.558  68.106  67.843  1.00 38.84           A
ATOM    201  CD1  PHE A  32      10.952  68.494  69.116  1.00 38.84           A
ATOM    202  CD2  PHE A  32      10.728  66.788  67.474  1.00 38.84           A
ATOM    203  CE1  PHE A  32      11.500  67.571  70.013  1.00 38.84           A
ATOM    204  CE2  PHE A  32      11.274  65.862  68.364  1.00 38.84           A
ATOM    205  CZ   PHE A  32      11.657  66.255  69.634  1.00 38.84           A
ATOM    206  C    PHE A  32      10.403  70.661  65.041  1.00 70.02           A
ATOM    207  O    PHE A  32      10.872  70.158  64.020  1.00 70.02           A
ATOM    208  N    GLY A  33       9.507  71.642  65.019  1.00 52.43           A
ATOM    209  CA   GLY A  33       9.022  72.160  63.754  1.00 52.43           A
ATOM    210  C    GLY A  33      10.150  72.311  62.758  1.00 52.43           A
ATOM    211  O    GLY A  33       9.926  72.368  61.550  1.00 52.43           A
ATOM    212  N    VAL A  34      11.371  72.386  63.279  1.00 71.93           A
ATOM    213  CA   VAL A  34      12.560  72.495  62.451  1.00 71.93           A
ATOM    214  CB   VAL A  34      13.449  73.635  62.897  1.00 70.76           A
```

| ATOM | 215 | CG1 | VAL A | 34 | 12.679 | 74.928 | 62.857 | 1.00 | 70.76 | A |
|------|-----|-----|-------|----|--------|--------|--------|------|-------|---|
| ATOM | 216 | CG2 | VAL A | 34 | 13.962 | 73.349 | 64.280 | 1.00 | 70.76 | A |
| ATOM | 217 | C | VAL A | 34 | 13.356 | 71.201 | 62.560 | 1.00 | 71.93 | A |
| ATOM | 218 | O | VAL A | 34 | 13.984 | 70.771 | 61.596 | 1.00 | 71.93 | A |
| ATOM | 219 | N | THR A | 35 | 13.328 | 70.584 | 63.737 | 1.00 | 58.19 | A |
| ATOM | 220 | CA | THR A | 35 | 14.040 | 69.329 | 63.952 | 1.00 | 58.19 | A |
| ATOM | 221 | CB | THR A | 35 | 13.727 | 68.750 | 65.344 | 1.00 | 96.03 | A |
| ATOM | 222 | OG1 | THR A | 35 | 14.468 | 69.479 | 66.330 | 1.00 | 96.03 | A |
| ATOM | 223 | CG2 | THR A | 35 | 14.097 | 67.278 | 65.416 | 1.00 | 96.03 | A |
| ATOM | 224 | C | THR A | 35 | 13.690 | 68.295 | 62.881 | 1.00 | 58.19 | A |
| ATOM | 225 | O | THR A | 35 | 14.418 | 67.317 | 62.682 | 1.00 | 58.19 | A |
| ATOM | 226 | N | LEU A | 36 | 12.580 | 68.509 | 62.183 | 1.00 | 45.88 | A |
| ATOM | 227 | CA | LEU A | 36 | 12.201 | 67.580 | 61.134 | 1.00 | 45.88 | A |
| ATOM | 228 | CB | LEU A | 36 | 11.105 | 66.616 | 61.617 | 1.00 | 72.17 | A |
| ATOM | 229 | CG | LEU A | 36 | 9.905 | 67.087 | 62.438 | 1.00 | 72.17 | A |
| ATOM | 230 | CD1 | LEU A | 36 | 8.883 | 65.962 | 62.562 | 1.00 | 72.17 | A |
| ATOM | 231 | CD2 | LEU A | 36 | 10.379 | 67.502 | 63.809 | 1.00 | 72.17 | A |
| ATOM | 232 | C | LEU A | 36 | 11.793 | 68.227 | 59.820 | 1.00 | 45.88 | A |
| ATOM | 233 | O | LEU A | 36 | 12.138 | 67.725 | 58.752 | 1.00 | 45.88 | A |
| ATOM | 234 | N | GLY A | 37 | 11.077 | 69.342 | 59.888 | 1.00 | 100.07 | A |
| ATOM | 235 | CA | GLY A | 37 | 10.649 | 69.998 | 58.666 | 1.00 | 100.07 | A |
| ATOM | 236 | C | GLY A | 37 | 11.797 | 70.359 | 57.744 | 1.00 | 100.07 | A |
| ATOM | 237 | O | GLY A | 37 | 11.598 | 70.576 | 56.549 | 1.00 | 100.07 | A |
| ATOM | 238 | N | ASN A | 38 | 13.006 | 70.411 | 58.289 | 1.00 | 62.51 | A |
| ATOM | 239 | CA | ASN A | 38 | 14.175 | 70.767 | 57.495 | 1.00 | 62.51 | A |
| ATOM | 240 | CB | ASN A | 38 | 15.222 | 71.433 | 58.389 | 1.00 | 44.82 | A |
| ATOM | 241 | CG | ASN A | 38 | 16.323 | 72.078 | 57.600 | 1.00 | 44.82 | A |
| ATOM | 242 | OD1 | ASN A | 38 | 17.140 | 71.392 | 57.002 | 1.00 | 44.82 | A |
| ATOM | 243 | ND2 | ASN A | 38 | 16.345 | 73.410 | 57.582 | 1.00 | 44.82 | A |
| ATOM | 244 | C | ASN A | 38 | 14.810 | 69.612 | 56.715 | 1.00 | 62.51 | A |
| ATOM | 245 | O | ASN A | 38 | 14.766 | 69.608 | 55.485 | 1.00 | 62.51 | A |
| ATOM | 246 | N | PRO A | 39 | 15.403 | 68.618 | 57.413 | 1.00 | 32.75 | A |
| ATOM | 247 | CD | PRO A | 39 | 15.306 | 68.316 | 58.852 | 1.00 | 32.40 | A |
| ATOM | 248 | CA | PRO A | 39 | 16.025 | 67.496 | 56.706 | 1.00 | 32.75 | A |
| ATOM | 249 | CB | PRO A | 39 | 16.090 | 66.408 | 57.768 | 1.00 | 32.40 | A |
| ATOM | 250 | CG | PRO A | 39 | 16.281 | 67.167 | 59.007 | 1.00 | 32.40 | A |
| ATOM | 251 | C | PRO A | 39 | 15.153 | 67.093 | 55.542 | 1.00 | 32.75 | A |
| ATOM | 252 | O | PRO A | 39 | 15.644 | 66.776 | 54.456 | 1.00 | 32.75 | A |
| ATOM | 253 | N | LEU A | 40 | 13.845 | 67.112 | 55.776 | 1.00 | 61.43 | A |
| ATOM | 254 | CA | LEU A | 40 | 12.903 | 66.745 | 54.733 | 1.00 | 61.43 | A |
| ATOM | 255 | CB | LEU A | 40 | 11.464 | 67.042 | 55.183 | 1.00 | 62.67 | A |
| ATOM | 256 | CG | LEU A | 40 | 11.008 | 66.513 | 56.555 | 1.00 | 62.67 | A |
| ATOM | 257 | CD1 | LEU A | 40 | 9.508 | 66.718 | 56.683 | 1.00 | 62.67 | A |
| ATOM | 258 | CD2 | LEU A | 40 | 11.345 | 65.039 | 56.723 | 1.00 | 62.67 | A |
| ATOM | 259 | C | LEU A | 40 | 13.283 | 67.576 | 53.514 | 1.00 | 61.43 | A |
| ATOM | 260 | O | LEU A | 40 | 13.648 | 67.027 | 52.472 | 1.00 | 61.43 | A |
| ATOM | 261 | N | ALA A | 41 | 13.235 | 68.899 | 53.674 | 1.00 | 76.41 | A |
| ATOM | 262 | CA | ALA A | 41 | 13.570 | 69.831 | 52.598 | 1.00 | 76.41 | A |
| ATOM | 263 | CB | ALA A | 41 | 13.664 | 71.271 | 53.135 | 1.00 | 17.66 | A |
| ATOM | 264 | C | ALA A | 41 | 14.888 | 69.424 | 51.965 | 1.00 | 76.41 | A |
| ATOM | 265 | O | ALA A | 41 | 14.999 | 69.288 | 50.743 | 1.00 | 76.41 | A |
| ATOM | 266 | N | ARG A | 42 | 15.891 | 69.241 | 52.811 | 1.00 | 55.18 | A |
| ATOM | 267 | CA | ARG A | 42 | 17.195 | 68.835 | 52.331 | 1.00 | 55.18 | A |
| ATOM | 268 | CB | ARG A | 42 | 18.081 | 68.423 | 53.505 | 1.00 | 50.68 | A |
| ATOM | 269 | CG | ARG A | 42 | 18.327 | 69.551 | 54.476 | 1.00 | 50.68 | A |
| ATOM | 270 | CD | ARG A | 42 | 19.592 | 70.268 | 54.136 | 1.00 | 50.68 | A |
| ATOM | 271 | NE | ARG A | 42 | 20.706 | 69.661 | 54.843 | 1.00 | 50.68 | A |
| ATOM | 272 | CZ | ARG A | 42 | 21.938 | 69.590 | 54.361 | 1.00 | 50.68 | A |
| ATOM | 273 | NH1 | ARG A | 42 | 22.213 | 70.085 | 53.156 | 1.00 | 50.68 | A |
| ATOM | 274 | NH2 | ARG A | 42 | 22.895 | 69.034 | 55.095 | 1.00 | 50.68 | A |
| ATOM | 275 | C | ARG A | 42 | 16.918 | 67.642 | 51.432 | 1.00 | 55.18 | A |
| ATOM | 276 | O | ARG A | 42 | 16.989 | 67.750 | 50.209 | 1.00 | 55.18 | A |
| ATOM | 277 | N | ILE A | 43 | 16.561 | 66.520 | 52.051 | 1.00 | 20.10 | A |
| ATOM | 278 | CA | ILE A | 43 | 16.269 | 65.302 | 51.317 | 1.00 | 20.10 | A |
| ATOM | 279 | CB | ILE A | 43 | 15.440 | 64.319 | 52.162 | 1.00 | 22.38 | A |
| ATOM | 280 | CG2 | ILE A | 43 | 15.404 | 62.952 | 51.482 | 1.00 | 22.38 | A |
| ATOM | 281 | CG1 | ILE A | 43 | 16.062 | 64.166 | 53.541 | 1.00 | 22.38 | A |
| ATOM | 282 | CD | ILE A | 43 | 17.339 | 63.403 | 53.534 | 1.00 | 22.38 | A |
| ATOM | 283 | C | ILE A | 43 | 15.468 | 65.641 | 50.066 | 1.00 | 20.10 | A |
| ATOM | 284 | O | ILE A | 43 | 15.890 | 65.356 | 48.943 | 1.00 | 20.10 | A |
| ATOM | 285 | N | LEU A | 44 | 14.310 | 66.260 | 50.281 | 1.00 | 46.55 | A |
| ATOM | 286 | CA | LEU A | 44 | 13.419 | 66.648 | 49.196 | 1.00 | 46.55 | A |
| ATOM | 287 | CB | LEU A | 44 | 12.410 | 67.689 | 49.686 | 1.00 | 52.98 | A |
| ATOM | 288 | CG | LEU A | 44 | 11.436 | 67.147 | 50.731 | 1.00 | 52.98 | A |
| ATOM | 289 | CD1 | LEU A | 44 | 10.608 | 68.269 | 51.320 | 1.00 | 52.98 | A |
| ATOM | 290 | CD2 | LEU A | 44 | 10.550 | 66.110 | 50.077 | 1.00 | 52.98 | A |
| ATOM | 291 | C | LEU A | 44 | 14.189 | 67.204 | 48.002 | 1.00 | 46.55 | A |
| ATOM | 292 | O | LEU A | 44 | 14.084 | 66.692 | 46.881 | 1.00 | 46.55 | A |
| ATOM | 293 | N | LEU A | 45 | 14.970 | 68.250 | 48.247 | 1.00 | 40.73 | A |
| ATOM | 294 | CA | LEU A | 45 | 15.757 | 68.877 | 47.192 | 1.00 | 40.73 | A |
| ATOM | 295 | CB | LEU A | 45 | 16.322 | 70.203 | 47.690 | 1.00 | 25.17 | A |
| ATOM | 296 | CG | LEU A | 45 | 15.338 | 71.271 | 48.150 | 1.00 | 25.17 | A |
| ATOM | 297 | CD1 | LEU A | 45 | 16.096 | 72.346 | 48.868 | 1.00 | 25.17 | A |
| ATOM | 298 | CD2 | LEU A | 45 | 14.609 | 71.867 | 46.976 | 1.00 | 25.17 | A |

| ATOM | 299 | C   | LEU A | 45 | 16.914 | 67.985 | 46.744 | 1.00 | 40.73  | A |
|------|-----|-----|-------|----|--------|--------|--------|------|--------|---|
| ATOM | 300 | O   | LEU A | 45 | 17.466 | 68.168 | 45.660 | 1.00 | 40.73  | A |
| ATOM | 301 | N   | SER A | 46 | 17.270 | 67.023 | 47.592 | 1.00 | 49.02  | A |
| ATOM | 302 | CA  | SER A | 46 | 18.375 | 66.112 | 47.326 | 1.00 | 49.02  | A |
| ATOM | 303 | CB  | SER A | 46 | 19.145 | 65.831 | 48.619 | 1.00 | 100.07 | A |
| ATOM | 304 | OG  | SER A | 46 | 19.335 | 67.007 | 49.381 | 1.00 | 100.07 | A |
| ATOM | 305 | C   | SER A | 46 | 17.915 | 64.782 | 46.753 | 1.00 | 49.02  | A |
| ATOM | 306 | O   | SER A | 46 | 17.264 | 64.709 | 45.714 | 1.00 | 49.02  | A |
| ATOM | 307 | N   | SER A | 47 | 18.276 | 63.726 | 47.461 | 1.00 | 43.33  | A |
| ATOM | 308 | CA  | SER A | 47 | 17.935 | 62.367 | 47.083 | 1.00 | 43.33  | A |
| ATOM | 309 | CB  | SER A | 47 | 18.397 | 61.419 | 48.196 | 1.00 | 99.93  | A |
| ATOM | 310 | OG  | SER A | 47 | 19.629 | 61.851 | 48.751 | 1.00 | 99.93  | A |
| ATOM | 311 | C   | SER A | 47 | 16.435 | 62.137 | 46.802 | 1.00 | 43.33  | A |
| ATOM | 312 | O   | SER A | 47 | 15.624 | 62.121 | 47.733 | 1.00 | 43.33  | A |
| ATOM | 313 | N   | ILE A | 48 | 16.073 | 61.959 | 45.531 | 1.00 | 85.43  | A |
| ATOM | 314 | CA  | ILE A | 48 | 14.684 | 61.695 | 45.128 | 1.00 | 85.43  | A |
| ATOM | 315 | CB  | ILE A | 48 | 13.746 | 62.916 | 45.278 | 1.00 | 25.46  | A |
| ATOM | 316 | CG2 | ILE A | 48 | 12.484 | 62.694 | 44.442 | 1.00 | 25.46  | A |
| ATOM | 317 | CG1 | ILE A | 48 | 13.377 | 63.159 | 46.745 | 1.00 | 25.46  | A |
| ATOM | 318 | CD  | ILE A | 48 | 12.100 | 62.507 | 47.206 | 1.00 | 25.46  | A |
| ATOM | 319 | C   | ILE A | 48 | 14.616 | 61.324 | 43.660 | 1.00 | 85.43  | A |
| ATOM | 320 | O   | ILE A | 48 | 14.911 | 62.151 | 42.796 | 1.00 | 85.43  | A |
| ATOM | 321 | N   | PRO A | 49 | 14.191 | 60.089 | 43.354 | 1.00 | 54.50  | A |
| ATOM | 322 | CD  | PRO A | 49 | 13.855 | 59.002 | 44.287 | 1.00 | 98.88  | A |
| ATOM | 323 | CA  | PRO A | 49 | 14.090 | 59.628 | 41.968 | 1.00 | 54.50  | A |
| ATOM | 324 | CB  | PRO A | 49 | 13.472 | 58.243 | 42.115 | 1.00 | 98.88  | A |
| ATOM | 325 | CG  | PRO A | 49 | 14.029 | 57.779 | 43.417 | 1.00 | 98.88  | A |
| ATOM | 326 | C   | PRO A | 49 | 13.235 | 60.555 | 41.113 | 1.00 | 54.50  | A |
| ATOM | 327 | O   | PRO A | 49 | 12.143 | 60.947 | 41.518 | 1.00 | 54.50  | A |
| ATOM | 328 | N   | GLY A | 50 | 13.749 | 60.903 | 39.937 | 1.00 | 44.57  | A |
| ATOM | 329 | CA  | GLY A | 50 | 13.041 | 61.776 | 39.021 | 1.00 | 44.57  | A |
| ATOM | 330 | C   | GLY A | 50 | 13.338 | 61.313 | 37.613 | 1.00 | 44.57  | A |
| ATOM | 331 | O   | GLY A | 50 | 13.775 | 60.182 | 37.424 | 1.00 | 44.57  | A |
| ATOM | 332 | N   | THR A | 51 | 13.134 | 62.178 | 36.624 | 1.00 | 54.82  | A |
| ATOM | 333 | CA  | THR A | 51 | 13.368 | 61.808 | 35.229 | 1.00 | 54.82  | A |
| ATOM | 334 | CB  | THR A | 51 | 12.086 | 61.266 | 34.624 | 1.00 | 88.12  | A |
| ATOM | 335 | OG1 | THR A | 51 | 11.121 | 62.326 | 34.566 | 1.00 | 88.12  | A |
| ATOM | 336 | CG2 | THR A | 51 | 11.528 | 60.129 | 35.480 | 1.00 | 88.12  | A |
| ATOM | 337 | C   | THR A | 51 | 13.793 | 63.019 | 34.397 | 1.00 | 54.82  | A |
| ATOM | 338 | O   | THR A | 51 | 13.311 | 64.123 | 34.624 | 1.00 | 54.82  | A |
| ATOM | 339 | N   | ALA A | 52 | 14.680 | 62.812 | 33.425 | 1.00 | 32.19  | A |
| ATOM | 340 | CA  | ALA A | 52 | 15.134 | 63.907 | 32.571 | 1.00 | 32.19  | A |
| ATOM | 341 | CB  | ALA A | 52 | 16.008 | 64.856 | 33.371 | 1.00 | 100.07 | A |
| ATOM | 342 | C   | ALA A | 52 | 15.876 | 63.456 | 31.313 | 1.00 | 32.19  | A |
| ATOM | 343 | O   | ALA A | 52 | 16.463 | 62.375 | 31.280 | 1.00 | 32.19  | A |
| ATOM | 344 | N   | VAL A | 53 | 15.847 | 64.298 | 30.282 | 1.00 | 31.84  | A |
| ATOM | 345 | CA  | VAL A | 53 | 16.510 | 64.001 | 29.016 | 1.00 | 31.84  | A |
| ATOM | 346 | CB  | VAL A | 53 | 16.542 | 65.251 | 28.123 | 1.00 | 36.17  | A |
| ATOM | 347 | CG1 | VAL A | 53 | 17.906 | 65.430 | 27.504 | 1.00 | 36.17  | A |
| ATOM | 348 | CG2 | VAL A | 53 | 15.501 | 65.126 | 27.036 | 1.00 | 36.17  | A |
| ATOM | 349 | C   | VAL A | 53 | 17.930 | 63.524 | 29.281 | 1.00 | 31.84  | A |
| ATOM | 350 | O   | VAL A | 53 | 18.460 | 63.735 | 30.365 | 1.00 | 31.84  | A |
| ATOM | 351 | N   | THR A | 54 | 18.562 | 62.900 | 28.294 | 1.00 | 38.47  | A |
| ATOM | 352 | CA  | THR A | 54 | 19.915 | 62.400 | 28.495 | 1.00 | 38.47  | A |
| ATOM | 353 | CB  | THR A | 54 | 19.866 | 60.958 | 28.965 | 1.00 | 69.18  | A |
| ATOM | 354 | OG1 | THR A | 54 | 18.933 | 60.849 | 30.043 | 1.00 | 69.18  | A |
| ATOM | 355 | CG2 | THR A | 54 | 21.238 | 60.497 | 29.413 | 1.00 | 69.18  | A |
| ATOM | 356 | C   | THR A | 54 | 20.810 | 62.434 | 27.264 | 1.00 | 38.47  | A |
| ATOM | 357 | O   | THR A | 54 | 22.038 | 62.464 | 27.391 | 1.00 | 38.47  | A |
| ATOM | 358 | N   | SER A | 55 | 20.192 | 62.403 | 26.082 | 1.00 | 48.54  | A |
| ATOM | 359 | CA  | SER A | 55 | 20.919 | 62.424 | 24.810 | 1.00 | 48.54  | A |
| ATOM | 360 | CB  | SER A | 55 | 21.768 | 61.157 | 24.684 | 1.00 | 72.28  | A |
| ATOM | 361 | OG  | SER A | 55 | 22.265 | 61.011 | 23.369 | 1.00 | 72.28  | A |
| ATOM | 362 | C   | SER A | 55 | 19.970 | 62.520 | 23.611 | 1.00 | 48.54  | A |
| ATOM | 363 | O   | SER A | 55 | 18.924 | 61.864 | 23.582 | 1.00 | 48.54  | A |
| ATOM | 364 | N   | VAL A | 56 | 20.331 | 63.334 | 22.622 | 1.00 | 74.20  | A |
| ATOM | 365 | CA  | VAL A | 56 | 19.483 | 63.476 | 21.440 | 1.00 | 74.20  | A |
| ATOM | 366 | CB  | VAL A | 56 | 18.765 | 64.875 | 21.357 | 1.00 | 15.45  | A |
| ATOM | 367 | CG1 | VAL A | 56 | 18.329 | 65.339 | 22.717 | 1.00 | 15.45  | A |
| ATOM | 368 | CG2 | VAL A | 56 | 19.664 | 65.896 | 20.712 | 1.00 | 15.45  | A |
| ATOM | 369 | C   | VAL A | 56 | 20.216 | 63.290 | 20.120 | 1.00 | 74.20  | A |
| ATOM | 370 | O   | VAL A | 56 | 21.439 | 63.384 | 20.048 | 1.00 | 74.20  | A |
| ATOM | 371 | N   | TYR A | 57 | 19.439 | 63.014 | 19.079 | 1.00 | 62.63  | A |
| ATOM | 372 | CA  | TYR A | 57 | 19.954 | 62.864 | 17.731 | 1.00 | 62.63  | A |
| ATOM | 373 | CB  | TYR A | 57 | 19.964 | 61.401 | 17.266 | 1.00 | 52.17  | A |
| ATOM | 374 | CG  | TYR A | 57 | 20.310 | 61.202 | 15.788 | 1.00 | 52.17  | A |
| ATOM | 375 | CD1 | TYR A | 57 | 20.875 | 60.010 | 15.335 | 1.00 | 52.17  | A |
| ATOM | 376 | CE1 | TYR A | 57 | 21.190 | 59.822 | 13.980 | 1.00 | 52.17  | A |
| ATOM | 377 | CD2 | TYR A | 57 | 20.065 | 62.199 | 14.844 | 1.00 | 52.17  | A |
| ATOM | 378 | CE2 | TYR A | 57 | 20.371 | 62.022 | 13.492 | 1.00 | 52.17  | A |
| ATOM | 379 | CZ  | TYR A | 57 | 20.935 | 60.837 | 13.066 | 1.00 | 52.17  | A |
| ATOM | 380 | OH  | TYR A | 57 | 21.253 | 60.688 | 11.732 | 1.00 | 52.17  | A |
| ATOM | 381 | C   | TYR A | 57 | 18.991 | 63.644 | 16.881 | 1.00 | 62.63  | A |
| ATOM | 382 | O   | TYR A | 57 | 17.850 | 63.227 | 16.690 | 1.00 | 62.63  | A |

| ATOM | 383 | N | ILE A | 58 | 19.444 | 64.793 | 16.399 | 1.00 | 40.99 | A |
|------|-----|-----|-------|----|--------|--------|--------|------|-------|---|
| ATOM | 384 | CA | ILE A | 58 | 18.623 | 65.611 | 15.519 | 1.00 | 40.99 | A |
| ATOM | 385 | CB | ILE A | 58 | 18.849 | 67.138 | 15.730 | 1.00 | 48.67 | A |
| ATOM | 386 | CG2 | ILE A | 58 | 17.754 | 67.919 | 15.058 | 1.00 | 48.67 | A |
| ATOM | 387 | CG1 | ILE A | 58 | 18.808 | 67.490 | 17.209 | 1.00 | 48.67 | A |
| ATOM | 388 | CD | ILE A | 58 | 20.002 | 66.996 | 17.960 | 1.00 | 48.67 | A |
| ATOM | 389 | C | ILE A | 58 | 19.166 | 65.206 | 14.148 | 1.00 | 40.99 | A |
| ATOM | 390 | O | ILE A | 58 | 20.378 | 65.247 | 13.930 | 1.00 | 40.99 | A |
| ATOM | 391 | N | GLU A | 59 | 18.286 | 64.789 | 13.241 | 1.00 | 100.07 | A |
| ATOM | 392 | CA | GLU A | 59 | 18.698 | 64.361 | 11.903 | 1.00 | 100.07 | A |
| ATOM | 393 | CB | GLU A | 59 | 17.461 | 64.209 | 11.008 | 1.00 | 100.07 | A |
| ATOM | 394 | CG | GLU A | 59 | 17.757 | 63.710 | 9.605 | 1.00 | 100.07 | A |
| ATOM | 395 | CD | GLU A | 59 | 17.088 | 62.377 | 9.299 | 1.00 | 100.07 | A |
| ATOM | 396 | OE1 | GLU A | 59 | 17.258 | 61.420 | 10.086 | 1.00 | 100.07 | A |
| ATOM | 397 | OE2 | GLU A | 59 | 16.396 | 62.285 | 8.264 | 1.00 | 100.07 | A |
| ATOM | 398 | C | GLU A | 59 | 19.683 | 65.326 | 11.243 | 1.00 | 100.07 | A |
| ATOM | 399 | O | GLU A | 59 | 19.293 | 66.422 | 10.835 | 1.00 | 100.07 | A |
| ATOM | 400 | N | ASP A | 60 | 20.947 | 64.901 | 11.150 | 1.00 | 100.07 | A |
| ATOM | 401 | CA | ASP A | 60 | 22.050 | 65.669 | 10.544 | 1.00 | 100.07 | A |
| ATOM | 402 | CB | ASP A | 60 | 21.514 | 66.695 | 9.536 | 1.00 | 81.65 | A |
| ATOM | 403 | CG | ASP A | 60 | 20.699 | 66.058 | 8.429 | 1.00 | 81.65 | A |
| ATOM | 404 | OD1 | ASP A | 60 | 21.295 | 65.438 | 7.526 | 1.00 | 81.65 | A |
| ATOM | 405 | OD2 | ASP A | 60 | 19.457 | 66.170 | 8.465 | 1.00 | 81.65 | A |
| ATOM | 406 | C | ASP A | 60 | 22.969 | 66.394 | 11.539 | 1.00 | 100.07 | A |
| ATOM | 407 | O | ASP A | 60 | 22.543 | 66.839 | 12.606 | 1.00 | 100.07 | A |
| ATOM | 408 | N | VAL A | 61 | 24.239 | 66.507 | 11.157 | 1.00 | 87.49 | A |
| ATOM | 409 | CA | VAL A | 61 | 25.279 | 67.175 | 11.944 | 1.00 | 87.49 | A |
| ATOM | 410 | CB | VAL A | 61 | 25.121 | 68.709 | 11.901 | 1.00 | 76.95 | A |
| ATOM | 411 | CG1 | VAL A | 61 | 26.437 | 69.359 | 12.288 | 1.00 | 76.95 | A |
| ATOM | 412 | CG2 | VAL A | 61 | 24.679 | 69.160 | 10.516 | 1.00 | 76.95 | A |
| ATOM | 413 | C | VAL A | 61 | 25.392 | 66.763 | 13.401 | 1.00 | 87.49 | A |
| ATOM | 414 | O | VAL A | 61 | 24.406 | 66.751 | 14.140 | 1.00 | 87.49 | A |
| ATOM | 415 | N | LEU A | 62 | 26.611 | 66.427 | 13.808 | 1.00 | 69.94 | A |
| ATOM | 416 | CA | LEU A | 62 | 26.859 | 66.051 | 15.191 | 1.00 | 69.94 | A |
| ATOM | 417 | CB | LEU A | 62 | 27.936 | 64.971 | 15.280 | 1.00 | 99.97 | A |
| ATOM | 418 | CG | LEU A | 62 | 29.229 | 65.175 | 14.498 | 1.00 | 99.97 | A |
| ATOM | 419 | CD1 | LEU A | 62 | 30.181 | 64.026 | 14.818 | 1.00 | 99.97 | A |
| ATOM | 420 | CD2 | LEU A | 62 | 28.936 | 65.237 | 13.002 | 1.00 | 99.97 | A |
| ATOM | 421 | C | LEU A | 62 | 27.275 | 67.293 | 15.966 | 1.00 | 69.94 | A |
| ATOM | 422 | O | LEU A | 62 | 26.962 | 68.411 | 15.553 | 1.00 | 69.94 | A |
| ATOM | 423 | N | HIS A | 63 | 27.987 | 67.094 | 17.071 | 1.00 | 43.02 | A |
| ATOM | 424 | CA | HIS A | 63 | 28.420 | 68.187 | 17.939 | 1.00 | 43.02 | A |
| ATOM | 425 | CB | HIS A | 63 | 29.691 | 68.855 | 17.388 | 1.00 | 100.07 | A |
| ATOM | 426 | CG | HIS A | 63 | 29.495 | 69.617 | 16.115 | 1.00 | 100.07 | A |
| ATOM | 427 | CD2 | HIS A | 63 | 30.027 | 69.439 | 14.883 | 1.00 | 100.07 | A |
| ATOM | 428 | ND1 | HIS A | 63 | 28.726 | 70.757 | 16.039 | 1.00 | 100.07 | A |
| ATOM | 429 | CE1 | HIS A | 63 | 28.799 | 71.251 | 14.815 | 1.00 | 100.07 | A |
| ATOM | 430 | NE2 | HIS A | 63 | 29.582 | 70.471 | 14.094 | 1.00 | 100.07 | A |
| ATOM | 431 | C | HIS A | 63 | 27.319 | 69.220 | 18.223 | 1.00 | 43.02 | A |
| ATOM | 432 | O | HIS A | 63 | 26.556 | 69.622 | 17.344 | 1.00 | 43.02 | A |
| ATOM | 433 | N | GLU A | 64 | 27.235 | 69.621 | 19.484 | 1.00 | 83.05 | A |
| ATOM | 434 | CA | GLU A | 64 | 26.243 | 70.580 | 19.932 | 1.00 | 83.05 | A |
| ATOM | 435 | CB | GLU A | 64 | 26.253 | 70.639 | 21.463 | 1.00 | 95.17 | A |
| ATOM | 436 | CG | GLU A | 64 | 25.040 | 71.323 | 22.070 | 1.00 | 95.17 | A |
| ATOM | 437 | CD | GLU A | 64 | 25.059 | 71.329 | 23.587 | 1.00 | 95.17 | A |
| ATOM | 438 | OE1 | GLU A | 64 | 25.330 | 70.265 | 24.189 | 1.00 | 95.17 | A |
| ATOM | 439 | OE2 | GLU A | 64 | 24.788 | 72.397 | 24.176 | 1.00 | 95.17 | A |
| ATOM | 440 | C | GLU A | 64 | 26.506 | 71.969 | 19.364 | 1.00 | 83.05 | A |
| ATOM | 441 | O | GLU A | 64 | 25.830 | 72.919 | 19.734 | 1.00 | 83.05 | A |
| ATOM | 442 | N | PHE A | 65 | 27.477 | 72.097 | 18.465 | 1.00 | 17.45 | A |
| ATOM | 443 | CA | PHE A | 65 | 27.794 | 73.409 | 17.884 | 1.00 | 17.45 | A |
| ATOM | 444 | CB | PHE A | 65 | 29.272 | 73.719 | 18.095 | 1.00 | 18.31 | A |
| ATOM | 445 | CG | PHE A | 65 | 29.709 | 73.551 | 19.508 | 1.00 | 18.31 | A |
| ATOM | 446 | CD1 | PHE A | 65 | 29.899 | 72.295 | 20.040 | 1.00 | 18.31 | A |
| ATOM | 447 | CD2 | PHE A | 65 | 29.873 | 74.648 | 20.331 | 1.00 | 18.31 | A |
| ATOM | 448 | CE1 | PHE A | 65 | 30.243 | 72.135 | 21.367 | 1.00 | 18.31 | A |
| ATOM | 449 | CE2 | PHE A | 65 | 30.215 | 74.487 | 21.657 | 1.00 | 18.31 | A |
| ATOM | 450 | CZ | PHE A | 65 | 30.399 | 73.227 | 22.170 | 1.00 | 18.31 | A |
| ATOM | 451 | C | PHE A | 65 | 27.463 | 73.526 | 16.402 | 1.00 | 17.45 | A |
| ATOM | 452 | O | PHE A | 65 | 28.275 | 74.024 | 15.619 | 1.00 | 17.45 | A |
| ATOM | 453 | N | SER A | 66 | 26.268 | 73.079 | 16.023 | 1.00 | 52.72 | A |
| ATOM | 454 | CA | SER A | 66 | 25.846 | 73.092 | 14.624 | 1.00 | 52.72 | A |
| ATOM | 455 | CB | SER A | 66 | 25.300 | 71.711 | 14.251 | 1.00 | 48.15 | A |
| ATOM | 456 | OG | SER A | 66 | 26.072 | 70.662 | 14.825 | 1.00 | 48.15 | A |
| ATOM | 457 | C | SER A | 66 | 24.768 | 74.139 | 14.351 | 1.00 | 52.72 | A |
| ATOM | 458 | O | SER A | 66 | 24.640 | 75.117 | 15.084 | 1.00 | 52.72 | A |
| ATOM | 459 | N | THR A | 67 | 23.996 | 73.927 | 13.288 | 1.00 | 44.34 | A |
| ATOM | 460 | CA | THR A | 67 | 22.920 | 74.843 | 12.922 | 1.00 | 44.34 | A |
| ATOM | 461 | CB | THR A | 67 | 23.470 | 76.169 | 12.362 | 1.00 | 40.81 | A |
| ATOM | 462 | OG1 | THR A | 67 | 22.381 | 76.976 | 11.891 | 1.00 | 40.81 | A |
| ATOM | 463 | CG2 | THR A | 67 | 24.449 | 75.907 | 11.221 | 1.00 | 40.81 | A |
| ATOM | 464 | C | THR A | 67 | 21.976 | 74.228 | 11.887 | 1.00 | 44.34 | A |
| ATOM | 465 | O | THR A | 67 | 22.298 | 74.178 | 10.701 | 1.00 | 44.34 | A |
| ATOM | 466 | N | ILE A | 68 | 20.808 | 73.766 | 12.336 | 1.00 | 68.89 | A |

| ATOM | 467 | CA  | ILE A | 68 | 19.825 | 73.136 | 11.444 | 1.00 | 68.89 | A |
|------|-----|-----|-------|----|--------|--------|--------|------|-------|---|
| ATOM | 468 | CB  | ILE A | 68 | 18.866 | 72.182 | 12.216 | 1.00 | 47.46 | A |
| ATOM | 469 | CG2 | ILE A | 68 | 18.420 | 71.048 | 11.306 | 1.00 | 47.46 | A |
| ATOM | 470 | CG1 | ILE A | 68 | 19.574 | 71.570 | 13.424 | 1.00 | 47.46 | A |
| ATOM | 471 | CD  | ILE A | 68 | 18.671 | 70.752 | 14.283 | 1.00 | 47.46 | A |
| ATOM | 472 | C   | ILE A | 68 | 18.962 | 74.172 | 10.719 | 1.00 | 68.89 | A |
| ATOM | 473 | O   | ILE A | 68 | 18.215 | 74.927 | 11.348 | 1.00 | 68.89 | A |
| ATOM | 474 | N   | PRO A | 69 | 19.035 | 74.189 | 9.375  | 1.00 | 69.72 | A |
| ATOM | 475 | CD  | PRO A | 69 | 19.754 | 73.147 | 8.619  | 1.00 | 34.85 | A |
| ATOM | 476 | CA  | PRO A | 69 | 18.316 | 75.088 | 8.454  | 1.00 | 69.72 | A |
| ATOM | 477 | CB  | PRO A | 69 | 18.767 | 74.604 | 7.077  | 1.00 | 34.85 | A |
| ATOM | 478 | CG  | PRO A | 69 | 18.999 | 73.140 | 7.306  | 1.00 | 34.85 | A |
| ATOM | 479 | C   | PRO A | 69 | 16.800 | 75.116 | 8.569  | 1.00 | 69.72 | A |
| ATOM | 480 | O   | PRO A | 69 | 16.187 | 74.160 | 9.033  | 1.00 | 69.72 | A |
| ATOM | 481 | N   | GLY A | 70 | 16.212 | 76.222 | 8.116  | 1.00 | 92.95 | A |
| ATOM | 482 | CA  | GLY A | 70 | 14.772 | 76.388 | 8.174  | 1.00 | 92.95 | A |
| ATOM | 483 | C   | GLY A | 70 | 14.338 | 76.526 | 9.618  | 1.00 | 92.95 | A |
| ATOM | 484 | O   | GLY A | 70 | 13.167 | 76.771 | 9.905  | 1.00 | 92.95 | A |
| ATOM | 485 | N   | VAL A | 71 | 15.296 | 76.377 | 10.528 | 1.00 | 56.58 | A |
| ATOM | 486 | CA  | VAL A | 71 | 15.033 | 76.454 | 11.955 | 1.00 | 56.58 | A |
| ATOM | 487 | CB  | VAL A | 71 | 15.624 | 75.233 | 12.690 | 1.00 | 36.59 | A |
| ATOM | 488 | CG1 | VAL A | 71 | 15.017 | 75.097 | 14.074 | 1.00 | 36.59 | A |
| ATOM | 489 | CG2 | VAL A | 71 | 15.422 | 73.988 | 11.876 | 1.00 | 36.59 | A |
| ATOM | 490 | C   | VAL A | 71 | 15.712 | 77.683 | 12.536 | 1.00 | 56.58 | A |
| ATOM | 491 | O   | VAL A | 71 | 16.927 | 77.701 | 12.689 | 1.00 | 56.58 | A |
| ATOM | 492 | N   | LYS A | 72 | 14.928 | 78.700 | 12.869 | 1.00 | 65.96 | A |
| ATOM | 493 | CA  | LYS A | 72 | 15.459 | 79.925 | 13.473 | 1.00 | 65.96 | A |
| ATOM | 494 | CB  | LYS A | 72 | 14.290 | 80.823 | 13.902 | 1.00 | 99.92 | A |
| ATOM | 495 | CG  | LYS A | 72 | 14.647 | 81.927 | 14.895 | 1.00 | 99.92 | A |
| ATOM | 496 | CD  | LYS A | 72 | 13.387 | 82.534 | 15.506 | 1.00 | 99.92 | A |
| ATOM | 497 | CE  | LYS A | 72 | 13.686 | 83.308 | 16.781 | 1.00 | 99.92 | A |
| ATOM | 498 | NZ  | LYS A | 72 | 12.437 | 83.682 | 17.502 | 1.00 | 99.92 | A |
| ATOM | 499 | C   | LYS A | 72 | 16.346 | 79.620 | 14.688 | 1.00 | 65.96 | A |
| ATOM | 500 | O   | LYS A | 72 | 17.428 | 80.197 | 14.840 | 1.00 | 65.96 | A |
| ATOM | 501 | N   | GLU A | 73 | 15.868 | 78.730 | 15.555 | 1.00 | 56.97 | A |
| ATOM | 502 | CA  | GLU A | 73 | 16.607 | 78.315 | 16.744 | 1.00 | 56.97 | A |
| ATOM | 503 | CB  | GLU A | 73 | 15.973 | 77.066 | 17.361 | 1.00 | 64.77 | A |
| ATOM | 504 | CG  | GLU A | 73 | 15.259 | 77.297 | 18.646 | 1.00 | 64.77 | A |
| ATOM | 505 | CD  | GLU A | 73 | 14.292 | 78.429 | 18.525 | 1.00 | 64.77 | A |
| ATOM | 506 | OE1 | GLU A | 73 | 13.611 | 78.489 | 17.484 | 1.00 | 64.77 | A |
| ATOM | 507 | OE2 | GLU A | 73 | 14.205 | 79.254 | 19.460 | 1.00 | 64.77 | A |
| ATOM | 508 | C   | GLU A | 73 | 18.028 | 77.951 | 16.344 | 1.00 | 56.97 | A |
| ATOM | 509 | O   | GLU A | 73 | 18.369 | 77.943 | 15.163 | 1.00 | 56.97 | A |
| ATOM | 510 | N   | ASP A | 74 | 18.840 | 77.627 | 17.344 | 1.00 | 56.37 | A |
| ATOM | 511 | CA  | ASP A | 74 | 20.227 | 77.213 | 17.143 | 1.00 | 56.37 | A |
| ATOM | 512 | CB  | ASP A | 74 | 21.111 | 77.836 | 18.232 | 1.00 | 68.46 | A |
| ATOM | 513 | CG  | ASP A | 74 | 22.589 | 77.652 | 17.969 | 1.00 | 68.46 | A |
| ATOM | 514 | OD1 | ASP A | 74 | 23.082 | 76.509 | 18.057 | 1.00 | 68.46 | A |
| ATOM | 515 | OD2 | ASP A | 74 | 23.260 | 78.663 | 17.675 | 1.00 | 68.46 | A |
| ATOM | 516 | C   | ASP A | 74 | 20.176 | 75.695 | 17.301 | 1.00 | 56.37 | A |
| ATOM | 517 | O   | ASP A | 74 | 19.332 | 75.039 | 16.700 | 1.00 | 56.37 | A |
| ATOM | 518 | N   | VAL A | 75 | 21.064 | 75.132 | 18.107 | 1.00 | 47.58 | A |
| ATOM | 519 | CA  | VAL A | 75 | 21.052 | 73.694 | 18.331 | 1.00 | 47.58 | A |
| ATOM | 520 | CB  | VAL A | 75 | 22.004 | 72.915 | 17.374 | 1.00 | 71.89 | A |
| ATOM | 521 | CG1 | VAL A | 75 | 21.598 | 73.139 | 15.923 | 1.00 | 71.89 | A |
| ATOM | 522 | CG2 | VAL A | 75 | 23.438 | 73.342 | 17.593 | 1.00 | 71.89 | A |
| ATOM | 523 | C   | VAL A | 75 | 21.480 | 73.467 | 19.761 | 1.00 | 47.58 | A |
| ATOM | 524 | O   | VAL A | 75 | 21.212 | 72.415 | 20.341 | 1.00 | 47.58 | A |
| ATOM | 525 | N   | VAL A | 76 | 22.150 | 74.470 | 20.325 | 1.00 | 47.65 | A |
| ATOM | 526 | CA  | VAL A | 76 | 22.606 | 74.387 | 21.705 | 1.00 | 47.65 | A |
| ATOM | 527 | CB  | VAL A | 76 | 23.711 | 75.429 | 22.029 | 1.00 | 53.08 | A |
| ATOM | 528 | CG1 | VAL A | 76 | 24.565 | 74.932 | 23.186 | 1.00 | 53.08 | A |
| ATOM | 529 | CG2 | VAL A | 76 | 24.561 | 75.700 | 20.806 | 1.00 | 53.08 | A |
| ATOM | 530 | C   | VAL A | 76 | 21.361 | 74.716 | 22.502 | 1.00 | 47.65 | A |
| ATOM | 531 | O   | VAL A | 76 | 20.969 | 73.976 | 23.415 | 1.00 | 47.65 | A |
| ATOM | 532 | N   | GLU A | 77 | 20.738 | 75.833 | 22.118 | 1.00 | 51.13 | A |
| ATOM | 533 | CA  | GLU A | 77 | 19.512 | 76.305 | 22.750 | 1.00 | 51.13 | A |
| ATOM | 534 | CB  | GLU A | 77 | 18.912 | 77.446 | 21.935 | 1.00 | 99.63 | A |
| ATOM | 535 | CG  | GLU A | 77 | 18.429 | 78.606 | 22.766 | 1.00 | 99.63 | A |
| ATOM | 536 | CD  | GLU A | 77 | 17.254 | 79.306 | 22.125 | 1.00 | 99.63 | A |
| ATOM | 537 | OE1 | GLU A | 77 | 16.118 | 78.791 | 22.241 | 1.00 | 99.63 | A |
| ATOM | 538 | OE2 | GLU A | 77 | 17.469 | 80.362 | 21.493 | 1.00 | 99.63 | A |
| ATOM | 539 | C   | GLU A | 77 | 18.566 | 75.106 | 22.752 | 1.00 | 51.13 | A |
| ATOM | 540 | O   | GLU A | 77 | 18.148 | 74.627 | 23.805 | 1.00 | 51.13 | A |
| ATOM | 541 | N   | ILE A | 78 | 18.239 | 74.623 | 21.557 | 1.00 | 41.27 | A |
| ATOM | 542 | CA  | ILE A | 78 | 17.374 | 73.468 | 21.425 | 1.00 | 41.27 | A |
| ATOM | 543 | CB  | ILE A | 78 | 17.596 | 72.782 | 20.080 | 1.00 | 44.04 | A |
| ATOM | 544 | CG2 | ILE A | 78 | 16.831 | 71.480 | 20.035 | 1.00 | 44.04 | A |
| ATOM | 545 | CG1 | ILE A | 78 | 17.197 | 73.735 | 18.951 | 1.00 | 44.04 | A |
| ATOM | 546 | CD  | ILE A | 78 | 17.541 | 73.234 | 17.560 | 1.00 | 44.04 | A |
| ATOM | 547 | C   | ILE A | 78 | 17.786 | 72.519 | 22.530 | 1.00 | 41.27 | A |
| ATOM | 548 | O   | ILE A | 78 | 16.984 | 72.174 | 23.385 | 1.00 | 41.27 | A |
| ATOM | 549 | N   | ILE A | 79 | 19.049 | 72.118 | 22.538 | 1.00 | 42.42 | A |
| ATOM | 550 | CA  | ILE A | 79 | 19.491 | 71.211 | 23.576 | 1.00 | 42.42 | A |

| ATOM | 551 | CB | ILE A | 79 | 21.013 | 71.013 | 23.586 | 1.00 | 35.69 | A |
|------|-----|-----|-------|----|--------|--------|--------|------|-------|---|
| ATOM | 552 | CG2 | ILE A | 79 | 21.426 | 70.226 | 24.837 | 1.00 | 35.69 | A |
| ATOM | 553 | CG1 | ILE A | 79 | 21.450 | 70.237 | 22.349 | 1.00 | 35.69 | A |
| ATOM | 554 | CD | ILE A | 79 | 21.040 | 68.792 | 22.370 | 1.00 | 35.69 | A |
| ATOM | 555 | C | ILE A | 79 | 19.089 | 71.752 | 24.927 | 1.00 | 42.42 | A |
| ATOM | 556 | O | ILE A | 79 | 18.740 | 70.980 | 25.811 | 1.00 | 42.42 | A |
| ATOM | 557 | N | LEU A | 80 | 19.136 | 73.074 | 25.084 | 1.00 | 70.11 | A |
| ATOM | 558 | CA | LEU A | 80 | 18.779 | 73.710 | 26.354 | 1.00 | 70.11 | A |
| ATOM | 559 | CB | LEU A | 80 | 19.257 | 75.173 | 26.380 | 1.00 | 34.05 | A |
| ATOM | 560 | CG | LEU A | 80 | 20.732 | 75.506 | 26.083 | 1.00 | 34.05 | A |
| ATOM | 561 | CD1 | LEU A | 80 | 20.959 | 76.988 | 26.339 | 1.00 | 34.05 | A |
| ATOM | 562 | CD2 | LEU A | 80 | 21.677 | 74.686 | 26.952 | 1.00 | 34.05 | A |
| ATOM | 563 | C | LEU A | 80 | 17.276 | 73.644 | 26.654 | 1.00 | 70.11 | A |
| ATOM | 564 | O | LEU A | 80 | 16.892 | 73.356 | 27.789 | 1.00 | 70.11 | A |
| ATOM | 565 | N | ASN A | 81 | 16.423 | 73.924 | 25.665 | 1.00 | 34.19 | A |
| ATOM | 566 | CA | ASN A | 81 | 14.981 | 73.826 | 25.903 | 1.00 | 34.19 | A |
| ATOM | 567 | CB | ASN A | 81 | 14.178 | 74.115 | 24.622 | 1.00 | 38.34 | A |
| ATOM | 568 | CG | ASN A | 81 | 14.037 | 75.611 | 24.326 | 1.00 | 38.34 | A |
| ATOM | 569 | OD1 | ASN A | 81 | 14.858 | 76.211 | 23.631 | 1.00 | 38.34 | A |
| ATOM | 570 | ND2 | ASN A | 81 | 12.984 | 76.215 | 24.859 | 1.00 | 38.34 | A |
| ATOM | 571 | C | ASN A | 81 | 14.754 | 72.381 | 26.350 | 1.00 | 34.19 | A |
| ATOM | 572 | O | ASN A | 81 | 14.429 | 72.100 | 27.508 | 1.00 | 34.19 | A |
| ATOM | 573 | N | LEU A | 82 | 14.976 | 71.473 | 25.407 | 1.00 | 59.07 | A |
| ATOM | 574 | CA | LEU A | 82 | 14.849 | 70.030 | 25.594 | 1.00 | 59.07 | A |
| ATOM | 575 | CB | LEU A | 82 | 15.567 | 69.353 | 24.409 | 1.00 | 58.84 | A |
| ATOM | 576 | CG | LEU A | 82 | 15.719 | 67.852 | 24.181 | 1.00 | 58.84 | A |
| ATOM | 577 | CD1 | LEU A | 82 | 15.984 | 67.607 | 22.702 | 1.00 | 58.84 | A |
| ATOM | 578 | CD2 | LEU A | 82 | 16.848 | 67.312 | 25.036 | 1.00 | 58.84 | A |
| ATOM | 579 | C | LEU A | 82 | 15.404 | 69.563 | 26.944 | 1.00 | 59.07 | A |
| ATOM | 580 | O | LEU A | 82 | 15.077 | 68.478 | 27.415 | 1.00 | 59.07 | A |
| ATOM | 581 | N | LYS A | 83 | 16.238 | 70.389 | 27.565 | 1.00 | 40.47 | A |
| ATOM | 582 | CA | LYS A | 83 | 16.819 | 70.056 | 28.860 | 1.00 | 40.47 | A |
| ATOM | 583 | CB | LYS A | 83 | 17.902 | 71.066 | 29.260 | 1.00 | 71.50 | A |
| ATOM | 584 | CG | LYS A | 83 | 19.280 | 70.837 | 28.666 | 1.00 | 71.50 | A |
| ATOM | 585 | CD | LYS A | 83 | 20.261 | 71.900 | 29.148 | 1.00 | 71.50 | A |
| ATOM | 586 | CE | LYS A | 83 | 20.472 | 71.818 | 30.645 | 1.00 | 71.50 | A |
| ATOM | 587 | NZ | LYS A | 83 | 21.299 | 72.948 | 31.147 | 1.00 | 71.50 | A |
| ATOM | 588 | C | LYS A | 83 | 15.739 | 70.082 | 29.928 | 1.00 | 40.47 | A |
| ATOM | 589 | O | LYS A | 83 | 15.774 | 69.300 | 30.885 | 1.00 | 40.47 | A |
| ATOM | 590 | N | GLU A | 84 | 14.791 | 71.002 | 29.767 | 1.00 | 100.07 | A |
| ATOM | 591 | CA | GLU A | 84 | 13.698 | 71.163 | 30.719 | 1.00 | 100.07 | A |
| ATOM | 592 | CB | GLU A | 84 | 13.113 | 72.561 | 30.617 | 1.00 | 99.88 | A |
| ATOM | 593 | CG | GLU A | 84 | 13.981 | 73.587 | 31.279 | 1.00 | 99.88 | A |
| ATOM | 594 | CD | GLU A | 84 | 13.730 | 74.954 | 30.735 | 1.00 | 99.88 | A |
| ATOM | 595 | OE1 | GLU A | 84 | 12.552 | 75.369 | 30.714 | 1.00 | 99.88 | A |
| ATOM | 596 | OE2 | GLU A | 84 | 14.710 | 75.609 | 30.326 | 1.00 | 99.88 | A |
| ATOM | 597 | C | GLU A | 84 | 12.599 | 70.134 | 30.557 | 1.00 | 100.07 | A |
| ATOM | 598 | O | GLU A | 84 | 12.089 | 69.613 | 31.550 | 1.00 | 100.07 | A |
| ATOM | 599 | N | LEU A | 85 | 12.229 | 69.856 | 29.311 | 1.00 | 31.70 | A |
| ATOM | 600 | CA | LEU A | 85 | 11.204 | 68.863 | 29.023 | 1.00 | 31.70 | A |
| ATOM | 601 | CB | LEU A | 85 | 11.528 | 68.157 | 27.705 | 1.00 | 36.11 | A |
| ATOM | 602 | CG | LEU A | 85 | 10.661 | 66.947 | 27.364 | 1.00 | 36.11 | A |
| ATOM | 603 | CD1 | LEU A | 85 | 9.209 | 67.333 | 27.506 | 1.00 | 36.11 | A |
| ATOM | 604 | CD2 | LEU A | 85 | 10.950 | 66.480 | 25.947 | 1.00 | 36.11 | A |
| ATOM | 605 | C | LEU A | 85 | 11.097 | 67.819 | 30.138 | 1.00 | 31.70 | A |
| ATOM | 606 | O | LEU A | 85 | 12.002 | 67.003 | 30.332 | 1.00 | 31.70 | A |
| ATOM | 607 | N | VAL A | 86 | 9.988 | 67.867 | 30.872 | 1.00 | 64.02 | A |
| ATOM | 608 | CA | VAL A | 86 | 9.746 | 66.938 | 31.967 | 1.00 | 64.02 | A |
| ATOM | 609 | CB | VAL A | 86 | 9.075 | 67.640 | 33.155 | 1.00 | 43.35 | A |
| ATOM | 610 | CG1 | VAL A | 86 | 7.761 | 68.241 | 32.738 | 1.00 | 43.35 | A |
| ATOM | 611 | CG2 | VAL A | 86 | 8.865 | 66.662 | 34.267 | 1.00 | 43.35 | A |
| ATOM | 612 | C | VAL A | 86 | 8.889 | 65.760 | 31.528 | 1.00 | 64.02 | A |
| ATOM | 613 | O | VAL A | 86 | 7.912 | 65.945 | 30.798 | 1.00 | 64.02 | A |
| ATOM | 614 | N | VAL A | 87 | 9.247 | 64.551 | 31.969 | 1.00 | 31.91 | A |
| ATOM | 615 | CA | VAL A | 87 | 8.491 | 63.355 | 31.584 | 1.00 | 31.91 | A |
| ATOM | 616 | CB | VAL A | 87 | 9.341 | 62.361 | 30.760 | 1.00 | 48.32 | A |
| ATOM | 617 | CG1 | VAL A | 87 | 9.363 | 62.762 | 29.307 | 1.00 | 48.32 | A |
| ATOM | 618 | CG2 | VAL A | 87 | 10.751 | 62.321 | 31.304 | 1.00 | 48.32 | A |
| ATOM | 619 | C | VAL A | 87 | 7.925 | 62.575 | 32.752 | 1.00 | 31.91 | A |
| ATOM | 620 | O | VAL A | 87 | 8.558 | 62.430 | 33.784 | 1.00 | 31.91 | A |
| ATOM | 621 | N | ARG A | 88 | 6.707 | 62.091 | 32.569 | 1.00 | 62.79 | A |
| ATOM | 622 | CA | ARG A | 88 | 6.028 | 61.273 | 33.557 | 1.00 | 62.79 | A |
| ATOM | 623 | CB | ARG A | 88 | 4.565 | 61.715 | 33.684 | 1.00 | 68.82 | A |
| ATOM | 624 | CG | ARG A | 88 | 3.661 | 60.775 | 34.489 | 1.00 | 68.82 | A |
| ATOM | 625 | CD | ARG A | 88 | 2.337 | 61.461 | 34.886 | 1.00 | 68.82 | A |
| ATOM | 626 | NE | ARG A | 88 | 1.402 | 60.584 | 35.594 | 1.00 | 68.82 | A |
| ATOM | 627 | CZ | ARG A | 88 | 1.705 | 59.860 | 36.671 | 1.00 | 68.82 | A |
| ATOM | 628 | NH1 | ARG A | 88 | 0.785 | 59.099 | 37.239 | 1.00 | 68.82 | A |
| ATOM | 629 | NH2 | ARG A | 88 | 2.928 | 59.880 | 37.184 | 1.00 | 68.82 | A |
| ATOM | 630 | C | ARG A | 88 | 6.131 | 59.906 | 32.892 | 1.00 | 62.79 | A |
| ATOM | 631 | O | ARG A | 88 | 5.583 | 59.699 | 31.811 | 1.00 | 62.79 | A |
| ATOM | 632 | N | PHE A | 89 | 6.842 | 58.980 | 33.524 | 1.00 | 88.02 | A |
| ATOM | 633 | CA | PHE A | 89 | 7.055 | 57.662 | 32.938 | 1.00 | 88.02 | A |
| ATOM | 634 | CB | PHE A | 89 | 8.420 | 57.135 | 33.409 | 1.00 | 36.30 | A |

| | | | | | | | | | | |
|---|---|---|---|---|---|---|---|---|---|---|
| ATOM | 635 | CG | PHE | A | 89 | 9.547 | 57.385 | 32.429 | 1.00 36.30 | A |
| ATOM | 636 | CD1 | PHE | A | 89 | 9.441 | 58.369 | 31.444 | 1.00 36.30 | A |
| ATOM | 637 | CD2 | PHE | A | 89 | 10.717 | 56.620 | 32.483 | 1.00 36.30 | A |
| ATOM | 638 | CE1 | PHE | A | 89 | 10.493 | 58.578 | 30.514 | 1.00 36.30 | A |
| ATOM | 639 | CE2 | PHE | A | 89 | 11.769 | 56.822 | 31.562 | 1.00 36.30 | A |
| ATOM | 640 | CZ | PHE | A | 89 | 11.655 | 57.800 | 30.582 | 1.00 36.30 | A |
| ATOM | 641 | C | PHE | A | 89 | 5.986 | 56.568 | 33.069 | 1.00 88.02 | A |
| ATOM | 642 | O | PHE | A | 89 | 5.719 | 55.858 | 32.099 | 1.00 88.02 | A |
| ATOM | 643 | N | LEU | A | 90 | 5.375 | 56.428 | 34.240 | 1.00100.03 | A |
| ATOM | 644 | CA | LEU | A | 90 | 4.355 | 55.398 | 34.452 | 1.00100.03 | A |
| ATOM | 645 | CB | LEU | A | 90 | 3.385 | 55.335 | 33.268 | 1.00 43.38 | A |
| ATOM | 646 | CG | LEU | A | 90 | 2.587 | 56.623 | 33.037 | 1.00 43.38 | A |
| ATOM | 647 | CD1 | LEU | A | 90 | 1.514 | 56.436 | 31.972 | 1.00 43.38 | A |
| ATOM | 648 | CD2 | LEU | A | 90 | 1.932 | 57.016 | 34.341 | 1.00 43.38 | A |
| ATOM | 649 | C | LEU | A | 90 | 4.990 | 54.028 | 34.683 | 1.00100.03 | A |
| ATOM | 650 | O | LEU | A | 90 | 5.794 | 53.853 | 35.600 | 1.00100.03 | A |
| ATOM | 651 | N | ASP | A | 91 | 4.627 | 53.064 | 33.845 | 1.00 82.00 | A |
| ATOM | 652 | CA | ASP | A | 91 | 5.131 | 51.692 | 33.935 | 1.00 82.00 | A |
| ATOM | 653 | CB | ASP | A | 91 | 5.334 | 51.115 | 32.531 | 1.00100.07 | A |
| ATOM | 654 | CG | ASP | A | 91 | 6.270 | 51.954 | 31.685 | 1.00100.07 | A |
| ATOM | 655 | OD1 | ASP | A | 91 | 7.485 | 51.991 | 31.985 | 1.00100.07 | A |
| ATOM | 656 | OD2 | ASP | A | 91 | 5.783 | 52.582 | 30.717 | 1.00100.07 | A |
| ATOM | 657 | C | ASP | A | 91 | 6.391 | 51.442 | 34.752 | 1.00 82.00 | A |
| ATOM | 658 | O | ASP | A | 91 | 7.498 | 51.752 | 34.318 | 1.00 82.00 | A |
| ATOM | 659 | N | PRO | A | 92 | 6.230 | 50.878 | 35.958 | 1.00 75.04 | A |
| ATOM | 660 | CD | PRO | A | 92 | 4.953 | 50.554 | 36.616 | 1.00100.07 | A |
| ATOM | 661 | CA | PRO | A | 92 | 7.356 | 50.571 | 36.837 | 1.00 75.04 | A |
| ATOM | 662 | CB | PRO | A | 92 | 6.721 | 49.688 | 37.893 | 1.00100.07 | A |
| ATOM | 663 | CG | PRO | A | 92 | 5.374 | 50.328 | 38.051 | 1.00100.07 | A |
| ATOM | 664 | C | PRO | A | 92 | 8.396 | 49.840 | 36.007 | 1.00 75.04 | A |
| ATOM | 665 | O | PRO | A | 92 | 8.216 | 48.664 | 35.655 | 1.00 75.04 | A |
| ATOM | 666 | N | ARG | A | 93 | 9.457 | 50.578 | 35.680 | 1.00100.07 | A |
| ATOM | 667 | CA | ARG | A | 93 | 10.584 | 50.115 | 34.869 | 1.00100.07 | A |
| ATOM | 668 | CB | ARG | A | 93 | 10.444 | 48.626 | 34.537 | 1.00100.07 | A |
| ATOM | 669 | CG | ARG | A | 93 | 11.763 | 47.913 | 34.422 | 1.00100.07 | A |
| ATOM | 670 | CD | ARG | A | 93 | 12.626 | 48.210 | 35.641 | 1.00100.07 | A |
| ATOM | 671 | NE | ARG | A | 93 | 13.974 | 47.675 | 35.493 | 1.00100.07 | A |
| ATOM | 672 | CZ | ARG | A | 93 | 15.043 | 48.171 | 36.105 | 1.00100.07 | A |
| ATOM | 673 | NH1 | ARG | A | 93 | 14.919 | 49.220 | 36.909 | 1.00100.07 | A |
| ATOM | 674 | NH2 | ARG | A | 93 | 16.235 | 47.624 | 35.903 | 1.00100.07 | A |
| ATOM | 675 | C | ARG | A | 93 | 10.591 | 50.940 | 33.581 | 1.00100.07 | A |
| ATOM | 676 | O | ARG | A | 93 | 9.553 | 51.079 | 32.934 | 1.00100.07 | A |
| ATOM | 677 | N | TRP | A | 94 | 11.740 | 51.503 | 33.210 | 1.00 75.71 | A |
| ATOM | 678 | CA | TRP | A | 94 | 11.794 | 52.301 | 31.987 | 1.00 75.71 | A |
| ATOM | 679 | CB | TRP | A | 94 | 10.774 | 53.442 | 32.089 | 1.00 99.15 | A |
| ATOM | 680 | CG | TRP | A | 94 | 9.927 | 53.683 | 30.853 | 1.00 99.15 | A |
| ATOM | 681 | CD2 | TRP | A | 94 | 9.912 | 52.919 | 29.642 | 1.00 99.15 | A |
| ATOM | 682 | CE2 | TRP | A | 94 | 8.990 | 53.540 | 28.769 | 1.00 99.15 | A |
| ATOM | 683 | CE3 | TRP | A | 94 | 10.585 | 51.772 | 29.207 | 1.00 99.15 | A |
| ATOM | 684 | CD1 | TRP | A | 94 | 9.035 | 54.699 | 30.666 | 1.00 99.15 | A |
| ATOM | 685 | NE1 | TRP | A | 94 | 8.472 | 54.624 | 29.421 | 1.00 99.15 | A |
| ATOM | 686 | CZ2 | TRP | A | 94 | 8.726 | 53.055 | 27.485 | 1.00 99.15 | A |
| ATOM | 687 | CZ3 | TRP | A | 94 | 10.323 | 51.289 | 27.926 | 1.00 99.15 | A |
| ATOM | 688 | CH2 | TRP | A | 94 | 9.399 | 51.932 | 27.081 | 1.00 99.15 | A |
| ATOM | 689 | C | TRP | A | 94 | 13.181 | 52.860 | 31.622 | 1.00 75.71 | A |
| ATOM | 690 | O | TRP | A | 94 | 14.204 | 52.300 | 32.021 | 1.00 75.71 | A |
| ATOM | 691 | N | ARG | A | 95 | 13.168 | 53.951 | 30.846 | 1.00 54.02 | A |
| ATOM | 692 | CA | ARG | A | 95 | 14.330 | 54.700 | 30.336 | 1.00 54.02 | A |
| ATOM | 693 | CB | ARG | A | 95 | 15.670 | 54.103 | 30.811 | 1.00100.06 | A |
| ATOM | 694 | CG | ARG | A | 95 | 15.943 | 54.246 | 32.325 | 1.00100.06 | A |
| ATOM | 695 | CD | ARG | A | 95 | 17.394 | 53.909 | 32.698 | 1.00100.06 | A |
| ATOM | 696 | NE | ARG | A | 95 | 17.546 | 53.545 | 34.111 | 1.00100.06 | A |
| ATOM | 697 | CZ | ARG | A | 95 | 18.714 | 53.439 | 34.748 | 1.00100.06 | A |
| ATOM | 698 | NH1 | ARG | A | 95 | 19.855 | 53.674 | 34.114 | 1.00100.06 | A |
| ATOM | 699 | NH2 | ARG | A | 95 | 18.745 | 53.077 | 36.025 | 1.00100.06 | A |
| ATOM | 700 | C | ARG | A | 95 | 14.278 | 54.722 | 28.811 | 1.00 54.02 | A |
| ATOM | 701 | O | ARG | A | 95 | 15.299 | 54.555 | 28.157 | 1.00 54.02 | A |
| ATOM | 702 | N | THR | A | 96 | 13.080 | 54.976 | 28.270 | 1.00 42.25 | A |
| ATOM | 703 | CA | THR | A | 96 | 12.785 | 54.978 | 26.817 | 1.00 42.25 | A |
| ATOM | 704 | CB | THR | A | 96 | 11.251 | 54.979 | 26.574 | 1.00 64.26 | A |
| ATOM | 705 | OG1 | THR | A | 96 | 10.987 | 54.595 | 25.221 | 1.00 64.26 | A |
| ATOM | 706 | CG2 | THR | A | 96 | 10.659 | 56.357 | 26.820 | 1.00 64.26 | A |
| ATOM | 707 | C | THR | A | 96 | 13.397 | 56.022 | 25.870 | 1.00 42.25 | A |
| ATOM | 708 | O | THR | A | 96 | 14.484 | 56.530 | 26.109 | 1.00 42.25 | A |
| ATOM | 709 | N | THR | A | 97 | 12.691 | 56.311 | 24.780 | 1.00 37.72 | A |
| ATOM | 710 | CA | THR | A | 97 | 13.146 | 57.277 | 23.781 | 1.00 37.72 | A |
| ATOM | 711 | CB | THR | A | 97 | 13.999 | 56.625 | 22.731 | 1.00 16.48 | A |
| ATOM | 712 | OG1 | THR | A | 97 | 15.101 | 55.984 | 23.369 | 1.00 16.48 | A |
| ATOM | 713 | CG2 | THR | A | 97 | 14.492 | 57.667 | 21.735 | 1.00 16.48 | A |
| ATOM | 714 | C | THR | A | 97 | 12.004 | 57.939 | 23.029 | 1.00 37.72 | A |
| ATOM | 715 | O | THR | A | 97 | 10.949 | 57.347 | 22.842 | 1.00 37.72 | A |
| ATOM | 716 | N | LEU | A | 98 | 12.218 | 59.158 | 22.562 | 1.00 50.75 | A |
| ATOM | 717 | CA | LEU | A | 98 | 11.151 | 59.825 | 21.859 | 1.00 50.75 | A |
| ATOM | 718 | CB | LEU | A | 98 | 10.672 | 61.041 | 22.648 | 1.00 14.35 | A |

```
ATOM    719  CG  LEU A  98      10.225  60.667  24.070  1.00 14.35           A
ATOM    720  CD1 LEU A  98       9.781  61.881  24.863  1.00 14.35           A
ATOM    721  CD2 LEU A  98       9.095  59.657  23.960  1.00 14.35           A
ATOM    722  C   LEU A  98      11.518  60.220  20.451  1.00 50.75           A
ATOM    723  O   LEU A  98      12.700  60.311  20.095  1.00 50.75           A
ATOM    724  N   ILE A  99      10.475  60.437  19.654  1.00 47.11           A
ATOM    725  CA  ILE A  99      10.587  60.809  18.262  1.00 47.11           A
ATOM    726  CB  ILE A  99       9.811  59.852  17.384  1.00 41.20           A
ATOM    727  CG2 ILE A  99       9.582  60.479  16.034  1.00 41.20           A
ATOM    728  CG1 ILE A  99      10.541  58.514  17.290  1.00 41.20           A
ATOM    729  CD  ILE A  99      11.838  58.567  16.494  1.00 41.20           A
ATOM    730  C   ILE A  99       9.962  62.158  18.094  1.00 47.11           A
ATOM    731  O   ILE A  99       9.129  62.560  18.888  1.00 47.11           A
ATOM    732  N   LEU A 100      10.362  62.855  17.047  1.00 24.91           A
ATOM    733  CA  LEU A 100       9.826  64.172  16.751  1.00 24.91           A
ATOM    734  CB  LEU A 100      10.314  65.222  17.746  1.00 89.32           A
ATOM    735  CG  LEU A 100      10.260  66.662  17.209  1.00 89.32           A
ATOM    736  CD1 LEU A 100       8.948  66.937  16.494  1.00 89.32           A
ATOM    737  CD2 LEU A 100      10.458  67.625  18.347  1.00 89.32           A
ATOM    738  C   LEU A 100      10.312  64.540  15.389  1.00 24.91           A
ATOM    739  O   LEU A 100      11.282  65.277  15.254  1.00 24.91           A
ATOM    740  N   ARG A 101       9.637  64.010  14.380  1.00 83.85           A
ATOM    741  CA  ARG A 101      10.007  64.266  13.002  1.00 83.85           A
ATOM    742  CB  ARG A 101       9.584  63.072  12.126  1.00100.07           A
ATOM    743  CG  ARG A 101      10.640  62.603  11.118  1.00100.07           A
ATOM    744  CD  ARG A 101      10.512  61.104  10.804  1.00100.07           A
ATOM    745  NE  ARG A 101      11.748  60.552  10.237  1.00100.07           A
ATOM    746  CZ  ARG A 101      11.980  59.255  10.026  1.00100.07           A
ATOM    747  NH1 ARG A 101      11.055  58.354  10.334  1.00100.07           A
ATOM    748  NH2 ARG A 101      13.143  58.854   9.515  1.00100.07           A
ATOM    749  C   ARG A 101       9.348  65.555  12.520  1.00 83.85           A
ATOM    750  O   ARG A 101       9.977  66.373  11.845  1.00 83.85           A
ATOM    751  N   ALA A 102       8.088  65.733  12.908  1.00 35.68           A
ATOM    752  CA  ALA A 102       7.281  66.885  12.516  1.00 35.68           A
ATOM    753  CB  ALA A 102       6.218  67.171  13.578  1.00 52.49           A
ATOM    754  C   ALA A 102       8.099  68.130  12.234  1.00 35.68           A
ATOM    755  O   ALA A 102       8.750  68.679  13.124  1.00 35.68           A
ATOM    756  N   ALA A 103       8.047  68.566  10.980  1.00 42.28           A
ATOM    757  CA  ALA A 103       8.787  69.731  10.539  1.00 42.28           A
ATOM    758  CB  ALA A 103       9.994  69.286   9.739  1.00100.07           A
ATOM    759  C   ALA A 103       7.947  70.713   9.735  1.00 42.28           A
ATOM    760  O   ALA A 103       8.442  71.411   8.847  1.00 42.28           A
ATOM    761  N   GLY A 104       6.662  70.769  10.046  1.00100.07           A
ATOM    762  CA  GLY A 104       5.816  71.702   9.338  1.00100.07           A
ATOM    763  C   GLY A 104       6.221  73.106   9.744  1.00100.07           A
ATOM    764  O   GLY A 104       6.073  73.475  10.913  1.00100.07           A
ATOM    765  N   PRO A 105       6.764  73.904   8.811  1.00 83.24           A
ATOM    766  CD  PRO A 105       7.061  73.545   7.412  1.00 87.70           A
ATOM    767  CA  PRO A 105       7.183  75.276   9.088  1.00 83.24           A
ATOM    768  CB  PRO A 105       7.210  75.887   7.701  1.00 87.70           A
ATOM    769  CG  PRO A 105       7.817  74.760   6.914  1.00 87.70           A
ATOM    770  C   PRO A 105       6.241  76.006  10.048  1.00 83.24           A
ATOM    771  O   PRO A 105       5.326  76.710   9.617  1.00 83.24           A
ATOM    772  N   LYS A 106       6.479  75.815  11.346  1.00 72.93           A
ATOM    773  CA  LYS A 106       5.689  76.430  12.411  1.00 72.93           A
ATOM    774  CB  LYS A 106       4.307  75.787  12.495  1.00 99.49           A
ATOM    775  CG  LYS A 106       4.326  74.377  13.040  1.00 99.49           A
ATOM    776  CD  LYS A 106       2.920  73.858  13.249  1.00 99.49           A
ATOM    777  CE  LYS A 106       2.936  72.521  13.974  1.00 99.49           A
ATOM    778  NZ  LYS A 106       1.564  72.035  14.306  1.00 99.49           A
ATOM    779  C   LYS A 106       6.410  76.237  13.746  1.00 72.93           A
ATOM    780  O   LYS A 106       7.586  75.869  13.776  1.00 72.93           A
ATOM    781  N   GLU A 107       5.700  76.477  14.845  1.00 85.68           A
ATOM    782  CA  GLU A 107       6.272  76.332  16.185  1.00 85.68           A
ATOM    783  CB  GLU A 107       5.506  77.187  17.190  1.00 99.92           A
ATOM    784  CG  GLU A 107       5.735  78.668  17.095  1.00 99.92           A
ATOM    785  CD  GLU A 107       5.712  79.314  18.467  1.00 99.92           A
ATOM    786  OE1 GLU A 107       4.768  79.039  19.242  1.00 99.92           A
ATOM    787  OE2 GLU A 107       6.640  80.092  18.772  1.00 99.92           A
ATOM    788  C   GLU A 107       6.265  74.896  16.710  1.00 85.68           A
ATOM    789  O   GLU A 107       5.197  74.339  16.978  1.00 85.68           A
ATOM    790  N   VAL A 108       7.443  74.300  16.875  1.00 77.04           A
ATOM    791  CA  VAL A 108       7.505  72.942  17.405  1.00 77.04           A
ATOM    792  CB  VAL A 108       8.715  72.136  16.849  1.00 16.82           A
ATOM    793  CG1 VAL A 108       8.635  70.668  17.318  1.00 16.82           A
ATOM    794  CG2 VAL A 108       8.742  72.207  15.321  1.00 16.82           A
ATOM    795  C   VAL A 108       7.624  73.011  18.926  1.00 77.04           A
ATOM    796  O   VAL A 108       8.637  73.456  19.464  1.00 77.04           A
ATOM    797  N   ARG A 109       6.567  72.584  19.606  1.00 23.54           A
ATOM    798  CA  ARG A 109       6.496  72.558  21.066  1.00 23.54           A
ATOM    799  CB  ARG A 109       5.194  73.211  21.505  1.00100.07           A
ATOM    800  CG  ARG A 109       4.015  72.742  20.673  1.00100.07           A
ATOM    801  CD  ARG A 109       2.715  73.404  21.074  1.00100.07           A
ATOM    802  NE  ARG A 109       1.634  73.012  20.178  1.00100.07           A
```

```
ATOM    803  CZ   ARG A 109       0.382  73.423  20.306  1.00100.07           A
ATOM    804  NH1  ARG A 109       0.053  74.238  21.298  1.00100.07           A
ATOM    805  NH2  ARG A 109      -0.536  73.027  19.438  1.00100.07           A
ATOM    806  C    ARG A 109       6.520  71.091  21.492  1.00 23.54           A
ATOM    807  O    ARG A 109       6.398  70.210  20.648  1.00 23.54           A
ATOM    808  N    ALA A 110       6.655  70.823  22.786  1.00 50.26           A
ATOM    809  CA   ALA A 110       6.725  69.446  23.295  1.00 50.26           A
ATOM    810  CB   ALA A 110       6.742  69.455  24.823  1.00 70.58           A
ATOM    811  C    ALA A 110       5.652  68.478  22.808  1.00 50.26           A
ATOM    812  O    ALA A 110       5.957  67.321  22.510  1.00 50.26           A
ATOM    813  N    VAL A 111       4.405  68.936  22.748  1.00 98.69           A
ATOM    814  CA   VAL A 111       3.293  68.098  22.300  1.00 98.69           A
ATOM    815  CB   VAL A 111       2.064  68.967  21.939  1.00100.07           A
ATOM    816  CG1  VAL A 111       0.896  68.091  21.485  1.00100.07           A
ATOM    817  CG2  VAL A 111       1.663  69.801  23.140  1.00100.07           A
ATOM    818  C    VAL A 111       3.692  67.281  21.082  1.00 98.69           A
ATOM    819  O    VAL A 111       3.751  66.051  21.139  1.00 98.69           A
ATOM    820  N    ASP A 112       3.974  67.989  19.991  1.00 65.07           A
ATOM    821  CA   ASP A 112       4.371  67.396  18.720  1.00 65.07           A
ATOM    822  CB   ASP A 112       5.018  68.476  17.865  1.00 99.77           A
ATOM    823  CG   ASP A 112       4.079  69.630  17.595  1.00 99.77           A
ATOM    824  OD1  ASP A 112       3.135  69.448  16.801  1.00 99.77           A
ATOM    825  OD2  ASP A 112       4.271  70.713  18.185  1.00 99.77           A
ATOM    826  C    ASP A 112       5.308  66.207  18.869  1.00 65.07           A
ATOM    827  O    ASP A 112       5.536  65.458  17.926  1.00 65.07           A
ATOM    828  N    PHE A 113       5.860  66.035  20.058  1.00 61.73           A
ATOM    829  CA   PHE A 113       6.746  64.921  20.301  1.00 61.73           A
ATOM    830  CB   PHE A 113       7.319  65.006  21.705  1.00 56.73           A
ATOM    831  CG   PHE A 113       8.798  65.124  21.730  1.00 56.73           A
ATOM    832  CD1  PHE A 113       9.407  66.335  21.469  1.00 56.73           A
ATOM    833  CD2  PHE A 113       9.588  64.012  21.984  1.00 56.73           A
ATOM    834  CE1  PHE A 113      10.789  66.442  21.461  1.00 56.73           A
ATOM    835  CE2  PHE A 113      10.962  64.108  21.977  1.00 56.73           A
ATOM    836  CZ   PHE A 113      11.567  65.327  21.715  1.00 56.73           A
ATOM    837  C    PHE A 113       5.964  63.630  20.159  1.00 61.73           A
ATOM    838  O    PHE A 113       5.220  63.259  21.071  1.00 61.73           A
ATOM    839  N    THR A 114       6.143  62.953  19.023  1.00 51.46           A
ATOM    840  CA   THR A 114       5.463  61.689  18.735  1.00 51.46           A
ATOM    841  CB   THR A 114       6.451  60.574  18.353  1.00 52.59           A
ATOM    842  OG1  THR A 114       5.754  59.322  18.281  1.00 52.59           A
ATOM    843  CG2  THR A 114       7.530  60.453  19.391  1.00 52.59           A
ATOM    844  C    THR A 114       4.627  61.158  19.886  1.00 51.46           A
ATOM    845  O    THR A 114       5.152  60.816  20.957  1.00 51.46           A
ATOM    846  N    PRO A 115       3.302  61.095  19.688  1.00 41.98           A
ATOM    847  CD   PRO A 115       2.489  61.486  18.519  1.00 51.61           A
ATOM    848  CA   PRO A 115       2.468  60.581  20.775  1.00 41.98           A
ATOM    849  CB   PRO A 115       1.097  60.452  20.117  1.00 51.61           A
ATOM    850  CG   PRO A 115       1.103  61.597  19.113  1.00 51.61           A
ATOM    851  C    PRO A 115       3.082  59.234  21.150  1.00 41.98           A
ATOM    852  O    PRO A 115       3.723  58.579  20.320  1.00 41.98           A
ATOM    853  N    SER A 116       2.920  58.833  22.399  1.00 71.44           A
ATOM    854  CA   SER A 116       3.477  57.568  22.825  1.00 71.44           A
ATOM    855  CB   SER A 116       4.994  57.593  22.699  1.00 81.81           A
ATOM    856  OG   SER A 116       5.547  56.438  23.297  1.00 81.81           A
ATOM    857  C    SER A 116       3.101  57.329  24.263  1.00 71.44           A
ATOM    858  O    SER A 116       3.800  57.796  25.167  1.00 71.44           A
ATOM    859  N    ALA A 117       1.999  56.605  24.469  1.00100.07           A
ATOM    860  CA   ALA A 117       1.496  56.304  25.813  1.00100.07           A
ATOM    861  CB   ALA A 117       0.308  55.325  25.741  1.00 89.40           A
ATOM    862  C    ALA A 117       2.600  55.731  26.696  1.00100.07           A
ATOM    863  O    ALA A 117       3.788  55.878  26.391  1.00100.07           A
ATOM    864  N    ASP A 118       2.211  55.071  27.785  1.00 68.67           A
ATOM    865  CA   ASP A 118       3.183  54.496  28.708  1.00 68.67           A
ATOM    866  CB   ASP A 118       3.846  53.268  28.082  1.00 77.30           A
ATOM    867  CG   ASP A 118       4.291  53.511  26.643  1.00 77.30           A
ATOM    868  OD1  ASP A 118       3.434  53.509  25.733  1.00 77.30           A
ATOM    869  OD2  ASP A 118       5.496  53.729  26.415  1.00 77.30           A
ATOM    870  C    ASP A 118       4.243  55.545  29.034  1.00 68.67           A
ATOM    871  O    ASP A 118       5.300  55.229  29.582  1.00 68.67           A
ATOM    872  N    VAL A 119       3.928  56.797  28.697  1.00 84.27           A
ATOM    873  CA   VAL A 119       4.804  57.948  28.899  1.00 84.27           A
ATOM    874  CB   VAL A 119       5.951  57.944  27.867  1.00 70.32           A
ATOM    875  CG1  VAL A 119       6.553  59.328  27.744  1.00 70.32           A
ATOM    876  CG2  VAL A 119       7.019  56.947  28.282  1.00 70.32           A
ATOM    877  C    VAL A 119       4.008  59.247  28.718  1.00 84.27           A
ATOM    878  O    VAL A 119       3.488  59.510  27.635  1.00 84.27           A
ATOM    879  N    GLU A 120       3.919  60.055  29.774  1.00 94.10           A
ATOM    880  CA   GLU A 120       3.197  61.329  29.717  1.00 94.10           A
ATOM    881  CB   GLU A 120       2.408  61.574  31.007  1.00100.07           A
ATOM    882  CG   GLU A 120       1.097  60.818  31.143  1.00100.07           A
ATOM    883  CD   GLU A 120       0.374  61.162  32.439  1.00100.07           A
ATOM    884  OE1  GLU A 120       0.063  62.356  32.654  1.00100.07           A
ATOM    885  OE2  GLU A 120       0.123  60.238  33.243  1.00100.07           A
ATOM    886  C    GLU A 120       4.138  62.512  29.518  1.00 94.10           A
```

```
ATOM    887  O   GLU A 120       5.307  62.459  29.901  1.00 94.10           A
ATOM    888  N   ILE A 121       3.618  63.586  28.932  1.00 65.61           A
ATOM    889  CA  ILE A 121       4.414  64.785  28.706  1.00 65.61           A
ATOM    890  CB  ILE A 121       4.379  65.212  27.231  1.00 99.99           A
ATOM    891  CG2 ILE A 121       5.350  66.360  26.993  1.00 99.99           A
ATOM    892  CG1 ILE A 121       4.740  64.019  26.349  1.00 99.99           A
ATOM    893  CD  ILE A 121       5.999  63.297  26.775  1.00 99.99           A
ATOM    894  C   ILE A 121       3.890  65.924  29.573  1.00 65.61           A
ATOM    895  O   ILE A 121       3.383  66.932  29.074  1.00 65.61           A
ATOM    896  N   MET A 122       4.022  65.738  30.881  1.00 73.05           A
ATOM    897  CA  MET A 122       3.583  66.696  31.883  1.00 73.05           A
ATOM    898  CB  MET A 122       4.516  66.614  33.095  1.00100.07           A
ATOM    899  CG  MET A 122       3.825  66.738  34.449  1.00100.07           A
ATOM    900  SD  MET A 122       3.484  65.141  35.256  1.00100.07           A
ATOM    901  CE  MET A 122       2.173  64.515  34.188  1.00100.07           A
ATOM    902  C   MET A 122       3.520  68.138  31.385  1.00 73.05           A
ATOM    903  O   MET A 122       2.609  68.887  31.745  1.00 73.05           A
ATOM    904  N   ASN A 123       4.484  68.531  30.558  1.00 98.98           A
ATOM    905  CA  ASN A 123       4.509  69.896  30.054  1.00 98.98           A
ATOM    906  CB  ASN A 123       5.772  70.619  30.526  1.00 99.41           A
ATOM    907  CG  ASN A 123       7.021  70.152  29.800  1.00 99.41           A
ATOM    908  OD1 ASN A 123       7.420  68.994  29.902  1.00 99.41           A
ATOM    909  ND2 ASN A 123       7.639  71.056  29.055  1.00 99.41           A
ATOM    910  C   ASN A 123       4.437  69.985  28.543  1.00 98.98           A
ATOM    911  O   ASN A 123       5.416  69.724  27.849  1.00 98.98           A
ATOM    912  N   PRO A 124       3.265  70.337  28.005  1.00 50.62           A
ATOM    913  CD  PRO A 124       2.027  70.802  28.648  1.00100.07           A
ATOM    914  CA  PRO A 124       3.169  70.452  26.551  1.00 50.62           A
ATOM    915  CB  PRO A 124       1.679  70.610  26.327  1.00100.07           A
ATOM    916  CG  PRO A 124       1.289  71.460  27.488  1.00100.07           A
ATOM    917  C   PRO A 124       3.921  71.758  26.316  1.00 50.62           A
ATOM    918  O   PRO A 124       4.892  72.051  27.024  1.00 50.62           A
ATOM    919  N   ASP A 125       3.473  72.561  25.362  1.00100.07           A
ATOM    920  CA  ASP A 125       4.131  73.839  25.117  1.00100.07           A
ATOM    921  CB  ASP A 125       3.710  74.842  26.199  1.00 71.33           A
ATOM    922  CG  ASP A 125       2.506  74.361  27.017  1.00 71.33           A
ATOM    923  OD1 ASP A 125       1.415  74.196  26.440  1.00 71.33           A
ATOM    924  OD2 ASP A 125       2.648  74.143  28.241  1.00 71.33           A
ATOM    925  C   ASP A 125       5.666  73.702  25.089  1.00100.07           A
ATOM    926  O   ASP A 125       6.229  73.191  24.122  1.00100.07           A
ATOM    927  N   LEU A 126       6.333  74.162  26.146  1.00 27.66           A
ATOM    928  CA  LEU A 126       7.789  74.085  26.264  1.00 27.66           A
ATOM    929  CB  LEU A 126       8.174  72.657  26.651  1.00 48.42           A
ATOM    930  CG  LEU A 126       9.651  72.263  26.779  1.00 48.42           A
ATOM    931  CD1 LEU A 126      10.257  72.842  28.048  1.00 48.42           A
ATOM    932  CD2 LEU A 126       9.759  70.747  26.804  1.00 48.42           A
ATOM    933  C   LEU A 126       8.538  74.486  24.989  1.00 27.66           A
ATOM    934  O   LEU A 126       9.587  73.915  24.698  1.00 27.66           A
ATOM    935  N   HIS A 127       8.018  75.469  24.249  1.00 55.30           A
ATOM    936  CA  HIS A 127       8.623  75.917  22.982  1.00 55.30           A
ATOM    937  CB  HIS A 127       8.847  77.433  22.963  1.00 78.31           A
ATOM    938  CG  HIS A 127       9.335  77.957  21.640  1.00 78.31           A
ATOM    939  CD2 HIS A 127       8.997  79.067  20.940  1.00 78.31           A
ATOM    940  ND1 HIS A 127      10.305  77.318  20.894  1.00 78.31           A
ATOM    941  CE1 HIS A 127      10.541  78.011  19.794  1.00 78.31           A
ATOM    942  NE2 HIS A 127       9.761  79.077  19.797  1.00 78.31           A
ATOM    943  C   HIS A 127       9.945  75.246  22.645  1.00 55.30           A
ATOM    944  O   HIS A 127      11.003  75.862  22.756  1.00 55.30           A
ATOM    945  N   ILE A 128       9.900  73.992  22.224  1.00 32.89           A
ATOM    946  CA  ILE A 128      11.143  73.328  21.912  1.00 32.89           A
ATOM    947  CB  ILE A 128      10.933  71.841  21.579  1.00 28.75           A
ATOM    948  CG2 ILE A 128      11.983  71.355  20.562  1.00 28.75           A
ATOM    949  CG1 ILE A 128      10.986  71.030  22.871  1.00 28.75           A
ATOM    950  CD  ILE A 128      11.375  69.573  22.673  1.00 28.75           A
ATOM    951  C   ILE A 128      11.870  73.994  20.762  1.00 32.89           A
ATOM    952  O   ILE A 128      13.098  74.063  20.783  1.00 32.89           A
ATOM    953  N   ALA A 129      11.150  74.484  19.755  1.00 35.51           A
ATOM    954  CA  ALA A 129      11.844  75.135  18.640  1.00 35.51           A
ATOM    955  CB  ALA A 129      12.968  74.222  18.105  1.00 64.61           A
ATOM    956  C   ALA A 129      11.002  75.620  17.468  1.00 35.51           A
ATOM    957  O   ALA A 129      10.142  74.912  16.941  1.00 35.51           A
ATOM    958  N   THR A 130      11.284  76.847  17.062  1.00 56.00           A
ATOM    959  CA  THR A 130      10.614  77.454  15.938  1.00 56.00           A
ATOM    960  CB  THR A 130      10.783  78.977  15.963  1.00 97.43           A
ATOM    961  OG1 THR A 130      10.089  79.515  17.095  1.00 97.43           A
ATOM    962  CG2 THR A 130      10.263  79.600  14.668  1.00 97.43           A
ATOM    963  C   THR A 130      11.324  76.926  14.716  1.00 56.00           A
ATOM    964  O   THR A 130      12.433  76.425  14.819  1.00 56.00           A
ATOM    965  N   LEU A 131      10.678  77.017  13.566  1.00 96.96           A
ATOM    966  CA  LEU A 131      11.262  76.591  12.303  1.00 96.96           A
ATOM    967  CB  LEU A 131      11.596  75.069  12.278  1.00 14.70           A
ATOM    968  CG  LEU A 131      10.673  73.901  12.679  1.00 14.70           A
ATOM    969  CD1 LEU A 131       9.538  73.750  11.686  1.00 14.70           A
ATOM    970  CD2 LEU A 131      11.487  72.612  12.725  1.00 14.70           A
```

| ATOM | 971 | C | LEU A 131 | 10.225 | 76.982 | 11.276 | 1.00 96.96 | A |
|------|------|-----|-----------|--------|--------|--------|------------|---|
| ATOM | 972 | O | LEU A 131 | 9.037 | 77.057 | 11.586 | 1.00 96.96 | A |
| ATOM | 973 | N | GLU A 132 | 10.676 | 77.294 | 10.071 | 1.00 33.61 | A |
| ATOM | 974 | CA | GLU A 132 | 9.758 | 77.690 | 9.030 | 1.00 33.61 | A |
| ATOM | 975 | CB | GLU A 132 | 9.275 | 79.126 | 9.262 | 1.00100.07 | A |
| ATOM | 976 | CG | GLU A 132 | 10.357 | 80.190 | 9.227 | 1.00100.07 | A |
| ATOM | 977 | CD | GLU A 132 | 9.840 | 81.549 | 9.680 | 1.00100.07 | A |
| ATOM | 978 | OE1 | GLU A 132 | 9.431 | 81.657 | 10.860 | 1.00100.07 | A |
| ATOM | 979 | OE2 | GLU A 132 | 9.838 | 82.502 | 8.863 | 1.00100.07 | A |
| ATOM | 980 | C | GLU A 132 | 10.375 | 77.546 | 7.658 | 1.00 33.61 | A |
| ATOM | 981 | O | GLU A 132 | 11.603 | 77.496 | 7.520 | 1.00 33.61 | A |
| ATOM | 982 | N | GLU A 133 | 9.488 | 77.448 | 6.667 | 1.00 83.31 | A |
| ATOM | 983 | CA | GLU A 133 | 9.816 | 77.309 | 5.253 | 1.00 83.31 | A |
| ATOM | 984 | CB | GLU A 133 | 10.514 | 78.582 | 4.768 | 1.00100.07 | A |
| ATOM | 985 | CG | GLU A 133 | 10.593 | 78.703 | 3.256 | 1.00100.07 | A |
| ATOM | 986 | CD | GLU A 133 | 11.146 | 80.045 | 2.793 | 1.00100.07 | A |
| ATOM | 987 | OE1 | GLU A 133 | 10.642 | 81.092 | 3.266 | 1.00100.07 | A |
| ATOM | 988 | OE2 | GLU A 133 | 12.072 | 80.049 | 1.946 | 1.00100.07 | A |
| ATOM | 989 | C | GLU A 133 | 10.652 | 76.073 | 4.879 | 1.00 83.31 | A |
| ATOM | 990 | O | GLU A 133 | 10.635 | 75.630 | 3.728 | 1.00 83.31 | A |
| ATOM | 991 | N | GLY A 134 | 11.370 | 75.504 | 5.841 | 1.00 99.81 | A |
| ATOM | 992 | CA | GLY A 134 | 12.190 | 74.345 | 5.535 | 1.00 99.81 | A |
| ATOM | 993 | C | GLY A 134 | 12.147 | 73.242 | 6.571 | 1.00 99.81 | A |
| ATOM | 994 | O | GLY A 134 | 13.135 | 72.953 | 7.251 | 1.00 99.81 | A |
| ATOM | 995 | N | GLY A 135 | 10.986 | 72.615 | 6.678 | 1.00100.07 | A |
| ATOM | 996 | CA | GLY A 135 | 10.808 | 71.535 | 7.625 | 1.00100.07 | A |
| ATOM | 997 | C | GLY A 135 | 11.883 | 70.469 | 7.656 | 1.00100.07 | A |
| ATOM | 998 | O | GLY A 135 | 11.861 | 69.498 | 6.894 | 1.00100.07 | A |
| ATOM | 999 | N | LYS A 136 | 12.828 | 70.642 | 8.561 | 1.00 72.43 | A |
| ATOM | 1000 | CA | LYS A 136 | 13.899 | 69.685 | 8.702 | 1.00 72.43 | A |
| ATOM | 1001 | CB | LYS A 136 | 15.189 | 70.282 | 8.133 | 1.00100.07 | A |
| ATOM | 1002 | CG | LYS A 136 | 16.330 | 69.291 | 7.911 | 1.00100.07 | A |
| ATOM | 1003 | CD | LYS A 136 | 16.063 | 68.365 | 6.724 | 1.00100.07 | A |
| ATOM | 1004 | CE | LYS A 136 | 17.254 | 67.452 | 6.455 | 1.00100.07 | A |
| ATOM | 1005 | NZ | LYS A 136 | 16.977 | 66.466 | 5.374 | 1.00100.07 | A |
| ATOM | 1006 | C | LYS A 136 | 14.006 | 69.535 | 10.199 | 1.00 72.43 | A |
| ATOM | 1007 | O | LYS A 136 | 14.514 | 70.438 | 10.852 | 1.00 72.43 | A |
| ATOM | 1008 | N | LEU A 137 | 13.513 | 68.441 | 10.774 | 1.00 56.42 | A |
| ATOM | 1009 | CA | LEU A 137 | 13.650 | 68.333 | 12.220 | 1.00 56.42 | A |
| ATOM | 1010 | CB | LEU A 137 | 12.468 | 69.017 | 12.903 | 1.00 27.01 | A |
| ATOM | 1011 | CG | LEU A 137 | 12.654 | 69.167 | 14.421 | 1.00 27.01 | A |
| ATOM | 1012 | CD1 | LEU A 137 | 14.017 | 69.743 | 14.728 | 1.00 27.01 | A |
| ATOM | 1013 | CD2 | LEU A 137 | 11.548 | 70.047 | 14.998 | 1.00 27.01 | A |
| ATOM | 1014 | C | LEU A 137 | 13.904 | 66.971 | 12.866 | 1.00 56.42 | A |
| ATOM | 1015 | O | LEU A 137 | 14.781 | 66.865 | 13.726 | 1.00 56.42 | A |
| ATOM | 1016 | N | TYR A 138 | 13.160 | 65.942 | 12.463 | 1.00 42.82 | A |
| ATOM | 1017 | CA | TYR A 138 | 13.313 | 64.596 | 13.041 | 1.00 42.82 | A |
| ATOM | 1018 | CB | TYR A 138 | 13.670 | 63.566 | 11.961 | 1.00 53.06 | A |
| ATOM | 1019 | CG | TYR A 138 | 13.835 | 62.165 | 12.522 | 1.00 53.06 | A |
| ATOM | 1020 | CD1 | TYR A 138 | 12.800 | 61.560 | 13.238 | 1.00 53.06 | A |
| ATOM | 1021 | CE1 | TYR A 138 | 12.951 | 60.307 | 13.817 | 1.00 53.06 | A |
| ATOM | 1022 | CD2 | TYR A 138 | 15.034 | 61.467 | 12.390 | 1.00 53.06 | A |
| ATOM | 1023 | CE2 | TYR A 138 | 15.195 | 60.203 | 12.968 | 1.00 53.06 | A |
| ATOM | 1024 | CZ | TYR A 138 | 14.145 | 59.639 | 13.687 | 1.00 53.06 | A |
| ATOM | 1025 | OH | TYR A 138 | 14.297 | 58.439 | 14.329 | 1.00 53.06 | A |
| ATOM | 1026 | C | TYR A 138 | 14.350 | 64.479 | 14.164 | 1.00 42.82 | A |
| ATOM | 1027 | O | TYR A 138 | 15.546 | 64.369 | 13.897 | 1.00 42.82 | A |
| ATOM | 1028 | N | MET A 139 | 13.881 | 64.498 | 15.411 | 1.00 77.85 | A |
| ATOM | 1029 | CA | MET A 139 | 14.761 | 64.385 | 16.572 | 1.00 77.85 | A |
| ATOM | 1030 | CB | MET A 139 | 14.628 | 65.614 | 17.464 | 1.00100.07 | A |
| ATOM | 1031 | CG | MET A 139 | 14.947 | 66.909 | 16.760 | 1.00100.07 | A |
| ATOM | 1032 | SD | MET A 139 | 15.042 | 68.272 | 17.916 | 1.00100.07 | A |
| ATOM | 1033 | CE | MET A 139 | 13.373 | 68.931 | 17.827 | 1.00100.07 | A |
| ATOM | 1034 | C | MET A 139 | 14.455 | 63.137 | 17.395 | 1.00 77.85 | A |
| ATOM | 1035 | O | MET A 139 | 13.321 | 62.915 | 17.812 | 1.00 77.85 | A |
| ATOM | 1036 | N | GLU A 140 | 15.477 | 62.327 | 17.631 | 1.00 29.15 | A |
| ATOM | 1037 | CA | GLU A 140 | 15.324 | 61.100 | 18.387 | 1.00 29.15 | A |
| ATOM | 1038 | CB | GLU A 140 | 15.984 | 59.966 | 17.604 | 1.00 74.04 | A |
| ATOM | 1039 | CG | GLU A 140 | 15.658 | 58.564 | 18.069 | 1.00 74.04 | A |
| ATOM | 1040 | CD | GLU A 140 | 16.472 | 57.505 | 17.331 | 1.00 74.04 | A |
| ATOM | 1041 | OE1 | GLU A 140 | 17.696 | 57.415 | 17.574 | 1.00 74.04 | A |
| ATOM | 1042 | OE2 | GLU A 140 | 15.892 | 56.766 | 16.504 | 1.00 74.04 | A |
| ATOM | 1043 | C | GLU A 140 | 16.079 | 61.368 | 19.685 | 1.00 29.15 | A |
| ATOM | 1044 | O | GLU A 140 | 17.310 | 61.253 | 19.707 | 1.00 29.15 | A |
| ATOM | 1045 | N | VAL A 141 | 15.354 | 61.701 | 20.765 | 1.00 7.41 | A |
| ATOM | 1046 | CA | VAL A 141 | 15.979 | 62.060 | 22.059 | 1.00 7.41 | A |
| ATOM | 1047 | CB | VAL A 141 | 15.594 | 63.490 | 22.436 | 1.00 73.37 | A |
| ATOM | 1048 | CG1 | VAL A 141 | 14.110 | 63.667 | 22.270 | 1.00 73.37 | A |
| ATOM | 1049 | CG2 | VAL A 141 | 15.979 | 63.775 | 23.874 | 1.00 73.37 | A |
| ATOM | 1050 | C | VAL A 141 | 15.735 | 61.219 | 23.301 | 1.00 7.41 | A |
| ATOM | 1051 | O | VAL A 141 | 14.745 | 61.401 | 23.987 | 1.00 7.41 | A |
| ATOM | 1052 | N | ARG A 142 | 16.675 | 60.353 | 23.631 | 1.00 25.95 | A |
| ATOM | 1053 | CA | ARG A 142 | 16.529 | 59.479 | 24.789 | 1.00 25.95 | A |
| ATOM | 1054 | CB | ARG A 142 | 17.838 | 58.742 | 25.040 | 1.00 45.39 | A |

```
ATOM   1055  CG   ARG A 142      17.775  57.735  26.157  1.00 45.39           A
ATOM   1056  CD   ARG A 142      19.112  57.119  26.362  1.00 45.39           A
ATOM   1057  NE   ARG A 142      19.050  56.066  27.351  1.00 45.39           A
ATOM   1058  CZ   ARG A 142      20.061  55.753  28.146  1.00 45.39           A
ATOM   1059  NH1  ARG A 142      21.197  56.430  28.051  1.00 45.39           A
ATOM   1060  NH2  ARG A 142      19.939  54.768  29.030  1.00 45.39           A
ATOM   1061  C    ARG A 142      16.148  60.222  26.057  1.00 25.95           A
ATOM   1062  O    ARG A 142      16.176  61.443  26.086  1.00 25.95           A
ATOM   1063  N    VAL A 143      15.795  59.455  27.092  1.00100.07           A
ATOM   1064  CA   VAL A 143      15.426  59.953  28.421  1.00100.07           A
ATOM   1065  CB   VAL A 143      13.951  60.446  28.483  1.00100.07           A
ATOM   1066  CG1  VAL A 143      13.727  61.579  27.495  1.00100.07           A
ATOM   1067  CG2  VAL A 143      13.007  59.312  28.189  1.00100.07           A
ATOM   1068  C    VAL A 143      15.616  58.797  29.416  1.00100.07           A
ATOM   1069  O    VAL A 143      15.115  57.694  29.202  1.00100.07           A
ATOM   1070  N    ASP A 144      16.332  59.053  30.506  1.00 51.55           A
ATOM   1071  CA   ASP A 144      16.632  58.012  31.495  1.00 51.55           A
ATOM   1072  CB   ASP A 144      18.153  57.902  31.686  1.00 39.57           A
ATOM   1073  CG   ASP A 144      18.863  57.204  30.532  1.00 39.57           A
ATOM   1074  OD1  ASP A 144      18.664  57.585  29.353  1.00 39.57           A
ATOM   1075  OD2  ASP A 144      19.645  56.272  30.822  1.00 39.57           A
ATOM   1076  C    ASP A 144      16.017  58.180  32.881  1.00 51.55           A
ATOM   1077  O    ASP A 144      15.578  59.262  33.263  1.00 51.55           A
ATOM   1078  N    ARG A 145      16.003  57.093  33.644  1.00 64.20           A
ATOM   1079  CA   ARG A 145      15.492  57.149  35.001  1.00 64.20           A
ATOM   1080  CB   ARG A 145      15.285  55.736  35.561  1.00 99.82           A
ATOM   1081  CG   ARG A 145      14.184  55.627  36.619  1.00 99.82           A
ATOM   1082  CD   ARG A 145      12.803  55.635  35.970  1.00 99.82           A
ATOM   1083  NE   ARG A 145      11.743  56.001  36.906  1.00 99.82           A
ATOM   1084  CZ   ARG A 145      10.455  56.077  36.585  1.00 99.82           A
ATOM   1085  NH1  ARG A 145      10.059  55.806  35.351  1.00 99.82           A
ATOM   1086  NH2  ARG A 145       9.565  56.442  37.494  1.00 99.82           A
ATOM   1087  C    ARG A 145      16.642  57.841  35.721  1.00 64.20           A
ATOM   1088  O    ARG A 145      17.790  57.689  35.318  1.00 64.20           A
ATOM   1089  N    GLY A 146      16.368  58.608  36.766  1.00 85.65           A
ATOM   1090  CA   GLY A 146      17.482  59.259  37.424  1.00 85.65           A
ATOM   1091  C    GLY A 146      17.289  59.789  38.825  1.00 85.65           A
ATOM   1092  O    GLY A 146      16.175  59.926  39.330  1.00 85.65           A
ATOM   1093  N    VAL A 147      18.421  60.099  39.443  1.00 74.35           A
ATOM   1094  CA   VAL A 147      18.476  60.624  40.792  1.00 74.35           A
ATOM   1095  CB   VAL A 147      18.627  59.499  41.796  1.00 36.54           A
ATOM   1096  CG1  VAL A 147      18.898  60.070  43.181  1.00 36.54           A
ATOM   1097  CG2  VAL A 147      17.383  58.628  41.771  1.00 36.54           A
ATOM   1098  C    VAL A 147      19.695  61.514  40.878  1.00 74.35           A
ATOM   1099  O    VAL A 147      20.760  61.174  40.357  1.00 74.35           A
ATOM   1100  N    GLY A 148      19.547  62.650  41.538  1.00 50.28           A
ATOM   1101  CA   GLY A 148      20.673  63.553  41.650  1.00 50.28           A
ATOM   1102  C    GLY A 148      20.896  64.253  40.322  1.00 50.28           A
ATOM   1103  O    GLY A 148      20.062  64.160  39.411  1.00 50.28           A
ATOM   1104  N    TYR A 149      22.031  64.941  40.212  1.00 65.06           A
ATOM   1105  CA   TYR A 149      22.396  65.694  39.015  1.00 65.06           A
ATOM   1106  CB   TYR A 149      22.614  67.157  39.419  1.00 46.08           A
ATOM   1107  CG   TYR A 149      23.368  68.042  38.448  1.00 46.08           A
ATOM   1108  CD1  TYR A 149      23.036  68.092  37.098  1.00 46.08           A
ATOM   1109  CE1  TYR A 149      23.700  68.964  36.226  1.00 46.08           A
ATOM   1110  CD2  TYR A 149      24.385  68.882  38.904  1.00 46.08           A
ATOM   1111  CE2  TYR A 149      25.052  69.750  38.043  1.00 46.08           A
ATOM   1112  CZ   TYR A 149      24.708  69.787  36.708  1.00 46.08           A
ATOM   1113  OH   TYR A 149      25.384  70.637  35.866  1.00 46.08           A
ATOM   1114  C    TYR A 149      23.645  65.122  38.380  1.00 65.06           A
ATOM   1115  O    TYR A 149      24.665  64.975  39.043  1.00 65.06           A
ATOM   1116  N    VAL A 150      23.557  64.778  37.100  1.00 45.82           A
ATOM   1117  CA   VAL A 150      24.702  64.230  36.381  1.00 45.82           A
ATOM   1118  CB   VAL A 150      24.612  62.709  36.233  1.00 23.65           A
ATOM   1119  CG1  VAL A 150      25.897  62.185  35.631  1.00 23.65           A
ATOM   1120  CG2  VAL A 150      24.388  62.075  37.588  1.00 23.65           A
ATOM   1121  C    VAL A 150      24.774  64.872  35.012  1.00 45.82           A
ATOM   1122  O    VAL A 150      23.782  64.947  34.298  1.00 45.82           A
ATOM   1123  N    PRO A 151      25.962  65.347  34.630  1.00 38.98           A
ATOM   1124  CD   PRO A 151      27.109  65.558  35.532  1.00 32.54           A
ATOM   1125  CA   PRO A 151      26.179  66.006  33.340  1.00 38.98           A
ATOM   1126  CB   PRO A 151      26.842  67.290  33.764  1.00 32.54           A
ATOM   1127  CG   PRO A 151      27.754  66.801  34.962  1.00 32.54           A
ATOM   1128  C    PRO A 151      27.057  65.214  32.397  1.00 38.98           A
ATOM   1129  O    PRO A 151      27.363  64.055  32.666  1.00 38.98           A
ATOM   1130  N    ALA A 152      27.456  65.851  31.296  1.00 38.13           A
ATOM   1131  CA   ALA A 152      28.338  65.221  30.315  1.00 38.13           A
ATOM   1132  CB   ALA A 152      28.853  66.249  29.321  1.00 57.22           A
ATOM   1133  C    ALA A 152      29.507  64.555  31.041  1.00 38.13           A
ATOM   1134  O    ALA A 152      30.630  65.079  31.115  1.00 38.13           A
ATOM   1135  N    GLU A 153      29.184  63.394  31.595  1.00100.07           A
ATOM   1136  CA   GLU A 153      30.083  62.531  32.330  1.00100.07           A
ATOM   1137  CB   GLU A 153      29.921  62.750  33.830  1.00 63.28           A
ATOM   1138  CG   GLU A 153      30.804  61.861  34.672  1.00 63.28           A
```

```
ATOM   1139  CD   GLU A 153      30.083  61.327  35.895  1.00 63.28       A
ATOM   1140  OE1  GLU A 153      29.707  62.134  36.775  1.00 63.28       A
ATOM   1141  OE2  GLU A 153      29.884  60.094  35.972  1.00 63.28       A
ATOM   1142  C    GLU A 153      29.514  61.186  31.918  1.00100.07       A
ATOM   1143  O    GLU A 153      30.248  60.266  31.557  1.00100.07       A
ATOM   1144  N    ARG A 154      28.184  61.101  31.948  1.00 97.84       A
ATOM   1145  CA   ARG A 154      27.480  59.892  31.549  1.00 97.84       A
ATOM   1146  CB   ARG A 154      26.333  59.588  32.509  1.00100.07       A
ATOM   1147  CG   ARG A 154      26.835  59.067  33.858  1.00100.07       A
ATOM   1148  CD   ARG A 154      25.753  58.328  34.644  1.00100.07       A
ATOM   1149  NE   ARG A 154      26.273  57.725  35.874  1.00100.07       A
ATOM   1150  CZ   ARG A 154      25.573  56.915  36.665  1.00100.07       A
ATOM   1151  NH1  ARG A 154      24.319  56.607  36.358  1.00100.07       A
ATOM   1152  NH2  ARG A 154      26.128  56.407  37.760  1.00100.07       A
ATOM   1153  C    ARG A 154      26.980  60.063  30.130  1.00 97.84       A
ATOM   1154  O    ARG A 154      25.929  60.668  29.889  1.00 97.84       A
ATOM   1155  N    HIS A 155      27.777  59.526  29.206  1.00 33.73       A
ATOM   1156  CA   HIS A 155      27.547  59.567  27.759  1.00 33.73       A
ATOM   1157  CB   HIS A 155      28.605  58.703  27.087  1.00100.07       A
ATOM   1158  CG   HIS A 155      28.798  57.374  27.753  1.00100.07       A
ATOM   1159  CD2  HIS A 155      28.156  56.191  27.590  1.00100.07       A
ATOM   1160  ND1  HIS A 155      29.743  57.164  28.734  1.00100.07       A
ATOM   1161  CE1  HIS A 155      29.680  55.908  29.141  1.00100.07       A
ATOM   1162  NE2  HIS A 155      28.725  55.296  28.462  1.00100.07       A
ATOM   1163  C    HIS A 155      26.181  59.164  27.167  1.00 33.73       A
ATOM   1164  O    HIS A 155      25.329  58.515  27.808  1.00 33.73       A
ATOM   1165  N    GLY A 156      26.008  59.551  25.906  1.00 73.63       A
ATOM   1166  CA   GLY A 156      24.810  59.225  25.156  1.00 73.63       A
ATOM   1167  C    GLY A 156      25.191  58.230  24.065  1.00 73.63       A
ATOM   1168  O    GLY A 156      24.863  58.409  22.889  1.00 73.63       A
ATOM   1169  N    ILE A 157      25.909  57.180  24.462  1.00100.07       A
ATOM   1170  CA   ILE A 157      26.344  56.139  23.535  1.00100.07       A
ATOM   1171  CB   ILE A 157      27.412  55.195  24.182  1.00100.07       A
ATOM   1172  CG2  ILE A 157      27.894  54.156  23.169  1.00100.07       A
ATOM   1173  CG1  ILE A 157      28.614  56.005  24.683  1.00100.07       A
ATOM   1174  CD   ILE A 157      29.309  56.847  23.646  1.00100.07       A
ATOM   1175  C    ILE A 157      25.139  55.307  23.103  1.00100.07       A
ATOM   1176  O    ILE A 157      25.145  54.081  23.220  1.00100.07       A
ATOM   1177  N    LYS A 158      24.103  55.985  22.615  1.00 86.89       A
ATOM   1178  CA   LYS A 158      22.887  55.322  22.154  1.00 86.89       A
ATOM   1179  CB   LYS A 158      21.673  56.195  22.471  1.00 94.08       A
ATOM   1180  CG   LYS A 158      20.346  55.588  22.071  1.00 94.08       A
ATOM   1181  CD   LYS A 158      19.275  56.658  21.978  1.00 94.08       A
ATOM   1182  CE   LYS A 158      18.080  56.183  21.166  1.00 94.08       A
ATOM   1183  NZ   LYS A 158      17.231  57.331  20.740  1.00 94.08       A
ATOM   1184  C    LYS A 158      23.019  55.136  20.647  1.00 86.89       A
ATOM   1185  O    LYS A 158      23.473  54.091  20.170  1.00 86.89       A
ATOM   1186  N    ASP A 159      22.618  56.159  19.902  1.00 37.45       A
ATOM   1187  CA   ASP A 159      22.722  56.139  18.448  1.00 37.45       A
ATOM   1188  CB   ASP A 159      21.834  57.243  17.857  1.00100.07       A
ATOM   1189  CG   ASP A 159      21.704  57.154  16.349  1.00100.07       A
ATOM   1190  OD1  ASP A 159      22.702  57.415  15.642  1.00100.07       A
ATOM   1191  OD2  ASP A 159      20.598  56.825  15.869  1.00100.07       A
ATOM   1192  C    ASP A 159      24.198  56.424  18.190  1.00 37.45       A
ATOM   1193  O    ASP A 159      24.554  57.212  17.305  1.00 37.45       A
ATOM   1194  N    ARG A 160      25.040  55.776  18.998  1.00100.07       A
ATOM   1195  CA   ARG A 160      26.490  55.930  18.945  1.00100.07       A
ATOM   1196  CB   ARG A 160      27.194  54.577  19.099  1.00100.07       A
ATOM   1197  CG   ARG A 160      28.723  54.671  18.980  1.00100.07       A
ATOM   1198  CD   ARG A 160      29.369  55.377  20.176  1.00100.07       A
ATOM   1199  NE   ARG A 160      30.564  56.136  19.801  1.00100.07       A
ATOM   1200  CZ   ARG A 160      31.557  56.443  20.634  1.00100.07       A
ATOM   1201  NH1  ARG A 160      31.515  56.051  21.903  1.00100.07       A
ATOM   1202  NH2  ARG A 160      32.592  57.152  20.199  1.00100.07       A
ATOM   1203  C    ARG A 160      26.941  56.589  17.664  1.00100.07       A
ATOM   1204  O    ARG A 160      27.352  55.892  16.737  1.00100.07       A
ATOM   1205  N    ILE A 161      26.860  57.922  17.610  1.00 52.94       A
ATOM   1206  CA   ILE A 161      27.275  58.641  16.413  1.00 52.94       A
ATOM   1207  CB   ILE A 161      26.764  57.886  15.141  1.00 60.99       A
ATOM   1208  CG2  ILE A 161      26.149  58.843  14.152  1.00 60.99       A
ATOM   1209  CG1  ILE A 161      27.925  57.115  14.500  1.00 60.99       A
ATOM   1210  CD   ILE A 161      27.504  55.849  13.786  1.00 60.99       A
ATOM   1211  C    ILE A 161      26.923  60.117  16.264  1.00 52.94       A
ATOM   1212  O    ILE A 161      27.590  60.840  15.522  1.00 52.94       A
ATOM   1213  N    ASN A 162      25.878  60.572  16.939  1.00 99.95       A
ATOM   1214  CA   ASN A 162      25.502  61.975  16.837  1.00 99.95       A
ATOM   1215  CB   ASN A 162      24.505  62.166  15.694  1.00 96.68       A
ATOM   1216  CG   ASN A 162      24.995  61.559  14.386  1.00 96.68       A
ATOM   1217  OD1  ASN A 162      26.119  61.810  13.947  1.00 96.68       A
ATOM   1218  ND2  ASN A 162      24.146  60.756  13.757  1.00 96.68       A
ATOM   1219  C    ASN A 162      24.905  62.399  18.163  1.00 99.95       A
ATOM   1220  O    ASN A 162      24.515  63.544  18.365  1.00 99.95       A
ATOM   1221  N    ALA A 163      24.872  61.437  19.066  1.00 51.97       A
ATOM   1222  CA   ALA A 163      24.337  61.587  20.402  1.00 51.97       A
```

```
ATOM   1223  CB  ALA A 163      25.087  60.647  21.333  1.00100.07           A
ATOM   1224  C   ALA A 163      24.279  62.980  21.037  1.00 51.97           A
ATOM   1225  O   ALA A 163      23.253  63.358  21.607  1.00 51.97           A
ATOM   1226  N   ILE A 164      25.369  63.737  20.948  1.00 40.41           A
ATOM   1227  CA  ILE A 164      25.456  65.060  21.588  1.00 40.41           A
ATOM   1228  CB  ILE A 164      24.715  66.208  20.805  1.00 22.84           A
ATOM   1229  CG2 ILE A 164      25.247  66.343  19.377  1.00 22.84           A
ATOM   1230  CG1 ILE A 164      23.215  65.966  20.793  1.00 22.84           A
ATOM   1231  CD  ILE A 164      22.472  67.120  20.245  1.00 22.84           A
ATOM   1232  C   ILE A 164      24.834  64.991  22.976  1.00 40.41           A
ATOM   1233  O   ILE A 164      24.163  65.921  23.396  1.00 40.41           A
ATOM   1234  N   PRO A 165      25.101  63.912  23.728  1.00 16.22           A
ATOM   1235  CD  PRO A 165      26.390  63.209  23.641  1.00 26.38           A
ATOM   1236  CA  PRO A 165      24.531  63.743  25.075  1.00 16.22           A
ATOM   1237  CB  PRO A 165      25.573  62.880  25.799  1.00 26.38           A
ATOM   1238  CG  PRO A 165      26.835  63.215  25.077  1.00 26.38           A
ATOM   1239  C   PRO A 165      24.240  65.048  25.793  1.00 16.22           A
ATOM   1240  O   PRO A 165      25.107  65.913  25.890  1.00 16.22           A
ATOM   1241  N   VAL A 166      23.003  65.197  26.256  1.00 48.47           A
ATOM   1242  CA  VAL A 166      22.601  66.395  26.971  1.00 48.47           A
ATOM   1243  CB  VAL A 166      21.175  66.826  26.611  1.00 39.93           A
ATOM   1244  CG1 VAL A 166      20.750  67.993  27.472  1.00 39.93           A
ATOM   1245  CG2 VAL A 166      21.121  67.231  25.174  1.00 39.93           A
ATOM   1246  C   VAL A 166      22.680  66.107  28.453  1.00 48.47           A
ATOM   1247  O   VAL A 166      22.681  64.943  28.875  1.00 48.47           A
ATOM   1248  N   ASP A 167      22.754  67.174  29.240  1.00 51.97           A
ATOM   1249  CA  ASP A 167      22.861  67.049  30.679  1.00 51.97           A
ATOM   1250  CB  ASP A 167      23.156  68.417  31.292  1.00 67.98           A
ATOM   1251  CG  ASP A 167      24.547  68.917  30.956  1.00 67.98           A
ATOM   1252  OD1 ASP A 167      25.538  68.343  31.461  1.00 67.98           A
ATOM   1253  OD2 ASP A 167      24.646  69.885  30.178  1.00 67.98           A
ATOM   1254  C   ASP A 167      21.621  66.456  31.316  1.00 51.97           A
ATOM   1255  O   ASP A 167      20.568  66.354  30.690  1.00 51.97           A
ATOM   1256  N   ALA A 168      21.769  66.051  32.570  1.00 49.41           A
ATOM   1257  CA  ALA A 168      20.669  65.486  33.333  1.00 49.41           A
ATOM   1258  CB  ALA A 168      21.119  64.225  34.076  1.00100.07           A
ATOM   1259  C   ALA A 168      20.158  66.525  34.328  1.00 49.41           A
ATOM   1260  O   ALA A 168      20.790  67.541  34.598  1.00 49.41           A
ATOM   1261  N   ILE A 169      18.981  66.271  34.851  1.00 47.41           A
ATOM   1262  CA  ILE A 169      18.382  67.153  35.809  1.00 47.41           A
ATOM   1263  CB  ILE A 169      17.881  68.479  35.193  1.00100.07           A
ATOM   1264  CG2 ILE A 169      18.325  69.629  36.057  1.00100.07           A
ATOM   1265  CG1 ILE A 169      18.410  68.675  33.774  1.00100.07           A
ATOM   1266  CD  ILE A 169      17.772  67.765  32.752  1.00100.07           A
ATOM   1267  C   ILE A 169      17.193  66.341  36.232  1.00 47.41           A
ATOM   1268  O   ILE A 169      16.077  66.563  35.763  1.00 47.41           A
ATOM   1269  N   PHE A 170      17.437  65.364  37.091  1.00 56.10           A
ATOM   1270  CA  PHE A 170      16.359  64.515  37.552  1.00 56.10           A
ATOM   1271  CB  PHE A 170      16.939  63.223  38.115  1.00 52.95           A
ATOM   1272  CG  PHE A 170      17.797  62.481  37.132  1.00 52.95           A
ATOM   1273  CD1 PHE A 170      17.279  62.070  35.907  1.00 52.95           A
ATOM   1274  CD2 PHE A 170      19.125  62.197  37.422  1.00 52.95           A
ATOM   1275  CE1 PHE A 170      18.072  61.392  34.994  1.00 52.95           A
ATOM   1276  CE2 PHE A 170      19.923  61.516  36.510  1.00 52.95           A
ATOM   1277  CZ  PHE A 170      19.396  61.115  35.298  1.00 52.95           A
ATOM   1278  C   PHE A 170      15.510  65.248  38.595  1.00 56.10           A
ATOM   1279  O   PHE A 170      14.856  66.241  38.274  1.00 56.10           A
ATOM   1280  N   SER A 171      15.532  64.761  39.834  1.00 56.78           A
ATOM   1281  CA  SER A 171      14.767  65.346  40.936  1.00 56.78           A
ATOM   1282  CB  SER A 171      15.698  65.978  41.967  1.00 41.35           A
ATOM   1283  OG  SER A 171      14.944  66.683  42.937  1.00 41.35           A
ATOM   1284  C   SER A 171      13.739  66.380  40.513  1.00 56.78           A
ATOM   1285  O   SER A 171      14.081  67.507  40.180  1.00 56.78           A
ATOM   1286  N   PRO A 172      12.456  66.013  40.543  1.00 38.33           A
ATOM   1287  CD  PRO A 172      11.908  64.678  40.827  1.00 27.85           A
ATOM   1288  CA  PRO A 172      11.389  66.931  40.151  1.00 38.33           A
ATOM   1289  CB  PRO A 172      10.276  65.991  39.742  1.00 27.85           A
ATOM   1290  CG  PRO A 172      10.409  64.935  40.774  1.00 27.85           A
ATOM   1291  C   PRO A 172      10.942  67.887  41.228  1.00 38.33           A
ATOM   1292  O   PRO A 172      10.072  68.717  40.988  1.00 38.33           A
ATOM   1293  N   VAL A 173      11.496  67.758  42.424  1.00 21.94           A
ATOM   1294  CA  VAL A 173      11.142  68.684  43.481  1.00 21.94           A
ATOM   1295  CB  VAL A 173      11.833  68.295  44.775  1.00 56.09           A
ATOM   1296  CG1 VAL A 173      11.568  69.332  45.820  1.00 56.09           A
ATOM   1297  CG2 VAL A 173      11.333  66.934  45.235  1.00 56.09           A
ATOM   1298  C   VAL A 173      11.715  69.992  42.956  1.00 21.94           A
ATOM   1299  O   VAL A 173      12.922  70.083  42.732  1.00 21.94           A
ATOM   1300  N   ARG A 174      10.860  70.994  42.747  1.00 51.23           A
ATOM   1301  CA  ARG A 174      11.293  72.279  42.182  1.00 51.23           A
ATOM   1302  CB  ARG A 174      10.345  72.661  41.028  1.00100.00           A
ATOM   1303  CG  ARG A 174      10.795  73.840  40.182  1.00100.00           A
ATOM   1304  CD  ARG A 174      12.272  73.730  39.908  1.00100.00           A
ATOM   1305  NE  ARG A 174      12.736  74.650  38.880  1.00100.00           A
ATOM   1306  CZ  ARG A 174      14.021  74.882  38.630  1.00100.00           A
```

| ATOM | 1307 | NH1 | ARG | A | 174 | 14.956 | 74.265 | 39.343 | 1.00 | 100.00 | A |
| --- | --- | --- | --- | --- | --- | --- | --- | --- | --- | --- | --- |
| ATOM | 1308 | NH2 | ARG | A | 174 | 14.376 | 75.714 | 37.656 | 1.00 | 100.00 | A |
| ATOM | 1309 | C | ARG | A | 174 | 11.452 | 73.469 | 43.137 | 1.00 | 51.23 | A |
| ATOM | 1310 | O | ARG | A | 174 | 11.802 | 74.567 | 42.717 | 1.00 | 51.23 | A |
| ATOM | 1311 | N | ARG | A | 175 | 11.221 | 73.245 | 44.422 | 1.00 | 24.40 | A |
| ATOM | 1312 | CA | ARG | A | 175 | 11.333 | 74.302 | 45.419 | 1.00 | 24.40 | A |
| ATOM | 1313 | CB | ARG | A | 175 | 10.472 | 75.484 | 44.973 | 1.00 | 46.83 | A |
| ATOM | 1314 | CG | ARG | A | 175 | 10.416 | 76.649 | 45.911 | 1.00 | 46.83 | A |
| ATOM | 1315 | CD | ARG | A | 175 | 9.769 | 77.818 | 45.203 | 1.00 | 46.83 | A |
| ATOM | 1316 | NE | ARG | A | 175 | 9.080 | 78.729 | 46.115 | 1.00 | 46.83 | A |
| ATOM | 1317 | CZ | ARG | A | 175 | 8.459 | 79.841 | 45.725 | 1.00 | 46.83 | A |
| ATOM | 1318 | NH1 | ARG | A | 175 | 8.449 | 80.181 | 44.437 | 1.00 | 46.83 | A |
| ATOM | 1319 | NH2 | ARG | A | 175 | 7.837 | 80.608 | 46.616 | 1.00 | 46.83 | A |
| ATOM | 1320 | C | ARG | A | 175 | 10.808 | 73.652 | 46.703 | 1.00 | 24.40 | A |
| ATOM | 1321 | O | ARG | A | 175 | 9.964 | 72.769 | 46.633 | 1.00 | 24.40 | A |
| ATOM | 1322 | N | VAL | A | 176 | 11.312 | 74.057 | 47.864 | 1.00 | 50.40 | A |
| ATOM | 1323 | CA | VAL | A | 176 | 10.875 | 73.467 | 49.137 | 1.00 | 50.40 | A |
| ATOM | 1324 | CB | VAL | A | 176 | 11.639 | 72.126 | 49.452 | 1.00 | 5.23 | A |
| ATOM | 1325 | CG1 | VAL | A | 176 | 11.188 | 71.565 | 50.791 | 1.00 | 5.23 | A |
| ATOM | 1326 | CG2 | VAL | A | 176 | 11.447 | 71.110 | 48.351 | 1.00 | 5.23 | A |
| ATOM | 1327 | C | VAL | A | 176 | 11.108 | 74.403 | 50.333 | 1.00 | 50.40 | A |
| ATOM | 1328 | O | VAL | A | 176 | 12.242 | 74.536 | 50.827 | 1.00 | 50.40 | A |
| ATOM | 1329 | N | ALA | A | 177 | 10.038 | 75.040 | 50.802 | 1.00 | 73.68 | A |
| ATOM | 1330 | CA | ALA | A | 177 | 10.125 | 75.936 | 51.955 | 1.00 | 73.68 | A |
| ATOM | 1331 | CB | ALA | A | 177 | 9.717 | 77.367 | 51.551 | 1.00 | 18.59 | A |
| ATOM | 1332 | C | ALA | A | 177 | 9.208 | 75.400 | 53.057 | 1.00 | 73.68 | A |
| ATOM | 1333 | O | ALA | A | 177 | 8.647 | 74.312 | 52.927 | 1.00 | 73.68 | A |
| ATOM | 1334 | N | PHE | A | 178 | 9.082 | 76.144 | 54.148 | 1.00 | 100.07 | A |
| ATOM | 1335 | CA | PHE | A | 178 | 8.196 | 75.751 | 55.239 | 1.00 | 100.07 | A |
| ATOM | 1336 | CB | PHE | A | 178 | 8.518 | 74.313 | 55.714 | 1.00 | 30.14 | A |
| ATOM | 1337 | CG | PHE | A | 178 | 9.759 | 74.172 | 56.548 | 1.00 | 30.14 | A |
| ATOM | 1338 | CD1 | PHE | A | 178 | 9.782 | 74.587 | 57.876 | 1.00 | 30.14 | A |
| ATOM | 1339 | CD2 | PHE | A | 178 | 10.877 | 73.523 | 56.038 | 1.00 | 30.14 | A |
| ATOM | 1340 | CE1 | PHE | A | 178 | 10.905 | 74.343 | 58.685 | 1.00 | 30.14 | A |
| ATOM | 1341 | CE2 | PHE | A | 178 | 12.005 | 73.279 | 56.844 | 1.00 | 30.14 | A |
| ATOM | 1342 | CZ | PHE | A | 178 | 12.014 | 73.686 | 58.162 | 1.00 | 30.14 | A |
| ATOM | 1343 | C | PHE | A | 178 | 8.211 | 76.770 | 56.372 | 1.00 | 100.07 | A |
| ATOM | 1344 | O | PHE | A | 178 | 8.983 | 77.725 | 56.325 | 1.00 | 100.07 | A |
| ATOM | 1345 | N | GLN | A | 179 | 7.350 | 76.605 | 57.370 | 1.00 | 51.57 | A |
| ATOM | 1346 | CA | GLN | A | 179 | 7.318 | 77.579 | 58.457 | 1.00 | 51.57 | A |
| ATOM | 1347 | CB | GLN | A | 179 | 6.322 | 78.681 | 58.113 | 1.00 | 99.76 | A |
| ATOM | 1348 | CG | GLN | A | 179 | 6.833 | 79.639 | 57.071 | 1.00 | 99.76 | A |
| ATOM | 1349 | CD | GLN | A | 179 | 5.748 | 80.537 | 56.544 | 1.00 | 99.76 | A |
| ATOM | 1350 | OE1 | GLN | A | 179 | 4.724 | 80.740 | 57.200 | 1.00 | 99.76 | A |
| ATOM | 1351 | NE2 | GLN | A | 179 | 5.966 | 81.094 | 55.356 | 1.00 | 99.76 | A |
| ATOM | 1352 | C | GLN | A | 179 | 6.960 | 76.979 | 59.805 | 1.00 | 51.57 | A |
| ATOM | 1353 | O | GLN | A | 179 | 6.040 | 76.175 | 59.915 | 1.00 | 51.57 | A |
| ATOM | 1354 | N | VAL | A | 180 | 7.693 | 77.362 | 60.835 | 1.00 | 86.87 | A |
| ATOM | 1355 | CA | VAL | A | 180 | 7.386 | 76.852 | 62.154 | 1.00 | 86.87 | A |
| ATOM | 1356 | CB | VAL | A | 180 | 8.669 | 76.574 | 62.958 | 1.00 | 48.36 | A |
| ATOM | 1357 | CG1 | VAL | A | 180 | 8.313 | 76.074 | 64.349 | 1.00 | 48.36 | A |
| ATOM | 1358 | CG2 | VAL | A | 180 | 9.525 | 75.543 | 62.231 | 1.00 | 48.36 | A |
| ATOM | 1359 | C | VAL | A | 180 | 6.541 | 77.915 | 62.845 | 1.00 | 86.87 | A |
| ATOM | 1360 | O | VAL | A | 180 | 7.072 | 78.856 | 63.437 | 1.00 | 86.87 | A |
| ATOM | 1361 | N | GLU | A | 181 | 5.221 | 77.768 | 62.746 | 1.00 | 100.07 | A |
| ATOM | 1362 | CA | GLU | A | 181 | 4.273 | 78.712 | 63.343 | 1.00 | 100.07 | A |
| ATOM | 1363 | CB | GLU | A | 181 | 2.938 | 78.666 | 62.596 | 1.00 | 72.17 | A |
| ATOM | 1364 | CG | GLU | A | 181 | 3.031 | 78.951 | 61.128 | 1.00 | 72.17 | A |
| ATOM | 1365 | CD | GLU | A | 181 | 3.100 | 80.429 | 60.840 | 1.00 | 72.17 | A |
| ATOM | 1366 | OE1 | GLU | A | 181 | 3.556 | 81.181 | 61.734 | 1.00 | 72.17 | A |
| ATOM | 1367 | OE2 | GLU | A | 181 | 2.707 | 80.832 | 59.718 | 1.00 | 72.17 | A |
| ATOM | 1368 | C | GLU | A | 181 | 3.978 | 78.365 | 64.784 | 1.00 | 100.07 | A |
| ATOM | 1369 | O | GLU | A | 181 | 4.394 | 77.320 | 65.290 | 1.00 | 100.07 | A |
| ATOM | 1370 | N | ASP | A | 182 | 3.236 | 79.254 | 65.431 | 1.00 | 99.56 | A |
| ATOM | 1371 | CA | ASP | A | 182 | 2.823 | 79.048 | 66.805 | 1.00 | 99.56 | A |
| ATOM | 1372 | CB | ASP | A | 182 | 2.886 | 80.361 | 67.581 | 1.00 | 100.07 | A |
| ATOM | 1373 | CG | ASP | A | 182 | 4.304 | 80.790 | 67.867 | 1.00 | 100.07 | A |
| ATOM | 1374 | OD1 | ASP | A | 182 | 5.052 | 79.988 | 68.473 | 1.00 | 100.07 | A |
| ATOM | 1375 | OD2 | ASP | A | 182 | 4.664 | 81.923 | 67.488 | 1.00 | 100.07 | A |
| ATOM | 1376 | C | ASP | A | 182 | 1.391 | 78.534 | 66.733 | 1.00 | 99.56 | A |
| ATOM | 1377 | O | ASP | A | 182 | 0.493 | 79.223 | 66.240 | 1.00 | 99.56 | A |
| ATOM | 1378 | N | THR | A | 183 | 1.189 | 77.308 | 67.205 | 1.00 | 100.07 | A |
| ATOM | 1379 | CA | THR | A | 183 | -0.129 | 76.702 | 67.180 | 1.00 | 100.07 | A |
| ATOM | 1380 | CB | THR | A | 183 | -0.071 | 75.216 | 67.606 | 1.00 | 100.07 | A |
| ATOM | 1381 | OG1 | THR | A | 183 | -1.405 | 74.709 | 67.744 | 1.00 | 100.07 | A |
| ATOM | 1382 | CG2 | THR | A | 183 | 0.677 | 75.057 | 68.924 | 1.00 | 100.07 | A |
| ATOM | 1383 | C | THR | A | 183 | -1.123 | 77.431 | 68.063 | 1.00 | 100.07 | A |
| ATOM | 1384 | O | THR | A | 183 | -1.615 | 78.512 | 67.708 | 1.00 | 100.07 | A |
| ATOM | 1385 | N | ARG | A | 184 | -1.393 | 76.822 | 69.217 | 1.00 | 69.50 | A |
| ATOM | 1386 | CA | ARG | A | 184 | -2.334 | 77.313 | 70.216 | 1.00 | 69.50 | A |
| ATOM | 1387 | CB | ARG | A | 184 | -3.382 | 78.244 | 69.568 | 1.00 | 100.07 | A |
| ATOM | 1388 | CG | ARG | A | 184 | -4.731 | 78.353 | 70.288 | 1.00 | 100.07 | A |
| ATOM | 1389 | CD | ARG | A | 184 | -5.779 | 77.375 | 69.723 | 1.00 | 100.07 | A |
| ATOM | 1390 | NE | ARG | A | 184 | -7.057 | 77.467 | 70.440 | 1.00 | 100.07 | A |

-17-

```
ATOM   1391  CZ   ARG A 184     -8.110  76.672  70.234  1.00100.07      A
ATOM   1392  NH1  ARG A 184     -8.056  75.707  69.322  1.00100.07      A
ATOM   1393  NH2  ARG A 184     -9.219  76.834  70.953  1.00100.07      A
ATOM   1394  C    ARG A 184     -3.021  76.056  70.750  1.00 69.50      A
ATOM   1395  O    ARG A 184     -3.281  75.096  70.013  1.00 69.50      A
ATOM   1396  N    LEU A 185     -3.315  76.099  72.041  1.00100.07      A
ATOM   1397  CA   LEU A 185     -3.944  75.016  72.775  1.00100.07      A
ATOM   1398  CB   LEU A 185     -5.447  74.934  72.482  1.00 86.73      A
ATOM   1399  CG   LEU A 185     -6.248  75.931  73.343  1.00 86.73      A
ATOM   1400  CD1  LEU A 185     -7.725  75.600  73.244  1.00 86.73      A
ATOM   1401  CD2  LEU A 185     -5.800  75.865  74.810  1.00 86.73      A
ATOM   1402  C    LEU A 185     -3.293  73.641  72.709  1.00100.07      A
ATOM   1403  O    LEU A 185     -3.091  73.043  71.649  1.00100.07      A
ATOM   1404  N    GLY A 186     -2.973  73.175  73.910  1.00100.07      A
ATOM   1405  CA   GLY A 186     -2.315  71.908  74.137  1.00100.07      A
ATOM   1406  C    GLY A 186     -1.383  72.200  75.302  1.00100.07      A
ATOM   1407  O    GLY A 186     -0.848  71.295  75.959  1.00100.07      A
ATOM   1408  N    GLN A 187     -1.226  73.504  75.546  1.00100.07      A
ATOM   1409  CA   GLN A 187     -0.386  74.080  76.597  1.00100.07      A
ATOM   1410  CB   GLN A 187      0.836  73.186  76.860  1.00 98.59      A
ATOM   1411  CG   GLN A 187      1.811  73.705  77.904  1.00 98.59      A
ATOM   1412  CD   GLN A 187      2.936  72.722  78.190  1.00 98.59      A
ATOM   1413  OE1  GLN A 187      3.609  72.250  77.276  1.00 98.59      A
ATOM   1414  NE2  GLN A 187      3.146  72.414  79.464  1.00 98.59      A
ATOM   1415  C    GLN A 187      0.065  75.445  76.086  1.00100.07      A
ATOM   1416  O    GLN A 187     -0.259  75.827  74.960  1.00100.07      A
ATOM   1417  N    ARG A 188      0.820  76.176  76.899  1.00 99.87      A
ATOM   1418  CA   ARG A 188      1.279  77.503  76.506  1.00 99.87      A
ATOM   1419  CB   ARG A 188      2.149  78.112  77.612  1.00100.07      A
ATOM   1420  CG   ARG A 188      1.317  78.786  78.700  1.00100.07      A
ATOM   1421  CD   ARG A 188      2.167  79.285  79.857  1.00100.07      A
ATOM   1422  NE   ARG A 188      1.411  80.204  80.707  1.00100.07      A
ATOM   1423  CZ   ARG A 188      1.877  80.766  81.820  1.00100.07      A
ATOM   1424  NH1  ARG A 188      3.111  80.505  82.239  1.00100.07      A
ATOM   1425  NH2  ARG A 188      1.107  81.602  82.509  1.00100.07      A
ATOM   1426  C    ARG A 188      1.980  77.592  75.153  1.00 99.87      A
ATOM   1427  O    ARG A 188      2.854  76.787  74.831  1.00 99.87      A
ATOM   1428  N    THR A 189      1.559  78.587  74.374  1.00100.07      A
ATOM   1429  CA   THR A 189      2.077  78.863  73.033  1.00100.07      A
ATOM   1430  CB   THR A 189      2.503  80.348  72.881  1.00100.07      A
ATOM   1431  OG1  THR A 189      1.332  81.167  72.741  1.00100.07      A
ATOM   1432  CG2  THR A 189      3.408  80.534  71.651  1.00100.07      A
ATOM   1433  C    THR A 189      3.238  77.991  72.568  1.00100.07      A
ATOM   1434  O    THR A 189      3.096  77.227  71.605  1.00100.07      A
ATOM   1435  N    ASP A 190      4.382  78.137  73.240  1.00 96.21      A
ATOM   1436  CA   ASP A 190      5.588  77.376  72.926  1.00 96.21      A
ATOM   1437  CB   ASP A 190      5.867  76.334  74.019  1.00 99.97      A
ATOM   1438  CG   ASP A 190      6.367  76.943  75.313  1.00 99.97      A
ATOM   1439  OD1  ASP A 190      7.403  77.643  75.273  1.00 99.97      A
ATOM   1440  OD2  ASP A 190      5.732  76.708  76.368  1.00 99.97      A
ATOM   1441  C    ASP A 190      5.452  76.630  71.616  1.00 96.21      A
ATOM   1442  O    ASP A 190      5.961  77.051  70.580  1.00 96.21      A
ATOM   1443  N    LEU A 191      4.745  75.510  71.706  1.00 88.88      A
ATOM   1444  CA   LEU A 191      4.483  74.620  70.594  1.00 88.88      A
ATOM   1445  CB   LEU A 191      3.076  74.051  70.700  1.00 82.14      A
ATOM   1446  CG   LEU A 191      2.676  73.433  72.032  1.00 82.14      A
ATOM   1447  CD1  LEU A 191      1.383  72.671  71.805  1.00 82.14      A
ATOM   1448  CD2  LEU A 191      3.769  72.508  72.566  1.00 82.14      A
ATOM   1449  C    LEU A 191      4.660  75.214  69.212  1.00 88.88      A
ATOM   1450  O    LEU A 191      4.358  76.388  68.967  1.00 88.88      A
ATOM   1451  N    ASP A 192      5.134  74.360  68.310  1.00 97.03      A
ATOM   1452  CA   ASP A 192      5.383  74.718  66.927  1.00 97.03      A
ATOM   1453  CB   ASP A 192      6.744  74.172  66.494  1.00100.07      A
ATOM   1454  CG   ASP A 192      7.785  74.256  67.596  1.00100.07      A
ATOM   1455  OD1  ASP A 192      8.067  75.379  68.066  1.00100.07      A
ATOM   1456  OD2  ASP A 192      8.321  73.198  67.994  1.00100.07      A
ATOM   1457  C    ASP A 192      4.294  74.099  66.052  1.00 97.03      A
ATOM   1458  O    ASP A 192      3.673  73.110  66.439  1.00 97.03      A
ATOM   1459  N    LYS A 193      4.066  74.685  64.880  1.00 30.13      A
ATOM   1460  CA   LYS A 193      3.073  74.182  63.936  1.00 30.13      A
ATOM   1461  CB   LYS A 193      1.833  75.071  63.963  1.00 88.42      A
ATOM   1462  CG   LYS A 193      0.919  74.908  62.762  1.00 88.42      A
ATOM   1463  CD   LYS A 193      0.025  76.119  62.617  1.00 88.42      A
ATOM   1464  CE   LYS A 193     -0.670  76.138  61.280  1.00 88.42      A
ATOM   1465  NZ   LYS A 193     -1.297  77.462  61.048  1.00 88.42      A
ATOM   1466  C    LYS A 193      3.670  74.183  62.527  1.00 30.13      A
ATOM   1467  O    LYS A 193      3.632  75.212  61.836  1.00 30.13      A
ATOM   1468  N    LEU A 194      4.205  73.030  62.105  1.00 31.31      A
ATOM   1469  CA   LEU A 194      4.850  72.873  60.790  1.00 31.31      A
ATOM   1470  CB   LEU A 194      5.268  71.422  60.604  1.00 34.90      A
ATOM   1471  CG   LEU A 194      6.671  71.285  60.020  1.00 34.90      A
ATOM   1472  CD1  LEU A 194      7.490  70.294  60.834  1.00 34.90      A
ATOM   1473  CD2  LEU A 194      6.566  70.857  58.590  1.00 34.90      A
ATOM   1474  C    LEU A 194      3.964  73.315  59.630  1.00 31.31      A
```

| | | | | | | | | | |
|---|---|---|---|---|---|---|---|---|---|
| ATOM | 1475 | O | LEU | A | 194 | 2.958 | 73.993 | 59.844 | 1.00 31.31 | A |
| ATOM | 1476 | N | THR | A | 195 | 4.321 | 72.941 | 58.404 | 1.00 32.61 | A |
| ATOM | 1477 | CA | THR | A | 195 | 3.510 | 73.364 | 57.265 | 1.00 32.61 | A |
| ATOM | 1478 | CB | THR | A | 195 | 3.084 | 74.840 | 57.441 | 1.00 82.69 | A |
| ATOM | 1479 | OG1 | THR | A | 195 | 2.132 | 75.199 | 56.436 | 1.00 82.69 | A |
| ATOM | 1480 | CG2 | THR | A | 195 | 4.301 | 75.756 | 57.332 | 1.00 82.69 | A |
| ATOM | 1481 | C | THR | A | 195 | 4.193 | 73.264 | 55.900 | 1.00 32.61 | A |
| ATOM | 1482 | O | THR | A | 195 | 3.767 | 73.942 | 54.966 | 1.00 32.61 | A |
| ATOM | 1483 | N | LEU | A | 196 | 5.217 | 72.424 | 55.751 | 1.00 44.55 | A |
| ATOM | 1484 | CA | LEU | A | 196 | 5.933 | 72.366 | 54.470 | 1.00 44.55 | A |
| ATOM | 1485 | CB | LEU | A | 196 | 7.018 | 71.281 | 54.486 | 1.00 31.90 | A |
| ATOM | 1486 | CG | LEU | A | 196 | 6.714 | 69.816 | 54.729 | 1.00 31.90 | A |
| ATOM | 1487 | CD1 | LEU | A | 196 | 7.990 | 69.100 | 55.175 | 1.00 31.90 | A |
| ATOM | 1488 | CD2 | LEU | A | 196 | 5.669 | 69.706 | 55.793 | 1.00 31.90 | A |
| ATOM | 1489 | C | LEU | A | 196 | 5.105 | 72.265 | 53.216 | 1.00 44.55 | A |
| ATOM | 1490 | O | LEU | A | 196 | 4.207 | 71.433 | 53.108 | 1.00 44.55 | A |
| ATOM | 1491 | N | ARG | A | 197 | 5.433 | 73.146 | 52.273 | 1.00 46.84 | A |
| ATOM | 1492 | CA | ARG | A | 197 | 4.737 | 73.253 | 50.997 | 1.00 46.84 | A |
| ATOM | 1493 | CB | ARG | A | 197 | 4.976 | 74.644 | 50.402 | 1.00 54.72 | A |
| ATOM | 1494 | CG | ARG | A | 197 | 4.749 | 75.804 | 51.384 | 1.00 54.72 | A |
| ATOM | 1495 | CD | ARG | A | 197 | 4.243 | 77.010 | 50.621 | 1.00 54.72 | A |
| ATOM | 1496 | NE | ARG | A | 197 | 4.582 | 78.285 | 51.237 | 1.00 54.72 | A |
| ATOM | 1497 | CZ | ARG | A | 197 | 4.340 | 79.459 | 50.659 | 1.00 54.72 | A |
| ATOM | 1498 | NH1 | ARG | A | 197 | 3.755 | 79.497 | 49.467 | 1.00 54.72 | A |
| ATOM | 1499 | NH2 | ARG | A | 197 | 4.703 | 80.592 | 51.249 | 1.00 54.72 | A |
| ATOM | 1500 | C | ARG | A | 197 | 5.129 | 72.167 | 49.986 | 1.00 46.84 | A |
| ATOM | 1501 | O | ARG | A | 197 | 4.317 | 71.298 | 49.667 | 1.00 46.84 | A |
| ATOM | 1502 | N | ILE | A | 198 | 6.365 | 72.221 | 49.491 | 1.00 33.53 | A |
| ATOM | 1503 | CA | ILE | A | 198 | 6.876 | 71.260 | 48.508 | 1.00 33.53 | A |
| ATOM | 1504 | CB | ILE | A | 198 | 6.366 | 69.829 | 48.798 | 1.00 31.98 | A |
| ATOM | 1505 | CG2 | ILE | A | 198 | 6.661 | 68.896 | 47.640 | 1.00 31.98 | A |
| ATOM | 1506 | CG1 | ILE | A | 198 | 7.039 | 69.321 | 50.082 | 1.00 31.98 | A |
| ATOM | 1507 | CD | ILE | A | 198 | 7.115 | 67.786 | 50.217 | 1.00 31.98 | A |
| ATOM | 1508 | C | ILE | A | 198 | 6.472 | 71.698 | 47.114 | 1.00 33.53 | A |
| ATOM | 1509 | O | ILE | A | 198 | 6.077 | 70.905 | 46.284 | 1.00 33.53 | A |
| ATOM | 1510 | N | TRP | A | 199 | 6.622 | 72.991 | 46.875 | 1.00100.07 | A |
| ATOM | 1511 | CA | TRP | A | 199 | 6.251 | 73.655 | 45.632 | 1.00100.07 | A |
| ATOM | 1512 | CB | TRP | A | 199 | 7.323 | 74.658 | 45.251 | 1.00 99.57 | A |
| ATOM | 1513 | CG | TRP | A | 199 | 6.687 | 75.861 | 44.709 | 1.00 99.57 | A |
| ATOM | 1514 | CD2 | TRP | A | 199 | 6.225 | 76.980 | 45.466 | 1.00 99.57 | A |
| ATOM | 1515 | CE2 | TRP | A | 199 | 5.583 | 77.852 | 44.565 | 1.00 99.57 | A |
| ATOM | 1516 | CE3 | TRP | A | 199 | 6.292 | 77.330 | 46.823 | 1.00 99.57 | A |
| ATOM | 1517 | CD1 | TRP | A | 199 | 6.323 | 76.086 | 43.421 | 1.00 99.57 | A |
| ATOM | 1518 | NE1 | TRP | A | 199 | 5.657 | 77.280 | 43.322 | 1.00 99.57 | A |
| ATOM | 1519 | CZ2 | TRP | A | 199 | 5.005 | 79.064 | 44.976 | 1.00 99.57 | A |
| ATOM | 1520 | CZ3 | TRP | A | 199 | 5.719 | 78.532 | 47.232 | 1.00 99.57 | A |
| ATOM | 1521 | CH2 | TRP | A | 199 | 5.084 | 79.386 | 46.309 | 1.00 99.57 | A |
| ATOM | 1522 | C | TRP | A | 199 | 5.790 | 72.979 | 44.352 | 1.00100.07 | A |
| ATOM | 1523 | O | TRP | A | 199 | 4.617 | 72.644 | 44.209 | 1.00100.07 | A |
| ATOM | 1524 | N | THR | A | 200 | 6.692 | 72.835 | 43.391 | 1.00 68.48 | A |
| ATOM | 1525 | CA | THR | A | 200 | 6.319 | 72.236 | 42.111 | 1.00 68.48 | A |
| ATOM | 1526 | CB | THR | A | 200 | 6.737 | 73.178 | 40.936 | 1.00 87.15 | A |
| ATOM | 1527 | OG1 | THR | A | 200 | 6.139 | 74.467 | 41.122 | 1.00 87.15 | A |
| ATOM | 1528 | CG2 | THR | A | 200 | 6.291 | 72.627 | 39.594 | 1.00 87.15 | A |
| ATOM | 1529 | C | THR | A | 200 | 6.976 | 70.870 | 41.935 | 1.00 68.48 | A |
| ATOM | 1530 | O | THR | A | 200 | 7.706 | 70.386 | 42.806 | 1.00 68.48 | A |
| ATOM | 1531 | N | ASP | A | 201 | 6.692 | 70.252 | 40.800 | 1.00 31.77 | A |
| ATOM | 1532 | CA | ASP | A | 201 | 7.241 | 68.964 | 40.483 | 1.00 31.77 | A |
| ATOM | 1533 | CB | ASP | A | 201 | 6.380 | 67.867 | 41.088 | 1.00 88.26 | A |
| ATOM | 1534 | CG | ASP | A | 201 | 6.183 | 68.052 | 42.561 | 1.00 88.26 | A |
| ATOM | 1535 | OD1 | ASP | A | 201 | 5.102 | 68.533 | 42.952 | 1.00 88.26 | A |
| ATOM | 1536 | OD2 | ASP | A | 201 | 7.117 | 67.738 | 43.327 | 1.00 88.26 | A |
| ATOM | 1537 | C | ASP | A | 201 | 7.385 | 68.754 | 38.980 | 1.00 31.77 | A |
| ATOM | 1538 | O | ASP | A | 201 | 6.566 | 69.236 | 38.169 | 1.00 31.77 | A |
| ATOM | 1539 | N | GLY | A | 202 | 8.463 | 68.059 | 38.618 | 1.00 58.84 | A |
| ATOM | 1540 | CA | GLY | A | 202 | 8.681 | 67.736 | 37.230 | 1.00 58.84 | A |
| ATOM | 1541 | C | GLY | A | 202 | 7.467 | 66.868 | 36.954 | 1.00 58.84 | A |
| ATOM | 1542 | O | GLY | A | 202 | 6.430 | 67.366 | 36.485 | 1.00 58.84 | A |
| ATOM | 1543 | N | SER | A | 203 | 7.580 | 65.581 | 37.302 | 1.00 66.27 | A |
| ATOM | 1544 | CA | SER | A | 203 | 6.497 | 64.618 | 37.102 | 1.00 66.27 | A |
| ATOM | 1545 | CB | SER | A | 203 | 7.030 | 63.309 | 36.511 | 1.00 89.23 | A |
| ATOM | 1546 | OG | SER | A | 203 | 7.849 | 62.622 | 37.432 | 1.00 89.23 | A |
| ATOM | 1547 | C | SER | A | 203 | 5.691 | 64.315 | 38.366 | 1.00 66.27 | A |
| ATOM | 1548 | O | SER | A | 203 | 4.597 | 64.856 | 38.530 | 1.00 66.27 | A |
| ATOM | 1549 | N | VAL | A | 204 | 6.243 | 63.465 | 39.243 | 1.00 42.74 | A |
| ATOM | 1550 | CA | VAL | A | 204 | 5.610 | 63.032 | 40.508 | 1.00 42.74 | A |
| ATOM | 1551 | CB | VAL | A | 204 | 6.607 | 62.209 | 41.417 | 1.00 21.15 | A |
| ATOM | 1552 | CG1 | VAL | A | 204 | 7.944 | 62.046 | 40.738 | 1.00 21.15 | A |
| ATOM | 1553 | CG2 | VAL | A | 204 | 6.793 | 62.879 | 42.764 | 1.00 21.15 | A |
| ATOM | 1554 | C | VAL | A | 204 | 4.972 | 64.117 | 41.390 | 1.00 42.74 | A |
| ATOM | 1555 | O | VAL | A | 204 | 5.099 | 65.314 | 41.127 | 1.00 42.74 | A |
| ATOM | 1556 | N | THR | A | 205 | 4.293 | 63.684 | 42.452 | 1.00 21.70 | A |
| ATOM | 1557 | CA | THR | A | 205 | 3.617 | 64.619 | 43.348 | 1.00 21.70 | A |
| ATOM | 1558 | CB | THR | A | 205 | 2.108 | 64.347 | 43.399 | 1.00 74.21 | A |

```
ATOM   1559  OG1 THR A 205       1.876  63.080  44.030  1.00 74.21           A
ATOM   1560  CG2 THR A 205       1.521  64.351  41.985  1.00 74.21           A
ATOM   1561  C   THR A 205       4.120  64.675  44.794  1.00 21.70           A
ATOM   1562  O   THR A 205       4.462  63.656  45.402  1.00 21.70           A
ATOM   1563  N   PRO A 206       4.121  65.890  45.368  1.00 17.57           A
ATOM   1564  CD  PRO A 206       3.336  67.024  44.848  1.00 23.29           A
ATOM   1565  CA  PRO A 206       4.563  66.175  46.725  1.00 17.57           A
ATOM   1566  CB  PRO A 206       3.730  67.384  47.102  1.00 23.29           A
ATOM   1567  CG  PRO A 206       3.667  68.108  45.834  1.00 23.29           A
ATOM   1568  C   PRO A 206       4.290  65.002  47.621  1.00 17.57           A
ATOM   1569  O   PRO A 206       5.221  64.344  48.070  1.00 17.57           A
ATOM   1570  N   LEU A 207       3.012  64.740  47.883  1.00 66.62           A
ATOM   1571  CA  LEU A 207       2.637  63.621  48.739  1.00 66.62           A
ATOM   1572  CB  LEU A 207       1.264  63.075  48.348  1.00100.07           A
ATOM   1573  CG  LEU A 207       0.807  61.885  49.197  1.00100.07           A
ATOM   1574  CD1 LEU A 207       0.394  62.392  50.572  1.00100.07           A
ATOM   1575  CD2 LEU A 207      -0.347  61.153  48.516  1.00100.07           A
ATOM   1576  C   LEU A 207       3.677  62.516  48.567  1.00 66.62           A
ATOM   1577  O   LEU A 207       4.303  62.063  49.533  1.00 66.62           A
ATOM   1578  N   GLU A 208       3.861  62.104  47.316  1.00 83.94           A
ATOM   1579  CA  GLU A 208       4.828  61.073  46.987  1.00 83.94           A
ATOM   1580  CB  GLU A 208       4.791  60.763  45.484  1.00 86.72           A
ATOM   1581  CG  GLU A 208       3.448  60.239  44.974  1.00 86.72           A
ATOM   1582  CD  GLU A 208       3.461  59.883  43.485  1.00 86.72           A
ATOM   1583  OE1 GLU A 208       4.193  58.946  43.086  1.00 86.72           A
ATOM   1584  OE2 GLU A 208       2.729  60.544  42.715  1.00 86.72           A
ATOM   1585  C   GLU A 208       6.223  61.548  47.386  1.00 83.94           A
ATOM   1586  O   GLU A 208       6.928  60.855  48.120  1.00 83.94           A
ATOM   1587  N   ALA A 209       6.613  62.732  46.906  1.00 96.12           A
ATOM   1588  CA  ALA A 209       7.929  63.298  47.221  1.00 96.12           A
ATOM   1589  CB  ALA A 209       8.053  64.748  46.668  1.00 27.97           A
ATOM   1590  C   ALA A 209       8.153  63.282  48.735  1.00 96.12           A
ATOM   1591  O   ALA A 209       9.192  62.824  49.213  1.00 96.12           A
ATOM   1592  N   LEU A 210       7.165  63.771  49.480  1.00 44.94           A
ATOM   1593  CA  LEU A 210       7.227  63.812  50.934  1.00 44.94           A
ATOM   1594  CB  LEU A 210       5.929  64.413  51.482  1.00 31.43           A
ATOM   1595  CG  LEU A 210       5.568  64.066  52.931  1.00 31.43           A
ATOM   1596  CD1 LEU A 210       6.619  64.625  53.863  1.00 31.43           A
ATOM   1597  CD2 LEU A 210       4.174  64.600  53.278  1.00 31.43           A
ATOM   1598  C   LEU A 210       7.464  62.430  51.554  1.00 44.94           A
ATOM   1599  O   LEU A 210       8.495  62.197  52.201  1.00 44.94           A
ATOM   1600  N   ASN A 211       6.508  61.519  51.374  1.00100.07           A
ATOM   1601  CA  ASN A 211       6.648  60.172  51.927  1.00100.07           A
ATOM   1602  CB  ASN A 211       5.497  59.264  51.479  1.00100.07           A
ATOM   1603  CG  ASN A 211       4.154  59.701  52.033  1.00100.07           A
ATOM   1604  OD1 ASN A 211       3.527  60.633  51.527  1.00100.07           A
ATOM   1605  ND2 ASN A 211       3.711  59.030  53.089  1.00100.07           A
ATOM   1606  C   ASN A 211       7.959  59.609  51.412  1.00100.07           A
ATOM   1607  O   ASN A 211       8.701  58.944  52.137  1.00100.07           A
ATOM   1608  N   GLN A 212       8.233  59.883  50.144  1.00 85.92           A
ATOM   1609  CA  GLN A 212       9.457  59.426  49.522  1.00 85.92           A
ATOM   1610  CB  GLN A 212       9.571  60.013  48.120  1.00100.07           A
ATOM   1611  CG  GLN A 212      10.776  59.549  47.342  1.00100.07           A
ATOM   1612  CD  GLN A 212      10.393  58.736  46.124  1.00100.07           A
ATOM   1613  OE1 GLN A 212       9.550  59.151  45.323  1.00100.07           A
ATOM   1614  NE2 GLN A 212      11.016  57.571  45.971  1.00100.07           A
ATOM   1615  C   GLN A 212      10.605  59.930  50.382  1.00 85.92           A
ATOM   1616  O   GLN A 212      11.534  59.186  50.703  1.00 85.92           A
ATOM   1617  N   ALA A 213      10.516  61.200  50.768  1.00 41.35           A
ATOM   1618  CA  ALA A 213      11.546  61.840  51.581  1.00 41.35           A
ATOM   1619  CB  ALA A 213      11.154  63.271  51.881  1.00 45.50           A
ATOM   1620  C   ALA A 213      11.828  61.112  52.883  1.00 41.35           A
ATOM   1621  O   ALA A 213      12.922  60.579  53.088  1.00 41.35           A
ATOM   1622  N   VAL A 214      10.829  61.112  53.761  1.00 83.40           A
ATOM   1623  CA  VAL A 214      10.925  60.472  55.069  1.00 83.40           A
ATOM   1624  CB  VAL A 214       9.521  60.254  55.678  1.00 48.39           A
ATOM   1625  CG1 VAL A 214       9.196  61.363  56.670  1.00 48.39           A
ATOM   1626  CG2 VAL A 214       8.486  60.244  54.582  1.00 48.39           A
ATOM   1627  C   VAL A 214      11.650  59.136  55.029  1.00 83.40           A
ATOM   1628  O   VAL A 214      12.493  58.839  55.881  1.00 83.40           A
ATOM   1629  N   ALA A 215      11.311  58.339  54.026  1.00 68.64           A
ATOM   1630  CA  ALA A 215      11.905  57.024  53.843  1.00 68.64           A
ATOM   1631  CB  ALA A 215      11.617  56.527  52.434  1.00100.07           A
ATOM   1632  C   ALA A 215      13.401  57.036  54.093  1.00 68.64           A
ATOM   1633  O   ALA A 215      13.874  56.577  55.129  1.00 68.64           A
ATOM   1634  N   ILE A 216      14.136  57.576  53.129  1.00 99.55           A
ATOM   1635  CA  ILE A 216      15.585  57.651  53.204  1.00 99.55           A
ATOM   1636  CB  ILE A 216      16.104  58.623  52.160  1.00 59.90           A
ATOM   1637  CG2 ILE A 216      17.570  58.348  51.892  1.00 59.90           A
ATOM   1638  CG1 ILE A 216      15.296  58.447  50.872  1.00 59.90           A
ATOM   1639  CD  ILE A 216      15.592  59.487  49.835  1.00 59.90           A
ATOM   1640  C   ILE A 216      16.060  58.067  54.590  1.00 99.55           A
ATOM   1641  O   ILE A 216      16.869  57.375  55.208  1.00 99.55           A
ATOM   1642  N   LEU A 217      15.547  59.193  55.074  1.00 64.91           A
```

```
ATOM   1643  CA   LEU A 217      15.903  59.698  56.394  1.00 64.91           A
ATOM   1644  CB   LEU A 217      14.980  60.861  56.762  1.00 37.93           A
ATOM   1645  CG   LEU A 217      14.969  61.401  58.195  1.00 37.93           A
ATOM   1646  CD1  LEU A 217      16.343  61.850  58.656  1.00 37.93           A
ATOM   1647  CD2  LEU A 217      14.007  62.561  58.228  1.00 37.93           A
ATOM   1648  C    LEU A 217      15.729  58.560  57.387  1.00 64.91           A
ATOM   1649  O    LEU A 217      16.632  58.242  58.164  1.00 64.91           A
ATOM   1650  N    LYS A 218      14.558  57.939  57.345  1.00 40.33           A
ATOM   1651  CA   LYS A 218      14.264  56.828  58.236  1.00 40.33           A
ATOM   1652  CB   LYS A 218      12.867  56.267  57.932  1.00100.07           A
ATOM   1653  CG   LYS A 218      12.883  55.002  57.080  1.00100.07           A
ATOM   1654  CD   LYS A 218      11.633  54.839  56.237  1.00100.07           A
ATOM   1655  CE   LYS A 218      11.820  53.728  55.201  1.00100.07           A
ATOM   1656  NZ   LYS A 218      10.636  53.558  54.307  1.00100.07           A
ATOM   1657  C    LYS A 218      15.313  55.737  58.027  1.00 40.33           A
ATOM   1658  O    LYS A 218      15.919  55.237  58.980  1.00 40.33           A
ATOM   1659  N    GLU A 219      15.509  55.399  56.752  1.00 47.87           A
ATOM   1660  CA   GLU A 219      16.434  54.370  56.286  1.00 47.87           A
ATOM   1661  CB   GLU A 219      16.394  54.331  54.759  1.00 87.82           A
ATOM   1662  CG   GLU A 219      17.156  53.201  54.110  1.00 87.82           A
ATOM   1663  CD   GLU A 219      16.986  53.206  52.595  1.00 87.82           A
ATOM   1664  OE1  GLU A 219      15.837  53.058  52.115  1.00 87.82           A
ATOM   1665  OE2  GLU A 219      18.000  53.364  51.882  1.00 87.82           A
ATOM   1666  C    GLU A 219      17.852  54.641  56.762  1.00 47.87           A
ATOM   1667  O    GLU A 219      18.588  53.716  57.096  1.00 47.87           A
ATOM   1668  N    HIS A 220      18.239  55.912  56.779  1.00 65.57           A
ATOM   1669  CA   HIS A 220      19.570  56.281  57.237  1.00 65.57           A
ATOM   1670  CB   HIS A 220      19.877  57.739  56.929  1.00 34.75           A
ATOM   1671  CG   HIS A 220      20.172  58.005  55.489  1.00 34.75           A
ATOM   1672  CD2  HIS A 220      19.422  58.576  54.516  1.00 34.75           A
ATOM   1673  ND1  HIS A 220      21.384  57.700  54.912  1.00 34.75           A
ATOM   1674  CE1  HIS A 220      21.369  58.076  53.645  1.00 34.75           A
ATOM   1675  NE2  HIS A 220      20.191  58.611  53.380  1.00 34.75           A
ATOM   1676  C    HIS A 220      19.613  56.090  58.735  1.00 65.57           A
ATOM   1677  O    HIS A 220      20.464  55.380  59.255  1.00 65.57           A
ATOM   1678  N    LEU A 221      18.688  56.748  59.422  1.00 50.48           A
ATOM   1679  CA   LEU A 221      18.591  56.645  60.869  1.00 50.48           A
ATOM   1680  CB   LEU A 221      17.158  56.994  61.308  1.00 48.41           A
ATOM   1681  CG   LEU A 221      16.772  58.342  61.941  1.00 48.41           A
ATOM   1682  CD1  LEU A 221      17.653  58.559  63.162  1.00 48.41           A
ATOM   1683  CD2  LEU A 221      16.900  59.501  60.954  1.00 48.41           A
ATOM   1684  C    LEU A 221      18.941  55.227  61.336  1.00 50.48           A
ATOM   1685  O    LEU A 221      19.723  55.030  62.272  1.00 50.48           A
ATOM   1686  N    ASN A 222      18.359  54.238  60.666  1.00 79.78           A
ATOM   1687  CA   ASN A 222      18.589  52.845  61.014  1.00 79.78           A
ATOM   1688  CB   ASN A 222      17.833  51.948  60.042  1.00 64.26           A
ATOM   1689  CG   ASN A 222      16.330  52.115  60.167  1.00 64.26           A
ATOM   1690  OD1  ASN A 222      15.777  52.007  61.261  1.00 64.26           A
ATOM   1691  ND2  ASN A 222      15.662  52.381  59.050  1.00 64.26           A
ATOM   1692  C    ASN A 222      20.057  52.466  61.093  1.00 79.78           A
ATOM   1693  O    ASN A 222      20.462  51.742  61.995  1.00 79.78           A
ATOM   1694  N    TYR A 223      20.859  52.971  60.166  1.00 81.32           A
ATOM   1695  CA   TYR A 223      22.280  52.670  60.169  1.00 81.32           A
ATOM   1696  CB   TYR A 223      23.029  53.617  59.234  1.00 81.85           A
ATOM   1697  CG   TYR A 223      22.680  53.484  57.769  1.00 81.85           A
ATOM   1698  CD1  TYR A 223      22.719  52.249  57.137  1.00 81.85           A
ATOM   1699  CE1  TYR A 223      22.450  52.132  55.795  1.00 81.85           A
ATOM   1700  CD2  TYR A 223      22.357  54.606  57.009  1.00 81.85           A
ATOM   1701  CE2  TYR A 223      22.087  54.502  55.669  1.00 81.85           A
ATOM   1702  CZ   TYR A 223      22.135  53.261  55.064  1.00 81.85           A
ATOM   1703  OH   TYR A 223      21.868  53.139  53.719  1.00 81.85           A
ATOM   1704  C    TYR A 223      22.867  52.786  61.574  1.00 81.32           A
ATOM   1705  O    TYR A 223      23.876  52.152  61.874  1.00 81.32           A
ATOM   1706  N    PHE A 224      22.243  53.589  62.436  1.00 65.20           A
ATOM   1707  CA   PHE A 224      22.755  53.765  63.799  1.00 65.20           A
ATOM   1708  CB   PHE A 224      22.110  54.988  64.473  1.00 70.91           A
ATOM   1709  CG   PHE A 224      22.403  56.303  63.781  1.00 70.91           A
ATOM   1710  CD1  PHE A 224      21.497  56.852  62.880  1.00 70.91           A
ATOM   1711  CD2  PHE A 224      23.596  56.977  64.015  1.00 70.91           A
ATOM   1712  CE1  PHE A 224      21.772  58.043  62.224  1.00 70.91           A
ATOM   1713  CE2  PHE A 224      23.878  58.168  63.362  1.00 70.91           A
ATOM   1714  CZ   PHE A 224      22.962  58.701  62.463  1.00 70.91           A
ATOM   1715  C    PHE A 224      22.515  52.510  64.644  1.00 65.20           A
ATOM   1716  O    PHE A 224      22.260  52.576  65.850  1.00 65.20           A
ATOM   1717  N    ALA A 225      22.621  51.362  63.987  1.00 42.35           A
ATOM   1718  CA   ALA A 225      22.412  50.070  64.618  1.00 42.35           A
ATOM   1719  CB   ALA A 225      22.202  49.004  63.547  1.00100.07           A
ATOM   1720  C    ALA A 225      23.563  49.668  65.522  1.00 42.35           A
ATOM   1721  O    ALA A 225      24.054  50.485  66.297  1.00 42.35           A
ATOM   1722  N    ASN A 226      23.981  48.404  65.421  1.00 61.29           A
ATOM   1723  CA   ASN A 226      25.074  47.880  66.240  1.00 61.29           A
ATOM   1724  CB   ASN A 226      25.162  46.352  66.127  1.00100.07           A
ATOM   1725  CG   ASN A 226      24.423  45.635  67.257  1.00100.07           A
ATOM   1726  OD1  ASN A 226      24.404  44.402  67.322  1.00100.07           A
```

```
ATOM   1727  ND2 ASN A 226      23.816  46.408  68.154  1.00100.07      A
ATOM   1728  C   ASN A 226      26.408  48.508  65.870  1.00 61.29      A
ATOM   1729  O   ASN A 226      26.799  48.521  64.706  1.00 61.29      A
ATOM   1730  N   PRO A 227      27.117  49.048  66.868  1.00 40.31      A
ATOM   1731  CD  PRO A 227      26.527  49.417  68.167  1.00 59.71      A
ATOM   1732  CA  PRO A 227      28.412  49.703  66.712  1.00 40.31      A
ATOM   1733  CB  PRO A 227      28.206  50.984  67.487  1.00 59.71      A
ATOM   1734  CG  PRO A 227      27.521  50.456  68.713  1.00 59.71      A
ATOM   1735  C   PRO A 227      29.549  48.893  67.313  1.00 40.31      A
ATOM   1736  O   PRO A 227      29.310  47.992  68.110  1.00 40.31      A
ATOM   1737  N   GLU A 228      30.784  49.246  66.962  1.00 59.63      A
ATOM   1738  CA  GLU A 228      31.964  48.552  67.476  1.00 59.63      A
ATOM   1739  CB  GLU A 228      32.915  48.224  66.326  1.00100.07      A
ATOM   1740  CG  GLU A 228      33.255  49.422  65.465  1.00100.07      A
ATOM   1741  CD  GLU A 228      34.162  49.065  64.309  1.00100.07      A
ATOM   1742  OE1 GLU A 228      33.737  48.260  63.448  1.00100.07      A
ATOM   1743  OE2 GLU A 228      35.299  49.592  64.265  1.00100.07      A
ATOM   1744  C   GLU A 228      32.684  49.388  68.534  1.00 59.63      A
ATOM   1745  O   GLU A 228      32.123  49.679  69.587  1.00 59.63      A
ATOM   1746  N   ALA A 229      33.934  49.743  68.247  1.00100.07      A
ATOM   1747  CA  ALA A 229      34.773  50.566  69.119  1.00100.07      A
ATOM   1748  CB  ALA A 229      34.435  52.038  68.894  1.00 56.47      A
ATOM   1749  C   ALA A 229      34.789  50.255  70.622  1.00100.07      A
ATOM   1750  O   ALA A 229      34.070  49.374  71.102  1.00100.07      A
ATOM   1751  N   SER A 230      35.639  50.989  71.346  1.00100.07      A
ATOM   1752  CA  SER A 230      35.799  50.856  72.800  1.00100.07      A
ATOM   1753  CB  SER A 230      37.154  50.233  73.130  1.00 57.13      A
ATOM   1754  OG  SER A 230      37.372  50.230  74.531  1.00 57.13      A
ATOM   1755  C   SER A 230      35.685  52.219  73.501  1.00100.07      A
ATOM   1756  O   SER A 230      34.764  52.982  73.219  1.00100.07      A
ATOM   1757  N   ALA A 231      36.612  52.528  74.411  1.00100.07      A
ATOM   1758  CA  ALA A 231      36.574  53.813  75.124  1.00100.07      A
ATOM   1759  CB  ALA A 231      35.302  53.907  75.890  1.00 66.54      A
ATOM   1760  C   ALA A 231      37.742  54.071  76.077  1.00100.07      A
ATOM   1761  O   ALA A 231      38.231  53.088  76.677  1.00100.07      A
ATOM   1762  OT  ALA A 231      38.121  55.259  76.240  1.00 66.54      A
ATOM   1763  CB  ALA B   6      27.155  51.553  47.423  1.00 79.56      B
ATOM   1764  C   ALA B   6      27.338  52.268  49.835  1.00100.07      B
ATOM   1765  O   ALA B   6      28.190  51.919  50.660  1.00100.07      B
ATOM   1766  N   ALA B   6      29.209  52.643  48.225  1.00100.07      B
ATOM   1767  CA  ALA B   6      27.726  52.605  48.381  1.00100.07      B
ATOM   1768  N   ALA B   7      26.035  52.373  50.100  1.00100.07      B
ATOM   1769  CA  ALA B   7      25.360  52.131  51.384  1.00100.07      B
ATOM   1770  CB  ALA B   7      23.995  51.490  51.113  1.00 82.99      B
ATOM   1771  C   ALA B   7      26.025  51.387  52.545  1.00100.07      B
ATOM   1772  O   ALA B   7      27.244  51.216  52.605  1.00100.07      B
ATOM   1773  N   ALA B   8      25.168  50.977  53.481  1.00 78.31      B
ATOM   1774  CA  ALA B   8      25.552  50.243  54.678  1.00 78.31      B
ATOM   1775  CB  ALA B   8      25.669  48.777  54.336  1.00 59.34      B
ATOM   1776  C   ALA B   8      26.836  50.736  55.352  1.00 78.31      B
ATOM   1777  O   ALA B   8      27.845  50.037  55.357  1.00 78.31      B
ATOM   1778  N   PRO B   9      26.808  51.938  55.956  1.00 67.12      B
ATOM   1779  CD  PRO B   9      25.683  52.886  56.059  1.00 58.31      B
ATOM   1780  CA  PRO B   9      27.999  52.480  56.619  1.00 67.12      B
ATOM   1781  CB  PRO B   9      27.659  53.954  56.775  1.00 58.31      B
ATOM   1782  CG  PRO B   9      26.204  53.908  57.060  1.00 58.31      B
ATOM   1783  C   PRO B   9      28.303  51.814  57.958  1.00 67.12      B
ATOM   1784  O   PRO B   9      27.549  50.963  58.428  1.00 67.12      B
ATOM   1785  N   VAL B  10      29.413  52.213  58.568  1.00 72.37      B
ATOM   1786  CA  VAL B  10      29.830  51.657  59.847  1.00 72.37      B
ATOM   1787  CB  VAL B  10      31.334  51.424  59.891  1.00 48.12      B
ATOM   1788  CG1 VAL B  10      31.740  50.974  61.282  1.00 48.12      B
ATOM   1789  CG2 VAL B  10      31.730  50.403  58.846  1.00 48.12      B
ATOM   1790  C   VAL B  10      29.508  52.578  60.995  1.00 72.37      B
ATOM   1791  O   VAL B  10      29.775  53.771  60.912  1.00 72.37      B
ATOM   1792  N   PHE B  11      28.978  52.017  62.079  1.00 72.74      B
ATOM   1793  CA  PHE B  11      28.611  52.808  63.247  1.00 72.74      B
ATOM   1794  CB  PHE B  11      27.223  52.372  63.731  1.00 78.84      B
ATOM   1795  CG  PHE B  11      26.595  53.303  64.734  1.00 78.84      B
ATOM   1796  CD1 PHE B  11      26.622  54.678  64.544  1.00 78.84      B
ATOM   1797  CD2 PHE B  11      25.941  52.795  65.860  1.00 78.84      B
ATOM   1798  CE1 PHE B  11      26.005  55.533  65.461  1.00 78.84      B
ATOM   1799  CE2 PHE B  11      25.321  53.640  66.783  1.00 78.84      B
ATOM   1800  CZ  PHE B  11      25.352  55.010  66.584  1.00 78.84      B
ATOM   1801  C   PHE B  11      29.637  52.713  64.373  1.00 72.74      B
ATOM   1802  O   PHE B  11      29.281  52.462  65.514  1.00 72.74      B
ATOM   1803  N   THR B  12      30.914  52.911  64.040  1.00 59.90      B
ATOM   1804  CA  THR B  12      31.999  52.875  65.029  1.00 59.90      B
ATOM   1805  CB  THR B  12      33.338  53.340  64.411  1.00100.07      B
ATOM   1806  OG1 THR B  12      33.135  54.564  63.690  1.00100.07      B
ATOM   1807  CG2 THR B  12      33.889  52.283  63.463  1.00100.07      B
ATOM   1808  C   THR B  12      31.633  53.800  66.185  1.00 59.90      B
ATOM   1809  O   THR B  12      31.427  54.996  65.986  1.00 59.90      B
ATOM   1810  N   ALA B  13      31.547  53.251  67.391  1.00 48.11      B
```

| | | | | | | | | | | |
|---|---|---|---|---|---|---|---|---|---|---|
| ATOM | 1811 | CA | ALA | B | 13 | 31.168 | 54.063 | 68.538 | 1.00 48.11 | B |
| ATOM | 1812 | CB | ALA | B | 13 | 29.736 | 53.737 | 68.962 | 1.00 30.65 | B |
| ATOM | 1813 | C | ALA | B | 13 | 32.093 | 53.927 | 69.730 | 1.00 48.11 | B |
| ATOM | 1814 | O | ALA | B | 13 | 31.844 | 53.126 | 70.634 | 1.00 48.11 | B |
| ATOM | 1815 | N | THR | B | 14 | 33.160 | 54.719 | 69.734 | 1.00 65.33 | B |
| ATOM | 1816 | CA | THR | B | 14 | 34.104 | 54.698 | 70.838 | 1.00 65.33 | B |
| ATOM | 1817 | CB | THR | B | 14 | 35.351 | 55.548 | 70.521 | 1.00100.07 | B |
| ATOM | 1818 | OG1 | THR | B | 14 | 35.977 | 55.053 | 69.327 | 1.00100.07 | B |
| ATOM | 1819 | CG2 | THR | B | 14 | 36.345 | 55.480 | 71.673 | 1.00100.07 | B |
| ATOM | 1820 | C | THR | B | 14 | 33.379 | 55.242 | 72.073 | 1.00 65.33 | B |
| ATOM | 1821 | O | THR | B | 14 | 33.225 | 56.451 | 72.243 | 1.00 65.33 | B |
| ATOM | 1822 | N | THR | B | 15 | 32.920 | 54.316 | 72.909 | 1.00100.01 | B |
| ATOM | 1823 | CA | THR | B | 15 | 32.182 | 54.596 | 74.137 | 1.00100.01 | B |
| ATOM | 1824 | CB | THR | B | 15 | 31.609 | 53.294 | 74.719 | 1.00100.07 | B |
| ATOM | 1825 | OG1 | THR | B | 15 | 32.638 | 52.611 | 75.448 | 1.00100.07 | B |
| ATOM | 1826 | CG2 | THR | B | 15 | 31.115 | 52.377 | 73.599 | 1.00100.07 | B |
| ATOM | 1827 | C | THR | B | 15 | 33.032 | 55.232 | 75.232 | 1.00100.01 | B |
| ATOM | 1828 | O | THR | B | 15 | 33.978 | 55.961 | 74.950 | 1.00100.01 | B |
| ATOM | 1829 | N | GLN | B | 16 | 32.689 | 54.900 | 76.482 | 1.00 99.07 | B |
| ATOM | 1830 | CA | GLN | B | 16 | 33.371 | 55.391 | 77.688 | 1.00 99.07 | B |
| ATOM | 1831 | CB | GLN | B | 16 | 33.434 | 56.926 | 77.678 | 1.00 91.47 | B |
| ATOM | 1832 | CG | GLN | B | 16 | 34.322 | 57.534 | 78.750 | 1.00 91.47 | B |
| ATOM | 1833 | CD | GLN | B | 16 | 35.695 | 56.888 | 78.811 | 1.00 91.47 | B |
| ATOM | 1834 | OE1 | GLN | B | 16 | 36.428 | 56.856 | 77.822 | 1.00 91.47 | B |
| ATOM | 1835 | NE2 | GLN | B | 16 | 36.049 | 56.369 | 79.980 | 1.00 91.47 | B |
| ATOM | 1836 | C | GLN | B | 16 | 32.578 | 54.891 | 78.905 | 1.00 99.07 | B |
| ATOM | 1837 | O | GLN | B | 16 | 31.914 | 53.853 | 78.821 | 1.00 99.07 | B |
| ATOM | 1838 | N | GLY | B | 17 | 32.662 | 55.606 | 80.029 | 1.00100.07 | B |
| ATOM | 1839 | CA | GLY | B | 17 | 31.908 | 55.232 | 81.220 | 1.00100.07 | B |
| ATOM | 1840 | C | GLY | B | 17 | 30.481 | 55.693 | 80.971 | 1.00100.07 | B |
| ATOM | 1841 | O | GLY | B | 17 | 29.639 | 54.897 | 80.556 | 1.00100.07 | B |
| ATOM | 1842 | N | ASP | B | 18 | 30.194 | 56.968 | 81.230 | 1.00 77.15 | B |
| ATOM | 1843 | CA | ASP | B | 18 | 28.868 | 57.503 | 80.932 | 1.00 77.15 | B |
| ATOM | 1844 | CB | ASP | B | 18 | 27.875 | 57.280 | 82.090 | 1.00100.07 | B |
| ATOM | 1845 | CG | ASP | B | 18 | 28.244 | 58.021 | 83.349 | 1.00100.07 | B |
| ATOM | 1846 | OD1 | ASP | B | 18 | 29.429 | 57.976 | 83.735 | 1.00100.07 | B |
| ATOM | 1847 | OD2 | ASP | B | 18 | 27.333 | 58.627 | 83.962 | 1.00100.07 | B |
| ATOM | 1848 | C | ASP | B | 18 | 28.890 | 58.957 | 80.473 | 1.00 77.15 | B |
| ATOM | 1849 | O | ASP | B | 18 | 28.073 | 59.786 | 80.870 | 1.00 77.15 | B |
| ATOM | 1850 | N | HIS | B | 19 | 29.848 | 59.231 | 79.596 | 1.00 59.01 | B |
| ATOM | 1851 | CA | HIS | B | 19 | 30.036 | 60.536 | 79.001 | 1.00 59.01 | B |
| ATOM | 1852 | CB | HIS | B | 19 | 30.554 | 61.546 | 80.031 | 1.00 99.93 | B |
| ATOM | 1853 | CG | HIS | B | 19 | 31.642 | 61.027 | 80.915 | 1.00 99.93 | B |
| ATOM | 1854 | CD2 | HIS | B | 19 | 32.186 | 59.794 | 81.041 | 1.00 99.93 | B |
| ATOM | 1855 | ND1 | HIS | B | 19 | 32.300 | 61.829 | 81.823 | 1.00 99.93 | B |
| ATOM | 1856 | CE1 | HIS | B | 19 | 33.202 | 61.113 | 82.469 | 1.00 99.93 | B |
| ATOM | 1857 | NE2 | HIS | B | 19 | 33.153 | 59.874 | 82.014 | 1.00 99.93 | B |
| ATOM | 1858 | C | HIS | B | 19 | 30.952 | 60.441 | 77.799 | 1.00 59.01 | B |
| ATOM | 1859 | O | HIS | B | 19 | 31.723 | 59.490 | 77.653 | 1.00 59.01 | B |
| ATOM | 1860 | N | TYR | B | 20 | 30.841 | 61.432 | 76.927 | 1.00 64.52 | B |
| ATOM | 1861 | CA | TYR | B | 20 | 31.639 | 61.483 | 75.712 | 1.00 64.52 | B |
| ATOM | 1862 | CB | TYR | B | 20 | 33.132 | 61.667 | 76.040 | 1.00 86.15 | B |
| ATOM | 1863 | CG | TYR | B | 20 | 33.940 | 62.278 | 74.909 | 1.00 86.15 | B |
| ATOM | 1864 | CD1 | TYR | B | 20 | 35.331 | 62.327 | 74.965 | 1.00 86.15 | B |
| ATOM | 1865 | CE1 | TYR | B | 20 | 36.076 | 62.865 | 73.911 | 1.00 86.15 | B |
| ATOM | 1866 | CD2 | TYR | B | 20 | 33.313 | 62.790 | 73.773 | 1.00 86.15 | B |
| ATOM | 1867 | CE2 | TYR | B | 20 | 34.046 | 63.325 | 72.724 | 1.00 86.15 | B |
| ATOM | 1868 | CZ | TYR | B | 20 | 35.420 | 63.359 | 72.794 | 1.00 86.15 | B |
| ATOM | 1869 | OH | TYR | B | 20 | 36.128 | 63.872 | 71.735 | 1.00 86.15 | B |
| ATOM | 1870 | C | TYR | B | 20 | 31.415 | 60.178 | 74.973 | 1.00 64.52 | B |
| ATOM | 1871 | O | TYR | B | 20 | 32.296 | 59.325 | 74.909 | 1.00 64.52 | B |
| ATOM | 1872 | N | GLY | B | 21 | 30.212 | 60.024 | 74.437 | 1.00 99.59 | B |
| ATOM | 1873 | CA | GLY | B | 21 | 29.896 | 58.823 | 73.700 | 1.00 99.59 | B |
| ATOM | 1874 | C | GLY | B | 21 | 30.171 | 59.065 | 72.238 | 1.00 99.59 | B |
| ATOM | 1875 | O | GLY | B | 21 | 29.258 | 59.179 | 71.429 | 1.00 99.59 | B |
| ATOM | 1876 | N | GLU | B | 22 | 31.444 | 59.186 | 71.901 | 1.00 60.24 | B |
| ATOM | 1877 | CA | GLU | B | 22 | 31.824 | 59.388 | 70.519 | 1.00 60.24 | B |
| ATOM | 1878 | CB | GLU | B | 22 | 33.345 | 59.257 | 70.402 | 1.00 99.88 | B |
| ATOM | 1879 | CG | GLU | B | 22 | 33.884 | 59.121 | 68.987 | 1.00 99.88 | B |
| ATOM | 1880 | CD | GLU | B | 22 | 33.951 | 57.676 | 68.499 | 1.00 99.88 | B |
| ATOM | 1881 | OE1 | GLU | B | 22 | 32.894 | 57.011 | 68.410 | 1.00 99.88 | B |
| ATOM | 1882 | OE2 | GLU | B | 22 | 35.074 | 57.206 | 68.195 | 1.00 99.88 | B |
| ATOM | 1883 | C | GLU | B | 22 | 31.118 | 58.294 | 69.716 | 1.00 60.24 | B |
| ATOM | 1884 | O | GLU | B | 22 | 31.180 | 57.111 | 70.060 | 1.00 60.24 | B |
| ATOM | 1885 | N | PHE | B | 23 | 30.427 | 58.703 | 68.661 | 1.00 68.91 | B |
| ATOM | 1886 | CA | PHE | B | 23 | 29.709 | 57.786 | 67.792 | 1.00 68.91 | B |
| ATOM | 1887 | CB | PHE | B | 23 | 28.222 | 57.955 | 68.023 | 1.00 73.38 | B |
| ATOM | 1888 | CG | PHE | B | 23 | 27.833 | 57.680 | 69.426 | 1.00 73.38 | B |
| ATOM | 1889 | CD1 | PHE | B | 23 | 26.914 | 58.480 | 70.082 | 1.00 73.38 | B |
| ATOM | 1890 | CD2 | PHE | B | 23 | 28.437 | 56.634 | 70.118 | 1.00 73.38 | B |
| ATOM | 1891 | CE1 | PHE | B | 23 | 26.601 | 58.245 | 71.421 | 1.00 73.38 | B |
| ATOM | 1892 | CE2 | PHE | B | 23 | 28.139 | 56.387 | 71.446 | 1.00 73.38 | B |
| ATOM | 1893 | CZ | PHE | B | 23 | 27.217 | 57.194 | 72.105 | 1.00 73.38 | B |
| ATOM | 1894 | C | PHE | B | 23 | 30.110 | 58.192 | 66.394 | 1.00 68.91 | B |

-23-

```
ATOM   1895  O    PHE B  23      30.427  59.359  66.170  1.00 68.91           B
ATOM   1896  N    VAL B  24      30.125  57.249  65.455  1.00 81.71           B
ATOM   1897  CA   VAL B  24      30.531  57.594  64.095  1.00 81.71           B
ATOM   1898  CB   VAL B  24      32.070  57.615  63.953  1.00  8.17           B
ATOM   1899  CG1  VAL B  24      32.448  57.871  62.510  1.00  8.17           B
ATOM   1900  CG2  VAL B  24      32.667  58.680  64.852  1.00  8.17           B
ATOM   1901  C    VAL B  24      30.036  56.748  62.936  1.00 81.71           B
ATOM   1902  O    VAL B  24      30.568  55.667  62.698  1.00 81.71           B
ATOM   1903  N    LEU B  25      29.035  57.236  62.208  1.00 73.45           B
ATOM   1904  CA   LEU B  25      28.584  56.505  61.036  1.00 73.45           B
ATOM   1905  CB   LEU B  25      27.119  56.808  60.684  1.00 20.54           B
ATOM   1906  CG   LEU B  25      26.676  58.027  59.875  1.00 20.54           B
ATOM   1907  CD1  LEU B  25      27.419  58.135  58.550  1.00 20.54           B
ATOM   1908  CD2  LEU B  25      25.182  57.890  59.639  1.00 20.54           B
ATOM   1909  C    LEU B  25      29.557  57.067  60.007  1.00 73.45           B
ATOM   1910  O    LEU B  25      29.912  58.241  60.086  1.00 73.45           B
ATOM   1911  N    GLU B  26      29.986  56.257  59.044  1.00100.07           B
ATOM   1912  CA   GLU B  26      30.984  56.734  58.100  1.00100.07           B
ATOM   1913  CB   GLU B  26      32.048  55.648  57.958  1.00 99.35           B
ATOM   1914  CG   GLU B  26      33.440  56.186  57.747  1.00 99.35           B
ATOM   1915  CD   GLU B  26      34.499  55.165  58.101  1.00 99.35           B
ATOM   1916  OE1  GLU B  26      34.482  54.054  57.519  1.00 99.35           B
ATOM   1917  OE2  GLU B  26      35.348  55.473  58.967  1.00 99.35           B
ATOM   1918  C    GLU B  26      30.568  57.311  56.738  1.00100.07           B
ATOM   1919  O    GLU B  26      30.080  58.440  56.690  1.00100.07           B
ATOM   1920  N    PRO B  27      30.744  56.575  55.619  1.00 70.02           B
ATOM   1921  CD   PRO B  27      31.438  55.321  55.290  1.00 23.02           B
ATOM   1922  CA   PRO B  27      30.323  57.235  54.379  1.00 70.02           B
ATOM   1923  CB   PRO B  27      30.851  56.310  53.288  1.00 23.02           B
ATOM   1924  CG   PRO B  27      32.009  55.647  53.931  1.00 23.02           B
ATOM   1925  C    PRO B  27      28.837  57.482  54.213  1.00 70.02           B
ATOM   1926  O    PRO B  27      28.011  56.617  54.484  1.00 70.02           B
ATOM   1927  N    LEU B  28      28.520  58.683  53.755  1.00 44.22           B
ATOM   1928  CA   LEU B  28      27.157  59.101  53.491  1.00 44.22           B
ATOM   1929  CB   LEU B  28      26.538  59.786  54.702  1.00 59.23           B
ATOM   1930  CG   LEU B  28      26.298  58.974  55.970  1.00 59.23           B
ATOM   1931  CD1  LEU B  28      25.541  59.835  56.960  1.00 59.23           B
ATOM   1932  CD2  LEU B  28      25.506  57.721  55.656  1.00 59.23           B
ATOM   1933  C    LEU B  28      27.267  60.096  52.354  1.00 44.22           B
ATOM   1934  O    LEU B  28      28.034  61.055  52.445  1.00 44.22           B
ATOM   1935  N    GLU B  29      26.525  59.867  51.277  1.00 55.67           B
ATOM   1936  CA   GLU B  29      26.566  60.777  50.138  1.00 55.67           B
ATOM   1937  CB   GLU B  29      25.359  60.531  49.226  1.00 99.81           B
ATOM   1938  CG   GLU B  29      25.318  61.360  47.942  1.00 99.81           B
ATOM   1939  CD   GLU B  29      26.308  60.890  46.890  1.00 99.81           B
ATOM   1940  OE1  GLU B  29      27.528  61.069  47.097  1.00 99.81           B
ATOM   1941  OE2  GLU B  29      25.860  60.339  45.857  1.00 99.81           B
ATOM   1942  C    GLU B  29      26.534  62.204  50.690  1.00 55.67           B
ATOM   1943  O    GLU B  29      25.783  62.504  51.626  1.00 55.67           B
ATOM   1944  N    ARG B  30      27.358  63.077  50.120  1.00 83.37           B
ATOM   1945  CA   ARG B  30      27.434  64.451  50.593  1.00 83.37           B
ATOM   1946  CB   ARG B  30      28.133  65.358  49.576  1.00100.07           B
ATOM   1947  CG   ARG B  30      27.367  65.502  48.289  1.00100.07           B
ATOM   1948  CD   ARG B  30      27.615  66.840  47.621  1.00100.07           B
ATOM   1949  NE   ARG B  30      26.938  66.895  46.326  1.00100.07           B
ATOM   1950  CZ   ARG B  30      26.924  67.957  45.531  1.00100.07           B
ATOM   1951  NH1  ARG B  30      27.547  69.067  45.901  1.00100.07           B
ATOM   1952  NH2  ARG B  30      26.304  67.901  44.360  1.00100.07           B
ATOM   1953  C    ARG B  30      26.059  65.018  50.892  1.00 83.37           B
ATOM   1954  O    ARG B  30      25.145  64.948  50.067  1.00 83.37           B
ATOM   1955  N    GLY B  31      25.910  65.559  52.094  1.00 49.44           B
ATOM   1956  CA   GLY B  31      24.651  66.165  52.449  1.00 49.44           B
ATOM   1957  C    GLY B  31      23.870  65.507  53.561  1.00 49.44           B
ATOM   1958  O    GLY B  31      22.820  66.018  53.934  1.00 49.44           B
ATOM   1959  N    PHE B  32      24.340  64.390  54.106  1.00 58.66           B
ATOM   1960  CA   PHE B  32      23.569  63.761  55.172  1.00 58.66           B
ATOM   1961  CB   PHE B  32      23.214  62.318  54.798  1.00 45.85           B
ATOM   1962  CG   PHE B  32      22.292  62.218  53.610  1.00 45.85           B
ATOM   1963  CD1  PHE B  32      21.055  62.856  53.619  1.00 45.85           B
ATOM   1964  CD2  PHE B  32      22.681  61.542  52.457  1.00 45.85           B
ATOM   1965  CE1  PHE B  32      20.220  62.831  52.489  1.00 45.85           B
ATOM   1966  CE2  PHE B  32      21.849  61.512  51.322  1.00 45.85           B
ATOM   1967  CZ   PHE B  32      20.618  62.160  51.342  1.00 45.85           B
ATOM   1968  C    PHE B  32      24.227  63.814  56.532  1.00 58.66           B
ATOM   1969  O    PHE B  32      23.565  63.645  57.549  1.00 58.66           B
ATOM   1970  N    GLY B  33      25.529  64.054  56.556  1.00 34.05           B
ATOM   1971  CA   GLY B  33      26.207  64.160  57.831  1.00 34.05           B
ATOM   1972  C    GLY B  33      25.363  65.108  58.647  1.00 34.05           B
ATOM   1973  O    GLY B  33      24.979  64.805  59.766  1.00 34.05           B
ATOM   1974  N    VAL B  34      25.042  66.244  58.040  1.00 70.95           B
ATOM   1975  CA   VAL B  34      24.234  67.296  58.651  1.00 70.95           B
ATOM   1976  CB   VAL B  34      24.452  68.648  57.902  1.00 46.05           B
ATOM   1977  CG1  VAL B  34      23.311  69.620  58.172  1.00 46.05           B
ATOM   1978  CG2  VAL B  34      25.764  69.259  58.336  1.00 46.05           B
```

| | | | | | | | | | | |
|---|---|---|---|---|---|---|---|---|---|---|
| ATOM | 1979 | C | VAL | B | 34 | 22.737 | 67.005 | 58.676 | 1.00 70.95 | B |
| ATOM | 1980 | O | VAL | B | 34 | 22.072 | 67.333 | 59.657 | 1.00 70.95 | B |
| ATOM | 1981 | N | THR | B | 35 | 22.202 | 66.411 | 57.609 | 1.00 92.67 | B |
| ATOM | 1982 | CA | THR | B | 35 | 20.769 | 66.136 | 57.569 | 1.00 92.67 | B |
| ATOM | 1983 | CB | THR | B | 35 | 20.329 | 65.470 | 56.254 | 1.00 31.42 | B |
| ATOM | 1984 | OG1 | THR | B | 35 | 20.804 | 66.240 | 55.146 | 1.00 31.42 | B |
| ATOM | 1985 | CG2 | THR | B | 35 | 18.800 | 65.441 | 56.171 | 1.00 31.42 | B |
| ATOM | 1986 | C | THR | B | 35 | 20.357 | 65.284 | 58.756 | 1.00 92.67 | B |
| ATOM | 1987 | O | THR | B | 35 | 19.205 | 65.294 | 59.170 | 1.00 92.67 | B |
| ATOM | 1988 | N | LEU | B | 36 | 21.306 | 64.533 | 59.290 | 1.00 29.62 | B |
| ATOM | 1989 | CA | LEU | B | 36 | 21.080 | 63.741 | 60.496 | 1.00 29.62 | B |
| ATOM | 1990 | CB | LEU | B | 36 | 21.480 | 62.274 | 60.310 | 1.00 35.43 | B |
| ATOM | 1991 | CG | LEU | B | 36 | 20.969 | 61.455 | 59.122 | 1.00 35.43 | B |
| ATOM | 1992 | CD1 | LEU | B | 36 | 21.285 | 59.989 | 59.391 | 1.00 35.43 | B |
| ATOM | 1993 | CD2 | LEU | B | 36 | 19.476 | 61.644 | 58.921 | 1.00 35.43 | B |
| ATOM | 1994 | C | LEU | B | 36 | 22.121 | 64.420 | 61.369 | 1.00 29.62 | B |
| ATOM | 1995 | O | LEU | B | 36 | 22.434 | 65.583 | 61.138 | 1.00 29.62 | B |
| ATOM | 1996 | N | GLY | B | 37 | 22.685 | 63.722 | 62.342 | 1.00100.07 | B |
| ATOM | 1997 | CA | GLY | B | 37 | 23.714 | 64.353 | 63.147 | 1.00100.07 | B |
| ATOM | 1998 | C | GLY | B | 37 | 23.376 | 65.699 | 63.763 | 1.00100.07 | B |
| ATOM | 1999 | O | GLY | B | 37 | 24.056 | 66.134 | 64.688 | 1.00100.07 | B |
| ATOM | 2000 | N | ASN | B | 38 | 22.349 | 66.369 | 63.252 | 1.00 74.19 | B |
| ATOM | 2001 | CA | ASN | B | 38 | 21.927 | 67.656 | 63.792 | 1.00 74.19 | B |
| ATOM | 2002 | CB | ASN | B | 38 | 21.734 | 68.669 | 62.668 | 1.00 66.42 | B |
| ATOM | 2003 | CG | ASN | B | 38 | 21.004 | 69.900 | 63.128 | 1.00 66.42 | B |
| ATOM | 2004 | OD1 | ASN | B | 38 | 19.779 | 69.895 | 63.254 | 1.00 66.42 | B |
| ATOM | 2005 | ND2 | ASN | B | 38 | 21.748 | 70.962 | 63.399 | 1.00 66.42 | B |
| ATOM | 2006 | C | ASN | B | 38 | 20.641 | 67.489 | 64.622 | 1.00 74.19 | B |
| ATOM | 2007 | O | ASN | B | 38 | 20.634 | 67.848 | 65.804 | 1.00 74.19 | B |
| ATOM | 2008 | N | PRO | B | 39 | 19.540 | 66.953 | 64.023 | 1.00 63.64 | B |
| ATOM | 2009 | CD | PRO | B | 39 | 19.280 | 66.698 | 62.591 | 1.00 38.03 | B |
| ATOM | 2010 | CA | PRO | B | 39 | 18.300 | 66.762 | 64.787 | 1.00 63.64 | B |
| ATOM | 2011 | CB | PRO | B | 39 | 17.389 | 66.067 | 63.778 | 1.00 38.03 | B |
| ATOM | 2012 | CG | PRO | B | 39 | 17.756 | 66.727 | 62.514 | 1.00 38.03 | B |
| ATOM | 2013 | C | PRO | B | 39 | 18.553 | 65.901 | 66.036 | 1.00 63.64 | B |
| ATOM | 2014 | O | PRO | B | 39 | 17.856 | 66.026 | 67.045 | 1.00 63.64 | B |
| ATOM | 2015 | N | LEU | B | 40 | 19.556 | 65.029 | 65.960 | 1.00 37.49 | B |
| ATOM | 2016 | CA | LEU | B | 40 | 19.912 | 64.169 | 67.088 | 1.00 37.49 | B |
| ATOM | 2017 | CB | LEU | B | 40 | 20.729 | 62.953 | 66.623 | 1.00 37.14 | B |
| ATOM | 2018 | CG | LEU | B | 40 | 20.066 | 61.926 | 65.699 | 1.00 37.14 | B |
| ATOM | 2019 | CD1 | LEU | B | 40 | 19.043 | 61.090 | 66.451 | 1.00 37.14 | B |
| ATOM | 2020 | CD2 | LEU | B | 40 | 19.425 | 62.664 | 64.524 | 1.00 37.14 | B |
| ATOM | 2021 | C | LEU | B | 40 | 20.711 | 64.951 | 68.131 | 1.00 37.49 | B |
| ATOM | 2022 | O | LEU | B | 40 | 21.082 | 64.419 | 69.179 | 1.00 37.49 | B |
| ATOM | 2023 | N | ALA | B | 41 | 20.997 | 66.209 | 67.819 | 1.00 46.88 | B |
| ATOM | 2024 | CA | ALA | B | 41 | 21.713 | 67.088 | 68.732 | 1.00 46.88 | B |
| ATOM | 2025 | CB | ALA | B | 41 | 22.657 | 68.005 | 67.956 | 1.00 38.70 | B |
| ATOM | 2026 | C | ALA | B | 41 | 20.575 | 67.892 | 69.333 | 1.00 46.88 | B |
| ATOM | 2027 | O | ALA | B | 41 | 20.412 | 67.984 | 70.551 | 1.00 46.88 | B |
| ATOM | 2028 | N | ARG | B | 42 | 19.771 | 68.452 | 68.443 | 1.00 83.52 | B |
| ATOM | 2029 | CA | ARG | B | 42 | 18.626 | 69.239 | 68.838 | 1.00 83.52 | B |
| ATOM | 2030 | CB | ARG | B | 42 | 17.852 | 69.664 | 67.588 | 1.00 47.50 | B |
| ATOM | 2031 | CG | ARG | B | 42 | 16.967 | 70.854 | 67.795 | 1.00 47.50 | B |
| ATOM | 2032 | CD | ARG | B | 42 | 16.745 | 71.594 | 66.505 | 1.00 47.50 | B |
| ATOM | 2033 | NE | ARG | B | 42 | 16.086 | 72.869 | 66.766 | 1.00 47.50 | B |
| ATOM | 2034 | CZ | ARG | B | 42 | 16.180 | 73.943 | 65.982 | 1.00 47.50 | B |
| ATOM | 2035 | NH1 | ARG | B | 42 | 16.915 | 73.896 | 64.872 | 1.00 47.50 | B |
| ATOM | 2036 | NH2 | ARG | B | 42 | 15.538 | 75.068 | 66.304 | 1.00 47.50 | B |
| ATOM | 2037 | C | ARG | B | 42 | 17.763 | 68.393 | 69.767 | 1.00 83.52 | B |
| ATOM | 2038 | O | ARG | B | 42 | 17.449 | 68.810 | 70.880 | 1.00 83.52 | B |
| ATOM | 2039 | N | ILE | B | 43 | 17.402 | 67.193 | 69.323 | 1.00 45.38 | B |
| ATOM | 2040 | CA | ILE | B | 43 | 16.582 | 66.310 | 70.144 | 1.00 45.38 | B |
| ATOM | 2041 | CB | ILE | B | 43 | 16.111 | 65.095 | 69.327 | 1.00 28.38 | B |
| ATOM | 2042 | CG2 | ILE | B | 43 | 15.238 | 64.199 | 70.162 | 1.00 28.38 | B |
| ATOM | 2043 | CG1 | ILE | B | 43 | 15.302 | 65.586 | 68.134 | 1.00 28.38 | B |
| ATOM | 2044 | CD | ILE | B | 43 | 14.384 | 66.738 | 68.483 | 1.00 28.38 | B |
| ATOM | 2045 | C | ILE | B | 43 | 17.365 | 65.859 | 71.362 | 1.00 45.38 | B |
| ATOM | 2046 | O | ILE | B | 43 | 16.832 | 65.822 | 72.461 | 1.00 45.38 | B |
| ATOM | 2047 | N | LEU | B | 44 | 18.641 | 65.546 | 71.159 | 1.00 45.50 | B |
| ATOM | 2048 | CA | LEU | B | 44 | 19.514 | 65.096 | 72.235 | 1.00 45.50 | B |
| ATOM | 2049 | CB | LEU | B | 44 | 20.947 | 64.963 | 71.711 | 1.00 98.53 | B |
| ATOM | 2050 | CG | LEU | B | 44 | 21.892 | 63.909 | 72.293 | 1.00 98.53 | B |
| ATOM | 2051 | CD1 | LEU | B | 44 | 21.212 | 63.119 | 73.402 | 1.00 98.53 | B |
| ATOM | 2052 | CD2 | LEU | B | 44 | 22.317 | 62.980 | 71.177 | 1.00 98.53 | B |
| ATOM | 2053 | C | LEU | B | 44 | 19.486 | 66.066 | 73.405 | 1.00 45.50 | B |
| ATOM | 2054 | O | LEU | B | 44 | 19.348 | 65.647 | 74.557 | 1.00 45.50 | B |
| ATOM | 2055 | N | LEU | B | 45 | 19.627 | 67.359 | 73.102 | 1.00 99.98 | B |
| ATOM | 2056 | CA | LEU | B | 45 | 19.623 | 68.414 | 74.119 | 1.00 99.98 | B |
| ATOM | 2057 | CB | LEU | B | 45 | 20.164 | 69.734 | 73.546 | 1.00 40.52 | B |
| ATOM | 2058 | CG | LEU | B | 45 | 21.635 | 69.861 | 73.113 | 1.00 40.52 | B |
| ATOM | 2059 | CD1 | LEU | B | 45 | 21.895 | 71.293 | 72.646 | 1.00 40.52 | B |
| ATOM | 2060 | CD2 | LEU | B | 45 | 22.579 | 69.500 | 74.272 | 1.00 40.52 | B |
| ATOM | 2061 | C | LEU | B | 45 | 18.213 | 68.641 | 74.624 | 1.00 99.98 | B |
| ATOM | 2062 | O | LEU | B | 45 | 18.015 | 69.006 | 75.781 | 1.00 99.98 | B |

| ATOM | 2063 | N   | SER | B | 46 | 17.246 | 68.415 | 73.737  | 1.00 | 100.07 | B |
|------|------|-----|-----|---|----|--------|--------|---------|------|--------|---|
| ATOM | 2064 | CA  | SER | B | 46 | 15.826 | 68.592 | 74.033  | 1.00 | 100.07 | B |
| ATOM | 2065 | CB  | SER | B | 46 | 15.059 | 68.930 | 72.750  | 1.00 | 84.56  | B |
| ATOM | 2066 | OG  | SER | B | 46 | 15.629 | 70.035 | 72.075  | 1.00 | 84.56  | B |
| ATOM | 2067 | C   | SER | B | 46 | 15.195 | 67.350 | 74.642  | 1.00 | 100.07 | B |
| ATOM | 2068 | O   | SER | B | 46 | 15.648 | 66.813 | 75.657  | 1.00 | 100.07 | B |
| ATOM | 2069 | N   | SER | B | 47 | 14.124 | 66.918 | 73.993  | 1.00 | 38.59  | B |
| ATOM | 2070 | CA  | SER | B | 47 | 13.366 | 65.745 | 74.386  | 1.00 | 38.59  | B |
| ATOM | 2071 | CB  | SER | B | 47 | 12.578 | 65.294 | 73.161  | 1.00 | 100.07 | B |
| ATOM | 2072 | OG  | SER | B | 47 | 13.127 | 65.891 | 71.990  | 1.00 | 100.07 | B |
| ATOM | 2073 | C   | SER | B | 47 | 14.209 | 64.584 | 74.939  | 1.00 | 38.59  | B |
| ATOM | 2074 | O   | SER | B | 47 | 14.948 | 63.947 | 74.213  | 1.00 | 38.59  | B |
| ATOM | 2075 | N   | ILE | B | 48 | 14.104 | 64.311 | 76.227  | 1.00 | 70.20  | B |
| ATOM | 2076 | CA  | ILE | B | 48 | 14.852 | 63.212 | 76.811  | 1.00 | 70.20  | B |
| ATOM | 2077 | CB  | ILE | B | 48 | 16.377 | 63.476 | 76.803  | 1.00 | 23.12  | B |
| ATOM | 2078 | CG2 | ILE | B | 48 | 16.930 | 63.501 | 78.213  | 1.00 | 23.12  | B |
| ATOM | 2079 | CG1 | ILE | B | 48 | 17.104 | 62.308 | 76.163  | 1.00 | 23.12  | B |
| ATOM | 2080 | CD  | ILE | B | 48 | 16.633 | 61.975 | 74.779  | 1.00 | 23.12  | B |
| ATOM | 2081 | C   | ILE | B | 48 | 14.374 | 63.060 | 78.238  | 1.00 | 70.20  | B |
| ATOM | 2082 | O   | ILE | B | 48 | 13.969 | 64.031 | 78.877  | 1.00 | 70.20  | B |
| ATOM | 2083 | N   | PRO | B | 49 | 14.377 | 61.829 | 78.748  | 1.00 | 58.07  | B |
| ATOM | 2084 | CD  | PRO | B | 49 | 14.511 | 60.549 | 78.028  | 1.00 | 100.07 | B |
| ATOM | 2085 | CA  | PRO | B | 49 | 13.933 | 61.621 | 80.122  | 1.00 | 58.07  | B |
| ATOM | 2086 | CB  | PRO | B | 49 | 13.453 | 60.177 | 80.103  | 1.00 | 100.07 | B |
| ATOM | 2087 | CG  | PRO | B | 49 | 14.412 | 59.536 | 79.140  | 1.00 | 100.07 | B |
| ATOM | 2088 | C   | PRO | B | 49 | 15.115 | 61.844 | 81.055  | 1.00 | 58.07  | B |
| ATOM | 2089 | O   | PRO | B | 49 | 16.239 | 61.457 | 80.733  | 1.00 | 58.07  | B |
| ATOM | 2090 | N   | GLY | B | 50 | 14.860 | 62.482 | 82.195  | 1.00 | 100.07 | B |
| ATOM | 2091 | CA  | GLY | B | 50 | 15.912 | 62.746 | 83.165  | 1.00 | 100.07 | B |
| ATOM | 2092 | C   | GLY | B | 50 | 15.371 | 63.398 | 84.427  | 1.00 | 100.07 | B |
| ATOM | 2093 | O   | GLY | B | 50 | 14.303 | 64.004 | 84.398  | 1.00 | 100.07 | B |
| ATOM | 2094 | N   | THR | B | 51 | 16.092 | 63.283 | 85.538  | 1.00 | 100.07 | B |
| ATOM | 2095 | CA  | THR | B | 51 | 15.631 | 63.887 | 86.784  | 1.00 | 100.07 | B |
| ATOM | 2096 | CB  | THR | B | 51 | 15.778 | 62.923 | 87.966  | 1.00 | 84.35  | B |
| ATOM | 2097 | OG1 | THR | B | 51 | 17.167 | 62.773 | 88.297  | 1.00 | 84.35  | B |
| ATOM | 2098 | CG2 | THR | B | 51 | 15.193 | 61.575 | 87.611  | 1.00 | 84.35  | B |
| ATOM | 2099 | C   | THR | B | 51 | 16.406 | 65.153 | 87.119  | 1.00 | 100.07 | B |
| ATOM | 2100 | O   | THR | B | 51 | 17.380 | 65.481 | 86.440  | 1.00 | 100.07 | B |
| ATOM | 2101 | N   | ALA | B | 52 | 15.978 | 65.854 | 88.170  | 1.00 | 100.07 | B |
| ATOM | 2102 | CA  | ALA | B | 52 | 16.643 | 67.090 | 88.593  | 1.00 | 100.07 | B |
| ATOM | 2103 | CB  | ALA | B | 52 | 16.751 | 68.046 | 87.397  | 1.00 | 86.61  | B |
| ATOM | 2104 | C   | ALA | B | 52 | 15.947 | 67.807 | 89.763  | 1.00 | 100.07 | B |
| ATOM | 2105 | O   | ALA | B | 52 | 14.722 | 67.951 | 89.769  | 1.00 | 100.07 | B |
| ATOM | 2106 | N   | VAL | B | 53 | 16.733 | 68.260 | 90.742  | 1.00 | 64.65  | B |
| ATOM | 2107 | CA  | VAL | B | 53 | 16.196 | 68.983 | 91.895  | 1.00 | 64.65  | B |
| ATOM | 2108 | CB  | VAL | B | 53 | 17.323 | 69.551 | 92.777  | 1.00 | 34.06  | B |
| ATOM | 2109 | CG1 | VAL | B | 53 | 16.729 | 70.441 | 93.838  | 1.00 | 34.06  | B |
| ATOM | 2110 | CG2 | VAL | B | 53 | 18.126 | 68.430 | 93.409  | 1.00 | 34.06  | B |
| ATOM | 2111 | C   | VAL | B | 53 | 15.374 | 70.155 | 91.380  | 1.00 | 64.65  | B |
| ATOM | 2112 | O   | VAL | B | 53 | 15.663 | 70.691 | 90.309  | 1.00 | 64.65  | B |
| ATOM | 2113 | N   | THR | B | 54 | 14.359 | 70.572 | 92.126  | 1.00 | 82.03  | B |
| ATOM | 2114 | CA  | THR | B | 54 | 13.561 | 71.684 | 91.645  | 1.00 | 82.03  | B |
| ATOM | 2115 | CB  | THR | B | 54 | 12.352 | 71.169 | 90.825  | 1.00 | 79.61  | B |
| ATOM | 2116 | OG1 | THR | B | 54 | 11.675 | 72.280 | 90.213  | 1.00 | 79.61  | B |
| ATOM | 2117 | CG2 | THR | B | 54 | 11.396 | 70.386 | 91.717  | 1.00 | 79.61  | B |
| ATOM | 2118 | C   | THR | B | 54 | 13.103 | 72.710 | 92.687  | 1.00 | 82.03  | B |
| ATOM | 2119 | O   | THR | B | 54 | 12.698 | 73.819 | 92.320  | 1.00 | 82.03  | B |
| ATOM | 2120 | N   | SER | B | 55 | 13.179 | 72.369 | 93.973  | 1.00 | 99.98  | B |
| ATOM | 2121 | CA  | SER | B | 55 | 12.760 | 73.305 | 95.025  | 1.00 | 99.98  | B |
| ATOM | 2122 | CB  | SER | B | 55 | 11.230 | 73.419 | 95.045  | 1.00 | 44.96  | B |
| ATOM | 2123 | OG  | SER | B | 55 | 10.811 | 74.693 | 95.506  | 1.00 | 44.96  | B |
| ATOM | 2124 | C   | SER | B | 55 | 13.281 | 72.847 | 96.387  | 1.00 | 99.98  | B |
| ATOM | 2125 | O   | SER | B | 55 | 13.313 | 71.652 | 96.664  | 1.00 | 99.98  | B |
| ATOM | 2126 | N   | VAL | B | 56 | 13.685 | 73.787 | 97.241  | 1.00 | 57.66  | B |
| ATOM | 2127 | CA  | VAL | B | 56 | 14.225 | 73.407 | 98.546  | 1.00 | 57.66  | B |
| ATOM | 2128 | CB  | VAL | B | 56 | 15.783 | 73.495 | 98.563  | 1.00 | 56.04  | B |
| ATOM | 2129 | CG1 | VAL | B | 56 | 16.360 | 72.603 | 99.672  | 1.00 | 56.04  | B |
| ATOM | 2130 | CG2 | VAL | B | 56 | 16.349 | 73.120 | 97.212  | 1.00 | 56.04  | B |
| ATOM | 2131 | C   | VAL | B | 56 | 13.725 | 74.223 | 99.745  | 1.00 | 57.66  | B |
| ATOM | 2132 | O   | VAL | B | 56 | 13.389 | 75.404 | 99.638  | 1.00 | 57.66  | B |
| ATOM | 2133 | N   | TYR | B | 57 | 13.692 | 73.558 | 100.893 | 1.00 | 97.06  | B |
| ATOM | 2134 | CA  | TYR | B | 57 | 13.297 | 74.172 | 102.149 | 1.00 | 97.06  | B |
| ATOM | 2135 | CB  | TYR | B | 57 | 12.014 | 73.532 | 102.694 | 1.00 | 68.12  | B |
| ATOM | 2136 | CG  | TYR | B | 57 | 11.517 | 74.134 | 104.004 | 1.00 | 68.12  | B |
| ATOM | 2137 | CD1 | TYR | B | 57 | 10.393 | 73.617 | 104.654 | 1.00 | 68.12  | B |
| ATOM | 2138 | CE1 | TYR | B | 57 | 9.943  | 74.162 | 105.855 | 1.00 | 68.12  | B |
| ATOM | 2139 | CD2 | TYR | B | 57 | 12.175 | 75.217 | 104.596 | 1.00 | 68.12  | B |
| ATOM | 2140 | CE2 | TYR | B | 57 | 11.733 | 75.765 | 105.792 | 1.00 | 68.12  | B |
| ATOM | 2141 | CZ  | TYR | B | 57 | 10.623 | 75.234 | 106.413 | 1.00 | 68.12  | B |
| ATOM | 2142 | OH  | TYR | B | 57 | 10.210 | 75.775 | 107.602 | 1.00 | 68.12  | B |
| ATOM | 2143 | C   | TYR | B | 57 | 14.476 | 73.880 | 103.075 | 1.00 | 97.06  | B |
| ATOM | 2144 | O   | TYR | B | 57 | 14.679 | 72.738 | 103.502 | 1.00 | 97.06  | B |
| ATOM | 2145 | N   | ILE | B | 58 | 15.252 | 74.917 | 103.374 | 1.00 | 100.07 | B |
| ATOM | 2146 | CA  | ILE | B | 58 | 16.440 | 74.781 | 104.215 | 1.00 | 100.07 | B |

```
ATOM   2147  CB   ILE B  58      17.664  75.444 103.525  1.00100.07           B
ATOM   2148  CG2  ILE B  58      18.924  75.227 104.360  1.00100.07           B
ATOM   2149  CG1  ILE B  58      17.849  74.861 102.116  1.00100.07           B
ATOM   2150  CD   ILE B  58      16.813  75.317 101.116  1.00100.07           B
ATOM   2151  C    ILE B  58      16.277  75.366 105.619  1.00100.07           B
ATOM   2152  O    ILE B  58      17.025  76.261 106.026  1.00100.07           B
ATOM   2153  N    GLU B  59      15.304  74.831 106.352  1.00100.07           B
ATOM   2154  CA   GLU B  59      14.995  75.268 107.709  1.00100.07           B
ATOM   2155  CB   GLU B  59      15.542  74.270 108.729  1.00100.07           B
ATOM   2156  CG   GLU B  59      15.261  74.684 110.174  1.00100.07           B
ATOM   2157  CD   GLU B  59      13.787  75.006 110.432  1.00100.07           B
ATOM   2158  OE1  GLU B  59      13.222  75.870 109.724  1.00100.07           B
ATOM   2159  OE2  GLU B  59      13.195  74.399 111.353  1.00100.07           B
ATOM   2160  C    GLU B  59      15.462  76.678 108.078  1.00100.07           B
ATOM   2161  O    GLU B  59      16.634  76.883 108.402  1.00100.07           B
ATOM   2162  N    ASP B  60      14.522  77.626 108.014  1.00100.07           B
ATOM   2163  CA   ASP B  60      14.697  79.051 108.350  1.00100.07           B
ATOM   2164  CB   ASP B  60      16.106  79.341 108.903  1.00100.07           B
ATOM   2165  CG   ASP B  60      16.198  79.114 110.421  1.00100.07           B
ATOM   2166  OD1  ASP B  60      15.478  79.798 111.181  1.00100.07           B
ATOM   2167  OD2  ASP B  60      16.987  78.252 110.858  1.00100.07           B
ATOM   2168  C    ASP B  60      14.314  80.089 107.269  1.00100.07           B
ATOM   2169  O    ASP B  60      13.188  80.055 106.757  1.00100.07           B
ATOM   2170  N    VAL B  61      15.224  81.003 106.922  1.00 30.98           B
ATOM   2171  CA   VAL B  61      14.915  82.070 105.954  1.00 30.98           B
ATOM   2172  CB   VAL B  61      16.120  83.004 105.737  1.00 99.92           B
ATOM   2173  CG1  VAL B  61      15.640  84.320 105.139  1.00 99.92           B
ATOM   2174  CG2  VAL B  61      16.850  83.236 107.052  1.00 99.92           B
ATOM   2175  C    VAL B  61      14.423  81.641 104.572  1.00 30.98           B
ATOM   2176  O    VAL B  61      14.744  80.556 104.077  1.00 30.98           B
ATOM   2177  N    LEU B  62      13.647  82.522 103.949  1.00 90.28           B
ATOM   2178  CA   LEU B  62      13.080  82.253 102.636  1.00 90.28           B
ATOM   2179  CB   LEU B  62      11.783  83.057 102.446  1.00100.07           B
ATOM   2180  CG   LEU B  62      11.089  83.054 101.074  1.00100.07           B
ATOM   2181  CD1  LEU B  62      10.931  81.636 100.557  1.00100.07           B
ATOM   2182  CD2  LEU B  62       9.741  83.742 101.187  1.00100.07           B
ATOM   2183  C    LEU B  62      14.028  82.520 101.470  1.00 90.28           B
ATOM   2184  O    LEU B  62      15.025  81.821 101.302  1.00 90.28           B
ATOM   2185  N    HIS B  63      13.707  83.538 100.676  1.00 50.34           B
ATOM   2186  CA   HIS B  63      14.475  83.909  99.487  1.00 50.34           B
ATOM   2187  CB   HIS B  63      14.419  85.434  99.257  1.00100.07           B
ATOM   2188  CG   HIS B  63      15.116  86.251 100.305  1.00100.07           B
ATOM   2189  CD2  HIS B  63      16.013  87.260 100.193  1.00100.07           B
ATOM   2190  ND1  HIS B  63      14.862  86.114 101.653  1.00100.07           B
ATOM   2191  CE1  HIS B  63      15.571  87.004 102.326  1.00100.07           B
ATOM   2192  NE2  HIS B  63      16.278  87.712 101.463  1.00100.07           B
ATOM   2193  C    HIS B  63      15.923  83.435  99.419  1.00 50.34           B
ATOM   2194  O    HIS B  63      16.675  83.534 100.391  1.00 50.34           B
ATOM   2195  N    GLU B  64      16.304  82.921  98.252  1.00 64.80           B
ATOM   2196  CA   GLU B  64      17.659  82.421  98.020  1.00 64.80           B
ATOM   2197  CB   GLU B  64      17.907  82.200  96.523  1.00100.07           B
ATOM   2198  CG   GLU B  64      19.341  81.801  96.198  1.00100.07           B
ATOM   2199  CD   GLU B  64      19.621  81.714  94.707  1.00100.07           B
ATOM   2200  OE1  GLU B  64      19.506  82.748  94.012  1.00100.07           B
ATOM   2201  OE2  GLU B  64      19.962  80.608  94.231  1.00100.07           B
ATOM   2202  C    GLU B  64      18.719  83.380  98.549  1.00 64.80           B
ATOM   2203  O    GLU B  64      19.885  83.022  98.691  1.00 64.80           B
ATOM   2204  N    PHE B  65      18.291  84.601  98.839  1.00 78.74           B
ATOM   2205  CA   PHE B  65      19.187  85.634  99.318  1.00 78.74           B
ATOM   2206  CB   PHE B  65      18.838  86.964  98.639  1.00100.07           B
ATOM   2207  CG   PHE B  65      18.214  86.807  97.268  1.00100.07           B
ATOM   2208  CD1  PHE B  65      16.855  86.496  97.136  1.00100.07           B
ATOM   2209  CD2  PHE B  65      18.983  86.962  96.111  1.00100.07           B
ATOM   2210  CE1  PHE B  65      16.272  86.342  95.871  1.00100.07           B
ATOM   2211  CE2  PHE B  65      18.412  86.809  94.840  1.00100.07           B
ATOM   2212  CZ   PHE B  65      17.057  86.499  94.719  1.00100.07           B
ATOM   2213  C    PHE B  65      19.125  85.784 100.833  1.00 78.74           B
ATOM   2214  O    PHE B  65      18.567  86.748 101.355  1.00 78.74           B
ATOM   2215  N    SER B  66      19.706  84.821 101.535  1.00100.07           B
ATOM   2216  CA   SER B  66      19.735  84.855 102.988  1.00100.07           B
ATOM   2217  CB   SER B  66      18.663  83.929 103.558  1.00100.07           B
ATOM   2218  OG   SER B  66      17.381  84.320 103.099  1.00100.07           B
ATOM   2219  C    SER B  66      21.116  84.422 103.437  1.00100.07           B
ATOM   2220  O    SER B  66      22.079  84.571 102.682  1.00100.07           B
ATOM   2221  N    THR B  67      21.220  83.901 104.658  1.00100.07           B
ATOM   2222  CA   THR B  67      22.505  83.430 105.179  1.00100.07           B
ATOM   2223  CB   THR B  67      23.479  84.621 105.500  1.00100.07           B
ATOM   2224  OG1  THR B  67      23.948  85.214 104.280  1.00100.07           B
ATOM   2225  CG2  THR B  67      24.689  84.132 106.301  1.00100.07           B
ATOM   2226  C    THR B  67      22.356  82.572 106.434  1.00100.07           B
ATOM   2227  O    THR B  67      22.077  83.079 107.524  1.00100.07           B
ATOM   2228  N    ILE B  68      22.525  81.265 106.270  1.00 43.12           B
ATOM   2229  CA   ILE B  68      22.460  80.366 107.405  1.00 43.12           B
ATOM   2230  CB   ILE B  68      22.307  78.888 106.978  1.00 99.22           B
```

| | | | | | | | | | |
|---|---|---|---|---|---|---|---|---|---|
|ATOM|2231|CG2|ILE|B|68|20.840|78.547|106.831|1.00 99.22|B|
|ATOM|2232|CG1|ILE|B|68|23.070|78.624|105.675|1.00 99.22|B|
|ATOM|2233|CD|ILE|B|68|24.567|78.813|105.764|1.00 99.22|B|
|ATOM|2234|C|ILE|B|68|23.782|80.530|108.144|1.00 43.12|B|
|ATOM|2235|O|ILE|B|68|24.797|80.913|107.551|1.00 43.12|B|
|ATOM|2236|N|PRO|B|69|23.774|80.285|109.459|1.00 70.41|B|
|ATOM|2237|CD|PRO|B|69|22.564|80.388|110.294|1.00100.07|B|
|ATOM|2238|CA|PRO|B|69|24.979|80.397|110.284|1.00 70.41|B|
|ATOM|2239|CB|PRO|B|69|24.468|81.105|111.526|1.00100.07|B|
|ATOM|2240|CG|PRO|B|69|23.140|80.455|111.706|1.00100.07|B|
|ATOM|2241|C|PRO|B|69|25.594|79.023|110.592|1.00 70.41|B|
|ATOM|2242|O|PRO|B|69|24.975|77.974|110.366|1.00 70.41|B|
|ATOM|2243|N|GLY|B|70|26.818|79.039|111.105|1.00 91.68|B|
|ATOM|2244|CA|GLY|B|70|27.495|77.799|111.420|1.00 91.68|B|
|ATOM|2245|C|GLY|B|70|27.838|77.080|110.139|1.00 91.68|B|
|ATOM|2246|O|GLY|B|70|28.435|76.008|110.162|1.00 91.68|B|
|ATOM|2247|N|VAL|B|71|27.450|77.687|109.019|1.00100.07|B|
|ATOM|2248|CA|VAL|B|71|27.707|77.141|107.691|1.00100.07|B|
|ATOM|2249|CB|VAL|B|71|26.416|76.679|107.017|1.00 99.79|B|
|ATOM|2250|CG1|VAL|B|71|26.748|75.750|105.869|1.00 99.79|B|
|ATOM|2251|CG2|VAL|B|71|25.504|76.016|108.029|1.00 99.79|B|
|ATOM|2252|C|VAL|B|71|28.334|78.227|106.828|1.00100.07|B|
|ATOM|2253|O|VAL|B|71|27.660|79.177|106.425|1.00100.07|B|
|ATOM|2254|N|LYS|B|72|29.623|78.074|106.543|1.00 92.37|B|
|ATOM|2255|CA|LYS|B|72|30.364|79.052|105.756|1.00 92.37|B|
|ATOM|2256|CB|LYS|B|72|31.840|78.655|105.695|1.00 99.35|B|
|ATOM|2257|CG|LYS|B|72|32.502|78.707|107.057|1.00 99.35|B|
|ATOM|2258|CD|LYS|B|72|32.255|80.071|107.708|1.00 99.35|B|
|ATOM|2259|CE|LYS|B|72|32.632|80.090|109.189|1.00 99.35|B|
|ATOM|2260|NZ|LYS|B|72|32.395|81.428|109.816|1.00 99.35|B|
|ATOM|2261|C|LYS|B|72|29.819|79.297|104.355|1.00 92.37|B|
|ATOM|2262|O|LYS|B|72|29.843|80.421|103.854|1.00 92.37|B|
|ATOM|2263|N|GLU|B|73|29.315|78.250|103.725|1.00 76.40|B|
|ATOM|2264|CA|GLU|B|73|28.780|78.391|102.392|1.00 76.40|B|
|ATOM|2265|CB|GLU|B|73|28.687|77.015|101.766|1.00 93.16|B|
|ATOM|2266|CG|GLU|B|73|30.060|76.455|101.540|1.00 93.16|B|
|ATOM|2267|CD|GLU|B|73|30.054|74.997|101.206|1.00 93.16|B|
|ATOM|2268|OE1|GLU|B|73|29.239|74.575|100.365|1.00 93.16|B|
|ATOM|2269|OE2|GLU|B|73|30.882|74.271|101.778|1.00 93.16|B|
|ATOM|2270|C|GLU|B|73|27.436|79.085|102.413|1.00 76.40|B|
|ATOM|2271|O|GLU|B|73|26.526|78.645|103.098|1.00 76.40|B|
|ATOM|2272|N|ASP|B|74|27.318|80.181|101.671|1.00 37.10|B|
|ATOM|2273|CA|ASP|B|74|26.066|80.938|101.609|1.00 37.10|B|
|ATOM|2274|CB|ASP|B|74|26.264|82.215|100.798|1.00 88.96|B|
|ATOM|2275|CG|ASP|B|74|25.746|82.082|99.380|1.00 88.96|B|
|ATOM|2276|OD1|ASP|B|74|26.090|81.086|98.716|1.00 88.96|B|
|ATOM|2277|OD2|ASP|B|74|24.994|82.970|98.931|1.00 88.96|B|
|ATOM|2278|C|ASP|B|74|24.929|80.140|100.973|1.00 37.10|B|
|ATOM|2279|O|ASP|B|74|25.138|79.040|100.467|1.00 37.10|B|
|ATOM|2280|N|VAL|B|75|23.725|80.704|100.994|1.00 45.70|B|
|ATOM|2281|CA|VAL|B|75|22.567|80.056|100.376|1.00 45.70|B|
|ATOM|2282|CB|VAL|B|75|21.300|80.980|100.389|1.00 55.69|B|
|ATOM|2283|CG1|VAL|B|75|20.453|80.723|101.619|1.00 55.69|B|
|ATOM|2284|CG2|VAL|B|75|21.726|82.439|100.351|1.00 55.69|B|
|ATOM|2285|C|VAL|B|75|22.914|79.792|98.913|1.00 45.70|B|
|ATOM|2286|O|VAL|B|75|23.454|78.745|98.561|1.00 45.70|B|
|ATOM|2287|N|VAL|B|76|22.597|80.776|98.080|1.00 63.40|B|
|ATOM|2288|CA|VAL|B|76|22.824|80.726|96.645|1.00 63.40|B|
|ATOM|2289|CB|VAL|B|76|23.401|82.055|96.140|1.00 99.98|B|
|ATOM|2290|CG1|VAL|B|76|23.499|82.035|94.625|1.00 99.98|B|
|ATOM|2291|CG2|VAL|B|76|22.525|83.203|96.606|1.00 99.98|B|
|ATOM|2292|C|VAL|B|76|23.729|79.607|96.153|1.00 63.40|B|
|ATOM|2293|O|VAL|B|76|23.320|78.818|95.302|1.00 63.40|B|
|ATOM|2294|N|GLU|B|77|24.952|79.525|96.674|1.00 65.02|B|
|ATOM|2295|CA|GLU|B|77|25.864|78.483|96.209|1.00 65.02|B|
|ATOM|2296|CB|GLU|B|77|27.284|78.671|96.749|1.00 88.18|B|
|ATOM|2297|CG|GLU|B|77|28.295|77.797|96.008|1.00 88.18|B|
|ATOM|2298|CD|GLU|B|77|29.653|78.458|95.826|1.00 88.18|B|
|ATOM|2299|OE1|GLU|B|77|30.512|78.309|96.719|1.00 88.18|B|
|ATOM|2300|OE2|GLU|B|77|29.860|79.132|94.791|1.00 88.18|B|
|ATOM|2301|C|GLU|B|77|25.376|77.094|96.551|1.00 65.02|B|
|ATOM|2302|O|GLU|B|77|25.518|76.174|95.751|1.00 65.02|B|
|ATOM|2303|N|ILE|B|78|24.814|76.918|97.738|1.00 50.01|B|
|ATOM|2304|CA|ILE|B|78|24.287|75.608|98.061|1.00 50.01|B|
|ATOM|2305|CB|ILE|B|78|23.658|75.562|99.460|1.00 60.32|B|
|ATOM|2306|CG2|ILE|B|78|22.766|74.349|99.585|1.00 60.32|B|
|ATOM|2307|CG1|ILE|B|78|24.772|75.496|100.511|1.00 60.32|B|
|ATOM|2308|CD|ILE|B|78|24.294|75.467|101.944|1.00 60.32|B|
|ATOM|2309|C|ILE|B|78|23.248|75.341|96.983|1.00 50.01|B|
|ATOM|2310|O|ILE|B|78|23.340|74.344|96.266|1.00 50.01|B|
|ATOM|2311|N|ILE|B|79|22.291|76.259|96.847|1.00 57.29|B|
|ATOM|2312|CA|ILE|B|79|21.243|76.146|95.831|1.00 57.29|B|
|ATOM|2313|CB|ILE|B|79|20.613|77.521|95.478|1.00 74.38|B|
|ATOM|2314|CG2|ILE|B|79|19.882|77.435|94.140|1.00 74.38|B|

-28-

| | | | | | | | | | | |
|---|---|---|---|---|---|---|---|---|---|---|
| ATOM | 2315 | CG1 | ILE | B | 79 | 19.638 | 77.959 | 96.577 | 1.00 74.38 | B |
| ATOM | 2316 | CD | ILE | B | 79 | 20.258 | 78.119 | 97.955 | 1.00 74.38 | B |
| ATOM | 2317 | C | ILE | B | 79 | 21.870 | 75.589 | 94.571 | 1.00 57.29 | B |
| ATOM | 2318 | O | ILE | B | 79 | 21.400 | 74.600 | 94.018 | 1.00 57.29 | B |
| ATOM | 2319 | N | LEU | B | 80 | 22.940 | 76.230 | 94.121 | 1.00 99.36 | B |
| ATOM | 2320 | CA | LEU | B | 80 | 23.629 | 75.777 | 92.928 | 1.00 99.36 | B |
| ATOM | 2321 | CB | LEU | B | 80 | 24.823 | 76.671 | 92.628 | 1.00 53.04 | B |
| ATOM | 2322 | CG | LEU | B | 80 | 24.414 | 78.118 | 92.392 | 1.00 53.04 | B |
| ATOM | 2323 | CD1 | LEU | B | 80 | 25.616 | 78.903 | 91.898 | 1.00 53.04 | B |
| ATOM | 2324 | CD2 | LEU | B | 80 | 23.278 | 78.168 | 91.373 | 1.00 53.04 | B |
| ATOM | 2325 | C | LEU | B | 80 | 24.087 | 74.342 | 93.115 | 1.00 99.36 | B |
| ATOM | 2326 | O | LEU | B | 80 | 23.738 | 73.467 | 92.325 | 1.00 99.36 | B |
| ATOM | 2327 | N | ASN | B | 81 | 24.867 | 74.104 | 94.164 | 1.00 53.66 | B |
| ATOM | 2328 | CA | ASN | B | 81 | 25.363 | 72.770 | 94.451 | 1.00 53.66 | B |
| ATOM | 2329 | CB | ASN | B | 81 | 25.774 | 72.670 | 95.909 | 1.00 46.42 | B |
| ATOM | 2330 | CG | ASN | B | 81 | 27.002 | 73.492 | 96.221 | 1.00 46.42 | B |
| ATOM | 2331 | OD1 | ASN | B | 81 | 28.100 | 73.187 | 95.748 | 1.00 46.42 | B |
| ATOM | 2332 | ND2 | ASN | B | 81 | 26.829 | 74.546 | 97.022 | 1.00 46.42 | B |
| ATOM | 2333 | C | ASN | B | 81 | 24.252 | 71.775 | 94.177 | 1.00 53.66 | B |
| ATOM | 2334 | O | ASN | B | 81 | 24.300 | 71.013 | 93.211 | 1.00 53.66 | B |
| ATOM | 2335 | N | LEU | B | 82 | 23.235 | 71.798 | 95.024 | 1.00 89.22 | B |
| ATOM | 2336 | CA | LEU | B | 82 | 22.120 | 70.890 | 94.851 | 1.00 89.22 | B |
| ATOM | 2337 | CB | LEU | B | 82 | 20.923 | 71.322 | 95.691 | 1.00100.07 | B |
| ATOM | 2338 | CG | LEU | B | 82 | 21.135 | 71.451 | 97.195 | 1.00100.07 | B |
| ATOM | 2339 | CD1 | LEU | B | 82 | 19.782 | 71.769 | 97.825 | 1.00100.07 | B |
| ATOM | 2340 | CD2 | LEU | B | 82 | 21.743 | 70.163 | 97.782 | 1.00100.07 | B |
| ATOM | 2341 | C | LEU | B | 82 | 21.690 | 70.839 | 93.397 | 1.00 89.22 | B |
| ATOM | 2342 | O | LEU | B | 82 | 21.331 | 69.778 | 92.889 | 1.00 89.22 | B |
| ATOM | 2343 | N | LYS | B | 83 | 21.739 | 71.989 | 92.730 | 1.00 68.47 | B |
| ATOM | 2344 | CA | LYS | B | 83 | 21.317 | 72.079 | 91.340 | 1.00 68.47 | B |
| ATOM | 2345 | CB | LYS | B | 83 | 21.372 | 73.532 | 90.844 | 1.00 56.25 | B |
| ATOM | 2346 | CG | LYS | B | 83 | 20.603 | 73.751 | 89.557 | 1.00 56.25 | B |
| ATOM | 2347 | CD | LYS | B | 83 | 19.744 | 75.012 | 89.581 | 1.00 56.25 | B |
| ATOM | 2348 | CE | LYS | B | 83 | 20.558 | 76.290 | 89.398 | 1.00 56.25 | B |
| ATOM | 2349 | NZ | LYS | B | 83 | 19.686 | 77.513 | 89.264 | 1.00 56.25 | B |
| ATOM | 2350 | C | LYS | B | 83 | 22.146 | 71.182 | 90.444 | 1.00 68.47 | B |
| ATOM | 2351 | O | LYS | B | 83 | 21.905 | 71.096 | 89.239 | 1.00 68.47 | B |
| ATOM | 2352 | N | GLU | B | 84 | 23.114 | 70.496 | 91.039 | 1.00 76.12 | B |
| ATOM | 2353 | CA | GLU | B | 84 | 23.958 | 69.602 | 90.271 | 1.00 76.12 | B |
| ATOM | 2354 | CB | GLU | B | 84 | 25.357 | 70.194 | 90.136 | 1.00 90.31 | B |
| ATOM | 2355 | CG | GLU | B | 84 | 26.220 | 69.540 | 89.074 | 1.00 90.31 | B |
| ATOM | 2356 | CD | GLU | B | 84 | 27.502 | 70.312 | 88.847 | 1.00 90.31 | B |
| ATOM | 2357 | OE1 | GLU | B | 84 | 28.140 | 70.682 | 89.851 | 1.00 90.31 | B |
| ATOM | 2358 | OE2 | GLU | B | 84 | 27.873 | 70.551 | 87.678 | 1.00 90.31 | B |
| ATOM | 2359 | C | GLU | B | 84 | 24.028 | 68.227 | 90.910 | 1.00 76.12 | B |
| ATOM | 2360 | O | GLU | B | 84 | 24.938 | 67.456 | 90.625 | 1.00 76.12 | B |
| ATOM | 2361 | N | LEU | B | 85 | 23.083 | 67.921 | 91.793 | 1.00100.07 | B |
| ATOM | 2362 | CA | LEU | B | 85 | 23.062 | 66.596 | 92.395 | 1.00100.07 | B |
| ATOM | 2363 | CB | LEU | B | 85 | 22.049 | 66.515 | 93.537 | 1.00 57.77 | B |
| ATOM | 2364 | CG | LEU | B | 85 | 21.985 | 65.124 | 94.184 | 1.00 57.77 | B |
| ATOM | 2365 | CD1 | LEU | B | 85 | 23.352 | 64.756 | 94.747 | 1.00 57.77 | B |
| ATOM | 2366 | CD2 | LEU | B | 85 | 20.930 | 65.088 | 95.281 | 1.00 57.77 | B |
| ATOM | 2367 | C | LEU | B | 85 | 22.615 | 65.708 | 91.241 | 1.00100.07 | B |
| ATOM | 2368 | O | LEU | B | 85 | 22.203 | 66.224 | 90.202 | 1.00100.07 | B |
| ATOM | 2369 | N | VAL | B | 86 | 22.697 | 64.390 | 91.397 | 1.00 99.56 | B |
| ATOM | 2370 | CA | VAL | B | 86 | 22.271 | 63.486 | 90.325 | 1.00 99.56 | B |
| ATOM | 2371 | CB | VAL | B | 86 | 23.481 | 62.905 | 89.573 | 1.00 42.86 | B |
| ATOM | 2372 | CG1 | VAL | B | 86 | 23.065 | 62.469 | 88.177 | 1.00 42.86 | B |
| ATOM | 2373 | CG2 | VAL | B | 86 | 24.590 | 63.924 | 89.513 | 1.00 42.86 | B |
| ATOM | 2374 | C | VAL | B | 86 | 21.470 | 62.313 | 90.892 | 1.00 99.56 | B |
| ATOM | 2375 | O | VAL | B | 86 | 22.038 | 61.339 | 91.398 | 1.00 99.56 | B |
| ATOM | 2376 | N | VAL | B | 87 | 20.149 | 62.411 | 90.794 | 1.00100.07 | B |
| ATOM | 2377 | CA | VAL | B | 87 | 19.269 | 61.376 | 91.306 | 1.00100.07 | B |
| ATOM | 2378 | CB | VAL | B | 87 | 17.961 | 61.986 | 91.861 | 1.00 99.71 | B |
| ATOM | 2379 | CG1 | VAL | B | 87 | 17.043 | 60.886 | 92.365 | 1.00 99.71 | B |
| ATOM | 2380 | CG2 | VAL | B | 87 | 18.275 | 62.956 | 92.985 | 1.00 99.71 | B |
| ATOM | 2381 | C | VAL | B | 87 | 18.915 | 60.363 | 90.238 | 1.00100.07 | B |
| ATOM | 2382 | O | VAL | B | 87 | 18.779 | 60.710 | 89.061 | 1.00100.07 | B |
| ATOM | 2383 | N | ARG | B | 88 | 18.775 | 59.109 | 90.665 | 1.00100.07 | B |
| ATOM | 2384 | CA | ARG | B | 88 | 18.416 | 58.008 | 89.775 | 1.00100.07 | B |
| ATOM | 2385 | CB | ARG | B | 88 | 19.603 | 57.072 | 89.570 | 1.00100.07 | B |
| ATOM | 2386 | CG | ARG | B | 88 | 19.301 | 55.915 | 88.648 | 1.00100.07 | B |
| ATOM | 2387 | CD | ARG | B | 88 | 20.429 | 54.931 | 88.698 | 1.00100.07 | B |
| ATOM | 2388 | NE | ARG | B | 88 | 20.029 | 53.615 | 88.221 | 1.00100.07 | B |
| ATOM | 2389 | CZ | ARG | B | 88 | 20.732 | 52.509 | 88.443 | 1.00100.07 | B |
| ATOM | 2390 | NH1 | ARG | B | 88 | 21.867 | 52.577 | 89.135 | 1.00100.07 | B |
| ATOM | 2391 | NH2 | ARG | B | 88 | 20.303 | 51.335 | 87.984 | 1.00100.07 | B |
| ATOM | 2392 | C | ARG | B | 88 | 17.236 | 57.222 | 90.335 | 1.00100.07 | B |
| ATOM | 2393 | O | ARG | B | 88 | 17.420 | 56.208 | 91.014 | 1.00100.07 | B |
| ATOM | 2394 | N | PHE | B | 89 | 16.027 | 57.704 | 90.050 | 1.00100.07 | B |
| ATOM | 2395 | CA | PHE | B | 89 | 14.810 | 57.045 | 90.506 | 1.00100.07 | B |
| ATOM | 2396 | CB | PHE | B | 89 | 13.577 | 57.694 | 89.876 | 1.00 72.11 | B |
| ATOM | 2397 | CG | PHE | B | 89 | 13.375 | 59.130 | 90.269 | 1.00 72.11 | B |
| ATOM | 2398 | CD1 | PHE | B | 89 | 13.865 | 59.613 | 91.484 | 1.00 72.11 | B |

-29-

| | | | | | | | | | |
|---|---|---|---|---|---|---|---|---|---|
| ATOM | 2399 | CD2 | PHE | B | 89 | 12.631 | 59.984 | 89.458 | 1.00 72.11 | B |
| ATOM | 2400 | CE1 | PHE | B | 89 | 13.609 | 60.920 | 91.884 | 1.00 72.11 | B |
| ATOM | 2401 | CE2 | PHE | B | 89 | 12.369 | 61.296 | 89.849 | 1.00 72.11 | B |
| ATOM | 2402 | CZ | PHE | B | 89 | 12.856 | 61.764 | 91.062 | 1.00 72.11 | B |
| ATOM | 2403 | C | PHE | B | 89 | 14.878 | 55.583 | 90.080 | 1.00100.07 | B |
| ATOM | 2404 | O | PHE | B | 89 | 15.720 | 55.211 | 89.264 | 1.00100.07 | B |
| ATOM | 2405 | N | LEU | B | 90 | 13.993 | 54.754 | 90.619 | 1.00100.07 | B |
| ATOM | 2406 | CA | LEU | B | 90 | 14.003 | 53.341 | 90.263 | 1.00100.07 | B |
| ATOM | 2407 | CB | LEU | B | 90 | 14.628 | 52.522 | 91.389 | 1.00 93.06 | B |
| ATOM | 2408 | CG | LEU | B | 90 | 16.127 | 52.704 | 91.604 | 1.00 93.06 | B |
| ATOM | 2409 | CD1 | LEU | B | 90 | 16.568 | 51.930 | 92.851 | 1.00 93.06 | B |
| ATOM | 2410 | CD2 | LEU | B | 90 | 16.866 | 52.229 | 90.356 | 1.00 93.06 | B |
| ATOM | 2411 | C | LEU | B | 90 | 12.615 | 52.805 | 89.982 | 1.00100.07 | B |
| ATOM | 2412 | O | LEU | B | 90 | 12.437 | 51.956 | 89.102 | 1.00100.07 | B |
| ATOM | 2413 | N | ASP | B | 91 | 11.637 | 53.284 | 90.748 | 1.00100.07 | B |
| ATOM | 2414 | CA | ASP | B | 91 | 10.253 | 52.859 | 90.564 | 1.00100.07 | B |
| ATOM | 2415 | CB | ASP | B | 91 | 9.321 | 53.600 | 91.545 | 1.00100.07 | B |
| ATOM | 2416 | CG | ASP | B | 91 | 9.329 | 52.991 | 92.948 | 1.00100.07 | B |
| ATOM | 2417 | OD1 | ASP | B | 91 | 9.179 | 51.756 | 93.064 | 1.00100.07 | B |
| ATOM | 2418 | OD2 | ASP | B | 91 | 9.471 | 53.746 | 93.937 | 1.00100.07 | B |
| ATOM | 2419 | C | ASP | B | 91 | 9.845 | 53.161 | 89.117 | 1.00100.07 | B |
| ATOM | 2420 | O | ASP | B | 91 | 10.682 | 53.488 | 88.276 | 1.00100.07 | B |
| ATOM | 2421 | N | PRO | B | 92 | 8.554 | 53.042 | 88.801 | 1.00 99.91 | B |
| ATOM | 2422 | CD | PRO | B | 92 | 7.463 | 52.328 | 89.492 | 1.00100.07 | B |
| ATOM | 2423 | CA | PRO | B | 92 | 8.186 | 53.333 | 87.416 | 1.00 99.91 | B |
| ATOM | 2424 | CB | PRO | B | 92 | 7.138 | 52.280 | 87.132 | 1.00100.07 | B |
| ATOM | 2425 | CG | PRO | B | 92 | 6.360 | 52.296 | 88.434 | 1.00100.07 | B |
| ATOM | 2426 | C | PRO | B | 92 | 7.592 | 54.723 | 87.345 | 1.00 99.91 | B |
| ATOM | 2427 | O | PRO | B | 92 | 7.528 | 55.342 | 86.283 | 1.00 99.91 | B |
| ATOM | 2428 | N | ARG | B | 93 | 7.136 | 55.184 | 88.501 | 1.00 99.05 | B |
| ATOM | 2429 | CA | ARG | B | 93 | 6.524 | 56.490 | 88.647 | 1.00 99.05 | B |
| ATOM | 2430 | CB | ARG | B | 93 | 5.059 | 56.313 | 89.046 | 1.00100.07 | B |
| ATOM | 2431 | CG | ARG | B | 93 | 4.286 | 57.591 | 89.294 | 1.00100.07 | B |
| ATOM | 2432 | CD | ARG | B | 93 | 3.730 | 58.184 | 88.012 | 1.00100.07 | B |
| ATOM | 2433 | NE | ARG | B | 93 | 2.691 | 59.169 | 88.314 | 1.00100.07 | B |
| ATOM | 2434 | CZ | ARG | B | 93 | 1.973 | 59.818 | 87.400 | 1.00100.07 | B |
| ATOM | 2435 | NH1 | ARG | B | 93 | 2.179 | 59.589 | 86.106 | 1.00100.07 | B |
| ATOM | 2436 | NH2 | ARG | B | 93 | 1.042 | 60.691 | 87.779 | 1.00100.07 | B |
| ATOM | 2437 | C | ARG | B | 93 | 7.300 | 57.174 | 89.765 | 1.00 99.05 | B |
| ATOM | 2438 | O | ARG | B | 93 | 7.943 | 56.495 | 90.570 | 1.00 99.05 | B |
| ATOM | 2439 | N | TRP | B | 94 | 7.258 | 58.504 | 89.815 | 1.00100.07 | B |
| ATOM | 2440 | CA | TRP | B | 94 | 7.968 | 59.221 | 90.866 | 1.00100.07 | B |
| ATOM | 2441 | CB | TRP | B | 94 | 9.455 | 58.871 | 90.827 | 1.00100.07 | B |
| ATOM | 2442 | CG | TRP | B | 94 | 9.992 | 58.360 | 92.132 | 1.00100.07 | B |
| ATOM | 2443 | CD2 | TRP | B | 94 | 9.241 | 57.780 | 93.201 | 1.00100.07 | B |
| ATOM | 2444 | CE2 | TRP | B | 94 | 10.172 | 57.412 | 94.210 | 1.00100.07 | B |
| ATOM | 2445 | CE3 | TRP | B | 94 | 7.881 | 57.538 | 93.426 | 1.00100.07 | B |
| ATOM | 2446 | CD1 | TRP | B | 94 | 11.296 | 58.317 | 92.511 | 1.00100.07 | B |
| ATOM | 2447 | NE1 | TRP | B | 94 | 11.419 | 57.751 | 93.754 | 1.00100.07 | B |
| ATOM | 2448 | CZ2 | TRP | B | 94 | 9.785 | 56.805 | 95.406 | 1.00100.07 | B |
| ATOM | 2449 | CZ3 | TRP | B | 94 | 7.489 | 56.934 | 94.617 | 1.00100.07 | B |
| ATOM | 2450 | CH2 | TRP | B | 94 | 8.444 | 56.579 | 95.598 | 1.00100.07 | B |
| ATOM | 2451 | C | TRP | B | 94 | 7.817 | 60.741 | 90.843 | 1.00100.07 | B |
| ATOM | 2452 | O | TRP | B | 94 | 7.075 | 61.297 | 90.026 | 1.00100.07 | B |
| ATOM | 2453 | N | ARG | B | 95 | 8.552 | 61.379 | 91.760 | 1.00100.04 | B |
| ATOM | 2454 | CA | ARG | B | 95 | 8.607 | 62.831 | 91.981 | 1.00100.04 | B |
| ATOM | 2455 | CB | ARG | B | 95 | 7.344 | 63.530 | 91.450 | 1.00100.07 | B |
| ATOM | 2456 | CG | ARG | B | 95 | 7.514 | 64.026 | 90.017 | 1.00100.07 | B |
| ATOM | 2457 | CD | ARG | B | 95 | 6.233 | 64.517 | 89.363 | 1.00100.07 | B |
| ATOM | 2458 | NE | ARG | B | 95 | 6.537 | 65.143 | 88.075 | 1.00100.07 | B |
| ATOM | 2459 | CZ | ARG | B | 95 | 5.631 | 65.504 | 87.169 | 1.00100.07 | B |
| ATOM | 2460 | NH1 | ARG | B | 95 | 4.336 | 65.300 | 87.402 | 1.00100.07 | B |
| ATOM | 2461 | NH2 | ARG | B | 95 | 6.020 | 66.073 | 86.030 | 1.00100.07 | B |
| ATOM | 2462 | C | ARG | B | 95 | 8.732 | 63.047 | 93.489 | 1.00100.04 | B |
| ATOM | 2463 | O | ARG | B | 95 | 8.072 | 63.909 | 94.072 | 1.00100.04 | B |
| ATOM | 2464 | N | THR | B | 96 | 9.602 | 62.240 | 94.094 | 1.00 53.76 | B |
| ATOM | 2465 | CA | THR | B | 96 | 9.877 | 62.226 | 95.532 | 1.00 53.76 | B |
| ATOM | 2466 | CB | THR | B | 96 | 10.996 | 61.214 | 95.862 | 1.00100.07 | B |
| ATOM | 2467 | OG1 | THR | B | 96 | 11.042 | 60.200 | 94.852 | 1.00100.07 | B |
| ATOM | 2468 | CG2 | THR | B | 96 | 10.738 | 60.558 | 97.209 | 1.00100.07 | B |
| ATOM | 2469 | C | THR | B | 96 | 10.283 | 63.528 | 96.198 | 1.00 53.76 | B |
| ATOM | 2470 | O | THR | B | 96 | 9.967 | 64.620 | 95.736 | 1.00 53.76 | B |
| ATOM | 2471 | N | THR | B | 97 | 10.992 | 63.375 | 97.309 | 1.00 66.01 | B |
| ATOM | 2472 | CA | THR | B | 97 | 11.477 | 64.489 | 98.109 | 1.00 66.01 | B |
| ATOM | 2473 | CB | THR | B | 97 | 10.568 | 64.756 | 99.333 | 1.00 84.61 | B |
| ATOM | 2474 | OG1 | THR | B | 97 | 9.191 | 64.675 | 98.942 | 1.00 84.61 | B |
| ATOM | 2475 | CG2 | THR | B | 97 | 10.839 | 66.143 | 99.901 | 1.00 84.61 | B |
| ATOM | 2476 | C | THR | B | 97 | 12.828 | 64.041 | 98.618 | 1.00 66.01 | B |
| ATOM | 2477 | O | THR | B | 97 | 13.371 | 63.045 | 98.138 | 1.00 66.01 | B |
| ATOM | 2478 | N | LEU | B | 98 | 13.358 | 64.766 | 99.595 | 1.00 90.84 | B |
| ATOM | 2479 | CA | LEU | B | 98 | 14.645 | 64.432 | 100.179 | 1.00 90.84 | B |
| ATOM | 2480 | CB | LEU | B | 98 | 15.766 | 64.668 | 99.171 | 1.00100.07 | B |
| ATOM | 2481 | CG | LEU | B | 98 | 16.072 | 63.438 | 98.317 | 1.00100.07 | B |
| ATOM | 2482 | CD1 | LEU | B | 98 | 17.106 | 63.793 | 97.265 | 1.00100.07 | B |

| ATOM | 2483 | CD2 | LEU B 98 | 16.553 | 62.298 | 99.214 | 1.00 | 100.07 | B |
|---|---|---|---|---|---|---|---|---|---|
| ATOM | 2484 | C | LEU B 98 | 14.936 | 65.189 | 101.459 | 1.00 | 90.84 | B |
| ATOM | 2485 | O | LEU B 98 | 14.724 | 66.400 | 101.570 | 1.00 | 90.84 | B |
| ATOM | 2486 | N | ILE B 99 | 15.443 | 64.443 | 102.426 | 1.00 | 100.07 | B |
| ATOM | 2487 | CA | ILE B 99 | 15.764 | 64.996 | 103.715 | 1.00 | 100.07 | B |
| ATOM | 2488 | CB | ILE B 99 | 15.091 | 64.178 | 104.816 | 1.00 | 82.57 | B |
| ATOM | 2489 | CG2 | ILE B 99 | 15.535 | 64.666 | 106.177 | 1.00 | 82.57 | B |
| ATOM | 2490 | CG1 | ILE B 99 | 13.574 | 64.276 | 104.658 | 1.00 | 82.57 | B |
| ATOM | 2491 | CD | ILE B 99 | 13.049 | 65.709 | 104.586 | 1.00 | 82.57 | B |
| ATOM | 2492 | C | ILE B 99 | 17.258 | 65.039 | 103.958 | 1.00 | 100.07 | B |
| ATOM | 2493 | O | ILE B 99 | 18.018 | 64.203 | 103.473 | 1.00 | 100.07 | B |
| ATOM | 2494 | N | LEU B 100 | 17.661 | 66.048 | 104.711 | 1.00 | 94.32 | B |
| ATOM | 2495 | CA | LEU B 100 | 19.046 | 66.254 | 105.075 | 1.00 | 94.32 | B |
| ATOM | 2496 | CB | LEU B 100 | 19.776 | 67.066 | 104.001 | 1.00 | 96.49 | B |
| ATOM | 2497 | CG | LEU B 100 | 21.262 | 67.353 | 104.253 | 1.00 | 96.49 | B |
| ATOM | 2498 | CD1 | LEU B 100 | 22.084 | 66.077 | 104.097 | 1.00 | 96.49 | B |
| ATOM | 2499 | CD2 | LEU B 100 | 21.742 | 68.412 | 103.281 | 1.00 | 96.49 | B |
| ATOM | 2500 | C | LEU B 100 | 18.921 | 67.072 | 106.336 | 1.00 | 94.32 | B |
| ATOM | 2501 | O | LEU B 100 | 18.637 | 68.261 | 106.265 | 1.00 | 94.32 | B |
| ATOM | 2502 | N | ARG B 101 | 19.099 | 66.428 | 107.484 | 1.00 | 100.07 | B |
| ATOM | 2503 | CA | ARG B 101 | 18.996 | 67.124 | 108.756 | 1.00 | 100.07 | B |
| ATOM | 2504 | CB | ARG B 101 | 17.862 | 66.541 | 109.600 | 1.00 | 100.07 | B |
| ATOM | 2505 | CG | ARG B 101 | 16.645 | 66.117 | 108.811 | 1.00 | 100.07 | B |
| ATOM | 2506 | CD | ARG B 101 | 15.767 | 65.207 | 109.654 | 1.00 | 100.07 | B |
| ATOM | 2507 | NE | ARG B 101 | 14.936 | 64.329 | 108.833 | 1.00 | 100.07 | B |
| ATOM | 2508 | CZ | ARG B 101 | 14.128 | 63.392 | 109.319 | 1.00 | 100.07 | B |
| ATOM | 2509 | NH1 | ARG B 101 | 14.037 | 63.209 | 110.630 | 1.00 | 100.07 | B |
| ATOM | 2510 | NH2 | ARG B 101 | 13.411 | 62.636 | 108.493 | 1.00 | 100.07 | B |
| ATOM | 2511 | C | ARG B 101 | 20.302 | 66.991 | 109.522 | 1.00 | 100.07 | B |
| ATOM | 2512 | O | ARG B 101 | 20.391 | 67.439 | 110.663 | 1.00 | 100.07 | B |
| ATOM | 2513 | N | ALA B 102 | 21.311 | 66.366 | 108.917 | 1.00 | 84.36 | B |
| ATOM | 2514 | CA | ALA B 102 | 22.595 | 66.238 | 109.602 | 1.00 | 84.36 | B |
| ATOM | 2515 | CB | ALA B 102 | 23.664 | 65.684 | 108.668 | 1.00 | 31.29 | B |
| ATOM | 2516 | C | ALA B 102 | 22.951 | 67.654 | 110.027 | 1.00 | 84.36 | B |
| ATOM | 2517 | O | ALA B 102 | 22.259 | 68.604 | 109.659 | 1.00 | 84.36 | B |
| ATOM | 2518 | N | ALA B 103 | 24.021 | 67.816 | 110.790 | 1.00 | 98.79 | B |
| ATOM | 2519 | CA | ALA B 103 | 24.378 | 69.152 | 111.235 | 1.00 | 98.79 | B |
| ATOM | 2520 | CB | ALA B 103 | 23.258 | 69.718 | 112.084 | 1.00 | 36.97 | B |
| ATOM | 2521 | C | ALA B 103 | 25.663 | 69.114 | 112.033 | 1.00 | 98.79 | B |
| ATOM | 2522 | O | ALA B 103 | 26.061 | 70.105 | 112.646 | 1.00 | 98.79 | B |
| ATOM | 2523 | N | GLY B 104 | 26.301 | 67.952 | 112.049 | 1.00 | 99.66 | B |
| ATOM | 2524 | CA | GLY B 104 | 27.552 | 67.847 | 112.760 | 1.00 | 99.66 | B |
| ATOM | 2525 | C | GLY B 104 | 28.491 | 68.825 | 112.083 | 1.00 | 99.66 | B |
| ATOM | 2526 | O | GLY B 104 | 28.585 | 68.821 | 110.855 | 1.00 | 99.66 | B |
| ATOM | 2527 | N | PRO B 105 | 29.177 | 69.695 | 112.840 | 1.00 | 99.90 | B |
| ATOM | 2528 | CD | PRO B 105 | 28.942 | 69.919 | 114.281 | 1.00 | 61.68 | B |
| ATOM | 2529 | CA | PRO B 105 | 30.118 | 70.692 | 112.296 | 1.00 | 99.90 | B |
| ATOM | 2530 | CB | PRO B 105 | 30.670 | 71.345 | 113.565 | 1.00 | 61.68 | B |
| ATOM | 2531 | CG | PRO B 105 | 29.481 | 71.305 | 114.489 | 1.00 | 61.68 | B |
| ATOM | 2532 | C | PRO B 105 | 31.243 | 70.165 | 111.356 | 1.00 | 99.90 | B |
| ATOM | 2533 | O | PRO B 105 | 32.430 | 70.265 | 111.683 | 1.00 | 99.90 | B |
| ATOM | 2534 | N | LYS B 106 | 30.863 | 69.637 | 110.188 | 1.00 | 99.99 | B |
| ATOM | 2535 | CA | LYS B 106 | 31.815 | 69.084 | 109.213 | 1.00 | 99.99 | B |
| ATOM | 2536 | CB | LYS B 106 | 32.076 | 67.612 | 109.536 | 1.00 | 99.91 | B |
| ATOM | 2537 | CG | LYS B 106 | 32.565 | 67.373 | 110.958 | 1.00 | 99.91 | B |
| ATOM | 2538 | CD | LYS B 106 | 32.057 | 66.047 | 111.509 | 1.00 | 99.91 | B |
| ATOM | 2539 | CE | LYS B 106 | 32.273 | 65.964 | 113.010 | 1.00 | 99.91 | B |
| ATOM | 2540 | NZ | LYS B 106 | 31.590 | 64.787 | 113.598 | 1.00 | 99.91 | B |
| ATOM | 2541 | C | LYS B 106 | 31.306 | 69.223 | 107.765 | 1.00 | 99.99 | B |
| ATOM | 2542 | O | LYS B 106 | 30.276 | 69.855 | 107.536 | 1.00 | 99.99 | B |
| ATOM | 2543 | N | GLU B 107 | 32.005 | 68.619 | 106.797 | 1.00 | 61.16 | B |
| ATOM | 2544 | CA | GLU B 107 | 31.626 | 68.737 | 105.380 | 1.00 | 61.16 | B |
| ATOM | 2545 | CB | GLU B 107 | 32.835 | 68.423 | 104.478 | 1.00 | 100.07 | B |
| ATOM | 2546 | CG | GLU B 107 | 34.002 | 69.422 | 104.564 | 1.00 | 100.07 | B |
| ATOM | 2547 | CD | GLU B 107 | 34.986 | 69.333 | 103.382 | 1.00 | 100.07 | B |
| ATOM | 2548 | OE1 | GLU B 107 | 34.609 | 69.718 | 102.254 | 1.00 | 100.07 | B |
| ATOM | 2549 | OE2 | GLU B 107 | 36.138 | 68.883 | 103.581 | 1.00 | 100.07 | B |
| ATOM | 2550 | C | GLU B 107 | 30.422 | 67.956 | 104.845 | 1.00 | 61.16 | B |
| ATOM | 2551 | O | GLU B 107 | 30.571 | 66.820 | 104.398 | 1.00 | 61.16 | B |
| ATOM | 2552 | N | VAL B 108 | 29.241 | 68.574 | 104.863 | 1.00 | 55.48 | B |
| ATOM | 2553 | CA | VAL B 108 | 28.019 | 67.944 | 104.338 | 1.00 | 55.48 | B |
| ATOM | 2554 | CB | VAL B 108 | 26.806 | 68.899 | 104.429 | 1.00 | 80.68 | B |
| ATOM | 2555 | CG1 | VAL B 108 | 25.721 | 68.457 | 103.468 | 1.00 | 80.68 | B |
| ATOM | 2556 | CG2 | VAL B 108 | 26.259 | 68.913 | 105.846 | 1.00 | 80.68 | B |
| ATOM | 2557 | C | VAL B 108 | 28.256 | 67.612 | 102.871 | 1.00 | 55.48 | B |
| ATOM | 2558 | O | VAL B 108 | 28.874 | 68.395 | 102.167 | 1.00 | 55.48 | B |
| ATOM | 2559 | N | ARG B 109 | 27.759 | 66.472 | 102.399 | 1.00 | 92.03 | B |
| ATOM | 2560 | CA | ARG B 109 | 27.998 | 66.098 | 101.007 | 1.00 | 92.03 | B |
| ATOM | 2561 | CB | ARG B 109 | 29.477 | 65.782 | 100.833 | 1.00 | 100.07 | B |
| ATOM | 2562 | CG | ARG B 109 | 30.058 | 64.980 | 101.985 | 1.00 | 100.07 | B |
| ATOM | 2563 | CD | ARG B 109 | 31.512 | 64.666 | 101.726 | 1.00 | 100.07 | B |
| ATOM | 2564 | NE | ARG B 109 | 32.377 | 65.057 | 102.832 | 1.00 | 100.07 | B |
| ATOM | 2565 | CZ | ARG B 109 | 33.699 | 64.922 | 102.816 | 1.00 | 100.07 | B |
| ATOM | 2566 | NH1 | ARG B 109 | 34.299 | 64.406 | 101.753 | 1.00 | 100.07 | B |

| ATOM | 2567 | NH2 | ARG | B | 109 | 34.422 | 65.301 | 103.860 | 1.00 | 100.07 | B |
|------|------|-----|-----|---|-----|--------|--------|---------|------|--------|---|
| ATOM | 2568 | C | ARG | B | 109 | 27.177 | 64.938 | 100.448 | 1.00 | 92.03 | B |
| ATOM | 2569 | O | ARG | B | 109 | 27.539 | 63.777 | 100.629 | 1.00 | 92.03 | B |
| ATOM | 2570 | N | ALA | B | 110 | 26.094 | 65.269 | 99.745 | 1.00 | 100.07 | B |
| ATOM | 2571 | CA | ALA | B | 110 | 25.198 | 64.291 | 99.121 | 1.00 | 100.07 | B |
| ATOM | 2572 | CB | ALA | B | 110 | 25.788 | 63.809 | 97.803 | 1.00 | 80.83 | B |
| ATOM | 2573 | C | ALA | B | 110 | 24.821 | 63.091 | 99.994 | 1.00 | 100.07 | B |
| ATOM | 2574 | O | ALA | B | 110 | 23.686 | 63.005 | 100.453 | 1.00 | 100.07 | B |
| ATOM | 2575 | N | VAL | B | 111 | 25.763 | 62.166 | 100.203 | 1.00 | 100.07 | B |
| ATOM | 2576 | CA | VAL | B | 111 | 25.545 | 60.957 | 101.022 | 1.00 | 100.07 | B |
| ATOM | 2577 | CB | VAL | B | 111 | 26.891 | 60.379 | 101.574 | 1.00 | 71.79 | B |
| ATOM | 2578 | CG1 | VAL | B | 111 | 26.628 | 59.239 | 102.561 | 1.00 | 71.79 | B |
| ATOM | 2579 | CG2 | VAL | B | 111 | 27.743 | 59.878 | 100.433 | 1.00 | 71.79 | B |
| ATOM | 2580 | C | VAL | B | 111 | 24.627 | 61.166 | 102.230 | 1.00 | 100.07 | B |
| ATOM | 2581 | O | VAL | B | 111 | 23.600 | 60.501 | 102.381 | 1.00 | 100.07 | B |
| ATOM | 2582 | N | ASP | B | 112 | 25.019 | 62.091 | 103.092 | 1.00 | 86.11 | B |
| ATOM | 2583 | CA | ASP | B | 112 | 24.280 | 62.404 | 104.304 | 1.00 | 86.11 | B |
| ATOM | 2584 | CB | ASP | B | 112 | 25.011 | 63.522 | 105.052 | 1.00 | 100.07 | B |
| ATOM | 2585 | CG | ASP | B | 112 | 26.533 | 63.410 | 104.938 | 1.00 | 100.07 | B |
| ATOM | 2586 | OD1 | ASP | B | 112 | 27.230 | 64.364 | 105.352 | 1.00 | 100.07 | B |
| ATOM | 2587 | OD2 | ASP | B | 112 | 27.036 | 62.376 | 104.438 | 1.00 | 100.07 | B |
| ATOM | 2588 | C | ASP | B | 112 | 22.838 | 62.835 | 104.011 | 1.00 | 86.11 | B |
| ATOM | 2589 | O | ASP | B | 112 | 22.119 | 63.285 | 104.904 | 1.00 | 86.11 | B |
| ATOM | 2590 | N | PHE | B | 113 | 22.416 | 62.681 | 102.761 | 1.00 | 100.07 | B |
| ATOM | 2591 | CA | PHE | B | 113 | 21.078 | 63.086 | 102.335 | 1.00 | 100.07 | B |
| ATOM | 2592 | CB | PHE | B | 113 | 21.080 | 63.361 | 100.826 | 1.00 | 90.11 | B |
| ATOM | 2593 | CG | PHE | B | 113 | 20.489 | 64.683 | 100.447 | 1.00 | 90.11 | B |
| ATOM | 2594 | CD1 | PHE | B | 113 | 20.974 | 65.859 | 100.997 | 1.00 | 90.11 | B |
| ATOM | 2595 | CD2 | PHE | B | 113 | 19.466 | 64.758 | 99.516 | 1.00 | 90.11 | B |
| ATOM | 2596 | CE1 | PHE | B | 113 | 20.448 | 67.093 | 100.623 | 1.00 | 90.11 | B |
| ATOM | 2597 | CE2 | PHE | B | 113 | 18.934 | 65.989 | 99.135 | 1.00 | 90.11 | B |
| ATOM | 2598 | CZ | PHE | B | 113 | 19.427 | 67.156 | 99.689 | 1.00 | 90.11 | B |
| ATOM | 2599 | C | PHE | B | 113 | 19.949 | 62.105 | 102.655 | 1.00 | 100.07 | B |
| ATOM | 2600 | O | PHE | B | 113 | 19.202 | 61.717 | 101.756 | 1.00 | 100.07 | B |
| ATOM | 2601 | N | THR | B | 114 | 19.813 | 61.711 | 103.920 | 1.00 | 100.07 | B |
| ATOM | 2602 | CA | THR | B | 114 | 18.742 | 60.789 | 104.315 | 1.00 | 100.07 | B |
| ATOM | 2603 | CB | THR | B | 114 | 17.361 | 61.486 | 104.238 | 1.00 | 88.84 | B |
| ATOM | 2604 | OG1 | THR | B | 114 | 17.280 | 62.487 | 105.258 | 1.00 | 88.84 | B |
| ATOM | 2605 | CG2 | THR | B | 114 | 16.229 | 60.486 | 104.412 | 1.00 | 88.84 | B |
| ATOM | 2606 | C | THR | B | 114 | 18.704 | 59.555 | 103.409 | 1.00 | 100.07 | B |
| ATOM | 2607 | O | THR | B | 114 | 18.027 | 59.555 | 102.379 | 1.00 | 100.07 | B |
| ATOM | 2608 | N | PRO | B | 115 | 19.409 | 58.477 | 103.798 | 1.00 | 99.99 | B |
| ATOM | 2609 | CD | PRO | B | 115 | 20.172 | 58.342 | 105.052 | 1.00 | 100.07 | B |
| ATOM | 2610 | CA | PRO | B | 115 | 19.467 | 57.231 | 103.021 | 1.00 | 99.99 | B |
| ATOM | 2611 | CB | PRO | B | 115 | 20.439 | 56.364 | 103.825 | 1.00 | 100.07 | B |
| ATOM | 2612 | CG | PRO | B | 115 | 20.235 | 56.840 | 105.223 | 1.00 | 100.07 | B |
| ATOM | 2613 | C | PRO | B | 115 | 18.169 | 56.495 | 102.696 | 1.00 | 99.99 | B |
| ATOM | 2614 | O | PRO | B | 115 | 17.844 | 55.486 | 103.319 | 1.00 | 99.99 | B |
| ATOM | 2615 | N | SER | B | 116 | 17.452 | 56.995 | 101.693 | 1.00 | 100.07 | B |
| ATOM | 2616 | CA | SER | B | 116 | 16.196 | 56.402 | 101.246 | 1.00 | 100.07 | B |
| ATOM | 2617 | CB | SER | B | 116 | 15.185 | 57.509 | 100.928 | 1.00 | 61.15 | B |
| ATOM | 2618 | OG | SER | B | 116 | 14.031 | 56.989 | 100.286 | 1.00 | 61.15 | B |
| ATOM | 2619 | C | SER | B | 116 | 16.414 | 55.533 | 100.001 | 1.00 | 100.07 | B |
| ATOM | 2620 | O | SER | B | 116 | 17.012 | 55.977 | 99.022 | 1.00 | 100.07 | B |
| ATOM | 2621 | N | ALA | B | 117 | 15.940 | 54.290 | 100.046 | 1.00 | 67.48 | B |
| ATOM | 2622 | CA | ALA | B | 117 | 16.071 | 53.394 | 98.904 | 1.00 | 67.48 | B |
| ATOM | 2623 | CB | ALA | B | 117 | 15.756 | 51.942 | 99.309 | 1.00 | 19.78 | B |
| ATOM | 2624 | C | ALA | B | 117 | 15.080 | 53.894 | 97.864 | 1.00 | 67.48 | B |
| ATOM | 2625 | O | ALA | B | 117 | 14.692 | 55.060 | 97.903 | 1.00 | 67.48 | B |
| ATOM | 2626 | N | ASP | B | 118 | 14.666 | 53.021 | 96.948 | 1.00 | 81.51 | B |
| ATOM | 2627 | CA | ASP | B | 118 | 13.727 | 53.380 | 95.879 | 1.00 | 81.51 | B |
| ATOM | 2628 | CB | ASP | B | 118 | 12.296 | 53.561 | 96.428 | 1.00 | 99.81 | B |
| ATOM | 2629 | CG | ASP | B | 118 | 12.189 | 54.653 | 97.481 | 1.00 | 99.81 | B |
| ATOM | 2630 | OD1 | ASP | B | 118 | 12.482 | 54.391 | 98.670 | 1.00 | 99.81 | B |
| ATOM | 2631 | OD2 | ASP | B | 118 | 11.809 | 55.782 | 97.110 | 1.00 | 99.81 | B |
| ATOM | 2632 | C | ASP | B | 118 | 14.169 | 54.632 | 95.117 | 1.00 | 81.51 | B |
| ATOM | 2633 | O | ASP | B | 118 | 13.482 | 55.097 | 94.202 | 1.00 | 81.51 | B |
| ATOM | 2634 | N | VAL | B | 119 | 15.326 | 55.163 | 95.506 | 1.00 | 99.55 | B |
| ATOM | 2635 | CA | VAL | B | 119 | 15.917 | 56.345 | 94.886 | 1.00 | 99.55 | B |
| ATOM | 2636 | CB | VAL | B | 119 | 15.337 | 57.668 | 95.467 | 1.00 | 47.33 | B |
| ATOM | 2637 | CG1 | VAL | B | 119 | 15.695 | 58.823 | 94.556 | 1.00 | 47.33 | B |
| ATOM | 2638 | CG2 | VAL | B | 119 | 13.830 | 57.580 | 95.614 | 1.00 | 47.33 | B |
| ATOM | 2639 | C | VAL | B | 119 | 17.419 | 56.317 | 95.168 | 1.00 | 99.55 | B |
| ATOM | 2640 | O | VAL | B | 119 | 17.832 | 56.326 | 96.327 | 1.00 | 99.55 | B |
| ATOM | 2641 | N | GLU | B | 120 | 18.232 | 56.268 | 94.115 | 1.00 | 100.07 | B |
| ATOM | 2642 | CA | GLU | B | 120 | 19.686 | 56.242 | 94.281 | 1.00 | 100.07 | B |
| ATOM | 2643 | CB | GLU | B | 120 | 20.347 | 55.297 | 93.259 | 1.00 | 100.07 | B |
| ATOM | 2644 | CG | GLU | B | 120 | 20.584 | 53.863 | 93.765 | 1.00 | 100.07 | B |
| ATOM | 2645 | CD | GLU | B | 120 | 21.693 | 53.132 | 92.999 | 1.00 | 100.07 | B |
| ATOM | 2646 | OE1 | GLU | B | 120 | 22.851 | 53.609 | 93.029 | 1.00 | 100.07 | B |
| ATOM | 2647 | OE2 | GLU | B | 120 | 21.410 | 52.082 | 92.373 | 1.00 | 100.07 | B |
| ATOM | 2648 | C | GLU | B | 120 | 20.334 | 57.622 | 94.176 | 1.00 | 100.07 | B |
| ATOM | 2649 | O | GLU | B | 120 | 19.760 | 58.562 | 93.617 | 1.00 | 100.07 | B |
| ATOM | 2650 | N | ILE | B | 121 | 21.540 | 57.722 | 94.730 | 1.00 | 86.75 | B |

| | | | | | | | | | |
|---|---|---|---|---|---|---|---|---|---|
| ATOM | 2651 | CA | ILE | B | 121 | 22.320 | 58.952 | 94.725 | 1.00 86.75 | B |
| ATOM | 2652 | CB | ILE | B | 121 | 22.667 | 59.395 | 96.176 | 1.00 60.89 | B |
| ATOM | 2653 | CG2 | ILE | B | 121 | 23.796 | 60.419 | 96.169 | 1.00 60.89 | B |
| ATOM | 2654 | CG1 | ILE | B | 121 | 21.408 | 59.954 | 96.864 | 1.00 60.89 | B |
| ATOM | 2655 | CD | ILE | B | 121 | 20.766 | 61.159 | 96.164 | 1.00 60.89 | B |
| ATOM | 2656 | C | ILE | B | 121 | 23.593 | 58.669 | 93.948 | 1.00 86.75 | B |
| ATOM | 2657 | O | ILE | B | 121 | 24.635 | 58.360 | 94.526 | 1.00 86.75 | B |
| ATOM | 2658 | N | MET | B | 122 | 23.483 | 58.756 | 92.628 | 1.00 68.28 | B |
| ATOM | 2659 | CA | MET | B | 122 | 24.607 | 58.510 | 91.736 | 1.00 68.28 | B |
| ATOM | 2660 | CB | MET | B | 122 | 24.272 | 59.014 | 90.331 | 1.00100.07 | B |
| ATOM | 2661 | CG | MET | B | 122 | 24.003 | 57.901 | 89.333 | 1.00100.07 | B |
| ATOM | 2662 | SD | MET | B | 122 | 22.975 | 56.597 | 90.026 | 1.00100.07 | B |
| ATOM | 2663 | CE | MET | B | 122 | 24.226 | 55.365 | 90.479 | 1.00100.07 | B |
| ATOM | 2664 | C | MET | B | 122 | 25.891 | 59.178 | 92.235 | 1.00 68.28 | B |
| ATOM | 2665 | O | MET | B | 122 | 26.891 | 58.508 | 92.514 | 1.00 68.28 | B |
| ATOM | 2666 | N | ASN | B | 123 | 25.857 | 60.501 | 92.341 | 1.00 99.82 | B |
| ATOM | 2667 | CA | ASN | B | 123 | 27.009 | 61.257 | 92.807 | 1.00 99.82 | B |
| ATOM | 2668 | CB | ASN | B | 123 | 27.095 | 62.579 | 92.045 | 1.00 54.79 | B |
| ATOM | 2669 | CG | ASN | B | 123 | 25.800 | 63.352 | 92.084 | 1.00 54.79 | B |
| ATOM | 2670 | OD1 | ASN | B | 123 | 24.718 | 62.769 | 92.119 | 1.00 54.79 | B |
| ATOM | 2671 | ND2 | ASN | B | 123 | 25.900 | 64.673 | 92.058 | 1.00 54.79 | B |
| ATOM | 2672 | C | ASN | B | 123 | 26.908 | 61.495 | 94.314 | 1.00 99.82 | B |
| ATOM | 2673 | O | ASN | B | 123 | 26.147 | 62.348 | 94.773 | 1.00 99.82 | B |
| ATOM | 2674 | N | PRO | B | 124 | 27.699 | 60.743 | 95.098 | 1.00 35.86 | B |
| ATOM | 2675 | CD | PRO | B | 124 | 28.697 | 59.817 | 94.528 | 1.00100.07 | B |
| ATOM | 2676 | CA | PRO | B | 124 | 27.800 | 60.747 | 96.562 | 1.00 35.86 | B |
| ATOM | 2677 | CB | PRO | B | 124 | 28.588 | 59.484 | 96.840 | 1.00100.07 | B |
| ATOM | 2678 | CG | PRO | B | 124 | 29.581 | 59.509 | 95.726 | 1.00100.07 | B |
| ATOM | 2679 | C | PRO | B | 124 | 28.453 | 61.931 | 97.208 | 1.00 35.86 | B |
| ATOM | 2680 | O | PRO | B | 124 | 27.993 | 62.399 | 98.241 | 1.00 35.86 | B |
| ATOM | 2681 | N | ASP | B | 125 | 29.550 | 62.386 | 96.620 | 1.00100.07 | B |
| ATOM | 2682 | CA | ASP | B | 125 | 30.287 | 63.514 | 97.160 | 1.00100.07 | B |
| ATOM | 2683 | CB | ASP | B | 125 | 31.677 | 63.542 | 96.541 | 1.00100.07 | B |
| ATOM | 2684 | CG | ASP | B | 125 | 32.258 | 62.150 | 96.400 | 1.00100.07 | B |
| ATOM | 2685 | OD1 | ASP | B | 125 | 31.872 | 61.267 | 97.195 | 1.00100.07 | B |
| ATOM | 2686 | OD2 | ASP | B | 125 | 33.096 | 61.932 | 95.504 | 1.00100.07 | B |
| ATOM | 2687 | C | ASP | B | 125 | 29.525 | 64.795 | 96.873 | 1.00100.07 | B |
| ATOM | 2688 | O | ASP | B | 125 | 28.635 | 65.159 | 97.639 | 1.00100.07 | B |
| ATOM | 2689 | N | LEU | B | 126 | 29.842 | 65.465 | 95.770 | 1.00 99.82 | B |
| ATOM | 2690 | CA | LEU | B | 126 | 29.157 | 66.711 | 95.441 | 1.00 99.82 | B |
| ATOM | 2691 | CB | LEU | B | 126 | 27.736 | 66.440 | 94.950 | 1.00 92.04 | B |
| ATOM | 2692 | CG | LEU | B | 126 | 26.955 | 67.718 | 94.631 | 1.00 92.04 | B |
| ATOM | 2693 | CD1 | LEU | B | 126 | 27.485 | 68.342 | 93.347 | 1.00 92.04 | B |
| ATOM | 2694 | CD2 | LEU | B | 126 | 25.485 | 67.397 | 94.491 | 1.00 92.04 | B |
| ATOM | 2695 | C | LEU | B | 126 | 29.098 | 67.545 | 96.714 | 1.00 99.82 | B |
| ATOM | 2696 | O | LEU | B | 126 | 28.062 | 67.603 | 97.378 | 1.00 99.82 | B |
| ATOM | 2697 | N | HIS | B | 127 | 30.213 | 68.187 | 97.043 | 1.00 68.55 | B |
| ATOM | 2698 | CA | HIS | B | 127 | 30.334 | 68.991 | 98.251 | 1.00 68.55 | B |
| ATOM | 2699 | CB | HIS | B | 127 | 31.320 | 70.123 | 98.019 | 1.00100.07 | B |
| ATOM | 2700 | CG | HIS | B | 127 | 31.805 | 70.734 | 99.290 | 1.00100.07 | B |
| ATOM | 2701 | CD2 | HIS | B | 127 | 33.002 | 70.653 | 99.919 | 1.00100.07 | B |
| ATOM | 2702 | ND1 | HIS | B | 127 | 30.976 | 71.443 | 100.132 | 1.00100.07 | B |
| ATOM | 2703 | CE1 | HIS | B | 127 | 31.640 | 71.767 | 101.227 | 1.00100.07 | B |
| ATOM | 2704 | NE2 | HIS | B | 127 | 32.872 | 71.300 | 101.124 | 1.00100.07 | B |
| ATOM | 2705 | C | HIS | B | 127 | 29.088 | 69.566 | 98.933 | 1.00 68.55 | B |
| ATOM | 2706 | O | HIS | B | 127 | 29.066 | 69.676 | 100.151 | 1.00 68.55 | B |
| ATOM | 2707 | N | ILE | B | 128 | 28.063 | 69.933 | 98.174 | 1.00100.07 | B |
| ATOM | 2708 | CA | ILE | B | 128 | 26.829 | 70.503 | 98.737 | 1.00100.07 | B |
| ATOM | 2709 | CB | ILE | B | 128 | 25.911 | 69.420 | 99.377 | 1.00 98.44 | B |
| ATOM | 2710 | CG2 | ILE | B | 128 | 24.688 | 70.087 | 100.028 | 1.00 98.44 | B |
| ATOM | 2711 | CG1 | ILE | B | 128 | 25.426 | 68.448 | 98.291 | 1.00 98.44 | B |
| ATOM | 2712 | CD | ILE | B | 128 | 24.313 | 67.505 | 98.725 | 1.00 98.44 | B |
| ATOM | 2713 | C | ILE | B | 128 | 27.018 | 71.661 | 99.728 | 1.00100.07 | B |
| ATOM | 2714 | O | ILE | B | 128 | 26.510 | 72.760 | 99.488 | 1.00100.07 | B |
| ATOM | 2715 | N | ALA | B | 129 | 27.721 | 71.432 | 100.835 | 1.00 55.59 | B |
| ATOM | 2716 | CA | ALA | B | 129 | 27.953 | 72.499 | 101.801 | 1.00 55.59 | B |
| ATOM | 2717 | CB | ALA | B | 129 | 26.619 | 73.108 | 102.249 | 1.00 17.18 | B |
| ATOM | 2718 | C | ALA | B | 129 | 28.785 | 72.115 | 103.016 | 1.00 55.59 | B |
| ATOM | 2719 | O | ALA | B | 129 | 28.753 | 70.975 | 103.487 | 1.00 55.59 | B |
| ATOM | 2720 | N | THR | B | 130 | 29.530 | 73.101 | 103.511 | 1.00 98.41 | B |
| ATOM | 2721 | CA | THR | B | 130 | 30.400 | 72.962 | 104.678 | 1.00 98.41 | B |
| ATOM | 2722 | CB | THR | B | 130 | 31.868 | 73.431 | 104.348 | 1.00 63.09 | B |
| ATOM | 2723 | OG1 | THR | B | 130 | 32.586 | 72.385 | 103.676 | 1.00 63.09 | B |
| ATOM | 2724 | CG2 | THR | B | 130 | 32.615 | 73.823 | 105.613 | 1.00 63.09 | B |
| ATOM | 2725 | C | THR | B | 130 | 29.835 | 73.820 | 105.823 | 1.00 98.41 | B |
| ATOM | 2726 | O | THR | B | 130 | 29.439 | 74.973 | 105.621 | 1.00 98.41 | B |
| ATOM | 2727 | N | LEU | B | 131 | 29.780 | 73.241 | 107.018 | 1.00 76.18 | B |
| ATOM | 2728 | CA | LEU | B | 131 | 29.298 | 73.950 | 108.199 | 1.00 76.18 | B |
| ATOM | 2729 | CB | LEU | B | 131 | 27.789 | 73.742 | 108.390 | 1.00 99.38 | B |
| ATOM | 2730 | CG | LEU | B | 131 | 27.202 | 72.343 | 108.600 | 1.00 99.38 | B |
| ATOM | 2731 | CD1 | LEU | B | 131 | 25.750 | 72.447 | 109.035 | 1.00 99.38 | B |
| ATOM | 2732 | CD2 | LEU | B | 131 | 27.307 | 71.557 | 107.319 | 1.00 99.38 | B |
| ATOM | 2733 | C | LEU | B | 131 | 30.066 | 73.470 | 109.438 | 1.00 76.18 | B |
| ATOM | 2734 | O | LEU | B | 131 | 30.284 | 72.269 | 109.617 | 1.00 76.18 | B |

| | | | | | | | | | |
|---|---|---|---|---|---|---|---|---|---|
|ATOM|2735|N|GLU|B|132|30.475|74.417|110.283|1.00 97.11|B|
|ATOM|2736|CA|GLU|B|132|31.255|74.123|111.486|1.00 97.11|B|
|ATOM|2737|CB|GLU|B|132|32.533|74.981|111.482|1.00100.00|B|
|ATOM|2738|CG|GLU|B|132|33.555|74.656|112.575|1.00100.00|B|
|ATOM|2739|CD|GLU|B|132|34.748|75.610|112.586|1.00100.00|B|
|ATOM|2740|OE1|GLU|B|132|35.586|75.552|111.658|1.00100.00|B|
|ATOM|2741|OE2|GLU|B|132|34.845|76.423|113.530|1.00100.00|B|
|ATOM|2742|C|GLU|B|132|30.470|74.372|112.769|1.00 97.11|B|
|ATOM|2743|O|GLU|B|132|29.253|74.529|112.721|1.00 97.11|B|
|ATOM|2744|N|GLU|B|133|31.187|74.411|113.898|1.00 80.07|B|
|ATOM|2745|CA|GLU|B|133|30.617|74.621|115.235|1.00 80.07|B|
|ATOM|2746|CB|GLU|B|133|30.981|76.006|115.796|1.00100.07|B|
|ATOM|2747|CG|GLU|B|133|32.189|75.989|116.753|1.00100.07|B|
|ATOM|2748|CD|GLU|B|133|32.288|77.233|117.655|1.00100.07|B|
|ATOM|2749|OE1|GLU|B|133|31.285|77.575|118.330|1.00100.07|B|
|ATOM|2750|OE2|GLU|B|133|33.374|77.859|117.701|1.00100.07|B|
|ATOM|2751|C|GLU|B|133|29.116|74.438|115.274|1.00 80.07|B|
|ATOM|2752|O|GLU|B|133|28.625|73.426|115.764|1.00 80.07|B|
|ATOM|2753|N|GLY|B|134|28.388|75.422|114.760|1.00100.07|B|
|ATOM|2754|CA|GLY|B|134|26.943|75.316|114.728|1.00100.07|B|
|ATOM|2755|C|GLY|B|134|26.552|74.003|114.073|1.00100.07|B|
|ATOM|2756|O|GLY|B|134|27.403|73.183|113.716|1.00100.07|B|
|ATOM|2757|N|GLY|B|135|25.256|73.795|113.915|1.00 82.84|B|
|ATOM|2758|CA|GLY|B|135|24.799|72.571|113.299|1.00 82.84|B|
|ATOM|2759|C|GLY|B|135|23.382|72.791|112.835|1.00 82.84|B|
|ATOM|2760|O|GLY|B|135|22.486|72.022|113.165|1.00 82.84|B|
|ATOM|2761|N|LYS|B|136|23.175|73.874|112.097|1.00100.07|B|
|ATOM|2762|CA|LYS|B|136|21.855|74.186|111.564|1.00100.07|B|
|ATOM|2763|CB|LYS|B|136|21.897|75.511|110.784|1.00 99.93|B|
|ATOM|2764|CG|LYS|B|136|21.306|76.691|111.515|1.00 99.93|B|
|ATOM|2765|CD|LYS|B|136|19.839|76.447|111.797|1.00 99.93|B|
|ATOM|2766|CE|LYS|B|136|19.267|77.505|112.716|1.00 99.93|B|
|ATOM|2767|NZ|LYS|B|136|17.844|77.213|113.027|1.00 99.93|B|
|ATOM|2768|C|LYS|B|136|21.464|73.048|110.621|1.00100.07|B|
|ATOM|2769|O|LYS|B|136|21.312|71.895|111.036|1.00100.07|B|
|ATOM|2770|N|LEU|B|137|21.293|73.393|109.350|1.00 98.57|B|
|ATOM|2771|CA|LEU|B|137|20.974|72.424|108.322|1.00 98.57|B|
|ATOM|2772|CB|LEU|B|137|21.786|71.149|108.557|1.00100.07|B|
|ATOM|2773|CG|LEU|B|137|22.513|70.536|107.362|1.00100.07|B|
|ATOM|2774|CD1|LEU|B|137|21.497|70.114|106.316|1.00100.07|B|
|ATOM|2775|CD2|LEU|B|137|23.509|71.538|106.785|1.00100.07|B|
|ATOM|2776|C|LEU|B|137|19.509|72.062|108.158|1.00 98.57|B|
|ATOM|2777|O|LEU|B|137|18.635|72.925|108.038|1.00 98.57|B|
|ATOM|2778|N|TYR|B|138|19.270|70.758|108.165|1.00 93.30|B|
|ATOM|2779|CA|TYR|B|138|17.955|70.177|107.964|1.00 93.30|B|
|ATOM|2780|CB|TYR|B|138|17.083|70.282|109.216|1.00100.07|B|
|ATOM|2781|CG|TYR|B|138|15.841|69.401|109.163|1.00100.07|B|
|ATOM|2782|CD1|TYR|B|138|15.311|68.831|110.326|1.00100.07|B|
|ATOM|2783|CE1|TYR|B|138|14.121|68.096|110.290|1.00100.07|B|
|ATOM|2784|CD2|TYR|B|138|15.152|69.200|107.962|1.00100.07|B|
|ATOM|2785|CE2|TYR|B|138|13.975|68.474|107.919|1.00100.07|B|
|ATOM|2786|CZ|TYR|B|138|13.456|67.929|109.078|1.00100.07|B|
|ATOM|2787|OH|TYR|B|138|12.252|67.257|109.023|1.00100.07|B|
|ATOM|2788|C|TYR|B|138|17.275|70.792|106.752|1.00 93.30|B|
|ATOM|2789|O|TYR|B|138|16.477|71.731|106.850|1.00 93.30|B|
|ATOM|2790|N|MET|B|139|17.631|70.240|105.599|1.00 55.15|B|
|ATOM|2791|CA|MET|B|139|17.089|70.663|104.331|1.00 55.15|B|
|ATOM|2792|CB|MET|B|139|18.193|70.789|103.283|1.00 80.40|B|
|ATOM|2793|CG|MET|B|139|19.147|71.949|103.447|1.00 80.40|B|
|ATOM|2794|SD|MET|B|139|19.904|72.301|101.841|1.00 80.40|B|
|ATOM|2795|CE|MET|B|139|21.380|71.247|101.910|1.00 80.40|B|
|ATOM|2796|C|MET|B|139|16.108|69.607|103.863|1.00 55.15|B|
|ATOM|2797|O|MET|B|139|16.340|68.406|104.037|1.00 55.15|B|
|ATOM|2798|N|GLU|B|140|15.017|70.068|103.265|1.00 77.01|B|
|ATOM|2799|CA|GLU|B|140|13.997|69.186|102.732|1.00 77.01|B|
|ATOM|2800|CB|GLU|B|140|12.729|69.274|103.582|1.00 82.89|B|
|ATOM|2801|CG|GLU|B|140|13.000|68.994|105.054|1.00 82.89|B|
|ATOM|2802|CD|GLU|B|140|11.743|68.800|105.872|1.00 82.89|B|
|ATOM|2803|OE1|GLU|B|140|10.858|69.677|105.824|1.00 82.89|B|
|ATOM|2804|OE2|GLU|B|140|11.645|67.771|106.570|1.00 82.89|B|
|ATOM|2805|C|GLU|B|140|13.756|69.644|101.305|1.00 77.01|B|
|ATOM|2806|O|GLU|B|140|12.992|70.574|101.044|1.00 77.01|B|
|ATOM|2807|N|VAL|B|141|14.446|68.985|100.386|1.00 92.65|B|
|ATOM|2808|CA|VAL|B|141|14.359|69.322|98.979|1.00 92.65|B|
|ATOM|2809|CB|VAL|B|141|15.766|69.498|98.379|1.00100.07|B|
|ATOM|2810|CG1|VAL|B|141|16.551|68.198|98.494|1.00100.07|B|
|ATOM|2811|CG2|VAL|B|141|15.659|69.928|96.933|1.00100.07|B|
|ATOM|2812|C|VAL|B|141|13.606|68.280|98.162|1.00 92.65|B|
|ATOM|2813|O|VAL|B|141|13.829|67.072|98.286|1.00 92.65|B|
|ATOM|2814|N|ARG|B|142|12.705|68.770|97.323|1.00100.07|B|
|ATOM|2815|CA|ARG|B|142|11.932|67.911|96.451|1.00100.07|B|
|ATOM|2816|CB|ARG|B|142|10.620|68.591|96.034|1.00100.07|B|
|ATOM|2817|CG|ARG|B|142|10.609|70.116|96.158|1.00100.07|B|
|ATOM|2818|CD|ARG|B|142|10.544|70.568|97.632|1.00100.07|B|

```
ATOM   2819  NE   ARG B 142      10.382  72.019  97.785  1.00100.07      B
ATOM   2820  CZ   ARG B 142      10.316  72.652  98.957  1.00100.07      B
ATOM   2821  NH1  ARG B 142      10.399  71.965 100.089  1.00100.07      B
ATOM   2822  NH2  ARG B 142      10.168  73.971  99.001  1.00100.07      B
ATOM   2823  C    ARG B 142      12.771  67.626  95.226  1.00100.07      B
ATOM   2824  O    ARG B 142      13.922  68.046  95.138  1.00100.07      B
ATOM   2825  N    VAL B 143      12.197  66.888  94.291  1.00100.07      B
ATOM   2826  CA   VAL B 143      12.869  66.565  93.044  1.00100.07      B
ATOM   2827  CB   VAL B 143      13.654  65.222  93.138  1.00 61.67      B
ATOM   2828  CG1  VAL B 143      14.587  65.088  91.954  1.00 61.67      B
ATOM   2829  CG2  VAL B 143      14.480  65.172  94.425  1.00 61.67      B
ATOM   2830  C    VAL B 143      11.693  66.476  92.072  1.00100.07      B
ATOM   2831  O    VAL B 143      10.574  66.841  92.442  1.00100.07      B
ATOM   2832  N    ASP B 144      11.924  66.007  90.851  1.00 95.21      B
ATOM   2833  CA   ASP B 144      10.846  65.926  89.867  1.00 95.21      B
ATOM   2834  CB   ASP B 144      10.515  67.329  89.344  1.00 72.03      B
ATOM   2835  CG   ASP B 144       9.111  67.775  89.695  1.00 72.03      B
ATOM   2836  OD1  ASP B 144       8.828  67.943  90.900  1.00 72.03      B
ATOM   2837  OD2  ASP B 144       8.292  67.961  88.769  1.00 72.03      B
ATOM   2838  C    ASP B 144      11.207  65.049  88.672  1.00 95.21      B
ATOM   2839  O    ASP B 144      12.376  64.724  88.456  1.00 95.21      B
ATOM   2840  N    ARG B 145      10.191  64.659  87.904  1.00100.07      B
ATOM   2841  CA   ARG B 145      10.410  63.881  86.691  1.00100.07      B
ATOM   2842  CB   ARG B 145       9.142  63.134  86.261  1.00 99.83      B
ATOM   2843  CG   ARG B 145       8.137  63.998  85.489  1.00 99.83      B
ATOM   2844  CD   ARG B 145       7.010  63.161  84.877  1.00 99.83      B
ATOM   2845  NE   ARG B 145       6.077  63.960  84.075  1.00 99.83      B
ATOM   2846  CZ   ARG B 145       4.988  63.473  83.475  1.00 99.83      B
ATOM   2847  NH1  ARG B 145       4.684  62.186  83.580  1.00 99.83      B
ATOM   2848  NH2  ARG B 145       4.195  64.274  82.769  1.00 99.83      B
ATOM   2849  C    ARG B 145      10.654  65.037  85.735  1.00100.07      B
ATOM   2850  O    ARG B 145      10.125  66.128  85.961  1.00100.07      B
ATOM   2851  N    GLY B 146      11.422  64.827  84.672  1.00 98.78      B
ATOM   2852  CA   GLY B 146      11.685  65.944  83.783  1.00 98.78      B
ATOM   2853  C    GLY B 146      11.575  65.771  82.286  1.00 98.78      B
ATOM   2854  O    GLY B 146      10.806  64.953  81.787  1.00 98.78      B
ATOM   2855  N    VAL B 147      12.360  66.577  81.577  1.00 42.75      B
ATOM   2856  CA   VAL B 147      12.412  66.600  80.112  1.00 42.75      B
ATOM   2857  CB   VAL B 147      11.075  67.070  79.506  1.00100.07      B
ATOM   2858  CG1  VAL B 147      10.278  65.878  79.025  1.00100.07      B
ATOM   2859  CG2  VAL B 147      10.276  67.864  80.548  1.00100.07      B
ATOM   2860  C    VAL B 147      13.490  67.610  79.738  1.00 42.75      B
ATOM   2861  O    VAL B 147      14.608  67.517  80.226  1.00 42.75      B
ATOM   2862  N    GLY B 148      13.153  68.584  78.899  1.00 59.44      B
ATOM   2863  CA   GLY B 148      14.124  69.601  78.532  1.00 59.44      B
ATOM   2864  C    GLY B 148      14.693  70.368  79.721  1.00 59.44      B
ATOM   2865  O    GLY B 148      15.242  69.767  80.648  1.00 59.44      B
ATOM   2866  N    TYR B 149      14.574  71.696  79.697  1.00 61.94      B
ATOM   2867  CA   TYR B 149      15.084  72.552  80.783  1.00 61.94      B
ATOM   2868  CB   TYR B 149      16.250  73.427  80.288  1.00 40.16      B
ATOM   2869  CG   TYR B 149      17.066  74.178  81.346  1.00 40.16      B
ATOM   2870  CD1  TYR B 149      18.019  73.518  82.119  1.00 40.16      B
ATOM   2871  CE1  TYR B 149      18.853  74.224  83.004  1.00 40.16      B
ATOM   2872  CD2  TYR B 149      16.958  75.571  81.493  1.00 40.16      B
ATOM   2873  CE2  TYR B 149      17.792  76.289  82.378  1.00 40.16      B
ATOM   2874  CZ   TYR B 149      18.739  75.605  83.128  1.00 40.16      B
ATOM   2875  OH   TYR B 149      19.576  76.283  83.998  1.00 40.16      B
ATOM   2876  C    TYR B 149      13.950  73.465  81.216  1.00 61.94      B
ATOM   2877  O    TYR B 149      13.169  73.911  80.381  1.00 61.94      B
ATOM   2878  N    VAL B 150      13.845  73.724  82.516  1.00 99.87      B
ATOM   2879  CA   VAL B 150      12.824  74.629  83.036  1.00 99.87      B
ATOM   2880  CB   VAL B 150      11.508  73.938  83.379  1.00 90.50      B
ATOM   2881  CG1  VAL B 150      10.516  74.987  83.887  1.00 90.50      B
ATOM   2882  CG2  VAL B 150      10.953  73.226  82.161  1.00 90.50      B
ATOM   2883  C    VAL B 150      13.328  75.286  84.313  1.00 99.87      B
ATOM   2884  O    VAL B 150      13.768  74.615  85.247  1.00 99.87      B
ATOM   2885  N    PRO B 151      13.253  76.619  84.371  1.00100.07      B
ATOM   2886  CD   PRO B 151      13.023  77.508  83.215  1.00 74.65      B
ATOM   2887  CA   PRO B 151      13.710  77.381  85.532  1.00100.07      B
ATOM   2888  CB   PRO B 151      14.412  78.552  84.881  1.00 74.65      B
ATOM   2889  CG   PRO B 151      13.440  78.880  83.752  1.00 74.65      B
ATOM   2890  C    PRO B 151      12.600  77.848  86.466  1.00100.07      B
ATOM   2891  O    PRO B 151      11.637  77.126  86.726  1.00100.07      B
ATOM   2892  N    ALA B 152      12.767  79.073  86.964  1.00 59.87      B
ATOM   2893  CA   ALA B 152      11.803  79.716  87.851  1.00 59.87      B
ATOM   2894  CB   ALA B 152      12.429  80.935  88.505  1.00100.07      B
ATOM   2895  C    ALA B 152      10.555  80.126  87.052  1.00 59.87      B
ATOM   2896  O    ALA B 152      10.185  81.308  86.957  1.00 59.87      B
ATOM   2897  N    GLU B 153       9.942  79.111  86.455  1.00100.07      B
ATOM   2898  CA   GLU B 153       8.720  79.230  85.669  1.00100.07      B
ATOM   2899  CB   GLU B 153       8.982  78.839  84.212  1.00 88.53      B
ATOM   2900  CG   GLU B 153       7.738  78.417  83.439  1.00 88.53      B
ATOM   2901  CD   GLU B 153       6.629  79.446  83.505  1.00 88.53      B
ATOM   2902  OE1  GLU B 153       6.884  80.616  83.160  1.00 88.53      B
```

| | | | | | | | | | |
|---|---|---|---|---|---|---|---|---|---|
|ATOM|2903|OE2|GLU|B|153|5.500|79.086|83.898|1.00 88.53|B|
|ATOM|2904|C|GLU|B|153|7.821|78.185|86.324|1.00100.07|B|
|ATOM|2905|O|GLU|B|153|6.604|78.349|86.459|1.00100.07|B|
|ATOM|2906|N|ARG|B|154|8.468|77.099|86.726|1.00 89.73|B|
|ATOM|2907|CA|ARG|B|154|7.811|76.002|87.398|1.00 89.73|B|
|ATOM|2908|CB|ARG|B|154|8.359|74.676|86.871|1.00100.07|B|
|ATOM|2909|CG|ARG|B|154|7.792|73.455|87.555|1.00100.07|B|
|ATOM|2910|CD|ARG|B|154|7.363|72.400|86.546|1.00100.07|B|
|ATOM|2911|NE|ARG|B|154|6.815|71.222|87.213|1.00100.07|B|
|ATOM|2912|CZ|ARG|B|154|6.216|70.216|86.587|1.00100.07|B|
|ATOM|2913|NH1|ARG|B|154|6.081|70.239|85.266|1.00100.07|B|
|ATOM|2914|NH2|ARG|B|154|5.756|69.188|87.286|1.00100.07|B|
|ATOM|2915|C|ARG|B|154|8.163|76.184|88.871|1.00 89.73|B|
|ATOM|2916|O|ARG|B|154|9.236|75.772|89.331|1.00 89.73|B|
|ATOM|2917|N|HIS|B|155|7.238|76.815|89.588|1.00 81.81|B|
|ATOM|2918|CA|HIS|B|155|7.382|77.134|91.006|1.00 81.81|B|
|ATOM|2919|CB|HIS|B|155|6.327|78.176|91.384|1.00100.07|B|
|ATOM|2920|CG|HIS|B|155|5.950|79.084|90.252|1.00100.07|B|
|ATOM|2921|CD2|HIS|B|155|4.746|79.552|89.844|1.00100.07|B|
|ATOM|2922|ND1|HIS|B|155|6.879|79.607|89.378|1.00100.07|B|
|ATOM|2923|CE1|HIS|B|155|6.264|80.355|88.479|1.00100.07|B|
|ATOM|2924|NE2|HIS|B|155|4.969|80.338|88.739|1.00100.07|B|
|ATOM|2925|C|HIS|B|155|7.331|75.958|91.987|1.00 81.81|B|
|ATOM|2926|O|HIS|B|155|6.701|74.932|91.720|1.00 81.81|B|
|ATOM|2927|N|GLY|B|156|8.010|76.132|93.123|1.00 78.05|B|
|ATOM|2928|CA|GLY|B|156|8.060|75.111|94.158|1.00 78.05|B|
|ATOM|2929|C|GLY|B|156|6.987|75.314|95.213|1.00 78.05|B|
|ATOM|2930|O|GLY|B|156|7.278|75.574|96.378|1.00 78.05|B|
|ATOM|2931|N|ILE|B|157|5.733|75.192|94.785|1.00100.07|B|
|ATOM|2932|CA|ILE|B|157|4.583|75.351|95.666|1.00100.07|B|
|ATOM|2933|CB|ILE|B|157|3.276|74.823|94.995|1.00 83.13|B|
|ATOM|2934|CG2|ILE|B|157|2.063|75.472|95.639|1.00 83.13|B|
|ATOM|2935|CG1|ILE|B|157|3.253|75.165|93.503|1.00 83.13|B|
|ATOM|2936|CD|ILE|B|157|3.110|76.638|93.196|1.00 83.13|B|
|ATOM|2937|C|ILE|B|157|4.817|74.567|96.962|1.00100.07|B|
|ATOM|2938|O|ILE|B|157|4.783|75.139|98.047|1.00100.07|B|
|ATOM|2939|N|LYS|B|158|5.062|73.262|96.827|1.00100.07|B|
|ATOM|2940|CA|LYS|B|158|5.302|72.353|97.953|1.00100.07|B|
|ATOM|2941|CB|LYS|B|158|6.715|71.773|97.885|1.00 99.97|B|
|ATOM|2942|CG|LYS|B|158|6.765|70.380|97.301|1.00 99.97|B|
|ATOM|2943|CD|LYS|B|158|7.549|69.436|98.190|1.00 99.97|B|
|ATOM|2944|CE|LYS|B|158|7.530|68.029|97.618|1.00 99.97|B|
|ATOM|2945|NZ|LYS|B|158|8.255|67.062|98.482|1.00 99.97|B|
|ATOM|2946|C|LYS|B|158|5.076|72.916|99.354|1.00100.07|B|
|ATOM|2947|O|LYS|B|158|3.934|73.086|99.786|1.00100.07|B|
|ATOM|2948|N|ASP|B|159|6.178|73.174|100.060|1.00 83.66|B|
|ATOM|2949|CA|ASP|B|159|6.164|73.723|101.420|1.00 83.66|B|
|ATOM|2950|CB|ASP|B|159|7.601|73.816|101.958|1.00 85.27|B|
|ATOM|2951|CG|ASP|B|159|7.675|74.397|103.367|1.00 85.27|B|
|ATOM|2952|OD1|ASP|B|159|7.208|73.722|104.310|1.00 85.27|B|
|ATOM|2953|OD2|ASP|B|159|8.206|75.525|103.529|1.00 85.27|B|
|ATOM|2954|C|ASP|B|159|5.550|75.122|101.407|1.00 83.66|B|
|ATOM|2955|O|ASP|B|159|5.956|75.989|102.178|1.00 83.66|B|
|ATOM|2956|N|ARG|B|160|4.581|75.334|100.520|1.00 80.11|B|
|ATOM|2957|CA|ARG|B|160|3.902|76.619|100.385|1.00 80.11|B|
|ATOM|2958|CB|ARG|B|160|3.040|76.901|101.622|1.00100.07|B|
|ATOM|2959|CG|ARG|B|160|2.240|75.714|102.162|1.00100.07|B|
|ATOM|2960|CD|ARG|B|160|1.668|76.058|103.536|1.00100.07|B|
|ATOM|2961|NE|ARG|B|160|1.012|74.935|104.200|1.00100.07|B|
|ATOM|2962|CZ|ARG|B|160|0.587|74.967|105.461|1.00100.07|B|
|ATOM|2963|NH1|ARG|B|160|0.751|76.063|106.191|1.00100.07|B|
|ATOM|2964|NH2|ARG|B|160|-0.001|73.905|105.996|1.00100.07|B|
|ATOM|2965|C|ARG|B|160|4.933|77.725|100.241|1.00 80.11|B|
|ATOM|2966|O|ARG|B|160|5.280|78.126|99.129|1.00 80.11|B|
|ATOM|2967|N|ILE|B|161|5.403|78.233|101.379|1.00100.07|B|
|ATOM|2968|CA|ILE|B|161|6.423|79.263|101.361|1.00100.07|B|
|ATOM|2969|CB|ILE|B|161|5.817|80.686|101.585|1.00 93.92|B|
|ATOM|2970|CG2|ILE|B|161|6.914|81.701|101.919|1.00 93.92|B|
|ATOM|2971|CG1|ILE|B|161|5.092|81.117|100.298|1.00 93.92|B|
|ATOM|2972|CD|ILE|B|161|4.737|82.588|100.223|1.00 93.92|B|
|ATOM|2973|C|ILE|B|161|7.639|78.996|102.240|1.00100.07|B|
|ATOM|2974|O|ILE|B|161|7.548|78.840|103.460|1.00100.07|B|
|ATOM|2975|N|ASN|B|162|8.767|78.921|101.534|1.00100.07|B|
|ATOM|2976|CA|ASN|B|162|10.119|78.653|102.024|1.00100.07|B|
|ATOM|2977|CB|ASN|B|162|10.114|77.925|103.377|1.00 87.12|B|
|ATOM|2978|CG|ASN|B|162|9.859|78.855|104.552|1.00 87.12|B|
|ATOM|2979|OD1|ASN|B|162|10.393|79.968|104.627|1.00 87.12|B|
|ATOM|2980|ND2|ASN|B|162|9.049|78.389|105.489|1.00 87.12|B|
|ATOM|2981|C|ASN|B|162|10.683|77.717|100.949|1.00100.07|B|
|ATOM|2982|O|ASN|B|162|11.729|77.077|101.108|1.00100.07|B|
|ATOM|2983|N|ALA|B|163|9.955|77.661|99.842|1.00 85.63|B|
|ATOM|2984|CA|ALA|B|163|10.297|76.816|98.718|1.00 85.63|B|
|ATOM|2985|CB|ALA|B|163|9.130|76.789|97.745|1.00 66.82|B|
|ATOM|2986|C|ALA|B|163|11.575|77.194|97.975|1.00 85.63|B|

-36-

| ATOM | 2987 | O   | ALA B 163 | 12.384 | 76.318 | 97.646 | 1.00 | 85.63 | B |
| ATOM | 2988 | N   | ILE B 164 | 11.755 | 78.489 | 97.717 | 1.00 | 83.16 | B |
| ATOM | 2989 | CA  | ILE B 164 | 12.914 | 78.972 | 96.964 | 1.00 | 83.16 | B |
| ATOM | 2990 | CB  | ILE B 164 | 14.184 | 79.126 | 97.855 | 1.00 | 54.32 | B |
| ATOM | 2991 | CG2 | ILE B 164 | 13.875 | 80.052 | 99.028 | 1.00 | 54.32 | B |
| ATOM | 2992 | CG1 | ILE B 164 | 14.678 | 77.763 | 98.348 | 1.00 | 54.32 | B |
| ATOM | 2993 | CD  | ILE B 164 | 16.115 | 77.780 | 98.826 | 1.00 | 54.32 | B |
| ATOM | 2994 | C   | ILE B 164 | 13.199 | 77.979 | 95.831 | 1.00 | 83.16 | B |
| ATOM | 2995 | O   | ILE B 164 | 14.308 | 77.455 | 95.703 | 1.00 | 83.16 | B |
| ATOM | 2996 | N   | PRO B 165 | 12.188 | 77.724 | 94.982 | 1.00 | 89.68 | B |
| ATOM | 2997 | CD  | PRO B 165 | 10.966 | 78.534 | 94.853 | 1.00 | 34.51 | B |
| ATOM | 2998 | CA  | PRO B 165 | 12.291 | 76.797 | 93.855 | 1.00 | 89.68 | B |
| ATOM | 2999 | CB  | PRO B 165 | 10.987 | 77.035 | 93.096 | 1.00 | 34.51 | B |
| ATOM | 3000 | CG  | PRO B 165 | 10.694 | 78.458 | 93.371 | 1.00 | 34.51 | B |
| ATOM | 3001 | C   | PRO B 165 | 13.531 | 76.951 | 92.975 | 1.00 | 89.68 | B |
| ATOM | 3002 | O   | PRO B 165 | 13.738 | 77.969 | 92.311 | 1.00 | 89.68 | B |
| ATOM | 3003 | N   | VAL B 166 | 14.349 | 75.909 | 92.990 | 1.00 | 93.92 | B |
| ATOM | 3004 | CA  | VAL B 166 | 15.572 | 75.852 | 92.215 | 1.00 | 93.92 | B |
| ATOM | 3005 | CB  | VAL B 166 | 16.404 | 74.635 | 92.638 | 1.00 | 34.28 | B |
| ATOM | 3006 | CG1 | VAL B 166 | 17.695 | 74.570 | 91.845 | 1.00 | 34.28 | B |
| ATOM | 3007 | CG2 | VAL B 166 | 16.691 | 74.705 | 94.124 | 1.00 | 34.28 | B |
| ATOM | 3008 | C   | VAL B 166 | 15.209 | 75.699 | 90.747 | 1.00 | 93.92 | B |
| ATOM | 3009 | O   | VAL B 166 | 14.030 | 75.601 | 90.398 | 1.00 | 93.92 | B |
| ATOM | 3010 | N   | ASP B 167 | 16.224 | 75.680 | 89.888 | 1.00 | 54.81 | B |
| ATOM | 3011 | CA  | ASP B 167 | 16.001 | 75.515 | 88.460 | 1.00 | 54.81 | B |
| ATOM | 3012 | CB  | ASP B 167 | 17.027 | 76.309 | 87.649 | 1.00 | 79.60 | B |
| ATOM | 3013 | CG  | ASP B 167 | 16.789 | 77.801 | 87.714 | 1.00 | 79.60 | B |
| ATOM | 3014 | OD1 | ASP B 167 | 15.643 | 78.220 | 87.437 | 1.00 | 79.60 | B |
| ATOM | 3015 | OD2 | ASP B 167 | 17.744 | 78.546 | 88.037 | 1.00 | 79.60 | B |
| ATOM | 3016 | C   | ASP B 167 | 16.089 | 74.042 | 88.102 | 1.00 | 54.81 | B |
| ATOM | 3017 | O   | ASP B 167 | 16.657 | 73.231 | 88.840 | 1.00 | 54.81 | B |
| ATOM | 3018 | N   | ALA B 168 | 15.533 | 73.699 | 86.953 | 1.00 | 35.06 | B |
| ATOM | 3019 | CA  | ALA B 168 | 15.530 | 72.319 | 86.520 | 1.00 | 35.06 | B |
| ATOM | 3020 | CB  | ALA B 168 | 14.148 | 71.957 | 86.055 | 1.00 | 82.11 | B |
| ATOM | 3021 | C   | ALA B 168 | 16.536 | 71.986 | 85.431 | 1.00 | 35.06 | B |
| ATOM | 3022 | O   | ALA B 168 | 16.595 | 72.639 | 84.390 | 1.00 | 35.06 | B |
| ATOM | 3023 | N   | ILE B 169 | 17.314 | 70.945 | 85.672 | 1.00 | 64.88 | B |
| ATOM | 3024 | CA  | ILE B 169 | 18.298 | 70.515 | 84.709 | 1.00 | 64.88 | B |
| ATOM | 3025 | CB  | ILE B 169 | 19.728 | 70.753 | 85.232 | 1.00 | 96.76 | B |
| ATOM | 3026 | CG2 | ILE B 169 | 20.131 | 72.181 | 84.980 | 1.00 | 96.76 | B |
| ATOM | 3027 | CG1 | ILE B 169 | 19.813 | 70.443 | 86.730 | 1.00 | 96.76 | B |
| ATOM | 3028 | CD  | ILE B 169 | 19.959 | 68.976 | 87.076 | 1.00 | 96.76 | B |
| ATOM | 3029 | C   | ILE B 169 | 18.111 | 69.048 | 84.410 | 1.00 | 64.88 | B |
| ATOM | 3030 | O   | ILE B 169 | 19.037 | 68.259 | 84.571 | 1.00 | 64.88 | B |
| ATOM | 3031 | N   | PHE B 170 | 16.906 | 68.665 | 83.998 | 1.00 | 36.37 | B |
| ATOM | 3032 | CA  | PHE B 170 | 16.683 | 67.265 | 83.656 | 1.00 | 36.37 | B |
| ATOM | 3033 | CB  | PHE B 170 | 15.251 | 66.815 | 83.946 | 1.00 | 77.26 | B |
| ATOM | 3034 | CG  | PHE B 170 | 14.299 | 67.930 | 84.272 | 1.00 | 77.26 | B |
| ATOM | 3035 | CD1 | PHE B 170 | 13.755 | 68.717 | 83.264 | 1.00 | 77.26 | B |
| ATOM | 3036 | CD2 | PHE B 170 | 13.869 | 68.131 | 85.584 | 1.00 | 77.26 | B |
| ATOM | 3037 | CE1 | PHE B 170 | 12.784 | 69.682 | 83.557 | 1.00 | 77.26 | B |
| ATOM | 3038 | CE2 | PHE B 170 | 12.904 | 69.089 | 85.880 | 1.00 | 77.26 | B |
| ATOM | 3039 | CZ  | PHE B 170 | 12.359 | 69.864 | 84.863 | 1.00 | 77.26 | B |
| ATOM | 3040 | C   | PHE B 170 | 17.009 | 67.059 | 82.197 | 1.00 | 36.37 | B |
| ATOM | 3041 | O   | PHE B 170 | 16.539 | 67.801 | 81.350 | 1.00 | 36.37 | B |
| ATOM | 3042 | N   | SER B 171 | 17.841 | 66.051 | 81.951 | 1.00 | 62.92 | B |
| ATOM | 3043 | CA  | SER B 171 | 18.358 | 65.651 | 80.640 | 1.00 | 62.92 | B |
| ATOM | 3044 | CB  | SER B 171 | 18.434 | 66.831 | 79.657 | 1.00 | 62.68 | B |
| ATOM | 3045 | OG  | SER B 171 | 17.176 | 67.196 | 79.129 | 1.00 | 62.68 | B |
| ATOM | 3046 | C   | SER B 171 | 19.786 | 65.250 | 80.962 | 1.00 | 62.92 | B |
| ATOM | 3047 | O   | SER B 171 | 20.656 | 66.109 | 81.037 | 1.00 | 62.92 | B |
| ATOM | 3048 | N   | PRO B 172 | 20.048 | 63.960 | 81.206 | 1.00 | 94.48 | B |
| ATOM | 3049 | CD  | PRO B 172 | 19.176 | 62.890 | 81.712 | 1.00 | 90.02 | B |
| ATOM | 3050 | CA  | PRO B 172 | 21.449 | 63.660 | 81.501 | 1.00 | 94.48 | B |
| ATOM | 3051 | CB  | PRO B 172 | 21.388 | 62.238 | 82.024 | 1.00 | 90.02 | B |
| ATOM | 3052 | CG  | PRO B 172 | 20.071 | 62.220 | 82.728 | 1.00 | 90.02 | B |
| ATOM | 3053 | C   | PRO B 172 | 22.345 | 63.828 | 80.254 | 1.00 | 94.48 | B |
| ATOM | 3054 | O   | PRO B 172 | 23.250 | 63.029 | 80.000 | 1.00 | 94.48 | B |
| ATOM | 3055 | N   | VAL B 173 | 22.057 | 64.872 | 79.473 | 1.00 | 92.81 | B |
| ATOM | 3056 | CA  | VAL B 173 | 22.833 | 65.224 | 78.284 | 1.00 | 92.81 | B |
| ATOM | 3057 | CB  | VAL B 173 | 22.018 | 65.161 | 76.960 | 1.00 | 51.56 | B |
| ATOM | 3058 | CG1 | VAL B 173 | 21.733 | 63.730 | 76.600 | 1.00 | 51.56 | B |
| ATOM | 3059 | CG2 | VAL B 173 | 20.733 | 65.957 | 77.084 | 1.00 | 51.56 | B |
| ATOM | 3060 | C   | VAL B 173 | 23.348 | 66.648 | 78.451 | 1.00 | 92.81 | B |
| ATOM | 3061 | O   | VAL B 173 | 22.621 | 67.618 | 78.231 | 1.00 | 92.81 | B |
| ATOM | 3062 | N   | ARG B 174 | 24.601 | 66.766 | 78.873 | 1.00 | 100.07 | B |
| ATOM | 3063 | CA  | ARG B 174 | 25.228 | 68.067 | 79.045 | 1.00 | 100.07 | B |
| ATOM | 3064 | CB  | ARG B 174 | 26.141 | 68.072 | 80.270 | 1.00 | 100.07 | B |
| ATOM | 3065 | CG  | ARG B 174 | 25.640 | 67.291 | 81.482 | 1.00 | 100.07 | B |
| ATOM | 3066 | CD  | ARG B 174 | 25.106 | 68.215 | 82.555 | 1.00 | 100.07 | B |
| ATOM | 3067 | NE  | ARG B 174 | 24.912 | 67.536 | 83.830 | 1.00 | 100.07 | B |
| ATOM | 3068 | CZ  | ARG B 174 | 24.206 | 68.043 | 84.835 | 1.00 | 100.07 | B |
| ATOM | 3069 | NH1 | ARG B 174 | 23.631 | 69.232 | 84.699 | 1.00 | 100.07 | B |
| ATOM | 3070 | NH2 | ARG B 174 | 24.078 | 67.368 | 85.972 | 1.00 | 100.07 | B |

| ATOM | 3071 | C | ARG B 174 | 26.097 | 68.212 | 77.803 | 1.00 | 100.07 | B |
|------|------|------|---------|--------|--------|--------|------|--------|---|
| ATOM | 3072 | O | ARG B 174 | 27.015 | 67.416 | 77.607 | 1.00 | 100.07 | B |
| ATOM | 3073 | N | ARG B 175 | 25.796 | 69.182 | 76.945 | 1.00 | 74.17 | B |
| ATOM | 3074 | CA | ARG B 175 | 26.609 | 69.394 | 75.746 | 1.00 | 74.17 | B |
| ATOM | 3075 | CB | ARG B 175 | 28.078 | 69.481 | 76.168 | 1.00 | 38.79 | B |
| ATOM | 3076 | CG | ARG B 175 | 29.043 | 69.844 | 75.084 | 1.00 | 38.79 | B |
| ATOM | 3077 | CD | ARG B 175 | 30.429 | 70.017 | 75.644 | 1.00 | 38.79 | B |
| ATOM | 3078 | NE | ARG B 175 | 31.346 | 70.404 | 74.587 | 1.00 | 38.79 | B |
| ATOM | 3079 | CZ | ARG B 175 | 32.663 | 70.394 | 74.709 | 1.00 | 38.79 | B |
| ATOM | 3080 | NH1 | ARG B 175 | 33.219 | 70.018 | 75.851 | 1.00 | 38.79 | B |
| ATOM | 3081 | NH2 | ARG B 175 | 33.423 | 70.740 | 73.682 | 1.00 | 38.79 | B |
| ATOM | 3082 | C | ARG B 175 | 26.457 | 68.356 | 74.625 | 1.00 | 74.17 | B |
| ATOM | 3083 | O | ARG B 175 | 26.337 | 67.167 | 74.894 | 1.00 | 74.17 | B |
| ATOM | 3084 | N | VAL B 176 | 26.481 | 68.827 | 73.374 | 1.00 | 73.32 | B |
| ATOM | 3085 | CA | VAL B 176 | 26.354 | 67.986 | 72.168 | 1.00 | 73.32 | B |
| ATOM | 3086 | CB | VAL B 176 | 24.870 | 67.629 | 71.870 | 1.00 | 75.21 | B |
| ATOM | 3087 | CG1 | VAL B 176 | 24.740 | 66.997 | 70.486 | 1.00 | 75.21 | B |
| ATOM | 3088 | CG2 | VAL B 176 | 24.342 | 66.675 | 72.922 | 1.00 | 75.21 | B |
| ATOM | 3089 | C | VAL B 176 | 26.924 | 68.687 | 70.919 | 1.00 | 73.32 | B |
| ATOM | 3090 | O | VAL B 176 | 26.322 | 69.634 | 70.403 | 1.00 | 73.32 | B |
| ATOM | 3091 | N | ALA B 177 | 28.072 | 68.213 | 70.436 | 1.00 | 100.07 | B |
| ATOM | 3092 | CA | ALA B 177 | 28.715 | 68.785 | 69.248 | 1.00 | 100.07 | B |
| ATOM | 3093 | CB | ALA B 177 | 29.906 | 69.654 | 69.661 | 1.00 | 100.07 | B |
| ATOM | 3094 | C | ALA B 177 | 29.175 | 67.684 | 68.281 | 1.00 | 100.07 | B |
| ATOM | 3095 | O | ALA B 177 | 29.308 | 66.525 | 68.679 | 1.00 | 100.07 | B |
| ATOM | 3096 | N | PHE B 178 | 29.441 | 68.051 | 67.025 | 1.00 | 43.26 | B |
| ATOM | 3097 | CA | PHE B 178 | 29.835 | 67.070 | 66.013 | 1.00 | 43.26 | B |
| ATOM | 3098 | CB | PHE B 178 | 28.632 | 66.240 | 65.639 | 1.00 | 35.05 | B |
| ATOM | 3099 | CG | PHE B 178 | 27.584 | 67.029 | 64.936 | 1.00 | 35.05 | B |
| ATOM | 3100 | CD1 | PHE B 178 | 27.631 | 67.202 | 63.564 | 1.00 | 35.05 | B |
| ATOM | 3101 | CD2 | PHE B 178 | 26.580 | 67.650 | 65.653 | 1.00 | 35.05 | B |
| ATOM | 3102 | CE1 | PHE B 178 | 26.683 | 67.987 | 62.915 | 1.00 | 35.05 | B |
| ATOM | 3103 | CE2 | PHE B 178 | 25.634 | 68.435 | 65.014 | 1.00 | 35.05 | B |
| ATOM | 3104 | CZ | PHE B 178 | 25.683 | 68.606 | 63.641 | 1.00 | 35.05 | B |
| ATOM | 3105 | C | PHE B 178 | 30.310 | 67.741 | 64.739 | 1.00 | 43.26 | B |
| ATOM | 3106 | O | PHE B 178 | 29.889 | 68.850 | 64.435 | 1.00 | 43.26 | B |
| ATOM | 3107 | N | GLN B 179 | 31.136 | 67.051 | 63.959 | 1.00 | 38.06 | B |
| ATOM | 3108 | CA | GLN B 179 | 31.611 | 67.643 | 62.714 | 1.00 | 38.06 | B |
| ATOM | 3109 | CB | GLN B 179 | 32.986 | 68.313 | 62.899 | 1.00 | 100.07 | B |
| ATOM | 3110 | CG | GLN B 179 | 34.162 | 67.389 | 63.204 | 1.00 | 100.07 | B |
| ATOM | 3111 | CD | GLN B 179 | 35.513 | 68.090 | 63.038 | 1.00 | 100.07 | B |
| ATOM | 3112 | OE1 | GLN B 179 | 35.650 | 69.279 | 63.337 | 1.00 | 100.07 | B |
| ATOM | 3113 | NE2 | GLN B 179 | 36.516 | 67.350 | 62.574 | 1.00 | 100.07 | B |
| ATOM | 3114 | C | GLN B 179 | 31.659 | 66.744 | 61.494 | 1.00 | 38.06 | B |
| ATOM | 3115 | O | GLN B 179 | 32.255 | 65.671 | 61.518 | 1.00 | 38.06 | B |
| ATOM | 3116 | N | VAL B 180 | 31.049 | 67.227 | 60.416 | 1.00 | 32.81 | B |
| ATOM | 3117 | CA | VAL B 180 | 30.958 | 66.509 | 59.154 | 1.00 | 32.81 | B |
| ATOM | 3118 | CB | VAL B 180 | 29.708 | 66.997 | 58.367 | 1.00 | 57.30 | B |
| ATOM | 3119 | CG1 | VAL B 180 | 29.811 | 68.502 | 58.089 | 1.00 | 57.30 | B |
| ATOM | 3120 | CG2 | VAL B 180 | 29.548 | 66.195 | 57.084 | 1.00 | 57.30 | B |
| ATOM | 3121 | C | VAL B 180 | 32.217 | 66.620 | 58.278 | 1.00 | 32.81 | B |
| ATOM | 3122 | O | VAL B 180 | 32.298 | 67.459 | 57.374 | 1.00 | 32.81 | B |
| ATOM | 3123 | N | GLU B 181 | 33.189 | 65.751 | 58.550 | 1.00 | 53.70 | B |
| ATOM | 3124 | CA | GLU B 181 | 34.448 | 65.718 | 57.814 | 1.00 | 53.70 | B |
| ATOM | 3125 | CB | GLU B 181 | 35.491 | 64.914 | 58.573 | 1.00 | 100.07 | B |
| ATOM | 3126 | CG | GLU B 181 | 36.276 | 65.714 | 59.569 | 1.00 | 100.07 | B |
| ATOM | 3127 | CD | GLU B 181 | 37.403 | 64.901 | 60.167 | 1.00 | 100.07 | B |
| ATOM | 3128 | OE1 | GLU B 181 | 37.112 | 63.883 | 60.837 | 1.00 | 100.07 | B |
| ATOM | 3129 | OE2 | GLU B 181 | 38.580 | 65.276 | 59.959 | 1.00 | 100.07 | B |
| ATOM | 3130 | C | GLU B 181 | 34.358 | 65.164 | 56.401 | 1.00 | 53.70 | B |
| ATOM | 3131 | O | GLU B 181 | 33.310 | 65.167 | 55.771 | 1.00 | 53.70 | B |
| ATOM | 3132 | N | ASP B 182 | 35.481 | 64.673 | 55.910 | 1.00 | 62.55 | B |
| ATOM | 3133 | CA | ASP B 182 | 35.517 | 64.133 | 54.576 | 1.00 | 62.55 | B |
| ATOM | 3134 | CB | ASP B 182 | 36.163 | 65.152 | 53.647 | 1.00 | 38.34 | B |
| ATOM | 3135 | CG | ASP B 182 | 35.158 | 66.105 | 53.079 | 1.00 | 38.34 | B |
| ATOM | 3136 | OD1 | ASP B 182 | 33.967 | 65.850 | 53.352 | 1.00 | 38.34 | B |
| ATOM | 3137 | OD2 | ASP B 182 | 35.534 | 67.074 | 52.365 | 1.00 | 38.34 | B |
| ATOM | 3138 | C | ASP B 182 | 36.195 | 62.775 | 54.422 | 1.00 | 62.55 | B |
| ATOM | 3139 | O | ASP B 182 | 37.403 | 62.693 | 54.183 | 1.00 | 62.55 | B |
| ATOM | 3140 | N | THR B 183 | 35.423 | 61.702 | 54.575 | 1.00 | 47.37 | B |
| ATOM | 3141 | CA | THR B 183 | 35.984 | 60.369 | 54.399 | 1.00 | 47.37 | B |
| ATOM | 3142 | CB | THR B 183 | 35.006 | 59.252 | 54.821 | 1.00 | 99.56 | B |
| ATOM | 3143 | OG1 | THR B 183 | 34.865 | 59.248 | 56.245 | 1.00 | 99.56 | B |
| ATOM | 3144 | CG2 | THR B 183 | 35.525 | 57.894 | 54.375 | 1.00 | 99.56 | B |
| ATOM | 3145 | C | THR B 183 | 36.194 | 60.313 | 52.888 | 1.00 | 47.37 | B |
| ATOM | 3146 | O | THR B 183 | 35.378 | 60.844 | 52.113 | 1.00 | 47.37 | B |
| ATOM | 3147 | N | ARG B 184 | 37.277 | 59.671 | 52.461 | 1.00 | 59.20 | B |
| ATOM | 3148 | CA | ARG B 184 | 37.554 | 59.632 | 51.041 | 1.00 | 59.20 | B |
| ATOM | 3149 | CB | ARG B 184 | 38.788 | 60.510 | 50.720 | 1.00 | 100.07 | B |
| ATOM | 3150 | CG | ARG B 184 | 39.992 | 60.404 | 51.680 | 1.00 | 100.07 | B |
| ATOM | 3151 | CD | ARG B 184 | 41.190 | 61.266 | 51.203 | 1.00 | 100.07 | B |
| ATOM | 3152 | NE | ARG B 184 | 42.352 | 61.199 | 52.101 | 1.00 | 100.07 | B |
| ATOM | 3153 | CZ | ARG B 184 | 43.544 | 61.740 | 51.840 | 1.00 | 100.07 | B |
| ATOM | 3154 | NH1 | ARG B 184 | 43.747 | 62.394 | 50.701 | 1.00 | 100.07 | B |

| | | | | | | | | | |
|---|---|---|---|---|---|---|---|---|---|
| ATOM | 3155 | NH2 | ARG | B | 184 | 44.534 | 61.633 | 52.721 | 1.00100.07 | B |
| ATOM | 3156 | C | ARG | B | 184 | 37.633 | 58.367 | 50.219 | 1.00 59.20 | B |
| ATOM | 3157 | O | ARG | B | 184 | 38.097 | 58.418 | 49.084 | 1.00 59.20 | B |
| ATOM | 3158 | N | LEU | B | 185 | 37.191 | 57.236 | 50.748 | 1.00100.07 | B |
| ATOM | 3159 | CA | LEU | B | 185 | 37.232 | 56.028 | 49.937 | 1.00100.07 | B |
| ATOM | 3160 | CB | LEU | B | 185 | 37.320 | 54.768 | 50.811 | 1.00100.07 | B |
| ATOM | 3161 | CG | LEU | B | 185 | 37.645 | 53.426 | 50.121 | 1.00100.07 | B |
| ATOM | 3162 | CD1 | LEU | B | 185 | 38.340 | 53.635 | 48.765 | 1.00100.07 | B |
| ATOM | 3163 | CD2 | LEU | B | 185 | 38.521 | 52.594 | 51.060 | 1.00100.07 | B |
| ATOM | 3164 | C | LEU | B | 185 | 35.957 | 56.062 | 49.124 | 1.00100.07 | B |
| ATOM | 3165 | O | LEU | B | 185 | 35.588 | 57.137 | 48.645 | 1.00100.07 | B |
| ATOM | 3166 | N | GLY | B | 186 | 35.260 | 54.933 | 48.994 | 1.00 99.96 | B |
| ATOM | 3167 | CA | GLY | B | 186 | 34.074 | 54.934 | 48.156 | 1.00 99.96 | B |
| ATOM | 3168 | C | GLY | B | 186 | 34.675 | 55.719 | 47.009 | 1.00 99.96 | B |
| ATOM | 3169 | O | GLY | B | 186 | 35.829 | 55.470 | 46.633 | 1.00 99.96 | B |
| ATOM | 3170 | N | GLN | B | 187 | 33.943 | 56.673 | 46.455 | 1.00 99.57 | B |
| ATOM | 3171 | CA | GLN | B | 187 | 34.557 | 57.492 | 45.428 | 1.00 99.57 | B |
| ATOM | 3172 | CB | GLN | B | 187 | 34.412 | 56.898 | 44.023 | 1.00100.07 | B |
| ATOM | 3173 | CG | GLN | B | 187 | 35.795 | 56.577 | 43.378 | 1.00100.07 | B |
| ATOM | 3174 | CD | GLN | B | 187 | 36.923 | 57.556 | 43.791 | 1.00100.07 | B |
| ATOM | 3175 | OE1 | GLN | B | 187 | 37.484 | 57.466 | 44.891 | 1.00100.07 | B |
| ATOM | 3176 | NE2 | GLN | B | 187 | 37.245 | 58.488 | 42.902 | 1.00100.07 | B |
| ATOM | 3177 | C | GLN | B | 187 | 34.179 | 58.950 | 45.440 | 1.00 99.57 | B |
| ATOM | 3178 | O | GLN | B | 187 | 33.039 | 59.332 | 45.721 | 1.00 99.57 | B |
| ATOM | 3179 | N | ARG | B | 188 | 35.195 | 59.743 | 45.129 | 1.00 99.66 | B |
| ATOM | 3180 | CA | ARG | B | 188 | 35.143 | 61.188 | 45.132 | 1.00 99.66 | B |
| ATOM | 3181 | CB | ARG | B | 188 | 33.701 | 61.725 | 45.252 | 1.00100.07 | B |
| ATOM | 3182 | CG | ARG | B | 188 | 32.757 | 61.473 | 44.071 | 1.00100.07 | B |
| ATOM | 3183 | CD | ARG | B | 188 | 31.370 | 62.082 | 44.347 | 1.00100.07 | B |
| ATOM | 3184 | NE | ARG | B | 188 | 30.927 | 62.984 | 43.280 | 1.00100.07 | B |
| ATOM | 3185 | CZ | ARG | B | 188 | 29.800 | 63.692 | 43.314 | 1.00100.07 | B |
| ATOM | 3186 | NH1 | ARG | B | 188 | 28.997 | 63.605 | 44.365 | 1.00100.07 | B |
| ATOM | 3187 | NH2 | ARG | B | 188 | 29.470 | 64.477 | 42.293 | 1.00100.07 | B |
| ATOM | 3188 | C | ARG | B | 188 | 35.886 | 61.498 | 46.422 | 1.00 99.66 | B |
| ATOM | 3189 | O | ARG | B | 188 | 36.796 | 60.768 | 46.823 | 1.00 99.66 | B |
| ATOM | 3190 | N | THR | B | 189 | 35.474 | 62.573 | 47.076 | 1.00 98.98 | B |
| ATOM | 3191 | CA | THR | B | 189 | 36.058 | 62.983 | 48.333 | 1.00 98.98 | B |
| ATOM | 3192 | CB | THR | B | 189 | 37.406 | 63.686 | 48.114 | 1.00 51.63 | B |
| ATOM | 3193 | OG1 | THR | B | 189 | 37.983 | 63.237 | 46.881 | 1.00 51.63 | B |
| ATOM | 3194 | CG2 | THR | B | 189 | 38.369 | 63.355 | 49.257 | 1.00 51.63 | B |
| ATOM | 3195 | C | THR | B | 189 | 35.031 | 63.960 | 48.857 | 1.00 98.98 | B |
| ATOM | 3196 | O | THR | B | 189 | 35.329 | 64.845 | 49.653 | 1.00 98.98 | B |
| ATOM | 3197 | N | ASP | B | 190 | 33.809 | 63.789 | 48.366 | 1.00 43.16 | B |
| ATOM | 3198 | CA | ASP | B | 190 | 32.688 | 64.614 | 48.765 | 1.00 43.16 | B |
| ATOM | 3199 | CB | ASP | B | 190 | 31.751 | 64.831 | 47.586 | 1.00 79.99 | B |
| ATOM | 3200 | CG | ASP | B | 190 | 32.479 | 65.324 | 46.361 | 1.00 79.99 | B |
| ATOM | 3201 | OD1 | ASP | B | 190 | 33.289 | 66.263 | 46.502 | 1.00 79.99 | B |
| ATOM | 3202 | OD2 | ASP | B | 190 | 32.240 | 64.783 | 45.257 | 1.00 79.99 | B |
| ATOM | 3203 | C | ASP | B | 190 | 31.948 | 63.919 | 49.901 | 1.00 43.16 | B |
| ATOM | 3204 | O | ASP | B | 190 | 31.161 | 64.545 | 50.621 | 1.00 43.16 | B |
| ATOM | 3205 | N | LEU | B | 191 | 32.240 | 62.631 | 50.072 | 1.00 54.68 | B |
| ATOM | 3206 | CA | LEU | B | 191 | 31.609 | 61.788 | 51.083 | 1.00 54.68 | B |
| ATOM | 3207 | CB | LEU | B | 191 | 32.085 | 60.363 | 50.871 | 1.00 32.62 | B |
| ATOM | 3208 | CG | LEU | B | 191 | 31.728 | 59.969 | 49.439 | 1.00 32.62 | B |
| ATOM | 3209 | CD1 | LEU | B | 191 | 32.125 | 58.538 | 49.153 | 1.00 32.62 | B |
| ATOM | 3210 | CD2 | LEU | B | 191 | 30.240 | 60.144 | 49.247 | 1.00 32.62 | B |
| ATOM | 3211 | C | LEU | B | 191 | 31.773 | 62.188 | 52.548 | 1.00 54.68 | B |
| ATOM | 3212 | O | LEU | B | 191 | 32.863 | 62.083 | 53.112 | 1.00 54.68 | B |
| ATOM | 3213 | N | ASP | B | 192 | 30.666 | 62.622 | 53.154 | 1.00 56.67 | B |
| ATOM | 3214 | CA | ASP | B | 192 | 30.616 | 63.063 | 54.552 | 1.00 56.67 | B |
| ATOM | 3215 | CB | ASP | B | 192 | 29.190 | 63.505 | 54.903 | 1.00 66.03 | B |
| ATOM | 3216 | CG | ASP | B | 192 | 28.745 | 64.727 | 54.116 | 1.00 66.03 | B |
| ATOM | 3217 | OD1 | ASP | B | 192 | 29.508 | 65.167 | 53.227 | 1.00 66.03 | B |
| ATOM | 3218 | OD2 | ASP | B | 192 | 27.635 | 65.243 | 54.383 | 1.00 66.03 | B |
| ATOM | 3219 | C | ASP | B | 192 | 31.080 | 62.007 | 55.554 | 1.00 56.67 | B |
| ATOM | 3220 | O | ASP | B | 192 | 31.352 | 60.865 | 55.182 | 1.00 56.67 | B |
| ATOM | 3221 | N | LYS | B | 193 | 31.160 | 62.405 | 56.825 | 1.00 24.44 | B |
| ATOM | 3222 | CA | LYS | B | 193 | 31.598 | 61.524 | 57.902 | 1.00 24.44 | B |
| ATOM | 3223 | CB | LYS | B | 193 | 33.104 | 61.303 | 57.834 | 1.00 62.39 | B |
| ATOM | 3224 | CG | LYS | B | 193 | 33.637 | 60.548 | 59.031 | 1.00 62.39 | B |
| ATOM | 3225 | CD | LYS | B | 193 | 35.078 | 60.165 | 58.836 | 1.00 62.39 | B |
| ATOM | 3226 | CE | LYS | B | 193 | 35.466 | 59.022 | 59.747 | 1.00 62.39 | B |
| ATOM | 3227 | NZ | LYS | B | 193 | 36.737 | 58.393 | 59.292 | 1.00 62.39 | B |
| ATOM | 3228 | C | LYS | B | 193 | 31.254 | 62.168 | 59.239 | 1.00 24.44 | B |
| ATOM | 3229 | O | LYS | B | 193 | 32.036 | 62.955 | 59.762 | 1.00 24.44 | B |
| ATOM | 3230 | N | LEU | B | 194 | 30.109 | 61.807 | 59.811 | 1.00 74.01 | B |
| ATOM | 3231 | CA | LEU | B | 194 | 29.660 | 62.381 | 61.082 | 1.00 74.01 | B |
| ATOM | 3232 | CB | LEU | B | 194 | 28.415 | 61.656 | 61.592 | 1.00 60.97 | B |
| ATOM | 3233 | CG | LEU | B | 194 | 27.093 | 62.293 | 61.178 | 1.00 60.97 | B |
| ATOM | 3234 | CD1 | LEU | B | 194 | 26.151 | 62.229 | 62.343 | 1.00 60.97 | B |
| ATOM | 3235 | CD2 | LEU | B | 194 | 27.296 | 63.734 | 60.782 | 1.00 60.97 | B |
| ATOM | 3236 | C | LEU | B | 194 | 30.590 | 62.585 | 62.279 | 1.00 74.01 | B |
| ATOM | 3237 | O | LEU | B | 194 | 31.403 | 63.505 | 62.292 | 1.00 74.01 | B |
| ATOM | 3238 | N | THR | B | 195 | 30.418 | 61.741 | 63.294 | 1.00 32.39 | B |

| ATOM | 3239 | CA | THR | B | 195 | 31.168 | 61.788 | 64.560 | 1.00 | 32.39 | B |
|---|---|---|---|---|---|---|---|---|---|---|---|
| ATOM | 3240 | CB | THR | B | 195 | 32.573 | 62.420 | 64.443 | 1.00 | 35.71 | B |
| ATOM | 3241 | OG1 | THR | B | 195 | 33.113 | 62.192 | 63.140 | 1.00 | 35.71 | B |
| ATOM | 3242 | CG2 | THR | B | 195 | 33.501 | 61.817 | 65.470 | 1.00 | 35.71 | B |
| ATOM | 3243 | C | THR | B | 195 | 30.405 | 62.682 | 65.533 | 1.00 | 32.39 | B |
| ATOM | 3244 | O | THR | B | 195 | 30.448 | 63.902 | 65.412 | 1.00 | 32.39 | B |
| ATOM | 3245 | N | LEU | B | 196 | 29.686 | 62.078 | 66.474 | 1.00 | 77.38 | B |
| ATOM | 3246 | CA | LEU | B | 196 | 28.937 | 62.821 | 67.490 | 1.00 | 77.38 | B |
| ATOM | 3247 | CB | LEU | B | 196 | 27.503 | 62.305 | 67.603 | 1.00 | 58.80 | B |
| ATOM | 3248 | CG | LEU | B | 196 | 26.441 | 62.921 | 66.705 | 1.00 | 58.80 | B |
| ATOM | 3249 | CD1 | LEU | B | 196 | 27.034 | 63.307 | 65.374 | 1.00 | 58.80 | B |
| ATOM | 3250 | CD2 | LEU | B | 196 | 25.319 | 61.923 | 66.531 | 1.00 | 58.80 | B |
| ATOM | 3251 | C | LEU | B | 196 | 29.662 | 62.521 | 68.793 | 1.00 | 77.38 | B |
| ATOM | 3252 | O | LEU | B | 196 | 30.028 | 61.371 | 69.054 | 1.00 | 77.38 | B |
| ATOM | 3253 | N | ARG | B | 197 | 29.875 | 63.536 | 69.619 | 1.00 | 31.83 | B |
| ATOM | 3254 | CA | ARG | B | 197 | 30.563 | 63.283 | 70.869 | 1.00 | 31.83 | B |
| ATOM | 3255 | CB | ARG | B | 197 | 31.742 | 64.232 | 70.995 | 1.00 | 99.56 | B |
| ATOM | 3256 | CG | ARG | B | 197 | 31.445 | 65.622 | 70.537 | 1.00 | 99.56 | B |
| ATOM | 3257 | CD | ARG | B | 197 | 32.713 | 66.429 | 70.491 | 1.00 | 99.56 | B |
| ATOM | 3258 | NE | ARG | B | 197 | 32.691 | 67.361 | 69.373 | 1.00 | 99.56 | B |
| ATOM | 3259 | CZ | ARG | B | 197 | 33.640 | 68.254 | 69.124 | 1.00 | 99.56 | B |
| ATOM | 3260 | NH1 | ARG | B | 197 | 34.697 | 68.345 | 69.923 | 1.00 | 99.56 | B |
| ATOM | 3261 | NH2 | ARG | B | 197 | 33.530 | 69.051 | 68.068 | 1.00 | 99.56 | B |
| ATOM | 3262 | C | ARG | B | 197 | 29.697 | 63.346 | 72.122 | 1.00 | 31.83 | B |
| ATOM | 3263 | O | ARG | B | 197 | 30.217 | 63.306 | 73.230 | 1.00 | 31.83 | B |
| ATOM | 3264 | N | ILE | B | 198 | 28.383 | 63.425 | 71.927 | 1.00 | 14.50 | B |
| ATOM | 3265 | CA | ILE | B | 198 | 27.396 | 63.474 | 73.005 | 1.00 | 14.50 | B |
| ATOM | 3266 | CB | ILE | B | 198 | 26.389 | 62.311 | 72.908 | 1.00 | 39.02 | B |
| ATOM | 3267 | CG2 | ILE | B | 198 | 25.250 | 62.539 | 73.860 | 1.00 | 39.02 | B |
| ATOM | 3268 | CG1 | ILE | B | 198 | 25.835 | 62.204 | 71.481 | 1.00 | 39.02 | B |
| ATOM | 3269 | CD | ILE | B | 198 | 25.264 | 63.497 | 70.916 | 1.00 | 39.02 | B |
| ATOM | 3270 | C | ILE | B | 198 | 28.108 | 63.381 | 74.319 | 1.00 | 14.50 | B |
| ATOM | 3271 | O | ILE | B | 198 | 28.323 | 62.289 | 74.840 | 1.00 | 14.50 | B |
| ATOM | 3272 | N | TRP | B | 199 | 28.482 | 64.556 | 74.826 | 1.00 | 99.86 | B |
| ATOM | 3273 | CA | TRP | B | 199 | 29.225 | 64.710 | 76.068 | 1.00 | 99.86 | B |
| ATOM | 3274 | CB | TRP | B | 199 | 29.499 | 66.179 | 76.356 | 1.00 | 59.10 | B |
| ATOM | 3275 | CG | TRP | B | 199 | 30.839 | 66.521 | 75.920 | 1.00 | 59.10 | B |
| ATOM | 3276 | CD2 | TRP | B | 199 | 32.049 | 66.258 | 76.631 | 1.00 | 59.10 | B |
| ATOM | 3277 | CE2 | TRP | B | 199 | 33.112 | 66.662 | 75.802 | 1.00 | 59.10 | B |
| ATOM | 3278 | CE3 | TRP | B | 199 | 32.340 | 65.720 | 77.894 | 1.00 | 59.10 | B |
| ATOM | 3279 | CD1 | TRP | B | 199 | 31.195 | 67.054 | 74.727 | 1.00 | 59.10 | B |
| ATOM | 3280 | NE1 | TRP | B | 199 | 32.559 | 67.144 | 74.643 | 1.00 | 59.10 | B |
| ATOM | 3281 | CZ2 | TRP | B | 199 | 34.462 | 66.545 | 76.191 | 1.00 | 59.10 | B |
| ATOM | 3282 | CZ3 | TRP | B | 199 | 33.686 | 65.602 | 78.285 | 1.00 | 59.10 | B |
| ATOM | 3283 | CH2 | TRP | B | 199 | 34.726 | 66.017 | 77.433 | 1.00 | 59.10 | B |
| ATOM | 3284 | C | TRP | B | 199 | 28.670 | 64.067 | 77.315 | 1.00 | 99.86 | B |
| ATOM | 3285 | O | TRP | B | 199 | 27.878 | 63.126 | 77.256 | 1.00 | 99.86 | B |
| ATOM | 3286 | N | THR | B | 200 | 29.090 | 64.604 | 78.452 | 1.00 | 95.79 | B |
| ATOM | 3287 | CA | THR | B | 200 | 28.703 | 64.038 | 79.725 | 1.00 | 95.79 | B |
| ATOM | 3288 | CB | THR | B | 200 | 29.306 | 64.869 | 80.925 | 1.00 | 100.07 | B |
| ATOM | 3289 | OG1 | THR | B | 200 | 29.330 | 64.055 | 82.108 | 1.00 | 100.07 | B |
| ATOM | 3290 | CG2 | THR | B | 200 | 28.510 | 66.128 | 81.196 | 1.00 | 100.07 | B |
| ATOM | 3291 | C | THR | B | 200 | 27.229 | 63.693 | 79.950 | 1.00 | 95.79 | B |
| ATOM | 3292 | O | THR | B | 200 | 26.359 | 63.933 | 79.103 | 1.00 | 95.79 | B |
| ATOM | 3293 | N | ASP | B | 201 | 26.982 | 63.098 | 81.109 | 1.00 | 100.07 | B |
| ATOM | 3294 | CA | ASP | B | 201 | 25.671 | 62.624 | 81.497 | 1.00 | 100.07 | B |
| ATOM | 3295 | CB | ASP | B | 201 | 25.846 | 61.298 | 82.237 | 1.00 | 90.30 | B |
| ATOM | 3296 | CG | ASP | B | 201 | 26.462 | 61.478 | 83.629 | 1.00 | 90.30 | B |
| ATOM | 3297 | OD1 | ASP | B | 201 | 27.544 | 62.097 | 83.736 | 1.00 | 90.30 | B |
| ATOM | 3298 | OD2 | ASP | B | 201 | 25.855 | 61.005 | 84.615 | 1.00 | 90.30 | B |
| ATOM | 3299 | C | ASP | B | 201 | 24.792 | 63.515 | 82.353 | 1.00 | 100.07 | B |
| ATOM | 3300 | O | ASP | B | 201 | 24.389 | 64.605 | 81.957 | 1.00 | 100.07 | B |
| ATOM | 3301 | N | GLY | B | 202 | 24.502 | 62.995 | 83.541 | 1.00 | 99.57 | B |
| ATOM | 3302 | CA | GLY | B | 202 | 23.648 | 63.640 | 84.509 | 1.00 | 99.57 | B |
| ATOM | 3303 | C | GLY | B | 202 | 22.712 | 62.514 | 84.877 | 1.00 | 99.57 | B |
| ATOM | 3304 | O | GLY | B | 202 | 21.551 | 62.746 | 85.215 | 1.00 | 99.57 | B |
| ATOM | 3305 | N | SER | B | 203 | 23.243 | 61.289 | 84.764 | 1.00 | 92.91 | B |
| ATOM | 3306 | CA | SER | B | 203 | 22.544 | 60.029 | 85.061 | 1.00 | 92.91 | B |
| ATOM | 3307 | CB | SER | B | 203 | 21.470 | 60.260 | 86.135 | 1.00 | 100.07 | B |
| ATOM | 3308 | OG | SER | B | 203 | 20.227 | 59.678 | 85.778 | 1.00 | 100.07 | B |
| ATOM | 3309 | C | SER | B | 203 | 21.908 | 59.353 | 83.835 | 1.00 | 92.91 | B |
| ATOM | 3310 | O | SER | B | 203 | 20.772 | 59.647 | 83.478 | 1.00 | 92.91 | B |
| ATOM | 3311 | N | VAL | B | 204 | 22.668 | 58.444 | 83.226 | 1.00 | 71.61 | B |
| ATOM | 3312 | CA | VAL | B | 204 | 22.332 | 57.634 | 82.035 | 1.00 | 71.61 | B |
| ATOM | 3313 | CB | VAL | B | 204 | 21.272 | 58.246 | 81.056 | 1.00 | 44.92 | B |
| ATOM | 3314 | CG1 | VAL | B | 204 | 19.887 | 58.225 | 81.655 | 1.00 | 44.92 | B |
| ATOM | 3315 | CG2 | VAL | B | 204 | 21.671 | 59.618 | 80.656 | 1.00 | 44.92 | B |
| ATOM | 3316 | C | VAL | B | 204 | 23.623 | 57.517 | 81.237 | 1.00 | 71.61 | B |
| ATOM | 3317 | O | VAL | B | 204 | 24.717 | 57.580 | 81.799 | 1.00 | 71.61 | B |
| ATOM | 3318 | N | THR | B | 205 | 23.507 | 57.348 | 79.929 | 1.00 | 50.50 | B |
| ATOM | 3319 | CA | THR | B | 205 | 24.696 | 57.264 | 79.107 | 1.00 | 50.50 | B |
| ATOM | 3320 | CB | THR | B | 205 | 25.324 | 55.853 | 79.150 | 1.00 | 100.07 | B |
| ATOM | 3321 | OG1 | THR | B | 205 | 26.748 | 55.974 | 79.228 | 1.00 | 100.07 | B |
| ATOM | 3322 | CG2 | THR | B | 205 | 24.978 | 55.064 | 77.894 | 1.00 | 100.07 | B |

| | | | | | | | | | | |
|---|---|---|---|---|---|---|---|---|---|---|
| ATOM | 3323 | C | THR | B | 205 | 24.348 | 57.635 | 77.673 | 1.00 50.50 | B |
| ATOM | 3324 | O | THR | B | 205 | 23.270 | 57.293 | 77.172 | 1.00 50.50 | B |
| ATOM | 3325 | N | PRO | B | 206 | 25.261 | 58.352 | 76.998 | 1.00 43.13 | B |
| ATOM | 3326 | CD | PRO | B | 206 | 26.627 | 58.645 | 77.464 | 1.00100.07 | B |
| ATOM | 3327 | CA | PRO | B | 206 | 25.077 | 58.786 | 75.611 | 1.00 43.13 | B |
| ATOM | 3328 | CB | PRO | B | 206 | 26.482 | 59.241 | 75.199 | 1.00100.07 | B |
| ATOM | 3329 | CG | PRO | B | 206 | 27.402 | 58.539 | 76.194 | 1.00100.07 | B |
| ATOM | 3330 | C | PRO | B | 206 | 24.523 | 57.671 | 74.734 | 1.00 43.13 | B |
| ATOM | 3331 | O | PRO | B | 206 | 23.477 | 57.834 | 74.094 | 1.00 43.13 | B |
| ATOM | 3332 | N | LEU | B | 207 | 25.228 | 56.539 | 74.719 | 1.00 99.23 | B |
| ATOM | 3333 | CA | LEU | B | 207 | 24.818 | 55.379 | 73.933 | 1.00 99.23 | B |
| ATOM | 3334 | CB | LEU | B | 207 | 25.383 | 54.090 | 74.553 | 1.00 83.32 | B |
| ATOM | 3335 | CG | LEU | B | 207 | 26.693 | 54.157 | 75.352 | 1.00 83.32 | B |
| ATOM | 3336 | CD1 | LEU | B | 207 | 27.121 | 52.755 | 75.746 | 1.00 83.32 | B |
| ATOM | 3337 | CD2 | LEU | B | 207 | 27.776 | 54.817 | 74.534 | 1.00 83.32 | B |
| ATOM | 3338 | C | LEU | B | 207 | 23.304 | 55.371 | 74.014 | 1.00 99.23 | B |
| ATOM | 3339 | O | LEU | B | 207 | 22.608 | 55.505 | 73.006 | 1.00 99.23 | B |
| ATOM | 3340 | N | GLU | B | 208 | 22.812 | 55.256 | 75.241 | 1.00 58.63 | B |
| ATOM | 3341 | CA | GLU | B | 208 | 21.389 | 55.238 | 75.502 | 1.00 58.63 | B |
| ATOM | 3342 | CB | GLU | B | 208 | 21.177 | 55.007 | 76.990 | 1.00 99.97 | B |
| ATOM | 3343 | CG | GLU | B | 208 | 21.996 | 53.829 | 77.496 | 1.00 99.97 | B |
| ATOM | 3344 | CD | GLU | B | 208 | 22.353 | 53.957 | 78.960 | 1.00 99.97 | B |
| ATOM | 3345 | OE1 | GLU | B | 208 | 22.448 | 55.110 | 79.431 | 1.00 99.97 | B |
| ATOM | 3346 | OE2 | GLU | B | 208 | 22.559 | 52.917 | 79.629 | 1.00 99.97 | B |
| ATOM | 3347 | C | GLU | B | 208 | 20.771 | 56.558 | 75.041 | 1.00 58.63 | B |
| ATOM | 3348 | O | GLU | B | 208 | 19.789 | 56.570 | 74.299 | 1.00 58.63 | B |
| ATOM | 3349 | N | ALA | B | 209 | 21.368 | 57.668 | 75.462 | 1.00 50.18 | B |
| ATOM | 3350 | CA | ALA | B | 209 | 20.877 | 58.991 | 75.092 | 1.00 50.18 | B |
| ATOM | 3351 | CB | ALA | B | 209 | 21.902 | 60.045 | 75.465 | 1.00 17.32 | B |
| ATOM | 3352 | C | ALA | B | 209 | 20.584 | 59.066 | 73.606 | 1.00 50.18 | B |
| ATOM | 3353 | O | ALA | B | 209 | 19.504 | 59.505 | 73.204 | 1.00 50.18 | B |
| ATOM | 3354 | N | LEU | B | 210 | 21.551 | 58.620 | 72.804 | 1.00 86.85 | B |
| ATOM | 3355 | CA | LEU | B | 210 | 21.452 | 58.639 | 71.345 | 1.00 86.85 | B |
| ATOM | 3356 | CB | LEU | B | 210 | 22.800 | 58.266 | 70.722 | 1.00 41.12 | B |
| ATOM | 3357 | CG | LEU | B | 210 | 22.734 | 57.913 | 69.232 | 1.00 41.12 | B |
| ATOM | 3358 | CD1 | LEU | B | 210 | 22.029 | 59.007 | 68.449 | 1.00 41.12 | B |
| ATOM | 3359 | CD2 | LEU | B | 210 | 24.132 | 57.687 | 68.708 | 1.00 41.12 | B |
| ATOM | 3360 | C | LEU | B | 210 | 20.344 | 57.772 | 70.738 | 1.00 86.85 | B |
| ATOM | 3361 | O | LEU | B | 210 | 19.483 | 58.278 | 70.011 | 1.00 86.85 | B |
| ATOM | 3362 | N | ASN | B | 211 | 20.375 | 56.468 | 71.002 | 1.00 97.57 | B |
| ATOM | 3363 | CA | ASN | B | 211 | 19.339 | 55.597 | 70.464 | 1.00 97.57 | B |
| ATOM | 3364 | CB | ASN | B | 211 | 19.578 | 54.144 | 70.872 | 1.00 43.62 | B |
| ATOM | 3365 | CG | ASN | B | 211 | 20.712 | 53.501 | 70.088 | 1.00 43.62 | B |
| ATOM | 3366 | OD1 | ASN | B | 211 | 20.635 | 53.344 | 68.861 | 1.00 43.62 | B |
| ATOM | 3367 | ND2 | ASN | B | 211 | 21.776 | 53.129 | 70.790 | 1.00 43.62 | B |
| ATOM | 3368 | C | ASN | B | 211 | 18.025 | 56.104 | 71.017 | 1.00 97.57 | B |
| ATOM | 3369 | O | ASN | B | 211 | 16.987 | 56.053 | 70.351 | 1.00 97.57 | B |
| ATOM | 3370 | N | GLN | B | 212 | 18.087 | 56.615 | 72.242 | 1.00 83.52 | B |
| ATOM | 3371 | CA | GLN | B | 212 | 16.916 | 57.170 | 72.883 | 1.00 83.52 | B |
| ATOM | 3372 | CB | GLN | B | 212 | 17.201 | 57.487 | 74.346 | 1.00 62.48 | B |
| ATOM | 3373 | CG | GLN | B | 212 | 17.271 | 56.262 | 75.233 | 1.00 62.48 | B |
| ATOM | 3374 | CD | GLN | B | 212 | 17.292 | 56.619 | 76.703 | 1.00 62.48 | B |
| ATOM | 3375 | OE1 | GLN | B | 212 | 16.398 | 57.310 | 77.202 | 1.00 62.48 | B |
| ATOM | 3376 | NE2 | GLN | B | 212 | 18.308 | 56.147 | 77.408 | 1.00 62.48 | B |
| ATOM | 3377 | C | GLN | B | 212 | 16.536 | 58.437 | 72.151 | 1.00 83.52 | B |
| ATOM | 3378 | O | GLN | B | 212 | 15.401 | 58.885 | 72.238 | 1.00 83.52 | B |
| ATOM | 3379 | N | ALA | B | 213 | 17.494 | 59.004 | 71.422 | 1.00 61.59 | B |
| ATOM | 3380 | CA | ALA | B | 213 | 17.270 | 60.236 | 70.675 | 1.00 61.59 | B |
| ATOM | 3381 | CB | ALA | B | 213 | 18.589 | 60.956 | 70.460 | 1.00 62.72 | B |
| ATOM | 3382 | C | ALA | B | 213 | 16.611 | 59.946 | 69.342 | 1.00 61.59 | B |
| ATOM | 3383 | O | ALA | B | 213 | 15.651 | 60.607 | 68.953 | 1.00 61.59 | B |
| ATOM | 3384 | N | VAL | B | 214 | 17.145 | 58.961 | 68.636 | 1.00 47.91 | B |
| ATOM | 3385 | CA | VAL | B | 214 | 16.601 | 58.567 | 67.345 | 1.00 47.91 | B |
| ATOM | 3386 | CB | VAL | B | 214 | 17.178 | 57.228 | 66.930 | 1.00 47.00 | B |
| ATOM | 3387 | CG1 | VAL | B | 214 | 16.548 | 56.774 | 65.648 | 1.00 47.00 | B |
| ATOM | 3388 | CG2 | VAL | B | 214 | 18.677 | 57.347 | 66.798 | 1.00 47.00 | B |
| ATOM | 3389 | C | VAL | B | 214 | 15.093 | 58.413 | 67.489 | 1.00 47.91 | B |
| ATOM | 3390 | O | VAL | B | 214 | 14.301 | 59.113 | 66.855 | 1.00 47.91 | B |
| ATOM | 3391 | N | ALA | B | 215 | 14.726 | 57.481 | 68.356 | 1.00 44.43 | B |
| ATOM | 3392 | CA | ALA | B | 215 | 13.343 | 57.157 | 68.658 | 1.00 44.43 | B |
| ATOM | 3393 | CB | ALA | B | 215 | 13.250 | 56.718 | 70.106 | 1.00100.07 | B |
| ATOM | 3394 | C | ALA | B | 215 | 12.304 | 58.247 | 68.390 | 1.00 44.43 | B |
| ATOM | 3395 | O | ALA | B | 215 | 11.409 | 58.072 | 67.563 | 1.00 44.43 | B |
| ATOM | 3396 | N | ILE | B | 216 | 12.424 | 59.358 | 69.109 | 1.00 44.46 | B |
| ATOM | 3397 | CA | ILE | B | 216 | 11.488 | 60.479 | 68.996 | 1.00 44.46 | B |
| ATOM | 3398 | CB | ILE | B | 216 | 11.940 | 61.708 | 69.839 | 1.00 28.99 | B |
| ATOM | 3399 | CG2 | ILE | B | 216 | 10.747 | 62.624 | 70.115 | 1.00 28.99 | B |
| ATOM | 3400 | CG1 | ILE | B | 216 | 12.558 | 61.260 | 71.166 | 1.00 28.99 | B |
| ATOM | 3401 | CD | ILE | B | 216 | 13.887 | 60.591 | 71.008 | 1.00 28.99 | B |
| ATOM | 3402 | C | ILE | B | 216 | 11.351 | 60.973 | 67.566 | 1.00 44.46 | B |
| ATOM | 3403 | O | ILE | B | 216 | 10.248 | 61.063 | 67.021 | 1.00 44.46 | B |
| ATOM | 3404 | N | LEU | B | 217 | 12.486 | 61.335 | 66.980 | 1.00 80.63 | B |
| ATOM | 3405 | CA | LEU | B | 217 | 12.501 | 61.818 | 65.616 | 1.00 80.63 | B |
| ATOM | 3406 | CB | LEU | B | 217 | 13.935 | 62.049 | 65.149 | 1.00 65.28 | B |

-41-

```
ATOM   3407  CG   LEU B 217      14.051  62.148  63.627  1.00 65.28           B
ATOM   3408  CD1  LEU B 217      13.182  63.301  63.122  1.00 65.28           B
ATOM   3409  CD2  LEU B 217      15.513  62.319  63.227  1.00 65.28           B
ATOM   3410  C    LEU B 217      11.832  60.761  64.755  1.00 80.63           B
ATOM   3411  O    LEU B 217      10.972  61.058  63.922  1.00 80.63           B
ATOM   3412  N    LYS B 218      12.241  59.519  64.981  1.00 92.37           B
ATOM   3413  CA   LYS B 218      11.706  58.373  64.269  1.00 92.37           B
ATOM   3414  CB   LYS B 218      12.358  57.110  64.829  1.00100.07           B
ATOM   3415  CG   LYS B 218      12.257  55.867  63.972  1.00100.07           B
ATOM   3416  CD   LYS B 218      13.025  54.735  64.654  1.00100.07           B
ATOM   3417  CE   LYS B 218      12.794  53.374  64.007  1.00100.07           B
ATOM   3418  NZ   LYS B 218      13.420  52.274  64.806  1.00100.07           B
ATOM   3419  C    LYS B 218      10.199  58.376  64.522  1.00 92.37           B
ATOM   3420  O    LYS B 218       9.414  58.637  63.612  1.00 92.37           B
ATOM   3421  N    GLU B 219       9.801  58.133  65.769  1.00 79.01           B
ATOM   3422  CA   GLU B 219       8.386  58.099  66.113  1.00 79.01           B
ATOM   3423  CB   GLU B 219       8.196  57.858  67.612  1.00100.07           B
ATOM   3424  CG   GLU B 219       8.450  59.058  68.500  1.00100.07           B
ATOM   3425  CD   GLU B 219       8.105  58.780  69.964  1.00100.07           B
ATOM   3426  OE1  GLU B 219       8.764  57.912  70.583  1.00100.07           B
ATOM   3427  OE2  GLU B 219       7.172  59.423  70.497  1.00100.07           B
ATOM   3428  C    GLU B 219       7.631  59.345  65.689  1.00 79.01           B
ATOM   3429  O    GLU B 219       6.407  59.329  65.600  1.00 79.01           B
ATOM   3430  N    HIS B 220       8.357  60.424  65.426  1.00 99.82           B
ATOM   3431  CA   HIS B 220       7.730  61.662  64.990  1.00 99.82           B
ATOM   3432  CB   HIS B 220       8.626  62.848  65.334  1.00 99.10           B
ATOM   3433  CG   HIS B 220       8.309  63.475  66.654  1.00 99.10           B
ATOM   3434  CD2  HIS B 220       8.813  63.255  67.890  1.00 99.10           B
ATOM   3435  ND1  HIS B 220       7.335  64.441  66.806  1.00 99.10           B
ATOM   3436  CE1  HIS B 220       7.256  64.789  68.079  1.00 99.10           B
ATOM   3437  NE2  HIS B 220       8.143  64.083  68.757  1.00 99.10           B
ATOM   3438  C    HIS B 220       7.464  61.605  63.493  1.00 99.82           B
ATOM   3439  O    HIS B 220       6.385  61.984  63.032  1.00 99.82           B
ATOM   3440  N    LEU B 221       8.441  61.120  62.733  1.00 59.35           B
ATOM   3441  CA   LEU B 221       8.285  61.021  61.287  1.00 59.35           B
ATOM   3442  CB   LEU B 221       9.488  60.320  60.672  1.00 41.22           B
ATOM   3443  CG   LEU B 221      10.769  61.140  60.790  1.00 41.22           B
ATOM   3444  CD1  LEU B 221      11.934  60.247  60.380  1.00 41.22           B
ATOM   3445  CD2  LEU B 221      11.006  61.856  59.475  1.00 41.22           B
ATOM   3446  C    LEU B 221       7.014  60.239  60.998  1.00 59.35           B
ATOM   3447  O    LEU B 221       6.330  60.510  60.016  1.00 59.35           B
ATOM   3448  N    ASN B 222       6.704  59.278  61.868  1.00 72.61           B
ATOM   3449  CA   ASN B 222       5.506  58.457  61.727  1.00 72.61           B
ATOM   3450  CB   ASN B 222       5.130  57.790  63.046  1.00 98.73           B
ATOM   3451  CG   ASN B 222       6.276  57.075  63.686  1.00 98.73           B
ATOM   3452  OD1  ASN B 222       6.132  56.492  64.762  1.00 98.73           B
ATOM   3453  ND2  ASN B 222       7.428  57.106  63.035  1.00 98.73           B
ATOM   3454  C    ASN B 222       4.355  59.375  61.380  1.00 72.61           B
ATOM   3455  O    ASN B 222       3.698  59.218  60.353  1.00 72.61           B
ATOM   3456  N    TYR B 223       4.113  60.326  62.277  1.00 53.49           B
ATOM   3457  CA   TYR B 223       3.044  61.303  62.125  1.00 53.49           B
ATOM   3458  CB   TYR B 223       3.401  62.584  62.879  1.00 66.70           B
ATOM   3459  CG   TYR B 223       3.589  62.418  64.376  1.00 66.70           B
ATOM   3460  CD1  TYR B 223       4.271  63.383  65.115  1.00 66.70           B
ATOM   3461  CE1  TYR B 223       4.464  63.244  66.485  1.00 66.70           B
ATOM   3462  CD2  TYR B 223       3.093  61.301  65.055  1.00 66.70           B
ATOM   3463  CE2  TYR B 223       3.281  61.153  66.432  1.00 66.70           B
ATOM   3464  CZ   TYR B 223       3.974  62.129  67.137  1.00 66.70           B
ATOM   3465  OH   TYR B 223       4.217  61.983  68.486  1.00 66.70           B
ATOM   3466  C    TYR B 223       2.753  61.636  60.667  1.00 53.49           B
ATOM   3467  O    TYR B 223       1.606  61.907  60.308  1.00 53.49           B
ATOM   3468  N    PHE B 224       3.796  61.634  59.837  1.00 66.70           B
ATOM   3469  CA   PHE B 224       3.633  61.904  58.410  1.00 66.70           B
ATOM   3470  CB   PHE B 224       4.970  62.275  57.738  1.00 53.82           B
ATOM   3471  CG   PHE B 224       5.693  63.448  58.376  1.00 53.82           B
ATOM   3472  CD1  PHE B 224       6.431  63.281  59.556  1.00 53.82           B
ATOM   3473  CD2  PHE B 224       5.655  64.714  57.787  1.00 53.82           B
ATOM   3474  CE1  PHE B 224       7.113  64.352  60.130  1.00 53.82           B
ATOM   3475  CE2  PHE B 224       6.337  65.791  58.362  1.00 53.82           B
ATOM   3476  CZ   PHE B 224       7.066  65.609  59.532  1.00 53.82           B
ATOM   3477  C    PHE B 224       3.099  60.619  57.796  1.00 66.70           B
ATOM   3478  O    PHE B 224       3.780  59.953  57.006  1.00 66.70           B
ATOM   3479  N    ALA B 225       1.881  60.271  58.194  1.00 79.03           B
ATOM   3480  CA   ALA B 225       1.198  59.079  57.716  1.00 79.03           B
ATOM   3481  CB   ALA B 225       1.362  57.950  58.720  1.00 49.79           B
ATOM   3482  C    ALA B 225      -0.268  59.455  57.571  1.00 79.03           B
ATOM   3483  O    ALA B 225      -0.787  60.238  58.364  1.00 79.03           B
ATOM   3484  N    ASN B 226      -0.930  58.904  56.559  1.00 83.64           B
ATOM   3485  CA   ASN B 226      -2.343  59.185  56.311  1.00 83.64           B
ATOM   3486  CB   ASN B 226      -3.229  58.265  57.158  1.00100.07           B
ATOM   3487  CG   ASN B 226      -2.620  57.949  58.496  1.00100.07           B
ATOM   3488  OD1  ASN B 226      -1.858  56.994  58.624  1.00100.07           B
ATOM   3489  ND2  ASN B 226      -2.934  58.761  59.504  1.00100.07           B
ATOM   3490  C    ASN B 226      -2.738  60.638  56.556  1.00 83.64           B
```

| ATOM | 3491 | O | ASN | B | 226 | -2.819 | 61.102 | 57.696 | 1.00 | 83.64 | B |
|------|------|----|-----|---|-----|--------|--------|--------|------|-------|---|
| ATOM | 3492 | N | PRO | B | 227 | -2.992 | 61.373 | 55.469 | 1.00 | 99.93 | B |
| ATOM | 3493 | CD | PRO | B | 227 | -2.459 | 61.008 | 54.141 | 1.00 | 100.07 | B |
| ATOM | 3494 | CA | PRO | B | 227 | -3.383 | 62.783 | 55.503 | 1.00 | 99.93 | B |
| ATOM | 3495 | CB | PRO | B | 227 | -2.469 | 63.390 | 54.457 | 1.00 | 100.07 | B |
| ATOM | 3496 | CG | PRO | B | 227 | -2.510 | 62.324 | 53.381 | 1.00 | 100.07 | B |
| ATOM | 3497 | C | PRO | B | 227 | -4.867 | 63.041 | 55.193 | 1.00 | 99.93 | B |
| ATOM | 3498 | O | PRO | B | 227 | -5.677 | 62.114 | 55.106 | 1.00 | 99.93 | B |
| ATOM | 3499 | N | GLU | B | 228 | -5.193 | 64.322 | 55.034 | 1.00 | 94.63 | B |
| ATOM | 3500 | CA | GLU | B | 228 | -6.535 | 64.800 | 54.702 | 1.00 | 94.63 | B |
| ATOM | 3501 | CB | GLU | B | 228 | -7.334 | 65.083 | 55.972 | 1.00 | 100.07 | B |
| ATOM | 3502 | CG | GLU | B | 228 | -7.381 | 63.944 | 56.966 | 1.00 | 100.07 | B |
| ATOM | 3503 | CD | GLU | B | 228 | -8.436 | 64.167 | 58.030 | 1.00 | 100.07 | B |
| ATOM | 3504 | OE1 | GLU | B | 228 | -8.364 | 65.204 | 58.727 | 1.00 | 100.07 | B |
| ATOM | 3505 | OE2 | GLU | B | 228 | -9.337 | 63.308 | 58.161 | 1.00 | 100.07 | B |
| ATOM | 3506 | C | GLU | B | 228 | -6.259 | 66.119 | 53.991 | 1.00 | 94.63 | B |
| ATOM | 3507 | O | GLU | B | 228 | -5.305 | 66.805 | 54.344 | 1.00 | 94.63 | B |
| ATOM | 3508 | N | ALA | B | 229 | -7.070 | 66.505 | 53.015 | 1.00 | 52.60 | B |
| ATOM | 3509 | CA | ALA | B | 229 | -6.754 | 67.753 | 52.343 | 1.00 | 52.60 | B |
| ATOM | 3510 | CB | ALA | B | 229 | -5.594 | 67.519 | 51.423 | 1.00 | 61.53 | B |
| ATOM | 3511 | C | ALA | B | 229 | -7.841 | 68.485 | 51.583 | 1.00 | 52.60 | B |
| ATOM | 3512 | O | ALA | B | 229 | -8.541 | 69.333 | 52.148 | 1.00 | 52.60 | B |
| ATOM | 3513 | N | ALA | B | 230 | -7.935 | 68.183 | 50.286 | 1.00 | 100.07 | B |
| ATOM | 3514 | CA | ALA | B | 230 | -8.904 | 68.802 | 49.378 | 1.00 | 100.07 | B |
| ATOM | 3515 | CB | ALA | B | 230 | -10.315 | 68.785 | 50.000 | 1.00 | 86.00 | B |
| ATOM | 3516 | C | ALA | B | 230 | -8.485 | 70.238 | 49.053 | 1.00 | 100.07 | B |
| ATOM | 3517 | O | ALA | B | 230 | -9.093 | 71.192 | 49.541 | 1.00 | 100.07 | B |
| ATOM | 3518 | N | ALA | B | 231 | -7.458 | 70.391 | 48.219 | 1.00 | 99.41 | B |
| ATOM | 3519 | CA | ALA | B | 231 | -6.959 | 71.718 | 47.861 | 1.00 | 99.41 | B |
| ATOM | 3520 | CB | ALA | B | 231 | -5.487 | 71.637 | 47.519 | 1.00 | 67.22 | B |
| ATOM | 3521 | C | ALA | B | 231 | -7.708 | 72.376 | 46.712 | 1.00 | 99.41 | B |
| ATOM | 3522 | O | ALA | B | 231 | -8.433 | 71.649 | 45.999 | 1.00 | 99.41 | B |
| ATOM | 3523 | OT | ALA | B | 231 | -7.534 | 73.609 | 46.537 | 1.00 | 67.22 | B |
| ATOM | 3524 | CB | ALA | C | 2 | 8.451 | 96.575 | 31.813 | 1.00 | 53.37 | C |
| ATOM | 3525 | C | ALA | C | 2 | 10.543 | 97.948 | 31.601 | 1.00 | 100.07 | C |
| ATOM | 3526 | O | ALA | C | 2 | 11.375 | 97.053 | 31.752 | 1.00 | 100.07 | C |
| ATOM | 3527 | N | ALA | C | 2 | 9.353 | 97.162 | 29.585 | 1.00 | 100.07 | C |
| ATOM | 3528 | CA | ALA | C | 2 | 9.179 | 97.641 | 30.982 | 1.00 | 100.07 | C |
| ATOM | 3529 | N | ILE | C | 3 | 10.767 | 99.214 | 31.947 | 1.00 | 81.15 | C |
| ATOM | 3530 | CA | ILE | C | 3 | 12.023 | 99.650 | 32.559 | 1.00 | 81.15 | C |
| ATOM | 3531 | CB | ILE | C | 3 | 13.110 | 99.940 | 31.495 | 1.00 | 93.79 | C |
| ATOM | 3532 | CG2 | ILE | C | 3 | 14.432 | 100.195 | 32.189 | 1.00 | 93.79 | C |
| ATOM | 3533 | CG1 | ILE | C | 3 | 13.238 | 98.780 | 30.507 | 1.00 | 93.79 | C |
| ATOM | 3534 | CD | ILE | C | 3 | 14.326 | 98.989 | 29.475 | 1.00 | 100.07 | C |
| ATOM | 3535 | C | ILE | C | 3 | 11.802 | 100.958 | 33.327 | 1.00 | 81.15 | C |
| ATOM | 3536 | O | ILE | C | 3 | 10.910 | 101.732 | 32.994 | 1.00 | 81.15 | C |
| ATOM | 3537 | N | LYS | C | 4 | 12.612 | 101.207 | 34.350 | 1.00 | 44.10 | C |
| ATOM | 3538 | CA | LYS | C | 4 | 12.499 | 102.454 | 35.094 | 1.00 | 44.10 | C |
| ATOM | 3539 | CB | LYS | C | 4 | 12.878 | 102.253 | 36.557 | 1.00 | 100.07 | C |
| ATOM | 3540 | CG | LYS | C | 4 | 11.725 | 101.814 | 37.447 | 1.00 | 100.07 | C |
| ATOM | 3541 | CD | LYS | C | 4 | 10.552 | 102.791 | 37.379 | 1.00 | 100.07 | C |
| ATOM | 3542 | CE | LYS | C | 4 | 9.385 | 102.339 | 38.260 | 1.00 | 100.07 | C |
| ATOM | 3543 | NZ | LYS | C | 4 | 8.140 | 103.097 | 37.957 | 1.00 | 100.07 | C |
| ATOM | 3544 | C | LYS | C | 4 | 13.431 | 103.477 | 34.462 | 1.00 | 44.10 | C |
| ATOM | 3545 | O | LYS | C | 4 | 14.417 | 103.115 | 33.821 | 1.00 | 44.10 | C |
| ATOM | 3546 | N | ARG | C | 5 | 13.134 | 104.755 | 34.646 | 1.00 | 69.39 | C |
| ATOM | 3547 | CA | ARG | C | 5 | 13.965 | 105.793 | 34.055 | 1.00 | 69.39 | C |
| ATOM | 3548 | CB | ARG | C | 5 | 13.426 | 106.148 | 32.657 | 1.00 | 100.07 | C |
| ATOM | 3549 | CG | ARG | C | 5 | 13.674 | 105.075 | 31.584 | 1.00 | 100.07 | C |
| ATOM | 3550 | CD | ARG | C | 5 | 13.416 | 105.601 | 30.150 | 1.00 | 100.07 | C |
| ATOM | 3551 | NE | ARG | C | 5 | 14.206 | 104.883 | 29.142 | 1.00 | 100.07 | C |
| ATOM | 3552 | CZ | ARG | C | 5 | 14.259 | 105.194 | 27.846 | 1.00 | 100.07 | C |
| ATOM | 3553 | NH1 | ARG | C | 5 | 13.562 | 106.222 | 27.370 | 1.00 | 100.07 | C |
| ATOM | 3554 | NH2 | ARG | C | 5 | 15.026 | 104.479 | 27.027 | 1.00 | 100.07 | C |
| ATOM | 3555 | C | ARG | C | 5 | 14.093 | 107.064 | 34.902 | 1.00 | 69.39 | C |
| ATOM | 3556 | O | ARG | C | 5 | 13.120 | 107.801 | 35.079 | 1.00 | 69.39 | C |
| ATOM | 3557 | N | PHE | C | 6 | 15.292 | 107.315 | 35.423 | 1.00 | 100.07 | C |
| ATOM | 3558 | CA | PHE | C | 6 | 15.548 | 108.513 | 36.223 | 1.00 | 100.07 | C |
| ATOM | 3559 | CB | PHE | C | 6 | 15.612 | 108.195 | 37.731 | 1.00 | 99.71 | C |
| ATOM | 3560 | CG | PHE | C | 6 | 15.918 | 106.737 | 38.077 | 1.00 | 99.71 | C |
| ATOM | 3561 | CD1 | PHE | C | 6 | 16.705 | 105.933 | 37.252 | 1.00 | 99.71 | C |
| ATOM | 3562 | CD2 | PHE | C | 6 | 15.452 | 106.193 | 39.283 | 1.00 | 99.71 | C |
| ATOM | 3563 | CE1 | PHE | C | 6 | 17.019 | 104.621 | 37.626 | 1.00 | 99.71 | C |
| ATOM | 3564 | CE2 | PHE | C | 6 | 15.765 | 104.890 | 39.656 | 1.00 | 99.71 | C |
| ATOM | 3565 | CZ | PHE | C | 6 | 16.549 | 104.106 | 38.829 | 1.00 | 99.71 | C |
| ATOM | 3566 | C | PHE | C | 6 | 16.846 | 109.201 | 35.809 | 1.00 | 100.07 | C |
| ATOM | 3567 | O | PHE | C | 6 | 17.869 | 108.537 | 35.661 | 1.00 | 100.07 | C |
| ATOM | 3568 | N | GLY | C | 7 | 16.807 | 110.527 | 35.636 | 1.00 | 100.07 | C |
| ATOM | 3569 | CA | GLY | C | 7 | 17.999 | 111.262 | 35.234 | 1.00 | 100.07 | C |
| ATOM | 3570 | C | GLY | C | 7 | 17.800 | 112.707 | 34.786 | 1.00 | 100.07 | C |
| ATOM | 3571 | O | GLY | C | 7 | 16.872 | 113.377 | 35.236 | 1.00 | 100.07 | C |
| ATOM | 3572 | N | ARG | C | 8 | 18.680 | 113.192 | 33.907 | 1.00 | 100.07 | C |
| ATOM | 3573 | CA | ARG | C | 8 | 18.598 | 114.567 | 33.397 | 1.00 | 100.07 | C |
| ATOM | 3574 | CB | ARG | C | 8 | 19.496 | 115.481 | 34.225 | 1.00 | 100.07 | C |

```
ATOM   3575  CG   ARG C   8      18.927 115.746  35.607  1.00100.07           C
ATOM   3576  CD   ARG C   8      19.469 117.043  36.189  1.00100.07           C
ATOM   3577  NE   ARG C   8      18.818 117.431  37.441  1.00100.07           C
ATOM   3578  CZ   ARG C   8      19.094 118.552  38.102  1.00100.07           C
ATOM   3579  NH1  ARG C   8      20.008 119.390  37.630  1.00100.07           C
ATOM   3580  NH2  ARG C   8      18.457 118.839  39.231  1.00100.07           C
ATOM   3581  C    ARG C   8      18.882 114.767  31.894  1.00100.07           C
ATOM   3582  O    ARG C   8      19.199 113.813  31.185  1.00100.07           C
ATOM   3583  N    ILE C   9      18.751 116.014  31.431  1.00 85.07           C
ATOM   3584  CA   ILE C   9      18.926 116.420  30.023  1.00 85.07           C
ATOM   3585  CB   ILE C   9      20.126 117.398  29.855  1.00100.07           C
ATOM   3586  CG2  ILE C   9      19.985 118.164  28.559  1.00100.07           C
ATOM   3587  CG1  ILE C   9      20.143 118.438  30.981  1.00100.07           C
ATOM   3588  CD   ILE C   9      20.695 117.922  32.299  1.00100.07           C
ATOM   3589  C    ILE C   9      19.057 115.295  28.985  1.00 85.07           C
ATOM   3590  O    ILE C   9      18.302 114.318  29.031  1.00 85.07           C
ATOM   3591  N    ARG C  10      20.005 115.455  28.057  1.00 99.59           C
ATOM   3592  CA   ARG C  10      20.296 114.509  26.965  1.00 99.59           C
ATOM   3593  CB   ARG C  10      19.120 113.546  26.737  1.00100.07           C
ATOM   3594  CG   ARG C  10      19.272 112.570  25.575  1.00100.07           C
ATOM   3595  CD   ARG C  10      17.906 112.005  25.201  1.00100.07           C
ATOM   3596  NE   ARG C  10      17.909 111.286  23.926  1.00100.07           C
ATOM   3597  CZ   ARG C  10      16.810 110.992  23.233  1.00100.07           C
ATOM   3598  NH1  ARG C  10      15.619 111.358  23.693  1.00100.07           C
ATOM   3599  NH2  ARG C  10      16.895 110.335  22.080  1.00100.07           C
ATOM   3600  C    ARG C  10      20.530 115.345  25.701  1.00 99.59           C
ATOM   3601  O    ARG C  10      20.543 114.831  24.577  1.00 99.59           C
ATOM   3602  N    GLU C  11      20.709 116.644  25.921  1.00 95.59           C
ATOM   3603  CA   GLU C  11      20.938 117.651  24.886  1.00 95.59           C
ATOM   3604  CB   GLU C  11      21.781 118.774  25.511  1.00100.07           C
ATOM   3605  CG   GLU C  11      22.184 119.942  24.628  1.00100.07           C
ATOM   3606  CD   GLU C  11      22.520 121.210  25.446  1.00100.07           C
ATOM   3607  OE1  GLU C  11      22.983 121.095  26.608  1.00100.07           C
ATOM   3608  OE2  GLU C  11      22.320 122.331  24.924  1.00100.07           C
ATOM   3609  C    GLU C  11      21.563 117.139  23.587  1.00 95.59           C
ATOM   3610  O    GLU C  11      21.159 117.543  22.499  1.00 95.59           C
ATOM   3611  N    VAL C  12      22.512 116.218  23.702  1.00 56.92           C
ATOM   3612  CA   VAL C  12      23.217 115.671  22.550  1.00 56.92           C
ATOM   3613  CB   VAL C  12      24.625 116.262  22.499  1.00 43.85           C
ATOM   3614  CG1  VAL C  12      25.498 115.474  21.577  1.00 43.85           C
ATOM   3615  CG2  VAL C  12      24.546 117.685  22.058  1.00 43.85           C
ATOM   3616  C    VAL C  12      23.328 114.146  22.545  1.00 56.92           C
ATOM   3617  O    VAL C  12      23.437 113.518  23.598  1.00 56.92           C
ATOM   3618  N    ILE C  13      23.300 113.553  21.355  1.00 99.52           C
ATOM   3619  CA   ILE C  13      23.432 112.108  21.241  1.00 99.52           C
ATOM   3620  CB   ILE C  13      23.132 111.590  19.820  1.00100.07           C
ATOM   3621  CG2  ILE C  13      22.625 110.156  19.893  1.00100.07           C
ATOM   3622  CG1  ILE C  13      22.054 112.449  19.155  1.00100.07           C
ATOM   3623  CD   ILE C  13      22.575 113.725  18.488  1.00100.07           C
ATOM   3624  C    ILE C  13      24.894 111.855  21.544  1.00 99.52           C
ATOM   3625  O    ILE C  13      25.757 112.650  21.163  1.00 99.52           C
ATOM   3626  N    PRO C  14      25.200 110.736  22.227  1.00100.07           C
ATOM   3627  CD   PRO C  14      24.342 109.569  22.493  1.00100.07           C
ATOM   3628  CA   PRO C  14      26.593 110.446  22.556  1.00100.07           C
ATOM   3629  CB   PRO C  14      26.490 109.130  23.332  1.00100.07           C
ATOM   3630  CG   PRO C  14      25.350 108.445  22.665  1.00100.07           C
ATOM   3631  C    PRO C  14      27.476 110.327  21.320  1.00100.07           C
ATOM   3632  O    PRO C  14      28.511 109.674  21.365  1.00100.07           C
ATOM   3633  N    LEU C  15      27.078 110.958  20.219  1.00 99.37           C
ATOM   3634  CA   LEU C  15      27.881 110.878  19.005  1.00 99.37           C
ATOM   3635  CB   LEU C  15      29.251 111.501  19.246  1.00100.07           C
ATOM   3636  CG   LEU C  15      30.244 111.561  18.075  1.00100.07           C
ATOM   3637  CD1  LEU C  15      29.893 112.702  17.119  1.00100.07           C
ATOM   3638  CD2  LEU C  15      31.651 111.754  18.636  1.00100.07           C
ATOM   3639  C    LEU C  15      28.070 109.407  18.699  1.00 99.37           C
ATOM   3640  O    LEU C  15      29.199 108.923  18.664  1.00 99.37           C
ATOM   3641  N    PRO C  16      26.971 108.679  18.437  1.00100.07           C
ATOM   3642  CD   PRO C  16      25.660 109.213  18.031  1.00100.07           C
ATOM   3643  CA   PRO C  16      27.061 107.240  18.140  1.00100.07           C
ATOM   3644  CB   PRO C  16      25.775 106.966  17.360  1.00100.07           C
ATOM   3645  CG   PRO C  16      24.841 107.955  17.909  1.00100.07           C
ATOM   3646  C    PRO C  16      28.302 106.699  17.406  1.00100.07           C
ATOM   3647  O    PRO C  16      28.760 105.584  17.681  1.00100.07           C
ATOM   3648  N    PRO C  17      28.854 107.471  16.450  1.00 99.96           C
ATOM   3649  CD   PRO C  17      28.398 108.764  15.935  1.00 64.04           C
ATOM   3650  CA   PRO C  17      30.028 107.035  15.703  1.00 99.96           C
ATOM   3651  CB   PRO C  17      30.477 108.311  14.983  1.00 64.04           C
ATOM   3652  CG   PRO C  17      29.696 109.415  15.628  1.00 64.04           C
ATOM   3653  C    PRO C  17      31.161 106.357  16.457  1.00 99.96           C
ATOM   3654  O    PRO C  17      31.907 105.604  15.853  1.00 99.96           C
ATOM   3655  N    LEU C  18      31.301 106.626  17.752  1.00 50.16           C
ATOM   3656  CA   LEU C  18      32.350 106.007  18.582  1.00 50.16           C
ATOM   3657  CB   LEU C  18      31.787 104.823  19.361  1.00 59.86           C
ATOM   3658  CG   LEU C  18      30.732 105.193  20.405  1.00 59.86           C
```

-44-

```
ATOM   3659  CD1 LEU C  18      30.211 103.942  21.081  1.00 59.86           C
ATOM   3660  CD2 LEU C  18      31.331 106.124  21.437  1.00 59.86           C
ATOM   3661  C   LEU C  18      33.578 105.557  17.810  1.00 50.16           C
ATOM   3662  O   LEU C  18      34.634 106.132  17.970  1.00 50.16           C
ATOM   3663  N   THR C  19      33.466 104.514  16.996  1.00 32.85           C
ATOM   3664  CA  THR C  19      34.601 104.091  16.188  1.00 32.85           C
ATOM   3665  CB  THR C  19      34.215 103.051  15.154  1.00 36.99           C
ATOM   3666  OG1 THR C  19      32.891 102.580  15.411  1.00 36.99           C
ATOM   3667  CG2 THR C  19      35.177 101.885  15.207  1.00 36.99           C
ATOM   3668  C   THR C  19      35.015 105.327  15.417  1.00 32.85           C
ATOM   3669  O   THR C  19      36.025 105.339  14.725  1.00 32.85           C
ATOM   3670  N   GLU C  20      34.206 106.369  15.521  1.00 32.76           C
ATOM   3671  CA  GLU C  20      34.486 107.618  14.854  1.00 32.76           C
ATOM   3672  CB  GLU C  20      33.607 108.721  15.422  1.00100.07           C
ATOM   3673  CG  GLU C  20      33.657 110.004  14.618  1.00100.07           C
ATOM   3674  CD  GLU C  20      33.655 111.242  15.479  1.00100.07           C
ATOM   3675  OE1 GLU C  20      33.507 112.342  14.908  1.00100.07           C
ATOM   3676  OE2 GLU C  20      33.810 111.121  16.715  1.00100.07           C
ATOM   3677  C   GLU C  20      35.938 108.001  15.064  1.00 32.76           C
ATOM   3678  O   GLU C  20      36.460 108.812  14.316  1.00 32.76           C
ATOM   3679  N   ILE C  21      36.577 107.425  16.085  1.00 35.52           C
ATOM   3680  CA  ILE C  21      37.971 107.736  16.404  1.00 35.52           C
ATOM   3681  CB  ILE C  21      38.569 106.773  17.419  1.00 65.40           C
ATOM   3682  CG2 ILE C  21      39.876 107.347  17.923  1.00 65.40           C
ATOM   3683  CG1 ILE C  21      37.598 106.551  18.578  1.00 65.40           C
ATOM   3684  CD  ILE C  21      37.203 107.819  19.338  1.00100.07           C
ATOM   3685  C   ILE C  21      38.802 107.632  15.160  1.00 35.52           C
ATOM   3686  O   ILE C  21      39.426 108.604  14.729  1.00 35.52           C
ATOM   3687  N   GLN C  22      38.803 106.432  14.597  1.00 55.89           C
ATOM   3688  CA  GLN C  22      39.516 106.164  13.376  1.00 55.89           C
ATOM   3689  CB  GLN C  22      40.142 104.778  13.451  1.00 99.33           C
ATOM   3690  CG  GLN C  22      40.993 104.623  14.694  1.00 99.33           C
ATOM   3691  CD  GLN C  22      41.568 103.237  14.869  1.00 99.33           C
ATOM   3692  OE1 GLN C  22      40.839 102.250  14.883  1.00 99.33           C
ATOM   3693  NE2 GLN C  22      42.886 103.157  15.016  1.00 99.33           C
ATOM   3694  C   GLN C  22      38.423 106.240  12.326  1.00 55.89           C
ATOM   3695  O   GLN C  22      37.927 107.324  12.026  1.00 55.89           C
ATOM   3696  N   VAL C  23      38.021 105.098  11.796  1.00 60.15           C
ATOM   3697  CA  VAL C  23      36.971 105.082  10.799  1.00 60.15           C
ATOM   3698  CB  VAL C  23      35.585 105.203  11.433  1.00 77.73           C
ATOM   3699  CG1 VAL C  23      34.519 105.126  10.355  1.00 77.73           C
ATOM   3700  CG2 VAL C  23      35.386 104.111  12.448  1.00 77.73           C
ATOM   3701  C   VAL C  23      37.148 106.268   9.889  1.00 60.15           C
ATOM   3702  O   VAL C  23      37.848 106.183   8.887  1.00 60.15           C
ATOM   3703  N   GLU C  24      36.520 107.380  10.262  1.00 55.50           C
ATOM   3704  CA  GLU C  24      36.583 108.605   9.476  1.00 55.50           C
ATOM   3705  CB  GLU C  24      35.516 109.589   9.954  1.00 99.93           C
ATOM   3706  CG  GLU C  24      34.191 109.379   9.248  1.00 99.93           C
ATOM   3707  CD  GLU C  24      33.005 109.889  10.034  1.00 99.93           C
ATOM   3708  OE1 GLU C  24      32.655 109.287  11.070  1.00 99.93           C
ATOM   3709  OE2 GLU C  24      32.415 110.899   9.612  1.00 99.93           C
ATOM   3710  C   GLU C  24      37.954 109.256   9.437  1.00 55.50           C
ATOM   3711  O   GLU C  24      38.154 110.262   8.748  1.00 55.50           C
ATOM   3712  N   SER C  25      38.898 108.675  10.170  1.00 42.32           C
ATOM   3713  CA  SER C  25      40.260 109.177  10.159  1.00 42.32           C
ATOM   3714  CB  SER C  25      41.079 108.583  11.304  1.00 98.36           C
ATOM   3715  OG  SER C  25      40.465 108.848  12.545  1.00 98.36           C
ATOM   3716  C   SER C  25      40.798 108.663   8.840  1.00 42.32           C
ATOM   3717  O   SER C  25      40.875 109.392   7.861  1.00 42.32           C
ATOM   3718  N   TYR C  26      41.145 107.384   8.816  1.00 75.16           C
ATOM   3719  CA  TYR C  26      41.678 106.783   7.611  1.00 75.16           C
ATOM   3720  CB  TYR C  26      41.438 105.282   7.618  1.00100.07           C
ATOM   3721  CG  TYR C  26      42.516 104.534   6.899  1.00100.07           C
ATOM   3722  CD1 TYR C  26      43.832 104.630   7.321  1.00100.07           C
ATOM   3723  CE1 TYR C  26      44.845 103.972   6.663  1.00100.07           C
ATOM   3724  CD2 TYR C  26      42.236 103.751   5.786  1.00100.07           C
ATOM   3725  CE2 TYR C  26      43.250 103.080   5.116  1.00100.07           C
ATOM   3726  CZ  TYR C  26      44.555 103.202   5.565  1.00100.07           C
ATOM   3727  OH  TYR C  26      45.588 102.560   4.935  1.00100.07           C
ATOM   3728  C   TYR C  26      41.002 107.397   6.395  1.00 75.16           C
ATOM   3729  O   TYR C  26      41.646 108.057   5.580  1.00 75.16           C
ATOM   3730  N   LYS C  27      39.691 107.190   6.305  1.00 67.08           C
ATOM   3731  CA  LYS C  27      38.881 107.683   5.194  1.00 67.08           C
ATOM   3732  CB  LYS C  27      37.415 107.691   5.594  1.00100.07           C
ATOM   3733  CG  LYS C  27      36.458 107.978   4.472  1.00100.07           C
ATOM   3734  CD  LYS C  27      35.049 107.654   4.925  1.00100.07           C
ATOM   3735  CE  LYS C  27      34.041 107.911   3.830  1.00100.07           C
ATOM   3736  NZ  LYS C  27      32.669 107.557   4.281  1.00100.07           C
ATOM   3737  C   LYS C  27      39.282 109.070   4.733  1.00 67.08           C
ATOM   3738  O   LYS C  27      39.199 109.383   3.551  1.00 67.08           C
ATOM   3739  N   LYS C  28      39.695 109.893   5.692  1.00 59.84           C
ATOM   3740  CA  LYS C  28      40.134 111.261   5.412  1.00 59.84           C
ATOM   3741  CB  LYS C  28      40.065 112.147   6.671  1.00100.07           C
ATOM   3742  CG  LYS C  28      38.706 112.797   6.947  1.00100.07           C
```

| | | | | | | | | | |
|---|---|---|---|---|---|---|---|---|---|
| ATOM | 3743 | CD | LYS | C | 28 | 38.404 | 113.913 | 5.950 | 1.00 100.07 | C |
| ATOM | 3744 | CE | LYS | C | 28 | 37.034 | 114.523 | 6.218 | 1.00 100.07 | C |
| ATOM | 3745 | NZ | LYS | C | 28 | 36.619 | 115.506 | 5.170 | 1.00 100.07 | C |
| ATOM | 3746 | C | LYS | C | 28 | 41.564 | 111.243 | 4.916 | 1.00 59.84 | C |
| ATOM | 3747 | O | LYS | C | 28 | 41.858 | 111.780 | 3.854 | 1.00 59.84 | C |
| ATOM | 3748 | N | ALA | C | 29 | 42.455 | 110.638 | 5.698 | 1.00 51.31 | C |
| ATOM | 3749 | CA | ALA | C | 29 | 43.851 | 110.559 | 5.307 | 1.00 51.31 | C |
| ATOM | 3750 | CB | ALA | C | 29 | 44.602 | 109.621 | 6.214 | 1.00 88.35 | C |
| ATOM | 3751 | C | ALA | C | 29 | 43.860 | 110.038 | 3.882 | 1.00 51.31 | C |
| ATOM | 3752 | O | ALA | C | 29 | 44.590 | 110.549 | 3.042 | 1.00 51.31 | C |
| ATOM | 3753 | N | LEU | C | 30 | 43.026 | 109.033 | 3.636 | 1.00 91.88 | C |
| ATOM | 3754 | CA | LEU | C | 30 | 42.881 | 108.405 | 2.339 | 1.00 91.88 | C |
| ATOM | 3755 | CB | LEU | C | 30 | 42.478 | 106.948 | 2.546 | 1.00 100.07 | C |
| ATOM | 3756 | CG | LEU | C | 30 | 42.047 | 106.095 | 1.358 | 1.00 100.07 | C |
| ATOM | 3757 | CD1 | LEU | C | 30 | 43.199 | 105.879 | 0.382 | 1.00 100.07 | C |
| ATOM | 3758 | CD2 | LEU | C | 30 | 41.536 | 104.771 | 1.898 | 1.00 100.07 | C |
| ATOM | 3759 | C | LEU | C | 30 | 41.797 | 109.150 | 1.542 | 1.00 91.88 | C |
| ATOM | 3760 | O | LEU | C | 30 | 40.646 | 108.706 | 1.455 | 1.00 91.88 | C |
| ATOM | 3761 | N | GLN | C | 31 | 42.175 | 110.296 | 0.983 | 1.00 74.59 | C |
| ATOM | 3762 | CA | GLN | C | 31 | 41.281 | 111.140 | 0.187 | 1.00 74.59 | C |
| ATOM | 3763 | CB | GLN | C | 31 | 42.088 | 112.024 | -0.753 | 1.00 86.91 | C |
| ATOM | 3764 | CG | GLN | C | 31 | 43.415 | 112.501 | -0.149 | 1.00 86.91 | C |
| ATOM | 3765 | CD | GLN | C | 31 | 43.279 | 113.804 | 0.586 | 1.00 86.91 | C |
| ATOM | 3766 | OE1 | GLN | C | 31 | 42.168 | 114.243 | 0.884 | 1.00 86.91 | C |
| ATOM | 3767 | NE2 | GLN | C | 31 | 44.407 | 114.436 | 0.879 | 1.00 86.91 | C |
| ATOM | 3768 | C | GLN | C | 31 | 40.338 | 110.323 | -0.643 | 1.00 74.59 | C |
| ATOM | 3769 | O | GLN | C | 31 | 39.253 | 110.778 | -0.967 | 1.00 74.59 | C |
| ATOM | 3770 | N | ALA | C | 32 | 40.792 | 109.117 | -0.993 | 1.00 100.07 | C |
| ATOM | 3771 | CA | ALA | C | 32 | 40.055 | 108.150 | -1.800 | 1.00 100.07 | C |
| ATOM | 3772 | CB | ALA | C | 32 | 40.292 | 106.764 | -1.247 | 1.00 90.82 | C |
| ATOM | 3773 | C | ALA | C | 32 | 38.545 | 108.380 | -1.981 | 1.00 100.07 | C |
| ATOM | 3774 | O | ALA | C | 32 | 37.872 | 108.891 | -1.094 | 1.00 100.07 | C |
| ATOM | 3775 | N | ASP | C | 33 | 38.026 | 107.953 | -3.146 | 1.00 57.55 | C |
| ATOM | 3776 | CA | ASP | C | 33 | 36.605 | 108.101 | -3.465 | 1.00 57.55 | C |
| ATOM | 3777 | CB | ASP | C | 33 | 35.774 | 107.377 | -2.407 | 1.00 100.07 | C |
| ATOM | 3778 | CG | ASP | C | 33 | 34.822 | 106.382 | -3.030 | 1.00 100.07 | C |
| ATOM | 3779 | OD1 | ASP | C | 33 | 34.015 | 106.799 | -3.884 | 1.00 100.07 | C |
| ATOM | 3780 | OD2 | ASP | C | 33 | 34.878 | 105.176 | -2.662 | 1.00 100.07 | C |
| ATOM | 3781 | C | ASP | C | 33 | 36.124 | 109.528 | -3.589 | 1.00 57.55 | C |
| ATOM | 3782 | O | ASP | C | 33 | 34.998 | 109.845 | -3.209 | 1.00 57.55 | C |
| ATOM | 3783 | N | VAL | C | 34 | 37.005 | 110.363 | -4.125 | 1.00 71.46 | C |
| ATOM | 3784 | CA | VAL | C | 34 | 36.753 | 111.782 | -4.358 | 1.00 71.46 | C |
| ATOM | 3785 | CB | VAL | C | 34 | 37.561 | 112.629 | -3.350 | 1.00 100.07 | C |
| ATOM | 3786 | CG1 | VAL | C | 34 | 37.598 | 114.073 | -3.769 | 1.00 100.07 | C |
| ATOM | 3787 | CG2 | VAL | C | 34 | 36.953 | 112.475 | -1.962 | 1.00 100.07 | C |
| ATOM | 3788 | C | VAL | C | 34 | 37.234 | 112.075 | -5.768 | 1.00 71.46 | C |
| ATOM | 3789 | O | VAL | C | 34 | 38.048 | 111.329 | -6.308 | 1.00 71.46 | C |
| ATOM | 3790 | N | PRO | C | 35 | 36.727 | 113.133 | -6.402 | 1.00 40.20 | C |
| ATOM | 3791 | CD | PRO | C | 35 | 35.675 | 114.131 | -6.165 | 1.00 100.07 | C |
| ATOM | 3792 | CA | PRO | C | 35 | 37.300 | 113.274 | -7.744 | 1.00 40.20 | C |
| ATOM | 3793 | CB | PRO | C | 35 | 36.415 | 114.335 | -8.382 | 1.00 100.07 | C |
| ATOM | 3794 | CG | PRO | C | 35 | 35.973 | 115.170 | -7.224 | 1.00 100.07 | C |
| ATOM | 3795 | C | PRO | C | 35 | 38.737 | 113.731 | -7.519 | 1.00 40.20 | C |
| ATOM | 3796 | O | PRO | C | 35 | 38.993 | 114.627 | -6.707 | 1.00 40.20 | C |
| ATOM | 3797 | N | PRO | C | 36 | 39.690 | 113.075 | -8.187 | 1.00 61.53 | C |
| ATOM | 3798 | CD | PRO | C | 36 | 39.478 | 112.085 | -9.256 | 1.00 99.99 | C |
| ATOM | 3799 | CA | PRO | C | 36 | 41.109 | 113.404 | -8.051 | 1.00 61.53 | C |
| ATOM | 3800 | CB | PRO | C | 36 | 41.781 | 112.359 | -8.924 | 1.00 99.99 | C |
| ATOM | 3801 | CG | PRO | C | 36 | 40.775 | 112.169 | -10.027 | 1.00 99.99 | C |
| ATOM | 3802 | C | PRO | C | 36 | 41.413 | 114.817 | -8.511 | 1.00 61.53 | C |
| ATOM | 3803 | O | PRO | C | 36 | 42.157 | 115.010 | -9.461 | 1.00 61.53 | C |
| ATOM | 3804 | N | GLU | C | 37 | 40.845 | 115.804 | -7.826 | 1.00 98.76 | C |
| ATOM | 3805 | CA | GLU | C | 37 | 41.050 | 117.192 | -8.205 | 1.00 98.76 | C |
| ATOM | 3806 | CB | GLU | C | 37 | 40.113 | 117.549 | -9.354 | 1.00 99.98 | C |
| ATOM | 3807 | CG | GLU | C | 37 | 39.001 | 116.546 | -9.533 | 1.00 99.98 | C |
| ATOM | 3808 | CD | GLU | C | 37 | 38.120 | 116.890 | -10.691 | 1.00 99.98 | C |
| ATOM | 3809 | OE1 | GLU | C | 37 | 37.466 | 117.951 | -10.639 | 1.00 99.98 | C |
| ATOM | 3810 | OE2 | GLU | C | 37 | 38.086 | 116.097 | -11.649 | 1.00 99.98 | C |
| ATOM | 3811 | C | GLU | C | 37 | 40.791 | 118.120 | -7.035 | 1.00 98.76 | C |
| ATOM | 3812 | O | GLU | C | 37 | 40.722 | 119.337 | -7.204 | 1.00 98.76 | C |
| ATOM | 3813 | N | LYS | C | 38 | 40.651 | 117.538 | -5.849 | 1.00 70.78 | C |
| ATOM | 3814 | CA | LYS | C | 38 | 40.376 | 118.297 | -4.638 | 1.00 70.78 | C |
| ATOM | 3815 | CB | LYS | C | 38 | 38.906 | 118.749 | -4.632 | 1.00 100.07 | C |
| ATOM | 3816 | CG | LYS | C | 38 | 38.554 | 119.782 | -5.696 | 1.00 100.07 | C |
| ATOM | 3817 | CD | LYS | C | 38 | 37.056 | 120.027 | -5.825 | 1.00 100.07 | C |
| ATOM | 3818 | CE | LYS | C | 38 | 36.763 | 121.178 | -6.788 | 1.00 100.07 | C |
| ATOM | 3819 | NZ | LYS | C | 38 | 35.295 | 121.278 | -7.073 | 1.00 100.07 | C |
| ATOM | 3820 | C | LYS | C | 38 | 40.667 | 117.469 | -3.401 | 1.00 70.78 | C |
| ATOM | 3821 | O | LYS | C | 38 | 39.973 | 116.489 | -3.132 | 1.00 70.78 | C |
| ATOM | 3822 | N | ALA | C | 39 | 41.700 | 117.879 | -2.667 | 1.00 97.46 | C |
| ATOM | 3823 | CA | ALA | C | 39 | 42.127 | 117.217 | -1.435 | 1.00 97.46 | C |
| ATOM | 3824 | CB | ALA | C | 39 | 41.930 | 115.719 | -1.538 | 1.00 100.07 | C |
| ATOM | 3825 | C | ALA | C | 39 | 43.588 | 117.513 | -1.102 | 1.00 97.46 | C |
| ATOM | 3826 | O | ALA | C | 39 | 44.317 | 118.122 | -1.883 | 1.00 97.46 | C |

-46-

```
ATOM   3827  N   GLU C  40      44.004 117.062   0.074  1.00 81.94           C
ATOM   3828  CA  GLU C  40      45.366 117.233   0.587  1.00 81.94           C
ATOM   3829  CB  GLU C  40      45.814 118.684   0.455  1.00100.07           C
ATOM   3830  CG  GLU C  40      44.826 119.635   1.114  1.00100.07           C
ATOM   3831  CD  GLU C  40      45.454 120.949   1.573  1.00100.07           C
ATOM   3832  OE1 GLU C  40      45.907 121.737   0.714  1.00100.07           C
ATOM   3833  OE2 GLU C  40      45.491 121.204   2.799  1.00100.07           C
ATOM   3834  C   GLU C  40      45.323 116.859   2.067  1.00 81.94           C
ATOM   3835  O   GLU C  40      46.356 116.673   2.708  1.00 81.94           C
ATOM   3836  N   ASN C  41      44.105 116.769   2.597  1.00 99.27           C
ATOM   3837  CA  ASN C  41      43.874 116.422   4.001  1.00 99.27           C
ATOM   3838  CB  ASN C  41      42.415 115.967   4.210  1.00100.07           C
ATOM   3839  CG  ASN C  41      41.398 117.093   3.998  1.00100.07           C
ATOM   3840  OD1 ASN C  41      41.190 117.943   4.873  1.00100.07           C
ATOM   3841  ND2 ASN C  41      40.754 117.095   2.831  1.00100.07           C
ATOM   3842  C   ASN C  41      44.834 115.315   4.437  1.00 99.27           C
ATOM   3843  O   ASN C  41      44.878 114.246   3.817  1.00 99.27           C
ATOM   3844  N   VAL C  42      45.593 115.580   5.504  1.00100.07           C
ATOM   3845  CA  VAL C  42      46.580 114.640   6.035  1.00100.07           C
ATOM   3846  CB  VAL C  42      45.904 113.475   6.763  1.00 76.43           C
ATOM   3847  CG1 VAL C  42      46.951 112.652   7.502  1.00 76.43           C
ATOM   3848  CG2 VAL C  42      44.876 114.012   7.729  1.00 76.43           C
ATOM   3849  C   VAL C  42      47.472 114.103   4.911  1.00100.07           C
ATOM   3850  O   VAL C  42      48.464 113.420   5.156  1.00100.07           C
ATOM   3851  N   GLY C  43      47.078 114.408   3.678  1.00100.07           C
ATOM   3852  CA  GLY C  43      47.831 114.037   2.500  1.00100.07           C
ATOM   3853  C   GLY C  43      48.117 112.624   2.045  1.00100.07           C
ATOM   3854  O   GLY C  43      49.272 112.325   1.723  1.00100.07           C
ATOM   3855  N   ILE C  44      47.113 111.750   1.995  1.00 69.51           C
ATOM   3856  CA  ILE C  44      47.371 110.402   1.483  1.00 69.51           C
ATOM   3857  CB  ILE C  44      46.064 109.560   1.304  1.00100.02           C
ATOM   3858  CG2 ILE C  44      45.539 109.670  -0.132  1.00100.02           C
ATOM   3859  CG1 ILE C  44      46.323 108.087   1.627  1.00100.02           C
ATOM   3860  CD  ILE C  44      47.299 107.415   0.709  1.00100.07           C
ATOM   3861  C   ILE C  44      47.870 110.798   0.109  1.00 69.51           C
ATOM   3862  O   ILE C  44      48.617 110.069  -0.549  1.00 69.51           C
ATOM   3863  N   GLN C  45      47.414 111.994  -0.277  1.00 86.09           C
ATOM   3864  CA  GLN C  45      47.715 112.635  -1.544  1.00 86.09           C
ATOM   3865  CB  GLN C  45      46.484 113.385  -2.064  1.00100.07           C
ATOM   3866  CG  GLN C  45      46.638 113.864  -3.492  1.00100.07           C
ATOM   3867  CD  GLN C  45      45.850 115.117  -3.778  1.00100.07           C
ATOM   3868  OE1 GLN C  45      46.128 116.183  -3.224  1.00100.07           C
ATOM   3869  NE2 GLN C  45      44.864 114.998  -4.649  1.00100.07           C
ATOM   3870  C   GLN C  45      48.868 113.623  -1.419  1.00 86.09           C
ATOM   3871  O   GLN C  45      49.804 113.599  -2.222  1.00 86.09           C
ATOM   3872  N   ALA C  46      48.801 114.499  -0.422  1.00 99.82           C
ATOM   3873  CA  ALA C  46      49.862 115.473  -0.261  1.00 99.82           C
ATOM   3874  CB  ALA C  46      49.792 116.140   1.096  1.00100.07           C
ATOM   3875  C   ALA C  46      51.158 114.726  -0.406  1.00 99.82           C
ATOM   3876  O   ALA C  46      51.988 115.092  -1.226  1.00 99.82           C
ATOM   3877  N   ALA C  47      51.314 113.664   0.380  1.00 56.81           C
ATOM   3878  CA  ALA C  47      52.527 112.846   0.341  1.00 56.81           C
ATOM   3879  CB  ALA C  47      52.207 111.423   0.808  1.00 69.85           C
ATOM   3880  C   ALA C  47      53.126 112.834  -1.077  1.00 56.81           C
ATOM   3881  O   ALA C  47      54.343 112.959  -1.267  1.00 56.81           C
ATOM   3882  N   PHE C  48      52.264 112.685  -2.074  1.00 97.93           C
ATOM   3883  CA  PHE C  48      52.714 112.707  -3.447  1.00 97.93           C
ATOM   3884  CB  PHE C  48      51.545 112.430  -4.390  1.00 99.49           C
ATOM   3885  CG  PHE C  48      51.143 110.988  -4.446  1.00 99.49           C
ATOM   3886  CD1 PHE C  48      51.027 110.241  -3.285  1.00 99.49           C
ATOM   3887  CD2 PHE C  48      50.883 110.375  -5.662  1.00 99.49           C
ATOM   3888  CE1 PHE C  48      50.661 108.908  -3.332  1.00 99.49           C
ATOM   3889  CE2 PHE C  48      50.517 109.041  -5.716  1.00 99.49           C
ATOM   3890  CZ  PHE C  48      50.406 108.307  -4.548  1.00 99.49           C
ATOM   3891  C   PHE C  48      53.200 114.128  -3.616  1.00 97.93           C
ATOM   3892  O   PHE C  48      54.404 114.375  -3.673  1.00 97.93           C
ATOM   3893  N   LYS C  49      52.256 115.066  -3.655  1.00 55.20           C
ATOM   3894  CA  LYS C  49      52.605 116.466  -3.817  1.00 55.20           C
ATOM   3895  CB  LYS C  49      51.444 117.372  -3.413  1.00100.07           C
ATOM   3896  CG  LYS C  49      50.465 117.612  -4.557  1.00100.07           C
ATOM   3897  CD  LYS C  49      49.132 118.170  -4.088  1.00100.07           C
ATOM   3898  CE  LYS C  49      48.202 118.374  -5.284  1.00100.07           C
ATOM   3899  NZ  LYS C  49      46.814 118.754  -4.903  1.00100.07           C
ATOM   3900  C   LYS C  49      53.821 116.719  -2.965  1.00 55.20           C
ATOM   3901  O   LYS C  49      54.805 117.274  -3.433  1.00 55.20           C
ATOM   3902  N   GLU C  50      53.777 116.254  -1.724  1.00 44.34           C
ATOM   3903  CA  GLU C  50      54.905 116.439  -0.815  1.00 44.34           C
ATOM   3904  CB  GLU C  50      54.722 115.640   0.488  1.00100.07           C
ATOM   3905  CG  GLU C  50      53.460 115.940   1.288  1.00100.07           C
ATOM   3906  CD  GLU C  50      53.351 117.385   1.757  1.00100.07           C
ATOM   3907  OE1 GLU C  50      53.412 118.307   0.910  1.00100.07           C
ATOM   3908  OE2 GLU C  50      53.181 117.596   2.979  1.00100.07           C
ATOM   3909  C   GLU C  50      56.220 116.020  -1.473  1.00 44.34           C
ATOM   3910  O   GLU C  50      57.013 116.875  -1.865  1.00 44.34           C
```

-47-

```
ATOM   3911  N    THR C  51      56.452 114.714  -1.584  1.00 92.95           C
ATOM   3912  CA   THR C  51      57.673 114.214  -2.185  1.00 92.95           C
ATOM   3913  CB   THR C  51      57.591 112.736  -2.476  1.00 76.00           C
ATOM   3914  OG1  THR C  51      57.002 112.067  -1.354  1.00 76.00           C
ATOM   3915  CG2  THR C  51      58.995 112.197  -2.724  1.00 76.00           C
ATOM   3916  C    THR C  51      57.864 114.972  -3.483  1.00 92.95           C
ATOM   3917  O    THR C  51      57.014 114.930  -4.370  1.00 92.95           C
ATOM   3918  N    PHE C  52      58.994 115.666  -3.575  1.00100.07           C
ATOM   3919  CA   PHE C  52      59.315 116.498  -4.724  1.00100.07           C
ATOM   3920  CB   PHE C  52      60.744 117.038  -4.598  1.00100.07           C
ATOM   3921  CG   PHE C  52      60.847 118.279  -3.748  1.00100.07           C
ATOM   3922  CD1  PHE C  52      61.702 118.323  -2.652  1.00100.07           C
ATOM   3923  CD2  PHE C  52      60.083 119.413  -4.047  1.00100.07           C
ATOM   3924  CE1  PHE C  52      61.794 119.492  -1.857  1.00100.07           C
ATOM   3925  CE2  PHE C  52      60.164 120.578  -3.268  1.00100.07           C
ATOM   3926  CZ   PHE C  52      61.019 120.619  -2.172  1.00100.07           C
ATOM   3927  C    PHE C  52      59.111 115.903  -6.105  1.00100.07           C
ATOM   3928  O    PHE C  52      59.649 114.840  -6.417  1.00100.07           C
ATOM   3929  N    PRO C  53      58.298 116.591  -6.942  1.00 91.92           C
ATOM   3930  CD   PRO C  53      57.487 117.764  -6.573  1.00 49.19           C
ATOM   3931  CA   PRO C  53      57.997 116.184  -8.311  1.00 91.92           C
ATOM   3932  CB   PRO C  53      57.281 117.407  -8.862  1.00 49.19           C
ATOM   3933  CG   PRO C  53      56.481 117.827  -7.694  1.00 49.19           C
ATOM   3934  C    PRO C  53      59.317 115.898  -9.008  1.00 91.92           C
ATOM   3935  O    PRO C  53      59.735 116.614  -9.913  1.00 91.92           C
ATOM   3936  N    ILE C  54      59.963 114.837  -8.528  1.00100.07           C
ATOM   3937  CA   ILE C  54      61.248 114.330  -8.990  1.00100.07           C
ATOM   3938  CB   ILE C  54      61.068 112.912  -9.529  1.00100.07           C
ATOM   3939  CG2  ILE C  54      62.264 112.529 -10.409  1.00100.07           C
ATOM   3940  CG1  ILE C  54      60.753 111.962  -8.358  1.00100.07           C
ATOM   3941  CD   ILE C  54      61.570 112.186  -7.095  1.00100.07           C
ATOM   3942  C    ILE C  54      62.105 115.129  -9.960  1.00100.07           C
ATOM   3943  O    ILE C  54      61.810 115.253 -11.155  1.00100.07           C
ATOM   3944  N    GLU C  55      63.202 115.636  -9.412  1.00100.07           C
ATOM   3945  CA   GLU C  55      64.160 116.433 -10.162  1.00100.07           C
ATOM   3946  CB   GLU C  55      64.719 117.563  -9.289  1.00100.07           C
ATOM   3947  CG   GLU C  55      63.714 118.412  -8.512  1.00100.07           C
ATOM   3948  CD   GLU C  55      64.137 118.662  -7.056  1.00100.07           C
ATOM   3949  OE1  GLU C  55      65.344 118.839  -6.784  1.00100.07           C
ATOM   3950  OE2  GLU C  55      63.243 118.689  -6.182  1.00100.07           C
ATOM   3951  C    GLU C  55      65.322 115.529 -10.518  1.00100.07           C
ATOM   3952  O    GLU C  55      65.555 114.522  -9.844  1.00100.07           C
ATOM   3953  N    GLU C  56      66.057 115.890 -11.565  1.00 85.09           C
ATOM   3954  CA   GLU C  56      67.240 115.136 -11.970  1.00 85.09           C
ATOM   3955  CB   GLU C  56      67.546 115.301 -13.476  1.00100.07           C
ATOM   3956  CG   GLU C  56      67.905 116.716 -13.971  1.00100.07           C
ATOM   3957  CD   GLU C  56      66.718 117.457 -14.580  1.00100.07           C
ATOM   3958  OE1  GLU C  56      66.059 116.895 -15.480  1.00100.07           C
ATOM   3959  OE2  GLU C  56      66.445 118.607 -14.161  1.00100.07           C
ATOM   3960  C    GLU C  56      68.392 115.721 -11.146  1.00 85.09           C
ATOM   3961  O    GLU C  56      68.261 115.954  -9.955  1.00 85.09           C
ATOM   3962  N    ALA C  57      69.520 115.952 -11.800  1.00100.07           C
ATOM   3963  CA   ALA C  57      70.688 116.533 -11.159  1.00100.07           C
ATOM   3964  CB   ALA C  57      71.891 115.528 -11.220  1.00 81.58           C
ATOM   3965  C    ALA C  57      71.031 117.860 -11.876  1.00100.07           C
ATOM   3966  O    ALA C  57      70.352 118.274 -12.832  1.00100.07           C
ATOM   3967  N    ALA C  58      72.060 118.534 -11.372  1.00100.07           C
ATOM   3968  CA   ALA C  58      72.523 119.799 -11.951  1.00100.07           C
ATOM   3969  CB   ALA C  58      72.832 119.603 -13.456  1.00 88.65           C
ATOM   3970  C    ALA C  58      71.633 121.040 -11.756  1.00100.07           C
ATOM   3971  O    ALA C  58      72.164 122.124 -11.511  1.00100.07           C
ATOM   3972  N    ALA C  59      70.308 120.878 -11.818  1.00100.07           C
ATOM   3973  CA   ALA C  59      69.363 121.990 -11.701  1.00100.07           C
ATOM   3974  CB   ALA C  59      69.776 122.953 -10.549  1.00 73.41           C
ATOM   3975  C    ALA C  59      69.274 122.733 -13.046  1.00100.07           C
ATOM   3976  O    ALA C  59      69.697 123.879 -13.169  1.00100.07           C
ATOM   3977  N    ALA C  60      68.704 122.033 -14.025  1.00100.07           C
ATOM   3978  CA   ALA C  60      68.501 122.478 -15.418  1.00100.07           C
ATOM   3979  CB   ALA C  60      68.734 123.996 -15.594  1.00100.07           C
ATOM   3980  C    ALA C  60      69.436 121.675 -16.322  1.00100.07           C
ATOM   3981  O    ALA C  60      70.038 120.695 -15.872  1.00100.07           C
ATOM   3982  N    ALA C  61      69.533 122.076 -17.592  1.00100.07           C
ATOM   3983  CA   ALA C  61      70.363 121.410 -18.618  1.00100.07           C
ATOM   3984  CB   ALA C  61      71.570 120.723 -17.987  1.00100.07           C
ATOM   3985  C    ALA C  61      69.512 120.385 -19.390  1.00100.07           C
ATOM   3986  O    ALA C  61      68.289 120.457 -19.351  1.00100.07           C
ATOM   3987  N    ALA C  62      70.141 119.462 -20.123  1.00100.07           C
ATOM   3988  CA   ALA C  62      69.400 118.433 -20.882  1.00100.07           C
ATOM   3989  CB   ALA C  62      70.375 117.395 -21.466  1.00100.07           C
ATOM   3990  C    ALA C  62      68.382 117.756 -19.943  1.00100.07           C
ATOM   3991  O    ALA C  62      68.690 116.784 -19.235  1.00100.07           C
ATOM   3992  N    ALA C  63      67.169 118.311 -19.947  1.00100.07           C
ATOM   3993  CA   ALA C  63      66.061 117.889 -19.093  1.00100.07           C
ATOM   3994  CB   ALA C  63      64.807 118.689 -19.493  1.00 31.37           C
```

```
ATOM   3995  C   ALA C  63      65.714 116.399 -18.943  1.00100.07           C
ATOM   3996  O   ALA C  63      65.621 115.655 -19.923  1.00100.07           C
ATOM   3997  N   LEU C  64      65.526 115.992 -17.683  1.00 99.55           C
ATOM   3998  CA  LEU C  64      65.169 114.621 -17.292  1.00 99.55           C
ATOM   3999  CB  LEU C  64      66.422 113.733 -17.185  1.00100.07           C
ATOM   4000  CG  LEU C  64      66.507 112.380 -17.922  1.00100.07           C
ATOM   4001  CD1 LEU C  64      67.912 111.798 -17.726  1.00100.07           C
ATOM   4002  CD2 LEU C  64      65.450 111.407 -17.415  1.00100.07           C
ATOM   4003  C   LEU C  64      64.499 114.708 -15.918  1.00 99.55           C
ATOM   4004  O   LEU C  64      65.121 114.385 -14.908  1.00 99.55           C
ATOM   4005  N   VAL C  65      63.244 115.163 -15.890  1.00100.07           C
ATOM   4006  CA  VAL C  65      62.472 115.304 -14.650  1.00100.07           C
ATOM   4007  CB  VAL C  65      62.309 116.786 -14.251  1.00100.07           C
ATOM   4008  CG1 VAL C  65      60.950 117.010 -13.573  1.00100.07           C
ATOM   4009  CG2 VAL C  65      63.439 117.185 -13.299  1.00100.07           C
ATOM   4010  C   VAL C  65      61.079 114.671 -14.675  1.00100.07           C
ATOM   4011  O   VAL C  65      60.302 114.859 -15.618  1.00100.07           C
ATOM   4012  N   LEU C  66      60.769 113.947 -13.600  1.00 57.88           C
ATOM   4013  CA  LEU C  66      59.485 113.276 -13.454  1.00 57.88           C
ATOM   4014  CB  LEU C  66      59.680 111.955 -12.699  1.00100.07           C
ATOM   4015  CG  LEU C  66      58.465 111.064 -12.426  1.00100.07           C
ATOM   4016  CD1 LEU C  66      57.672 110.829 -13.702  1.00100.07           C
ATOM   4017  CD2 LEU C  66      58.949 109.741 -11.833  1.00100.07           C
ATOM   4018  C   LEU C  66      58.546 114.199 -12.687  1.00 57.88           C
ATOM   4019  O   LEU C  66      58.964 115.238 -12.189  1.00 57.88           C
ATOM   4020  N   ASP C  67      57.273 113.840 -12.617  1.00 64.25           C
ATOM   4021  CA  ASP C  67      56.315 114.654 -11.890  1.00 64.25           C
ATOM   4022  CB  ASP C  67      55.975 115.941 -12.664  1.00100.07           C
ATOM   4023  CG  ASP C  67      55.108 115.691 -13.890  1.00100.07           C
ATOM   4024  OD1 ASP C  67      55.411 114.752 -14.659  1.00100.07           C
ATOM   4025  OD2 ASP C  67      54.130 116.451 -14.090  1.00100.07           C
ATOM   4026  C   ASP C  67      55.074 113.829 -11.638  1.00 64.25           C
ATOM   4027  O   ASP C  67      54.707 112.963 -12.432  1.00 64.25           C
ATOM   4028  N   PHE C  68      54.425 114.114 -10.522  1.00 66.57           C
ATOM   4029  CA  PHE C  68      53.252 113.379 -10.105  1.00 66.57           C
ATOM   4030  CB  PHE C  68      53.213 113.339  -8.573  1.00100.07           C
ATOM   4031  CG  PHE C  68      54.531 112.924  -7.950  1.00100.07           C
ATOM   4032  CD1 PHE C  68      55.624 113.793  -7.936  1.00100.07           C
ATOM   4033  CD2 PHE C  68      54.703 111.639  -7.447  1.00100.07           C
ATOM   4034  CE1 PHE C  68      56.867 113.376  -7.436  1.00100.07           C
ATOM   4035  CE2 PHE C  68      55.942 111.218  -6.947  1.00100.07           C
ATOM   4036  CZ  PHE C  68      57.022 112.088  -6.945  1.00100.07           C
ATOM   4037  C   PHE C  68      51.944 113.889 -10.658  1.00 66.57           C
ATOM   4038  O   PHE C  68      51.899 114.866 -11.396  1.00 66.57           C
ATOM   4039  N   LEU C  69      50.881 113.195 -10.280  1.00 95.34           C
ATOM   4040  CA  LEU C  69      49.531 113.507 -10.709  1.00 95.34           C
ATOM   4041  CB  LEU C  69      49.391 113.331 -12.216  1.00100.07           C
ATOM   4042  CG  LEU C  69      49.315 114.595 -13.058  1.00100.07           C
ATOM   4043  CD1 LEU C  69      48.891 114.220 -14.471  1.00100.07           C
ATOM   4044  CD2 LEU C  69      48.312 115.564 -12.442  1.00100.07           C
ATOM   4045  C   LEU C  69      48.583 112.538 -10.044  1.00 95.34           C
ATOM   4046  O   LEU C  69      49.005 111.644  -9.309  1.00 95.34           C
ATOM   4047  N   GLU C  70      47.299 112.726 -10.316  1.00100.07           C
ATOM   4048  CA  GLU C  70      46.256 111.859  -9.791  1.00100.07           C
ATOM   4049  CB  GLU C  70      45.807 110.893 -10.891  1.00100.07           C
ATOM   4050  CG  GLU C  70      45.425 111.524 -12.218  1.00100.07           C
ATOM   4051  CD  GLU C  70      43.941 111.500 -12.426  1.00100.07           C
ATOM   4052  OE1 GLU C  70      43.246 112.323 -11.799  1.00100.07           C
ATOM   4053  OE2 GLU C  70      43.472 110.641 -13.198  1.00100.07           C
ATOM   4054  C   GLU C  70      46.670 111.040  -8.563  1.00100.07           C
ATOM   4055  O   GLU C  70      47.365 111.521  -7.660  1.00100.07           C
ATOM   4056  N   TYR C  71      46.230 109.786  -8.582  1.00 75.56           C
ATOM   4057  CA  TYR C  71      46.433 108.778  -7.553  1.00 75.56           C
ATOM   4058  CB  TYR C  71      46.438 109.401  -6.147  1.00100.07           C
ATOM   4059  CG  TYR C  71      45.178 110.178  -5.798  1.00100.07           C
ATOM   4060  CD1 TYR C  71      44.012 109.522  -5.395  1.00100.07           C
ATOM   4061  CE1 TYR C  71      42.834 110.238  -5.105  1.00100.07           C
ATOM   4062  CD2 TYR C  71      45.144 111.570  -5.899  1.00100.07           C
ATOM   4063  CE2 TYR C  71      43.977 112.293  -5.613  1.00100.07           C
ATOM   4064  CZ  TYR C  71      42.826 111.625  -5.216  1.00100.07           C
ATOM   4065  OH  TYR C  71      41.690 112.358  -4.932  1.00100.07           C
ATOM   4066  C   TYR C  71      45.219 107.865  -7.720  1.00 75.56           C
ATOM   4067  O   TYR C  71      44.085 108.338  -7.858  1.00 75.56           C
ATOM   4068  N   ARG C  72      45.438 106.560  -7.753  1.00 57.59           C
ATOM   4069  CA  ARG C  72      44.301 105.674  -7.914  1.00 57.59           C
ATOM   4070  CB  ARG C  72      43.982 105.494  -9.401  1.00100.07           C
ATOM   4071  CG  ARG C  72      43.500 106.759 -10.104  1.00100.07           C
ATOM   4072  CD  ARG C  72      43.271 106.502 -11.593  1.00100.07           C
ATOM   4073  NE  ARG C  72      42.780 107.675 -12.329  1.00100.07           C
ATOM   4074  CZ  ARG C  72      42.475 107.665 -13.629  1.00100.07           C
ATOM   4075  NH1 ARG C  72      42.614 106.543 -14.330  1.00100.07           C
ATOM   4076  NH2 ARG C  72      42.029 108.767 -14.233  1.00100.07           C
ATOM   4077  C   ARG C  72      44.448 104.310  -7.257  1.00 57.59           C
ATOM   4078  O   ARG C  72      45.223 103.465  -7.718  1.00 57.59           C
```

-49-

| ATOM | 4079 | N | ILE | C | 73 | 43.729 | 104.102 | -6.155 | 1.00 | 63.88 | C |
|------|------|------|-----|---|----|--------|---------|--------|------|-------|---|
| ATOM | 4080 | CA | ILE | C | 73 | 43.753 | 102.805 | -5.486 | 1.00 | 63.88 | C |
| ATOM | 4081 | CB | ILE | C | 73 | 43.574 | 102.891 | -3.953 | 1.00 | 100.07 | C |
| ATOM | 4082 | CG2 | ILE | C | 73 | 44.622 | 102.078 | -3.267 | 1.00 | 100.07 | C |
| ATOM | 4083 | CG1 | ILE | C | 73 | 43.566 | 104.335 | -3.483 | 1.00 | 100.07 | C |
| ATOM | 4084 | CD | ILE | C | 73 | 42.175 | 104.768 | -3.007 | 1.00 | 100.07 | C |
| ATOM | 4085 | C | ILE | C | 73 | 42.480 | 102.205 | -6.020 | 1.00 | 63.88 | C |
| ATOM | 4086 | O | ILE | C | 73 | 41.550 | 102.952 | -6.328 | 1.00 | 63.88 | C |
| ATOM | 4087 | N | GLY | C | 74 | 42.399 | 100.888 | -6.138 | 1.00 | 44.96 | C |
| ATOM | 4088 | CA | GLY | C | 74 | 41.148 | 100.354 | -6.632 | 1.00 | 44.96 | C |
| ATOM | 4089 | C | GLY | C | 74 | 40.924 | 98.877 | -6.468 | 1.00 | 44.96 | C |
| ATOM | 4090 | O | GLY | C | 74 | 41.841 | 98.124 | -6.132 | 1.00 | 44.96 | C |
| ATOM | 4091 | N | ASP | C | 75 | 39.677 | 98.474 | -6.688 | 1.00 | 61.25 | C |
| ATOM | 4092 | CA | ASP | C | 75 | 39.300 | 97.078 | -6.613 | 1.00 | 61.25 | C |
| ATOM | 4093 | CB | ASP | C | 75 | 39.288 | 96.480 | -8.028 | 1.00 | 100.07 | C |
| ATOM | 4094 | CG | ASP | C | 75 | 40.471 | 96.965 | -8.906 | 1.00 | 100.07 | C |
| ATOM | 4095 | OD1 | ASP | C | 75 | 40.641 | 98.191 | -9.095 | 1.00 | 100.07 | C |
| ATOM | 4096 | OD2 | ASP | C | 75 | 41.226 | 96.119 | -9.436 | 1.00 | 100.07 | C |
| ATOM | 4097 | C | ASP | C | 75 | 40.181 | 96.218 | -5.713 | 1.00 | 61.25 | C |
| ATOM | 4098 | O | ASP | C | 75 | 41.273 | 95.786 | -6.117 | 1.00 | 61.25 | C |
| ATOM | 4099 | N | PRO | C | 76 | 39.734 | 95.979 | -4.466 | 1.00 | 77.46 | C |
| ATOM | 4100 | CD | PRO | C | 76 | 38.632 | 96.635 | -3.745 | 1.00 | 86.05 | C |
| ATOM | 4101 | CA | PRO | C | 76 | 40.526 | 95.146 | -3.560 | 1.00 | 77.46 | C |
| ATOM | 4102 | CB | PRO | C | 76 | 39.699 | 95.140 | -2.265 | 1.00 | 86.05 | C |
| ATOM | 4103 | CG | PRO | C | 76 | 38.326 | 95.626 | -2.678 | 1.00 | 86.05 | C |
| ATOM | 4104 | C | PRO | C | 76 | 40.700 | 93.761 | -4.196 | 1.00 | 77.46 | C |
| ATOM | 4105 | O | PRO | C | 76 | 39.734 | 93.129 | -4.598 | 1.00 | 77.46 | C |
| ATOM | 4106 | N | PRO | C | 77 | 41.945 | 93.278 | -4.278 | 1.00 | 54.01 | C |
| ATOM | 4107 | CD | PRO | C | 77 | 42.936 | 93.689 | -3.269 | 1.00 | 64.03 | C |
| ATOM | 4108 | CA | PRO | C | 77 | 42.324 | 91.991 | -4.859 | 1.00 | 54.01 | C |
| ATOM | 4109 | CB | PRO | C | 77 | 43.742 | 91.799 | -4.366 | 1.00 | 64.03 | C |
| ATOM | 4110 | CG | PRO | C | 77 | 43.682 | 92.410 | -3.004 | 1.00 | 64.03 | C |
| ATOM | 4111 | C | PRO | C | 77 | 41.414 | 90.884 | -4.392 | 1.00 | 54.01 | C |
| ATOM | 4112 | O | PRO | C | 77 | 40.760 | 90.225 | -5.202 | 1.00 | 54.01 | C |
| ATOM | 4113 | N | PHE | C | 78 | 41.390 | 90.676 | -3.079 | 1.00 | 58.09 | C |
| ATOM | 4114 | CA | PHE | C | 78 | 40.554 | 89.647 | -2.454 | 1.00 | 58.09 | C |
| ATOM | 4115 | CB | PHE | C | 78 | 41.398 | 88.629 | -1.699 | 1.00 | 98.77 | C |
| ATOM | 4116 | CG | PHE | C | 78 | 41.846 | 87.485 | -2.530 | 1.00 | 98.77 | C |
| ATOM | 4117 | CD1 | PHE | C | 78 | 43.037 | 87.554 | -3.225 | 1.00 | 98.77 | C |
| ATOM | 4118 | CD2 | PHE | C | 78 | 41.091 | 86.321 | -2.588 | 1.00 | 98.77 | C |
| ATOM | 4119 | CE1 | PHE | C | 78 | 43.483 | 86.476 | -3.965 | 1.00 | 98.77 | C |
| ATOM | 4120 | CE2 | PHE | C | 78 | 41.526 | 85.234 | -3.328 | 1.00 | 98.77 | C |
| ATOM | 4121 | CZ | PHE | C | 78 | 42.728 | 85.310 | -4.018 | 1.00 | 98.77 | C |
| ATOM | 4122 | C | PHE | C | 78 | 39.607 | 90.303 | -1.473 | 1.00 | 58.09 | C |
| ATOM | 4123 | O | PHE | C | 78 | 39.590 | 91.533 | -1.366 | 1.00 | 58.09 | C |
| ATOM | 4124 | N | SER | C | 79 | 38.828 | 89.489 | -0.763 | 1.00 | 60.18 | C |
| ATOM | 4125 | CA | SER | C | 79 | 37.869 | 89.992 | 0.207 | 1.00 | 60.18 | C |
| ATOM | 4126 | CB | SER | C | 79 | 36.446 | 89.566 | -0.171 | 1.00 | 100.07 | C |
| ATOM | 4127 | OG | SER | C | 79 | 36.154 | 88.258 | 0.298 | 1.00 | 100.07 | C |
| ATOM | 4128 | C | SER | C | 79 | 38.130 | 89.512 | 1.619 | 1.00 | 60.18 | C |
| ATOM | 4129 | O | SER | C | 79 | 38.856 | 88.550 | 1.843 | 1.00 | 60.18 | C |
| ATOM | 4130 | N | GLN | C | 80 | 37.517 | 90.209 | 2.567 | 1.00 | 78.53 | C |
| ATOM | 4131 | CA | GLN | C | 80 | 37.615 | 89.851 | 3.962 | 1.00 | 78.53 | C |
| ATOM | 4132 | CB | GLN | C | 80 | 36.744 | 90.789 | 4.805 | 1.00 | 100.07 | C |
| ATOM | 4133 | CG | GLN | C | 80 | 35.437 | 91.250 | 4.115 | 1.00 | 100.07 | C |
| ATOM | 4134 | CD | GLN | C | 80 | 34.297 | 91.448 | 5.105 | 1.00 | 100.07 | C |
| ATOM | 4135 | OE1 | GLN | C | 80 | 34.394 | 92.274 | 6.017 | 1.00 | 100.07 | C |
| ATOM | 4136 | NE2 | GLN | C | 80 | 33.215 | 90.678 | 4.937 | 1.00 | 100.07 | C |
| ATOM | 4137 | C | GLN | C | 80 | 37.117 | 88.408 | 4.078 | 1.00 | 78.53 | C |
| ATOM | 4138 | O | GLN | C | 80 | 36.103 | 88.057 | 3.489 | 1.00 | 78.53 | C |
| ATOM | 4139 | N | ASP | C | 81 | 37.848 | 87.597 | 4.838 | 1.00 | 87.72 | C |
| ATOM | 4140 | CA | ASP | C | 81 | 37.545 | 86.181 | 5.067 | 1.00 | 87.72 | C |
| ATOM | 4141 | CB | ASP | C | 81 | 36.031 | 85.894 | 5.051 | 1.00 | 100.07 | C |
| ATOM | 4142 | CG | ASP | C | 81 | 35.464 | 85.571 | 6.445 | 1.00 | 100.07 | C |
| ATOM | 4143 | OD1 | ASP | C | 81 | 34.766 | 86.436 | 7.028 | 1.00 | 100.07 | C |
| ATOM | 4144 | OD2 | ASP | C | 81 | 35.716 | 84.461 | 6.962 | 1.00 | 100.07 | C |
| ATOM | 4145 | C | ASP | C | 81 | 38.255 | 85.294 | 4.057 | 1.00 | 87.72 | C |
| ATOM | 4146 | O | ASP | C | 81 | 38.748 | 84.229 | 4.416 | 1.00 | 87.72 | C |
| ATOM | 4147 | N | GLU | C | 82 | 38.292 | 85.718 | 2.794 | 1.00 | 77.33 | C |
| ATOM | 4148 | CA | GLU | C | 82 | 39.032 | 84.953 | 1.787 | 1.00 | 77.33 | C |
| ATOM | 4149 | CB | GLU | C | 82 | 38.857 | 85.492 | 0.365 | 1.00 | 100.07 | C |
| ATOM | 4150 | CG | GLU | C | 82 | 37.467 | 85.559 | -0.184 | 1.00 | 100.07 | C |
| ATOM | 4151 | CD | GLU | C | 82 | 37.465 | 86.160 | -1.571 | 1.00 | 100.07 | C |
| ATOM | 4152 | OE1 | GLU | C | 82 | 38.085 | 87.235 | -1.743 | 1.00 | 100.07 | C |
| ATOM | 4153 | OE2 | GLU | C | 82 | 36.845 | 85.559 | -2.480 | 1.00 | 100.07 | C |
| ATOM | 4154 | C | GLU | C | 82 | 40.428 | 85.312 | 2.203 | 1.00 | 77.33 | C |
| ATOM | 4155 | O | GLU | C | 82 | 41.351 | 84.507 | 2.124 | 1.00 | 77.33 | C |
| ATOM | 4156 | N | CYS | C | 83 | 40.556 | 86.561 | 2.637 | 1.00 | 33.66 | C |
| ATOM | 4157 | CA | CYS | C | 83 | 41.819 | 87.108 | 3.081 | 1.00 | 33.66 | C |
| ATOM | 4158 | CB | CYS | C | 83 | 41.656 | 88.559 | 3.479 | 1.00 | 42.30 | C |
| ATOM | 4159 | SG | CYS | C | 83 | 42.498 | 89.654 | 2.355 | 1.00 | 42.30 | C |
| ATOM | 4160 | C | CYS | C | 83 | 42.335 | 86.335 | 4.253 | 1.00 | 33.66 | C |
| ATOM | 4161 | O | CYS | C | 83 | 43.341 | 85.642 | 4.145 | 1.00 | 33.66 | C |
| ATOM | 4162 | N | ARG | C | 84 | 41.645 | 86.438 | 5.382 | 1.00 | 40.55 | C |

-50-

```
ATOM  4163  CA   ARG C  84    42.079  85.720   6.580  1.00 40.55      C
ATOM  4164  CB   ARG C  84    41.086  85.954   7.715  1.00 60.20      C
ATOM  4165  CG   ARG C  84    40.630  87.404   7.827  1.00 60.20      C
ATOM  4166  CD   ARG C  84    39.392  87.509   8.709  1.00 60.20      C
ATOM  4167  NE   ARG C  84    38.602  88.714   8.456  1.00 60.20      C
ATOM  4168  CZ   ARG C  84    37.357  88.888   8.890  1.00 60.20      C
ATOM  4169  NH1  ARG C  84    36.762  87.933   9.597  1.00 60.20      C
ATOM  4170  NH2  ARG C  84    36.705  90.008   8.609  1.00 60.20      C
ATOM  4171  C    ARG C  84    42.205  84.224   6.288  1.00 40.55      C
ATOM  4172  O    ARG C  84    43.157  83.579   6.717  1.00 40.55      C
ATOM  4173  N    GLU C  85    41.249  83.684   5.539  1.00 54.53      C
ATOM  4174  CA   GLU C  85    41.271  82.268   5.205  1.00 54.53      C
ATOM  4175  CB   GLU C  85    40.133  81.925   4.241  1.00100.07      C
ATOM  4176  CG   GLU C  85    39.920  80.430   4.047  1.00100.07      C
ATOM  4177  CD   GLU C  85    38.512  80.088   3.584  1.00100.07      C
ATOM  4178  OE1  GLU C  85    38.111  80.537   2.485  1.00100.07      C
ATOM  4179  OE2  GLU C  85    37.801  79.367   4.327  1.00100.07      C
ATOM  4180  C    GLU C  85    42.606  81.896   4.587  1.00 54.53      C
ATOM  4181  O    GLU C  85    43.318  81.043   5.111  1.00 54.53      C
ATOM  4182  N    LYS C  86    42.947  82.563   3.488  1.00 65.18      C
ATOM  4183  CA   LYS C  86    44.186  82.301   2.773  1.00 65.18      C
ATOM  4184  CB   LYS C  86    43.964  82.518   1.274  1.00100.07      C
ATOM  4185  CG   LYS C  86    43.028  81.487   0.660  1.00100.07      C
ATOM  4186  CD   LYS C  86    42.558  81.876  -0.726  1.00100.07      C
ATOM  4187  CE   LYS C  86    41.580  80.846  -1.281  1.00100.07      C
ATOM  4188  NZ   LYS C  86    40.652  81.452  -2.278  1.00100.07      C
ATOM  4189  C    LYS C  86    45.317  83.187   3.259  1.00 65.18      C
ATOM  4190  O    LYS C  86    46.149  83.611   2.470  1.00 65.18      C
ATOM  4191  N    ASP C  87    45.359  83.452   4.560  1.00100.07      C
ATOM  4192  CA   ASP C  87    46.399  84.302   5.129  1.00100.07      C
ATOM  4193  CB   ASP C  87    47.588  83.475   5.619  1.00 70.60      C
ATOM  4194  CG   ASP C  87    47.361  82.870   6.997  1.00 70.60      C
ATOM  4195  OD1  ASP C  87    46.695  83.499   7.841  1.00 70.60      C
ATOM  4196  OD2  ASP C  87    47.874  81.766   7.254  1.00 70.60      C
ATOM  4197  C    ASP C  87    46.897  85.329   4.132  1.00100.07      C
ATOM  4198  O    ASP C  87    48.034  85.261   3.682  1.00100.07      C
ATOM  4199  N    LEU C  88    46.035  86.271   3.778  1.00100.04      C
ATOM  4200  CA   LEU C  88    46.408  87.329   2.854  1.00100.04      C
ATOM  4201  CB   LEU C  88    45.838  87.060   1.458  1.00 94.76      C
ATOM  4202  CG   LEU C  88    46.548  85.963   0.653  1.00 94.76      C
ATOM  4203  CD1  LEU C  88    46.111  86.008  -0.807  1.00 94.76      C
ATOM  4204  CD2  LEU C  88    48.045  86.167   0.729  1.00 94.76      C
ATOM  4205  C    LEU C  88    45.891  88.665   3.374  1.00100.04      C
ATOM  4206  O    LEU C  88    44.699  88.811   3.631  1.00100.04      C
ATOM  4207  N    THR C  89    46.794  89.626   3.548  1.00 71.47      C
ATOM  4208  CA   THR C  89    46.444  90.958   4.042  1.00 71.47      C
ATOM  4209  CB   THR C  89    47.664  91.895   3.980  1.00100.07      C
ATOM  4210  OG1  THR C  89    48.741  91.340   4.752  1.00100.07      C
ATOM  4211  CG2  THR C  89    47.314  93.242   4.547  1.00100.07      C
ATOM  4212  C    THR C  89    45.309  91.572   3.217  1.00 71.47      C
ATOM  4213  O    THR C  89    45.170  91.264   2.035  1.00 71.47      C
ATOM  4214  N    TYR C  90    44.509  92.440   3.826  1.00 76.50      C
ATOM  4215  CA   TYR C  90    43.387  93.050   3.117  1.00 76.50      C
ATOM  4216  CB   TYR C  90    42.228  93.284   4.074  1.00 99.63      C
ATOM  4217  CG   TYR C  90    40.981  93.806   3.406  1.00 99.63      C
ATOM  4218  CD1  TYR C  90    40.580  93.323   2.163  1.00 99.63      C
ATOM  4219  CE1  TYR C  90    39.449  93.803   1.555  1.00 99.63      C
ATOM  4220  CD2  TYR C  90    40.204  94.786   4.013  1.00 99.63      C
ATOM  4221  CE2  TYR C  90    39.062  95.269   3.403  1.00 99.63      C
ATOM  4222  CZ   TYR C  90    38.699  94.776   2.171  1.00 99.63      C
ATOM  4223  OH   TYR C  90    37.596  95.283   1.532  1.00 99.63      C
ATOM  4224  C    TYR C  90    43.779  94.361   2.458  1.00 76.50      C
ATOM  4225  O    TYR C  90    43.243  95.411   2.797  1.00 76.50      C
ATOM  4226  N    GLN C  91    44.698  94.282   1.523  1.00 31.86      C
ATOM  4227  CA   GLN C  91    45.180  95.451   0.793  1.00 31.86      C
ATOM  4228  CB   GLN C  91    46.666  95.294   0.493  1.00100.07      C
ATOM  4229  CG   GLN C  91    47.560  95.167   1.722  1.00100.07      C
ATOM  4230  CD   GLN C  91    48.954  94.690   1.372  1.00100.07      C
ATOM  4231  OE1  GLN C  91    49.097  93.788   0.548  1.00100.07      C
ATOM  4232  NE2  GLN C  91    49.979  95.265   2.000  1.00100.07      C
ATOM  4233  C    GLN C  91    44.443  95.672  -0.535  1.00 31.86      C
ATOM  4234  O    GLN C  91    43.605  94.859  -0.943  1.00 31.86      C
ATOM  4235  N    ALA C  92    44.763  96.766  -1.193  1.00 44.62      C
ATOM  4236  CA   ALA C  92    44.155  97.116  -2.482  1.00 44.62      C
ATOM  4237  CB   ALA C  92    42.937  97.984  -2.259  1.00 77.59      C
ATOM  4238  C    ALA C  92    45.176  97.864  -3.331  1.00 44.62      C
ATOM  4239  O    ALA C  92    45.713  98.879  -2.933  1.00 44.62      C
ATOM  4240  N    PRO C  93    45.445  97.360  -4.531  1.00 71.69      C
ATOM  4241  CD   PRO C  93    44.722  96.322  -5.271  1.00 83.08      C
ATOM  4242  CA   PRO C  93    46.426  98.053  -5.370  1.00 71.69      C
ATOM  4243  CB   PRO C  93    46.297  97.338  -6.709  1.00 83.08      C
ATOM  4244  CG   PRO C  93    44.880  96.804  -6.673  1.00 83.08      C
ATOM  4245  C    PRO C  93    46.229  99.558  -5.498  1.00 71.69      C
ATOM  4246  O    PRO C  93    45.096 100.046  -5.586  1.00 71.69      C
```

| ATOM | 4247 | N | LEU | C | 94 | 47.335 | 100.295 | -5.501 | 1.00 | 46.46 | C |
| ATOM | 4248 | CA | LEU | C | 94 | 47.299 | 101.746 | -5.644 | 1.00 | 46.46 | C |
| ATOM | 4249 | CB | LEU | C | 94 | 47.569 | 102.450 | -4.301 | 1.00 | 100.07 | C |
| ATOM | 4250 | CG | LEU | C | 94 | 47.791 | 103.983 | -4.362 | 1.00 | 100.07 | C |
| ATOM | 4251 | CD1 | LEU | C | 94 | 46.785 | 104.634 | -5.345 | 1.00 | 100.07 | C |
| ATOM | 4252 | CD2 | LEU | C | 94 | 47.710 | 104.596 | -2.953 | 1.00 | 100.07 | C |
| ATOM | 4253 | C | LEU | C | 94 | 48.333 | 102.204 | -6.653 | 1.00 | 46.46 | C |
| ATOM | 4254 | O | LEU | C | 94 | 49.527 | 102.007 | -6.444 | 1.00 | 46.46 | C |
| ATOM | 4255 | N | TYR | C | 95 | 47.875 | 102.814 | -7.738 | 1.00 | 38.72 | C |
| ATOM | 4256 | CA | TYR | C | 95 | 48.785 | 103.327 | -8.755 | 1.00 | 38.72 | C |
| ATOM | 4257 | CB | TYR | C | 95 | 48.677 | 102.477 | -10.034 | 1.00 | 99.71 | C |
| ATOM | 4258 | CG | TYR | C | 95 | 47.277 | 102.114 | -10.492 | 1.00 | 99.71 | C |
| ATOM | 4259 | CD1 | TYR | C | 95 | 46.387 | 103.090 | -10.940 | 1.00 | 99.71 | C |
| ATOM | 4260 | CE1 | TYR | C | 95 | 45.122 | 102.750 | -11.458 | 1.00 | 99.71 | C |
| ATOM | 4261 | CD2 | TYR | C | 95 | 46.870 | 100.784 | -10.557 | 1.00 | 99.71 | C |
| ATOM | 4262 | CE2 | TYR | C | 95 | 45.613 | 100.432 | -11.071 | 1.00 | 99.71 | C |
| ATOM | 4263 | CZ | TYR | C | 95 | 44.746 | 101.421 | -11.526 | 1.00 | 99.71 | C |
| ATOM | 4264 | OH | TYR | C | 95 | 43.531 | 101.094 | -12.096 | 1.00 | 99.71 | C |
| ATOM | 4265 | C | TYR | C | 95 | 48.472 | 104.817 | -9.027 | 1.00 | 38.72 | C |
| ATOM | 4266 | O | TYR | C | 95 | 47.469 | 105.347 | -8.527 | 1.00 | 38.72 | C |
| ATOM | 4267 | N | ALA | C | 96 | 49.335 | 105.497 | -9.785 | 1.00 | 49.87 | C |
| ATOM | 4268 | CA | ALA | C | 96 | 49.115 | 106.910 | -10.109 | 1.00 | 49.87 | C |
| ATOM | 4269 | CB | ALA | C | 96 | 49.384 | 107.775 | -8.892 | 1.00 | 87.08 | C |
| ATOM | 4270 | C | ALA | C | 96 | 49.998 | 107.360 | -11.276 | 1.00 | 49.87 | C |
| ATOM | 4271 | O | ALA | C | 96 | 51.215 | 107.232 | -11.198 | 1.00 | 49.87 | C |
| ATOM | 4272 | N | ARG | C | 97 | 49.390 | 107.895 | -12.339 | 1.00 | 37.17 | C |
| ATOM | 4273 | CA | ARG | C | 97 | 50.116 | 108.347 | -13.539 | 1.00 | 37.17 | C |
| ATOM | 4274 | CB | ARG | C | 97 | 49.146 | 108.899 | -14.587 | 1.00 | 100.07 | C |
| ATOM | 4275 | CG | ARG | C | 97 | 48.033 | 107.979 | -15.033 | 1.00 | 100.07 | C |
| ATOM | 4276 | CD | ARG | C | 97 | 47.021 | 108.749 | -15.880 | 1.00 | 100.07 | C |
| ATOM | 4277 | NE | ARG | C | 97 | 45.816 | 107.967 | -16.137 | 1.00 | 100.07 | C |
| ATOM | 4278 | CZ | ARG | C | 97 | 44.762 | 108.405 | -16.820 | 1.00 | 100.07 | C |
| ATOM | 4279 | NH1 | ARG | C | 97 | 44.754 | 109.633 | -17.327 | 1.00 | 100.07 | C |
| ATOM | 4280 | NH2 | ARG | C | 97 | 43.712 | 107.610 | -16.994 | 1.00 | 100.07 | C |
| ATOM | 4281 | C | ARG | C | 97 | 51.139 | 109.440 | -13.270 | 1.00 | 37.17 | C |
| ATOM | 4282 | O | ARG | C | 97 | 50.789 | 110.494 | -12.749 | 1.00 | 37.17 | C |
| ATOM | 4283 | N | LEU | C | 98 | 52.390 | 109.200 | -13.656 | 1.00 | 70.64 | C |
| ATOM | 4284 | CA | LEU | C | 98 | 53.468 | 110.172 | -13.472 | 1.00 | 70.64 | C |
| ATOM | 4285 | CB | LEU | C | 98 | 54.628 | 109.533 | -12.708 | 1.00 | 99.56 | C |
| ATOM | 4286 | CG | LEU | C | 98 | 54.248 | 108.906 | -11.363 | 1.00 | 99.56 | C |
| ATOM | 4287 | CD1 | LEU | C | 98 | 55.483 | 108.366 | -10.655 | 1.00 | 99.56 | C |
| ATOM | 4288 | CD2 | LEU | C | 98 | 53.566 | 109.951 | -10.503 | 1.00 | 99.56 | C |
| ATOM | 4289 | C | LEU | C | 98 | 53.927 | 110.598 | -14.860 | 1.00 | 70.64 | C |
| ATOM | 4290 | O | LEU | C | 98 | 53.318 | 110.195 | -15.847 | 1.00 | 70.64 | C |
| ATOM | 4291 | N | GLN | C | 99 | 54.994 | 111.390 | -14.952 | 1.00 | 48.44 | C |
| ATOM | 4292 | CA | GLN | C | 99 | 55.470 | 111.848 | -16.261 | 1.00 | 48.44 | C |
| ATOM | 4293 | CB | GLN | C | 99 | 54.624 | 113.013 | -16.761 | 1.00 | 99.92 | C |
| ATOM | 4294 | CG | GLN | C | 99 | 53.177 | 112.716 | -16.978 | 1.00 | 99.92 | C |
| ATOM | 4295 | CD | GLN | C | 99 | 52.391 | 113.959 | -17.330 | 1.00 | 99.92 | C |
| ATOM | 4296 | OE1 | GLN | C | 99 | 52.616 | 114.573 | -18.373 | 1.00 | 99.92 | C |
| ATOM | 4297 | NE2 | GLN | C | 99 | 51.460 | 114.341 | -16.458 | 1.00 | 99.92 | C |
| ATOM | 4298 | C | GLN | C | 99 | 56.906 | 112.329 | -16.282 | 1.00 | 48.44 | C |
| ATOM | 4299 | O | GLN | C | 99 | 57.297 | 113.132 | -15.440 | 1.00 | 48.44 | C |
| ATOM | 4300 | N | LEU | C | 100 | 57.692 | 111.864 | -17.247 | 1.00 | 56.30 | C |
| ATOM | 4301 | CA | LEU | C | 100 | 59.062 | 112.349 | -17.359 | 1.00 | 56.30 | C |
| ATOM | 4302 | CB | LEU | C | 100 | 59.944 | 111.394 | -18.142 | 1.00 | 97.08 | C |
| ATOM | 4303 | CG | LEU | C | 100 | 59.726 | 109.908 | -17.952 | 1.00 | 97.08 | C |
| ATOM | 4304 | CD1 | LEU | C | 100 | 59.622 | 109.289 | -19.323 | 1.00 | 97.08 | C |
| ATOM | 4305 | CD2 | LEU | C | 100 | 60.856 | 109.297 | -17.144 | 1.00 | 97.08 | C |
| ATOM | 4306 | C | LEU | C | 100 | 58.909 | 113.606 | -18.188 | 1.00 | 56.30 | C |
| ATOM | 4307 | O | LEU | C | 100 | 57.952 | 113.741 | -18.951 | 1.00 | 56.30 | C |
| ATOM | 4308 | N | ILE | C | 101 | 59.842 | 114.530 | -18.054 | 1.00 | 99.85 | C |
| ATOM | 4309 | CA | ILE | C | 101 | 59.772 | 115.747 | -18.829 | 1.00 | 99.85 | C |
| ATOM | 4310 | CB | ILE | C | 101 | 59.283 | 116.908 | -17.950 | 1.00 | 100.07 | C |
| ATOM | 4311 | CG2 | ILE | C | 101 | 59.308 | 118.217 | -18.735 | 1.00 | 100.07 | C |
| ATOM | 4312 | CG1 | ILE | C | 101 | 57.860 | 116.578 | -17.460 | 1.00 | 100.07 | C |
| ATOM | 4313 | CD | ILE | C | 101 | 57.155 | 117.678 | -16.675 | 1.00 | 100.07 | C |
| ATOM | 4314 | C | ILE | C | 101 | 61.176 | 115.948 | -19.362 | 1.00 | 99.85 | C |
| ATOM | 4315 | O | ILE | C | 101 | 62.139 | 115.500 | -18.740 | 1.00 | 99.85 | C |
| ATOM | 4316 | N | HIS | C | 102 | 61.299 | 116.579 | -20.523 | 1.00 | 77.59 | C |
| ATOM | 4317 | CA | HIS | C | 102 | 62.614 | 116.754 | -21.123 | 1.00 | 77.59 | C |
| ATOM | 4318 | CB | HIS | C | 102 | 62.802 | 115.728 | -22.235 | 1.00 | 100.07 | C |
| ATOM | 4319 | CG | HIS | C | 102 | 62.959 | 114.319 | -21.750 | 1.00 | 100.07 | C |
| ATOM | 4320 | CD2 | HIS | C | 102 | 63.493 | 113.821 | -20.608 | 1.00 | 100.07 | C |
| ATOM | 4321 | ND1 | HIS | C | 102 | 62.602 | 113.227 | -22.515 | 1.00 | 100.07 | C |
| ATOM | 4322 | CE1 | HIS | C | 102 | 62.914 | 112.119 | -21.867 | 1.00 | 100.07 | C |
| ATOM | 4323 | NE2 | HIS | C | 102 | 63.455 | 112.447 | -20.714 | 1.00 | 100.07 | C |
| ATOM | 4324 | C | HIS | C | 102 | 62.939 | 118.128 | -21.678 | 1.00 | 77.59 | C |
| ATOM | 4325 | O | HIS | C | 102 | 62.096 | 119.024 | -21.743 | 1.00 | 77.59 | C |
| ATOM | 4326 | N | LYS | C | 103 | 64.203 | 118.257 | -22.071 | 1.00 | 100.07 | C |
| ATOM | 4327 | CA | LYS | C | 103 | 64.743 | 119.474 | -22.658 | 1.00 | 100.07 | C |
| ATOM | 4328 | CB | LYS | C | 103 | 66.151 | 119.759 | -22.120 | 1.00 | 100.07 | C |
| ATOM | 4329 | CG | LYS | C | 103 | 66.675 | 121.111 | -22.547 | 1.00 | 100.07 | C |
| ATOM | 4330 | CD | LYS | C | 103 | 65.645 | 122.170 | -22.196 | 1.00 | 100.07 | C |

| ATOM | 4331 | CE  | LYS | C | 103 | 66.091 | 123.545 | -22.632 | 1.00 | 100.07 | C |
| ATOM | 4332 | NZ  | LYS | C | 103 | 65.001 | 124.542 | -22.380 | 1.00 | 100.07 | C |
| ATOM | 4333 | C   | LYS | C | 103 | 64.825 | 119.269 | -24.160 | 1.00 | 100.07 | C |
| ATOM | 4334 | O   | LYS | C | 103 | 65.009 | 120.214 | -24.925 | 1.00 | 100.07 | C |
| ATOM | 4335 | N   | ASP | C | 104 | 64.708 | 118.003 | -24.555 | 1.00 |  67.51 | C |
| ATOM | 4336 | CA  | ASP | C | 104 | 64.742 | 117.584 | -25.943 | 1.00 |  67.51 | C |
| ATOM | 4337 | CB  | ASP | C | 104 | 65.471 | 116.239 | -26.057 | 1.00 | 100.07 | C |
| ATOM | 4338 | CG  | ASP | C | 104 | 65.095 | 115.273 | -24.945 | 1.00 | 100.07 | C |
| ATOM | 4339 | OD1 | ASP | C | 104 | 65.371 | 115.584 | -23.762 | 1.00 | 100.07 | C |
| ATOM | 4340 | OD2 | ASP | C | 104 | 64.526 | 114.207 | -25.258 | 1.00 | 100.07 | C |
| ATOM | 4341 | C   | ASP | C | 104 | 63.296 | 117.457 | -26.389 | 1.00 |  67.51 | C |
| ATOM | 4342 | O   | ASP | C | 104 | 62.995 | 116.842 | -27.408 | 1.00 |  67.51 | C |
| ATOM | 4343 | N   | THR | C | 105 | 62.398 | 118.065 | -25.624 | 1.00 | 100.07 | C |
| ATOM | 4344 | CA  | THR | C | 105 | 60.978 | 117.999 | -25.942 | 1.00 | 100.07 | C |
| ATOM | 4345 | CB  | THR | C | 105 | 60.687 | 118.617 | -27.355 | 1.00 | 100.07 | C |
| ATOM | 4346 | OG1 | THR | C | 105 | 60.778 | 120.047 | -27.268 | 1.00 | 100.07 | C |
| ATOM | 4347 | CG2 | THR | C | 105 | 59.297 | 118.238 | -27.859 | 1.00 | 100.07 | C |
| ATOM | 4348 | C   | THR | C | 105 | 60.531 | 116.526 | -25.867 | 1.00 | 100.07 | C |
| ATOM | 4349 | O   | THR | C | 105 | 60.421 | 115.833 | -26.885 | 1.00 | 100.07 | C |
| ATOM | 4350 | N   | GLY | C | 106 | 60.307 | 116.058 | -24.639 | 1.00 |  91.69 | C |
| ATOM | 4351 | CA  | GLY | C | 106 | 59.873 | 114.694 | -24.395 | 1.00 |  91.69 | C |
| ATOM | 4352 | C   | GLY | C | 106 | 58.988 | 114.721 | -23.168 | 1.00 |  91.69 | C |
| ATOM | 4353 | O   | GLY | C | 106 | 59.471 | 114.980 | -22.067 | 1.00 |  91.69 | C |
| ATOM | 4354 | N   | LEU | C | 107 | 57.695 | 114.467 | -23.359 | 1.00 |  83.98 | C |
| ATOM | 4355 | CA  | LEU | C | 107 | 56.726 | 114.468 | -22.264 | 1.00 |  83.98 | C |
| ATOM | 4356 | CB  | LEU | C | 107 | 55.796 | 115.661 | -22.419 | 1.00 | 100.07 | C |
| ATOM | 4357 | CG  | LEU | C | 107 | 56.562 | 116.956 | -22.681 | 1.00 | 100.07 | C |
| ATOM | 4358 | CD1 | LEU | C | 107 | 55.603 | 118.031 | -23.146 | 1.00 | 100.07 | C |
| ATOM | 4359 | CD2 | LEU | C | 107 | 57.319 | 117.376 | -21.420 | 1.00 | 100.07 | C |
| ATOM | 4360 | C   | LEU | C | 107 | 55.891 | 113.188 | -22.215 | 1.00 |  83.98 | C |
| ATOM | 4361 | O   | LEU | C | 107 | 54.809 | 113.134 | -22.795 | 1.00 |  83.98 | C |
| ATOM | 4362 | N   | ILE | C | 108 | 56.389 | 112.174 | -21.508 | 1.00 |  99.90 | C |
| ATOM | 4363 | CA  | ILE | C | 108 | 55.699 | 110.890 | -21.392 | 1.00 |  99.90 | C |
| ATOM | 4364 | CB  | ILE | C | 108 | 56.715 | 109.716 | -21.334 | 1.00 |  98.56 | C |
| ATOM | 4365 | CG2 | ILE | C | 108 | 55.985 | 108.389 | -21.242 | 1.00 |  98.56 | C |
| ATOM | 4366 | CG1 | ILE | C | 108 | 57.624 | 109.731 | -22.568 | 1.00 |  98.56 | C |
| ATOM | 4367 | CD  | ILE | C | 108 | 58.798 | 110.695 | -22.462 | 1.00 | 100.07 | C |
| ATOM | 4368 | C   | ILE | C | 108 | 54.769 | 110.761 | -20.173 | 1.00 |  99.90 | C |
| ATOM | 4369 | O   | ILE | C | 108 | 54.928 | 111.461 | -19.166 | 1.00 |  99.90 | C |
| ATOM | 4370 | N   | LYS | C | 109 | 53.798 | 109.851 | -20.291 | 1.00 |  83.23 | C |
| ATOM | 4371 | CA  | LYS | C | 109 | 52.824 | 109.545 | -19.237 | 1.00 |  83.23 | C |
| ATOM | 4372 | CB  | LYS | C | 109 | 51.456 | 110.164 | -19.541 | 1.00 |  63.06 | C |
| ATOM | 4373 | CG  | LYS | C | 109 | 51.423 | 111.668 | -19.522 | 1.00 |  63.06 | C |
| ATOM | 4374 | CD  | LYS | C | 109 | 50.018 | 112.171 | -19.298 | 1.00 |  63.06 | C |
| ATOM | 4375 | CE  | LYS | C | 109 | 49.999 | 113.681 | -19.374 | 1.00 |  63.06 | C |
| ATOM | 4376 | NZ  | LYS | C | 109 | 48.740 | 114.222 | -18.831 | 1.00 |  63.06 | C |
| ATOM | 4377 | C   | LYS | C | 109 | 52.652 | 108.029 | -19.143 | 1.00 |  83.23 | C |
| ATOM | 4378 | O   | LYS | C | 109 | 52.062 | 107.411 | -20.031 | 1.00 |  83.23 | C |
| ATOM | 4379 | N   | GLU | C | 110 | 53.165 | 107.427 | -18.077 | 1.00 |  77.31 | C |
| ATOM | 4380 | CA  | GLU | C | 110 | 53.030 | 105.989 | -17.918 | 1.00 |  77.31 | C |
| ATOM | 4381 | CB  | GLU | C | 110 | 54.172 | 105.414 | -17.089 | 1.00 | 100.07 | C |
| ATOM | 4382 | CG  | GLU | C | 110 | 55.357 | 105.003 | -17.924 | 1.00 | 100.07 | C |
| ATOM | 4383 | CD  | GLU | C | 110 | 55.059 | 103.793 | -18.771 | 1.00 | 100.07 | C |
| ATOM | 4384 | OE1 | GLU | C | 110 | 54.516 | 102.810 | -18.216 | 1.00 | 100.07 | C |
| ATOM | 4385 | OE2 | GLU | C | 110 | 55.368 | 103.820 | -19.984 | 1.00 | 100.07 | C |
| ATOM | 4386 | C   | GLU | C | 110 | 51.710 | 105.629 | -17.285 | 1.00 |  77.31 | C |
| ATOM | 4387 | O   | GLU | C | 110 | 51.303 | 106.202 | -16.269 | 1.00 |  77.31 | C |
| ATOM | 4388 | N   | ASP | C | 111 | 51.052 | 104.662 | -17.902 | 1.00 | 100.07 | C |
| ATOM | 4389 | CA  | ASP | C | 111 | 49.759 | 104.205 | -17.433 | 1.00 | 100.07 | C |
| ATOM | 4390 | CB  | ASP | C | 111 | 49.245 | 103.058 | -18.298 | 1.00 | 100.07 | C |
| ATOM | 4391 | CG  | ASP | C | 111 | 48.849 | 103.516 | -19.679 | 1.00 | 100.07 | C |
| ATOM | 4392 | OD1 | ASP | C | 111 | 48.002 | 104.435 | -19.768 | 1.00 | 100.07 | C |
| ATOM | 4393 | OD2 | ASP | C | 111 | 49.382 | 102.961 | -20.665 | 1.00 | 100.07 | C |
| ATOM | 4394 | C   | ASP | C | 111 | 49.703 | 103.773 | -15.984 | 1.00 | 100.07 | C |
| ATOM | 4395 | O   | ASP | C | 111 | 50.098 | 102.661 | -15.635 | 1.00 | 100.07 | C |
| ATOM | 4396 | N   | GLU | C | 112 | 49.193 | 104.673 | -15.155 | 1.00 |  60.24 | C |
| ATOM | 4397 | CA  | GLU | C | 112 | 49.015 | 104.385 | -13.757 | 1.00 |  60.24 | C |
| ATOM | 4398 | CB  | GLU | C | 112 | 48.143 | 103.135 | -13.599 | 1.00 | 100.07 | C |
| ATOM | 4399 | CG  | GLU | C | 112 | 46.899 | 103.094 | -14.486 | 1.00 | 100.07 | C |
| ATOM | 4400 | CD  | GLU | C | 112 | 45.965 | 104.272 | -14.275 | 1.00 | 100.07 | C |
| ATOM | 4401 | OE1 | GLU | C | 112 | 46.219 | 105.068 | -13.347 | 1.00 | 100.07 | C |
| ATOM | 4402 | OE2 | GLU | C | 112 | 44.974 | 104.396 | -15.030 | 1.00 | 100.07 | C |
| ATOM | 4403 | C   | GLU | C | 112 | 50.340 | 104.145 | -13.080 | 1.00 |  60.24 | C |
| ATOM | 4404 | O   | GLU | C | 112 | 50.612 | 104.731 | -12.038 | 1.00 |  60.24 | C |
| ATOM | 4405 | N   | VAL | C | 113 | 51.159 | 103.280 | -13.661 | 1.00 |  82.31 | C |
| ATOM | 4406 | CA  | VAL | C | 113 | 52.428 | 102.960 | -13.046 | 1.00 |  82.31 | C |
| ATOM | 4407 | CB  | VAL | C | 113 | 53.241 | 104.206 | -12.822 | 1.00 | 100.07 | C |
| ATOM | 4408 | CG1 | VAL | C | 113 | 54.650 | 103.836 | -12.419 | 1.00 | 100.07 | C |
| ATOM | 4409 | CG2 | VAL | C | 113 | 53.204 | 105.051 | -14.067 | 1.00 | 100.07 | C |
| ATOM | 4410 | C   | VAL | C | 113 | 52.007 | 102.384 | -11.702 | 1.00 |  82.31 | C |
| ATOM | 4411 | O   | VAL | C | 113 | 52.154 | 103.006 | -10.645 | 1.00 |  82.31 | C |
| ATOM | 4412 | N   | PHE | C | 114 | 51.436 | 101.192 | -11.770 | 1.00 |  52.03 | C |
| ATOM | 4413 | CA  | PHE | C | 114 | 50.933 | 100.486 | -10.606 | 1.00 |  52.03 | C |
| ATOM | 4414 | CB  | PHE | C | 114 | 50.599 |  99.042 | -11.019 | 1.00 | 100.07 | C |

```
ATOM   4415  CG  PHE C 114      49.751  98.951 -12.287  1.00100.07           C
ATOM   4416  CD1 PHE C 114      50.295  99.269 -13.538  1.00100.07           C
ATOM   4417  CD2 PHE C 114      48.401  98.590 -12.224  1.00100.07           C
ATOM   4418  CE1 PHE C 114      49.507  99.236 -14.706  1.00100.07           C
ATOM   4419  CE2 PHE C 114      47.607  98.556 -13.391  1.00100.07           C
ATOM   4420  CZ  PHE C 114      48.165  98.879 -14.629  1.00100.07           C
ATOM   4421  C   PHE C 114      51.935 100.561  -9.454  1.00 52.03           C
ATOM   4422  O   PHE C 114      53.125 100.791  -9.664  1.00 52.03           C
ATOM   4423  N   LEU C 115      51.456 100.380  -8.233  1.00 99.90           C
ATOM   4424  CA  LEU C 115      52.350 100.469  -7.096  1.00 99.90           C
ATOM   4425  CB  LEU C 115      52.359 101.915  -6.594  1.00100.07           C
ATOM   4426  CG  LEU C 115      53.452 102.402  -5.645  1.00100.07           C
ATOM   4427  CD1 LEU C 115      54.793 101.762  -5.993  1.00100.07           C
ATOM   4428  CD2 LEU C 115      53.526 103.917  -5.746  1.00100.07           C
ATOM   4429  C   LEU C 115      52.000  99.514  -5.964  1.00 99.90           C
ATOM   4430  O   LEU C 115      51.373  98.468  -6.172  1.00 99.90           C
ATOM   4431  N   GLY C 116      52.433  99.890  -4.765  1.00 61.19           C
ATOM   4432  CA  GLY C 116      52.197  99.086  -3.590  1.00 61.19           C
ATOM   4433  C   GLY C 116      50.750  98.997  -3.178  1.00 61.19           C
ATOM   4434  O   GLY C 116      49.893  99.733  -3.664  1.00 61.19           C
ATOM   4435  N   HIS C 117      50.490  98.067  -2.268  1.00 50.40           C
ATOM   4436  CA  HIS C 117      49.157  97.833  -1.737  1.00 50.40           C
ATOM   4437  CB  HIS C 117      48.960  96.340  -1.472  1.00 99.90           C
ATOM   4438  CG  HIS C 117      48.949  95.495  -2.706  1.00 99.90           C
ATOM   4439  CD2 HIS C 117      49.883  94.670  -3.234  1.00 99.90           C
ATOM   4440  ND1 HIS C 117      47.847  95.402  -3.534  1.00 99.90           C
ATOM   4441  CE1 HIS C 117      48.108  94.551  -4.514  1.00 99.90           C
ATOM   4442  NE2 HIS C 117      49.336  94.096  -4.353  1.00 99.90           C
ATOM   4443  C   HIS C 117      49.001  98.600  -0.418  1.00 50.40           C
ATOM   4444  O   HIS C 117      49.831  98.475   0.482  1.00 50.40           C
ATOM   4445  N   LEU C 118      47.932  99.383  -0.308  1.00 44.36           C
ATOM   4446  CA  LEU C 118      47.687 100.162   0.898  1.00 44.36           C
ATOM   4447  CB  LEU C 118      47.320 101.600   0.529  1.00100.07           C
ATOM   4448  CG  LEU C 118      47.573 102.670   1.592  1.00100.07           C
ATOM   4449  CD1 LEU C 118      46.828 103.957   1.238  1.00100.07           C
ATOM   4450  CD2 LEU C 118      47.106 102.159   2.922  1.00100.07           C
ATOM   4451  C   LEU C 118      46.537  99.527   1.659  1.00 44.36           C
ATOM   4452  O   LEU C 118      45.391  99.674   1.260  1.00 44.36           C
ATOM   4453  N   PRO C 119      46.836  98.832   2.771  1.00 33.57           C
ATOM   4454  CD  PRO C 119      48.155  98.733   3.398  1.00100.07           C
ATOM   4455  CA  PRO C 119      45.815  98.161   3.609  1.00 33.57           C
ATOM   4456  CB  PRO C 119      46.560  97.900   4.925  1.00100.07           C
ATOM   4457  CG  PRO C 119      47.805  98.748   4.853  1.00100.07           C
ATOM   4458  C   PRO C 119      44.476  98.877   3.812  1.00 33.57           C
ATOM   4459  O   PRO C 119      44.404 100.014   4.272  1.00 33.57           C
ATOM   4460  N   LEU C 120      43.403  98.179   3.460  1.00 48.29           C
ATOM   4461  CA  LEU C 120      42.067  98.726   3.572  1.00 48.29           C
ATOM   4462  CB  LEU C 120      41.163  98.034   2.563  1.00100.07           C
ATOM   4463  CG  LEU C 120      41.822  98.110   1.183  1.00100.07           C
ATOM   4464  CD1 LEU C 120      41.022  97.315   0.181  1.00100.07           C
ATOM   4465  CD2 LEU C 120      41.940  99.561   0.745  1.00100.07           C
ATOM   4466  C   LEU C 120      41.599  98.497   4.980  1.00 48.29           C
ATOM   4467  O   LEU C 120      42.148  97.645   5.672  1.00 48.29           C
ATOM   4468  N   MET C 121      40.609  99.277   5.407  1.00 38.60           C
ATOM   4469  CA  MET C 121      40.074  99.175   6.757  1.00 38.60           C
ATOM   4470  CB  MET C 121      40.019 100.551   7.423  1.00 99.86           C
ATOM   4471  CG  MET C 121      39.742 100.513   8.924  1.00 99.86           C
ATOM   4472  SD  MET C 121      39.254 102.116   9.631  1.00 99.86           C
ATOM   4473  CE  MET C 121      40.791 103.008   9.614  1.00 99.86           C
ATOM   4474  C   MET C 121      38.681  98.605   6.675  1.00 38.60           C
ATOM   4475  O   MET C 121      37.857  99.072   5.894  1.00 38.60           C
ATOM   4476  N   THR C 122      38.418  97.582   7.475  1.00 51.97           C
ATOM   4477  CA  THR C 122      37.107  96.977   7.472  1.00 51.97           C
ATOM   4478  CB  THR C 122      37.073  95.780   8.410  1.00 98.89           C
ATOM   4479  OG1 THR C 122      35.866  95.042   8.200  1.00 98.89           C
ATOM   4480  CG2 THR C 122      37.143  96.235   9.844  1.00 98.89           C
ATOM   4481  C   THR C 122      36.170  98.071   7.964  1.00 51.97           C
ATOM   4482  O   THR C 122      36.554  99.232   7.991  1.00 51.97           C
ATOM   4483  N   GLU C 123      34.952  97.722   8.359  1.00 43.02           C
ATOM   4484  CA  GLU C 123      34.006  98.729   8.841  1.00 43.02           C
ATOM   4485  CB  GLU C 123      32.602  98.148   8.913  1.00100.07           C
ATOM   4486  CG  GLU C 123      32.119  97.584   7.611  1.00100.07           C
ATOM   4487  CD  GLU C 123      32.953  96.407   7.159  1.00100.07           C
ATOM   4488  OE1 GLU C 123      32.957  95.369   7.863  1.00100.07           C
ATOM   4489  OE2 GLU C 123      33.613  96.528   6.107  1.00100.07           C
ATOM   4490  C   GLU C 123      34.373  99.258  10.217  1.00 43.02           C
ATOM   4491  O   GLU C 123      33.592  99.969  10.834  1.00 43.02           C
ATOM   4492  N   ASP C 124      35.558  98.900  10.696  1.00100.07           C
ATOM   4493  CA  ASP C 124      36.023  99.326  12.008  1.00100.07           C
ATOM   4494  CB  ASP C 124      35.333  98.487  13.093  1.00100.07           C
ATOM   4495  CG  ASP C 124      34.916  97.114  12.597  1.00100.07           C
ATOM   4496  OD1 ASP C 124      34.106  97.044  11.650  1.00100.07           C
ATOM   4497  OD2 ASP C 124      35.391  96.101  13.153  1.00100.07           C
ATOM   4498  C   ASP C 124      37.553  99.255  12.164  1.00100.07           C
```

-54-

| ATOM | 4499 | O | ASP | C | 124 | 38.246 | 100.268 | 12.042 | 1.00 | 100.07 | C |
|------|------|------|-----|---|-----|--------|---------|--------|------|--------|---|
| ATOM | 4500 | N | GLY | C | 125 | 38.082 | 98.064 | 12.434 | 1.00 | 100.06 | C |
| ATOM | 4501 | CA | GLY | C | 125 | 39.519 | 97.916 | 12.599 | 1.00 | 100.06 | C |
| ATOM | 4502 | C | GLY | C | 125 | 40.209 | 97.514 | 11.310 | 1.00 | 100.06 | C |
| ATOM | 4503 | O | GLY | C | 125 | 39.708 | 97.784 | 10.221 | 1.00 | 100.06 | C |
| ATOM | 4504 | N | SER | C | 126 | 41.356 | 96.856 | 11.426 | 1.00 | 42.10 | C |
| ATOM | 4505 | CA | SER | C | 126 | 42.125 | 96.434 | 10.255 | 1.00 | 42.10 | C |
| ATOM | 4506 | CB | SER | C | 126 | 43.470 | 97.167 | 10.226 | 1.00 | 16.52 | C |
| ATOM | 4507 | OG | SER | C | 126 | 43.449 | 98.352 | 9.437 | 1.00 | 16.52 | C |
| ATOM | 4508 | C | SER | C | 126 | 42.388 | 94.931 | 10.253 | 1.00 | 42.10 | C |
| ATOM | 4509 | O | SER | C | 126 | 43.047 | 94.420 | 11.157 | 1.00 | 42.10 | C |
| ATOM | 4510 | N | PHE | C | 127 | 41.875 | 94.232 | 9.237 | 1.00 | 43.59 | C |
| ATOM | 4511 | CA | PHE | C | 127 | 42.066 | 92.779 | 9.092 | 1.00 | 43.59 | C |
| ATOM | 4512 | CB | PHE | C | 127 | 40.895 | 92.134 | 8.329 | 1.00 | 100.07 | C |
| ATOM | 4513 | CG | PHE | C | 127 | 39.595 | 92.076 | 9.114 | 1.00 | 100.07 | C |
| ATOM | 4514 | CD1 | PHE | C | 127 | 38.522 | 92.902 | 8.783 | 1.00 | 100.07 | C |
| ATOM | 4515 | CD2 | PHE | C | 127 | 39.441 | 91.192 | 10.184 | 1.00 | 100.07 | C |
| ATOM | 4516 | CE1 | PHE | C | 127 | 37.318 | 92.848 | 9.505 | 1.00 | 100.07 | C |
| ATOM | 4517 | CE2 | PHE | C | 127 | 38.241 | 91.134 | 10.912 | 1.00 | 100.07 | C |
| ATOM | 4518 | CZ | PHE | C | 127 | 37.180 | 91.966 | 10.568 | 1.00 | 100.07 | C |
| ATOM | 4519 | C | PHE | C | 127 | 43.355 | 92.557 | 8.316 | 1.00 | 43.59 | C |
| ATOM | 4520 | O | PHE | C | 127 | 43.393 | 91.799 | 7.353 | 1.00 | 43.59 | C |
| ATOM | 4521 | N | ILE | C | 128 | 44.392 | 93.262 | 8.765 | 1.00 | 62.47 | C |
| ATOM | 4522 | CA | ILE | C | 128 | 45.743 | 93.247 | 8.201 | 1.00 | 62.47 | C |
| ATOM | 4523 | CB | ILE | C | 128 | 46.441 | 94.595 | 8.432 | 1.00 | 99.55 | C |
| ATOM | 4524 | CG2 | ILE | C | 128 | 47.326 | 94.931 | 7.244 | 1.00 | 99.55 | C |
| ATOM | 4525 | CG1 | ILE | C | 128 | 45.398 | 95.688 | 8.677 | 1.00 | 99.55 | C |
| ATOM | 4526 | CD | ILE | C | 128 | 44.307 | 95.814 | 7.606 | 1.00 | 100.07 | C |
| ATOM | 4527 | C | ILE | C | 128 | 46.592 | 92.172 | 8.866 | 1.00 | 62.47 | C |
| ATOM | 4528 | O | ILE | C | 128 | 46.199 | 91.618 | 9.889 | 1.00 | 62.47 | C |
| ATOM | 4529 | N | ILE | C | 129 | 47.767 | 91.903 | 8.307 | 1.00 | 40.50 | C |
| ATOM | 4530 | CA | ILE | C | 129 | 48.634 | 90.854 | 8.840 | 1.00 | 40.50 | C |
| ATOM | 4531 | CB | ILE | C | 129 | 48.634 | 90.807 | 10.375 | 1.00 | 100.07 | C |
| ATOM | 4532 | CG2 | ILE | C | 129 | 49.187 | 89.462 | 10.837 | 1.00 | 100.07 | C |
| ATOM | 4533 | CG1 | ILE | C | 129 | 49.425 | 91.975 | 10.955 | 1.00 | 100.07 | C |
| ATOM | 4534 | CD | ILE | C | 129 | 50.894 | 91.681 | 11.206 | 1.00 | 100.07 | C |
| ATOM | 4535 | C | ILE | C | 129 | 48.070 | 89.509 | 8.395 | 1.00 | 40.50 | C |
| ATOM | 4536 | O | ILE | C | 129 | 48.771 | 88.696 | 7.798 | 1.00 | 40.50 | C |
| ATOM | 4537 | N | ASN | C | 130 | 46.799 | 89.308 | 8.748 | 1.00 | 72.40 | C |
| ATOM | 4538 | CA | ASN | C | 130 | 45.993 | 88.123 | 8.471 | 1.00 | 72.40 | C |
| ATOM | 4539 | CB | ASN | C | 130 | 46.859 | 86.892 | 8.262 | 1.00 | 100.07 | C |
| ATOM | 4540 | CG | ASN | C | 130 | 47.369 | 86.807 | 6.849 | 1.00 | 100.07 | C |
| ATOM | 4541 | OD1 | ASN | C | 130 | 46.818 | 87.438 | 5.951 | 1.00 | 100.07 | C |
| ATOM | 4542 | ND2 | ASN | C | 130 | 48.415 | 86.029 | 6.637 | 1.00 | 100.07 | C |
| ATOM | 4543 | C | ASN | C | 130 | 45.013 | 87.900 | 9.614 | 1.00 | 72.40 | C |
| ATOM | 4544 | O | ASN | C | 130 | 43.972 | 87.265 | 9.446 | 1.00 | 72.40 | C |
| ATOM | 4545 | N | GLY | C | 131 | 45.363 | 88.429 | 10.780 | 1.00 | 86.95 | C |
| ATOM | 4546 | CA | GLY | C | 131 | 44.499 | 88.344 | 11.944 | 1.00 | 86.95 | C |
| ATOM | 4547 | C | GLY | C | 131 | 44.131 | 89.787 | 12.247 | 1.00 | 86.95 | C |
| ATOM | 4548 | O | GLY | C | 131 | 45.017 | 90.612 | 12.455 | 1.00 | 86.95 | C |
| ATOM | 4549 | N | ALA | C | 132 | 42.842 | 90.109 | 12.265 | 1.00 | 40.44 | C |
| ATOM | 4550 | CA | ALA | C | 132 | 42.398 | 91.483 | 12.511 | 1.00 | 40.44 | C |
| ATOM | 4551 | CB | ALA | C | 132 | 40.893 | 91.487 | 12.835 | 1.00 | 5.07 | C |
| ATOM | 4552 | C | ALA | C | 132 | 43.195 | 92.180 | 13.630 | 1.00 | 40.44 | C |
| ATOM | 4553 | O | ALA | C | 132 | 43.742 | 91.517 | 14.507 | 1.00 | 40.44 | C |
| ATOM | 4554 | N | ASP | C | 133 | 43.278 | 93.514 | 13.571 | 1.00 | 39.16 | C |
| ATOM | 4555 | CA | ASP | C | 133 | 43.986 | 94.315 | 14.583 | 1.00 | 39.16 | C |
| ATOM | 4556 | CB | ASP | C | 133 | 45.476 | 93.952 | 14.614 | 1.00 | 100.07 | C |
| ATOM | 4557 | CG | ASP | C | 133 | 46.090 | 93.891 | 13.238 | 1.00 | 100.07 | C |
| ATOM | 4558 | OD1 | ASP | C | 133 | 45.994 | 94.891 | 12.496 | 1.00 | 100.07 | C |
| ATOM | 4559 | OD2 | ASP | C | 133 | 46.675 | 92.839 | 12.903 | 1.00 | 100.07 | C |
| ATOM | 4560 | C | ASP | C | 133 | 43.825 | 95.842 | 14.446 | 1.00 | 39.16 | C |
| ATOM | 4561 | O | ASP | C | 133 | 43.762 | 96.367 | 13.334 | 1.00 | 39.16 | C |
| ATOM | 4562 | N | ARG | C | 134 | 43.753 | 96.531 | 15.593 | 1.00 | 19.49 | C |
| ATOM | 4563 | CA | ARG | C | 134 | 43.591 | 97.984 | 15.652 | 1.00 | 19.49 | C |
| ATOM | 4564 | CB | ARG | C | 134 | 42.913 | 98.402 | 16.961 | 1.00 | 100.07 | C |
| ATOM | 4565 | CG | ARG | C | 134 | 41.449 | 97.991 | 17.112 | 1.00 | 100.07 | C |
| ATOM | 4566 | CD | ARG | C | 134 | 40.466 | 98.872 | 16.307 | 1.00 | 100.07 | C |
| ATOM | 4567 | NE | ARG | C | 134 | 39.064 | 98.581 | 16.647 | 1.00 | 100.07 | C |
| ATOM | 4568 | CZ | ARG | C | 134 | 38.006 | 99.211 | 16.139 | 1.00 | 100.07 | C |
| ATOM | 4569 | NH1 | ARG | C | 134 | 38.173 | 100.181 | 15.253 | 1.00 | 100.07 | C |
| ATOM | 4570 | NH2 | ARG | C | 134 | 36.780 | 98.874 | 16.521 | 1.00 | 100.07 | C |
| ATOM | 4571 | C | ARG | C | 134 | 44.929 | 98.702 | 15.544 | 1.00 | 19.49 | C |
| ATOM | 4572 | O | ARG | C | 134 | 45.983 | 98.084 | 15.692 | 1.00 | 19.49 | C |
| ATOM | 4573 | N | VAL | C | 135 | 44.872 | 100.014 | 15.307 | 1.00 | 40.37 | C |
| ATOM | 4574 | CA | VAL | C | 135 | 46.063 | 100.842 | 15.169 | 1.00 | 40.37 | C |
| ATOM | 4575 | CB | VAL | C | 135 | 45.918 | 101.800 | 13.997 | 1.00 | 49.11 | C |
| ATOM | 4576 | CG1 | VAL | C | 135 | 47.062 | 101.588 | 13.020 | 1.00 | 49.11 | C |
| ATOM | 4577 | CG2 | VAL | C | 135 | 44.587 | 101.577 | 13.319 | 1.00 | 49.11 | C |
| ATOM | 4578 | C | VAL | C | 135 | 46.395 | 101.645 | 16.430 | 1.00 | 40.37 | C |
| ATOM | 4579 | O | VAL | C | 135 | 47.556 | 101.738 | 16.821 | 1.00 | 40.37 | C |
| ATOM | 4580 | N | ILE | C | 136 | 45.385 | 102.236 | 17.059 | 1.00 | 46.74 | C |
| ATOM | 4581 | CA | ILE | C | 136 | 45.576 | 102.992 | 18.304 | 1.00 | 46.74 | C |
| ATOM | 4582 | CB | ILE | C | 136 | 46.534 | 102.285 | 19.265 | 1.00 | 33.21 | C |

```
ATOM   4583  CG2 ILE C 136      46.542 103.009  20.579  1.00 33.21           C
ATOM   4584  CG1 ILE C 136      46.118 100.835  19.448  1.00 33.21           C
ATOM   4585  CD  ILE C 136      44.644 100.653  19.701  1.00 73.39           C
ATOM   4586  C   ILE C 136      46.080 104.413  18.193  1.00 46.74           C
ATOM   4587  O   ILE C 136      47.275 104.659  18.067  1.00 46.74           C
ATOM   4588  N   VAL C 137      45.157 105.353  18.281  1.00 30.06           C
ATOM   4589  CA  VAL C 137      45.500 106.753  18.203  1.00 30.06           C
ATOM   4590  CB  VAL C 137      44.342 107.561  18.740  1.00 64.43           C
ATOM   4591  CG1 VAL C 137      44.443 108.968  18.263  1.00 64.43           C
ATOM   4592  CG2 VAL C 137      43.034 106.931  18.293  1.00 64.43           C
ATOM   4593  C   VAL C 137      46.771 107.022  19.018  1.00 30.06           C
ATOM   4594  O   VAL C 137      46.769 106.871  20.232  1.00 30.06           C
ATOM   4595  N   SER C 138      47.841 107.431  18.336  1.00 32.80           C
ATOM   4596  CA  SER C 138      49.162 107.692  18.946  1.00 32.80           C
ATOM   4597  CB  SER C 138      50.210 108.075  17.891  1.00 91.01           C
ATOM   4598  OG  SER C 138      51.464 108.350  18.526  1.00 91.01           C
ATOM   4599  C   SER C 138      49.362 108.705  20.063  1.00 32.80           C
ATOM   4600  O   SER C 138      49.628 109.872  19.793  1.00 32.80           C
ATOM   4601  N   GLN C 139      49.276 108.247  21.307  1.00 52.72           C
ATOM   4602  CA  GLN C 139      49.538 109.057  22.504  1.00 52.72           C
ATOM   4603  CB  GLN C 139      50.884 108.618  23.049  1.00 81.44           C
ATOM   4604  CG  GLN C 139      51.087 108.824  24.493  1.00 81.44           C
ATOM   4605  CD  GLN C 139      52.080 107.836  25.010  1.00 81.44           C
ATOM   4606  OE1 GLN C 139      53.249 107.855  24.633  1.00 81.44           C
ATOM   4607  NE2 GLN C 139      51.616 106.933  25.849  1.00 81.44           C
ATOM   4608  C   GLN C 139      49.552 110.582  22.381  1.00 52.72           C
ATOM   4609  O   GLN C 139      48.756 111.267  23.031  1.00 52.72           C
ATOM   4610  N   ILE C 140      50.524 111.076  21.602  1.00 61.34           C
ATOM   4611  CA  ILE C 140      50.750 112.497  21.303  1.00 61.34           C
ATOM   4612  CB  ILE C 140      49.900 113.403  22.199  1.00 66.08           C
ATOM   4613  CG2 ILE C 140      50.546 114.766  22.332  1.00 66.08           C
ATOM   4614  CG1 ILE C 140      48.496 113.506  21.617  1.00 66.08           C
ATOM   4615  CD  ILE C 140      47.519 114.182  22.530  1.00100.07           C
ATOM   4616  C   ILE C 140      52.205 113.021  21.323  1.00 61.34           C
ATOM   4617  O   ILE C 140      53.090 112.481  22.008  1.00 61.34           C
ATOM   4618  N   HIS C 141      52.411 114.106  20.573  1.00 41.62           C
ATOM   4619  CA  HIS C 141      53.707 114.758  20.410  1.00 41.62           C
ATOM   4620  CB  HIS C 141      53.935 115.022  18.931  1.00100.07           C
ATOM   4621  CG  HIS C 141      52.958 114.314  18.057  1.00100.07           C
ATOM   4622  CD2 HIS C 141      51.763 114.699  17.555  1.00100.07           C
ATOM   4623  ND1 HIS C 141      53.115 112.992  17.700  1.00100.07           C
ATOM   4624  CE1 HIS C 141      52.052 112.595  17.019  1.00100.07           C
ATOM   4625  NE2 HIS C 141      51.218 113.615  16.920  1.00100.07           C
ATOM   4626  C   HIS C 141      53.739 116.083  21.126  1.00 41.62           C
ATOM   4627  O   HIS C 141      54.450 116.995  20.709  1.00 41.62           C
ATOM   4628  N   ARG C 142      52.959 116.202  22.189  1.00 38.29           C
ATOM   4629  CA  ARG C 142      52.895 117.457  22.929  1.00 38.29           C
ATOM   4630  CB  ARG C 142      54.275 117.834  23.503  1.00 51.20           C
ATOM   4631  CG  ARG C 142      54.308 119.222  24.142  1.00 51.20           C
ATOM   4632  CD  ARG C 142      55.067 119.258  25.457  1.00 51.20           C
ATOM   4633  NE  ARG C 142      56.399 119.819  25.309  1.00 51.20           C
ATOM   4634  CZ  ARG C 142      57.359 119.264  24.583  1.00 51.20           C
ATOM   4635  NH1 ARG C 142      57.125 118.128  23.940  1.00 51.20           C
ATOM   4636  NH2 ARG C 142      58.552 119.844  24.501  1.00 51.20           C
ATOM   4637  C   ARG C 142      52.370 118.601  22.048  1.00 38.29           C
ATOM   4638  O   ARG C 142      52.106 119.689  22.561  1.00 38.29           C
ATOM   4639  N   SER C 143      52.233 118.346  20.736  1.00 13.32           C
ATOM   4640  CA  SER C 143      51.724 119.314  19.744  1.00 13.32           C
ATOM   4641  CB  SER C 143      50.630 120.195  20.356  1.00 74.48           C
ATOM   4642  OG  SER C 143      50.188 121.169  19.431  1.00 74.48           C
ATOM   4643  C   SER C 143      52.803 120.186  19.133  1.00 13.32           C
ATOM   4644  O   SER C 143      53.581 120.798  19.844  1.00 13.32           C
ATOM   4645  N   PRO C 144      52.833 120.286  17.798  1.00 33.41           C
ATOM   4646  CD  PRO C 144      51.686 119.989  16.927  1.00 47.73           C
ATOM   4647  CA  PRO C 144      53.826 121.084  17.070  1.00 33.41           C
ATOM   4648  CB  PRO C 144      53.307 121.048  15.637  1.00 47.73           C
ATOM   4649  CG  PRO C 144      51.838 121.029  15.834  1.00 47.73           C
ATOM   4650  C   PRO C 144      54.038 122.514  17.569  1.00 33.41           C
ATOM   4651  O   PRO C 144      53.157 123.103  18.210  1.00 33.41           C
ATOM   4652  N   GLY C 145      55.225 123.057  17.286  1.00 44.08           C
ATOM   4653  CA  GLY C 145      55.528 124.422  17.690  1.00 44.08           C
ATOM   4654  C   GLY C 145      56.897 124.751  18.269  1.00 44.08           C
ATOM   4655  O   GLY C 145      57.934 124.315  17.770  1.00 44.08           C
ATOM   4656  N   VAL C 146      56.873 125.555  19.331  1.00 43.75           C
ATOM   4657  CA  VAL C 146      58.064 126.017  20.054  1.00 43.75           C
ATOM   4658  CB  VAL C 146      58.742 127.196  19.320  1.00 46.92           C
ATOM   4659  CG1 VAL C 146      59.609 127.995  20.293  1.00 46.92           C
ATOM   4660  CG2 VAL C 146      59.576 126.669  18.152  1.00 46.92           C
ATOM   4661  C   VAL C 146      57.581 126.512  21.416  1.00 43.75           C
ATOM   4662  O   VAL C 146      56.627 127.296  21.470  1.00 43.75           C
ATOM   4663  N   TYR C 147      58.212 126.071  22.510  1.00 41.76           C
ATOM   4664  CA  TYR C 147      57.755 126.524  23.821  1.00 41.76           C
ATOM   4665  CB  TYR C 147      56.340 125.986  24.091  1.00 49.74           C
ATOM   4666  CG  TYR C 147      56.027 124.619  23.509  1.00 49.74           C
```

```
ATOM   4667  CD1 TYR C 147      56.758 123.497  23.888  1.00 49.74           C
ATOM   4668  CE1 TYR C 147      56.441 122.235  23.398  1.00 49.74           C
ATOM   4669  CD2 TYR C 147      54.965 124.444  22.610  1.00 49.74           C
ATOM   4670  CE2 TYR C 147      54.644 123.188  22.114  1.00 49.74           C
ATOM   4671  CZ  TYR C 147      55.387 122.085  22.515  1.00 49.74           C
ATOM   4672  OH  TYR C 147      55.092 120.822  22.055  1.00 49.74           C
ATOM   4673  C   TYR C 147      58.590 126.375  25.088  1.00 41.76           C
ATOM   4674  O   TYR C 147      58.032 126.250  26.177  1.00 41.76           C
ATOM   4675  N   PHE C 148      59.912 126.413  24.959  1.00100.02           C
ATOM   4676  CA  PHE C 148      60.814 126.367  26.119  1.00100.02           C
ATOM   4677  CB  PHE C 148      60.589 127.621  26.972  1.00 35.32           C
ATOM   4678  CG  PHE C 148      60.547 128.865  26.161  1.00 35.32           C
ATOM   4679  CD1 PHE C 148      59.437 129.150  25.366  1.00 35.32           C
ATOM   4680  CD2 PHE C 148      61.663 129.676  26.064  1.00 35.32           C
ATOM   4681  CE1 PHE C 148      59.440 130.200  24.478  1.00 35.32           C
ATOM   4682  CE2 PHE C 148      61.678 130.737  25.172  1.00 35.32           C
ATOM   4683  CZ  PHE C 148      60.558 130.994  24.377  1.00 35.32           C
ATOM   4684  C   PHE C 148      60.800 125.145  27.021  1.00100.02           C
ATOM   4685  O   PHE C 148      60.861 124.012  26.539  1.00100.02           C
ATOM   4686  N   THR C 149      60.739 125.410  28.330  1.00 52.16           C
ATOM   4687  CA  THR C 149      60.737 124.404  29.398  1.00 52.16           C
ATOM   4688  CB  THR C 149      60.741 122.966  28.849  1.00100.07           C
ATOM   4689  OG1 THR C 149      59.541 122.732  28.104  1.00100.07           C
ATOM   4690  CG2 THR C 149      60.854 121.961  29.984  1.00100.07           C
ATOM   4691  C   THR C 149      62.017 124.567  30.215  1.00 52.16           C
ATOM   4692  O   THR C 149      63.101 124.674  29.643  1.00 52.16           C
ATOM   4693  N   PRO C 150      61.913 124.600  31.556  1.00 47.65           C
ATOM   4694  CD  PRO C 150      60.678 124.839  32.314  1.00 61.69           C
ATOM   4695  CA  PRO C 150      63.084 124.745  32.436  1.00 47.65           C
ATOM   4696  CB  PRO C 150      62.465 124.908  33.829  1.00 61.69           C
ATOM   4697  CG  PRO C 150      61.081 124.376  33.679  1.00 61.69           C
ATOM   4698  C   PRO C 150      64.140 123.631  32.380  1.00 47.65           C
ATOM   4699  O   PRO C 150      63.826 122.444  32.362  1.00 47.65           C
ATOM   4700  N   ASP C 151      65.401 124.055  32.352  1.00 78.09           C
ATOM   4701  CA  ASP C 151      66.547 123.158  32.275  1.00 78.09           C
ATOM   4702  CB  ASP C 151      67.816 123.960  31.947  1.00 82.31           C
ATOM   4703  CG  ASP C 151      69.004 123.072  31.597  1.00 82.31           C
ATOM   4704  OD1 ASP C 151      69.257 122.103  32.341  1.00 82.31           C
ATOM   4705  OD2 ASP C 151      69.693 123.349  30.586  1.00 82.31           C
ATOM   4706  C   ASP C 151      66.733 122.438  33.596  1.00 78.09           C
ATOM   4707  O   ASP C 151      67.020 123.066  34.613  1.00 78.09           C
ATOM   4708  N   PRO C 152      66.580 121.105  33.596  1.00100.07           C
ATOM   4709  CD  PRO C 152      66.281 120.281  32.410  1.00100.07           C
ATOM   4710  CA  PRO C 152      66.728 120.264  34.791  1.00100.07           C
ATOM   4711  CB  PRO C 152      66.297 118.887  34.293  1.00100.07           C
ATOM   4712  CG  PRO C 152      66.732 118.906  32.851  1.00100.07           C
ATOM   4713  C   PRO C 152      68.149 120.259  35.364  1.00100.07           C
ATOM   4714  O   PRO C 152      68.400 119.688  36.430  1.00100.07           C
ATOM   4715  N   ALA C 153      69.074 120.890  34.645  1.00 77.78           C
ATOM   4716  CA  ALA C 153      70.463 120.983  35.083  1.00 77.78           C
ATOM   4717  CB  ALA C 153      71.398 120.750  33.910  1.00 75.78           C
ATOM   4718  C   ALA C 153      70.679 122.378  35.662  1.00 77.78           C
ATOM   4719  O   ALA C 153      71.014 123.314  34.930  1.00 77.78           C
ATOM   4720  N   ARG C 154      70.494 122.495  36.979  1.00 94.66           C
ATOM   4721  CA  ARG C 154      70.616 123.764  37.695  1.00 94.66           C
ATOM   4722  CB  ARG C 154      72.080 124.201  37.803  1.00100.07           C
ATOM   4723  CG  ARG C 154      72.969 123.242  38.612  1.00100.07           C
ATOM   4724  CD  ARG C 154      73.766 123.969  39.701  1.00100.07           C
ATOM   4725  NE  ARG C 154      72.902 124.445  40.786  1.00100.07           C
ATOM   4726  CZ  ARG C 154      73.318 125.157  41.832  1.00100.07           C
ATOM   4727  NH1 ARG C 154      74.599 125.493  41.949  1.00100.07           C
ATOM   4728  NH2 ARG C 154      72.451 125.529  42.768  1.00100.07           C
ATOM   4729  C   ARG C 154      69.790 124.800  36.941  1.00 94.66           C
ATOM   4730  O   ARG C 154      70.141 125.210  35.839  1.00 94.66           C
ATOM   4731  N   PRO C 155      68.676 125.237  37.539  1.00 99.90           C
ATOM   4732  CD  PRO C 155      68.500 125.126  39.000  1.00 66.32           C
ATOM   4733  CA  PRO C 155      67.739 126.218  36.982  1.00 99.90           C
ATOM   4734  CB  PRO C 155      67.365 127.035  38.208  1.00 66.32           C
ATOM   4735  CG  PRO C 155      67.258 125.954  39.252  1.00 66.32           C
ATOM   4736  C   PRO C 155      68.239 127.073  35.802  1.00 99.90           C
ATOM   4737  O   PRO C 155      68.902 128.094  35.995  1.00 99.90           C
ATOM   4738  N   GLY C 156      67.900 126.653  34.581  1.00 82.77           C
ATOM   4739  CA  GLY C 156      68.337 127.381  33.401  1.00 82.77           C
ATOM   4740  C   GLY C 156      67.451 127.278  32.168  1.00 82.77           C
ATOM   4741  O   GLY C 156      67.945 127.289  31.036  1.00 82.77           C
ATOM   4742  N   ARG C 157      66.145 127.181  32.383  1.00100.07           C
ATOM   4743  CA  ARG C 157      65.163 127.100  31.298  1.00100.07           C
ATOM   4744  CB  ARG C 157      64.694 128.495  30.913  1.00 63.00           C
ATOM   4745  CG  ARG C 157      64.524 129.435  32.075  1.00 63.00           C
ATOM   4746  CD  ARG C 157      64.051 128.739  33.335  1.00 63.00           C
ATOM   4747  NE  ARG C 157      63.404 129.700  34.216  1.00 63.00           C
ATOM   4748  CZ  ARG C 157      63.177 129.511  35.511  1.00 63.00           C
ATOM   4749  NH1 ARG C 157      63.552 128.380  36.108  1.00 63.00           C
ATOM   4750  NH2 ARG C 157      62.560 130.463  36.207  1.00 63.00           C
```

| | | | | | | | | | |
|---|---|---|---|---|---|---|---|---|---|
| ATOM | 4751 | C | ARG | C | 157 | 65.592 | 126.380 | 30.022 | 1.00 100.07 C |
| ATOM | 4752 | O | ARG | C | 157 | 65.856 | 125.179 | 30.038 | 1.00 100.07 C |
| ATOM | 4753 | N | TYR | C | 158 | 65.629 | 127.133 | 28.922 | 1.00 80.15 C |
| ATOM | 4754 | CA | TYR | C | 158 | 65.999 | 126.639 | 27.587 | 1.00 80.15 C |
| ATOM | 4755 | CB | TYR | C | 158 | 66.807 | 125.340 | 27.661 | 1.00 100.07 C |
| ATOM | 4756 | CG | TYR | C | 158 | 66.052 | 124.174 | 27.103 | 1.00 100.07 C |
| ATOM | 4757 | CD1 | TYR | C | 158 | 65.109 | 123.493 | 27.870 | 1.00 100.07 C |
| ATOM | 4758 | CE1 | TYR | C | 158 | 64.327 | 122.479 | 27.320 | 1.00 100.07 C |
| ATOM | 4759 | CD2 | TYR | C | 158 | 66.207 | 123.814 | 25.772 | 1.00 100.07 C |
| ATOM | 4760 | CE2 | TYR | C | 158 | 65.435 | 122.807 | 25.205 | 1.00 100.07 C |
| ATOM | 4761 | CZ | TYR | C | 158 | 64.493 | 122.139 | 25.978 | 1.00 100.07 C |
| ATOM | 4762 | OH | TYR | C | 158 | 63.718 | 121.148 | 25.394 | 1.00 100.07 C |
| ATOM | 4763 | C | TYR | C | 158 | 64.755 | 126.407 | 26.723 | 1.00 80.15 C |
| ATOM | 4764 | O | TYR | C | 158 | 63.676 | 126.098 | 27.232 | 1.00 80.15 C |
| ATOM | 4765 | N | ILE | C | 159 | 64.925 | 126.514 | 25.409 | 1.00 23.07 C |
| ATOM | 4766 | CA | ILE | C | 159 | 63.802 | 126.366 | 24.494 | 1.00 23.07 C |
| ATOM | 4767 | CB | ILE | C | 159 | 63.603 | 127.614 | 23.606 | 1.00 100.07 C |
| ATOM | 4768 | CG2 | ILE | C | 159 | 62.118 | 127.883 | 23.421 | 1.00 100.07 C |
| ATOM | 4769 | CG1 | ILE | C | 159 | 64.308 | 128.822 | 24.212 | 1.00 100.07 C |
| ATOM | 4770 | CD | ILE | C | 159 | 65.809 | 128.767 | 24.080 | 1.00 100.07 C |
| ATOM | 4771 | C | ILE | C | 159 | 63.843 | 125.195 | 23.542 | 1.00 23.07 C |
| ATOM | 4772 | O | ILE | C | 159 | 64.884 | 124.840 | 22.983 | 1.00 23.07 C |
| ATOM | 4773 | N | ALA | C | 160 | 62.662 | 124.631 | 23.339 | 1.00 47.25 C |
| ATOM | 4774 | CA | ALA | C | 160 | 62.475 | 123.511 | 22.446 | 1.00 47.25 C |
| ATOM | 4775 | CB | ALA | C | 160 | 61.698 | 122.408 | 23.175 | 1.00 16.84 C |
| ATOM | 4776 | C | ALA | C | 160 | 61.713 | 123.998 | 21.204 | 1.00 47.25 C |
| ATOM | 4777 | O | ALA | C | 160 | 60.667 | 124.642 | 21.320 | 1.00 47.25 C |
| ATOM | 4778 | N | SER | C | 161 | 62.257 | 123.725 | 20.022 | 1.00 99.36 C |
| ATOM | 4779 | CA | SER | C | 161 | 61.606 | 124.115 | 18.772 | 1.00 99.36 C |
| ATOM | 4780 | CB | SER | C | 161 | 62.640 | 124.628 | 17.753 | 1.00 42.46 C |
| ATOM | 4781 | OG | SER | C | 161 | 62.631 | 126.046 | 17.644 | 1.00 42.46 C |
| ATOM | 4782 | C | SER | C | 161 | 60.904 | 122.873 | 18.228 | 1.00 99.36 C |
| ATOM | 4783 | O | SER | C | 161 | 61.546 | 121.999 | 17.638 | 1.00 99.36 C |
| ATOM | 4784 | N | ILE | C | 162 | 59.591 | 122.794 | 18.436 | 1.00 100.02 C |
| ATOM | 4785 | CA | ILE | C | 162 | 58.806 | 121.647 | 17.984 | 1.00 100.02 C |
| ATOM | 4786 | CB | ILE | C | 162 | 57.395 | 121.632 | 18.588 | 1.00 100.07 C |
| ATOM | 4787 | CG2 | ILE | C | 162 | 56.686 | 120.346 | 18.211 | 1.00 100.07 C |
| ATOM | 4788 | CG1 | ILE | C | 162 | 57.472 | 121.682 | 20.110 | 1.00 100.07 C |
| ATOM | 4789 | CD | ILE | C | 162 | 58.042 | 122.957 | 20.665 | 1.00 100.07 C |
| ATOM | 4790 | C | ILE | C | 162 | 58.672 | 121.582 | 16.484 | 1.00 100.02 C |
| ATOM | 4791 | O | ILE | C | 162 | 59.157 | 122.455 | 15.774 | 1.00 100.02 C |
| ATOM | 4792 | N | ILE | C | 163 | 58.002 | 120.546 | 15.998 | 1.00 27.30 C |
| ATOM | 4793 | CA | ILE | C | 163 | 57.839 | 120.380 | 14.571 | 1.00 27.30 C |
| ATOM | 4794 | CB | ILE | C | 163 | 58.935 | 119.477 | 14.050 | 1.00 37.66 C |
| ATOM | 4795 | CG2 | ILE | C | 163 | 58.549 | 118.894 | 12.717 | 1.00 37.66 C |
| ATOM | 4796 | CG1 | ILE | C | 163 | 60.237 | 120.269 | 13.991 | 1.00 37.66 C |
| ATOM | 4797 | CD | ILE | C | 163 | 60.127 | 121.562 | 13.217 | 1.00 37.66 C |
| ATOM | 4798 | C | ILE | C | 163 | 56.486 | 119.803 | 14.208 | 1.00 27.30 C |
| ATOM | 4799 | O | ILE | C | 163 | 55.944 | 118.980 | 14.948 | 1.00 27.30 C |
| ATOM | 4800 | N | PRO | C | 164 | 55.921 | 120.222 | 13.055 | 1.00 100.07 C |
| ATOM | 4801 | CD | PRO | C | 164 | 56.538 | 121.109 | 12.051 | 1.00 96.76 C |
| ATOM | 4802 | CA | PRO | C | 164 | 54.614 | 119.749 | 12.576 | 1.00 100.07 C |
| ATOM | 4803 | CB | PRO | C | 164 | 54.589 | 120.207 | 11.107 | 1.00 96.76 C |
| ATOM | 4804 | CG | PRO | C | 164 | 56.036 | 120.516 | 10.768 | 1.00 96.76 C |
| ATOM | 4805 | C | PRO | C | 164 | 54.360 | 118.244 | 12.722 | 1.00 100.07 C |
| ATOM | 4806 | O | PRO | C | 164 | 53.236 | 117.772 | 12.520 | 1.00 100.07 C |
| ATOM | 4807 | N | LEU | C | 165 | 55.406 | 117.507 | 13.083 | 1.00 69.74 C |
| ATOM | 4808 | CA | LEU | C | 165 | 55.330 | 116.062 | 13.255 | 1.00 69.74 C |
| ATOM | 4809 | CB | LEU | C | 165 | 54.893 | 115.414 | 11.943 | 1.00 100.07 C |
| ATOM | 4810 | CG | LEU | C | 165 | 54.813 | 113.890 | 11.877 | 1.00 100.07 C |
| ATOM | 4811 | CD1 | LEU | C | 165 | 53.422 | 113.447 | 12.315 | 1.00 100.07 C |
| ATOM | 4812 | CD2 | LEU | C | 165 | 55.111 | 113.420 | 10.459 | 1.00 100.07 C |
| ATOM | 4813 | C | LEU | C | 165 | 56.727 | 115.576 | 13.600 | 1.00 69.74 C |
| ATOM | 4814 | O | LEU | C | 165 | 57.701 | 116.279 | 13.357 | 1.00 69.74 C |
| ATOM | 4815 | N | PRO | C | 166 | 56.850 | 114.379 | 14.192 | 1.00 90.60 C |
| ATOM | 4816 | CD | PRO | C | 166 | 55.844 | 113.495 | 14.807 | 1.00 49.54 C |
| ATOM | 4817 | CA | PRO | C | 166 | 58.208 | 113.925 | 14.504 | 1.00 90.60 C |
| ATOM | 4818 | CB | PRO | C | 166 | 57.969 | 112.786 | 15.505 | 1.00 49.54 C |
| ATOM | 4819 | CG | PRO | C | 166 | 56.647 | 112.240 | 15.083 | 1.00 49.54 C |
| ATOM | 4820 | C | PRO | C | 166 | 58.918 | 113.481 | 13.206 | 1.00 90.60 C |
| ATOM | 4821 | O | PRO | C | 166 | 60.122 | 113.209 | 13.192 | 1.00 90.60 C |
| ATOM | 4822 | N | LYS | C | 167 | 58.151 | 113.430 | 12.116 | 1.00 100.01 C |
| ATOM | 4823 | CA | LYS | C | 167 | 58.668 | 113.048 | 10.800 | 1.00 100.01 C |
| ATOM | 4824 | CB | LYS | C | 167 | 58.156 | 111.655 | 10.396 | 1.00 100.07 C |
| ATOM | 4825 | CG | LYS | C | 167 | 58.679 | 110.494 | 11.256 | 1.00 100.07 C |
| ATOM | 4826 | CD | LYS | C | 167 | 58.161 | 109.131 | 10.759 | 1.00 100.07 C |
| ATOM | 4827 | CE | LYS | C | 167 | 58.618 | 107.963 | 11.653 | 1.00 100.07 C |
| ATOM | 4828 | NZ | LYS | C | 167 | 58.148 | 106.610 | 11.188 | 1.00 100.07 C |
| ATOM | 4829 | C | LYS | C | 167 | 58.235 | 114.083 | 9.755 | 1.00 100.01 C |
| ATOM | 4830 | O | LYS | C | 167 | 57.872 | 113.739 | 8.627 | 1.00 100.01 C |
| ATOM | 4831 | N | ARG | C | 168 | 58.276 | 115.354 | 10.146 | 1.00 64.31 C |
| ATOM | 4832 | CA | ARG | C | 168 | 57.900 | 116.453 | 9.263 | 1.00 64.31 C |
| ATOM | 4833 | CB | ARG | C | 168 | 56.396 | 116.704 | 9.374 | 1.00 77.54 C |
| ATOM | 4834 | CG | ARG | C | 168 | 55.723 | 117.009 | 8.053 | 1.00 77.54 C |

```
ATOM   4835  CD   ARG C 168      56.177 118.346   7.512  1.00 77.54           C
ATOM   4836  NE   ARG C 168      55.819 118.499   6.109  1.00 77.54           C
ATOM   4837  CZ   ARG C 168      56.249 117.690   5.147  1.00 77.54           C
ATOM   4838  NH1  ARG C 168      57.049 116.673   5.444  1.00 77.54           C
ATOM   4839  NH2  ARG C 168      55.885 117.898   3.888  1.00 77.54           C
ATOM   4840  C    ARG C 168      58.691 117.720   9.630  1.00 64.31           C
ATOM   4841  O    ARG C 168      58.182 118.842   9.536  1.00 64.31           C
ATOM   4842  N    GLY C 169      59.943 117.516  10.042  1.00 72.47           C
ATOM   4843  CA   GLY C 169      60.812 118.617  10.429  1.00 72.47           C
ATOM   4844  C    GLY C 169      61.723 118.316  11.617  1.00 72.47           C
ATOM   4845  O    GLY C 169      61.381 117.508  12.482  1.00 72.47           C
ATOM   4846  N    PRO C 170      62.898 118.961  11.694  1.00 89.12           C
ATOM   4847  CD   PRO C 170      63.498 119.758  10.609  1.00100.07           C
ATOM   4848  CA   PRO C 170      63.861 118.759  12.784  1.00 89.12           C
ATOM   4849  CB   PRO C 170      65.157 119.298  12.193  1.00100.07           C
ATOM   4850  CG   PRO C 170      64.676 120.391  11.299  1.00100.07           C
ATOM   4851  C    PRO C 170      63.543 119.380  14.155  1.00 89.12           C
ATOM   4852  O    PRO C 170      63.020 120.494  14.262  1.00 89.12           C
ATOM   4853  N    TRP C 171      63.898 118.625  15.191  1.00 65.36           C
ATOM   4854  CA   TRP C 171      63.716 118.969  16.607  1.00 65.36           C
ATOM   4855  CB   TRP C 171      63.716 117.648  17.400  1.00 59.97           C
ATOM   4856  CG   TRP C 171      63.110 117.578  18.806  1.00 59.97           C
ATOM   4857  CD2  TRP C 171      61.945 118.255  19.311  1.00 59.97           C
ATOM   4858  CE2  TRP C 171      61.694 117.749  20.606  1.00 59.97           C
ATOM   4859  CE3  TRP C 171      61.082 119.228  18.794  1.00 59.97           C
ATOM   4860  CD1  TRP C 171      63.505 116.725  19.804  1.00 59.97           C
ATOM   4861  NE1  TRP C 171      62.662 116.820  20.881  1.00 59.97           C
ATOM   4862  CZ2  TRP C 171      60.625 118.188  21.391  1.00 59.97           C
ATOM   4863  CZ3  TRP C 171      60.020 119.658  19.581  1.00 59.97           C
ATOM   4864  CH2  TRP C 171      59.801 119.138  20.858  1.00 59.97           C
ATOM   4865  C    TRP C 171      64.931 119.822  17.005  1.00 65.36           C
ATOM   4866  O    TRP C 171      66.047 119.310  17.078  1.00 65.36           C
ATOM   4867  N    ILE C 172      64.730 121.116  17.236  1.00 75.20           C
ATOM   4868  CA   ILE C 172      65.842 121.984  17.626  1.00 75.20           C
ATOM   4869  CB   ILE C 172      65.914 123.297  16.774  1.00 49.67           C
ATOM   4870  CG2  ILE C 172      66.771 124.342  17.478  1.00 49.67           C
ATOM   4871  CG1  ILE C 172      66.553 123.049  15.411  1.00 49.67           C
ATOM   4872  CD   ILE C 172      66.740 124.339  14.603  1.00 49.67           C
ATOM   4873  C    ILE C 172      65.686 122.412  19.076  1.00 75.20           C
ATOM   4874  O    ILE C 172      64.570 122.463  19.596  1.00 75.20           C
ATOM   4875  N    ASP C 173      66.812 122.717  19.723  1.00 45.64           C
ATOM   4876  CA   ASP C 173      66.807 123.196  21.100  1.00 45.64           C
ATOM   4877  CB   ASP C 173      66.997 122.054  22.091  1.00 58.55           C
ATOM   4878  CG   ASP C 173      65.687 121.431  22.510  1.00 58.55           C
ATOM   4879  OD1  ASP C 173      64.666 122.142  22.491  1.00 58.55           C
ATOM   4880  OD2  ASP C 173      65.675 120.239  22.877  1.00 58.55           C
ATOM   4881  C    ASP C 173      67.866 124.255  21.360  1.00 45.64           C
ATOM   4882  O    ASP C 173      69.064 123.955  21.365  1.00 45.64           C
ATOM   4883  N    LEU C 174      67.412 125.498  21.535  1.00 26.43           C
ATOM   4884  CA   LEU C 174      68.296 126.612  21.859  1.00 26.43           C
ATOM   4885  CB   LEU C 174      67.575 127.939  21.695  1.00 44.43           C
ATOM   4886  CG   LEU C 174      66.944 128.213  20.335  1.00 44.43           C
ATOM   4887  CD1  LEU C 174      65.633 128.952  20.541  1.00 44.43           C
ATOM   4888  CD2  LEU C 174      67.901 129.010  19.456  1.00 44.43           C
ATOM   4889  C    LEU C 174      68.476 126.309  23.331  1.00 26.43           C
ATOM   4890  O    LEU C 174      67.490 126.161  24.060  1.00 26.43           C
ATOM   4891  N    GLU C 175      69.718 126.215  23.780  1.00 54.85           C
ATOM   4892  CA   GLU C 175      69.955 125.839  25.163  1.00 54.85           C
ATOM   4893  CB   GLU C 175      70.220 124.337  25.181  1.00100.07           C
ATOM   4894  CG   GLU C 175      70.503 123.710  26.510  1.00100.07           C
ATOM   4895  CD   GLU C 175      70.747 122.223  26.358  1.00100.07           C
ATOM   4896  OE1  GLU C 175      71.643 121.857  25.568  1.00100.07           C
ATOM   4897  OE2  GLU C 175      70.046 121.423  27.015  1.00100.07           C
ATOM   4898  C    GLU C 175      71.100 126.593  25.818  1.00 54.85           C
ATOM   4899  O    GLU C 175      72.247 126.151  25.753  1.00 54.85           C
ATOM   4900  N    VAL C 176      70.784 127.722  26.455  1.00 99.89           C
ATOM   4901  CA   VAL C 176      71.799 128.533  27.126  1.00 99.89           C
ATOM   4902  CB   VAL C 176      71.243 129.893  27.605  1.00100.07           C
ATOM   4903  CG1  VAL C 176      72.351 130.689  28.289  1.00100.07           C
ATOM   4904  CG2  VAL C 176      70.695 130.680  26.428  1.00100.07           C
ATOM   4905  C    VAL C 176      72.341 127.791  28.335  1.00 99.89           C
ATOM   4906  O    VAL C 176      71.575 127.336  29.186  1.00 99.89           C
ATOM   4907  N    GLU C 177      73.667 127.683  28.396  1.00 99.82           C
ATOM   4908  CA   GLU C 177      74.368 126.985  29.469  1.00 99.82           C
ATOM   4909  CB   GLU C 177      75.119 125.780  28.892  1.00 87.63           C
ATOM   4910  CG   GLU C 177      76.130 126.137  27.801  1.00 87.63           C
ATOM   4911  CD   GLU C 177      76.448 124.968  26.882  1.00 87.63           C
ATOM   4912  OE1  GLU C 177      75.514 124.469  26.217  1.00 87.63           C
ATOM   4913  OE2  GLU C 177      77.625 124.548  26.822  1.00 87.63           C
ATOM   4914  C    GLU C 177      75.353 127.930  30.136  1.00 99.82           C
ATOM   4915  O    GLU C 177      75.239 129.148  30.001  1.00 99.82           C
ATOM   4916  N    ALA C 178      76.319 127.366  30.855  1.00 74.18           C
ATOM   4917  CA   ALA C 178      77.328 128.176  31.530  1.00 74.18           C
ATOM   4918  CB   ALA C 178      77.666 127.569  32.909  1.00 22.45           C
```

| ATOM | 4919 | C | ALA C 178 | 78.579 | 128.251 | 30.656 | 1.00 | 74.18 | C |
|------|------|-----|-----------|--------|---------|--------|------|-------|---|
| ATOM | 4920 | O | ALA C 178 | 78.916 | 129.309 | 30.115 | 1.00 | 74.18 | C |
| ATOM | 4921 | N | SER C 179 | 79.250 | 127.113 | 30.508 | 1.00 | 60.33 | C |
| ATOM | 4922 | CA | SER C 179 | 80.469 | 127.036 | 29.717 | 1.00 | 60.33 | C |
| ATOM | 4923 | CB | SER C 179 | 81.451 | 126.053 | 30.375 | 1.00 | 64.32 | C |
| ATOM | 4924 | OG | SER C 179 | 80.799 | 124.875 | 30.810 | 1.00 | 64.32 | C |
| ATOM | 4925 | C | SER C 179 | 80.212 | 126.651 | 28.261 | 1.00 | 60.33 | C |
| ATOM | 4926 | O | SER C 179 | 80.744 | 125.657 | 27.756 | 1.00 | 60.33 | C |
| ATOM | 4927 | N | GLY C 180 | 79.395 | 127.463 | 27.594 | 1.00 | 100.07 | C |
| ATOM | 4928 | CA | GLY C 180 | 79.049 | 127.242 | 26.197 | 1.00 | 100.07 | C |
| ATOM | 4929 | C | GLY C 180 | 78.168 | 128.387 | 25.721 | 1.00 | 100.07 | C |
| ATOM | 4930 | O | GLY C 180 | 78.378 | 128.961 | 24.652 | 1.00 | 100.07 | C |
| ATOM | 4931 | N | VAL C 181 | 77.180 | 128.722 | 26.546 | 1.00 | 88.90 | C |
| ATOM | 4932 | CA | VAL C 181 | 76.236 | 129.803 | 26.283 | 1.00 | 88.90 | C |
| ATOM | 4933 | CB | VAL C 181 | 76.915 | 131.185 | 26.413 | 1.00 | 94.12 | C |
| ATOM | 4934 | CG1 | VAL C 181 | 75.873 | 132.285 | 26.277 | 1.00 | 94.12 | C |
| ATOM | 4935 | CG2 | VAL C 181 | 77.626 | 131.293 | 27.758 | 1.00 | 94.12 | C |
| ATOM | 4936 | C | VAL C 181 | 75.552 | 129.722 | 24.927 | 1.00 | 88.90 | C |
| ATOM | 4937 | O | VAL C 181 | 76.198 | 129.610 | 23.892 | 1.00 | 88.90 | C |
| ATOM | 4938 | N | VAL C 182 | 74.227 | 129.775 | 24.960 | 1.00 | 41.38 | C |
| ATOM | 4939 | CA | VAL C 182 | 73.406 | 129.729 | 23.766 | 1.00 | 41.38 | C |
| ATOM | 4940 | CB | VAL C 182 | 73.349 | 131.117 | 23.122 | 1.00 | 48.32 | C |
| ATOM | 4941 | CG1 | VAL C 182 | 72.150 | 131.204 | 22.205 | 1.00 | 48.32 | C |
| ATOM | 4942 | CG2 | VAL C 182 | 73.280 | 132.187 | 24.201 | 1.00 | 48.32 | C |
| ATOM | 4943 | C | VAL C 182 | 73.883 | 128.700 | 22.728 | 1.00 | 41.38 | C |
| ATOM | 4944 | O | VAL C 182 | 74.699 | 129.007 | 21.846 | 1.00 | 41.38 | C |
| ATOM | 4945 | N | THR C 183 | 73.349 | 127.481 | 22.838 | 1.00 | 81.84 | C |
| ATOM | 4946 | CA | THR C 183 | 73.685 | 126.370 | 21.943 | 1.00 | 81.84 | C |
| ATOM | 4947 | CB | THR C 183 | 74.093 | 125.113 | 22.722 | 1.00 | 64.23 | C |
| ATOM | 4948 | OG1 | THR C 183 | 75.115 | 125.435 | 23.673 | 1.00 | 64.23 | C |
| ATOM | 4949 | CG2 | THR C 183 | 74.606 | 124.059 | 21.767 | 1.00 | 64.23 | C |
| ATOM | 4950 | C | THR C 183 | 72.498 | 125.969 | 21.081 | 1.00 | 81.84 | C |
| ATOM | 4951 | O | THR C 183 | 71.344 | 126.077 | 21.499 | 1.00 | 81.84 | C |
| ATOM | 4952 | N | MET C 184 | 72.792 | 125.482 | 19.881 | 1.00 | 87.56 | C |
| ATOM | 4953 | CA | MET C 184 | 71.755 | 125.051 | 18.952 | 1.00 | 87.56 | C |
| ATOM | 4954 | CB | MET C 184 | 71.859 | 125.831 | 17.641 | 1.00 | 35.60 | C |
| ATOM | 4955 | CG | MET C 184 | 70.544 | 126.411 | 17.140 | 1.00 | 35.60 | C |
| ATOM | 4956 | SD | MET C 184 | 69.546 | 125.324 | 16.116 | 1.00 | 35.60 | C |
| ATOM | 4957 | CE | MET C 184 | 69.895 | 125.965 | 14.526 | 1.00 | 35.60 | C |
| ATOM | 4958 | C | MET C 184 | 71.959 | 123.580 | 18.666 | 1.00 | 87.56 | C |
| ATOM | 4959 | O | MET C 184 | 72.660 | 123.227 | 17.721 | 1.00 | 87.56 | C |
| ATOM | 4960 | N | LYS C 185 | 71.369 | 122.717 | 19.487 | 1.00 | 47.66 | C |
| ATOM | 4961 | CA | LYS C 185 | 71.514 | 121.284 | 19.259 | 1.00 | 47.66 | C |
| ATOM | 4962 | CB | LYS C 185 | 71.545 | 120.525 | 20.587 | 1.00 | 100.07 | C |
| ATOM | 4963 | CG | LYS C 185 | 70.406 | 120.864 | 21.522 | 1.00 | 100.07 | C |
| ATOM | 4964 | CD | LYS C 185 | 70.432 | 119.985 | 22.768 | 1.00 | 100.07 | C |
| ATOM | 4965 | CE | LYS C 185 | 69.298 | 120.357 | 23.729 | 1.00 | 100.07 | C |
| ATOM | 4966 | NZ | LYS C 185 | 69.183 | 119.465 | 24.924 | 1.00 | 100.07 | C |
| ATOM | 4967 | C | LYS C 185 | 70.350 | 120.800 | 18.409 | 1.00 | 47.66 | C |
| ATOM | 4968 | O | LYS C 185 | 69.194 | 121.048 | 18.752 | 1.00 | 47.66 | C |
| ATOM | 4969 | N | VAL C 186 | 70.651 | 120.144 | 17.286 | 1.00 | 53.45 | C |
| ATOM | 4970 | CA | VAL C 186 | 69.598 | 119.631 | 16.412 | 1.00 | 53.45 | C |
| ATOM | 4971 | CB | VAL C 186 | 69.804 | 120.007 | 14.934 | 1.00 | 38.28 | C |
| ATOM | 4972 | CG1 | VAL C 186 | 68.477 | 119.930 | 14.209 | 1.00 | 38.28 | C |
| ATOM | 4973 | CG2 | VAL C 186 | 70.390 | 121.384 | 14.806 | 1.00 | 38.28 | C |
| ATOM | 4974 | C | VAL C 186 | 69.624 | 118.119 | 16.505 | 1.00 | 53.45 | C |
| ATOM | 4975 | O | VAL C 186 | 69.587 | 117.558 | 17.604 | 1.00 | 53.45 | C |
| ATOM | 4976 | N | ASN C 187 | 69.688 | 117.457 | 15.354 | 1.00 | 49.25 | C |
| ATOM | 4977 | CA | ASN C 187 | 69.739 | 116.005 | 15.347 | 1.00 | 49.25 | C |
| ATOM | 4978 | CB | ASN C 187 | 69.646 | 115.476 | 13.912 | 1.00 | 100.07 | C |
| ATOM | 4979 | CG | ASN C 187 | 70.553 | 116.219 | 12.952 | 1.00 | 100.07 | C |
| ATOM | 4980 | OD1 | ASN C 187 | 71.684 | 116.558 | 13.288 | 1.00 | 100.07 | C |
| ATOM | 4981 | ND2 | ASN C 187 | 70.063 | 116.459 | 11.739 | 1.00 | 100.07 | C |
| ATOM | 4982 | C | ASN C 187 | 71.051 | 115.557 | 16.003 | 1.00 | 49.25 | C |
| ATOM | 4983 | O | ASN C 187 | 71.154 | 114.453 | 16.555 | 1.00 | 49.25 | C |
| ATOM | 4984 | N | LYS C 188 | 72.037 | 116.450 | 15.969 | 1.00 | 96.97 | C |
| ATOM | 4985 | CA | LYS C 188 | 73.361 | 116.185 | 16.529 | 1.00 | 96.97 | C |
| ATOM | 4986 | CB | LYS C 188 | 74.092 | 115.171 | 15.633 | 1.00 | 100.07 | C |
| ATOM | 4987 | CG | LYS C 188 | 75.556 | 114.905 | 15.983 | 1.00 | 100.07 | C |
| ATOM | 4988 | CD | LYS C 188 | 76.295 | 114.220 | 14.832 | 1.00 | 100.07 | C |
| ATOM | 4989 | CE | LYS C 188 | 75.670 | 112.879 | 14.465 | 1.00 | 100.07 | C |
| ATOM | 4990 | NZ | LYS C 188 | 75.753 | 111.881 | 15.572 | 1.00 | 100.07 | C |
| ATOM | 4991 | C | LYS C 188 | 74.168 | 117.489 | 16.596 | 1.00 | 96.97 | C |
| ATOM | 4992 | O | LYS C 188 | 73.862 | 118.445 | 15.880 | 1.00 | 96.97 | C |
| ATOM | 4993 | N | ALA C 189 | 75.171 | 117.518 | 17.478 | 1.00 | 79.36 | C |
| ATOM | 4994 | CA | ALA C 189 | 76.092 | 118.654 | 17.646 | 1.00 | 79.36 | C |
| ATOM | 4995 | CB | ALA C 189 | 76.488 | 119.205 | 16.270 | 1.00 | 100.07 | C |
| ATOM | 4996 | C | ALA C 189 | 75.738 | 119.819 | 18.569 | 1.00 | 79.36 | C |
| ATOM | 4997 | O | ALA C 189 | 74.586 | 120.225 | 18.705 | 1.00 | 79.36 | C |
| ATOM | 4998 | N | LYS C 190 | 76.781 | 120.360 | 19.182 | 1.00 | 67.78 | C |
| ATOM | 4999 | CA | LYS C 190 | 76.676 | 121.487 | 20.098 | 1.00 | 67.78 | C |
| ATOM | 5000 | CB | LYS C 190 | 77.584 | 121.238 | 21.323 | 1.00 | 100.07 | C |
| ATOM | 5001 | CG | LYS C 190 | 77.626 | 122.351 | 22.396 | 1.00 | 100.07 | C |
| ATOM | 5002 | CD | LYS C 190 | 78.597 | 122.004 | 23.549 | 1.00 | 100.07 | C |

| ATOM | 5003 | CE | LYS C 190 | 78.694 123.119 24.602 | 1.00100.07 | C |
|---|---|---|---|---|---|---|
| ATOM | 5004 | NZ | LYS C 190 | 79.616 122.794 25.735 | 1.00100.07 | C |
| ATOM | 5005 | C | LYS C 190 | 77.134 122.739 19.347 | 1.00 67.78 | C |
| ATOM | 5006 | O | LYS C 190 | 77.673 123.674 19.951 | 1.00 67.78 | C |
| ATOM | 5007 | N | PHE C 191 | 76.924 122.762 18.031 | 1.00 66.37 | C |
| ATOM | 5008 | CA | PHE C 191 | 77.354 123.912 17.241 | 1.00 66.37 | C |
| ATOM | 5009 | CB | PHE C 191 | 76.927 123.754 15.776 | 1.00 74.59 | C |
| ATOM | 5010 | CG | PHE C 191 | 75.594 124.358 15.452 | 1.00 74.59 | C |
| ATOM | 5011 | CD1 | PHE C 191 | 75.479 125.718 15.187 | 1.00 74.59 | C |
| ATOM | 5012 | CD2 | PHE C 191 | 74.452 123.566 15.389 | 1.00 74.59 | C |
| ATOM | 5013 | CE1 | PHE C 191 | 74.243 126.280 14.860 | 1.00 74.59 | C |
| ATOM | 5014 | CE2 | PHE C 191 | 73.215 124.120 15.065 | 1.00 74.59 | C |
| ATOM | 5015 | CZ | PHE C 191 | 73.112 125.477 14.799 | 1.00 74.59 | C |
| ATOM | 5016 | C | PHE C 191 | 76.804 125.200 17.846 | 1.00 66.37 | C |
| ATOM | 5017 | O | PHE C 191 | 75.608 125.322 18.120 | 1.00 66.37 | C |
| ATOM | 5018 | N | PRO C 192 | 77.688 126.173 18.089 | 1.00 40.46 | C |
| ATOM | 5019 | CD | PRO C 192 | 79.145 126.072 17.906 | 1.00 76.02 | C |
| ATOM | 5020 | CA | PRO C 192 | 77.328 127.466 18.672 | 1.00 40.46 | C |
| ATOM | 5021 | CB | PRO C 192 | 78.641 128.232 18.617 | 1.00 76.02 | C |
| ATOM | 5022 | CG | PRO C 192 | 79.654 127.142 18.834 | 1.00 76.02 | C |
| ATOM | 5023 | C | PRO C 192 | 76.192 128.195 17.961 | 1.00 40.46 | C |
| ATOM | 5024 | O | PRO C 192 | 76.264 128.486 16.758 | 1.00 40.46 | C |
| ATOM | 5025 | N | LEU C 193 | 75.151 128.497 18.734 | 1.00 60.89 | C |
| ATOM | 5026 | CA | LEU C 193 | 73.963 129.188 18.234 | 1.00 60.89 | C |
| ATOM | 5027 | CB | LEU C 193 | 73.038 129.533 19.409 | 1.00 48.89 | C |
| ATOM | 5028 | CG | LEU C 193 | 71.762 130.334 19.125 | 1.00 48.89 | C |
| ATOM | 5029 | CD1 | LEU C 193 | 72.105 131.774 18.814 | 1.00 48.89 | C |
| ATOM | 5030 | CD2 | LEU C 193 | 71.008 129.705 17.976 | 1.00 48.89 | C |
| ATOM | 5031 | C | LEU C 193 | 74.265 130.454 17.436 | 1.00 60.89 | C |
| ATOM | 5032 | O | LEU C 193 | 73.502 130.847 16.552 | 1.00 60.89 | C |
| ATOM | 5033 | N | VAL C 194 | 75.375 131.097 17.757 | 1.00 71.15 | C |
| ATOM | 5034 | CA | VAL C 194 | 75.743 132.315 17.069 | 1.00 71.15 | C |
| ATOM | 5035 | CB | VAL C 194 | 76.998 132.936 17.682 | 1.00100.02 | C |
| ATOM | 5036 | CG1 | VAL C 194 | 77.129 134.381 17.226 | 1.00100.02 | C |
| ATOM | 5037 | CG2 | VAL C 194 | 76.947 132.824 19.196 | 1.00100.02 | C |
| ATOM | 5038 | C | VAL C 194 | 76.029 132.059 15.596 | 1.00 71.15 | C |
| ATOM | 5039 | O | VAL C 194 | 75.603 132.829 14.727 | 1.00 71.15 | C |
| ATOM | 5040 | N | LEU C 195 | 76.748 130.977 15.311 | 1.00 47.15 | C |
| ATOM | 5041 | CA | LEU C 195 | 77.094 130.699 13.935 | 1.00 47.15 | C |
| ATOM | 5042 | CB | LEU C 195 | 77.851 129.380 13.801 | 1.00 30.73 | C |
| ATOM | 5043 | CG | LEU C 195 | 78.273 129.060 12.353 | 1.00 30.73 | C |
| ATOM | 5044 | CD1 | LEU C 195 | 79.236 130.113 11.840 | 1.00 30.73 | C |
| ATOM | 5045 | CD2 | LEU C 195 | 78.916 127.672 12.281 | 1.00 30.73 | C |
| ATOM | 5046 | C | LEU C 195 | 75.872 130.687 13.051 | 1.00 47.15 | C |
| ATOM | 5047 | O | LEU C 195 | 75.874 131.334 12.014 | 1.00 47.15 | C |
| ATOM | 5048 | N | LEU C 196 | 74.818 129.977 13.440 | 1.00 31.79 | C |
| ATOM | 5049 | CA | LEU C 196 | 73.651 129.963 12.567 | 1.00 31.79 | C |
| ATOM | 5050 | CB | LEU C 196 | 72.472 129.190 13.160 | 1.00 36.06 | C |
| ATOM | 5051 | CG | LEU C 196 | 71.180 129.532 12.380 | 1.00 36.06 | C |
| ATOM | 5052 | CD1 | LEU C 196 | 71.322 129.076 10.942 | 1.00 36.06 | C |
| ATOM | 5053 | CD2 | LEU C 196 | 69.952 128.902 13.028 | 1.00 36.06 | C |
| ATOM | 5054 | C | LEU C 196 | 73.189 131.380 12.284 | 1.00 31.79 | C |
| ATOM | 5055 | O | LEU C 196 | 73.044 131.763 11.120 | 1.00 31.79 | C |
| ATOM | 5056 | N | LEU C 197 | 72.943 132.139 13.352 | 1.00 53.35 | C |
| ATOM | 5057 | CA | LEU C 197 | 72.486 133.520 13.238 | 1.00 53.35 | C |
| ATOM | 5058 | CB | LEU C 197 | 72.559 134.212 14.586 | 1.00 13.56 | C |
| ATOM | 5059 | CG | LEU C 197 | 71.501 133.713 15.560 | 1.00 13.56 | C |
| ATOM | 5060 | CD1 | LEU C 197 | 71.666 134.372 16.901 | 1.00 13.56 | C |
| ATOM | 5061 | CD2 | LEU C 197 | 70.134 134.019 14.988 | 1.00 13.56 | C |
| ATOM | 5062 | C | LEU C 197 | 73.354 134.255 12.253 | 1.00 53.35 | C |
| ATOM | 5063 | O | LEU C 197 | 72.851 134.933 11.347 | 1.00 53.35 | C |
| ATOM | 5064 | N | ARG C 198 | 74.664 134.119 12.451 | 1.00 53.87 | C |
| ATOM | 5065 | CA | ARG C 198 | 75.662 134.727 11.573 | 1.00 53.87 | C |
| ATOM | 5066 | CB | ARG C 198 | 76.960 133.909 11.681 | 1.00100.07 | C |
| ATOM | 5067 | CG | ARG C 198 | 78.258 134.508 11.127 | 1.00100.07 | C |
| ATOM | 5068 | CD | ARG C 198 | 79.423 133.535 11.476 | 1.00100.07 | C |
| ATOM | 5069 | NE | ARG C 198 | 80.659 133.698 10.692 | 1.00100.07 | C |
| ATOM | 5070 | CZ | ARG C 198 | 81.727 132.896 10.778 | 1.00100.07 | C |
| ATOM | 5071 | NH1 | ARG C 198 | 81.735 131.861 11.614 | 1.00100.07 | C |
| ATOM | 5072 | NH2 | ARG C 198 | 82.794 133.126 10.021 | 1.00100.07 | C |
| ATOM | 5073 | C | ARG C 198 | 75.027 134.622 10.180 | 1.00 53.87 | C |
| ATOM | 5074 | O | ARG C 198 | 74.616 135.628 9.594 | 1.00 53.87 | C |
| ATOM | 5075 | N | VAL C 199 | 74.889 133.391 9.692 | 1.00 47.34 | C |
| ATOM | 5076 | CA | VAL C 199 | 74.284 133.145 8.392 | 1.00 47.34 | C |
| ATOM | 5077 | CB | VAL C 199 | 74.040 131.641 8.155 | 1.00 80.39 | C |
| ATOM | 5078 | CG1 | VAL C 199 | 72.734 131.430 7.410 | 1.00 80.39 | C |
| ATOM | 5079 | CG2 | VAL C 199 | 75.188 131.057 7.347 | 1.00 80.39 | C |
| ATOM | 5080 | C | VAL C 199 | 72.965 133.877 8.254 | 1.00 47.34 | C |
| ATOM | 5081 | O | VAL C 199 | 72.821 134.734 7.395 | 1.00 47.34 | C |
| ATOM | 5082 | N | LEU C 200 | 72.004 133.548 9.105 | 1.00 54.72 | C |
| ATOM | 5083 | CA | LEU C 200 | 70.702 134.188 9.028 | 1.00 54.72 | C |
| ATOM | 5084 | CB | LEU C 200 | 69.822 133.750 10.209 | 1.00 51.02 | C |
| ATOM | 5085 | CG | LEU C 200 | 69.795 132.231 10.424 | 1.00 51.02 | C |
| ATOM | 5086 | CD1 | LEU C 200 | 68.560 131.831 11.201 | 1.00 51.02 | C |

| ATOM | 5087 | CD2 | LEU C 200 | 69.817 | 131.531 | 9.088 | 1.00 | 51.02 | C |
|------|------|-----|-----------|--------|---------|-------|------|-------|---|
| ATOM | 5088 | C | LEU C 200 | 70.826 | 135.714 | 8.956 | 1.00 | 54.72 | C |
| ATOM | 5089 | O | LEU C 200 | 69.850 | 136.420 | 8.653 | 1.00 | 54.72 | C |
| ATOM | 5090 | N | GLY C 201 | 72.025 | 136.227 | 9.221 | 1.00 | 88.81 | C |
| ATOM | 5091 | CA | GLY C 201 | 72.227 | 137.661 | 9.126 | 1.00 | 88.81 | C |
| ATOM | 5092 | C | GLY C 201 | 72.626 | 138.423 | 10.373 | 1.00 | 88.81 | C |
| ATOM | 5093 | O | GLY C 201 | 73.504 | 139.284 | 10.309 | 1.00 | 88.81 | C |
| ATOM | 5094 | N | TYR C 202 | 71.983 | 138.133 | 11.500 | 1.00 | 50.03 | C |
| ATOM | 5095 | CA | TYR C 202 | 72.304 | 138.830 | 12.736 | 1.00 | 50.03 | C |
| ATOM | 5096 | CB | TYR C 202 | 71.568 | 138.221 | 13.923 | 1.00 | 91.56 | C |
| ATOM | 5097 | CG | TYR C 202 | 70.107 | 138.029 | 13.669 | 1.00 | 91.56 | C |
| ATOM | 5098 | CD1 | TYR C 202 | 69.642 | 136.875 | 13.064 | 1.00 | 91.56 | C |
| ATOM | 5099 | CE1 | TYR C 202 | 68.305 | 136.705 | 12.786 | 1.00 | 91.56 | C |
| ATOM | 5100 | CD2 | TYR C 202 | 69.192 | 139.018 | 13.993 | 1.00 | 91.56 | C |
| ATOM | 5101 | CE2 | TYR C 202 | 67.846 | 138.861 | 13.719 | 1.00 | 91.56 | C |
| ATOM | 5102 | CZ | TYR C 202 | 67.406 | 137.700 | 13.117 | 1.00 | 91.56 | C |
| ATOM | 5103 | OH | TYR C 202 | 66.063 | 137.510 | 12.877 | 1.00 | 91.56 | C |
| ATOM | 5104 | C | TYR C 202 | 73.786 | 138.717 | 12.963 | 1.00 | 50.03 | C |
| ATOM | 5105 | O | TYR C 202 | 74.435 | 137.843 | 12.396 | 1.00 | 50.03 | C |
| ATOM | 5106 | N | ASP C 203 | 74.318 | 139.609 | 13.788 | 1.00 | 56.36 | C |
| ATOM | 5107 | CA | ASP C 203 | 75.738 | 139.628 | 14.095 | 1.00 | 56.36 | C |
| ATOM | 5108 | CB | ASP C 203 | 76.587 | 139.377 | 12.833 | 1.00 | 100.07 | C |
| ATOM | 5109 | CG | ASP C 203 | 76.061 | 140.117 | 11.599 | 1.00 | 100.07 | C |
| ATOM | 5110 | OD1 | ASP C 203 | 75.712 | 141.316 | 11.712 | 1.00 | 100.07 | C |
| ATOM | 5111 | OD2 | ASP C 203 | 76.011 | 139.493 | 10.511 | 1.00 | 100.07 | C |
| ATOM | 5112 | C | ASP C 203 | 76.152 | 140.949 | 14.716 | 1.00 | 56.36 | C |
| ATOM | 5113 | O | ASP C 203 | 75.904 | 142.018 | 14.165 | 1.00 | 56.36 | C |
| ATOM | 5114 | N | GLN C 204 | 76.785 | 140.846 | 15.876 | 1.00 | 72.47 | C |
| ATOM | 5115 | CA | GLN C 204 | 77.287 | 141.989 | 16.621 | 1.00 | 72.47 | C |
| ATOM | 5116 | CB | GLN C 204 | 78.592 | 142.483 | 15.997 | 1.00 | 72.98 | C |
| ATOM | 5117 | CG | GLN C 204 | 79.460 | 143.213 | 16.987 | 1.00 | 72.98 | C |
| ATOM | 5118 | CD | GLN C 204 | 79.751 | 142.357 | 18.206 | 1.00 | 72.98 | C |
| ATOM | 5119 | OE1 | GLN C 204 | 78.831 | 141.861 | 18.867 | 1.00 | 72.98 | C |
| ATOM | 5120 | NE2 | GLN C 204 | 81.035 | 142.176 | 18.510 | 1.00 | 72.98 | C |
| ATOM | 5121 | C | GLN C 204 | 76.332 | 143.159 | 16.742 | 1.00 | 72.47 | C |
| ATOM | 5122 | O | GLN C 204 | 75.809 | 143.650 | 15.750 | 1.00 | 72.47 | C |
| ATOM | 5123 | N | GLU C 205 | 76.124 | 143.613 | 17.968 | 1.00 | 53.41 | C |
| ATOM | 5124 | CA | GLU C 205 | 75.254 | 144.749 | 18.200 | 1.00 | 53.41 | C |
| ATOM | 5125 | CB | GLU C 205 | 75.979 | 146.045 | 17.820 | 1.00 | 100.07 | C |
| ATOM | 5126 | CG | GLU C 205 | 77.134 | 146.410 | 18.755 | 1.00 | 100.07 | C |
| ATOM | 5127 | CD | GLU C 205 | 77.684 | 147.806 | 18.493 | 1.00 | 100.07 | C |
| ATOM | 5128 | OE1 | GLU C 205 | 78.190 | 148.044 | 17.375 | 1.00 | 100.07 | C |
| ATOM | 5129 | OE2 | GLU C 205 | 77.609 | 148.666 | 19.401 | 1.00 | 100.07 | C |
| ATOM | 5130 | C | GLU C 205 | 73.933 | 144.642 | 17.444 | 1.00 | 53.41 | C |
| ATOM | 5131 | O | GLU C 205 | 72.900 | 144.391 | 18.058 | 1.00 | 53.41 | C |
| ATOM | 5132 | N | THR C 206 | 73.946 | 144.842 | 16.125 | 1.00 | 100.07 | C |
| ATOM | 5133 | CA | THR C 206 | 72.708 | 144.727 | 15.349 | 1.00 | 100.07 | C |
| ATOM | 5134 | CB | THR C 206 | 72.987 | 144.559 | 13.806 | 1.00 | 92.33 | C |
| ATOM | 5135 | OG1 | THR C 206 | 71.781 | 144.790 | 13.064 | 1.00 | 92.33 | C |
| ATOM | 5136 | CG2 | THR C 206 | 73.487 | 143.159 | 13.481 | 1.00 | 92.33 | C |
| ATOM | 5137 | C | THR C 206 | 72.031 | 143.481 | 15.916 | 1.00 | 100.07 | C |
| ATOM | 5138 | O | THR C 206 | 70.806 | 143.345 | 15.898 | 1.00 | 100.07 | C |
| ATOM | 5139 | N | LEU C 207 | 72.866 | 142.589 | 16.447 | 1.00 | 55.66 | C |
| ATOM | 5140 | CA | LEU C 207 | 72.407 | 141.361 | 17.070 | 1.00 | 55.66 | C |
| ATOM | 5141 | CB | LEU C 207 | 73.581 | 140.389 | 17.240 | 1.00 | 81.45 | C |
| ATOM | 5142 | CG | LEU C 207 | 73.260 | 139.010 | 17.825 | 1.00 | 81.45 | C |
| ATOM | 5143 | CD1 | LEU C 207 | 72.044 | 138.425 | 17.132 | 1.00 | 81.45 | C |
| ATOM | 5144 | CD2 | LEU C 207 | 74.456 | 138.090 | 17.667 | 1.00 | 81.45 | C |
| ATOM | 5145 | C | LEU C 207 | 71.859 | 141.782 | 18.423 | 1.00 | 55.66 | C |
| ATOM | 5146 | O | LEU C 207 | 70.789 | 142.388 | 18.501 | 1.00 | 55.66 | C |
| ATOM | 5147 | N | VAL C 208 | 72.583 | 141.458 | 19.488 | 1.00 | 65.79 | C |
| ATOM | 5148 | CA | VAL C 208 | 72.161 | 141.863 | 20.820 | 1.00 | 65.79 | C |
| ATOM | 5149 | CB | VAL C 208 | 72.873 | 141.073 | 21.921 | 1.00 | 100.07 | C |
| ATOM | 5150 | CG1 | VAL C 208 | 72.747 | 141.797 | 23.244 | 1.00 | 100.07 | C |
| ATOM | 5151 | CG2 | VAL C 208 | 72.273 | 139.693 | 22.029 | 1.00 | 100.07 | C |
| ATOM | 5152 | C | VAL C 208 | 72.612 | 143.302 | 20.871 | 1.00 | 65.79 | C |
| ATOM | 5153 | O | VAL C 208 | 73.547 | 143.674 | 20.158 | 1.00 | 65.79 | C |
| ATOM | 5154 | N | ARG C 209 | 71.979 | 144.089 | 21.735 | 1.00 | 99.95 | C |
| ATOM | 5155 | CA | ARG C 209 | 72.252 | 145.519 | 21.840 | 1.00 | 99.95 | C |
| ATOM | 5156 | CB | ARG C 209 | 73.729 | 145.826 | 21.533 | 1.00 | 100.07 | C |
| ATOM | 5157 | CG | ARG C 209 | 74.700 | 145.161 | 22.527 | 1.00 | 100.07 | C |
| ATOM | 5158 | CD | ARG C 209 | 76.155 | 145.589 | 22.327 | 1.00 | 100.07 | C |
| ATOM | 5159 | NE | ARG C 209 | 77.002 | 145.186 | 23.453 | 1.00 | 100.07 | C |
| ATOM | 5160 | CZ | ARG C 209 | 78.293 | 145.491 | 23.580 | 1.00 | 100.07 | C |
| ATOM | 5161 | NH1 | ARG C 209 | 78.910 | 146.206 | 22.648 | 1.00 | 100.07 | C |
| ATOM | 5162 | NH2 | ARG C 209 | 78.971 | 145.085 | 24.648 | 1.00 | 100.07 | C |
| ATOM | 5163 | C | ARG C 209 | 71.313 | 145.972 | 20.730 | 1.00 | 99.95 | C |
| ATOM | 5164 | O | ARG C 209 | 71.573 | 146.903 | 19.970 | 1.00 | 99.95 | C |
| ATOM | 5165 | N | GLU C 210 | 70.207 | 145.231 | 20.683 | 1.00 | 71.12 | C |
| ATOM | 5166 | CA | GLU C 210 | 69.107 | 145.358 | 19.738 | 1.00 | 71.12 | C |
| ATOM | 5167 | CB | GLU C 210 | 69.636 | 145.502 | 18.308 | 1.00 | 100.07 | C |
| ATOM | 5168 | CG | GLU C 210 | 69.087 | 146.704 | 17.548 | 1.00 | 100.07 | C |
| ATOM | 5169 | CD | GLU C 210 | 69.703 | 148.018 | 17.998 | 1.00 | 100.07 | C |
| ATOM | 5170 | OE1 | GLU C 210 | 70.945 | 148.141 | 17.931 | 1.00 | 100.07 | C |

| ATOM | 5171 | OE2 | GLU C 210 | 68.946 148.927 18.410 | 1.00 100.07 | C |
|------|------|-----|-----------|------------------------|-------------|---|
| ATOM | 5172 | C   | GLU C 210 | 68.385 144.008 19.900 | 1.00 71.12  | C |
| ATOM | 5173 | O   | GLU C 210 | 67.498 143.633 19.121 | 1.00 71.12  | C |
| ATOM | 5174 | N   | LEU C 211 | 68.819 143.273 20.921 | 1.00 54.95  | C |
| ATOM | 5175 | CA  | LEU C 211 | 68.251 141.980 21.264 | 1.00 54.95  | C |
| ATOM | 5176 | CB  | LEU C 211 | 69.046 140.836 20.631 | 1.00 69.50  | C |
| ATOM | 5177 | CG  | LEU C 211 | 68.786 139.481 21.316 | 1.00 69.50  | C |
| ATOM | 5178 | CD1 | LEU C 211 | 67.314 139.125 21.179 | 1.00 69.50  | C |
| ATOM | 5179 | CD2 | LEU C 211 | 69.652 138.389 20.723 | 1.00 69.50  | C |
| ATOM | 5180 | C   | LEU C 211 | 68.321 141.826 22.768 | 1.00 54.95  | C |
| ATOM | 5181 | O   | LEU C 211 | 67.340 142.025 23.493 | 1.00 54.95  | C |
| ATOM | 5182 | N   | SER C 212 | 69.509 141.459 23.222 | 1.00 99.88  | C |
| ATOM | 5183 | CA  | SER C 212 | 69.743 141.255 24.632 | 1.00 99.88  | C |
| ATOM | 5184 | CB  | SER C 212 | 70.710 140.092 24.827 | 1.00 100.07 | C |
| ATOM | 5185 | OG  | SER C 212 | 70.406 139.040 23.925 | 1.00 100.07 | C |
| ATOM | 5186 | C   | SER C 212 | 70.316 142.534 25.214 | 1.00 99.88  | C |
| ATOM | 5187 | O   | SER C 212 | 70.620 143.474 24.480 | 1.00 99.88  | C |
| ATOM | 5188 | N   | ALA C 213 | 70.461 142.553 26.534 | 1.00 65.46  | C |
| ATOM | 5189 | CA  | ALA C 213 | 70.968 143.699 27.270 | 1.00 65.46  | C |
| ATOM | 5190 | CB  | ALA C 213 | 70.391 144.994 26.729 | 1.00 50.68  | C |
| ATOM | 5191 | C   | ALA C 213 | 70.424 143.442 28.645 | 1.00 65.46  | C |
| ATOM | 5192 | O   | ALA C 213 | 71.167 143.102 29.563 | 1.00 65.46  | C |
| ATOM | 5193 | N   | TYR C 214 | 69.109 143.589 28.779 | 1.00 100.07 | C |
| ATOM | 5194 | CA  | TYR C 214 | 68.478 143.334 30.059 | 1.00 100.07 | C |
| ATOM | 5195 | CB  | TYR C 214 | 66.943 143.486 29.966 | 1.00 65.35  | C |
| ATOM | 5196 | CG  | TYR C 214 | 66.223 142.649 28.912 | 1.00 65.35  | C |
| ATOM | 5197 | CD1 | TYR C 214 | 66.765 141.448 28.420 | 1.00 65.35  | C |
| ATOM | 5198 | CE1 | TYR C 214 | 66.079 140.661 27.496 | 1.00 65.35  | C |
| ATOM | 5199 | CD2 | TYR C 214 | 64.967 143.034 28.446 | 1.00 65.35  | C |
| ATOM | 5200 | CE2 | TYR C 214 | 64.270 142.249 27.523 | 1.00 65.35  | C |
| ATOM | 5201 | CZ  | TYR C 214 | 64.833 141.070 27.052 | 1.00 65.35  | C |
| ATOM | 5202 | OH  | TYR C 214 | 64.154 140.331 26.113 | 1.00 65.35  | C |
| ATOM | 5203 | C   | TYR C 214 | 68.883 141.914 30.470 | 1.00 100.07 | C |
| ATOM | 5204 | O   | TYR C 214 | 69.010 141.597 31.654 | 1.00 100.07 | C |
| ATOM | 5205 | N   | GLY C 215 | 69.107 141.072 29.467 | 1.00 80.24  | C |
| ATOM | 5206 | CA  | GLY C 215 | 69.520 139.712 29.711 | 1.00 80.24  | C |
| ATOM | 5207 | C   | GLY C 215 | 70.896 139.628 29.099 | 1.00 80.24  | C |
| ATOM | 5208 | O   | GLY C 215 | 71.041 139.784 27.887 | 1.00 80.24  | C |
| ATOM | 5209 | N   | ASP C 216 | 71.912 139.421 29.931 | 1.00 73.01  | C |
| ATOM | 5210 | CA  | ASP C 216 | 73.282 139.326 29.439 | 1.00 73.01  | C |
| ATOM | 5211 | CB  | ASP C 216 | 74.256 139.267 30.613 | 1.00 100.07 | C |
| ATOM | 5212 | CG  | ASP C 216 | 74.180 140.505 31.482 | 1.00 100.07 | C |
| ATOM | 5213 | OD1 | ASP C 216 | 73.091 140.775 32.028 | 1.00 100.07 | C |
| ATOM | 5214 | OD2 | ASP C 216 | 75.198 141.217 31.613 | 1.00 100.07 | C |
| ATOM | 5215 | C   | ASP C 216 | 73.394 138.082 28.589 | 1.00 73.01  | C |
| ATOM | 5216 | O   | ASP C 216 | 72.720 137.959 27.569 | 1.00 73.01  | C |
| ATOM | 5217 | N   | LEU C 217 | 74.243 137.153 28.999 | 1.00 98.70  | C |
| ATOM | 5218 | CA  | LEU C 217 | 74.384 135.915 28.249 | 1.00 98.70  | C |
| ATOM | 5219 | CB  | LEU C 217 | 73.049 135.152 28.263 | 1.00 100.07 | C |
| ATOM | 5220 | CG  | LEU C 217 | 72.003 135.553 29.323 | 1.00 100.07 | C |
| ATOM | 5221 | CD1 | LEU C 217 | 70.897 134.520 29.360 | 1.00 100.07 | C |
| ATOM | 5222 | CD2 | LEU C 217 | 72.634 135.656 30.701 | 1.00 100.07 | C |
| ATOM | 5223 | C   | LEU C 217 | 74.801 136.221 26.811 | 1.00 98.70  | C |
| ATOM | 5224 | O   | LEU C 217 | 74.785 135.344 25.943 | 1.00 98.70  | C |
| ATOM | 5225 | N   | VAL C 218 | 75.160 137.480 26.570 | 1.00 98.49  | C |
| ATOM | 5226 | CA  | VAL C 218 | 75.601 137.918 25.253 | 1.00 98.49  | C |
| ATOM | 5227 | CB  | VAL C 218 | 75.181 139.364 24.954 | 1.00 59.59  | C |
| ATOM | 5228 | CG1 | VAL C 218 | 75.392 139.661 23.475 | 1.00 59.59  | C |
| ATOM | 5229 | CG2 | VAL C 218 | 73.744 139.585 25.370 | 1.00 59.59  | C |
| ATOM | 5230 | C   | VAL C 218 | 77.116 137.865 25.264 | 1.00 98.49  | C |
| ATOM | 5231 | O   | VAL C 218 | 77.741 137.482 24.279 | 1.00 98.49  | C |
| ATOM | 5232 | N   | GLN C 219 | 77.699 138.265 26.392 | 1.00 84.51  | C |
| ATOM | 5233 | CA  | GLN C 219 | 79.146 138.236 26.560 | 1.00 84.51  | C |
| ATOM | 5234 | CB  | GLN C 219 | 79.528 138.715 27.965 | 1.00 100.03 | C |
| ATOM | 5235 | CG  | GLN C 219 | 79.308 140.201 28.224 | 1.00 100.03 | C |
| ATOM | 5236 | CD  | GLN C 219 | 79.498 140.581 29.696 | 1.00 100.03 | C |
| ATOM | 5237 | OE1 | GLN C 219 | 80.426 140.112 30.362 | 1.00 100.03 | C |
| ATOM | 5238 | NE2 | GLN C 219 | 78.622 141.446 30.202 | 1.00 100.03 | C |
| ATOM | 5239 | C   | GLN C 219 | 79.592 136.784 26.365 | 1.00 84.51  | C |
| ATOM | 5240 | O   | GLN C 219 | 80.743 136.426 26.620 | 1.00 84.51  | C |
| ATOM | 5241 | N   | GLY C 220 | 78.650 135.955 25.926 | 1.00 93.33  | C |
| ATOM | 5242 | CA  | GLY C 220 | 78.918 134.554 25.679 | 1.00 93.33  | C |
| ATOM | 5243 | C   | GLY C 220 | 78.294 134.174 24.352 | 1.00 93.33  | C |
| ATOM | 5244 | O   | GLY C 220 | 78.074 132.997 24.059 | 1.00 93.33  | C |
| ATOM | 5245 | N   | LEU C 221 | 78.004 135.194 23.551 | 1.00 91.77  | C |
| ATOM | 5246 | CA  | LEU C 221 | 77.402 135.018 22.233 | 1.00 91.77  | C |
| ATOM | 5247 | CB  | LEU C 221 | 75.948 135.498 22.252 | 1.00 48.22  | C |
| ATOM | 5248 | CG  | LEU C 221 | 75.104 135.084 21.051 | 1.00 48.22  | C |
| ATOM | 5249 | CD1 | LEU C 221 | 74.677 133.644 21.284 | 1.00 48.22  | C |
| ATOM | 5250 | CD2 | LEU C 221 | 73.891 135.998 20.877 | 1.00 48.22  | C |
| ATOM | 5251 | C   | LEU C 221 | 78.191 135.868 21.239 | 1.00 91.77  | C |
| ATOM | 5252 | O   | LEU C 221 | 77.843 135.961 20.063 | 1.00 91.77  | C |
| ATOM | 5253 | N   | LEU C 222 | 79.263 136.481 21.728 | 1.00 68.85  | C |
| ATOM | 5254 | CA  | LEU C 222 | 80.083 137.355 20.913 | 1.00 68.85  | C |

```
ATOM   5255  CB  LEU C 222      80.269 138.670  21.652  1.00 50.24           C
ATOM   5256  CG  LEU C 222      78.933 139.159  22.213  1.00 50.24           C
ATOM   5257  CD1 LEU C 222      79.164 140.356  23.113  1.00 50.24           C
ATOM   5258  CD2 LEU C 222      77.983 139.500  21.082  1.00 50.24           C
ATOM   5259  C   LEU C 222      81.434 136.778  20.514  1.00 68.85           C
ATOM   5260  O   LEU C 222      81.876 136.979  19.391  1.00 68.85           C
ATOM   5261  N   ASP C 223      82.112 136.079  21.417  1.00100.07           C
ATOM   5262  CA  ASP C 223      83.399 135.502  21.040  1.00100.07           C
ATOM   5263  CB  ASP C 223      84.250 135.159  22.255  1.00 99.92           C
ATOM   5264  CG  ASP C 223      85.546 134.498  21.862  1.00 99.92           C
ATOM   5265  OD1 ASP C 223      86.279 135.089  21.043  1.00 99.92           C
ATOM   5266  OD2 ASP C 223      85.821 133.388  22.359  1.00 99.92           C
ATOM   5267  C   ASP C 223      83.191 134.252  20.201  1.00100.07           C
ATOM   5268  O   ASP C 223      82.099 133.676  20.188  1.00100.07           C
ATOM   5269  N   GLU C 224      84.242 133.823  19.512  1.00100.07           C
ATOM   5270  CA  GLU C 224      84.145 132.669  18.625  1.00100.07           C
ATOM   5271  CB  GLU C 224      83.543 131.453  19.340  1.00100.07           C
ATOM   5272  CG  GLU C 224      83.776 130.126  18.610  1.00100.07           C
ATOM   5273  CD  GLU C 224      85.253 129.726  18.548  1.00100.07           C
ATOM   5274  OE1 GLU C 224      85.869 129.546  19.621  1.00100.07           C
ATOM   5275  OE2 GLU C 224      85.800 129.585  17.430  1.00100.07           C
ATOM   5276  C   GLU C 224      83.196 133.179  17.547  1.00100.07           C
ATOM   5277  O   GLU C 224      82.964 132.537  16.525  1.00100.07           C
ATOM   5278  N   ALA C 225      82.656 134.364  17.819  1.00100.07           C
ATOM   5279  CA  ALA C 225      81.744 135.081  16.940  1.00100.07           C
ATOM   5280  CB  ALA C 225      80.427 135.373  17.650  1.00100.07           C
ATOM   5281  C   ALA C 225      82.491 136.370  16.648  1.00100.07           C
ATOM   5282  O   ALA C 225      82.201 137.079  15.678  1.00100.07           C
ATOM   5283  N   VAL C 226      83.446 136.669  17.532  1.00100.07           C
ATOM   5284  CA  VAL C 226      84.315 137.823  17.364  1.00100.07           C
ATOM   5285  CB  VAL C 226      85.339 137.943  18.525  1.00 78.06           C
ATOM   5286  CG1 VAL C 226      86.249 139.144  18.302  1.00 78.06           C
ATOM   5287  CG2 VAL C 226      84.615 138.086  19.846  1.00 78.06           C
ATOM   5288  C   VAL C 226      85.009 137.314  16.111  1.00100.07           C
ATOM   5289  O   VAL C 226      85.512 138.069  15.277  1.00100.07           C
ATOM   5290  N   LEU C 227      85.002 135.987  16.008  1.00100.07           C
ATOM   5291  CA  LEU C 227      85.553 135.281  14.875  1.00100.07           C
ATOM   5292  CB  LEU C 227      85.899 133.836  15.249  1.00 73.25           C
ATOM   5293  CG  LEU C 227      86.534 133.549  16.611  1.00 73.25           C
ATOM   5294  CD1 LEU C 227      86.971 132.090  16.656  1.00 73.25           C
ATOM   5295  CD2 LEU C 227      87.718 134.470  16.844  1.00 73.25           C
ATOM   5296  C   LEU C 227      84.398 135.273  13.885  1.00100.07           C
ATOM   5297  O   LEU C 227      84.449 135.929  12.848  1.00100.07           C
ATOM   5298  N   ALA C 228      83.340 134.551  14.245  1.00 73.62           C
ATOM   5299  CA  ALA C 228      82.159 134.419  13.400  1.00 73.62           C
ATOM   5300  CB  ALA C 228      81.008 133.853  14.213  1.00  5.07           C
ATOM   5301  C   ALA C 228      81.718 135.697  12.672  1.00 73.62           C
ATOM   5302  O   ALA C 228      80.865 136.452  13.153  1.00 73.62           C
ATOM   5303  N   MET C 229      82.307 135.907  11.493  1.00 77.26           C
ATOM   5304  CA  MET C 229      82.021 137.056  10.637  1.00 77.26           C
ATOM   5305  CB  MET C 229      82.959 138.218  10.986  1.00 99.54           C
ATOM   5306  CG  MET C 229      83.253 138.388  12.465  1.00 99.54           C
ATOM   5307  SD  MET C 229      81.831 138.883  13.422  1.00 99.54           C
ATOM   5308  CE  MET C 229      82.273 140.581  13.802  1.00 99.54           C
ATOM   5309  C   MET C 229      82.247 136.652   9.165  1.00 77.26           C
ATOM   5310  O   MET C 229      83.396 136.541   8.730  1.00 77.26           C
ATOM   5311  N   ARG C 230      81.156 136.434   8.421  1.00100.07           C
ATOM   5312  CA  ARG C 230      81.176 136.049   6.993  1.00100.07           C
ATOM   5313  CB  ARG C 230      82.581 135.579   6.559  1.00100.07           C
ATOM   5314  CG  ARG C 230      82.762 135.220   5.064  1.00100.07           C
ATOM   5315  CD  ARG C 230      84.259 135.064   4.733  1.00100.07           C
ATOM   5316  NE  ARG C 230      84.556 134.258   3.545  1.00100.07           C
ATOM   5317  CZ  ARG C 230      84.164 134.547   2.305  1.00100.07           C
ATOM   5318  NH1 ARG C 230      83.441 135.634   2.071  1.00100.07           C
ATOM   5319  NH2 ARG C 230      84.513 133.757   1.291  1.00100.07           C
ATOM   5320  C   ARG C 230      80.153 134.947   6.692  1.00100.07           C
ATOM   5321  O   ARG C 230      80.460 133.758   6.792  1.00100.07           C
ATOM   5322  N   PRO C 231      78.924 135.330   6.304  1.00 40.50           C
ATOM   5323  CD  PRO C 231      78.526 136.671   5.859  1.00 42.04           C
ATOM   5324  CA  PRO C 231      77.866 134.361   5.994  1.00 40.50           C
ATOM   5325  CB  PRO C 231      76.813 135.205   5.295  1.00 42.04           C
ATOM   5326  CG  PRO C 231      77.617 136.335   4.719  1.00 42.04           C
ATOM   5327  C   PRO C 231      78.360 133.232   5.124  1.00 40.50           C
ATOM   5328  O   PRO C 231      78.371 132.080   5.546  1.00 40.50           C
ATOM   5329  N   GLU C 232      78.762 133.573   3.905  1.00 92.40           C
ATOM   5330  CA  GLU C 232      79.277 132.582   2.973  1.00 92.40           C
ATOM   5331  CB  GLU C 232      80.204 133.251   1.952  1.00100.07           C
ATOM   5332  CG  GLU C 232      80.567 132.408   0.722  1.00100.07           C
ATOM   5333  CD  GLU C 232      81.568 131.294   1.003  1.00100.07           C
ATOM   5334  OE1 GLU C 232      81.189 130.297   1.650  1.00100.07           C
ATOM   5335  OE2 GLU C 232      82.738 131.418   0.570  1.00100.07           C
ATOM   5336  C   GLU C 232      80.059 131.608   3.831  1.00 92.40           C
ATOM   5337  O   GLU C 232      79.703 130.437   3.942  1.00 92.40           C
ATOM   5338  N   GLU C 233      81.104 132.119   4.472  1.00 52.83           C
```

```
ATOM   5339  CA  GLU C 233      81.941 131.309   5.336  1.00 52.83           C
ATOM   5340  CB  GLU C 233      82.932 132.177   6.098  1.00 82.05           C
ATOM   5341  CG  GLU C 233      84.350 131.927   5.695  1.00 82.05           C
ATOM   5342  CD  GLU C 233      84.679 130.463   5.754  1.00 82.05           C
ATOM   5343  OE1 GLU C 233      84.626 129.893   6.864  1.00 82.05           C
ATOM   5344  OE2 GLU C 233      84.977 129.883   4.688  1.00 82.05           C
ATOM   5345  C   GLU C 233      81.076 130.575   6.322  1.00 52.83           C
ATOM   5346  O   GLU C 233      81.131 129.354   6.405  1.00 52.83           C
ATOM   5347  N   ALA C 234      80.269 131.332   7.059  1.00 72.93           C
ATOM   5348  CA  ALA C 234      79.377 130.774   8.068  1.00 72.93           C
ATOM   5349  CB  ALA C 234      78.211 131.711   8.305  1.00 11.79           C
ATOM   5350  C   ALA C 234      78.858 129.396   7.693  1.00 72.93           C
ATOM   5351  O   ALA C 234      79.104 128.424   8.407  1.00 72.93           C
ATOM   5352  N   MET C 235      78.149 129.311   6.573  1.00 69.38           C
ATOM   5353  CA  MET C 235      77.592 128.044   6.114  1.00 69.38           C
ATOM   5354  CB  MET C 235      77.031 128.204   4.715  1.00 63.02           C
ATOM   5355  CG  MET C 235      76.343 129.507   4.493  1.00 63.02           C
ATOM   5356  SD  MET C 235      75.998 129.651   2.762  1.00 63.02           C
ATOM   5357  CE  MET C 235      74.270 129.324   2.748  1.00 63.02           C
ATOM   5358  C   MET C 235      78.626 126.924   6.095  1.00 69.38           C
ATOM   5359  O   MET C 235      78.380 125.831   6.607  1.00 69.38           C
ATOM   5360  N   VAL C 236      79.776 127.193   5.487  1.00 79.28           C
ATOM   5361  CA  VAL C 236      80.842 126.201   5.403  1.00 79.28           C
ATOM   5362  CB  VAL C 236      82.046 126.740   4.577  1.00 68.86           C
ATOM   5363  CG1 VAL C 236      83.247 125.810   4.713  1.00 68.86           C
ATOM   5364  CG2 VAL C 236      81.655 126.857   3.110  1.00 68.86           C
ATOM   5365  C   VAL C 236      81.317 125.795   6.797  1.00 79.28           C
ATOM   5366  O   VAL C 236      81.317 124.613   7.148  1.00 79.28           C
ATOM   5367  N   ARG C 237      81.713 126.778   7.595  1.00 71.28           C
ATOM   5368  CA  ARG C 237      82.190 126.500   8.938  1.00 71.28           C
ATOM   5369  CB  ARG C 237      82.357 127.798   9.726  1.00100.07           C
ATOM   5370  CG  ARG C 237      82.899 127.579  11.124  1.00100.07           C
ATOM   5371  CD  ARG C 237      82.447 128.678  12.069  1.00100.07           C
ATOM   5372  NE  ARG C 237      82.653 128.298  13.467  1.00100.07           C
ATOM   5373  CZ  ARG C 237      82.152 128.959  14.506  1.00100.07           C
ATOM   5374  NH1 ARG C 237      81.408 130.044  14.315  1.00100.07           C
ATOM   5375  NH2 ARG C 237      82.394 128.530  15.738  1.00100.07           C
ATOM   5376  C   ARG C 237      81.211 125.592   9.665  1.00 71.28           C
ATOM   5377  O   ARG C 237      81.595 124.851  10.567  1.00 71.28           C
ATOM   5378  N   LEU C 238      79.946 125.653   9.263  1.00 96.52           C
ATOM   5379  CA  LEU C 238      78.897 124.845   9.875  1.00 96.52           C
ATOM   5380  CB  LEU C 238      77.562 125.572   9.765  1.00 29.95           C
ATOM   5381  CG  LEU C 238      76.433 125.042  10.639  1.00 29.95           C
ATOM   5382  CD1 LEU C 238      76.794 125.328  12.090  1.00 29.95           C
ATOM   5383  CD2 LEU C 238      75.105 125.699  10.265  1.00 29.95           C
ATOM   5384  C   LEU C 238      78.782 123.473   9.206  1.00 96.52           C
ATOM   5385  O   LEU C 238      78.873 122.433   9.870  1.00 96.52           C
ATOM   5386  N   PHE C 239      78.560 123.485   7.891  1.00 77.89           C
ATOM   5387  CA  PHE C 239      78.444 122.259   7.106  1.00 77.89           C
ATOM   5388  CB  PHE C 239      78.727 122.562   5.635  1.00 99.87           C
ATOM   5389  CG  PHE C 239      77.738 121.957   4.684  1.00 99.87           C
ATOM   5390  CD1 PHE C 239      77.187 122.723   3.660  1.00 99.87           C
ATOM   5391  CD2 PHE C 239      77.390 120.616   4.777  1.00 99.87           C
ATOM   5392  CE1 PHE C 239      76.306 122.164   2.740  1.00 99.87           C
ATOM   5393  CE2 PHE C 239      76.514 120.045   3.861  1.00 99.87           C
ATOM   5394  CZ  PHE C 239      75.970 120.822   2.840  1.00 99.87           C
ATOM   5395  C   PHE C 239      79.509 121.339   7.671  1.00 77.89           C
ATOM   5396  O   PHE C 239      79.265 120.168   7.939  1.00 77.89           C
ATOM   5397  N   THR C 240      80.692 121.907   7.866  1.00 42.59           C
ATOM   5398  CA  THR C 240      81.806 121.184   8.443  1.00 42.59           C
ATOM   5399  CB  THR C 240      82.940 122.145   8.869  1.00 59.06           C
ATOM   5400  OG1 THR C 240      83.463 122.801   7.709  1.00 59.06           C
ATOM   5401  CG2 THR C 240      84.064 121.386   9.585  1.00 59.06           C
ATOM   5402  C   THR C 240      81.299 120.475   9.685  1.00 42.59           C
ATOM   5403  O   THR C 240      81.233 119.251   9.718  1.00 42.59           C
ATOM   5404  N   LEU C 241      80.938 121.261  10.697  1.00100.07           C
ATOM   5405  CA  LEU C 241      80.440 120.742  11.967  1.00100.07           C
ATOM   5406  CB  LEU C 241      79.885 121.880  12.818  1.00 44.55           C
ATOM   5407  CG  LEU C 241      80.862 123.035  13.055  1.00 44.55           C
ATOM   5408  CD1 LEU C 241      80.105 124.199  13.661  1.00 44.55           C
ATOM   5409  CD2 LEU C 241      82.011 122.600  13.950  1.00 44.55           C
ATOM   5410  C   LEU C 241      79.376 119.678  11.762  1.00100.07           C
ATOM   5411  O   LEU C 241      79.093 118.892  12.667  1.00100.07           C
ATOM   5412  N   LEU C 242      78.771 119.671  10.579  1.00 72.59           C
ATOM   5413  CA  LEU C 242      77.781 118.654  10.245  1.00 72.59           C
ATOM   5414  CB  LEU C 242      76.519 119.298   9.674  1.00 85.83           C
ATOM   5415  CG  LEU C 242      75.641 119.902  10.779  1.00 85.83           C
ATOM   5416  CD1 LEU C 242      76.424 120.948  11.554  1.00 85.83           C
ATOM   5417  CD2 LEU C 242      74.388 120.509  10.172  1.00 85.83           C
ATOM   5418  C   LEU C 242      78.452 117.697   9.249  1.00 72.59           C
ATOM   5419  O   LEU C 242      77.998 117.494   8.115  1.00 72.59           C
ATOM   5420  N   ARG C 243      79.560 117.142   9.747  1.00 80.45           C
ATOM   5421  CA  ARG C 243      80.477 116.195   9.107  1.00 80.45           C
ATOM   5422  CB  ARG C 243      80.728 115.021  10.066  1.00100.07           C
```

```
ATOM   5423  CG   ARG C 243      81.593 115.348  11.287  1.00100.07           C
ATOM   5424  CD   ARG C 243      81.309 114.390  12.458  1.00100.07           C
ATOM   5425  NE   ARG C 243      81.285 112.979  12.063  1.00100.07           C
ATOM   5426  CZ   ARG C 243      80.944 111.970  12.865  1.00100.07           C
ATOM   5427  NH1  ARG C 243      80.593 112.193  14.124  1.00100.07           C
ATOM   5428  NH2  ARG C 243      80.947 110.728  12.401  1.00100.07           C
ATOM   5429  C    ARG C 243      80.221 115.630   7.713  1.00 80.45           C
ATOM   5430  O    ARG C 243      81.092 115.718   6.848  1.00 80.45           C
ATOM   5431  N    PRO C 244      79.040 115.026   7.479  1.00100.07           C
ATOM   5432  CD   PRO C 244      77.926 114.899   8.442  1.00100.07           C
ATOM   5433  CA   PRO C 244      78.662 114.428   6.189  1.00100.07           C
ATOM   5434  CB   PRO C 244      77.137 114.414   6.258  1.00100.07           C
ATOM   5435  CG   PRO C 244      76.910 114.036   7.682  1.00100.07           C
ATOM   5436  C    PRO C 244      79.182 115.035   4.880  1.00100.07           C
ATOM   5437  O    PRO C 244      79.316 116.258   4.736  1.00100.07           C
ATOM   5438  N    GLY C 245      79.464 114.145   3.929  1.00100.07           C
ATOM   5439  CA   GLY C 245      79.958 114.546   2.626  1.00100.07           C
ATOM   5440  C    GLY C 245      81.149 115.481   2.650  1.00100.07           C
ATOM   5441  O    GLY C 245      81.632 115.863   1.585  1.00100.07           C
ATOM   5442  N    ASP C 246      81.633 115.831   3.844  1.00 94.17           C
ATOM   5443  CA   ASP C 246      82.760 116.752   3.983  1.00 94.17           C
ATOM   5444  CB   ASP C 246      84.082 115.985   4.017  1.00100.07           C
ATOM   5445  CG   ASP C 246      84.160 115.025   5.186  1.00100.07           C
ATOM   5446  OD1  ASP C 246      83.824 115.444   6.316  1.00100.07           C
ATOM   5447  OD2  ASP C 246      84.562 113.858   4.979  1.00100.07           C
ATOM   5448  C    ASP C 246      82.711 117.697   2.785  1.00 94.17           C
ATOM   5449  O    ASP C 246      83.503 117.583   1.841  1.00 94.17           C
ATOM   5450  N    PRO C 247      81.755 118.643   2.813  1.00100.07           C
ATOM   5451  CD   PRO C 247      80.680 118.638   3.826  1.00100.07           C
ATOM   5452  CA   PRO C 247      81.486 119.659   1.788  1.00100.07           C
ATOM   5453  CB   PRO C 247      79.997 119.917   1.977  1.00100.07           C
ATOM   5454  CG   PRO C 247      79.879 119.860   3.462  1.00100.07           C
ATOM   5455  C    PRO C 247      82.270 120.982   1.720  1.00100.07           C
ATOM   5456  O    PRO C 247      81.725 121.972   1.231  1.00100.07           C
ATOM   5457  N    PRO C 248      83.533 121.032   2.197  1.00 72.68           C
ATOM   5458  CD   PRO C 248      84.379 120.051   2.903  1.00100.07           C
ATOM   5459  CA   PRO C 248      84.222 122.324   2.092  1.00 72.68           C
ATOM   5460  CB   PRO C 248      85.658 121.971   2.459  1.00100.07           C
ATOM   5461  CG   PRO C 248      85.459 120.925   3.516  1.00100.07           C
ATOM   5462  C    PRO C 248      84.088 122.925   0.689  1.00 72.68           C
ATOM   5463  O    PRO C 248      84.942 122.741  -0.186  1.00 72.68           C
ATOM   5464  N    LYS C 249      82.985 123.642   0.506  1.00 69.22           C
ATOM   5465  CA   LYS C 249      82.628 124.292  -0.743  1.00 69.22           C
ATOM   5466  CB   LYS C 249      82.582 123.285  -1.896  1.00 87.67           C
ATOM   5467  CG   LYS C 249      81.946 123.851  -3.167  1.00 87.67           C
ATOM   5468  CD   LYS C 249      82.165 122.950  -4.375  1.00 87.67           C
ATOM   5469  CE   LYS C 249      81.743 123.648  -5.664  1.00 87.67           C
ATOM   5470  NZ   LYS C 249      82.217 122.925  -6.877  1.00 87.67           C
ATOM   5471  C    LYS C 249      81.239 124.855  -0.537  1.00 69.22           C
ATOM   5472  O    LYS C 249      80.285 124.096  -0.383  1.00 69.22           C
ATOM   5473  N    LYS C 250      81.129 126.178  -0.516  1.00 32.54           C
ATOM   5474  CA   LYS C 250      79.839 126.843  -0.340  1.00 32.54           C
ATOM   5475  CB   LYS C 250      79.882 128.204  -1.043  1.00100.07           C
ATOM   5476  CG   LYS C 250      80.749 128.202  -2.308  1.00100.07           C
ATOM   5477  CD   LYS C 250      80.961 129.609  -2.869  1.00100.07           C
ATOM   5478  CE   LYS C 250      81.923 129.608  -4.060  1.00100.07           C
ATOM   5479  NZ   LYS C 250      82.124 130.976  -4.631  1.00100.07           C
ATOM   5480  C    LYS C 250      78.712 125.982  -0.911  1.00 32.54           C
ATOM   5481  O    LYS C 250      78.908 125.290  -1.910  1.00 32.54           C
ATOM   5482  N    ASP C 251      77.539 126.007  -0.286  1.00100.07           C
ATOM   5483  CA   ASP C 251      76.431 125.196  -0.786  1.00100.07           C
ATOM   5484  CB   ASP C 251      76.517 123.777  -0.233  1.00100.07           C
ATOM   5485  CG   ASP C 251      77.281 122.859  -1.149  1.00100.07           C
ATOM   5486  OD1  ASP C 251      76.846 122.701  -2.311  1.00100.07           C
ATOM   5487  OD2  ASP C 251      78.317 122.308  -0.718  1.00100.07           C
ATOM   5488  C    ASP C 251      75.029 125.720  -0.560  1.00100.07           C
ATOM   5489  O    ASP C 251      74.193 125.652  -1.464  1.00100.07           C
ATOM   5490  N    LYS C 252      74.762 126.227   0.638  1.00100.07           C
ATOM   5491  CA   LYS C 252      73.437 126.743   0.944  1.00100.07           C
ATOM   5492  CB   LYS C 252      72.988 127.725  -0.136  1.00 81.51           C
ATOM   5493  CG   LYS C 252      71.546 128.170  -0.011  1.00 81.51           C
ATOM   5494  CD   LYS C 252      71.222 129.287  -0.994  1.00 81.51           C
ATOM   5495  CE   LYS C 252      69.844 129.868  -0.732  1.00 81.51           C
ATOM   5496  NZ   LYS C 252      69.602 131.058  -1.578  1.00 81.51           C
ATOM   5497  C    LYS C 252      72.474 125.576   1.007  1.00100.07           C
ATOM   5498  O    LYS C 252      71.506 125.594   1.768  1.00100.07           C
ATOM   5499  N    ALA C 253      72.744 124.561   0.193  1.00100.07           C
ATOM   5500  CA   ALA C 253      71.922 123.362   0.166  1.00100.07           C
ATOM   5501  CB   ALA C 253      72.496 122.352  -0.808  1.00100.07           C
ATOM   5502  C    ALA C 253      71.959 122.813   1.580  1.00100.07           C
ATOM   5503  O    ALA C 253      72.704 123.324   2.424  1.00100.07           C
ATOM   5504  N    LEU C 254      71.186 121.765   1.840  1.00 81.03           C
ATOM   5505  CA   LEU C 254      71.133 121.211   3.183  1.00 81.03           C
ATOM   5506  CB   LEU C 254      72.543 121.064   3.761  1.00 10.72           C
```

-66-

```
ATOM   5507  CG   LEU C 254      72.617 120.785   5.262  1.00 10.72           C
ATOM   5508  CD1  LEU C 254      71.649 119.664   5.693  1.00 10.72           C
ATOM   5509  CD2  LEU C 254      74.029 120.414   5.586  1.00 10.72           C
ATOM   5510  C    LEU C 254      70.335 122.252   3.959  1.00 81.03           C
ATOM   5511  O    LEU C 254      69.256 121.962   4.482  1.00 81.03           C
ATOM   5512  N    ALA C 255      70.875 123.469   4.023  1.00 39.51           C
ATOM   5513  CA   ALA C 255      70.185 124.579   4.670  1.00 39.51           C
ATOM   5514  CB   ALA C 255      71.140 125.786   4.834  1.00 16.33           C
ATOM   5515  C    ALA C 255      69.057 124.878   3.664  1.00 39.51           C
ATOM   5516  O    ALA C 255      68.135 125.649   3.919  1.00 39.51           C
ATOM   5517  N    TYR C 256      69.154 124.224   2.510  1.00 72.15           C
ATOM   5518  CA   TYR C 256      68.158 124.340   1.455  1.00 72.15           C
ATOM   5519  CB   TYR C 256      68.586 123.493   0.247  1.00100.07           C
ATOM   5520  CG   TYR C 256      68.440 124.166  -1.112  1.00100.07           C
ATOM   5521  CD1  TYR C 256      69.177 125.309  -1.437  1.00100.07           C
ATOM   5522  CE1  TYR C 256      69.056 125.920  -2.704  1.00100.07           C
ATOM   5523  CD2  TYR C 256      67.575 123.647  -2.084  1.00100.07           C
ATOM   5524  CE2  TYR C 256      67.447 124.250  -3.352  1.00100.07           C
ATOM   5525  CZ   TYR C 256      68.188 125.385  -3.654  1.00100.07           C
ATOM   5526  OH   TYR C 256      68.051 125.988  -4.889  1.00100.07           C
ATOM   5527  C    TYR C 256      66.905 123.752   2.106  1.00 72.15           C
ATOM   5528  O    TYR C 256      65.813 123.773   1.544  1.00 72.15           C
ATOM   5529  N    LEU C 257      67.103 123.209   3.303  1.00 82.61           C
ATOM   5530  CA   LEU C 257      66.042 122.616   4.107  1.00 82.61           C
ATOM   5531  CB   LEU C 257      66.359 121.153   4.437  1.00100.07           C
ATOM   5532  CG   LEU C 257      66.487 120.060   3.373  1.00100.07           C
ATOM   5533  CD1  LEU C 257      66.967 118.776   4.050  1.00100.07           C
ATOM   5534  CD2  LEU C 257      65.161 119.825   2.685  1.00100.07           C
ATOM   5535  C    LEU C 257      66.001 123.419   5.407  1.00 82.61           C
ATOM   5536  O    LEU C 257      65.991 124.650   5.369  1.00 82.61           C
ATOM   5537  N    PHE C 258      65.991 122.708   6.541  1.00 51.05           C
ATOM   5538  CA   PHE C 258      65.976 123.303   7.877  1.00 51.05           C
ATOM   5539  CB   PHE C 258      67.381 123.254   8.482  1.00 99.09           C
ATOM   5540  CG   PHE C 258      68.011 121.890   8.464  1.00 99.09           C
ATOM   5541  CD1  PHE C 258      68.064 121.142   7.290  1.00 99.09           C
ATOM   5542  CD2  PHE C 258      68.599 121.372   9.614  1.00 99.09           C
ATOM   5543  CE1  PHE C 258      68.691 119.896   7.258  1.00 99.09           C
ATOM   5544  CE2  PHE C 258      69.231 120.126   9.597  1.00 99.09           C
ATOM   5545  CZ   PHE C 258      69.280 119.387   8.414  1.00 99.09           C
ATOM   5546  C    PHE C 258      65.498 124.757   7.841  1.00 51.05           C
ATOM   5547  O    PHE C 258      66.114 125.655   8.430  1.00 51.05           C
ATOM   5548  N    GLY C 259      64.391 124.979   7.145  1.00 53.98           C
ATOM   5549  CA   GLY C 259      63.862 126.316   7.019  1.00 53.98           C
ATOM   5550  C    GLY C 259      63.382 126.452   5.600  1.00 53.98           C
ATOM   5551  O    GLY C 259      62.180 126.551   5.364  1.00 53.98           C
ATOM   5552  N    LEU C 260      64.318 126.434   4.653  1.00 49.38           C
ATOM   5553  CA   LEU C 260      63.981 126.550   3.231  1.00 49.38           C
ATOM   5554  CB   LEU C 260      65.271 126.554   2.348  1.00 43.29           C
ATOM   5555  CG   LEU C 260      65.306 126.925   0.832  1.00 43.29           C
ATOM   5556  CD1  LEU C 260      66.711 127.330   0.447  1.00 43.29           C
ATOM   5557  CD2  LEU C 260      64.848 125.776  -0.058  1.00 43.29           C
ATOM   5558  C    LEU C 260      63.076 125.378   2.842  1.00 49.38           C
ATOM   5559  O    LEU C 260      63.017 124.371   3.545  1.00 49.38           C
ATOM   5560  N    LEU C 261      62.372 125.551   1.726  1.00100.07           C
ATOM   5561  CA   LEU C 261      61.466 124.565   1.150  1.00100.07           C
ATOM   5562  CB   LEU C 261      62.272 123.548   0.315  1.00 79.47           C
ATOM   5563  CG   LEU C 261      62.716 122.180   0.856  1.00 79.47           C
ATOM   5564  CD1  LEU C 261      63.559 121.476  -0.194  1.00 79.47           C
ATOM   5565  CD2  LEU C 261      63.511 122.331   2.123  1.00 79.47           C
ATOM   5566  C    LEU C 261      60.552 123.835   2.130  1.00100.07           C
ATOM   5567  O    LEU C 261      60.971 123.425   3.209  1.00100.07           C
ATOM   5568  N    ALA C 262      59.289 123.683   1.740  1.00 66.60           C
ATOM   5569  CA   ALA C 262      58.306 122.982   2.557  1.00 66.60           C
ATOM   5570  CB   ALA C 262      56.894 123.410   2.173  1.00 19.85           C
ATOM   5571  C    ALA C 262      58.465 121.479   2.349  1.00 66.60           C
ATOM   5572  O    ALA C 262      57.476 120.754   2.215  1.00 66.60           C
ATOM   5573  N    ASP C 263      59.711 121.021   2.297  1.00 87.18           C
ATOM   5574  CA   ASP C 263      59.982 119.603   2.128  1.00 87.18           C
ATOM   5575  CB   ASP C 263      61.383 119.377   1.546  1.00 93.30           C
ATOM   5576  CG   ASP C 263      61.993 118.054   1.986  1.00 93.30           C
ATOM   5577  OD1  ASP C 263      61.307 117.016   1.862  1.00 93.30           C
ATOM   5578  OD2  ASP C 263      63.154 118.052   2.456  1.00 93.30           C
ATOM   5579  C    ASP C 263      59.859 118.915   3.481  1.00 87.18           C
ATOM   5580  O    ASP C 263      59.160 117.907   3.605  1.00 87.18           C
ATOM   5581  N    PRO C 264      60.556 119.439   4.510  1.00100.07           C
ATOM   5582  CD   PRO C 264      61.872 120.081   4.360  1.00100.07           C
ATOM   5583  CA   PRO C 264      60.486 118.836   5.841  1.00100.07           C
ATOM   5584  CB   PRO C 264      61.847 118.156   5.957  1.00100.07           C
ATOM   5585  CG   PRO C 264      62.789 119.085   5.086  1.00100.07           C
ATOM   5586  C    PRO C 264      60.256 119.856   6.973  1.00100.07           C
ATOM   5587  O    PRO C 264      60.894 119.776   8.023  1.00100.07           C
ATOM   5588  N    LYS C 265      59.349 120.804   6.758  1.00 72.31           C
ATOM   5589  CA   LYS C 265      59.048 121.836   7.753  1.00 72.31           C
ATOM   5590  CB   LYS C 265      60.196 122.857   7.820  1.00 61.50           C
```

```
ATOM   5591  CG   LYS C 265      60.204 123.796   9.035  1.00 61.50           C
ATOM   5592  CD   LYS C 265      60.899 123.147  10.239  1.00 61.50           C
ATOM   5593  CE   LYS C 265      61.087 124.124  11.387  1.00 61.50           C
ATOM   5594  NZ   LYS C 265      61.852 123.539  12.524  1.00 61.50           C
ATOM   5595  C    LYS C 265      57.807 122.536   7.242  1.00 72.31           C
ATOM   5596  O    LYS C 265      57.822 123.041   6.120  1.00 72.31           C
ATOM   5597  N    ARG C 266      56.732 122.573   8.025  1.00100.07           C
ATOM   5598  CA   ARG C 266      55.543 123.258   7.532  1.00100.07           C
ATOM   5599  CB   ARG C 266      54.941 122.482   6.353  1.00100.07           C
ATOM   5600  CG   ARG C 266      53.930 123.275   5.517  1.00100.07           C
ATOM   5601  CD   ARG C 266      53.633 122.575   4.186  1.00100.07           C
ATOM   5602  NE   ARG C 266      52.774 123.371   3.310  1.00100.07           C
ATOM   5603  CZ   ARG C 266      52.493 123.057   2.049  1.00100.07           C
ATOM   5604  NH1  ARG C 266      53.005 121.959   1.509  1.00100.07           C
ATOM   5605  NH2  ARG C 266      51.707 123.846   1.325  1.00100.07           C
ATOM   5606  C    ARG C 266      54.447 123.558   8.540  1.00100.07           C
ATOM   5607  O    ARG C 266      53.804 124.607   8.454  1.00100.07           C
ATOM   5608  N    TYR C 267      54.234 122.656   9.496  1.00 84.65           C
ATOM   5609  CA   TYR C 267      53.173 122.841  10.490  1.00 84.65           C
ATOM   5610  CB   TYR C 267      53.466 124.029  11.401  1.00 86.36           C
ATOM   5611  CG   TYR C 267      54.922 124.194  11.775  1.00 86.36           C
ATOM   5612  CD1  TYR C 267      55.839 124.731  10.871  1.00 86.36           C
ATOM   5613  CE1  TYR C 267      57.162 124.942  11.228  1.00 86.36           C
ATOM   5614  CD2  TYR C 267      55.374 123.868  13.048  1.00 86.36           C
ATOM   5615  CE2  TYR C 267      56.696 124.078  13.416  1.00 86.36           C
ATOM   5616  CZ   TYR C 267      57.583 124.616  12.504  1.00 86.36           C
ATOM   5617  OH   TYR C 267      58.890 124.827  12.867  1.00 86.36           C
ATOM   5618  C    TYR C 267      51.891 123.103   9.707  1.00 84.65           C
ATOM   5619  O    TYR C 267      50.884 123.568  10.255  1.00 84.65           C
ATOM   5620  N    ALA C 268      51.984 122.803   8.409  1.00100.07           C
ATOM   5621  CA   ALA C 268      50.920 122.939   7.411  1.00100.07           C
ATOM   5622  CB   ALA C 268      50.044 121.675   7.419  1.00100.07           C
ATOM   5623  C    ALA C 268      50.037 124.189   7.495  1.00100.07           C
ATOM   5624  O    ALA C 268      48.819 124.080   7.718  1.00100.07           C
ATOM   5625  N    ALA C 269      50.646 125.361   7.283  1.00100.07           C
ATOM   5626  CA   ALA C 269      49.934 126.646   7.335  1.00100.07           C
ATOM   5627  CB   ALA C 269      49.281 126.949   5.977  1.00100.07           C
ATOM   5628  C    ALA C 269      48.875 126.637   8.440  1.00100.07           C
ATOM   5629  O    ALA C 269      47.958 127.469   8.452  1.00100.07           C
ATOM   5630  N    GLY C 270      49.030 125.682   9.360  1.00 89.18           C
ATOM   5631  CA   GLY C 270      48.118 125.515  10.469  1.00 89.18           C
ATOM   5632  C    GLY C 270      48.834 125.823  11.762  1.00 89.18           C
ATOM   5633  O    GLY C 270      50.049 125.625  11.875  1.00 89.18           C
ATOM   5634  N    ALA C 271      48.058 126.312  12.726  1.00 96.46           C
ATOM   5635  CA   ALA C 271      48.535 126.702  14.051  1.00 96.46           C
ATOM   5636  CB   ALA C 271      47.351 126.775  15.015  1.00 65.34           C
ATOM   5637  C    ALA C 271      49.624 125.792  14.615  1.00 96.46           C
ATOM   5638  O    ALA C 271      49.810 124.668  14.141  1.00 96.46           C
ATOM   5639  N    ALA C 272      50.328 126.287  15.635  1.00 66.27           C
ATOM   5640  CA   ALA C 272      51.422 125.546  16.265  1.00 66.27           C
ATOM   5641  CB   ALA C 272      50.971 124.154  16.673  1.00100.07           C
ATOM   5642  C    ALA C 272      52.488 125.464  15.199  1.00 66.27           C
ATOM   5643  O    ALA C 272      52.524 124.527  14.402  1.00 66.27           C
ATOM   5644  N    GLY C 273      53.360 126.458  15.201  1.00 72.04           C
ATOM   5645  CA   GLY C 273      54.401 126.555  14.199  1.00 72.04           C
ATOM   5646  C    GLY C 273      54.035 127.902  13.644  1.00 72.04           C
ATOM   5647  O    GLY C 273      54.708 128.483  12.797  1.00 72.04           C
ATOM   5648  N    ALA C 274      52.916 128.381  14.178  1.00 17.99           C
ATOM   5649  CA   ALA C 274      52.341 129.672  13.865  1.00 17.99           C
ATOM   5650  CB   ALA C 274      51.802 129.688  12.429  1.00 26.15           C
ATOM   5651  C    ALA C 274      51.211 129.906  14.874  1.00 17.99           C
ATOM   5652  O    ALA C 274      51.170 129.285  15.951  1.00 17.99           C
ATOM   5653  N    ALA C 275      50.305 130.808  14.509  1.00100.07           C
ATOM   5654  CA   ALA C 275      49.160 131.172  15.331  1.00100.07           C
ATOM   5655  CB   ALA C 275      47.865 130.813  14.600  1.00 36.93           C
ATOM   5656  C    ALA C 275      49.172 130.551  16.728  1.00100.07           C
ATOM   5657  O    ALA C 275      49.986 130.940  17.570  1.00100.07           C
ATOM   5658  N    ALA C 276      48.281 129.580  16.950  1.00 99.84           C
ATOM   5659  CA   ALA C 276      48.108 128.890  18.236  1.00 99.84           C
ATOM   5660  CB   ALA C 276      47.739 127.437  18.016  1.00  5.07           C
ATOM   5661  C    ALA C 276      49.263 128.956  19.207  1.00 99.84           C
ATOM   5662  O    ALA C 276      49.059 128.866  20.417  1.00 99.84           C
ATOM   5663  N    ALA C 277      50.477 129.090  18.693  1.00 75.88           C
ATOM   5664  CA   ALA C 277      51.622 129.160  19.574  1.00 75.88           C
ATOM   5665  CB   ALA C 277      52.113 127.747  19.908  1.00100.07           C
ATOM   5666  C    ALA C 277      52.756 129.983  18.998  1.00 75.88           C
ATOM   5667  O    ALA C 277      53.021 131.091  19.463  1.00 75.88           C
ATOM   5668  N    ALA C 278      53.428 129.426  17.994  1.00 47.49           C
ATOM   5669  CA   ALA C 278      54.558 130.089  17.371  1.00 47.49           C
ATOM   5670  CB   ALA C 278      54.720 129.613  15.966  1.00 23.99           C
ATOM   5671  C    ALA C 278      54.351 131.588  17.394  1.00 47.49           C
ATOM   5672  O    ALA C 278      54.982 132.291  18.189  1.00 47.49           C
ATOM   5673  N    GLU C 279      53.454 132.069  16.534  1.00100.07           C
ATOM   5674  CA   GLU C 279      53.156 133.493  16.458  1.00100.07           C
```

| ATOM | 5675 | CB | GLU | C | 279 | 52.197 | 133.787 | 15.298 | 1.00 | 100.07 | C |
| ATOM | 5676 | CG | GLU | C | 279 | 52.880 | 133.871 | 13.939 | 1.00 | 100.07 | C |
| ATOM | 5677 | CD | GLU | C | 279 | 51.981 | 134.458 | 12.859 | 1.00 | 100.07 | C |
| ATOM | 5678 | OE1 | GLU | C | 279 | 51.425 | 135.562 | 13.075 | 1.00 | 100.07 | C |
| ATOM | 5679 | OE2 | GLU | C | 279 | 51.838 | 133.818 | 11.791 | 1.00 | 100.07 | C |
| ATOM | 5680 | C | GLU | C | 279 | 52.567 | 134.021 | 17.762 | 1.00 | 100.07 | C |
| ATOM | 5681 | O | GLU | C | 279 | 52.471 | 135.233 | 17.960 | 1.00 | 100.07 | C |
| ATOM | 5682 | N | LYS | C | 280 | 52.175 | 133.120 | 18.657 | 1.00 | 81.12 | C |
| ATOM | 5683 | CA | LYS | C | 280 | 51.618 | 133.552 | 19.928 | 1.00 | 81.12 | C |
| ATOM | 5684 | CB | LYS | C | 280 | 50.574 | 132.564 | 20.431 | 1.00 | 49.89 | C |
| ATOM | 5685 | CG | LYS | C | 280 | 49.621 | 133.205 | 21.430 | 1.00 | 49.89 | C |
| ATOM | 5686 | CD | LYS | C | 280 | 49.261 | 134.642 | 21.000 | 1.00 | 49.89 | C |
| ATOM | 5687 | CE | LYS | C | 280 | 48.687 | 134.698 | 19.577 | 1.00 | 49.89 | C |
| ATOM | 5688 | NZ | LYS | C | 280 | 48.550 | 136.094 | 19.073 | 1.00 | 49.89 | C |
| ATOM | 5689 | C | LYS | C | 280 | 52.696 | 133.742 | 20.983 | 1.00 | 81.12 | C |
| ATOM | 5690 | O | LYS | C | 280 | 52.419 | 133.738 | 22.181 | 1.00 | 81.12 | C |
| ATOM | 5691 | N | LEU | C | 281 | 53.925 | 133.908 | 20.508 | 1.00 | 61.88 | C |
| ATOM | 5692 | CA | LEU | C | 281 | 55.108 | 134.127 | 21.334 | 1.00 | 61.88 | C |
| ATOM | 5693 | CB | LEU | C | 281 | 55.520 | 132.839 | 22.056 | 1.00 | 76.71 | C |
| ATOM | 5694 | CG | LEU | C | 281 | 54.539 | 132.276 | 23.087 | 1.00 | 76.71 | C |
| ATOM | 5695 | CD1 | LEU | C | 281 | 55.055 | 130.969 | 23.676 | 1.00 | 76.71 | C |
| ATOM | 5696 | CD2 | LEU | C | 281 | 54.333 | 133.317 | 24.168 | 1.00 | 76.71 | C |
| ATOM | 5697 | C | LEU | C | 281 | 56.170 | 134.524 | 20.321 | 1.00 | 61.88 | C |
| ATOM | 5698 | O | LEU | C | 281 | 57.237 | 133.905 | 20.232 | 1.00 | 61.88 | C |
| ATOM | 5699 | N | GLY | C | 282 | 55.844 | 135.548 | 19.534 | 1.00 | 89.14 | C |
| ATOM | 5700 | CA | GLY | C | 282 | 56.754 | 136.028 | 18.505 | 1.00 | 89.14 | C |
| ATOM | 5701 | C | GLY | C | 282 | 56.138 | 137.047 | 17.556 | 1.00 | 89.14 | C |
| ATOM | 5702 | O | GLY | C | 282 | 56.759 | 137.462 | 16.570 | 1.00 | 89.14 | C |
| ATOM | 5703 | N | VAL | C | 283 | 54.903 | 137.439 | 17.851 | 1.00 | 88.20 | C |
| ATOM | 5704 | CA | VAL | C | 283 | 54.199 | 138.428 | 17.052 | 1.00 | 88.20 | C |
| ATOM | 5705 | CB | VAL | C | 283 | 55.091 | 139.670 | 16.821 | 1.00 | 100.07 | C |
| ATOM | 5706 | CG1 | VAL | C | 283 | 54.280 | 140.781 | 16.169 | 1.00 | 100.07 | C |
| ATOM | 5707 | CG2 | VAL | C | 283 | 55.691 | 140.135 | 18.145 | 1.00 | 100.07 | C |
| ATOM | 5708 | C | VAL | C | 283 | 53.714 | 137.913 | 15.699 | 1.00 | 88.20 | C |
| ATOM | 5709 | O | VAL | C | 283 | 52.506 | 137.821 | 15.460 | 1.00 | 88.20 | C |
| ATOM | 5710 | N | GLY | C | 284 | 54.648 | 137.582 | 14.812 | 1.00 | 54.85 | C |
| ATOM | 5711 | CA | GLY | C | 284 | 54.254 | 137.109 | 13.497 | 1.00 | 54.85 | C |
| ATOM | 5712 | C | GLY | C | 284 | 55.070 | 135.958 | 12.939 | 1.00 | 54.85 | C |
| ATOM | 5713 | O | GLY | C | 284 | 55.853 | 135.323 | 13.657 | 1.00 | 54.85 | C |
| ATOM | 5714 | N | LEU | C | 285 | 54.859 | 135.682 | 11.651 | 1.00 | 56.96 | C |
| ATOM | 5715 | CA | LEU | C | 285 | 55.566 | 134.615 | 10.938 | 1.00 | 56.96 | C |
| ATOM | 5716 | CB | LEU | C | 285 | 55.563 | 133.330 | 11.769 | 1.00 | 65.06 | C |
| ATOM | 5717 | CG | LEU | C | 285 | 56.924 | 132.701 | 12.073 | 1.00 | 65.06 | C |
| ATOM | 5718 | CD1 | LEU | C | 285 | 56.706 | 131.522 | 12.993 | 1.00 | 65.06 | C |
| ATOM | 5719 | CD2 | LEU | C | 285 | 57.614 | 132.256 | 10.793 | 1.00 | 65.06 | C |
| ATOM | 5720 | C | LEU | C | 285 | 54.972 | 134.331 | 9.554 | 1.00 | 56.96 | C |
| ATOM | 5721 | O | LEU | C | 285 | 54.267 | 135.165 | 8.979 | 1.00 | 56.96 | C |
| ATOM | 5722 | N | SER | C | 286 | 55.274 | 133.141 | 9.034 | 1.00 | 100.07 | C |
| ATOM | 5723 | CA | SER | C | 286 | 54.802 | 132.695 | 7.723 | 1.00 | 100.07 | C |
| ATOM | 5724 | CB | SER | C | 286 | 55.404 | 133.573 | 6.614 | 1.00 | 92.37 | C |
| ATOM | 5725 | OG | SER | C | 286 | 55.095 | 134.946 | 6.798 | 1.00 | 92.37 | C |
| ATOM | 5726 | C | SER | C | 286 | 55.214 | 131.237 | 7.485 | 1.00 | 100.07 | C |
| ATOM | 5727 | O | SER | C | 286 | 56.104 | 130.971 | 6.680 | 1.00 | 100.07 | C |
| ATOM | 5728 | N | GLY | C | 287 | 54.575 | 130.295 | 8.172 | 1.00 | 81.48 | C |
| ATOM | 5729 | CA | GLY | C | 287 | 54.944 | 128.903 | 7.985 | 1.00 | 81.48 | C |
| ATOM | 5730 | C | GLY | C | 287 | 56.365 | 128.649 | 8.468 | 1.00 | 81.48 | C |
| ATOM | 5731 | O | GLY | C | 287 | 56.907 | 129.455 | 9.227 | 1.00 | 81.48 | C |
| ATOM | 5732 | N | ALA | C | 288 | 56.969 | 127.546 | 8.018 | 1.00 | 69.71 | C |
| ATOM | 5733 | CA | ALA | C | 288 | 58.337 | 127.125 | 8.393 | 1.00 | 69.71 | C |
| ATOM | 5734 | CB | ALA | C | 288 | 58.997 | 126.395 | 7.223 | 1.00 | 54.40 | C |
| ATOM | 5735 | C | ALA | C | 288 | 59.338 | 128.138 | 8.952 | 1.00 | 69.71 | C |
| ATOM | 5736 | O | ALA | C | 288 | 59.283 | 129.335 | 8.681 | 1.00 | 69.71 | C |
| ATOM | 5737 | N | THR | C | 289 | 60.280 | 127.602 | 9.717 | 1.00 | 100.07 | C |
| ATOM | 5738 | CA | THR | C | 289 | 61.337 | 128.373 | 10.358 | 1.00 | 100.07 | C |
| ATOM | 5739 | CB | THR | C | 289 | 62.183 | 127.468 | 11.290 | 1.00 | 67.47 | C |
| ATOM | 5740 | OG1 | THR | C | 289 | 61.347 | 126.892 | 12.301 | 1.00 | 67.47 | C |
| ATOM | 5741 | CG2 | THR | C | 289 | 63.286 | 128.261 | 11.947 | 1.00 | 67.47 | C |
| ATOM | 5742 | C | THR | C | 289 | 62.284 | 128.994 | 9.337 | 1.00 | 100.07 | C |
| ATOM | 5743 | O | THR | C | 289 | 62.572 | 128.384 | 8.307 | 1.00 | 100.07 | C |
| ATOM | 5744 | N | LEU | C | 290 | 62.756 | 130.208 | 9.631 | 1.00 | 25.23 | C |
| ATOM | 5745 | CA | LEU | C | 290 | 63.710 | 130.912 | 8.770 | 1.00 | 25.23 | C |
| ATOM | 5746 | CB | LEU | C | 290 | 65.067 | 130.239 | 8.929 | 1.00 | 100.07 | C |
| ATOM | 5747 | CG | LEU | C | 290 | 66.237 | 130.717 | 8.087 | 1.00 | 100.07 | C |
| ATOM | 5748 | CD1 | LEU | C | 290 | 66.668 | 132.100 | 8.534 | 1.00 | 100.07 | C |
| ATOM | 5749 | CD2 | LEU | C | 290 | 67.374 | 129.727 | 8.248 | 1.00 | 100.07 | C |
| ATOM | 5750 | C | LEU | C | 290 | 63.332 | 130.942 | 7.287 | 1.00 | 25.23 | C |
| ATOM | 5751 | O | LEU | C | 290 | 63.176 | 129.891 | 6.671 | 1.00 | 25.23 | C |
| ATOM | 5752 | N | VAL | C | 291 | 63.195 | 132.131 | 6.703 | 1.00 | 100.07 | C |
| ATOM | 5753 | CA | VAL | C | 291 | 62.858 | 132.202 | 5.282 | 1.00 | 100.07 | C |
| ATOM | 5754 | CB | VAL | C | 291 | 62.652 | 133.652 | 4.797 | 1.00 | 71.19 | C |
| ATOM | 5755 | CG1 | VAL | C | 291 | 62.031 | 133.642 | 3.403 | 1.00 | 71.19 | C |
| ATOM | 5756 | CG2 | VAL | C | 291 | 61.752 | 134.407 | 5.767 | 1.00 | 71.19 | C |
| ATOM | 5757 | C | VAL | C | 291 | 64.031 | 131.577 | 4.532 | 1.00 | 100.07 | C |
| ATOM | 5758 | O | VAL | C | 291 | 64.780 | 130.797 | 5.119 | 1.00 | 100.07 | C |

| ATOM | 5759 | N | ALA C 292 | 64.215 131.905 | 3.254 | 1.00 100.07 | C |
|---|---|---|---|---|---|---|---|
| ATOM | 5760 | CA | ALA C 292 | 65.321 131.299 | 2.513 | 1.00 100.07 | C |
| ATOM | 5761 | CB | ALA C 292 | 65.063 129.801 | 2.355 | 1.00 100.07 | C |
| ATOM | 5762 | C | ALA C 292 | 65.684 131.890 | 1.154 | 1.00 100.07 | C |
| ATOM | 5763 | O | ALA C 292 | 65.429 133.061 | 0.867 | 1.00 100.07 | C |
| ATOM | 5764 | N | ALA C 293 | 66.299 131.038 | 0.335 | 1.00 100.07 | C |
| ATOM | 5765 | CA | ALA C 293 | 66.748 131.371 | −1.008 | 1.00 100.07 | C |
| ATOM | 5766 | CB | ALA C 293 | 66.909 130.084 | −1.819 | 1.00 63.42 | C |
| ATOM | 5767 | C | ALA C 293 | 65.845 132.360 | −1.755 | 1.00 100.07 | C |
| ATOM | 5768 | O | ALA C 293 | 64.958 131.970 | −2.524 | 1.00 100.07 | C |
| ATOM | 5769 | N | GLU C 294 | 66.087 133.647 | −1.523 | 1.00 99.91 | C |
| ATOM | 5770 | CA | GLU C 294 | 65.330 134.712 | −2.168 | 1.00 99.91 | C |
| ATOM | 5771 | CB | GLU C 294 | 64.719 135.635 | −1.119 | 1.00 100.07 | C |
| ATOM | 5772 | CG | GLU C 294 | 63.552 135.032 | −0.378 | 1.00 100.07 | C |
| ATOM | 5773 | CD | GLU C 294 | 62.824 136.059 | 0.451 | 1.00 100.07 | C |
| ATOM | 5774 | OE1 | GLU C 294 | 61.710 135.751 | 0.933 | 1.00 100.07 | C |
| ATOM | 5775 | OE2 | GLU C 294 | 63.372 137.173 | 0.617 | 1.00 100.07 | C |
| ATOM | 5776 | C | GLU C 294 | 66.284 135.504 | −3.037 | 1.00 99.91 | C |
| ATOM | 5777 | O | GLU C 294 | 66.307 135.363 | −4.261 | 1.00 99.91 | C |
| ATOM | 5778 | N | ASP C 295 | 67.065 136.348 | −2.380 | 1.00 95.05 | C |
| ATOM | 5779 | CA | ASP C 295 | 68.054 137.153 | −3.060 | 1.00 95.05 | C |
| ATOM | 5780 | CB | ASP C 295 | 68.041 138.580 | −2.516 | 1.00 100.07 | C |
| ATOM | 5781 | CG | ASP C 295 | 66.651 139.158 | −2.449 | 1.00 100.07 | C |
| ATOM | 5782 | OD1 | ASP C 295 | 65.914 139.028 | −3.448 | 1.00 100.07 | C |
| ATOM | 5783 | OD2 | ASP C 295 | 66.301 139.746 | −1.402 | 1.00 100.07 | C |
| ATOM | 5784 | C | ASP C 295 | 69.393 136.492 | −2.758 | 1.00 95.05 | C |
| ATOM | 5785 | O | ASP C 295 | 70.361 136.646 | −3.506 | 1.00 95.05 | C |
| ATOM | 5786 | N | GLY C 296 | 69.431 135.749 | −1.653 | 1.00 100.07 | C |
| ATOM | 5787 | CA | GLY C 296 | 70.645 135.064 | −1.244 | 1.00 100.07 | C |
| ATOM | 5788 | C | GLY C 296 | 70.417 134.198 | −0.018 | 1.00 100.07 | C |
| ATOM | 5789 | O | GLY C 296 | 69.728 133.180 | −0.092 | 1.00 100.07 | C |
| ATOM | 5790 | N | ALA C 297 | 70.989 134.597 | 1.114 | 1.00 100.03 | C |
| ATOM | 5791 | CA | ALA C 297 | 70.835 133.835 | 2.348 | 1.00 100.03 | C |
| ATOM | 5792 | CB | ALA C 297 | 71.762 134.378 | 3.425 | 1.00 32.08 | C |
| ATOM | 5793 | C | ALA C 297 | 69.397 133.907 | 2.822 | 1.00 100.03 | C |
| ATOM | 5794 | O | ALA C 297 | 68.624 134.743 | 2.355 | 1.00 100.03 | C |
| ATOM | 5795 | N | ALA C 298 | 69.040 133.030 | 3.750 | 1.00 52.31 | C |
| ATOM | 5796 | CA | ALA C 298 | 67.687 133.016 | 4.283 | 1.00 52.31 | C |
| ATOM | 5797 | CB | ALA C 298 | 67.437 131.684 | 4.964 | 1.00 100.07 | C |
| ATOM | 5798 | C | ALA C 298 | 67.547 134.166 | 5.287 | 1.00 52.31 | C |
| ATOM | 5799 | O | ALA C 298 | 68.532 134.849 | 5.577 | 1.00 52.31 | C |
| ATOM | 5800 | N | LYS C 299 | 66.337 134.409 | 5.795 | 1.00 94.40 | C |
| ATOM | 5801 | CA | LYS C 299 | 66.154 135.450 | 6.815 | 1.00 94.40 | C |
| ATOM | 5802 | CB | LYS C 299 | 65.529 136.722 | 6.242 | 1.00 99.97 | C |
| ATOM | 5803 | CG | LYS C 299 | 65.443 137.853 | 7.288 | 1.00 99.97 | C |
| ATOM | 5804 | CD | LYS C 299 | 66.813 138.136 | 7.929 | 1.00 99.97 | C |
| ATOM | 5805 | CE | LYS C 299 | 66.751 139.280 | 8.934 | 1.00 99.97 | C |
| ATOM | 5806 | NZ | LYS C 299 | 68.101 139.620 | 9.472 | 1.00 99.97 | C |
| ATOM | 5807 | C | LYS C 299 | 65.301 134.950 | 7.981 | 1.00 94.40 | C |
| ATOM | 5808 | O | LYS C 299 | 64.147 134.557 | 7.797 | 1.00 94.40 | C |
| ATOM | 5809 | N | ALA C 300 | 65.879 134.975 | 9.181 | 1.00 78.57 | C |
| ATOM | 5810 | CA | ALA C 300 | 65.192 134.493 | 10.372 | 1.00 78.57 | C |
| ATOM | 5811 | CB | ALA C 300 | 65.948 134.906 | 11.623 | 1.00 37.12 | C |
| ATOM | 5812 | C | ALA C 300 | 63.764 134.987 | 10.450 | 1.00 78.57 | C |
| ATOM | 5813 | O | ALA C 300 | 63.427 136.021 | 9.870 | 1.00 78.57 | C |
| ATOM | 5814 | N | GLU C 301 | 62.934 134.233 | 11.168 | 1.00 100.07 | C |
| ATOM | 5815 | CA | GLU C 301 | 61.527 134.575 | 11.354 | 1.00 100.07 | C |
| ATOM | 5816 | CB | GLU C 301 | 60.739 134.290 | 10.072 | 1.00 96.06 | C |
| ATOM | 5817 | CG | GLU C 301 | 59.407 135.016 | 9.988 | 1.00 96.06 | C |
| ATOM | 5818 | CD | GLU C 301 | 58.773 134.905 | 8.616 | 1.00 96.06 | C |
| ATOM | 5819 | OE1 | GLU C 301 | 59.454 135.229 | 7.621 | 1.00 96.06 | C |
| ATOM | 5820 | OE2 | GLU C 301 | 57.595 134.501 | 8.533 | 1.00 96.06 | C |
| ATOM | 5821 | C | GLU C 301 | 60.944 133.776 | 12.522 | 1.00 100.07 | C |
| ATOM | 5822 | O | GLU C 301 | 59.741 133.840 | 12.796 | 1.00 100.07 | C |
| ATOM | 5823 | N | VAL C 302 | 61.814 133.030 | 13.204 | 1.00 33.68 | C |
| ATOM | 5824 | CA | VAL C 302 | 61.427 132.210 | 14.351 | 1.00 33.68 | C |
| ATOM | 5825 | CB | VAL C 302 | 61.028 130.774 | 13.930 | 1.00 36.28 | C |
| ATOM | 5826 | CG1 | VAL C 302 | 60.952 129.861 | 15.149 | 1.00 36.28 | C |
| ATOM | 5827 | CG2 | VAL C 302 | 59.693 130.796 | 13.227 | 1.00 36.28 | C |
| ATOM | 5828 | C | VAL C 302 | 62.552 132.083 | 15.352 | 1.00 33.68 | C |
| ATOM | 5829 | O | VAL C 302 | 62.309 132.106 | 16.547 | 1.00 33.68 | C |
| ATOM | 5830 | N | PHE C 303 | 63.782 131.965 | 14.868 | 1.00 65.41 | C |
| ATOM | 5831 | CA | PHE C 303 | 64.914 131.789 | 15.763 | 1.00 65.41 | C |
| ATOM | 5832 | CB | PHE C 303 | 66.206 131.736 | 14.960 | 1.00 34.09 | C |
| ATOM | 5833 | CG | PHE C 303 | 66.554 130.360 | 14.558 | 1.00 34.09 | C |
| ATOM | 5834 | CD1 | PHE C 303 | 66.046 129.814 | 13.399 | 1.00 34.09 | C |
| ATOM | 5835 | CD2 | PHE C 303 | 67.264 129.545 | 15.420 | 1.00 34.09 | C |
| ATOM | 5836 | CE1 | PHE C 303 | 66.229 128.465 | 13.104 | 1.00 34.09 | C |
| ATOM | 5837 | CE2 | PHE C 303 | 67.453 128.191 | 15.136 | 1.00 34.09 | C |
| ATOM | 5838 | CZ | PHE C 303 | 66.931 127.653 | 13.976 | 1.00 34.09 | C |
| ATOM | 5839 | C | PHE C 303 | 65.059 132.718 | 16.966 | 1.00 65.41 | C |
| ATOM | 5840 | O | PHE C 303 | 64.229 132.676 | 17.881 | 1.00 65.41 | C |
| ATOM | 5841 | N | LEU C 304 | 66.109 133.539 | 16.991 | 1.00 61.39 | C |
| ATOM | 5842 | CA | LEU C 304 | 66.317 134.450 | 18.115 | 1.00 61.39 | C |

| ATOM | 5843 | CB | LEU | C | 304 | 67.266 | 135.588 | 17.751 | 1.00 | 60.59 | C |
|------|------|-----|-----|---|-----|--------|---------|--------|------|-------|---|
| ATOM | 5844 | CG | LEU | C | 304 | 66.753 | 136.531 | 16.671 | 1.00 | 60.59 | C |
| ATOM | 5845 | CD1 | LEU | C | 304 | 67.520 | 137.823 | 16.693 | 1.00 | 60.59 | C |
| ATOM | 5846 | CD2 | LEU | C | 304 | 66.864 | 135.837 | 15.338 | 1.00 | 60.59 | C |
| ATOM | 5847 | C | LEU | C | 304 | 65.011 | 135.032 | 18.633 | 1.00 | 61.39 | C |
| ATOM | 5848 | O | LEU | C | 304 | 64.885 | 135.278 | 19.825 | 1.00 | 61.39 | C |
| ATOM | 5849 | N | PRO | C | 305 | 64.027 | 135.289 | 17.747 | 1.00 | 59.52 | C |
| ATOM | 5850 | CD | PRO | C | 305 | 63.954 | 135.319 | 16.274 | 1.00 | 50.13 | C |
| ATOM | 5851 | CA | PRO | C | 305 | 62.800 | 135.836 | 18.333 | 1.00 | 59.52 | C |
| ATOM | 5852 | CB | PRO | C | 305 | 61.814 | 135.839 | 17.147 | 1.00 | 50.13 | C |
| ATOM | 5853 | CG | PRO | C | 305 | 62.515 | 135.048 | 16.032 | 1.00 | 50.13 | C |
| ATOM | 5854 | C | PRO | C | 305 | 62.356 | 134.970 | 19.525 | 1.00 | 59.52 | C |
| ATOM | 5855 | O | PRO | C | 305 | 61.641 | 135.421 | 20.426 | 1.00 | 59.52 | C |
| ATOM | 5856 | N | THR | C | 306 | 62.809 | 133.722 | 19.509 | 1.00 | 78.49 | C |
| ATOM | 5857 | CA | THR | C | 306 | 62.549 | 132.777 | 20.580 | 1.00 | 78.49 | C |
| ATOM | 5858 | CB | THR | C | 306 | 62.677 | 131.321 | 20.098 | 1.00 | 57.87 | C |
| ATOM | 5859 | OG1 | THR | C | 306 | 61.564 | 131.001 | 19.263 | 1.00 | 57.87 | C |
| ATOM | 5860 | CG2 | THR | C | 306 | 62.705 | 130.361 | 21.268 | 1.00 | 57.87 | C |
| ATOM | 5861 | C | THR | C | 306 | 63.685 | 133.060 | 21.539 | 1.00 | 78.49 | C |
| ATOM | 5862 | O | THR | C | 306 | 63.474 | 133.359 | 22.715 | 1.00 | 78.49 | C |
| ATOM | 5863 | N | LEU | C | 307 | 64.899 | 132.965 | 21.002 | 1.00 | 55.35 | C |
| ATOM | 5864 | CA | LEU | C | 307 | 66.120 | 133.218 | 21.753 | 1.00 | 55.35 | C |
| ATOM | 5865 | CB | LEU | C | 307 | 67.262 | 133.478 | 20.762 | 1.00 | 34.85 | C |
| ATOM | 5866 | CG | LEU | C | 307 | 68.700 | 133.765 | 21.181 | 1.00 | 34.85 | C |
| ATOM | 5867 | CD1 | LEU | C | 307 | 69.181 | 132.720 | 22.176 | 1.00 | 34.85 | C |
| ATOM | 5868 | CD2 | LEU | C | 307 | 69.568 | 133.797 | 19.932 | 1.00 | 34.85 | C |
| ATOM | 5869 | C | LEU | C | 307 | 65.831 | 134.438 | 22.615 | 1.00 | 55.35 | C |
| ATOM | 5870 | O | LEU | C | 307 | 66.080 | 134.435 | 23.820 | 1.00 | 55.35 | C |
| ATOM | 5871 | N | ARG | C | 308 | 65.280 | 135.471 | 21.983 | 1.00 | 44.73 | C |
| ATOM | 5872 | CA | ARG | C | 308 | 64.905 | 136.692 | 22.672 | 1.00 | 44.73 | C |
| ATOM | 5873 | CB | ARG | C | 308 | 64.143 | 137.610 | 21.726 | 1.00 | 95.84 | C |
| ATOM | 5874 | CG | ARG | C | 308 | 63.347 | 138.700 | 22.417 | 1.00 | 95.84 | C |
| ATOM | 5875 | CD | ARG | C | 308 | 62.874 | 139.715 | 21.399 | 1.00 | 95.84 | C |
| ATOM | 5876 | NE | ARG | C | 308 | 62.047 | 139.105 | 20.361 | 1.00 | 95.84 | C |
| ATOM | 5877 | CZ | ARG | C | 308 | 62.205 | 139.314 | 19.057 | 1.00 | 95.84 | C |
| ATOM | 5878 | NH1 | ARG | C | 308 | 63.164 | 140.116 | 18.613 | 1.00 | 95.84 | C |
| ATOM | 5879 | NH2 | ARG | C | 308 | 61.392 | 138.731 | 18.193 | 1.00 | 95.84 | C |
| ATOM | 5880 | C | ARG | C | 308 | 64.001 | 136.283 | 23.818 | 1.00 | 44.73 | C |
| ATOM | 5881 | O | ARG | C | 308 | 64.323 | 136.512 | 24.982 | 1.00 | 44.73 | C |
| ATOM | 5882 | N | TYR | C | 309 | 62.879 | 135.657 | 23.468 | 1.00 | 45.25 | C |
| ATOM | 5883 | CA | TYR | C | 309 | 61.897 | 135.187 | 24.440 | 1.00 | 45.25 | C |
| ATOM | 5884 | CB | TYR | C | 309 | 60.753 | 134.461 | 23.723 | 1.00 | 43.04 | C |
| ATOM | 5885 | CG | TYR | C | 309 | 59.551 | 134.084 | 24.588 | 1.00 | 43.04 | C |
| ATOM | 5886 | CD1 | TYR | C | 309 | 58.537 | 133.274 | 24.076 | 1.00 | 43.04 | C |
| ATOM | 5887 | CE1 | TYR | C | 309 | 57.457 | 132.897 | 24.845 | 1.00 | 43.04 | C |
| ATOM | 5888 | CD2 | TYR | C | 309 | 59.436 | 134.514 | 25.902 | 1.00 | 43.04 | C |
| ATOM | 5889 | CE2 | TYR | C | 309 | 58.350 | 134.146 | 26.683 | 1.00 | 43.04 | C |
| ATOM | 5890 | CZ | TYR | C | 309 | 57.363 | 133.333 | 26.150 | 1.00 | 43.04 | C |
| ATOM | 5891 | OH | TYR | C | 309 | 56.285 | 132.945 | 26.925 | 1.00 | 43.04 | C |
| ATOM | 5892 | C | TYR | C | 309 | 62.503 | 134.268 | 25.497 | 1.00 | 45.25 | C |
| ATOM | 5893 | O | TYR | C | 309 | 61.970 | 134.170 | 26.595 | 1.00 | 45.25 | C |
| ATOM | 5894 | N | LEU | C | 310 | 63.602 | 133.587 | 25.185 | 1.00 | 57.81 | C |
| ATOM | 5895 | CA | LEU | C | 310 | 64.215 | 132.719 | 26.189 | 1.00 | 57.81 | C |
| ATOM | 5896 | CB | LEU | C | 310 | 65.342 | 131.868 | 25.590 | 1.00 | 33.86 | C |
| ATOM | 5897 | CG | LEU | C | 310 | 66.035 | 131.019 | 26.667 | 1.00 | 33.86 | C |
| ATOM | 5898 | CD1 | LEU | C | 310 | 65.131 | 129.873 | 27.070 | 1.00 | 33.86 | C |
| ATOM | 5899 | CD2 | LEU | C | 310 | 67.351 | 130.488 | 26.169 | 1.00 | 33.86 | C |
| ATOM | 5900 | C | LEU | C | 310 | 64.775 | 133.580 | 27.332 | 1.00 | 57.81 | C |
| ATOM | 5901 | O | LEU | C | 310 | 64.361 | 133.451 | 28.487 | 1.00 | 57.81 | C |
| ATOM | 5902 | N | PHE | C | 311 | 65.718 | 134.458 | 27.005 | 1.00 | 46.11 | C |
| ATOM | 5903 | CA | PHE | C | 311 | 66.313 | 135.338 | 27.997 | 1.00 | 46.11 | C |
| ATOM | 5904 | CB | PHE | C | 311 | 67.144 | 136.421 | 27.297 | 1.00 | 36.49 | C |
| ATOM | 5905 | CG | PHE | C | 311 | 68.366 | 135.893 | 26.587 | 1.00 | 36.49 | C |
| ATOM | 5906 | CD1 | PHE | C | 311 | 69.079 | 136.701 | 25.709 | 1.00 | 36.49 | C |
| ATOM | 5907 | CD2 | PHE | C | 311 | 68.828 | 134.596 | 26.815 | 1.00 | 36.49 | C |
| ATOM | 5908 | CE1 | PHE | C | 311 | 70.235 | 136.226 | 25.060 | 1.00 | 36.49 | C |
| ATOM | 5909 | CE2 | PHE | C | 311 | 69.989 | 134.110 | 26.166 | 1.00 | 36.49 | C |
| ATOM | 5910 | CZ | PHE | C | 311 | 70.689 | 134.932 | 25.295 | 1.00 | 36.49 | C |
| ATOM | 5911 | C | PHE | C | 311 | 65.194 | 135.974 | 28.825 | 1.00 | 46.11 | C |
| ATOM | 5912 | O | PHE | C | 311 | 65.212 | 135.929 | 30.056 | 1.00 | 46.11 | C |
| ATOM | 5913 | N | ALA | C | 312 | 64.211 | 136.548 | 28.137 | 1.00 | 65.23 | C |
| ATOM | 5914 | CA | ALA | C | 312 | 63.078 | 137.196 | 28.794 | 1.00 | 65.23 | C |
| ATOM | 5915 | CB | ALA | C | 312 | 62.204 | 137.902 | 27.761 | 1.00 | 88.15 | C |
| ATOM | 5916 | C | ALA | C | 312 | 62.237 | 136.197 | 29.586 | 1.00 | 65.23 | C |
| ATOM | 5917 | O | ALA | C | 312 | 61.073 | 136.466 | 29.900 | 1.00 | 65.23 | C |
| ATOM | 5918 | N | LEU | C | 313 | 62.832 | 135.045 | 29.886 | 1.00 | 36.75 | C |
| ATOM | 5919 | CA | LEU | C | 313 | 62.190 | 133.979 | 30.654 | 1.00 | 36.75 | C |
| ATOM | 5920 | CB | LEU | C | 313 | 61.676 | 132.868 | 29.718 | 1.00 | 36.31 | C |
| ATOM | 5921 | CG | LEU | C | 313 | 61.429 | 131.406 | 30.147 | 1.00 | 36.31 | C |
| ATOM | 5922 | CD1 | LEU | C | 313 | 60.547 | 131.314 | 31.371 | 1.00 | 36.31 | C |
| ATOM | 5923 | CD2 | LEU | C | 313 | 60.789 | 130.651 | 28.990 | 1.00 | 36.31 | C |
| ATOM | 5924 | C | LEU | C | 313 | 63.299 | 133.469 | 31.549 | 1.00 | 36.75 | C |
| ATOM | 5925 | O | LEU | C | 313 | 63.201 | 132.420 | 32.173 | 1.00 | 36.75 | C |
| ATOM | 5926 | N | THR | C | 314 | 64.369 | 134.244 | 31.601 | 1.00 | 37.84 | C |

```
ATOM   5927  CA  THR C 314      65.520 133.903  32.413  1.00 37.84           C
ATOM   5928  CB  THR C 314      66.764 133.782  31.528  1.00 42.48           C
ATOM   5929  OG1 THR C 314      66.361 133.433  30.197  1.00 42.48           C
ATOM   5930  CG2 THR C 314      67.693 132.702  32.057  1.00 42.48           C
ATOM   5931  C   THR C 314      65.699 135.037  33.420  1.00 37.84           C
ATOM   5932  O   THR C 314      66.753 135.168  34.053  1.00 37.84           C
ATOM   5933  N   ALA C 315      64.645 135.851  33.541  1.00 99.46           C
ATOM   5934  CA  ALA C 315      64.583 137.009  34.443  1.00 99.46           C
ATOM   5935  CB  ALA C 315      65.806 137.909  34.228  1.00 90.21           C
ATOM   5936  C   ALA C 315      63.286 137.816  34.214  1.00 99.46           C
ATOM   5937  O   ALA C 315      62.393 137.820  35.062  1.00 99.46           C
ATOM   5938  N   GLY C 316      63.212 138.480  33.056  1.00 46.37           C
ATOM   5939  CA  GLY C 316      62.078 139.307  32.640  1.00 46.37           C
ATOM   5940  C   GLY C 316      60.711 139.226  33.301  1.00 46.37           C
ATOM   5941  O   GLY C 316      60.598 139.102  34.512  1.00 46.37           C
ATOM   5942  N   VAL C 317      59.659 139.311  32.492  1.00 94.07           C
ATOM   5943  CA  VAL C 317      58.294 139.273  33.007  1.00 94.07           C
ATOM   5944  CB  VAL C 317      57.619 140.651  32.831  1.00 37.23           C
ATOM   5945  CG1 VAL C 317      56.113 140.546  33.042  1.00 37.23           C
ATOM   5946  CG2 VAL C 317      58.211 141.622  33.821  1.00 37.23           C
ATOM   5947  C   VAL C 317      57.372 138.182  32.443  1.00 94.07           C
ATOM   5948  O   VAL C 317      56.591 137.592  33.198  1.00 94.07           C
ATOM   5949  N   PRO C 318      57.443 137.894  31.121  1.00100.07           C
ATOM   5950  CD  PRO C 318      58.415 138.347  30.106  1.00 86.80           C
ATOM   5951  CA  PRO C 318      56.568 136.853  30.563  1.00100.07           C
ATOM   5952  CB  PRO C 318      56.898 136.884  29.072  1.00 86.80           C
ATOM   5953  CG  PRO C 318      58.347 137.242  29.064  1.00 86.80           C
ATOM   5954  C   PRO C 318      56.861 135.496  31.199  1.00100.07           C
ATOM   5955  O   PRO C 318      55.947 134.746  31.544  1.00100.07           C
ATOM   5956  N   GLY C 319      58.145 135.193  31.356  1.00 77.43           C
ATOM   5957  CA  GLY C 319      58.533 133.938  31.964  1.00 77.43           C
ATOM   5958  C   GLY C 319      57.845 132.752  31.331  1.00 77.43           C
ATOM   5959  O   GLY C 319      58.306 132.243  30.310  1.00 77.43           C
ATOM   5960  N   HIS C 320      56.727 132.328  31.914  1.00 37.14           C
ATOM   5961  CA  HIS C 320      56.018 131.166  31.395  1.00 37.14           C
ATOM   5962  CB  HIS C 320      55.453 131.420  29.988  1.00100.07           C
ATOM   5963  CG  HIS C 320      54.381 132.465  29.920  1.00100.07           C
ATOM   5964  CD2 HIS C 320      54.251 133.553  29.123  1.00100.07           C
ATOM   5965  ND1 HIS C 320      53.237 132.416  30.689  1.00100.07           C
ATOM   5966  CE1 HIS C 320      52.448 133.427  30.366  1.00100.07           C
ATOM   5967  NE2 HIS C 320      53.041 134.131  29.418  1.00100.07           C
ATOM   5968  C   HIS C 320      57.066 130.060  31.285  1.00 37.14           C
ATOM   5969  O   HIS C 320      57.671 129.871  30.229  1.00 37.14           C
ATOM   5970  N   GLU C 321      57.316 129.351  32.375  1.00 67.45           C
ATOM   5971  CA  GLU C 321      58.284 128.273  32.322  1.00 67.45           C
ATOM   5972  CB  GLU C 321      58.701 127.843  33.732  1.00100.07           C
ATOM   5973  CG  GLU C 321      59.628 128.825  34.461  1.00100.07           C
ATOM   5974  CD  GLU C 321      59.757 128.532  35.963  1.00100.07           C
ATOM   5975  OE1 GLU C 321      58.746 128.684  36.681  1.00100.07           C
ATOM   5976  OE2 GLU C 321      60.858 128.150  36.428  1.00100.07           C
ATOM   5977  C   GLU C 321      57.566 127.136  31.623  1.00 67.45           C
ATOM   5978  O   GLU C 321      57.979 125.990  31.735  1.00 67.45           C
ATOM   5979  N   VAL C 322      56.491 127.474  30.904  1.00 58.94           C
ATOM   5980  CA  VAL C 322      55.655 126.512  30.168  1.00 58.94           C
ATOM   5981  CB  VAL C 322      55.035 127.144  28.879  1.00 62.46           C
ATOM   5982  CG1 VAL C 322      56.125 127.660  27.963  1.00 62.46           C
ATOM   5983  CG2 VAL C 322      54.192 126.109  28.139  1.00 62.46           C
ATOM   5984  C   VAL C 322      56.349 125.218  29.760  1.00 58.94           C
ATOM   5985  O   VAL C 322      57.447 125.230  29.192  1.00 58.94           C
ATOM   5986  N   ALA C 323      55.686 124.103  30.051  1.00 99.69           C
ATOM   5987  CA  ALA C 323      56.207 122.778  29.729  1.00 99.69           C
ATOM   5988  CB  ALA C 323      57.113 122.273  30.868  1.00 65.57           C
ATOM   5989  C   ALA C 323      55.017 121.845  29.550  1.00 99.69           C
ATOM   5990  O   ALA C 323      54.364 121.490  30.532  1.00 99.69           C
ATOM   5991  N   ASP C 324      54.724 121.451  28.311  1.00 55.65           C
ATOM   5992  CA  ASP C 324      53.584 120.581  28.076  1.00 55.65           C
ATOM   5993  CB  ASP C 324      53.814 119.223  28.756  1.00 50.97           C
ATOM   5994  CG  ASP C 324      52.518 118.577  29.260  1.00 50.97           C
ATOM   5995  OD1 ASP C 324      51.850 119.149  30.142  1.00 50.97           C
ATOM   5996  OD2 ASP C 324      52.163 117.486  28.784  1.00 50.97           C
ATOM   5997  C   ASP C 324      52.351 121.272  28.659  1.00 55.65           C
ATOM   5998  O   ASP C 324      51.217 120.823  28.457  1.00 55.65           C
ATOM   5999  N   ALA C 325      52.592 122.374  29.370  1.00100.07           C
ATOM   6000  CA  ALA C 325      51.546 123.156  30.018  1.00100.07           C
ATOM   6001  CB  ALA C 325      50.528 123.623  28.982  1.00100.07           C
ATOM   6002  C   ALA C 325      50.859 122.316  31.092  1.00100.07           C
ATOM   6003  O   ALA C 325      50.878 122.644  32.284  1.00100.07           C
ATOM   6004  N   ALA C 326      50.252 121.227  30.636  1.00100.07           C
ATOM   6005  CA  ALA C 326      49.545 120.273  31.475  1.00100.07           C
ATOM   6006  CB  ALA C 326      48.507 120.981  32.345  1.00100.07           C
ATOM   6007  C   ALA C 326      48.861 119.364  30.479  1.00100.07           C
ATOM   6008  O   ALA C 326      47.672 119.090  30.602  1.00100.07           C
ATOM   6009  N   ALA C 327      49.618 118.909  29.483  1.00 83.77           C
ATOM   6010  CA  ALA C 327      49.062 118.059  28.439  1.00 83.77           C
```

```
ATOM   6011  CB  ALA C 327      48.566 116.742  29.035  1.00100.07       C
ATOM   6012  C   ALA C 327      47.896 118.882  27.915  1.00 83.77       C
ATOM   6013  O   ALA C 327      46.886 118.358  27.413  1.00 83.77       C
ATOM   6014  N   LEU C 328      48.066 120.193  28.049  1.00 42.59       C
ATOM   6015  CA  LEU C 328      47.050 121.145  27.666  1.00 42.59       C
ATOM   6016  CB  LEU C 328      47.357 122.477  28.361  1.00 39.91       C
ATOM   6017  CG  LEU C 328      46.236 123.450  28.735  1.00 39.91       C
ATOM   6018  CD1 LEU C 328      44.939 122.754  29.142  1.00 39.91       C
ATOM   6019  CD2 LEU C 328      46.753 124.267  29.879  1.00 39.91       C
ATOM   6020  C   LEU C 328      46.947 121.304  26.152  1.00 42.59       C
ATOM   6021  O   LEU C 328      46.797 120.320  25.413  1.00 42.59       C
ATOM   6022  N   GLY C 329      46.991 122.551  25.694  1.00100.07       C
ATOM   6023  CA  GLY C 329      46.926 122.817  24.270  1.00100.07       C
ATOM   6024  C   GLY C 329      48.262 122.387  23.719  1.00100.07       C
ATOM   6025  O   GLY C 329      48.749 122.908  22.718  1.00100.07       C
ATOM   6026  N   ASN C 330      48.860 121.432  24.418  1.00 28.65       C
ATOM   6027  CA  ASN C 330      50.146 120.883  24.055  1.00 28.65       C
ATOM   6028  CB  ASN C 330      51.213 121.388  25.021  1.00 44.56       C
ATOM   6029  CG  ASN C 330      51.338 122.912  25.021  1.00 44.56       C
ATOM   6030  OD1 ASN C 330      51.807 123.496  26.001  1.00 44.56       C
ATOM   6031  ND2 ASN C 330      50.935 123.557  23.926  1.00 44.56       C
ATOM   6032  C   ASN C 330      50.033 119.363  24.116  1.00 28.65       C
ATOM   6033  O   ASN C 330      50.403 118.721  25.109  1.00 28.65       C
ATOM   6034  N   ALA C 331      49.503 118.802  23.034  1.00 20.61       C
ATOM   6035  CA  ALA C 331      49.316 117.367  22.934  1.00 20.61       C
ATOM   6036  CB  ALA C 331      48.399 116.895  24.066  1.00  5.07       C
ATOM   6037  C   ALA C 331      48.740 116.969  21.565  1.00 20.61       C
ATOM   6038  O   ALA C 331      47.548 116.694  21.429  1.00 20.61       C
ATOM   6039  N   ALA C 332      49.589 116.930  20.547  1.00100.07       C
ATOM   6040  CA  ALA C 332      49.106 116.575  19.218  1.00100.07       C
ATOM   6041  CB  ALA C 332      50.079 117.058  18.141  1.00 71.55       C
ATOM   6042  C   ALA C 332      48.852 115.081  19.061  1.00100.07       C
ATOM   6043  O   ALA C 332      49.709 114.250  19.357  1.00100.07       C
ATOM   6044  N   ILE C 333      47.652 114.759  18.594  1.00 69.05       C
ATOM   6045  CA  ILE C 333      47.227 113.387  18.361  1.00 69.05       C
ATOM   6046  CB  ILE C 333      45.710 113.268  18.608  1.00 45.11       C
ATOM   6047  CG2 ILE C 333      45.224 111.888  18.289  1.00 45.11       C
ATOM   6048  CG1 ILE C 333      45.407 113.544  20.075  1.00 45.11       C
ATOM   6049  CD  ILE C 333      45.688 112.362  20.972  1.00 45.11       C
ATOM   6050  C   ILE C 333      47.546 112.994  16.916  1.00 69.05       C
ATOM   6051  O   ILE C 333      47.965 113.823  16.103  1.00 69.05       C
ATOM   6052  N   ARG C 334      47.368 111.719  16.610  1.00 26.87       C
ATOM   6053  CA  ARG C 334      47.610 111.214  15.270  1.00 26.87       C
ATOM   6054  CB  ARG C 334      49.059 110.751  15.117  1.00 28.56       C
ATOM   6055  CG  ARG C 334      49.983 111.909  14.867  1.00 28.56       C
ATOM   6056  CD  ARG C 334      51.142 111.584  13.941  1.00 28.56       C
ATOM   6057  NE  ARG C 334      52.127 110.690  14.528  1.00 28.56       C
ATOM   6058  CZ  ARG C 334      53.219 110.295  13.884  1.00 28.56       C
ATOM   6059  NH1 ARG C 334      53.451 110.722  12.651  1.00 28.56       C
ATOM   6060  NH2 ARG C 334      54.069 109.453  14.453  1.00 28.56       C
ATOM   6061  C   ARG C 334      46.668 110.084  14.910  1.00 26.87       C
ATOM   6062  O   ARG C 334      46.963 108.913  15.132  1.00 26.87       C
ATOM   6063  N   THR C 335      45.513 110.437  14.375  1.00 43.35       C
ATOM   6064  CA  THR C 335      44.591 109.407  13.977  1.00 43.35       C
ATOM   6065  CB  THR C 335      43.301 110.013  13.380  1.00 44.39       C
ATOM   6066  OG1 THR C 335      43.574 111.329  12.886  1.00 44.39       C
ATOM   6067  CG2 THR C 335      42.208 110.089  14.438  1.00 44.39       C
ATOM   6068  C   THR C 335      45.331 108.568  12.931  1.00 43.35       C
ATOM   6069  O   THR C 335      46.145 109.092  12.162  1.00 43.35       C
ATOM   6070  N   VAL C 336      45.075 107.262  12.943  1.00  9.90       C
ATOM   6071  CA  VAL C 336      45.686 106.327  12.011  1.00  9.90       C
ATOM   6072  CB  VAL C 336      44.735 105.196  11.684  1.00 10.63       C
ATOM   6073  CG1 VAL C 336      45.434 104.171  10.854  1.00 10.63       C
ATOM   6074  CG2 VAL C 336      44.197 104.601  12.952  1.00 10.63       C
ATOM   6075  C   VAL C 336      46.002 107.039  10.722  1.00  9.90       C
ATOM   6076  O   VAL C 336      47.115 106.971  10.223  1.00  9.90       C
ATOM   6077  N   GLY C 337      45.002 107.736  10.195  1.00 33.04       C
ATOM   6078  CA  GLY C 337      45.183 108.453   8.951  1.00 33.04       C
ATOM   6079  C   GLY C 337      46.562 109.058   8.856  1.00 33.04       C
ATOM   6080  O   GLY C 337      47.302 108.818   7.904  1.00 33.04       C
ATOM   6081  N   GLU C 338      46.904 109.837   9.871  1.00 39.99       C
ATOM   6082  CA  GLU C 338      48.191 110.493   9.937  1.00 39.99       C
ATOM   6083  CB  GLU C 338      48.255 111.322  11.226  1.00 46.47       C
ATOM   6084  CG  GLU C 338      48.869 112.717  11.109  1.00 46.47       C
ATOM   6085  CD  GLU C 338      48.639 113.553  12.368  1.00 46.47       C
ATOM   6086  OE1 GLU C 338      49.372 114.537  12.587  1.00 46.47       C
ATOM   6087  OE2 GLU C 338      47.716 113.235  13.146  1.00 46.47       C
ATOM   6088  C   GLU C 338      49.319 109.445   9.889  1.00 39.99       C
ATOM   6089  O   GLU C 338      50.140 109.477   8.973  1.00 39.99       C
ATOM   6090  N   LEU C 339      49.342 108.508  10.846  1.00 16.83       C
ATOM   6091  CA  LEU C 339      50.393 107.475  10.909  1.00 16.83       C
ATOM   6092  CB  LEU C 339      50.096 106.439  12.002  1.00  9.52       C
ATOM   6093  CG  LEU C 339      49.716 106.874  13.429  1.00  9.52       C
ATOM   6094  CD1 LEU C 339      48.216 107.139  13.435  1.00  9.52       C
```

```
ATOM   6095  CD2 LEU C 339      50.064 105.799  14.488  1.00  9.52           C
ATOM   6096  C   LEU C 339      50.606 106.724   9.597  1.00 16.83           C
ATOM   6097  O   LEU C 339      51.731 106.624   9.101  1.00 16.83           C
ATOM   6098  N   MET C 340      49.522 106.175   9.053  1.00 35.16           C
ATOM   6099  CA  MET C 340      49.557 105.431   7.795  1.00 35.16           C
ATOM   6100  CB  MET C 340      48.144 104.929   7.466  1.00 52.11           C
ATOM   6101  CG  MET C 340      47.974 104.323   6.086  1.00 52.11           C
ATOM   6102  SD  MET C 340      48.305 105.523   4.786  1.00 52.11           C
ATOM   6103  CE  MET C 340      47.118 106.781   5.204  1.00 52.11           C
ATOM   6104  C   MET C 340      50.076 106.365   6.702  1.00 35.16           C
ATOM   6105  O   MET C 340      50.874 105.978   5.841  1.00 35.16           C
ATOM   6106  N   ALA C 341      49.598 107.600   6.742  1.00 35.96           C
ATOM   6107  CA  ALA C 341      50.016 108.602   5.791  1.00 35.96           C
ATOM   6108  CB  ALA C 341      49.380 109.924   6.127  1.00 14.91           C
ATOM   6109  C   ALA C 341      51.529 108.713   5.880  1.00 35.96           C
ATOM   6110  O   ALA C 341      52.225 108.387   4.925  1.00 35.96           C
ATOM   6111  N   ASP C 342      52.035 109.163   7.029  1.00 42.69           C
ATOM   6112  CA  ASP C 342      53.475 109.309   7.235  1.00 42.69           C
ATOM   6113  CB  ASP C 342      53.801 109.389   8.727  1.00 55.31           C
ATOM   6114  CG  ASP C 342      53.325 110.682   9.358  1.00 55.31           C
ATOM   6115  OD1 ASP C 342      53.634 111.752   8.798  1.00 55.31           C
ATOM   6116  OD2 ASP C 342      52.650 110.635  10.411  1.00 55.31           C
ATOM   6117  C   ASP C 342      54.276 108.169   6.613  1.00 42.69           C
ATOM   6118  O   ASP C 342      55.328 108.395   6.004  1.00 42.69           C
ATOM   6119  N   GLN C 343      53.774 106.947   6.763  1.00 63.10           C
ATOM   6120  CA  GLN C 343      54.445 105.777   6.212  1.00 63.10           C
ATOM   6121  CB  GLN C 343      53.656 104.520   6.536  1.00 61.98           C
ATOM   6122  CG  GLN C 343      54.535 103.434   7.111  1.00 61.98           C
ATOM   6123  CD  GLN C 343      55.534 103.969   8.134  1.00 61.98           C
ATOM   6124  OE1 GLN C 343      55.155 104.570   9.150  1.00 61.98           C
ATOM   6125  NE2 GLN C 343      56.821 103.754   7.866  1.00 61.98           C
ATOM   6126  C   GLN C 343      54.616 105.921   4.713  1.00 63.10           C
ATOM   6127  O   GLN C 343      55.556 105.392   4.137  1.00 63.10           C
ATOM   6128  N   PHE C 344      53.689 106.628   4.083  1.00 69.38           C
ATOM   6129  CA  PHE C 344      53.780 106.884   2.657  1.00 69.38           C
ATOM   6130  CB  PHE C 344      52.519 107.573   2.141  1.00 29.38           C
ATOM   6131  CG  PHE C 344      51.854 106.863   1.006  1.00 29.38           C
ATOM   6132  CD1 PHE C 344      50.631 107.304   0.532  1.00 29.38           C
ATOM   6133  CD2 PHE C 344      52.417 105.722   0.449  1.00 29.38           C
ATOM   6134  CE1 PHE C 344      49.971 106.616  -0.476  1.00 29.38           C
ATOM   6135  CE2 PHE C 344      51.766 105.018  -0.564  1.00 29.38           C
ATOM   6136  CZ  PHE C 344      50.540 105.464  -1.029  1.00 29.38           C
ATOM   6137  C   PHE C 344      54.935 107.858   2.545  1.00 69.38           C
ATOM   6138  O   PHE C 344      55.911 107.602   1.839  1.00 69.38           C
ATOM   6139  N   ARG C 345      54.803 108.983   3.252  1.00 63.64           C
ATOM   6140  CA  ARG C 345      55.827 110.016   3.260  1.00 63.64           C
ATOM   6141  CB  ARG C 345      55.636 110.950   4.456  1.00 50.37           C
ATOM   6142  CG  ARG C 345      54.277 111.641   4.500  1.00 50.37           C
ATOM   6143  CD  ARG C 345      53.992 112.212   5.892  1.00 50.37           C
ATOM   6144  NE  ARG C 345      52.564 112.431   6.141  1.00 50.37           C
ATOM   6145  CZ  ARG C 345      51.892 113.525   5.795  1.00 50.37           C
ATOM   6146  NH1 ARG C 345      52.507 114.526   5.179  1.00 50.37           C
ATOM   6147  NH2 ARG C 345      50.602 113.623   6.076  1.00 50.37           C
ATOM   6148  C   ARG C 345      57.140 109.270   3.375  1.00 63.64           C
ATOM   6149  O   ARG C 345      58.081 109.529   2.630  1.00 63.64           C
ATOM   6150  N   VAL C 346      57.179 108.313   4.297  1.00 64.40           C
ATOM   6151  CA  VAL C 346      58.367 107.494   4.507  1.00 64.40           C
ATOM   6152  CB  VAL C 346      58.214 106.589   5.743  1.00100.07           C
ATOM   6153  CG1 VAL C 346      59.487 105.781   5.948  1.00100.07           C
ATOM   6154  CG2 VAL C 346      57.908 107.423   6.970  1.00100.07           C
ATOM   6155  C   VAL C 346      58.600 106.588   3.298  1.00 64.40           C
ATOM   6156  O   VAL C 346      59.740 106.331   2.906  1.00 64.40           C
ATOM   6157  N   GLY C 347      57.505 106.096   2.725  1.00 21.03           C
ATOM   6158  CA  GLY C 347      57.595 105.221   1.579  1.00 21.03           C
ATOM   6159  C   GLY C 347      58.234 105.932   0.414  1.00 21.03           C
ATOM   6160  O   GLY C 347      59.384 105.656   0.064  1.00 21.03           C
ATOM   6161  N   LEU C 348      57.481 106.848  -0.187  1.00 55.93           C
ATOM   6162  CA  LEU C 348      57.953 107.615  -1.327  1.00 55.93           C
ATOM   6163  CB  LEU C 348      57.077 108.850  -1.524  1.00 33.94           C
ATOM   6164  CG  LEU C 348      55.662 108.617  -2.052  1.00 33.94           C
ATOM   6165  CD1 LEU C 348      54.842 107.776  -1.083  1.00 33.94           C
ATOM   6166  CD2 LEU C 348      55.004 109.971  -2.263  1.00 33.94           C
ATOM   6167  C   LEU C 348      59.402 108.030  -1.116  1.00 55.93           C
ATOM   6168  O   LEU C 348      60.152 108.230  -2.071  1.00 55.93           C
ATOM   6169  N   ALA C 349      59.789 108.147   0.151  1.00 98.46           C
ATOM   6170  CA  ALA C 349      61.149 108.530   0.516  1.00 98.46           C
ATOM   6171  CB  ALA C 349      61.304 108.533   2.039  1.00100.07           C
ATOM   6172  C   ALA C 349      62.175 107.593  -0.113  1.00 98.46           C
ATOM   6173  O   ALA C 349      63.357 107.926  -0.209  1.00 98.46           C
ATOM   6174  N   ARG C 350      61.726 106.417  -0.535  1.00 29.60           C
ATOM   6175  CA  ARG C 350      62.637 105.482  -1.159  1.00 29.60           C
ATOM   6176  CB  ARG C 350      62.231 104.039  -0.870  1.00100.07           C
ATOM   6177  CG  ARG C 350      63.181 103.028  -1.506  1.00100.07           C
ATOM   6178  CD  ARG C 350      62.729 101.594  -1.289  1.00100.07           C
```

| ATOM | 6179 | NE  | ARG | C | 350 | 63.506 | 100.653 | -2.091  | 1.00 | 100.07 | C |
|------|------|-----|-----|---|-----|--------|---------|---------|------|--------|---|
| ATOM | 6180 | CZ  | ARG | C | 350 | 63.147 | 99.395  | -2.328  | 1.00 | 100.07 | C |
| ATOM | 6181 | NH1 | ARG | C | 350 | 62.011 | 98.917  | -1.825  | 1.00 | 100.07 | C |
| ATOM | 6182 | NH2 | ARG | C | 350 | 63.931 | 98.616  | -3.068  | 1.00 | 100.07 | C |
| ATOM | 6183 | C   | ARG | C | 350 | 62.722 | 105.701 | -2.669  | 1.00 | 29.60  | C |
| ATOM | 6184 | O   | ARG | C | 350 | 63.713 | 106.255 | -3.151  | 1.00 | 29.60  | C |
| ATOM | 6185 | N   | LEU | C | 351 | 61.697 | 105.282 | -3.413  | 1.00 | 85.61  | C |
| ATOM | 6186 | CA  | LEU | C | 351 | 61.717 | 105.445 | -4.867  | 1.00 | 85.61  | C |
| ATOM | 6187 | CB  | LEU | C | 351 | 60.315 | 105.339 | -5.477  | 1.00 | 22.25  | C |
| ATOM | 6188 | CG  | LEU | C | 351 | 59.479 | 106.627 | -5.477  | 1.00 | 22.25  | C |
| ATOM | 6189 | CD1 | LEU | C | 351 | 58.370 | 106.525 | -6.500  | 1.00 | 22.25  | C |
| ATOM | 6190 | CD2 | LEU | C | 351 | 58.915 | 106.879 | -4.091  | 1.00 | 22.25  | C |
| ATOM | 6191 | C   | LEU | C | 351 | 62.285 | 106.813 | -5.203  | 1.00 | 85.61  | C |
| ATOM | 6192 | O   | LEU | C | 351 | 62.921 | 106.992 | -6.239  | 1.00 | 85.61  | C |
| ATOM | 6193 | N   | ALA | C | 352 | 62.033 | 107.781 | -4.325  | 1.00 | 59.25  | C |
| ATOM | 6194 | CA  | ALA | C | 352 | 62.541 | 109.128 | -4.523  | 1.00 | 59.25  | C |
| ATOM | 6195 | CB  | ALA | C | 352 | 62.459 | 109.908 | -3.223  | 1.00 | 100.07 | C |
| ATOM | 6196 | C   | ALA | C | 352 | 63.990 | 108.975 | -4.966  | 1.00 | 59.25  | C |
| ATOM | 6197 | O   | ALA | C | 352 | 64.339 | 109.302 | -6.098  | 1.00 | 59.25  | C |
| ATOM | 6198 | N   | ARG | C | 353 | 64.825 | 108.455 | -4.070  | 1.00 | 45.38  | C |
| ATOM | 6199 | CA  | ARG | C | 353 | 66.228 | 108.234 | -4.382  | 1.00 | 45.38  | C |
| ATOM | 6200 | CB  | ARG | C | 353 | 66.905 | 107.463 | -3.255  | 1.00 | 100.07 | C |
| ATOM | 6201 | CG  | ARG | C | 353 | 68.038 | 108.201 | -2.586  | 1.00 | 100.07 | C |
| ATOM | 6202 | CD  | ARG | C | 353 | 67.540 | 109.352 | -1.730  | 1.00 | 100.07 | C |
| ATOM | 6203 | NE  | ARG | C | 353 | 68.628 | 109.920 | -0.938  | 1.00 | 100.07 | C |
| ATOM | 6204 | CZ  | ARG | C | 353 | 68.484 | 110.884 | -0.035  | 1.00 | 100.07 | C |
| ATOM | 6205 | NH1 | ARG | C | 353 | 67.285 | 111.403 | 0.204   | 1.00 | 100.07 | C |
| ATOM | 6206 | NH2 | ARG | C | 353 | 69.543 | 111.325 | 0.633   | 1.00 | 100.07 | C |
| ATOM | 6207 | C   | ARG | C | 353 | 66.252 | 107.394 | -5.644  | 1.00 | 45.38  | C |
| ATOM | 6208 | O   | ARG | C | 353 | 67.009 | 107.659 | -6.575  | 1.00 | 45.38  | C |
| ATOM | 6209 | N   | GLY | C | 354 | 65.397 | 106.379 | -5.661  | 1.00 | 74.85  | C |
| ATOM | 6210 | CA  | GLY | C | 354 | 65.314 | 105.487 | -6.799  | 1.00 | 74.85  | C |
| ATOM | 6211 | C   | GLY | C | 354 | 64.899 | 106.175 | -8.082  | 1.00 | 74.85  | C |
| ATOM | 6212 | O   | GLY | C | 354 | 64.875 | 105.542 | -9.134  | 1.00 | 74.85  | C |
| ATOM | 6213 | N   | VAL | C | 355 | 64.550 | 107.457 | -8.018  | 1.00 | 59.81  | C |
| ATOM | 6214 | CA  | VAL | C | 355 | 64.167 | 108.164 | -9.236  | 1.00 | 59.81  | C |
| ATOM | 6215 | CB  | VAL | C | 355 | 63.149 | 109.304 | -8.970  | 1.00 | 34.18  | C |
| ATOM | 6216 | CG1 | VAL | C | 355 | 63.878 | 110.644 | -8.773  | 1.00 | 34.18  | C |
| ATOM | 6217 | CG2 | VAL | C | 355 | 62.153 | 109.374 | -10.120 | 1.00 | 34.18  | C |
| ATOM | 6218 | C   | VAL | C | 355 | 65.446 | 108.739 | -9.842  | 1.00 | 59.81  | C |
| ATOM | 6219 | O   | VAL | C | 355 | 65.691 | 108.595 | -11.035 | 1.00 | 59.81  | C |
| ATOM | 6220 | N   | ARG | C | 356 | 66.268 | 109.382 | -9.018  | 1.00 | 74.77  | C |
| ATOM | 6221 | CA  | ARG | C | 356 | 67.523 | 109.916 | -9.513  | 1.00 | 74.77  | C |
| ATOM | 6222 | CB  | ARG | C | 356 | 68.282 | 110.649 | -8.398  | 1.00 | 100.07 | C |
| ATOM | 6223 | CG  | ARG | C | 356 | 67.593 | 111.935 | -7.890  | 1.00 | 100.07 | C |
| ATOM | 6224 | CD  | ARG | C | 356 | 68.564 | 112.821 | -7.076  | 1.00 | 100.07 | C |
| ATOM | 6225 | NE  | ARG | C | 356 | 67.955 | 114.049 | -6.546  | 1.00 | 100.07 | C |
| ATOM | 6226 | CZ  | ARG | C | 356 | 68.616 | 114.979 | -5.857  | 1.00 | 100.07 | C |
| ATOM | 6227 | NH1 | ARG | C | 356 | 69.910 | 114.833 | -5.612  | 1.00 | 100.07 | C |
| ATOM | 6228 | NH2 | ARG | C | 356 | 67.985 | 116.055 | -5.405  | 1.00 | 100.07 | C |
| ATOM | 6229 | C   | ARG | C | 356 | 68.304 | 108.693 | -10.014 | 1.00 | 74.77  | C |
| ATOM | 6230 | O   | ARG | C | 356 | 69.253 | 108.813 | -10.784 | 1.00 | 74.77  | C |
| ATOM | 6231 | N   | GLU | C | 357 | 67.869 | 107.514 | -9.575  | 1.00 | 67.64  | C |
| ATOM | 6232 | CA  | GLU | C | 357 | 68.463 | 106.239 | -9.971  | 1.00 | 67.64  | C |
| ATOM | 6233 | CB  | GLU | C | 357 | 67.613 | 105.082 | -9.416  | 1.00 | 99.66  | C |
| ATOM | 6234 | CG  | GLU | C | 357 | 67.872 | 103.684 | -10.033 | 1.00 | 99.66  | C |
| ATOM | 6235 | CD  | GLU | C | 357 | 66.706 | 103.150 | -10.879 | 1.00 | 99.66  | C |
| ATOM | 6236 | OE1 | GLU | C | 357 | 66.743 | 101.958 | -11.258 | 1.00 | 99.66  | C |
| ATOM | 6237 | OE2 | GLU | C | 357 | 65.760 | 103.914 | -11.166 | 1.00 | 99.66  | C |
| ATOM | 6238 | C   | GLU | C | 357 | 68.533 | 106.125 | -11.491 | 1.00 | 67.64  | C |
| ATOM | 6239 | O   | GLU | C | 357 | 69.540 | 106.482 | -12.109 | 1.00 | 67.64  | C |
| ATOM | 6240 | N   | ALA | C | 358 | 67.452 | 105.613 | -12.078 | 1.00 | 90.74  | C |
| ATOM | 6241 | CA  | ALA | C | 358 | 67.349 | 105.437 | -13.520 | 1.00 | 90.74  | C |
| ATOM | 6242 | CB  | ALA | C | 358 | 66.112 | 104.623 | -13.861 | 1.00 | 25.37  | C |
| ATOM | 6243 | C   | ALA | C | 358 | 67.267 | 106.812 | -14.156 | 1.00 | 90.74  | C |
| ATOM | 6244 | O   | ALA | C | 358 | 67.279 | 106.951 | -15.376 | 1.00 | 90.74  | C |
| ATOM | 6245 | N   | MET | C | 359 | 67.167 | 107.826 | -13.304 | 1.00 | 78.14  | C |
| ATOM | 6246 | CA  | MET | C | 359 | 67.112 | 109.204 | -13.756 | 1.00 | 78.14  | C |
| ATOM | 6247 | CB  | MET | C | 359 | 67.267 | 110.160 | -12.568 | 1.00 | 74.02  | C |
| ATOM | 6248 | CG  | MET | C | 359 | 66.745 | 111.570 | -12.777 | 1.00 | 74.02  | C |
| ATOM | 6249 | SD  | MET | C | 359 | 64.977 | 111.670 | -12.459 | 1.00 | 74.02  | C |
| ATOM | 6250 | CE  | MET | C | 359 | 64.287 | 111.107 | -14.064 | 1.00 | 74.02  | C |
| ATOM | 6251 | C   | MET | C | 359 | 68.329 | 109.323 | -14.655 | 1.00 | 78.14  | C |
| ATOM | 6252 | O   | MET | C | 359 | 68.242 | 109.112 | -15.864 | 1.00 | 78.14  | C |
| ATOM | 6253 | N   | VAL | C | 360 | 69.471 | 109.627 | -14.043 | 1.00 | 84.79  | C |
| ATOM | 6254 | CA  | VAL | C | 360 | 70.715 | 109.782 | -14.776 | 1.00 | 84.79  | C |
| ATOM | 6255 | CB  | VAL | C | 360 | 71.879 | 110.153 | -13.848 | 1.00 | 40.83  | C |
| ATOM | 6256 | CG1 | VAL | C | 360 | 73.122 | 110.454 | -14.678 | 1.00 | 40.83  | C |
| ATOM | 6257 | CG2 | VAL | C | 360 | 71.508 | 111.351 | -13.005 | 1.00 | 40.83  | C |
| ATOM | 6258 | C   | VAL | C | 360 | 71.068 | 108.493 | -15.490 | 1.00 | 84.79  | C |
| ATOM | 6259 | O   | VAL | C | 360 | 70.723 | 108.311 | -16.658 | 1.00 | 84.79  | C |
| ATOM | 6260 | N   | MET | C | 361 | 71.765 | 107.601 | -14.794 | 1.00 | 64.36  | C |
| ATOM | 6261 | CA  | MET | C | 361 | 72.144 | 106.333 | -15.392 | 1.00 | 64.36  | C |
| ATOM | 6262 | CB  | MET | C | 361 | 72.657 | 105.380 | -14.315 | 1.00 | 100.07 | C |

| ATOM | 6263 | CG | MET | C | 361 | 72.980 | 103.976 | -14.808 | 1.00 | 100.07 | C |
| ATOM | 6264 | SD | MET | C | 361 | 71.516 | 103.001 | -15.211 | 1.00 | 100.07 | C |
| ATOM | 6265 | CE | MET | C | 361 | 71.038 | 102.450 | -13.616 | 1.00 | 100.07 | C |
| ATOM | 6266 | C | MET | C | 361 | 70.890 | 105.771 | -16.042 | 1.00 | 64.36 | C |
| ATOM | 6267 | O | MET | C | 361 | 69.960 | 105.354 | -15.345 | 1.00 | 64.36 | C |
| ATOM | 6268 | N | GLY | C | 362 | 70.853 | 105.783 | -17.374 | 1.00 | 40.07 | C |
| ATOM | 6269 | CA | GLY | C | 362 | 69.687 | 105.269 | -18.075 | 1.00 | 40.07 | C |
| ATOM | 6270 | C | GLY | C | 362 | 69.531 | 105.835 | -19.468 | 1.00 | 40.07 | C |
| ATOM | 6271 | O | GLY | C | 362 | 70.290 | 106.724 | -19.856 | 1.00 | 40.07 | C |
| ATOM | 6272 | N | SER | C | 363 | 68.543 | 105.326 | -20.209 | 1.00 | 66.93 | C |
| ATOM | 6273 | CA | SER | C | 363 | 68.272 | 105.750 | -21.590 | 1.00 | 66.93 | C |
| ATOM | 6274 | CB | SER | C | 363 | 67.563 | 104.629 | -22.355 | 1.00 | 100.07 | C |
| ATOM | 6275 | OG | SER | C | 363 | 67.247 | 105.034 | -23.676 | 1.00 | 100.07 | C |
| ATOM | 6276 | C | SER | C | 363 | 67.432 | 107.021 | -21.678 | 1.00 | 66.93 | C |
| ATOM | 6277 | O | SER | C | 363 | 66.202 | 106.966 | -21.709 | 1.00 | 66.93 | C |
| ATOM | 6278 | N | PRO | C | 364 | 68.097 | 108.181 | -21.773 | 1.00 | 63.54 | C |
| ATOM | 6279 | CD | PRO | C | 364 | 69.500 | 108.289 | -22.209 | 1.00 | 93.74 | C |
| ATOM | 6280 | CA | PRO | C | 364 | 67.436 | 109.487 | -21.856 | 1.00 | 63.54 | C |
| ATOM | 6281 | CB | PRO | C | 364 | 68.535 | 110.390 | -22.425 | 1.00 | 93.74 | C |
| ATOM | 6282 | CG | PRO | C | 364 | 69.431 | 109.431 | -23.172 | 1.00 | 93.74 | C |
| ATOM | 6283 | C | PRO | C | 364 | 66.124 | 109.562 | -22.651 | 1.00 | 63.54 | C |
| ATOM | 6284 | O | PRO | C | 364 | 65.233 | 110.345 | -22.302 | 1.00 | 63.54 | C |
| ATOM | 6285 | N | ASP | C | 365 | 65.998 | 108.754 | -23.704 | 1.00 | 99.87 | C |
| ATOM | 6286 | CA | ASP | C | 365 | 64.785 | 108.774 | -24.525 | 1.00 | 99.87 | C |
| ATOM | 6287 | CB | ASP | C | 365 | 65.149 | 108.753 | -26.020 | 1.00 | 100.07 | C |
| ATOM | 6288 | CG | ASP | C | 365 | 64.028 | 109.302 | -26.917 | 1.00 | 100.07 | C |
| ATOM | 6289 | OD1 | ASP | C | 365 | 64.179 | 109.263 | -28.161 | 1.00 | 100.07 | C |
| ATOM | 6290 | OD2 | ASP | C | 365 | 62.999 | 109.781 | -26.385 | 1.00 | 100.07 | C |
| ATOM | 6291 | C | ASP | C | 365 | 63.842 | 107.610 | -24.204 | 1.00 | 99.87 | C |
| ATOM | 6292 | O | ASP | C | 365 | 62.645 | 107.666 | -24.505 | 1.00 | 99.87 | C |
| ATOM | 6293 | N | THR | C | 366 | 64.376 | 106.558 | -23.595 | 1.00 | 100.07 | C |
| ATOM | 6294 | CA | THR | C | 366 | 63.553 | 105.408 | -23.247 | 1.00 | 100.07 | C |
| ATOM | 6295 | CB | THR | C | 366 | 64.290 | 104.088 | -23.523 | 1.00 | 81.24 | C |
| ATOM | 6296 | OG1 | THR | C | 366 | 64.670 | 104.036 | -24.905 | 1.00 | 81.24 | C |
| ATOM | 6297 | CG2 | THR | C | 366 | 63.386 | 102.900 | -23.206 | 1.00 | 81.24 | C |
| ATOM | 6298 | C | THR | C | 366 | 63.158 | 105.463 | -21.780 | 1.00 | 100.07 | C |
| ATOM | 6299 | O | THR | C | 366 | 62.175 | 104.847 | -21.369 | 1.00 | 100.07 | C |
| ATOM | 6300 | N | LEU | C | 367 | 63.933 | 106.208 | -20.999 | 1.00 | 87.14 | C |
| ATOM | 6301 | CA | LEU | C | 367 | 63.670 | 106.360 | -19.578 | 1.00 | 87.14 | C |
| ATOM | 6302 | CB | LEU | C | 367 | 64.690 | 107.305 | -18.942 | 1.00 | 100.07 | C |
| ATOM | 6303 | CG | LEU | C | 367 | 66.110 | 106.775 | -18.731 | 1.00 | 100.07 | C |
| ATOM | 6304 | CD1 | LEU | C | 367 | 67.010 | 107.904 | -18.244 | 1.00 | 100.07 | C |
| ATOM | 6305 | CD2 | LEU | C | 367 | 66.086 | 105.624 | -17.730 | 1.00 | 100.07 | C |
| ATOM | 6306 | C | LEU | C | 367 | 62.273 | 106.911 | -19.367 | 1.00 | 87.14 | C |
| ATOM | 6307 | O | LEU | C | 367 | 62.079 | 108.122 | -19.331 | 1.00 | 87.14 | C |
| ATOM | 6308 | N | THR | C | 368 | 61.303 | 106.012 | -19.245 | 1.00 | 88.45 | C |
| ATOM | 6309 | CA | THR | C | 368 | 59.918 | 106.400 | -19.024 | 1.00 | 88.45 | C |
| ATOM | 6310 | CB | THR | C | 368 | 58.979 | 105.804 | -20.094 | 1.00 | 85.27 | C |
| ATOM | 6311 | OG1 | THR | C | 368 | 58.938 | 104.378 | -19.960 | 1.00 | 85.27 | C |
| ATOM | 6312 | CG2 | THR | C | 368 | 59.467 | 106.177 | -21.496 | 1.00 | 85.27 | C |
| ATOM | 6313 | C | THR | C | 368 | 59.495 | 105.898 | -17.654 | 1.00 | 88.45 | C |
| ATOM | 6314 | O | THR | C | 368 | 60.098 | 104.966 | -17.118 | 1.00 | 88.45 | C |
| ATOM | 6315 | N | PRO | C | 369 | 58.464 | 106.514 | -17.054 | 1.00 | 100.07 | C |
| ATOM | 6316 | CD | PRO | C | 369 | 57.546 | 107.569 | -17.523 | 1.00 | 36.65 | C |
| ATOM | 6317 | CA | PRO | C | 369 | 58.081 | 106.002 | -15.735 | 1.00 | 100.07 | C |
| ATOM | 6318 | CB | PRO | C | 369 | 56.970 | 106.960 | -15.296 | 1.00 | 36.65 | C |
| ATOM | 6319 | CG | PRO | C | 369 | 56.378 | 107.440 | -16.579 | 1.00 | 36.65 | C |
| ATOM | 6320 | C | PRO | C | 369 | 57.631 | 104.546 | -15.865 | 1.00 | 100.07 | C |
| ATOM | 6321 | O | PRO | C | 369 | 57.699 | 103.970 | -16.951 | 1.00 | 100.07 | C |
| ATOM | 6322 | N | ALA | C | 370 | 57.190 | 103.942 | -14.771 | 1.00 | 74.49 | C |
| ATOM | 6323 | CA | ALA | C | 370 | 56.755 | 102.550 | -14.810 | 1.00 | 74.49 | C |
| ATOM | 6324 | CB | ALA | C | 370 | 55.466 | 102.422 | -15.599 | 1.00 | 100.07 | C |
| ATOM | 6325 | C | ALA | C | 370 | 57.839 | 101.685 | -15.438 | 1.00 | 74.49 | C |
| ATOM | 6326 | O | ALA | C | 370 | 57.616 | 100.517 | -15.754 | 1.00 | 74.49 | C |
| ATOM | 6327 | N | LYS | C | 371 | 59.009 | 102.285 | -15.630 | 1.00 | 40.41 | C |
| ATOM | 6328 | CA | LYS | C | 371 | 60.170 | 101.609 | -16.193 | 1.00 | 40.41 | C |
| ATOM | 6329 | CB | LYS | C | 371 | 60.349 | 101.946 | -17.681 | 1.00 | 65.26 | C |
| ATOM | 6330 | CG | LYS | C | 371 | 59.268 | 101.393 | -18.604 | 1.00 | 65.26 | C |
| ATOM | 6331 | CD | LYS | C | 371 | 59.603 | 101.655 | -20.071 | 1.00 | 65.26 | C |
| ATOM | 6332 | CE | LYS | C | 371 | 58.542 | 101.087 | -21.005 | 1.00 | 65.26 | C |
| ATOM | 6333 | NZ | LYS | C | 371 | 57.221 | 101.740 | -20.824 | 1.00 | 65.26 | C |
| ATOM | 6334 | C | LYS | C | 371 | 61.325 | 102.177 | -15.396 | 1.00 | 40.41 | C |
| ATOM | 6335 | O | LYS | C | 371 | 62.455 | 101.674 | -15.444 | 1.00 | 40.41 | C |
| ATOM | 6336 | N | LEU | C | 372 | 61.005 | 103.244 | -14.667 | 1.00 | 98.56 | C |
| ATOM | 6337 | CA | LEU | C | 372 | 61.951 | 103.960 | -13.825 | 1.00 | 98.56 | C |
| ATOM | 6338 | CB | LEU | C | 372 | 61.964 | 105.444 | -14.198 | 1.00 | 84.70 | C |
| ATOM | 6339 | CG | LEU | C | 372 | 63.228 | 106.258 | -13.899 | 1.00 | 84.70 | C |
| ATOM | 6340 | CD1 | LEU | C | 372 | 62.983 | 107.709 | -14.289 | 1.00 | 84.70 | C |
| ATOM | 6341 | CD2 | LEU | C | 372 | 63.607 | 106.149 | -12.433 | 1.00 | 84.70 | C |
| ATOM | 6342 | C | LEU | C | 372 | 61.471 | 103.819 | -12.393 | 1.00 | 98.56 | C |
| ATOM | 6343 | O | LEU | C | 372 | 62.230 | 104.023 | -11.449 | 1.00 | 98.56 | C |
| ATOM | 6344 | N | VAL | C | 373 | 60.199 | 103.462 | -12.250 | 1.00 | 83.09 | C |
| ATOM | 6345 | CA | VAL | C | 373 | 59.562 | 103.302 | -10.945 | 1.00 | 83.09 | C |
| ATOM | 6346 | CB | VAL | C | 373 | 58.215 | 104.049 | -10.916 | 1.00 | 71.59 | C |

```
ATOM   6347  CG1 VAL C 373      57.413 103.633  -9.710  1.00 71.59           C
ATOM   6348  CG2 VAL C 373      58.462 105.547 -10.900  1.00 71.59           C
ATOM   6349  C   VAL C 373      59.319 101.854 -10.547  1.00 83.09           C
ATOM   6350  O   VAL C 373      58.975 101.019 -11.377  1.00 83.09           C
ATOM   6351  N   ASN C 374      59.498 101.567  -9.263  1.00 53.47           C
ATOM   6352  CA  ASN C 374      59.283 100.222  -8.746  1.00 53.47           C
ATOM   6353  CB  ASN C 374      60.617  99.578  -8.370  1.00100.07           C
ATOM   6354  CG  ASN C 374      61.586  99.530  -9.539  1.00100.07           C
ATOM   6355  OD1 ASN C 374      61.214  99.159 -10.658  1.00100.07           C
ATOM   6356  ND2 ASN C 374      62.839  99.897  -9.284  1.00100.07           C
ATOM   6357  C   ASN C 374      58.340 100.233  -7.541  1.00 53.47           C
ATOM   6358  O   ASN C 374      58.368 101.153  -6.716  1.00 53.47           C
ATOM   6359  N   SER C 375      57.502  99.204  -7.444  1.00 68.54           C
ATOM   6360  CA  SER C 375      56.534  99.115  -6.362  1.00 68.54           C
ATOM   6361  CB  SER C 375      55.250  98.475  -6.878  1.00100.07           C
ATOM   6362  OG  SER C 375      54.754  99.187  -7.999  1.00100.07           C
ATOM   6363  C   SER C 375      57.051  98.340  -5.169  1.00 68.54           C
ATOM   6364  O   SER C 375      56.412  97.396  -4.712  1.00 68.54           C
ATOM   6365  N   ARG C 376      58.216  98.739  -4.672  1.00 40.13           C
ATOM   6366  CA  ARG C 376      58.826  98.088  -3.518  1.00 40.13           C
ATOM   6367  CB  ARG C 376      60.207  97.525  -3.868  1.00100.07           C
ATOM   6368  CG  ARG C 376      60.149  96.199  -4.626  1.00100.07           C
ATOM   6369  CD  ARG C 376      61.510  95.505  -4.704  1.00100.07           C
ATOM   6370  NE  ARG C 376      61.388  94.123  -5.172  1.00100.07           C
ATOM   6371  CZ  ARG C 376      62.390  93.248  -5.208  1.00100.07           C
ATOM   6372  NH1 ARG C 376      63.604  93.607  -4.801  1.00100.07           C
ATOM   6373  NH2 ARG C 376      62.173  92.010  -5.644  1.00100.07           C
ATOM   6374  C   ARG C 376      58.936  99.080  -2.381  1.00 40.13           C
ATOM   6375  O   ARG C 376      58.538  98.795  -1.257  1.00 40.13           C
ATOM   6376  N   PRO C 377      59.475 100.267  -2.658  1.00 70.63           C
ATOM   6377  CD  PRO C 377      59.910 100.758  -3.972  1.00100.07           C
ATOM   6378  CA  PRO C 377      59.626 101.313  -1.645  1.00 70.63           C
ATOM   6379  CB  PRO C 377      59.967 102.554  -2.478  1.00100.07           C
ATOM   6380  CG  PRO C 377      59.513 102.193  -3.888  1.00100.07           C
ATOM   6381  C   PRO C 377      58.394 101.535  -0.760  1.00 70.63           C
ATOM   6382  O   PRO C 377      58.501 101.506   0.463  1.00 70.63           C
ATOM   6383  N   LEU C 378      57.238 101.760  -1.386  1.00 70.91           C
ATOM   6384  CA  LEU C 378      55.985 101.992  -0.665  1.00 70.91           C
ATOM   6385  CB  LEU C 378      54.940 102.613  -1.586  1.00 81.51           C
ATOM   6386  CG  LEU C 378      55.158 104.095  -1.863  1.00 81.51           C
ATOM   6387  CD1 LEU C 378      56.464 104.313  -2.625  1.00 81.51           C
ATOM   6388  CD2 LEU C 378      53.980 104.609  -2.648  1.00 81.51           C
ATOM   6389  C   LEU C 378      55.421 100.727  -0.040  1.00 70.91           C
ATOM   6390  O   LEU C 378      54.634 100.785   0.909  1.00 70.91           C
ATOM   6391  N   GLU C 379      55.792  99.581  -0.594  1.00 69.76           C
ATOM   6392  CA  GLU C 379      55.356  98.330  -0.014  1.00 69.76           C
ATOM   6393  CB  GLU C 379      55.325  97.216  -1.054  1.00100.07           C
ATOM   6394  CG  GLU C 379      54.327  96.139  -0.699  1.00100.07           C
ATOM   6395  CD  GLU C 379      53.041  96.733  -0.149  1.00100.07           C
ATOM   6396  OE1 GLU C 379      52.484  97.637  -0.810  1.00100.07           C
ATOM   6397  OE2 GLU C 379      52.590  96.306   0.939  1.00100.07           C
ATOM   6398  C   GLU C 379      56.470  98.107   0.993  1.00 69.76           C
ATOM   6399  O   GLU C 379      57.489  98.796   0.934  1.00 69.76           C
ATOM   6400  N   ALA C 380      56.298  97.169   1.915  1.00 99.83           C
ATOM   6401  CA  ALA C 380      57.319  96.939   2.931  1.00 99.83           C
ATOM   6402  CB  ALA C 380      58.694  96.751   2.287  1.00 68.20           C
ATOM   6403  C   ALA C 380      57.324  98.175   3.818  1.00 99.83           C
ATOM   6404  O   ALA C 380      56.989  98.105   4.996  1.00 99.83           C
ATOM   6405  N   ALA C 381      57.695  99.313   3.244  1.00 58.39           C
ATOM   6406  CA  ALA C 381      57.717 100.555   3.993  1.00 58.39           C
ATOM   6407  CB  ALA C 381      57.894 101.725   3.065  1.00100.07           C
ATOM   6408  C   ALA C 381      56.394 100.655   4.712  1.00 58.39           C
ATOM   6409  O   ALA C 381      56.291 101.318   5.736  1.00 58.39           C
ATOM   6410  N   LEU C 382      55.385  99.993   4.150  1.00 82.05           C
ATOM   6411  CA  LEU C 382      54.046  99.939   4.731  1.00 82.05           C
ATOM   6412  CB  LEU C 382      52.978 100.171   3.672  1.00  5.55           C
ATOM   6413  CG  LEU C 382      52.716 101.595   3.216  1.00  5.55           C
ATOM   6414  CD1 LEU C 382      51.793 101.569   2.028  1.00  5.55           C
ATOM   6415  CD2 LEU C 382      52.099 102.391   4.345  1.00  5.55           C
ATOM   6416  C   LEU C 382      53.854  98.547   5.306  1.00 82.05           C
ATOM   6417  O   LEU C 382      53.592  98.381   6.500  1.00 82.05           C
ATOM   6418  N   ARG C 383      53.981  97.547   4.436  1.00 94.25           C
ATOM   6419  CA  ARG C 383      53.841  96.156   4.837  1.00 94.25           C
ATOM   6420  CB  ARG C 383      54.454  95.227   3.778  1.00100.07           C
ATOM   6421  CG  ARG C 383      54.527  93.756   4.184  1.00100.07           C
ATOM   6422  CD  ARG C 383      55.108  92.872   3.072  1.00100.07           C
ATOM   6423  NE  ARG C 383      54.186  92.700   1.945  1.00100.07           C
ATOM   6424  CZ  ARG C 383      54.338  91.799   0.970  1.00100.07           C
ATOM   6425  NH1 ARG C 383      55.381  90.975   0.975  1.00100.07           C
ATOM   6426  NH2 ARG C 383      53.439  91.709  -0.009  1.00100.07           C
ATOM   6427  C   ARG C 383      54.557  95.981   6.163  1.00 94.25           C
ATOM   6428  O   ARG C 383      54.186  95.130   6.969  1.00 94.25           C
ATOM   6429  N   GLU C 384      55.583  96.796   6.391  1.00 56.29           C
ATOM   6430  CA  GLU C 384      56.308  96.713   7.634  1.00 56.29           C
```

-77-

| | | | | | | | | | | |
|---|---|---|---|---|---|---|---|---|---|---|
| ATOM | 6431 | CB | GLU | C | 384 | 57.712 | 97.282 | 7.523 | 1.00 84.63 | C |
| ATOM | 6432 | CG | GLU | C | 384 | 58.655 | 96.650 | 8.525 | 1.00 84.63 | C |
| ATOM | 6433 | CD | GLU | C | 384 | 59.980 | 97.370 | 8.618 | 1.00 84.63 | C |
| ATOM | 6434 | OE1 | GLU | C | 384 | 60.038 | 98.424 | 9.291 | 1.00 84.63 | C |
| ATOM | 6435 | OE2 | GLU | C | 384 | 60.962 | 96.887 | 8.010 | 1.00 84.63 | C |
| ATOM | 6436 | C | GLU | C | 384 | 55.535 | 97.481 | 8.675 | 1.00 56.29 | C |
| ATOM | 6437 | O | GLU | C | 384 | 55.254 | 96.945 | 9.742 | 1.00 56.29 | C |
| ATOM | 6438 | N | PHE | C | 385 | 55.163 | 98.726 | 8.402 | 1.00 53.87 | C |
| ATOM | 6439 | CA | PHE | C | 385 | 54.421 | 99.423 | 9.439 | 1.00 53.87 | C |
| ATOM | 6440 | CB | PHE | C | 385 | 54.222 | 100.908 | 9.165 | 1.00 31.97 | C |
| ATOM | 6441 | CG | PHE | C | 385 | 53.353 | 101.582 | 10.214 | 1.00 31.97 | C |
| ATOM | 6442 | CD1 | PHE | C | 385 | 53.785 | 101.677 | 11.540 | 1.00 31.97 | C |
| ATOM | 6443 | CD2 | PHE | C | 385 | 52.078 | 102.045 | 9.900 | 1.00 31.97 | C |
| ATOM | 6444 | CE1 | PHE | C | 385 | 52.972 | 102.214 | 12.527 | 1.00 31.97 | C |
| ATOM | 6445 | CE2 | PHE | C | 385 | 51.263 | 102.581 | 10.885 | 1.00 31.97 | C |
| ATOM | 6446 | CZ | PHE | C | 385 | 51.714 | 102.663 | 12.200 | 1.00 31.97 | C |
| ATOM | 6447 | C | PHE | C | 385 | 53.052 | 98.832 | 9.728 | 1.00 53.87 | C |
| ATOM | 6448 | O | PHE | C | 385 | 52.946 | 97.856 | 10.462 | 1.00 53.87 | C |
| ATOM | 6449 | N | PHE | C | 386 | 52.014 | 99.425 | 9.140 | 1.00 46.11 | C |
| ATOM | 6450 | CA | PHE | C | 386 | 50.639 | 99.012 | 9.381 | 1.00 46.11 | C |
| ATOM | 6451 | CB | PHE | C | 386 | 49.834 | 98.926 | 8.081 | 1.00 42.42 | C |
| ATOM | 6452 | CG | PHE | C | 386 | 48.394 | 99.267 | 8.272 | 1.00 42.42 | C |
| ATOM | 6453 | CD1 | PHE | C | 386 | 47.875 | 100.451 | 7.768 | 1.00 42.42 | C |
| ATOM | 6454 | CD2 | PHE | C | 386 | 47.581 | 98.465 | 9.076 | 1.00 42.42 | C |
| ATOM | 6455 | CE1 | PHE | C | 386 | 46.555 | 100.840 | 8.071 | 1.00 42.42 | C |
| ATOM | 6456 | CE2 | PHE | C | 386 | 46.261 | 98.844 | 9.386 | 1.00 42.42 | C |
| ATOM | 6457 | CZ | PHE | C | 386 | 45.745 | 100.033 | 8.888 | 1.00 42.42 | C |
| ATOM | 6458 | C | PHE | C | 386 | 50.535 | 97.694 | 10.134 | 1.00 46.11 | C |
| ATOM | 6459 | O | PHE | C | 386 | 50.323 | 97.674 | 11.353 | 1.00 46.11 | C |
| ATOM | 6460 | N | SER | C | 387 | 50.696 | 96.589 | 9.423 | 1.00 23.33 | C |
| ATOM | 6461 | CA | SER | C | 387 | 50.619 | 95.294 | 10.078 | 1.00 23.33 | C |
| ATOM | 6462 | CB | SER | C | 387 | 50.407 | 94.188 | 9.038 | 1.00100.07 | C |
| ATOM | 6463 | OG | SER | C | 387 | 49.034 | 93.837 | 8.945 | 1.00100.07 | C |
| ATOM | 6464 | C | SER | C | 387 | 51.886 | 95.050 | 10.875 | 1.00 23.33 | C |
| ATOM | 6465 | O | SER | C | 387 | 52.297 | 95.891 | 11.652 | 1.00 23.33 | C |
| ATOM | 6466 | N | ARG | C | 388 | 52.495 | 93.897 | 10.676 | 1.00 84.80 | C |
| ATOM | 6467 | CA | ARG | C | 388 | 53.716 | 93.533 | 11.361 | 1.00 84.80 | C |
| ATOM | 6468 | CB | ARG | C | 388 | 54.832 | 93.413 | 10.327 | 1.00100.07 | C |
| ATOM | 6469 | CG | ARG | C | 388 | 54.634 | 92.229 | 9.379 | 1.00100.07 | C |
| ATOM | 6470 | CD | ARG | C | 388 | 55.745 | 92.147 | 8.349 | 1.00100.07 | C |
| ATOM | 6471 | NE | ARG | C | 388 | 56.133 | 90.770 | 8.059 | 1.00100.07 | C |
| ATOM | 6472 | CZ | ARG | C | 388 | 57.221 | 90.434 | 7.369 | 1.00100.07 | C |
| ATOM | 6473 | NH1 | ARG | C | 388 | 58.026 | 91.378 | 6.897 | 1.00100.07 | C |
| ATOM | 6474 | NH2 | ARG | C | 388 | 57.517 | 89.157 | 7.162 | 1.00100.07 | C |
| ATOM | 6475 | C | ARG | C | 388 | 54.163 | 94.399 | 12.553 | 1.00 84.80 | C |
| ATOM | 6476 | O | ARG | C | 388 | 53.417 | 94.569 | 13.516 | 1.00 84.80 | C |
| ATOM | 6477 | N | SER | C | 389 | 55.372 | 94.948 | 12.487 | 1.00 15.17 | C |
| ATOM | 6478 | CA | SER | C | 389 | 55.938 | 95.743 | 13.591 | 1.00 15.17 | C |
| ATOM | 6479 | CB | SER | C | 389 | 57.466 | 95.729 | 13.482 | 1.00100.07 | C |
| ATOM | 6480 | OG | SER | C | 389 | 57.900 | 96.390 | 12.301 | 1.00100.07 | C |
| ATOM | 6481 | C | SER | C | 389 | 55.498 | 97.197 | 13.797 | 1.00 15.17 | C |
| ATOM | 6482 | O | SER | C | 389 | 55.539 | 98.003 | 12.868 | 1.00 15.17 | C |
| ATOM | 6483 | N | ALA | C | 390 | 55.130 | 97.520 | 15.034 | 1.00 74.60 | C |
| ATOM | 6484 | CA | ALA | C | 390 | 54.695 | 98.860 | 15.437 | 1.00 74.60 | C |
| ATOM | 6485 | CB | ALA | C | 390 | 54.061 | 99.607 | 14.271 | 1.00 54.82 | C |
| ATOM | 6486 | C | ALA | C | 390 | 53.680 | 98.725 | 16.561 | 1.00 74.60 | C |
| ATOM | 6487 | O | ALA | C | 390 | 52.511 | 98.422 | 16.299 | 1.00 74.60 | C |
| ATOM | 6488 | N | LEU | C | 391 | 54.128 | 98.943 | 17.800 | 1.00 99.21 | C |
| ATOM | 6489 | CA | LEU | C | 391 | 53.259 | 98.846 | 18.973 | 1.00 99.21 | C |
| ATOM | 6490 | CB | LEU | C | 391 | 53.669 | 99.858 | 20.047 | 1.00100.07 | C |
| ATOM | 6491 | CG | LEU | C | 391 | 54.523 | 99.374 | 21.223 | 1.00100.07 | C |
| ATOM | 6492 | CD1 | LEU | C | 391 | 54.940 | 100.571 | 22.082 | 1.00100.07 | C |
| ATOM | 6493 | CD2 | LEU | C | 391 | 53.733 | 98.361 | 22.048 | 1.00100.07 | C |
| ATOM | 6494 | C | LEU | C | 391 | 51.833 | 99.122 | 18.557 | 1.00 99.21 | C |
| ATOM | 6495 | O | LEU | C | 391 | 50.907 | 98.427 | 18.965 | 1.00 99.21 | C |
| ATOM | 6496 | N | SER | C | 392 | 51.668 | 100.138 | 17.723 | 1.00 41.66 | C |
| ATOM | 6497 | CA | SER | C | 392 | 50.358 | 100.503 | 17.242 | 1.00 41.66 | C |
| ATOM | 6498 | CB | SER | C | 392 | 50.422 | 101.884 | 16.574 | 1.00 44.66 | C |
| ATOM | 6499 | OG | SER | C | 392 | 50.865 | 102.887 | 17.483 | 1.00 44.66 | C |
| ATOM | 6500 | C | SER | C | 392 | 49.798 | 99.439 | 16.283 | 1.00 41.66 | C |
| ATOM | 6501 | O | SER | C | 392 | 49.167 | 99.757 | 15.276 | 1.00 41.66 | C |
| ATOM | 6502 | N | GLN | C | 393 | 50.035 | 98.170 | 16.595 | 1.00 45.63 | C |
| ATOM | 6503 | CA | GLN | C | 393 | 49.507 | 97.080 | 15.782 | 1.00 45.63 | C |
| ATOM | 6504 | CB | GLN | C | 393 | 50.576 | 96.515 | 14.841 | 1.00 68.19 | C |
| ATOM | 6505 | CG | GLN | C | 393 | 50.051 | 95.603 | 13.683 | 1.00 68.19 | C |
| ATOM | 6506 | CD | GLN | C | 393 | 49.662 | 94.150 | 14.073 | 1.00 68.19 | C |
| ATOM | 6507 | OE1 | GLN | C | 393 | 49.587 | 93.277 | 13.212 | 1.00 68.19 | C |
| ATOM | 6508 | NE2 | GLN | C | 393 | 49.406 | 93.905 | 15.349 | 1.00 68.19 | C |
| ATOM | 6509 | C | GLN | C | 393 | 49.024 | 95.970 | 16.707 | 1.00 45.63 | C |
| ATOM | 6510 | O | GLN | C | 393 | 49.827 | 95.367 | 17.415 | 1.00 45.63 | C |
| ATOM | 6511 | N | PHE | C | 394 | 47.720 | 95.704 | 16.700 | 1.00 88.56 | C |
| ATOM | 6512 | CA | PHE | C | 394 | 47.133 | 94.642 | 17.513 | 1.00 88.56 | C |
| ATOM | 6513 | CB | PHE | C | 394 | 47.728 | 94.634 | 18.941 | 1.00 62.03 | C |
| ATOM | 6514 | CG | PHE | C | 394 | 47.836 | 96.016 | 19.621 | 1.00 62.03 | C |

```
ATOM   6515  CD1 PHE C 394      46.727  96.841  19.784  1.00 62.03           C
ATOM   6516  CD2 PHE C 394      49.036  96.426  20.217  1.00 62.03           C
ATOM   6517  CE1 PHE C 394      46.804  98.040  20.536  1.00 62.03           C
ATOM   6518  CE2 PHE C 394      49.109  97.625  20.967  1.00 62.03           C
ATOM   6519  CZ  PHE C 394      47.989  98.422  21.123  1.00 62.03           C
ATOM   6520  C   PHE C 394      45.608  94.717  17.565  1.00 88.56           C
ATOM   6521  O   PHE C 394      45.041  95.805  17.458  1.00 88.56           C
ATOM   6522  N   LYS C 395      44.947  93.562  17.689  1.00 92.90           C
ATOM   6523  CA  LYS C 395      43.477  93.501  17.773  1.00 92.90           C
ATOM   6524  CB  LYS C 395      42.921  92.323  16.983  1.00 92.45           C
ATOM   6525  CG  LYS C 395      43.378  90.975  17.521  1.00 92.45           C
ATOM   6526  CD  LYS C 395      42.263  89.937  17.495  1.00 92.45           C
ATOM   6527  CE  LYS C 395      41.844  89.561  16.081  1.00 92.45           C
ATOM   6528  NZ  LYS C 395      40.691  88.615  16.087  1.00 92.45           C
ATOM   6529  C   LYS C 395      43.150  93.275  19.229  1.00 92.90           C
ATOM   6530  O   LYS C 395      44.019  93.448  20.079  1.00 92.90           C
ATOM   6531  N   ASP C 396      41.919  92.880  19.541  1.00 39.25           C
ATOM   6532  CA  ASP C 396      41.618  92.631  20.953  1.00 39.25           C
ATOM   6533  CB  ASP C 396      41.626  93.950  21.736  1.00 83.72           C
ATOM   6534  CG  ASP C 396      42.032  93.762  23.190  1.00 83.72           C
ATOM   6535  OD1 ASP C 396      41.329  93.032  23.913  1.00 83.72           C
ATOM   6536  OD2 ASP C 396      43.054  94.344  23.610  1.00 83.72           C
ATOM   6537  C   ASP C 396      40.357  91.843  21.299  1.00 39.25           C
ATOM   6538  O   ASP C 396      39.245  92.384  21.347  1.00 39.25           C
ATOM   6539  N   GLU C 397      40.576  90.551  21.537  1.00 48.65           C
ATOM   6540  CA  GLU C 397      39.564  89.576  21.942  1.00 48.65           C
ATOM   6541  CB  GLU C 397      39.712  89.342  23.455  1.00 45.27           C
ATOM   6542  CG  GLU C 397      38.793  88.295  24.073  1.00 45.27           C
ATOM   6543  CD  GLU C 397      37.623  88.895  24.826  1.00 45.27           C
ATOM   6544  OE1 GLU C 397      36.931  89.783  24.286  1.00 45.27           C
ATOM   6545  OE2 GLU C 397      37.393  88.452  25.965  1.00 45.27           C
ATOM   6546  C   GLU C 397      38.080  89.793  21.600  1.00 48.65           C
ATOM   6547  O   GLU C 397      37.703  90.722  20.888  1.00 48.65           C
ATOM   6548  N   THR C 398      37.270  88.884  22.140  1.00100.07           C
ATOM   6549  CA  THR C 398      35.820  88.792  21.993  1.00100.07           C
ATOM   6550  CB  THR C 398      35.313  87.505  22.676  1.00 56.66           C
ATOM   6551  OG1 THR C 398      35.825  87.433  24.011  1.00 56.66           C
ATOM   6552  CG2 THR C 398      35.764  86.296  21.912  1.00 56.66           C
ATOM   6553  C   THR C 398      34.937  89.940  22.478  1.00100.07           C
ATOM   6554  O   THR C 398      34.511  90.772  21.673  1.00100.07           C
ATOM   6555  N   ASN C 399      34.639  89.958  23.781  1.00 47.47           C
ATOM   6556  CA  ASN C 399      33.766  90.977  24.375  1.00 47.47           C
ATOM   6557  CB  ASN C 399      34.267  91.388  25.747  1.00 55.14           C
ATOM   6558  CG  ASN C 399      33.471  92.536  26.325  1.00 55.14           C
ATOM   6559  OD1 ASN C 399      33.833  93.106  27.355  1.00 55.14           C
ATOM   6560  ND2 ASN C 399      32.373  92.880  25.667  1.00 55.14           C
ATOM   6561  C   ASN C 399      33.651  92.229  23.521  1.00 47.47           C
ATOM   6562  O   ASN C 399      34.444  93.151  23.673  1.00 47.47           C
ATOM   6563  N   PRO C 400      32.634  92.292  22.644  1.00 35.05           C
ATOM   6564  CD  PRO C 400      31.385  91.528  22.747  1.00 36.44           C
ATOM   6565  CA  PRO C 400      32.436  93.445  21.769  1.00 35.05           C
ATOM   6566  CB  PRO C 400      30.950  93.363  21.414  1.00 36.44           C
ATOM   6567  CG  PRO C 400      30.365  92.600  22.543  1.00 36.44           C
ATOM   6568  C   PRO C 400      32.834  94.790  22.380  1.00 35.05           C
ATOM   6569  O   PRO C 400      33.244  95.707  21.657  1.00 35.05           C
ATOM   6570  N   LEU C 401      32.722  94.934  23.698  1.00 23.41           C
ATOM   6571  CA  LEU C 401      33.120  96.205  24.278  1.00 23.41           C
ATOM   6572  CB  LEU C 401      32.995  96.209  25.793  1.00 13.07           C
ATOM   6573  CG  LEU C 401      33.447  97.565  26.326  1.00 13.07           C
ATOM   6574  CD1 LEU C 401      32.501  98.595  25.793  1.00 13.07           C
ATOM   6575  CD2 LEU C 401      33.451  97.609  27.834  1.00 13.07           C
ATOM   6576  C   LEU C 401      34.574  96.312  23.911  1.00 23.41           C
ATOM   6577  O   LEU C 401      35.009  97.279  23.292  1.00 23.41           C
ATOM   6578  N   SER C 402      35.307  95.271  24.285  1.00 37.62           C
ATOM   6579  CA  SER C 402      36.735  95.159  24.027  1.00 37.62           C
ATOM   6580  CB  SER C 402      37.159  93.699  24.206  1.00 58.42           C
ATOM   6581  OG  SER C 402      36.598  93.170  25.395  1.00 58.42           C
ATOM   6582  C   SER C 402      37.094  95.648  22.622  1.00 37.62           C
ATOM   6583  O   SER C 402      37.676  96.720  22.443  1.00 37.62           C
ATOM   6584  N   SER C 403      36.746  94.856  21.623  1.00 59.01           C
ATOM   6585  CA  SER C 403      37.027  95.232  20.256  1.00 59.01           C
ATOM   6586  CB  SER C 403      36.280  94.302  19.304  1.00100.07           C
ATOM   6587  OG  SER C 403      34.880  94.375  19.519  1.00100.07           C
ATOM   6588  C   SER C 403      36.616  96.678  19.975  1.00 59.01           C
ATOM   6589  O   SER C 403      36.816  97.171  18.868  1.00 59.01           C
ATOM   6590  N   LEU C 404      36.031  97.353  20.963  1.00 29.86           C
ATOM   6591  CA  LEU C 404      35.601  98.741  20.787  1.00 29.86           C
ATOM   6592  CB  LEU C 404      34.121  98.884  21.167  1.00 33.94           C
ATOM   6593  CG  LEU C 404      33.424 100.196  20.787  1.00 33.94           C
ATOM   6594  CD1 LEU C 404      33.246 100.275  19.289  1.00 33.94           C
ATOM   6595  CD2 LEU C 404      32.070 100.258  21.448  1.00 33.94           C
ATOM   6596  C   LEU C 404      36.459  99.719  21.610  1.00 29.86           C
ATOM   6597  O   LEU C 404      37.066 100.646  21.052  1.00 29.86           C
ATOM   6598  N   ARG C 405      36.508  99.498  22.928  1.00 41.17           C
```

```
ATOM  6599  CA   ARG C 405      37.286 100.332  23.852  1.00 41.17           C
ATOM  6600  CB   ARG C 405      37.154  99.815  25.300  1.00100.07           C
ATOM  6601  CG   ARG C 405      38.471  99.334  25.985  1.00100.07           C
ATOM  6602  CD   ARG C 405      39.043  98.062  25.331  1.00100.07           C
ATOM  6603  NE   ARG C 405      40.331  97.622  25.879  1.00100.07           C
ATOM  6604  CZ   ARG C 405      41.087  96.663  25.335  1.00100.07           C
ATOM  6605  NH1  ARG C 405      40.690  96.045  24.232  1.00100.07           C
ATOM  6606  NH2  ARG C 405      42.242  96.317  25.890  1.00100.07           C
ATOM  6607  C    ARG C 405      38.740 100.293  23.451  1.00 41.17           C
ATOM  6608  O    ARG C 405      39.570 101.003  24.008  1.00 41.17           C
ATOM  6609  N    HIS C 406      39.042  99.447  22.479  1.00 24.77           C
ATOM  6610  CA   HIS C 406      40.404  99.278  22.030  1.00 24.77           C
ATOM  6611  CB   HIS C 406      40.645  97.818  21.701  1.00 25.51           C
ATOM  6612  CG   HIS C 406      42.032  97.532  21.235  1.00 25.51           C
ATOM  6613  CD2  HIS C 406      43.080  96.957  21.867  1.00 25.51           C
ATOM  6614  ND1  HIS C 406      42.466  97.843  19.966  1.00 25.51           C
ATOM  6615  CE1  HIS C 406      43.721  97.468  19.836  1.00 25.51           C
ATOM  6616  NE2  HIS C 406      44.118  96.927  20.973  1.00 25.51           C
ATOM  6617  C    HIS C 406      40.785 100.138  20.850  1.00 24.77           C
ATOM  6618  O    HIS C 406      41.967 100.355  20.605  1.00 24.77           C
ATOM  6619  N    ALA C 407      39.803 100.600  20.092  1.00 38.45           C
ATOM  6620  CA   ALA C 407      40.115 101.471  18.970  1.00 38.45           C
ATOM  6621  CB   ALA C 407      39.042 101.398  17.932  1.00 26.31           C
ATOM  6622  C    ALA C 407      40.098 102.826  19.624  1.00 38.45           C
ATOM  6623  O    ALA C 407      40.726 103.776  19.156  1.00 38.45           C
ATOM  6624  N    ARG C 408      39.377 102.864  20.742  1.00 53.76           C
ATOM  6625  CA   ARG C 408      39.171 104.055  21.549  1.00 53.76           C
ATOM  6626  CB   ARG C 408      37.830 103.924  22.284  1.00 38.44           C
ATOM  6627  CG   ARG C 408      37.253 105.223  22.770  1.00 38.44           C
ATOM  6628  CD   ARG C 408      35.952 105.034  23.549  1.00 38.44           C
ATOM  6629  NE   ARG C 408      35.174 106.269  23.554  1.00 38.44           C
ATOM  6630  CZ   ARG C 408      34.881 106.954  22.447  1.00 38.44           C
ATOM  6631  NH1  ARG C 408      35.300 106.516  21.260  1.00 38.44           C
ATOM  6632  NH2  ARG C 408      34.181 108.081  22.516  1.00 38.44           C
ATOM  6633  C    ARG C 408      40.308 104.335  22.543  1.00 53.76           C
ATOM  6634  O    ARG C 408      40.254 105.321  23.276  1.00 53.76           C
ATOM  6635  N    ARG C 409      41.324 103.471  22.588  1.00 53.14           C
ATOM  6636  CA   ARG C 409      42.462 103.699  23.486  1.00 53.14           C
ATOM  6637  CB   ARG C 409      43.333 102.453  23.647  1.00 56.81           C
ATOM  6638  CG   ARG C 409      43.025 101.587  24.855  1.00 56.81           C
ATOM  6639  CD   ARG C 409      44.033 100.433  24.942  1.00 56.81           C
ATOM  6640  NE   ARG C 409      43.760  99.503  26.040  1.00 56.81           C
ATOM  6641  CZ   ARG C 409      44.543  98.477  26.377  1.00 56.81           C
ATOM  6642  NH1  ARG C 409      45.671  98.233  25.710  1.00 56.81           C
ATOM  6643  NH2  ARG C 409      44.179  97.679  27.373  1.00 56.81           C
ATOM  6644  C    ARG C 409      43.294 104.782  22.838  1.00 53.14           C
ATOM  6645  O    ARG C 409      43.048 105.153  21.689  1.00 53.14           C
ATOM  6646  N    ILE C 410      44.298 105.269  23.553  1.00 27.33           C
ATOM  6647  CA   ILE C 410      45.130 106.344  23.024  1.00 27.33           C
ATOM  6648  CB   ILE C 410      44.672 107.713  23.598  1.00 41.58           C
ATOM  6649  CG2  ILE C 410      45.571 108.843  23.096  1.00 41.58           C
ATOM  6650  CG1  ILE C 410      43.220 107.970  23.202  1.00 41.58           C
ATOM  6651  CD   ILE C 410      42.743 109.335  23.544  1.00 41.58           C
ATOM  6652  C    ILE C 410      46.597 106.159  23.350  1.00 27.33           C
ATOM  6653  O    ILE C 410      47.265 105.263  22.832  1.00 27.33           C
ATOM  6654  N    SER C 411      47.079 107.058  24.199  1.00 36.52           C
ATOM  6655  CA   SER C 411      48.443 107.066  24.691  1.00 36.52           C
ATOM  6656  CB   SER C 411      48.400 106.733  26.185  1.00 62.16           C
ATOM  6657  OG   SER C 411      47.111 106.239  26.551  1.00 62.16           C
ATOM  6658  C    SER C 411      49.383 106.110  23.959  1.00 36.52           C
ATOM  6659  O    SER C 411      49.423 106.074  22.732  1.00 36.52           C
ATOM  6660  N    ALA C 412      50.137 105.348  24.743  1.00 64.92           C
ATOM  6661  CA   ALA C 412      51.079 104.367  24.227  1.00 64.92           C
ATOM  6662  CB   ALA C 412      50.440 103.585  23.073  1.00 18.77           C
ATOM  6663  C    ALA C 412      52.397 104.989  23.780  1.00 64.92           C
ATOM  6664  O    ALA C 412      52.438 106.139  23.356  1.00 64.92           C
ATOM  6665  N    ALA C 413      53.472 104.215  23.888  1.00 57.15           C
ATOM  6666  CA   ALA C 413      54.794 104.668  23.478  1.00 57.15           C
ATOM  6667  CB   ALA C 413      55.835 103.618  23.849  1.00 81.91           C
ATOM  6668  C    ALA C 413      54.789 104.895  21.966  1.00 57.15           C
ATOM  6669  O    ALA C 413      54.967 103.955  21.195  1.00 57.15           C
ATOM  6670  N    ALA C 414      54.597 106.145  21.552  1.00100.07           C
ATOM  6671  CA   ALA C 414      54.538 106.498  20.131  1.00100.07           C
ATOM  6672  CB   ALA C 414      54.007 107.936  19.969  1.00 67.08           C
ATOM  6673  C    ALA C 414      55.854 106.348  19.372  1.00100.07           C
ATOM  6674  O    ALA C 414      56.673 105.470  19.669  1.00100.07           C
ATOM  6675  N    ALA C 415      56.035 107.211  18.376  1.00100.07           C
ATOM  6676  CA   ALA C 415      57.236 107.199  17.560  1.00100.07           C
ATOM  6677  CB   ALA C 415      56.975 107.914  16.240  1.00100.07           C
ATOM  6678  C    ALA C 415      58.383 107.868  18.312  1.00100.07           C
ATOM  6679  O    ALA C 415      58.186 108.439  19.388  1.00100.07           C
ATOM  6680  N    ALA C 416      59.579 107.791  17.731  1.00100.07           C
ATOM  6681  CA   ALA C 416      60.785 108.364  18.326  1.00100.07           C
ATOM  6682  CB   ALA C 416      61.988 108.113  17.413  1.00 91.00           C
```

-80-

```
ATOM   6683  C   ALA C 416      60.677 109.855  18.660  1.00100.07           C
ATOM   6684  O   ALA C 416      59.752 110.269  19.370  1.00100.07           C
ATOM   6685  N   ALA C 417      61.621 110.650  18.147  1.00100.07           C
ATOM   6686  CA  ALA C 417      61.670 112.095  18.405  1.00100.07           C
ATOM   6687  CB  ALA C 417      60.355 112.768  17.983  1.00 51.89           C
ATOM   6688  C   ALA C 417      61.930 112.304  19.906  1.00100.07           C
ATOM   6689  O   ALA C 417      63.084 112.323  20.345  1.00100.07           C
ATOM   6690  N   ALA C 418      60.863 112.441  20.693  1.00100.07           C
ATOM   6691  CA  ALA C 418      60.987 112.618  22.144  1.00100.07           C
ATOM   6692  CB  ALA C 418      61.465 114.040  22.477  1.00 65.97           C
ATOM   6693  C   ALA C 418      59.649 112.337  22.833  1.00100.07           C
ATOM   6694  O   ALA C 418      59.244 113.068  23.742  1.00100.07           C
ATOM   6695  N   ALA C 419      58.981 111.262  22.400  1.00100.07           C
ATOM   6696  CA  ALA C 419      57.677 110.872  22.937  1.00100.07           C
ATOM   6697  CB  ALA C 419      56.589 111.092  21.861  1.00 90.38           C
ATOM   6698  C   ALA C 419      57.578 109.445  23.485  1.00100.07           C
ATOM   6699  O   ALA C 419      57.508 108.477  22.722  1.00100.07           C
ATOM   6700  N   ALA C 420      57.572 109.344  24.814  1.00 96.61           C
ATOM   6701  CA  ALA C 420      57.423 108.083  25.534  1.00 96.61           C
ATOM   6702  CB  ALA C 420      56.034 107.527  25.260  1.00100.07           C
ATOM   6703  C   ALA C 420      58.434 106.959  25.397  1.00 96.61           C
ATOM   6704  O   ALA C 420      59.294 106.954  24.518  1.00 96.61           C
ATOM   6705  N   GLU C 421      58.266 105.990  26.291  1.00 64.31           C
ATOM   6706  CA  GLU C 421      59.073 104.785  26.406  1.00 64.31           C
ATOM   6707  CB  GLU C 421      60.558 105.115  26.425  1.00100.07           C
ATOM   6708  CG  GLU C 421      61.351 104.126  27.269  1.00100.07           C
ATOM   6709  CD  GLU C 421      62.822 104.450  27.322  1.00100.07           C
ATOM   6710  OE1 GLU C 421      63.162 105.631  27.559  1.00100.07           C
ATOM   6711  OE2 GLU C 421      63.636 103.519  27.131  1.00100.07           C
ATOM   6712  C   GLU C 421      58.693 104.147  27.744  1.00 64.31           C
ATOM   6713  O   GLU C 421      58.271 104.844  28.657  1.00 64.31           C
ATOM   6714  N   ARG C 422      58.854 102.837  27.873  1.00 72.83           C
ATOM   6715  CA  ARG C 422      58.494 102.138  29.104  1.00 72.83           C
ATOM   6716  CB  ARG C 422      58.571 100.615  28.891  1.00100.07           C
ATOM   6717  CG  ARG C 422      57.941 100.131  27.571  1.00100.07           C
ATOM   6718  CD  ARG C 422      57.685  98.612  27.524  1.00100.07           C
ATOM   6719  NE  ARG C 422      57.274  98.179  26.183  1.00100.07           C
ATOM   6720  CZ  ARG C 422      56.744  96.992  25.882  1.00100.07           C
ATOM   6721  NH1 ARG C 422      56.536  96.076  26.824  1.00100.07           C
ATOM   6722  NH2 ARG C 422      56.428  96.714  24.623  1.00100.07           C
ATOM   6723  C   ARG C 422      59.370 102.531  30.297  1.00 72.83           C
ATOM   6724  O   ARG C 422      59.663 101.696  31.155  1.00 72.83           C
ATOM   6725  N   ALA C 423      59.760 103.809  30.334  1.00 99.57           C
ATOM   6726  CA  ALA C 423      60.592 104.402  31.396  1.00 99.57           C
ATOM   6727  CB  ALA C 423      61.556 103.361  31.982  1.00 72.35           C
ATOM   6728  C   ALA C 423      61.388 105.585  30.839  1.00 99.57           C
ATOM   6729  O   ALA C 423      62.496 105.865  31.295  1.00 99.57           C
ATOM   6730  N   GLY C 424      60.814 106.285  29.864  1.00100.07           C
ATOM   6731  CA  GLY C 424      61.507 107.400  29.233  1.00100.07           C
ATOM   6732  C   GLY C 424      62.001 108.507  30.145  1.00100.07           C
ATOM   6733  O   GLY C 424      61.836 108.428  31.367  1.00100.07           C
ATOM   6734  N   ALA C 425      62.611 109.538  29.550  1.00100.07           C
ATOM   6735  CA  ALA C 425      63.127 110.692  30.289  1.00100.07           C
ATOM   6736  CB  ALA C 425      64.064 111.531  29.398  1.00 58.72           C
ATOM   6737  C   ALA C 425      61.935 111.533  30.775  1.00100.07           C
ATOM   6738  O   ALA C 425      62.025 112.752  30.940  1.00100.07           C
ATOM   6739  N   ALA C 426      60.812 110.848  30.987  1.00100.07           C
ATOM   6740  CA  ALA C 426      59.570 111.435  31.470  1.00100.07           C
ATOM   6741  CB  ALA C 426      58.880 112.230  30.363  1.00 94.56           C
ATOM   6742  C   ALA C 426      58.675 110.277  31.932  1.00100.07           C
ATOM   6743  O   ALA C 426      58.220 109.466  31.122  1.00100.07           C
ATOM   6744  N   VAL C 427      58.469 110.200  33.244  1.00100.07           C
ATOM   6745  CA  VAL C 427      57.641 109.182  33.897  1.00100.07           C
ATOM   6746  CB  VAL C 427      58.395 107.831  34.048  1.00100.07           C
ATOM   6747  CG1 VAL C 427      57.554 106.843  34.848  1.00100.07           C
ATOM   6748  CG2 VAL C 427      58.697 107.252  32.669  1.00100.07           C
ATOM   6749  C   VAL C 427      57.275 109.756  35.280  1.00100.07           C
ATOM   6750  O   VAL C 427      57.783 110.804  35.667  1.00100.07           C
ATOM   6751  N   ALA C 428      56.404 109.065  36.012  1.00 70.42           C
ATOM   6752  CA  ALA C 428      55.921 109.511  37.331  1.00 70.42           C
ATOM   6753  CB  ALA C 428      57.075 109.655  38.331  1.00 40.60           C
ATOM   6754  C   ALA C 428      55.180 110.835  37.217  1.00 70.42           C
ATOM   6755  O   ALA C 428      54.017 110.949  37.599  1.00 70.42           C
ATOM   6756  N   ASP C 429      55.870 111.829  36.670  1.00 98.97           C
ATOM   6757  CA  ASP C 429      55.327 113.167  36.493  1.00 98.97           C
ATOM   6758  CB  ASP C 429      56.434 114.101  36.011  1.00100.07           C
ATOM   6759  CG  ASP C 429      57.818 113.630  36.431  1.00100.07           C
ATOM   6760  OD1 ASP C 429      58.078 113.505  37.647  1.00100.07           C
ATOM   6761  OD2 ASP C 429      58.642 113.385  35.527  1.00100.07           C
ATOM   6762  C   ASP C 429      54.204 113.136  35.459  1.00 98.97           C
ATOM   6763  O   ASP C 429      53.097 113.621  35.700  1.00 98.97           C
ATOM   6764  N   VAL C 430      54.517 112.564  34.300  1.00 99.88           C
ATOM   6765  CA  VAL C 430      53.582 112.443  33.191  1.00 99.88           C
ATOM   6766  CB  VAL C 430      54.252 111.700  32.009  1.00100.07           C
```

| | | | | | | | | | |
|---|---|---|---|---|---|---|---|---|---|
| ATOM | 6767 | CG1 | VAL | C 430 | 53.323 | 111.669 | 30.818 | 1.00 100.07 | C |
| ATOM | 6768 | CG2 | VAL | C 430 | 55.559 | 112.379 | 31.646 | 1.00 100.07 | C |
| ATOM | 6769 | C | VAL | C 430 | 52.303 | 111.699 | 33.586 | 1.00 99.88 | C |
| ATOM | 6770 | O | VAL | C 430 | 51.216 | 112.292 | 33.634 | 1.00 99.88 | C |
| ATOM | 6771 | N | HIS | C 431 | 52.454 | 110.401 | 33.861 | 1.00 100.07 | C |
| ATOM | 6772 | CA | HIS | C 431 | 51.354 | 109.514 | 34.247 | 1.00 100.07 | C |
| ATOM | 6773 | CB | HIS | C 431 | 51.844 | 108.486 | 35.282 | 1.00 87.20 | C |
| ATOM | 6774 | CG | HIS | C 431 | 52.949 | 107.595 | 34.794 | 1.00 92.95 | C |
| ATOM | 6775 | CD2 | HIS | C 431 | 54.226 | 107.443 | 35.219 | 1.00 92.95 | C |
| ATOM | 6776 | ND1 | HIS | C 431 | 52.777 | 106.671 | 33.783 | 1.00 92.95 | C |
| ATOM | 6777 | CE1 | HIS | C 431 | 53.898 | 105.987 | 33.615 | 1.00 92.95 | C |
| ATOM | 6778 | NE2 | HIS | C 431 | 54.792 | 106.437 | 34.475 | 1.00 92.95 | C |
| ATOM | 6779 | C | HIS | C 431 | 50.116 | 110.239 | 34.801 | 1.00 100.07 | C |
| ATOM | 6780 | O | HIS | C 431 | 48.986 | 109.979 | 34.373 | 1.00 100.07 | C |
| ATOM | 6781 | N | ALA | C 432 | 50.335 | 111.163 | 35.732 | 1.00 61.37 | C |
| ATOM | 6782 | CA | ALA | C 432 | 49.251 | 111.919 | 36.361 | 1.00 61.37 | C |
| ATOM | 6783 | CB | ALA | C 432 | 49.822 | 113.072 | 37.203 | 1.00 46.95 | C |
| ATOM | 6784 | C | ALA | C 432 | 48.207 | 112.457 | 35.392 | 1.00 61.37 | C |
| ATOM | 6785 | O | ALA | C 432 | 48.404 | 112.472 | 34.183 | 1.00 61.37 | C |
| ATOM | 6786 | N | THR | C 433 | 47.085 | 112.878 | 35.961 | 1.00 38.18 | C |
| ATOM | 6787 | CA | THR | C 433 | 45.957 | 113.422 | 35.223 | 1.00 38.18 | C |
| ATOM | 6788 | CB | THR | C 433 | 44.633 | 112.950 | 35.844 | 1.00 100.07 | C |
| ATOM | 6789 | OG1 | THR | C 433 | 44.466 | 111.549 | 35.615 | 1.00 99.58 | C |
| ATOM | 6790 | CG2 | THR | C 433 | 43.475 | 113.708 | 35.239 | 1.00 99.58 | C |
| ATOM | 6791 | C | THR | C 433 | 45.934 | 114.942 | 35.267 | 1.00 38.18 | C |
| ATOM | 6792 | O | THR | C 433 | 45.799 | 115.511 | 36.341 | 1.00 38.18 | C |
| ATOM | 6793 | N | HIS | C 434 | 46.036 | 115.599 | 34.115 | 1.00 47.33 | C |
| ATOM | 6794 | CA | HIS | C 434 | 45.987 | 117.060 | 34.063 | 1.00 47.33 | C |
| ATOM | 6795 | CB | HIS | C 434 | 46.633 | 117.561 | 32.780 | 1.00 82.00 | C |
| ATOM | 6796 | CG | HIS | C 434 | 46.170 | 116.837 | 31.555 | 0.00 35.70 | C |
| ATOM | 6797 | CD2 | HIS | C 434 | 45.518 | 117.270 | 30.452 | 0.00 35.70 | C |
| ATOM | 6798 | ND1 | HIS | C 434 | 46.373 | 115.484 | 31.372 | 0.00 35.70 | C |
| ATOM | 6799 | CE1 | HIS | C 434 | 45.867 | 115.121 | 30.205 | 0.00 35.70 | C |
| ATOM | 6800 | NE2 | HIS | C 434 | 45.344 | 116.188 | 29.628 | 0.00 35.70 | C |
| ATOM | 6801 | C | HIS | C 434 | 44.527 | 117.476 | 34.095 | 1.00 47.33 | C |
| ATOM | 6802 | O | HIS | C 434 | 43.638 | 116.653 | 33.868 | 1.00 47.33 | C |
| ATOM | 6803 | N | TYR | C 435 | 44.262 | 118.744 | 34.373 | 1.00 99.57 | C |
| ATOM | 6804 | CA | TYR | C 435 | 42.878 | 119.177 | 34.416 | 1.00 99.57 | C |
| ATOM | 6805 | CB | TYR | C 435 | 42.759 | 120.593 | 34.975 | 1.00 14.53 | C |
| ATOM | 6806 | CG | TYR | C 435 | 43.626 | 121.605 | 34.293 | 0.00 5.07 | C |
| ATOM | 6807 | CD1 | TYR | C 435 | 43.315 | 122.059 | 33.017 | 0.00 5.07 | C |
| ATOM | 6808 | CE1 | TYR | C 435 | 44.090 | 123.011 | 32.394 | 0.00 5.07 | C |
| ATOM | 6809 | CD2 | TYR | C 435 | 44.745 | 122.129 | 34.931 | 0.00 5.07 | C |
| ATOM | 6810 | CE2 | TYR | C 435 | 45.532 | 123.084 | 34.318 | 0.00 5.07 | C |
| ATOM | 6811 | CZ | TYR | C 435 | 45.199 | 123.524 | 33.050 | 0.00 5.07 | C |
| ATOM | 6812 | OH | TYR | C 435 | 45.974 | 124.485 | 32.444 | 0.00 5.07 | C |
| ATOM | 6813 | C | TYR | C 435 | 42.235 | 119.088 | 33.044 | 1.00 99.57 | C |
| ATOM | 6814 | O | TYR | C 435 | 41.220 | 119.722 | 32.785 | 1.00 99.57 | C |
| ATOM | 6815 | N | GLY | C 436 | 42.857 | 118.315 | 32.162 | 1.00 98.61 | C |
| ATOM | 6816 | CA | GLY | C 436 | 42.294 | 118.122 | 30.848 | 1.00 98.61 | C |
| ATOM | 6817 | C | GLY | C 436 | 41.415 | 116.892 | 30.959 | 1.00 98.61 | C |
| ATOM | 6818 | O | GLY | C 436 | 41.855 | 115.773 | 30.711 | 1.00 98.61 | C |
| ATOM | 6819 | N | ARG | C 437 | 40.179 | 117.091 | 31.394 | 1.00 99.71 | C |
| ATOM | 6820 | CA | ARG | C 437 | 39.252 | 115.988 | 31.507 | 1.00 99.71 | C |
| ATOM | 6821 | CB | ARG | C 437 | 38.003 | 116.400 | 32.273 | 1.00 100.07 | C |
| ATOM | 6822 | CG | ARG | C 437 | 37.352 | 117.659 | 31.791 | 1.00 100.07 | C |
| ATOM | 6823 | CD | ARG | C 437 | 36.442 | 118.215 | 32.869 | 1.00 100.07 | C |
| ATOM | 6824 | NE | ARG | C 437 | 36.153 | 119.628 | 32.651 | 1.00 100.07 | C |
| ATOM | 6825 | CZ | ARG | C 437 | 35.708 | 120.458 | 33.591 | 1.00 100.07 | C |
| ATOM | 6826 | NH1 | ARG | C 437 | 35.495 | 120.013 | 34.824 | 1.00 100.07 | C |
| ATOM | 6827 | NH2 | ARG | C 437 | 35.482 | 121.738 | 33.301 | 1.00 100.07 | C |
| ATOM | 6828 | C | ARG | C 437 | 38.911 | 115.619 | 30.087 | 1.00 99.71 | C |
| ATOM | 6829 | O | ARG | C 437 | 39.340 | 116.291 | 29.153 | 1.00 99.71 | C |
| ATOM | 6830 | N | ILE | C 438 | 38.117 | 114.563 | 29.944 | 1.00 100.07 | C |
| ATOM | 6831 | CA | ILE | C 438 | 37.703 | 114.014 | 28.646 | 1.00 100.07 | C |
| ATOM | 6832 | CB | ILE | C 438 | 37.950 | 114.995 | 27.490 | 1.00 29.55 | C |
| ATOM | 6833 | CG2 | ILE | C 438 | 38.455 | 114.232 | 26.265 | 1.00 29.55 | C |
| ATOM | 6834 | CG1 | ILE | C 438 | 36.694 | 115.841 | 27.283 | 1.00 29.55 | C |
| ATOM | 6835 | CD | ILE | C 438 | 35.411 | 115.015 | 27.267 | 1.00 29.55 | C |
| ATOM | 6836 | C | ILE | C 438 | 38.524 | 112.745 | 28.413 | 1.00 100.07 | C |
| ATOM | 6837 | O | ILE | C 438 | 37.996 | 111.656 | 28.146 | 1.00 100.07 | C |
| ATOM | 6838 | N | CYS | C 439 | 39.834 | 112.902 | 28.468 | 1.00 91.77 | C |
| ATOM | 6839 | CA | CYS | C 439 | 40.686 | 111.749 | 28.358 | 1.00 91.77 | C |
| ATOM | 6840 | CB | CYS | C 439 | 42.151 | 112.179 | 28.355 | 1.00 75.81 | C |
| ATOM | 6841 | SG | CYS | C 439 | 43.343 | 110.833 | 28.162 | 1.00 75.81 | C |
| ATOM | 6842 | C | CYS | C 439 | 40.291 | 111.102 | 29.693 | 1.00 91.77 | C |
| ATOM | 6843 | O | CYS | C 439 | 40.270 | 111.762 | 30.726 | 1.00 91.77 | C |
| ATOM | 6844 | N | PRO | C 440 | 39.985 | 109.808 | 29.687 | 1.00 40.33 | C |
| ATOM | 6845 | CD | PRO | C 440 | 40.706 | 108.921 | 28.767 | 1.00 100.07 | C |
| ATOM | 6846 | CA | PRO | C 440 | 39.577 | 109.060 | 30.878 | 1.00 40.33 | C |
| ATOM | 6847 | CB | PRO | C 440 | 39.945 | 107.628 | 30.523 | 1.00 100.07 | C |
| ATOM | 6848 | CG | PRO | C 440 | 41.175 | 107.820 | 29.692 | 1.00 100.07 | C |
| ATOM | 6849 | C | PRO | C 440 | 40.251 | 109.507 | 32.155 | 1.00 40.33 | C |
| ATOM | 6850 | O | PRO | C 440 | 41.402 | 109.953 | 32.160 | 1.00 40.33 | C |

```
ATOM   6851  N   VAL C 441      39.530 109.369  33.250  1.00 52.92           C
ATOM   6852  CA  VAL C 441      40.059 109.761  34.532  1.00 52.92           C
ATOM   6853  CB  VAL C 441      39.084 110.718  35.231  1.00 44.78           C
ATOM   6854  CG1 VAL C 441      38.818 111.920  34.349  1.00 44.78           C
ATOM   6855  CG2 VAL C 441      37.776 110.009  35.504  1.00 44.78           C
ATOM   6856  C   VAL C 441      40.253 108.509  35.378  1.00 52.92           C
ATOM   6857  O   VAL C 441      41.299 108.337  36.015  1.00 52.92           C
ATOM   6858  N   ALA C 442      39.254 107.622  35.351  1.00 40.09           C
ATOM   6859  CA  ALA C 442      39.275 106.388  36.135  1.00 40.09           C
ATOM   6860  CB  ALA C 442      37.903 106.147  36.750  1.00 27.54           C
ATOM   6861  C   ALA C 442      39.691 105.152  35.365  1.00 40.09           C
ATOM   6862  O   ALA C 442      39.912 104.102  35.965  1.00 40.09           C
ATOM   6863  N   THR C 443      39.825 105.274  34.048  1.00 55.15           C
ATOM   6864  CA  THR C 443      40.164 104.107  33.234  1.00 55.15           C
ATOM   6865  CB  THR C 443      39.019 103.828  32.245  1.00100.07           C
ATOM   6866  OG1 THR C 443      37.771 104.218  32.847  1.00100.07           C
ATOM   6867  CG2 THR C 443      38.974 102.334  31.903  1.00100.07           C
ATOM   6868  C   THR C 443      41.503 104.025  32.473  1.00 55.15           C
ATOM   6869  O   THR C 443      41.563 104.177  31.249  1.00 55.15           C
ATOM   6870  N   PRO C 444      42.595 103.763  33.202  1.00 92.64           C
ATOM   6871  CD  PRO C 444      42.690 103.710  34.670  1.00100.07           C
ATOM   6872  CA  PRO C 444      43.923 103.646  32.616  1.00 92.64           C
ATOM   6873  CB  PRO C 444      44.812 104.177  33.712  1.00100.07           C
ATOM   6874  CG  PRO C 444      44.193 103.508  34.892  1.00100.07           C
ATOM   6875  C   PRO C 444      44.125 102.159  32.427  1.00 92.64           C
ATOM   6876  O   PRO C 444      43.165 101.403  32.308  1.00 92.64           C
ATOM   6877  N   GLU C 445      45.375 101.732  32.444  1.00 35.24           C
ATOM   6878  CA  GLU C 445      45.664 100.334  32.264  1.00 35.24           C
ATOM   6879  CB  GLU C 445      46.597 100.128  31.076  1.00100.07           C
ATOM   6880  CG  GLU C 445      45.882  99.957  29.747  1.00100.07           C
ATOM   6881  CD  GLU C 445      44.960  98.743  29.725  1.00100.07           C
ATOM   6882  OE1 GLU C 445      43.792  98.861  30.155  1.00100.07           C
ATOM   6883  OE2 GLU C 445      45.410  97.663  29.285  1.00100.07           C
ATOM   6884  C   GLU C 445      46.297  99.809  33.510  1.00 35.24           C
ATOM   6885  O   GLU C 445      46.975  98.796  33.477  1.00 35.24           C
ATOM   6886  N   GLY C 446      46.077 100.519  34.606  1.00 38.20           C
ATOM   6887  CA  GLY C 446      46.613 100.127  35.903  1.00 38.20           C
ATOM   6888  C   GLY C 446      47.905  99.337  36.014  1.00 38.20           C
ATOM   6889  O   GLY C 446      48.008  98.232  35.504  1.00 38.20           C
ATOM   6890  N   ALA C 447      48.882  99.904  36.714  1.00 49.32           C
ATOM   6891  CA  ALA C 447      50.190  99.278  36.927  1.00 49.32           C
ATOM   6892  CB  ALA C 447      50.063  97.756  36.993  1.00 91.95           C
ATOM   6893  C   ALA C 447      51.219  99.668  35.873  1.00 49.32           C
ATOM   6894  O   ALA C 447      50.939 100.464  34.974  1.00 49.32           C
ATOM   6895  N   ASN C 448      52.420  99.118  36.013  1.00 90.35           C
ATOM   6896  CA  ASN C 448      53.511  99.393  35.091  1.00 90.35           C
ATOM   6897  CB  ASN C 448      54.442  98.183  35.031  1.00100.07           C
ATOM   6898  CG  ASN C 448      53.701  96.898  34.709  1.00100.07           C
ATOM   6899  OD1 ASN C 448      52.552  96.712  35.119  1.00100.07           C
ATOM   6900  ND2 ASN C 448      54.360  95.995  33.984  1.00100.07           C
ATOM   6901  C   ASN C 448      52.970  99.709  33.708  1.00 90.35           C
ATOM   6902  O   ASN C 448      52.214  98.925  33.139  1.00 90.35           C
ATOM   6903  N   ILE C 449      53.337 100.875  33.186  1.00 36.73           C
ATOM   6904  CA  ILE C 449      52.894 101.305  31.862  1.00 36.73           C
ATOM   6905  CB  ILE C 449      53.504 100.414  30.749  1.00100.01           C
ATOM   6906  CG2 ILE C 449      52.756 100.599  29.430  1.00100.01           C
ATOM   6907  CG1 ILE C 449      54.997 100.737  30.609  1.00100.01           C
ATOM   6908  CD  ILE C 449      55.311 102.230  30.461  1.00100.01           C
ATOM   6909  C   ILE C 449      51.390 101.316  31.731  1.00 36.73           C
ATOM   6910  O   ILE C 449      50.853 101.883  30.796  1.00 36.73           C
ATOM   6911  N   GLY C 450      50.704 100.686  32.667  1.00100.07           C
ATOM   6912  CA  GLY C 450      49.263 100.689  32.607  1.00100.07           C
ATOM   6913  C   GLY C 450      48.840 102.093  32.968  1.00100.07           C
ATOM   6914  O   GLY C 450      47.670 102.353  33.250  1.00100.07           C
ATOM   6915  N   LEU C 451      49.812 103.001  32.955  1.00 27.08           C
ATOM   6916  CA  LEU C 451      49.562 104.393  33.296  1.00 27.08           C
ATOM   6917  CB  LEU C 451      50.470 104.744  34.450  1.00 19.71           C
ATOM   6918  CG  LEU C 451      50.422 103.577  35.424  1.00 19.71           C
ATOM   6919  CD1 LEU C 451      51.690 103.552  36.253  1.00 19.71           C
ATOM   6920  CD2 LEU C 451      49.176 103.691  36.298  1.00 19.71           C
ATOM   6921  C   LEU C 451      49.816 105.328  32.109  1.00 27.08           C
ATOM   6922  O   LEU C 451      49.077 106.287  31.853  1.00 27.08           C
ATOM   6923  N   ILE C 452      50.895 105.038  31.405  1.00 36.86           C
ATOM   6924  CA  ILE C 452      51.296 105.792  30.239  1.00 36.86           C
ATOM   6925  CB  ILE C 452      52.493 105.071  29.542  1.00 22.11           C
ATOM   6926  CG2 ILE C 452      52.370 105.206  28.045  1.00 22.11           C
ATOM   6927  CG1 ILE C 452      53.844 105.556  30.105  1.00 22.11           C
ATOM   6928  CD  ILE C 452      54.210 106.997  29.790  1.00 22.11           C
ATOM   6929  C   ILE C 452      50.093 105.843  29.303  1.00 36.86           C
ATOM   6930  O   ILE C 452      49.896 106.821  28.593  1.00 36.86           C
ATOM   6931  N   THR C 453      49.279 104.789  29.341  1.00 54.44           C
ATOM   6932  CA  THR C 453      48.100 104.651  28.485  1.00 54.44           C
ATOM   6933  CB  THR C 453      48.107 103.306  27.814  1.00 17.58           C
ATOM   6934  OG1 THR C 453      48.664 103.451  26.507  1.00 17.58           C
```

```
ATOM   6935  CG2 THR C 453      46.702 102.730  27.743  1.00 17.58           C
ATOM   6936  C   THR C 453      46.726 104.813  29.111  1.00 54.44           C
ATOM   6937  O   THR C 453      46.531 104.450  30.266  1.00 54.44           C
ATOM   6938  N   SER C 454      45.762 105.294  28.319  1.00 53.99           C
ATOM   6939  CA  SER C 454      44.395 105.521  28.804  1.00 53.99           C
ATOM   6940  CB  SER C 454      44.306 106.909  29.430  1.00 46.82           C
ATOM   6941  OG  SER C 454      44.811 107.883  28.534  1.00 46.82           C
ATOM   6942  C   SER C 454      43.327 105.416  27.719  1.00 53.99           C
ATOM   6943  O   SER C 454      43.647 105.469  26.531  1.00 53.99           C
ATOM   6944  N   LEU C 455      42.061 105.289  28.134  1.00 33.07           C
ATOM   6945  CA  LEU C 455      40.932 105.188  27.197  1.00 33.07           C
ATOM   6946  CB  LEU C 455      39.746 104.446  27.832  1.00 56.68           C
ATOM   6947  CG  LEU C 455      39.930 103.450  28.995  1.00 56.68           C
ATOM   6948  CD1 LEU C 455      38.787 102.452  28.960  1.00 56.68           C
ATOM   6949  CD2 LEU C 455      41.250 102.699  28.894  1.00 56.68           C
ATOM   6950  C   LEU C 455      40.513 106.614  26.843  1.00 33.07           C
ATOM   6951  O   LEU C 455      41.369 107.479  26.731  1.00 33.07           C
ATOM   6952  N   ALA C 456      39.219 106.866  26.665  1.00 73.31           C
ATOM   6953  CA  ALA C 456      38.726 108.215  26.343  1.00 73.31           C
ATOM   6954  CB  ALA C 456      39.063 108.596  24.904  1.00  5.07           C
ATOM   6955  C   ALA C 456      37.226 108.245  26.521  1.00 73.31           C
ATOM   6956  O   ALA C 456      36.607 107.203  26.723  1.00 73.31           C
ATOM   6957  N   ALA C 457      36.642 109.437  26.455  1.00 39.05           C
ATOM   6958  CA  ALA C 457      35.188 109.584  26.568  1.00 39.05           C
ATOM   6959  CB  ALA C 457      34.832 110.573  27.649  1.00 55.73           C
ATOM   6960  C   ALA C 457      34.762 110.118  25.219  1.00 39.05           C
ATOM   6961  O   ALA C 457      35.588 110.161  24.298  1.00 39.05           C
ATOM   6962  N   TYR C 458      33.500 110.513  25.070  1.00 33.57           C
ATOM   6963  CA  TYR C 458      33.127 111.057  23.775  1.00 33.57           C
ATOM   6964  CB  TYR C 458      31.603 111.238  23.660  1.00 98.79           C
ATOM   6965  CG  TYR C 458      31.043 112.606  23.985  1.00 98.79           C
ATOM   6966  CD1 TYR C 458      31.519 113.753  23.345  1.00 98.79           C
ATOM   6967  CE1 TYR C 458      30.981 114.998  23.613  1.00 98.79           C
ATOM   6968  CD2 TYR C 458      30.000 112.749  24.904  1.00 98.79           C
ATOM   6969  CE2 TYR C 458      29.445 113.994  25.177  1.00 98.79           C
ATOM   6970  CZ  TYR C 458      29.945 115.117  24.528  1.00 98.79           C
ATOM   6971  OH  TYR C 458      29.425 116.368  24.792  1.00 98.79           C
ATOM   6972  C   TYR C 458      33.900 112.384  23.646  1.00 33.57           C
ATOM   6973  O   TYR C 458      34.089 113.090  24.640  1.00 33.57           C
ATOM   6974  N   ALA C 459      34.359 112.703  22.433  1.00 22.09           C
ATOM   6975  CA  ALA C 459      35.141 113.915  22.172  1.00 22.09           C
ATOM   6976  CB  ALA C 459      36.318 113.935  23.038  1.00  5.07           C
ATOM   6977  C   ALA C 459      35.619 113.939  20.745  1.00 22.09           C
ATOM   6978  O   ALA C 459      35.297 113.049  19.979  1.00 22.09           C
ATOM   6979  N   ALA C 460      36.423 114.932  20.392  1.00 62.32           C
ATOM   6980  CA  ALA C 460      36.937 115.042  19.027  1.00 62.32           C
ATOM   6981  CB  ALA C 460      37.821 113.826  18.696  1.00  5.07           C
ATOM   6982  C   ALA C 460      35.789 115.152  18.009  1.00 62.32           C
ATOM   6983  O   ALA C 460      34.907 114.290  17.972  1.00 62.32           C
ATOM   6984  N   ALA C 461      35.803 116.219  17.200  1.00100.07           C
ATOM   6985  CA  ALA C 461      34.795 116.489  16.146  1.00100.07           C
ATOM   6986  CB  ALA C 461      33.401 115.988  16.560  1.00 72.39           C
ATOM   6987  C   ALA C 461      34.717 117.976  15.792  1.00100.07           C
ATOM   6988  O   ALA C 461      34.484 118.819  16.661  1.00100.07           C
ATOM   6989  N   ALA C 462      34.900 118.274  14.507  1.00100.07           C
ATOM   6990  CA  ALA C 462      34.877 119.642  13.972  1.00100.07           C
ATOM   6991  CB  ALA C 462      33.968 120.547  14.823  1.00100.07           C
ATOM   6992  C   ALA C 462      36.298 120.215  13.914  1.00100.07           C
ATOM   6993  O   ALA C 462      36.855 120.618  14.938  1.00100.07           C
ATOM   6994  N   ALA C 463      36.871 120.249  12.709  1.00100.07           C
ATOM   6995  CA  ALA C 463      38.230 120.739  12.488  1.00100.07           C
ATOM   6996  CB  ALA C 463      38.453 122.082  13.236  1.00 13.60           C
ATOM   6997  C   ALA C 463      39.252 119.670  12.935  1.00100.07           C
ATOM   6998  O   ALA C 463      39.422 119.395  14.134  1.00100.07           C
ATOM   6999  N   ALA C 464      39.910 119.058  11.950  1.00100.07           C
ATOM   7000  CA  ALA C 464      40.909 118.012  12.182  1.00100.07           C
ATOM   7001  CB  ALA C 464      41.279 117.336  10.864  1.00 95.64           C
ATOM   7002  C   ALA C 464      42.158 118.568  12.837  1.00100.07           C
ATOM   7003  O   ALA C 464      42.126 119.656  13.407  1.00100.07           C
ATOM   7004  N   GLY C 465      43.257 117.822  12.741  1.00 89.40           C
ATOM   7005  CA  GLY C 465      44.505 118.256  13.349  1.00 89.40           C
ATOM   7006  C   GLY C 465      44.156 119.057  14.579  1.00 89.40           C
ATOM   7007  O   GLY C 465      44.640 120.176  14.756  1.00 89.40           C
ATOM   7008  N   ALA C 466      43.282 118.470  15.401  1.00 67.76           C
ATOM   7009  CA  ALA C 466      42.772 119.082  16.623  1.00 67.76           C
ATOM   7010  CB  ALA C 466      41.215 119.152  16.548  1.00  5.07           C
ATOM   7011  C   ALA C 466      43.236 118.345  17.895  1.00 67.76           C
ATOM   7012  O   ALA C 466      44.175 117.539  17.850  1.00 67.76           C
ATOM   7013  N   ALA C 467      42.580 118.629  19.022  1.00 45.17           C
ATOM   7014  CA  ALA C 467      42.933 118.010  20.305  1.00 45.17           C
ATOM   7015  CB  ALA C 467      43.887 118.928  21.065  1.00100.07           C
ATOM   7016  C   ALA C 467      41.765 117.594  21.230  1.00 45.17           C
ATOM   7017  O   ALA C 467      41.395 118.307  22.171  1.00 45.17           C
ATOM   7018  N   ALA C 468      41.227 116.409  20.961  1.00 62.76           C
```

| ATOM | 7019 | CA  | ALA C 468 | 40.130 | 115.828 | 21.721 | 1.00 | 62.76 | C |
|------|------|-----|-----------|--------|---------|--------|------|-------|---|
| ATOM | 7020 | CB  | ALA C 468 | 40.641 | 115.345 | 23.074 | 1.00 |  5.07 | C |
| ATOM | 7021 | C   | ALA C 468 | 38.944 | 116.783 | 21.878 | 1.00 | 62.76 | C |
| ATOM | 7022 | O   | ALA C 468 | 37.877 | 116.520 | 21.335 | 1.00 | 62.76 | C |
| ATOM | 7023 | N   | THR C 469 | 39.121 | 117.870 | 22.624 | 1.00 | 53.13 | C |
| ATOM | 7024 | CA  | THR C 469 | 38.073 | 118.887 | 22.818 | 1.00 | 53.13 | C |
| ATOM | 7025 | CB  | THR C 469 | 38.116 | 119.904 | 21.648 | 1.00 | 41.18 | C |
| ATOM | 7026 | OG1 | THR C 469 | 37.438 | 119.380 | 20.501 | 1.00 | 41.18 | C |
| ATOM | 7027 | CG2 | THR C 469 | 39.539 | 120.150 | 21.251 | 1.00 | 41.18 | C |
| ATOM | 7028 | C   | THR C 469 | 36.608 | 118.427 | 23.009 | 1.00 | 53.13 | C |
| ATOM | 7029 | O   | THR C 469 | 35.883 | 118.210 | 22.044 | 1.00 | 53.13 | C |
| ATOM | 7030 | N   | PRO C 470 | 36.150 | 118.307 | 24.266 | 1.00 | 61.21 | C |
| ATOM | 7031 | CD  | PRO C 470 | 36.879 | 118.665 | 25.492 | 1.00 | 86.46 | C |
| ATOM | 7032 | CA  | PRO C 470 | 34.780 | 117.881 | 24.586 | 1.00 | 61.21 | C |
| ATOM | 7033 | CB  | PRO C 470 | 34.792 | 117.798 | 26.097 | 1.00 | 86.46 | C |
| ATOM | 7034 | CG  | PRO C 470 | 35.756 | 118.877 | 26.464 | 1.00 | 86.46 | C |
| ATOM | 7035 | C   | PRO C 470 | 33.738 | 118.876 | 24.095 | 1.00 | 61.21 | C |
| ATOM | 7036 | O   | PRO C 470 | 34.092 | 119.911 | 23.528 | 1.00 | 61.21 | C |
| ATOM | 7037 | N   | TYR C 471 | 32.458 | 118.568 | 24.314 | 1.00 | 26.59 | C |
| ATOM | 7038 | CA  | TYR C 471 | 31.387 | 119.458 | 23.878 | 1.00 | 26.59 | C |
| ATOM | 7039 | CB  | TYR C 471 | 30.331 | 118.715 | 23.047 | 1.00 | 99.64 | C |
| ATOM | 7040 | CG  | TYR C 471 | 30.826 | 117.874 | 21.878 | 1.00 | 99.64 | C |
| ATOM | 7041 | CD1 | TYR C 471 | 29.916 | 117.176 | 21.083 | 1.00 | 99.64 | C |
| ATOM | 7042 | CE1 | TYR C 471 | 30.341 | 116.342 | 20.068 | 1.00 | 99.64 | C |
| ATOM | 7043 | CD2 | TYR C 471 | 32.188 | 117.715 | 21.609 | 1.00 | 99.64 | C |
| ATOM | 7044 | CE2 | TYR C 471 | 32.625 | 116.878 | 20.591 | 1.00 | 99.64 | C |
| ATOM | 7045 | CZ  | TYR C 471 | 31.694 | 116.192 | 19.829 | 1.00 | 99.64 | C |
| ATOM | 7046 | OH  | TYR C 471 | 32.107 | 115.328 | 18.843 | 1.00 | 99.64 | C |
| ATOM | 7047 | C   | TYR C 471 | 30.716 | 119.983 | 25.122 | 1.00 | 26.59 | C |
| ATOM | 7048 | O   | TYR C 471 | 30.468 | 119.212 | 26.047 | 1.00 | 26.59 | C |
| ATOM | 7049 | N   | ARG C 472 | 30.422 | 121.282 | 25.152 | 1.00 | 42.17 | C |
| ATOM | 7050 | CA  | ARG C 472 | 29.752 | 121.883 | 26.310 | 1.00 | 42.17 | C |
| ATOM | 7051 | CB  | ARG C 472 | 30.780 | 122.539 | 27.238 | 1.00 | 67.73 | C |
| ATOM | 7052 | CG  | ARG C 472 | 30.962 | 121.786 | 28.542 | 1.00 | 67.73 | C |
| ATOM | 7053 | CD  | ARG C 472 | 32.154 | 122.279 | 29.336 | 1.00 | 67.73 | C |
| ATOM | 7054 | NE  | ARG C 472 | 33.422 | 122.064 | 28.644 | 1.00 | 67.73 | C |
| ATOM | 7055 | CZ  | ARG C 472 | 34.582 | 121.856 | 29.263 | 1.00 | 67.73 | C |
| ATOM | 7056 | NH1 | ARG C 472 | 34.637 | 121.831 | 30.589 | 1.00 | 67.73 | C |
| ATOM | 7057 | NH2 | ARG C 472 | 35.691 | 121.675 | 28.559 | 1.00 | 67.73 | C |
| ATOM | 7058 | C   | ARG C 472 | 28.644 | 122.886 | 25.957 | 1.00 | 42.17 | C |
| ATOM | 7059 | O   | ARG C 472 | 28.883 | 123.924 | 25.340 | 1.00 | 42.17 | C |
| ATOM | 7060 | N   | ALA C 473 | 27.423 | 122.558 | 26.361 | 1.00 |100.07 | C |
| ATOM | 7061 | CA  | ALA C 473 | 26.269 | 123.407 | 26.093 | 1.00 |100.07 | C |
| ATOM | 7062 | CB  | ALA C 473 | 25.046 | 122.874 | 26.869 | 1.00 | 11.39 | C |
| ATOM | 7063 | C   | ALA C 473 | 26.561 | 124.850 | 26.499 | 1.00 |100.07 | C |
| ATOM | 7064 | O   | ALA C 473 | 27.310 | 125.078 | 27.448 | 1.00 |100.07 | C |
| ATOM | 7065 | N   | VAL C 474 | 25.992 | 125.817 | 25.773 | 1.00 | 45.41 | C |
| ATOM | 7066 | CA  | VAL C 474 | 26.161 | 127.245 | 26.100 | 1.00 | 45.41 | C |
| ATOM | 7067 | CB  | VAL C 474 | 26.936 | 127.995 | 24.983 | 1.00 | 99.87 | C |
| ATOM | 7068 | CG1 | VAL C 474 | 27.150 | 129.452 | 25.373 | 1.00 | 99.87 | C |
| ATOM | 7069 | CG2 | VAL C 474 | 28.286 | 127.329 | 24.756 | 1.00 | 99.87 | C |
| ATOM | 7070 | C   | VAL C 474 | 24.768 | 127.882 | 26.297 | 1.00 | 45.41 | C |
| ATOM | 7071 | O   | VAL C 474 | 24.343 | 128.737 | 25.520 | 1.00 | 45.41 | C |
| ATOM | 7072 | N   | ALA C 475 | 24.080 | 127.454 | 27.358 | 1.00 | 55.11 | C |
| ATOM | 7073 | CA  | ALA C 475 | 22.712 | 127.889 | 27.682 | 1.00 | 55.11 | C |
| ATOM | 7074 | CB  | ALA C 475 | 22.716 | 129.277 | 28.250 | 1.00 | 74.41 | C |
| ATOM | 7075 | C   | ALA C 475 | 21.749 | 127.797 | 26.482 | 1.00 | 55.11 | C |
| ATOM | 7076 | O   | ALA C 475 | 21.796 | 128.597 | 25.538 | 1.00 | 55.11 | C |
| ATOM | 7077 | N   | ALA C 476 | 20.882 | 126.791 | 26.537 | 1.00 | 53.15 | C |
| ATOM | 7078 | CA  | ALA C 476 | 19.914 | 126.534 | 25.487 | 1.00 | 53.15 | C |
| ATOM | 7079 | CB  | ALA C 476 | 18.952 | 127.699 | 25.385 | 1.00 | 25.83 | C |
| ATOM | 7080 | C   | ALA C 476 | 20.579 | 126.276 | 24.132 | 1.00 | 53.15 | C |
| ATOM | 7081 | O   | ALA C 476 | 19.952 | 125.744 | 23.214 | 1.00 | 53.15 | C |
| ATOM | 7082 | N   | GLY C 477 | 21.850 | 126.643 | 24.016 | 1.00 | 63.12 | C |
| ATOM | 7083 | CA  | GLY C 477 | 22.572 | 126.465 | 22.768 | 1.00 | 63.12 | C |
| ATOM | 7084 | C   | GLY C 477 | 22.612 | 125.063 | 22.193 | 1.00 | 63.12 | C |
| ATOM | 7085 | O   | GLY C 477 | 21.673 | 124.280 | 22.332 | 1.00 | 63.12 | C |
| ATOM | 7086 | N   | ALA C 478 | 23.718 | 124.753 | 21.526 | 1.00 | 76.01 | C |
| ATOM | 7087 | CA  | ALA C 478 | 23.903 | 123.444 | 20.918 | 1.00 | 76.01 | C |
| ATOM | 7088 | CB  | ALA C 478 | 24.228 | 123.591 | 19.449 | 1.00 |100.07 | C |
| ATOM | 7089 | C   | ALA C 478 | 25.016 | 122.680 | 21.620 | 1.00 | 76.01 | C |
| ATOM | 7090 | O   | ALA C 478 | 24.746 | 121.757 | 22.390 | 1.00 | 76.01 | C |
| ATOM | 7091 | N   | ALA C 479 | 26.267 | 123.055 | 21.366 | 1.00 | 52.97 | C |
| ATOM | 7092 | CA  | ALA C 479 | 27.363 | 122.347 | 22.017 | 1.00 | 52.97 | C |
| ATOM | 7093 | CB  | ALA C 479 | 27.393 | 120.899 | 21.529 | 1.00 | 14.76 | C |
| ATOM | 7094 | C   | ALA C 479 | 28.761 | 122.959 | 21.914 | 1.00 | 52.97 | C |
| ATOM | 7095 | O   | ALA C 479 | 29.452 | 123.083 | 22.924 | 1.00 | 52.97 | C |
| ATOM | 7096 | N   | ALA C 480 | 29.185 | 123.329 | 20.710 | 1.00 | 64.02 | C |
| ATOM | 7097 | CA  | ALA C 480 | 30.516 | 123.907 | 20.523 | 1.00 | 64.02 | C |
| ATOM | 7098 | CB  | ALA C 480 | 30.622 | 125.259 | 21.263 | 1.00 | 25.96 | C |
| ATOM | 7099 | C   | ALA C 480 | 31.579 | 122.939 | 21.043 | 1.00 | 64.02 | C |
| ATOM | 7100 | O   | ALA C 480 | 31.650 | 122.662 | 22.242 | 1.00 | 64.02 | C |
| ATOM | 7101 | N   | ALA C 481 | 32.405 | 122.415 | 20.147 | 1.00 | 51.87 | C |
| ATOM | 7102 | CA  | ALA C 481 | 33.447 | 121.485 | 20.567 | 1.00 | 51.87 | C |

-85-

```
ATOM   7103  CB  ALA C 481      33.818 120.556  19.419  1.00 88.09           C
ATOM   7104  C   ALA C 481      34.670 122.263  21.038  1.00 51.87           C
ATOM   7105  O   ALA C 481      35.693 122.326  20.345  1.00 51.87           C
ATOM   7106  N   ALA C 482      34.557 122.843  22.230  1.00 70.79           C
ATOM   7107  CA  ALA C 482      35.626 123.651  22.811  1.00 70.79           C
ATOM   7108  CB  ALA C 482      35.196 124.184  24.189  1.00 84.75           C
ATOM   7109  C   ALA C 482      36.975 122.951  22.921  1.00 70.79           C
ATOM   7110  O   ALA C 482      37.091 121.889  23.532  1.00 70.79           C
ATOM   7111  N   ALA C 483      37.990 123.562  22.313  1.00 39.85           C
ATOM   7112  CA  ALA C 483      39.346 123.041  22.359  1.00 39.85           C
ATOM   7113  CB  ALA C 483      40.277 123.933  21.568  1.00 66.62           C
ATOM   7114  C   ALA C 483      39.744 123.045  23.822  1.00 39.85           C
ATOM   7115  O   ALA C 483      39.102 123.695  24.643  1.00 39.85           C
ATOM   7116  N   ALA C 484      40.789 122.314  24.165  1.00 45.49           C
ATOM   7117  CA  ALA C 484      41.210 122.296  25.553  1.00 45.49           C
ATOM   7118  CB  ALA C 484      42.503 121.510  25.698  1.00 83.60           C
ATOM   7119  C   ALA C 484      41.432 123.750  25.930  1.00 45.49           C
ATOM   7120  O   ALA C 484      41.262 124.135  27.078  1.00 45.49           C
ATOM   7121  N   ALA C 485      41.788 124.552  24.928  1.00 62.49           C
ATOM   7122  CA  ALA C 485      42.062 125.975  25.103  1.00 62.49           C
ATOM   7123  CB  ALA C 485      42.387 126.604  23.766  1.00 75.01           C
ATOM   7124  C   ALA C 485      40.939 126.750  25.776  1.00 62.49           C
ATOM   7125  O   ALA C 485      41.170 127.828  26.316  1.00 62.49           C
ATOM   7126  N   ALA C 486      39.721 126.224  25.735  1.00 68.78           C
ATOM   7127  CA  ALA C 486      38.613 126.907  26.385  1.00 68.78           C
ATOM   7128  CB  ALA C 486      37.278 126.262  26.000  1.00 45.92           C
ATOM   7129  C   ALA C 486      38.856 126.800  27.890  1.00 68.78           C
ATOM   7130  O   ALA C 486      38.016 126.309  28.646  1.00 68.78           C
ATOM   7131  N   ALA C 487      40.039 127.248  28.302  1.00100.07           C
ATOM   7132  CA  ALA C 487      40.446 127.243  29.700  1.00100.07           C
ATOM   7133  CB  ALA C 487      41.950 126.961  29.820  1.00  8.81           C
ATOM   7134  C   ALA C 487      40.123 128.623  30.260  1.00100.07           C
ATOM   7135  O   ALA C 487      40.944 129.249  30.936  1.00100.07           C
ATOM   7136  N   ALA C 488      38.918 129.092  29.957  1.00100.07           C
ATOM   7137  CA  ALA C 488      38.450 130.394  30.411  1.00100.07           C
ATOM   7138  CB  ALA C 488      38.844 131.475  29.380  1.00 44.69           C
ATOM   7139  C   ALA C 488      36.930 130.314  30.560  1.00100.07           C
ATOM   7140  O   ALA C 488      36.400 129.370  31.149  1.00100.07           C
ATOM   7141  N   ALA C 489      36.247 131.322  30.033  1.00 77.46           C
ATOM   7142  CA  ALA C 489      34.791 131.404  30.034  1.00 77.46           C
ATOM   7143  CB  ALA C 489      34.251 130.446  28.962  1.00 50.89           C
ATOM   7144  C   ALA C 489      34.006 131.223  31.355  1.00 77.46           C
ATOM   7145  O   ALA C 489      32.953 131.850  31.532  1.00 77.46           C
ATOM   7146  N   ALA C 490      34.500 130.382  32.266  1.00 46.88           C
ATOM   7147  CA  ALA C 490      33.826 130.117  33.547  1.00 46.88           C
ATOM   7148  CB  ALA C 490      33.077 131.362  34.034  1.00  5.07           C
ATOM   7149  C   ALA C 490      32.846 128.944  33.443  1.00 46.88           C
ATOM   7150  O   ALA C 490      31.669 129.085  33.763  1.00 46.88           C
ATOM   7151  N   ALA C 491      33.348 127.788  33.014  1.00 51.44           C
ATOM   7152  CA  ALA C 491      32.547 126.574  32.840  1.00 51.44           C
ATOM   7153  CB  ALA C 491      33.468 125.407  32.487  1.00 61.55           C
ATOM   7154  C   ALA C 491      31.638 126.175  34.007  1.00 51.44           C
ATOM   7155  O   ALA C 491      32.079 126.143  35.159  1.00 51.44           C
ATOM   7156  N   ALA C 492      30.379 125.845  33.700  1.00 44.47           C
ATOM   7157  CA  ALA C 492      29.408 125.443  34.733  1.00 44.47           C
ATOM   7158  CB  ALA C 492      28.175 126.339  34.676  1.00 47.73           C
ATOM   7159  C   ALA C 492      28.986 123.980  34.617  1.00 44.47           C
ATOM   7160  O   ALA C 492      28.338 123.594  33.644  1.00 44.47           C
ATOM   7161  N   ALA C 493      29.344 123.195  35.638  1.00 80.97           C
ATOM   7162  CA  ALA C 493      29.065 121.752  35.715  1.00 80.97           C
ATOM   7163  CB  ALA C 493      29.654 121.161  37.028  1.00 41.43           C
ATOM   7164  C   ALA C 493      27.593 121.381  35.597  1.00 80.97           C
ATOM   7165  O   ALA C 493      26.718 122.178  35.923  1.00 80.97           C
ATOM   7166  N   ALA C 494      27.343 120.156  35.134  1.00 52.40           C
ATOM   7167  CA  ALA C 494      25.995 119.627  34.945  1.00 52.40           C
ATOM   7168  CB  ALA C 494      26.064 118.183  34.567  1.00 11.52           C
ATOM   7169  C   ALA C 494      25.155 119.772  36.195  1.00 52.40           C
ATOM   7170  O   ALA C 494      25.678 119.660  37.306  1.00 52.40           C
ATOM   7171  N   ALA C 495      23.853 119.998  36.002  1.00 60.75           C
ATOM   7172  CA  ALA C 495      22.893 120.184  37.095  1.00 60.75           C
ATOM   7173  CB  ALA C 495      23.368 119.445  38.365  1.00 29.87           C
ATOM   7174  C   ALA C 495      22.643 121.670  37.412  1.00 60.75           C
ATOM   7175  O   ALA C 495      23.558 122.500  37.380  1.00 60.75           C
ATOM   7176  N   ALA C 496      21.388 121.987  37.720  1.00 91.47           C
ATOM   7177  CA  ALA C 496      20.953 123.344  38.053  1.00 91.47           C
ATOM   7178  CB  ALA C 496      21.526 124.346  37.057  1.00100.07           C
ATOM   7179  C   ALA C 496      19.432 123.331  37.965  1.00 91.47           C
ATOM   7180  O   ALA C 496      18.737 123.808  38.863  1.00 91.47           C
ATOM   7181  N   ALA C 497      18.955 122.758  36.860  1.00100.07           C
ATOM   7182  CA  ALA C 497      17.541 122.589  36.513  1.00100.07           C
ATOM   7183  CB  ALA C 497      17.111 121.140  36.806  1.00 69.36           C
ATOM   7184  C   ALA C 497      16.518 123.563  37.100  1.00100.07           C
ATOM   7185  O   ALA C 497      16.255 123.570  38.301  1.00100.07           C
ATOM   7186  N   ALA C 498      15.932 124.369  36.219  1.00100.07           C
```

```
ATOM   7187  CA  ALA C 498      14.913 125.352  36.579  1.00100.07           C
ATOM   7188  CB  ALA C 498      15.534 126.509  37.346  1.00 16.63           C
ATOM   7189  C   ALA C 498      14.296 125.850  35.275  1.00100.07           C
ATOM   7190  O   ALA C 498      14.681 126.900  34.752  1.00100.07           C
ATOM   7191  N   ALA C 499      13.337 125.082  34.760  1.00100.07           C
ATOM   7192  CA  ALA C 499      12.665 125.397  33.497  1.00100.07           C
ATOM   7193  CB  ALA C 499      12.067 126.811  33.541  1.00100.07           C
ATOM   7194  C   ALA C 499      13.732 125.300  32.412  1.00100.07           C
ATOM   7195  O   ALA C 499      14.198 124.208  32.083  1.00100.07           C
ATOM   7196  N   ALA C 500      14.108 126.445  31.858  1.00 75.11           C
ATOM   7197  CA  ALA C 500      15.155 126.509  30.850  1.00 75.11           C
ATOM   7198  CB  ALA C 500      14.578 126.921  29.504  1.00 12.62           C
ATOM   7199  C   ALA C 500      16.107 127.576  31.381  1.00 75.11           C
ATOM   7200  O   ALA C 500      17.127 127.884  30.767  1.00 75.11           C
ATOM   7201  N   ALA C 501      15.755 128.109  32.553  1.00 84.78           C
ATOM   7202  CA  ALA C 501      16.515 129.157  33.237  1.00 84.78           C
ATOM   7203  CB  ALA C 501      15.555 130.250  33.722  1.00100.07           C
ATOM   7204  C   ALA C 501      17.323 128.619  34.419  1.00 84.78           C
ATOM   7205  O   ALA C 501      16.785 127.908  35.263  1.00 84.78           C
ATOM   7206  N   ALA C 502      18.605 128.980  34.479  1.00 33.77           C
ATOM   7207  CA  ALA C 502      19.498 128.538  35.547  1.00 33.77           C
ATOM   7208  CB  ALA C 502      20.659 129.513  35.677  1.00  5.07           C
ATOM   7209  C   ALA C 502      18.741 128.414  36.868  1.00 33.77           C
ATOM   7210  O   ALA C 502      18.237 127.345  37.200  1.00 33.77           C
ATOM   7211  N   ALA C 503      18.675 129.503  37.622  1.00 99.79           C
ATOM   7212  CA  ALA C 503      17.937 129.537  38.885  1.00 99.79           C
ATOM   7213  CB  ALA C 503      16.459 129.284  38.612  1.00100.07           C
ATOM   7214  C   ALA C 503      18.399 128.645  40.042  1.00 99.79           C
ATOM   7215  O   ALA C 503      17.743 127.655  40.386  1.00 99.79           C
ATOM   7216  N   ALA C 504      19.518 129.028  40.649  1.00 99.95           C
ATOM   7217  CA  ALA C 504      20.092 128.337  41.799  1.00 99.95           C
ATOM   7218  CB  ALA C 504      20.960 127.181  41.365  1.00 27.97           C
ATOM   7219  C   ALA C 504      20.937 129.401  42.454  1.00 99.95           C
ATOM   7220  O   ALA C 504      21.435 129.226  43.562  1.00 99.95           C
ATOM   7221  N   GLY C 505      21.092 130.507  41.731  1.00 49.62           C
ATOM   7222  CA  GLY C 505      21.855 131.636  42.220  1.00 49.62           C
ATOM   7223  C   GLY C 505      23.106 131.257  42.983  1.00 49.62           C
ATOM   7224  O   GLY C 505      23.434 131.872  44.006  1.00 49.62           C
ATOM   7225  N   ALA C 506      23.797 130.235  42.483  1.00100.07           C
ATOM   7226  CA  ALA C 506      25.042 129.741  43.076  1.00100.07           C
ATOM   7227  CB  ALA C 506      24.738 128.744  44.194  1.00100.07           C
ATOM   7228  C   ALA C 506      25.861 129.072  41.965  1.00100.07           C
ATOM   7229  O   ALA C 506      26.998 129.464  41.686  1.00100.07           C
ATOM   7230  N   ALA C 507      25.266 128.062  41.338  1.00 69.47           C
ATOM   7231  CA  ALA C 507      25.898 127.355  40.239  1.00 69.47           C
ATOM   7232  CB  ALA C 507      25.920 128.259  39.011  1.00 11.32           C
ATOM   7233  C   ALA C 507      27.312 126.907  40.565  1.00 69.47           C
ATOM   7234  O   ALA C 507      28.223 127.733  40.571  1.00 69.47           C
ATOM   7235  N   ALA C 508      27.516 125.619  40.842  1.00 58.95           C
ATOM   7236  CA  ALA C 508      28.880 125.157  41.123  1.00 58.95           C
ATOM   7237  CB  ALA C 508      28.894 123.738  41.710  1.00  5.07           C
ATOM   7238  C   ALA C 508      29.537 125.155  39.765  1.00 58.95           C
ATOM   7239  O   ALA C 508      28.899 124.805  38.771  1.00 58.95           C
ATOM   7240  N   ALA C 509      30.796 125.557  39.696  1.00 36.57           C
ATOM   7241  CA  ALA C 509      31.445 125.563  38.396  1.00 36.57           C
ATOM   7242  CB  ALA C 509      30.896 126.694  37.549  1.00 16.32           C
ATOM   7243  C   ALA C 509      32.957 125.642  38.454  1.00 36.57           C
ATOM   7244  O   ALA C 509      33.561 125.630  39.535  1.00 36.57           C
ATOM   7245  N   ALA C 510      33.559 125.722  37.272  1.00 16.98           C
ATOM   7246  CA  ALA C 510      35.004 125.779  37.156  1.00 16.98           C
ATOM   7247  CB  ALA C 510      35.538 124.450  36.616  1.00 80.19           C
ATOM   7248  C   ALA C 510      35.442 126.906  36.250  1.00 16.98           C
ATOM   7249  O   ALA C 510      34.740 127.298  35.319  1.00 16.98           C
ATOM   7250  N   ALA C 511      36.626 127.416  36.533  1.00 77.42           C
ATOM   7251  CA  ALA C 511      37.192 128.482  35.742  1.00 77.42           C
ATOM   7252  CB  ALA C 511      36.873 129.836  36.380  1.00  5.07           C
ATOM   7253  C   ALA C 511      38.695 128.215  35.701  1.00 77.42           C
ATOM   7254  O   ALA C 511      39.383 128.268  36.725  1.00 77.42           C
ATOM   7255  N   ALA C 512      39.181 127.888  34.506  1.00 67.81           C
ATOM   7256  CA  ALA C 512      40.586 127.585  34.273  1.00 67.81           C
ATOM   7257  CB  ALA C 512      41.474 128.721  34.786  1.00 94.60           C
ATOM   7258  C   ALA C 512      40.970 126.270  34.933  1.00 67.81           C
ATOM   7259  O   ALA C 512      41.817 125.540  34.410  1.00 67.81           C
ATOM   7260  N   ALA C 513      40.341 125.963  36.068  1.00 86.56           C
ATOM   7261  CA  ALA C 513      40.619 124.724  36.803  1.00 86.56           C
ATOM   7262  CB  ALA C 513      42.117 124.620  37.101  1.00100.07           C
ATOM   7263  C   ALA C 513      39.832 124.619  38.110  1.00 86.56           C
ATOM   7264  O   ALA C 513      39.083 123.666  38.326  1.00 86.56           C
ATOM   7265  N   ALA C 514      40.030 125.606  38.978  1.00 54.32           C
ATOM   7266  CA  ALA C 514      39.378 125.673  40.275  1.00 54.32           C
ATOM   7267  CB  ALA C 514      39.504 127.077  40.841  1.00 86.08           C
ATOM   7268  C   ALA C 514      37.916 125.279  40.219  1.00 54.32           C
ATOM   7269  O   ALA C 514      37.228 125.524  39.231  1.00 54.32           C
ATOM   7270  N   ALA C 515      37.456 124.653  41.293  1.00 75.05           C
```

```
ATOM   7271  CA   ALA C 515      36.066 124.249 41.408  1.00 75.05           C
ATOM   7272  CB   ALA C 515      35.958 122.984 42.266  1.00 19.56           C
ATOM   7273  C    ALA C 515      35.369 125.430 42.089  1.00 75.05           C
ATOM   7274  O    ALA C 515      34.714 125.272 43.119  1.00 75.05           C
ATOM   7275  N    ALA C 516      35.527 126.615 41.502  1.00 33.77           C
ATOM   7276  CA   ALA C 516      34.962 127.851 42.041  1.00 33.77           C
ATOM   7277  CB   ALA C 516      35.715 129.048 41.450  1.00  5.07           C
ATOM   7278  C    ALA C 516      33.453 128.032 41.853  1.00 33.77           C
ATOM   7279  O    ALA C 516      32.946 127.977 40.732  1.00 33.77           C
ATOM   7280  N    ALA C 517      32.765 128.268 42.978  1.00 29.64           C
ATOM   7281  CA   ALA C 517      31.307 128.477 43.060  1.00 29.64           C
ATOM   7282  CB   ALA C 517      30.881 128.551 44.514  1.00 26.55           C
ATOM   7283  C    ALA C 517      30.825 129.731 42.319  1.00 29.64           C
ATOM   7284  O    ALA C 517      30.688 130.813 42.903  1.00 29.64           C
ATOM   7285  N    ALA C 518      30.559 129.531 41.026  1.00100.07           C
ATOM   7286  CA   ALA C 518      30.105 130.538 40.058  1.00100.07           C
ATOM   7287  CB   ALA C 518      29.288 129.857 38.961  1.00 96.52           C
ATOM   7288  C    ALA C 518      29.348 131.760 40.542  1.00100.07           C
ATOM   7289  O    ALA C 518      28.626 131.722 41.537  1.00100.07           C
ATOM   7290  N    GLY C 519      29.514 132.843 39.791  1.00 96.72           C
ATOM   7291  CA   GLY C 519      28.853 134.086 40.117  1.00 96.72           C
ATOM   7292  C    GLY C 519      27.441 134.128 39.568  1.00 96.72           C
ATOM   7293  O    GLY C 519      26.932 135.203 39.257  1.00 96.72           C
ATOM   7294  N    ALA C 520      26.810 132.962 39.439  1.00 72.63           C
ATOM   7295  CA   ALA C 520      25.435 132.866 38.934  1.00 72.63           C
ATOM   7296  CB   ALA C 520      24.493 133.622 39.859  1.00 80.18           C
ATOM   7297  C    ALA C 520      25.254 133.364 37.499  1.00 72.63           C
ATOM   7298  O    ALA C 520      24.257 133.054 36.850  1.00 72.63           C
ATOM   7299  N    ALA C 521      26.224 134.142 37.027  1.00 89.56           C
ATOM   7300  CA   ALA C 521      26.226 134.708 35.684  1.00 89.56           C
ATOM   7301  CB   ALA C 521      26.827 133.704 34.708  1.00 35.64           C
ATOM   7302  C    ALA C 521      24.850 135.167 35.194  1.00 89.56           C
ATOM   7303  O    ALA C 521      24.307 136.171 35.671  1.00 89.56           C
ATOM   7304  N    VAL C 522      24.303 134.441 34.219  1.00100.07           C
ATOM   7305  CA   VAL C 522      22.991 134.745 33.634  1.00100.07           C
ATOM   7306  CB   VAL C 522      23.114 134.979 32.084  1.00 83.70           C
ATOM   7307  CG1  VAL C 522      21.784 135.464 31.502  1.00 83.70           C
ATOM   7308  CG2  VAL C 522      24.215 136.011 31.801  1.00 83.70           C
ATOM   7309  C    VAL C 522      21.975 133.616 33.924  1.00100.07           C
ATOM   7310  O    VAL C 522      21.917 133.090 35.045  1.00100.07           C
ATOM   7311  N    ILE C 523      21.175 133.265 32.919  1.00100.07           C
ATOM   7312  CA   ILE C 523      20.161 132.216 33.027  1.00100.07           C
ATOM   7313  CB   ILE C 523      18.713 132.835 33.101  1.00100.07           C
ATOM   7314  CG2  ILE C 523      17.769 132.176 32.089  1.00100.07           C
ATOM   7315  CG1  ILE C 523      18.135 132.677 34.516  1.00100.07           C
ATOM   7316  CD   ILE C 523      16.702 133.203 34.668  1.00100.07           C
ATOM   7317  C    ILE C 523      20.310 131.359 31.777  1.00100.07           C
ATOM   7318  O    ILE C 523      20.599 130.162 31.851  1.00100.07           C
ATOM   7319  N    VAL C 524      20.129 131.989 30.622  1.00 99.13           C
ATOM   7320  CA   VAL C 524      20.276 131.291 29.360  1.00 99.13           C
ATOM   7321  CB   VAL C 524      18.952 130.788 28.798  1.00100.07           C
ATOM   7322  CG1  VAL C 524      19.235 129.833 27.645  1.00100.07           C
ATOM   7323  CG2  VAL C 524      18.184 130.073 29.858  1.00100.07           C
ATOM   7324  C    VAL C 524      20.929 132.214 28.354  1.00 99.13           C
ATOM   7325  O    VAL C 524      20.892 131.997 27.152  1.00 99.13           C
ATOM   7326  N    ALA C 525      21.506 133.285 28.873  1.00 99.85           C
ATOM   7327  CA   ALA C 525      22.274 134.218 28.062  1.00 99.85           C
ATOM   7328  CB   ALA C 525      21.930 135.638 28.432  1.00 54.65           C
ATOM   7329  C    ALA C 525      23.574 133.771 28.730  1.00 99.85           C
ATOM   7330  O    ALA C 525      24.447 134.587 29.042  1.00 99.85           C
ATOM   7331  N    PRO C 526      23.730 132.452 28.894  1.00100.07           C
ATOM   7332  CD   PRO C 526      23.555 132.065 27.477  1.00 69.64           C
ATOM   7333  CA   PRO C 526      24.693 131.491 29.469  1.00100.07           C
ATOM   7334  CB   PRO C 526      25.317 130.789 28.249  1.00 69.64           C
ATOM   7335  CG   PRO C 526      24.923 131.579 27.115  1.00 69.64           C
ATOM   7336  C    PRO C 526      25.745 131.972 30.462  1.00100.07           C
ATOM   7337  O    PRO C 526      25.488 132.773 31.371  1.00100.07           C
ATOM   7338  N    GLU C 527      26.930 131.398 30.294  1.00100.07           C
ATOM   7339  CA   GLU C 527      28.128 131.674 31.086  1.00100.07           C
ATOM   7340  CB   GLU C 527      28.148 130.875 32.387  1.00100.07           C
ATOM   7341  CG   GLU C 527      26.940 131.095 33.244  1.00100.07           C
ATOM   7342  CD   GLU C 527      26.644 129.911 34.133  1.00100.07           C
ATOM   7343  OE1  GLU C 527      27.364 129.714 35.139  1.00100.07           C
ATOM   7344  OE2  GLU C 527      25.689 129.165 33.811  1.00100.07           C
ATOM   7345  C    GLU C 527      29.125 131.078 30.118  1.00100.07           C
ATOM   7346  O    GLU C 527      30.330 131.104 30.344  1.00100.07           C
ATOM   7347  N    ALA C 528      28.554 130.540 29.038  1.00 81.93           C
ATOM   7348  CA   ALA C 528      29.270 129.893 27.939  1.00 81.93           C
ATOM   7349  CB   ALA C 528      30.618 130.565 27.708  1.00 95.44           C
ATOM   7350  C    ALA C 528      29.467 128.403 28.185  1.00 81.93           C
ATOM   7351  O    ALA C 528      29.770 127.647 27.251  1.00 81.93           C
ATOM   7352  N    VAL C 529      29.309 127.984 29.437  1.00 66.83           C
ATOM   7353  CA   VAL C 529      29.478 126.577 29.776  1.00 66.83           C
ATOM   7354  CB   VAL C 529      30.786 126.302 30.535  1.00100.07           C
```

| ATOM | 7355 | CG1 | VAL C 529 | 30.811 124.848 30.985 | 1.00100.07 | C |
|------|------|-----|-----------|------------------------|------------|---|
| ATOM | 7356 | CG2 | VAL C 529 | 31.989 126.578 29.650 | 1.00100.07 | C |
| ATOM | 7357 | C   | VAL C 529 | 28.375 125.984 30.621 | 1.00 66.83 | C |
| ATOM | 7358 | O   | VAL C 529 | 28.020 126.516 31.673 | 1.00 66.83 | C |
| ATOM | 7359 | N   | GLU C 530 | 27.869 124.851 30.156 | 1.00100.07 | C |
| ATOM | 7360 | CA  | GLU C 530 | 26.824 124.147 30.850 | 1.00100.07 | C |
| ATOM | 7361 | CB  | GLU C 530 | 25.593 124.011 29.960 | 1.00 94.66 | C |
| ATOM | 7362 | CG  | GLU C 530 | 24.485 123.198 30.601 | 1.00 94.66 | C |
| ATOM | 7363 | CD  | GLU C 530 | 24.056 123.758 31.951 | 1.00 94.66 | C |
| ATOM | 7364 | OE1 | GLU C 530 | 24.922 123.987 32.826 | 1.00 94.66 | C |
| ATOM | 7365 | OE2 | GLU C 530 | 22.842 123.966 32.140 | 1.00 94.66 | C |
| ATOM | 7366 | C   | GLU C 530 | 27.294 122.764 31.267 | 1.00100.07 | C |
| ATOM | 7367 | O   | GLU C 530 | 26.890 122.282 32.321 | 1.00100.07 | C |
| ATOM | 7368 | N   | PHE C 531 | 28.138 122.132 30.446 | 1.00 64.70 | C |
| ATOM | 7369 | CA  | PHE C 531 | 28.644 120.780 30.717 | 1.00 64.70 | C |
| ATOM | 7370 | CB  | PHE C 531 | 28.806 120.533 32.213 | 1.00 98.58 | C |
| ATOM | 7371 | CG  | PHE C 531 | 30.204 120.650 32.693 | 1.00 98.58 | C |
| ATOM | 7372 | CD1 | PHE C 531 | 30.876 121.860 32.625 | 1.00 98.58 | C |
| ATOM | 7373 | CD2 | PHE C 531 | 30.845 119.553 33.248 | 1.00 98.58 | C |
| ATOM | 7374 | CE1 | PHE C 531 | 32.169 121.973 33.106 | 1.00 98.58 | C |
| ATOM | 7375 | CE2 | PHE C 531 | 32.128 119.647 33.730 | 1.00 98.58 | C |
| ATOM | 7376 | CZ  | PHE C 531 | 32.794 120.858 33.663 | 1.00 98.58 | C |
| ATOM | 7377 | C   | PHE C 531 | 27.686 119.734 30.165 | 1.00 64.70 | C |
| ATOM | 7378 | O   | PHE C 531 | 26.923 119.120 30.910 | 1.00 64.70 | C |
| ATOM | 7379 | N   | MET C 532 | 27.726 119.542 28.852 | 1.00 37.81 | C |
| ATOM | 7380 | CA  | MET C 532 | 26.874 118.577 28.192 | 1.00 37.81 | C |
| ATOM | 7381 | CB  | MET C 532 | 27.489 118.185 26.858 | 1.00 90.89 | C |
| ATOM | 7382 | CG  | MET C 532 | 26.510 117.504 25.972 | 1.00 90.89 | C |
| ATOM | 7383 | SD  | MET C 532 | 24.970 118.422 26.043 | 1.00 90.89 | C |
| ATOM | 7384 | CE  | MET C 532 | 24.008 117.459 27.253 | 1.00 90.89 | C |
| ATOM | 7385 | C   | MET C 532 | 26.735 117.358 29.082 | 1.00 37.81 | C |
| ATOM | 7386 | O   | MET C 532 | 27.728 116.724 29.408 | 1.00 37.81 | C |
| ATOM | 7387 | N   | ASP C 533 | 25.506 117.066 29.500 | 1.00 43.33 | C |
| ATOM | 7388 | CA  | ASP C 533 | 25.176 115.920 30.356 | 1.00 43.33 | C |
| ATOM | 7389 | CB  | ASP C 533 | 24.084 115.102 29.673 | 1.00100.07 | C |
| ATOM | 7390 | CG  | ASP C 533 | 23.404 114.145 30.613 | 1.00100.07 | C |
| ATOM | 7391 | OD1 | ASP C 533 | 22.954 114.605 31.689 | 1.00100.07 | C |
| ATOM | 7392 | OD2 | ASP C 533 | 23.311 112.942 30.272 | 1.00100.07 | C |
| ATOM | 7393 | C   | ASP C 533 | 26.370 115.020 30.706 | 1.00 43.33 | C |
| ATOM | 7394 | O   | ASP C 533 | 26.489 113.890 30.228 | 1.00 43.33 | C |
| ATOM | 7395 | N   | VAL C 534 | 27.235 115.541 31.568 | 1.00 25.67 | C |
| ATOM | 7396 | CA  | VAL C 534 | 28.456 114.874 32.004 | 1.00 25.67 | C |
| ATOM | 7397 | CB  | VAL C 534 | 29.076 115.609 33.183 | 1.00100.07 | C |
| ATOM | 7398 | CG1 | VAL C 534 | 30.326 114.886 33.644 | 1.00100.07 | C |
| ATOM | 7399 | CG2 | VAL C 534 | 29.381 117.024 32.789 | 1.00100.07 | C |
| ATOM | 7400 | C   | VAL C 534 | 28.352 113.427 32.416 | 1.00 25.67 | C |
| ATOM | 7401 | O   | VAL C 534 | 27.803 113.136 33.484 | 1.00 25.67 | C |
| ATOM | 7402 | N   | SER C 535 | 28.918 112.547 31.583 | 1.00 30.45 | C |
| ATOM | 7403 | CA  | SER C 535 | 28.946 111.100 31.822 | 1.00 30.45 | C |
| ATOM | 7404 | CB  | SER C 535 | 27.842 110.674 32.796 | 1.00100.07 | C |
| ATOM | 7405 | OG  | SER C 535 | 26.559 110.974 32.270 | 1.00100.07 | C |
| ATOM | 7406 | C   | SER C 535 | 28.810 110.267 30.548 | 1.00 30.45 | C |
| ATOM | 7407 | O   | SER C 535 | 27.719 110.145 29.977 | 1.00 30.45 | C |
| ATOM | 7408 | N   | PRO C 536 | 29.919 109.660 30.104 | 1.00 87.03 | C |
| ATOM | 7409 | CD  | PRO C 536 | 29.947 108.621 29.055 | 1.00100.07 | C |
| ATOM | 7410 | CA  | PRO C 536 | 31.223 109.746 30.760 | 1.00 87.03 | C |
| ATOM | 7411 | CB  | PRO C 536 | 31.902 108.452 30.347 | 1.00100.07 | C |
| ATOM | 7412 | CG  | PRO C 536 | 31.440 108.309 28.935 | 1.00100.07 | C |
| ATOM | 7413 | C   | PRO C 536 | 32.028 110.958 30.326 | 1.00 87.03 | C |
| ATOM | 7414 | O   | PRO C 536 | 33.232 111.023 30.602 | 1.00 87.03 | C |
| ATOM | 7415 | N   | LYS C 537 | 31.389 111.901 29.630 | 1.00 27.01 | C |
| ATOM | 7416 | CA  | LYS C 537 | 32.111 113.087 29.219 | 1.00 27.01 | C |
| ATOM | 7417 | CB  | LYS C 537 | 31.162 114.239 28.909 | 1.00 57.11 | C |
| ATOM | 7418 | CG  | LYS C 537 | 31.877 115.472 28.347 | 1.00 57.11 | C |
| ATOM | 7419 | CD  | LYS C 537 | 31.083 116.769 28.515 | 1.00 57.11 | C |
| ATOM | 7420 | CE  | LYS C 537 | 31.019 117.179 29.977 | 1.00 57.11 | C |
| ATOM | 7421 | NZ  | LYS C 537 | 30.491 118.556 30.180 | 1.00 57.11 | C |
| ATOM | 7422 | C   | LYS C 537 | 32.747 113.347 30.543 | 1.00 27.01 | C |
| ATOM | 7423 | O   | LYS C 537 | 32.089 113.120 31.557 | 1.00 27.01 | C |
| ATOM | 7424 | N   | GLN C 538 | 33.998 113.778 30.585 | 1.00 77.89 | C |
| ATOM | 7425 | CA  | GLN C 538 | 34.623 114.035 31.884 | 1.00 77.89 | C |
| ATOM | 7426 | CB  | GLN C 538 | 33.738 114.961 32.738 | 1.00 99.92 | C |
| ATOM | 7427 | CG  | GLN C 538 | 34.161 115.106 34.209 | 1.00 99.92 | C |
| ATOM | 7428 | CD  | GLN C 538 | 34.642 116.512 34.562 | 1.00 99.92 | C |
| ATOM | 7429 | OE1 | GLN C 538 | 33.972 117.506 34.268 | 1.00 99.92 | C |
| ATOM | 7430 | NE2 | GLN C 538 | 35.807 116.598 35.203 | 1.00 99.92 | C |
| ATOM | 7431 | C   | GLN C 538 | 34.910 112.752 32.661 | 1.00 77.89 | C |
| ATOM | 7432 | O   | GLN C 538 | 35.965 112.150 32.473 | 1.00 77.89 | C |
| ATOM | 7433 | N   | VAL C 539 | 33.992 112.324 33.532 | 1.00 98.72 | C |
| ATOM | 7434 | CA  | VAL C 539 | 34.255 111.113 34.305 | 1.00 98.72 | C |
| ATOM | 7435 | CB  | VAL C 539 | 33.118 110.796 35.351 | 1.00 23.12 | C |
| ATOM | 7436 | CG1 | VAL C 539 | 32.004 110.010 34.722 | 1.00 23.12 | C |
| ATOM | 7437 | CG2 | VAL C 539 | 33.698 110.045 36.531 | 1.00 23.12 | C |
| ATOM | 7438 | C   | VAL C 539 | 34.513 109.925 33.369 | 1.00 98.72 | C |

—89—

```
ATOM   7439  O    VAL C 539      33.641 109.456  32.638  1.00 98.72           C
ATOM   7440  N    ALA C 540      35.774 109.506  33.385  1.00 88.30           C
ATOM   7441  CA   ALA C 540      36.330 108.398  32.614  1.00 88.30           C
ATOM   7442  CB   ALA C 540      36.431 107.154  33.516  1.00100.07           C
ATOM   7443  C    ALA C 540      35.758 107.993  31.253  1.00 88.30           C
ATOM   7444  O    ALA C 540      34.873 108.636  30.682  1.00 88.30           C
ATOM   7445  N    SER C 541      36.316 106.883  30.774  1.00 38.21           C
ATOM   7446  CA   SER C 541      36.031 106.254  29.492  1.00 38.21           C
ATOM   7447  CB   SER C 541      36.844 104.962  29.378  1.00 89.88           C
ATOM   7448  OG   SER C 541      36.477 104.210  28.232  1.00 89.88           C
ATOM   7449  C    SER C 541      34.609 105.942  29.075  1.00 38.21           C
ATOM   7450  O    SER C 541      33.662 106.051  29.843  1.00 38.21           C
ATOM   7451  N    LEU C 542      34.500 105.547  27.812  1.00 99.80           C
ATOM   7452  CA   LEU C 542      33.240 105.174  27.201  1.00 99.80           C
ATOM   7453  CB   LEU C 542      33.456 104.793  25.724  1.00 75.91           C
ATOM   7454  CG   LEU C 542      32.458 103.831  25.052  1.00 75.91           C
ATOM   7455  CD1  LEU C 542      31.112 104.494  24.846  1.00 75.91           C
ATOM   7456  CD2  LEU C 542      33.015 103.391  23.722  1.00 75.91           C
ATOM   7457  C    LEU C 542      32.720 103.974  27.948  1.00 99.80           C
ATOM   7458  O    LEU C 542      31.526 103.866  28.205  1.00 99.80           C
ATOM   7459  N    ASN C 543      33.633 103.084  28.320  1.00 45.16           C
ATOM   7460  CA   ASN C 543      33.232 101.861  28.988  1.00 45.16           C
ATOM   7461  CB   ASN C 543      33.892 100.665  28.302  1.00 31.59           C
ATOM   7462  CG   ASN C 543      35.270 100.403  28.814  1.00 31.59           C
ATOM   7463  OD1  ASN C 543      36.081 101.322  28.923  1.00 31.59           C
ATOM   7464  ND2  ASN C 543      35.549  99.149  29.146  1.00 31.59           C
ATOM   7465  C    ASN C 543      33.474 101.796  30.490  1.00 45.16           C
ATOM   7466  O    ASN C 543      34.131 100.881  30.991  1.00 45.16           C
ATOM   7467  N    THR C 544      32.912 102.761  31.205  1.00 77.59           C
ATOM   7468  CA   THR C 544      33.026 102.823  32.652  1.00 77.59           C
ATOM   7469  CB   THR C 544      34.288 103.652  33.069  1.00 53.19           C
ATOM   7470  OG1  THR C 544      34.200 104.061  34.438  1.00 53.19           C
ATOM   7471  CG2  THR C 544      34.452 104.849  32.178  1.00 53.19           C
ATOM   7472  C    THR C 544      31.717 103.418  33.171  1.00 77.59           C
ATOM   7473  O    THR C 544      31.579 103.726  34.352  1.00 77.59           C
ATOM   7474  N    ASN C 545      30.753 103.561  32.260  1.00 46.72           C
ATOM   7475  CA   ASN C 545      29.419 104.072  32.588  1.00 46.72           C
ATOM   7476  CB   ASN C 545      28.846 104.912  31.461  1.00 64.40           C
ATOM   7477  CG   ASN C 545      29.657 106.127  31.191  1.00 64.40           C
ATOM   7478  OD1  ASN C 545      29.461 107.170  31.812  1.00 64.40           C
ATOM   7479  ND2  ASN C 545      30.599 106.005  30.267  1.00 64.40           C
ATOM   7480  C    ASN C 545      28.535 102.857  32.755  1.00 46.72           C
ATOM   7481  O    ASN C 545      27.357 102.957  33.122  1.00 46.72           C
ATOM   7482  N    LEU C 546      29.103 101.701  32.441  1.00 51.64           C
ATOM   7483  CA   LEU C 546      28.359 100.471  32.594  1.00 51.64           C
ATOM   7484  CB   LEU C 546      29.008  99.333  31.795  1.00 67.44           C
ATOM   7485  CG   LEU C 546      29.403  99.578  30.331  1.00 67.44           C
ATOM   7486  CD1  LEU C 546      29.607  98.236  29.664  1.00 67.44           C
ATOM   7487  CD2  LEU C 546      28.343 100.352  29.585  1.00 67.44           C
ATOM   7488  C    LEU C 546      28.421 100.200  34.095  1.00 51.64           C
ATOM   7489  O    LEU C 546      28.235  99.069  34.549  1.00 51.64           C
ATOM   7490  N    ILE C 547      28.702 101.262  34.852  1.00 46.71           C
ATOM   7491  CA   ILE C 547      28.782 101.186  36.304  1.00 46.71           C
ATOM   7492  CB   ILE C 547      30.131 101.669  36.834  1.00 63.78           C
ATOM   7493  CG2  ILE C 547      30.102 101.656  38.338  1.00 63.78           C
ATOM   7494  CG1  ILE C 547      31.246 100.738  36.377  1.00 63.78           C
ATOM   7495  CD   ILE C 547      32.602 101.049  37.001  1.00 63.78           C
ATOM   7496  C    ILE C 547      27.693 102.032  36.960  1.00 46.71           C
ATOM   7497  O    ILE C 547      27.864 103.230  37.164  1.00 46.71           C
ATOM   7498  N    PRO C 548      26.571 101.401  37.330  1.00 86.11           C
ATOM   7499  CD   PRO C 548      26.375  99.946  37.374  1.00 48.30           C
ATOM   7500  CA   PRO C 548      25.439 102.062  37.961  1.00 86.11           C
ATOM   7501  CB   PRO C 548      24.546 100.889  38.354  1.00 48.30           C
ATOM   7502  CG   PRO C 548      25.505  99.797  38.578  1.00 48.30           C
ATOM   7503  C    PRO C 548      25.738 102.995  39.123  1.00 86.11           C
ATOM   7504  O    PRO C 548      24.984 103.939  39.369  1.00 86.11           C
ATOM   7505  N    PHE C 549      26.812 102.766  39.859  1.00 21.96           C
ATOM   7506  CA   PHE C 549      27.050 103.692  40.960  1.00 21.96           C
ATOM   7507  CB   PHE C 549      26.572 103.059  42.275  1.00 66.52           C
ATOM   7508  CG   PHE C 549      25.065 102.980  42.392  1.00 66.52           C
ATOM   7509  CD1  PHE C 549      24.322 102.171  41.540  1.00 66.52           C
ATOM   7510  CD2  PHE C 549      24.386 103.756  43.313  1.00 66.52           C
ATOM   7511  CE1  PHE C 549      22.926 102.143  41.598  1.00 66.52           C
ATOM   7512  CE2  PHE C 549      22.992 103.731  43.377  1.00 66.52           C
ATOM   7513  CZ   PHE C 549      22.265 102.923  42.515  1.00 66.52           C
ATOM   7514  C    PHE C 549      28.492 104.187  41.041  1.00 21.96           C
ATOM   7515  O    PHE C 549      29.106 104.276  42.110  1.00 21.96           C
ATOM   7516  N    LEU C 550      29.022 104.527  39.874  1.00 46.97           C
ATOM   7517  CA   LEU C 550      30.382 105.016  39.775  1.00 46.97           C
ATOM   7518  CB   LEU C 550      30.617 105.644  38.396  1.00 31.66           C
ATOM   7519  CG   LEU C 550      32.022 106.137  38.042  1.00 31.66           C
ATOM   7520  CD1  LEU C 550      33.081 105.267  38.708  1.00 31.66           C
ATOM   7521  CD2  LEU C 550      32.183 106.139  36.520  1.00 31.66           C
ATOM   7522  C    LEU C 550      30.553 106.030  40.873  1.00 46.97           C
```

```
ATOM   7523  O   LEU C 550      31.656 106.263 41.346  1.00 46.97           C
ATOM   7524  N   GLU C 551      29.436 106.618 41.283  1.00 44.84           C
ATOM   7525  CA  GLU C 551      29.442 107.598 42.349  1.00 44.84           C
ATOM   7526  CB  GLU C 551      28.027 108.102 42.594  1.00 99.26           C
ATOM   7527  CG  GLU C 551      27.216 108.214 41.331  1.00 99.26           C
ATOM   7528  CD  GLU C 551      26.115 109.231 41.453  1.00 99.26           C
ATOM   7529  OE1 GLU C 551      26.442 110.419 41.654  1.00 99.26           C
ATOM   7530  OE2 GLU C 551      24.929 108.850 41.347  1.00 99.26           C
ATOM   7531  C   GLU C 551      29.975 106.890 43.591  1.00 44.84           C
ATOM   7532  O   GLU C 551      31.178 106.866 43.827  1.00 44.84           C
ATOM   7533  N   HIS C 552      29.078 106.308 44.377  1.00 62.12           C
ATOM   7534  CA  HIS C 552      29.467 105.580 45.581  1.00 62.12           C
ATOM   7535  CB  HIS C 552      28.235 104.955 46.218  1.00 38.24           C
ATOM   7536  CG  HIS C 552      27.002 105.779 46.059  1.00 38.24           C
ATOM   7537  CD2 HIS C 552      26.139 105.892 45.024  1.00 38.24           C
ATOM   7538  ND1 HIS C 552      26.555 106.648 47.030  1.00 38.24           C
ATOM   7539  CE1 HIS C 552      25.467 107.258 46.599  1.00 38.24           C
ATOM   7540  NE2 HIS C 552      25.194 106.818 45.384  1.00 38.24           C
ATOM   7541  C   HIS C 552      30.412 104.472 45.144  1.00 62.12           C
ATOM   7542  O   HIS C 552      30.109 103.293 45.282  1.00 62.12           C
ATOM   7543  N   ASP C 553      31.563 104.852 44.620  1.00 74.17           C
ATOM   7544  CA  ASP C 553      32.513 103.881 44.131  1.00 74.17           C
ATOM   7545  CB  ASP C 553      31.994 103.313 42.802  1.00 24.87           C
ATOM   7546  CG  ASP C 553      31.498 101.878 42.926  1.00 24.87           C
ATOM   7547  OD1 ASP C 553      31.012 101.481 44.008  1.00 24.87           C
ATOM   7548  OD2 ASP C 553      31.596 101.146 41.925  1.00 24.87           C
ATOM   7549  C   ASP C 553      33.859 104.577 43.958  1.00 74.17           C
ATOM   7550  O   ASP C 553      34.060 105.377 43.038  1.00 74.17           C
ATOM   7551  N   ASP C 554      34.776 104.272 44.868  1.00 18.17           C
ATOM   7552  CA  ASP C 554      36.111 104.856 44.854  1.00 18.17           C
ATOM   7553  CB  ASP C 554      36.932 104.285 46.013  1.00 45.40           C
ATOM   7554  CG  ASP C 554      38.371 104.734 45.975  1.00 45.40           C
ATOM   7555  OD1 ASP C 554      39.035 104.475 44.955  1.00 45.40           C
ATOM   7556  OD2 ASP C 554      38.847 105.342 46.954  1.00 45.40           C
ATOM   7557  C   ASP C 554      36.845 104.614 43.539  1.00 18.17           C
ATOM   7558  O   ASP C 554      37.094 103.472 43.173  1.00 18.17           C
ATOM   7559  N   ALA C 555      37.203 105.691 42.846  1.00 34.34           C
ATOM   7560  CA  ALA C 555      37.926 105.597 41.580  1.00 34.34           C
ATOM   7561  CB  ALA C 555      38.827 106.789 41.404  1.00 19.00           C
ATOM   7562  C   ALA C 555      38.755 104.335 41.517  1.00 34.34           C
ATOM   7563  O   ALA C 555      38.446 103.425 40.758  1.00 34.34           C
ATOM   7564  N   ASN C 556      39.810 104.284 42.319  1.00 29.63           C
ATOM   7565  CA  ASN C 556      40.681 103.116 42.356  1.00 29.63           C
ATOM   7566  CB  ASN C 556      41.334 103.000 43.732  1.00 71.66           C
ATOM   7567  CG  ASN C 556      42.832 102.801 43.643  1.00 71.66           C
ATOM   7568  OD1 ASN C 556      43.301 101.768 43.169  1.00 71.66           C
ATOM   7569  ND2 ASN C 556      43.594 103.797 44.090  1.00 71.66           C
ATOM   7570  C   ASN C 556      39.969 101.798 41.993  1.00 29.63           C
ATOM   7571  O   ASN C 556      40.089 101.325 40.855  1.00 29.63           C
ATOM   7572  N   ALA C 557      39.232 101.201 42.934  1.00 54.73           C
ATOM   7573  CA  ALA C 557      38.533  99.947 42.630  1.00 54.73           C
ATOM   7574  CB  ALA C 557      37.690  99.458 43.844  1.00  5.07           C
ATOM   7575  C   ALA C 557      37.644 100.141 41.394  1.00 54.73           C
ATOM   7576  O   ALA C 557      37.436  99.214 40.612  1.00 54.73           C
ATOM   7577  N   ALA C 558      37.137 101.352 41.202  1.00 39.66           C
ATOM   7578  CA  ALA C 558      36.294 101.610 40.048  1.00 39.66           C
ATOM   7579  CB  ALA C 558      35.826 103.058 40.029  1.00 39.20           C
ATOM   7580  C   ALA C 558      37.071 101.296 38.782  1.00 39.66           C
ATOM   7581  O   ALA C 558      36.537 100.660 37.870  1.00 39.66           C
ATOM   7582  N   LEU C 559      38.330 101.731 38.716  1.00 11.82           C
ATOM   7583  CA  LEU C 559      39.141 101.469 37.524  1.00 11.82           C
ATOM   7584  CB  LEU C 559      40.577 101.995 37.696  1.00 16.16           C
ATOM   7585  CG  LEU C 559      41.761 101.011 37.705  1.00 16.16           C
ATOM   7586  CD1 LEU C 559      41.950 100.452 36.320  1.00 16.16           C
ATOM   7587  CD2 LEU C 559      43.045 101.689 38.123  1.00 16.16           C
ATOM   7588  C   LEU C 559      39.161  99.967 37.376  1.00 11.82           C
ATOM   7589  O   LEU C 559      38.990  99.435 36.279  1.00 11.82           C
ATOM   7590  N   MET C 560      39.339  99.300 38.515  1.00 13.81           C
ATOM   7591  CA  MET C 560      39.414  97.849 38.594  1.00 13.81           C
ATOM   7592  CB  MET C 560      39.743  97.442 40.014  1.00 42.89           C
ATOM   7593  CG  MET C 560      40.569  96.205 40.106  1.00 42.89           C
ATOM   7594  SD  MET C 560      41.238  96.047 41.758  1.00 42.89           C
ATOM   7595  CE  MET C 560      42.037  97.722 41.973  1.00 42.89           C
ATOM   7596  C   MET C 560      38.138  97.153 38.157  1.00 13.81           C
ATOM   7597  O   MET C 560      38.024  95.935 38.275  1.00 13.81           C
ATOM   7598  N   GLY C 561      37.181  97.940 37.668  1.00 10.47           C
ATOM   7599  CA  GLY C 561      35.912  97.418 37.187  1.00 10.47           C
ATOM   7600  C   GLY C 561      35.818  97.899 35.759  1.00 10.47           C
ATOM   7601  O   GLY C 561      35.297  97.218 34.883  1.00 10.47           C
ATOM   7602  N   SER C 562      36.340  99.090 35.516  1.00 24.81           C
ATOM   7603  CA  SER C 562      36.330  99.619 34.167  1.00 24.81           C
ATOM   7604  CB  SER C 562      36.930 101.022 34.142  1.00 62.72           C
ATOM   7605  OG  SER C 562      35.974 101.982 34.558  1.00 62.72           C
ATOM   7606  C   SER C 562      37.109  98.693 33.222  1.00 24.81           C
```

```
ATOM   7607  O   SER C 562      36.697  98.465  32.083  1.00 24.81           C
ATOM   7608  N   ASN C 563      38.239  98.168  33.688  1.00 10.93           C
ATOM   7609  CA  ASN C 563      39.037  97.259  32.864  1.00 10.93           C
ATOM   7610  CB  ASN C 563      40.478  97.127  33.390  1.00 27.67           C
ATOM   7611  CG  ASN C 563      41.293  98.406  33.230  1.00 27.67           C
ATOM   7612  OD1 ASN C 563      42.277  98.627  33.944  1.00 27.67           C
ATOM   7613  ND2 ASN C 563      40.898  99.244  32.286  1.00 27.67           C
ATOM   7614  C   ASN C 563      38.327  95.947  33.042  1.00 10.93           C
ATOM   7615  O   ASN C 563      37.815  95.361  32.103  1.00 10.93           C
ATOM   7616  N   MET C 564      38.277  95.526  34.292  1.00 15.33           C
ATOM   7617  CA  MET C 564      37.652  94.282  34.680  1.00 15.33           C
ATOM   7618  CB  MET C 564      36.993  94.463  36.043  1.00 33.53           C
ATOM   7619  CG  MET C 564      36.804  93.175  36.812  1.00 33.53           C
ATOM   7620  SD  MET C 564      38.294  92.697  37.662  1.00 33.53           C
ATOM   7621  CE  MET C 564      39.226  92.028  36.304  1.00 33.53           C
ATOM   7622  C   MET C 564      36.632  93.741  33.665  1.00 15.33           C
ATOM   7623  O   MET C 564      36.609  92.541  33.397  1.00 15.33           C
ATOM   7624  N   GLN C 565      35.793  94.613  33.108  1.00 39.06           C
ATOM   7625  CA  GLN C 565      34.793  94.184  32.131  1.00 39.06           C
ATOM   7626  CB  GLN C 565      33.836  95.322  31.797  1.00 43.60           C
ATOM   7627  CG  GLN C 565      32.579  95.396  32.619  1.00 43.60           C
ATOM   7628  CD  GLN C 565      31.681  96.528  32.142  1.00 43.60           C
ATOM   7629  OE1 GLN C 565      32.043  97.702  32.249  1.00 43.60           C
ATOM   7630  NE2 GLN C 565      30.513  96.181  31.602  1.00 43.60           C
ATOM   7631  C   GLN C 565      35.376  93.669  30.812  1.00 39.06           C
ATOM   7632  O   GLN C 565      35.095  92.535  30.425  1.00 39.06           C
ATOM   7633  N   THR C 566      36.168  94.503  30.128  1.00 12.13           C
ATOM   7634  CA  THR C 566      36.761  94.137  28.833  1.00 12.13           C
ATOM   7635  CB  THR C 566      38.150  94.755  28.583  1.00  7.27           C
ATOM   7636  OG1 THR C 566      38.058  96.180  28.557  1.00  7.27           C
ATOM   7637  CG2 THR C 566      38.673  94.306  27.241  1.00  7.27           C
ATOM   7638  C   THR C 566      36.959  92.655  28.700  1.00 12.13           C
ATOM   7639  O   THR C 566      36.752  92.099  27.627  1.00 12.13           C
ATOM   7640  N   GLN C 567      37.374  92.033  29.803  1.00 17.53           C
ATOM   7641  CA  GLN C 567      37.634  90.601  29.861  1.00 17.53           C
ATOM   7642  CB  GLN C 567      38.664  90.340  30.968  1.00 67.31           C
ATOM   7643  CG  GLN C 567      39.641  91.526  31.163  1.00 67.31           C
ATOM   7644  CD  GLN C 567      40.991  91.138  31.769  1.00 67.31           C
ATOM   7645  OE1 GLN C 567      41.734  90.337  31.195  1.00 67.31           C
ATOM   7646  NE2 GLN C 567      41.317  91.715  32.923  1.00 67.31           C
ATOM   7647  C   GLN C 567      36.328  89.845  30.110  1.00 17.53           C
ATOM   7648  O   GLN C 567      36.272  88.900  30.885  1.00 17.53           C
ATOM   7649  N   ALA C 568      35.286  90.282  29.418  1.00 24.15           C
ATOM   7650  CA  ALA C 568      33.954  89.712  29.517  1.00 24.15           C
ATOM   7651  CB  ALA C 568      33.059  90.322  28.462  1.00 67.54           C
ATOM   7652  C   ALA C 568      33.887  88.205  29.411  1.00 24.15           C
ATOM   7653  O   ALA C 568      33.919  87.526  30.424  1.00 24.15           C
ATOM   7654  N   VAL C 569      33.770  87.700  28.182  1.00 12.59           C
ATOM   7655  CA  VAL C 569      33.661  86.261  27.868  1.00 12.59           C
ATOM   7656  CB  VAL C 569      34.095  85.348  29.017  1.00 21.13           C
ATOM   7657  CG1 VAL C 569      33.927  83.908  28.615  1.00 21.13           C
ATOM   7658  CG2 VAL C 569      35.520  85.602  29.362  1.00 21.13           C
ATOM   7659  C   VAL C 569      32.219  85.900  27.553  1.00 12.59           C
ATOM   7660  O   VAL C 569      31.514  85.362  28.396  1.00 12.59           C
ATOM   7661  N   PRO C 570      31.769  86.176  26.321  1.00 35.39           C
ATOM   7662  CD  PRO C 570      32.588  86.473  25.137  1.00 74.38           C
ATOM   7663  CA  PRO C 570      30.397  85.874  25.924  1.00 35.39           C
ATOM   7664  CB  PRO C 570      30.456  85.939  24.397  1.00 74.38           C
ATOM   7665  CG  PRO C 570      31.890  85.670  24.083  1.00 74.38           C
ATOM   7666  C   PRO C 570      29.906  84.539  26.443  1.00 35.39           C
ATOM   7667  O   PRO C 570      30.664  83.568  26.495  1.00 35.39           C
ATOM   7668  N   LEU C 571      28.630  84.518  26.831  1.00 33.95           C
ATOM   7669  CA  LEU C 571      27.971  83.330  27.372  1.00 33.95           C
ATOM   7670  CB  LEU C 571      27.508  83.600  28.816  1.00 10.32           C
ATOM   7671  CG  LEU C 571      28.562  83.994  29.866  1.00 10.32           C
ATOM   7672  CD1 LEU C 571      29.173  85.305  29.463  1.00 10.32           C
ATOM   7673  CD2 LEU C 571      27.950  84.129  31.252  1.00 10.32           C
ATOM   7674  C   LEU C 571      26.768  82.909  26.512  1.00 33.95           C
ATOM   7675  O   LEU C 571      26.221  83.718  25.761  1.00 33.95           C
ATOM   7676  N   ILE C 572      26.384  81.636  26.629  1.00 47.12           C
ATOM   7677  CA  ILE C 572      25.251  81.056  25.901  1.00 47.12           C
ATOM   7678  CB  ILE C 572      24.997  79.581  26.317  1.00 48.48           C
ATOM   7679  CG2 ILE C 572      25.477  78.643  25.246  1.00 48.48           C
ATOM   7680  CG1 ILE C 572      25.719  79.268  27.626  1.00 48.48           C
ATOM   7681  CD  ILE C 572      25.270  80.112  28.819  1.00 48.48           C
ATOM   7682  C   ILE C 572      23.972  81.829  26.182  1.00 47.12           C
ATOM   7683  O   ILE C 572      23.140  82.039  25.299  1.00 47.12           C
ATOM   7684  N   ARG C 573      23.825  82.246  27.431  1.00 32.55           C
ATOM   7685  CA  ARG C 573      22.656  82.991  27.866  1.00 32.55           C
ATOM   7686  CB  ARG C 573      21.923  82.192  28.929  1.00 40.55           C
ATOM   7687  CG  ARG C 573      22.003  80.690  28.738  1.00 40.55           C
ATOM   7688  CD  ARG C 573      21.791  79.987  30.064  1.00 40.55           C
ATOM   7689  NE  ARG C 573      20.407  79.593  30.339  1.00 40.55           C
ATOM   7690  CZ  ARG C 573      19.327  80.363  30.189  1.00 40.55           C
```

```
ATOM   7691  NH1 ARG C 573      19.417  81.615  29.748  1.00 40.55           C
ATOM   7692  NH2 ARG C 573      18.138  79.866  30.503  1.00 40.55           C
ATOM   7693  C   ARG C 573      23.145  84.294  28.468  1.00 32.55           C
ATOM   7694  O   ARG C 573      22.933  84.551  29.658  1.00 32.55           C
ATOM   7695  N   ALA C 574      23.815  85.110  27.657  1.00 30.93           C
ATOM   7696  CA  ALA C 574      24.322  86.384  28.155  1.00 30.93           C
ATOM   7697  CB  ALA C 574      24.866  87.214  27.023  1.00 67.20           C
ATOM   7698  C   ALA C 574      23.147  87.080  28.812  1.00 30.93           C
ATOM   7699  O   ALA C 574      22.037  86.559  28.793  1.00 30.93           C
ATOM   7700  N   GLN C 575      23.366  88.243  29.399  1.00 34.78           C
ATOM   7701  CA  GLN C 575      22.261  88.942  30.037  1.00 34.78           C
ATOM   7702  CB  GLN C 575      21.855  88.261  31.358  1.00 54.90           C
ATOM   7703  CG  GLN C 575      21.124  86.920  31.217  1.00 54.90           C
ATOM   7704  CD  GLN C 575      20.546  86.406  32.531  1.00 54.90           C
ATOM   7705  OE1 GLN C 575      21.250  86.299  33.532  1.00 54.90           C
ATOM   7706  NE2 GLN C 575      19.257  86.079  32.526  1.00 54.90           C
ATOM   7707  C   GLN C 575      22.618  90.389  30.310  1.00 34.78           C
ATOM   7708  O   GLN C 575      23.762  90.713  30.634  1.00 34.78           C
ATOM   7709  N   ALA C 576      21.638  91.265  30.148  1.00 16.83           C
ATOM   7710  CA  ALA C 576      21.867  92.660  30.403  1.00 16.83           C
ATOM   7711  CB  ALA C 576      20.782  93.492  29.776  1.00 86.29           C
ATOM   7712  C   ALA C 576      21.800  92.751  31.908  1.00 16.83           C
ATOM   7713  O   ALA C 576      21.265  91.850  32.560  1.00 16.83           C
ATOM   7714  N   PRO C 577      22.385  93.810  32.487  1.00 73.42           C
ATOM   7715  CD  PRO C 577      23.386  94.675  31.841  1.00 80.42           C
ATOM   7716  CA  PRO C 577      22.383  94.023  33.937  1.00 73.42           C
ATOM   7717  CB  PRO C 577      23.661  94.822  34.165  1.00 80.42           C
ATOM   7718  CG  PRO C 577      23.743  95.646  32.949  1.00 80.42           C
ATOM   7719  C   PRO C 577      21.119  94.796  34.336  1.00 73.42           C
ATOM   7720  O   PRO C 577      20.716  95.731  33.642  1.00 73.42           C
ATOM   7721  N   VAL C 578      20.500  94.383  35.444  1.00 99.09           C
ATOM   7722  CA  VAL C 578      19.272  95.004  35.945  1.00 99.09           C
ATOM   7723  CB  VAL C 578      18.863  94.421  37.317  1.00100.07           C
ATOM   7724  CG1 VAL C 578      17.598  95.097  37.813  1.00100.07           C
ATOM   7725  CG2 VAL C 578      18.625  92.925  37.202  1.00100.07           C
ATOM   7726  C   VAL C 578      19.426  96.511  36.078  1.00 99.09           C
ATOM   7727  O   VAL C 578      18.650  97.284  35.521  1.00 99.09           C
ATOM   7728  N   VAL C 579      20.415  96.927  36.839  1.00 45.44           C
ATOM   7729  CA  VAL C 579      20.688  98.339  36.987  1.00 45.44           C
ATOM   7730  CB  VAL C 579      21.447  98.569  38.277  1.00100.07           C
ATOM   7731  CG1 VAL C 579      21.223  99.976  38.774  1.00100.07           C
ATOM   7732  CG2 VAL C 579      21.039  97.541  39.303  1.00100.07           C
ATOM   7733  C   VAL C 579      21.647  98.529  35.816  1.00 45.44           C
ATOM   7734  O   VAL C 579      22.797  98.136  35.952  1.00 45.44           C
ATOM   7735  N   MET C 580      21.230  99.110  34.688  1.00 79.50           C
ATOM   7736  CA  MET C 580      22.168  99.142  33.569  1.00 79.50           C
ATOM   7737  CB  MET C 580      21.563  98.394  32.373  1.00100.07           C
ATOM   7738  CG  MET C 580      20.210  98.889  31.904  1.00 82.47           C
ATOM   7739  SD  MET C 580      19.895  98.194  30.273  1.00 82.47           C
ATOM   7740  CE  MET C 580      20.423  99.579  29.251  1.00 82.47           C
ATOM   7741  C   MET C 580      22.916 100.362  33.033  1.00 79.50           C
ATOM   7742  O   MET C 580      24.029 100.216  32.529  1.00 79.50           C
ATOM   7743  N   ILE C 581      22.334 101.560  33.120  1.00 65.73           C
ATOM   7744  CA  ILE C 581      22.975 102.787  32.630  1.00 65.73           C
ATOM   7745  CB  ILE C 581      24.498 102.859  32.951  1.00100.07           C
ATOM   7746  CG2 ILE C 581      24.958 104.302  32.849  1.00100.07           C
ATOM   7747  CG1 ILE C 581      24.806 102.273  34.341  1.00100.07           C
ATOM   7748  CD  ILE C 581      23.853 102.712  35.427  1.00100.07           C
ATOM   7749  C   ILE C 581      22.857 103.009  31.142  1.00 65.73           C
ATOM   7750  O   ILE C 581      23.857 103.118  30.468  1.00 65.73           C
ATOM   7751  N   GLY C 582      21.641 103.082  30.602  1.00 92.71           C
ATOM   7752  CA  GLY C 582      21.451 103.312  29.180  1.00 92.71           C
ATOM   7753  C   GLY C 582      22.516 102.818  28.210  1.00 92.71           C
ATOM   7754  O   GLY C 582      22.376 101.748  27.644  1.00 92.71           C
ATOM   7755  N   LEU C 583      23.556 103.625  28.010  1.00 60.27           C
ATOM   7756  CA  LEU C 583      24.672 103.311  27.119  1.00 60.27           C
ATOM   7757  CB  LEU C 583      25.998 103.553  27.834  1.00 91.16           C
ATOM   7758  CG  LEU C 583      26.573 104.961  27.793  1.00 96.91           C
ATOM   7759  CD1 LEU C 583      27.928 104.981  28.460  1.00 96.91           C
ATOM   7760  CD2 LEU C 583      26.700 105.404  26.357  1.00 96.91           C
ATOM   7761  C   LEU C 583      24.665 101.890  26.585  1.00 60.27           C
ATOM   7762  O   LEU C 583      24.815 101.667  25.379  1.00 60.27           C
ATOM   7763  N   GLU C 584      24.510 100.934  27.497  1.00 51.86           C
ATOM   7764  CA  GLU C 584      24.494  99.514  27.168  1.00 51.86           C
ATOM   7765  CB  GLU C 584      23.645  98.795  28.190  1.00 93.84           C
ATOM   7766  CG  GLU C 584      23.700  99.453  29.542  1.00 99.59           C
ATOM   7767  CD  GLU C 584      24.354  98.573  30.557  1.00 99.59           C
ATOM   7768  OE1 GLU C 584      23.760  97.536  30.868  1.00 99.59           C
ATOM   7769  OE2 GLU C 584      25.456  98.897  31.046  1.00 99.59           C
ATOM   7770  C   GLU C 584      23.927  99.282  25.779  1.00 51.86           C
ATOM   7771  O   GLU C 584      24.264  98.297  25.122  1.00 51.86           C
ATOM   7772  N   GLU C 585      23.075 100.208  25.341  1.00 60.51           C
ATOM   7773  CA  GLU C 585      22.408 100.139  24.045  1.00 60.51           C
ATOM   7774  CB  GLU C 585      21.237 101.123  24.007  1.00100.07           C
```

```
ATOM   7775  CG  GLU C 585      20.166 100.866  25.071  1.00100.07           C
ATOM   7776  CD  GLU C 585      18.936 101.773  24.936  1.00100.07           C
ATOM   7777  OE1 GLU C 585      18.381 101.880  23.820  1.00100.07           C
ATOM   7778  OE2 GLU C 585      18.513 102.370  25.952  1.00100.07           C
ATOM   7779  C   GLU C 585      23.306 100.415  22.858  1.00 60.51           C
ATOM   7780  O   GLU C 585      23.404  99.581  21.968  1.00 60.51           C
ATOM   7781  N   ARG C 586      23.944 101.588  22.850  1.00 61.97           C
ATOM   7782  CA  ARG C 586      24.821 102.019  21.758  1.00 61.97           C
ATOM   7783  CB  ARG C 586      25.092 103.525  21.871  1.00 98.61           C
ATOM   7784  CG  ARG C 586      25.195 104.259  20.543  1.00100.07           C
ATOM   7785  CD  ARG C 586      24.884 105.725  20.715  1.00100.07           C
ATOM   7786  NE  ARG C 586      23.925 106.189  19.717  1.00100.07           C
ATOM   7787  CZ  ARG C 586      22.909 107.013  19.973  1.00100.07           C
ATOM   7788  NH1 ARG C 586      22.710 107.467  21.206  1.00100.07           C
ATOM   7789  NH2 ARG C 586      22.098 107.395  18.992  1.00100.07           C
ATOM   7790  C   ARG C 586      26.149 101.266  21.660  1.00 61.97           C
ATOM   7791  O   ARG C 586      26.610 100.981  20.556  1.00 61.97           C
ATOM   7792  N   VAL C 587      26.760 100.943  22.801  1.00 51.35           C
ATOM   7793  CA  VAL C 587      28.048 100.239  22.802  1.00 51.35           C
ATOM   7794  CB  VAL C 587      28.440  99.735  24.201  1.00 47.36           C
ATOM   7795  CG1 VAL C 587      29.595  98.751  24.098  1.00 53.11           C
ATOM   7796  CG2 VAL C 587      28.850 100.916  25.073  1.00 53.11           C
ATOM   7797  C   VAL C 587      28.085  99.062  21.854  1.00 51.35           C
ATOM   7798  O   VAL C 587      29.153  98.711  21.370  1.00 51.35           C
ATOM   7799  N   VAL C 588      26.928  98.456  21.587  1.00 37.60           C
ATOM   7800  CA  VAL C 588      26.854  97.322  20.667  1.00 37.60           C
ATOM   7801  CB  VAL C 588      25.792  96.316  21.070  1.00 36.67           C
ATOM   7802  CG1 VAL C 588      25.879  95.115  20.167  1.00 42.42           C
ATOM   7803  CG2 VAL C 588      25.971  95.915  22.504  1.00 42.42           C
ATOM   7804  C   VAL C 588      26.451  97.822  19.298  1.00 37.60           C
ATOM   7805  O   VAL C 588      27.110  97.555  18.295  1.00 37.60           C
ATOM   7806  N   ARG C 589      25.349  98.555  19.273  1.00 38.69           C
ATOM   7807  CA  ARG C 589      24.824  99.103  18.037  1.00 38.69           C
ATOM   7808  CB  ARG C 589      23.519  99.846  18.344  1.00100.07           C
ATOM   7809  CG  ARG C 589      22.627  98.988  19.247  1.00100.07           C
ATOM   7810  CD  ARG C 589      21.220  99.517  19.492  1.00100.07           C
ATOM   7811  NE  ARG C 589      20.448  98.541  20.269  1.00100.07           C
ATOM   7812  CZ  ARG C 589      19.127  98.572  20.405  1.00100.07           C
ATOM   7813  NH1 ARG C 589      18.410  99.534  19.860  1.00100.07           C
ATOM   7814  NH2 ARG C 589      18.519  97.630  21.134  1.00100.07           C
ATOM   7815  C   ARG C 589      25.862  99.998  17.392  1.00 38.69           C
ATOM   7816  O   ARG C 589      25.555 100.815  16.531  1.00 38.69           C
ATOM   7817  N   ASP C 590      27.101  99.821  17.830  1.00 31.50           C
ATOM   7818  CA  ASP C 590      28.244 100.564  17.330  1.00 31.50           C
ATOM   7819  CB  ASP C 590      28.617 101.708  18.283  1.00100.07           C
ATOM   7820  CG  ASP C 590      27.563 102.801  18.338  1.00 99.80           C
ATOM   7821  OD1 ASP C 590      27.195 103.343  17.275  1.00 99.80           C
ATOM   7822  OD2 ASP C 590      27.116 103.129  19.455  1.00 99.80           C
ATOM   7823  C   ASP C 590      29.417  99.587  17.221  1.00 31.50           C
ATOM   7824  O   ASP C 590      30.320  99.764  16.399  1.00 31.50           C
ATOM   7825  N   SER C 591      29.402  98.556  18.061  1.00 51.99           C
ATOM   7826  CA  SER C 591      30.453  97.541  18.050  1.00 51.99           C
ATOM   7827  CB  SER C 591      30.404  96.698  19.321  1.00100.07           C
ATOM   7828  OG  SER C 591      29.322  95.776  19.273  1.00 80.96           C
ATOM   7829  C   SER C 591      30.156  96.635  16.879  1.00 51.99           C
ATOM   7830  O   SER C 591      30.402  95.439  16.950  1.00 51.99           C
ATOM   7831  N   LEU C 592      29.613  97.224  15.817  1.00 23.57           C
ATOM   7832  CA  LEU C 592      29.214  96.516  14.599  1.00 23.57           C
ATOM   7833  CB  LEU C 592      30.106  96.919  13.421  1.00 93.77           C
ATOM   7834  CG  LEU C 592      30.020  98.360  12.917  1.00 99.52           C
ATOM   7835  CD1 LEU C 592      30.845  98.502  11.649  1.00 99.52           C
ATOM   7836  CD2 LEU C 592      28.571  98.717  12.639  1.00 99.52           C
ATOM   7837  C   LEU C 592      29.248  95.014  14.748  1.00 23.57           C
ATOM   7838  O   LEU C 592      29.919  94.354  13.969  1.00 23.57           C
ATOM   7839  N   ALA C 593      28.547  94.470  15.740  1.00 47.38           C
ATOM   7840  CA  ALA C 593      28.548  93.025  15.956  1.00 47.38           C
ATOM   7841  CB  ALA C 593      29.304  92.672  17.243  1.00  5.07           C
ATOM   7842  C   ALA C 593      27.126  92.514  16.026  1.00 47.38           C
ATOM   7843  O   ALA C 593      26.823  91.538  16.714  1.00 47.38           C
ATOM   7844  N   ALA C 594      26.249  93.188  15.302  1.00 31.85           C
ATOM   7845  CA  ALA C 594      24.850  92.807  15.276  1.00 31.85           C
ATOM   7846  CB  ALA C 594      24.105  93.525  16.391  1.00 24.88           C
ATOM   7847  C   ALA C 594      24.310  93.198  13.903  1.00 31.85           C
ATOM   7848  O   ALA C 594      24.983  93.913  13.161  1.00 31.85           C
ATOM   7849  N   LEU C 595      23.112  92.737  13.557  1.00 69.24           C
ATOM   7850  CA  LEU C 595      22.553  93.042  12.247  1.00 69.24           C
ATOM   7851  CB  LEU C 595      21.615  91.919  11.809  1.00100.07           C
ATOM   7852  CG  LEU C 595      22.337  90.891  10.931  1.00 94.58           C
ATOM   7853  CD1 LEU C 595      21.598  89.561  10.892  1.00 94.58           C
ATOM   7854  CD2 LEU C 595      22.481  91.476   9.544  1.00 94.58           C
ATOM   7855  C   LEU C 595      21.873  94.399  12.102  1.00 69.24           C
ATOM   7856  O   LEU C 595      22.364  95.254  11.372  1.00 69.24           C
ATOM   7857  N   TYR C 596      20.749  94.609  12.775  1.00100.07           C
ATOM   7858  CA  TYR C 596      20.058  95.897  12.679  1.00100.07           C
```

| ATOM | 7859 | CB | TYR C 596 | 20.961 | 97.014 | 13.216 | 1.00 100.07 | C |
|------|------|-----|-----------|--------|--------|--------|-------------|---|
| ATOM | 7860 | CG | TYR C 596 | 21.503 | 96.783 | 14.606 | 1.00 99.93 | C |
| ATOM | 7861 | CD1 | TYR C 596 | 22.692 | 97.380 | 15.012 | 1.00 99.93 | C |
| ATOM | 7862 | CE1 | TYR C 596 | 23.193 | 97.187 | 16.292 | 1.00 99.93 | C |
| ATOM | 7863 | CD2 | TYR C 596 | 20.823 | 95.983 | 15.524 | 1.00 99.93 | C |
| ATOM | 7864 | CE2 | TYR C 596 | 21.316 | 95.787 | 16.812 | 1.00 99.93 | C |
| ATOM | 7865 | CZ | TYR C 596 | 22.503 | 96.393 | 17.188 | 1.00 99.93 | C |
| ATOM | 7866 | OH | TYR C 596 | 23.000 | 96.209 | 18.458 | 1.00 99.93 | C |
| ATOM | 7867 | C | TYR C 596 | 19.658 | 96.242 | 11.238 | 1.00 100.07 | C |
| ATOM | 7868 | O | TYR C 596 | 20.467 | 96.773 | 10.470 | 1.00 100.07 | C |
| ATOM | 7869 | N | ALA C 597 | 18.413 | 95.948 | 10.872 | 1.00 54.19 | C |
| ATOM | 7870 | CA | ALA C 597 | 17.936 | 96.258 | 9.535 | 1.00 54.19 | C |
| ATOM | 7871 | CB | ALA C 597 | 16.704 | 95.443 | 9.214 | 1.00 32.33 | C |
| ATOM | 7872 | C | ALA C 597 | 17.600 | 97.740 | 9.492 | 1.00 54.19 | C |
| ATOM | 7873 | O | ALA C 597 | 17.241 | 98.339 | 10.522 | 1.00 54.19 | C |
| ATOM | 7874 | N | GLU C 598 | 17.705 | 98.324 | 8.298 | 1.00 99.93 | C |
| ATOM | 7875 | CA | GLU C 598 | 17.417 | 99.745 | 8.103 | 1.00 99.93 | C |
| ATOM | 7876 | CB | GLU C 598 | 18.736 | 100.480 | 7.802 | 1.00 100.07 | C |
| ATOM | 7877 | CG | GLU C 598 | 19.822 | 100.153 | 8.842 | 1.00 100.07 | C |
| ATOM | 7878 | CD | GLU C 598 | 21.097 | 100.975 | 8.698 | 1.00 100.07 | C |
| ATOM | 7879 | OE1 | GLU C 598 | 21.686 | 100.999 | 7.596 | 1.00 100.07 | C |
| ATOM | 7880 | OE2 | GLU C 598 | 21.518 | 101.588 | 9.703 | 1.00 100.07 | C |
| ATOM | 7881 | C | GLU C 598 | 16.348 | 100.027 | 7.019 | 1.00 99.93 | C |
| ATOM | 7882 | O | GLU C 598 | 16.629 | 100.657 | 5.994 | 1.00 99.93 | C |
| ATOM | 7883 | N | ALA C 599 | 15.123 | 99.553 | 7.278 | 1.00 100.07 | C |
| ATOM | 7884 | CA | ALA C 599 | 13.974 | 99.725 | 6.385 | 1.00 100.07 | C |
| ATOM | 7885 | CB | ALA C 599 | 14.323 | 99.246 | 4.996 | 1.00 29.73 | C |
| ATOM | 7886 | C | ALA C 599 | 12.697 | 99.017 | 6.892 | 1.00 100.07 | C |
| ATOM | 7887 | O | ALA C 599 | 11.751 | 99.694 | 7.298 | 1.00 100.07 | C |
| ATOM | 7888 | N | ALA C 600 | 12.683 | 97.675 | 6.865 | 1.00 95.62 | C |
| ATOM | 7889 | CA | ALA C 600 | 11.560 | 96.817 | 7.322 | 1.00 95.62 | C |
| ATOM | 7890 | CB | ALA C 600 | 10.331 | 97.653 | 7.652 | 1.00 64.11 | C |
| ATOM | 7891 | C | ALA C 600 | 11.189 | 95.768 | 6.267 | 1.00 95.62 | C |
| ATOM | 7892 | O | ALA C 600 | 11.626 | 95.872 | 5.125 | 1.00 95.62 | C |
| ATOM | 7893 | N | ALA C 601 | 10.393 | 94.769 | 6.665 | 1.00 65.54 | C |
| ATOM | 7894 | CA | ALA C 601 | 9.918 | 93.678 | 5.787 | 1.00 65.54 | C |
| ATOM | 7895 | CB | ALA C 601 | 10.703 | 93.652 | 4.461 | 1.00 14.47 | C |
| ATOM | 7896 | C | ALA C 601 | 9.983 | 92.289 | 6.451 | 1.00 65.54 | C |
| ATOM | 7897 | O | ALA C 601 | 9.246 | 92.019 | 7.403 | 1.00 65.54 | C |
| ATOM | 7898 | N | ALA C 602 | 10.859 | 91.425 | 5.922 | 1.00 66.42 | C |
| ATOM | 7899 | CA | ALA C 602 | 11.083 | 90.048 | 6.392 | 1.00 66.42 | C |
| ATOM | 7900 | CB | ALA C 602 | 10.170 | 89.709 | 7.582 | 1.00 16.02 | C |
| ATOM | 7901 | C | ALA C 602 | 10.869 | 89.027 | 5.275 | 1.00 66.42 | C |
| ATOM | 7902 | O | ALA C 602 | 10.611 | 89.388 | 4.123 | 1.00 66.42 | C |
| ATOM | 7903 | N | ALA C 603 | 10.961 | 87.750 | 5.641 | 1.00 37.55 | C |
| ATOM | 7904 | CA | ALA C 603 | 10.800 | 86.610 | 4.736 | 1.00 37.55 | C |
| ATOM | 7905 | CB | ALA C 603 | 11.384 | 86.915 | 3.400 | 1.00 37.88 | C |
| ATOM | 7906 | C | ALA C 603 | 11.526 | 85.422 | 5.347 | 1.00 37.55 | C |
| ATOM | 7907 | O | ALA C 603 | 10.990 | 84.327 | 5.409 | 1.00 37.55 | C |
| ATOM | 7908 | N | ALA C 604 | 12.768 | 85.651 | 5.752 | 1.00 99.65 | C |
| ATOM | 7909 | CA | ALA C 604 | 13.632 | 84.662 | 6.398 | 1.00 99.65 | C |
| ATOM | 7910 | CB | ALA C 604 | 13.520 | 84.811 | 7.935 | 1.00 51.23 | C |
| ATOM | 7911 | C | ALA C 604 | 13.500 | 83.201 | 6.037 | 1.00 99.65 | C |
| ATOM | 7912 | O | ALA C 604 | 13.322 | 82.809 | 4.881 | 1.00 99.65 | C |
| ATOM | 7913 | N | ALA C 605 | 13.580 | 82.417 | 7.108 | 1.00 100.07 | C |
| ATOM | 7914 | CA | ALA C 605 | 13.532 | 80.962 | 7.128 | 1.00 100.07 | C |
| ATOM | 7915 | CB | ALA C 605 | 14.319 | 80.356 | 5.950 | 1.00 100.07 | C |
| ATOM | 7916 | C | ALA C 605 | 14.350 | 80.900 | 8.406 | 1.00 100.07 | C |
| ATOM | 7917 | O | ALA C 605 | 14.036 | 80.155 | 9.343 | 1.00 100.07 | C |
| ATOM | 7918 | N | ALA C 606 | 15.357 | 81.772 | 8.431 | 1.00 100.07 | C |
| ATOM | 7919 | CA | ALA C 606 | 16.279 | 81.944 | 9.532 | 1.00 100.07 | C |
| ATOM | 7920 | CB | ALA C 606 | 15.509 | 82.407 | 10.753 | 1.00 100.07 | C |
| ATOM | 7921 | C | ALA C 606 | 17.170 | 80.760 | 9.906 | 1.00 100.07 | C |
| ATOM | 7922 | O | ALA C 606 | 17.039 | 79.661 | 9.387 | 1.00 100.07 | C |
| ATOM | 7923 | N | ALA C 607 | 18.112 | 81.070 | 10.800 | 1.00 100.07 | C |
| ATOM | 7924 | CA | ALA C 607 | 19.116 | 80.162 | 11.399 | 1.00 100.07 | C |
| ATOM | 7925 | CB | ALA C 607 | 18.754 | 78.710 | 11.132 | 1.00 71.68 | C |
| ATOM | 7926 | C | ALA C 607 | 20.571 | 80.410 | 10.979 | 1.00 100.07 | C |
| ATOM | 7927 | O | ALA C 607 | 21.436 | 80.813 | 11.783 | 1.00 100.07 | C |
| ATOM | 7928 | N | ALA C 608 | 20.829 | 80.153 | 9.706 | 1.00 100.07 | C |
| ATOM | 7929 | CA | ALA C 608 | 22.144 | 80.336 | 9.139 | 1.00 100.07 | C |
| ATOM | 7930 | CB | ALA C 608 | 22.712 | 78.971 | 8.757 | 1.00 17.73 | C |
| ATOM | 7931 | C | ALA C 608 | 22.065 | 81.250 | 7.935 | 1.00 100.07 | C |
| ATOM | 7932 | O | ALA C 608 | 22.907 | 81.197 | 7.037 | 1.00 100.07 | C |
| ATOM | 7933 | N | ALA C 609 | 21.039 | 82.091 | 7.903 | 1.00 100.07 | C |
| ATOM | 7934 | CA | ALA C 609 | 20.835 | 83.005 | 6.778 | 1.00 100.07 | C |
| ATOM | 7935 | CB | ALA C 609 | 20.646 | 82.208 | 5.488 | 1.00 100.07 | C |
| ATOM | 7936 | C | ALA C 609 | 19.634 | 83.895 | 7.014 | 1.00 100.07 | C |
| ATOM | 7937 | O | ALA C 609 | 18.568 | 83.684 | 6.407 | 1.00 100.07 | C |
| ATOM | 7938 | N | ALA C 610 | 19.783 | 84.899 | 7.874 | 1.00 87.78 | C |
| ATOM | 7939 | CA | ALA C 610 | 18.669 | 85.774 | 8.200 | 1.00 87.78 | C |
| ATOM | 7940 | CB | ALA C 610 | 19.071 | 86.781 | 9.255 | 1.00 43.39 | C |
| ATOM | 7941 | C | ALA C 610 | 18.031 | 86.537 | 7.064 | 1.00 87.78 | C |
| ATOM | 7942 | O | ALA C 610 | 18.593 | 87.502 | 6.553 | 1.00 87.78 | C |

| | | | | | | | | |
|---|---|---|---|---|---|---|---|---|
|ATOM|7943|N|ALA C 611|16.851|86.081|6.660|1.00|100.07|C|
|ATOM|7944|CA|ALA C 611|16.009|86.707|5.636|1.00|100.07|C|
|ATOM|7945|CB|ALA C 611|14.871|87.498|6.311|1.00|39.23|C|
|ATOM|7946|C|ALA C 611|16.626|87.588|4.565|1.00|100.07|C|
|ATOM|7947|O|ALA C 611|17.848|87.598|4.307|1.00|100.07|C|
|ATOM|7948|N|ALA C 612|15.733|88.331|3.928|1.00|99.99|C|
|ATOM|7949|CA|ALA C 612|16.043|89.241|2.848|1.00|99.99|C|
|ATOM|7950|CB|ALA C 612|15.416|88.711|1.572|1.00|59.80|C|
|ATOM|7951|C|ALA C 612|15.451|90.595|3.225|1.00|99.99|C|
|ATOM|7952|O|ALA C 612|15.919|91.649|2.780|1.00|99.99|C|
|ATOM|7953|N|ALA C 613|14.446|90.562|4.102|1.00|84.37|C|
|ATOM|7954|CA|ALA C 613|13.773|91.778|4.533|1.00|84.37|C|
|ATOM|7955|CB|ALA C 613|14.670|92.551|5.454|1.00|97.27|C|
|ATOM|7956|C|ALA C 613|13.474|92.580|3.265|1.00|84.37|C|
|ATOM|7957|O|ALA C 613|14.145|93.557|2.948|1.00|84.37|C|
|ATOM|7958|N|ALA C 614|12.463|92.131|2.536|1.00|99.71|C|
|ATOM|7959|CA|ALA C 614|12.070|92.753|1.283|1.00|99.71|C|
|ATOM|7960|CB|ALA C 614|11.047|91.865|0.572|1.00|98.58|C|
|ATOM|7961|C|ALA C 614|11.504|94.160|1.499|1.00|99.71|C|
|ATOM|7962|O|ALA C 614|10.311|94.409|1.300|1.00|99.71|C|
|ATOM|7963|N|ALA C 615|12.374|95.086|1.896|1.00|100.07|C|
|ATOM|7964|CA|ALA C 615|11.987|96.473|2.153|1.00|100.07|C|
|ATOM|7965|CB|ALA C 615|13.136|97.195|2.835|1.00|80.06|C|
|ATOM|7966|C|ALA C 615|11.587|97.193|0.875|1.00|100.07|C|
|ATOM|7967|O|ALA C 615|10.970|96.598|-0.016|1.00|100.07|C|
|ATOM|7968|N|ALA C 616|11.929|98.479|0.813|1.00|100.07|C|
|ATOM|7969|CA|ALA C 616|11.643|99.332|-0.349|1.00|100.07|C|
|ATOM|7970|CB|ALA C 616|11.801|100.814|0.017|1.00|100.07|C|
|ATOM|7971|C|ALA C 616|12.614|98.970|-1.465|1.00|100.07|C|
|ATOM|7972|O|ALA C 616|12.761|99.695|-2.447|1.00|100.07|C|
|ATOM|7973|N|ALA C 617|13.293|97.845|-1.278|1.00|100.07|C|
|ATOM|7974|CA|ALA C 617|14.248|97.335|-2.254|1.00|100.07|C|
|ATOM|7975|CB|ALA C 617|15.671|97.762|-1.890|1.00|100.07|C|
|ATOM|7976|C|ALA C 617|14.132|95.823|-2.244|1.00|100.07|C|
|ATOM|7977|O|ALA C 617|13.599|95.239|-1.301|1.00|100.07|C|
|ATOM|7978|N|ALA C 618|14.629|95.201|-3.307|1.00|100.07|C|
|ATOM|7979|CA|ALA C 618|14.583|93.751|-3.454|1.00|100.07|C|
|ATOM|7980|CB|ALA C 618|15.319|93.336|-4.737|1.00|100.07|C|
|ATOM|7981|C|ALA C 618|15.174|93.027|-2.242|1.00|100.07|C|
|ATOM|7982|O|ALA C 618|15.940|93.605|-1.470|1.00|100.07|C|
|ATOM|7983|N|ALA C 619|14.798|91.760|-2.086|1.00|92.15|C|
|ATOM|7984|CA|ALA C 619|15.276|90.928|-0.994|1.00|92.15|C|
|ATOM|7985|CB|ALA C 619|15.049|89.454|-1.344|1.00|50.50|C|
|ATOM|7986|C|ALA C 619|16.764|91.199|-0.716|1.00|92.15|C|
|ATOM|7987|O|ALA C 619|17.499|91.656|-1.601|1.00|92.15|C|
|ATOM|7988|N|ALA C 620|17.203|90.923|0.514|1.00|96.86|C|
|ATOM|7989|CA|ALA C 620|18.594|91.149|0.914|1.00|96.86|C|
|ATOM|7990|CB|ALA C 620|18.657|92.302|1.890|1.00|84.06|C|
|ATOM|7991|C|ALA C 320|19.285|89.921|1.513|1.00|96.86|C|
|ATOM|7992|O|ALA C 620|18.658|89.091|2.171|1.00|96.86|C|
|ATOM|7993|N|ALA C 621|20.593|89.828|1.288|1.00|100.07|C|
|ATOM|7994|CA|ALA C 621|21.386|88.704|1.776|1.00|100.07|C|
|ATOM|7995|CB|ALA C 621|22.492|88.377|0.777|1.00|92.04|C|
|ATOM|7996|C|ALA C 621|21.997|88.943|3.149|1.00|100.07|C|
|ATOM|7997|O|ALA C 621|23.221|88.941|3.301|1.00|100.07|C|
|ATOM|7998|N|ALA C 622|21.145|89.150|4.148|1.00|54.52|C|
|ATOM|7999|CA|ALA C 622|21.620|89.374|5.504|1.00|54.52|C|
|ATOM|8000|CB|ALA C 622|20.587|90.187|6.294|1.00|13.56|C|
|ATOM|8001|C|ALA C 622|21.866|88.004|6.153|1.00|54.52|C|
|ATOM|8002|O|ALA C 622|20.938|87.363|6.652|1.00|54.52|C|
|ATOM|8003|N|ALA C 623|23.120|87.547|6.110|1.00|43.18|C|
|ATOM|8004|CA|ALA C 623|23.487|86.251|6.690|1.00|43.18|C|
|ATOM|8005|CB|ALA C 623|24.431|85.480|5.737|1.00|13.47|C|
|ATOM|8006|C|ALA C 623|24.143|86.421|8.059|1.00|43.18|C|
|ATOM|8007|O|ALA C 623|25.019|87.267|8.238|1.00|43.18|C|
|ATOM|8008|N|ALA C 624|23.710|85.616|9.024|1.00|55.35|C|
|ATOM|8009|CA|ALA C 624|24.265|85.689|10.367|1.00|55.35|C|
|ATOM|8010|CB|ALA C 624|23.149|85.310|11.424|1.00|5.07|C|
|ATOM|8011|C|ALA C 624|25.497|84.757|10.472|1.00|55.35|C|
|ATOM|8012|O|ALA C 624|25.467|83.639|9.950|1.00|55.35|C|
|ATOM|8013|N|ALA C 625|26.569|85.237|11.123|1.00|43.11|C|
|ATOM|8014|CA|ALA C 625|27.815|84.478|11.329|1.00|43.11|C|
|ATOM|8015|CB|ALA C 625|28.944|85.410|11.736|1.00|65.80|C|
|ATOM|8016|C|ALA C 625|27.651|83.381|12.383|1.00|43.11|C|
|ATOM|8017|O|ALA C 625|27.222|83.638|13.509|1.00|43.11|C|
|ATOM|8018|N|ALA C 626|28.024|82.166|11.992|1.00|33.96|C|
|ATOM|8019|CA|ALA C 626|27.915|80.956|12.812|1.00|33.96|C|
|ATOM|8020|CB|ALA C 626|28.559|79.792|12.082|1.00|93.68|C|
|ATOM|8021|C|ALA C 626|28.443|81.008|14.225|1.00|33.96|C|
|ATOM|8022|O|ALA C 626|27.829|81.621|15.076|1.00|33.96|C|
|ATOM|8023|N|ALA C 627|29.553|80.300|14.466|1.00|41.98|C|
|ATOM|8024|CA|ALA C 627|30.251|80.228|15.761|1.00|41.98|C|
|ATOM|8025|CB|ALA C 627|29.982|78.866|16.461|1.00|5.07|C|
|ATOM|8026|C|ALA C 627|31.762|80.397|15.491|1.00|41.98|C|

| | | | | | | | | | |
|---|---|---|---|---|---|---|---|---|---|
| ATOM | 8027 | O | ALA | C | 627 | 32.518 | 79.419 | 15.508 | 1.00 41.98 | C |
| ATOM | 8028 | N | ALA | C | 628 | 32.190 | 81.636 | 15.245 | 1.00100.07 | C |
| ATOM | 8029 | CA | ALA | C | 628 | 33.587 | 81.963 | 14.948 | 1.00100.07 | C |
| ATOM | 8030 | CB | ALA | C | 628 | 33.709 | 83.422 | 14.600 | 1.00100.07 | C |
| ATOM | 8031 | C | ALA | C | 628 | 34.554 | 81.621 | 16.070 | 1.00100.07 | C |
| ATOM | 8032 | O | ALA | C | 628 | 34.253 | 80.755 | 16.890 | 1.00100.07 | C |
| ATOM | 8033 | N | ALA | C | 629 | 35.713 | 82.283 | 16.119 | 1.00 24.80 | C |
| ATOM | 8034 | CA | ALA | C | 629 | 36.684 | 81.968 | 17.176 | 1.00 24.80 | C |
| ATOM | 8035 | CB | ALA | C | 629 | 37.117 | 80.502 | 17.042 | 1.00 66.11 | C |
| ATOM | 8036 | C | ALA | C | 629 | 37.919 | 82.863 | 17.237 | 1.00 24.80 | C |
| ATOM | 8037 | O | ALA | C | 629 | 37.807 | 84.089 | 17.159 | 1.00 24.80 | C |
| ATOM | 8038 | N | ALA | C | 630 | 39.076 | 82.212 | 17.420 | 1.00 99.68 | C |
| ATOM | 8039 | CA | ALA | C | 630 | 40.430 | 82.800 | 17.506 | 1.00 99.68 | C |
| ATOM | 8040 | CB | ALA | C | 630 | 41.170 | 82.533 | 16.194 | 1.00 88.40 | C |
| ATOM | 8041 | C | ALA | C | 630 | 40.564 | 84.291 | 17.899 | 1.00 99.68 | C |
| ATOM | 8042 | O | ALA | C | 630 | 39.715 | 85.096 | 17.542 | 1.00 99.68 | C |
| ATOM | 8043 | N | ALA | C | 631 | 41.660 | 84.652 | 18.584 | 1.00 60.35 | C |
| ATOM | 8044 | CA | ALA | C | 631 | 41.895 | 86.025 | 19.077 | 1.00 60.35 | C |
| ATOM | 8045 | CB | ALA | C | 631 | 41.838 | 87.057 | 17.936 | 1.00 5.07 | C |
| ATOM | 8046 | C | ALA | C | 631 | 40.702 | 86.171 | 19.989 | 1.00 60.35 | C |
| ATOM | 8047 | O | ALA | C | 631 | 40.819 | 86.388 | 21.200 | 1.00 60.35 | C |
| ATOM | 8048 | N | ALA | C | 632 | 39.551 | 86.027 | 19.349 | 1.00100.07 | C |
| ATOM | 8049 | CA | ALA | C | 632 | 38.267 | 86.012 | 19.992 | 1.00100.07 | C |
| ATOM | 8050 | CB | ALA | C | 632 | 37.161 | 86.033 | 18.954 | 1.00 5.07 | C |
| ATOM | 8051 | C | ALA | C | 632 | 38.366 | 84.635 | 20.599 | 1.00100.07 | C |
| ATOM | 8052 | O | ALA | C | 632 | 37.631 | 83.731 | 20.210 | 1.00100.07 | C |
| ATOM | 8053 | N | ALA | C | 633 | 39.322 | 84.463 | 21.506 | 1.00100.07 | C |
| ATOM | 8054 | CA | ALA | C | 633 | 39.517 | 83.185 | 22.166 | 1.00100.07 | C |
| ATOM | 8055 | CB | ALA | C | 633 | 40.373 | 83.372 | 23.399 | 1.00 46.63 | C |
| ATOM | 8056 | C | ALA | C | 633 | 38.140 | 82.628 | 22.541 | 1.00100.07 | C |
| ATOM | 8057 | O | ALA | C | 633 | 37.993 | 81.436 | 22.813 | 1.00100.07 | C |
| ATOM | 8058 | N | ALA | C | 634 | 37.139 | 83.510 | 22.537 | 1.00 86.54 | C |
| ATOM | 8059 | CA | ALA | C | 634 | 35.766 | 83.152 | 22.858 | 1.00 86.54 | C |
| ATOM | 8060 | CB | ALA | C | 634 | 35.220 | 84.115 | 23.902 | 1.00100.07 | C |
| ATOM | 8061 | C | ALA | C | 634 | 34.854 | 83.137 | 21.619 | 1.00 86.54 | C |
| ATOM | 8062 | O | ALA | C | 634 | 34.893 | 84.039 | 20.783 | 1.00 86.54 | C |
| ATOM | 8063 | N | ALA | C | 635 | 34.034 | 82.094 | 21.525 | 1.00 19.09 | C |
| ATOM | 8064 | CA | ALA | C | 635 | 33.100 | 81.889 | 20.424 | 1.00 19.09 | C |
| ATOM | 8065 | CB | ALA | C | 635 | 32.201 | 80.710 | 20.742 | 1.00100.07 | C |
| ATOM | 8066 | C | ALA | C | 635 | 32.258 | 83.115 | 20.163 | 1.00 19.09 | C |
| ATOM | 8067 | O | ALA | C | 635 | 31.335 | 83.387 | 20.914 | 1.00 19.09 | C |
| ATOM | 8068 | N | ALA | C | 636 | 32.545 | 83.831 | 19.082 | 1.00 11.13 | C |
| ATOM | 8069 | CA | ALA | C | 636 | 31.803 | 85.055 | 18.779 | 1.00 11.13 | C |
| ATOM | 8070 | CB | ALA | C | 636 | 32.768 | 86.193 | 18.415 | 1.00 57.46 | C |
| ATOM | 8071 | C | ALA | C | 636 | 30.774 | 84.902 | 17.697 | 1.00 11.13 | C |
| ATOM | 8072 | O | ALA | C | 636 | 30.923 | 85.469 | 16.610 | 1.00 11.13 | C |
| ATOM | 8073 | N | ALA | C | 637 | 29.713 | 84.183 | 18.049 | 1.00 99.58 | C |
| ATOM | 8074 | CA | ALA | C | 637 | 28.589 | 83.870 | 17.175 | 1.00 99.58 | C |
| ATOM | 8075 | CB | ALA | C | 637 | 28.088 | 82.484 | 17.515 | 1.00 21.95 | C |
| ATOM | 8076 | C | ALA | C | 637 | 27.417 | 84.849 | 17.223 | 1.00 99.58 | C |
| ATOM | 8077 | O | ALA | C | 637 | 26.987 | 85.274 | 18.292 | 1.00 99.58 | C |
| ATOM | 8078 | N | ALA | C | 638 | 26.894 | 85.187 | 16.051 | 1.00 53.59 | C |
| ATOM | 8079 | CA | ALA | C | 638 | 25.754 | 86.084 | 15.951 | 1.00 53.59 | C |
| ATOM | 8080 | CB | ALA | C | 638 | 25.761 | 86.768 | 14.566 | 1.00 12.66 | C |
| ATOM | 8081 | C | ALA | C | 638 | 24.525 | 85.164 | 16.123 | 1.00 53.59 | C |
| ATOM | 8082 | O | ALA | C | 638 | 24.686 | 83.937 | 16.078 | 1.00 53.59 | C |
| ATOM | 8083 | N | ALA | C | 639 | 23.322 | 85.723 | 16.337 | 1.00 64.18 | C |
| ATOM | 8084 | CA | ALA | C | 639 | 22.101 | 84.901 | 16.499 | 1.00 64.18 | C |
| ATOM | 8085 | CB | ALA | C | 639 | 21.651 | 84.896 | 17.941 | 1.00 5.07 | C |
| ATOM | 8086 | C | ALA | C | 639 | 20.905 | 85.232 | 15.600 | 1.00 64.18 | C |
| ATOM | 8087 | O | ALA | C | 639 | 21.040 | 85.302 | 14.376 | 1.00 64.18 | C |
| ATOM | 8088 | N | ALA | C | 640 | 19.733 | 85.433 | 16.198 | 1.00 81.73 | C |
| ATOM | 8089 | CA | ALA | C | 640 | 18.538 | 85.696 | 15.402 | 1.00 81.73 | C |
| ATOM | 8090 | CB | ALA | C | 640 | 17.832 | 84.368 | 15.146 | 1.00 6.94 | C |
| ATOM | 8091 | C | ALA | C | 640 | 17.545 | 86.735 | 15.965 | 1.00 81.73 | C |
| ATOM | 8092 | O | ALA | C | 640 | 17.739 | 87.266 | 17.055 | 1.00 81.73 | C |
| ATOM | 8093 | N | ALA | C | 641 | 16.490 | 87.031 | 15.200 | 1.00100.07 | C |
| ATOM | 8094 | CA | ALA | C | 641 | 15.458 | 87.994 | 15.610 | 1.00100.07 | C |
| ATOM | 8095 | CB | ALA | C | 641 | 15.698 | 89.335 | 14.941 | 1.00 89.32 | C |
| ATOM | 8096 | C | ALA | C | 641 | 14.010 | 87.515 | 15.350 | 1.00100.07 | C |
| ATOM | 8097 | O | ALA | C | 641 | 13.554 | 86.581 | 16.007 | 1.00100.07 | C |
| ATOM | 8098 | N | ALA | C | 642 | 13.286 | 88.127 | 14.406 | 1.00100.07 | C |
| ATOM | 8099 | CA | ALA | C | 642 | 11.886 | 87.720 | 14.147 | 1.00100.07 | C |
| ATOM | 8100 | CB | ALA | C | 642 | 10.940 | 88.852 | 14.547 | 1.00100.07 | C |
| ATOM | 8101 | C | ALA | C | 642 | 11.543 | 87.248 | 12.726 | 1.00100.07 | C |
| ATOM | 8102 | O | ALA | C | 642 | 12.437 | 86.988 | 11.924 | 1.00100.07 | C |
| ATOM | 8103 | N | ALA | C | 643 | 10.245 | 87.144 | 12.421 | 1.00 99.66 | C |
| ATOM | 8104 | CA | ALA | C | 643 | 9.788 | 86.691 | 11.097 | 1.00 99.66 | C |
| ATOM | 8105 | CB | ALA | C | 643 | 9.862 | 85.175 | 11.024 | 1.00 9.74 | C |
| ATOM | 8106 | C | ALA | C | 643 | 8.376 | 87.150 | 10.691 | 1.00 99.66 | C |
| ATOM | 8107 | O | ALA | C | 643 | 7.386 | 86.502 | 11.039 | 1.00 99.66 | C |
| ATOM | 8108 | N | ALA | C | 644 | 8.306 | 88.250 | 9.936 | 1.00 96.96 | C |
| ATOM | 8109 | CA | ALA | C | 644 | 7.054 | 88.850 | 9.445 | 1.00 96.96 | C |
| ATOM | 8110 | CB | ALA | C | 644 | 5.916 | 87.825 | 9.444 | 1.00 78.40 | C |

| ATOM | 8111 | C | ALA C 644 | 6.634 | 90.091 | 10.240 | 1.00 96.96 | C |
| ATOM | 8112 | O | ALA C 644 | 5.518 | 90.163 | 10.769 | 1.00 96.96 | C |
| ATOM | 8113 | N | ALA C 645 | 7.539 | 91.064 | 10.306 | 1.00100.07 | C |
| ATOM | 8114 | CA | ALA C 645 | 7.309 | 92.321 | 11.017 | 1.00100.07 | C |
| ATOM | 8115 | CB | ALA C 645 | 8.166 | 92.379 | 12.290 | 1.00100.07 | C |
| ATOM | 8116 | C | ALA C 645 | 7.677 | 93.476 | 10.094 | 1.00100.07 | C |
| ATOM | 8117 | O | ALA C 645 | 7.401 | 93.430 | 8.892 | 1.00100.07 | C |
| ATOM | 8118 | N | ALA C 646 | 8.315 | 94.501 | 10.652 | 1.00100.07 | C |
| ATOM | 8119 | CA | ALA C 646 | 8.714 | 95.655 | 9.861 | 1.00100.07 | C |
| ATOM | 8120 | CB | ALA C 646 | 7.475 | 96.434 | 9.430 | 1.00100.07 | C |
| ATOM | 8121 | C | ALA C 646 | 9.645 | 96.548 | 10.663 | 1.00100.07 | C |
| ATOM | 8122 | O | ALA C 646 | 9.238 | 97.117 | 11.669 | 1.00100.07 | C |
| ATOM | 8123 | N | ALA C 647 | 10.893 | 96.659 | 10.218 | 1.00100.07 | C |
| ATOM | 8124 | CA | ALA C 647 | 11.902 | 97.489 | 10.877 | 1.00100.07 | C |
| ATOM | 8125 | CB | ALA C 647 | 11.552 | 98.993 | 10.715 | 1.00 43.12 | C |
| ATOM | 8126 | C | ALA C 647 | 12.127 | 97.153 | 12.357 | 1.00100.07 | C |
| ATOM | 8127 | O | ALA C 647 | 13.271 | 97.110 | 12.819 | 1.00100.07 | C |
| ATOM | 8128 | N | ALA C 648 | 11.047 | 96.902 | 13.096 | 1.00100.07 | C |
| ATOM | 8129 | CA | ALA C 648 | 11.142 | 96.590 | 14.521 | 1.00100.07 | C |
| ATOM | 8130 | CB | ALA C 648 | 12.314 | 95.638 | 14.784 | 1.00100.07 | C |
| ATOM | 8131 | C | ALA C 648 | 11.365 | 97.907 | 15.260 | 1.00100.07 | C |
| ATOM | 8132 | O | ALA C 648 | 12.443 | 98.480 | 15.175 | 1.00100.07 | C |
| ATOM | 8133 | N | ALA C 649 | 10.356 | 98.377 | 15.990 | 1.00100.07 | C |
| ATOM | 8134 | CA | ALA C 649 | 10.475 | 99.652 | 16.710 | 1.00100.07 | C |
| ATOM | 8135 | CB | ALA C 649 | 9.850 | 100.778 | 15.858 | 1.00100.07 | C |
| ATOM | 8136 | C | ALA C 649 | 9.920 | 99.720 | 18.147 | 1.00100.07 | C |
| ATOM | 8137 | O | ALA C 649 | 9.275 | 100.708 | 18.528 | 1.00100.07 | C |
| ATOM | 8138 | N | ALA C 650 | 10.164 | 98.689 | 18.947 | 1.00100.07 | C |
| ATOM | 8139 | CA | ALA C 650 | 9.689 | 98.712 | 20.325 | 1.00100.07 | C |
| ATOM | 8140 | CB | ALA C 650 | 9.852 | 97.344 | 20.963 | 1.00100.07 | C |
| ATOM | 8141 | C | ALA C 650 | 10.494 | 99.769 | 21.098 | 1.00100.07 | C |
| ATOM | 8142 | O | ALA C 650 | 9.979 | 100.438 | 22.001 | 1.00100.07 | C |
| ATOM | 8143 | N | ALA C 651 | 11.762 | 99.912 | 20.721 | 1.00100.07 | C |
| ATOM | 8144 | CA | ALA C 651 | 12.680 | 100.885 | 21.319 | 1.00100.07 | C |
| ATOM | 8145 | CB | ALA C 651 | 13.060 | 100.461 | 22.755 | 1.00 68.86 | C |
| ATOM | 8146 | C | ALA C 651 | 13.922 | 100.944 | 20.414 | 1.00100.07 | C |
| ATOM | 8147 | O | ALA C 651 | 14.869 | 101.710 | 20.662 | 1.00100.07 | C |
| ATOM | 8148 | N | GLY C 652 | 13.879 | 100.131 | 19.354 | 1.00100.07 | C |
| ATOM | 8149 | CA | GLY C 652 | 14.961 | 100.048 | 18.381 | 1.00100.07 | C |
| ATOM | 8150 | C | GLY C 652 | 14.658 | 99.059 | 17.252 | 1.00100.07 | C |
| ATOM | 8151 | O | GLY C 652 | 13.848 | 98.137 | 17.427 | 1.00100.07 | C |
| ATOM | 8152 | N | ASP C 653 | 15.318 | 99.241 | 16.102 | 1.00100.07 | C |
| ATOM | 8153 | CA | ASP C 653 | 15.130 | 98.390 | 14.913 | 1.00100.07 | C |
| ATOM | 8154 | CB | ASP C 653 | 15.022 | 99.277 | 13.663 | 1.00100.07 | C |
| ATOM | 8155 | CG | ASP C 653 | 14.086 | 100.464 | 13.867 | 1.00100.07 | C |
| ATOM | 8156 | OD1 | ASP C 653 | 12.857 | 100.264 | 14.005 | 1.00100.07 | C |
| ATOM | 8157 | OD2 | ASP C 653 | 14.593 | 101.608 | 13.893 | 1.00100.07 | C |
| ATOM | 8158 | C | ASP C 653 | 16.239 | 97.343 | 14.711 | 1.00100.07 | C |
| ATOM | 8159 | O | ASP C 653 | 16.973 | 97.372 | 13.719 | 1.00100.07 | C |
| ATOM | 8160 | N | LEU C 654 | 16.316 | 96.410 | 15.656 | 1.00100.07 | C |
| ATOM | 8161 | CA | LEU C 654 | 17.307 | 95.338 | 15.672 | 1.00100.07 | C |
| ATOM | 8162 | CB | LEU C 654 | 17.106 | 94.454 | 16.895 | 1.00 94.26 | C |
| ATOM | 8163 | CG | LEU C 654 | 16.722 | 95.116 | 18.216 | 1.00100.01 | C |
| ATOM | 8164 | CD1 | LEU C 654 | 15.989 | 94.100 | 19.103 | 1.00100.01 | C |
| ATOM | 8165 | CD2 | LEU C 654 | 17.971 | 95.663 | 18.905 | 1.00100.01 | C |
| ATOM | 8166 | C | LEU C 654 | 17.275 | 94.418 | 14.474 | 1.00100.07 | C |
| ATOM | 8167 | O | LEU C 654 | 16.743 | 94.747 | 13.417 | 1.00100.07 | C |
| ATOM | 8168 | N | LEU C 655 | 17.850 | 93.241 | 14.706 | 1.00100.07 | C |
| ATOM | 8169 | CA | LEU C 655 | 17.970 | 92.142 | 13.759 | 1.00100.07 | C |
| ATOM | 8170 | CB | LEU C 655 | 18.557 | 92.593 | 12.424 | 1.00 88.96 | C |
| ATOM | 8171 | CG | LEU C 655 | 17.708 | 93.228 | 11.332 | 1.00 81.76 | C |
| ATOM | 8172 | CD1 | LEU C 655 | 18.496 | 93.174 | 10.040 | 1.00 81.76 | C |
| ATOM | 8173 | CD2 | LEU C 655 | 16.402 | 92.492 | 11.164 | 1.00 81.76 | C |
| ATOM | 8174 | C | LEU C 655 | 18.942 | 91.162 | 14.395 | 1.00100.07 | C |
| ATOM | 8175 | O | LEU C 655 | 20.037 | 91.548 | 14.803 | 1.00100.07 | C |
| ATOM | 8176 | N | ALA C 656 | 18.554 | 89.897 | 14.468 | 1.00 99.65 | C |
| ATOM | 8177 | CA | ALA C 656 | 19.421 | 88.897 | 15.068 | 1.00 99.65 | C |
| ATOM | 8178 | CB | ALA C 656 | 20.639 | 88.640 | 14.191 | 1.00 70.74 | C |
| ATOM | 8179 | C | ALA C 656 | 19.864 | 89.458 | 16.393 | 1.00 99.65 | C |
| ATOM | 8180 | O | ALA C 656 | 19.109 | 90.176 | 17.048 | 1.00 99.65 | C |
| ATOM | 8181 | N | ASP C 657 | 21.102 | 89.141 | 16.764 | 1.00 66.20 | C |
| ATOM | 8182 | CA | ASP C 657 | 21.700 | 89.601 | 18.012 | 1.00 66.20 | C |
| ATOM | 8183 | CB | ASP C 657 | 21.322 | 88.684 | 19.187 | 1.00100.07 | C |
| ATOM | 8184 | CG | ASP C 657 | 20.486 | 89.390 | 20.262 | 1.00100.07 | C |
| ATOM | 8185 | OD1 | ASP C 657 | 20.406 | 90.638 | 20.258 | 1.00100.07 | C |
| ATOM | 8186 | OD2 | ASP C 657 | 19.921 | 88.687 | 21.129 | 1.00100.07 | C |
| ATOM | 8187 | C | ASP C 657 | 23.189 | 89.521 | 17.778 | 1.00 66.20 | C |
| ATOM | 8188 | O | ASP C 657 | 23.638 | 89.676 | 16.647 | 1.00 66.20 | C |
| ATOM | 8189 | N | GLY C 658 | 23.948 | 89.255 | 18.833 | 1.00 44.26 | C |
| ATOM | 8190 | CA | GLY C 658 | 25.390 | 89.170 | 18.701 | 1.00 44.26 | C |
| ATOM | 8191 | C | GLY C 658 | 26.107 | 88.359 | 19.772 | 1.00 44.26 | C |
| ATOM | 8192 | O | GLY C 658 | 25.648 | 87.275 | 20.142 | 1.00 44.26 | C |
| ATOM | 8193 | N | PRO C 659 | 27.241 | 88.863 | 20.301 | 1.00 25.56 | C |
| ATOM | 8194 | CD | PRO C 659 | 28.004 | 90.021 | 19.797 | 1.00 70.81 | C |

```
ATOM   8195  CA  PRO C 659      28.013  88.167  21.325  1.00 25.56           C
ATOM   8196  CB  PRO C 659      29.435  88.553  20.967  1.00 65.06           C
ATOM   8197  CG  PRO C 659      29.270  89.992  20.657  1.00 70.81           C
ATOM   8198  C   PRO C 659      27.669  88.551  22.753  1.00 25.56           C
ATOM   8199  O   PRO C 659      28.353  88.138  23.690  1.00 25.56           C
ATOM   8200  N   ALA C 660      26.634  89.357  22.934  1.00 72.37           C
ATOM   8201  CA  ALA C 660      26.241  89.754  24.279  1.00 72.37           C
ATOM   8202  CB  ALA C 660      27.325  90.609  24.912  1.00 11.08           C
ATOM   8203  C   ALA C 660      24.933  90.509  24.254  1.00 72.37           C
ATOM   8204  O   ALA C 660      24.361  90.818  25.293  1.00 72.37           C
ATOM   8205  N   SER C 661      24.451  90.816  23.065  1.00 88.91           C
ATOM   8206  CA  SER C 661      23.209  91.539  22.998  1.00 88.91           C
ATOM   8207  CB  SER C 661      22.787  91.776  21.554  1.00 73.45           C
ATOM   8208  OG  SER C 661      22.669  90.543  20.875  1.00 73.45           C
ATOM   8209  C   SER C 661      22.138  90.756  23.715  1.00 88.91           C
ATOM   8210  O   SER C 661      21.669  89.721  23.238  1.00 88.91           C
ATOM   8211  N   GLU C 662      21.789  91.230  24.903  1.00 99.95           C
ATOM   8212  CA  GLU C 662      20.702  90.610  25.624  1.00 99.95           C
ATOM   8213  CB  GLU C 662      20.658  91.047  27.097  1.00100.07           C
ATOM   8214  CG  GLU C 662      20.078  89.978  28.037  1.00100.07           C
ATOM   8215  CD  GLU C 662      18.634  89.639  27.735  1.00100.07           C
ATOM   8216  OE1 GLU C 662      17.777  90.537  27.881  1.00100.07           C
ATOM   8217  OE2 GLU C 662      18.353  88.482  27.352  1.00100.07           C
ATOM   8218  C   GLU C 662      19.653  91.330  24.803  1.00 99.95           C
ATOM   8219  O   GLU C 662      18.768  92.007  25.319  1.00 99.95           C
ATOM   8220  N   GLU C 663      19.816  91.202  23.492  1.00 42.52           C
ATOM   8221  CA  GLU C 663      18.943  91.832  22.537  1.00 42.52           C
ATOM   8222  CB  GLU C 663      17.481  91.645  22.955  1.00100.07           C
ATOM   8223  CG  GLU C 663      17.078  90.185  23.126  1.00100.07           C
ATOM   8224  CD  GLU C 663      15.632  90.013  23.557  1.00100.07           C
ATOM   8225  OE1 GLU C 663      14.958  91.020  23.869  1.00100.07           C
ATOM   8226  OE2 GLU C 663      15.168  88.857  23.589  1.00100.07           C
ATOM   8227  C   GLU C 663      19.321  93.293  22.563  1.00 42.52           C
ATOM   8228  O   GLU C 663      18.893  94.024  23.448  1.00 42.52           C
ATOM   8229  N   GLY C 664      20.163  93.697  21.619  1.00 65.62           C
ATOM   8230  CA  GLY C 664      20.585  95.084  21.529  1.00 65.62           C
ATOM   8231  C   GLY C 664      21.279  95.676  22.746  1.00 65.62           C
ATOM   8232  O   GLY C 664      22.170  96.515  22.602  1.00 65.62           C
ATOM   8233  N   PHE C 665      20.867  95.277  23.945  1.00 23.68           C
ATOM   8234  CA  PHE C 665      21.488  95.800  25.141  1.00 23.68           C
ATOM   8235  CB  PHE C 665      20.546  95.667  26.329  1.00 74.15           C
ATOM   8236  CG  PHE C 665      19.294  96.475  26.176  1.00 74.15           C
ATOM   8237  CD1 PHE C 665      18.172  95.932  25.569  1.00 74.15           C
ATOM   8238  CD2 PHE C 665      19.263  97.811  26.562  1.00 74.15           C
ATOM   8239  CE1 PHE C 665      17.032  96.710  25.342  1.00 74.15           C
ATOM   8240  CE2 PHE C 665      18.134  98.596  26.342  1.00 74.15           C
ATOM   8241  CZ  PHE C 665      17.016  98.046  25.729  1.00 74.15           C
ATOM   8242  C   PHE C 665      22.743  94.999  25.339  1.00 23.68           C
ATOM   8243  O   PHE C 665      22.845  93.900  24.820  1.00 23.68           C
ATOM   8244  N   LEU C 366      23.718  95.546  26.050  1.00 42.54           C
ATOM   8245  CA  LEU C 666      24.960  94.820  26.261  1.00 42.54           C
ATOM   8246  CB  LEU C 666      26.082  95.803  26.597  1.00 72.22           C
ATOM   8247  CG  LEU C 666      27.452  95.248  26.990  1.00 72.22           C
ATOM   8248  CD1 LEU C 666      27.825  94.066  26.118  1.00 72.22           C
ATOM   8249  CD2 LEU C 666      28.478  96.357  26.857  1.00 72.22           C
ATOM   8250  C   LEU C 666      24.802  93.788  27.374  1.00 42.54           C
ATOM   8251  O   LEU C 666      24.065  94.010  28.334  1.00 42.54           C
ATOM   8252  N   ALA C 667      25.478  92.652  27.240  1.00 50.65           C
ATOM   8253  CA  ALA C 667      25.388  91.614  28.256  1.00 50.65           C
ATOM   8254  CB  ALA C 667      24.253  90.654  27.924  1.00  5.07           C
ATOM   8255  C   ALA C 667      26.702  90.856  28.384  1.00 50.65           C
ATOM   8256  O   ALA C 667      27.093  90.101  27.492  1.00 50.65           C
ATOM   8257  N   LEU C 668      27.390  91.066  29.498  1.00 31.94           C
ATOM   8258  CA  LEU C 668      28.650  90.390  29.725  1.00 31.94           C
ATOM   8259  CB  LEU C 668      29.698  91.373  30.227  1.00 62.68           C
ATOM   8260  CG  LEU C 668      29.964  92.516  29.246  1.00 62.68           C
ATOM   8261  CD1 LEU C 668      31.213  93.289  29.664  1.00 62.68           C
ATOM   8262  CD2 LEU C 668      30.151  91.952  27.852  1.00 62.68           C
ATOM   8263  C   LEU C 668      28.420  89.296  30.736  1.00 31.94           C
ATOM   8264  O   LEU C 668      28.607  88.125  30.439  1.00 31.94           C
ATOM   8265  N   GLY C 669      28.005  89.674  31.934  1.00 40.01           C
ATOM   8266  CA  GLY C 669      27.744  88.677  32.951  1.00 40.01           C
ATOM   8267  C   GLY C 669      26.274  88.339  32.945  1.00 40.01           C
ATOM   8268  O   GLY C 669      25.545  88.765  32.059  1.00 40.01           C
ATOM   8269  N   GLN C 670      25.837  87.571  33.929  1.00 37.92           C
ATOM   8270  CA  GLN C 670      24.442  87.200  34.024  1.00 37.92           C
ATOM   8271  CB  GLN C 670      24.243  85.723  33.729  1.00 99.48           C
ATOM   8272  CG  GLN C 670      24.932  85.190  32.513  1.00 99.48           C
ATOM   8273  CD  GLN C 670      24.602  83.731  32.308  1.00 99.48           C
ATOM   8274  OE1 GLN C 670      23.436  83.370  32.170  1.00 99.48           C
ATOM   8275  NE2 GLN C 670      25.620  82.881  32.300  1.00 99.48           C
ATOM   8276  C   GLN C 670      24.074  87.418  35.467  1.00 37.92           C
ATOM   8277  O   GLN C 670      24.299  86.523  36.271  1.00 37.92           C
ATOM   8278  N   ASN C 671      23.506  88.577  35.800  1.00 55.65           C
```

| ATOM | 8279 | CA | ASN C 671 | 23.124 | 88.903 | 37.184 | 1.00 | 55.65 | C |
|---|---|---|---|---|---|---|---|---|---|
| ATOM | 8280 | CB | ASN C 671 | 22.488 | 90.304 | 37.237 | 1.00 | 36.47 | C |
| ATOM | 8281 | CG | ASN C 671 | 21.422 | 90.517 | 36.171 | 1.00 | 36.47 | C |
| ATOM | 8282 | OD1 | ASN C 671 | 21.022 | 89.585 | 35.474 | 1.00 | 36.47 | C |
| ATOM | 8283 | ND2 | ASN C 671 | 20.953 | 91.752 | 36.046 | 1.00 | 36.47 | C |
| ATOM | 8284 | C | ASN C 671 | 22.225 | 87.903 | 37.930 | 1.00 | 55.65 | C |
| ATOM | 8285 | O | ASN C 671 | 21.169 | 87.513 | 37.436 | 1.00 | 55.65 | C |
| ATOM | 8286 | N | VAL C 672 | 22.657 | 87.500 | 39.125 | 1.00 | 60.20 | C |
| ATOM | 8287 | CA | VAL C 672 | 21.907 | 86.553 | 39.950 | 1.00 | 60.20 | C |
| ATOM | 8288 | CB | VAL C 672 | 22.636 | 85.198 | 40.078 | 1.00 | 49.89 | C |
| ATOM | 8289 | CG1 | VAL C 672 | 22.828 | 84.575 | 38.710 | 1.00 | 49.89 | C |
| ATOM | 8290 | CG2 | VAL C 672 | 23.966 | 85.383 | 40.772 | 1.00 | 49.89 | C |
| ATOM | 8291 | C | VAL C 672 | 21.648 | 87.088 | 41.360 | 1.00 | 60.20 | C |
| ATOM | 8292 | O | VAL C 672 | 22.086 | 88.185 | 41.708 | 1.00 | 60.20 | C |
| ATOM | 8293 | N | LEU C 673 | 20.950 | 86.297 | 42.172 | 1.00 | 44.28 | C |
| ATOM | 8294 | CA | LEU C 673 | 20.599 | 86.692 | 43.532 | 1.00 | 44.28 | C |
| ATOM | 8295 | CB | LEU C 673 | 19.350 | 85.928 | 43.978 | 1.00 | 43.43 | C |
| ATOM | 8296 | CG | LEU C 673 | 18.399 | 86.621 | 44.956 | 1.00 | 43.43 | C |
| ATOM | 8297 | CD1 | LEU C 673 | 17.069 | 85.881 | 45.034 | 1.00 | 43.43 | C |
| ATOM | 8298 | CD2 | LEU C 673 | 19.064 | 86.685 | 46.304 | 1.00 | 43.43 | C |
| ATOM | 8299 | C | LEU C 673 | 21.754 | 86.455 | 44.493 | 1.00 | 44.28 | C |
| ATOM | 8300 | O | LEU C 673 | 22.061 | 85.324 | 44.864 | 1.00 | 44.28 | C |
| ATOM | 8301 | N | VAL C 674 | 22.371 | 87.551 | 44.910 | 1.00 | 15.07 | C |
| ATOM | 8302 | CA | VAL C 674 | 23.531 | 87.527 | 45.783 | 1.00 | 15.07 | C |
| ATOM | 8303 | CB | VAL C 674 | 24.529 | 88.604 | 45.331 | 1.00 | 100.07 | C |
| ATOM | 8304 | CG1 | VAL C 674 | 25.701 | 88.670 | 46.287 | 1.00 | 100.07 | C |
| ATOM | 8305 | CG2 | VAL C 674 | 24.998 | 88.313 | 43.917 | 1.00 | 100.07 | C |
| ATOM | 8306 | C | VAL C 674 | 23.284 | 87.728 | 47.265 | 1.00 | 15.07 | C |
| ATOM | 8307 | O | VAL C 674 | 22.549 | 88.621 | 47.663 | 1.00 | 15.07 | C |
| ATOM | 8308 | N | ALA C 675 | 23.913 | 86.903 | 48.090 | 1.00 | 32.76 | C |
| ATOM | 8309 | CA | ALA C 675 | 23.785 | 87.047 | 49.534 | 1.00 | 32.76 | C |
| ATOM | 8310 | CB | ALA C 675 | 23.792 | 85.690 | 50.203 | 1.00 | 72.15 | C |
| ATOM | 8311 | C | ALA C 675 | 25.036 | 87.831 | 49.911 | 1.00 | 32.76 | C |
| ATOM | 8312 | O | ALA C 675 | 25.918 | 88.006 | 49.064 | 1.00 | 32.76 | C |
| ATOM | 8313 | N | ILE C 676 | 25.130 | 88.305 | 51.155 | 1.00 | 19.32 | C |
| ATOM | 8314 | CA | ILE C 676 | 26.312 | 89.062 | 51.571 | 1.00 | 19.32 | C |
| ATOM | 8315 | CB | ILE C 676 | 26.072 | 90.593 | 51.550 | 1.00 | 5.39 | C |
| ATOM | 8316 | CG2 | ILE C 676 | 27.194 | 91.287 | 52.235 | 1.00 | 5.39 | C |
| ATOM | 8317 | CG1 | ILE C 676 | 25.994 | 91.115 | 50.107 | 1.00 | 5.39 | C |
| ATOM | 8318 | CD | ILE C 676 | 25.831 | 92.648 | 49.974 | 1.00 | 5.39 | C |
| ATOM | 8319 | C | ILE C 676 | 26.653 | 88.688 | 52.979 | 1.00 | 19.32 | C |
| ATOM | 8320 | O | ILE C 676 | 26.248 | 89.380 | 53.885 | 1.00 | 19.32 | C |
| ATOM | 8321 | N | MET C 677 | 27.401 | 87.611 | 53.173 | 1.00 | 20.03 | C |
| ATOM | 8322 | CA | MET C 677 | 27.769 | 87.180 | 54.521 | 1.00 | 20.03 | C |
| ATOM | 8323 | CB | MET C 677 | 26.571 | 86.531 | 55.174 | 1.00 | 33.10 | C |
| ATOM | 8324 | CG | MET C 677 | 25.752 | 85.732 | 54.199 | 1.00 | 33.10 | C |
| ATOM | 8325 | SD | MET C 677 | 24.619 | 84.686 | 55.075 | 1.00 | 33.10 | C |
| ATOM | 8326 | CE | MET C 677 | 25.749 | 83.629 | 56.015 | 1.00 | 33.10 | C |
| ATOM | 8327 | C | MET C 677 | 28.961 | 86.224 | 54.556 | 1.00 | 20.03 | C |
| ATOM | 8328 | O | MET C 677 | 29.150 | 85.397 | 53.668 | 1.00 | 20.03 | C |
| ATOM | 8329 | N | PRO C 678 | 29.800 | 86.337 | 55.581 | 1.00 | 42.63 | C |
| ATOM | 8330 | CD | PRO C 678 | 29.751 | 87.187 | 56.779 | 1.00 | 15.40 | C |
| ATOM | 8331 | CA | PRO C 678 | 30.947 | 85.430 | 55.633 | 1.00 | 42.63 | C |
| ATOM | 8332 | CB | PRO C 678 | 31.701 | 85.907 | 56.872 | 1.00 | 15.40 | C |
| ATOM | 8333 | CG | PRO C 678 | 30.601 | 86.393 | 57.759 | 1.00 | 15.40 | C |
| ATOM | 8334 | C | PRO C 678 | 30.482 | 83.992 | 55.769 | 1.00 | 42.63 | C |
| ATOM | 8335 | O | PRO C 678 | 29.890 | 83.644 | 56.786 | 1.00 | 42.63 | C |
| ATOM | 8336 | N | PHE C 679 | 30.740 | 83.157 | 54.762 | 1.00 | 29.34 | C |
| ATOM | 8337 | CA | PHE C 679 | 30.322 | 81.747 | 54.828 | 1.00 | 29.34 | C |
| ATOM | 8338 | CB | PHE C 679 | 29.673 | 81.313 | 53.494 | 1.00 | 50.07 | C |
| ATOM | 8339 | CG | PHE C 679 | 28.584 | 80.269 | 53.648 | 1.00 | 50.07 | C |
| ATOM | 8340 | CD1 | PHE C 679 | 27.287 | 80.638 | 53.969 | 1.00 | 50.07 | C |
| ATOM | 8341 | CD2 | PHE C 679 | 28.869 | 78.920 | 53.504 | 1.00 | 50.07 | C |
| ATOM | 8342 | CE1 | PHE C 679 | 26.292 | 79.676 | 54.150 | 1.00 | 50.07 | C |
| ATOM | 8343 | CE2 | PHE C 679 | 27.883 | 77.959 | 53.683 | 1.00 | 50.07 | C |
| ATOM | 8344 | CZ | PHE C 679 | 26.595 | 78.335 | 54.008 | 1.00 | 50.07 | C |
| ATOM | 8345 | C | PHE C 679 | 31.490 | 80.802 | 55.176 | 1.00 | 29.34 | C |
| ATOM | 8346 | O | PHE C 679 | 32.302 | 80.457 | 54.324 | 1.00 | 29.34 | C |
| ATOM | 8347 | N | ASP C 680 | 31.554 | 80.401 | 56.440 | 1.00 | 14.67 | C |
| ATOM | 8348 | CA | ASP C 680 | 32.582 | 79.508 | 56.967 | 1.00 | 14.67 | C |
| ATOM | 8349 | CB | ASP C 680 | 32.037 | 78.085 | 57.041 | 1.00 | 41.08 | C |
| ATOM | 8350 | CG | ASP C 680 | 30.826 | 77.970 | 57.936 | 1.00 | 41.08 | C |
| ATOM | 8351 | OD1 | ASP C 680 | 29.786 | 78.574 | 57.598 | 1.00 | 41.08 | C |
| ATOM | 8352 | OD2 | ASP C 680 | 30.916 | 77.275 | 58.971 | 1.00 | 41.08 | C |
| ATOM | 8353 | C | ASP C 680 | 33.969 | 79.454 | 56.320 | 1.00 | 14.67 | C |
| ATOM | 8354 | O | ASP C 680 | 34.714 | 78.520 | 56.579 | 1.00 | 14.67 | C |
| ATOM | 8355 | N | GLY C 681 | 34.331 | 80.435 | 55.502 | 1.00 | 31.79 | C |
| ATOM | 8356 | CA | GLY C 681 | 35.654 | 80.420 | 54.892 | 1.00 | 31.79 | C |
| ATOM | 8357 | C | GLY C 681 | 35.663 | 80.347 | 53.377 | 1.00 | 31.79 | C |
| ATOM | 8358 | O | GLY C 681 | 36.491 | 80.959 | 52.698 | 1.00 | 31.79 | C |
| ATOM | 8359 | N | TYR C 682 | 34.716 | 79.598 | 52.840 | 1.00 | 19.16 | C |
| ATOM | 8360 | CA | TYR C 682 | 34.627 | 79.429 | 51.419 | 1.00 | 19.16 | C |
| ATOM | 8361 | CB | TYR C 682 | 33.422 | 78.546 | 51.110 | 1.00 | 28.99 | C |
| ATOM | 8362 | CG | TYR C 682 | 33.624 | 77.236 | 51.847 | 1.00 | 28.99 | C |

```
ATOM   8363  CD1 TYR C 682      34.634  76.349  51.472  1.00 28.99           C
ATOM   8364  CE1 TYR C 682      35.004  75.281  52.293  1.00 28.99           C
ATOM   8365  CD2 TYR C 682      32.981  76.995  53.055  1.00 28.99           C
ATOM   8366  CE2 TYR C 682      33.346  75.934  53.874  1.00 28.99           C
ATOM   8367  CZ  TYR C 682      34.356  75.092  53.493  1.00 28.99           C
ATOM   8368  OH  TYR C 682      34.727  74.087  54.349  1.00 28.99           C
ATOM   8369  C   TYR C 682      34.615  80.776  50.760  1.00 19.16           C
ATOM   8370  O   TYR C 682      34.868  80.878  49.562  1.00 19.16           C
ATOM   8371  N   ASN C 683      34.361  81.827  51.535  1.00 18.87           C
ATOM   8372  CA  ASN C 683      34.411  83.170  50.964  1.00 18.87           C
ATOM   8373  CB  ASN C 683      33.009  83.791  50.764  1.00 62.59           C
ATOM   8374  CG  ASN C 683      32.288  84.097  52.062  1.00 62.59           C
ATOM   8375  OD1 ASN C 683      32.728  83.699  53.140  1.00 62.59           C
ATOM   8376  ND2 ASN C 683      31.156  84.802  51.958  1.00 62.59           C
ATOM   8377  C   ASN C 683      35.286  84.055  51.812  1.00 18.87           C
ATOM   8378  O   ASN C 683      34.949  85.193  52.092  1.00 18.87           C
ATOM   8379  N   PHE C 684      36.417  83.492  52.225  1.00 40.54           C
ATOM   8380  CA  PHE C 684      37.444  84.179  53.014  1.00 40.54           C
ATOM   8381  CB  PHE C 684      38.366  83.120  53.608  1.00 13.84           C
ATOM   8382  CG  PHE C 684      39.643  83.642  54.244  1.00 13.84           C
ATOM   8383  CD1 PHE C 684      39.729  83.816  55.619  1.00 13.84           C
ATOM   8384  CD2 PHE C 684      40.807  83.761  53.490  1.00 13.84           C
ATOM   8385  CE1 PHE C 684      40.944  84.074  56.227  1.00 13.84           C
ATOM   8386  CE2 PHE C 684      42.026  84.022  54.103  1.00 13.84           C
ATOM   8387  CZ  PHE C 684      42.089  84.172  55.473  1.00 13.84           C
ATOM   8388  C   PHE C 684      38.187  85.042  51.997  1.00 40.54           C
ATOM   8389  O   PHE C 684      38.327  84.661  50.837  1.00 40.54           C
ATOM   8390  N   GLU C 685      38.674  86.200  52.408  1.00 88.25           C
ATOM   8391  CA  GLU C 685      39.337  87.056  51.442  1.00 88.25           C
ATOM   8392  CB  GLU C 685      40.546  86.360  50.829  1.00 83.88           C
ATOM   8393  CG  GLU C 685      41.750  86.366  51.732  1.00 83.88           C
ATOM   8394  CD  GLU C 685      42.012  87.736  52.332  1.00 83.88           C
ATOM   8395  OE1 GLU C 685      41.819  88.745  51.623  1.00 83.88           C
ATOM   8396  OE2 GLU C 685      42.418  87.807  53.511  1.00 83.88           C
ATOM   8397  C   GLU C 685      38.317  87.365  50.358  1.00 88.25           C
ATOM   8398  O   GLU C 685      37.157  87.658  50.661  1.00 88.25           C
ATOM   8399  N   ASP C 686      38.723  87.280  49.097  1.00 55.13           C
ATOM   8400  CA  ASP C 686      37.788  87.591  48.028  1.00 55.13           C
ATOM   8401  CB  ASP C 686      38.470  88.488  46.995  1.00100.07           C
ATOM   8402  CG  ASP C 686      38.885  89.830  47.577  1.00100.07           C
ATOM   8403  OD1 ASP C 686      38.008  90.556  48.093  1.00100.07           C
ATOM   8404  OD2 ASP C 686      40.088  90.158  47.518  1.00100.07           C
ATOM   8405  C   ASP C 686      37.161  86.368  47.355  1.00 55.13           C
ATOM   8406  O   ASP C 686      36.494  86.488  46.316  1.00 55.13           C
ATOM   8407  N   ALA C 687      37.368  85.192  47.946  1.00 61.11           C
ATOM   8408  CA  ALA C 687      36.784  83.972  47.400  1.00 61.11           C
ATOM   8409  CB  ALA C 687      37.206  82.785  48.210  1.00 31.25           C
ATOM   8410  C   ALA C 687      35.267  84.128  47.446  1.00 61.11           C
ATOM   8411  O   ALA C 687      34.726  84.789  48.334  1.00 61.11           C
ATOM   8412  N   ILE C 688      34.583  83.500  46.500  1.00 23.75           C
ATOM   8413  CA  ILE C 688      33.139  83.615  46.407  1.00 23.75           C
ATOM   8414  CB  ILE C 688      32.785  84.463  45.224  1.00 35.11           C
ATOM   8415  CG2 ILE C 688      31.292  84.628  45.144  1.00 35.11           C
ATOM   8416  CG1 ILE C 688      33.543  85.776  45.314  1.00 35.11           C
ATOM   8417  CD  ILE C 688      33.348  86.641  44.117  1.00 35.11           C
ATOM   8418  C   ILE C 688      32.447  82.293  46.199  1.00 23.75           C
ATOM   8419  O   ILE C 688      32.639  81.676  45.162  1.00 23.75           C
ATOM   8420  N   VAL C 689      31.620  81.872  47.146  1.00 15.37           C
ATOM   8421  CA  VAL C 689      30.903  80.607  47.014  1.00 15.37           C
ATOM   8422  CB  VAL C 689      30.151  80.301  48.300  1.00 12.44           C
ATOM   8423  CG1 VAL C 689      29.438  78.980  48.168  1.00 12.44           C
ATOM   8424  CG2 VAL C 689      31.112  80.264  49.464  1.00 12.44           C
ATOM   8425  C   VAL C 689      29.887  80.589  45.840  1.00 15.37           C
ATOM   8426  O   VAL C 689      29.391  81.638  45.440  1.00 15.37           C
ATOM   8427  N   ILE C 690      29.590  79.414  45.276  1.00 38.82           C
ATOM   8428  CA  ILE C 690      28.607  79.326  44.186  1.00 38.82           C
ATOM   8429  CB  ILE C 690      29.187  78.832  42.835  1.00 64.94           C
ATOM   8430  CG2 ILE C 690      28.147  79.006  41.753  1.00 64.94           C
ATOM   8431  CG1 ILE C 690      30.395  79.633  42.390  1.00 64.94           C
ATOM   8432  CD  ILE C 690      30.920  79.167  41.030  1.00 64.94           C
ATOM   8433  C   ILE C 690      27.546  78.283  44.530  1.00 38.82           C
ATOM   8434  O   ILE C 690      27.840  77.301  45.231  1.00 38.82           C
ATOM   8435  N   SER C 691      26.324  78.495  44.019  1.00 26.09           C
ATOM   8436  CA  SER C 691      25.208  77.555  44.206  1.00 26.09           C
ATOM   8437  CB  SER C 691      23.880  78.275  44.414  1.00 77.43           C
ATOM   8438  OG  SER C 691      22.809  77.362  44.232  1.00 77.43           C
ATOM   8439  C   SER C 691      25.093  76.694  42.954  1.00 26.09           C
ATOM   8440  O   SER C 691      24.718  77.173  41.885  1.00 26.09           C
ATOM   8441  N   GLU C 692      25.429  75.422  43.117  1.00  5.07           C
ATOM   8442  CA  GLU C 692      25.418  74.442  42.055  1.00  5.07           C
ATOM   8443  CB  GLU C 692      25.182  73.065  42.660  1.00 41.10           C
ATOM   8444  CG  GLU C 692      25.056  71.944  41.668  1.00 41.10           C
ATOM   8445  CD  GLU C 692      25.390  70.606  42.289  1.00 41.10           C
ATOM   8446  OE1 GLU C 692      24.959  70.356  43.429  1.00 41.10           C
```

```
ATOM   8447  OE2 GLU C 692      26.079  69.798  41.639  1.00 41.10           C
ATOM   8448  C   GLU C 692      24.390  74.747  40.994  1.00  5.07           C
ATOM   8449  O   GLU C 692      24.638  74.546  39.809  1.00  5.07           C
ATOM   8450  N   GLU C 693      23.243  75.261  41.417  1.00 37.66           C
ATOM   8451  CA  GLU C 693      22.179  75.576  40.477  1.00 37.66           C
ATOM   8452  CB  GLU C 693      21.149  76.493  41.140  1.00 74.69           C
ATOM   8453  CG  GLU C 693      19.718  76.122  40.808  1.00 74.69           C
ATOM   8454  CD  GLU C 693      19.369  74.712  41.257  1.00 74.69           C
ATOM   8455  OE1 GLU C 693      20.030  73.749  40.808  1.00 74.69           C
ATOM   8456  OE2 GLU C 693      18.432  74.561  42.064  1.00 74.69           C
ATOM   8457  C   GLU C 693      22.688  76.199  39.163  1.00 37.66           C
ATOM   8458  O   GLU C 693      22.480  75.636  38.090  1.00 37.66           C
ATOM   8459  N   LEU C 694      23.365  77.345  39.244  1.00 30.35           C
ATOM   8460  CA  LEU C 694      23.887  78.019  38.047  1.00 30.35           C
ATOM   8461  CB  LEU C 694      24.924  79.084  38.435  1.00 24.48           C
ATOM   8462  CG  LEU C 694      24.530  80.143  39.461  1.00 24.48           C
ATOM   8463  CD1 LEU C 694      25.612  81.220  39.574  1.00 24.48           C
ATOM   8464  CD2 LEU C 694      23.226  80.765  39.022  1.00 24.48           C
ATOM   8465  C   LEU C 694      24.539  77.014  37.089  1.00 30.35           C
ATOM   8466  O   LEU C 694      24.555  77.198  35.867  1.00 30.35           C
ATOM   8467  N   ALA C 695      25.094  75.957  37.662  1.00 18.21           C
ATOM   8468  CA  ALA C 695      25.739  74.948  36.864  1.00 18.21           C
ATOM   8469  CB  ALA C 695      26.728  74.141  37.736  1.00  5.07           C
ATOM   8470  C   ALA C 695      24.599  74.081  36.344  1.00 18.21           C
ATOM   8471  O   ALA C 695      24.553  73.750  35.155  1.00 18.21           C
ATOM   8472  N   ALA C 696      23.664  73.748  37.236  1.00 37.13           C
ATOM   8473  CA  ALA C 696      22.507  72.924  36.887  1.00 37.13           C
ATOM   8474  CB  ALA C 696      21.666  72.630  38.131  1.00  5.07           C
ATOM   8475  C   ALA C 696      21.678  73.627  35.812  1.00 37.13           C
ATOM   8476  O   ALA C 696      21.115  72.976  34.943  1.00 37.13           C
ATOM   8477  N   ARG C 697      21.584  74.950  35.875  1.00 78.06           C
ATOM   8478  CA  ARG C 697      20.881  75.688  34.830  1.00 78.06           C
ATOM   8479  CB  ARG C 697      20.485  77.090  35.300  1.00 67.10           C
ATOM   8480  CG  ARG C 697      19.715  77.116  36.617  1.00 67.10           C
ATOM   8481  CD  ARG C 697      18.453  77.963  36.515  1.00 67.10           C
ATOM   8482  NE  ARG C 697      18.659  79.355  36.904  1.00 67.10           C
ATOM   8483  CZ  ARG C 697      18.069  80.388  36.308  1.00 67.10           C
ATOM   8484  NH1 ARG C 697      17.239  80.186  35.280  1.00 67.10           C
ATOM   8485  NH2 ARG C 697      18.295  81.621  36.751  1.00 67.10           C
ATOM   8486  C   ARG C 697      22.061  75.791  33.893  1.00 78.06           C
ATOM   8487  O   ARG C 697      23.192  75.662  34.354  1.00 78.06           C
ATOM   8488  N   ASP C 698      21.858  75.996  32.599  1.00 49.34           C
ATOM   8489  CA  ASP C 698      23.042  76.096  31.756  1.00 49.34           C
ATOM   8490  CB  ASP C 698      22.773  75.619  30.332  1.00 70.47           C
ATOM   8491  CG  ASP C 698      23.540  74.349  29.999  1.00 70.47           C
ATOM   8492  OD1 ASP C 698      24.680  74.205  30.499  1.00 70.47           C
ATOM   8493  OD2 ASP C 698      23.012  73.506  29.237  1.00 70.47           C
ATOM   8494  C   ASP C 698      23.542  77.524  31.757  1.00 49.34           C
ATOM   8495  O   ASP C 698      23.818  78.107  30.716  1.00 49.34           C
ATOM   8496  N   PHE C 699      23.674  78.064  32.963  1.00 70.88           C
ATOM   8497  CA  PHE C 699      24.128  79.429  33.167  1.00 70.88           C
ATOM   8498  CB  PHE C 699      24.091  79.798  34.652  1.00 48.70           C
ATOM   8499  CG  PHE C 699      23.152  80.930  34.968  1.00 48.70           C
ATOM   8500  CD1 PHE C 699      21.864  80.678  35.431  1.00 48.70           C
ATOM   8501  CD2 PHE C 699      23.554  82.250  34.793  1.00 48.70           C
ATOM   8502  CE1 PHE C 699      20.998  81.716  35.713  1.00 48.70           C
ATOM   8503  CE2 PHE C 699      22.692  83.291  35.073  1.00 48.70           C
ATOM   8504  CZ  PHE C 699      21.411  83.021  35.536  1.00 48.70           C
ATOM   8505  C   PHE C 699      25.512  79.718  32.638  1.00 70.88           C
ATOM   8506  O   PHE C 699      25.871  79.311  31.537  1.00 70.88           C
ATOM   8507  N   TYR C 700      26.271  80.436  33.457  1.00 47.29           C
ATOM   8508  CA  TYR C 700      27.624  80.871  33.151  1.00 47.29           C
ATOM   8509  CB  TYR C 700      28.431  80.951  34.451  1.00 41.89           C
ATOM   8510  CG  TYR C 700      28.040  82.145  35.294  1.00 41.89           C
ATOM   8511  CD1 TYR C 700      28.574  82.343  36.562  1.00 41.89           C
ATOM   8512  CE1 TYR C 700      28.198  83.452  37.334  1.00 41.89           C
ATOM   8513  CD2 TYR C 700      27.119  83.088  34.817  1.00 41.89           C
ATOM   8514  CE2 TYR C 700      26.740  84.195  35.587  1.00 41.89           C
ATOM   8515  CZ  TYR C 700      27.285  84.363  36.834  1.00 41.89           C
ATOM   8516  OH  TYR C 700      26.914  85.447  37.572  1.00 41.89           C
ATOM   8517  C   TYR C 700      28.421  80.138  32.081  1.00 47.29           C
ATOM   8518  O   TYR C 700      29.404  80.686  31.579  1.00 47.29           C
ATOM   8519  N   THR C 701      28.020  78.916  31.734  1.00 21.71           C
ATOM   8520  CA  THR C 701      28.710  78.156  30.700  1.00 21.71           C
ATOM   8521  CB  THR C 701      27.838  77.003  30.204  1.00 56.54           C
ATOM   8522  OG1 THR C 701      26.583  77.513  29.742  1.00 56.54           C
ATOM   8523  CG2 THR C 701      27.596  76.020  31.327  1.00 56.54           C
ATOM   8524  C   THR C 701      29.072  79.063  29.512  1.00 21.71           C
ATOM   8525  O   THR C 701      28.208  79.751  28.955  1.00 21.71           C
ATOM   8526  N   SER C 702      30.362  79.065  29.158  1.00 45.58           C
ATOM   8527  CA  SER C 702      30.906  79.872  28.060  1.00 45.58           C
ATOM   8528  CB  SER C 702      31.925  80.872  28.604  1.00 89.52           C
ATOM   8529  OG  SER C 702      32.947  80.210  29.330  1.00 89.52           C
ATOM   8530  C   SER C 702      31.590  78.965  27.045  1.00 45.58           C
```

```
ATOM   8531  O   SER C 702      32.369  78.085  27.428  1.00 45.58           C
ATOM   8532  N   ILE C 703      31.315  79.189  25.759  1.00 22.39           C
ATOM   8533  CA  ILE C 703      31.883  78.362  24.696  1.00 22.39           C
ATOM   8534  CB  ILE C 703      30.898  78.228  23.545  1.00 67.44           C
ATOM   8535  CG2 ILE C 703      31.615  77.685  22.327  1.00 67.44           C
ATOM   8536  CG1 ILE C 703      29.733  77.331  23.962  1.00 67.44           C
ATOM   8537  CD  ILE C 703      28.625  77.228  22.922  1.00 67.44           C
ATOM   8538  C   ILE C 703      33.191  78.881  24.116  1.00 22.39           C
ATOM   8539  O   ILE C 703      33.252  80.028  23.679  1.00 22.39           C
ATOM   8540  N   HIS C 704      34.219  78.030  24.071  1.00 45.20           C
ATOM   8541  CA  HIS C 704      35.522  78.431  23.537  1.00 45.20           C
ATOM   8542  CB  HIS C 704      36.554  78.432  24.659  1.00100.07           C
ATOM   8543  CG  HIS C 704      36.214  79.360  25.785  1.00100.07           C
ATOM   8544  CD2 HIS C 704      36.807  80.500  26.213  1.00100.07           C
ATOM   8545  ND1 HIS C 704      35.143  79.148  26.626  1.00100.07           C
ATOM   8546  CE1 HIS C 704      35.093  80.116  27.527  1.00100.07           C
ATOM   8547  NE2 HIS C 704      36.093  80.949  27.297  1.00100.07           C
ATOM   8548  C   HIS C 704      36.011  77.590  22.337  1.00 45.20           C
ATOM   8549  O   HIS C 704      35.769  76.387  22.260  1.00 45.20           C
ATOM   8550  N   ILE C 705      36.730  78.237  21.420  1.00 15.98           C
ATOM   8551  CA  ILE C 705      37.191  77.603  20.191  1.00 15.98           C
ATOM   8552  CB  ILE C 705      36.301  78.039  19.052  1.00 14.22           C
ATOM   8553  CG2 ILE C 705      36.793  77.477  17.763  1.00 14.22           C
ATOM   8554  CG1 ILE C 705      34.877  77.633  19.321  1.00 14.22           C
ATOM   8555  CD  ILE C 705      33.946  78.211  18.296  1.00 14.22           C
ATOM   8556  C   ILE C 705      38.601  77.953  19.719  1.00 15.98           C
ATOM   8557  O   ILE C 705      38.815  79.066  19.224  1.00 15.98           C
ATOM   8558  N   GLU C 706      39.561  77.039  19.808  1.00 60.09           C
ATOM   8559  CA  GLU C 706      40.865  77.411  19.288  1.00 60.09           C
ATOM   8560  CB  GLU C 706      41.907  77.489  20.387  1.00 99.45           C
ATOM   8561  CG  GLU C 706      42.925  78.553  20.032  1.00 99.45           C
ATOM   8562  CD  GLU C 706      42.359  79.560  19.022  1.00 99.45           C
ATOM   8563  OE1 GLU C 706      41.317  80.195  19.306  1.00 99.45           C
ATOM   8564  OE2 GLU C 706      42.951  79.707  17.934  1.00 99.45           C
ATOM   8565  C   GLU C 706      41.354  76.526  18.160  1.00 60.09           C
ATOM   8566  O   GLU C 706      40.903  75.398  18.042  1.00 60.09           C
ATOM   8567  N   ARG C 707      42.263  77.045  17.327  1.00 49.03           C
ATOM   8568  CA  ARG C 707      42.787  76.300  16.175  1.00 49.03           C
ATOM   8569  CB  ARG C 707      42.993  77.238  14.990  1.00 93.56           C
ATOM   8570  CG  ARG C 707      43.782  78.489  15.307  1.00 93.56           C
ATOM   8571  CD  ARG C 707      43.374  79.616  14.358  1.00 93.56           C
ATOM   8572  NE  ARG C 707      43.814  80.938  14.805  1.00 93.56           C
ATOM   8573  CZ  ARG C 707      43.295  82.087  14.374  1.00 93.56           C
ATOM   8574  NH1 ARG C 707      42.313  82.091  13.481  1.00 93.56           C
ATOM   8575  NH2 ARG C 707      43.747  83.239  14.853  1.00 93.56           C
ATOM   8576  C   ARG C 707      44.072  75.539  16.434  1.00 49.03           C
ATOM   8577  O   ARG C 707      44.622  75.604  17.525  1.00 49.03           C
ATOM   8578  N   TYR C 708      44.532  74.804  15.425  1.00 37.77           C
ATOM   8579  CA  TYR C 708      45.756  74.014  15.512  1.00 37.77           C
ATOM   8580  CB  TYR C 708      45.440  72.598  15.963  1.00 25.12           C
ATOM   8581  CG  TYR C 708      45.123  72.493  17.427  1.00 25.12           C
ATOM   8582  CD1 TYR C 708      43.815  72.342  17.872  1.00 25.12           C
ATOM   8583  CE1 TYR C 708      43.518  72.323  19.227  1.00 25.12           C
ATOM   8584  CD2 TYR C 708      46.127  72.613  18.372  1.00 25.12           C
ATOM   8585  CE2 TYR C 708      45.843  72.598  19.721  1.00 25.12           C
ATOM   8586  CZ  TYR C 708      44.539  72.461  20.150  1.00 25.12           C
ATOM   8587  OH  TYR C 708      44.264  72.536  21.507  1.00 25.12           C
ATOM   8588  C   TYR C 708      46.403  73.949  14.142  1.00 37.77           C
ATOM   8589  O   TYR C 708      45.719  73.655  13.154  1.00 37.77           C
ATOM   8590  N   GLU C 709      47.709  74.201  14.065  1.00 45.83           C
ATOM   8591  CA  GLU C 709      48.404  74.179  12.773  1.00 45.83           C
ATOM   8592  CB  GLU C 709      49.109  75.510  12.522  1.00 77.60           C
ATOM   8593  CG  GLU C 709      48.216  76.646  12.101  1.00 77.60           C
ATOM   8594  CD  GLU C 709      48.921  77.589  11.134  1.00 77.60           C
ATOM   8595  OE1 GLU C 709      50.074  77.990  11.427  1.00 77.60           C
ATOM   8596  OE2 GLU C 709      48.324  77.927  10.083  1.00 77.60           C
ATOM   8597  C   GLU C 709      49.442  73.081  12.603  1.00 45.83           C
ATOM   8598  O   GLU C 709      50.160  72.761  13.544  1.00 45.83           C
ATOM   8599  N   ILE C 710      49.522  72.516  11.398  1.00 21.14           C
ATOM   8600  CA  ILE C 710      50.517  71.487  11.070  1.00 21.14           C
ATOM   8601  CB  ILE C 710      49.935  70.077  10.971  1.00 43.13           C
ATOM   8602  CG2 ILE C 710      51.075  69.065  10.953  1.00 43.13           C
ATOM   8603  CG1 ILE C 710      48.943  69.823  12.117  1.00 43.13           C
ATOM   8604  CD  ILE C 710      49.473  69.976  13.553  1.00 43.13           C
ATOM   8605  C   ILE C 710      51.067  71.822   9.697  1.00 21.14           C
ATOM   8606  O   ILE C 710      50.306  71.986   8.732  1.00 21.14           C
ATOM   8607  N   GLU C 711      52.389  71.930   9.610  1.00 56.98           C
ATOM   8608  CA  GLU C 711      53.037  72.268   8.353  1.00 56.98           C
ATOM   8609  CB  GLU C 711      54.179  73.256   8.616  1.00 84.91           C
ATOM   8610  CG  GLU C 711      53.672  74.550   9.240  1.00 84.91           C
ATOM   8611  CD  GLU C 711      54.765  75.544   9.583  1.00 84.91           C
ATOM   8612  OE1 GLU C 711      55.392  76.097   8.656  1.00 84.91           C
ATOM   8613  OE2 GLU C 711      54.988  75.777  10.790  1.00 84.91           C
ATOM   8614  C   GLU C 711      53.546  71.031   7.623  1.00 56.98           C
```

| ATOM | 8615 | O   | GLU | C | 711 | 53.816 | 70.004 | 8.247  | 1.00 | 56.98  | C |
|------|------|-----|-----|---|-----|--------|--------|--------|------|--------|---|
| ATOM | 8616 | N   | ALA | C | 712 | 53.638 | 71.136 | 6.297  | 1.00 | 41.22  | C |
| ATOM | 8617 | CA  | ALA | C | 712 | 54.129 | 70.060 | 5.436  | 1.00 | 41.22  | C |
| ATOM | 8618 | CB  | ALA | C | 712 | 53.034 | 69.613 | 4.481  | 1.00 | 85.63  | C |
| ATOM | 8619 | C   | ALA | C | 712 | 55.338 | 70.596 | 4.661  | 1.00 | 41.22  | C |
| ATOM | 8620 | O   | ALA | C | 712 | 55.215 | 71.100 | 3.542  | 1.00 | 41.22  | C |
| ATOM | 8621 | N   | ARG | C | 713 | 56.507 | 70.487 | 5.284  | 1.00 | 58.37  | C |
| ATOM | 8622 | CA  | ARG | C | 713 | 57.761 | 70.966 | 4.717  | 1.00 | 58.37  | C |
| ATOM | 8623 | CB  | ARG | C | 713 | 58.882 | 70.792 | 5.744  | 1.00 | 99.84  | C |
| ATOM | 8624 | CG  | ARG | C | 713 | 58.633 | 71.525 | 7.061  | 1.00 | 99.84  | C |
| ATOM | 8625 | CD  | ARG | C | 713 | 58.850 | 73.031 | 6.919  | 1.00 | 99.84  | C |
| ATOM | 8626 | NE  | ARG | C | 713 | 58.432 | 73.782 | 8.107  | 1.00 | 99.84  | C |
| ATOM | 8627 | CZ  | ARG | C | 713 | 58.703 | 75.072 | 8.323  | 1.00 | 99.84  | C |
| ATOM | 8628 | NH1 | ARG | C | 713 | 59.403 | 75.767 | 7.434  | 1.00 | 99.84  | C |
| ATOM | 8629 | NH2 | ARG | C | 713 | 58.258 | 75.677 | 9.420  | 1.00 | 99.84  | C |
| ATOM | 8630 | C   | ARG | C | 713 | 58.147 | 70.292 | 3.402  | 1.00 | 58.37  | C |
| ATOM | 8631 | O   | ARG | C | 713 | 57.289 | 69.784 | 2.667  | 1.00 | 58.37  | C |
| ATOM | 8632 | N   | ASP | C | 714 | 59.448 | 70.292 | 3.117  | 1.00 | 68.42  | C |
| ATOM | 8633 | CA  | ASP | C | 714 | 59.961 | 69.711 | 1.884  | 1.00 | 68.42  | C |
| ATOM | 8634 | CB  | ASP | C | 714 | 59.791 | 70.729 | 0.751  | 1.00 | 80.11  | C |
| ATOM | 8635 | CG  | ASP | C | 714 | 59.750 | 70.087 | -0.622 | 1.00 | 80.11  | C |
| ATOM | 8636 | OD1 | ASP | C | 714 | 60.800 | 69.587 | -1.072 | 1.00 | 80.11  | C |
| ATOM | 8637 | OD2 | ASP | C | 714 | 58.666 | 70.084 | -1.250 | 1.00 | 80.11  | C |
| ATOM | 8638 | C   | ASP | C | 714 | 61.436 | 69.369 | 2.065  | 1.00 | 68.42  | C |
| ATOM | 8639 | O   | ASP | C | 714 | 62.166 | 69.219 | 1.093  | 1.00 | 68.42  | C |
| ATOM | 8640 | N   | ALA | C | 715 | 61.853 | 69.235 | 3.321  | 1.00 | 42.90  | C |
| ATOM | 8641 | CA  | ALA | C | 715 | 63.243 | 68.939 | 3.691  | 1.00 | 42.90  | C |
| ATOM | 8642 | CB  | ALA | C | 715 | 63.294 | 68.439 | 5.119  | 1.00 | 50.27  | C |
| ATOM | 8643 | C   | ALA | C | 715 | 64.015 | 67.982 | 2.789  | 1.00 | 42.90  | C |
| ATOM | 8644 | O   | ALA | C | 715 | 63.434 | 67.259 | 1.984  | 1.00 | 42.90  | C |
| ATOM | 8645 | N   | ALA | C | 716 | 65.335 | 67.981 | 2.962  | 1.00 | 88.79  | C |
| ATOM | 8646 | CA  | ALA | C | 716 | 66.264 | 67.162 | 2.186  | 1.00 | 88.79  | C |
| ATOM | 8647 | CB  | ALA | C | 716 | 67.684 | 67.451 | 2.632  | 1.00 |100.07  | C |
| ATOM | 8648 | C   | ALA | C | 716 | 66.042 | 65.656 | 2.177  | 1.00 | 88.79  | C |
| ATOM | 8649 | O   | ALA | C | 716 | 66.296 | 65.007 | 1.173  | 1.00 | 88.79  | C |
| ATOM | 8650 | N   | LEU | C | 717 | 65.595 | 65.090 | 3.289  | 1.00 | 39.98  | C |
| ATOM | 8651 | CA  | LEU | C | 717 | 65.367 | 63.650 | 3.349  | 1.00 | 39.98  | C |
| ATOM | 8652 | CB  | LEU | C | 717 | 65.426 | 63.187 | 4.795  | 1.00 | 76.08  | C |
| ATOM | 8653 | CG  | LEU | C | 717 | 66.660 | 63.744 | 5.484  | 1.00 | 81.83  | C |
| ATOM | 8654 | CD1 | LEU | C | 717 | 66.716 | 63.226 | 6.896  | 1.00 | 81.83  | C |
| ATOM | 8655 | CD2 | LEU | C | 717 | 67.898 | 63.364 | 4.690  | 1.00 | 81.83  | C |
| ATOM | 8656 | C   | LEU | C | 717 | 64.024 | 63.235 | 2.732  | 1.00 | 39.98  | C |
| ATOM | 8657 | O   | LEU | C | 717 | 63.399 | 62.264 | 3.163  | 1.00 | 39.98  | C |
| ATOM | 8658 | N   | GLY | C | 718 | 63.586 | 63.972 | 1.719  | 1.00 | 79.48  | C |
| ATOM | 8659 | CA  | GLY | C | 718 | 62.323 | 63.656 | 1.079  | 1.00 | 79.48  | C |
| ATOM | 8660 | C   | GLY | C | 718 | 61.206 | 64.576 | 1.526  | 1.00 | 79.48  | C |
| ATOM | 8661 | O   | GLY | C | 718 | 61.352 | 65.301 | 2.506  | 1.00 | 79.48  | C |
| ATOM | 8662 | N   | PRO | C | 719 | 60.067 | 64.564 | 0.822  | 1.00 | 23.76  | C |
| ATOM | 8663 | CD  | PRO | C | 719 | 59.891 | 63.891 | -0.472 | 1.00 | 98.16  | C |
| ATOM | 8664 | CA  | PRO | C | 719 | 58.900 | 65.391 | 1.120  | 1.00 | 23.76  | C |
| ATOM | 8665 | CB  | PRO | C | 719 | 58.102 | 65.333 | -0.177 | 1.00 | 92.41  | C |
| ATOM | 8666 | CG  | PRO | C | 719 | 58.398 | 63.973 | -0.672 | 1.00 | 98.16  | C |
| ATOM | 8667 | C   | PRO | C | 719 | 58.054 | 64.971 | 2.313  | 1.00 | 23.76  | C |
| ATOM | 8668 | O   | PRO | C | 719 | 57.677 | 63.809 | 2.448  | 1.00 | 23.76  | C |
| ATOM | 8669 | N   | GLU | C | 720 | 57.743 | 65.939 | 3.169  | 1.00 | 52.29  | C |
| ATOM | 8670 | CA  | GLU | C | 720 | 56.905 | 65.702 | 4.331  | 1.00 | 52.29  | C |
| ATOM | 8671 | CB  | GLU | C | 720 | 57.114 | 66.826 | 5.342  | 1.00 | 72.46  | C |
| ATOM | 8672 | CG  | GLU | C | 720 | 56.463 | 66.580 | 6.673  | 1.00 | 76.24  | C |
| ATOM | 8673 | CD  | GLU | C | 720 | 57.469 | 66.576 | 7.798  | 1.00 | 76.24  | C |
| ATOM | 8674 | OE1 | GLU | C | 720 | 58.039 | 67.653 | 8.077  | 1.00 | 76.24  | C |
| ATOM | 8675 | OE2 | GLU | C | 720 | 57.700 | 65.501 | 8.394  | 1.00 | 76.24  | C |
| ATOM | 8676 | C   | GLU | C | 720 | 55.470 | 65.724 | 3.794  | 1.00 | 52.29  | C |
| ATOM | 8677 | O   | GLU | C | 720 | 55.026 | 66.738 | 3.256  | 1.00 | 52.29  | C |
| ATOM | 8678 | N   | ARG | C | 721 | 54.748 | 64.614 | 3.920  | 1.00 | 29.36  | C |
| ATOM | 8679 | CA  | ARG | C | 721 | 53.370 | 64.548 | 3.413  | 1.00 | 29.36  | C |
| ATOM | 8680 | CB  | ARG | C | 721 | 53.325 | 63.548 | 2.257  | 1.00 |100.07  | C |
| ATOM | 8681 | CG  | ARG | C | 721 | 54.254 | 62.364 | 2.471  | 1.00 |100.07  | C |
| ATOM | 8682 | CD  | ARG | C | 721 | 54.414 | 61.509 | 1.225  | 1.00 |100.07  | C |
| ATOM | 8683 | NE  | ARG | C | 721 | 55.261 | 60.352 | 1.502  | 1.00 |100.07  | C |
| ATOM | 8684 | CZ  | ARG | C | 721 | 55.579 | 59.426 | 0.605  | 1.00 |100.07  | C |
| ATOM | 8685 | NH1 | ARG | C | 721 | 55.118 | 59.526 | -0.636 | 1.00 |100.07  | C |
| ATOM | 8686 | NH2 | ARG | C | 721 | 56.347 | 58.395 | 0.949  | 1.00 |100.07  | C |
| ATOM | 8687 | C   | ARG | C | 721 | 52.287 | 64.213 | 4.469  | 1.00 | 29.36  | C |
| ATOM | 8688 | O   | ARG | C | 721 | 52.589 | 63.688 | 5.545  | 1.00 | 29.36  | C |
| ATOM | 8689 | N   | ILE | C | 722 | 51.028 | 64.524 | 4.155  | 1.00 | 94.25  | C |
| ATOM | 8690 | CA  | ILE | C | 722 | 49.914 | 64.281 | 5.075  | 1.00 | 94.25  | C |
| ATOM | 8691 | CB  | ILE | C | 722 | 48.942 | 65.455 | 5.068  | 1.00 | 50.71  | C |
| ATOM | 8692 | CG2 | ILE | C | 722 | 47.901 | 65.249 | 6.118  | 1.00 | 56.46  | C |
| ATOM | 8693 | CG1 | ILE | C | 722 | 49.684 | 66.758 | 5.320  | 1.00 | 56.46  | C |
| ATOM | 8694 | CD  | ILE | C | 722 | 50.429 | 66.777 | 6.606  | 1.00 | 96.64  | C |
| ATOM | 8695 | C   | ILE | C | 722 | 49.096 | 63.039 | 4.737  | 1.00 | 94.25  | C |
| ATOM | 8696 | O   | ILE | C | 722 | 48.291 | 63.066 | 3.803  | 1.00 | 94.25  | C |
| ATOM | 8697 | N   | THR | C | 723 | 49.262 | 61.970 | 5.513  | 1.00 | 43.74  | C |
| ATOM | 8698 | CA  | THR | C | 723 | 48.533 | 60.734 | 5.236  | 1.00 | 43.74  | C |

```
ATOM   8699  CB  THR C 723      49.460  59.607   4.797  1.00100.07           C
ATOM   8700  OG1 THR C 723      50.769  60.127   4.545  1.00100.07           C
ATOM   8701  CG2 THR C 723      48.917  58.945   3.546  1.00100.07           C
ATOM   8702  C   THR C 723      47.776  60.173   6.391  1.00 43.74           C
ATOM   8703  O   THR C 723      48.185  60.305   7.534  1.00 43.74           C
ATOM   8704  N   ALA C 724      46.656  59.539   6.080  1.00 50.34           C
ATOM   8705  CA  ALA C 724      45.863  58.890   7.102  1.00 50.34           C
ATOM   8706  CB  ALA C 724      44.413  58.712   6.636  1.00 50.32           C
ATOM   8707  C   ALA C 724      46.568  57.544   7.218  1.00 50.34           C
ATOM   8708  O   ALA C 724      46.122  56.627   7.912  1.00 50.34           C
ATOM   8709  N   ASP C 725      47.696  57.459   6.518  1.00 53.08           C
ATOM   8710  CA  ASP C 725      48.536  56.277   6.467  1.00 53.08           C
ATOM   8711  CB  ASP C 725      49.102  56.129   5.048  1.00100.07           C
ATOM   8712  CG  ASP C 725      50.033  54.938   4.903  1.00100.07           C
ATOM   8713  OD1 ASP C 725      49.561  53.796   5.102  1.00100.07           C
ATOM   8714  OD2 ASP C 725      51.234  55.132   4.594  1.00100.07           C
ATOM   8715  C   ASP C 725      49.691  56.361   7.463  1.00 53.08           C
ATOM   8716  O   ASP C 725      50.802  55.937   7.169  1.00 53.08           C
ATOM   8717  N   ILE C 726      49.452  56.921   8.639  1.00 48.00           C
ATOM   8718  CA  ILE C 726      50.516  57.025   9.628  1.00 48.00           C
ATOM   8719  CB  ILE C 726      49.974  57.672  10.901  1.00 93.84           C
ATOM   8720  CG2 ILE C 726      50.552  56.995  12.117  1.00 99.59           C
ATOM   8721  CG1 ILE C 726      50.266  59.173  10.860  1.00 99.59           C
ATOM   8722  CD  ILE C 726      49.790  59.971  12.079  1.00100.07           C
ATOM   8723  C   ILE C 726      51.101  55.633   9.904  1.00 48.00           C
ATOM   8724  O   ILE C 726      50.374  54.640   9.985  1.00 48.00           C
ATOM   8725  N   PRO C 727      52.425  55.545  10.053  1.00 42.25           C
ATOM   8726  CD  PRO C 727      53.347  56.684  10.162  1.00 89.60           C
ATOM   8727  CA  PRO C 727      53.131  54.286  10.306  1.00 42.25           C
ATOM   8728  CB  PRO C 727      54.587  54.734  10.399  1.00100.07           C
ATOM   8729  CG  PRO C 727      54.460  56.102  10.995  1.00 89.60           C
ATOM   8730  C   PRO C 727      52.707  53.393  11.493  1.00 42.25           C
ATOM   8731  O   PRO C 727      51.525  53.315  11.844  1.00 42.25           C
ATOM   8732  N   HIS C 728      53.694  52.700  12.066  1.00 99.61           C
ATOM   8733  CA  HIS C 728      53.512  51.773  13.182  1.00 99.61           C
ATOM   8734  CB  HIS C 728      54.689  51.886  14.151  1.00100.07           C
ATOM   8735  CG  HIS C 728      56.011  51.538  13.541  1.00100.07           C
ATOM   8736  CD2 HIS C 728      57.214  52.156  13.596  1.00100.07           C
ATOM   8737  ND1 HIS C 728      56.205  50.392  12.798  1.00100.07           C
ATOM   8738  CE1 HIS C 728      57.474  50.326  12.421  1.00100.07           C
ATOM   8739  NE2 HIS C 728      58.104  51.385  12.896  1.00100.07           C
ATOM   8740  C   HIS C 728      52.209  51.944  13.941  1.00 99.61           C
ATOM   8741  O   HIS C 728      51.412  51.015  14.043  1.00 99.61           C
ATOM   8742  N   ALA C 729      51.998  53.141  14.483  1.00100.04           C
ATOM   8743  CA  ALA C 729      50.775  53.438  15.231  1.00100.04           C
ATOM   8744  CB  ALA C 729      50.808  54.870  15.754  1.00100.07           C
ATOM   8745  C   ALA C 729      49.558  53.247  14.343  1.00100.04           C
ATOM   8746  O   ALA C 729      48.578  53.977  14.446  1.00100.04           C
ATOM   8747  N   ALA C 730      49.646  52.266  13.453  1.00100.07           C
ATOM   8748  CA  ALA C 730      48.580  51.963  12.524  1.00100.07           C
ATOM   8749  CB  ALA C 730      49.024  50.880  11.571  1.00100.07           C
ATOM   8750  C   ALA C 730      47.324  51.535  13.276  1.00100.07           C
ATOM   8751  O   ALA C 730      46.266  51.364  12.685  1.00100.07           C
ATOM   8752  N   GLU C 731      47.454  51.373  14.589  1.00 61.05           C
ATOM   8753  CA  GLU C 731      46.358  50.965  15.472  1.00 61.05           C
ATOM   8754  CB  GLU C 731      46.572  51.602  16.847  1.00100.07           C
ATOM   8755  CG  GLU C 731      46.024  50.809  18.005  1.00100.07           C
ATOM   8756  CD  GLU C 731      47.123  50.340  18.945  1.00100.07           C
ATOM   8757  OE1 GLU C 731      47.665  51.174  19.707  1.00100.07           C
ATOM   8758  OE2 GLU C 731      47.456  49.131  18.912  1.00100.07           C
ATOM   8759  C   GLU C 731      45.005  51.376  14.916  1.00 61.05           C
ATOM   8760  O   GLU C 731      44.914  52.382  14.224  1.00 61.05           C
ATOM   8761  N   ALA C 732      43.957  50.628  15.223  1.00100.07           C
ATOM   8762  CA  ALA C 732      42.623  50.953  14.709  1.00100.07           C
ATOM   8763  CB  ALA C 732      41.683  49.751  14.917  1.00 79.24           C
ATOM   8764  C   ALA C 732      42.037  52.212  15.354  1.00100.07           C
ATOM   8765  O   ALA C 732      40.864  52.254  15.711  1.00100.07           C
ATOM   8766  N   ALA C 733      42.860  53.233  15.518  1.00 80.09           C
ATOM   8767  CA  ALA C 733      42.421  54.478  16.127  1.00 80.09           C
ATOM   8768  CB  ALA C 733      43.222  54.764  17.379  1.00100.07           C
ATOM   8769  C   ALA C 733      42.633  55.581  15.118  1.00 80.09           C
ATOM   8770  O   ALA C 733      41.900  56.560  15.086  1.00 80.09           C
ATOM   8771  N   LEU C 734      43.653  55.419  14.289  1.00 48.09           C
ATOM   8772  CA  LEU C 734      43.935  56.410  13.257  1.00 48.09           C
ATOM   8773  CB  LEU C 734      45.040  55.915  12.318  1.00100.07           C
ATOM   8774  CG  LEU C 734      46.317  55.365  12.942  1.00100.07           C
ATOM   8775  CD1 LEU C 734      47.075  54.626  11.852  1.00100.07           C
ATOM   8776  CD2 LEU C 734      47.182  56.491  13.542  1.00100.07           C
ATOM   8777  C   LEU C 734      42.663  56.621  12.448  1.00 48.09           C
ATOM   8778  O   LEU C 734      41.776  57.383  12.840  1.00 48.09           C
ATOM   8779  N   ARG C 735      42.590  55.924  11.317  1.00100.07           C
ATOM   8780  CA  ARG C 735      41.436  55.990  10.434  1.00100.07           C
ATOM   8781  CB  ARG C 735      41.520  54.876   9.365  1.00100.07           C
ATOM   8782  CG  ARG C 735      42.741  54.972   8.414  1.00100.07           C
```

```
ATOM   8783  CD   ARG C 735      42.943  53.698   7.548  1.00100.07           C
ATOM   8784  NE   ARG C 735      44.189  53.734   6.763  1.00100.07           C
ATOM   8785  CZ   ARG C 735      44.584  52.792   5.897  1.00100.07           C
ATOM   8786  NH1  ARG C 735      43.838  51.715   5.683  1.00100.07           C
ATOM   8787  NH2  ARG C 735      45.727  52.930   5.228  1.00100.07           C
ATOM   8788  C    ARG C 735      40.162  55.871  11.274  1.00100.07           C
ATOM   8789  O    ARG C 735      39.075  56.200  10.809  1.00100.07           C
ATOM   8790  N    ASP C 736      40.306  55.408  12.521  1.00 70.13           C
ATOM   8791  CA   ASP C 736      39.180  55.274  13.450  1.00 70.13           C
ATOM   8792  CB   ASP C 736      39.676  54.692  14.789  1.00100.07           C
ATOM   8793  CG   ASP C 736      38.570  54.566  15.854  1.00100.07           C
ATOM   8794  OD1  ASP C 736      38.027  55.608  16.288  1.00100.07           C
ATOM   8795  OD2  ASP C 736      38.251  53.429  16.273  1.00100.07           C
ATOM   8796  C    ASP C 736      38.622  56.679  13.625  1.00 70.13           C
ATOM   8797  O    ASP C 736      37.693  56.929  14.399  1.00 70.13           C
ATOM   8798  N    LEU C 737      39.224  57.582  12.866  1.00 26.72           C
ATOM   8799  CA   LEU C 737      38.901  58.998  12.798  1.00 26.72           C
ATOM   8800  CB   LEU C 737      39.105  59.688  14.158  1.00100.07           C
ATOM   8801  CG   LEU C 737      37.982  59.625  15.209  1.00 86.39           C
ATOM   8802  CD1  LEU C 737      38.380  60.286  16.522  1.00 86.39           C
ATOM   8803  CD2  LEU C 737      36.748  60.301  14.621  1.00 86.39           C
ATOM   8804  C    LEU C 737      39.971  59.432  11.796  1.00 26.72           C
ATOM   8805  O    LEU C 737      40.588  58.587  11.146  1.00 26.72           C
ATOM   8806  N    ALA C 738      40.223  60.726  11.658  1.00100.07           C
ATOM   8807  CA   ALA C 738      41.231  61.171  10.708  1.00100.07           C
ATOM   8808  CB   ALA C 738      42.596  60.643  11.117  1.00 53.72           C
ATOM   8809  C    ALA C 738      40.859  60.644   9.319  1.00100.07           C
ATOM   8810  O    ALA C 738      41.594  59.856   8.730  1.00100.07           C
ATOM   8811  N    GLU C 739      39.711  61.090   8.809  1.00 27.26           C
ATOM   8812  CA   GLU C 739      39.227  60.648   7.510  1.00 27.26           C
ATOM   8813  CB   GLU C 739      37.806  61.155   7.255  1.00100.07           C
ATOM   8814  CG   GLU C 739      37.751  62.594   6.741  1.00100.07           C
ATOM   8815  CD   GLU C 739      36.379  62.993   6.196  1.00100.07           C
ATOM   8816  OE1  GLU C 739      35.469  63.299   7.009  1.00100.07           C
ATOM   8817  OE2  GLU C 739      36.219  62.987   4.951  1.00100.07           C
ATOM   8818  C    GLU C 739      40.123  61.134   6.393  1.00 27.26           C
ATOM   8819  O    GLU C 739      40.191  62.336   6.129  1.00 27.26           C
ATOM   8820  N    GLU C 740      40.789  60.179   5.737  1.00 70.52           C
ATOM   8821  CA   GLU C 740      41.728  60.406   4.629  1.00 70.52           C
ATOM   8822  CB   GLU C 740      40.953  60.506   3.322  1.00100.07           C
ATOM   8823  CG   GLU C 740      40.329  59.186   2.956  1.00 99.90           C
ATOM   8824  CD   GLU C 740      39.561  59.240   1.664  1.00 99.90           C
ATOM   8825  OE1  GLU C 740      40.109  59.750   0.656  1.00 99.90           C
ATOM   8826  OE2  GLU C 740      38.406  58.760   1.656  1.00 99.90           C
ATOM   8827  C    GLU C 740      42.693  61.579   4.787  1.00 70.52           C
ATOM   8828  O    GLU C 740      43.906  61.383   4.874  1.00 70.52           C
ATOM   8829  N    GLY C 741      42.155  62.790   4.786  1.00100.07           C
ATOM   8830  CA   GLY C 741      42.969  63.973   4.980  1.00100.07           C
ATOM   8831  C    GLY C 741      43.075  64.250   6.468  1.00100.07           C
ATOM   8832  O    GLY C 741      43.345  65.378   6.917  1.00100.07           C
ATOM   8833  N    ILE C 742      42.812  63.207   7.240  1.00 70.03           C
ATOM   8834  CA   ILE C 742      42.901  63.285   8.680  1.00 70.03           C
ATOM   8835  CB   ILE C 742      44.371  63.393   9.077  1.00 63.79           C
ATOM   8836  CG2  ILE C 742      44.494  63.363  10.547  1.00 69.54           C
ATOM   8837  CG1  ILE C 742      45.155  62.201   8.527  1.00 69.54           C
ATOM   8838  CD   ILE C 742      45.330  62.194   7.030  1.00100.07           C
ATOM   8839  C    ILE C 742      42.099  64.413   9.363  1.00 70.03           C
ATOM   8840  O    ILE C 742      42.200  65.581   8.992  1.00 70.03           C
ATOM   8841  N    ALA C 743      41.331  64.021  10.390  1.00 64.34           C
ATOM   8842  CA   ALA C 743      40.479  64.896  11.201  1.00 64.34           C
ATOM   8843  CB   ALA C 743      41.138  66.259  11.397  1.00100.07           C
ATOM   8844  C    ALA C 743      39.131  65.051  10.520  1.00 64.34           C
ATOM   8845  O    ALA C 743      39.062  65.350   9.322  1.00 64.34           C
ATOM   8846  N    ALA C 744      38.060  64.819  11.272  1.00 94.10           C
ATOM   8847  CA   ALA C 744      36.700  64.940  10.744  1.00 94.10           C
ATOM   8848  CB   ALA C 744      36.043  63.565  10.627  1.00 89.11           C
ATOM   8849  C    ALA C 744      35.887  65.830  11.671  1.00 94.10           C
ATOM   8850  O    ALA C 744      36.208  65.957  12.850  1.00 94.10           C
ATOM   8851  N    ILE C 745      34.828  66.435  11.143  1.00 35.81           C
ATOM   8852  CA   ILE C 745      34.000  67.323  11.943  1.00 35.81           C
ATOM   8853  CB   ILE C 745      33.016  68.070  11.080  1.00 35.21           C
ATOM   8854  CG2  ILE C 745      32.377  69.193  11.881  1.00 35.21           C
ATOM   8855  CG1  ILE C 745      33.741  68.663   9.884  1.00 35.21           C
ATOM   8856  CD   ILE C 745      32.787  69.118   8.806  1.00 35.21           C
ATOM   8857  C    ILE C 745      33.212  66.623  13.039  1.00 35.81           C
ATOM   8858  O    ILE C 745      33.143  65.402  13.094  1.00 35.81           C
ATOM   8859  N    GLY C 746      32.614  67.419  13.915  1.00 31.59           C
ATOM   8860  CA   GLY C 746      31.840  66.877  15.006  1.00 31.59           C
ATOM   8861  C    GLY C 746      32.644  65.859  15.771  1.00 31.59           C
ATOM   8862  O    GLY C 746      32.188  65.317  16.771  1.00 31.59           C
ATOM   8863  N    ALA C 747      33.858  65.604  15.317  1.00 55.00           C
ATOM   8864  CA   ALA C 747      34.681  64.619  15.975  1.00 55.00           C
ATOM   8865  CB   ALA C 747      35.924  64.369  15.153  1.00 64.03           C
ATOM   8866  C    ALA C 747      35.061  65.029  17.392  1.00 55.00           C
```

```
ATOM   8867  O    ALA C 747      35.763  66.020  17.591  1.00 55.00           C
ATOM   8868  N    GLU C 748      34.589  64.270  18.377  1.00 20.56           C
ATOM   8869  CA   GLU C 748      34.923  64.553  19.767  1.00 20.56           C
ATOM   8870  CB   GLU C 748      33.974  63.782  20.687  1.00 57.88           C
ATOM   8871  CG   GLU C 748      34.306  63.851  22.156  1.00 57.88           C
ATOM   8872  CD   GLU C 748      35.313  62.802  22.565  1.00 57.88           C
ATOM   8873  OE1  GLU C 748      35.630  62.725  23.767  1.00 57.88           C
ATOM   8874  OE2  GLU C 748      35.787  62.047  21.689  1.00 57.88           C
ATOM   8875  C    GLU C 748      36.385  64.130  19.959  1.00 20.56           C
ATOM   8876  O    GLU C 748      36.742  62.985  19.702  1.00 20.56           C
ATOM   8877  N    VAL C 749      37.223  65.068  20.400  1.00 40.79           C
ATOM   8878  CA   VAL C 749      38.663  64.844  20.566  1.00 40.79           C
ATOM   8879  CB   VAL C 749      39.437  65.824  19.728  1.00 14.31           C
ATOM   8880  CG1  VAL C 749      40.899  65.652  19.996  1.00 14.31           C
ATOM   8881  CG2  VAL C 749      39.078  65.652  18.262  1.00 14.31           C
ATOM   8882  C    VAL C 749      39.240  64.983  21.963  1.00 40.79           C
ATOM   8883  O    VAL C 749      39.147  66.050  22.569  1.00 40.79           C
ATOM   8884  N    LYS C 750      39.891  63.925  22.440  1.00 31.19           C
ATOM   8885  CA   LYS C 750      40.512  63.899  23.773  1.00 31.19           C
ATOM   8886  CB   LYS C 750      40.345  62.511  24.401  1.00 99.75           C
ATOM   8887  CG   LYS C 750      39.318  61.629  23.698  1.00 99.75           C
ATOM   8888  CD   LYS C 750      39.797  60.179  23.585  1.00 99.75           C
ATOM   8889  CE   LYS C 750      38.861  59.333  22.726  1.00 99.75           C
ATOM   8890  NZ   LYS C 750      39.316  57.916  22.630  1.00 99.75           C
ATOM   8891  C    LYS C 750      41.999  64.184  23.561  1.00 31.19           C
ATOM   8892  O    LYS C 750      42.495  64.089  22.443  1.00 31.19           C
ATOM   8893  N    PRO C 751      42.735  64.520  24.627  1.00 51.92           C
ATOM   8894  CD   PRO C 751      42.445  64.330  26.057  1.00 76.09           C
ATOM   8895  CA   PRO C 751      44.157  64.799  24.435  1.00 51.92           C
ATOM   8896  CB   PRO C 751      44.612  65.182  25.831  1.00 76.09           C
ATOM   8897  CG   PRO C 751      43.839  64.232  26.664  1.00 76.09           C
ATOM   8898  C    PRO C 751      44.842  63.540  23.945  1.00 51.92           C
ATOM   8899  O    PRO C 751      44.493  62.439  24.379  1.00 51.92           C
ATOM   8900  N    GLY C 752      45.813  63.696  23.052  1.00 71.81           C
ATOM   8901  CA   GLY C 752      46.512  62.538  22.530  1.00 71.81           C
ATOM   8902  C    GLY C 752      46.007  62.142  21.155  1.00 71.81           C
ATOM   8903  O    GLY C 752      46.794  62.040  20.214  1.00 71.81           C
ATOM   8904  N    ASP C 753      44.700  61.920  21.033  1.00 39.11           C
ATOM   8905  CA   ASP C 753      44.095  61.540  19.758  1.00 39.11           C
ATOM   8906  CB   ASP C 753      42.607  61.923  19.743  1.00 68.10           C
ATOM   8907  CG   ASP C 753      41.815  61.300  20.893  1.00 68.10           C
ATOM   8908  OD1  ASP C 753      40.573  61.464  20.911  1.00 68.10           C
ATOM   8909  OD2  ASP C 753      42.424  60.656  21.774  1.00 68.10           C
ATOM   8910  C    ASP C 753      44.813  62.224  18.581  1.00 39.11           C
ATOM   8911  O    ASP C 753      45.092  63.425  18.619  1.00 39.11           C
ATOM   8912  N    ILE C 754      45.113  61.454  17.537  1.00 41.60           C
ATOM   8913  CA   ILE C 754      45.814  61.980  16.362  1.00 41.60           C
ATOM   8914  CB   ILE C 754      46.086  60.853  15.336  1.00 54.36           C
ATOM   8915  CG2  ILE C 754      47.123  61.297  14.333  1.00 54.36           C
ATOM   8916  CG1  ILE C 754      46.586  59.598  16.053  1.00 54.36           C
ATOM   8917  CD   ILE C 754      47.856  59.798  16.872  1.00 54.36           C
ATOM   8918  C    ILE C 754      44.987  63.069  15.688  1.00 41.60           C
ATOM   8919  O    ILE C 754      44.251  62.797  14.752  1.00 41.60           C
ATOM   8920  N    LEU C 755      45.109  64.304  16.160  1.00 11.80           C
ATOM   8921  CA   LEU C 755      44.338  65.410  15.589  1.00 11.80           C
ATOM   8922  CB   LEU C 755      44.839  66.744  16.140  1.00 51.18           C
ATOM   8923  CG   LEU C 755      43.886  67.928  16.001  1.00 51.18           C
ATOM   8924  CD1  LEU C 755      43.545  68.176  14.544  1.00 51.18           C
ATOM   8925  CD2  LEU C 755      42.634  67.635  16.799  1.00 51.18           C
ATOM   8926  C    LEU C 755      44.456  65.418  14.080  1.00 11.80           C
ATOM   8927  O    LEU C 755      43.465  65.547  13.386  1.00 11.80           C
ATOM   8928  N    VAL C 756      45.691  65.318  13.603  1.00 62.68           C
ATOM   8929  CA   VAL C 756      46.035  65.268  12.183  1.00 62.68           C
ATOM   8930  CB   VAL C 756      46.447  66.638  11.628  1.00  5.07           C
ATOM   8931  CG1  VAL C 756      47.100  66.509  10.256  1.00  5.07           C
ATOM   8932  CG2  VAL C 756      45.221  67.517  11.545  1.00  5.07           C
ATOM   8933  C    VAL C 756      47.234  64.350  12.172  1.00 62.68           C
ATOM   8934  O    VAL C 756      47.608  63.832  13.225  1.00 62.68           C
ATOM   8935  N    GLY C 757      47.843  64.131  11.015  1.00 37.71           C
ATOM   8936  CA   GLY C 757      48.997  63.259  11.003  1.00 37.71           C
ATOM   8937  C    GLY C 757      49.795  63.315   9.730  1.00 37.71           C
ATOM   8938  O    GLY C 757      49.238  63.477   8.643  1.00 37.71           C
ATOM   8939  N    ARG C 758      51.114  63.212   9.867  1.00 26.61           C
ATOM   8940  CA   ARG C 758      51.989  63.191   8.700  1.00 26.61           C
ATOM   8941  CB   ARG C 758      52.266  64.605   8.174  1.00 41.79           C
ATOM   8942  CG   ARG C 758      53.357  65.337   8.879  1.00 41.79           C
ATOM   8943  CD   ARG C 758      52.865  65.913  10.171  1.00 41.79           C
ATOM   8944  NE   ARG C 758      53.909  66.693  10.822  1.00 41.79           C
ATOM   8945  CZ   ARG C 758      54.637  67.606  10.198  1.00 41.79           C
ATOM   8946  NH1  ARG C 758      54.434  67.846   8.912  1.00 41.79           C
ATOM   8947  NH2  ARG C 758      55.562  68.276  10.860  1.00 41.79           C
ATOM   8948  C    ARG C 758      53.294  62.453   9.014  1.00 26.61           C
ATOM   8949  O    ARG C 758      53.518  62.009  10.145  1.00 26.61           C
ATOM   8950  N    THR C 759      54.145  62.308   8.005  1.00 62.22           C
```

```
ATOM   8951  CA  THR C 759      55.391  61.594   8.197  1.00 62.22           C
ATOM   8952  CB  THR C 759      55.285  60.171   7.655  1.00 75.33           C
ATOM   8953  OG1 THR C 759      56.565  59.535   7.760  1.00 75.33           C
ATOM   8954  CG2 THR C 759      54.833  60.190   6.193  1.00 75.33           C
ATOM   8955  C   THR C 759      56.632  62.219   7.578  1.00 62.22           C
ATOM   8956  O   THR C 759      56.592  62.767   6.474  1.00 62.22           C
ATOM   8957  N   SER C 760      57.736  62.111   8.309  1.00100.06           C
ATOM   8958  CA  SER C 760      59.032  62.611   7.878  1.00100.06           C
ATOM   8959  CB  SER C 760      59.641  63.501   8.964  1.00 57.66           C
ATOM   8960  OG  SER C 760      60.934  63.954   8.596  1.00 57.66           C
ATOM   8961  C   SER C 760      59.891  61.365   7.664  1.00100.06           C
ATOM   8962  O   SER C 760      59.889  60.460   8.502  1.00100.06           C
ATOM   8963  N   PHE C 761      60.614  61.312   6.546  1.00 19.65           C
ATOM   8964  CA  PHE C 761      61.449  60.151   6.238  1.00 19.65           C
ATOM   8965  CB  PHE C 761      62.065  60.286   4.846  1.00 64.09           C
ATOM   8966  CG  PHE C 761      61.064  60.404   3.744  1.00 64.09           C
ATOM   8967  CD1 PHE C 761      60.578  61.647   3.360  1.00 64.09           C
ATOM   8968  CD2 PHE C 761      60.612  59.270   3.080  1.00 64.09           C
ATOM   8969  CE1 PHE C 761      59.657  61.759   2.327  1.00 64.09           C
ATOM   8970  CE2 PHE C 761      59.689  59.368   2.044  1.00 64.09           C
ATOM   8971  CZ  PHE C 761      59.210  60.614   1.665  1.00 64.09           C
ATOM   8972  C   PHE C 761      62.573  59.870   7.239  1.00 19.65           C
ATOM   8973  O   PHE C 761      62.848  58.709   7.544  1.00 19.65           C
ATOM   8974  N   LYS C 762      63.213  60.934   7.725  1.00 68.08           C
ATOM   8975  CA  LYS C 762      64.326  60.842   8.672  1.00 68.08           C
ATOM   8976  CB  LYS C 762      63.854  61.093  10.111  1.00 70.03           C
ATOM   8977  CG  LYS C 762      63.351  62.504  10.408  1.00 70.03           C
ATOM   8978  CD  LYS C 762      63.369  62.783  11.914  1.00 70.03           C
ATOM   8979  CE  LYS C 762      62.080  63.432  12.393  1.00 70.03           C
ATOM   8980  NZ  LYS C 762      60.919  62.500  12.312  1.00 70.03           C
ATOM   8981  C   LYS C 762      65.037  59.496   8.619  1.00 68.08           C
ATOM   8982  O   LYS C 762      64.486  58.480   9.044  1.00 68.08           C
ATOM   8983  N   GLY C 763      66.268  59.491   8.114  1.00 34.35           C
ATOM   8984  CA  GLY C 763      67.006  58.244   8.024  1.00 34.35           C
ATOM   8985  C   GLY C 763      68.279  58.187   8.839  1.00 34.35           C
ATOM   8986  O   GLY C 763      69.294  57.725   8.335  1.00 34.35           C
ATOM   8987  N   GLU C 764      68.222  58.627  10.095  1.00100.04           C
ATOM   8988  CA  GLU C 764      69.389  58.632  10.986  1.00100.04           C
ATOM   8989  CB  GLU C 764      68.971  58.866  12.448  1.00100.07           C
ATOM   8990  CG  GLU C 764      68.110  60.104  12.728  1.00100.07           C
ATOM   8991  CD  GLU C 764      66.668  59.962  12.242  1.00100.07           C
ATOM   8992  OE1 GLU C 764      66.406  60.235  11.050  1.00100.07           C
ATOM   8993  OE2 GLU C 764      65.800  59.568  13.053  1.00100.07           C
ATOM   8994  C   GLU C 764      70.207  57.340  10.929  1.00100.04           C
ATOM   8995  O   GLU C 764      71.391  57.343  11.271  1.00100.04           C
ATOM   8996  N   GLN C 765      69.572  56.244  10.513  1.00 88.05           C
ATOM   8997  CA  GLN C 765      70.240  54.946  10.421  1.00 88.05           C
ATOM   8998  CB  GLN C 765      70.082  54.182  11.734  1.00100.07           C
ATOM   8999  CG  GLN C 765      70.803  54.838  12.897  1.00100.07           C
ATOM   9000  CD  GLN C 765      70.537  54.154  14.225  1.00100.07           C
ATOM   9001  OE1 GLN C 765      70.681  52.934  14.349  1.00100.07           C
ATOM   9002  NE2 GLN C 765      70.158  54.941  15.232  1.00100.07           C
ATOM   9003  C   GLN C 765      69.714  54.094   9.274  1.00 88.05           C
ATOM   9004  O   GLN C 765      68.770  54.480   8.581  1.00 88.05           C
ATOM   9005  N   GLU C 766      70.338  52.934   9.085  1.00100.07           C
ATOM   9006  CA  GLU C 766      69.964  51.995   8.028  1.00100.07           C
ATOM   9007  CB  GLU C 766      70.875  52.189   6.815  1.00 99.76           C
ATOM   9008  CG  GLU C 766      70.973  53.643   6.359  1.00 99.76           C
ATOM   9009  CD  GLU C 766      71.499  53.793   4.942  1.00 99.76           C
ATOM   9010  OE1 GLU C 766      71.672  54.948   4.497  1.00 99.76           C
ATOM   9011  OE2 GLU C 766      71.731  52.762   4.273  1.00 99.76           C
ATOM   9012  C   GLU C 766      70.100  50.572   8.568  1.00100.07           C
ATOM   9013  O   GLU C 766      71.176  50.181   9.027  1.00100.07           C
ATOM   9014  N   PRO C 767      69.019  49.767   8.490  1.00 98.58           C
ATOM   9015  CD  PRO C 767      67.808  49.957   7.672  1.00 32.75           C
ATOM   9016  CA  PRO C 767      69.087  48.394   9.008  1.00 98.58           C
ATOM   9017  CB  PRO C 767      67.760  47.766   8.555  1.00 32.75           C
ATOM   9018  CG  PRO C 767      67.411  48.524   7.338  1.00 32.75           C
ATOM   9019  C   PRO C 767      70.289  47.564   8.599  1.00 98.58           C
ATOM   9020  O   PRO C 767      70.335  47.023   7.496  1.00 98.58           C
ATOM   9021  N   SER C 768      71.270  47.484   9.495  1.00 27.79           C
ATOM   9022  CA  SER C 768      72.448  46.669   9.247  1.00 27.79           C
ATOM   9023  CB  SER C 768      73.363  46.679  10.466  1.00 46.09           C
ATOM   9024  OG  SER C 768      72.821  45.857  11.485  1.00 46.09           C
ATOM   9025  C   SER C 768      71.829  45.283   9.110  1.00 27.79           C
ATOM   9026  O   SER C 768      70.766  45.033   9.678  1.00 27.79           C
ATOM   9027  N   PRO C 769      72.473  44.362   8.375  1.00 38.14           C
ATOM   9028  CD  PRO C 769      73.871  44.382   7.919  1.00 71.74           C
ATOM   9029  CA  PRO C 769      71.892  43.019   8.229  1.00 38.14           C
ATOM   9030  CB  PRO C 769      73.041  42.207   7.635  1.00 71.74           C
ATOM   9031  CG  PRO C 769      74.270  42.950   8.112  1.00 71.74           C
ATOM   9032  C   PRO C 769      71.394  42.452   9.558  1.00 38.14           C
ATOM   9033  O   PRO C 769      71.317  43.166  10.559  1.00 38.14           C
ATOM   9034  N   GLU C 770      71.086  41.163   9.588  1.00 70.11           C
```

```
ATOM   9035  CA  GLU C 770      70.572  40.565  10.813  1.00 70.11           C
ATOM   9036  CB  GLU C 770      71.501  40.817  12.006  1.00100.07           C
ATOM   9037  CG  GLU C 770      72.966  40.478  11.799  1.00100.07           C
ATOM   9038  CD  GLU C 770      73.769  41.638  11.242  1.00100.07           C
ATOM   9039  OE1 GLU C 770      73.574  42.781  11.714  1.00100.07           C
ATOM   9040  OE2 GLU C 770      74.607  41.401  10.345  1.00100.07           C
ATOM   9041  C   GLU C 770      69.265  41.298  11.049  1.00 70.11           C
ATOM   9042  O   GLU C 770      68.221  40.874  10.571  1.00 70.11           C
ATOM   9043  N   GLU C 771      69.334  42.410  11.778  1.00 44.18           C
ATOM   9044  CA  GLU C 771      68.155  43.222  12.051  1.00 44.18           C
ATOM   9045  CB  GLU C 771      68.580  44.532  12.721  1.00100.07           C
ATOM   9046  CG  GLU C 771      67.529  45.183  13.618  1.00100.07           C
ATOM   9047  CD  GLU C 771      66.710  46.262  12.914  1.00100.07           C
ATOM   9048  OE1 GLU C 771      65.912  45.918  12.011  1.00100.07           C
ATOM   9049  OE2 GLU C 771      66.866  47.458  13.265  1.00100.07           C
ATOM   9050  C   GLU C 771      67.503  43.479  10.682  1.00 44.18           C
ATOM   9051  O   GLU C 771      66.282  43.371  10.514  1.00 44.18           C
ATOM   9052  N   ARG C 772      68.328  43.798   9.692  1.00 35.17           C
ATOM   9053  CA  ARG C 772      67.809  44.029   8.356  1.00 35.17           C
ATOM   9054  CB  ARG C 772      68.928  44.482   7.414  1.00100.07           C
ATOM   9055  CG  ARG C 772      68.529  44.489   5.941  1.00100.07           C
ATOM   9056  CD  ARG C 772      69.583  45.128   5.035  1.00100.07           C
ATOM   9057  NE  ARG C 772      69.532  46.591   5.042  1.00100.07           C
ATOM   9058  CZ  ARG C 772      68.457  47.315   4.734  1.00100.07           C
ATOM   9059  NH1 ARG C 772      67.316  46.725   4.395  1.00100.07           C
ATOM   9060  NH2 ARG C 772      68.524  48.640   4.750  1.00100.07           C
ATOM   9061  C   ARG C 772      67.229  42.703   7.882  1.00 35.17           C
ATOM   9062  O   ARG C 772      66.147  42.653   7.295  1.00 35.17           C
ATOM   9063  N   LEU C 773      67.958  41.628   8.152  1.00 84.17           C
ATOM   9064  CA  LEU C 773      67.521  40.294   7.769  1.00 84.17           C
ATOM   9065  CB  LEU C 773      68.610  39.271   8.089  1.00 54.45           C
ATOM   9066  CG  LEU C 773      68.142  37.826   8.307  1.00 54.45           C
ATOM   9067  CD1 LEU C 773      67.332  37.321   7.119  1.00 54.45           C
ATOM   9068  CD2 LEU C 773      69.362  36.960   8.534  1.00 54.45           C
ATOM   9069  C   LEU C 773      66.229  39.886   8.468  1.00 84.17           C
ATOM   9070  O   LEU C 773      65.241  39.552   7.810  1.00 84.17           C
ATOM   9071  N   LEU C 774      66.248  39.900   9.800  1.00 74.93           C
ATOM   9072  CA  LEU C 774      65.081  39.523  10.583  1.00 74.93           C
ATOM   9073  CB  LEU C 774      65.252  39.885  12.057  1.00 69.96           C
ATOM   9074  CG  LEU C 774      66.088  38.975  12.955  1.00 69.96           C
ATOM   9075  CD1 LEU C 774      67.569  39.139  12.642  1.00 69.96           C
ATOM   9076  CD2 LEU C 774      65.807  39.328  14.417  1.00 69.96           C
ATOM   9077  C   LEU C 774      63.845  40.212  10.072  1.00 74.93           C
ATOM   9078  O   LEU C 774      62.747  39.698  10.238  1.00 74.93           C
ATOM   9079  N   ARG C 775      64.025  41.377   9.455  1.00 99.83           C
ATOM   9080  CA  ARG C 775      62.910  42.159   8.923  1.00 99.83           C
ATOM   9081  CB  ARG C 775      63.440  43.481   8.381  1.00 74.88           C
ATOM   9082  CG  ARG C 775      63.789  44.488   9.469  1.00 74.88           C
ATOM   9083  CD  ARG C 775      62.532  45.102  10.047  1.00 74.88           C
ATOM   9084  NE  ARG C 775      62.829  46.227  10.921  1.00 74.88           C
ATOM   9085  CZ  ARG C 775      61.900  47.007  11.457  1.00 74.88           C
ATOM   9086  NH1 ARG C 775      60.615  46.781  11.202  1.00 74.88           C
ATOM   9087  NH2 ARG C 775      62.253  48.011  12.249  1.00 74.88           C
ATOM   9088  C   ARG C 775      62.082  41.428   7.860  1.00 99.83           C
ATOM   9089  O   ARG C 775      60.876  41.661   7.722  1.00 99.83           C
ATOM   9090  N   SER C 776      62.735  40.547   7.107  1.00 43.10           C
ATOM   9091  CA  SER C 776      62.043  39.760   6.095  1.00 43.10           C
ATOM   9092  CB  SER C 776      63.003  38.720   5.505  1.00 84.13           C
ATOM   9093  OG  SER C 776      63.794  38.110   6.513  1.00 84.13           C
ATOM   9094  C   SER C 776      60.858  39.077   6.779  1.00 43.10           C
ATOM   9095  O   SER C 776      59.745  39.099   6.273  1.00 43.10           C
ATOM   9096  N   ILE C 777      61.137  38.493   7.943  1.00 80.96           C
ATOM   9097  CA  ILE C 777      60.172  37.793   8.796  1.00 80.96           C
ATOM   9098  CB  ILE C 777      60.761  37.617  10.230  1.00 54.14           C
ATOM   9099  CG2 ILE C 777      59.788  36.854  11.139  1.00 54.14           C
ATOM   9100  CG1 ILE C 777      62.153  36.972  10.130  1.00 54.14           C
ATOM   9101  CD  ILE C 777      62.361  36.078   8.908  1.00 54.14           C
ATOM   9102  C   ILE C 777      58.839  38.528   8.903  1.00 80.96           C
ATOM   9103  O   ILE C 777      58.447  38.986   9.982  1.00 80.96           C
ATOM   9104  N   PHE C 778      58.145  38.621   7.775  1.00100.07           C
ATOM   9105  CA  PHE C 778      56.852  39.286   7.687  1.00100.07           C
ATOM   9106  CB  PHE C 778      55.840  38.638   8.640  1.00100.07           C
ATOM   9107  CG  PHE C 778      55.982  37.140   8.774  1.00100.07           C
ATOM   9108  CD1 PHE C 778      56.525  36.583   9.936  1.00100.07           C
ATOM   9109  CD2 PHE C 778      55.552  36.283   7.756  1.00100.07           C
ATOM   9110  CE1 PHE C 778      56.635  35.197  10.086  1.00100.07           C
ATOM   9111  CE2 PHE C 778      55.658  34.891   7.896  1.00100.07           C
ATOM   9112  CZ  PHE C 778      56.200  34.349   9.063  1.00100.07           C
ATOM   9113  C   PHE C 778      56.949  40.775   8.013  1.00100.07           C
ATOM   9114  O   PHE C 778      56.220  41.589   7.443  1.00100.07           C
ATOM   9115  N   GLY C 779      57.852  41.124   8.927  1.00 53.09           C
ATOM   9116  CA  GLY C 779      58.005  42.512   9.334  1.00 53.09           C
ATOM   9117  C   GLY C 779      58.845  43.371   8.410  1.00 53.09           C
ATOM   9118  O   GLY C 779      59.991  43.710   8.732  1.00 53.09           C
```

```
ATOM   9119  N   GLU C 780      58.259  43.739   7.272  1.00 55.93           C
ATOM   9120  CA  GLU C 780      58.934  44.554   6.263  1.00 55.93           C
ATOM   9121  CB  GLU C 780      57.924  45.069   5.234  1.00100.07           C
ATOM   9122  CG  GLU C 780      57.068  43.982   4.592  1.00100.07           C
ATOM   9123  CD  GLU C 780      56.017  44.547   3.642  1.00100.07           C
ATOM   9124  OE1 GLU C 780      56.380  44.984   2.524  1.00100.07           C
ATOM   9125  OE2 GLU C 780      54.824  44.562   4.022  1.00100.07           C
ATOM   9126  C   GLU C 780      59.645  45.734   6.902  1.00 55.93           C
ATOM   9127  O   GLU C 780      59.339  46.105   8.035  1.00 55.93           C
ATOM   9128  N   LYS C 781      60.601  46.310   6.178  1.00 99.18           C
ATOM   9129  CA  LYS C 781      61.345  47.460   6.680  1.00 99.18           C
ATOM   9130  CB  LYS C 781      62.604  47.687   5.843  1.00 85.95           C
ATOM   9131  CG  LYS C 781      62.312  47.909   4.368  1.00 85.95           C
ATOM   9132  CD  LYS C 781      63.511  48.493   3.628  1.00 85.95           C
ATOM   9133  CE  LYS C 781      63.151  48.856   2.188  1.00 85.95           C
ATOM   9134  NZ  LYS C 781      64.235  49.605   1.491  1.00 85.95           C
ATOM   9135  C   LYS C 781      60.424  48.667   6.563  1.00 99.18           C
ATOM   9136  O   LYS C 781      59.351  48.561   5.972  1.00 99.18           C
ATOM   9137  N   ALA C 782      60.832  49.805   7.121  1.00 56.09           C
ATOM   9138  CA  ALA C 782      60.020  51.025   7.058  1.00 56.09           C
ATOM   9139  CB  ALA C 782      59.096  51.108   8.278  1.00 99.75           C
ATOM   9140  C   ALA C 782      60.882  52.288   6.961  1.00 56.09           C
ATOM   9141  O   ALA C 782      62.115  52.222   7.040  1.00 56.09           C
ATOM   9142  N   ARG C 783      60.225  53.435   6.786  1.00 97.54           C
ATOM   9143  CA  ARG C 783      60.916  54.724   6.665  1.00 97.54           C
ATOM   9144  CB  ARG C 783      61.433  54.909   5.223  1.00 86.06           C
ATOM   9145  CG  ARG C 783      60.639  54.163   4.122  1.00 86.06           C
ATOM   9146  CD  ARG C 783      59.209  54.695   3.917  1.00 86.06           C
ATOM   9147  NE  ARG C 783      58.446  53.884   2.961  1.00 86.06           C
ATOM   9148  CZ  ARG C 783      57.262  54.217   2.447  1.00 86.06           C
ATOM   9149  NH1 ARG C 783      56.674  55.359   2.782  1.00 86.06           C
ATOM   9150  NH2 ARG C 783      56.663  53.402   1.589  1.00 86.06           C
ATOM   9151  C   ARG C 783      60.062  55.935   7.061  1.00 97.54           C
ATOM   9152  O   ARG C 783      60.210  57.009   6.481  1.00 97.54           C
ATOM   9153  N   ASP C 784      59.197  55.777   8.062  1.00100.07           C
ATOM   9154  CA  ASP C 784      58.322  56.872   8.473  1.00100.07           C
ATOM   9155  CB  ASP C 784      57.030  56.792   7.685  1.00 39.87           C
ATOM   9156  CG  ASP C 784      57.251  56.947   6.216  1.00 39.87           C
ATOM   9157  OD1 ASP C 784      57.775  58.004   5.813  1.00 39.87           C
ATOM   9158  OD2 ASP C 784      56.907  56.017   5.461  1.00 39.87           C
ATOM   9159  C   ASP C 784      57.966  57.008   9.951  1.00100.07           C
ATOM   9160  O   ASP C 784      57.837  56.017  10.677  1.00100.07           C
ATOM   9161  N   VAL C 785      57.777  58.258  10.370  1.00 78.78           C
ATOM   9162  CA  VAL C 785      57.421  58.592  11.746  1.00 78.78           C
ATOM   9163  CB  VAL C 785      58.449  59.563  12.369  1.00 99.50           C
ATOM   9164  CG1 VAL C 785      58.043  59.913  13.798  1.00 99.50           C
ATOM   9165  CG2 VAL C 785      59.836  58.950  12.331  1.00 99.50           C
ATOM   9166  C   VAL C 785      56.062  59.286  11.753  1.00 78.78           C
ATOM   9167  O   VAL C 785      55.799  60.156  10.922  1.00 78.78           C
ATOM   9168  N   LYS C 786      55.192  58.904  12.680  1.00 99.29           C
ATOM   9169  CA  LYS C 786      53.886  59.542  12.749  1.00 99.29           C
ATOM   9170  CB  LYS C 786      52.964  58.786  13.692  1.00100.07           C
ATOM   9171  CG  LYS C 786      53.517  58.643  15.076  1.00100.07           C
ATOM   9172  CD  LYS C 786      52.894  57.448  15.740  1.00100.07           C
ATOM   9173  CE  LYS C 786      53.713  56.992  16.927  1.00100.07           C
ATOM   9174  NZ  LYS C 786      53.301  55.634  17.397  1.00100.07           C
ATOM   9175  C   LYS C 786      54.135  60.919  13.301  1.00 99.29           C
ATOM   9176  O   LYS C 786      55.175  61.153  13.909  1.00 99.29           C
ATOM   9177  N   ASP C 787      53.198  61.833  13.078  1.00 89.06           C
ATOM   9178  CA  ASP C 787      53.341  63.188  13.598  1.00 89.06           C
ATOM   9179  CB  ASP C 787      54.167  64.066  12.644  1.00 38.50           C
ATOM   9180  CG  ASP C 787      55.542  63.479  12.340  1.00 38.50           C
ATOM   9181  OD1 ASP C 787      56.297  63.133  13.268  1.00 38.50           C
ATOM   9182  OD2 ASP C 787      55.876  63.371  11.153  1.00 38.50           C
ATOM   9183  C   ASP C 787      51.972  63.810  13.842  1.00 89.06           C
ATOM   9184  O   ASP C 787      50.956  63.307  13.363  1.00 89.06           C
ATOM   9185  N   THR C 788      51.970  64.906  14.594  1.00 72.43           C
ATOM   9186  CA  THR C 788      50.760  65.636  14.976  1.00 72.43           C
ATOM   9187  CB  THR C 788      49.879  66.033  13.783  1.00100.04           C
ATOM   9188  OG1 THR C 788      50.675  66.665  12.772  1.00100.04           C
ATOM   9189  CG2 THR C 788      48.781  67.000  14.259  1.00100.04           C
ATOM   9190  C   THR C 788      49.903  64.786  15.891  1.00 72.43           C
ATOM   9191  O   THR C 788      50.010  63.563  15.883  1.00 72.43           C
ATOM   9192  N   SER C 789      49.046  65.449  16.660  1.00 45.06           C
ATOM   9193  CA  SER C 789      48.144  64.809  17.625  1.00 45.06           C
ATOM   9194  CB  SER C 789      48.863  63.754  18.482  1.00 50.11           C
ATOM   9195  OG  SER C 789      48.895  62.472  17.880  1.00 50.11           C
ATOM   9196  C   SER C 789      47.709  65.935  18.541  1.00 45.06           C
ATOM   9197  O   SER C 789      48.369  66.977  18.590  1.00 45.06           C
ATOM   9198  N   LEU C 790      46.629  65.722  19.288  1.00 18.16           C
ATOM   9199  CA  LEU C 790      46.110  66.753  20.196  1.00 18.16           C
ATOM   9200  CB  LEU C 790      44.639  66.504  20.513  1.00 17.00           C
ATOM   9201  CG  LEU C 790      44.249  67.121  21.841  1.00 17.00           C
ATOM   9202  CD1 LEU C 790      44.518  68.596  21.829  1.00 17.00           C
```

```
ATOM   9203  CD2 LEU C 790      42.808  66.858  22.074  1.00 17.00           C
ATOM   9204  C   LEU C 790      46.861  66.966  21.504  1.00 18.16           C
ATOM   9205  O   LEU C 790      47.034  66.049  22.304  1.00 18.16           C
ATOM   9206  N   ARG C 791      47.240  68.224  21.709  1.00 45.09           C
ATOM   9207  CA  ARG C 791      47.989  68.664  22.868  1.00 45.09           C
ATOM   9208  CB  ARG C 791      47.940  70.194  22.993  1.00100.07           C
ATOM   9209  CG  ARG C 791      49.028  70.752  23.909  1.00100.07           C
ATOM   9210  CD  ARG C 791      48.640  72.069  24.570  1.00100.07           C
ATOM   9211  NE  ARG C 791      49.497  72.357  25.724  1.00100.07           C
ATOM   9212  CZ  ARG C 791      49.251  73.300  26.632  1.00100.07           C
ATOM   9213  NH1 ARG C 791      48.166  74.064  26.527  1.00100.07           C
ATOM   9214  NH2 ARG C 791      50.082  73.466  27.658  1.00100.07           C
ATOM   9215  C   ARG C 791      47.519  68.031  24.166  1.00 45.09           C
ATOM   9216  O   ARG C 791      46.558  67.268  24.189  1.00 45.09           C
ATOM   9217  N   VAL C 792      48.233  68.358  25.238  1.00 24.83           C
ATOM   9218  CA  VAL C 792      47.964  67.870  26.575  1.00 24.83           C
ATOM   9219  CB  VAL C 792      49.249  67.941  27.404  1.00 55.01           C
ATOM   9220  CG1 VAL C 792      50.257  66.956  26.857  1.00 55.01           C
ATOM   9221  CG2 VAL C 792      49.842  69.339  27.327  1.00 55.01           C
ATOM   9222  C   VAL C 792      46.857  68.720  27.213  1.00 24.83           C
ATOM   9223  O   VAL C 792      46.885  69.949  27.164  1.00 24.83           C
ATOM   9224  N   PRO C 793      45.888  68.075  27.865  1.00 61.06           C
ATOM   9225  CD  PRO C 793      46.311  66.994  28.776  1.00100.07           C
ATOM   9226  CA  PRO C 793      44.779  68.793  28.491  1.00 61.06           C
ATOM   9227  CB  PRO C 793      45.286  68.961  29.911  1.00100.07           C
ATOM   9228  CG  PRO C 793      45.859  67.531  30.169  1.00100.07           C
ATOM   9229  C   PRO C 793      44.210  70.085  27.871  1.00 61.06           C
ATOM   9230  O   PRO C 793      44.005  71.074  28.576  1.00 61.06           C
ATOM   9231  N   PRO C 794      43.953  70.087  26.545  1.00 99.26           C
ATOM   9232  CD  PRO C 794      44.723  69.290  25.576  1.00100.07           C
ATOM   9233  CA  PRO C 794      43.401  71.238  25.831  1.00 99.26           C
ATOM   9234  CB  PRO C 794      44.583  71.695  25.006  1.00100.07           C
ATOM   9235  CG  PRO C 794      45.126  70.353  24.516  1.00100.07           C
ATOM   9236  C   PRO C 794      42.272  70.695  24.945  1.00 99.26           C
ATOM   9237  O   PRO C 794      41.624  71.427  24.192  1.00 99.26           C
ATOM   9238  N   GLY C 795      42.073  69.385  25.038  1.00 46.52           C
ATOM   9239  CA  GLY C 795      41.042  68.728  24.269  1.00 46.52           C
ATOM   9240  C   GLY C 795      39.761  68.629  25.070  1.00 46.52           C
ATOM   9241  O   GLY C 795      38.771  69.258  24.689  1.00 46.52           C
ATOM   9242  N   GLU C 796      39.788  67.849  26.166  1.00 75.64           C
ATOM   9243  CA  GLU C 796      38.645  67.628  27.083  1.00 75.64           C
ATOM   9244  CB  GLU C 796      38.259  68.942  27.779  1.00 79.10           C
ATOM   9245  CG  GLU C 796      37.040  68.851  28.699  1.00 79.10           C
ATOM   9246  CD  GLU C 796      36.127  70.067  28.592  1.00 79.10           C
ATOM   9247  OE1 GLU C 796      35.550  70.280  27.504  1.00 79.10           C
ATOM   9248  OE2 GLU C 796      35.987  70.806  29.592  1.00 79.10           C
ATOM   9249  C   GLU C 796      37.408  67.059  26.385  1.00 75.64           C
ATOM   9250  O   GLU C 796      36.369  66.824  27.007  1.00 75.64           C
ATOM   9251  N   GLY C 797      37.542  66.823  25.088  1.00100.07           C
ATOM   9252  CA  GLY C 797      36.433  66.329  24.303  1.00100.07           C
ATOM   9253  C   GLY C 797      36.133  67.432  23.312  1.00100.07           C
ATOM   9254  O   GLY C 797      34.996  67.614  22.877  1.00100.07           C
ATOM   9255  N   GLY C 798      37.171  68.191  22.972  1.00 29.78           C
ATOM   9256  CA  GLY C 798      36.997  69.269  22.031  1.00 29.78           C
ATOM   9257  C   GLY C 798      36.429  68.635  20.786  1.00 29.78           C
ATOM   9258  O   GLY C 798      37.158  68.067  19.975  1.00 29.78           C
ATOM   9259  N   ILE C 799      35.120  68.709  20.626  1.00 45.20           C
ATOM   9260  CA  ILE C 799      34.511  68.100  19.463  1.00 45.20           C
ATOM   9261  CB  ILE C 799      32.993  67.954  19.686  1.00 36.50           C
ATOM   9262  CG2 ILE C 799      32.731  67.156  20.966  1.00 36.50           C
ATOM   9263  CG1 ILE C 799      32.348  69.319  19.871  1.00 36.50           C
ATOM   9264  CD  ILE C 799      30.922  69.207  20.278  1.00 36.50           C
ATOM   9265  C   ILE C 799      34.819  68.880  18.179  1.00 45.20           C
ATOM   9266  O   ILE C 799      34.157  69.862  17.865  1.00 45.20           C
ATOM   9267  N   VAL C 800      35.844  68.434  17.455  1.00 35.42           C
ATOM   9268  CA  VAL C 800      36.278  69.056  16.204  1.00 35.42           C
ATOM   9269  CB  VAL C 800      36.891  68.007  15.264  1.00 28.90           C
ATOM   9270  CG1 VAL C 800      36.999  68.569  13.853  1.00 28.90           C
ATOM   9271  CG2 VAL C 800      38.269  67.608  15.779  1.00 28.90           C
ATOM   9272  C   VAL C 800      35.167  69.790  15.466  1.00 35.42           C
ATOM   9273  O   VAL C 800      34.279  69.170  14.903  1.00 35.42           C
ATOM   9274  N   VAL C 801      35.249  71.115  15.448  1.00 28.85           C
ATOM   9275  CA  VAL C 801      34.231  71.940  14.826  1.00 28.85           C
ATOM   9276  CB  VAL C 801      34.009  73.238  15.588  1.00 19.72           C
ATOM   9277  CG1 VAL C 801      32.615  73.732  15.314  1.00 19.72           C
ATOM   9278  CG2 VAL C 801      34.265  73.050  17.067  1.00 19.72           C
ATOM   9279  C   VAL C 801      34.520  72.371  13.414  1.00 28.85           C
ATOM   9280  O   VAL C 801      33.670  72.998  12.779  1.00 28.85           C
ATOM   9281  N   GLY C 802      35.714  72.086  12.918  1.00 80.75           C
ATOM   9282  CA  GLY C 802      36.017  72.494  11.562  1.00 80.75           C
ATOM   9283  C   GLY C 802      37.467  72.315  11.193  1.00 80.75           C
ATOM   9284  O   GLY C 802      38.331  72.198  12.063  1.00 80.75           C
ATOM   9285  N   ARG C 803      37.733  72.292   9.893  1.00 20.60           C
ATOM   9286  CA  ARG C 803      39.095  72.133   9.399  1.00 20.60           C
```

```
ATOM   9287  CB  ARG C 803      39.365  70.656   9.057  1.00100.07           C
ATOM   9288  CG  ARG C 803      38.142  69.883   8.562  1.00100.07           C
ATOM   9289  CD  ARG C 803      38.180  69.580   7.062  1.00100.07           C
ATOM   9290  NE  ARG C 803      36.883  69.820   6.424  1.00100.07           C
ATOM   9291  CZ  ARG C 803      36.583  69.500   5.168  1.00100.07           C
ATOM   9292  NH1 ARG C 803      37.484  68.911   4.389  1.00100.07           C
ATOM   9293  NH2 ARG C 803      35.385  69.790   4.682  1.00100.07           C
ATOM   9294  C   ARG C 803      39.288  73.025   8.179  1.00 20.60           C
ATOM   9295  O   ARG C 803      38.327  73.363   7.488  1.00 20.60           C
ATOM   9296  N   LEU C 804      40.525  73.444   7.949  1.00 50.03           C
ATOM   9297  CA  LEU C 804      40.863  74.271   6.801  1.00 50.03           C
ATOM   9298  CB  LEU C 804      41.066  75.731   7.196  1.00 45.33           C
ATOM   9299  CG  LEU C 804      41.890  76.518   6.166  1.00 45.33           C
ATOM   9300  CD1 LEU C 804      41.250  76.369   4.799  1.00 45.33           C
ATOM   9301  CD2 LEU C 804      41.997  77.994   6.554  1.00 45.33           C
ATOM   9302  C   LEU C 804      42.160  73.724   6.243  1.00 50.03           C
ATOM   9303  O   LEU C 804      43.031  73.265   6.991  1.00 50.03           C
ATOM   9304  N   ARG C 805      42.292  73.777   4.928  1.00 57.38           C
ATOM   9305  CA  ARG C 805      43.481  73.265   4.291  1.00 57.38           C
ATOM   9306  CB  ARG C 805      43.224  71.858   3.758  1.00100.02           C
ATOM   9307  CG  ARG C 805      42.202  71.780   2.619  1.00100.02           C
ATOM   9308  CD  ARG C 805      40.873  72.462   2.962  1.00100.02           C
ATOM   9309  NE  ARG C 805      39.797  72.075   2.047  1.00100.02           C
ATOM   9310  CZ  ARG C 805      38.539  72.506   2.131  1.00100.02           C
ATOM   9311  NH1 ARG C 805      38.177  73.354   3.089  1.00100.02           C
ATOM   9312  NH2 ARG C 805      37.637  72.072   1.261  1.00100.02           C
ATOM   9313  C   ARG C 805      43.879  74.155   3.153  1.00 57.38           C
ATOM   9314  O   ARG C 805      43.126  74.318   2.196  1.00 57.38           C
ATOM   9315  N   LEU C 806      45.051  74.760   3.259  1.00 48.35           C
ATOM   9316  CA  LEU C 806      45.515  75.582   2.161  1.00 48.35           C
ATOM   9317  CB  LEU C 806      45.464  77.082   2.517  1.00 33.54           C
ATOM   9318  CG  LEU C 806      46.212  77.798   3.635  1.00 33.54           C
ATOM   9319  CD1 LEU C 806      47.687  77.828   3.334  1.00 33.54           C
ATOM   9320  CD2 LEU C 806      45.701  79.223   3.725  1.00 33.54           C
ATOM   9321  C   LEU C 806      46.911  75.112   1.759  1.00 48.35           C
ATOM   9322  O   LEU C 806      47.836  75.099   2.569  1.00 48.35           C
ATOM   9323  N   ARG C 807      47.033  74.679   0.504  1.00 97.68           C
ATOM   9324  CA  ARG C 807      48.290  74.170  -0.044  1.00 97.68           C
ATOM   9325  CB  ARG C 807      48.071  72.749  -0.592  1.00 98.93           C
ATOM   9326  CG  ARG C 807      46.648  72.436  -1.106  1.00 98.93           C
ATOM   9327  CD  ARG C 807      46.246  73.311  -2.300  1.00 98.93           C
ATOM   9328  NE  ARG C 807      45.070  72.803  -3.014  1.00 98.93           C
ATOM   9329  CZ  ARG C 807      44.615  73.301  -4.165  1.00 98.93           C
ATOM   9330  NH1 ARG C 807      45.231  74.326  -4.742  1.00 98.93           C
ATOM   9331  NH2 ARG C 807      43.548  72.765  -4.745  1.00 98.93           C
ATOM   9332  C   ARG C 807      48.868  75.080  -1.131  1.00 97.68           C
ATOM   9333  O   ARG C 807      48.127  75.599  -1.972  1.00 97.68           C
ATOM   9334  N   ARG C 808      50.188  75.276  -1.120  1.00 35.28           C
ATOM   9335  CA  ARG C 808      50.791  76.147  -2.125  1.00 35.28           C
ATOM   9336  CB  ARG C 808      52.322  76.153  -2.037  1.00 50.51           C
ATOM   9337  CG  ARG C 808      52.998  74.942  -2.613  1.00 50.51           C
ATOM   9338  CD  ARG C 808      54.506  75.143  -2.752  1.00 50.51           C
ATOM   9339  NE  ARG C 808      55.163  73.862  -3.018  1.00 50.51           C
ATOM   9340  CZ  ARG C 808      56.475  73.680  -3.108  1.00 50.51           C
ATOM   9341  NH1 ARG C 808      57.303  74.701  -2.961  1.00 50.51           C
ATOM   9342  NH2 ARG C 808      56.958  72.467  -3.323  1.00 50.51           C
ATOM   9343  C   ARG C 808      50.352  75.682  -3.500  1.00 35.28           C
ATOM   9344  O   ARG C 808      50.152  74.488  -3.732  1.00 35.28           C
ATOM   9345  N   GLY C 809      50.194  76.627  -4.411  1.00 99.53           C
ATOM   9346  CA  GLY C 809      49.754  76.270  -5.740  1.00 99.53           C
ATOM   9347  C   GLY C 809      48.247  76.353  -5.753  1.00 99.53           C
ATOM   9348  O   GLY C 809      47.585  75.666  -6.525  1.00 99.53           C
ATOM   9349  N   ASP C 810      47.711  77.186  -4.866  1.00 72.09           C
ATOM   9350  CA  ASP C 810      46.272  77.399  -4.770  1.00 72.09           C
ATOM   9351  CB  ASP C 810      45.848  77.349  -3.301  1.00 95.21           C
ATOM   9352  CG  ASP C 810      44.457  76.769  -3.114  1.00 95.21           C
ATOM   9353  OD1 ASP C 810      43.556  77.113  -3.910  1.00 95.21           C
ATOM   9354  OD2 ASP C 810      44.265  75.979  -2.163  1.00 95.21           C
ATOM   9355  C   ASP C 810      46.033  78.781  -5.419  1.00 72.09           C
ATOM   9356  O   ASP C 810      46.612  79.058  -6.464  1.00 72.09           C
ATOM   9357  N   PRO C 811      45.209  79.669  -4.834  1.00 68.87           C
ATOM   9358  CD  PRO C 811      44.476  79.824  -3.564  1.00 47.95           C
ATOM   9359  CA  PRO C 811      45.119  80.909  -5.603  1.00 68.87           C
ATOM   9360  CB  PRO C 811      43.955  81.619  -4.949  1.00 47.95           C
ATOM   9361  CG  PRO C 811      44.205  81.326  -3.517  1.00 47.95           C
ATOM   9362  C   PRO C 811      46.395  81.743  -5.519  1.00 68.87           C
ATOM   9363  O   PRO C 811      46.915  82.199  -6.542  1.00 68.87           C
ATOM   9364  N   GLY C 812      46.889  81.951  -4.298  1.00100.07           C
ATOM   9365  CA  GLY C 812      48.096  82.746  -4.109  1.00100.07           C
ATOM   9366  C   GLY C 812      48.864  82.466  -2.824  1.00100.07           C
ATOM   9367  O   GLY C 812      50.098  82.427  -2.826  1.00100.07           C
ATOM   9368  N   VAL C 813      48.132  82.295  -1.728  1.00 30.10           C
ATOM   9369  CA  VAL C 813      48.715  81.994  -0.428  1.00 30.10           C
ATOM   9370  CB  VAL C 813      48.208  80.633   0.086  1.00 57.90           C
```

| ATOM | 9371 | CG1 | VAL C 813 | 47.903 | 80.728 | 1.579 | 1.00 57.90 | C |
|---|---|---|---|---|---|---|---|---|
| ATOM | 9372 | CG2 | VAL C 813 | 47.000 | 80.180 | -0.725 | 1.00 57.90 | C |
| ATOM | 9373 | C | VAL C 813 | 50.251 | 81.950 | -0.341 | 1.00 30.10 | C |
| ATOM | 9374 | O | VAL C 813 | 50.910 | 81.077 | -0.930 | 1.00 30.10 | C |
| ATOM | 9375 | N | GLU C 814 | 50.834 | 82.888 | 0.394 | 1.00 41.78 | C |
| ATOM | 9376 | CA | GLU C 814 | 52.274 | 82.846 | 0.552 | 1.00 41.78 | C |
| ATOM | 9377 | CB | GLU C 814 | 52.847 | 84.172 | 1.085 | 1.00100.07 | C |
| ATOM | 9378 | CG | GLU C 814 | 54.401 | 84.176 | 1.136 | 1.00100.07 | C |
| ATOM | 9379 | CD | GLU C 814 | 55.026 | 85.350 | 1.910 | 1.00100.07 | C |
| ATOM | 9380 | OE1 | GLU C 814 | 54.991 | 85.345 | 3.165 | 1.00100.07 | C |
| ATOM | 9381 | OE2 | GLU C 814 | 55.565 | 86.277 | 1.257 | 1.00100.07 | C |
| ATOM | 9382 | C | GLU C 814 | 52.488 | 81.761 | 1.598 | 1.00 41.78 | C |
| ATOM | 9383 | O | GLU C 814 | 51.749 | 81.689 | 2.586 | 1.00 41.78 | C |
| ATOM | 9384 | N | LEU C 815 | 53.469 | 80.897 | 1.369 | 1.00 57.51 | C |
| ATOM | 9385 | CA | LEU C 815 | 53.775 | 79.858 | 2.336 | 1.00 57.51 | C |
| ATOM | 9386 | CB | LEU C 815 | 53.208 | 78.508 | 1.903 | 1.00 57.31 | C |
| ATOM | 9387 | CG | LEU C 815 | 51.743 | 78.345 | 2.307 | 1.00 57.31 | C |
| ATOM | 9388 | CD1 | LEU C 815 | 50.871 | 79.124 | 1.343 | 1.00 57.31 | C |
| ATOM | 9389 | CD2 | LEU C 815 | 51.358 | 76.874 | 2.307 | 1.00 57.31 | C |
| ATOM | 9390 | C | LEU C 815 | 55.269 | 79.748 | 2.571 | 1.00 57.51 | C |
| ATOM | 9391 | O | LEU C 815 | 56.022 | 79.367 | 1.679 | 1.00 57.51 | C |
| ATOM | 9392 | N | LYS C 816 | 55.677 | 80.105 | 3.787 | 1.00 66.37 | C |
| ATOM | 9393 | CA | LYS C 816 | 57.069 | 80.057 | 4.206 | 1.00 66.37 | C |
| ATOM | 9394 | CB | LYS C 816 | 57.166 | 79.641 | 5.676 | 1.00 92.74 | C |
| ATOM | 9395 | CG | LYS C 816 | 58.588 | 79.379 | 6.159 | 1.00 92.74 | C |
| ATOM | 9396 | CD | LYS C 816 | 59.456 | 80.630 | 6.064 | 1.00 92.74 | C |
| ATOM | 9397 | CE | LYS C 816 | 60.908 | 80.356 | 6.453 | 1.00 92.74 | C |
| ATOM | 9398 | NZ | LYS C 816 | 61.600 | 79.349 | 5.584 | 1.00 92.74 | C |
| ATOM | 9399 | C | LYS C 816 | 57.849 | 79.077 | 3.355 | 1.00 66.37 | C |
| ATOM | 9400 | O | LYS C 816 | 57.446 | 77.930 | 3.189 | 1.00 66.37 | C |
| ATOM | 9401 | N | PRO C 817 | 58.973 | 79.526 | 2.786 | 1.00 80.61 | C |
| ATOM | 9402 | CD | PRO C 817 | 59.620 | 80.837 | 2.935 | 1.00 71.98 | C |
| ATOM | 9403 | CA | PRO C 817 | 59.789 | 78.648 | 1.952 | 1.00 80.61 | C |
| ATOM | 9404 | CB | PRO C 817 | 61.119 | 79.401 | 1.855 | 1.00 71.98 | C |
| ATOM | 9405 | CG | PRO C 817 | 61.051 | 80.448 | 2.970 | 1.00 71.98 | C |
| ATOM | 9406 | C | PRO C 817 | 59.938 | 77.242 | 2.525 | 1.00 80.61 | C |
| ATOM | 9407 | O | PRO C 817 | 60.220 | 77.056 | 3.712 | 1.00 80.61 | C |
| ATOM | 9408 | N | GLY C 818 | 59.747 | 76.254 | 1.660 | 1.00 76.22 | C |
| ATOM | 9409 | CA | GLY C 818 | 59.847 | 74.876 | 2.087 | 1.00 76.22 | C |
| ATOM | 9410 | C | GLY C 818 | 58.445 | 74.459 | 2.442 | 1.00 76.22 | C |
| ATOM | 9411 | O | GLY C 818 | 57.922 | 73.474 | 1.928 | 1.00 76.22 | C |
| ATOM | 9412 | N | VAL C 819 | 57.824 | 75.236 | 3.318 | 1.00 43.58 | C |
| ATOM | 9413 | CA | VAL C 819 | 56.470 | 74.942 | 3.736 | 1.00 43.58 | C |
| ATOM | 9414 | CB | VAL C 919 | 55.876 | 76.087 | 4.557 | 1.00100.07 | C |
| ATOM | 9415 | CG1 | VAL C 819 | 54.455 | 75.749 | 4.963 | 1.00100.07 | C |
| ATOM | 9416 | CG2 | VAL C 819 | 56.739 | 76.339 | 5.777 | 1.00100.07 | C |
| ATOM | 9417 | C | VAL C 819 | 55.631 | 74.737 | 2.495 | 1.00 43.58 | C |
| ATOM | 9418 | O | VAL C 819 | 55.767 | 75.465 | 1.512 | 1.00 43.58 | C |
| ATOM | 9419 | N | ARG C 820 | 54.782 | 73.722 | 2.556 | 1.00 37.99 | C |
| ATOM | 9420 | CA | ARG C 820 | 53.893 | 73.365 | 1.468 | 1.00 37.99 | C |
| ATOM | 9421 | CB | ARG C 820 | 54.561 | 72.321 | 0.589 | 1.00 77.32 | C |
| ATOM | 9422 | CG | ARG C 820 | 53.585 | 71.441 | -0.143 | 1.00 77.32 | C |
| ATOM | 9423 | CD | ARG C 820 | 54.189 | 70.075 | -0.377 | 1.00 77.32 | C |
| ATOM | 9424 | NE | ARG C 820 | 53.154 | 69.089 | -0.659 | 1.00 77.32 | C |
| ATOM | 9425 | CZ | ARG C 820 | 53.374 | 67.784 | -0.726 | 1.00 77.32 | C |
| ATOM | 9426 | NH1 | ARG C 820 | 54.599 | 67.314 | -0.531 | 1.00 77.32 | C |
| ATOM | 9427 | NH2 | ARG C 820 | 52.370 | 66.954 | -0.981 | 1.00 77.32 | C |
| ATOM | 9428 | C | ARG C 820 | 52.662 | 72.773 | 2.129 | 1.00 37.99 | C |
| ATOM | 9429 | O | ARG C 820 | 52.784 | 71.870 | 2.944 | 1.00 37.99 | C |
| ATOM | 9430 | N | GLU C 821 | 51.480 | 73.266 | 1.785 | 1.00 34.34 | C |
| ATOM | 9431 | CA | GLU C 821 | 50.271 | 72.760 | 2.410 | 1.00 34.34 | C |
| ATOM | 9432 | CB | GLU C 821 | 50.140 | 71.259 | 2.174 | 1.00 45.30 | C |
| ATOM | 9433 | CG | GLU C 821 | 48.816 | 70.696 | 2.628 | 1.00 45.30 | C |
| ATOM | 9434 | CD | GLU C 821 | 48.768 | 69.184 | 2.553 | 1.00 45.30 | C |
| ATOM | 9435 | OE1 | GLU C 821 | 49.573 | 68.535 | 3.250 | 1.00 45.30 | C |
| ATOM | 9436 | OE2 | GLU C 821 | 47.925 | 68.644 | 1.802 | 1.00 45.30 | C |
| ATOM | 9437 | C | GLU C 821 | 50.424 | 73.035 | 3.902 | 1.00 34.34 | C |
| ATOM | 9438 | O | GLU C 821 | 51.495 | 72.842 | 4.459 | 1.00 34.34 | C |
| ATOM | 9439 | N | VAL C 822 | 49.360 | 73.493 | 4.553 | 1.00 22.98 | C |
| ATOM | 9440 | CA | VAL C 822 | 49.416 | 73.796 | 5.986 | 1.00 22.98 | C |
| ATOM | 9441 | CB | VAL C 822 | 49.744 | 75.267 | 6.221 | 1.00 37.56 | C |
| ATOM | 9442 | CG1 | VAL C 822 | 50.024 | 75.494 | 7.676 | 1.00 37.56 | C |
| ATOM | 9443 | CG2 | VAL C 822 | 50.914 | 75.690 | 5.351 | 1.00 37.56 | C |
| ATOM | 9444 | C | VAL C 822 | 48.091 | 73.509 | 6.677 | 1.00 22.98 | C |
| ATOM | 9445 | O | VAL C 822 | 47.341 | 74.421 | 6.978 | 1.00 22.98 | C |
| ATOM | 9446 | N | VAL C 823 | 47.815 | 72.234 | 6.910 | 1.00 23.45 | C |
| ATOM | 9447 | CA | VAL C 823 | 46.602 | 71.783 | 7.574 | 1.00 23.45 | C |
| ATOM | 9448 | CB | VAL C 823 | 46.804 | 70.364 | 8.146 | 1.00 59.29 | C |
| ATOM | 9449 | CG1 | VAL C 823 | 45.911 | 70.137 | 9.345 | 1.00 59.29 | C |
| ATOM | 9450 | CG2 | VAL C 823 | 46.502 | 69.336 | 7.080 | 1.00 59.29 | C |
| ATOM | 9451 | C | VAL C 823 | 46.229 | 72.707 | 8.717 | 1.00 23.45 | C |
| ATOM | 9452 | O | VAL C 823 | 47.103 | 73.287 | 9.360 | 1.00 23.45 | C |
| ATOM | 9453 | N | ARG C 824 | 44.936 | 72.839 | 8.982 | 1.00 44.37 | C |
| ATOM | 9454 | CA | ARG C 824 | 44.486 | 73.687 | 10.069 | 1.00 44.37 | C |

```
ATOM   9455  CB   ARG C 824      44.201  75.089   9.542  1.00 64.53           C
ATOM   9456  CG   ARG C 824      44.423  76.177  10.562  1.00 64.53           C
ATOM   9457  CD   ARG C 824      43.578  77.423  10.280  1.00 64.53           C
ATOM   9458  NE   ARG C 824      44.062  78.249   9.175  1.00 64.53           C
ATOM   9459  CZ   ARG C 824      45.188  78.958   9.197  1.00 64.53           C
ATOM   9460  NH1  ARG C 824      45.967  78.946  10.271  1.00 64.53           C
ATOM   9461  NH2  ARG C 824      45.523  79.701   8.148  1.00 64.53           C
ATOM   9462  C    ARG C 824      43.211  73.050  10.608  1.00 44.37           C
ATOM   9463  O    ARG C 824      42.293  72.763   9.837  1.00 44.37           C
ATOM   9464  N    VAL C 825      43.151  72.804  11.917  1.00 18.28           C
ATOM   9465  CA   VAL C 825      41.966  72.185  12.524  1.00 18.28           C
ATOM   9466  CB   VAL C 825      42.222  70.742  12.969  1.00  8.45           C
ATOM   9467  CG1  VAL C 825      40.958  70.182  13.592  1.00  8.45           C
ATOM   9468  CG2  VAL C 825      42.694  69.894  11.825  1.00  8.45           C
ATOM   9469  C    VAL C 825      41.520  72.918  13.781  1.00 18.28           C
ATOM   9470  O    VAL C 825      42.290  73.016  14.753  1.00 18.28           C
ATOM   9471  N    PHE C 826      40.271  73.387  13.775  1.00 35.68           C
ATOM   9472  CA   PHE C 826      39.681  74.117  14.902  1.00 35.68           C
ATOM   9473  CB   PHE C 826      38.703  75.141  14.374  1.00 16.17           C
ATOM   9474  CG   PHE C 826      39.335  76.171  13.532  1.00 16.17           C
ATOM   9475  CD1  PHE C 826      39.761  77.355  14.078  1.00 16.17           C
ATOM   9476  CD2  PHE C 926      39.530  75.954  12.186  1.00 16.17           C
ATOM   9477  CE1  PHE C 826      40.376  78.321  13.282  1.00 16.17           C
ATOM   9478  CE2  PHE C 826      40.145  76.909  11.382  1.00 16.17           C
ATOM   9479  CZ   PHE C 826      40.568  78.093  11.927  1.00 16.17           C
ATOM   9480  C    PHE C 826      38.948  73.219  15.884  1.00 35.68           C
ATOM   9481  O    PHE C 826      38.472  72.162  15.513  1.00 35.68           C
ATOM   9482  N    VAL C 827      38.845  73.644  17.136  1.00 41.76           C
ATOM   9483  CA   VAL C 827      38.149  72.845  18.137  1.00 41.76           C
ATOM   9484  CB   VAL C 827      39.107  71.964  18.959  1.00  8.72           C
ATOM   9485  CG1  VAL C 827      38.301  71.151  19.917  1.00  8.72           C
ATOM   9486  CG2  VAL C 827      39.921  71.049  18.068  1.00  8.72           C
ATOM   9487  C    VAL C 827      37.402  73.728  19.125  1.00 41.76           C
ATOM   9488  O    VAL C 827      37.891  74.789  19.518  1.00 41.76           C
ATOM   9489  N    ALA C 828      36.227  73.278  19.547  1.00 35.26           C
ATOM   9490  CA   ALA C 828      35.426  74.051  20.483  1.00 35.26           C
ATOM   9491  CB   ALA C 828      34.094  74.401  19.850  1.00 55.74           C
ATOM   9492  C    ALA C 828      35.193  73.313  21.790  1.00 35.26           C
ATOM   9493  O    ALA C 828      35.120  72.083  21.817  1.00 35.26           C
ATOM   9494  N    GLN C 829      35.077  74.077  22.873  1.00 33.29           C
ATOM   9495  CA   GLN C 829      34.827  73.509  24.191  1.00 33.29           C
ATOM   9496  CB   GLN C 829      36.016  73.744  25.126  1.00 43.24           C
ATOM   9497  CG   GLN C 829      37.247  72.928  24.816  1.00 43.24           C
ATOM   9498  CD   GLN C 829      38.339  73.108  25.856  1.00 43.24           C
ATOM   9499  OE1  GLN C 829      38.204  72.661  26.996  1.00 43.24           C
ATOM   9500  NE2  GLN C 829      39.426  73.773  25.471  1.00 43.24           C
ATOM   9501  C    GLN C 829      33.556  74.047  24.864  1.00 33.29           C
ATOM   9502  O    GLN C 829      33.061  75.155  24.577  1.00 33.29           C
ATOM   9503  N    LYS C 830      33.051  73.220  25.771  1.00 76.54           C
ATOM   9504  CA   LYS C 830      31.866  73.489  26.570  1.00 76.54           C
ATOM   9505  CB   LYS C 830      31.462  72.190  27.258  1.00 67.00           C
ATOM   9506  CG   LYS C 830      32.665  71.354  27.716  1.00 67.00           C
ATOM   9507  CD   LYS C 830      32.328  69.865  27.797  1.00 67.00           C
ATOM   9508  CE   LYS C 830      31.698  69.332  26.497  1.00 67.00           C
ATOM   9509  NZ   LYS C 830      32.531  69.581  25.291  1.00 67.00           C
ATOM   9510  C    LYS C 830      32.167  74.562  27.613  1.00 76.54           C
ATOM   9511  O    LYS C 830      31.812  75.727  27.447  1.00 76.54           C
ATOM   9512  N    ARG C 831      32.827  74.152  28.689  1.00 61.12           C
ATOM   9513  CA   ARG C 831      33.203  75.059  29.762  1.00 61.12           C
ATOM   9514  CB   ARG C 831      34.043  76.230  29.238  1.00 67.15           C
ATOM   9515  CG   ARG C 831      35.478  75.862  28.908  1.00 67.15           C
ATOM   9516  CD   ARG C 831      36.324  77.076  28.549  1.00 67.15           C
ATOM   9517  NE   ARG C 831      37.547  76.672  27.867  1.00 67.15           C
ATOM   9518  CZ   ARG C 831      38.416  75.798  28.356  1.00 67.15           C
ATOM   9519  NH1  ARG C 831      38.202  75.241  29.536  1.00 67.15           C
ATOM   9520  NH2  ARG C 831      39.486  75.459  27.653  1.00 67.15           C
ATOM   9521  C    ARG C 831      32.041  75.623  30.536  1.00 61.12           C
ATOM   9522  O    ARG C 831      31.408  76.591  30.112  1.00 61.12           C
ATOM   9523  N    LYS C 832      31.762  74.994  31.670  1.00 73.93           C
ATOM   9524  CA   LYS C 832      30.716  75.439  32.569  1.00 73.93           C
ATOM   9525  CB   LYS C 832      29.955  74.244  33.138  1.00 52.92           C
ATOM   9526  CG   LYS C 832      29.265  73.396  32.087  1.00 52.92           C
ATOM   9527  CD   LYS C 832      28.761  72.096  32.673  1.00 52.92           C
ATOM   9528  CE   LYS C 832      27.673  72.341  33.700  1.00 52.92           C
ATOM   9529  NZ   LYS C 832      27.416  71.142  34.549  1.00 52.92           C
ATOM   9530  C    LYS C 832      31.570  76.105  33.636  1.00 73.93           C
ATOM   9531  O    LYS C 832      32.720  76.444  33.363  1.00 73.93           C
ATOM   9532  N    LEU C 833      31.050  76.280  34.843  1.00 36.60           C
ATOM   9533  CA   LEU C 833      31.838  76.935  35.879  1.00 36.60           C
ATOM   9534  CB   LEU C 833      30.934  77.862  36.695  1.00 25.51           C
ATOM   9535  CG   LEU C 833      31.589  78.991  37.492  1.00 25.51           C
ATOM   9536  CD1  LEU C 833      32.612  79.700  36.636  1.00 25.51           C
ATOM   9537  CD2  LEU C 833      30.521  79.961  37.957  1.00 25.51           C
ATOM   9538  C    LEU C 833      32.564  75.937  36.783  1.00 36.60           C
```

```
ATOM   9539  O    LEU C 833      32.094  74.815  37.004  1.00 36.60           C
ATOM   9540  N    GLN C 834      33.721  76.341  37.295  1.00 37.55           C
ATOM   9541  CA   GLN C 834      34.502  75.461  38.157  1.00 37.55           C
ATOM   9542  CB   GLN C 834      35.602  74.750  37.370  1.00 71.12           C
ATOM   9543  CG   GLN C 834      35.162  73.912  36.191  1.00 71.12           C
ATOM   9544  CD   GLN C 834      36.352  73.324  35.467  1.00 71.12           C
ATOM   9545  OE1  GLN C 834      37.283  74.043  35.114  1.00 71.12           C
ATOM   9546  NE2  GLN C 834      36.332  72.015  35.244  1.00 71.12           C
ATOM   9547  C    GLN C 834      35.187  76.242  39.246  1.00 37.55           C
ATOM   9548  O    GLN C 834      35.138  77.463  39.272  1.00 37.55           C
ATOM   9549  N    VAL C 835      35.853  75.521  40.132  1.00  9.55           C
ATOM   9550  CA   VAL C 835      36.578  76.157  41.199  1.00  9.55           C
ATOM   9551  CB   VAL C 835      36.994  75.115  42.196  1.00 16.09           C
ATOM   9552  CG1  VAL C 835      37.661  75.777  43.396  1.00 16.09           C
ATOM   9553  CG2  VAL C 835      35.777  74.304  42.597  1.00 16.09           C
ATOM   9554  C    VAL C 835      37.820  76.863  40.616  1.00  9.55           C
ATOM   9555  O    VAL C 835      38.775  76.217  40.169  1.00  9.55           C
ATOM   9556  N    GLY C 836      37.803  78.191  40.626  1.00 25.08           C
ATOM   9557  CA   GLY C 836      38.901  78.974  40.086  1.00 25.08           C
ATOM   9558  C    GLY C 836      38.199  80.124  39.413  1.00 25.08           C
ATOM   9559  O    GLY C 836      37.379  80.798  40.043  1.00 25.08           C
ATOM   9560  N    ASP C 837      38.502  80.355  38.144  1.00 24.55           C
ATOM   9561  CA   ASP C 837      37.841  81.405  37.351  1.00 24.55           C
ATOM   9562  CB   ASP C 837      36.629  80.804  36.614  1.00 59.95           C
ATOM   9563  CG   ASP C 837      36.406  79.310  36.916  1.00 59.95           C
ATOM   9564  OD1  ASP C 837      35.493  78.722  36.298  1.00 59.95           C
ATOM   9565  OD2  ASP C 837      37.117  78.711  37.754  1.00 59.95           C
ATOM   9566  C    ASP C 837      37.391  82.715  38.038  1.00 24.55           C
ATOM   9567  O    ASP C 837      36.486  82.723  38.880  1.00 24.55           C
ATOM   9568  N    LYS C 838      38.016  83.826  37.654  1.00 41.85           C
ATOM   9569  CA   LYS C 838      37.662  85.126  38.215  1.00 41.85           C
ATOM   9570  CB   LYS C 838      38.535  86.226  37.599  1.00 53.43           C
ATOM   9571  CG   LYS C 838      39.899  86.354  38.250  1.00 53.43           C
ATOM   9572  CD   LYS C 838      40.838  87.249  37.462  1.00 53.43           C
ATOM   9573  CE   LYS C 838      40.427  88.704  37.500  1.00 53.43           C
ATOM   9574  NZ   LYS C 838      41.269  89.528  36.569  1.00 53.43           C
ATOM   9575  C    LYS C 838      36.184  85.424  37.952  1.00 41.85           C
ATOM   9576  O    LYS C 838      35.688  85.190  36.845  1.00 41.85           C
ATOM   9577  N    LEU C 839      35.480  85.946  38.960  1.00 17.69           C
ATOM   9578  CA   LEU C 839      34.070  86.246  38.791  1.00 17.69           C
ATOM   9579  CB   LEU C 839      33.275  85.643  39.936  1.00 20.55           C
ATOM   9580  CG   LEU C 839      32.093  84.833  39.411  1.00 20.55           C
ATOM   9581  CD1  LEU C 839      32.491  84.172  38.102  1.00 20.55           C
ATOM   9582  CD2  LEU C 839      31.654  83.798  40.442  1.00 20.55           C
ATOM   9583  C    LEU C 839      33.750  87.715  38.648  1.00 17.69           C
ATOM   9584  O    LEU C 839      32.777  88.067  38.013  1.00 17.69           C
ATOM   9585  N    ALA C 840      34.569  88.559  39.250  1.00 14.32           C
ATOM   9586  CA   ALA C 840      34.428  90.013  39.192  1.00 14.32           C
ATOM   9587  CB   ALA C 840      35.651  90.590  38.514  1.00 78.31           C
ATOM   9588  C    ALA C 840      33.178  90.666  38.584  1.00 14.32           C
ATOM   9589  O    ALA C 840      32.643  90.225  37.566  1.00 14.32           C
ATOM   9590  N    ASN C 841      32.754  91.770  39.195  1.00 36.59           C
ATOM   9591  CA   ASN C 841      31.582  92.514  38.733  1.00 36.59           C
ATOM   9592  CB   ASN C 841      30.602  92.699  39.875  1.00 16.19           C
ATOM   9593  CG   ASN C 841      31.234  93.358  41.057  1.00 16.19           C
ATOM   9594  OD1  ASN C 841      30.674  93.327  42.144  1.00 16.19           C
ATOM   9595  ND2  ASN C 841      32.410  93.958  40.863  1.00 16.19           C
ATOM   9596  C    ASN C 841      31.946  93.881  38.187  1.00 36.59           C
ATOM   9597  O    ASN C 841      33.083  94.112  37.808  1.00 36.59           C
ATOM   9598  N    ARG C 842      30.978  94.793  38.171  1.00 31.18           C
ATOM   9599  CA   ARG C 842      31.207  96.138  37.646  1.00 31.18           C
ATOM   9600  CB   ARG C 842      29.885  96.764  37.215  1.00 36.79           C
ATOM   9601  CG   ARG C 842      29.286  96.115  36.003  1.00 36.79           C
ATOM   9602  CD   ARG C 842      27.890  96.610  35.763  1.00 36.79           C
ATOM   9603  NE   ARG C 842      27.016  96.327  36.894  1.00 36.79           C
ATOM   9604  CZ   ARG C 842      25.725  96.630  36.910  1.00 36.79           C
ATOM   9605  NH1  ARG C 842      25.190  97.219  35.852  1.00 36.79           C
ATOM   9606  NH2  ARG C 842      24.974  96.343  37.967  1.00 36.79           C
ATOM   9607  C    ARG C 842      31.912  97.083  38.606  1.00 31.18           C
ATOM   9608  O    ARG C 842      32.655  97.962  38.177  1.00 31.18           C
ATOM   9609  N    HIS C 843      31.668  96.909  39.901  1.00 15.36           C
ATOM   9610  CA   HIS C 843      32.284  97.751  40.914  1.00 15.36           C
ATOM   9611  CB   HIS C 843      31.318  97.975  42.065  1.00 20.07           C
ATOM   9612  CG   HIS C 843      29.971  98.462  41.639  1.00 20.07           C
ATOM   9613  CD2  HIS C 843      28.730  98.015  41.937  1.00 20.07           C
ATOM   9614  ND1  HIS C 843      29.797  99.567  40.834  1.00 20.07           C
ATOM   9615  CE1  HIS C 843      28.507  99.785  40.656  1.00 20.07           C
ATOM   9616  NE2  HIS C 843      27.837  98.857  41.316  1.00 20.07           C
ATOM   9617  C    HIS C 843      33.521  97.036  41.422  1.00 15.36           C
ATOM   9618  O    HIS C 843      33.739  96.903  42.617  1.00 15.36           C
ATOM   9619  N    GLY C 844      34.324  96.555  40.491  1.00 24.47           C
ATOM   9620  CA   GLY C 844      35.539  95.855  40.850  1.00 24.47           C
ATOM   9621  C    GLY C 844      35.520  94.975  42.089  1.00 24.47           C
ATOM   9622  O    GLY C 844      36.492  94.994  42.837  1.00 24.47           C
```

```
ATOM   9623  N    ASN C 845      34.464  94.203  42.337  1.00  7.29           C
ATOM   9624  CA   ASN C 845      34.507  93.357  43.524  1.00  7.29           C
ATOM   9625  CB   ASN C 845      33.149  93.291  44.212  1.00 47.87           C
ATOM   9626  CG   ASN C 845      33.268  92.875  45.664  1.00 47.87           C
ATOM   9627  OD1  ASN C 845      33.543  91.710  45.967  1.00 47.87           C
ATOM   9628  ND2  ASN C 845      33.088  93.833  46.573  1.00 47.87           C
ATOM   9629  C    ASN C 845      35.024  91.940  43.228  1.00  7.29           C
ATOM   9630  O    ASN C 845      34.633  90.952  43.882  1.00  7.29           C
ATOM   9631  N    LYS C 846      35.939  91.888  42.257  1.00  9.29           C
ATOM   9632  CA   LYS C 846      36.598  90.682  41.768  1.00  9.29           C
ATOM   9633  CB   LYS C 846      37.791  91.103  40.914  1.00 51.12           C
ATOM   9634  CG   LYS C 846      38.785  92.033  41.613  1.00 51.12           C
ATOM   9635  CD   LYS C 846      39.735  91.294  42.568  1.00 51.12           C
ATOM   9636  CE   LYS C 846      41.023  92.086  42.781  1.00 51.12           C
ATOM   9637  NZ   LYS C 846      41.715  92.422  41.490  1.00 51.12           C
ATOM   9638  C    LYS C 846      37.054  89.663  42.804  1.00  9.29           C
ATOM   9639  O    LYS C 846      37.600  90.023  43.842  1.00  9.29           C
ATOM   9640  N    GLY C 847      36.847  88.385  42.496  1.00 48.33           C
ATOM   9641  CA   GLY C 847      37.238  87.307  43.395  1.00 48.33           C
ATOM   9642  C    GLY C 847      37.167  85.970  42.673  1.00 48.33           C
ATOM   9643  O    GLY C 847      36.453  85.849  41.670  1.00 48.33           C
ATOM   9644  N    VAL C 848      37.893  84.966  43.164  1.00 41.93           C
ATOM   9645  CA   VAL C 848      37.901  83.646  42.519  1.00 41.93           C
ATOM   9646  CB   VAL C 848      39.305  83.025  42.527  1.00 26.52           C
ATOM   9647  CG1  VAL C 848      39.875  83.044  43.918  1.00 26.52           C
ATOM   9648  CG2  VAL C 848      39.237  81.604  42.063  1.00 26.52           C
ATOM   9649  C    VAL C 848      36.968  82.666  43.203  1.00 41.93           C
ATOM   9650  O    VAL C 848      36.833  82.692  44.434  1.00 41.93           C
ATOM   9651  N    VAL C 849      36.344  81.790  42.413  1.00 19.39           C
ATOM   9652  CA   VAL C 849      35.413  80.799  42.967  1.00 19.39           C
ATOM   9653  CB   VAL C 849      34.630  80.056  41.884  1.00  7.09           C
ATOM   9654  CG1  VAL C 849      33.978  78.865  42.501  1.00  7.09           C
ATOM   9655  CG2  VAL C 849      33.578  80.954  41.248  1.00  7.09           C
ATOM   9656  C    VAL C 849      36.064  79.707  43.808  1.00 19.39           C
ATOM   9657  O    VAL C 849      36.707  78.810  43.261  1.00 19.39           C
ATOM   9658  N    ALA C 850      35.880  79.773  45.125  1.00 18.37           C
ATOM   9659  CA   ALA C 850      36.424  78.764  46.028  1.00 18.37           C
ATOM   9660  CB   ALA C 850      36.501  79.307  47.446  1.00 49.09           C
ATOM   9661  C    ALA C 850      35.455  77.584  45.951  1.00 18.37           C
ATOM   9662  O    ALA C 850      35.198  77.103  44.862  1.00 18.37           C
ATOM   9663  N    LYS C 851      34.906  77.128  47.078  1.00 34.64           C
ATOM   9664  CA   LYS C 851      33.952  76.008  47.070  1.00 34.64           C
ATOM   9665  CB   LYS C 851      33.610  75.601  48.494  1.00 58.68           C
ATOM   9666  CG   LYS C 851      32.571  74.521  48.569  1.00 58.68           C
ATOM   9667  CD   LYS C 951      32.523  73.929  49.956  1.00 58.68           C
ATOM   9668  CE   LYS C 851      33.809  73.163  50.282  1.00 58.68           C
ATOM   9669  NZ   LYS C 851      33.884  72.688  51.703  1.00 58.68           C
ATOM   9670  C    LYS C 851      32.650  76.330  46.315  1.00 34.64           C
ATOM   9671  O    LYS C 851      32.371  77.497  46.016  1.00 34.64           C
ATOM   9672  N    ILE C 852      31.866  75.295  45.994  1.00 27.52           C
ATOM   9673  CA   ILE C 852      30.588  75.470  45.287  1.00 27.52           C
ATOM   9674  CB   ILE C 852      30.777  75.306  43.795  1.00 24.22           C
ATOM   9675  CG2  ILE C 852      31.297  73.931  43.488  1.00 24.22           C
ATOM   9676  CG1  ILE C 852      29.473  75.588  43.079  1.00 24.22           C
ATOM   9677  CD   ILE C 852      29.642  75.618  41.572  1.00 24.22           C
ATOM   9678  C    ILE C 852      29.536  74.480  45.812  1.00 27.52           C
ATOM   9679  O    ILE C 852      29.545  73.287  45.495  1.00 27.52           C
ATOM   9680  N    LEU C 853      28.642  75.028  46.635  1.00 36.16           C
ATOM   9681  CA   LEU C 853      27.572  74.321  47.336  1.00 36.16           C
ATOM   9682  CB   LEU C 853      27.129  75.165  48.532  1.00 26.55           C
ATOM   9683  CG   LEU C 853      27.737  74.884  49.906  1.00 26.55           C
ATOM   9684  CD1  LEU C 853      29.124  74.292  49.792  1.00 26.55           C
ATOM   9685  CD2  LEU C 853      27.756  76.172  50.679  1.00 26.55           C
ATOM   9686  C    LEU C 853      26.330  73.919  46.568  1.00 36.16           C
ATOM   9687  O    LEU C 853      26.056  74.421  45.486  1.00 36.16           C
ATOM   9688  N    PRO C 854      25.552  73.000  47.148  1.00 33.52           C
ATOM   9689  CD   PRO C 854      26.021  72.171  48.275  1.00 11.97           C
ATOM   9690  CA   PRO C 854      24.307  72.465  46.602  1.00 33.52           C
ATOM   9691  CB   PRO C 854      24.311  71.041  47.116  1.00 11.97           C
ATOM   9692  CG   PRO C 854      24.864  71.231  48.518  1.00 11.97           C
ATOM   9693  C    PRO C 854      23.150  73.247  47.186  1.00 33.52           C
ATOM   9694  O    PRO C 854      23.273  73.770  48.293  1.00 33.52           C
ATOM   9695  N    VAL C 855      22.035  73.319  46.458  1.00 14.10           C
ATOM   9696  CA   VAL C 855      20.834  74.025  46.927  1.00 14.10           C
ATOM   9697  CB   VAL C 855      19.641  73.738  46.023  1.00 16.59           C
ATOM   9698  CG1  VAL C 855      19.706  74.570  44.773  1.00 16.59           C
ATOM   9699  CG2  VAL C 855      19.668  72.283  45.642  1.00 16.59           C
ATOM   9700  C    VAL C 855      20.482  73.533  48.326  1.00 14.10           C
ATOM   9701  O    VAL C 855      20.052  74.310  49.171  1.00 14.10           C
ATOM   9702  N    GLU C 856      20.870  72.234  48.555  1.00 35.45           C
ATOM   9703  CA   GLU C 856      20.402  71.619  49.852  1.00 35.45           C
ATOM   9704  CB   GLU C 856      21.115  70.282  49.971  1.00 62.29           C
ATOM   9705  CG   GLU C 856      20.921  69.332  48.827  1.00 62.29           C
ATOM   9706  CD   GLU C 856      21.821  68.125  48.981  1.00 62.29           C
```

```
ATOM   9707  OE1 GLU C 856      21.750  67.452  50.038  1.00 62.29           C
ATOM   9708  OE2 GLU C 856      22.609  67.855  48.051  1.00 62.29           C
ATOM   9709  C   GLU C 856      20.924  72.508  50.969  1.00 35.45           C
ATOM   9710  O   GLU C 856      20.382  72.534  52.067  1.00 35.45           C
ATOM   9711  N   ASP C 857      22.015  73.203  50.696  1.00 52.98           C
ATOM   9712  CA  ASP C 857      22.582  74.101  51.676  1.00 52.98           C
ATOM   9713  CB  ASP C 857      24.080  73.858  51.793  1.00 31.39           C
ATOM   9714  CG  ASP C 857      24.387  72.454  52.271  1.00 31.39           C
ATOM   9715  OD1 ASP C 857      23.670  71.995  53.181  1.00 31.39           C
ATOM   9716  OD2 ASP C 857      25.330  71.810  51.753  1.00 31.39           C
ATOM   9717  C   ASP C 857      22.267  75.521  51.230  1.00 52.98           C
ATOM   9718  O   ASP C 857      21.123  75.812  50.867  1.00 52.98           C
ATOM   9719  N   MET C 858      23.259  76.404  51.230  1.00 35.76           C
ATOM   9720  CA  MET C 858      23.011  77.787  50.830  1.00 35.76           C
ATOM   9721  CB  MET C 858      22.194  77.820  49.530  1.00 16.55           C
ATOM   9722  CG  MET C 858      22.960  77.257  48.370  1.00 16.55           C
ATOM   9723  SD  MET C 858      24.634  77.926  48.386  1.00 16.55           C
ATOM   9724  CE  MET C 858      24.321  79.453  47.528  1.00 16.55           C
ATOM   9725  C   MET C 858      22.265  78.517  51.945  1.00 35.76           C
ATOM   9726  O   MET C 858      22.374  78.155  53.116  1.00 35.76           C
ATOM   9727  N   PRO C 859      21.546  79.589  51.607  1.00 59.65           C
ATOM   9728  CD  PRO C 859      21.970  80.618  50.641  1.00 69.85           C
ATOM   9729  CA  PRO C 859      20.859  80.221  52.725  1.00 59.65           C
ATOM   9730  CB  PRO C 859      21.655  81.502  52.896  1.00 69.85           C
ATOM   9731  CG  PRO C 859      21.903  81.910  51.466  1.00 69.85           C
ATOM   9732  C   PRO C 859      19.364  80.460  52.439  1.00 59.65           C
ATOM   9733  O   PRO C 859      18.931  81.603  52.283  1.00 59.65           C
ATOM   9734  N   ALA C 860      18.588  79.375  52.379  1.00 57.41           C
ATOM   9735  CA  ALA C 860      17.142  79.431  52.115  1.00 57.41           C
ATOM   9736  CB  ALA C 860      16.391  78.318  52.933  1.00  5.07           C
ATOM   9737  C   ALA C 860      16.553  80.793  52.452  1.00 57.41           C
ATOM   9738  O   ALA C 860      16.683  81.263  53.580  1.00 57.41           C
ATOM   9739  N   LEU C 861      15.934  81.450  51.479  1.00 31.25           C
ATOM   9740  CA  LEU C 861      15.300  82.726  51.778  1.00 31.25           C
ATOM   9741  CB  LEU C 861      14.834  83.423  50.498  1.00 26.02           C
ATOM   9742  CG  LEU C 861      14.736  84.960  50.547  1.00 26.02           C
ATOM   9743  CD1 LEU C 861      16.093  85.533  50.919  1.00 26.02           C
ATOM   9744  CD2 LEU C 861      14.258  85.528  49.209  1.00 26.02           C
ATOM   9745  C   LEU C 861      14.107  82.209  52.576  1.00 31.25           C
ATOM   9746  O   LEU C 861      13.994  80.998  52.771  1.00 31.25           C
ATOM   9747  N   PRO C 862      13.202  83.085  53.048  1.00 45.19           C
ATOM   9748  CD  PRO C 862      13.204  84.553  53.087  1.00 49.83           C
ATOM   9749  CA  PRO C 862      12.066  82.568  53.815  1.00 45.19           C
ATOM   9750  CB  PRO C 862      11.422  83.830  54.363  1.00 49.83           C
ATOM   9751  CG  PRO C 862      11.756  84.844  53.340  1.00 49.83           C
ATOM   9752  C   PRO C 862      11.056  81.664  53.121  1.00 45.19           C
ATOM   9753  O   PRO C 862      10.532  80.740  53.747  1.00 45.19           C
ATOM   9754  N   ASP C 863      10.789  81.916  51.840  1.00 19.47           C
ATOM   9755  CA  ASP C 863       9.811  81.120  51.090  1.00 19.47           C
ATOM   9756  CB  ASP C 863       8.980  82.036  50.215  1.00 32.30           C
ATOM   9757  CG  ASP C 863       9.775  82.584  49.074  1.00 32.30           C
ATOM   9758  OD1 ASP C 863       9.360  83.601  48.496  1.00 32.30           C
ATOM   9759  OD2 ASP C 863      10.822  81.990  48.746  1.00 32.30           C
ATOM   9760  C   ASP C 863      10.467  80.091  50.192  1.00 19.47           C
ATOM   9761  O   ASP C 863       9.867  79.626  49.228  1.00 19.47           C
ATOM   9762  N   GLY C 864      11.710  79.757  50.497  1.00 53.01           C
ATOM   9763  CA  GLY C 864      12.434  78.805  49.680  1.00 53.01           C
ATOM   9764  C   GLY C 864      13.495  79.544  48.891  1.00 53.01           C
ATOM   9765  O   GLY C 864      14.421  80.116  49.464  1.00 53.01           C
ATOM   9766  N   THR C 865      13.346  79.549  47.574  1.00 38.13           C
ATOM   9767  CA  THR C 865      14.291  80.218  46.694  1.00 38.13           C
ATOM   9768  CB  THR C 865      13.911  81.698  46.462  1.00 56.51           C
ATOM   9769  OG1 THR C 865      13.730  82.342  47.726  1.00 56.51           C
ATOM   9770  CG2 THR C 865      12.630  81.811  45.633  1.00 56.51           C
ATOM   9771  C   THR C 865      15.696  80.181  47.269  1.00 38.13           C
ATOM   9772  O   THR C 865      16.038  80.983  48.133  1.00 38.13           C
ATOM   9773  N   PRO C 866      16.536  79.250  46.793  1.00 19.58           C
ATOM   9774  CD  PRO C 866      16.488  78.478  45.538  1.00 57.39           C
ATOM   9775  CA  PRO C 866      17.886  79.219  47.345  1.00 19.58           C
ATOM   9776  CB  PRO C 866      18.512  78.048  46.620  1.00 57.39           C
ATOM   9777  CG  PRO C 866      17.971  78.243  45.249  1.00 57.39           C
ATOM   9778  C   PRO C 866      18.506  80.515  46.905  1.00 19.58           C
ATOM   9779  O   PRO C 866      17.885  81.292  46.180  1.00 19.58           C
ATOM   9780  N   VAL C 867      19.729  80.756  47.332  1.00 52.39           C
ATOM   9781  CA  VAL C 867      20.383  81.963  46.907  1.00 52.39           C
ATOM   9782  CB  VAL C 867      21.013  82.694  48.090  1.00 22.98           C
ATOM   9783  CG1 VAL C 867      21.695  83.958  47.613  1.00 22.98           C
ATOM   9784  CG2 VAL C 867      19.940  83.057  49.072  1.00 22.98           C
ATOM   9785  C   VAL C 867      21.429  81.595  45.866  1.00 52.39           C
ATOM   9786  O   VAL C 867      22.191  80.646  46.035  1.00 52.39           C
ATOM   9787  N   ASP C 868      21.426  82.334  44.767  1.00 36.26           C
ATOM   9788  CA  ASP C 868      22.368  82.101  43.706  1.00 36.26           C
ATOM   9789  CB  ASP C 868      22.234  83.169  42.622  1.00 64.66           C
ATOM   9790  CG  ASP C 868      21.019  82.961  41.747  1.00 64.66           C
```

| ATOM | 9791 | OD1 | ASP | C | 868 | 20.744 | 81.796 | 41.397 | 1.00 | 64.66 | C |
| ATOM | 9792 | OD2 | ASP | C | 868 | 20.346 | 83.954 | 41.394 | 1.00 | 64.66 | C |
| ATOM | 9793 | C | ASP | C | 868 | 23.792 | 82.102 | 44.236 | 1.00 | 36.26 | C |
| ATOM | 9794 | O | ASP | C | 868 | 24.351 | 81.043 | 44.510 | 1.00 | 36.26 | C |
| ATOM | 9795 | N | VAL | C | 869 | 24.379 | 83.286 | 44.407 | 1.00 | 20.02 | C |
| ATOM | 9796 | CA | VAL | C | 869 | 25.764 | 83.361 | 44.849 | 1.00 | 20.02 | C |
| ATOM | 9797 | CB | VAL | C | 869 | 26.652 | 83.772 | 43.688 | 1.00 | 36.58 | C |
| ATOM | 9798 | CG1 | VAL | C | 869 | 27.459 | 85.022 | 44.042 | 1.00 | 36.58 | C |
| ATOM | 9799 | CG2 | VAL | C | 869 | 27.536 | 82.576 | 43.299 | 1.00 | 36.58 | C |
| ATOM | 9800 | C | VAL | C | 869 | 26.044 | 84.269 | 46.016 | 1.00 | 20.02 | C |
| ATOM | 9801 | O | VAL | C | 869 | 25.534 | 85.374 | 46.076 | 1.00 | 20.02 | C |
| ATOM | 9802 | N | ILE | C | 870 | 26.878 | 83.783 | 46.929 | 1.00 | 44.04 | C |
| ATOM | 9803 | CA | ILE | C | 870 | 27.270 | 84.494 | 48.143 | 1.00 | 44.04 | C |
| ATOM | 9804 | CB | ILE | C | 870 | 27.496 | 83.509 | 49.294 | 1.00 | 15.22 | C |
| ATOM | 9805 | CG2 | ILE | C | 870 | 28.318 | 84.174 | 50.408 | 1.00 | 15.22 | C |
| ATOM | 9806 | CG1 | ILE | C | 870 | 26.174 | 82.957 | 49.795 | 1.00 | 15.22 | C |
| ATOM | 9807 | CD | ILE | C | 870 | 26.377 | 81.914 | 50.899 | 1.00 | 15.22 | C |
| ATOM | 9808 | C | ILE | C | 870 | 28.590 | 85.241 | 47.981 | 1.00 | 44.04 | C |
| ATOM | 9809 | O | ILE | C | 870 | 29.575 | 84.661 | 47.530 | 1.00 | 44.04 | C |
| ATOM | 9810 | N | LEU | C | 871 | 28.609 | 86.514 | 48.372 | 1.00 | 16.83 | C |
| ATOM | 9811 | CA | LEU | C | 871 | 29.818 | 87.335 | 48.325 | 1.00 | 16.83 | C |
| ATOM | 9812 | CB | LEU | C | 871 | 29.553 | 88.652 | 47.580 | 1.00 | 35.83 | C |
| ATOM | 9813 | CG | LEU | C | 871 | 29.890 | 88.781 | 46.078 | 1.00 | 35.83 | C |
| ATOM | 9814 | CD1 | LEU | C | 871 | 29.426 | 87.574 | 45.300 | 1.00 | 35.83 | C |
| ATOM | 9815 | CD2 | LEU | C | 871 | 29.241 | 90.029 | 45.514 | 1.00 | 35.83 | C |
| ATOM | 9816 | C | LEU | C | 871 | 30.179 | 87.590 | 49.792 | 1.00 | 16.83 | C |
| ATOM | 9817 | O | LEU | C | 871 | 29.319 | 87.498 | 50.671 | 1.00 | 16.83 | C |
| ATOM | 9818 | N | ASN | C | 872 | 31.443 | 87.895 | 50.069 | 1.00 | 57.66 | C |
| ATOM | 9819 | CA | ASN | C | 872 | 31.867 | 88.127 | 51.449 | 1.00 | 57.66 | C |
| ATOM | 9820 | CB | ASN | C | 872 | 33.271 | 87.615 | 51.690 | 1.00 | 30.76 | C |
| ATOM | 9821 | CG | ASN | C | 872 | 33.717 | 87.867 | 53.101 | 1.00 | 30.76 | C |
| ATOM | 9822 | OD1 | ASN | C | 872 | 32.923 | 88.300 | 53.946 | 1.00 | 30.76 | C |
| ATOM | 9823 | ND2 | ASN | C | 872 | 34.984 | 87.588 | 53.381 | 1.00 | 30.76 | C |
| ATOM | 9824 | C | ASN | C | 872 | 31.829 | 89.564 | 51.931 | 1.00 | 57.66 | C |
| ATOM | 9825 | O | ASN | C | 872 | 32.784 | 90.315 | 51.759 | 1.00 | 57.66 | C |
| ATOM | 9826 | N | PRO | C | 873 | 30.756 | 89.930 | 52.630 | 1.00 | 24.13 | C |
| ATOM | 9827 | CD | PRO | C | 873 | 30.040 | 88.951 | 53.463 | 1.00100.07 | | C |
| ATOM | 9828 | CA | PRO | C | 873 | 30.552 | 91.276 | 53.164 | 1.00 | 24.13 | C |
| ATOM | 9829 | CB | PRO | C | 873 | 29.469 | 91.067 | 54.208 | 1.00100.07 | | C |
| ATOM | 9830 | CG | PRO | C | 873 | 29.821 | 89.726 | 54.747 | 1.00100.07 | | C |
| ATOM | 9831 | C | PRO | C | 873 | 31.804 | 91.791 | 53.804 | 1.00 | 24.13 | C |
| ATOM | 9832 | O | PRO | C | 873 | 32.051 | 92.977 | 53.801 | 1.00 | 24.13 | C |
| ATOM | 9833 | N | LEU | C | 874 | 32.592 | 90.893 | 54.371 | 1.00 | 33.95 | C |
| ATOM | 9834 | CA | LEU | C | 874 | 33.804 | 91.322 | 55.039 | 1.00 | 33.95 | C |
| ATOM | 9835 | CB | LEU | C | 874 | 34.558 | 90.139 | 55.634 | 1.00 | 49.91 | C |
| ATOM | 9836 | CG | LEU | C | 874 | 35.833 | 90.534 | 56.372 | 1.00 | 49.91 | C |
| ATOM | 9837 | CD1 | LEU | C | 874 | 35.580 | 91.720 | 57.284 | 1.00 | 49.91 | C |
| ATOM | 9838 | CD2 | LEU | C | 874 | 36.313 | 89.342 | 57.147 | 1.00 | 49.91 | C |
| ATOM | 9839 | C | LEU | C | 874 | 34.713 | 92.074 | 54.115 | 1.00 | 33.95 | C |
| ATOM | 9840 | O | LEU | C | 874 | 34.532 | 92.041 | 52.903 | 1.00 | 33.95 | C |
| ATOM | 9841 | N | GLY | C | 875 | 35.688 | 92.749 | 54.716 | 1.00 | 57.62 | C |
| ATOM | 9842 | CA | GLY | C | 875 | 36.644 | 93.538 | 53.973 | 1.00 | 57.62 | C |
| ATOM | 9843 | C | GLY | C | 875 | 36.093 | 94.038 | 52.655 | 1.00 | 57.62 | C |
| ATOM | 9844 | O | GLY | C | 875 | 35.702 | 95.206 | 52.526 | 1.00 | 57.62 | C |
| ATOM | 9845 | N | VAL | C | 876 | 36.050 | 93.117 | 51.694 | 1.00 | 49.45 | C |
| ATOM | 9846 | CA | VAL | C | 876 | 35.597 | 93.353 | 50.332 | 1.00 | 49.45 | C |
| ATOM | 9847 | CB | VAL | C | 876 | 34.764 | 92.167 | 49.811 | 1.00100.07 | | C |
| ATOM | 9848 | CG1 | VAL | C | 876 | 34.738 | 92.195 | 48.294 | 1.00100.07 | | C |
| ATOM | 9849 | CG2 | VAL | C | 876 | 35.366 | 90.848 | 50.294 | 1.00100.07 | | C |
| ATOM | 9850 | C | VAL | C | 876 | 34.852 | 94.661 | 50.075 | 1.00 | 49.45 | C |
| ATOM | 9851 | O | VAL | C | 876 | 35.052 | 95.285 | 49.022 | 1.00 | 49.45 | C |
| ATOM | 9852 | N | PRO | C | 877 | 33.942 | 95.070 | 50.981 | 1.00 | 75.50 | C |
| ATOM | 9853 | CD | PRO | C | 877 | 33.070 | 94.231 | 51.819 | 1.00 | 39.36 | C |
| ATOM | 9854 | CA | PRO | C | 877 | 33.283 | 96.345 | 50.681 | 1.00 | 75.50 | C |
| ATOM | 9855 | CB | PRO | C | 877 | 31.821 | 96.081 | 51.042 | 1.00 | 39.36 | C |
| ATOM | 9856 | CG | PRO | C | 877 | 31.947 | 95.197 | 52.210 | 1.00 | 39.36 | C |
| ATOM | 9857 | C | PRO | C | 877 | 33.904 | 97.499 | 51.482 | 1.00 | 75.50 | C |
| ATOM | 9858 | O | PRO | C | 877 | 34.278 | 98.523 | 50.909 | 1.00 | 75.50 | C |
| ATOM | 9859 | N | SER | C | 878 | 34.058 | 97.324 | 52.791 | 1.00 | 21.99 | C |
| ATOM | 9860 | CA | SER | C | 878 | 34.611 | 98.394 | 53.618 | 1.00 | 21.99 | C |
| ATOM | 9861 | CB | SER | C | 878 | 34.824 | 97.909 | 55.024 | 1.00 | 16.84 | C |
| ATOM | 9862 | OG | SER | C | 878 | 35.856 | 96.954 | 54.973 | 1.00 | 16.84 | C |
| ATOM | 9863 | C | SER | C | 878 | 35.943 | 98.894 | 53.090 | 1.00 | 21.99 | C |
| ATOM | 9864 | O | SER | C | 878 | 35.992 | 99.890 | 52.368 | 1.00 | 21.99 | C |
| ATOM | 9865 | N | ARG | C | 879 | 37.013 | 98.191 | 53.470 | 1.00 | 38.33 | C |
| ATOM | 9866 | CA | ARG | C | 879 | 38.391 | 98.508 | 53.087 | 1.00 | 38.33 | C |
| ATOM | 9867 | CB | ARG | C | 879 | 39.207 | 97.232 | 52.927 | 1.00 | 66.17 | C |
| ATOM | 9868 | CG | ARG | C | 879 | 38.944 | 96.148 | 53.944 | 1.00 | 66.17 | C |
| ATOM | 9869 | CD | ARG | C | 879 | 39.707 | 94.908 | 53.531 | 1.00 | 66.17 | C |
| ATOM | 9870 | NE | ARG | C | 879 | 40.075 | 94.062 | 54.658 | 1.00 | 66.17 | C |
| ATOM | 9871 | CZ | ARG | C | 879 | 40.983 | 93.094 | 54.579 | 1.00 | 66.17 | C |
| ATOM | 9872 | NH1 | ARG | C | 879 | 41.597 | 92.868 | 53.425 | 1.00 | 66.17 | C |
| ATOM | 9873 | NH2 | ARG | C | 879 | 41.283 | 92.358 | 55.648 | 1.00 | 66.17 | C |
| ATOM | 9874 | C | ARG | C | 879 | 38.452 | 99.221 | 51.756 | 1.00 | 38.33 | C |

| ATOM | 9875 | O | ARG C 879 | 38.993 100.323 51.633 1.00 38.33 | C |
|---|---|---|---|---|---|
| ATOM | 9876 | N | MET C 880 | 37.871 98.547 50.770 1.00 35.34 | C |
| ATOM | 9877 | CA | MET C 880 | 37.830 98.960 49.384 1.00 35.34 | C |
| ATOM | 9878 | CB | MET C 880 | 37.513 97.705 48.579 1.00 95.06 | C |
| ATOM | 9879 | CG | MET C 880 | 37.955 96.454 49.345 1.00 95.06 | C |
| ATOM | 9880 | SD | MET C 880 | 37.783 94.867 48.513 1.00 95.06 | C |
| ATOM | 9881 | CE | MET C 880 | 39.395 94.119 48.842 1.00 95.06 | C |
| ATOM | 9882 | C | MET C 880 | 36.913 100.135 48.993 1.00 35.34 | C |
| ATOM | 9883 | O | MET C 880 | 37.002 100.636 47.865 1.00 35.34 | C |
| ATOM | 9884 | N | ASN C 881 | 36.045 100.576 49.907 1.00 7.65 | C |
| ATOM | 9885 | CA | ASN C 881 | 35.136 101.713 49.658 1.00 7.65 | C |
| ATOM | 9886 | CB | ASN C 881 | 35.912 103.058 49.617 1.00 29.82 | C |
| ATOM | 9887 | CG | ASN C 881 | 37.019 103.188 50.695 1.00 29.82 | C |
| ATOM | 9888 | OD1 | ASN C 881 | 37.795 104.154 50.679 1.00 29.82 | C |
| ATOM | 9889 | ND2 | ASN C 881 | 37.091 102.232 51.617 1.00 29.82 | C |
| ATOM | 9890 | C | ASN C 881 | 34.362 101.601 48.330 1.00 7.65 | C |
| ATOM | 9891 | O | ASN C 881 | 34.843 102.077 47.316 1.00 7.65 | C |
| ATOM | 9892 | N | LEU C 882 | 33.175 101.001 48.323 1.00 45.54 | C |
| ATOM | 9893 | CA | LEU C 882 | 32.390 100.878 47.085 1.00 45.54 | C |
| ATOM | 9894 | CB | LEU C 882 | 32.932 99.735 46.223 1.00 13.17 | C |
| ATOM | 9895 | CG | LEU C 882 | 33.340 98.477 46.999 1.00 13.17 | C |
| ATOM | 9896 | CD1 | LEU C 882 | 33.223 97.214 46.156 1.00 13.17 | C |
| ATOM | 9897 | CD2 | LEU C 882 | 34.756 98.670 47.469 1.00 13.17 | C |
| ATOM | 9898 | C | LEU C 882 | 30.889 100.644 47.301 1.00 45.54 | C |
| ATOM | 9899 | O | LEU C 882 | 30.497 99.632 47.869 1.00 45.54 | C |
| ATOM | 9900 | N | GLY C 883 | 30.053 101.574 46.845 1.00 28.44 | C |
| ATOM | 9901 | CA | GLY C 883 | 28.620 101.407 46.979 1.00 28.44 | C |
| ATOM | 9902 | C | GLY C 883 | 28.130 100.495 45.856 1.00 28.44 | C |
| ATOM | 9903 | O | GLY C 883 | 27.422 100.929 44.934 1.00 28.44 | C |
| ATOM | 9904 | N | GLN C 884 | 28.552 99.229 45.889 1.00 100.07 | C |
| ATOM | 9905 | CA | GLN C 884 | 28.121 98.234 44.894 1.00 100.07 | C |
| ATOM | 9906 | CB | GLN C 884 | 28.981 96.962 44.971 1.00 20.42 | C |
| ATOM | 9907 | CG | GLN C 884 | 29.085 96.368 46.371 1.00 20.42 | C |
| ATOM | 9908 | CD | GLN C 884 | 30.264 95.417 46.546 1.00 20.42 | C |
| ATOM | 9909 | OE1 | GLN C 884 | 30.266 94.296 46.025 1.00 20.42 | C |
| ATOM | 9910 | NE2 | GLN C 884 | 31.275 95.862 47.291 1.00 20.42 | C |
| ATOM | 9911 | C | GLN C 884 | 26.743 97.922 45.400 1.00 100.07 | C |
| ATOM | 9912 | O | GLN C 884 | 25.778 97.745 44.656 1.00 100.07 | C |
| ATOM | 9913 | N | ILE C 885 | 26.707 97.877 46.719 1.00 48.67 | C |
| ATOM | 9914 | CA | ILE C 885 | 25.539 97.624 47.502 1.00 48.67 | C |
| ATOM | 9915 | CB | ILE C 885 | 25.816 98.135 48.890 1.00 5.07 | C |
| ATOM | 9916 | CG2 | ILE C 885 | 24.652 97.826 49.810 1.00 5.07 | C |
| ATOM | 9917 | CG1 | ILE C 885 | 27.111 97.499 49.390 1.00 5.07 | C |
| ATOM | 9918 | CD | ILE C 885 | 27.175 95.993 49.180 1.00 5.07 | C |
| ATOM | 9919 | C | ILE C 885 | 24.287 98.271 46.921 1.00 48.67 | C |
| ATOM | 9920 | O | ILE C 985 | 23.231 97.640 46.864 1.00 48.67 | C |
| ATOM | 9921 | N | LEU C 886 | 24.395 99.520 46.483 1.00 44.11 | C |
| ATOM | 9922 | CA | LEU C 886 | 23.240 100.186 45.901 1.00 44.11 | C |
| ATOM | 9923 | CB | LEU C 886 | 23.497 101.683 45.749 1.00 20.52 | C |
| ATOM | 9924 | CG | LEU C 886 | 23.731 102.478 47.042 1.00 20.52 | C |
| ATOM | 9925 | CD1 | LEU C 886 | 24.076 103.893 46.651 1.00 20.52 | C |
| ATOM | 9926 | CD2 | LEU C 886 | 22.520 102.459 47.950 1.00 20.52 | C |
| ATOM | 9927 | C | LEU C 886 | 22.914 99.554 44.553 1.00 44.11 | C |
| ATOM | 9928 | O | LEU C 886 | 22.866 100.208 43.516 1.00 44.11 | C |
| ATOM | 9929 | N | GLU C 887 | 22.707 98.249 44.603 1.00 46.04 | C |
| ATOM | 9930 | CA | GLU C 887 | 22.359 97.446 43.452 1.00 46.04 | C |
| ATOM | 9931 | CB | GLU C 887 | 23.604 96.979 42.697 1.00 47.41 | C |
| ATOM | 9932 | CG | GLU C 887 | 23.277 96.054 41.527 1.00 47.41 | C |
| ATOM | 9933 | CD | GLU C 887 | 24.510 95.534 40.793 1.00 47.41 | C |
| ATOM | 9934 | OE1 | GLU C 887 | 25.343 96.353 40.346 1.00 47.41 | C |
| ATOM | 9935 | OE2 | GLU C 887 | 24.640 94.300 40.651 1.00 47.41 | C |
| ATOM | 9936 | C | GLU C 887 | 21.670 96.256 44.084 1.00 46.04 | C |
| ATOM | 9937 | O | GLU C 887 | 20.512 95.973 43.822 1.00 46.04 | C |
| ATOM | 9938 | N | THR C 888 | 22.400 95.572 44.944 1.00 15.52 | C |
| ATOM | 9939 | CA | THR C 888 | 21.879 94.422 45.646 1.00 15.52 | C |
| ATOM | 9940 | CB | THR C 888 | 22.929 93.960 46.629 1.00 39.97 | C |
| ATOM | 9941 | OG1 | THR C 888 | 24.218 94.175 46.049 1.00 39.97 | C |
| ATOM | 9942 | CG2 | THR C 888 | 22.750 92.496 46.967 1.00 39.97 | C |
| ATOM | 9943 | C | THR C 888 | 20.596 94.826 46.414 1.00 15.52 | C |
| ATOM | 9944 | O | THR C 888 | 19.844 93.969 46.913 1.00 15.52 | C |
| ATOM | 9945 | N | HIS C 889 | 20.377 96.140 46.537 1.00 46.14 | C |
| ATOM | 9946 | CA | HIS C 889 | 19.202 96.680 47.221 1.00 46.14 | C |
| ATOM | 9947 | CB | HIS C 889 | 19.553 97.940 48.004 1.00 27.47 | C |
| ATOM | 9948 | CG | HIS C 889 | 20.365 97.674 49.238 1.00 27.47 | C |
| ATOM | 9949 | CD2 | HIS C 889 | 20.865 96.521 49.748 1.00 27.47 | C |
| ATOM | 9950 | ND1 | HIS C 889 | 20.758 98.673 50.105 1.00 27.47 | C |
| ATOM | 9951 | CE1 | HIS C 889 | 21.464 98.149 51.092 1.00 27.47 | C |
| ATOM | 9952 | NE2 | HIS C 889 | 21.546 96.846 50.900 1.00 27.47 | C |
| ATOM | 9953 | C | HIS C 889 | 18.164 96.984 46.161 1.00 46.14 | C |
| ATOM | 9954 | O | HIS C 889 | 17.050 96.473 46.228 1.00 46.14 | C |
| ATOM | 9955 | N | LEU C 890 | 18.506 97.811 45.177 1.00 12.42 | C |
| ATOM | 9956 | CA | LEU C 890 | 17.556 98.061 44.097 1.00 12.42 | C |
| ATOM | 9957 | CB | LEU C 890 | 17.953 99.282 43.255 1.00 5.07 | C |
| ATOM | 9958 | CG | LEU C 890 | 17.402 99.344 41.815 1.00 5.07 | C |

```
ATOM   9959  CD1 LEU C 890      15.901  99.132  41.832  1.00  5.07           C
ATOM   9960  CD2 LEU C 890      17.759 100.655  41.155  1.00  5.07           C
ATOM   9961  C   LEU C 890      17.662  96.782  43.271  1.00 12.42           C
ATOM   9962  O   LEU C 890      17.508  96.780  42.047  1.00 12.42           C
ATOM   9963  N   GLY C 891      17.957  95.689  43.977  1.00 80.89           C
ATOM   9964  CA  GLY C 891      18.101  94.378  43.368  1.00 80.89           C
ATOM   9965  C   GLY C 891      16.847  93.573  43.603  1.00 80.89           C
ATOM   9966  O   GLY C 891      16.156  93.221  42.650  1.00 80.89           C
ATOM   9967  N   LEU C 892      16.552  93.266  44.862  1.00 28.36           C
ATOM   9968  CA  LEU C 892      15.327  92.537  45.141  1.00 28.36           C
ATOM   9969  CB  LEU C 892      15.209  92.169  46.621  1.00 22.53           C
ATOM   9970  CG  LEU C 892      15.498  93.223  47.673  1.00 22.53           C
ATOM   9971  CD1 LEU C 892      15.167  92.669  49.058  1.00 22.53           C
ATOM   9972  CD2 LEU C 892      16.968  93.612  47.574  1.00 22.53           C
ATOM   9973  C   LEU C 892      14.201  93.477  44.730  1.00 28.36           C
ATOM   9974  O   LEU C 892      13.146  93.049  44.240  1.00 28.36           C
ATOM   9975  N   ALA C 893      14.435  94.770  44.911  1.00 61.38           C
ATOM   9976  CA  ALA C 893      13.450  95.767  44.512  1.00 61.38           C
ATOM   9977  CB  ALA C 893      13.846  97.133  45.041  1.00 75.49           C
ATOM   9978  C   ALA C 893      13.458  95.759  42.985  1.00 61.38           C
ATOM   9979  O   ALA C 893      13.635  96.791  42.330  1.00 61.38           C
ATOM   9980  N   GLY C 894      13.278  94.567  42.434  1.00 25.17           C
ATOM   9981  CA  GLY C 894      13.289  94.396  41.002  1.00 25.17           C
ATOM   9982  C   GLY C 894      13.146  92.922  40.706  1.00 25.17           C
ATOM   9983  O   GLY C 894      12.765  92.526  39.612  1.00 25.17           C
ATOM   9984  N   TYR C 895      13.484  92.092  41.679  1.00 33.29           C
ATOM   9985  CA  TYR C 895      13.336  90.658  41.493  1.00 33.29           C
ATOM   9986  CB  TYR C 895      13.982  89.895  42.654  1.00 53.00           C
ATOM   9987  CG  TYR C 895      13.958  88.386  42.546  1.00 53.00           C
ATOM   9988  CD1 TYR C 895      14.226  87.743  41.342  1.00 53.00           C
ATOM   9989  CE1 TYR C 895      14.276  86.336  41.262  1.00 53.00           C
ATOM   9990  CD2 TYR C 895      13.732  87.596  43.675  1.00 53.00           C
ATOM   9991  CE2 TYR C 895      13.779  86.191  43.617  1.00 53.00           C
ATOM   9992  CZ  TYR C 895      14.052  85.561  42.408  1.00 53.00           C
ATOM   9993  OH  TYR C 895      14.109  84.172  42.349  1.00 53.00           C
ATOM   9994  C   TYR C 895      11.830  90.532  41.542  1.00 33.29           C
ATOM   9995  O   TYR C 895      11.190  90.167  40.558  1.00 33.29           C
ATOM   9996  N   PHE C 896      11.259  90.905  42.681  1.00 57.33           C
ATOM   9997  CA  PHE C 896       9.822  90.831  42.866  1.00 57.33           C
ATOM   9998  CB  PHE C 896       9.481  91.161  44.313  1.00 57.92           C
ATOM   9999  CG  PHE C 896      10.191  90.289  45.306  1.00 57.92           C
ATOM  10000  CD1 PHE C 896      11.390  90.696  45.873  1.00 57.92           C
ATOM  10001  CD2 PHE C 896       9.665  89.050  45.662  1.00 57.92           C
ATOM  10002  CE1 PHE C 896      12.057  89.882  46.785  1.00 57.92           C
ATOM  10003  CE2 PHE C 896      10.318  88.226  46.570  1.00 57.92           C
ATOM  10004  CZ  PHE C 896      11.517  88.641  47.135  1.00 57.92           C
ATOM  10005  C   PHE C 896       9.025  91.723  41.915  1.00 57.33           C
ATOM  10006  O   PHE C 896       7.803  91.599  41.825  1.00 57.33           C
ATOM  10007  N   LEU C 897       9.709  92.615  41.203  1.00 54.76           C
ATOM  10008  CA  LEU C 897       9.026  93.489  40.253  1.00 54.76           C
ATOM  10009  CB  LEU C 897       9.285  94.961  40.580  1.00 52.32           C
ATOM  10010  CG  LEU C 897       8.561  95.498  41.812  1.00 52.32           C
ATOM  10011  CD1 LEU C 897       9.077  94.773  43.033  1.00 52.32           C
ATOM  10012  CD2 LEU C 897       8.780  96.996  41.951  1.00 52.32           C
ATOM  10013  C   LEU C 897       9.437  93.210  38.808  1.00 54.76           C
ATOM  10014  O   LEU C 897       8.915  93.821  37.868  1.00 54.76           C
ATOM  10015  N   GLY C 898      10.358  92.272  38.620  1.00100.02           C
ATOM  10016  CA  GLY C 398      10.800  91.973  37.274  1.00100.02           C
ATOM  10017  C   GLY C 588      11.122  93.283  36.588  1.00100.02           C
ATOM  10018  O   GLY C 898      10.993  93.410  35.370  1.00100.02           C
ATOM  10019  N   GLN C 899      11.522  94.269  37.389  1.00 60.70           C
ATOM  10020  CA  GLN C 899      11.874  95.584  36.879  1.00 60.70           C
ATOM  10021  CB  GLN C 899      11.585  96.674  37.912  1.00 98.42           C
ATOM  10022  CG  GLN C 899      10.129  96.925  38.210  1.00 98.42           C
ATOM  10023  CD  GLN C 899       9.872  98.365  38.620  1.00 98.42           C
ATOM  10024  OE1 GLN C 899       9.825  99.262  37.777  1.00 98.42           C
ATOM  10025  NE2 GLN C 899       9.717  98.596  39.917  1.00 98.42           C
ATOM  10026  C   GLN C 899      13.347  95.652  36.502  1.00 60.70           C
ATOM  10027  O   GLN C 899      14.216  95.137  37.214  1.00 60.70           C
ATOM  10028  N   ARG C 900      13.609  96.289  35.367  1.00 66.63           C
ATOM  10029  CA  ARG C 900      14.961  96.471  34.861  1.00 66.63           C
ATOM  10030  CB  ARG C 900      15.017  96.079  33.387  1.00100.07           C
ATOM  10031  CG  ARG C 900      14.205  94.835  33.049  1.00100.07           C
ATOM  10032  CD  ARG C 900      14.849  93.561  33.574  1.00100.07           C
ATOM  10033  NE  ARG C 900      13.891  92.457  33.624  1.00100.07           C
ATOM  10034  CZ  ARG C 900      13.227  91.980  32.574  1.00100.07           C
ATOM  10035  NH1 ARG C 900      13.411  92.504  31.368  1.00100.07           C
ATOM  10036  NH2 ARG C 900      12.366  90.982  32.731  1.00100.07           C
ATOM  10037  C   ARG C 900      15.194  97.968  35.019  1.00 66.63           C
ATOM  10038  O   ARG C 900      14.322  98.763  34.675  1.00 66.63           C
ATOM  10039  N   TYR C 901      16.349  98.366  35.534  1.00 35.63           C
ATOM  10040  CA  TYR C 901      16.576  99.785  35.734  1.00 35.63           C
ATOM  10041  CB  TYR C 901      16.743 100.077  37.215  1.00 71.06           C
ATOM  10042  CG  TYR C 901      15.606  99.585  38.064  1.00 71.06           C
```

```
ATOM  10043  CD1 TYR C 901     15.321  98.229  38.159  1.00 71.06           C
ATOM  10044  CE1 TYR C 901     14.298  97.767  38.982  1.00 71.06           C
ATOM  10045  CD2 TYR C 901     14.833 100.473  38.809  1.00 71.06           C
ATOM  10046  CE2 TYR C 901     13.807 100.020  39.632  1.00 71.06           C
ATOM  10047  CZ  TYR C 901     13.548  98.668  39.716  1.00 71.06           C
ATOM  10048  OH  TYR C 901     12.559  98.209  40.545  1.00 71.06           C
ATOM  10049  C   TYR C 901     17.736 100.420  35.003  1.00 35.63           C
ATOM  10050  O   TYR C 901     18.665  99.759  34.546  1.00 35.63           C
ATOM  10051  N   ILE C 902     17.668 101.736  34.913  1.00 63.08           C
ATOM  10052  CA  ILE C 902     18.717 102.496  34.286  1.00 63.08           C
ATOM  10053  CB  ILE C 902     18.319 102.961  32.901  1.00 46.56           C
ATOM  10054  CG2 ILE C 902     19.411 103.828  32.313  1.00 46.56           C
ATOM  10055  CG1 ILE C 902     18.090 101.747  32.012  1.00 46.56           C
ATOM  10056  CD  ILE C 902     17.913 102.092  30.539  1.00 46.56           C
ATOM  10057  C   ILE C 902     18.979 103.700  35.167  1.00 63.08           C
ATOM  10058  O   ILE C 902     18.351 104.751  35.011  1.00 63.08           C
ATOM  10059  N   SER C 903     19.893 103.516  36.118  1.00 61.88           C
ATOM  10060  CA  SER C 903     20.295 104.558  37.057  1.00 61.88           C
ATOM  10061  CB  SER C 903     20.390 103.992  38.474  1.00 76.79           C
ATOM  10062  OG  SER C 903     21.504 103.133  38.631  1.00 76.79           C
ATOM  10063  C   SER C 903     21.664 105.021  36.604  1.00 61.88           C
ATOM  10064  O   SER C 903     22.676 104.654  37.186  1.00 61.88           C
ATOM  10065  N   PRO C 904     21.709 105.843  35.553  1.00 11.83           C
ATOM  10066  CD  PRO C 904     20.609 106.624  34.970  1.00 47.87           C
ATOM  10067  CA  PRO C 904     22.990 106.324  35.050  1.00 11.83           C
ATOM  10068  CB  PRO C 904     22.582 107.471  34.123  1.00 47.87           C
ATOM  10069  CG  PRO C 904     21.282 107.924  34.702  1.00 47.87           C
ATOM  10070  C   PRO C 904     24.032 106.743  36.090  1.00 11.83           C
ATOM  10071  O   PRO C 904     23.742 106.859  37.285  1.00 11.83           C
ATOM  10072  N   VAL C 905     25.251 106.951  35.592  1.00 12.06           C
ATOM  10073  CA  VAL C 905     26.419 107.381  36.354  1.00 12.06           C
ATOM  10074  CB  VAL C 905     27.656 107.246  35.487  1.00 25.52           C
ATOM  10075  CG1 VAL C 905     28.740 108.164  35.972  1.00 25.52           C
ATOM  10076  CG2 VAL C 905     28.118 105.832  35.509  1.00 25.52           C
ATOM  10077  C   VAL C 905     26.336 108.841  36.820  1.00 12.06           C
ATOM  10078  O   VAL C 905     26.450 109.768  36.004  1.00 12.06           C
ATOM  10079  N   PHE C 906     26.147 109.037  38.123  1.00 53.53           C
ATOM  10080  CA  PHE C 906     26.060 110.375  38.708  1.00 53.53           C
ATOM  10081  CB  PHE C 906     27.130 111.287  38.109  1.00 22.89           C
ATOM  10082  CG  PHE C 906     28.524 110.944  38.531  1.00 22.89           C
ATOM  10083  CD1 PHE C 906     29.574 111.028  37.624  1.00 22.89           C
ATOM  10084  CD2 PHE C 906     28.787 110.549  39.838  1.00 22.89           C
ATOM  10085  CE1 PHE C 906     30.861 110.726  38.002  1.00 22.89           C
ATOM  10086  CE2 PHE C 906     30.073 110.242  40.236  1.00 22.89           C
ATOM  10087  CZ  PHE C 906     31.117 110.330  39.315  1.00 22.89           C
ATOM  10088  C   PHE C 906     24.709 111.039  38.530  1.00 53.53           C
ATOM  10089  O   PHE C 906     24.550 112.211  38.852  1.00 53.53           C
ATOM  10090  N   ASP C 907     23.729 110.299  38.033  1.00 49.14           C
ATOM  10091  CA  ASP C 907     22.426 110.898  37.810  1.00 49.14           C
ATOM  10092  CB  ASP C 907     22.307 111.325  36.345  1.00 77.54           C
ATOM  10093  CG  ASP C 907     21.211 112.342  36.119  1.00 77.54           C
ATOM  10094  OD1 ASP C 907     20.134 112.185  36.728  1.00 77.54           C
ATOM  10095  OD2 ASP C 907     21.424 113.289  35.324  1.00 77.54           C
ATOM  10096  C   ASP C 907     21.276 109.966  38.152  1.00 49.14           C
ATOM  10097  O   ASP C 907     21.051 108.979  37.452  1.00 49.14           C
ATOM  10098  N   GLY C 908     20.567 110.282  39.237  1.00 38.42           C
ATOM  10099  CA  GLY C 908     19.406 109.503  39.647  1.00 38.42           C
ATOM  10100  C   GLY C 908     19.552 108.240  40.484  1.00 38.42           C
ATOM  10101  O   GLY C 908     20.625 107.920  40.984  1.00 38.42           C
ATOM  10102  N   ALA C 909     18.441 107.520  40.624  1.00 18.76           C
ATOM  10103  CA  ALA C 909     18.400 106.291  41.394  1.00 18.76           C
ATOM  10104  CB  ALA C 909     19.181 105.242  40.702  1.00  9.59           C
ATOM  10105  C   ALA C 909     18.988 106.543  42.769  1.00 18.76           C
ATOM  10106  O   ALA C 909     20.125 106.157  43.016  1.00 18.76           C
ATOM  10107  N   THR C 910     18.195 107.154  43.659  1.00 27.07           C
ATOM  10108  CA  THR C 910     18.621 107.526  45.021  1.00 27.07           C
ATOM  10109  CB  THR C 910     17.957 108.841  45.460  1.00 80.71           C
ATOM  10110  OG1 THR C 910     17.176 109.372  44.385  1.00 80.71           C
ATOM  10111  CG2 THR C 910     19.011 109.844  45.890  1.00 80.71           C
ATOM  10112  C   THR C 910     18.451 106.577  46.207  1.00 27.07           C
ATOM  10113  O   THR C 910     17.704 105.601  46.161  1.00 27.07           C
ATOM  10114  N   GLU C 911     19.145 106.926  47.288  1.00 33.40           C
ATOM  10115  CA  GLU C 911     19.126 106.180  48.546  1.00 33.40           C
ATOM  10116  CB  GLU C 911     20.024 106.875  49.571  1.00 46.53           C
ATOM  10117  CG  GLU C 911     19.694 106.565  51.019  1.00 46.53           C
ATOM  10118  CD  GLU C 911     20.338 105.300  51.506  1.00 46.53           C
ATOM  10119  OE1 GLU C 911     21.584 105.265  51.541  1.00 46.53           C
ATOM  10120  OE2 GLU C 911     19.605 104.350  51.852  1.00 46.53           C
ATOM  10121  C   GLU C 911     17.722 106.010  49.128  1.00 33.40           C
ATOM  10122  O   GLU C 911     17.502 105.133  49.965  1.00 33.40           C
ATOM  10123  N   PRO C 912     16.771 106.891  48.754  1.00 69.29           C
ATOM  10124  CD  PRO C 912     17.016 108.298  48.387  1.00 32.33           C
ATOM  10125  CA  PRO C 912     15.405 106.770  49.262  1.00 69.29           C
ATOM  10126  CB  PRO C 912     15.084 108.185  49.686  1.00 32.33           C
```

| | | | | | | | | | |
|---|---|---|---|---|---|---|---|---|---|
| ATOM | 10127 | CG | PRO | C | 912 | 15.632 | 108.940 | 48.564 | 1.00 32.33 | C |
| ATOM | 10128 | C | PRO | C | 912 | 14.533 | 106.342 | 48.093 | 1.00 69.29 | C |
| ATOM | 10129 | O | PRO | C | 912 | 13.562 | 105.606 | 48.251 | 1.00 69.29 | C |
| ATOM | 10130 | N | GLU | C | 913 | 14.905 | 106.826 | 46.914 | 1.00 66.75 | C |
| ATOM | 10131 | CA | GLU | C | 913 | 14.185 | 106.530 | 45.687 | 1.00 66.75 | C |
| ATOM | 10132 | CB | GLU | C | 913 | 14.948 | 107.078 | 44.484 | 1.00 51.23 | C |
| ATOM | 10133 | CG | GLU | C | 913 | 14.042 | 107.683 | 43.441 | 1.00 51.23 | C |
| ATOM | 10134 | CD | GLU | C | 913 | 14.636 | 108.931 | 42.818 | 1.00 51.23 | C |
| ATOM | 10135 | OE1 | GLU | C | 913 | 15.610 | 108.801 | 42.044 | 1.00 51.23 | C |
| ATOM | 10136 | OE2 | GLU | C | 913 | 14.129 | 110.041 | 43.111 | 1.00 51.23 | C |
| ATOM | 10137 | C | GLU | C | 913 | 14.079 | 105.033 | 45.595 | 1.00 66.75 | C |
| ATOM | 10138 | O | GLU | C | 913 | 13.136 | 104.494 | 45.022 | 1.00 66.75 | C |
| ATOM | 10139 | N | ILE | C | 914 | 15.072 | 104.376 | 46.181 | 1.00 47.22 | C |
| ATOM | 10140 | CA | ILE | C | 914 | 15.142 | 102.929 | 46.215 | 1.00 47.22 | C |
| ATOM | 10141 | CB | ILE | C | 914 | 16.556 | 102.490 | 46.592 | 1.00 36.83 | C |
| ATOM | 10142 | CG2 | ILE | C | 914 | 16.545 | 101.059 | 47.104 | 1.00 36.83 | C |
| ATOM | 10143 | CG1 | ILE | C | 914 | 17.474 | 102.678 | 45.381 | 1.00 36.83 | C |
| ATOM | 10144 | CD | ILE | C | 914 | 18.925 | 102.965 | 45.746 | 1.00 36.83 | C |
| ATOM | 10145 | C | ILE | C | 914 | 14.137 | 102.424 | 47.238 | 1.00 47.22 | C |
| ATOM | 10146 | O | ILE | C | 914 | 13.233 | 101.657 | 46.906 | 1.00 47.22 | C |
| ATOM | 10147 | N | LYS | C | 915 | 14.293 | 102.870 | 48.480 | 1.00 83.17 | C |
| ATOM | 10148 | CA | LYS | C | 915 | 13.383 | 102.480 | 49.547 | 1.00 83.17 | C |
| ATOM | 10149 | CB | LYS | C | 915 | 13.551 | 103.410 | 50.745 | 1.00 42.61 | C |
| ATOM | 10150 | CG | LYS | C | 915 | 14.938 | 103.374 | 51.372 | 1.00 42.61 | C |
| ATOM | 10151 | CD | LYS | C | 915 | 15.264 | 102.017 | 52.002 | 1.00 42.61 | C |
| ATOM | 10152 | CE | LYS | C | 915 | 16.398 | 102.149 | 53.021 | 1.00 42.61 | C |
| ATOM | 10153 | NZ | LYS | C | 915 | 17.566 | 102.917 | 52.482 | 1.00 42.61 | C |
| ATOM | 10154 | C | LYS | C | 915 | 11.952 | 102.560 | 49.025 | 1.00 83.17 | C |
| ATOM | 10155 | O | LYS | C | 915 | 11.190 | 101.611 | 49.153 | 1.00 83.17 | C |
| ATOM | 10156 | N | GLU | C | 916 | 11.593 | 103.701 | 48.439 | 1.00 47.84 | C |
| ATOM | 10157 | CA | GLU | C | 916 | 10.259 | 103.886 | 47.871 | 1.00 47.84 | C |
| ATOM | 10158 | CB | GLU | C | 916 | 10.201 | 105.195 | 47.064 | 1.00100.07 | C |
| ATOM | 10159 | CG | GLU | C | 916 | 9.106 | 105.238 | 45.991 | 1.00100.07 | C |
| ATOM | 10160 | CD | GLU | C | 916 | 9.412 | 106.226 | 44.863 | 1.00100.07 | C |
| ATOM | 10161 | OE1 | GLU | C | 916 | 10.559 | 106.227 | 44.360 | 1.00100.07 | C |
| ATOM | 10162 | OE2 | GLU | C | 916 | 8.505 | 106.990 | 44.465 | 1.00100.07 | C |
| ATOM | 10163 | C | GLU | C | 916 | 10.059 | 102.703 | 46.937 | 1.00 47.84 | C |
| ATOM | 10164 | O | GLU | C | 916 | 9.176 | 101.861 | 47.122 | 1.00 47.84 | C |
| ATOM | 10165 | N | LEU | C | 917 | 10.934 | 102.649 | 45.945 | 1.00 81.59 | C |
| ATOM | 10166 | CA | LEU | C | 917 | 10.925 | 101.618 | 44.933 | 1.00 81.59 | C |
| ATOM | 10167 | CB | LEU | C | 917 | 12.010 | 101.918 | 43.924 | 1.00 30.02 | C |
| ATOM | 10168 | CG | LEU | C | 917 | 11.620 | 101.641 | 42.486 | 1.00 30.02 | C |
| ATOM | 10169 | CD1 | LEU | C | 917 | 12.712 | 102.187 | 41.575 | 1.00 30.02 | C |
| ATOM | 10170 | CD2 | LEU | C | 917 | 11.397 | 100.153 | 42.281 | 1.00 30.02 | C |
| ATOM | 10171 | C | LEU | C | 917 | 11.183 | 100.262 | 45.547 | 1.00 81.59 | C |
| ATOM | 10172 | O | LEU | C | 917 | 11.348 | 99.269 | 44.845 | 1.00 81.59 | C |
| ATOM | 10173 | N | LEU | C | 918 | 11.215 | 100.216 | 46.866 | 1.00 38.74 | C |
| ATOM | 10174 | CA | LEU | C | 918 | 11.487 | 98.969 | 47.536 | 1.00 38.74 | C |
| ATOM | 10175 | CB | LEU | C | 918 | 12.849 | 99.064 | 48.216 | 1.00 71.95 | C |
| ATOM | 10176 | CG | LEU | C | 918 | 13.477 | 97.784 | 48.746 | 1.00 71.95 | C |
| ATOM | 10177 | CD1 | LEU | C | 918 | 14.882 | 97.678 | 48.198 | 1.00 71.95 | C |
| ATOM | 10178 | CD2 | LEU | C | 918 | 13.476 | 97.789 | 50.269 | 1.00 71.95 | C |
| ATOM | 10179 | C | LEU | C | 918 | 10.397 | 98.707 | 48.548 | 1.00 38.74 | C |
| ATOM | 10180 | O | LEU | C | 918 | 10.032 | 97.556 | 48.795 | 1.00 38.74 | C |
| ATOM | 10181 | N | ALA | C | 919 | 9.888 | 99.785 | 49.142 | 1.00 24.80 | C |
| ATOM | 10182 | CA | ALA | C | 919 | 8.825 | 99.676 | 50.132 | 1.00 24.80 | C |
| ATOM | 10183 | CB | ALA | C | 919 | 8.133 | 101.017 | 50.319 | 1.00 74.22 | C |
| ATOM | 10184 | C | ALA | C | 919 | 7.908 | 98.699 | 49.455 | 1.00 24.80 | C |
| ATOM | 10185 | O | ALA | C | 919 | 7.547 | 97.668 | 50.024 | 1.00 24.80 | C |
| ATOM | 10186 | N | GLU | C | 920 | 7.590 | 99.024 | 48.203 | 1.00 30.78 | C |
| ATOM | 10187 | CA | GLU | C | 920 | 6.750 | 98.175 | 47.379 | 1.00 30.78 | C |
| ATOM | 10188 | CB | GLU | C | 920 | 6.616 | 98.747 | 45.964 | 1.00100.07 | C |
| ATOM | 10189 | CG | GLU | C | 920 | 5.893 | 100.081 | 45.889 | 1.00100.07 | C |
| ATOM | 10190 | CD | GLU | C | 920 | 5.895 | 100.672 | 44.490 | 1.00100.07 | C |
| ATOM | 10191 | OE1 | GLU | C | 920 | 5.373 | 100.015 | 43.563 | 1.00100.07 | C |
| ATOM | 10192 | OE2 | GLU | C | 920 | 6.419 | 101.796 | 44.322 | 1.00100.07 | C |
| ATOM | 10193 | C | GLU | C | 920 | 7.476 | 96.843 | 47.328 | 1.00 30.78 | C |
| ATOM | 10194 | O | GLU | C | 920 | 8.187 | 96.488 | 48.271 | 1.00 30.78 | C |
| ATOM | 10195 | N | ALA | C | 921 | 7.321 | 96.113 | 46.229 | 1.00 33.07 | C |
| ATOM | 10196 | CA | ALA | C | 921 | 7.978 | 94.821 | 46.118 | 1.00 33.07 | C |
| ATOM | 10197 | CB | ALA | C | 921 | 9.469 | 95.013 | 46.090 | 1.00 35.08 | C |
| ATOM | 10198 | C | ALA | C | 921 | 7.567 | 94.069 | 47.370 | 1.00 33.07 | C |
| ATOM | 10199 | O | ALA | C | 921 | 6.745 | 93.156 | 47.323 | 1.00 33.07 | C |
| ATOM | 10200 | N | PHE | C | 922 | 8.148 | 94.468 | 48.493 | 1.00 42.33 | C |
| ATOM | 10201 | CA | PHE | C | 922 | 7.808 | 93.876 | 49.762 | 1.00 42.33 | C |
| ATOM | 10202 | CB | PHE | C | 922 | 8.342 | 94.716 | 50.907 | 1.00 22.01 | C |
| ATOM | 10203 | CG | PHE | C | 922 | 7.877 | 94.245 | 52.260 | 1.00 22.01 | C |
| ATOM | 10204 | CD1 | PHE | C | 922 | 8.712 | 93.471 | 53.068 | 1.00 22.01 | C |
| ATOM | 10205 | CD2 | PHE | C | 922 | 6.604 | 94.590 | 52.734 | 1.00 22.01 | C |
| ATOM | 10206 | CE1 | PHE | C | 922 | 8.291 | 93.053 | 54.324 | 1.00 22.01 | C |
| ATOM | 10207 | CE2 | PHE | C | 922 | 6.176 | 94.179 | 53.981 | 1.00 22.01 | C |
| ATOM | 10208 | CZ | PHE | C | 922 | 7.017 | 93.412 | 54.782 | 1.00 22.01 | C |
| ATOM | 10209 | C | PHE | C | 922 | 6.292 | 93.851 | 49.852 | 1.00 42.33 | C |
| ATOM | 10210 | O | PHE | C | 922 | 5.701 | 92.806 | 50.119 | 1.00 42.33 | C |

```
ATOM  10211  N   ASN C 923       5.667  95.007  49.626  1.00 62.06           C
ATOM  10212  CA  ASN C 923       4.212  95.118  49.688  1.00 62.06           C
ATOM  10213  CB  ASN C 923       3.742  96.518  49.281  1.00 89.21           C
ATOM  10214  CG  ASN C 923       3.670  97.473  50.463  1.00 89.21           C
ATOM  10215  OD1 ASN C 923       3.197  97.110  51.544  1.00 89.21           C
ATOM  10216  ND2 ASN C 923       4.125  98.702  50.260  1.00 89.21           C
ATOM  10217  C   ASN C 923       3.506  94.078  48.841  1.00 62.06           C
ATOM  10218  O   ASN C 923       2.294  94.129  48.662  1.00 62.06           C
ATOM  10219  N   LEU C 924       4.281  93.146  48.303  1.00 47.73           C
ATOM  10220  CA  LEU C 924       3.742  92.057  47.514  1.00 47.73           C
ATOM  10221  CB  LEU C 924       3.881  92.316  46.019  1.00 23.71           C
ATOM  10222  CG  LEU C 924       4.708  93.489  45.513  1.00 23.71           C
ATOM  10223  CD1 LEU C 924       4.658  93.419  43.992  1.00 23.71           C
ATOM  10224  CD2 LEU C 924       4.178  94.850  46.032  1.00 23.71           C
ATOM  10225  C   LEU C 924       4.517  90.818  47.886  1.00 47.73           C
ATOM  10226  O   LEU C 924       3.945  89.739  48.032  1.00 47.73           C
ATOM  10227  N   TYR C 925       5.828  90.977  48.038  1.00 29.69           C
ATOM  10228  CA  TYR C 925       6.668  89.857  48.416  1.00 29.69           C
ATOM  10229  CB  TYR C 925       8.094  90.305  48.698  1.00 48.02           C
ATOM  10230  CG  TYR C 925       8.743  89.505  49.804  1.00 48.02           C
ATOM  10231  CD1 TYR C 925       9.045  88.150  49.640  1.00 48.02           C
ATOM  10232  CE1 TYR C 925       9.594  87.401  50.683  1.00 48.02           C
ATOM  10233  CD2 TYR C 925       9.010  90.089  51.036  1.00 48.02           C
ATOM  10234  CE2 TYR C 925       9.554  89.351  52.075  1.00 48.02           C
ATOM  10235  CZ  TYR C 925       9.843  88.013  51.896  1.00 48.02           C
ATOM  10236  OH  TYR C 925      10.378  87.305  52.941  1.00 48.02           C
ATOM  10237  C   TYR C 925       6.056  89.350  49.689  1.00 29.69           C
ATOM  10238  O   TYR C 925       6.118  88.165  49.998  1.00 29.69           C
ATOM  10239  N   PHE C 926       5.469  90.269  50.436  1.00 98.59           C
ATOM  10240  CA  PHE C 926       4.832  89.893  51.668  1.00 98.59           C
ATOM  10241  CB  PHE C 926       5.189  90.854  52.787  1.00 51.90           C
ATOM  10242  CG  PHE C 926       4.920  90.292  54.131  1.00 51.90           C
ATOM  10243  CD1 PHE C 926       5.135  88.937  54.371  1.00 51.90           C
ATOM  10244  CD2 PHE C 926       4.475  91.091  55.160  1.00 51.90           C
ATOM  10245  CE1 PHE C 926       4.913  88.382  55.620  1.00 51.90           C
ATOM  10246  CE2 PHE C 926       4.249  90.547  56.423  1.00 51.90           C
ATOM  10247  CZ  PHE C 926       4.470  89.186  56.652  1.00 51.90           C
ATOM  10248  C   PHE C 926       3.333  89.847  51.478  1.00 98.59           C
ATOM  10249  O   PHE C 926       2.590  89.526  52.404  1.00 98.59           C
ATOM  10250  N   GLY C 927       2.893  90.184  50.271  1.00 98.95           C
ATOM  10251  CA  GLY C 927       1.477  90.135  49.963  1.00 98.95           C
ATOM  10252  C   GLY C 927       1.133  88.669  49.783  1.00 98.95           C
ATOM  10253  O   GLY C 927      -0.022  88.259  49.904  1.00 98.95           C
ATOM  10254  N   LYS C 928       2.165  87.880  49.490  1.00 49.42           C
ATOM  10255  CA  LYS C 928       2.027  86.441  49.302  1.00 49.42           C
ATOM  10256  CB  LYS C 928       3.387  85.786  49.020  1.00 99.83           C
ATOM  10257  CG  LYS C 928       4.359  86.565  48.138  1.00 99.83           C
ATOM  10258  CD  LYS C 928       5.699  85.820  48.044  1.00 99.83           C
ATOM  10259  CE  LYS C 928       6.749  86.622  47.285  1.00 99.83           C
ATOM  10260  NZ  LYS C 928       8.028  85.873  47.109  1.00 99.83           C
ATOM  10261  C   LYS C 928       1.498  85.864  50.606  1.00 49.42           C
ATOM  10262  O   LYS C 928       0.299  85.873  50.868  1.00 49.42           C
ATOM  10263  N   ARG C 929       2.430  85.364  51.409  1.00 37.71           C
ATOM  10264  CA  ARG C 929       2.140  84.779  52.700  1.00 37.71           C
ATOM  10265  CB  ARG C 929       3.271  85.128  53.657  1.00 81.61           C
ATOM  10266  CG  ARG C 929       4.619  84.729  53.097  1.00 81.61           C
ATOM  10267  CD  ARG C 929       5.742  85.373  53.857  1.00 81.61           C
ATOM  10268  NE  ARG C 929       5.714  85.008  55.262  1.00 81.61           C
ATOM  10269  CZ  ARG C 929       6.634  85.392  56.133  1.00 81.61           C
ATOM  10270  NH1 ARG C 929       7.647  86.149  55.736  1.00 81.61           C
ATOM  10271  NH2 ARG C 929       6.541  85.019  57.399  1.00 81.61           C
ATOM  10272  C   ARG C 929       0.813  85.313  53.209  1.00 37.71           C
ATOM  10273  O   ARG C 929      -0.153  84.559  53.353  1.00 37.71           C
ATOM  10274  N   GLN C 930       0.764  86.612  53.487  1.00 73.92           C
ATOM  10275  CA  GLN C 930      -0.481  87.221  53.924  1.00 73.92           C
ATOM  10276  CB  GLN C 930      -0.255  88.660  54.374  1.00 92.26           C
ATOM  10277  CG  GLN C 930       0.750  88.787  55.499  1.00 92.26           C
ATOM  10278  CD  GLN C 930       0.625  90.099  56.247  1.00 92.26           C
ATOM  10279  OE1 GLN C 930       0.654  91.178  55.649  1.00 92.26           C
ATOM  10280  NE2 GLN C 930       0.485  90.012  57.567  1.00 92.26           C
ATOM  10281  C   GLN C 930      -1.310  87.174  52.650  1.00 73.92           C
ATOM  10282  O   GLN C 930      -1.453  88.163  51.926  1.00 73.92           C
ATOM  10283  N   GLY C 931      -1.813  85.975  52.385  1.00 45.05           C
ATOM  10284  CA  GLY C 931      -2.604  85.683  51.210  1.00 45.05           C
ATOM  10285  C   GLY C 931      -2.421  84.190  51.048  1.00 45.05           C
ATOM  10286  O   GLY C 931      -3.281  83.408  51.461  1.00 45.05           C
ATOM  10287  N   GLU C 932      -1.277  83.797  50.488  1.00 60.13           C
ATOM  10288  CA  GLU C 932      -0.955  82.388  50.281  1.00 60.13           C
ATOM  10289  CB  GLU C 932       0.548  82.206  50.044  1.00 98.24           C
ATOM  10290  CG  GLU C 932       1.063  82.817  48.754  1.00 98.24           C
ATOM  10291  CD  GLU C 932       2.266  82.068  48.198  1.00 98.24           C
ATOM  10292  OE1 GLU C 932       3.247  81.870  48.948  1.00 98.24           C
ATOM  10293  OE2 GLU C 932       2.229  81.679  47.010  1.00 98.24           C
ATOM  10294  C   GLU C 932      -1.378  81.547  51.483  1.00 60.13           C
```

| | | | | | | | | | |
|---|---|---|---|---|---|---|---|---|---|
|ATOM|10295|O|GLU|C 932|-1.697|80.360|51.344|1.00 60.13|C|
|ATOM|10296|N|GLY|C 933|-1.364|82.171|52.660|1.00100.07|C|
|ATOM|10297|CA|GLY|C 933|-1.760|81.487|53.877|1.00100.07|C|
|ATOM|10298|C|GLY|C 933|-0.697|81.361|54.957|1.00100.07|C|
|ATOM|10299|O|GLY|C 933|-0.694|80.383|55.705|1.00100.07|C|
|ATOM|10300|N|PHE|C 934|0.208|82.331|55.055|1.00 85.74|C|
|ATOM|10301|CA|PHE|C 934|1.252|82.269|56.077|1.00 85.74|C|
|ATOM|10302|CB|PHE|C 934|2.532|81.644|55.520|1.00 99.77|C|
|ATOM|10303|CG|PHE|C 934|2.350|80.262|54.960|1.00 99.77|C|
|ATOM|10304|CD1|PHE|C 934|2.053|80.076|53.610|1.00 99.77|C|
|ATOM|10305|CD2|PHE|C 934|2.507|79.144|55.772|1.00 99.77|C|
|ATOM|10306|CE1|PHE|C 934|1.922|78.793|53.072|1.00 99.77|C|
|ATOM|10307|CE2|PHE|C 934|2.377|77.855|55.244|1.00 99.77|C|
|ATOM|10308|CZ|PHE|C 934|2.085|77.681|53.890|1.00 99.77|C|
|ATOM|10309|C|PHE|C 934|1.602|83.626|56.671|1.00 85.74|C|
|ATOM|10310|O|PHE|C 934|1.214|84.675|56.158|1.00 85.74|C|
|ATOM|10311|N|GLY|C 935|2.351|83.589|57.763|1.00 45.71|C|
|ATOM|10312|CA|GLY|C 935|2.755|84.816|58.409|1.00 45.71|C|
|ATOM|10313|C|GLY|C 935|3.878|84.583|59.401|1.00 45.71|C|
|ATOM|10314|O|GLY|C 935|3.860|83.591|60.128|1.00 45.71|C|
|ATOM|10315|N|VAL|C 936|4.856|85.492|59.408|1.00 13.93|C|
|ATOM|10316|CA|VAL|C 936|6.001|85.448|60.306|1.00 13.93|C|
|ATOM|10317|CB|VAL|C 936|6.082|86.757|61.074|1.00 41.62|C|
|ATOM|10318|CG1|VAL|C 936|7.195|86.695|62.124|1.00 41.62|C|
|ATOM|10319|CG2|VAL|C 936|6.263|87.900|60.080|1.00 41.62|C|
|ATOM|10320|C|VAL|C 936|5.983|84.307|61.315|1.00 13.93|C|
|ATOM|10321|O|VAL|C 936|5.042|84.161|62.098|1.00 13.93|C|
|ATOM|10322|N|ASP|C 937|7.033|83.500|61.308|1.00 25.57|C|
|ATOM|10323|CA|ASP|C 937|7.113|82.385|62.241|1.00 25.57|C|
|ATOM|10324|CB|ASP|C 937|7.294|81.071|61.479|1.00 50.57|C|
|ATOM|10325|CG|ASP|C 937|8.599|81.012|60.706|1.00 50.57|C|
|ATOM|10326|OD1|ASP|C 937|9.643|80.752|61.345|1.00 50.57|C|
|ATOM|10327|OD2|ASP|C 937|8.575|81.228|59.468|1.00 50.57|C|
|ATOM|10328|C|ASP|C 937|8.269|82.614|63.192|1.00 25.57|C|
|ATOM|10329|O|ASP|C 937|9.162|83.418|62.920|1.00 25.57|C|
|ATOM|10330|N|LYS|C 938|8.246|81.911|64.312|1.00 54.70|C|
|ATOM|10331|CA|LYS|C 938|9.287|82.076|65.307|1.00 54.70|C|
|ATOM|10332|CB|LYS|C 938|9.449|80.790|66.123|1.00100.07|C|
|ATOM|10333|CG|LYS|C 938|8.154|80.293|66.769|1.00100.07|C|
|ATOM|10334|CD|LYS|C 938|7.598|81.261|67.820|1.00100.07|C|
|ATOM|10335|CE|LYS|C 938|8.309|81.127|69.166|1.00100.07|C|
|ATOM|10336|NZ|LYS|C 938|7.648|81.906|70.267|1.00100.07|C|
|ATOM|10337|C|LYS|C 938|10.613|82.463|64.654|1.00 54.70|C|
|ATOM|10338|O|LYS|C 938|11.248|83.443|65.044|1.00 54.70|C|
|ATOM|10339|N|ARG|C 939|11.008|81.721|63.627|1.00 52.19|C|
|ATOM|10340|CA|ARG|C 939|12.279|81.999|62.973|1.00 52.19|C|
|ATOM|10341|CB|ARG|C 939|12.419|81.167|61.698|1.00 98.27|C|
|ATOM|10342|CG|ARG|C 939|12.252|79.675|61.940|1.00 98.27|C|
|ATOM|10343|CD|ARG|C 939|13.016|79.198|63.182|1.00 98.27|C|
|ATOM|10344|NE|ARG|C 939|12.664|79.981|64.372|1.00 98.27|C|
|ATOM|10345|CZ|ARG|C 939|12.968|79.671|65.631|1.00 98.27|C|
|ATOM|10346|NH1|ARG|C 939|13.644|78.561|65.917|1.00 98.27|C|
|ATOM|10347|NH2|ARG|C 939|12.605|80.493|66.611|1.00 98.27|C|
|ATOM|10348|C|ARG|C 939|12.487|83.472|62.706|1.00 52.19|C|
|ATOM|10349|O|ARG|C 939|13.542|84.013|63.013|1.00 52.19|C|
|ATOM|10350|N|GLU|C 940|11.495|84.137|62.142|1.00 22.52|C|
|ATOM|10351|CA|GLU|C 940|11.662|85.551|61.922|1.00 22.52|C|
|ATOM|10352|CB|GLU|C 940|10.625|86.067|60.926|1.00 50.73|C|
|ATOM|10353|CG|GLU|C 940|10.768|85.405|59.559|1.00 50.73|C|
|ATOM|10354|CD|GLU|C 940|9.697|85.801|58.557|1.00 50.73|C|
|ATOM|10355|OE1|GLU|C 940|9.648|86.984|58.162|1.00 50.73|C|
|ATOM|10356|OE2|GLU|C 940|8.907|84.921|58.156|1.00 50.73|C|
|ATOM|10357|C|GLU|C 940|11.421|86.069|63.323|1.00 22.52|C|
|ATOM|10358|O|GLU|C 940|12.299|85.953|64.184|1.00 22.52|C|
|ATOM|10359|N|LYS|C 941|10.219|86.592|63.565|1.00 61.51|C|
|ATOM|10360|CA|LYS|C 941|9.828|87.127|64.876|1.00 61.51|C|
|ATOM|10361|CB|LYS|C 941|8.385|86.705|65.206|1.00100.07|C|
|ATOM|10362|CG|LYS|C 941|7.926|87.054|66.626|1.00100.07|C|
|ATOM|10363|CD|LYS|C 941|6.502|86.574|66.918|1.00100.07|C|
|ATOM|10364|CE|LYS|C 941|6.024|87.098|68.277|1.00100.07|C|
|ATOM|10365|NZ|LYS|C 941|4.574|86.854|68.560|1.00100.07|C|
|ATOM|10366|C|LYS|C 941|10.748|86.670|65.999|1.00 61.51|C|
|ATOM|10367|O|LYS|C 941|11.813|87.245|66.224|1.00 61.51|C|
|ATOM|10368|N|GLU|C 942|10.317|85.618|66.685|1.00 80.51|C|
|ATOM|10369|CA|GLU|C 942|11.052|85.043|67.798|1.00 80.51|C|
|ATOM|10370|CB|GLU|C 942|10.944|83.512|67.767|1.00100.07|C|
|ATOM|10371|CG|GLU|C 942|11.971|82.771|68.626|1.00100.07|C|
|ATOM|10372|CD|GLU|C 942|12.028|83.277|70.062|1.00100.07|C|
|ATOM|10373|OE1|GLU|C 942|10.994|83.219|70.769|1.00100.07|C|
|ATOM|10374|OE2|GLU|C 942|13.116|83.733|70.482|1.00100.07|C|
|ATOM|10375|C|GLU|C 942|12.514|85.459|67.854|1.00 80.51|C|
|ATOM|10376|O|GLU|C 942|12.908|86.272|68.686|1.00 80.51|C|
|ATOM|10377|N|VAL|C 943|13.328|84.925|66.963|1.00 48.32|C|
|ATOM|10378|CA|VAL|C 943|14.725|85.277|67.030|1.00 48.32|C|

```
ATOM  10379  CB   VAL C 943      15.567  84.348  66.134  1.00100.07           C
ATOM  10380  CG1  VAL C 943      17.035  84.407  66.560  1.00100.07           C
ATOM  10381  CG2  VAL C 943      15.039  82.921  66.233  1.00100.07           C
ATOM  10382  C    VAL C 943      14.976  86.737  66.670  1.00 48.32           C
ATOM  10383  O    VAL C 943      14.757  87.628  67.497  1.00 48.32           C
ATOM  10384  N    LEU C 944      15.422  86.969  65.436  1.00 40.93           C
ATOM  10385  CA   LEU C 944      15.757  88.302  64.932  1.00 40.93           C
ATOM  10386  CB   LEU C 944      15.659  88.329  63.411  1.00 60.07           C
ATOM  10387  CG   LEU C 944      16.688  87.441  62.715  1.00 60.07           C
ATOM  10388  CD1  LEU C 944      16.246  85.985  62.777  1.00 60.07           C
ATOM  10389  CD2  LEU C 944      16.842  87.890  61.274  1.00 60.07           C
ATOM  10390  C    LEU C 944      14.957  89.454  65.512  1.00 40.93           C
ATOM  10391  O    LEU C 944      15.479  90.230  66.310  1.00 40.93           C
ATOM  10392  N    ALA C 945      13.704  89.572  65.091  1.00 38.12           C
ATOM  10393  CA   ALA C 945      12.836  90.625  65.584  1.00 38.12           C
ATOM  10394  CB   ALA C 945      11.407  90.114  65.671  1.00100.07           C
ATOM  10395  C    ALA C 945      13.320  91.096  66.958  1.00 38.12           C
ATOM  10396  O    ALA C 945      13.366  92.289  67.228  1.00 38.12           C
ATOM  10397  N    ARG C 946      13.661  90.160  67.836  1.00 48.91           C
ATOM  10398  CA   ARG C 946      14.181  90.556  69.131  1.00 48.91           C
ATOM  10399  CB   ARG C 946      14.446  89.335  70.025  1.00100.07           C
ATOM  10400  CG   ARG C 946      13.193  88.586  70.477  1.00100.07           C
ATOM  10401  CD   ARG C 946      13.519  87.373  71.369  1.00100.07           C
ATOM  10402  NE   ARG C 946      12.321  86.590  71.697  1.00100.07           C
ATOM  10403  CZ   ARG C 946      12.314  85.492  72.451  1.00100.07           C
ATOM  10404  NH1  ARG C 946      13.445  85.029  72.970  1.00100.07           C
ATOM  10405  NH2  ARG C 946      11.173  84.852  72.687  1.00100.07           C
ATOM  10406  C    ARG C 946      15.498  91.207  68.736  1.00 48.91           C
ATOM  10407  O    ARG C 946      15.535  92.375  68.347  1.00 48.91           C
ATOM  10408  N    ALA C 947      16.566  90.416  68.779  1.00 34.81           C
ATOM  10409  CA   ALA C 947      17.919  90.862  68.440  1.00 34.81           C
ATOM  10410  CB   ALA C 947      18.625  89.778  67.616  1.00 33.10           C
ATOM  10411  C    ALA C 947      18.065  92.220  67.749  1.00 34.81           C
ATOM  10412  O    ALA C 947      18.525  93.177  68.359  1.00 34.81           C
ATOM  10413  N    GLU C 948      17.663  92.332  66.494  1.00 31.69           C
ATOM  10414  CA   GLU C 948      17.858  93.602  65.823  1.00 31.69           C
ATOM  10415  CB   GLU C 948      17.310  93.566  64.395  1.00100.07           C
ATOM  10416  CG   GLU C 948      15.905  94.088  64.237  1.00100.07           C
ATOM  10417  CD   GLU C 948      14.945  93.447  65.212  1.00100.07           C
ATOM  10418  OE1  GLU C 948      15.056  92.225  65.428  1.00100.07           C
ATOM  10419  OE2  GLU C 948      14.080  94.164  65.759  1.00100.07           C
ATOM  10420  C    GLU C 948      17.326  94.834  66.551  1.00 31.69           C
ATOM  10421  O    GLU C 948      18.046  95.827  66.661  1.00 31.69           C
ATOM  10422  N    LYS C 949      16.098  94.803  67.066  1.00 68.91           C
ATOM  10423  CA   LYS C 949      15.586  95.995  67.742  1.00 68.91           C
ATOM  10424  CB   LYS C 949      14.186  95.773  68.332  1.00 46.24           C
ATOM  10425  CG   LYS C 949      14.140  95.089  69.686  1.00 46.24           C
ATOM  10426  CD   LYS C 949      12.816  95.354  70.398  1.00 46.24           C
ATOM  10427  CE   LYS C 949      11.632  94.708  69.688  1.00 46.24           C
ATOM  10428  NZ   LYS C 949      11.372  95.219  68.310  1.00 46.24           C
ATOM  10429  C    LYS C 949      16.564  96.359  68.840  1.00 68.91           C
ATOM  10430  O    LYS C 949      16.754  97.532  69.150  1.00 68.91           C
ATOM  10431  N    LEU C 950      17.193  95.340  69.417  1.00 30.74           C
ATOM  10432  CA   LEU C 950      18.179  95.549  70.458  1.00 30.74           C
ATOM  10433  CB   LEU C 950      18.600  94.206  71.067  1.00 99.55           C
ATOM  10434  CG   LEU C 950      17.569  93.391  71.869  1.00 99.55           C
ATOM  10435  CD1  LEU C 950      16.345  93.102  71.026  1.00 99.55           C
ATOM  10436  CD2  LEU C 950      18.194  92.080  72.340  1.00 99.55           C
ATOM  10437  C    LEU C 950      19.359  96.211  69.756  1.00 30.74           C
ATOM  10438  O    LEU C 950      20.496  95.767  69.868  1.00 30.74           C
ATOM  10439  N    GLY C 951      19.068  97.275  69.016  1.00 56.95           C
ATOM  10440  CA   GLY C 951      20.095  97.992  68.288  1.00 56.95           C
ATOM  10441  C    GLY C 951      19.926  97.793  66.797  1.00 56.95           C
ATOM  10442  O    GLY C 951      20.687  97.029  66.199  1.00 56.95           C
ATOM  10443  N    LEU C 952      18.929  98.474  66.218  1.00 89.26           C
ATOM  10444  CA   LEU C 952      18.592  98.417  64.786  1.00 89.26           C
ATOM  10445  CB   LEU C 952      19.331  97.274  64.100  1.00 36.22           C
ATOM  10446  CG   LEU C 952      18.842  96.852  62.717  1.00 36.22           C
ATOM  10447  CD1  LEU C 952      18.763  98.082  61.807  1.00 36.22           C
ATOM  10448  CD2  LEU C 952      19.790  95.785  62.145  1.00 36.22           C
ATOM  10449  C    LEU C 952      17.088  98.227  64.576  1.00 89.26           C
ATOM  10450  O    LEU C 952      16.434  97.588  65.395  1.00 89.26           C
ATOM  10451  N    VAL C 953      16.551  98.771  63.478  1.00 34.55           C
ATOM  10452  CA   VAL C 953      15.111  98.679  63.138  1.00 34.55           C
ATOM  10453  CB   VAL C 953      14.627  97.220  63.000  1.00 40.33           C
ATOM  10454  CG1  VAL C 953      14.110  96.691  64.342  1.00 40.33           C
ATOM  10455  CG2  VAL C 953      13.513  97.162  61.987  1.00 40.33           C
ATOM  10456  C    VAL C 953      14.119  99.349  64.109  1.00 34.55           C
ATOM  10457  O    VAL C 953      14.311  99.343  65.335  1.00 34.55           C
ATOM  10458  N    SER C 954      13.039  99.895  63.556  1.00 75.53           C
ATOM  10459  CA   SER C 954      12.016 100.559  64.363  1.00 75.53           C
ATOM  10460  CB   SER C 954      10.830 100.943  63.474  1.00 67.76           C
ATOM  10461  OG   SER C 954      11.212 101.907  62.504  1.00 67.76           C
ATOM  10462  C    SER C 954      11.548  99.653  65.507  1.00 75.53           C
```

| | | | | | | | | | |
|---|---|---|---|---|---|---|---|---|---|
| ATOM | 10463 | O | SER C 954 | 10.861 | 98.663 | 65.270 | 1.00 | 75.53 | C |
| ATOM | 10464 | N | PRO C 955 | 11.909 | 99.989 | 66.764 | 1.00 | 69.46 | C |
| ATOM | 10465 | CD | PRO C 955 | 12.816 | 101.089 | 67.139 | 1.00 | 94.74 | C |
| ATOM | 10466 | CA | PRO C 955 | 11.541 | 99.212 | 67.957 | 1.00 | 69.46 | C |
| ATOM | 10467 | CB | PRO C 955 | 12.649 | 99.558 | 68.936 | 1.00 | 94.74 | C |
| ATOM | 10468 | CG | PRO C 955 | 12.816 | 101.013 | 68.672 | 1.00 | 94.74 | C |
| ATOM | 10469 | C | PRO C 955 | 10.184 | 99.525 | 68.550 | 1.00 | 69.46 | C |
| ATOM | 10470 | O | PRO C 955 | 9.579 | 100.547 | 68.247 | 1.00 | 69.46 | C |
| ATOM | 10471 | N | GLY C 956 | 9.714 | 98.630 | 69.409 | 1.00 | 71.64 | C |
| ATOM | 10472 | CA | GLY C 956 | 8.438 | 98.847 | 70.055 | 1.00 | 71.64 | C |
| ATOM | 10473 | C | GLY C 956 | 7.165 | 98.338 | 69.398 | 1.00 | 71.64 | C |
| ATOM | 10474 | O | GLY C 956 | 6.475 | 97.512 | 69.992 | 1.00 | 71.64 | C |
| ATOM | 10475 | N | LYS C 957 | 6.840 | 98.791 | 68.187 | 1.00 | 34.57 | C |
| ATOM | 10476 | CA | LYS C 957 | 5.583 | 98.353 | 67.590 | 1.00 | 34.57 | C |
| ATOM | 10477 | CB | LYS C 957 | 4.733 | 99.574 | 67.232 | 1.00 | 100.07 | C |
| ATOM | 10478 | CG | LYS C 957 | 3.255 | 99.242 | 66.987 | 1.00 | 100.07 | C |
| ATOM | 10479 | CD | LYS C 957 | 2.572 | 98.743 | 68.266 | 1.00 | 100.07 | C |
| ATOM | 10480 | CE | LYS C 957 | 1.092 | 98.432 | 68.044 | 1.00 | 100.07 | C |
| ATOM | 10481 | NZ | LYS C 957 | 0.391 | 98.021 | 69.301 | 1.00 | 100.07 | C |
| ATOM | 10482 | C | LYS C 957 | 5.516 | 97.371 | 66.418 | 1.00 | 34.57 | C |
| ATOM | 10483 | O | LYS C 957 | 5.900 | 97.677 | 65.279 | 1.00 | 34.57 | C |
| ATOM | 10484 | N | SER C 958 | 4.976 | 96.195 | 66.736 | 1.00 | 53.75 | C |
| ATOM | 10485 | CA | SER C 958 | 4.735 | 95.105 | 65.796 | 1.00 | 53.75 | C |
| ATOM | 10486 | CB | SER C 958 | 3.728 | 95.542 | 64.738 | 1.00 | 27.38 | C |
| ATOM | 10487 | OG | SER C 958 | 3.760 | 94.645 | 63.637 | 1.00 | 27.38 | C |
| ATOM | 10488 | C | SER C 958 | 5.874 | 94.427 | 65.070 | 1.00 | 53.75 | C |
| ATOM | 10489 | O | SER C 958 | 6.828 | 95.071 | 64.641 | 1.00 | 53.75 | C |
| ATOM | 10490 | N | PRO C 959 | 5.751 | 93.099 | 64.887 | 1.00 | 40.02 | C |
| ATOM | 10491 | CD | PRO C 959 | 4.633 | 92.332 | 65.465 | 1.00 | 84.92 | C |
| ATOM | 10492 | CA | PRO C 959 | 6.689 | 92.196 | 64.215 | 1.00 | 40.02 | C |
| ATOM | 10493 | CB | PRO C 959 | 6.268 | 90.833 | 64.732 | 1.00 | 84.92 | C |
| ATOM | 10494 | CG | PRO C 959 | 4.786 | 90.981 | 64.805 | 1.00 | 84.92 | C |
| ATOM | 10495 | C | PRO C 959 | 6.523 | 92.306 | 62.702 | 1.00 | 40.02 | C |
| ATOM | 10496 | O | PRO C 959 | 7.487 | 92.474 | 61.966 | 1.00 | 40.02 | C |
| ATOM | 10497 | N | GLU C 960 | 5.287 | 92.198 | 62.242 | 1.00 | 17.23 | C |
| ATOM | 10498 | CA | GLU C 960 | 5.022 | 92.321 | 60.828 | 1.00 | 17.23 | C |
| ATOM | 10499 | CB | GLU C 960 | 3.527 | 92.186 | 60.563 | 1.00 | 99.51 | C |
| ATOM | 10500 | CG | GLU C 960 | 3.123 | 92.591 | 59.159 | 1.00 | 99.51 | C |
| ATOM | 10501 | CD | GLU C 960 | 1.634 | 92.485 | 58.936 | 1.00 | 99.51 | C |
| ATOM | 10502 | OE1 | GLU C 960 | 1.171 | 92.850 | 57.831 | 1.00 | 99.51 | C |
| ATOM | 10503 | OE2 | GLU C 960 | 0.929 | 92.035 | 59.867 | 1.00 | 99.51 | C |
| ATOM | 10504 | C | GLU C 960 | 5.498 | 93.705 | 60.402 | 1.00 | 17.23 | C |
| ATOM | 10505 | O | GLU C 960 | 5.744 | 93.964 | 59.223 | 1.00 | 17.23 | C |
| ATOM | 10506 | N | GLU C 961 | 5.616 | 94.606 | 61.370 | 1.00 | 57.30 | C |
| ATOM | 10507 | CA | GLU C 961 | 6.058 | 95.959 | 61.072 | 1.00 | 57.30 | C |
| ATOM | 10508 | CB | GLU C 961 | 5.621 | 96.925 | 62.177 | 1.00 | 100.07 | C |
| ATOM | 10509 | CG | GLU C 961 | 4.189 | 97.431 | 62.010 | 1.00 | 100.07 | C |
| ATOM | 10510 | CD | GLU C 961 | 3.820 | 98.501 | 63.019 | 1.00 | 100.07 | C |
| ATOM | 10511 | OE1 | GLU C 961 | 4.637 | 99.425 | 63.225 | 1.00 | 100.07 | C |
| ATOM | 10512 | OE2 | GLU C 961 | 2.712 | 98.425 | 63.597 | 1.00 | 100.07 | C |
| ATOM | 10513 | C | GLU C 961 | 7.560 | 95.987 | 60.914 | 1.00 | 57.30 | C |
| ATOM | 10514 | O | GLU C 961 | 8.089 | 96.782 | 60.132 | 1.00 | 57.30 | C |
| ATOM | 10515 | N | GLN C 962 | 8.231 | 95.102 | 61.654 | 1.00 | 62.87 | C |
| ATOM | 10516 | CA | GLN C 962 | 9.693 | 94.966 | 61.639 | 1.00 | 62.87 | C |
| ATOM | 10517 | CB | GLN C 962 | 10.139 | 93.938 | 62.686 | 1.00 | 100.07 | C |
| ATOM | 10518 | CG | GLN C 962 | 9.924 | 94.373 | 64.126 | 1.00 | 100.07 | C |
| ATOM | 10519 | CD | GLN C 962 | 10.982 | 95.344 | 64.608 | 1.00 | 100.07 | C |
| ATOM | 10520 | OE1 | GLN C 962 | 11.282 | 96.339 | 63.946 | 1.00 | 100.07 | C |
| ATOM | 10521 | NE2 | GLN C 962 | 11.550 | 95.062 | 65.774 | 1.00 | 100.07 | C |
| ATOM | 10522 | C | GLN C 962 | 10.235 | 94.548 | 60.273 | 1.00 | 62.87 | C |
| ATOM | 10523 | O | GLN C 962 | 11.320 | 94.969 | 59.869 | 1.00 | 62.87 | C |
| ATOM | 10524 | N | LEU C 963 | 9.487 | 93.707 | 59.568 | 1.00 | 62.04 | C |
| ATOM | 10525 | CA | LEU C 963 | 9.930 | 93.276 | 58.264 | 1.00 | 62.04 | C |
| ATOM | 10526 | CB | LEU C 963 | 9.018 | 92.191 | 57.715 | 1.00 | 60.02 | C |
| ATOM | 10527 | CG | LEU C 963 | 9.717 | 90.850 | 57.913 | 1.00 | 60.02 | C |
| ATOM | 10528 | CD1 | LEU C 963 | 10.990 | 90.832 | 57.084 | 1.00 | 60.02 | C |
| ATOM | 10529 | CD2 | LEU C 963 | 10.056 | 90.654 | 59.380 | 1.00 | 60.02 | C |
| ATOM | 10530 | C | LEU C 963 | 10.015 | 94.447 | 57.312 | 1.00 | 62.04 | C |
| ATOM | 10531 | O | LEU C 963 | 11.111 | 94.939 | 57.062 | 1.00 | 62.04 | C |
| ATOM | 10532 | N | LYS C 964 | 8.882 | 94.908 | 56.783 | 1.00 | 69.67 | C |
| ATOM | 10533 | CA | LYS C 964 | 8.900 | 96.052 | 55.867 | 1.00 | 69.67 | C |
| ATOM | 10534 | CB | LYS C 964 | 7.554 | 96.768 | 55.871 | 1.00 | 42.42 | C |
| ATOM | 10535 | CG | LYS C 964 | 7.465 | 97.952 | 54.930 | 1.00 | 42.42 | C |
| ATOM | 10536 | CD | LYS C 964 | 6.329 | 98.870 | 55.343 | 1.00 | 42.42 | C |
| ATOM | 10537 | CE | LYS C 964 | 5.962 | 99.848 | 54.245 | 1.00 | 42.42 | C |
| ATOM | 10538 | NZ | LYS C 964 | 5.250 | 99.167 | 53.131 | 1.00 | 42.42 | C |
| ATOM | 10539 | C | LYS C 964 | 9.982 | 97.011 | 56.352 | 1.00 | 69.67 | C |
| ATOM | 10540 | O | LYS C 964 | 10.799 | 97.500 | 55.566 | 1.00 | 69.67 | C |
| ATOM | 10541 | N | GLU C 965 | 9.984 | 97.254 | 57.661 | 1.00 | 61.72 | C |
| ATOM | 10542 | CA | GLU C 965 | 10.972 | 98.121 | 58.279 | 1.00 | 61.72 | C |
| ATOM | 10543 | CB | GLU C 965 | 10.805 | 98.101 | 59.799 | 1.00 | 100.07 | C |
| ATOM | 10544 | CG | GLU C 965 | 11.591 | 99.171 | 60.534 | 1.00 | 100.07 | C |
| ATOM | 10545 | CD | GLU C 965 | 11.095 | 100.571 | 60.233 | 1.00 | 100.07 | C |
| ATOM | 10546 | OE1 | GLU C 965 | 9.898 | 100.836 | 60.475 | 1.00 | 100.07 | C |

```
ATOM  10547  OE2 GLU C 965      11.896 101.411  59.763  1.00100.07           C
ATOM  10548  C   GLU C 965      12.359  97.597  57.894  1.00 61.72           C
ATOM  10549  O   GLU C 965      13.142  98.300  57.252  1.00 61.72           C
ATOM  10550  N   LEU C 966      12.651  96.353  58.269  1.00 45.84           C
ATOM  10551  CA  LEU C 966      13.943  95.751  57.957  1.00 45.84           C
ATOM  10552  CB  LEU C 966      14.109  94.427  58.709  1.00  8.60           C
ATOM  10553  CG  LEU C 966      15.510  94.226  59.291  1.00  8.60           C
ATOM  10554  CD1 LEU C 966      16.008  95.572  59.726  1.00  8.60           C
ATOM  10555  CD2 LEU C 966      15.524  93.254  60.475  1.00  8.60           C
ATOM  10556  C   LEU C 966      14.122  95.548  56.454  1.00 45.84           C
ATOM  10557  O   LEU C 966      14.981  96.185  55.858  1.00 45.84           C
ATOM  10558  N   PHE C 967      13.315  94.677  55.847  1.00 69.08           C
ATOM  10559  CA  PHE C 967      13.369  94.412  54.404  1.00 69.08           C
ATOM  10560  CB  PHE C 967      11.963  94.000  53.895  1.00 24.53           C
ATOM  10561  CG  PHE C 967      11.933  93.483  52.460  1.00 24.53           C
ATOM  10562  CD1 PHE C 967      12.185  92.145  52.177  1.00 24.53           C
ATOM  10563  CD2 PHE C 967      11.678  94.349  51.392  1.00 24.53           C
ATOM  10564  CE1 PHE C 967      12.186  91.686  50.858  1.00 24.53           C
ATOM  10565  CE2 PHE C 967      11.680  93.890  50.080  1.00 24.53           C
ATOM  10566  CZ  PHE C 967      11.935  92.560  49.815  1.00 24.53           C
ATOM  10567  C   PHE C 967      13.871  95.664  53.657  1.00 69.08           C
ATOM  10568  O   PHE C 967      14.595  95.545  52.670  1.00 69.08           C
ATOM  10569  N   ASP C 968      13.491  96.855  54.128  1.00 38.84           C
ATOM  10570  CA  ASP C 968      13.938  98.117  53.508  1.00 38.84           C
ATOM  10571  CB  ASP C 968      13.864  99.275  54.503  1.00 91.58           C
ATOM  10572  CG  ASP C 968      12.492  99.892  54.587  1.00 91.58           C
ATOM  10573  OD1 ASP C 968      11.950 100.277  53.530  1.00 91.58           C
ATOM  10574  OD2 ASP C 968      11.963 100.004  55.711  1.00 91.58           C
ATOM  10575  C   ASP C 968      15.382  98.003  53.048  1.00 38.84           C
ATOM  10576  O   ASP C 968      15.678  97.992  51.849  1.00 38.84           C
ATOM  10577  N   LEU C 969      16.273  97.954  54.035  1.00 45.27           C
ATOM  10578  CA  LEU C 969      17.696  97.799  53.805  1.00 45.27           C
ATOM  10579  CB  LEU C 969      18.482  98.524  54.919  1.00 54.46           C
ATOM  10580  CG  LEU C 969      18.235  98.367  56.439  1.00 54.46           C
ATOM  10581  CD1 LEU C 969      19.381  99.039  57.216  1.00 54.46           C
ATOM  10582  CD2 LEU C 969      16.895  98.968  56.852  1.00 54.46           C
ATOM  10583  C   LEU C 969      17.993  96.278  53.755  1.00 45.27           C
ATOM  10584  O   LEU C 969      17.916  95.671  52.689  1.00 45.27           C
ATOM  10585  N   GLY C 970      18.306  95.659  54.892  1.00 36.39           C
ATOM  10586  CA  GLY C 970      18.562  94.224  54.914  1.00 36.39           C
ATOM  10587  C   GLY C 970      17.373  93.385  54.455  1.00 36.39           C
ATOM  10588  O   GLY C 970      16.356  93.921  54.003  1.00 36.39           C
ATOM  10589  N   LYS C 971      17.478  92.065  54.606  1.00 36.78           C
ATOM  10590  CA  LYS C 971      16.418  91.164  54.150  1.00 36.78           C
ATOM  10591  CB  LYS C 971      16.852  90.452  52.866  1.00100.07           C
ATOM  10592  CG  LYS C 971      15.954  89.274  52.468  1.00100.07           C
ATOM  10593  CD  LYS C 971      14.505  89.718  52.264  1.00100.07           C
ATOM  10594  CE  LYS C 971      13.604  88.591  51.750  1.00100.07           C
ATOM  10595  NZ  LYS C 971      13.814  88.244  50.305  1.00100.07           C
ATOM  10596  C   LYS C 971      15.898  90.102  55.090  1.00 36.78           C
ATOM  10597  O   LYS C 971      16.662  89.448  55.809  1.00 36.78           C
ATOM  10598  N   VAL C 972      14.579  89.919  54.997  1.00 72.35           C
ATOM  10599  CA  VAL C 972      13.779  88.955  55.761  1.00 72.35           C
ATOM  10600  CB  VAL C 972      12.639  88.342  54.881  1.00 55.95           C
ATOM  10601  CG1 VAL C 972      11.804  87.360  55.691  1.00 55.95           C
ATOM  10602  CG2 VAL C 972      11.755  89.448  54.333  1.00 55.95           C
ATOM  10603  C   VAL C 972      14.556  87.812  56.387  1.00 72.35           C
ATOM  10604  O   VAL C 972      14.689  86.734  55.817  1.00 72.35           C
ATOM  10605  N   VAL C 973      15.061  88.072  57.578  1.00 22.24           C
ATOM  10606  CA  VAL C 973      15.799  87.097  58.324  1.00 22.24           C
ATOM  10607  CB  VAL C 973      14.835  86.115  58.976  1.00 51.82           C
ATOM  10608  CG1 VAL C 973      15.610  85.033  59.708  1.00 51.82           C
ATOM  10609  CG2 VAL C 973      13.925  86.859  59.935  1.00 51.82           C
ATOM  10610  C   VAL C 973      16.868  86.305  57.589  1.00 22.24           C
ATOM  10611  O   VAL C 373      18.028  86.319  58.006  1.00 22.24           C
ATOM  10612  N   LEU C 974      16.491  85.632  56.504  1.00 37.73           C
ATOM  10613  CA  LEU C 974      17.393  84.750  55.737  1.00 37.73           C
ATOM  10614  CB  LEU C 974      18.761  85.383  55.473  1.00 19.58           C
ATOM  10615  CG  LEU C 974      19.560  84.725  54.341  1.00 19.58           C
ATOM  10616  CD1 LEU C 974      18.862  84.860  52.988  1.00 19.58           C
ATOM  10617  CD2 LEU C 974      20.886  85.399  54.272  1.00 19.58           C
ATOM  10618  C   LEU C 974      17.537  83.531  56.652  1.00 37.73           C
ATOM  10619  O   LEU C 974      17.785  83.675  57.851  1.00 37.73           C
ATOM  10620  N   TYR C 975      17.393  82.329  56.114  1.00 47.42           C
ATOM  10621  CA  TYR C 975      17.421  81.185  57.001  1.00 47.42           C
ATOM  10622  CB  TYR C 975      16.285  80.247  56.639  1.00 23.93           C
ATOM  10623  CG  TYR C 975      14.889  80.746  57.007  1.00 23.93           C
ATOM  10624  CD1 TYR C 975      13.999  81.186  56.029  1.00 23.93           C
ATOM  10625  CE1 TYR C 975      12.688  81.461  56.335  1.00 23.93           C
ATOM  10626  CD2 TYR C 975      14.410  80.629  58.299  1.00 23.93           C
ATOM  10627  CE2 TYR C 975      13.100  80.908  58.601  1.00 23.93           C
ATOM  10628  CZ  TYR C 975      12.248  81.312  57.616  1.00 23.93           C
ATOM  10629  OH  TYR C 975      10.923  81.507  57.900  1.00 23.93           C
ATOM  10630  C   TYR C 975      18.684  80.372  57.243  1.00 47.42           C
```

```
ATOM  10631  O    TYR C 975      19.150  80.319  58.380  1.00 47.42           C
ATOM  10632  N    ASP C 976      19.215  79.727  56.207  1.00 24.95           C
ATOM  10633  CA   ASP C 976      20.433  78.896  56.306  1.00 24.95           C
ATOM  10634  CB   ASP C 976      21.222  79.150  57.614  1.00 61.71           C
ATOM  10635  CG   ASP C 976      22.563  78.392  57.675  1.00 61.71           C
ATOM  10636  OD1  ASP C 976      23.352  78.469  56.708  1.00 61.71           C
ATOM  10637  OD2  ASP C 976      22.840  77.732  58.702  1.00 61.71           C
ATOM  10638  C    ASP C 976      20.024  77.436  56.220  1.00 24.95           C
ATOM  10639  O    ASP C 976      20.222  76.655  57.157  1.00 24.95           C
ATOM  10640  N    GLY C 977      19.452  77.100  55.064  1.00 32.37           C
ATOM  10641  CA   GLY C 977      18.982  75.757  54.759  1.00 32.37           C
ATOM  10642  C    GLY C 977      19.751  74.550  55.279  1.00 32.37           C
ATOM  10643  O    GLY C 977      19.296  73.409  55.098  1.00 32.37           C
ATOM  10644  N    ARG C 978      20.910  74.772  55.892  1.00 45.31           C
ATOM  10645  CA   ARG C 978      21.653  73.658  56.436  1.00 45.31           C
ATOM  10646  CB   ARG C 978      22.922  74.130  57.128  1.00 40.73           C
ATOM  10647  CG   ARG C 978      23.865  74.893  56.235  1.00 40.73           C
ATOM  10648  CD   ARG C 978      25.173  75.112  56.953  1.00 40.73           C
ATOM  10649  NE   ARG C 978      26.230  75.584  56.070  1.00 40.73           C
ATOM  10650  CZ   ARG C 978      27.525  75.487  56.355  1.00 40.73           C
ATOM  10651  NH1  ARG C 978      27.933  74.938  57.496  1.00 40.73           C
ATOM  10652  NH2  ARG C 978      28.421  75.938  55.497  1.00 40.73           C
ATOM  10653  C    ARG C 978      20.711  73.021  57.448  1.00 45.31           C
ATOM  10654  O    ARG C 978      20.507  71.807  57.429  1.00 45.31           C
ATOM  10655  N    THR C 979      20.126  73.846  58.319  1.00 29.33           C
ATOM  10656  CA   THR C 979      19.172  73.373  59.326  1.00 29.33           C
ATOM  10657  CB   THR C 979      19.787  72.292  60.253  1.00 99.95           C
ATOM  10658  OG1  THR C 979      19.884  71.047  59.551  1.00 99.95           C
ATOM  10659  CG2  THR C 979      18.915  72.090  61.491  1.00 99.95           C
ATOM  10660  C    THR C 979      18.666  74.499  60.214  1.00 29.33           C
ATOM  10661  O    THR C 979      17.515  74.950  60.087  1.00 29.33           C
ATOM  10662  N    GLY C 980      19.562  74.923  61.110  1.00 49.26           C
ATOM  10663  CA   GLY C 980      19.318  75.973  62.091  1.00 49.26           C
ATOM  10664  C    GLY C 980      18.201  76.976  61.893  1.00 49.26           C
ATOM  10665  O    GLY C 980      17.653  77.458  62.866  1.00 49.26           C
ATOM  10666  N    GLU C 981      17.878  77.287  60.643  1.00100.07           C
ATOM  10667  CA   GLU C 981      16.830  78.239  60.282  1.00100.07           C
ATOM  10668  CB   GLU C 981      15.481  77.895  60.957  1.00100.07           C
ATOM  10669  CG   GLU C 981      14.551  76.979  60.111  1.00100.07           C
ATOM  10670  CD   GLU C 981      13.055  77.391  60.125  1.00100.07           C
ATOM  10671  OE1  GLU C 981      12.668  78.375  59.451  1.00100.07           C
ATOM  10672  OE2  GLU C 981      12.255  76.719  60.811  1.00100.07           C
ATOM  10673  C    GLU C 981      17.139  79.728  60.485  1.00100.07           C
ATOM  10674  O    GLU C 981      17.034  80.505  59.536  1.00100.07           C
ATOM  10675  N    PRO C 982      17.519  80.166  61.701  1.00 33.96           C
ATOM  10676  CD   PRO C 982      17.191  79.843  63.099  1.00 37.75           C
ATOM  10677  CA   PRO C 982      17.731  81.609  61.565  1.00 33.96           C
ATOM  10678  CB   PRO C 982      16.926  82.173  62.717  1.00 37.75           C
ATOM  10679  CG   PRO C 982      17.300  81.212  63.795  1.00 37.75           C
ATOM  10680  C    PRO C 982      19.178  82.044  61.633  1.00 33.96           C
ATOM  10681  O    PRO C 982      20.030  81.405  62.271  1.00 33.96           C
ATOM  10682  N    PHE C 983      19.440  83.136  60.939  1.00 15.71           C
ATOM  10683  CA   PHE C 983      20.750  83.727  60.933  1.00 15.71           C
ATOM  10684  CB   PHE C 983      21.157  84.070  59.507  1.00 51.89           C
ATOM  10685  CG   PHE C 983      22.133  83.099  58.906  1.00 51.89           C
ATOM  10686  CD1  PHE C 983      22.171  82.895  57.533  1.00 51.89           C
ATOM  10687  CD2  PHE C 983      23.034  82.410  59.710  1.00 51.89           C
ATOM  10688  CE1  PHE C 983      23.089  82.020  56.971  1.00 51.89           C
ATOM  10689  CE2  PHE C 983      23.958  81.533  59.154  1.00 51.89           C
ATOM  10690  CZ   PHE C 983      23.983  81.340  57.782  1.00 51.89           C
ATOM  10691  C    PHE C 983      20.500  84.975  61.757  1.00 15.71           C
ATOM  10692  O    PHE C 983      20.055  85.996  61.234  1.00 15.71           C
ATOM  10693  N    GLU C 984      20.749  84.862  63.056  1.00 26.64           C
ATOM  10694  CA   GLU C 984      20.537  85.951  63.998  1.00 26.64           C
ATOM  10695  CB   GLU C 984      21.262  85.633  65.310  1.00 85.70           C
ATOM  10696  CG   GLU C 984      22.694  85.131  65.125  1.00 85.70           C
ATOM  10697  CD   GLU C 984      23.174  84.266  66.288  1.00 85.70           C
ATOM  10698  OE1  GLU C 984      22.524  83.236  66.560  1.00 85.70           C
ATOM  10699  OE2  GLU C 984      24.195  84.604  66.928  1.00 85.70           C
ATOM  10700  C    GLU C 984      20.995  87.290  63.462  1.00 26.64           C
ATOM  10701  O    GLU C 984      22.172  87.599  63.542  1.00 26.64           C
ATOM  10702  N    GLY C 985      20.070  88.088  62.928  1.00 28.68           C
ATOM  10703  CA   GLY C 985      20.436  89.389  62.375  1.00 28.68           C
ATOM  10704  C    GLY C 985      20.371  89.361  60.855  1.00 28.68           C
ATOM  10705  O    GLY C 985      21.150  88.650  60.224  1.00 28.68           C
ATOM  10706  N    PRO C 986      19.472  90.146  60.237  1.00 60.08           C
ATOM  10707  CD   PRO C 986      18.942  91.340  60.912  1.00 54.17           C
ATOM  10708  CA   PRO C 986      19.248  90.253  58.786  1.00 60.08           C
ATOM  10709  CB   PRO C 986      18.557  91.603  58.645  1.00 54.17           C
ATOM  10710  CG   PRO C 986      19.064  92.369  59.828  1.00 54.17           C
ATOM  10711  C    PRO C 986      20.483  90.171  57.905  1.00 60.08           C
ATOM  10712  O    PRO C 986      21.591  90.407  58.375  1.00 60.08           C
ATOM  10713  N    ILE C 987      20.282  89.840  56.627  1.00 19.00           C
ATOM  10714  CA   ILE C 987      21.383  89.743  55.662  1.00 19.00           C
```

| | | | | | | | | | |
|---|---|---|---|---|---|---|---|---|---|
| ATOM | 10715 | CB | ILE | C 987 | 21.830 | 88.304 | 55.405 | 1.00 5.60 | C |
| ATOM | 10716 | CG2 | ILE | C 987 | 22.717 | 88.247 | 54.179 | 1.00 5.60 | C |
| ATOM | 10717 | CG1 | ILE | C 987 | 22.575 | 87.761 | 56.603 | 1.00 5.60 | C |
| ATOM | 10718 | CD | ILE | C 987 | 21.653 | 87.194 | 57.600 | 1.00 5.60 | C |
| ATOM | 10719 | C | ILE | C 987 | 20.995 | 90.287 | 54.305 | 1.00 19.00 | C |
| ATOM | 10720 | O | ILE | C 987 | 20.447 | 89.543 | 53.506 | 1.00 19.00 | C |
| ATOM | 10721 | N | VAL | C 988 | 21.291 | 91.552 | 54.015 | 1.00 71.61 | C |
| ATOM | 10722 | CA | VAL | C 988 | 20.911 | 92.103 | 52.719 | 1.00 71.61 | C |
| ATOM | 10723 | CB | VAL | C 988 | 21.744 | 93.340 | 52.350 | 1.00 10.10 | C |
| ATOM | 10724 | CG1 | VAL | C 988 | 22.612 | 93.720 | 53.498 | 1.00 10.10 | C |
| ATOM | 10725 | CG2 | VAL | C 988 | 22.573 | 93.077 | 51.110 | 1.00 10.10 | C |
| ATOM | 10726 | C | VAL | C 988 | 21.081 | 91.029 | 51.654 | 1.00 71.61 | C |
| ATOM | 10727 | O | VAL | C 988 | 22.146 | 90.418 | 51.533 | 1.00 71.61 | C |
| ATOM | 10728 | N | VAL | C 989 | 20.003 | 90.793 | 50.914 | 1.00 12.86 | C |
| ATOM | 10729 | CA | VAL | C 989 | 19.948 | 89.790 | 49.857 | 1.00 12.86 | C |
| ATOM | 10730 | CB | VAL | C 989 | 18.932 | 88.706 | 50.249 | 1.00 18.05 | C |
| ATOM | 10731 | CG1 | VAL | C 989 | 18.448 | 87.963 | 49.030 | 1.00 18.05 | C |
| ATOM | 10732 | CG2 | VAL | C 989 | 19.566 | 87.751 | 51.238 | 1.00 18.05 | C |
| ATOM | 10733 | C | VAL | C 989 | 19.516 | 90.459 | 48.548 | 1.00 12.86 | C |
| ATOM | 10734 | O | VAL | C 989 | 18.571 | 91.244 | 48.550 | 1.00 12.86 | C |
| ATOM | 10735 | N | GLY | C 990 | 20.180 | 90.167 | 47.434 | 1.00 15.70 | C |
| ATOM | 10736 | CA | GLY | C 990 | 19.774 | 90.815 | 46.194 | 1.00 15.70 | C |
| ATOM | 10737 | C | GLY | C 990 | 20.474 | 90.417 | 44.901 | 1.00 15.70 | C |
| ATOM | 10738 | O | GLY | C 990 | 21.599 | 89.901 | 44.904 | 1.00 15.70 | C |
| ATOM | 10739 | N | GLN | C 991 | 19.803 | 90.667 | 43.778 | 1.00 44.81 | C |
| ATOM | 10740 | CA | GLN | C 991 | 20.354 | 90.331 | 42.469 | 1.00 44.81 | C |
| ATOM | 10741 | CB | GLN | C 991 | 19.261 | 90.377 | 41.413 | 1.00 67.84 | C |
| ATOM | 10742 | CG | GLN | C 991 | 18.042 | 89.567 | 41.745 | 1.00 67.84 | C |
| ATOM | 10743 | CD | GLN | C 991 | 17.152 | 89.406 | 40.542 | 1.00 67.84 | C |
| ATOM | 10744 | OE1 | GLN | C 991 | 16.740 | 90.390 | 39.920 | 1.00 67.84 | C |
| ATOM | 10745 | NE2 | GLN | C 991 | 16.853 | 88.160 | 40.195 | 1.00 67.84 | C |
| ATOM | 10746 | C | GLN | C 991 | 21.465 | 91.281 | 42.058 | 1.00 44.81 | C |
| ATOM | 10747 | O | GLN | C 991 | 21.224 | 92.459 | 41.814 | 1.00 44.81 | C |
| ATOM | 10748 | N | MET | C 992 | 22.684 | 90.777 | 41.961 | 1.00 34.86 | C |
| ATOM | 10749 | CA | MET | C 992 | 23.772 | 91.650 | 41.580 | 1.00 34.86 | C |
| ATOM | 10750 | CB | MET | C 992 | 25.035 | 91.337 | 42.365 | 1.00 37.01 | C |
| ATOM | 10751 | CG | MET | C 992 | 26.069 | 92.436 | 42.285 | 1.00 37.01 | C |
| ATOM | 10752 | SD | MET | C 992 | 27.484 | 92.047 | 43.296 | 1.00 37.01 | C |
| ATOM | 10753 | CE | MET | C 992 | 26.771 | 92.246 | 44.909 | 1.00 37.01 | C |
| ATOM | 10754 | C | MET | C 992 | 24.063 | 91.569 | 40.105 | 1.00 34.86 | C |
| ATOM | 10755 | O | MET | C 992 | 23.283 | 92.087 | 39.309 | 1.00 34.86 | C |
| ATOM | 10756 | N | PHE | C 993 | 25.168 | 90.914 | 39.738 | 1.00 45.01 | C |
| ATOM | 10757 | CA | PHE | C 993 | 25.573 | 90.804 | 38.328 | 1.00 45.01 | C |
| ATOM | 10758 | CB | PHE | C 993 | 25.326 | 92.145 | 37.663 | 1.00 24.03 | C |
| ATOM | 10759 | CG | PHE | C 993 | 25.888 | 92.271 | 36.314 | 1.00 24.03 | C |
| ATOM | 10760 | CD1 | PHE | C 993 | 27.132 | 92.843 | 36.127 | 1.00 24.03 | C |
| ATOM | 10761 | CD2 | PHE | C 993 | 25.119 | 91.964 | 35.206 | 1.00 24.03 | C |
| ATOM | 10762 | CE1 | PHE | C 993 | 27.600 | 93.127 | 34.838 | 1.00 24.03 | C |
| ATOM | 10763 | CE2 | PHE | C 993 | 25.575 | 92.242 | 33.916 | 1.00 24.03 | C |
| ATOM | 10764 | CZ | PHE | C 993 | 26.816 | 92.829 | 33.736 | 1.00 24.03 | C |
| ATOM | 10765 | C | PHE | C 993 | 27.042 | 90.427 | 38.235 | 1.00 45.01 | C |
| ATOM | 10766 | O | PHE | C 993 | 27.910 | 91.272 | 38.408 | 1.00 45.01 | C |
| ATOM | 10767 | N | ILE | C 994 | 27.323 | 89.159 | 37.957 | 1.00 48.02 | C |
| ATOM | 10768 | CA | ILE | C 994 | 28.708 | 88.694 | 37.894 | 1.00 48.02 | C |
| ATOM | 10769 | CB | ILE | C 994 | 28.968 | 87.672 | 38.980 | 1.00 27.84 | C |
| ATOM | 10770 | CG2 | ILE | C 994 | 30.441 | 87.598 | 39.231 | 1.00 27.84 | C |
| ATOM | 10771 | CG1 | ILE | C 994 | 28.158 | 88.022 | 40.239 | 1.00 27.84 | C |
| ATOM | 10772 | CD | ILE | C 994 | 28.305 | 89.456 | 40.722 | 1.00 27.84 | C |
| ATOM | 10773 | C | ILE | C 994 | 29.199 | 88.092 | 36.565 | 1.00 48.02 | C |
| ATOM | 10774 | O | ILE | C 994 | 28.906 | 86.937 | 36.226 | 1.00 48.02 | C |
| ATOM | 10775 | N | MET | C 995 | 29.973 | 88.895 | 35.841 | 1.00 17.58 | C |
| ATOM | 10776 | CA | MET | C 995 | 30.538 | 88.537 | 34.556 | 1.00 17.58 | C |
| ATOM | 10777 | CB | MET | C 995 | 31.076 | 89.804 | 33.930 | 1.00 19.94 | C |
| ATOM | 10778 | CG | MET | C 995 | 31.195 | 90.898 | 34.976 | 1.00 19.94 | C |
| ATOM | 10779 | SD | MET | C 995 | 31.878 | 92.444 | 34.388 | 1.00 19.94 | C |
| ATOM | 10780 | CE | MET | C 995 | 31.076 | 92.559 | 32.790 | 1.00 19.94 | C |
| ATOM | 10781 | C | MET | C 995 | 31.645 | 87.536 | 34.821 | 1.00 17.58 | C |
| ATOM | 10782 | O | MET | C 995 | 32.257 | 87.562 | 35.885 | 1.00 17.58 | C |
| ATOM | 10783 | N | LYS | C 996 | 31.893 | 86.645 | 33.865 | 1.00 48.97 | C |
| ATOM | 10784 | CA | LYS | C 996 | 32.927 | 85.624 | 34.026 | 1.00 48.97 | C |
| ATOM | 10785 | CB | LYS | C 996 | 32.368 | 84.251 | 33.686 | 1.00 14.40 | C |
| ATOM | 10786 | CG | LYS | C 996 | 33.415 | 83.160 | 33.589 | 1.00 14.40 | C |
| ATOM | 10787 | CD | LYS | C 996 | 32.785 | 81.923 | 32.997 | 1.00 14.40 | C |
| ATOM | 10788 | CE | LYS | C 996 | 33.745 | 80.763 | 32.926 | 1.00 14.40 | C |
| ATOM | 10789 | NZ | LYS | C 996 | 33.030 | 79.579 | 32.379 | 1.00 14.40 | C |
| ATOM | 10790 | C | LYS | C 996 | 34.166 | 85.856 | 33.180 | 1.00 48.97 | C |
| ATOM | 10791 | O | LYS | C 996 | 34.215 | 85.465 | 32.015 | 1.00 48.97 | C |
| ATOM | 10792 | N | LEU | C 997 | 35.174 | 86.465 | 33.788 | 1.00 24.30 | C |
| ATOM | 10793 | CA | LEU | C 997 | 36.432 | 86.758 | 33.125 | 1.00 24.30 | C |
| ATOM | 10794 | CB | LEU | C 997 | 37.354 | 87.378 | 34.150 | 1.00 5.72 | C |
| ATOM | 10795 | CG | LEU | C 997 | 36.767 | 88.633 | 34.757 | 1.00 5.72 | C |
| ATOM | 10796 | CD1 | LEU | C 997 | 37.621 | 89.100 | 35.903 | 1.00 5.72 | C |
| ATOM | 10797 | CD2 | LEU | C 997 | 36.700 | 89.692 | 33.692 | 1.00 5.72 | 'C |
| ATOM | 10798 | C | LEU | C 997 | 37.149 | 85.574 | 32.450 | 1.00 24.30 | C |

```
ATOM  10799  O    LEU C  997      37.304  84.499  33.039  1.00 24.30           C
ATOM  10800  N    TYR C  998      37.595  85.784  31.215  1.00 42.50           C
ATOM  10801  CA   TYR C  998      38.327  84.764  30.465  1.00 42.50           C
ATOM  10802  CB   TYR C  998      38.642  85.278  29.056  1.00100.07           C
ATOM  10803  CG   TYR C  998      39.674  84.484  28.280  1.00100.07           C
ATOM  10804  CD1  TYR C  998      39.579  83.097  28.162  1.00100.07           C
ATOM  10805  CE1  TYR C  998      40.505  82.367  27.388  1.00100.07           C
ATOM  10806  CD2  TYR C  998      40.720  85.132  27.613  1.00100.07           C
ATOM  10807  CE2  TYR C  998      41.649  84.416  26.837  1.00100.07           C
ATOM  10808  CZ   TYR C  998      41.534  83.035  26.729  1.00100.07           C
ATOM  10809  OH   TYR C  998      42.434  82.323  25.961  1.00100.07           C
ATOM  10810  C    TYR C  998      39.616  84.545  31.222  1.00 42.50           C
ATOM  10811  O    TYR C  998      40.652  85.079  30.843  1.00 42.50           C
ATOM  10812  N    HIS C  999      39.546  83.776  32.302  1.00 11.23           C
ATOM  10813  CA   HIS C  999      40.710  83.510  33.130  1.00 11.23           C
ATOM  10814  CB   HIS C  999      40.871  84.633  34.147  1.00 51.32           C
ATOM  10815  CG   HIS C  999      42.177  85.354  34.060  1.00 51.32           C
ATOM  10816  CD2  HIS C  999      43.176  85.493  34.965  1.00 51.32           C
ATOM  10817  ND1  HIS C  999      42.566  86.062  32.949  1.00 51.32           C
ATOM  10818  CE1  HIS C  999      43.747  86.607  33.166  1.00 51.32           C
ATOM  10819  NE2  HIS C  999      44.143  86.279  34.383  1.00 51.32           C
ATOM  10820  C    HIS C  999      40.423  82.218  33.864  1.00 11.23           C
ATOM  10821  O    HIS C  999      40.959  81.975  34.954  1.00 11.23           C
ATOM  10822  N    MET C1000      39.553  81.403  33.269  1.00 39.96           C
ATOM  10823  CA   MET C1000      39.146  80.133  33.866  1.00 39.96           C
ATOM  10824  CB   MET C1000      38.187  79.382  32.926  1.00 53.24           C
ATOM  10825  CG   MET C1000      38.441  79.604  31.431  1.00 53.24           C
ATOM  10826  SD   MET C1000      37.162  80.576  30.552  1.00 53.24           C
ATOM  10827  CE   MET C1000      35.760  79.532  30.760  1.00 53.24           C
ATOM  10828  C    MET C1000      40.337  79.265  34.249  1.00 39.96           C
ATOM  10829  O    MET C1000      41.431  79.425  33.722  1.00 39.96           C
ATOM  10830  N    VAL C1001      40.123  78.356  35.187  1.00 10.65           C
ATOM  10831  CA   VAL C1001      41.197  77.506  35.646  1.00 10.65           C
ATOM  10832  CB   VAL C1001      40.784  76.619  36.771  1.00 16.57           C
ATOM  10833  CG1  VAL C1001      41.968  75.785  37.171  1.00 16.57           C
ATOM  10834  CG2  VAL C1001      40.246  77.435  37.926  1.00 16.57           C
ATOM  10835  C    VAL C1001      41.639  76.570  34.578  1.00 10.65           C
ATOM  10836  O    VAL C1001      42.832  76.421  34.353  1.00 10.65           C
ATOM  10837  N    GLU C1002      40.658  75.909  33.957  1.00 34.63           C
ATOM  10838  CA   GLU C1002      40.889  74.935  32.890  1.00 34.63           C
ATOM  10839  CB   GLU C1002      39.742  74.953  31.873  1.00 85.36           C
ATOM  10840  CG   GLU C1002      38.372  74.570  32.419  1.00 85.36           C
ATOM  10841  CD   GLU C1002      37.778  73.335  31.743  1.00 85.36           C
ATOM  10842  OE1  GLU C1002      38.234  72.204  32.027  1.00 85.36           C
ATOM  10843  OE2  GLU C1002      36.852  73.498  30.920  1.00 85.36           C
ATOM  10844  C    GLU C1002      42.176  75.268  32.179  1.00 34.63           C
ATOM  10845  O    GLU C1002      43.158  74.541  32.281  1.00 34.63           C
ATOM  10846  N    ASP C1003      42.147  76.390  31.467  1.00 33.92           C
ATOM  10847  CA   ASP C1003      43.283  76.892  30.712  1.00 33.92           C
ATOM  10848  CB   ASP C1003      43.020  78.325  30.263  1.00 45.68           C
ATOM  10849  CG   ASP C1003      42.406  78.401  28.892  1.00 45.68           C
ATOM  10850  OD1  ASP C1003      43.059  77.932  27.935  1.00 45.68           C
ATOM  10851  OD2  ASP C1003      41.281  78.931  28.763  1.00 45.68           C
ATOM  10852  C    ASP C1003      44.598  76.864  31.463  1.00 33.92           C
ATOM  10853  O    ASP C1003      45.651  76.971  30.837  1.00 33.92           C
ATOM  10854  N    LYS C1004      44.550  76.726  32.788  1.00 32.49           C
ATOM  10855  CA   LYS C1004      45.764  76.704  33.603  1.00 32.49           C
ATOM  10856  CB   LYS C1004      45.699  77.846  34.611  1.00 61.48           C
ATOM  10857  CG   LYS C1004      45.652  79.198  33.946  1.00 61.48           C
ATOM  10858  CD   LYS C1004      45.287  80.289  34.922  1.00 61.48           C
ATOM  10859  CE   LYS C1004      45.072  81.610  34.196  1.00 61.48           C
ATOM  10860  NZ   LYS C1004      44.325  82.583  35.043  1.00 61.48           C
ATOM  10861  C    LYS C1004      46.068  75.378  34.317  1.00 32.49           C
ATOM  10862  O    LYS C1004      45.385  74.379  34.117  1.00 32.49           C
ATOM  10863  N    MET C1005      47.108  75.383  35.144  1.00 29.86           C
ATOM  10864  CA   MET C1005      47.541  74.208  35.898  1.00 29.86           C
ATOM  10865  CB   MET C1005      46.439  73.715  36.846  1.00 50.48           C
ATOM  10866  CG   MET C1005      45.484  72.657  36.299  1.00 50.48           C
ATOM  10867  SD   MET C1005      44.955  71.438  37.556  1.00 50.48           C
ATOM  10868  CE   MET C1005      45.992  70.076  37.147  1.00 50.48           C
ATOM  10869  C    MET C1005      48.023  73.036  35.041  1.00 29.86           C
ATOM  10870  O    MET C1005      47.222  72.370  34.365  1.00 29.86           C
ATOM  10871  N    HIS C1006      49.344  72.816  35.063  1.00 15.86           C
ATOM  10872  CA   HIS C1006      49.997  71.721  34.350  1.00 15.86           C
ATOM  10873  CB   HIS C1006      51.107  72.243  33.428  1.00 98.34           C
ATOM  10874  CG   HIS C1006      51.129  71.579  32.079  1.00 98.34           C
ATOM  10875  CD2  HIS C1006      50.775  70.329  31.693  1.00 98.34           C
ATOM  10876  ND1  HIS C1006      51.524  72.235  30.930  1.00 98.34           C
ATOM  10877  CE1  HIS C1006      51.407  71.419  29.897  1.00 98.34           C
ATOM  10878  NE2  HIS C1006      50.954  70.257  30.332  1.00 98.34           C
ATOM  10879  C    HIS C1006      50.563  70.916  35.494  1.00 15.86           C
ATOM  10880  O    HIS C1006      50.202  71.176  36.629  1.00 15.86           C
ATOM  10881  N    ALA C1007      51.417  69.938  35.229  1.00 45.08           C
ATOM  10882  CA   ALA C1007      52.004  69.141  36.312  1.00 45.08           C
```

-130-

| | | | | | | | | |
|---|---|---|---|---|---|---|---|---|
| ATOM | 10883 | CB | ALA | C1007 | 50.919 | 68.388 | 37.072 | 1.00 20.02 | C |
| ATOM | 10884 | C | ALA | C1007 | 53.018 | 68.161 | 35.751 | 1.00 45.08 | C |
| ATOM | 10885 | O | ALA | C1007 | 52.661 | 67.079 | 35.300 | 1.00 45.08 | C |
| ATOM | 10886 | N | ARG | C1008 | 54.288 | 68.535 | 35.784 | 1.00 33.31 | C |
| ATOM | 10887 | CA | ARG | C1008 | 55.319 | 67.675 | 35.242 | 1.00 33.31 | C |
| ATOM | 10888 | CB | ARG | C1008 | 56.346 | 68.515 | 34.481 | 1.00 50.90 | C |
| ATOM | 10889 | CG | ARG | C1008 | 57.556 | 67.717 | 34.042 | 1.00 50.90 | C |
| ATOM | 10890 | CD | ARG | C1008 | 58.295 | 68.383 | 32.908 | 1.00 50.90 | C |
| ATOM | 10891 | NE | ARG | C1008 | 59.433 | 67.577 | 32.492 | 1.00 50.90 | C |
| ATOM | 10892 | CZ | ARG | C1008 | 60.219 | 67.861 | 31.459 | 1.00 50.90 | C |
| ATOM | 10893 | NH1 | ARG | C1008 | 60.001 | 68.939 | 30.714 | 1.00 50.90 | C |
| ATOM | 10894 | NH2 | ARG | C1008 | 61.232 | 67.058 | 31.171 | 1.00 50.90 | C |
| ATOM | 10895 | C | ARG | C1008 | 56.040 | 66.780 | 36.247 | 1.00 33.31 | C |
| ATOM | 10896 | O | ARG | C1008 | 56.488 | 67.234 | 37.294 | 1.00 33.31 | C |
| ATOM | 10897 | N | SER | C1009 | 56.121 | 65.493 | 35.930 | 1.00 31.12 | C |
| ATOM | 10898 | CA | SER | C1009 | 56.841 | 64.554 | 36.765 | 1.00 31.12 | C |
| ATOM | 10899 | CB | SER | C1009 | 56.045 | 63.288 | 37.016 | 1.00 57.05 | C |
| ATOM | 10900 | OG | SER | C1009 | 56.545 | 62.647 | 38.175 | 1.00 57.05 | C |
| ATOM | 10901 | C | SER | C1009 | 57.988 | 64.260 | 35.841 | 1.00 31.12 | C |
| ATOM | 10902 | O | SER | C1009 | 58.720 | 65.170 | 35.501 | 1.00 31.12 | C |
| ATOM | 10903 | N | THR | C1010 | 58.136 | 63.018 | 35.402 | 1.00 59.25 | C |
| ATOM | 10904 | CA | THR | C1010 | 59.225 | 62.689 | 34.492 | 1.00 59.25 | C |
| ATOM | 10905 | CB | THR | C1010 | 59.061 | 61.263 | 33.944 | 1.00100.07 | C |
| ATOM | 10906 | OG1 | THR | C1010 | 58.629 | 60.398 | 35.000 | 1.00100.07 | C |
| ATOM | 10907 | CG2 | THR | C1010 | 60.381 | 60.743 | 33.399 | 1.00100.07 | C |
| ATOM | 10908 | C | THR | C1010 | 59.155 | 63.710 | 33.346 | 1.00 59.25 | C |
| ATOM | 10909 | O | THR | C1010 | 59.607 | 64.843 | 33.488 | 1.00 59.25 | C |
| ATOM | 10910 | N | GLY | C1011 | 58.592 | 63.323 | 32.208 | 1.00 58.45 | C |
| ATOM | 10911 | CA | GLY | C1011 | 58.464 | 64.263 | 31.108 | 1.00 58.45 | C |
| ATOM | 10912 | C | GLY | C1011 | 59.624 | 64.383 | 30.144 | 1.00 58.45 | C |
| ATOM | 10913 | O | GLY | C1011 | 60.682 | 63.797 | 30.363 | 1.00 58.45 | C |
| ATOM | 10914 | N | PRO | C1012 | 59.441 | 65.151 | 29.053 | 1.00 37.00 | C |
| ATOM | 10915 | CD | PRO | C1012 | 58.130 | 65.729 | 28.709 | 1.00 44.34 | C |
| ATOM | 10916 | CA | PRO | C1012 | 60.397 | 65.430 | 27.974 | 1.00 37.00 | C |
| ATOM | 10917 | CB | PRO | C1012 | 59.513 | 65.996 | 26.877 | 1.00 44.34 | C |
| ATOM | 10918 | CG | PRO | C1012 | 58.504 | 66.734 | 27.650 | 1.00 44.34 | C |
| ATOM | 10919 | C | PRO | C1012 | 61.520 | 66.387 | 28.318 | 1.00 37.00 | C |
| ATOM | 10920 | O | PRO | C1012 | 61.282 | 67.563 | 28.591 | 1.00 37.00 | C |
| ATOM | 10921 | N | TYR | C1013 | 62.734 | 65.850 | 28.270 | 1.00 62.41 | C |
| ATOM | 10922 | CA | TYR | C1013 | 64.000 | 66.534 | 28.538 | 1.00 62.41 | C |
| ATOM | 10923 | CB | TYR | C1013 | 65.120 | 65.604 | 28.081 | 1.00100.04 | C |
| ATOM | 10924 | CG | TYR | C1013 | 64.853 | 64.945 | 26.726 | 1.00100.04 | C |
| ATOM | 10925 | CD1 | TYR | C1013 | 64.768 | 65.703 | 25.547 | 1.00100.04 | C |
| ATOM | 10926 | CE1 | TYR | C1013 | 64.549 | 65.102 | 24.307 | 1.00100.04 | C |
| ATOM | 10927 | CD2 | TYR | C1013 | 64.705 | 63.559 | 26.620 | 1.00100.04 | C |
| ATOM | 10928 | CE2 | TYR | C1013 | 64.485 | 62.949 | 25.377 | 1.00100.04 | C |
| ATOM | 10929 | CZ | TYR | C1013 | 64.413 | 63.728 | 24.233 | 1.00100.04 | C |
| ATOM | 10930 | OH | TYR | C1013 | 64.227 | 63.125 | 23.017 | 1.00100.04 | C |
| ATOM | 10931 | C | TYR | C1013 | 64.218 | 67.924 | 27.906 | 1.00 62.41 | C |
| ATOM | 10932 | O | TYR | C1013 | 63.745 | 68.936 | 28.418 | 1.00 62.41 | C |
| ATOM | 10933 | N | SER | C1014 | 64.986 | 67.930 | 26.814 | 1.00 52.58 | C |
| ATOM | 10934 | CA | SER | C1014 | 65.367 | 69.086 | 25.995 | 1.00 52.58 | C |
| ATOM | 10935 | CB | SER | C1014 | 65.380 | 70.392 | 26.780 | 1.00 59.15 | C |
| ATOM | 10936 | OG | SER | C1014 | 65.978 | 71.421 | 26.000 | 1.00 59.15 | C |
| ATOM | 10937 | C | SER | C1014 | 66.776 | 68.824 | 25.481 | 1.00 52.58 | C |
| ATOM | 10938 | O | SER | C1014 | 67.646 | 68.403 | 26.244 | 1.00 52.58 | C |
| ATOM | 10939 | N | LEU | C1015 | 67.002 | 69.078 | 24.195 | 1.00 54.93 | C |
| ATOM | 10940 | CA | LEU | C1015 | 68.310 | 68.848 | 23.582 | 1.00 54.93 | C |
| ATOM | 10941 | CB | LEU | C1015 | 68.167 | 67.947 | 22.352 | 1.00 38.30 | C |
| ATOM | 10942 | CG | LEU | C1015 | 66.809 | 67.947 | 21.631 | 1.00 38.30 | C |
| ATOM | 10943 | CD1 | LEU | C1015 | 66.450 | 69.345 | 21.148 | 1.00 38.30 | C |
| ATOM | 10944 | CD2 | LEU | C1015 | 66.858 | 66.959 | 20.457 | 1.00 38.30 | C |
| ATOM | 10945 | C | LEU | C1015 | 69.046 | 70.115 | 23.189 | 1.00 54.93 | C |
| ATOM | 10946 | O | LEU | C1015 | 69.899 | 70.087 | 22.301 | 1.00 54.93 | C |
| ATOM | 10947 | N | ILE | C1016 | 68.713 | 71.225 | 23.840 | 1.00 64.83 | C |
| ATOM | 10948 | CA | ILE | C1016 | 69.376 | 72.487 | 23.552 | 1.00 64.83 | C |
| ATOM | 10949 | CB | ILE | C1016 | 68.432 | 73.527 | 22.965 | 1.00 83.86 | C |
| ATOM | 10950 | CG2 | ILE | C1016 | 69.248 | 74.637 | 22.329 | 1.00 83.86 | C |
| ATOM | 10951 | CG1 | ILE | C1016 | 67.502 | 72.882 | 21.936 | 1.00 83.86 | C |
| ATOM | 10952 | CD | ILE | C1016 | 66.285 | 72.200 | 22.550 | 1.00 83.86 | C |
| ATOM | 10953 | C | ILE | C1016 | 69.931 | 73.054 | 24.839 | 1.00 64.83 | C |
| ATOM | 10954 | O | ILE | C1016 | 71.100 | 73.437 | 24.890 | 1.00 64.83 | C |
| ATOM | 10955 | N | THR | C1017 | 69.090 | 73.117 | 25.874 | 1.00 26.78 | C |
| ATOM | 10956 | CA | THR | C1017 | 69.517 | 73.623 | 27.182 | 1.00 26.78 | C |
| ATOM | 10957 | CB | THR | C1017 | 68.554 | 74.683 | 27.726 | 1.00 35.77 | C |
| ATOM | 10958 | OG1 | THR | C1017 | 67.344 | 74.678 | 26.955 | 1.00 35.77 | C |
| ATOM | 10959 | CG2 | THR | C1017 | 69.207 | 76.051 | 27.679 | 1.00 35.77 | C |
| ATOM | 10960 | C | THR | C1017 | 69.631 | 72.508 | 28.218 | 1.00 26.78 | C |
| ATOM | 10961 | O | THR | C1017 | 70.092 | 72.733 | 29.328 | 1.00 26.78 | C |
| ATOM | 10962 | N | GLN | C1018 | 69.197 | 71.310 | 27.843 | 1.00 33.99 | C |
| ATOM | 10963 | CA | GLN | C1018 | 69.247 | 70.134 | 28.703 | 1.00 33.99 | C |
| ATOM | 10964 | CB | GLN | C1018 | 70.675 | 69.897 | 29.176 | 1.00 91.29 | C |
| ATOM | 10965 | CG | GLN | C1018 | 71.247 | 68.598 | 28.663 | 1.00 91.29 | C |
| ATOM | 10966 | CD | GLN | C1018 | 70.326 | 67.424 | 28.920 | 1.00 91.29 | C |

```
ATOM  10967  OE1 GLN C1018      69.218  67.364  28.388  1.00 91.29           C
ATOM  10968  NE2 GLN C1018      70.778  66.483  29.742  1.00 91.29           C
ATOM  10969  C   GLN C1018      68.305  70.096  29.907  1.00 33.99           C
ATOM  10970  O   GLN C1018      68.167  69.054  30.557  1.00 33.99           C
ATOM  10971  N   GLN C1019      67.666  71.217  30.223  1.00 44.02           C
ATOM  10972  CA  GLN C1019      66.731  71.232  31.342  1.00 44.02           C
ATOM  10973  CB  GLN C1019      67.025  72.415  32.273  1.00 30.53           C
ATOM  10974  CG  GLN C1019      67.290  73.725  31.560  1.00 30.53           C
ATOM  10975  CD  GLN C1019      67.411  74.907  32.515  1.00 30.53           C
ATOM  10976  OE1 GLN C1019      68.344  74.992  33.320  1.00 30.53           C
ATOM  10977  NE2 GLN C1019      66.459  75.829  32.425  1.00 30.53           C
ATOM  10978  C   GLN C1019      65.280  71.275  30.829  1.00 44.02           C
ATOM  10979  O   GLN C1019      64.965  72.004  29.884  1.00 44.02           C
ATOM  10980  N   PRO C1020      64.381  70.499  31.464  1.00 42.70           C
ATOM  10981  CD  PRO C1020      64.652  70.085  32.856  1.00 38.29           C
ATOM  10982  CA  PRO C1020      62.950  70.354  31.166  1.00 42.70           C
ATOM  10983  CB  PRO C1020      62.323  70.349  32.549  1.00 38.29           C
ATOM  10984  CG  PRO C1020      63.308  69.559  33.335  1.00 38.29           C
ATOM  10985  C   PRO C1020      62.323  71.409  30.257  1.00 42.70           C
ATOM  10986  O   PRO C1020      62.444  72.607  30.503  1.00 42.70           C
ATOM  10987  N   LEU C1021      61.642  70.951  29.212  1.00 85.35           C
ATOM  10988  CA  LEU C1021      60.982  71.844  28.262  1.00 85.35           C
ATOM  10989  CB  LEU C1021      61.970  72.872  27.711  1.00 99.93           C
ATOM  10990  CG  LEU C1021      61.389  74.271  27.509  1.00 99.93           C
ATOM  10991  CD1 LEU C1021      60.152  74.200  26.615  1.00 99.93           C
ATOM  10992  CD2 LEU C1021      61.038  74.865  28.866  1.00 99.93           C
ATOM  10993  C   LEU C1021      60.374  71.042  27.110  1.00 85.35           C
ATOM  10994  O   LEU C1021      60.953  70.058  26.644  1.00 85.35           C
ATOM  10995  N   GLY C1022      59.210  71.476  26.642  1.00100.07           C
ATOM  10996  CA  GLY C1022      58.537  70.754  25.581  1.00100.07           C
ATOM  10997  C   GLY C1022      57.750  69.623  26.228  1.00100.07           C
ATOM  10998  O   GLY C1022      57.907  69.367  27.428  1.00100.07           C
ATOM  10999  N   GLY C1023      56.897  68.954  25.450  1.00100.07           C
ATOM  11000  CA  GLY C1023      56.107  67.856  25.991  1.00100.07           C
ATOM  11001  C   GLY C1023      55.164  67.123  25.046  1.00100.07           C
ATOM  11002  O   GLY C1023      53.944  67.333  25.086  1.00100.07           C
ATOM  11003  N   LYS C1024      55.722  66.257  24.201  1.00100.07           C
ATOM  11004  CA  LYS C1024      54.920  65.478  23.266  1.00100.07           C
ATOM  11005  CB  LYS C1024      55.802  64.878  22.164  1.00 97.81           C
ATOM  11006  CG  LYS C1024      56.619  65.896  21.368  1.00 97.81           C
ATOM  11007  CD  LYS C1024      57.317  65.261  20.153  1.00 97.81           C
ATOM  11008  CE  LYS C1024      58.382  64.231  20.541  1.00 97.81           C
ATOM  11009  NZ  LYS C1024      58.971  63.543  19.354  1.00 97.81           C
ATOM  11010  C   LYS C1024      54.258  64.357  24.066  1.00100.07           C
ATOM  11011  O   LYS C1024      54.358  63.179  23.698  1.00100.07           C
ATOM  11012  N   ALA C1025      53.594  64.745  25.161  1.00 54.60           C
ATOM  11013  CA  ALA C1025      52.903  63.827  26.074  1.00 54.60           C
ATOM  11014  CB  ALA C1025      53.623  62.458  26.112  1.00 13.33           C
ATOM  11015  C   ALA C1025      52.851  64.425  27.485  1.00 54.60           C
ATOM  11016  O   ALA C1025      51.858  65.020  27.892  1.00 54.60           C
ATOM  11017  N   GLN C1026      53.942  64.263  28.223  1.00 68.80           C
ATOM  11018  CA  GLN C1026      54.028  64.768  29.589  1.00 68.80           C
ATOM  11019  CB  GLN C1026      55.327  64.297  30.255  1.00100.07           C
ATOM  11020  CG  GLN C1026      55.659  62.815  30.046  1.00100.07           C
ATOM  11021  CD  GLN C1026      56.471  62.555  28.782  1.00100.07           C
ATOM  11022  OE1 GLN C1026      56.049  62.885  27.673  1.00100.07           C
ATOM  11023  NE2 GLN C1026      57.645  61.955  28.949  1.00100.07           C
ATOM  11024  C   GLN C1026      53.971  66.283  29.625  1.00 68.80           C
ATOM  11025  O   GLN C1026      53.210  66.857  30.397  1.00 68.80           C
ATOM  11026  N   PHE C1027      54.793  66.918  28.795  1.00 58.78           C
ATOM  11027  CA  PHE C1027      54.853  68.372  28.711  1.00 58.78           C
ATOM  11028  CB  PHE C1027      53.586  68.887  28.011  1.00 99.80           C
ATOM  11029  CG  PHE C1027      53.797  70.128  27.168  1.00 99.80           C
ATOM  11030  CD1 PHE C1027      52.740  70.662  26.426  1.00 99.80           C
ATOM  11031  CD2 PHE C1027      55.038  70.761  27.107  1.00 99.80           C
ATOM  11032  CE1 PHE C1027      52.914  71.809  25.640  1.00 99.80           C
ATOM  11033  CE2 PHE C1027      55.224  71.910  26.323  1.00 99.80           C
ATOM  11034  CZ  PHE C1027      54.160  72.432  25.586  1.00 99.80           C
ATOM  11035  C   PHE C1027      54.994  68.985  30.109  1.00 58.78           C
ATOM  11036  O   PHE C1027      54.869  68.291  31.123  1.00 58.78           C
ATOM  11037  N   GLY C1028      55.267  70.283  30.162  1.00 82.86           C
ATOM  11038  CA  GLY C1028      55.409  70.946  31.444  1.00 82.86           C
ATOM  11039  C   GLY C1028      56.683  71.753  31.521  1.00 82.86           C
ATOM  11040  O   GLY C1028      56.936  72.593  30.656  1.00 82.86           C
ATOM  11041  N   GLY C1029      57.479  71.502  32.558  1.00 98.74           C
ATOM  11042  CA  GLY C1029      58.742  72.204  32.728  1.00 98.74           C
ATOM  11043  C   GLY C1029      58.689  73.359  33.711  1.00 98.74           C
ATOM  11044  O   GLY C1029      58.813  74.520  33.318  1.00 98.74           C
ATOM  11045  N   GLN C1030      58.530  73.045  34.993  1.00 59.66           C
ATOM  11046  CA  GLN C1030      58.433  74.076  36.015  1.00 59.66           C
ATOM  11047  CB  GLN C1030      58.390  73.457  37.395  1.00 22.64           C
ATOM  11048  CG  GLN C1030      57.748  74.394  38.355  1.00 22.64           C
ATOM  11049  CD  GLN C1030      56.727  75.281  37.672  1.00 22.64           C
ATOM  11050  OE1 GLN C1030      57.082  76.304  37.080  1.00 22.64           C
```

| | | | | | | | | |
|---|---|---|---|---|---|---|---|---|
| ATOM | 11051 | NE2 | GLN C1030 | 55.454 | 74.882 | 37.734 | 1.00 22.64 | C |
| ATOM | 11052 | C | GLN C1030 | 59.541 | 75.103 | 35.971 | 1.00 59.66 | C |
| ATOM | 11053 | O | GLN C1030 | 60.505 | 74.931 | 35.235 | 1.00 59.66 | C |
| ATOM | 11054 | N | ARG C1031 | 59.412 | 76.160 | 36.773 | 1.00 36.92 | C |
| ATOM | 11055 | CA | ARG C1031 | 60.405 | 77.244 | 36.795 | 1.00 36.92 | C |
| ATOM | 11056 | CB | ARG C1031 | 59.719 | 78.542 | 36.350 | 1.00100.07 | C |
| ATOM | 11057 | CG | ARG C1031 | 58.717 | 78.297 | 35.206 | 1.00100.07 | C |
| ATOM | 11058 | CD | ARG C1031 | 58.187 | 79.562 | 34.518 | 1.00100.07 | C |
| ATOM | 11059 | NE | ARG C1031 | 57.157 | 79.222 | 33.531 | 1.00100.07 | C |
| ATOM | 11060 | CZ | ARG C1031 | 56.562 | 80.093 | 32.717 | 1.00100.07 | C |
| ATOM | 11061 | NH1 | ARG C1031 | 56.890 | 81.379 | 32.757 | 1.00100.07 | C |
| ATOM | 11062 | NH2 | ARG C1031 | 55.627 | 79.675 | 31.867 | 1.00100.07 | C |
| ATOM | 11063 | C | ARG C1031 | 61.049 | 77.403 | 38.172 | 1.00 36.92 | C |
| ATOM | 11064 | O | ARG C1031 | 60.770 | 76.611 | 39.063 | 1.00 36.92 | C |
| ATOM | 11065 | N | PHE C1032 | 61.916 | 78.397 | 38.364 | 1.00 43.17 | C |
| ATOM | 11066 | CA | PHE C1032 | 62.534 | 78.567 | 39.692 | 1.00 43.17 | C |
| ATOM | 11067 | CB | PHE C1032 | 63.490 | 77.405 | 39.956 | 1.00 6.13 | C |
| ATOM | 11068 | CG | PHE C1032 | 63.661 | 77.066 | 41.415 | 1.00 6.13 | C |
| ATOM | 11069 | CD1 | PHE C1032 | 62.556 | 76.836 | 42.225 | 1.00 6.13 | C |
| ATOM | 11070 | CD2 | PHE C1032 | 64.939 | 76.906 | 41.967 | 1.00 6.13 | C |
| ATOM | 11071 | CE1 | PHE C1032 | 62.724 | 76.444 | 43.576 | 1.00 6.13 | C |
| ATOM | 11072 | CE2 | PHE C1032 | 65.115 | 76.516 | 43.301 | 1.00 6.13 | C |
| ATOM | 11073 | CZ | PHE C1032 | 64.006 | 76.285 | 44.107 | 1.00 6.13 | C |
| ATOM | 11074 | C | PHE C1032 | 63.271 | 79.900 | 39.902 | 1.00 43.17 | C |
| ATOM | 11075 | O | PHE C1032 | 64.346 | 79.938 | 40.514 | 1.00 43.17 | C |
| ATOM | 11076 | N | GLY C1033 | 62.664 | 80.983 | 39.410 | 1.00 98.19 | C |
| ATOM | 11077 | CA | GLY C1033 | 63.230 | 82.325 | 39.499 | 1.00 98.19 | C |
| ATOM | 11078 | C | GLY C1033 | 63.908 | 82.779 | 40.781 | 1.00 98.19 | C |
| ATOM | 11079 | O | GLY C1033 | 63.256 | 83.316 | 41.677 | 1.00 98.19 | C |
| ATOM | 11080 | N | GLU C1034 | 65.226 | 82.581 | 40.833 | 1.00 31.25 | C |
| ATOM | 11081 | CA | GLU C1034 | 66.091 | 82.939 | 41.952 | 1.00 31.25 | C |
| ATOM | 11082 | CB | GLU C1034 | 66.957 | 84.142 | 41.581 | 1.00 25.78 | C |
| ATOM | 11083 | CG | GLU C1034 | 66.193 | 85.436 | 41.478 | 1.00 25.78 | C |
| ATOM | 11084 | CD | GLU C1034 | 67.053 | 86.606 | 41.039 | 1.00 25.78 | C |
| ATOM | 11085 | OE1 | GLU C1034 | 68.183 | 86.747 | 41.562 | 1.00 25.78 | C |
| ATOM | 11086 | OE2 | GLU C1034 | 66.584 | 87.392 | 40.179 | 1.00 25.78 | C |
| ATOM | 11087 | C | GLU C1034 | 65.403 | 83.194 | 43.285 | 1.00 31.25 | C |
| ATOM | 11088 | O | GLU C1034 | 65.659 | 82.465 | 44.238 | 1.00 31.25 | C |
| ATOM | 11089 | N | MET C1035 | 64.550 | 84.217 | 43.370 | 1.00 33.31 | C |
| ATOM | 11090 | CA | MET C1035 | 63.844 | 84.540 | 44.619 | 1.00 33.31 | C |
| ATOM | 11091 | CB | MET C1035 | 62.454 | 85.087 | 44.318 | 1.00 55.27 | C |
| ATOM | 11092 | CG | MET C1035 | 62.458 | 86.351 | 43.500 | 1.00 55.27 | C |
| ATOM | 11093 | SD | MET C1035 | 62.842 | 87.802 | 44.457 | 1.00 55.27 | C |
| ATOM | 11094 | CE | MET C1035 | 62.370 | 89.055 | 43.311 | 1.00 55.27 | C |
| ATOM | 11095 | C | MET C1035 | 63.703 | 83.309 | 45.506 | 1.00 33.31 | C |
| ATOM | 11096 | O | MET C1035 | 64.017 | 83.345 | 46.695 | 1.00 33.31 | C |
| ATOM | 11097 | N | GLU C1036 | 63.225 | 82.221 | 44.909 | 1.00 25.45 | C |
| ATOM | 11098 | CA | GLU C1036 | 63.048 | 80.962 | 45.613 | 1.00 25.45 | C |
| ATOM | 11099 | CB | GLU C1036 | 62.514 | 79.902 | 44.651 | 1.00 47.40 | C |
| ATOM | 11100 | CG | GLU C1036 | 61.136 | 80.247 | 44.085 | 1.00 47.40 | C |
| ATOM | 11101 | CD | GLU C1036 | 61.124 | 81.520 | 43.246 | 1.00 47.40 | C |
| ATOM | 11102 | OE1 | GLU C1036 | 61.633 | 81.489 | 42.108 | 1.00 47.40 | C |
| ATOM | 11103 | OE2 | GLU C1036 | 60.610 | 82.552 | 43.724 | 1.00 47.40 | C |
| ATOM | 11104 | C | GLU C1036 | 64.373 | 80.517 | 46.221 | 1.00 25.45 | C |
| ATOM | 11105 | O | GLU C1036 | 64.438 | 80.208 | 47.417 | 1.00 25.45 | C |
| ATOM | 11106 | N | VAL C1037 | 65.426 | 80.500 | 45.404 | 1.00 52.60 | C |
| ATOM | 11107 | CA | VAL C1037 | 66.753 | 80.108 | 45.868 | 1.00 52.60 | C |
| ATOM | 11108 | CB | VAL C1037 | 67.870 | 80.648 | 44.992 | 1.00 23.51 | C |
| ATOM | 11109 | CG1 | VAL C1037 | 69.148 | 79.957 | 45.358 | 1.00 23.51 | C |
| ATOM | 11110 | CG2 | VAL C1037 | 67.551 | 80.446 | 43.540 | 1.00 23.51 | C |
| ATOM | 11111 | C | VAL C1037 | 67.017 | 80.656 | 47.254 | 1.00 52.60 | C |
| ATOM | 11112 | O | VAL C1037 | 67.216 | 79.890 | 48.194 | 1.00 52.60 | C |
| ATOM | 11113 | N | TRP C1038 | 67.047 | 81.982 | 47.380 | 1.00 23.44 | C |
| ATOM | 11114 | CA | TRP C1038 | 67.271 | 82.574 | 48.690 | 1.00 23.44 | C |
| ATOM | 11115 | CB | TRP C1038 | 66.816 | 84.048 | 48.752 | 1.00 30.22 | C |
| ATOM | 11116 | CG | TRP C1038 | 67.603 | 85.011 | 47.894 | 1.00 30.22 | C |
| ATOM | 11117 | CD2 | TRP C1038 | 67.071 | 86.005 | 47.018 | 1.00 30.22 | C |
| ATOM | 11118 | CE2 | TRP C1038 | 68.161 | 86.617 | 46.366 | 1.00 30.22 | C |
| ATOM | 11119 | CE3 | TRP C1038 | 65.775 | 86.438 | 46.721 | 1.00 30.22 | C |
| ATOM | 11120 | CD1 | TRP C1038 | 68.949 | 85.066 | 47.752 | 1.00 30.22 | C |
| ATOM | 11121 | NE1 | TRP C1038 | 69.298 | 86.023 | 46.831 | 1.00 30.22 | C |
| ATOM | 11122 | CZ2 | TRP C1038 | 68.003 | 87.628 | 45.429 | 1.00 30.22 | C |
| ATOM | 11123 | CZ3 | TRP C1038 | 65.616 | 87.446 | 45.786 | 1.00 30.22 | C |
| ATOM | 11124 | CH2 | TRP C1038 | 66.729 | 88.034 | 45.149 | 1.00 30.22 | C |
| ATOM | 11125 | C | TRP C1038 | 66.437 | 81.747 | 49.667 | 1.00 23.44 | C |
| ATOM | 11126 | O | TRP C1038 | 66.991 | 81.090 | 50.536 | 1.00 23.44 | C |
| ATOM | 11127 | N | ALA C1039 | 65.113 | 81.752 | 49.492 | 1.00 5.13 | C |
| ATOM | 11128 | CA | ALA C1039 | 64.202 | 81.009 | 50.368 | 1.00 5.13 | C |
| ATOM | 11129 | CB | ALA C1039 | 62.931 | 80.675 | 49.639 | 1.00 21.81 | C |
| ATOM | 11130 | C | ALA C1039 | 64.847 | 79.732 | 50.859 | 1.00 5.13 | C |
| ATOM | 11131 | O | ALA C1039 | 65.059 | 79.539 | 52.061 | 1.00 5.13 | C |
| ATOM | 11132 | N | LEU C1040 | 65.159 | 78.847 | 49.926 | 1.00 22.00 | C |
| ATOM | 11133 | CA | LEU C1040 | 65.783 | 77.610 | 50.327 | 1.00 22.00 | C |
| ATOM | 11134 | CB | LEU C1040 | 66.231 | 76.818 | 49.098 | 1.00 39.12 | C |

| ATOM | 11135 | CG | LEU | C1040 | 65.075 | 76.292 | 48.237 | 1.00 | 39.12 | C |
| ATOM | 11136 | CD1 | LEU | C1040 | 63.977 | 75.746 | 49.146 | 1.00 | 39.12 | C |
| ATOM | 11137 | CD2 | LEU | C1040 | 64.511 | 77.399 | 47.377 | 1.00 | 39.12 | C |
| ATOM | 11138 | C | LEU | C1040 | 66.952 | 77.945 | 51.246 | 1.00 | 22.00 | C |
| ATOM | 11139 | O | LEU | C1040 | 67.016 | 77.444 | 52.366 | 1.00 | 22.00 | C |
| ATOM | 11140 | N | GLU | C1041 | 67.853 | 78.812 | 50.789 | 1.00 | 24.23 | C |
| ATOM | 11141 | CA | GLU | C1041 | 69.008 | 79.223 | 51.593 | 1.00 | 24.23 | C |
| ATOM | 11142 | CB | GLU | C1041 | 69.848 | 80.280 | 50.854 | 1.00 | 17.57 | C |
| ATOM | 11143 | CG | GLU | C1041 | 70.602 | 79.823 | 49.595 | 1.00 | 17.57 | C |
| ATOM | 11144 | CD | GLU | C1041 | 71.273 | 80.994 | 48.855 | 1.00 | 17.57 | C |
| ATOM | 11145 | OE1 | GLU | C1041 | 70.549 | 81.939 | 48.505 | 1.00 | 17.57 | C |
| ATOM | 11146 | OE2 | GLU | C1041 | 72.500 | 80.988 | 48.618 | 1.00 | 17.57 | C |
| ATOM | 11147 | C | GLU | C1041 | 68.533 | 79.830 | 52.917 | 1.00 | 24.23 | C |
| ATOM | 11148 | O | GLU | C1041 | 68.859 | 79.317 | 53.990 | 1.00 | 24.23 | C |
| ATOM | 11149 | N | ALA | C1042 | 67.768 | 80.927 | 52.816 | 1.00 | 11.12 | C |
| ATOM | 11150 | CA | ALA | C1042 | 67.237 | 81.669 | 53.967 | 1.00 | 11.12 | C |
| ATOM | 11151 | CB | ALA | C1042 | 65.966 | 82.425 | 53.590 | 1.00 | 58.04 | C |
| ATOM | 11152 | C | ALA | C1042 | 66.962 | 80.687 | 55.062 | 1.00 | 11.12 | C |
| ATOM | 11153 | O | ALA | C1042 | 67.303 | 80.928 | 56.203 | 1.00 | 11.12 | C |
| ATOM | 11154 | N | TYR | C1043 | 66.341 | 79.569 | 54.722 | 1.00 | 37.76 | C |
| ATOM | 11155 | CA | TYR | C1043 | 66.110 | 78.552 | 55.734 | 1.00 | 37.76 | C |
| ATOM | 11156 | CB | TYR | C1043 | 65.239 | 77.400 | 55.214 | 1.00 | 32.84 | C |
| ATOM | 11157 | CG | TYR | C1043 | 63.763 | 77.658 | 55.144 | 1.00 | 32.84 | C |
| ATOM | 11158 | CD1 | TYR | C1043 | 63.196 | 78.229 | 54.024 | 1.00 | 32.84 | C |
| ATOM | 11159 | CE1 | TYR | C1043 | 61.838 | 78.423 | 53.948 | 1.00 | 32.84 | C |
| ATOM | 11160 | CD2 | TYR | C1043 | 62.927 | 77.292 | 56.193 | 1.00 | 32.84 | C |
| ATOM | 11161 | CE2 | TYR | C1043 | 61.572 | 77.484 | 56.125 | 1.00 | 32.84 | C |
| ATOM | 11162 | CZ | TYR | C1043 | 61.033 | 78.046 | 54.999 | 1.00 | 32.84 | C |
| ATOM | 11163 | OH | TYR | C1043 | 59.678 | 78.214 | 54.896 | 1.00 | 32.84 | C |
| ATOM | 11164 | C | TYR | C1043 | 67.486 | 77.970 | 55.979 | 1.00 | 37.76 | C |
| ATOM | 11165 | O | TYR | C1043 | 68.415 | 78.611 | 56.468 | 1.00 | 37.76 | C |
| ATOM | 11166 | N | GLY | C1044 | 67.577 | 76.724 | 55.572 | 1.00 | 30.65 | C |
| ATOM | 11167 | CA | GLY | C1044 | 68.772 | 75.941 | 55.667 | 1.00 | 30.65 | C |
| ATOM | 11168 | C | GLY | C1044 | 68.100 | 74.715 | 55.125 | 1.00 | 30.65 | C |
| ATOM | 11169 | O | GLY | C1044 | 67.077 | 74.293 | 55.663 | 1.00 | 30.65 | C |
| ATOM | 11170 | N | ALA | C1045 | 68.616 | 74.174 | 54.039 | 1.00 | 28.37 | C |
| ATOM | 11171 | CA | ALA | C1045 | 68.007 | 72.999 | 53.475 | 1.00 | 28.37 | C |
| ATOM | 11172 | CB | ALA | C1045 | 66.599 | 73.309 | 53.066 | 1.00 | 5.07 | C |
| ATOM | 11173 | C | ALA | C1045 | 68.818 | 72.594 | 52.278 | 1.00 | 28.37 | C |
| ATOM | 11174 | O | ALA | C1045 | 68.378 | 71.779 | 51.470 | 1.00 | 28.37 | C |
| ATOM | 11175 | N | ALA | C1046 | 70.008 | 73.175 | 52.175 | 1.00 | 24.84 | C |
| ATOM | 11176 | CA | ALA | C1046 | 70.913 | 72.916 | 51.066 | 1.00 | 24.84 | C |
| ATOM | 11177 | CB | ALA | C1046 | 72.342 | 72.826 | 51.574 | 1.00 | 42.88 | C |
| ATOM | 11178 | C | ALA | C1046 | 70.532 | 71.651 | 50.307 | 1.00 | 24.84 | C |
| ATOM | 11179 | O | ALA | C1046 | 70.229 | 71.710 | 49.108 | 1.00 | 24.84 | C |
| ATOM | 11180 | N | HIS | C1047 | 70.511 | 70.516 | 51.006 | 1.00 | 19.24 | C |
| ATOM | 11181 | CA | HIS | C1047 | 70.163 | 69.264 | 50.343 | 1.00 | 19.24 | C |
| ATOM | 11182 | CB | HIS | C1047 | 70.054 | 68.134 | 51.365 | 1.00 | 99.82 | C |
| ATOM | 11183 | CG | HIS | C1047 | 71.384 | 67.597 | 51.793 | 1.00 | 99.82 | C |
| ATOM | 11184 | CD2 | HIS | C1047 | 72.044 | 67.677 | 52.973 | 1.00 | 99.82 | C |
| ATOM | 11185 | ND1 | HIS | C1047 | 72.224 | 66.923 | 50.933 | 1.00 | 99.82 | C |
| ATOM | 11186 | CE1 | HIS | C1047 | 73.341 | 66.612 | 51.564 | 1.00 | 99.82 | C |
| ATOM | 11187 | NE2 | HIS | C1047 | 73.258 | 67.057 | 52.804 | 1.00 | 99.82 | C |
| ATOM | 11188 | C | HIS | C1047 | 68.897 | 69.378 | 49.507 | 1.00 | 19.24 | C |
| ATOM | 11189 | O | HIS | C1047 | 68.895 | 69.004 | 48.335 | 1.00 | 19.24 | C |
| ATOM | 11190 | N | THR | C1048 | 67.832 | 69.908 | 50.100 | 1.00 | 34.66 | C |
| ATOM | 11191 | CA | THR | C1048 | 66.573 | 70.091 | 49.387 | 1.00 | 34.66 | C |
| ATOM | 11192 | CB | THR | C1048 | 65.543 | 70.846 | 50.219 | 1.00 | 41.37 | C |
| ATOM | 11193 | OG1 | THR | C1048 | 65.303 | 70.152 | 51.449 | 1.00 | 41.37 | C |
| ATOM | 11194 | CG2 | THR | C1048 | 64.251 | 70.969 | 49.437 | 1.00 | 41.37 | C |
| ATOM | 11195 | C | THR | C1048 | 66.840 | 70.938 | 48.162 | 1.00 | 34.66 | C |
| ATOM | 11196 | O | THR | C1048 | 66.300 | 70.676 | 47.087 | 1.00 | 34.66 | C |
| ATOM | 11197 | N | LEU | C1049 | 67.667 | 71.967 | 48.345 | 1.00 | 27.07 | C |
| ATOM | 11198 | CA | LEU | C1049 | 68.023 | 72.868 | 47.257 | 1.00 | 27.07 | C |
| ATOM | 11199 | CB | LEU | C1049 | 68.731 | 74.114 | 47.780 | 1.00 | 22.64 | C |
| ATOM | 11200 | CG | LEU | C1049 | 69.247 | 74.954 | 46.612 | 1.00 | 22.64 | C |
| ATOM | 11201 | CD1 | LEU | C1049 | 68.099 | 75.267 | 45.712 | 1.00 | 22.64 | C |
| ATOM | 11202 | CD2 | LEU | C1049 | 69.876 | 76.229 | 47.092 | 1.00 | 22.64 | C |
| ATOM | 11203 | C | LEU | C1049 | 68.932 | 72.182 | 46.253 | 1.00 | 27.07 | C |
| ATOM | 11204 | O | LEU | C1049 | 68.747 | 72.327 | 45.050 | 1.00 | 27.07 | C |
| ATOM | 11205 | N | GLN | C1050 | 69.923 | 71.451 | 46.761 | 1.00 | 66.41 | C |
| ATOM | 11206 | CA | GLN | C1050 | 70.876 | 70.723 | 45.922 | 1.00 | 66.41 | C |
| ATOM | 11207 | CB | GLN | C1050 | 71.708 | 69.755 | 46.799 | 1.00 | 41.38 | C |
| ATOM | 11208 | CG | GLN | C1050 | 72.482 | 68.615 | 46.064 | 1.00 | 41.38 | C |
| ATOM | 11209 | CD | GLN | C1050 | 73.972 | 68.892 | 45.839 | 1.00 | 41.38 | C |
| ATOM | 11210 | OE1 | GLN | C1050 | 74.836 | 68.180 | 46.370 | 1.00 | 41.38 | C |
| ATOM | 11211 | NE2 | GLN | C1050 | 74.275 | 69.919 | 45.040 | 1.00 | 41.38 | C |
| ATOM | 11212 | C | GLN | C1050 | 70.112 | 69.955 | 44.842 | 1.00 | 66.41 | C |
| ATOM | 11213 | O | GLN | C1050 | 70.372 | 70.096 | 43.647 | 1.00 | 66.41 | C |
| ATOM | 11214 | N | GLU | C1051 | 69.149 | 69.155 | 45.277 | 1.00 | 40.71 | C |
| ATOM | 11215 | CA | GLU | C1051 | 68.348 | 68.356 | 44.369 | 1.00 | 40.71 | C |
| ATOM | 11216 | CB | GLU | C1051 | 67.360 | 67.539 | 45.202 | 1.00 | 62.66 | C |
| ATOM | 11217 | CG | GLU | C1051 | 66.053 | 67.266 | 44.533 | 1.00 | 62.66 | C |
| ATOM | 11218 | CD | GLU | C1051 | 64.899 | 67.678 | 45.406 | 1.00 | 62.66 | C |

```
ATOM  11219  OE1 GLU C1051     64.906  68.845  45.863  1.00 62.66           C
ATOM  11220  OE2 GLU C1051     63.993  66.845  45.634  1.00 62.66           C
ATOM  11221  C   GLU C1051     67.629  69.208  43.311  1.00 40.71           C
ATOM  11222  O   GLU C1051     67.284  68.722  42.232  1.00 40.71           C
ATOM  11223  N   MET C1052     67.430  70.485  43.619  1.00 32.41           C
ATOM  11224  CA  MET C1052     66.747  71.398  42.709  1.00 32.41           C
ATOM  11225  CB  MET C1052     66.161  72.579  43.502  1.00 42.69           C
ATOM  11226  CG  MET C1052     64.869  73.182  42.934  1.00 42.69           C
ATOM  11227  SD  MET C1052     63.531  73.306  44.174  1.00 42.69           C
ATOM  11228  CE  MET C1052     62.247  72.140  43.492  1.00 42.69           C
ATOM  11229  C   MET C1052     67.708  71.891  41.635  1.00 32.41           C
ATOM  11230  O   MET C1052     67.325  72.637  40.750  1.00 32.41           C
ATOM  11231  N   LEU C1053     68.962  71.470  41.719  1.00 43.50           C
ATOM  11232  CA  LEU C1053     69.964  71.856  40.725  1.00 43.50           C
ATOM  11233  CB  LEU C1053     70.862  72.978  41.248  1.00 50.10           C
ATOM  11234  CG  LEU C1053     70.235  74.357  41.380  1.00 50.10           C
ATOM  11235  CD1 LEU C1053     69.204  74.517  40.270  1.00 50.10           C
ATOM  11236  CD2 LEU C1053     69.596  74.515  42.737  1.00 50.10           C
ATOM  11237  C   LEU C1053     70.850  70.680  40.330  1.00 43.50           C
ATOM  11238  O   LEU C1053     71.884  70.863  39.688  1.00 43.50           C
ATOM  11239  N   THR C1054     70.436  69.477  40.709  1.00 33.33           C
ATOM  11240  CA  THR C1054     71.205  68.284  40.414  1.00 33.33           C
ATOM  11241  CB  THR C1054     71.851  67.779  41.679  1.00 40.94           C
ATOM  11242  OG1 THR C1054     72.488  68.884  42.327  1.00 40.94           C
ATOM  11243  CG2 THR C1054     72.881  66.704  41.372  1.00 40.94           C
ATOM  11244  C   THR C1054     70.324  67.197  39.849  1.00 33.33           C
ATOM  11245  O   THR C1054     70.114  67.115  38.649  1.00 33.33           C
ATOM  11246  N   ILE C1055     69.803  66.364  40.733  1.00 24.89           C
ATOM  11247  CA  ILE C1055     68.939  65.278  40.331  1.00 24.89           C
ATOM  11248  CB  ILE C1055     68.460  64.454  41.540  1.00 67.79           C
ATOM  11249  CG2 ILE C1055     68.880  63.009  41.383  1.00 67.79           C
ATOM  11250  CG1 ILE C1055     68.998  65.054  42.839  1.00 67.79           C
ATOM  11251  CD  ILE C1055     70.508  64.940  43.008  1.00 67.79           C
ATOM  11252  C   ILE C1055     67.691  65.788  39.641  1.00 24.89           C
ATOM  11253  O   ILE C1055     66.758  65.015  39.452  1.00 24.89           C
ATOM  11254  N   LYS C1056     67.644  67.062  39.250  1.00 42.15           C
ATOM  11255  CA  LYS C1056     66.423  67.568  38.619  1.00 42.15           C
ATOM  11256  CB  LYS C1056     65.529  68.248  39.689  1.00 23.57           C
ATOM  11257  CG  LYS C1056     64.829  67.265  40.664  1.00 23.57           C
ATOM  11258  CD  LYS C1056     63.533  67.836  41.280  1.00 23.57           C
ATOM  11259  CE  LYS C1056     63.761  68.665  42.566  1.00 23.57           C
ATOM  11260  NZ  LYS C1056     62.494  69.220  43.178  1.00 23.57           C
ATOM  11261  C   LYS C1056     66.473  68.456  37.371  1.00 42.15           C
ATOM  11262  O   LYS C1056     65.741  69.437  37.296  1.00 42.15           C
ATOM  11263  N   SER C1057     67.312  68.114  36.396  1.00 40.15           C
ATOM  11264  CA  SER C1057     67.382  68.869  35.130  1.00 40.15           C
ATOM  11265  CB  SER C1057     66.988  70.349  35.330  1.00 37.27           C
ATOM  11266  OG  SER C1057     67.872  71.033  36.192  1.00 37.27           C
ATOM  11267  C   SER C1057     68.681  68.817  34.307  1.00 40.15           C
ATOM  11268  O   SER C1057     68.688  68.326  33.174  1.00 40.15           C
ATOM  11269  N   ASP C1058     69.769  69.330  34.863  1.00 51.84           C
ATOM  11270  CA  ASP C1058     71.036  69.348  34.152  1.00 51.84           C
ATOM  11271  CB  ASP C1058     71.844  70.555  34.604  1.00 65.21           C
ATOM  11272  CG  ASP C1058     70.991  71.786  34.783  1.00 65.21           C
ATOM  11273  OD1 ASP C1058     70.361  72.206  33.794  1.00 65.21           C
ATOM  11274  OD2 ASP C1058     70.945  72.331  35.908  1.00 65.21           C
ATOM  11275  C   ASP C1058     71.861  68.078  34.361  1.00 51.84           C
ATOM  11276  O   ASP C1058     72.364  67.500  33.399  1.00 51.84           C
ATOM  11277  N   ASP C1059     72.006  67.663  35.622  1.00 29.52           C
ATOM  11278  CA  ASP C1059     72.782  66.475  36.006  1.00 29.52           C
ATOM  11279  CB  ASP C1059     72.965  66.428  37.527  1.00 52.58           C
ATOM  11280  CG  ASP C1059     73.736  65.193  37.995  1.00 52.58           C
ATOM  11281  OD1 ASP C1059     73.437  64.075  37.542  1.00 52.58           C
ATOM  11282  OD2 ASP C1059     74.640  65.334  38.842  1.00 52.58           C
ATOM  11283  C   ASP C1059     72.151  65.170  35.567  1.00 29.52           C
ATOM  11284  O   ASP C1059     71.623  64.421  36.391  1.00 29.52           C
ATOM  11285  N   ILE C1060     72.200  64.895  34.274  1.00 46.88           C
ATOM  11286  CA  ILE C1060     71.652  63.653  33.753  1.00 46.88           C
ATOM  11287  CB  ILE C1060     72.311  63.308  32.418  1.00 33.49           C
ATOM  11288  CG2 ILE C1060     71.391  63.699  31.292  1.00 33.49           C
ATOM  11289  CG1 ILE C1060     73.623  64.094  32.262  1.00 33.49           C
ATOM  11290  CD  ILE C1060     74.665  63.904  33.382  1.00 33.49           C
ATOM  11291  C   ILE C1060     71.824  62.488  34.742  1.00 46.88           C
ATOM  11292  O   ILE C1060     70.878  61.733  34.989  1.00 46.88           C
ATOM  11293  N   GLU C1061     73.023  62.353  35.312  1.00 35.88           C
ATOM  11294  CA  GLU C1061     73.293  61.303  36.286  1.00 35.88           C
ATOM  11295  CB  GLU C1061     74.505  61.660  37.144  1.00100.07           C
ATOM  11296  CG  GLU C1061     75.682  62.187  36.368  1.00100.07           C
ATOM  11297  CD  GLU C1061     76.374  61.106  35.582  1.00100.07           C
ATOM  11298  OE1 GLU C1061     75.690  60.418  34.794  1.00100.07           C
ATOM  11299  OE2 GLU C1061     77.601  60.946  35.756  1.00100.07           C
ATOM  11300  C   GLU C1061     72.076  61.279  37.183  1.00 35.88           C
ATOM  11301  O   GLU C1061     71.344  60.286  37.254  1.00 35.88           C
ATOM  11302  N   GLY C1062     71.869  62.409  37.852  1.00 36.80           C
```

```
ATOM  11303  CA   GLY C1062     70.754  62.561  38.763  1.00 36.80           C
ATOM  11304  C    GLY C1062     69.472  62.002  38.197  1.00 36.80           C
ATOM  11305  O    GLY C1062     68.936  61.012  38.702  1.00 36.80           C
ATOM  11306  N    ARG C1063     68.984  62.648  37.144  1.00 48.95           C
ATOM  11307  CA   ARG C1063     67.767  62.220  36.493  1.00 48.95           C
ATOM  11308  CB   ARG C1063     67.757  62.708  35.044  1.00 50.82           C
ATOM  11309  CG   ARG C1063     67.856  64.227  34.917  1.00 50.82           C
ATOM  11310  CD   ARG C1063     68.058  64.695  33.474  1.00 50.82           C
ATOM  11311  NE   ARG C1063     66.829  64.764  32.693  1.00 50.82           C
ATOM  11312  CZ   ARG C1063     66.756  65.344  31.502  1.00 50.82           C
ATOM  11313  NH1  ARG C1063     67.839  65.890  30.971  1.00 50.82           C
ATOM  11314  NH2  ARG C1063     65.601  65.402  30.854  1.00 50.82           C
ATOM  11315  C    ARG C1063     67.718  60.703  36.547  1.00 48.95           C
ATOM  11316  O    ARG C1063     66.868  60.137  37.229  1.00 48.95           C
ATOM  11317  N    ASN C1064     68.652  60.052  35.859  1.00 32.70           C
ATOM  11318  CA   ASN C1064     68.714  58.593  35.834  1.00 32.70           C
ATOM  11319  CB   ASN C1064     70.009  58.144  35.169  1.00100.07           C
ATOM  11320  CG   ASN C1064     70.322  58.948  33.930  1.00100.07           C
ATOM  11321  OD1  ASN C1064     69.509  59.034  33.009  1.00100.07           C
ATOM  11322  ND2  ASN C1064     71.502  59.552  33.902  1.00100.07           C
ATOM  11323  C    ASN C1064     68.622  57.999  37.238  1.00 32.70           C
ATOM  11324  O    ASN C1064     67.607  57.404  37.604  1.00 32.70           C
ATOM  11325  N    ALA C1065     69.680  58.161  38.023  1.00 73.60           C
ATOM  11326  CA   ALA C1065     69.694  57.638  39.386  1.00 73.60           C
ATOM  11327  CB   ALA C1065     70.828  58.264  40.167  1.00100.07           C
ATOM  11328  C    ALA C1065     68.373  57.966  40.054  1.00 73.60           C
ATOM  11329  O    ALA C1065     67.784  57.143  40.756  1.00 73.60           C
ATOM  11330  N    ALA C1066     67.922  59.189  39.818  1.00 80.92           C
ATOM  11331  CA   ALA C1066     66.676  59.681  40.367  1.00 80.92           C
ATOM  11332  CB   ALA C1066     66.451  61.119  39.906  1.00 19.44           C
ATOM  11333  C    ALA C1066     65.507  58.804  39.931  1.00 80.92           C
ATOM  11334  O    ALA C1066     64.862  58.156  40.758  1.00 80.92           C
ATOM  11335  N    TYR C1067     65.257  58.778  38.623  1.00 45.00           C
ATOM  11336  CA   TYR C1067     64.152  58.020  38.061  1.00 45.00           C
ATOM  11337  CB   TYR C1067     63.924  58.384  36.601  1.00 63.03           C
ATOM  11338  CG   TYR C1067     62.583  57.898  36.108  1.00 63.03           C
ATOM  11339  CD1  TYR C1067     61.411  58.551  36.473  1.00 63.03           C
ATOM  11340  CE1  TYR C1067     60.159  58.084  36.060  1.00 63.03           C
ATOM  11341  CD2  TYR C1067     62.475  56.762  35.315  1.00 63.03           C
ATOM  11342  CE2  TYR C1067     61.223  56.284  34.897  1.00 63.03           C
ATOM  11343  CZ   TYR C1067     60.071  56.951  35.273  1.00 63.03           C
ATOM  11344  OH   TYR C1067     58.831  56.495  34.873  1.00 63.03           C
ATOM  11345  C    TYR C1067     64.276  56.518  38.142  1.00 45.00           C
ATOM  11346  O    TYR C1067     63.302  55.823  37.879  1.00 45.00           C
ATOM  11347  N    GLN C1068     65.456  56.006  38.482  1.00 69.85           C
ATOM  11348  CA   GLN C1068     65.649  54.557  38.585  1.00 69.85           C
ATOM  11349  CB   GLN C1068     67.043  54.166  38.087  1.00100.07           C
ATOM  11350  CG   GLN C1068     67.251  54.421  36.599  1.00100.07           C
ATOM  11351  CD   GLN C1068     68.652  54.079  36.126  1.00100.07           C
ATOM  11352  OE1  GLN C1068     69.115  52.946  36.291  1.00100.07           C
ATOM  11353  NE2  GLN C1068     69.335  55.058  35.528  1.00100.07           C
ATOM  11354  C    GLN C1068     65.468  54.109  40.027  1.00 69.85           C
ATOM  11355  O    GLN C1068     64.844  53.084  40.309  1.00 69.85           C
ATOM  11356  N    ALA C1069     66.016  54.898  40.939  1.00 36.94           C
ATOM  11357  CA   ALA C1069     65.918  54.603  42.354  1.00 36.94           C
ATOM  11358  CB   ALA C1069     66.685  55.643  43.154  1.00100.07           C
ATOM  11359  C    ALA C1069     64.457  54.619  42.756  1.00 36.94           C
ATOM  11360  O    ALA C1069     64.009  53.799  43.558  1.00 36.94           C
ATOM  11361  N    ILE C1070     63.714  55.559  42.186  1.00 53.32           C
ATOM  11362  CA   ILE C1070     62.303  55.703  42.497  1.00 53.32           C
ATOM  11363  CB   ILE C1070     61.765  57.030  41.939  1.00 78.37           C
ATOM  11364  CG2  ILE C1070     60.252  57.085  42.075  1.00 78.37           C
ATOM  11365  CG1  ILE C1070     62.430  58.190  42.687  1.00 78.37           C
ATOM  11366  CD   ILE C1070     61.981  59.550  42.244  1.00 78.37           C
ATOM  11367  C    ILE C1070     61.438  54.545  42.025  1.00 53.32           C
ATOM  11368  O    ILE C1070     60.635  54.034  42.800  1.00 53.32           C
ATOM  11369  N    ILE C1071     61.592  54.132  40.768  1.00 68.00           C
ATOM  11370  CA   ILE C1071     60.809  53.010  40.247  1.00 68.00           C
ATOM  11371  CB   ILE C1071     61.319  52.512  38.876  1.00 78.64           C
ATOM  11372  CG2  ILE C1071     60.257  51.635  38.234  1.00 78.64           C
ATOM  11373  CG1  ILE C1071     61.648  53.680  37.949  1.00 78.64           C
ATOM  11374  CD   ILE C1071     60.449  54.406  37.416  1.00 78.64           C
ATOM  11375  C    ILE C1071     61.021  51.862  41.230  1.00 68.00           C
ATOM  11376  O    ILE C1071     60.163  50.993  41.421  1.00 68.00           C
ATOM  11377  N    LYS C1072     62.199  51.871  41.840  1.00 68.80           C
ATOM  11378  CA   LYS C1072     62.572  50.861  42.809  1.00 68.80           C
ATOM  11379  CB   LYS C1072     64.078  50.615  42.732  1.00100.07           C
ATOM  11380  CG   LYS C1072     64.617  50.468  41.317  1.00100.07           C
ATOM  11381  CD   LYS C1072     66.130  50.277  41.319  1.00100.07           C
ATOM  11382  CE   LYS C1072     66.528  48.958  41.985  1.00100.07           C
ATOM  11383  NZ   LYS C1072     68.010  48.754  42.062  1.00100.07           C
ATOM  11384  C    LYS C1072     62.208  51.393  44.192  1.00 68.80           C
ATOM  11385  O    LYS C1072     61.715  52.516  44.319  1.00 68.80           C
ATOM  11386  N    GLY C1073     62.455  50.589  45.224  1.00 74.04           C
```

| ATOM | 11387 | CA | GLY | C1073 | 62.156 | 51.019 | 46.578 | 1.00 | 74.04 | C |
|------|-------|-----|-----|-------|--------|--------|--------|------|-------|---|
| ATOM | 11388 | C | GLY | C1073 | 63.291 | 51.838 | 47.156 | 1.00 | 74.04 | C |
| ATOM | 11389 | O | GLY | C1073 | 63.435 | 51.942 | 48.372 | 1.00 | 74.04 | C |
| ATOM | 11390 | N | GLU | C1074 | 64.090 | 52.426 | 46.268 | 1.00 | 65.07 | C |
| ATOM | 11391 | CA | GLU | C1074 | 65.248 | 53.227 | 46.648 | 1.00 | 65.07 | C |
| ATOM | 11392 | CB | GLU | C1074 | 66.412 | 52.896 | 45.717 | 1.00 | 98.80 | C |
| ATOM | 11393 | CG | GLU | C1074 | 67.060 | 51.557 | 46.022 | 1.00 | 98.80 | C |
| ATOM | 11394 | CD | GLU | C1074 | 67.422 | 50.775 | 44.777 | 1.00 | 98.80 | C |
| ATOM | 11395 | OE1 | GLU | C1074 | 67.954 | 51.379 | 43.820 | 1.00 | 98.80 | C |
| ATOM | 11396 | OE2 | GLU | C1074 | 67.185 | 49.548 | 44.759 | 1.00 | 98.80 | C |
| ATOM | 11397 | C | GLU | C1074 | 65.006 | 54.732 | 46.668 | 1.00 | 65.07 | C |
| ATOM | 11398 | O | GLU | C1074 | 64.226 | 55.263 | 45.876 | 1.00 | 65.07 | C |
| ATOM | 11399 | N | ASP | C1075 | 65.696 | 55.412 | 47.580 | 1.00 | 31.63 | C |
| ATOM | 11400 | CA | ASP | C1075 | 65.563 | 56.852 | 47.742 | 1.00 | 31.63 | C |
| ATOM | 11401 | CB | ASP | C1075 | 65.923 | 57.250 | 49.166 | 1.00 | 51.36 | C |
| ATOM | 11402 | CG | ASP | C1075 | 67.418 | 57.370 | 49.364 | 1.00 | 51.36 | C |
| ATOM | 11403 | OD1 | ASP | C1075 | 68.129 | 56.376 | 49.097 | 1.00 | 51.36 | C |
| ATOM | 11404 | OD2 | ASP | C1075 | 67.881 | 58.457 | 49.774 | 1.00 | 51.36 | C |
| ATOM | 11405 | C | ASP | C1075 | 66.470 | 57.615 | 46.795 | 1.00 | 31.63 | C |
| ATOM | 11406 | O | ASP | C1075 | 67.678 | 57.376 | 46.757 | 1.00 | 31.63 | C |
| ATOM | 11407 | N | VAL | C1076 | 65.892 | 58.541 | 46.038 | 1.00 | 77.61 | C |
| ATOM | 11408 | CA | VAL | C1076 | 66.679 | 59.344 | 45.109 | 1.00 | 77.61 | C |
| ATOM | 11409 | CB | VAL | C1076 | 65.902 | 60.608 | 44.661 | 1.00 | 49.98 | C |
| ATOM | 11410 | CG1 | VAL | C1076 | 66.847 | 61.627 | 44.022 | 1.00 | 49.98 | C |
| ATOM | 11411 | CG2 | VAL | C1076 | 64.825 | 60.210 | 43.669 | 1.00 | 49.98 | C |
| ATOM | 11412 | C | VAL | C1076 | 67.985 | 59.749 | 45.787 | 1.00 | 77.61 | C |
| ATOM | 11413 | O | VAL | C1076 | 67.982 | 60.289 | 46.891 | 1.00 | 77.61 | C |
| ATOM | 11414 | N | PRO | C1077 | 69.121 | 59.455 | 45.143 | 1.00 | 98.85 | C |
| ATOM | 11415 | CD | PRO | C1077 | 69.220 | 58.474 | 44.048 | 1.00 | 88.18 | C |
| ATOM | 11416 | CA | PRO | C1077 | 70.452 | 59.773 | 45.657 | 1.00 | 98.85 | C |
| ATOM | 11417 | CB | PRO | C1077 | 71.275 | 58.605 | 45.154 | 1.00 | 88.18 | C |
| ATOM | 11418 | CG | PRO | C1077 | 70.708 | 58.421 | 43.789 | 1.00 | 88.18 | C |
| ATOM | 11419 | C | PRO | C1077 | 71.014 | 61.115 | 45.177 | 1.00 | 98.85 | C |
| ATOM | 11420 | O | PRO | C1077 | 70.274 | 61.991 | 44.729 | 1.00 | 98.85 | C |
| ATOM | 11421 | N | GLU | C1078 | 72.335 | 61.251 | 45.290 | 1.00 | 98.90 | C |
| ATOM | 11422 | CA | GLU | C1078 | 73.071 | 62.445 | 44.875 | 1.00 | 98.90 | C |
| ATOM | 11423 | CB | GLU | C1078 | 72.635 | 63.674 | 45.672 | 1.00 | 89.32 | C |
| ATOM | 11424 | CG | GLU | C1078 | 73.706 | 64.767 | 45.709 | 1.00 | 89.32 | C |
| ATOM | 11425 | CD | GLU | C1078 | 74.156 | 65.233 | 44.328 | 1.00 | 89.32 | C |
| ATOM | 11426 | OE1 | GLU | C1078 | 74.071 | 64.462 | 43.353 | 1.00 | 89.32 | C |
| ATOM | 11427 | OE2 | GLU | C1078 | 74.618 | 66.385 | 44.226 | 1.00 | 89.32 | C |
| ATOM | 11428 | C | GLU | C1078 | 74.579 | 62.272 | 45.039 | 1.00 | 98.90 | C |
| ATOM | 11429 | O | GLU | C1078 | 75.075 | 62.039 | 46.141 | 1.00 | 98.90 | C |
| ATOM | 11430 | N | PRO | C1079 | 75.323 | 62.372 | 43.933 | 1.00 | 52.54 | C |
| ATOM | 11431 | CD | PRO | C1079 | 74.759 | 62.060 | 42.601 | 1.00 | 100.07 | C |
| ATOM | 11432 | CA | PRO | C1079 | 76.787 | 62.234 | 43.916 | 1.00 | 52.54 | C |
| ATOM | 11433 | CB | PRO | C1079 | 77.010 | 61.283 | 42.756 | 1.00 | 100.07 | C |
| ATOM | 11434 | CG | PRO | C1079 | 76.003 | 61.818 | 41.745 | 1.00 | 100.07 | C |
| ATOM | 11435 | C | PRO | C1079 | 77.448 | 63.575 | 43.646 | 1.00 | 52.54 | C |
| ATOM | 11436 | O | PRO | C1079 | 77.019 | 64.596 | 44.170 | 1.00 | 52.54 | C |
| ATOM | 11437 | N | SER | C1080 | 78.489 | 63.565 | 42.818 | 1.00 | 66.25 | C |
| ATOM | 11438 | CA | SER | C1080 | 79.153 | 64.807 | 42.451 | 1.00 | 66.25 | C |
| ATOM | 11439 | CB | SER | C1080 | 80.380 | 64.553 | 41.584 | 1.00 | 80.40 | C |
| ATOM | 11440 | OG | SER | C1080 | 80.894 | 65.782 | 41.093 | 1.00 | 80.40 | C |
| ATOM | 11441 | C | SER | C1080 | 78.135 | 65.602 | 41.646 | 1.00 | 66.25 | C |
| ATOM | 11442 | O | SER | C1080 | 76.945 | 65.277 | 41.658 | 1.00 | 66.25 | C |
| ATOM | 11443 | N | VAL | C1081 | 78.586 | 66.625 | 40.927 | 1.00 | 23.51 | C |
| ATOM | 11444 | CA | VAL | C1081 | 77.640 | 67.439 | 40.172 | 1.00 | 23.51 | C |
| ATOM | 11445 | CB | VAL | C1081 | 77.078 | 68.589 | 41.033 | 1.00 | 100.04 | C |
| ATOM | 11446 | CG1 | VAL | C1081 | 75.938 | 69.253 | 40.301 | 1.00 | 100.04 | C |
| ATOM | 11447 | CG2 | VAL | C1081 | 76.613 | 68.070 | 42.390 | 1.00 | 100.04 | C |
| ATOM | 11448 | C | VAL | C1081 | 78.157 | 68.049 | 38.882 | 1.00 | 23.51 | C |
| ATOM | 11449 | O | VAL | C1081 | 79.067 | 68.883 | 38.874 | 1.00 | 23.51 | C |
| ATOM | 11450 | N | PRO | C1082 | 77.525 | 67.673 | 37.772 | 1.00 | 57.24 | C |
| ATOM | 11451 | CD | PRO | C1082 | 76.147 | 67.165 | 37.764 | 1.00 | 99.94 | C |
| ATOM | 11452 | CA | PRO | C1082 | 77.885 | 68.154 | 36.443 | 1.00 | 57.24 | C |
| ATOM | 11453 | CB | PRO | C1082 | 76.704 | 67.706 | 35.593 | 1.00 | 99.94 | C |
| ATOM | 11454 | CG | PRO | C1082 | 75.575 | 67.835 | 36.547 | 1.00 | 99.94 | C |
| ATOM | 11455 | C | PRO | C1082 | 78.026 | 69.657 | 36.472 | 1.00 | 57.24 | C |
| ATOM | 11456 | O | PRO | C1082 | 78.852 | 70.224 | 35.760 | 1.00 | 57.24 | C |
| ATOM | 11457 | N | GLU | C1083 | 77.205 | 70.298 | 37.300 | 1.00 | 42.40 | C |
| ATOM | 11458 | CA | GLU | C1083 | 77.250 | 71.743 | 37.410 | 1.00 | 42.40 | C |
| ATOM | 11459 | CB | GLU | C1083 | 76.488 | 72.207 | 38.642 | 1.00 | 100.07 | C |
| ATOM | 11460 | CG | GLU | C1083 | 75.037 | 71.797 | 38.607 | 1.00 | 100.07 | C |
| ATOM | 11461 | CD | GLU | C1083 | 74.296 | 72.411 | 37.447 | 1.00 | 100.07 | C |
| ATOM | 11462 | OE1 | GLU | C1083 | 74.960 | 72.882 | 36.500 | 1.00 | 100.07 | C |
| ATOM | 11463 | OE2 | GLU | C1083 | 73.047 | 72.414 | 37.480 | 1.00 | 100.07 | C |
| ATOM | 11464 | C | GLU | C1083 | 78.705 | 72.104 | 37.520 | 1.00 | 42.40 | C |
| ATOM | 11465 | O | GLU | C1083 | 79.150 | 73.070 | 36.909 | 1.00 | 42.40 | C |
| ATOM | 11466 | N | SER | C1084 | 79.445 | 71.302 | 38.283 | 1.00 | 53.04 | C |
| ATOM | 11467 | CA | SER | C1084 | 80.867 | 71.540 | 38.437 | 1.00 | 53.04 | C |
| ATOM | 11468 | CB | SER | C1084 | 81.370 | 71.138 | 39.825 | 1.00 | 58.80 | C |
| ATOM | 11469 | OG | SER | C1084 | 82.649 | 71.714 | 40.076 | 1.00 | 58.80 | C |
| ATOM | 11470 | C | SER | C1084 | 81.609 | 70.753 | 37.374 | 1.00 | 53.04 | C |

```
ATOM  11471  O    SER C1084      82.407  71.330  36.635  1.00 53.04           C
ATOM  11472  N    PHE C1085      81.341  69.445  37.291  1.00 51.88           C
ATOM  11473  CA   PHE C1085      81.991  68.597  36.294  1.00 51.88           C
ATOM  11474  CB   PHE C1085      81.083  67.419  35.890  1.00 84.41           C
ATOM  11475  CG   PHE C1085      81.210  66.179  36.767  1.00 84.41           C
ATOM  11476  CD1  PHE C1085      81.989  66.173  37.921  1.00 84.41           C
ATOM  11477  CD2  PHE C1085      80.531  65.003  36.425  1.00 84.41           C
ATOM  11478  CE1  PHE C1085      82.093  65.017  38.715  1.00 84.41           C
ATOM  11479  CE2  PHE C1085      80.631  63.845  37.216  1.00 84.41           C
ATOM  11480  CZ   PHE C1085      81.411  63.857  38.358  1.00 84.41           C
ATOM  11481  C    PHE C1085      82.243  69.480  35.071  1.00 51.88           C
ATOM  11482  O    PHE C1085      83.388  69.670  34.662  1.00 51.88           C
ATOM  11483  N    ARG C1086      81.167  70.055  34.527  1.00 54.45           C
ATOM  11484  CA   ARG C1086      81.229  70.916  33.343  1.00 54.45           C
ATOM  11485  CB   ARG C1086      79.822  71.280  32.861  1.00 76.54           C
ATOM  11486  CG   ARG C1086      79.819  72.179  31.612  1.00 76.54           C
ATOM  11487  CD   ARG C1086      78.552  73.040  31.477  1.00 76.54           C
ATOM  11488  NE   ARG C1086      78.614  74.262  32.287  1.00 76.54           C
ATOM  11489  CZ   ARG C1086      77.643  75.174  32.371  1.00 76.54           C
ATOM  11490  NH1  ARG C1086      76.514  75.015  31.691  1.00 76.54           C
ATOM  11491  NH2  ARG C1086      77.803  76.249  33.138  1.00 76.54           C
ATOM  11492  C    ARG C1086      82.013  72.215  33.466  1.00 54.45           C
ATOM  11493  O    ARG C1086      82.718  72.583  32.534  1.00 54.45           C
ATOM  11494  N    VAL C1087      81.887  72.921  34.586  1.00 65.75           C
ATOM  11495  CA   VAL C1087      82.589  74.195  34.726  1.00 65.75           C
ATOM  11496  CB   VAL C1087      82.750  74.651  36.196  1.00 36.34           C
ATOM  11497  CG1  VAL C1087      82.631  76.185  36.291  1.00 36.34           C
ATOM  11498  CG2  VAL C1087      81.737  73.994  37.054  1.00 36.34           C
ATOM  11499  C    VAL C1087      83.978  74.120  34.125  1.00 65.75           C
ATOM  11500  O    VAL C1087      84.156  74.353  32.933  1.00 65.75           C
ATOM  11501  N    LEU C1088      84.956  73.797  34.960  1.00 74.07           C
ATOM  11502  CA   LEU C1088      86.346  73.700  34.540  1.00 74.07           C
ATOM  11503  CB   LEU C1088      87.051  72.638  35.350  1.00 38.61           C
ATOM  11504  CG   LEU C1088      86.196  72.103  36.479  1.00 38.61           C
ATOM  11505  CD1  LEU C1088      86.871  70.878  37.098  1.00 38.61           C
ATOM  11506  CD2  LEU C1088      85.981  73.212  37.498  1.00 38.61           C
ATOM  11507  C    LEU C1088      86.525  73.357  33.074  1.00 74.07           C
ATOM  11508  O    LEU C1088      87.253  74.031  32.349  1.00 74.07           C
ATOM  11509  N    VAL C1089      85.867  72.292  32.638  1.00 39.99           C
ATOM  11510  CA   VAL C1089      86.002  71.870  31.263  1.00 39.99           C
ATOM  11511  CB   VAL C1089      85.228  70.581  31.022  1.00 29.96           C
ATOM  11512  CG1  VAL C1089      85.238  70.251  29.554  1.00 29.96           C
ATOM  11513  CG2  VAL C1089      85.873  69.438  31.826  1.00 29.96           C
ATOM  11514  C    VAL C1089      85.574  72.960  30.298  1.00 39.99           C
ATOM  11515  O    VAL C1089      85.983  72.965  29.147  1.00 39.99           C
ATOM  11516  N    LYS C1090      84.756  73.893  30.760  1.00 33.87           C
ATOM  11517  CA   LYS C1090      84.347  74.999  29.903  1.00 33.87           C
ATOM  11518  CB   LYS C1090      82.952  75.500  30.276  1.00 53.31           C
ATOM  11519  CG   LYS C1090      81.852  74.457  30.144  1.00 53.31           C
ATOM  11520  CD   LYS C1090      80.478  75.101  30.093  1.00 53.31           C
ATOM  11521  CE   LYS C1090      80.221  75.777  28.755  1.00 53.31           C
ATOM  11522  NZ   LYS C1090      81.179  76.865  28.435  1.00 53.31           C
ATOM  11523  C    LYS C1090      85.374  76.102  30.135  1.00 33.87           C
ATOM  11524  O    LYS C1090      85.407  77.100  29.417  1.00 33.87           C
ATOM  11525  N    GLU C1091      86.208  75.885  31.154  1.00 65.89           C
ATOM  11526  CA   GLU C1091      87.287  76.791  31.560  1.00 65.89           C
ATOM  11527  CB   GLU C1091      87.625  76.570  33.031  1.00 57.58           C
ATOM  11528  CG   GLU C1091      86.593  77.100  33.978  1.00 57.58           C
ATOM  11529  CD   GLU C1091      86.758  78.578  34.201  1.00 57.58           C
ATOM  11530  OE1  GLU C1091      87.135  79.279  33.234  1.00 57.58           C
ATOM  11531  OE2  GLU C1091      86.507  79.036  35.336  1.00 57.58           C
ATOM  11532  C    GLU C1091      88.542  76.532  30.738  1.00 65.89           C
ATOM  11533  O    GLU C1091      88.989  77.387  29.976  1.00 65.89           C
ATOM  11534  N    LEU C1092      89.122  75.349  30.926  1.00 55.18           C
ATOM  11535  CA   LEU C1092      90.312  74.968  30.184  1.00 55.18           C
ATOM  11536  CB   LEU C1092      90.609  73.475  30.353  1.00 23.92           C
ATOM  11537  CG   LEU C1092      89.821  72.609  31.339  1.00 23.92           C
ATOM  11538  CD1  LEU C1092      90.415  71.199  31.352  1.00 23.92           C
ATOM  11539  CD2  LEU C1092      89.873  73.218  32.725  1.00 23.92           C
ATOM  11540  C    LEU C1092      89.970  75.253  28.739  1.00 55.18           C
ATOM  11541  O    LEU C1092      90.822  75.627  27.940  1.00 55.18           C
ATOM  11542  N    GLN C1093      88.694  75.064  28.427  1.00 33.59           C
ATOM  11543  CA   GLN C1093      88.158  75.310  27.103  1.00 33.59           C
ATOM  11544  CB   GLN C1093      86.637  75.319  27.172  1.00100.07           C
ATOM  11545  CG   GLN C1093      85.955  76.005  26.010  1.00100.07           C
ATOM  11546  CD   GLN C1093      84.457  76.056  26.193  1.00100.07           C
ATOM  11547  OE1  GLN C1093      83.962  76.508  27.229  1.00100.07           C
ATOM  11548  NE2  GLN C1093      83.723  75.589  25.189  1.00100.07           C
ATOM  11549  C    GLN C1093      88.671  76.668  26.661  1.00 33.59           C
ATOM  11550  O    GLN C1093      88.684  77.007  25.470  1.00 33.59           C
ATOM  11551  N    ALA C1094      89.053  77.453  27.656  1.00 49.86           C
ATOM  11552  CA   ALA C1094      89.628  78.762  27.443  1.00 49.86           C
ATOM  11553  CB   ALA C1094      88.832  79.817  28.182  1.00 56.04           C
ATOM  11554  C    ALA C1094      90.999  78.562  28.073  1.00 49.86           C
```

```
ATOM  11555  O    ALA C1094    91.138  77.779  29.018  1.00 49.86        C
ATOM  11556  N    LEU C1095    92.007  79.245  27.544  1.00 96.35        C
ATOM  11557  CA   LEU C1095    93.367  79.096  28.042  1.00 96.35        C
ATOM  11558  CB   LEU C1095    94.199  80.342  27.705  1.00 99.56        C
ATOM  11559  CG   LEU C1095    94.526  80.615  26.226  1.00 99.56        C
ATOM  11560  CD1  LEU C1095    95.628  81.667  26.144  1.00 99.56        C
ATOM  11561  CD2  LEU C1095    94.986  79.337  25.520  1.00 99.56        C
ATOM  11562  C    LEU C1095    93.467  78.790  29.533  1.00 96.35        C
ATOM  11563  O    LEU C1095    94.422  78.146  29.974  1.00 96.35        C
ATOM  11564  N    ALA C1096    92.477  79.237  30.304  1.00 99.47        C
ATOM  11565  CA   ALA C1096    92.462  79.017  31.749  1.00 99.47        C
ATOM  11566  CB   ALA C1096    91.344  79.847  32.385  1.00 59.09        C
ATOM  11567  C    ALA C1096    92.309  77.546  32.141  1.00 99.47        C
ATOM  11568  O    ALA C1096    91.527  77.217  33.033  1.00 99.47        C
ATOM  11569  N    LEU C1097    93.060  76.662  31.488  1.00 99.01        C
ATOM  11570  CA   LEU C1097    92.975  75.242  31.812  1.00 99.01        C
ATOM  11571  CB   LEU C1097    93.854  74.395  30.866  1.00 80.69        C
ATOM  11572  CG   LEU C1097    93.611  72.870  30.762  1.00 80.69        C
ATOM  11573  CD1  LEU C1097    93.789  72.419  29.315  1.00 80.69        C
ATOM  11574  CD2  LEU C1097    94.541  72.099  31.687  1.00 80.69        C
ATOM  11575  C    LEU C1097    93.401  75.053  33.260  1.00 99.01        C
ATOM  11576  O    LEU C1097    93.713  76.015  33.963  1.00 99.01        C
ATOM  11577  N    ASP C1098    93.402  73.795  33.682  1.00100.07        C
ATOM  11578  CA   ASP C1098    93.758  73.418  35.040  1.00100.07        C
ATOM  11579  CB   ASP C1098    95.266  73.457  35.249  1.00100.07        C
ATOM  11580  CG   ASP C1098    95.804  72.141  35.762  1.00100.07        C
ATOM  11581  OD1  ASP C1098    95.137  71.531  36.629  1.00100.07        C
ATOM  11582  OD2  ASP C1098    96.893  71.726  35.297  1.00100.07        C
ATOM  11583  C    ASP C1098    93.101  74.345  36.030  1.00100.07        C
ATOM  11584  O    ASP C1098    93.772  75.180  36.647  1.00100.07        C
ATOM  11585  N    VAL C1099    91.786  74.221  36.164  1.00 52.69        C
ATOM  11586  CA   VAL C1099    91.072  75.037  37.121  1.00 52.69        C
ATOM  11587  CB   VAL C1099    89.621  74.624  37.240  1.00 42.70        C
ATOM  11588  CG1  VAL C1099    88.781  75.321  36.190  1.00 42.70        C
ATOM  11589  CG2  VAL C1099    89.541  73.121  37.115  1.00 42.70        C
ATOM  11590  C    VAL C1099    91.783  74.722  38.414  1.00 52.69        C
ATOM  11591  O    VAL C1099    91.812  75.541  39.321  1.00 52.69        C
ATOM  11592  N    GLN C1100    92.359  73.523  38.485  1.00 36.26        C
ATOM  11593  CA   GLN C1100    93.134  73.126  39.655  1.00 36.26        C
ATOM  11594  CB   GLN C1100    94.151  74.247  39.966  1.00100.07        C
ATOM  11595  CG   GLN C1100    95.150  73.996  41.090  1.00100.07        C
ATOM  11596  CD   GLN C1100    95.834  75.271  41.560  1.00100.07        C
ATOM  11597  OE1  GLN C1100    95.167  76.264  41.879  1.00100.07        C
ATOM  11598  NE2  GLN C1100    97.169  75.245  41.628  1.00100.07        C
ATOM  11599  C    GLN C1100    92.306  72.818  40.897  1.00 36.26        C
ATOM  11600  O    GLN C1100    92.481  73.463  41.924  1.00 36.26        C
ATOM  11601  N    LEU C1101    91.415  71.837  40.814  1.00 76.28        C
ATOM  11602  CA   LEU C1101    90.584  71.435  41.945  1.00 76.28        C
ATOM  11603  CB   LEU C1101    89.785  70.216  41.531  1.00 70.02        C
ATOM  11604  CG   LEU C1101    89.202  69.415  42.667  1.00 70.02        C
ATOM  11605  CD1  LEU C1101    88.296  70.299  43.506  1.00 70.02        C
ATOM  11606  CD2  LEU C1101    88.459  68.252  42.084  1.00 70.02        C
ATOM  11607  C    LEU C1101    91.452  71.137  43.188  1.00 76.28        C
ATOM  11608  O    LEU C1101    92.672  71.054  43.064  1.00 76.28        C
ATOM  11609  N    ALA C1102    90.857  71.018  44.377  1.00100.07        C
ATOM  11610  CA   ALA C1102    91.648  70.757  45.592  1.00100.07        C
ATOM  11611  CB   ALA C1102    92.425  72.020  45.984  1.00 78.12        C
ATOM  11612  C    ALA C1102    90.851  70.237  46.802  1.00100.07        C
ATOM  11613  O    ALA C1102    89.609  70.195  46.763  1.00100.07        C
ATOM  11614  N    ALA C1103    91.566  69.853  47.866  1.00100.07        C
ATOM  11615  CA   ALA C1103    90.953  69.278  49.077  1.00100.07        C
ATOM  11616  CB   ALA C1103    90.996  67.750  48.967  1.00 92.98        C
ATOM  11617  C    ALA C1103    91.607  69.731  50.394  1.00100.07        C
ATOM  11618  O    ALA C1103    92.781  69.445  50.626  1.00100.07        C
ATOM  11619  N    ALA C1104    90.839  70.414  51.250  1.00 64.19        C
ATOM  11620  CA   ALA C1104    91.331  70.926  52.539  1.00 64.19        C
ATOM  11621  CB   ALA C1104    91.043  69.931  53.654  1.00 36.28        C
ATOM  11622  C    ALA C1104    92.808  71.167  52.428  1.00 64.19        C
ATOM  11623  O    ALA C1104    93.250  72.104  51.770  1.00 64.19        C
ATOM  11624  N    ALA C1105    93.572  70.274  53.039  1.00100.07        C
ATOM  11625  CA   ALA C1105    95.025  70.361  52.999  1.00100.07        C
ATOM  11626  CB   ALA C1105    95.635  69.269  53.870  1.00 80.10        C
ATOM  11627  C    ALA C1105    95.528  70.242  51.577  1.00100.07        C
ATOM  11628  O    ALA C1105    95.880  69.155  51.134  1.00100.07        C
ATOM  11629  N    ALA C1106    95.536  71.374  50.878  1.00 72.55        C
ATOM  11630  CA   ALA C1106    95.986  71.473  49.492  1.00 72.55        C
ATOM  11631  CB   ALA C1106    96.904  72.628  49.359  1.00 18.54        C
ATOM  11632  C    ALA C1106    96.654  70.220  48.956  1.00 72.55        C
ATOM  11633  O    ALA C1106    97.873  70.184  48.744  1.00 72.55        C
ATOM  11634  N    ALA C1107    95.836  69.190  48.746  1.00100.07        C
ATOM  11635  CA   ALA C1107    96.308  67.912  48.232  1.00100.07        C
ATOM  11636  CB   ALA C1107    96.144  66.813  49.301  1.00 19.57        C
ATOM  11637  C    ALA C1107    95.565  67.530  46.948  1.00100.07        C
ATOM  11638  O    ALA C1107    95.438  68.338  46.026  1.00100.07        C
```

```
ATOM  11639  N    ALA C1108   95.063  66.303  46.893  1.00100.07        C
ATOM  11640  CA   ALA C1108   94.362  65.827  45.707  1.00100.07        C
ATOM  11641  CB   ALA C1108   93.883  64.396  45.932  1.00100.07        C
ATOM  11642  C    ALA C1108   93.188  66.702  45.290  1.00100.07        C
ATOM  11643  O    ALA C1108   92.782  67.628  46.001  1.00100.07        C
ATOM  11644  N    ALA C1109   92.658  66.390  44.114  1.00 95.74        C
ATOM  11645  CA   ALA C1109   91.520  67.098  43.551  1.00 95.74        C
ATOM  11646  CB   ALA C1109   91.944  67.853  42.317  1.00 90.04        C
ATOM  11647  C    ALA C1109   90.506  66.031  43.177  1.00 95.74        C
ATOM  11648  O    ALA C1109   89.333  66.121  43.532  1.00 95.74        C
ATOM  11649  N    ALA C1110   90.988  65.010  42.470  1.00100.07        C
ATOM  11650  CA   ALA C1110   90.171  63.888  42.013  1.00100.07        C
ATOM  11651  CB   ALA C1110   89.654  63.074  43.222  1.00 72.21        C
ATOM  11652  C    ALA C1110   89.008  64.357  41.147  1.00100.07        C
ATOM  11653  O    ALA C1110   87.851  64.031  41.423  1.00100.07        C
ATOM  11654  N    ILE C1111   89.333  65.132  40.105  1.00100.07        C
ATOM  11655  CA   ILE C1111   88.331  65.678  39.169  1.00100.07        C
ATOM  11656  CB   ILE C1111   88.996  66.442  37.940  1.00100.07        C
ATOM  11657  CG2  ILE C1111   87.946  67.297  37.213  1.00100.07        C
ATOM  11658  CG1  ILE C1111   90.155  67.330  38.410  1.00100.07        C
ATOM  11659  CD   ILE C1111   90.949  67.968  37.299  1.00100.07        C
ATOM  11660  C    ILE C1111   87.570  64.471  38.622  1.00100.07        C
ATOM  11661  O    ILE C1111   88.160  63.395  38.450  1.00100.07        C
ATOM  11662  N    PHE C1112   86.276  64.648  38.365  1.00100.07        C
ATOM  11663  CA   PHE C1112   85.413  63.593  37.829  1.00100.07        C
ATOM  11664  CB   PHE C1112   84.486  64.207  36.787  1.00 99.62        C
ATOM  11665  CG   PHE C1112   85.152  65.234  35.916  1.00 99.62        C
ATOM  11666  CD1  PHE C1112   86.233  64.895  35.116  1.00 99.62        C
ATOM  11667  CD2  PHE C1112   84.690  66.539  35.896  1.00 99.62        C
ATOM  11668  CE1  PHE C1112   86.843  65.854  34.299  1.00 99.62        C
ATOM  11669  CE2  PHE C1112   85.281  67.493  35.098  1.00 99.62        C
ATOM  11670  CZ   PHE C1112   86.360  67.158  34.291  1.00 99.62        C
ATOM  11671  C    PHE C1112   86.133  62.387  37.202  1.00100.07        C
ATOM  11672  O    PHE C1112   87.233  62.521  36.679  1.00100.07        C
ATOM  11673  N    PHE C1113   85.465  61.230  37.236  1.00100.07        C
ATOM  11674  CA   PHE C1113   85.933  59.937  36.694  1.00100.07        C
ATOM  11675  CB   PHE C1113   87.390  59.977  36.187  1.00100.07        C
ATOM  11676  CG   PHE C1113   87.532  60.489  34.783  1.00100.07        C
ATOM  11677  CD1  PHE C1113   88.194  61.694  34.537  1.00100.07        C
ATOM  11678  CD2  PHE C1113   86.989  59.789  33.707  1.00100.07        C
ATOM  11679  CE1  PHE C1113   88.312  62.211  33.237  1.00100.07        C
ATOM  11680  CE2  PHE C1113   87.096  60.288  32.402  1.00100.07        C
ATOM  11681  CZ   PHE C1113   87.765  61.509  32.168  1.00100.07        C
ATOM  11682  C    PHE C1113   85.801  58.859  37.763  1.00100.07        C
ATOM  11683  O    PHE C1113   86.836  58.479  38.346  1.00100.07        C
ATOM  11684  OT   PHE C1113   84.656  58.427  38.019  1.00100.07        C
ATOM  11685  CB   ALA D    4   87.384  60.671  46.589  1.00 22.94        D
ATOM  11686  C    ALA D    4   86.770  62.048  48.624  1.00100.07        D
ATOM  11687  O    ALA D    4   85.615  61.765  48.962  1.00100.07        D
ATOM  11688  N    ALA D    4   87.611  59.692  48.852  1.00100.07        D
ATOM  11689  CA   ALA D    4   87.709  60.959  48.069  1.00100.07        D
ATOM  11690  N    ALA D    5   87.277  63.283  48.715  1.00100.07        D
ATOM  11691  CA   ALA D    5   86.508  64.439  49.214  1.00100.07        D
ATOM  11692  CB   ALA D    5   86.951  64.778  50.637  1.00  5.07        D
ATOM  11693  C    ALA D    5   86.692  65.658  48.284  1.00100.07        D
ATOM  11694  O    ALA D    5   86.857  65.478  47.078  1.00100.07        D
ATOM  11695  N    ALA D    6   86.650  66.883  48.824  1.00 51.88        D
ATOM  11696  CA   ALA D    6   86.839  68.090  47.994  1.00 51.88        D
ATOM  11697  CB   ALA D    6   86.002  67.993  46.716  1.00 80.71        D
ATOM  11698  C    ALA D    6   86.548  69.426  48.676  1.00 51.88        D
ATOM  11699  O    ALA D    6   85.777  69.495  49.634  1.00 51.88        D
ATOM  11700  N    ALA D    7   87.169  70.484  48.154  1.00 70.29        D
ATOM  11701  CA   ALA D    7   87.014  71.857  48.658  1.00 70.29        D
ATOM  11702  CB   ALA D    7   87.136  71.913  50.199  1.00 10.37        D
ATOM  11703  C    ALA D    7   88.076  72.753  48.023  1.00 70.29        D
ATOM  11704  O    ALA D    7   89.197  72.314  47.759  1.00 70.29        D
ATOM  11705  N    ALA D    8   87.715  74.012  47.786  1.00 50.86        D
ATOM  11706  CA   ALA D    8   88.611  74.987  47.166  1.00 50.86        D
ATOM  11707  CB   ALA D    8   89.885  75.098  47.968  1.00 24.01        D
ATOM  11708  C    ALA D    8   88.925  74.617  45.715  1.00 50.86        D
ATOM  11709  O    ALA D    8   89.289  73.483  45.423  1.00 50.86        D
ATOM  11710  N    ALA D    9   88.773  75.583  44.814  1.00 53.95        D
ATOM  11711  CA   ALA D    9   89.027  75.375  43.394  1.00 53.95        D
ATOM  11712  CB   ALA D    9   87.953  76.055  42.579  1.00 11.88        D
ATOM  11713  C    ALA D    9   90.411  75.893  42.986  1.00 53.95        D
ATOM  11714  O    ALA D    9   91.296  75.114  42.645  1.00 53.95        D
ATOM  11715  N    ALA D   10   90.595  77.207  42.997  1.00 37.22        D
ATOM  11716  CA   ALA D   10   91.894  77.800  42.660  1.00 37.22        D
ATOM  11717  CB   ALA D   10   92.978  77.206  43.558  1.00 95.67        D
ATOM  11718  C    ALA D   10   92.331  77.688  41.201  1.00 37.22        D
ATOM  11719  O    ALA D   10   92.958  76.707  40.808  1.00 37.22        D
ATOM  11720  N    ALA D   11   92.020  78.721  40.419  1.00 40.99        D
ATOM  11721  CA   ALA D   11   92.378  78.776  39.007  1.00 40.99        D
ATOM  11722  CB   ALA D   11   91.406  79.688  38.260  1.00100.07        D
```

```
ATOM  11723  C   ALA D  11      93.806  79.293  38.842  1.00 40.99      D
ATOM  11724  O   ALA D  11      94.491  79.615  39.820  1.00 40.99      D
ATOM  11725  N   ALA D  12      94.247  79.380  37.594  1.00 56.28      D
ATOM  11726  CA  ALA D  12      95.584  79.855  37.293  1.00 56.28      D
ATOM  11727  CB  ALA D  12      96.607  79.036  38.049  1.00100.07      D
ATOM  11728  C   ALA D  12      95.794  79.708  35.804  1.00 56.28      D
ATOM  11729  O   ALA D  12      94.852  79.385  35.086  1.00 56.28      D
ATOM  11730  N   ALA D  13      97.026  79.935  35.344  1.00 84.89      D
ATOM  11731  CA  ALA D  13      97.355  79.831  33.922  1.00 84.89      D
ATOM  11732  CB  ALA D  13      98.469  80.804  33.568  1.00 17.96      D
ATOM  11733  C   ALA D  13      97.749  78.414  33.514  1.00 84.89      D
ATOM  11734  O   ALA D  13      98.235  77.625  34.329  1.00 84.89      D
ATOM  11735  N   ALA D  14      97.532  78.102  32.239  1.00100.07      D
ATOM  11736  CA  ALA D  14      97.839  76.781  31.709  1.00100.07      D
ATOM  11737  CB  ALA D  14      96.572  75.941  31.673  1.00 45.15      D
ATOM  11738  C   ALA D  14      98.447  76.861  30.314  1.00100.07      D
ATOM  11739  O   ALA D  14      97.862  77.458  29.408  1.00100.07      D
ATOM  11740  N   ALA D  15      99.617  76.250  30.141  1.00 72.38      D
ATOM  11741  CA  ALA D  15     100.295  76.257  28.847  1.00 72.38      D
ATOM  11742  CB  ALA D  15     101.630  76.978  28.956  1.00 83.66      D
ATOM  11743  C   ALA D  15     100.513  74.842  28.334  1.00 72.38      D
ATOM  11744  O   ALA D  15     100.406  73.873  29.098  1.00 72.38      D
ATOM  11745  N   ALA D  16     100.829  74.750  27.039  1.00 60.85      D
ATOM  11746  CA  ALA D  16     101.069  73.485  26.346  1.00 60.85      D
ATOM  11747  CB  ALA D  16     102.241  73.622  25.412  1.00 31.86      D
ATOM  11748  C   ALA D  16     101.304  72.332  27.305  1.00 60.85      D
ATOM  11749  O   ALA D  16     100.345  71.748  27.805  1.00 60.85      D
ATOM  11750  N   ALA D  17     102.574  72.016  27.556  1.00100.07      D
ATOM  11751  CA  ALA D  17     102.967  70.929  28.460  1.00100.07      D
ATOM  11752  CB  ALA D  17     103.967  71.451  29.496  1.00100.07      D
ATOM  11753  C   ALA D  17     101.781  70.253  29.162  1.00100.07      D
ATOM  11754  O   ALA D  17     101.555  69.051  28.995  1.00100.07      D
ATOM  11755  N   ALA D  18     101.030  71.023  29.948  1.00 99.82      D
ATOM  11756  CA  ALA D  18      99.863  70.484  30.636  1.00 99.82      D
ATOM  11757  CB  ALA D  18      99.522  71.328  31.869  1.00 52.21      D
ATOM  11758  C   ALA D  18      98.690  70.479  29.664  1.00 99.82      D
ATOM  11759  O   ALA D  18      98.154  69.423  29.342  1.00 99.82      D
ATOM  11760  N   ALA D  19      98.311  71.662  29.185  1.00 36.78      D
ATOM  11761  CA  ALA D  19      97.192  71.792  28.253  1.00 36.78      D
ATOM  11762  CB  ALA D  19      97.191  73.185  27.605  1.00 30.74      D
ATOM  11763  C   ALA D  19      97.221  70.718  27.171  1.00 36.78      D
ATOM  11764  O   ALA D  19      96.193  70.415  26.558  1.00 36.78      D
ATOM  11765  N   ALA D  20      98.400  70.154  26.930  1.00 75.15      D
ATOM  11766  CA  ALA D  20      98.554  69.114  25.924  1.00 75.15      D
ATOM  11767  CB  ALA D  20      99.997  69.072  25.426  1.00100.07      D
ATOM  11768  C   ALA D  20      98.166  67.783  26.553  1.00 75.15      D
ATOM  11769  O   ALA D  20      97.465  66.972  25.946  1.00 75.15      D
ATOM  11770  N   ALA D  21      98.630  67.561  27.775  1.00100.03      D
ATOM  11771  CA  ALA D  21      98.303  66.336  28.483  1.00100.03      D
ATOM  11772  CB  ALA D  21      98.746  66.434  29.943  1.00 73.74      D
ATOM  11773  C   ALA D  21      96.793  66.194  28.405  1.00100.03      D
ATOM  11774  O   ALA D  21      96.274  65.100  28.181  1.00100.03      D
ATOM  11775  N   ALA D  22      96.108  67.328  28.572  1.00 73.95      D
ATOM  11776  CA  ALA D  22      94.648  67.406  28.546  1.00 73.95      D
ATOM  11777  CB  ALA D  22      94.205  68.848  28.289  1.00 68.74      D
ATOM  11778  C   ALA D  22      94.046  66.477  27.504  1.00 73.95      D
ATOM  11779  O   ALA D  22      93.173  65.667  27.893  1.00 73.95      D
ATOM  11780  OT  ALA D  22      94.453  66.569  26.322  1.00 68.74      D
ATOM  11781  CB  ALA E  96      83.151  63.580  30.479  1.00100.07      E
ATOM  11782  C   ALA E  96      85.004  62.930  28.936  1.00 78.93      E
ATOM  11783  O   ALA E  96      85.578  62.500  29.939  1.00 78.93      E
ATOM  11784  N   ALA E  96      82.645  62.583  28.266  1.00 78.93      E
ATOM  11785  CA  ALA E  96      83.584  63.473  29.021  1.00 78.93      E
ATOM  11786  N   ALA E  97      85.562  62.969  27.727  1.00 77.94      E
ATOM  11787  CA  ALA E  97      86.905  62.466  27.469  1.00 77.94      E
ATOM  11788  CB  ALA E  97      86.870  61.499  26.311  1.00 12.82      E
ATOM  11789  C   ALA E  97      87.937  63.544  27.185  1.00 77.94      E
ATOM  11790  O   ALA E  97      87.603  64.720  26.999  1.00 77.94      E
ATOM  11791  N   ALA E  98      89.197  63.106  27.142  1.00100.07      E
ATOM  11792  CA  ALA E  98      90.343  63.971  26.868  1.00100.07      E
ATOM  11793  CB  ALA E  98      91.590  63.119  26.572  1.00 66.96      E
ATOM  11794  C   ALA E  98      90.028  64.860  25.676  1.00100.07      E
ATOM  11795  O   ALA E  98      90.056  64.403  24.535  1.00100.07      E
ATOM  11796  N   ALA E  99      89.727  66.124  25.954  1.00 53.81      E
ATOM  11797  CA  ALA E  99      89.397  67.102  24.921  1.00 53.81      E
ATOM  11798  CB  ALA E  99      89.463  68.510  25.516  1.00100.07      E
ATOM  11799  C   ALA E  99      90.273  67.024  23.665  1.00 53.81      E
ATOM  11800  O   ALA E  99      90.933  66.017  23.399  1.00 53.81      E
ATOM  11801  N   ALA E 100      90.283  68.104  22.893  1.00 34.66      E
ATOM  11802  CA  ALA E 100      91.068  68.133  21.665  1.00 34.66      E
ATOM  11803  CB  ALA E 100      90.251  68.742  20.538  1.00100.07      E
ATOM  11804  C   ALA E 100      92.387  68.872  21.811  1.00 34.66      E
ATOM  11805  O   ALA E 100      92.453  69.941  22.417  1.00 34.66      E
ATOM  11806  N   ALA E 101      93.434  68.294  21.242  1.00 97.06      E
```

```
ATOM  11807  CA  ALA E 101      94.749  68.893  21.318  1.00 97.06      E
ATOM  11808  CB  ALA E 101      95.797  67.807  21.565  1.00  9.06      E
ATOM  11809  C   ALA E 101      95.077  69.663  20.049  1.00 97.06      E
ATOM  11810  O   ALA E 101      96.031  69.326  19.357  1.00 97.06      E
ATOM  11811  N   ALA E 102      94.296  70.696  19.742  1.00 63.22      E
ATOM  11812  CA  ALA E 102      94.552  71.491  18.535  1.00 63.22      E
ATOM  11813  CB  ALA E 102      93.470  72.562  18.359  1.00 67.61      E
ATOM  11814  C   ALA E 102      95.938  72.146  18.599  1.00 63.22      E
ATOM  11815  O   ALA E 102      96.062  73.336  18.908  1.00 63.22      E
ATOM  11816  N   ALA E 103      96.969  71.357  18.280  1.00 52.63      E
ATOM  11817  CA  ALA E 103      98.375  71.784  18.313  1.00 52.63      E
ATOM  11818  CB  ALA E 103      99.271  70.635  17.830  1.00 26.71      E
ATOM  11819  C   ALA E 103      98.708  73.059  17.542  1.00 52.63      E
ATOM  11820  O   ALA E 103      99.853  73.511  17.552  1.00 52.63      E
ATOM  11821  N   ALA E 104      97.709  73.637  16.884  1.00 67.52      E
ATOM  11822  CA  ALA E 104      97.902  74.853  16.107  1.00 67.52      E
ATOM  11823  CB  ALA E 104      97.886  76.081  17.035  1.00 53.02      E
ATOM  11824  C   ALA E 104      99.229  74.766  15.356  1.00 67.52      E
ATOM  11825  O   ALA E 104      99.761  73.677  15.145  1.00 67.52      E
ATOM  11826  N   ALA E 105      99.748  75.919  14.948  1.00 72.23      E
ATOM  11827  CA  ALA E 105     101.018  76.025  14.236  1.00 72.23      E
ATOM  11828  CB  ALA E 105     100.811  75.897  12.737  1.00 77.95      E
ATOM  11829  C   ALA E 105     101.494  77.415  14.579  1.00 72.23      E
ATOM  11830  O   ALA E 105     100.733  78.193  15.135  1.00 72.23      E
ATOM  11831  N   ALA E 106     102.741  77.723  14.248  1.00 85.60      E
ATOM  11832  CA  ALA E 106     103.344  79.027  14.532  1.00 85.60      E
ATOM  11833  CB  ALA E 106     104.282  79.406  13.393  1.00 88.68      E
ATOM  11834  C   ALA E 106     102.370  80.183  14.808  1.00 85.60      E
ATOM  11835  O   ALA E 106     102.324  81.157  14.061  1.00 85.60      E
ATOM  11836  N   ALA E 107     101.618  80.085  15.898  1.00 59.61      E
ATOM  11837  CA  ALA E 107     100.650  81.111  16.267  1.00 59.61      E
ATOM  11838  CB  ALA E 107      99.245  80.633  15.968  1.00 73.41      E
ATOM  11839  C   ALA E 107     100.787  81.395  17.749  1.00 59.61      E
ATOM  11840  O   ALA E 107     101.642  80.809  18.416  1.00 59.61      E
ATOM  11841  N   ALA E 108      99.932  82.277  18.262  1.00 79.26      E
ATOM  11842  CA  ALA E 108      99.967  82.650  19.674  1.00 79.26      E
ATOM  11843  CB  ALA E 108     101.386  83.032  20.068  1.00100.07      E
ATOM  11844  C   ALA E 108      99.025  83.806  19.987  1.00 79.26      E
ATOM  11845  O   ALA E 108      99.461  84.933  20.224  1.00 79.26      E
ATOM  11846  N   ALA E 109      97.730  83.539  19.987  1.00 77.88      E
ATOM  11847  CA  ALA E 109      96.782  84.596  20.282  1.00 77.88      E
ATOM  11848  CB  ALA E 109      95.375  84.135  19.970  1.00100.07      E
ATOM  11849  C   ALA E 109      96.879  85.018  21.735  1.00 77.88      E
ATOM  11850  O   ALA E 109      97.890  84.786  22.403  1.00 77.88      E
ATOM  11851  N   ALA E 110      95.810  85.638  22.219  1.00 76.08      E
ATOM  11852  CA  ALA E 110      95.754  86.098  23.592  1.00 76.08      E
ATOM  11853  CB  ALA E 110      96.133  87.566  23.664  1.00 40.92      E
ATOM  11854  C   ALA E 110      94.354  85.888  24.136  1.00 76.08      E
ATOM  11855  O   ALA E 110      93.406  86.566  23.717  1.00 76.08      E
ATOM  11856  N   ALA E 111      94.238  84.935  25.059  1.00100.07      E
ATOM  11857  CA  ALA E 111      92.967  84.609  25.689  1.00100.07      E
ATOM  11858  CB  ALA E 111      93.132  83.433  26.625  1.00  5.07      E
ATOM  11859  C   ALA E 111      92.490  85.815  26.467  1.00100.07      E
ATOM  11860  O   ALA E 111      92.402  85.774  27.695  1.00100.07      E
ATOM  11861  N   ALA E 112      92.187  86.892  25.750  1.00100.07      E
ATOM  11862  CA  ALA E 112      91.729  88.116  26.386  1.00100.07      E
ATOM  11863  CB  ALA E 112      90.530  87.801  27.315  1.00 44.03      E
ATOM  11864  C   ALA E 112      92.898  88.726  27.179  1.00100.07      E
ATOM  11865  O   ALA E 112      92.891  89.919  27.513  1.00100.07      E
ATOM  11866  N   ALA E 113      93.912  87.900  27.446  1.00 33.55      E
ATOM  11867  CA  ALA E 113      95.087  88.319  28.205  1.00 33.55      E
ATOM  11868  CB  ALA E 113      95.984  87.098  28.498  1.00 18.80      E
ATOM  11869  C   ALA E 113      95.870  89.415  27.482  1.00 33.55      E
ATOM  11870  O   ALA E 113      96.768  90.030  28.061  1.00 33.55      E
ATOM  11871  N   ALA E 114      95.507  89.656  26.222  1.00 67.18      E
ATOM  11872  CA  ALA E 114      96.143  90.694  25.405  1.00 67.18      E
ATOM  11873  CB  ALA E 114      95.683  90.600  23.959  1.00100.07      E
ATOM  11874  C   ALA E 114      95.769  92.055  25.970  1.00 67.18      E
ATOM  11875  O   ALA E 114      94.991  92.806  25.363  1.00 67.18      E
ATOM  11876  N   ALA E 115      96.337  92.349  27.140  1.00 83.09      E
ATOM  11877  CA  ALA E 115      96.109  93.597  27.863  1.00 83.09      E
ATOM  11878  CB  ALA E 115      94.676  93.634  28.398  1.00100.07      E
ATOM  11879  C   ALA E 115      97.097  93.646  29.020  1.00 83.09      E
ATOM  11880  O   ALA E 115      97.790  94.639  29.226  1.00 83.09      E
ATOM  11881  N   ALA E 116      97.132  92.554  29.775  1.00 48.97      E
ATOM  11882  CA  ALA E 116      98.027  92.413  30.911  1.00 48.97      E
ATOM  11883  CB  ALA E 116      97.382  91.539  31.991  1.00 27.73      E
ATOM  11884  C   ALA E 116      99.278  91.744  30.360  1.00 48.97      E
ATOM  11885  O   ALA E 116     100.392  92.022  30.801  1.00 48.97      E
ATOM  11886  N   ALA E 117      99.084  90.862  29.382  1.00100.07      E
ATOM  11887  CA  ALA E 117     100.204  90.168  28.754  1.00100.07      E
ATOM  11888  CB  ALA E 117      99.713  89.277  27.613  1.00 72.40      E
ATOM  11889  C   ALA E 117     101.142  91.235  28.225  1.00100.07      E
ATOM  11890  O   ALA E 117     102.326  90.990  28.006  1.00100.07      E
```

```
ATOM  11891  N   ALA E 118     100.594  92.427  28.032  1.00 68.38      E
ATOM  11892  CA  ALA E 118     101.361  93.552  27.540  1.00 68.38      E
ATOM  11893  CB  ALA E 118     100.576  94.263  26.447  1.00100.07      E
ATOM  11894  C   ALA E 118     101.675  94.517  28.685  1.00 68.38      E
ATOM  11895  O   ALA E 118     102.702  95.201  28.680  1.00 68.38      E
ATOM  11896  N   ALA E 119     100.783  94.560  29.670  1.00 62.26      E
ATOM  11897  CA  ALA E 119     100.939  95.444  30.822  1.00 62.26      E
ATOM  11898  CB  ALA E 119      99.949  95.051  31.922  1.00 68.19      E
ATOM  11899  C   ALA E 119     102.354  95.417  31.370  1.00 62.26      E
ATOM  11900  O   ALA E 119     102.840  96.413  31.899  1.00 62.26      E
ATOM  11901  N   ALA E 120     103.016  94.276  31.222  1.00 78.26      E
ATOM  11902  CA  ALA E 120     104.367  94.114  31.732  1.00 78.26      E
ATOM  11903  CB  ALA E 120     104.514  92.699  32.341  1.00 20.11      E
ATOM  11904  C   ALA E 120     105.500  94.390  30.723  1.00 78.26      E
ATOM  11905  O   ALA E 120     106.483  93.644  30.668  1.00 78.26      E
ATOM  11906  N   ALA E 121     105.366  95.460  29.934  1.00 56.21      E
ATOM  11907  CA  ALA E 121     106.393  95.845  28.950  1.00 56.21      E
ATOM  11908  CB  ALA E 121     106.759  94.657  28.047  1.00 12.10      E
ATOM  11909  C   ALA E 121     105.987  97.043  28.090  1.00 56.21      E
ATOM  11910  O   ALA E 121     106.373  97.139  26.928  1.00 56.21      E
ATOM  11911  N   ALA E 122     105.205  97.946  28.672  1.00 92.97      E
ATOM  11912  CA  ALA E 122     104.751  99.158  27.994  1.00 92.97      E
ATOM  11913  CB  ALA E 122     105.766 100.268  28.215  1.00  6.62      E
ATOM  11914  C   ALA E 122     104.456  99.024  26.497  1.00 92.97      E
ATOM  11915  O   ALA E 122     105.324  99.280  25.662  1.00 92.97      E
ATOM  11916  N   ALA E 123     103.225  98.645  26.165  1.00 99.76      E
ATOM  11917  CA  ALA E 123     102.811  98.493  24.772  1.00 99.76      E
ATOM  11918  CB  ALA E 123     102.896  97.023  24.357  1.00100.07      E
ATOM  11919  C   ALA E 123     101.388  99.030  24.563  1.00 99.76      E
ATOM  11920  O   ALA E 123     101.126 100.199  24.844  1.00 99.76      E
ATOM  11921  N   ALA E 124     100.478  98.175  24.087  1.00 52.94      E
ATOM  11922  CA  ALA E 124      99.084  98.555  23.824  1.00 52.94      E
ATOM  11923  CB  ALA E 124      98.428  99.076  25.091  1.00 91.04      E
ATOM  11924  C   ALA E 124      99.108  99.635  22.761  1.00 52.94      E
ATOM  11925  O   ALA E 124      99.839 100.614  22.897  1.00 52.94      E
ATOM  11926  N   ALA E 125      98.305  99.476  21.713  1.00100.07      E
ATOM  11927  CA  ALA E 125      98.305 100.432  20.603  1.00100.07      E
ATOM  11928  CB  ALA E 125      98.183 101.866  21.107  1.00 62.84      E
ATOM  11929  C   ALA E 125      99.667 100.198  19.952  1.00100.07      E
ATOM  11930  O   ALA E 125      99.800 100.199  18.727  1.00100.07      E
ATOM  11931  N   ALA E 126     100.673  99.995  20.800  1.00 48.23      E
ATOM  11932  CA  ALA E 126     102.023  99.682  20.367  1.00 48.23      E
ATOM  11933  CB  ALA E 126     103.009  99.870  21.516  1.00 53.31      E
ATOM  11934  C   ALA E 126     101.887  98.204  20.022  1.00 48.23      E
ATOM  11935  O   ALA E 126     102.121  97.802  18.888  1.00 48.23      E
ATOM  11936  N   ALA E 127     101.481  97.403  21.009  1.00 42.94      E
ATOM  11937  CA  ALA E 127     101.272  95.969  20.807  1.00 42.94      E
ATOM  11938  CB  ALA E 127     100.888  95.266  22.138  1.00 27.39      E
ATOM  11939  C   ALA E 127     100.154  95.815  19.779  1.00 42.94      E
ATOM  11940  O   ALA E 127      99.945  94.735  19.245  1.00 42.94      E
ATOM  11941  N   ALA E 128      99.427  96.900  19.517  1.00 99.91      E
ATOM  11942  CA  ALA E 128      98.366  96.866  18.514  1.00 99.91      E
ATOM  11943  CB  ALA E 128      97.690  98.220  18.397  1.00100.07      E
ATOM  11944  C   ALA E 128      99.110  96.540  17.233  1.00 99.91      E
ATOM  11945  O   ALA E 128      98.584  95.889  16.327  1.00 99.91      E
ATOM  11946  N   ALA E 129     100.347  97.022  17.169  1.00 61.39      E
ATOM  11947  CA  ALA E 129     101.213  96.739  16.043  1.00 61.39      E
ATOM  11948  CB  ALA E 129     102.421  97.667  16.049  1.00 87.87      E
ATOM  11949  C   ALA E 129     101.627  95.304  16.353  1.00 61.39      E
ATOM  11950  O   ALA E 129     100.848  94.560  16.940  1.00 61.39      E
ATOM  11951  N   ALA E 130     102.843  94.915  15.997  1.00 85.96      E
ATOM  11952  CA  ALA E 130     103.290  93.549  16.252  1.00 85.96      E
ATOM  11953  CB  ALA E 130     103.762  93.398  17.705  1.00 36.23      E
ATOM  11954  C   ALA E 130     102.161  92.563  15.961  1.00 85.96      E
ATOM  11955  O   ALA E 130     102.185  91.423  16.430  1.00 85.96      E
ATOM  11956  N   ALA E 131     101.172  93.019  15.189  1.00100.07      E
ATOM  11957  CA  ALA E 131     100.021  92.202  14.807  1.00100.07      E
ATOM  11958  CB  ALA E 131      98.708  92.893  15.212  1.00 81.68      E
ATOM  11959  C   ALA E 131     100.055  91.970  13.297  1.00100.07      E
ATOM  11960  O   ALA E 131      99.037  92.079  12.607  1.00100.07      E
ATOM  11961  N   ALA E 132     101.248  91.669  12.794  1.00 94.68      E
ATOM  11962  CA  ALA E 132     101.441  91.396  11.383  1.00 94.68      E
ATOM  11963  CB  ALA E 132     102.918  91.571  11.012  1.00 38.26      E
ATOM  11964  C   ALA E 132     100.983  89.956  11.139  1.00 94.68      E
ATOM  11965  O   ALA E 132      99.954  89.798  10.458  1.00 94.68      E
ATOM  11966  OT  ALA E 132     101.624  89.004  11.646  1.00 38.26      E
ATOM  11967  CB  ALA F 462     101.935  86.175  18.086  1.00100.07      F
ATOM  11968  C   ALA F 462     104.317  85.854  18.755  1.00 66.01      F
ATOM  11969  O   ALA F 462     104.206  85.675  19.962  1.00 66.01      F
ATOM  11970  N   ALA F 462     103.736  86.958  16.581  1.00 66.01      F
ATOM  11971  CA  ALA F 462     103.342  86.757  18.011  1.00 66.01      F
ATOM  11972  N   ALA F 463     105.267  85.278  18.030  1.00 79.79      F
ATOM  11973  CA  ALA F 463     106.264  84.404  18.638  1.00 79.79      F
ATOM  11974  CB  ALA F 463     107.036  83.652  17.554  1.00100.07      F
```

```
ATOM  11975  C   ALA F 463     107.220  85.260  19.458  1.00 79.79      F
ATOM  11976  O   ALA F 463     107.693  84.852  20.519  1.00 79.79      F
ATOM  11977  N   ALA F 464     107.509  86.449  18.940  1.00 51.07      F
ATOM  11978  CA  ALA F 464     108.398  87.384  19.613  1.00 51.07      F
ATOM  11979  CB  ALA F 464     108.716  88.548  18.697  1.00100.07      F
ATOM  11980  C   ALA F 464     107.662  87.869  20.842  1.00 51.07      F
ATOM  11981  O   ALA F 464     108.170  87.781  21.962  1.00 51.07      F
ATOM  11982  N   ALA F 465     106.454  88.378  20.614  1.00100.07      F
ATOM  11983  CA  ALA F 465     105.611  88.853  21.693  1.00100.07      F
ATOM  11984  CB  ALA F 465     104.187  88.961  21.219  1.00 35.10      F
ATOM  11985  C   ALA F 465     105.737  87.777  22.756  1.00100.07      F
ATOM  11986  O   ALA F 465     105.584  88.035  23.953  1.00100.07      F
ATOM  11987  N   ALA F 466     106.031  86.564  22.288  1.00 63.24      F
ATOM  11988  CA  ALA F 466     106.215  85.412  23.159  1.00 63.24      F
ATOM  11989  CB  ALA F 466     105.942  84.090  22.385  1.00 14.05      F
ATOM  11990  C   ALA F 466     107.650  85.446  23.655  1.00 63.24      F
ATOM  11991  O   ALA F 466     107.916  85.791  24.808  1.00 63.24      F
ATOM  11992  N   ALA F 467     108.567  85.099  22.759  1.00 99.18      F
ATOM  11993  CA  ALA F 467     109.988  85.068  23.070  1.00 99.18      F
ATOM  11994  CB  ALA F 467     110.804  85.146  21.784  1.00 35.14      F
ATOM  11995  C   ALA F 467     110.342  86.218  23.993  1.00 99.18      F
ATOM  11996  O   ALA F 467     110.957  86.021  25.036  1.00 99.18      F
ATOM  11997  N   ALA F 468     109.935  87.420  23.610  1.00 62.05      F
ATOM  11998  CA  ALA F 468     110.217  88.592  24.414  1.00 62.05      F
ATOM  11999  CB  ALA F 468     109.595  89.838  23.757  1.00 54.99      F
ATOM  12000  C   ALA F 468     109.672  88.383  25.837  1.00 62.05      F
ATOM  12001  O   ALA F 468     110.357  88.669  26.833  1.00 62.05      F
ATOM  12002  N   ALA F 469     108.452  87.860  25.932  1.00 51.19      F
ATOM  12003  CA  ALA F 469     107.822  87.628  27.230  1.00 51.19      F
ATOM  12004  CB  ALA F 469     106.313  87.377  27.046  1.00 14.58      F
ATOM  12005  C   ALA F 469     108.490  86.466  27.973  1.00 51.19      F
ATOM  12006  O   ALA F 469     108.425  86.365  29.196  1.00 51.19      F
ATOM  12007  N   ALA F 470     109.145  85.590  27.231  1.00 74.88      F
ATOM  12008  CA  ALA F 470     109.827  84.472  27.860  1.00 74.88      F
ATOM  12009  CB  ALA F 470     109.917  83.297  26.881  1.00 88.67      F
ATOM  12010  C   ALA F 470     111.229  84.938  28.265  1.00 74.88      F
ATOM  12011  O   ALA F 470     111.863  84.371  29.161  1.00 74.88      F
ATOM  12012  N   ALA F 471     111.697  85.988  27.596  1.00100.07      F
ATOM  12013  CA  ALA F 471     113.027  86.540  27.840  1.00100.07      F
ATOM  12014  CB  ALA F 471     113.468  87.377  26.643  1.00100.07      F
ATOM  12015  C   ALA F 471     113.084  87.380  29.098  1.00100.07      F
ATOM  12016  O   ALA F 471     113.645  86.955  30.112  1.00100.07      F
ATOM  12017  N   ALA F 472     112.510  88.579  29.016  1.00 99.94      F
ATOM  12018  CA  ALA F 472     112.478  89.504  30.147  1.00 99.94      F
ATOM  12019  CB  ALA F 472     111.647  90.738  29.795  1.00100.07      F
ATOM  12020  C   ALA F 472     111.882  88.793  31.355  1.00 99.94      F
ATOM  12021  O   ALA F 472     111.852  89.333  32.465  1.00 99.94      F
ATOM  12022  N   ALA F 473     111.407  87.574  31.114  1.00100.07      F
ATOM  12023  CA  ALA F 473     110.817  86.738  32.143  1.00100.07      F
ATOM  12024  CB  ALA F 473     110.238  85.469  31.514  1.00 81.68      F
ATOM  12025  C   ALA F 473     111.899  86.388  33.160  1.00100.07      F
ATOM  12026  O   ALA F 473     111.839  85.349  33.825  1.00100.07      F
ATOM  12027  N   ALA F 474     112.891  87.269  33.266  1.00 72.28      F
ATOM  12028  CA  ALA F 474     113.988  87.087  34.200  1.00 72.28      F
ATOM  12029  CB  ALA F 474     115.041  88.169  33.987  1.00 82.76      F
ATOM  12030  C   ALA F 474     113.424  87.163  35.613  1.00 72.28      F
ATOM  12031  O   ALA F 474     114.162  87.369  36.579  1.00 72.28      F
ATOM  12032  N   ALA F 475     112.105  86.996  35.709  1.00100.07      F
ATOM  12033  CA  ALA F 475     111.365  87.021  36.970  1.00100.07      F
ATOM  12034  CB  ALA F 475     111.592  85.710  37.739  1.00100.07      F
ATOM  12035  C   ALA F 475     111.718  88.217  37.851  1.00100.07      F
ATOM  12036  O   ALA F 475     111.119  89.288  37.727  1.00100.07      F
ATOM  12037  N   ALA F 476     112.683  88.018  38.744  1.00 90.75      F
ATOM  12038  CA  ALA F 476     113.128  89.064  39.653  1.00 90.75      F
ATOM  12039  CB  ALA F 476     114.329  88.569  40.466  1.00100.07      F
ATOM  12040  C   ALA F 476     113.492  90.330  38.878  1.00 90.75      F
ATOM  12041  O   ALA F 476     112.616  91.012  38.352  1.00 90.75      F
ATOM  12042  N   ALA F 477     114.786  90.631  38.809  1.00 99.66      F
ATOM  12043  CA  ALA F 477     115.276  91.812  38.105  1.00 99.66      F
ATOM  12044  CB  ALA F 477     115.598  91.462  36.658  1.00 87.62      F
ATOM  12045  C   ALA F 477     114.255  92.941  38.156  1.00 99.66      F
ATOM  12046  O   ALA F 477     114.169  93.670  39.149  1.00 99.66      F
ATOM  12047  N   ALA F 478     113.481  93.070  37.080  1.00 99.82      F
ATOM  12048  CA  ALA F 478     112.449  94.095  36.977  1.00 99.82      F
ATOM  12049  CB  ALA F 478     111.446  93.716  35.887  1.00 47.43      F
ATOM  12050  C   ALA F 478     111.739  94.279  38.318  1.00 99.82      F
ATOM  12051  O   ALA F 478     111.186  95.341  38.602  1.00 99.82      F
ATOM  12052  N   ALA F 479     111.751  93.232  39.137  1.00100.07      F
ATOM  12053  CA  ALA F 479     111.141  93.297  40.453  1.00100.07      F
ATOM  12054  CB  ALA F 479     111.254  91.947  41.157  1.00 59.19      F
ATOM  12055  C   ALA F 479     111.924  94.360  41.213  1.00100.07      F
ATOM  12056  O   ALA F 479     111.421  95.456  41.453  1.00100.07      F
ATOM  12057  N   ALA F 480     113.167  94.035  41.568  1.00 71.00      F
ATOM  12058  CA  ALA F 480     114.031  94.960  42.296  1.00 71.00      F
```

| ATOM | 12059 | CB | ALA F 480 | 115.445 | 94.405 | 42.382 | 1.00 | 100.07 | F |
|---|---|---|---|---|---|---|---|---|---|
| ATOM | 12060 | C | ALA F 480 | 114.032 | 96.271 | 41.542 | 1.00 | 71.00 | F |
| ATOM | 12061 | O | ALA F 480 | 114.008 | 97.349 | 42.137 | 1.00 | 71.00 | F |
| ATOM | 12062 | N | ALA F 481 | 114.062 | 96.157 | 40.219 | 1.00 | 77.09 | F |
| ATOM | 12063 | CA | ALA F 481 | 114.051 | 97.319 | 39.348 | 1.00 | 77.09 | F |
| ATOM | 12064 | CB | ALA F 481 | 113.916 | 96.883 | 37.891 | 1.00 | 38.68 | F |
| ATOM | 12065 | C | ALA F 481 | 112.860 | 98.168 | 39.745 | 1.00 | 77.09 | F |
| ATOM | 12066 | O | ALA F 481 | 112.998 | 99.237 | 40.340 | 1.00 | 77.09 | F |
| ATOM | 12067 | N | ALA F 482 | 111.679 | 97.676 | 39.407 | 1.00 | 95.03 | F |
| ATOM | 12068 | CA | ALA F 482 | 110.464 | 98.383 | 39.739 | 1.00 | 95.03 | F |
| ATOM | 12069 | CB | ALA F 482 | 109.252 | 97.496 | 39.459 | 1.00 | 67.50 | F |
| ATOM | 12070 | C | ALA F 482 | 110.536 | 98.758 | 41.218 | 1.00 | 95.03 | F |
| ATOM | 12071 | O | ALA F 482 | 110.268 | 99.905 | 41.582 | 1.00 | 95.03 | F |
| ATOM | 12072 | N | ALA F 483 | 110.923 | 97.793 | 42.057 | 1.00 | 95.33 | F |
| ATOM | 12073 | CA | ALA F 483 | 111.034 | 98.008 | 43.502 | 1.00 | 95.33 | F |
| ATOM | 12074 | CB | ALA F 483 | 112.016 | 97.022 | 44.110 | 1.00 | 100.07 | F |
| ATOM | 12075 | C | ALA F 483 | 111.502 | 99.427 | 43.746 | 1.00 | 95.33 | F |
| ATOM | 12076 | O | ALA F 483 | 110.882 | 100.177 | 44.500 | 1.00 | 95.33 | F |
| ATOM | 12077 | N | ALA F 484 | 112.601 | 99.788 | 43.092 | 1.00 | 100.07 | F |
| ATOM | 12078 | CA | ALA F 484 | 113.149 | 101.133 | 43.197 | 1.00 | 100.07 | F |
| ATOM | 12079 | CB | ALA F 484 | 114.645 | 101.127 | 42.851 | 1.00 | 100.07 | F |
| ATOM | 12080 | C | ALA F 484 | 112.369 | 102.014 | 42.217 | 1.00 | 100.07 | F |
| ATOM | 12081 | O | ALA F 484 | 112.854 | 102.363 | 41.136 | 1.00 | 100.07 | F |
| ATOM | 12082 | N | ALA F 485 | 111.141 | 102.348 | 42.601 | 1.00 | 100.07 | F |
| ATOM | 12083 | CA | ALA F 485 | 110.276 | 103.178 | 41.778 | 1.00 | 100.07 | F |
| ATOM | 12084 | CB | ALA F 485 | 108.819 | 102.865 | 42.090 | 1.00 | 29.66 | F |
| ATOM | 12085 | C | ALA F 485 | 110.576 | 104.655 | 42.036 | 1.00 | 100.07 | F |
| ATOM | 12086 | O | ALA F 485 | 110.049 | 105.531 | 41.345 | 1.00 | 100.07 | F |
| ATOM | 12087 | N | ALA F 486 | 111.432 | 104.908 | 43.032 | 1.00 | 100.07 | F |
| ATOM | 12088 | CA | ALA F 486 | 111.859 | 106.256 | 43.445 | 1.00 | 100.07 | F |
| ATOM | 12089 | CB | ALA F 486 | 113.081 | 106.731 | 42.593 | 1.00 | 11.16 | F |
| ATOM | 12090 | C | ALA F 486 | 110.746 | 107.304 | 43.401 | 1.00 | 100.07 | F |
| ATOM | 12091 | O | ALA F 486 | 109.569 | 106.985 | 43.595 | 1.00 | 100.07 | F |
| ATOM | 12092 | N | ALA F 487 | 111.131 | 108.556 | 43.157 | 1.00 | 100.07 | F |
| ATOM | 12093 | CA | ALA F 487 | 110.181 | 109.661 | 43.089 | 1.00 | 100.07 | F |
| ATOM | 12094 | CB | ALA F 487 | 110.515 | 110.708 | 44.135 | 1.00 | 10.05 | F |
| ATOM | 12095 | C | ALA F 487 | 110.168 | 110.303 | 41.711 | 1.00 | 100.07 | F |
| ATOM | 12096 | O | ALA F 487 | 111.107 | 110.147 | 40.924 | 1.00 | 100.07 | F |
| ATOM | 12097 | N | ALA F 488 | 109.089 | 111.031 | 41.440 | 1.00 | 97.36 | F |
| ATOM | 12098 | CA | ALA F 488 | 108.885 | 111.722 | 40.172 | 1.00 | 97.36 | F |
| ATOM | 12099 | CB | ALA F 488 | 109.311 | 110.832 | 38.994 | 1.00 | 78.09 | F |
| ATOM | 12100 | C | ALA F 488 | 107.403 | 112.063 | 40.065 | 1.00 | 97.36 | F |
| ATOM | 12101 | O | ALA F 488 | 106.673 | 112.024 | 41.058 | 1.00 | 97.36 | F |
| ATOM | 12102 | N | ALA F 489 | 106.961 | 112.393 | 38.857 | 1.00 | 100.07 | F |
| ATOM | 12103 | CA | ALA F 489 | 105.565 | 112.739 | 38.624 | 1.00 | 100.07 | F |
| ATOM | 12104 | CB | ALA F 489 | 105.379 | 113.231 | 37.182 | 1.00 | 95.80 | F |
| ATOM | 12105 | C | ALA F 489 | 104.660 | 111.540 | 38.897 | 1.00 | 100.07 | F |
| ATOM | 12106 | O | ALA F 489 | 104.450 | 111.156 | 40.051 | 1.00 | 100.07 | F |
| ATOM | 12107 | N | ALA F 490 | 104.132 | 110.956 | 37.824 | 1.00 | 99.59 | F |
| ATOM | 12108 | CA | ALA F 490 | 103.245 | 109.804 | 37.921 | 1.00 | 99.59 | F |
| ATOM | 12109 | CB | ALA F 490 | 102.754 | 109.404 | 36.533 | 1.00 | 77.92 | F |
| ATOM | 12110 | C | ALA F 490 | 103.924 | 108.618 | 38.594 | 1.00 | 99.59 | F |
| ATOM | 12111 | O | ALA F 490 | 105.022 | 108.203 | 38.206 | 1.00 | 99.59 | F |
| ATOM | 12112 | N | ALA F 491 | 103.256 | 108.079 | 39.606 | 1.00 | 63.35 | F |
| ATOM | 12113 | CA | ALA F 491 | 103.771 | 106.941 | 40.344 | 1.00 | 63.35 | F |
| ATOM | 12114 | CB | ALA F 491 | 102.876 | 106.653 | 41.520 | 1.00 | 33.73 | F |
| ATOM | 12115 | C | ALA F 491 | 103.838 | 105.730 | 39.429 | 1.00 | 63.35 | F |
| ATOM | 12116 | O | ALA F 491 | 104.916 | 105.190 | 39.189 | 1.00 | 63.35 | F |
| ATOM | 12117 | N | ALA F 492 | 102.681 | 105.319 | 38.915 | 1.00 | 80.27 | F |
| ATOM | 12118 | CA | ALA F 492 | 102.594 | 104.167 | 38.024 | 1.00 | 80.27 | F |
| ATOM | 12119 | CB | ALA F 492 | 102.730 | 104.622 | 36.575 | 1.00 | 21.41 | F |
| ATOM | 12120 | C | ALA F 492 | 103.699 | 103.175 | 38.382 | 1.00 | 80.27 | F |
| ATOM | 12121 | O | ALA F 492 | 103.795 | 102.743 | 39.532 | 1.00 | 80.27 | F |
| ATOM | 12122 | N | ALA F 493 | 104.535 | 102.843 | 37.399 | 1.00 | 100.07 | F |
| ATOM | 12123 | CA | ALA F 493 | 105.661 | 101.913 | 37.562 | 1.00 | 100.07 | F |
| ATOM | 12124 | CB | ALA F 493 | 106.925 | 102.683 | 37.933 | 1.00 | 100.07 | F |
| ATOM | 12125 | C | ALA F 493 | 105.408 | 100.812 | 38.583 | 1.00 | 100.07 | F |
| ATOM | 12126 | O | ALA F 493 | 105.175 | 99.660 | 38.215 | 1.00 | 100.07 | F |
| ATOM | 12127 | N | ALA F 494 | 105.481 | 101.167 | 39.864 | 1.00 | 72.51 | F |
| ATOM | 12128 | CA | ALA F 494 | 105.235 | 100.213 | 40.935 | 1.00 | 72.51 | F |
| ATOM | 12129 | CB | ALA F 494 | 105.018 | 100.952 | 42.260 | 1.00 | 52.38 | F |
| ATOM | 12130 | C | ALA F 494 | 103.982 | 99.439 | 40.544 | 1.00 | 72.51 | F |
| ATOM | 12131 | O | ALA F 494 | 103.901 | 98.227 | 40.734 | 1.00 | 72.51 | F |
| ATOM | 12132 | N | ALA F 495 | 103.020 | 100.162 | 39.972 | 1.00 | 100.07 | F |
| ATOM | 12133 | CA | ALA F 495 | 101.753 | 99.588 | 39.526 | 1.00 | 100.07 | F |
| ATOM | 12134 | CB | ALA F 495 | 101.020 | 100.581 | 38.631 | 1.00 | 100.07 | F |
| ATOM | 12135 | C | ALA F 495 | 101.969 | 98.271 | 38.787 | 1.00 | 100.07 | F |
| ATOM | 12136 | O | ALA F 495 | 101.095 | 97.404 | 38.769 | 1.00 | 100.07 | F |
| ATOM | 12137 | N | ALA F 496 | 103.128 | 98.124 | 38.162 | 1.00 | 57.26 | F |
| ATOM | 12138 | CA | ALA F 496 | 103.420 | 96.888 | 37.465 | 1.00 | 57.26 | F |
| ATOM | 12139 | CB | ALA F 496 | 104.776 | 96.976 | 36.759 | 1.00 | 29.06 | F |
| ATOM | 12140 | C | ALA F 496 | 103.449 | 95.817 | 38.552 | 1.00 | 57.26 | F |
| ATOM | 12141 | O | ALA F 496 | 102.747 | 94.811 | 38.471 | 1.00 | 57.26 | F |
| ATOM | 12142 | N | ALA F 497 | 104.240 | 96.067 | 39.589 | 1.00 | 61.78 | F |

| ATOM | 12143 | CA | ALA F 497 | 104.390 | 95.130 | 40.698 | 1.00 | 61.78 | F |
|------|-------|-----|-----------|---------|--------|--------|------|-------|---|
| ATOM | 12144 | CB | ALA F 497 | 104.901 | 95.870 | 41.949 | 1.00 | 61.71 | F |
| ATOM | 12145 | C | ALA F 497 | 103.123 | 94.339 | 41.030 | 1.00 | 61.78 | F |
| ATOM | 12146 | O | ALA F 497 | 103.196 | 93.159 | 41.371 | 1.00 | 61.78 | F |
| ATOM | 12147 | N | ALA F 498 | 101.965 | 94.980 | 40.934 | 1.00 | 99.94 | F |
| ATOM | 12148 | CA | ALA F 498 | 100.718 | 94.289 | 41.232 | 1.00 | 99.94 | F |
| ATOM | 12149 | CB | ALA F 498 | 99.528 | 95.205 | 40.978 | 1.00 | 100.07 | F |
| ATOM | 12150 | C | ALA F 498 | 100.632 | 93.046 | 40.357 | 1.00 | 99.94 | F |
| ATOM | 12151 | O | ALA F 498 | 100.442 | 91.936 | 40.862 | 1.00 | 99.94 | F |
| ATOM | 12152 | N | ALA F 499 | 100.780 | 93.237 | 39.046 | 1.00 | 100.07 | F |
| ATOM | 12153 | CA | ALA F 499 | 100.740 | 92.124 | 38.100 | 1.00 | 100.07 | F |
| ATOM | 12154 | CB | ALA F 499 | 100.733 | 92.655 | 36.651 | 1.00 | 24.68 | F |
| ATOM | 12155 | C | ALA F 499 | 101.964 | 91.233 | 38.340 | 1.00 | 100.07 | F |
| ATOM | 12156 | O | ALA F 499 | 101.839 | 90.017 | 38.524 | 1.00 | 100.07 | F |
| ATOM | 12157 | N | ALA F 500 | 103.141 | 91.859 | 38.363 | 1.00 | 82.45 | F |
| ATOM | 12158 | CA | ALA F 500 | 104.408 | 91.158 | 38.571 | 1.00 | 82.45 | F |
| ATOM | 12159 | CB | ALA F 500 | 105.574 | 92.167 | 38.544 | 1.00 | 19.29 | F |
| ATOM | 12160 | C | ALA F 500 | 104.445 | 90.339 | 39.865 | 1.00 | 82.45 | F |
| ATOM | 12161 | O | ALA F 500 | 104.820 | 89.168 | 39.852 | 1.00 | 82.45 | F |
| ATOM | 12162 | N | ALA F 501 | 104.061 | 90.959 | 40.977 | 1.00 | 82.14 | F |
| ATOM | 12163 | CA | ALA F 501 | 104.054 | 90.284 | 42.273 | 1.00 | 82.14 | F |
| ATOM | 12164 | CB | ALA F 501 | 103.426 | 91.181 | 43.321 | 1.00 | 18.50 | F |
| ATOM | 12165 | C | ALA F 501 | 103.280 | 88.975 | 42.180 | 1.00 | 82.14 | F |
| ATOM | 12166 | O | ALA F 501 | 103.835 | 87.891 | 42.368 | 1.00 | 82.14 | F |
| ATOM | 12167 | N | ALA F 502 | 101.988 | 89.087 | 41.896 | 1.00 | 91.70 | F |
| ATOM | 12168 | CA | ALA F 502 | 101.144 | 87.913 | 41.762 | 1.00 | 91.70 | F |
| ATOM | 12169 | CB | ALA F 502 | 99.784 | 88.312 | 41.206 | 1.00 | 100.07 | F |
| ATOM | 12170 | C | ALA F 502 | 101.858 | 86.986 | 40.797 | 1.00 | 91.70 | F |
| ATOM | 12171 | O | ALA F 502 | 101.969 | 85.782 | 41.025 | 1.00 | 91.70 | F |
| ATOM | 12172 | N | ALA F 503 | 102.355 | 87.571 | 39.716 | 1.00 | 98.19 | F |
| ATOM | 12173 | CA | ALA F 503 | 103.064 | 86.805 | 38.711 | 1.00 | 98.19 | F |
| ATOM | 12174 | CB | ALA F 503 | 103.558 | 87.726 | 37.604 | 1.00 | 14.32 | F |
| ATOM | 12175 | C | ALA F 503 | 104.230 | 86.080 | 39.369 | 1.00 | 98.19 | F |
| ATOM | 12176 | O | ALA F 503 | 104.156 | 84.871 | 39.611 | 1.00 | 98.19 | F |
| ATOM | 12177 | N | ALA F 504 | 105.295 | 86.824 | 39.673 | 1.00 | 100.07 | F |
| ATOM | 12178 | CA | ALA F 504 | 106.486 | 86.256 | 40.304 | 1.00 | 100.07 | F |
| ATOM | 12179 | CB | ALA F 504 | 107.430 | 87.401 | 40.829 | 1.00 | 5.07 | F |
| ATOM | 12180 | C | ALA F 504 | 106.070 | 85.307 | 41.438 | 1.00 | 100.07 | F |
| ATOM | 12181 | O | ALA F 504 | 106.858 | 84.473 | 41.894 | 1.00 | 100.07 | F |
| ATOM | 12182 | N | ALA F 505 | 104.816 | 85.430 | 41.868 | 1.00 | 98.28 | F |
| ATOM | 12183 | CA | ALA F 505 | 104.276 | 84.589 | 42.924 | 1.00 | 98.28 | F |
| ATOM | 12184 | CB | ALA F 505 | 103.045 | 85.238 | 43.518 | 1.00 | 32.21 | F |
| ATOM | 12185 | C | ALA F 505 | 103.926 | 83.220 | 42.354 | 1.00 | 98.28 | F |
| ATOM | 12186 | O | ALA F 505 | 104.463 | 82.201 | 42.794 | 1.00 | 98.28 | F |
| ATOM | 12187 | N | GLY F 506 | 103.028 | 83.200 | 41.372 | 1.00 | 64.41 | F |
| ATOM | 12188 | CA | GLY F 506 | 102.632 | 81.946 | 40.756 | 1.00 | 64.41 | F |
| ATOM | 12189 | C | GLY F 506 | 102.075 | 82.191 | 39.370 | 1.00 | 64.41 | F |
| ATOM | 12190 | O | GLY F 506 | 100.863 | 82.299 | 39.216 | 1.00 | 64.41 | F |
| ATOM | 12191 | N | ALA F 507 | 102.952 | 82.280 | 38.366 | 1.00 | 100.07 | F |
| ATOM | 12192 | CA | ALA F 507 | 102.537 | 82.530 | 36.975 | 1.00 | 100.07 | F |
| ATOM | 12193 | CB | ALA F 507 | 102.296 | 84.033 | 36.769 | 1.00 | 100.07 | F |
| ATOM | 12194 | C | ALA F 507 | 103.522 | 82.019 | 35.907 | 1.00 | 100.07 | F |
| ATOM | 12195 | O | ALA F 507 | 103.974 | 80.875 | 35.966 | 1.00 | 100.07 | F |
| ATOM | 12196 | N | ALA F 508 | 103.820 | 82.889 | 34.935 | 1.00 | 78.66 | F |
| ATOM | 12197 | CA | ALA F 508 | 104.733 | 82.643 | 33.805 | 1.00 | 78.66 | F |
| ATOM | 12198 | CB | ALA F 508 | 104.817 | 81.156 | 33.471 | 1.00 | 8.77 | F |
| ATOM | 12199 | C | ALA F 508 | 104.190 | 83.400 | 32.595 | 1.00 | 78.66 | F |
| ATOM | 12200 | O | ALA F 508 | 103.188 | 84.098 | 32.700 | 1.00 | 78.66 | F |
| ATOM | 12201 | N | PRO F 509 | 104.867 | 83.303 | 31.441 | 1.00 | 37.13 | F |
| ATOM | 12202 | CD | PRO F 509 | 106.278 | 82.889 | 31.292 | 1.00 | 100.07 | F |
| ATOM | 12203 | CA | PRO F 509 | 104.416 | 83.979 | 30.221 | 1.00 | 37.13 | F |
| ATOM | 12204 | CB | PRO F 509 | 105.706 | 84.545 | 29.663 | 1.00 | 100.07 | F |
| ATOM | 12205 | CG | PRO F 509 | 106.642 | 83.385 | 29.874 | 1.00 | 100.07 | F |
| ATOM | 12206 | C | PRO F 509 | 103.860 | 82.849 | 29.340 | 1.00 | 37.13 | F |
| ATOM | 12207 | O | PRO F 509 | 104.193 | 82.729 | 28.153 | 1.00 | 37.13 | F |
| ATOM | 12208 | N | GLU F 510 | 103.048 | 81.996 | 29.968 | 1.00 | 99.79 | F |
| ATOM | 12209 | CA | GLU F 510 | 102.416 | 80.848 | 29.320 | 1.00 | 99.79 | F |
| ATOM | 12210 | CB | GLU F 510 | 102.211 | 79.729 | 30.347 | 1.00 | 60.32 | F |
| ATOM | 12211 | CG | GLU F 510 | 103.496 | 79.265 | 31.021 | 1.00 | 60.32 | F |
| ATOM | 12212 | CD | GLU F 510 | 103.286 | 78.189 | 32.093 | 1.00 | 60.32 | F |
| ATOM | 12213 | OE1 | GLU F 510 | 102.708 | 77.115 | 31.789 | 1.00 | 60.32 | F |
| ATOM | 12214 | OE2 | GLU F 510 | 103.719 | 78.416 | 33.248 | 1.00 | 60.32 | F |
| ATOM | 12215 | C | GLU F 510 | 101.070 | 81.266 | 28.729 | 1.00 | 99.79 | F |
| ATOM | 12216 | O | GLU F 510 | 100.292 | 80.439 | 28.256 | 1.00 | 99.79 | F |
| ATOM | 12217 | N | TRP F 511 | 100.807 | 82.564 | 28.769 | 1.00 | 37.61 | F |
| ATOM | 12218 | CA | TRP F 511 | 99.581 | 83.118 | 28.248 | 1.00 | 37.61 | F |
| ATOM | 12219 | CB | TRP F 511 | 98.986 | 84.108 | 29.249 | 1.00 | 99.43 | F |
| ATOM | 12220 | CG | TRP F 511 | 99.942 | 85.166 | 29.700 | 1.00 | 99.43 | F |
| ATOM | 12221 | CD2 | TRP F 511 | 99.611 | 86.427 | 30.293 | 1.00 | 99.43 | F |
| ATOM | 12222 | CE2 | TRP F 511 | 100.824 | 87.048 | 30.660 | 1.00 | 99.43 | F |
| ATOM | 12223 | CE3 | TRP F 511 | 98.407 | 87.090 | 30.555 | 1.00 | 99.43 | F |
| ATOM | 12224 | CD1 | TRP F 511 | 101.303 | 85.082 | 29.724 | 1.00 | 99.43 | F |
| ATOM | 12225 | NE1 | TRP F 511 | 101.842 | 86.206 | 30.300 | 1.00 | 99.43 | F |
| ATOM | 12226 | CZ2 | TRP F 511 | 100.869 | 88.302 | 31.279 | 1.00 | 99.43 | F |

| ATOM | 12227 | CZ3 | TRP F 511 | 98.454 | 88.339 | 31.173 | 1.00 | 99.43 | F |
|------|-------|-----|-----------|--------|--------|--------|------|-------|---|
| ATOM | 12228 | CH2 | TRP F 511 | 99.678 | 88.928 | 31.527 | 1.00 | 99.43 | F |
| ATOM | 12229 | C | TRP F 511 | 99.856 | 83.815 | 26.938 | 1.00 | 37.61 | F |
| ATOM | 12230 | O | TRP F 511 | 99.749 | 85.024 | 26.845 | 1.00 | 37.61 | F |
| ATOM | 12231 | N | MET F 512 | 100.246 | 83.044 | 25.936 | 1.00 | 34.52 | F |
| ATOM | 12232 | CA | MET F 512 | 100.501 | 83.558 | 24.596 | 1.00 | 34.52 | F |
| ATOM | 12233 | CB | MET F 512 | 101.934 | 84.073 | 24.470 | 1.00 | 100.07 | F |
| ATOM | 12234 | CG | MET F 512 | 102.083 | 85.472 | 25.067 | 1.00 | 100.07 | F |
| ATOM | 12235 | SD | MET F 512 | 103.768 | 86.097 | 25.387 | 1.00 | 100.07 | F |
| ATOM | 12236 | CE | MET F 512 | 104.123 | 85.297 | 26.972 | 1.00 | 100.07 | F |
| ATOM | 12237 | C | MET F 512 | 100.242 | 82.360 | 23.699 | 1.00 | 34.52 | F |
| ATOM | 12238 | O | MET F 512 | 100.638 | 82.324 | 22.542 | 1.00 | 34.52 | F |
| ATOM | 12239 | N | ALA F 513 | 99.536 | 81.399 | 24.300 | 1.00 | 99.70 | F |
| ATOM | 12240 | CA | ALA F 513 | 99.099 | 80.114 | 23.737 | 1.00 | 99.70 | F |
| ATOM | 12241 | CB | ALA F 513 | 97.557 | 80.056 | 23.722 | 1.00 | 47.92 | F |
| ATOM | 12242 | C | ALA F 513 | 99.621 | 79.622 | 22.394 | 1.00 | 99.70 | F |
| ATOM | 12243 | O | ALA F 513 | 99.696 | 80.364 | 21.415 | 1.00 | 99.70 | F |
| ATOM | 12244 | N | ALA F 514 | 99.953 | 78.333 | 22.377 | 1.00 | 55.02 | F |
| ATOM | 12245 | CA | ALA F 514 | 100.442 | 77.631 | 21.197 | 1.00 | 55.02 | F |
| ATOM | 12246 | CB | ALA F 514 | 101.959 | 77.489 | 21.244 | 1.00 | 57.22 | F |
| ATOM | 12247 | C | ALA F 514 | 99.789 | 76.258 | 21.254 | 1.00 | 55.02 | F |
| ATOM | 12248 | O | ALA F 514 | 100.477 | 75.237 | 21.237 | 1.00 | 55.02 | F |
| ATOM | 12249 | N | ALA F 515 | 98.459 | 76.255 | 21.349 | 1.00 | 100.07 | F |
| ATOM | 12250 | CA | ALA F 515 | 97.653 | 75.035 | 21.426 | 1.00 | 100.07 | F |
| ATOM | 12251 | CB | ALA F 515 | 98.305 | 74.023 | 22.378 | 1.00 | 70.16 | F |
| ATOM | 12252 | C | ALA F 515 | 96.233 | 75.354 | 21.908 | 1.00 | 100.07 | F |
| ATOM | 12253 | O | ALA F 515 | 95.969 | 75.373 | 23.115 | 1.00 | 100.07 | F |
| ATOM | 12254 | N | ALA F 516 | 95.324 | 75.599 | 20.966 | 1.00 | 58.93 | F |
| ATOM | 12255 | CA | ALA F 516 | 93.936 | 75.912 | 21.300 | 1.00 | 58.93 | F |
| ATOM | 12256 | CB | ALA F 516 | 93.247 | 76.589 | 20.101 | 1.00 | 5.07 | F |
| ATOM | 12257 | C | ALA F 516 | 93.171 | 74.652 | 21.729 | 1.00 | 58.93 | F |
| ATOM | 12258 | O | ALA F 516 | 93.619 | 73.525 | 21.490 | 1.00 | 58.93 | F |
| ATOM | 12259 | N | VAL F 517 | 92.014 | 74.841 | 22.361 | 1.00 | 44.96 | F |
| ATOM | 12260 | CA | VAL F 517 | 91.231 | 73.709 | 22.834 | 1.00 | 44.96 | F |
| ATOM | 12261 | CB | VAL F 517 | 91.518 | 73.456 | 24.331 | 1.00 | 100.07 | F |
| ATOM | 12262 | CG1 | VAL F 517 | 91.438 | 71.971 | 24.626 | 1.00 | 100.07 | F |
| ATOM | 12263 | CG2 | VAL F 517 | 92.875 | 74.024 | 24.716 | 1.00 | 100.07 | F |
| ATOM | 12264 | C | VAL F 517 | 89.697 | 73.777 | 22.667 | 1.00 | 44.96 | F |
| ATOM | 12265 | O | VAL F 517 | 89.036 | 74.713 | 23.134 | 1.00 | 44.96 | F |
| ATOM | 12266 | N | PRO F 518 | 89.118 | 72.797 | 21.959 | 1.00 | 66.62 | F |
| ATOM | 12267 | CD | PRO F 518 | 89.811 | 72.091 | 20.868 | 1.00 | 100.07 | F |
| ATOM | 12268 | CA | PRO F 518 | 87.666 | 72.745 | 21.757 | 1.00 | 66.62 | F |
| ATOM | 12269 | CB | PRO F 518 | 87.539 | 72.294 | 20.306 | 1.00 | 100.07 | F |
| ATOM | 12270 | CG | PRO F 518 | 88.672 | 71.392 | 20.146 | 1.00 | 100.07 | F |
| ATOM | 12271 | C | PRO F 518 | 87.105 | 71.719 | 22.748 | 1.00 | 66.62 | F |
| ATOM | 12272 | O | PRO F 518 | 87.635 | 70.611 | 22.859 | 1.00 | 66.62 | F |
| ATOM | 12273 | N | VAL F 519 | 86.052 | 72.078 | 23.475 | 1.00 | 19.90 | F |
| ATOM | 12274 | CA | VAL F 519 | 85.485 | 71.153 | 24.460 | 1.00 | 19.90 | F |
| ATOM | 12275 | CB | VAL F 519 | 84.279 | 71.779 | 25.175 | 1.00 | 65.64 | F |
| ATOM | 12276 | CG1 | VAL F 519 | 83.784 | 70.851 | 26.269 | 1.00 | 65.64 | F |
| ATOM | 12277 | CG2 | VAL F 519 | 84.660 | 73.104 | 25.744 | 1.00 | 65.64 | F |
| ATOM | 12278 | C | VAL F 519 | 85.028 | 69.842 | 23.823 | 1.00 | 19.90 | F |
| ATOM | 12279 | O | VAL F 519 | 84.744 | 69.812 | 22.617 | 1.00 | 19.90 | F |
| ATOM | 12280 | N | LEU F 520 | 84.961 | 68.772 | 24.624 | 1.00 | 49.79 | F |
| ATOM | 12281 | CA | LEU F 520 | 84.498 | 67.481 | 24.118 | 1.00 | 49.79 | F |
| ATOM | 12282 | CB | LEU F 520 | 84.374 | 66.454 | 25.243 | 1.00 | 100.07 | F |
| ATOM | 12283 | CG | LEU F 520 | 84.087 | 65.035 | 24.730 | 1.00 | 100.07 | F |
| ATOM | 12284 | CD1 | LEU F 520 | 85.405 | 64.439 | 24.244 | 1.00 | 100.07 | F |
| ATOM | 12285 | CD2 | LEU F 520 | 83.461 | 64.145 | 25.811 | 1.00 | 100.07 | F |
| ATOM | 12286 | C | LEU F 520 | 83.116 | 67.803 | 23.575 | 1.00 | 49.79 | F |
| ATOM | 12287 | O | LEU F 520 | 82.388 | 68.561 | 24.195 | 1.00 | 49.79 | F |
| ATOM | 12288 | N | PRO F 521 | 82.723 | 67.229 | 22.428 | 1.00 | 35.08 | F |
| ATOM | 12289 | CD | PRO F 521 | 83.381 | 66.123 | 21.719 | 1.00 | 93.02 | F |
| ATOM | 12290 | CA | PRO F 521 | 81.408 | 67.507 | 21.836 | 1.00 | 35.08 | F |
| ATOM | 12291 | CB | PRO F 521 | 81.305 | 66.466 | 20.719 | 1.00 | 93.02 | F |
| ATOM | 12292 | CG | PRO F 521 | 82.201 | 65.370 | 21.180 | 1.00 | 93.02 | F |
| ATOM | 12293 | C | PRO F 521 | 80.137 | 67.566 | 22.710 | 1.00 | 35.08 | F |
| ATOM | 12294 | O | PRO F 521 | 79.319 | 68.480 | 22.543 | 1.00 | 35.08 | F |
| ATOM | 12295 | N | PRO F 522 | 79.950 | 66.613 | 23.653 | 1.00 | 99.94 | F |
| ATOM | 12296 | CD | PRO F 522 | 80.867 | 65.541 | 24.089 | 1.00 | 100.07 | F |
| ATOM | 12297 | CA | PRO F 522 | 78.747 | 66.635 | 24.503 | 1.00 | 99.94 | F |
| ATOM | 12298 | CB | PRO F 522 | 78.891 | 65.364 | 25.340 | 1.00 | 100.07 | F |
| ATOM | 12299 | CG | PRO F 522 | 80.370 | 65.234 | 25.496 | 1.00 | 100.07 | F |
| ATOM | 12300 | C | PRO F 522 | 78.613 | 67.892 | 25.364 | 1.00 | 99.94 | F |
| ATOM | 12301 | O | PRO F 522 | 78.099 | 67.846 | 26.482 | 1.00 | 99.94 | F |
| ATOM | 12302 | N | ASP F 523 | 79.079 | 69.009 | 24.820 | 1.00 | 78.45 | F |
| ATOM | 12303 | CA | ASP F 523 | 79.038 | 70.299 | 25.485 | 1.00 | 78.45 | F |
| ATOM | 12304 | CB | ASP F 523 | 80.421 | 70.661 | 26.004 | 1.00 | 97.06 | F |
| ATOM | 12305 | CG | ASP F 523 | 80.428 | 71.963 | 26.745 | 1.00 | 97.06 | F |
| ATOM | 12306 | OD1 | ASP F 523 | 79.881 | 72.948 | 26.210 | 1.00 | 97.06 | F |
| ATOM | 12307 | OD2 | ASP F 523 | 80.983 | 72.003 | 27.860 | 1.00 | 97.06 | F |
| ATOM | 12308 | C | ASP F 523 | 78.577 | 71.347 | 24.475 | 1.00 | 78.45 | F |
| ATOM | 12309 | O | ASP F 523 | 77.781 | 72.230 | 24.852 | 1.00 | 78.45 | F |
| ATOM | 12310 | OT | ASP F 523 | 79.029 | 71.280 | 23.315 | 1.00 | 97.06 | F |

```
ATOM  12311  CB  ALA G 535      72.510  75.095  18.383  1.00100.07           G
ATOM  12312  C   ALA G 535      73.810  75.656  20.434  1.00100.07           G
ATOM  12313  O   ALA G 535      74.091  76.725  20.985  1.00100.07           G
ATOM  12314  N   ALA G 535      71.558  76.614  20.076  1.00100.07           G
ATOM  12315  CA  ALA G 535      72.415  75.409  19.874  1.00100.07           G
ATOM  12316  N   ALA G 536      74.672  74.651  20.322  1.00100.07           G
ATOM  12317  CA  ALA G 536      76.054  74.798  20.757  1.00100.07           G
ATOM  12318  CB  ALA G 536      76.562  73.506  21.400  1.00 75.75           G
ATOM  12319  C   ALA G 536      76.746  75.050  19.422  1.00100.07           G
ATOM  12320  O   ALA G 536      77.817  75.655  19.355  1.00100.07           G
ATOM  12321  N   THR G 537      76.067  74.595  18.367  1.00 73.01           G
ATOM  12322  CA  THR G 537      76.497  74.706  16.977  1.00 73.01           G
ATOM  12323  CB  THR G 537      75.266  74.720  16.022  1.00100.07           G
ATOM  12324  OG1 THR G 537      74.459  73.557  16.248  1.00100.07           G
ATOM  12325  CG2 THR G 537      75.712  74.724  14.573  1.00100.07           G
ATOM  12326  C   THR G 537      77.328  75.954  16.708  1.00 73.01           G
ATOM  12327  O   THR G 537      78.401  75.874  16.101  1.00 73.01           G
ATOM  12328  N   SER G 538      76.828  77.100  17.167  1.00 70.80           G
ATOM  12329  CA  SER G 538      77.498  78.388  16.968  1.00 70.80           G
ATOM  12330  CB  SER G 538      76.739  79.496  17.715  1.00 70.37           G
ATOM  12331  OG  SER G 538      77.174  80.789  17.315  1.00 70.37           G
ATOM  12332  C   SER G 538      78.977  78.415  17.375  1.00 70.80           G
ATOM  12333  O   SER G 538      79.708  79.334  17.016  1.00 70.80           G
ATOM  12334  N   ASP G 539      79.421  77.412  18.119  1.00 80.36           G
ATOM  12335  CA  ASP G 539      80.812  77.361  18.554  1.00 80.36           G
ATOM  12336  CB  ASP G 539      80.876  76.982  20.042  1.00 79.91           G
ATOM  12337  CG  ASP G 539      82.293  77.005  20.600  1.00 79.91           G
ATOM  12338  OD1 ASP G 539      82.833  78.102  20.864  1.00 79.91           G
ATOM  12339  OD2 ASP G 539      82.869  75.916  20.770  1.00 79.91           G
ATOM  12340  C   ASP G 539      81.600  76.349  17.725  1.00 80.36           G
ATOM  12341  O   ASP G 539      82.824  76.292  17.801  1.00 80.36           G
ATOM  12342  N   LEU G 540      80.886  75.556  16.932  1.00 47.23           G
ATOM  12343  CA  LEU G 540      81.496  74.526  16.095  1.00 47.23           G
ATOM  12344  CB  LEU G 540      80.603  73.286  16.041  1.00 72.45           G
ATOM  12345  CG  LEU G 540      80.626  72.347  17.243  1.00 72.45           G
ATOM  12346  CD1 LEU G 540      79.481  71.350  17.146  1.00 72.45           G
ATOM  12347  CD2 LEU G 540      81.972  71.637  17.295  1.00 72.45           G
ATOM  12348  C   LEU G 540      81.717  75.024  14.686  1.00 47.23           G
ATOM  12349  O   LEU G 540      82.824  75.432  14.326  1.00 47.23           G
ATOM  12350  N   ASN G 541      80.654  74.987  13.887  1.00 80.65           G
ATOM  12351  CA  ASN G 541      80.752  75.438  12.514  1.00 80.65           G
ATOM  12352  CB  ASN G 541      79.379  75.551  11.860  1.00100.07           G
ATOM  12353  CG  ASN G 541      79.474  75.926  10.385  1.00100.07           G
ATOM  12354  OD1 ASN G 541      80.015  75.166   9.572  1.00100.07           G
ATOM  12355  ND2 ASN G 541      78.960  77.106  10.036  1.00100.07           G
ATOM  12356  C   ASN G 541      81.403  76.800  12.549  1.00 80.65           G
ATOM  12357  O   ASN G 541      81.704  77.397  11.513  1.00 80.65           G
ATOM  12358  N   ASP G 542      81.608  77.292  13.762  1.00 99.61           G
ATOM  12359  CA  ASP G 542      82.237  78.576  13.960  1.00 99.61           G
ATOM  12360  CB  ASP G 542      81.293  79.527  14.705  1.00100.07           G
ATOM  12361  CG  ASP G 542      79.946  79.684  14.013  1.00100.07           G
ATOM  12362  OD1 ASP G 542      79.930  79.892  12.780  1.00100.07           G
ATOM  12363  OD2 ASP G 542      78.906  79.613  14.704  1.00100.07           G
ATOM  12364  C   ASP G 542      83.500  78.396  14.777  1.00 99.61           G
ATOM  12365  O   ASP G 542      83.602  77.477  15.588  1.00 99.61           G
ATOM  12366  N   LEU G 543      84.465  79.272  14.531  1.00 96.41           G
ATOM  12367  CA  LEU G 543      85.714  79.285  15.271  1.00 96.41           G
ATOM  12368  CB  LEU G 543      85.450  79.884  16.659  1.00 99.66           G
ATOM  12369  CG  LEU G 543      84.549  81.128  16.673  1.00 99.66           G
ATOM  12370  CD1 LEU G 543      84.315  81.601  18.092  1.00 99.66           G
ATOM  12371  CD2 LEU G 543      85.191  82.222  15.852  1.00 99.66           G
ATOM  12372  C   LEU G 543      86.411  77.935  15.411  1.00 96.41           G
ATOM  12373  O   LEU G 543      87.488  77.850  15.988  1.00 96.41           G
ATOM  12374  N   TYR G 544      85.800  76.875  14.910  1.00 98.18           G
ATOM  12375  CA  TYR G 544      86.427  75.567  14.989  1.00 98.18           G
ATOM  12376  CB  TYR G 544      85.666  74.657  15.945  1.00 70.00           G
ATOM  12377  CG  TYR G 544      86.036  74.883  17.394  1.00 70.00           G
ATOM  12378  CD1 TYR G 544      85.287  74.314  18.424  1.00 70.00           G
ATOM  12379  CE1 TYR G 544      85.628  74.511  19.759  1.00 70.00           G
ATOM  12380  CD2 TYR G 544      87.140  75.657  17.739  1.00 70.00           G
ATOM  12381  CE2 TYR G 544      87.491  75.858  19.072  1.00 70.00           G
ATOM  12382  CZ  TYR G 544      86.733  75.281  20.075  1.00 70.00           G
ATOM  12383  OH  TYR G 544      87.100  75.443  21.392  1.00 70.00           G
ATOM  12384  C   TYR G 544      86.420  75.036  13.579  1.00 98.18           G
ATOM  12385  O   TYR G 544      87.085  74.055  13.246  1.00 98.18           G
ATOM  12386  N   ARG G 545      85.639  75.712  12.752  1.00 90.26           G
ATOM  12387  CA  ARG G 545      85.563  75.403  11.344  1.00 90.26           G
ATOM  12388  CB  ARG G 545      84.124  75.552  10.841  1.00100.07           G
ATOM  12389  CG  ARG G 545      83.941  75.377   9.335  1.00100.07           G
ATOM  12390  CD  ARG G 545      82.605  75.953   8.881  1.00100.07           G
ATOM  12391  NE  ARG G 545      82.452  75.947   7.427  1.00100.07           G
ATOM  12392  CZ  ARG G 545      81.434  76.506   6.776  1.00100.07           G
ATOM  12393  NH1 ARG G 545      80.469  77.122   7.447  1.00100.07           G
ATOM  12394  NH2 ARG G 545      81.377  76.448   5.451  1.00100.07           G
```

| | | | | | | | | | |
|---|---|---|---|---|---|---|---|---|---|
|ATOM|12395|C|ARG G 545|86.428|76.548|10.839|1.00|90.26|G|
|ATOM|12396|O|ARG G 545|87.469|76.342|10.219|1.00|90.26|G|
|ATOM|12397|N|ARG G 546|86.002|77.762|11.175|1.00|66.99|G|
|ATOM|12398|CA|ARG G 546|86.701|78.979|10.789|1.00|66.99|G|
|ATOM|12399|CB|ARG G 546|86.083|80.172|11.515|1.00|100.07|G|
|ATOM|12400|CG|ARG G 546|84.731|80.627|10.984|1.00|100.07|G|
|ATOM|12401|CD|ARG G 546|84.886|81.547|9.777|1.00|100.07|G|
|ATOM|12402|NE|ARG G 546|83.664|82.306|9.512|1.00|100.07|G|
|ATOM|12403|CZ|ARG G 546|83.526|83.185|8.522|1.00|100.07|G|
|ATOM|12404|NH1|ARG G 546|84.539|83.418|7.699|1.00|100.07|G|
|ATOM|12405|NH2|ARG G 546|82.377|83.830|8.352|1.00|100.07|G|
|ATOM|12406|C|ARG G 546|88.191|78.937|11.103|1.00|66.99|G|
|ATOM|12407|O|ARG G 546|89.002|79.482|10.351|1.00|66.99|G|
|ATOM|12408|N|LEU G 547|88.534|78.292|12.217|1.00|99.98|G|
|ATOM|12409|CA|LEU G 547|89.919|78.187|12.681|1.00|99.98|G|
|ATOM|12410|CB|LEU G 547|89.953|78.026|14.203|1.00|77.26|G|
|ATOM|12411|CG|LEU G 547|91.316|78.113|14.900|1.00|77.26|G|
|ATOM|12412|CD1|LEU G 547|91.485|79.512|15.477|1.00|77.26|G|
|ATOM|12413|CD2|LEU G 547|91.412|77.077|16.010|1.00|77.26|G|
|ATOM|12414|C|LEU G 547|90.736|77.055|12.066|1.00|99.98|G|
|ATOM|12415|O|LEU G 547|91.610|77.294|11.231|1.00|99.98|G|
|ATOM|12416|N|ILE G 548|90.462|75.825|12.496|1.00|84.49|G|
|ATOM|12417|CA|ILE G 548|91.194|74.661|12.006|1.00|84.49|G|
|ATOM|12418|CB|ILE G 548|90.434|73.355|12.298|1.00|26.57|G|
|ATOM|12419|CG2|ILE G 548|91.328|72.167|12.013|1.00|26.57|G|
|ATOM|12420|CG1|ILE G 548|90.011|73.320|13.767|1.00|26.57|G|
|ATOM|12421|CD|ILE G 548|91.153|73.574|14.758|1.00|26.57|G|
|ATOM|12422|C|ILE G 548|91.521|74.727|10.515|1.00|84.49|G|
|ATOM|12423|O|ILE G 548|92.536|74.185|10.077|1.00|84.49|G|
|ATOM|12424|N|ASN G 549|90.668|75.386|9.736|1.00|100.07|G|
|ATOM|12425|CA|ASN G 549|90.927|75.522|8.308|1.00|100.07|G|
|ATOM|12426|CB|ASN G 549|89.700|76.076|7.565|1.00|85.42|G|
|ATOM|12427|CG|ASN G 549|88.679|74.993|7.217|1.00|85.42|G|
|ATOM|12428|OD1|ASN G 549|88.947|73.795|7.352|1.00|85.42|G|
|ATOM|12429|ND2|ASN G 549|87.507|75.416|6.753|1.00|85.42|G|
|ATOM|12430|C|ASN G 549|92.121|76.453|8.104|1.00|100.07|G|
|ATOM|12431|O|ASN G 549|93.116|76.065|7.496|1.00|100.07|G|
|ATOM|12432|N|ARG G 550|92.027|77.677|8.613|1.00|63.37|G|
|ATOM|12433|CA|ARG G 550|93.127|78.621|8.468|1.00|63.37|G|
|ATOM|12434|CB|ARG G 550|92.911|79.869|9.326|1.00|100.07|G|
|ATOM|12435|CG|ARG G 550|91.732|80.726|8.911|1.00|100.07|G|
|ATOM|12436|CD|ARG G 550|91.814|81.103|7.445|1.00|100.07|G|
|ATOM|12437|NE|ARG G 550|90.710|81.968|7.039|1.00|100.07|G|
|ATOM|12438|CZ|ARG G 550|90.463|82.319|5.780|1.00|100.07|G|
|ATOM|12439|NH1|ARG G 550|91.246|81.876|4.805|1.00|100.07|G|
|ATOM|12440|NH2|ARG G 550|89.430|83.104|5.492|1.00|100.07|G|
|ATOM|12441|C|ARG G 550|94.422|77.957|8.886|1.00|63.37|G|
|ATOM|12442|O|ARG G 550|95.391|77.956|8.129|1.00|63.37|G|
|ATOM|12443|N|ASN G 551|94.437|77.388|10.090|1.00|54.49|G|
|ATOM|12444|CA|ASN G 551|95.636|76.732|10.585|1.00|54.49|G|
|ATOM|12445|CB|ASN G 551|95.339|75.907|11.837|1.00|56.03|G|
|ATOM|12446|CG|ASN G 551|96.611|75.448|12.554|1.00|56.03|G|
|ATOM|12447|OD1|ASN G 551|97.074|74.321|12.379|1.00|56.03|G|
|ATOM|12448|ND2|ASN G 551|97.184|76.334|13.356|1.00|56.03|G|
|ATOM|12449|C|ASN G 551|96.162|75.834|9.484|1.00|54.49|G|
|ATOM|12450|O|ASN G 551|97.361|75.583|9.393|1.00|54.49|G|
|ATOM|12451|N|ASN G 552|95.264|75.354|8.634|1.00|61.89|G|
|ATOM|12452|CA|ASN G 552|95.683|74.503|7.535|1.00|61.89|G|
|ATOM|12453|CB|ASN G 552|94.642|73.406|7.268|1.00|71.57|G|
|ATOM|12454|CG|ASN G 552|94.599|72.354|8.384|1.00|71.57|G|
|ATOM|12455|OD1|ASN G 552|95.641|71.842|8.816|1.00|71.57|G|
|ATOM|12456|ND2|ASN G 552|93.392|72.024|8.846|1.00|71.57|G|
|ATOM|12457|C|ASN G 552|95.943|75.347|6.296|1.00|61.89|G|
|ATOM|12458|O|ASN G 552|96.691|74.945|5.410|1.00|61.89|G|
|ATOM|12459|N|ARG G 553|95.328|76.524|6.243|1.00|97.47|G|
|ATOM|12460|CA|ARG G 553|95.532|77.442|5.130|1.00|97.47|G|
|ATOM|12461|CB|ARG G 553|94.731|78.726|5.336|1.00|100.07|G|
|ATOM|12462|CG|ARG G 553|95.118|79.874|4.400|1.00|100.07|G|
|ATOM|12463|CD|ARG G 553|94.516|79.730|2.996|1.00|100.07|G|
|ATOM|12464|NE|ARG G 553|94.684|80.953|2.202|1.00|100.07|G|
|ATOM|12465|CZ|ARG G 553|94.022|81.221|1.077|1.00|100.07|G|
|ATOM|12466|NH1|ARG G 553|93.139|80.351|0.599|1.00|100.07|G|
|ATOM|12467|NH2|ARG G 553|94.232|82.369|0.438|1.00|100.07|G|
|ATOM|12468|C|ARG G 553|97.015|77.772|5.141|1.00|97.47|G|
|ATOM|12469|O|ARG G 553|97.572|78.249|4.152|1.00|97.47|G|
|ATOM|12470|N|LEU G 554|97.644|77.526|6.284|1.00|69.85|G|
|ATOM|12471|CA|LEU G 554|99.071|77.772|6.446|1.00|69.85|G|
|ATOM|12472|CB|LEU G 554|99.330|78.679|7.654|1.00|92.56|G|
|ATOM|12473|CG|LEU G 554|98.524|79.982|7.705|1.00|92.56|G|
|ATOM|12474|CD1|LEU G 554|99.053|80.839|8.847|1.00|92.56|G|
|ATOM|12475|CD2|LEU G 554|98.621|80.731|6.380|1.00|92.56|G|
|ATOM|12476|C|LEU G 554|99.741|76.424|6.649|1.00|69.85|G|
|ATOM|12477|O|LEU G 554|100.948|76.276|6.493|1.00|69.85|G|
|ATOM|12478|N|LYS G 555|98.930|75.435|6.993|1.00|100.07|G|

| ATOM | 12479 | CA | LYS | G | 555 | 99.422 | 74.090 | 7.211 | 1.00 | 100.07 | G |
|---|---|---|---|---|---|---|---|---|---|---|---|
| ATOM | 12480 | CB | LYS | G | 555 | 98.340 | 73.270 | 7.920 | 1.00 | 100.07 | G |
| ATOM | 12481 | CG | LYS | G | 555 | 98.785 | 71.950 | 8.481 | 1.00 | 100.07 | G |
| ATOM | 12482 | CD | LYS | G | 555 | 99.760 | 72.144 | 9.615 | 1.00 | 100.07 | G |
| ATOM | 12483 | CE | LYS | G | 555 | 100.189 | 70.804 | 10.163 | 1.00 | 100.07 | G |
| ATOM | 12484 | NZ | LYS | G | 555 | 101.195 | 70.971 | 11.227 | 1.00 | 100.07 | G |
| ATOM | 12485 | C | LYS | G | 555 | 99.766 | 73.468 | 5.851 | 1.00 | 100.07 | G |
| ATOM | 12486 | O | LYS | G | 555 | 100.197 | 72.310 | 5.781 | 1.00 | 100.07 | G |
| ATOM | 12487 | N | LYS | G | 556 | 99.576 | 74.243 | 4.777 | 1.00 | 67.24 | G |
| ATOM | 12488 | CA | LYS | G | 556 | 99.856 | 73.782 | 3.407 | 1.00 | 67.24 | G |
| ATOM | 12489 | CB | LYS | G | 556 | 98.622 | 73.118 | 2.790 | 1.00 | 100.07 | G |
| ATOM | 12490 | CG | LYS | G | 556 | 98.145 | 71.875 | 3.514 | 1.00 | 100.07 | G |
| ATOM | 12491 | CD | LYS | G | 556 | 96.753 | 71.496 | 3.047 | 1.00 | 100.07 | G |
| ATOM | 12492 | CE | LYS | G | 556 | 96.102 | 70.495 | 3.990 | 1.00 | 100.07 | G |
| ATOM | 12493 | NZ | LYS | G | 556 | 94.667 | 70.261 | 3.637 | 1.00 | 100.07 | G |
| ATOM | 12494 | C | LYS | G | 556 | 100.293 | 74.913 | 2.492 | 1.00 | 67.24 | G |
| ATOM | 12495 | O | LYS | G | 556 | 100.072 | 74.861 | 1.285 | 1.00 | 67.24 | G |
| ATOM | 12496 | N | LEU | G | 557 | 100.890 | 75.944 | 3.074 | 1.00 | 68.19 | G |
| ATOM | 12497 | CA | LEU | G | 557 | 101.382 | 77.089 | 2.315 | 1.00 | 68.19 | G |
| ATOM | 12498 | CB | LEU | G | 557 | 100.421 | 78.275 | 2.423 | 1.00 | 44.98 | G |
| ATOM | 12499 | CG | LEU | G | 557 | 100.486 | 79.376 | 1.356 | 1.00 | 44.98 | G |
| ATOM | 12500 | CD1 | LEU | G | 557 | 99.658 | 80.547 | 1.850 | 1.00 | 44.98 | G |
| ATOM | 12501 | CD2 | LEU | G | 557 | 101.913 | 79.833 | 1.074 | 1.00 | 44.98 | G |
| ATOM | 12502 | C | LEU | G | 557 | 102.689 | 77.424 | 3.005 | 1.00 | 68.19 | G |
| ATOM | 12503 | O | LEU | G | 557 | 103.102 | 78.580 | 3.080 | 1.00 | 68.19 | G |
| ATOM | 12504 | N | LEU | G | 558 | 103.317 | 76.386 | 3.540 | 1.00 | 96.46 | G |
| ATOM | 12505 | CA | LEU | G | 558 | 104.572 | 76.542 | 4.245 | 1.00 | 96.46 | G |
| ATOM | 12506 | CB | LEU | G | 558 | 104.320 | 76.748 | 5.740 | 1.00 | 99.58 | G |
| ATOM | 12507 | CG | LEU | G | 558 | 103.493 | 77.982 | 6.124 | 1.00 | 99.58 | G |
| ATOM | 12508 | CD1 | LEU | G | 558 | 103.404 | 78.042 | 7.637 | 1.00 | 99.58 | G |
| ATOM | 12509 | CD2 | LEU | G | 558 | 104.118 | 79.263 | 5.573 | 1.00 | 99.58 | G |
| ATOM | 12510 | C | LEU | G | 558 | 105.440 | 75.323 | 4.009 | 1.00 | 96.46 | G |
| ATOM | 12511 | O | LEU | G | 558 | 106.664 | 75.435 | 3.947 | 1.00 | 96.46 | G |
| ATOM | 12512 | N | ALA | G | 559 | 104.824 | 74.151 | 3.894 | 1.00 | 99.94 | G |
| ATOM | 12513 | CA | ALA | G | 559 | 105.618 | 72.971 | 3.596 | 1.00 | 99.94 | G |
| ATOM | 12514 | CB | ALA | G | 559 | 104.801 | 71.690 | 3.766 | 1.00 | 27.45 | G |
| ATOM | 12515 | C | ALA | G | 559 | 105.958 | 73.229 | 2.125 | 1.00 | 99.94 | G |
| ATOM | 12516 | O | ALA | G | 559 | 106.787 | 72.535 | 1.525 | 1.00 | 99.94 | G |
| ATOM | 12517 | N | GLN | G | 560 | 105.299 | 74.257 | 1.569 | 1.00 | 100.07 | G |
| ATOM | 12518 | CA | GLN | G | 560 | 105.504 | 74.711 | 0.188 | 1.00 | 100.07 | G |
| ATOM | 12519 | CB | GLN | G | 560 | 104.169 | 74.957 | -0.538 | 1.00 | 92.79 | G |
| ATOM | 12520 | CG | GLN | G | 560 | 104.093 | 76.349 | -1.215 | 1.00 | 92.79 | G |
| ATOM | 12521 | CD | GLN | G | 560 | 103.080 | 76.450 | -2.355 | 1.00 | 92.79 | G |
| ATOM | 12522 | OE1 | GLN | G | 560 | 101.893 | 76.159 | -2.186 | 1.00 | 92.79 | G |
| ATOM | 12523 | NE2 | GLN | G | 560 | 103.550 | 76.884 | -3.522 | 1.00 | 92.79 | G |
| ATOM | 12524 | C | GLN | G | 560 | 106.288 | 76.025 | 0.203 | 1.00 | 100.07 | G |
| ATOM | 12525 | O | GLN | G | 560 | 106.227 | 76.781 | 1.178 | 1.00 | 100.07 | G |
| ATOM | 12526 | N | GLY | G | 561 | 107.002 | 76.289 | -0.892 | 1.00 | 100.07 | G |
| ATOM | 12527 | CA | GLY | G | 561 | 107.791 | 77.503 | -1.022 | 1.00 | 100.07 | G |
| ATOM | 12528 | C | GLY | G | 561 | 107.257 | 78.611 | -0.146 | 1.00 | 100.07 | G |
| ATOM | 12529 | O | GLY | G | 561 | 107.978 | 79.154 | 0.689 | 1.00 | 100.07 | G |
| ATOM | 12530 | N | ALA | G | 562 | 105.986 | 78.943 | -0.339 | 1.00 | 70.43 | G |
| ATOM | 12531 | CA | ALA | G | 562 | 105.346 | 79.972 | 0.462 | 1.00 | 70.43 | G |
| ATOM | 12532 | CB | ALA | G | 562 | 105.333 | 79.534 | 1.915 | 1.00 | 100.07 | G |
| ATOM | 12533 | C | ALA | G | 562 | 106.011 | 81.347 | 0.329 | 1.00 | 70.43 | G |
| ATOM | 12534 | O | ALA | G | 562 | 107.090 | 81.598 | 0.874 | 1.00 | 70.43 | G |
| ATOM | 12535 | N | PRO | G | 563 | 105.359 | 82.261 | -0.400 | 1.00 | 66.56 | G |
| ATOM | 12536 | CD | PRO | G | 563 | 104.173 | 81.972 | -1.231 | 1.00 | 41.79 | G |
| ATOM | 12537 | CA | PRO | G | 563 | 105.848 | 83.625 | -0.631 | 1.00 | 66.56 | G |
| ATOM | 12538 | CB | PRO | G | 563 | 105.104 | 84.038 | -1.897 | 1.00 | 41.79 | G |
| ATOM | 12539 | CG | PRO | G | 563 | 103.780 | 83.350 | -1.732 | 1.00 | 41.79 | G |
| ATOM | 12540 | C | PRO | G | 563 | 105.588 | 84.588 | 0.530 | 1.00 | 66.56 | G |
| ATOM | 12541 | O | PRO | G | 563 | 104.591 | 85.300 | 0.523 | 1.00 | 66.56 | G |
| ATOM | 12542 | N | GLU | G | 564 | 106.500 | 84.615 | 1.501 | 1.00 | 94.32 | G |
| ATOM | 12543 | CA | GLU | G | 564 | 106.404 | 85.470 | 2.701 | 1.00 | 94.32 | G |
| ATOM | 12544 | CB | GLU | G | 564 | 107.634 | 86.382 | 2.822 | 1.00 | 100.07 | G |
| ATOM | 12545 | CG | GLU | G | 564 | 108.948 | 85.655 | 3.090 | 1.00 | 100.07 | G |
| ATOM | 12546 | CD | GLU | G | 564 | 109.908 | 86.473 | 3.943 | 1.00 | 100.07 | G |
| ATOM | 12547 | OE1 | GLU | G | 564 | 109.761 | 86.466 | 5.186 | 1.00 | 100.07 | G |
| ATOM | 12548 | OE2 | GLU | G | 564 | 110.801 | 87.131 | 3.369 | 1.00 | 100.07 | G |
| ATOM | 12549 | C | GLU | G | 564 | 105.155 | 86.333 | 2.886 | 1.00 | 94.32 | G |
| ATOM | 12550 | O | GLU | G | 564 | 104.384 | 86.103 | 3.812 | 1.00 | 94.32 | G |
| ATOM | 12551 | N | ILE | G | 565 | 104.974 | 87.335 | 2.026 | 1.00 | 62.48 | G |
| ATOM | 12552 | CA | ILE | G | 565 | 103.822 | 88.240 | 2.102 | 1.00 | 62.48 | G |
| ATOM | 12553 | CB | ILE | G | 565 | 103.733 | 89.144 | 0.852 | 1.00 | 100.07 | G |
| ATOM | 12554 | CG2 | ILE | G | 565 | 102.698 | 90.232 | 1.081 | 1.00 | 100.07 | G |
| ATOM | 12555 | CG1 | ILE | G | 565 | 105.093 | 89.794 | 0.571 | 1.00 | 100.07 | G |
| ATOM | 12556 | CD | ILE | G | 565 | 105.185 | 90.494 | -0.776 | 1.00 | 100.07 | G |
| ATOM | 12557 | C | ILE | G | 565 | 102.510 | 87.471 | 2.251 | 1.00 | 62.48 | G |
| ATOM | 12558 | O | ILE | G | 565 | 101.711 | 87.779 | 3.130 | 1.00 | 62.48 | G |
| ATOM | 12559 | N | ILE | G | 566 | 102.283 | 86.482 | 1.388 | 1.00 | 100.07 | G |
| ATOM | 12560 | CA | ILE | G | 566 | 101.081 | 85.651 | 1.469 | 1.00 | 100.07 | G |
| ATOM | 12561 | CB | ILE | G | 566 | 100.667 | 85.111 | 0.058 | 1.00 | 96.39 | G |
| ATOM | 12562 | CG2 | ILE | G | 566 | 99.762 | 83.893 | 0.174 | 1.00 | 96.39 | G |

| ATOM | 12563 | CG1 | ILE G 566 | 99.919 | 86.204 | -0.712 | 1.00 96.39 | G |
|---|---|---|---|---|---|---|---|---|
| ATOM | 12564 | CD | ILE G 566 | 98.630 | 86.663 | -0.042 | 1.00 96.39 | G |
| ATOM | 12565 | C | ILE G 566 | 101.403 | 84.513 | 2.452 | 1.00100.07 | G |
| ATOM | 12566 | O | ILE G 566 | 101.402 | 83.324 | 2.119 | 1.00100.07 | G |
| ATOM | 12567 | N | ILE G 567 | 101.705 | 84.938 | 3.675 | 1.00 97.69 | G |
| ATOM | 12568 | CA | ILE G 567 | 102.050 | 84.093 | 4.815 | 1.00 97.69 | G |
| ATOM | 12569 | CB | ILE G 567 | 103.515 | 83.605 | 4.759 | 1.00 60.58 | G |
| ATOM | 12570 | CG2 | ILE G 567 | 103.941 | 83.066 | 6.111 | 1.00 60.58 | G |
| ATOM | 12571 | CG1 | ILE G 567 | 103.670 | 82.534 | 3.689 | 1.00 60.58 | G |
| ATOM | 12572 | CD | ILE G 567 | 105.087 | 82.344 | 3.278 | 1.00 60.58 | G |
| ATOM | 12573 | C | ILE G 567 | 101.926 | 85.091 | 5.947 | 1.00 97.69 | G |
| ATOM | 12574 | O | ILE G 567 | 101.336 | 84.810 | 6.980 | 1.00 97.69 | G |
| ATOM | 12575 | N | ARG G 568 | 102.501 | 86.269 | 5.726 | 1.00100.07 | G |
| ATOM | 12576 | CA | ARG G 568 | 102.435 | 87.347 | 6.700 | 1.00100.07 | G |
| ATOM | 12577 | CB | ARG G 568 | 103.088 | 88.635 | 6.172 | 1.00100.07 | G |
| ATOM | 12578 | CG | ARG G 568 | 104.444 | 88.988 | 6.776 | 1.00100.07 | G |
| ATOM | 12579 | CD | ARG G 568 | 104.879 | 90.378 | 6.346 | 1.00100.07 | G |
| ATOM | 12580 | NE | ARG G 568 | 106.333 | 90.492 | 6.304 | 1.00100.07 | G |
| ATOM | 12581 | CZ | ARG G 568 | 106.988 | 91.553 | 5.841 | 1.00100.07 | G |
| ATOM | 12582 | NH1 | ARG G 568 | 106.322 | 92.605 | 5.381 | 1.00100.07 | G |
| ATOM | 12583 | NH2 | ARG G 568 | 108.314 | 91.559 | 5.819 | 1.00100.07 | G |
| ATOM | 12584 | C | ARG G 568 | 100.960 | 87.608 | 6.877 | 1.00100.07 | G |
| ATOM | 12585 | O | ARG G 568 | 100.307 | 86.994 | 7.721 | 1.00100.07 | G |
| ATOM | 12586 | N | ASN G 569 | 100.437 | 88.508 | 6.049 | 1.00100.07 | G |
| ATOM | 12587 | CA | ASN G 569 | 99.036 | 88.870 | 6.118 | 1.00100.07 | G |
| ATOM | 12588 | CB | ASN G 569 | 98.723 | 89.966 | 5.101 | 1.00 69.10 | G |
| ATOM | 12589 | CG | ASN G 569 | 98.361 | 89.417 | 3.759 | 1.00 69.10 | G |
| ATOM | 12590 | OD1 | ASN G 569 | 99.066 | 88.577 | 3.210 | 1.00 69.10 | G |
| ATOM | 12591 | ND2 | ASN G 569 | 97.254 | 89.890 | 3.211 | 1.00 69.10 | G |
| ATOM | 12592 | C | ASN G 569 | 98.159 | 87.645 | 5.886 | 1.00100.07 | G |
| ATOM | 12593 | O | ASN G 569 | 96.951 | 87.693 | 6.122 | 1.00100.07 | G |
| ATOM | 12594 | N | GLU G 570 | 98.768 | 86.548 | 5.432 | 1.00 58.80 | G |
| ATOM | 12595 | CA | GLU G 570 | 98.029 | 85.307 | 5.209 | 1.00 58.80 | G |
| ATOM | 12596 | CB | GLU G 570 | 98.686 | 84.478 | 4.108 | 1.00 99.33 | G |
| ATOM | 12597 | CG | GLU G 570 | 98.009 | 84.644 | 2.754 | 1.00 99.33 | G |
| ATOM | 12598 | CD | GLU G 570 | 96.751 | 83.805 | 2.623 | 1.00 99.33 | G |
| ATOM | 12599 | OE1 | GLU G 570 | 95.973 | 83.751 | 3.599 | 1.00 99.33 | G |
| ATOM | 12600 | OE2 | GLU G 570 | 96.539 | 83.207 | 1.543 | 1.00 99.33 | G |
| ATOM | 12601 | C | GLU G 570 | 97.949 | 84.502 | 6.503 | 1.00 58.80 | G |
| ATOM | 12602 | O | GLU G 570 | 97.381 | 83.411 | 6.534 | 1.00 58.80 | G |
| ATOM | 12603 | N | LYS G 571 | 98.536 | 85.060 | 7.563 | 1.00100.07 | G |
| ATOM | 12604 | CA | LYS G 571 | 98.534 | 84.467 | 8.903 | 1.00100.07 | G |
| ATOM | 12605 | CB | LYS G 571 | 99.955 | 84.321 | 9.463 | 1.00 99.54 | G |
| ATOM | 12606 | CG | LYS G 571 | 99.999 | 83.812 | 10.899 | 1.00 99.54 | G |
| ATOM | 12607 | CD | LYS G 571 | 101.396 | 83.904 | 11.500 | 1.00 99.54 | G |
| ATOM | 12608 | CE | LYS G 571 | 101.358 | 83.672 | 13.014 | 1.00 99.54 | G |
| ATOM | 12609 | NZ | LYS G 571 | 102.687 | 83.790 | 13.692 | 1.00 99.54 | G |
| ATOM | 12610 | C | LYS G 571 | 97.771 | 85.453 | 9.761 | 1.00100.07 | G |
| ATOM | 12611 | O | LYS G 571 | 97.320 | 85.129 | 10.859 | 1.00100.07 | G |
| ATOM | 12612 | N | ARG G 572 | 97.658 | 86.675 | 9.249 | 1.00 69.60 | G |
| ATOM | 12613 | CA | ARG G 572 | 96.922 | 87.717 | 9.933 | 1.00 69.60 | G |
| ATOM | 12614 | CB | ARG G 572 | 96.559 | 88.849 | 8.974 | 1.00 99.49 | G |
| ATOM | 12615 | CG | ARG G 572 | 95.402 | 89.698 | 9.487 | 1.00 99.49 | G |
| ATOM | 12616 | CD | ARG G 572 | 94.596 | 90.375 | 8.370 | 1.00 99.49 | G |
| ATOM | 12617 | NE | ARG G 572 | 93.357 | 90.966 | 8.888 | 1.00 99.49 | G |
| ATOM | 12618 | CZ | ARG G 572 | 92.505 | 91.698 | 8.174 | 1.00 99.49 | G |
| ATOM | 12619 | NH1 | ARG G 572 | 92.741 | 91.949 | 6.893 | 1.00 99.49 | G |
| ATOM | 12620 | NH2 | ARG G 572 | 91.411 | 92.181 | 8.745 | 1.00 99.49 | G |
| ATOM | 12621 | C | ARG G 572 | 95.644 | 87.034 | 10.361 | 1.00 69.60 | G |
| ATOM | 12622 | O | ARG G 572 | 95.180 | 87.188 | 11.495 | 1.00 69.60 | G |
| ATOM | 12623 | N | MET G 573 | 95.091 | 86.265 | 9.426 | 1.00100.07 | G |
| ATOM | 12624 | CA | MET G 573 | 93.855 | 85.535 | 9.645 | 1.00100.07 | G |
| ATOM | 12625 | CB | MET G 573 | 93.361 | 84.937 | 8.321 | 1.00100.07 | G |
| ATOM | 12626 | CG | MET G 573 | 94.473 | 84.422 | 7.425 | 1.00100.07 | G |
| ATOM | 12627 | SD | MET G 573 | 93.965 | 83.087 | 6.310 | 1.00100.07 | G |
| ATOM | 12628 | CE | MET G 573 | 94.860 | 81.678 | 7.053 | 1.00100.07 | G |
| ATOM | 12629 | C | MET G 573 | 93.918 | 84.443 | 10.722 | 1.00100.07 | G |
| ATOM | 12630 | O | MET G 573 | 92.951 | 84.277 | 11.468 | 1.00100.07 | G |
| ATOM | 12631 | N | LEU G 574 | 95.027 | 83.707 | 10.828 | 1.00 92.74 | G |
| ATOM | 12632 | CA | LEU G 574 | 95.091 | 82.650 | 11.840 | 1.00 92.74 | G |
| ATOM | 12633 | CB | LEU G 574 | 96.466 | 81.996 | 11.927 | 1.00 61.13 | G |
| ATOM | 12634 | CG | LEU G 574 | 96.448 | 81.011 | 13.106 | 1.00 61.13 | G |
| ATOM | 12635 | CD1 | LEU G 574 | 95.320 | 80.038 | 12.928 | 1.00 61.13 | G |
| ATOM | 12636 | CD2 | LEU G 574 | 97.731 | 80.264 | 13.193 | 1.00 61.13 | G |
| ATOM | 12637 | C | LEU G 574 | 94.733 | 83.152 | 13.222 | 1.00 92.74 | G |
| ATOM | 12638 | O | LEU G 574 | 93.666 | 82.831 | 13.746 | 1.00 92.74 | G |
| ATOM | 12639 | N | GLN G 575 | 95.636 | 83.918 | 13.827 | 1.00100.07 | G |
| ATOM | 12640 | CA | GLN G 575 | 95.364 | 84.459 | 15.151 | 1.00100.07 | G |
| ATOM | 12641 | CB | GLN G 575 | 96.471 | 85.414 | 15.598 | 1.00 98.80 | G |
| ATOM | 12642 | CG | GLN G 575 | 96.193 | 86.034 | 16.945 | 1.00 98.80 | G |
| ATOM | 12643 | CD | GLN G 575 | 97.410 | 86.057 | 17.823 | 1.00 98.80 | G |
| ATOM | 12644 | OE1 | GLN G 575 | 98.116 | 85.063 | 17.937 | 1.00 98.80 | G |
| ATOM | 12645 | NE2 | GLN G 575 | 97.659 | 87.184 | 18.464 | 1.00 98.80 | G |
| ATOM | 12646 | C | GLN G 575 | 94.038 | 85.205 | 15.094 | 1.00100.07 | G |

| | | | | | | | | | |
|---|---|---|---|---|---|---|---|---|---|
| ATOM | 12647 | O | GLN | G | 575 | 93.219 | 85.100 | 16.011 | 1.00 100.07 | G |
| ATOM | 12648 | N | GLU | G | 576 | 93.834 | 85.956 | 14.009 | 1.00 53.26 | G |
| ATOM | 12649 | CA | GLU | G | 576 | 92.600 | 86.694 | 13.831 | 1.00 53.26 | G |
| ATOM | 12650 | CB | GLU | G | 576 | 92.437 | 87.116 | 12.372 | 1.00 89.35 | G |
| ATOM | 12651 | CG | GLU | G | 576 | 91.068 | 87.670 | 12.025 | 1.00 89.35 | G |
| ATOM | 12652 | CD | GLU | G | 576 | 90.582 | 88.707 | 13.019 | 1.00 89.35 | G |
| ATOM | 12653 | OE1 | GLU | G | 576 | 91.385 | 89.602 | 13.368 | 1.00 89.35 | G |
| ATOM | 12654 | OE2 | GLU | G | 576 | 89.399 | 88.630 | 13.443 | 1.00 89.35 | G |
| ATOM | 12655 | C | GLU | G | 576 | 91.520 | 85.711 | 14.241 | 1.00 53.26 | G |
| ATOM | 12656 | O | GLU | G | 576 | 90.693 | 85.998 | 15.104 | 1.00 53.26 | G |
| ATOM | 12657 | N | ALA | G | 577 | 91.559 | 84.527 | 13.651 | 1.00 83.08 | G |
| ATOM | 12658 | CA | ALA | G | 577 | 90.586 | 83.509 | 13.984 | 1.00 83.08 | G |
| ATOM | 12659 | CB | ALA | G | 577 | 90.836 | 82.258 | 13.163 | 1.00 89.31 | G |
| ATOM | 12660 | C | ALA | G | 577 | 90.649 | 83.184 | 15.477 | 1.00 83.08 | G |
| ATOM | 12661 | O | ALA | G | 577 | 89.638 | 83.281 | 16.168 | 1.00 83.08 | G |
| ATOM | 12662 | N | VAL | G | 578 | 91.831 | 82.820 | 15.980 | 1.00 49.06 | G |
| ATOM | 12663 | CA | VAL | G | 578 | 91.979 | 82.460 | 17.396 | 1.00 49.06 | G |
| ATOM | 12664 | CB | VAL | G | 578 | 93.428 | 82.178 | 17.762 | 1.00 94.26 | G |
| ATOM | 12665 | CG1 | VAL | G | 578 | 93.482 | 81.450 | 19.106 | 1.00 94.26 | G |
| ATOM | 12666 | CG2 | VAL | G | 578 | 94.087 | 81.373 | 16.660 | 1.00 94.26 | G |
| ATOM | 12667 | C | VAL | G | 578 | 91.468 | 83.528 | 18.350 | 1.00 49.06 | G |
| ATOM | 12668 | O | VAL | G | 578 | 90.684 | 83.244 | 19.263 | 1.00 49.06 | G |
| ATOM | 12669 | N | ASP | G | 579 | 91.942 | 84.753 | 18.159 | 1.00 68.63 | G |
| ATOM | 12670 | CA | ASP | G | 579 | 91.483 | 85.843 | 18.993 | 1.00 68.63 | G |
| ATOM | 12671 | CB | ASP | G | 579 | 92.306 | 87.110 | 18.765 | 1.00 100.07 | G |
| ATOM | 12672 | CG | ASP | G | 579 | 93.656 | 87.057 | 19.457 | 1.00 100.07 | G |
| ATOM | 12673 | OD1 | ASP | G | 579 | 93.702 | 86.659 | 20.649 | 1.00 100.07 | G |
| ATOM | 12674 | OD2 | ASP | G | 579 | 94.664 | 87.422 | 18.810 | 1.00 100.07 | G |
| ATOM | 12675 | C | ASP | G | 579 | 90.058 | 86.056 | 18.547 | 1.00 68.63 | G |
| ATOM | 12676 | O | ASP | G | 579 | 89.722 | 87.088 | 17.955 | 1.00 68.63 | G |
| ATOM | 12677 | N | ALA | G | 580 | 89.244 | 85.037 | 18.818 | 1.00 74.70 | G |
| ATOM | 12678 | CA | ALA | G | 580 | 87.834 | 85.019 | 18.475 | 1.00 74.70 | G |
| ATOM | 12679 | CB | ALA | G | 580 | 87.660 | 84.922 | 16.968 | 1.00 87.10 | G |
| ATOM | 12680 | C | ALA | G | 580 | 87.188 | 83.826 | 19.162 | 1.00 74.70 | G |
| ATOM | 12681 | O | ALA | G | 580 | 86.262 | 83.990 | 19.956 | 1.00 74.70 | G |
| ATOM | 12682 | N | VAL | G | 581 | 87.680 | 82.627 | 18.859 | 1.00 85.22 | G |
| ATOM | 12683 | CA | VAL | G | 581 | 87.150 | 81.414 | 19.475 | 1.00 85.22 | G |
| ATOM | 12684 | CB | VAL | G | 581 | 88.129 | 80.242 | 19.364 | 1.00 54.15 | G |
| ATOM | 12685 | CG1 | VAL | G | 581 | 87.590 | 79.034 | 20.093 | 1.00 54.15 | G |
| ATOM | 12686 | CG2 | VAL | G | 581 | 88.348 | 79.903 | 17.925 | 1.00 54.15 | G |
| ATOM | 12687 | C | VAL | G | 581 | 86.960 | 81.724 | 20.941 | 1.00 85.22 | G |
| ATOM | 12688 | O | VAL | G | 581 | 86.075 | 81.183 | 21.601 | 1.00 85.22 | G |
| ATOM | 12689 | N | ILE | G | 582 | 87.813 | 82.609 | 21.439 | 1.00 66.09 | G |
| ATOM | 12690 | CA | ILE | G | 582 | 87.750 | 83.036 | 22.820 | 1.00 66.09 | G |
| ATOM | 12691 | CB | ILE | G | 582 | 89.108 | 83.595 | 23.265 | 1.00 99.33 | G |
| ATOM | 12692 | CG2 | ILE | G | 582 | 89.185 | 83.647 | 24.779 | 1.00 99.33 | G |
| ATOM | 12693 | CG1 | ILE | G | 582 | 90.220 | 82.681 | 22.747 | 1.00 99.33 | G |
| ATOM | 12694 | CD | ILE | G | 582 | 91.611 | 83.202 | 22.993 | 1.00 99.33 | G |
| ATOM | 12695 | C | ILE | G | 582 | 86.670 | 84.113 | 22.884 | 1.00 66.09 | G |
| ATOM | 12696 | O | ILE | G | 582 | 85.622 | 83.985 | 22.248 | 1.00 66.09 | G |
| ATOM | 12697 | N | ASP | G | 583 | 86.922 | 85.178 | 23.629 | 1.00 100.07 | G |
| ATOM | 12698 | CA | ASP | G | 583 | 85.936 | 86.238 | 23.760 | 1.00 100.07 | G |
| ATOM | 12699 | CB | ASP | G | 583 | 86.386 | 87.247 | 24.813 | 1.00 83.18 | G |
| ATOM | 12700 | CG | ASP | G | 583 | 86.599 | 86.601 | 26.153 | 1.00 83.18 | G |
| ATOM | 12701 | OD1 | ASP | G | 583 | 85.704 | 85.824 | 26.545 | 1.00 83.18 | G |
| ATOM | 12702 | OD2 | ASP | G | 583 | 87.642 | 86.858 | 26.803 | 1.00 83.18 | G |
| ATOM | 12703 | C | ASP | G | 583 | 85.618 | 86.949 | 22.460 | 1.00 100.07 | G |
| ATOM | 12704 | O | ASP | G | 583 | 85.399 | 88.158 | 22.457 | 1.00 100.07 | G |
| ATOM | 12705 | N | ASN | G | 584 | 85.603 | 86.185 | 21.370 | 1.00 30.51 | G |
| ATOM | 12706 | CA | ASN | G | 584 | 85.278 | 86.683 | 20.041 | 1.00 30.51 | G |
| ATOM | 12707 | CB | ASN | G | 584 | 84.303 | 85.708 | 19.391 | 1.00 69.42 | G |
| ATOM | 12708 | CG | ASN | G | 584 | 84.042 | 86.020 | 17.943 | 1.00 69.42 | G |
| ATOM | 12709 | OD1 | ASN | G | 584 | 83.782 | 87.167 | 17.576 | 1.00 69.42 | G |
| ATOM | 12710 | ND2 | ASN | G | 584 | 84.095 | 84.993 | 17.104 | 1.00 69.42 | G |
| ATOM | 12711 | C | ASN | G | 584 | 84.633 | 88.068 | 20.099 | 1.00 30.51 | G |
| ATOM | 12712 | O | ASN | G | 584 | 83.430 | 88.203 | 19.863 | 1.00 30.51 | G |
| ATOM | 12713 | N | GLY | G | 385 | 85.425 | 89.097 | 20.396 | 1.00 100.07 | G |
| ATOM | 12714 | CA | GLY | G | 585 | 84.870 | 90.437 | 20.510 | 1.00 100.07 | G |
| ATOM | 12715 | C | GLY | G | 585 | 85.441 | 91.513 | 19.609 | 1.00 100.07 | G |
| ATOM | 12716 | O | GLY | G | 585 | 86.646 | 91.556 | 19.369 | 1.00 100.07 | G |
| ATOM | 12717 | N | ARG | G | 586 | 84.558 | 92.389 | 19.126 | 1.00 100.07 | G |
| ATOM | 12718 | CA | ARG | G | 586 | 84.910 | 93.499 | 18.235 | 1.00 100.07 | G |
| ATOM | 12719 | CB | ARG | G | 586 | 86.133 | 94.256 | 18.779 | 1.00 99.49 | G |
| ATOM | 12720 | CG | ARG | G | 586 | 85.906 | 94.938 | 20.145 | 1.00 99.49 | G |
| ATOM | 12721 | CD | ARG | G | 586 | 87.091 | 95.843 | 20.536 | 1.00 99.49 | G |
| ATOM | 12722 | NE | ARG | G | 586 | 86.937 | 96.473 | 21.851 | 1.00 99.49 | G |
| ATOM | 12723 | CZ | ARG | G | 586 | 87.779 | 97.373 | 22.358 | 1.00 99.49 | G |
| ATOM | 12724 | NH1 | ARG | G | 586 | 88.848 | 97.764 | 21.672 | 1.00 99.49 | G |
| ATOM | 12725 | NH2 | ARG | G | 586 | 87.546 | 97.891 | 23.555 | 1.00 99.49 | G |
| ATOM | 12726 | C | ARG | G | 586 | 85.144 | 93.044 | 16.782 | 1.00 100.07 | G |
| ATOM | 12727 | O | ARG | G | 586 | 85.863 | 92.077 | 16.526 | 1.00 100.07 | G |
| ATOM | 12728 | N | ARG | G | 587 | 84.538 | 93.770 | 15.842 | 1.00 78.77 | G |
| ATOM | 12729 | CA | ARG | G | 587 | 84.601 | 93.455 | 14.418 | 1.00 78.77 | G |
| ATOM | 12730 | CB | ARG | G | 587 | 86.039 | 93.249 | 13.931 | 1.00 100.07 | G |

```
ATOM  12731  CG   ARG G 587      86.090  92.980  12.427  1.00100.07           G
ATOM  12732  CD   ARG G 587      87.409  92.388  11.909  1.00100.07           G
ATOM  12733  NE   ARG G 587      87.307  92.078  10.475  1.00100.07           G
ATOM  12734  CZ   ARG G 587      88.275  91.540   9.730  1.00100.07           G
ATOM  12735  NH1  ARG G 587      89.449  91.238  10.272  1.00100.07           G
ATOM  12736  NH2  ARG G 587      88.069  91.303   8.437  1.00100.07           G
ATOM  12737  C    ARG G 587      83.821  92.159  14.227  1.00 78.77           G
ATOM  12738  O    ARG G 587      84.336  91.200  13.658  1.00 78.77           G
ATOM  12739  N    GLY G 588      82.585  92.143  14.727  1.00 79.03           G
ATOM  12740  CA   GLY G 588      81.720  90.974  14.641  1.00 79.03           G
ATOM  12741  C    GLY G 588      82.142  89.901  13.655  1.00 79.03           G
ATOM  12742  O    GLY G 588      82.416  90.184  12.490  1.00 79.03           G
ATOM  12743  N    SER G 589      82.200  88.661  14.118  1.00 75.86           G
ATOM  12744  CA   SER G 589      82.588  87.554  13.254  1.00 75.86           G
ATOM  12745  CB   SER G 589      83.758  86.792  13.867  1.00 61.57           G
ATOM  12746  OG   SER G 589      83.412  86.293  15.146  1.00 61.57           G
ATOM  12747  C    SER G 589      81.395  86.624  13.092  1.00 75.86           G
ATOM  12748  O    SER G 589      81.317  85.571  13.725  1.00 75.86           G
ATOM  12749  N    PRO G 590      80.449  87.003  12.226  1.00 67.14           G
ATOM  12750  CD   PRO G 590      80.461  88.258  11.453  1.00 93.37           G
ATOM  12751  CA   PRO G 590      79.231  86.237  11.952  1.00 67.14           G
ATOM  12752  CB   PRO G 590      78.313  87.298  11.369  1.00 93.37           G
ATOM  12753  CG   PRO G 590      79.275  88.084  10.525  1.00 93.37           G
ATOM  12754  C    PRO G 590      79.368  85.033  11.015  1.00 67.14           G
ATOM  12755  O    PRO G 590      80.178  84.129  11.230  1.00 67.14           G
ATOM  12756  N    VAL G 591      78.527  85.047   9.986  1.00 87.84           G
ATOM  12757  CA   VAL G 591      78.463  84.026   8.951  1.00 87.84           G
ATOM  12758  CB   VAL G 591      77.511  82.878   9.365  1.00 38.71           G
ATOM  12759  CG1  VAL G 591      77.480  81.809   8.305  1.00 38.71           G
ATOM  12760  CG2  VAL G 591      77.965  82.276  10.656  1.00 38.71           G
ATOM  12761  C    VAL G 591      77.894  84.777   7.740  1.00 87.84           G
ATOM  12762  O    VAL G 591      77.555  85.956   7.862  1.00 87.84           G
ATOM  12763  N    THR G 592      77.788  84.105   6.591  1.00100.07           G
ATOM  12764  CA   THR G 592      77.278  84.697   5.339  1.00100.07           G
ATOM  12765  CB   THR G 592      75.727  84.452   5.146  1.00 89.62           G
ATOM  12766  OG1  THR G 592      74.992  84.963   6.263  1.00 89.62           G
ATOM  12767  CG2  THR G 592      75.434  82.964   4.993  1.00 89.62           G
ATOM  12768  C    THR G 592      77.579  86.196   5.132  1.00100.07           G
ATOM  12769  O    THR G 592      76.686  86.979   4.771  1.00100.07           G
ATOM  12770  N    ASN G 593      78.844  86.575   5.346  1.00100.07           G
ATOM  12771  CA   ASN G 593      79.310  87.962   5.184  1.00100.07           G
ATOM  12772  CB   ASN G 593      80.836  88.049   5.409  1.00100.07           G
ATOM  12773  CG   ASN G 593      81.213  88.389   6.850  1.00100.07           G
ATOM  12774  OD1  ASN G 593      80.748  89.387   7.411  1.00100.07           G
ATOM  12775  ND2  ASN G 593      82.075  87.569   7.445  1.00100.07           G
ATOM  12776  C    ASN G 593      78.980  88.521   3.787  1.00100.07           G
ATOM  12777  O    ASN G 593      78.645  87.766   2.862  1.00100.07           G
ATOM  12778  N    PRO G 594      79.088  89.851   3.611  0.00 58.09           G
ATOM  12779  CD   PRO G 594      79.220  90.419   2.255  0.00 58.09           G
ATOM  12780  CA   PRO G 594      79.490  90.843   4.615  0.00 58.09           G
ATOM  12781  CB   PRO G 594      80.389  91.770   3.816  0.00 58.09           G
ATOM  12782  CG   PRO G 594      79.641  91.862   2.528  0.00 58.09           G
ATOM  12783  C    PRO G 594      78.314  91.595   5.242  0.00 58.09           G
ATOM  12784  O    PRO G 594      78.493  92.359   6.190  0.00 58.09           G
ATOM  12785  N    GLY G 595      77.118  91.378   4.704  0.00 58.09           G
ATOM  12786  CA   GLY G 595      75.938  92.051   5.218  0.00 58.09           G
ATOM  12787  C    GLY G 595      75.720  91.874   6.709  0.00 58.09           G
ATOM  12788  O    GLY G 595      76.323  91.003   7.336  0.00 58.09           G
ATOM  12789  N    SER G 596      74.855  92.709   7.279  0.00 58.09           G
ATOM  12790  CA   SER G 596      74.549  92.646   8.704  0.00 58.09           G
ATOM  12791  CB   SER G 596      73.750  93.880   9.128  0.00 58.09           G
ATOM  12792  OG   SER G 596      72.537  93.979   8.401  0.00 58.09           G
ATOM  12793  C    SER G 596      73.754  91.383   9.014  0.00 58.09           G
ATOM  12794  O    SER G 596      72.936  90.941   8.206  0.00 58.09           G
ATOM  12795  N    GLU G 597      73.992  90.810  10.189  1.00100.07           G
ATOM  12796  CA   GLU G 597      73.301  89.586  10.594  1.00100.07           G
ATOM  12797  CB   GLU G 597      73.957  88.390   9.890  1.00 99.95           G
ATOM  12798  CG   GLU G 597      73.035  87.213   9.640  1.00 99.95           G
ATOM  12799  CD   GLU G 597      73.664  86.177   8.728  1.00 99.95           G
ATOM  12800  OE1  GLU G 597      74.698  85.593   9.114  1.00 99.95           G
ATOM  12801  OE2  GLU G 597      73.126  85.951   7.622  1.00 99.95           G
ATOM  12802  C    GLU G 597      73.328  89.398  12.125  1.00100.07           G
ATOM  12803  O    GLU G 597      72.897  90.281  12.879  1.00100.07           G
ATOM  12804  N    ARG G 598      73.822  88.246  12.577  1.00 81.01           G
ATOM  12805  CA   ARG G 598      73.922  87.945  14.007  1.00 81.01           G
ATOM  12806  CB   ARG G 598      72.696  87.154  14.492  1.00100.07           G
ATOM  12807  CG   ARG G 598      71.390  87.951  14.629  1.00100.07           G
ATOM  12808  CD   ARG G 598      70.279  87.036  15.167  1.00100.07           G
ATOM  12809  NE   ARG G 598      68.972  87.685  15.287  1.00100.07           G
ATOM  12810  CZ   ARG G 598      67.835  87.033  15.532  1.00100.07           G
ATOM  12811  NH1  ARG G 598      67.841  85.713  15.683  1.00100.07           G
ATOM  12812  NH2  ARG G 598      66.688  87.696  15.611  1.00100.07           G
ATOM  12813  C    ARG G 598      75.186  87.126  14.277  1.00 81.01           G
ATOM  12814  O    ARG G 598      75.288  85.979  13.849  1.00 81.01           G
```

```
ATOM  12815  N   PRO G 599      76.155  87.703  15.007  1.00 67.92           G
ATOM  12816  CD  PRO G 599      75.980  88.937  15.790  1.00 56.78           G
ATOM  12817  CA  PRO G 599      77.428  87.058  15.353  1.00 67.92           G
ATOM  12818  CB  PRO G 599      78.015  87.999  16.407  1.00 56.78           G
ATOM  12819  CG  PRO G 599      76.804  88.645  17.004  1.00 56.78           G
ATOM  12820  C   PRO G 599      77.312  85.611  15.846  1.00 67.92           G
ATOM  12821  O   PRO G 599      76.225  85.029  15.828  1.00 67.92           G
ATOM  12822  N   LEU G 600      78.434  85.040  16.290  1.00 33.54           G
ATOM  12823  CA  LEU G 600      78.468  83.655  16.759  1.00 33.54           G
ATOM  12824  CB  LEU G 600      79.523  82.885  15.969  1.00 50.34           G
ATOM  12825  CG  LEU G 600      79.547  83.272  14.489  1.00 50.34           G
ATOM  12826  CD1 LEU G 600      80.734  82.640  13.780  1.00 50.34           G
ATOM  12827  CD2 LEU G 600      78.242  82.856  13.857  1.00 50.34           G
ATOM  12828  C   LEU G 600      78.766  83.555  18.250  1.00 33.54           G
ATOM  12829  O   LEU G 600      79.576  84.315  18.790  1.00 33.54           G
ATOM  12830  N   ARG G 601      78.110  82.599  18.905  1.00 99.93           G
ATOM  12831  CA  ARG G 601      78.256  82.365  20.345  1.00 99.93           G
ATOM  12832  CB  ARG G 601      77.073  81.516  20.834  1.00100.07           G
ATOM  12833  CG  ARG G 601      75.721  82.173  20.517  1.00100.07           G
ATOM  12834  CD  ARG G 601      74.510  81.448  21.106  1.00100.07           G
ATOM  12835  NE  ARG G 601      73.274  82.207  20.883  1.00100.07           G
ATOM  12836  CZ  ARG G 601      72.044  81.744  21.106  1.00100.07           G
ATOM  12837  NH1 ARG G 301      71.855  80.511  21.563  1.00100.07           G
ATOM  12838  NH2 ARG G 601      70.997  82.519  20.867  1.00100.07           G
ATOM  12839  C   ARG G 601      79.594  81.707  20.697  1.00 99.93           G
ATOM  12840  O   ARG G 601      79.704  80.485  20.775  1.00 99.93           G
ATOM  12841  N   SER G 602      80.600  82.539  20.935  1.00 61.69           G
ATOM  12842  CA  SER G 602      81.942  82.065  21.235  1.00 61.69           G
ATOM  12843  CB  SER G 602      82.966  83.116  20.794  1.00 99.19           G
ATOM  12844  OG  SER G 602      82.786  84.339  21.488  1.00 99.19           G
ATOM  12845  C   SER G 602      82.228  81.686  22.680  1.00 61.69           G
ATOM  12846  O   SER G 602      81.469  82.028  23.591  1.00 61.69           G
ATOM  12847  N   LEU G 603      83.348  80.983  22.870  1.00 56.92           G
ATOM  12848  CA  LEU G 603      83.795  80.551  24.191  1.00 56.92           G
ATOM  12849  CB  LEU G 603      85.145  79.848  24.119  1.00 93.55           G
ATOM  12850  CG  LEU G 603      85.285  78.699  23.133  1.00 93.55           G
ATOM  12851  CD1 LEU G 603      86.633  78.018  23.356  1.00 93.55           G
ATOM  12852  CD2 LEU G 603      84.145  77.721  23.327  1.00 93.55           G
ATOM  12853  C   LEU G 603      83.952  81.766  25.068  1.00 56.92           G
ATOM  12854  O   LEU G 603      84.806  82.621  24.822  1.00 56.92           G
ATOM  12855  N   THR G 604      83.125  81.841  26.098  1.00 46.27           G
ATOM  12856  CA  THR G 604      83.177  82.960  27.022  1.00 46.27           G
ATOM  12857  CB  THR G 604      84.602  83.176  27.555  1.00100.07           G
ATOM  12858  OG1 THR G 604      85.347  81.954  27.453  1.00100.07           G
ATOM  12859  CG2 THR G 604      84.548  83.583  29.015  1.00100.07           G
ATOM  12860  C   THR G 604      82.689  84.217  26.316  1.00 46.27           G
ATOM  12861  O   THR G 604      83.409  85.212  26.188  1.00 46.27           G
ATOM  12862  N   ASP G 605      81.452  84.116  25.837  1.00 83.07           G
ATOM  12863  CA  ASP G 605      80.726  85.174  25.144  1.00 83.07           G
ATOM  12864  CB  ASP G 605      80.995  85.137  23.641  1.00100.07           G
ATOM  12865  CG  ASP G 605      80.070  86.054  22.867  1.00100.07           G
ATOM  12866  OD1 ASP G 605      78.897  85.674  22.676  1.00100.07           G
ATOM  12867  OD2 ASP G 605      80.504  87.158  22.463  1.00100.07           G
ATOM  12868  C   ASP G 605      79.285  84.796  25.423  1.00 83.07           G
ATOM  12869  O   ASP G 605      78.533  85.544  26.048  1.00 83.07           G
ATOM  12870  N   ILE G 606      78.916  83.616  24.941  1.00 79.89           G
ATOM  12871  CA  ILE G 606      77.593  83.055  25.180  1.00 79.89           G
ATOM  12872  CB  ILE G 606      76.939  82.510  23.869  1.00100.07           G
ATOM  12873  CG2 ILE G 606      75.871  81.453  24.176  1.00100.07           G
ATOM  12874  CG1 ILE G 606      76.303  83.677  23.097  1.00100.07           G
ATOM  12875  CD  ILE G 606      75.043  84.258  23.735  1.00100.07           G
ATOM  12876  C   ILE G 606      77.957  81.949  26.158  1.00 79.89           G
ATOM  12877  O   ILE G 606      77.261  80.954  26.335  1.00 79.89           G
ATOM  12878  N   LEU G 607      79.106  82.163  26.778  1.00 76.14           G
ATOM  12879  CA  LEU G 607      79.642  81.280  27.788  1.00 76.14           G
ATOM  12880  CB  LEU G 607      80.797  80.465  27.220  1.00 92.61           G
ATOM  12881  CG  LEU G 607      80.428  79.479  26.116  1.00 92.61           G
ATOM  12882  CD1 LEU G 607      81.671  78.738  25.679  1.00 92.61           G
ATOM  12883  CD2 LEU G 607      79.387  78.497  26.625  1.00 92.61           G
ATOM  12884  C   LEU G 607      80.137  82.259  28.842  1.00 76.14           G
ATOM  12885  O   LEU G 607      80.842  83.221  28.517  1.00 76.14           G
ATOM  12886  N   SER G 608      79.750  82.037  30.095  1.00 84.73           G
ATOM  12887  CA  SER G 608      80.141  82.940  31.172  1.00 84.73           G
ATOM  12888  CB  SER G 608      81.635  83.266  31.069  1.00 72.65           G
ATOM  12889  OG  SER G 608      82.397  82.079  30.879  1.00 72.65           G
ATOM  12890  C   SER G 608      79.304  84.216  31.040  1.00 84.73           G
ATOM  12891  O   SER G 608      78.362  84.429  31.802  1.00 84.73           G
ATOM  12892  N   GLY G 609      79.646  85.043  30.059  1.00 48.23           G
ATOM  12893  CA  GLY G 609      78.925  86.281  29.814  1.00 48.23           G
ATOM  12894  C   GLY G 609      77.513  86.397  30.366  1.00 48.23           G
ATOM  12895  O   GLY G 609      77.331  86.581  31.564  1.00 48.23           G
ATOM  12896  N   LYS G 610      76.507  86.298  29.500  1.00100.07           G
ATOM  12897  CA  LYS G 610      75.108  86.425  29.925  1.00100.07           G
ATOM  12898  CB  LYS G 610      74.213  86.723  28.715  1.00100.07           G
```

| ATOM | 12899 | CG | LYS | G | 610 | 74.583 | 87.986 | 27.951 | 1.00 | 100.07 | G |
|---|---|---|---|---|---|---|---|---|---|---|---|
| ATOM | 12900 | CD | LYS | G | 610 | 73.938 | 87.997 | 26.574 | 1.00 | 100.07 | G |
| ATOM | 12901 | CE | LYS | G | 610 | 74.635 | 88.981 | 25.643 | 1.00 | 100.07 | G |
| ATOM | 12902 | NZ | LYS | G | 610 | 74.195 | 88.837 | 24.221 | 1.00 | 100.07 | G |
| ATOM | 12903 | C | LYS | G | 610 | 74.595 | 85.177 | 30.636 | 1.00 | 100.07 | G |
| ATOM | 12904 | O | LYS | G | 610 | 75.364 | 84.488 | 31.306 | 1.00 | 100.07 | G |
| ATOM | 12905 | N | GLN | G | 611 | 73.292 | 84.913 | 30.492 | 1.00 | 54.57 | G |
| ATOM | 12906 | CA | GLN | G | 611 | 72.633 | 83.749 | 31.091 | 1.00 | 54.57 | G |
| ATOM | 12907 | CB | GLN | G | 611 | 71.281 | 83.493 | 30.403 | 1.00 | 100.07 | G |
| ATOM | 12908 | CG | GLN | G | 611 | 70.109 | 84.395 | 30.833 | 1.00 | 100.07 | G |
| ATOM | 12909 | CD | GLN | G | 611 | 68.775 | 84.030 | 30.135 | 1.00 | 100.07 | G |
| ATOM | 12910 | OE1 | GLN | G | 611 | 68.389 | 82.852 | 30.066 | 1.00 | 100.07 | G |
| ATOM | 12911 | NE2 | GLN | G | 611 | 68.068 | 85.046 | 29.630 | 1.00 | 100.07 | G |
| ATOM | 12912 | C | GLN | G | 611 | 73.497 | 82.493 | 30.950 | 1.00 | 54.57 | G |
| ATOM | 12913 | O | GLN | G | 611 | 73.199 | 81.624 | 30.143 | 1.00 | 54.57 | G |
| ATOM | 12914 | N | GLY | G | 612 | 74.563 | 82.384 | 31.734 | 1.00 | 79.93 | G |
| ATOM | 12915 | CA | GLY | G | 612 | 75.406 | 81.212 | 31.617 | 1.00 | 79.93 | G |
| ATOM | 12916 | C | GLY | G | 612 | 76.576 | 81.115 | 32.575 | 1.00 | 79.93 | G |
| ATOM | 12917 | O | GLY | G | 612 | 76.977 | 82.086 | 33.224 | 1.00 | 79.93 | G |
| ATOM | 12918 | N | ALA | G | 613 | 77.120 | 79.906 | 32.652 | 1.00 | 100.07 | G |
| ATOM | 12919 | CA | ALA | G | 613 | 78.257 | 79.598 | 33.502 | 1.00 | 100.07 | G |
| ATOM | 12920 | CB | ALA | G | 613 | 79.524 | 80.187 | 32.898 | 1.00 | 100.07 | G |
| ATOM | 12921 | C | ALA | G | 613 | 78.088 | 80.076 | 34.938 | 1.00 | 100.07 | G |
| ATOM | 12922 | O | ALA | G | 613 | 77.578 | 79.344 | 35.787 | 1.00 | 100.07 | G |
| ATOM | 12923 | N | PHE | G | 614 | 78.507 | 81.305 | 35.212 | 1.00 | 68.46 | G |
| ATOM | 12924 | CA | PHE | G | 614 | 78.421 | 81.825 | 36.566 | 1.00 | 68.46 | G |
| ATOM | 12925 | CB | PHE | G | 614 | 79.486 | 82.911 | 36.783 | 1.00 | 49.59 | G |
| ATOM | 12926 | CG | PHE | G | 614 | 80.898 | 82.426 | 36.598 | 1.00 | 49.59 | G |
| ATOM | 12927 | CD1 | PHE | G | 614 | 81.682 | 82.912 | 35.556 | 1.00 | 49.59 | G |
| ATOM | 12928 | CD2 | PHE | G | 614 | 81.421 | 81.450 | 37.432 | 1.00 | 49.59 | G |
| ATOM | 12929 | CE1 | PHE | G | 614 | 82.963 | 82.429 | 35.342 | 1.00 | 49.59 | G |
| ATOM | 12930 | CE2 | PHE | G | 614 | 82.698 | 80.958 | 37.231 | 1.00 | 49.59 | G |
| ATOM | 12931 | CZ | PHE | G | 614 | 83.473 | 81.446 | 36.181 | 1.00 | 49.59 | G |
| ATOM | 12932 | C | PHE | G | 614 | 77.051 | 82.361 | 36.971 | 1.00 | 68.46 | G |
| ATOM | 12933 | O | PHE | G | 614 | 76.956 | 83.193 | 37.874 | 1.00 | 68.46 | G |
| ATOM | 12934 | N | ARG | G | 615 | 75.987 | 81.891 | 36.325 | 1.00 | 38.15 | G |
| ATOM | 12935 | CA | ARG | G | 615 | 74.654 | 82.366 | 36.684 | 1.00 | 38.15 | G |
| ATOM | 12936 | CB | ARG | G | 615 | 74.219 | 83.507 | 35.768 | 1.00 | 68.40 | G |
| ATOM | 12937 | CG | ARG | G | 615 | 75.299 | 84.538 | 35.494 | 1.00 | 68.40 | G |
| ATOM | 12938 | CD | ARG | G | 615 | 74.687 | 85.884 | 35.161 | 1.00 | 68.40 | G |
| ATOM | 12939 | NE | ARG | G | 615 | 75.519 | 86.690 | 34.277 | 1.00 | 68.40 | G |
| ATOM | 12940 | CZ | ARG | G | 615 | 75.282 | 87.967 | 34.014 | 1.00 | 68.40 | G |
| ATOM | 12941 | NH1 | ARG | G | 615 | 74.246 | 88.576 | 34.575 | 1.00 | 68.40 | G |
| ATOM | 12942 | NH2 | ARG | G | 615 | 76.065 | 88.628 | 33.177 | 1.00 | 68.40 | G |
| ATOM | 12943 | C | ARG | G | 615 | 73.602 | 81.274 | 36.644 | 1.00 | 38.15 | G |
| ATOM | 12944 | O | ARG | G | 615 | 72.761 | 81.188 | 37.527 | 1.00 | 38.15 | G |
| ATOM | 12945 | N | GLN | G | 616 | 73.640 | 80.428 | 35.628 | 1.00 | 41.80 | G |
| ATOM | 12946 | CA | GLN | G | 616 | 72.637 | 79.385 | 35.554 | 1.00 | 41.80 | G |
| ATOM | 12947 | CB | GLN | G | 616 | 72.773 | 78.585 | 34.258 | 1.00 | 100.07 | G |
| ATOM | 12948 | CG | GLN | G | 616 | 71.518 | 77.788 | 33.932 | 1.00 | 100.07 | G |
| ATOM | 12949 | CD | GLN | G | 616 | 71.433 | 77.401 | 32.474 | 1.00 | 100.07 | G |
| ATOM | 12950 | OE1 | GLN | G | 616 | 71.313 | 78.256 | 31.595 | 1.00 | 100.07 | G |
| ATOM | 12951 | NE2 | GLN | G | 616 | 71.495 | 76.103 | 32.205 | 1.00 | 100.07 | G |
| ATOM | 12952 | C | GLN | G | 616 | 72.663 | 78.458 | 36.767 | 1.00 | 41.80 | G |
| ATOM | 12953 | O | GLN | G | 616 | 73.230 | 77.369 | 36.761 | 1.00 | 41.80 | G |
| ATOM | 12954 | N | ASN | G | 617 | 72.016 | 78.934 | 37.811 | 1.00 | 41.52 | G |
| ATOM | 12955 | CA | ASN | G | 617 | 71.875 | 78.241 | 39.071 | 1.00 | 41.52 | G |
| ATOM | 12956 | CB | ASN | G | 617 | 73.228 | 77.840 | 39.654 | 1.00 | 55.01 | G |
| ATOM | 12957 | CG | ASN | G | 617 | 73.694 | 76.488 | 39.157 | 1.00 | 55.01 | G |
| ATOM | 12958 | OD1 | ASN | G | 617 | 73.027 | 75.480 | 39.347 | 1.00 | 55.01 | G |
| ATOM | 12959 | ND2 | ASN | G | 617 | 74.845 | 76.464 | 38.518 | 1.00 | 55.01 | G |
| ATOM | 12960 | C | ASN | G | 617 | 71.207 | 79.306 | 39.907 | 1.00 | 41.52 | G |
| ATOM | 12961 | O | ASN | G | 617 | 70.217 | 79.053 | 40.591 | 1.00 | 41.52 | G |
| ATOM | 12962 | N | LEU | G | 618 | 71.756 | 80.511 | 39.832 | 1.00 | 38.70 | G |
| ATOM | 12963 | CA | LEU | G | 618 | 71.167 | 81.630 | 40.526 | 1.00 | 38.70 | G |
| ATOM | 12964 | CB | LEU | G | 618 | 71.997 | 82.889 | 40.295 | 1.00 | 19.94 | G |
| ATOM | 12965 | CG | LEU | G | 618 | 73.466 | 82.736 | 40.713 | 1.00 | 19.94 | G |
| ATOM | 12966 | CD1 | LEU | G | 618 | 74.257 | 83.963 | 40.314 | 1.00 | 19.94 | G |
| ATOM | 12967 | CD2 | LEU | G | 618 | 73.555 | 82.490 | 42.228 | 1.00 | 19.94 | G |
| ATOM | 12968 | C | LEU | G | 618 | 69.863 | 81.673 | 39.749 | 1.00 | 38.70 | G |
| ATOM | 12969 | O | LEU | G | 618 | 68.925 | 80.969 | 40.102 | 1.00 | 38.70 | G |
| ATOM | 12970 | N | LEU | G | 619 | 69.808 | 82.449 | 38.672 | 1.00 | 99.98 | G |
| ATOM | 12971 | CA | LEU | G | 619 | 68.598 | 82.510 | 37.855 | 1.00 | 99.98 | G |
| ATOM | 12972 | CB | LEU | G | 619 | 68.928 | 83.021 | 36.454 | 1.00 | 43.46 | G |
| ATOM | 12973 | CG | LEU | G | 619 | 69.107 | 84.510 | 36.169 | 1.00 | 43.46 | G |
| ATOM | 12974 | CD1 | LEU | G | 619 | 70.027 | 85.128 | 37.195 | 1.00 | 43.46 | G |
| ATOM | 12975 | CD2 | LEU | G | 619 | 69.651 | 84.684 | 34.748 | 1.00 | 43.46 | G |
| ATOM | 12976 | C | LEU | G | 619 | 67.958 | 81.121 | 37.738 | 1.00 | 99.98 | G |
| ATOM | 12977 | O | LEU | G | 619 | 68.639 | 80.132 | 37.466 | 1.00 | 99.98 | G |
| ATOM | 12978 | N | GLY | G | 620 | 66.645 | 81.076 | 37.944 | 1.00 | 79.93 | G |
| ATOM | 12979 | CA | GLY | G | 620 | 65.859 | 79.849 | 37.884 | 1.00 | 79.93 | G |
| ATOM | 12980 | C | GLY | G | 620 | 66.407 | 78.473 | 37.513 | 1.00 | 79.93 | G |
| ATOM | 12981 | O | GLY | G | 620 | 67.469 | 78.050 | 37.976 | 1.00 | 79.93 | G |
| ATOM | 12982 | N | LYS | G | 621 | 65.613 | 77.781 | 36.691 | 1.00 | 72.90 | G |

| ATOM | 12983 | CA | LYS G 621 | 65.844 | 76.429 | 36.169 | 1.00 | 72.90 | G |
| ATOM | 12984 | CB | LYS G 621 | 66.924 | 75.690 | 36.958 | 1.00 | 46.06 | G |
| ATOM | 12985 | CG | LYS G 621 | 68.324 | 75.911 | 36.404 | 1.00 | 46.06 | G |
| ATOM | 12986 | CD | LYS G 621 | 69.330 | 74.976 | 37.067 | 1.00 | 46.06 | G |
| ATOM | 12987 | CE | LYS G 621 | 70.722 | 75.151 | 36.490 | 1.00 | 46.06 | G |
| ATOM | 12988 | NZ | LYS G 621 | 71.698 | 74.369 | 37.268 | 1.00 | 46.06 | G |
| ATOM | 12989 | C | LYS G 621 | 64.526 | 75.652 | 36.235 | 1.00 | 72.90 | G |
| ATOM | 12990 | O | LYS G 621 | 63.762 | 75.803 | 37.184 | 1.00 | 72.90 | G |
| ATOM | 12991 | N | ARG G 622 | 64.261 | 74.829 | 35.226 | 1.00 | 28.55 | G |
| ATOM | 12992 | CA | ARG G 622 | 63.023 | 74.059 | 35.150 | 1.00 | 28.55 | G |
| ATOM | 12993 | CB | ARG G 622 | 62.770 | 73.590 | 33.711 | 1.00 | 99.38 | G |
| ATOM | 12994 | CG | ARG G 622 | 62.745 | 74.693 | 32.676 | 1.00 | 99.38 | G |
| ATOM | 12995 | CD | ARG G 622 | 61.448 | 75.469 | 32.695 | 1.00 | 99.38 | G |
| ATOM | 12996 | NE | ARG G 622 | 61.630 | 76.827 | 32.187 | 1.00 | 99.38 | G |
| ATOM | 12997 | CZ | ARG G 622 | 60.653 | 77.721 | 32.056 | 1.00 | 99.38 | G |
| ATOM | 12998 | NH1 | ARG G 622 | 59.407 | 77.403 | 32.392 | 1.00 | 99.38 | G |
| ATOM | 12999 | NH2 | ARG G 622 | 60.924 | 78.942 | 31.603 | 1.00 | 99.38 | G |
| ATOM | 13000 | C | ARG G 622 | 62.947 | 72.843 | 36.063 | 1.00 | 28.55 | G |
| ATOM | 13001 | O | ARG G 622 | 63.176 | 71.720 | 35.616 | 1.00 | 28.55 | G |
| ATOM | 13002 | N | VAL G 623 | 62.617 | 73.056 | 37.333 | 1.00 | 29.29 | G |
| ATOM | 13003 | CA | VAL G 623 | 62.469 | 71.937 | 38.259 | 1.00 | 29.29 | G |
| ATOM | 13004 | CB | VAL G 623 | 61.667 | 72.327 | 39.512 | 1.00 | 100.07 | G |
| ATOM | 13005 | CG1 | VAL G 623 | 61.412 | 71.093 | 40.369 | 1.00 | 100.07 | G |
| ATOM | 13006 | CG2 | VAL G 623 | 62.424 | 73.368 | 40.310 | 1.00 | 100.07 | G |
| ATOM | 13007 | C | VAL G 623 | 61.695 | 70.838 | 37.530 | 1.00 | 29.29 | G |
| ATOM | 13008 | O | VAL G 623 | 60.690 | 71.092 | 36.852 | 1.00 | 29.29 | G |
| ATOM | 13009 | N | ASP G 624 | 62.155 | 69.608 | 37.676 | 1.00 | 89.28 | G |
| ATOM | 13010 | CA | ASP G 624 | 61.512 | 68.520 | 36.983 | 1.00 | 89.28 | G |
| ATOM | 13011 | CB | ASP G 624 | 62.571 | 67.568 | 36.447 | 1.00 | 70.43 | G |
| ATOM | 13012 | CG | ASP G 624 | 62.035 | 66.655 | 35.383 | 1.00 | 70.43 | G |
| ATOM | 13013 | OD1 | ASP G 624 | 61.474 | 67.173 | 34.395 | 1.00 | 70.43 | G |
| ATOM | 13014 | OD2 | ASP G 624 | 62.176 | 65.424 | 35.536 | 1.00 | 70.43 | G |
| ATOM | 13015 | C | ASP G 624 | 60.500 | 67.755 | 37.812 | 1.00 | 89.28 | G |
| ATOM | 13016 | O | ASP G 624 | 60.294 | 66.569 | 37.589 | 1.00 | 89.28 | G |
| ATOM | 13017 | N | TYR G 625 | 59.864 | 68.421 | 38.765 | 1.00 | 78.71 | G |
| ATOM | 13018 | CA | TYR G 625 | 58.857 | 67.755 | 39.581 | 1.00 | 78.71 | G |
| ATOM | 13019 | CB | TYR G 625 | 59.495 | 67.007 | 40.746 | 1.00 | 49.45 | G |
| ATOM | 13020 | CG | TYR G 625 | 59.741 | 65.537 | 40.492 | 1.00 | 49.45 | G |
| ATOM | 13021 | CD1 | TYR G 625 | 60.922 | 65.105 | 39.900 | 1.00 | 49.45 | G |
| ATOM | 13022 | CE1 | TYR G 625 | 61.157 | 63.763 | 39.675 | 1.00 | 49.45 | G |
| ATOM | 13023 | CD2 | TYR G 625 | 58.796 | 64.579 | 40.851 | 1.00 | 49.45 | G |
| ATOM | 13024 | CE2 | TYR G 625 | 59.023 | 63.240 | 40.627 | 1.00 | 49.45 | G |
| ATOM | 13025 | CZ | TYR G 625 | 60.204 | 62.842 | 40.039 | 1.00 | 49.45 | G |
| ATOM | 13026 | OH | TYR G 625 | 60.451 | 61.519 | 39.797 | 1.00 | 49.45 | G |
| ATOM | 13027 | C | TYR G 625 | 57.866 | 68.744 | 40.141 | 1.00 | 78.71 | G |
| ATOM | 13028 | O | TYR G 625 | 57.678 | 68.815 | 41.354 | 1.00 | 78.71 | G |
| ATOM | 13029 | N | SER G 626 | 57.205 | 69.494 | 39.274 | 1.00 | 28.63 | G |
| ATOM | 13030 | CA | SER G 626 | 56.278 | 70.479 | 39.772 | 1.00 | 28.63 | G |
| ATOM | 13031 | CB | SER G 626 | 57.018 | 71.788 | 39.975 | 1.00 | 100.07 | G |
| ATOM | 13032 | OG | SER G 626 | 56.115 | 72.867 | 39.840 | 1.00 | 100.07 | G |
| ATOM | 13033 | C | SER G 626 | 55.033 | 70.769 | 38.969 | 1.00 | 28.63 | G |
| ATOM | 13034 | O | SER G 626 | 55.021 | 70.673 | 37.750 | 1.00 | 28.63 | G |
| ATOM | 13035 | N | GLY G 627 | 53.985 | 71.161 | 39.676 | 1.00 | 90.30 | G |
| ATOM | 13036 | CA | GLY G 627 | 52.740 | 71.523 | 39.030 | 1.00 | 90.30 | G |
| ATOM | 13037 | C | GLY G 627 | 52.401 | 72.899 | 39.566 | 1.00 | 90.30 | G |
| ATOM | 13038 | O | GLY G 627 | 53.085 | 73.379 | 40.468 | 1.00 | 90.30 | G |
| ATOM | 13039 | N | ARG G 628 | 51.374 | 73.547 | 39.030 | 1.00 | 16.46 | G |
| ATOM | 13040 | CA | ARG G 628 | 51.002 | 74.861 | 39.530 | 1.00 | 16.46 | G |
| ATOM | 13041 | CB | ARG G 628 | 52.085 | 75.890 | 39.206 | 1.00 | 93.47 | G |
| ATOM | 13042 | CG | ARG G 628 | 52.472 | 75.980 | 37.757 | 1.00 | 93.47 | G |
| ATOM | 13043 | CD | ARG G 628 | 52.690 | 77.424 | 37.386 | 1.00 | 93.47 | G |
| ATOM | 13044 | NE | ARG G 628 | 51.798 | 77.813 | 36.304 | 1.00 | 93.47 | G |
| ATOM | 13045 | CZ | ARG G 628 | 51.437 | 79.063 | 36.042 | 1.00 | 93.47 | G |
| ATOM | 13046 | NH1 | ARG G 628 | 51.893 | 80.055 | 36.795 | 1.00 | 93.47 | G |
| ATOM | 13047 | NH2 | ARG G 628 | 50.622 | 79.319 | 35.024 | 1.00 | 93.47 | G |
| ATOM | 13048 | C | ARG G 628 | 49.668 | 75.315 | 38.981 | 1.00 | 16.46 | G |
| ATOM | 13049 | O | ARG G 628 | 49.501 | 75.456 | 37.779 | 1.00 | 16.46 | G |
| ATOM | 13050 | N | SER G 629 | 48.709 | 75.548 | 39.867 | 1.00 | 25.34 | G |
| ATOM | 13051 | CA | SER G 629 | 47.382 | 75.965 | 39.440 | 1.00 | 25.34 | G |
| ATOM | 13052 | CB | SER G 629 | 46.411 | 74.800 | 39.566 | 1.00 | 100.07 | G |
| ATOM | 13053 | OG | SER G 629 | 45.122 | 75.168 | 39.115 | 1.00 | 100.07 | G |
| ATOM | 13054 | C | SER G 629 | 46.881 | 77.105 | 40.296 | 1.00 | 25.34 | G |
| ATOM | 13055 | O | SER G 629 | 47.650 | 77.709 | 41.052 | 1.00 | 25.34 | G |
| ATOM | 13056 | N | VAL G 630 | 45.584 | 77.384 | 40.179 | 1.00 | 11.98 | G |
| ATOM | 13057 | CA | VAL G 630 | 44.963 | 78.441 | 40.953 | 1.00 | 11.98 | G |
| ATOM | 13058 | CB | VAL G 630 | 43.650 | 78.871 | 40.364 | 1.00 | 7.52 | G |
| ATOM | 13059 | CG1 | VAL G 630 | 43.026 | 79.925 | 41.270 | 1.00 | 7.52 | G |
| ATOM | 13060 | CG2 | VAL G 630 | 43.858 | 79.409 | 38.988 | 1.00 | 7.52 | G |
| ATOM | 13061 | C | VAL G 630 | 44.694 | 78.052 | 42.403 | 1.00 | 11.98 | G |
| ATOM | 13062 | O | VAL G 630 | 44.238 | 76.951 | 42.716 | 1.00 | 11.98 | G |
| ATOM | 13063 | N | ILE G 631 | 44.960 | 78.995 | 43.286 | 1.00 | 34.03 | G |
| ATOM | 13064 | CA | ILE G 631 | 44.779 | 78.766 | 44.692 | 1.00 | 34.03 | G |
| ATOM | 13065 | CB | ILE G 631 | 45.829 | 79.585 | 45.471 | 1.00 | 68.49 | G |
| ATOM | 13066 | CG2 | ILE G 631 | 45.325 | 79.983 | 46.820 | 1.00 | 68.49 | G |

| | | | | | | | | | |
|---|---|---|---|---|---|---|---|---|---|
| ATOM | 13067 | CG1 | ILE G 631 | 47.086 | 78.742 | 45.631 | 1.00 | 68.49 | G |
| ATOM | 13068 | CD | ILE G 631 | 47.489 | 78.004 | 44.373 | 1.00 | 68.49 | G |
| ATOM | 13069 | C | ILE G 631 | 43.360 | 79.093 | 45.118 | 1.00 | 34.03 | G |
| ATOM | 13070 | O | ILE G 631 | 42.682 | 79.928 | 44.500 | 1.00 | 34.03 | G |
| ATOM | 13071 | N | VAL G 632 | 42.914 | 78.390 | 46.159 | 1.00 | 34.74 | G |
| ATOM | 13072 | CA | VAL G 632 | 41.587 | 78.552 | 46.738 | 1.00 | 34.74 | G |
| ATOM | 13073 | CB | VAL G 632 | 40.559 | 77.618 | 46.049 | 1.00 | 9.48 | G |
| ATOM | 13074 | CG1 | VAL G 632 | 39.632 | 77.010 | 47.063 | 1.00 | 9.48 | G |
| ATOM | 13075 | CG2 | VAL G 632 | 39.744 | 78.401 | 45.048 | 1.00 | 9.48 | G |
| ATOM | 13076 | C | VAL G 632 | 41.643 | 78.249 | 48.238 | 1.00 | 34.74 | G |
| ATOM | 13077 | O | VAL G 632 | 42.370 | 77.353 | 48.694 | 1.00 | 34.74 | G |
| ATOM | 13078 | N | VAL G 633 | 40.878 | 79.025 | 48.999 | 1.00 | 18.50 | G |
| ATOM | 13079 | CA | VAL G 633 | 40.798 | 78.870 | 50.436 | 1.00 | 18.50 | G |
| ATOM | 13080 | CB | VAL G 633 | 40.042 | 80.021 | 51.044 | 1.00 | 35.16 | G |
| ATOM | 13081 | CG1 | VAL G 633 | 38.677 | 80.106 | 50.397 | 1.00 | 35.16 | G |
| ATOM | 13082 | CG2 | VAL G 633 | 39.890 | 79.807 | 52.539 | 1.00 | 35.16 | G |
| ATOM | 13083 | C | VAL G 633 | 40.022 | 77.609 | 50.789 | 1.00 | 18.50 | G |
| ATOM | 13084 | O | VAL G 633 | 39.194 | 77.123 | 50.008 | 1.00 | 18.50 | G |
| ATOM | 13085 | N | GLY G 634 | 40.275 | 77.100 | 51.988 | 1.00 | 15.10 | G |
| ATOM | 13086 | CA | GLY G 634 | 39.578 | 75.923 | 52.465 | 1.00 | 15.10 | G |
| ATOM | 13087 | C | GLY G 634 | 40.061 | 75.554 | 53.850 | 1.00 | 15.10 | G |
| ATOM | 13088 | O | GLY G 634 | 41.266 | 75.446 | 54.061 | 1.00 | 15.10 | G |
| ATOM | 13089 | N | PRO G 635 | 39.159 | 75.386 | 54.821 | 1.00 | 29.71 | G |
| ATOM | 13090 | CD | PRO G 635 | 37.763 | 75.838 | 54.812 | 1.00 | 61.92 | G |
| ATOM | 13091 | CA | PRO G 635 | 39.576 | 75.018 | 56.177 | 1.00 | 29.71 | G |
| ATOM | 13092 | CB | PRO G 635 | 38.283 | 75.107 | 56.967 | 1.00 | 61.92 | G |
| ATOM | 13093 | CG | PRO G 635 | 37.552 | 76.173 | 56.259 | 1.00 | 61.92 | G |
| ATOM | 13094 | C | PRO G 635 | 40.189 | 73.602 | 56.224 | 1.00 | 29.71 | G |
| ATOM | 13095 | O | PRO G 635 | 39.640 | 72.686 | 56.846 | 1.00 | 29.71 | G |
| ATOM | 13096 | N | ALA G 636 | 41.319 | 73.424 | 55.538 | 1.00 | 69.68 | G |
| ATOM | 13097 | CA | ALA G 636 | 42.032 | 72.145 | 55.509 | 1.00 | 69.68 | G |
| ATOM | 13098 | CB | ALA G 636 | 43.073 | 72.138 | 54.341 | 1.00 | 5.07 | G |
| ATOM | 13099 | C | ALA G 636 | 42.729 | 72.080 | 56.866 | 1.00 | 69.68 | G |
| ATOM | 13100 | O | ALA G 636 | 42.862 | 73.110 | 57.514 | 1.00 | 69.68 | G |
| ATOM | 13101 | N | ALA G 637 | 43.151 | 70.900 | 57.316 | 1.00 | 64.90 | G |
| ATOM | 13102 | CA | ALA G 637 | 43.832 | 70.815 | 58.614 | 1.00 | 64.90 | G |
| ATOM | 13103 | CB | ALA G 637 | 44.521 | 69.484 | 58.788 | 1.00 | 100.07 | G |
| ATOM | 13104 | C | ALA G 637 | 44.850 | 71.928 | 58.601 | 1.00 | 64.90 | G |
| ATOM | 13105 | O | ALA G 637 | 45.944 | 71.792 | 58.055 | 1.00 | 64.90 | G |
| ATOM | 13106 | N | ALA G 638 | 44.456 | 73.044 | 59.190 | 1.00 | 92.94 | G |
| ATOM | 13107 | CA | ALA G 638 | 45.288 | 74.218 | 59.222 | 1.00 | 92.94 | G |
| ATOM | 13108 | CB | ALA G 638 | 45.005 | 75.022 | 60.440 | 1.00 | 25.01 | G |
| ATOM | 13109 | C | ALA G 638 | 46.753 | 73.911 | 59.166 | 1.00 | 92.94 | G |
| ATOM | 13110 | O | ALA G 638 | 47.239 | 72.985 | 59.814 | 1.00 | 92.94 | G |
| ATOM | 13111 | N | LEU G 639 | 47.445 | 74.708 | 58.367 | 1.00 | 63.12 | G |
| ATOM | 13112 | CA | LEU G 639 | 48.878 | 74.610 | 58.210 | 1.00 | 63.12 | G |
| ATOM | 13113 | CB | LEU G 639 | 49.560 | 75.097 | 59.496 | 1.00 | 30.13 | G |
| ATOM | 13114 | CG | LEU G 639 | 48.719 | 75.720 | 60.625 | 1.00 | 30.13 | G |
| ATOM | 13115 | CD1 | LEU G 639 | 49.628 | 76.005 | 61.813 | 1.00 | 30.13 | G |
| ATOM | 13116 | CD2 | LEU G 639 | 48.040 | 76.992 | 60.159 | 1.00 | 30.13 | G |
| ATOM | 13117 | C | LEU G 639 | 49.310 | 73.189 | 57.908 | 1.00 | 63.12 | G |
| ATOM | 13118 | O | LEU G 639 | 49.639 | 72.838 | 56.783 | 1.00 | 63.12 | G |
| ATOM | 13119 | N | HIS G 640 | 49.308 | 72.381 | 58.947 | 1.00 | 58.21 | G |
| ATOM | 13120 | CA | HIS G 640 | 49.691 | 71.000 | 58.872 | 1.00 | 58.21 | G |
| ATOM | 13121 | CB | HIS G 640 | 49.015 | 70.275 | 60.019 | 1.00 | 83.80 | G |
| ATOM | 13122 | CG | HIS G 640 | 49.760 | 69.077 | 60.489 | 1.00 | 83.80 | G |
| ATOM | 13123 | CD2 | HIS G 640 | 49.334 | 67.944 | 61.087 | 1.00 | 83.80 | G |
| ATOM | 13124 | ND1 | HIS G 640 | 51.132 | 68.988 | 60.422 | 1.00 | 83.80 | G |
| ATOM | 13125 | CE1 | HIS G 640 | 51.521 | 67.847 | 60.962 | 1.00 | 83.80 | G |
| ATOM | 13126 | NE2 | HIS G 640 | 50.451 | 67.195 | 61.376 | 1.00 | 83.80 | G |
| ATOM | 13127 | C | HIS G 640 | 49.422 | 70.253 | 57.556 | 1.00 | 58.21 | G |
| ATOM | 13128 | O | HIS G 640 | 49.986 | 69.181 | 57.359 | 1.00 | 58.21 | G |
| ATOM | 13129 | N | GLN G 641 | 48.592 | 70.787 | 56.652 | 1.00 | 37.38 | G |
| ATOM | 13130 | CA | GLN G 641 | 48.288 | 70.069 | 55.407 | 1.00 | 37.38 | G |
| ATOM | 13131 | CB | GLN G 641 | 46.961 | 69.326 | 55.561 | 1.00 | 45.66 | G |
| ATOM | 13132 | CG | GLN G 641 | 46.911 | 68.476 | 56.831 | 1.00 | 45.66 | G |
| ATOM | 13133 | CD | GLN G 641 | 45.771 | 67.479 | 56.865 | 1.00 | 45.66 | G |
| ATOM | 13134 | OE1 | GLN G 641 | 44.609 | 67.828 | 56.636 | 1.00 | 45.66 | G |
| ATOM | 13135 | NE2 | GLN G 641 | 46.101 | 66.224 | 57.172 | 1.00 | 45.66 | G |
| ATOM | 13136 | C | GLN G 641 | 48.259 | 70.931 | 54.158 | 1.00 | 37.38 | G |
| ATOM | 13137 | O | GLN G 641 | 48.869 | 71.982 | 54.139 | 1.00 | 37.38 | G |
| ATOM | 13138 | N | CYS G 642 | 47.546 | 70.501 | 53.116 | 1.00 | 91.93 | G |
| ATOM | 13139 | CA | CYS G 642 | 47.514 | 71.262 | 51.863 | 1.00 | 91.93 | G |
| ATOM | 13140 | CB | CYS G 642 | 48.696 | 70.842 | 50.997 | 1.00 | 28.38 | G |
| ATOM | 13141 | SG | CYS G 642 | 48.976 | 71.902 | 49.585 | 1.00 | 28.38 | G |
| ATOM | 13142 | C | CYS G 642 | 46.235 | 71.165 | 51.027 | 1.00 | 91.93 | G |
| ATOM | 13143 | O | CYS G 642 | 45.134 | 71.169 | 51.570 | 1.00 | 91.93 | G |
| ATOM | 13144 | N | GLY G 643 | 46.406 | 71.092 | 49.702 | 1.00 | 24.53 | G |
| ATOM | 13145 | CA | GLY G 643 | 45.296 | 71.008 | 48.753 | 1.00 | 24.53 | G |
| ATOM | 13146 | C | GLY G 643 | 45.601 | 70.019 | 47.634 | 1.00 | 24.53 | G |
| ATOM | 13147 | O | GLY G 643 | 45.687 | 68.822 | 47.901 | 1.00 | 24.53 | G |
| ATOM | 13148 | N | LEU G 644 | 45.768 | 70.490 | 46.394 | 1.00 | 40.04 | G |
| ATOM | 13149 | CA | LEU G 644 | 46.078 | 69.603 | 45.251 | 1.00 | 40.04 | G |
| ATOM | 13150 | CB | LEU G 644 | 47.129 | 68.551 | 45.622 | 1.00 | 19.81 | G |

| | | | | | | | | | | |
|---|---|---|---|---|---|---|---|---|---|---|
| ATOM | 13151 | CG | LEU | G | 644 | 48.596 | 68.886 | 45.827 | 1.00 19.81 | G |
| ATOM | 13152 | CD1 | LEU | G | 644 | 48.763 | 69.685 | 47.086 | 1.00 19.81 | G |
| ATOM | 13153 | CD2 | LEU | G | 644 | 49.379 | 67.595 | 45.946 | 1.00 19.81 | G |
| ATOM | 13154 | C | LEU | G | 644 | 44.914 | 68.828 | 44.635 | 1.00 40.04 | G |
| ATOM | 13155 | O | LEU | G | 644 | 44.300 | 67.997 | 45.296 | 1.00 40.04 | G |
| ATOM | 13156 | N | PRO | G | 645 | 44.626 | 69.049 | 43.348 | 1.00 38.50 | G |
| ATOM | 13157 | CD | PRO | G | 645 | 45.406 | 69.783 | 42.347 | 1.00 17.71 | G |
| ATOM | 13158 | CA | PRO | G | 645 | 43.521 | 68.314 | 42.720 | 1.00 38.50 | G |
| ATOM | 13159 | CB | PRO | G | 645 | 43.562 | 68.775 | 41.268 | 1.00 17.71 | G |
| ATOM | 13160 | CG | PRO | G | 645 | 44.372 | 70.066 | 41.310 | 1.00 17.71 | G |
| ATOM | 13161 | C | PRO | G | 645 | 43.922 | 66.858 | 42.831 | 1.00 38.50 | G |
| ATOM | 13162 | O | PRO | G | 645 | 45.116 | 66.567 | 42.882 | 1.00 38.50 | G |
| ATOM | 13163 | N | LYS | G | 646 | 42.973 | 65.932 | 42.865 | 1.00 80.83 | G |
| ATOM | 13164 | CA | LYS | G | 646 | 43.392 | 64.546 | 42.979 | 1.00 80.83 | G |
| ATOM | 13165 | CB | LYS | G | 646 | 42.257 | 63.646 | 43.454 | 1.00 39.56 | G |
| ATOM | 13166 | CG | LYS | G | 646 | 41.140 | 63.342 | 42.490 | 1.00 39.56 | G |
| ATOM | 13167 | CD | LYS | G | 646 | 40.197 | 62.424 | 43.240 | 1.00 39.56 | G |
| ATOM | 13168 | CE | LYS | G | 646 | 39.155 | 61.766 | 42.373 | 1.00 39.56 | G |
| ATOM | 13169 | NZ | LYS | G | 646 | 38.444 | 60.697 | 43.168 | 1.00 39.56 | G |
| ATOM | 13170 | C | LYS | G | 646 | 43.918 | 64.084 | 41.650 | 1.00 80.83 | G |
| ATOM | 13171 | O | LYS | G | 646 | 43.965 | 62.902 | 41.358 | 1.00 80.83 | G |
| ATOM | 13172 | N | ARG | G | 647 | 44.316 | 65.051 | 40.844 | 1.00 49.85 | G |
| ATOM | 13173 | CA | ARG | G | 647 | 44.868 | 64.794 | 39.534 | 1.00 49.85 | G |
| ATOM | 13174 | CB | ARG | G | 647 | 44.283 | 65.796 | 38.543 | 1.00 99.57 | G |
| ATOM | 13175 | CG | ARG | G | 647 | 44.334 | 65.362 | 37.102 | 1.00 99.57 | G |
| ATOM | 13176 | CD | ARG | G | 647 | 43.502 | 64.113 | 36.879 | 1.00 99.57 | G |
| ATOM | 13177 | NE | ARG | G | 647 | 43.402 | 63.777 | 35.460 | 1.00 99.57 | G |
| ATOM | 13178 | CZ | ARG | G | 647 | 42.906 | 62.634 | 34.990 | 1.00 99.57 | G |
| ATOM | 13179 | NH1 | ARG | G | 647 | 42.461 | 61.700 | 35.828 | 1.00 99.57 | G |
| ATOM | 13180 | NH2 | ARG | G | 647 | 42.859 | 62.427 | 33.677 | 1.00 99.57 | G |
| ATOM | 13181 | C | ARG | G | 647 | 46.367 | 65.015 | 39.710 | 1.00 49.85 | G |
| ATOM | 13182 | O | ARG | G | 647 | 47.125 | 64.056 | 39.787 | 1.00 49.85 | G |
| ATOM | 13183 | N | MET | G | 648 | 46.763 | 66.289 | 39.816 | 1.00 29.00 | G |
| ATOM | 13184 | CA | MET | G | 548 | 48.156 | 66.717 | 39.993 | 1.00 29.00 | G |
| ATOM | 13185 | CB | MET | G | 648 | 48.243 | 68.102 | 40.649 | 1.00 30.28 | G |
| ATOM | 13186 | CG | MET | G | 648 | 47.489 | 69.223 | 39.953 | 1.00 30.28 | G |
| ATOM | 13187 | SD | MET | G | 648 | 48.145 | 70.888 | 40.324 | 1.00 30.28 | G |
| ATOM | 13188 | CE | MET | G | 648 | 48.852 | 70.663 | 41.989 | 1.00 30.28 | G |
| ATOM | 13189 | C | MET | G | 648 | 48.936 | 65.761 | 40.858 | 1.00 29.00 | G |
| ATOM | 13190 | O | MET | G | 648 | 50.023 | 65.337 | 40.484 | 1.00 29.00 | G |
| ATOM | 13191 | N | ALA | G | 649 | 48.382 | 65.430 | 42.020 | 1.00 26.60 | G |
| ATOM | 13192 | CA | ALA | G | 649 | 49.066 | 64.528 | 42.939 | 1.00 26.60 | G |
| ATOM | 13193 | CB | ALA | G | 649 | 48.095 | 64.021 | 44.027 | 1.00 10.22 | G |
| ATOM | 13194 | C | ALA | G | 649 | 49.628 | 63.363 | 42.131 | 1.00 26.60 | G |
| ATOM | 13195 | O | ALA | G | 649 | 50.809 | 62.997 | 42.254 | 1.00 26.60 | G |
| ATOM | 13196 | N | LEU | G | 650 | 48.778 | 62.791 | 41.288 | 1.00 49.03 | G |
| ATOM | 13197 | CA | LEU | G | 650 | 49.195 | 61.683 | 40.447 | 1.00 49.03 | G |
| ATOM | 13198 | CB | LEU | G | 650 | 48.053 | 61.267 | 39.511 | 1.00 47.03 | G |
| ATOM | 13199 | CG | LEU | G | 650 | 48.350 | 60.182 | 38.470 | 1.00 47.03 | G |
| ATOM | 13200 | CD1 | LEU | G | 650 | 48.809 | 58.909 | 39.163 | 1.00 47.03 | G |
| ATOM | 13201 | CD2 | LEU | G | 650 | 47.102 | 59.920 | 37.639 | 1.00 47.03 | G |
| ATOM | 13202 | C | LEU | G | 650 | 50.408 | 62.105 | 39.627 | 1.00 49.03 | G |
| ATOM | 13203 | O | LEU | G | 650 | 51.540 | 61.729 | 39.936 | 1.00 49.03 | G |
| ATOM | 13204 | N | GLU | G | 651 | 50.159 | 62.915 | 38.600 | 1.00 48.76 | G |
| ATOM | 13205 | CA | GLU | G | 651 | 51.206 | 63.382 | 37.702 | 1.00 48.76 | G |
| ATOM | 13206 | CB | GLU | G | 651 | 50.737 | 64.594 | 36.904 | 1.00 84.05 | G |
| ATOM | 13207 | CG | GLU | G | 651 | 51.026 | 64.488 | 35.413 | 1.00 84.05 | G |
| ATOM | 13208 | CD | GLU | G | 651 | 52.443 | 64.041 | 35.119 | 1.00 84.05 | G |
| ATOM | 13209 | OE1 | GLU | G | 651 | 53.375 | 64.581 | 35.748 | 1.00 84.05 | G |
| ATOM | 13210 | OE2 | GLU | G | 651 | 52.626 | 63.160 | 34.252 | 1.00 84.05 | G |
| ATOM | 13211 | C | GLU | G | 651 | 52.501 | 63.719 | 38.410 | 1.00 48.76 | G |
| ATOM | 13212 | O | GLU | G | 651 | 53.559 | 63.655 | 37.801 | 1.00 48.76 | G |
| ATOM | 13213 | N | LEU | G | 652 | 52.431 | 64.083 | 39.687 | 1.00 47.24 | G |
| ATOM | 13214 | CA | LEU | G | 652 | 53.650 | 64.397 | 40.419 | 1.00 47.24 | G |
| ATOM | 13215 | CB | LEU | G | 652 | 53.376 | 65.324 | 41.613 | 1.00 47.90 | G |
| ATOM | 13216 | CG | LEU | G | 652 | 53.281 | 66.856 | 41.463 | 1.00 47.90 | G |
| ATOM | 13217 | CD1 | LEU | G | 652 | 54.230 | 67.347 | 40.356 | 1.00 47.90 | G |
| ATOM | 13218 | CD2 | LEU | G | 652 | 51.850 | 67.267 | 41.166 | 1.00 47.90 | G |
| ATOM | 13219 | C | LEU | G | 652 | 54.310 | 63.122 | 40.919 | 1.00 47.24 | G |
| ATOM | 13220 | O | LEU | G | 652 | 55.413 | 62.784 | 40.509 | 1.00 47.24 | G |
| ATOM | 13221 | N | PHE | G | 653 | 53.620 | 62.400 | 41.787 | 1.00 56.79 | G |
| ATOM | 13222 | CA | PHE | G | 653 | 54.175 | 61.179 | 42.354 | 1.00 56.79 | G |
| ATOM | 13223 | CB | PHE | G | 653 | 53.487 | 60.905 | 43.690 | 1.00 25.78 | G |
| ATOM | 13224 | CG | PHE | G | 653 | 53.758 | 61.954 | 44.725 | 1.00 25.78 | G |
| ATOM | 13225 | CD1 | PHE | G | 653 | 53.278 | 63.242 | 44.569 | 1.00 25.78 | G |
| ATOM | 13226 | CD2 | PHE | G | 653 | 54.540 | 61.666 | 45.830 | 1.00 25.78 | G |
| ATOM | 13227 | CE1 | PHE | G | 653 | 53.579 | 64.224 | 45.495 | 1.00 25.78 | G |
| ATOM | 13228 | CE2 | PHE | G | 653 | 54.841 | 62.649 | 46.754 | 1.00 25.78 | G |
| ATOM | 13229 | CZ | PHE | G | 653 | 54.361 | 63.928 | 46.584 | 1.00 25.78 | G |
| ATOM | 13230 | C | PHE | G | 653 | 54.133 | 59.924 | 41.473 | 1.00 56.79 | G |
| ATOM | 13231 | O | PHE | G | 653 | 54.311 | 58.806 | 41.963 | 1.00 56.79 | G |
| ATOM | 13232 | N | LYS | G | 654 | 53.916 | 60.105 | 40.174 | 1.00 40.62 | G |
| ATOM | 13233 | CA | LYS | G | 654 | 53.854 | 58.971 | 39.255 | 1.00 40.62 | G |
| ATOM | 13234 | CB | LYS | G | 654 | 53.914 | 59.473 | 37.808 | 1.00 99.70 | G |

| ATOM | 13235 | CG | LYS G 654 | 53.341 | 58.518 | 36.779 | 1.00 | 99.70 | G |
| ATOM | 13236 | CD | LYS G 654 | 52.932 | 59.276 | 35.524 | 1.00 | 99.70 | G |
| ATOM | 13237 | CE | LYS G 654 | 52.021 | 58.444 | 34.652 | 1.00 | 99.70 | G |
| ATOM | 13238 | NZ | LYS G 654 | 51.344 | 59.299 | 33.652 | 1.00 | 99.70 | G |
| ATOM | 13239 | C | LYS G 654 | 54.996 | 57.992 | 39.551 | 1.00 | 40.62 | G |
| ATOM | 13240 | O | LYS G 654 | 54.764 | 56.925 | 40.117 | 1.00 | 40.62 | G |
| ATOM | 13241 | N | PRO G 655 | 56.248 | 58.364 | 39.212 | 1.00 | 28.87 | G |
| ATOM | 13242 | CD | PRO G 655 | 56.711 | 59.692 | 38.775 | 1.00 | 54.28 | G |
| ATOM | 13243 | CA | PRO G 655 | 57.400 | 57.494 | 39.457 | 1.00 | 28.87 | G |
| ATOM | 13244 | CB | PRO G 655 | 58.588 | 58.421 | 39.247 | 1.00 | 54.28 | G |
| ATOM | 13245 | CG | PRO G 655 | 58.084 | 59.385 | 38.254 | 1.00 | 54.28 | G |
| ATOM | 13246 | C | PRO G 655 | 57.359 | 56.982 | 40.870 | 1.00 | 28.87 | G |
| ATOM | 13247 | O | PRO G 655 | 57.877 | 55.921 | 41.169 | 1.00 | 28.87 | G |
| ATOM | 13248 | N | PHE G 656 | 56.745 | 57.756 | 41.746 | 1.00 | 35.11 | G |
| ATOM | 13249 | CA | PHE G 656 | 56.658 | 57.361 | 43.133 | 1.00 | 35.11 | G |
| ATOM | 13250 | CB | PHE G 656 | 56.374 | 58.585 | 44.010 | 1.00 | 60.65 | G |
| ATOM | 13251 | CG | PHE G 656 | 57.544 | 58.999 | 44.841 | 1.00 | 60.65 | G |
| ATOM | 13252 | CD1 | PHE G 656 | 58.759 | 59.294 | 44.244 | 1.00 | 60.65 | G |
| ATOM | 13253 | CD2 | PHE G 656 | 57.459 | 59.003 | 46.225 | 1.00 | 60.65 | G |
| ATOM | 13254 | CE1 | PHE G 656 | 59.875 | 59.576 | 45.012 | 1.00 | 60.65 | G |
| ATOM | 13255 | CE2 | PHE G 656 | 58.570 | 59.283 | 47.008 | 1.00 | 60.65 | G |
| ATOM | 13256 | CZ | PHE G 656 | 59.782 | 59.568 | 46.402 | 1.00 | 60.65 | G |
| ATOM | 13257 | C | PHE G 656 | 55.568 | 56.334 | 43.280 | 1.00 | 35.11 | G |
| ATOM | 13258 | O | PHE G 656 | 55.662 | 55.425 | 44.102 | 1.00 | 35.11 | G |
| ATOM | 13259 | N | LEU G 657 | 54.537 | 56.489 | 42.464 | 1.00 | 65.32 | G |
| ATOM | 13260 | CA | LEU G 657 | 53.414 | 55.586 | 42.488 | 1.00 | 65.32 | G |
| ATOM | 13261 | CB | LEU G 657 | 52.169 | 56.265 | 41.898 | 1.00 | 19.03 | G |
| ATOM | 13262 | CG | LEU G 657 | 50.975 | 55.329 | 41.619 | 1.00 | 19.03 | G |
| ATOM | 13263 | CD1 | LEU G 657 | 50.680 | 54.490 | 42.870 | 1.00 | 19.03 | G |
| ATOM | 13264 | CD2 | LEU G 657 | 49.739 | 56.121 | 41.187 | 1.00 | 19.03 | G |
| ATOM | 13265 | C | LEU G 657 | 53.706 | 54.284 | 41.744 | 1.00 | 65.32 | G |
| ATOM | 13266 | O | LEU G 657 | 53.362 | 53.211 | 42.235 | 1.00 | 65.32 | G |
| ATOM | 13267 | N | LEU G 658 | 54.346 | 54.358 | 40.578 | 1.00 | 78.99 | G |
| ATOM | 13268 | CA | LEU G 658 | 54.639 | 53.146 | 39.805 | 1.00 | 78.99 | G |
| ATOM | 13269 | CB | LEU G 658 | 55.548 | 53.470 | 38.619 | 1.00 | 45.38 | G |
| ATOM | 13270 | CG | LEU G 658 | 55.077 | 54.636 | 37.735 | 1.00 | 45.38 | G |
| ATOM | 13271 | CD1 | LEU G 658 | 55.955 | 54.755 | 36.495 | 1.00 | 45.38 | G |
| ATOM | 13272 | CD2 | LEU G 658 | 53.636 | 54.419 | 37.334 | 1.00 | 45.38 | G |
| ATOM | 13273 | C | LEU G 658 | 55.258 | 52.033 | 40.646 | 1.00 | 78.99 | G |
| ATOM | 13274 | O | LEU G 658 | 55.009 | 50.860 | 40.397 | 1.00 | 78.99 | G |
| ATOM | 13275 | N | LYS G 659 | 56.061 | 52.401 | 41.639 | 1.00 | 75.27 | G |
| ATOM | 13276 | CA | LYS G 659 | 56.687 | 51.424 | 42.535 | 1.00 | 75.27 | G |
| ATOM | 13277 | CB | LYS G 659 | 57.680 | 52.121 | 43.476 | 1.00 | 100.07 | G |
| ATOM | 13278 | CG | LYS G 659 | 58.019 | 51.337 | 44.753 | 1.00 | 100.07 | G |
| ATOM | 13279 | CD | LYS G 659 | 58.850 | 52.187 | 45.715 | 1.00 | 100.07 | G |
| ATOM | 13280 | CE | LYS G 659 | 59.066 | 51.485 | 47.051 | 1.00 | 100.07 | G |
| ATOM | 13281 | NZ | LYS G 659 | 60.031 | 52.214 | 47.939 | 1.00 | 100.07 | G |
| ATOM | 13282 | C | LYS G 659 | 55.620 | 50.731 | 43.375 | 1.00 | 75.27 | G |
| ATOM | 13283 | O | LYS G 659 | 55.738 | 49.551 | 43.691 | 1.00 | 75.27 | G |
| ATOM | 13284 | N | LYS G 660 | 54.597 | 51.492 | 43.753 | 1.00 | 80.48 | G |
| ATOM | 13285 | CA | LYS G 660 | 53.489 | 50.986 | 44.551 | 1.00 | 80.48 | G |
| ATOM | 13286 | CB | LYS G 660 | 52.409 | 52.064 | 44.699 | 1.00 | 98.60 | G |
| ATOM | 13287 | CG | LYS G 660 | 51.235 | 51.702 | 45.600 | 1.00 | 98.60 | G |
| ATOM | 13288 | CD | LYS G 660 | 51.597 | 51.857 | 47.075 | 1.00 | 98.60 | G |
| ATOM | 13289 | CE | LYS G 660 | 50.384 | 51.647 | 47.984 | 1.00 | 98.60 | G |
| ATOM | 13290 | NZ | LYS G 660 | 50.742 | 51.783 | 49.432 | 1.00 | 98.60 | G |
| ATOM | 13291 | C | LYS G 660 | 52.911 | 49.804 | 43.803 | 1.00 | 80.48 | G |
| ATOM | 13292 | O | LYS G 660 | 53.372 | 48.677 | 43.952 | 1.00 | 80.48 | G |
| ATOM | 13293 | N | MET G 661 | 51.909 | 50.098 | 42.981 | 1.00 | 100.07 | G |
| ATOM | 13294 | CA | MET G 661 | 51.205 | 49.114 | 42.172 | 1.00 | 100.07 | G |
| ATOM | 13295 | CB | MET G 661 | 50.988 | 49.691 | 40.775 | 1.00 | 51.26 | G |
| ATOM | 13296 | CG | MET G 661 | 50.066 | 50.902 | 40.804 | 1.00 | 51.26 | G |
| ATOM | 13297 | SD | MET G 661 | 49.618 | 51.549 | 39.191 | 1.00 | 51.26 | G |
| ATOM | 13298 | CE | MET G 661 | 50.071 | 53.262 | 39.371 | 1.00 | 51.26 | G |
| ATOM | 13299 | C | MET G 661 | 51.825 | 47.716 | 42.101 | 1.00 | 100.07 | G |
| ATOM | 13300 | O | MET G 661 | 51.199 | 46.749 | 42.546 | 1.00 | 100.07 | G |
| ATOM | 13301 | N | GLU G 662 | 53.037 | 47.592 | 41.562 | 1.00 | 99.55 | G |
| ATOM | 13302 | CA | GLU G 662 | 53.666 | 46.272 | 41.482 | 1.00 | 99.55 | G |
| ATOM | 13303 | CB | GLU G 662 | 54.955 | 46.304 | 40.672 | 1.00 | 100.07 | G |
| ATOM | 13304 | CG | GLU G 662 | 55.505 | 44.904 | 40.447 | 1.00 | 100.07 | G |
| ATOM | 13305 | CD | GLU G 662 | 56.878 | 44.899 | 39.814 | 1.00 | 100.07 | G |
| ATOM | 13306 | OE1 | GLU G 662 | 57.849 | 45.282 | 40.500 | 1.00 | 100.07 | G |
| ATOM | 13307 | OE2 | GLU G 662 | 56.986 | 44.513 | 38.629 | 1.00 | 100.07 | G |
| ATOM | 13308 | C | GLU G 662 | 53.979 | 45.743 | 42.875 | 1.00 | 99.55 | G |
| ATOM | 13309 | O | GLU G 662 | 53.684 | 44.593 | 43.192 | 1.00 | 99.55 | G |
| ATOM | 13310 | N | GLU G 663 | 54.614 | 46.574 | 43.693 | 1.00 | 100.07 | G |
| ATOM | 13311 | CA | GLU G 663 | 54.911 | 46.188 | 45.065 | 1.00 | 100.07 | G |
| ATOM | 13312 | CB | GLU G 663 | 55.613 | 47.328 | 45.809 | 1.00 | 100.07 | G |
| ATOM | 13313 | CG | GLU G 663 | 55.546 | 47.179 | 47.324 | 1.00 | 100.07 | G |
| ATOM | 13314 | CD | GLU G 663 | 55.596 | 48.509 | 48.062 | 1.00 | 100.07 | G |
| ATOM | 13315 | OE1 | GLU G 663 | 55.020 | 49.502 | 47.556 | 1.00 | 100.07 | G |
| ATOM | 13316 | OE2 | GLU G 663 | 56.194 | 48.552 | 49.162 | 1.00 | 100.07 | G |
| ATOM | 13317 | C | GLU G 663 | 53.538 | 45.950 | 45.687 | 1.00 | 100.07 | G |
| ATOM | 13318 | O | GLU G 663 | 53.327 | 44.997 | 46.440 | 1.00 | 100.07 | G |

| | | | | | | | | | |
|---|---|---|---|---|---|---|---|---|---|
| ATOM | 13319 | N | LYS | G | 664 | 52.608 | 46.841 | 45.349 | 1.00 60.73 | G |
| ATOM | 13320 | CA | LYS | G | 664 | 51.229 | 46.778 | 45.823 | 1.00 60.73 | G |
| ATOM | 13321 | CB | LYS | G | 664 | 50.480 | 48.055 | 45.402 | 1.00100.07 | G |
| ATOM | 13322 | CG | LYS | G | 664 | 49.017 | 48.173 | 45.852 | 1.00100.07 | G |
| ATOM | 13323 | CD | LYS | G | 664 | 48.847 | 48.509 | 47.331 | 1.00100.07 | G |
| ATOM | 13324 | CE | LYS | G | 664 | 47.372 | 48.719 | 47.656 | 1.00100.07 | G |
| ATOM | 13325 | NZ | LYS | G | 664 | 47.100 | 48.884 | 49.106 | 1.00100.07 | G |
| ATOM | 13326 | C | LYS | G | 664 | 50.618 | 45.549 | 45.164 | 1.00 60.73 | G |
| ATOM | 13327 | O | LYS | G | 664 | 49.423 | 45.279 | 45.281 | 1.00 60.73 | G |
| ATOM | 13328 | N | ALA | G | 665 | 51.470 | 44.813 | 44.463 | 1.00100.07 | G |
| ATOM | 13329 | CA | ALA | G | 665 | 51.084 | 43.592 | 43.780 | 1.00100.07 | G |
| ATOM | 13330 | CB | ALA | G | 665 | 50.374 | 42.646 | 44.750 | 1.00100.07 | G |
| ATOM | 13331 | C | ALA | G | 665 | 50.233 | 43.798 | 42.535 | 1.00100.07 | G |
| ATOM | 13332 | O | ALA | G | 665 | 50.370 | 43.036 | 41.574 | 1.00100.07 | G |
| ATOM | 13333 | N | PHE | G | 666 | 49.361 | 44.805 | 42.515 | 1.00 33.07 | G |
| ATOM | 13334 | CA | PHE | G | 666 | 48.553 | 44.963 | 41.311 | 1.00 33.07 | G |
| ATOM | 13335 | CB | PHE | G | 666 | 47.475 | 46.016 | 41.454 | 1.00 72.87 | G |
| ATOM | 13336 | CG | PHE | G | 666 | 46.494 | 45.973 | 40.331 | 1.00 72.87 | G |
| ATOM | 13337 | CD1 | PHE | G | 666 | 45.872 | 44.768 | 40.001 | 1.00 72.87 | G |
| ATOM | 13338 | CD2 | PHE | G | 666 | 46.212 | 47.101 | 39.580 | 1.00 72.87 | G |
| ATOM | 13339 | CE1 | PHE | G | 666 | 44.981 | 44.683 | 38.938 | 1.00 72.87 | G |
| ATOM | 13340 | CE2 | PHE | G | 666 | 45.318 | 47.029 | 38.511 | 1.00 72.87 | G |
| ATOM | 13341 | CZ | PHE | G | 666 | 44.701 | 45.815 | 38.188 | 1.00 72.87 | G |
| ATOM | 13342 | C | PHE | G | 666 | 49.398 | 45.312 | 40.108 | 1.00 33.07 | G |
| ATOM | 13343 | O | PHE | G | 666 | 50.470 | 45.878 | 40.256 | 1.00 33.07 | G |
| ATOM | 13344 | N | ALA | G | 667 | 48.906 | 44.990 | 38.917 | 1.00 84.06 | G |
| ATOM | 13345 | CA | ALA | G | 667 | 49.659 | 45.255 | 37.695 | 1.00 84.06 | G |
| ATOM | 13346 | CB | ALA | G | 667 | 49.845 | 46.752 | 37.502 | 1.00100.07 | G |
| ATOM | 13347 | C | ALA | G | 667 | 51.017 | 44.550 | 37.815 | 1.00 84.06 | G |
| ATOM | 13348 | O | ALA | G | 667 | 51.907 | 44.994 | 38.542 | 1.00 84.06 | G |
| ATOM | 13349 | N | PRO | G | 668 | 51.191 | 43.439 | 37.088 | 1.00100.07 | G |
| ATOM | 13350 | CD | PRO | G | 668 | 50.284 | 42.977 | 36.021 | 1.00100.07 | G |
| ATOM | 13351 | CA | PRO | G | 668 | 52.423 | 42.645 | 37.102 | 1.00100.07 | G |
| ATOM | 13352 | CB | PRO | G | 668 | 52.097 | 41.502 | 36.152 | 1.00100.07 | G |
| ATOM | 13353 | CG | PRO | G | 668 | 51.206 | 42.169 | 35.146 | 1.00100.07 | G |
| ATOM | 13354 | C | PRO | G | 668 | 53.699 | 43.374 | 36.702 | 1.00100.07 | G |
| ATOM | 13355 | O | PRO | G | 668 | 54.733 | 43.223 | 37.359 | 1.00100.07 | G |
| ATOM | 13356 | N | ASN | G | 669 | 53.629 | 44.158 | 35.627 | 1.00100.04 | G |
| ATOM | 13357 | CA | ASN | G | 669 | 54.803 | 44.880 | 35.144 | 1.00100.04 | G |
| ATOM | 13358 | CB | ASN | G | 669 | 54.957 | 44.687 | 33.628 | 1.00100.07 | G |
| ATOM | 13359 | CG | ASN | G | 669 | 56.405 | 44.432 | 33.211 | 1.00100.07 | G |
| ATOM | 13360 | OD1 | ASN | G | 669 | 57.298 | 45.234 | 33.501 | 1.00100.07 | G |
| ATOM | 13361 | ND2 | ASN | G | 669 | 56.641 | 43.309 | 32.528 | 1.00100.07 | G |
| ATOM | 13362 | C | ASN | G | 669 | 54.774 | 46.369 | 35.469 | 1.00100.04 | G |
| ATOM | 13363 | O | ASN | G | 669 | 53.759 | 47.042 | 35.287 | 1.00100.04 | G |
| ATOM | 13364 | N | VAL | G | 670 | 55.895 | 46.873 | 35.977 | 1.00 69.38 | G |
| ATOM | 13365 | CA | VAL | G | 670 | 55.997 | 48.285 | 36.294 | 1.00 69.38 | G |
| ATOM | 13366 | CB | VAL | G | 670 | 57.381 | 48.643 | 36.873 | 1.00 35.05 | G |
| ATOM | 13367 | CG1 | VAL | G | 670 | 57.569 | 50.153 | 36.891 | 1.00 35.05 | G |
| ATOM | 13368 | CG2 | VAL | G | 670 | 57.515 | 48.086 | 38.276 | 1.00 35.05 | G |
| ATOM | 13369 | C | VAL | G | 670 | 55.837 | 48.968 | 34.955 | 1.00 69.38 | G |
| ATOM | 13370 | O | VAL | G | 670 | 55.227 | 50.025 | 34.851 | 1.00 69.38 | G |
| ATOM | 13371 | N | LYS | G | 671 | 56.386 | 48.342 | 33.922 | 1.00 52.67 | G |
| ATOM | 13372 | CA | LYS | G | 671 | 56.292 | 48.898 | 32.587 | 1.00 52.67 | G |
| ATOM | 13373 | CB | LYS | G | 671 | 57.126 | 48.068 | 31.603 | 1.00100.07 | G |
| ATOM | 13374 | CG | LYS | G | 671 | 58.581 | 47.894 | 32.052 | 1.00100.07 | G |
| ATOM | 13375 | CD | LYS | G | 671 | 59.523 | 47.496 | 30.910 | 1.00100.07 | G |
| ATOM | 13376 | CE | LYS | G | 671 | 60.981 | 47.401 | 31.395 | 1.00100.07 | G |
| ATOM | 13377 | NZ | LYS | G | 671 | 61.967 | 47.176 | 30.286 | 1.00100.07 | G |
| ATOM | 13378 | C | LYS | G | 671 | 54.824 | 48.879 | 32.211 | 1.00 52.67 | G |
| ATOM | 13379 | O | LYS | G | 671 | 54.383 | 49.636 | 31.348 | 1.00 52.67 | G |
| ATOM | 13380 | N | ALA | G | 672 | 54.068 | 48.017 | 32.887 | 1.00 73.77 | G |
| ATOM | 13381 | CA | ALA | G | 672 | 52.630 | 47.891 | 32.650 | 1.00 73.77 | G |
| ATOM | 13382 | CB | ALA | G | 672 | 52.113 | 46.565 | 33.223 | 1.00100.07 | G |
| ATOM | 13383 | C | ALA | G | 672 | 51.904 | 49.062 | 33.305 | 1.00 73.77 | G |
| ATOM | 13384 | O | ALA | G | 672 | 50.826 | 49.475 | 32.871 | 1.00 73.77 | G |
| ATOM | 13385 | N | ALA | G | 673 | 52.514 | 49.591 | 34.356 | 1.00 65.57 | G |
| ATOM | 13386 | CA | ALA | G | 673 | 51.947 | 50.712 | 35.084 | 1.00 65.57 | G |
| ATOM | 13387 | CB | ALA | G | 673 | 52.928 | 51.176 | 36.161 | 1.00100.07 | G |
| ATOM | 13388 | C | ALA | G | 673 | 51.571 | 51.880 | 34.166 | 1.00 65.57 | G |
| ATOM | 13389 | O | ALA | G | 673 | 50.408 | 52.018 | 33.784 | 1.00 65.57 | G |
| ATOM | 13390 | N | ALA | G | 674 | 52.552 | 52.712 | 33.816 | 1.00 99.66 | G |
| ATOM | 13391 | CA | ALA | G | 674 | 52.319 | 53.878 | 32.962 | 1.00 99.66 | G |
| ATOM | 13392 | CB | ALA | G | 674 | 53.630 | 54.293 | 32.258 | 1.00 43.29 | G |
| ATOM | 13393 | C | ALA | G | 674 | 51.209 | 53.640 | 31.933 | 1.00 99.66 | G |
| ATOM | 13394 | O | ALA | G | 674 | 50.588 | 54.583 | 31.449 | 1.00 99.66 | G |
| ATOM | 13395 | N | ALA | G | 675 | 50.958 | 52.373 | 31.619 | 1.00 67.37 | G |
| ATOM | 13396 | CA | ALA | G | 675 | 49.930 | 51.991 | 30.661 | 1.00 67.37 | G |
| ATOM | 13397 | CB | ALA | G | 675 | 50.269 | 50.636 | 30.056 | 1.00100.07 | G |
| ATOM | 13398 | C | ALA | G | 675 | 48.562 | 51.929 | 31.318 | 1.00 67.37 | G |
| ATOM | 13399 | O | ALA | G | 675 | 47.622 | 52.583 | 30.888 | 1.00 67.37 | G |
| ATOM | 13400 | N | MET | G | 676 | 48.457 | 51.118 | 32.358 | 1.00 87.94 | G |
| ATOM | 13401 | CA | MET | G | 676 | 47.207 | 50.960 | 33.081 | 1.00 87.94 | G |
| ATOM | 13402 | CB | MET | G | 676 | 47.460 | 50.109 | 34.313 | 1.00 58.41 | G |

```
ATOM  13403  CG   MET G 676      46.249  49.693  35.088  1.00 58.41           G
ATOM  13404  SD   MET G 676      46.864  48.497  36.277  1.00 58.41           G
ATOM  13405  CE   MET G 676      47.491  47.222  35.162  1.00 58.41           G
ATOM  13406  C    MET G 676      46.637  52.314  33.486  1.00 87.94           G
ATOM  13407  O    MET G 676      45.482  52.403  33.896  1.00 87.94           G
ATOM  13408  N    LEU G 677      47.457  53.360  33.393  1.00 72.25           G
ATOM  13409  CA   LEU G 677      47.018  54.712  33.724  1.00 72.25           G
ATOM  13410  CB   LEU G 677      48.045  55.446  34.594  1.00 26.85           G
ATOM  13411  CG   LEU G 677      48.854  54.754  35.700  1.00 26.85           G
ATOM  13412  CD1  LEU G 677      49.709  55.787  36.404  1.00 26.85           G
ATOM  13413  CD2  LEU G 677      47.952  54.080  36.701  1.00 26.85           G
ATOM  13414  C    LEU G 677      46.913  55.434  32.391  1.00 72.25           G
ATOM  13415  O    LEU G 677      46.217  56.441  32.261  1.00 72.25           G
ATOM  13416  N    GLU G 678      47.622  54.896  31.401  1.00100.07           G
ATOM  13417  CA   GLU G 678      47.658  55.455  30.050  1.00100.07           G
ATOM  13418  CB   GLU G 678      48.872  54.905  29.279  1.00100.07           G
ATOM  13419  CG   GLU G 678      49.657  55.956  28.480  1.00100.07           G
ATOM  13420  CD   GLU G 678      51.005  56.308  29.110  1.00100.07           G
ATOM  13421  OE1  GLU G 678      51.886  55.422  29.158  1.00100.07           G
ATOM  13422  OE2  GLU G 678      51.186  57.467  29.554  1.00100.07           G
ATOM  13423  C    GLU G 678      46.376  55.186  29.246  1.00100.07           G
ATOM  13424  O    GLU G 678      46.371  55.317  28.019  1.00100.07           G
ATOM  13425  N    ARG G 679      45.296  54.799  29.924  1.00100.07           G
ATOM  13426  CA   ARG G 679      44.024  54.567  29.239  1.00100.07           G
ATOM  13427  CB   ARG G 679      43.046  53.833  30.171  1.00100.07           G
ATOM  13428  CG   ARG G 679      41.582  53.754  29.693  1.00100.07           G
ATOM  13429  CD   ARG G 679      41.419  53.023  28.359  1.00100.07           G
ATOM  13430  NE   ARG G 679      40.018  52.701  28.074  1.00100.07           G
ATOM  13431  CZ   ARG G 679      39.603  52.017  27.008  1.00100.07           G
ATOM  13432  NH1  ARG G 679      40.480  51.579  26.111  1.00100.07           G
ATOM  13433  NH2  ARG G 679      38.311  51.751  26.845  1.00100.07           G
ATOM  13434  C    ARG G 679      43.501  55.963  28.895  1.00100.07           G
ATOM  13435  O    ARG G 679      42.337  56.143  28.538  1.00100.07           G
ATOM  13436  N    GLN G 680      44.406  56.937  29.010  1.00100.07           G
ATOM  13437  CA   GLN G 680      44.164  58.358  28.764  1.00100.07           G
ATOM  13438  CB   GLN G 680      43.680  58.597  27.316  1.00100.07           G
ATOM  13439  CG   GLN G 680      42.222  58.264  27.005  1.00100.07           G
ATOM  13440  CD   GLN G 680      41.919  58.299  25.507  1.00100.07           G
ATOM  13441  OE1  GLN G 680      42.237  59.273  24.820  1.00100.07           G
ATOM  13442  NE2  GLN G 680      41.300  57.235  25.000  1.00100.07           G
ATOM  13443  C    GLN G 680      43.185  58.926  29.796  1.00100.07           G
ATOM  13444  O    GLN G 680      43.281  60.099  30.181  1.00100.07           G
ATOM  13445  N    ARG G 681      42.273  58.065  30.257  1.00100.07           G
ATOM  13446  CA   ARG G 681      41.253  58.394  31.261  1.00100.07           G
ATOM  13447  CB   ARG G 681      40.134  59.242  30.630  1.00100.07           G
ATOM  13448  CG   ARG G 681      40.583  60.631  30.171  1.00100.07           G
ATOM  13449  CD   ARG G 681      39.496  61.380  29.411  1.00100.07           G
ATOM  13450  NE   ARG G 681      39.821  62.800  29.260  1.00100.07           G
ATOM  13451  CZ   ARG G 681      38.950  63.737  28.885  1.00100.07           G
ATOM  13452  NH1  ARG G 681      37.690  63.404  28.614  1.00100.07           G
ATOM  13453  NH2  ARG G 681      39.328  65.012  28.801  1.00100.07           G
ATOM  13454  C    ARG G 681      40.662  57.090  31.834  1.00100.07           G
ATOM  13455  O    ARG G 681      40.220  56.226  31.072  1.00100.07           G
ATOM  13456  N    ASP G 682      40.690  56.962  33.166  1.00 70.65           G
ATOM  13457  CA   ASP G 682      40.167  55.807  33.927  1.00 70.65           G
ATOM  13458  CB   ASP G 682      39.532  54.752  33.021  1.00100.07           G
ATOM  13459  CG   ASP G 682      38.153  55.148  32.556  1.00100.07           G
ATOM  13460  OD1  ASP G 682      37.364  55.607  33.412  1.00100.07           G
ATOM  13461  OD2  ASP G 682      37.859  54.995  31.347  1.00100.07           G
ATOM  13462  C    ASP G 682      41.162  55.100  34.834  1.00 70.65           G
ATOM  13463  O    ASP G 682      42.155  54.538  34.378  1.00 70.65           G
ATOM  13464  N    ILE G 683      40.865  55.135  36.129  1.00 38.32           G
ATOM  13465  CA   ILE G 683      41.675  54.505  37.170  1.00 38.32           G
ATOM  13466  CB   ILE G 683      42.678  55.479  37.791  1.00 59.54           G
ATOM  13467  CG2  ILE G 683      43.507  54.751  38.799  1.00 59.54           G
ATOM  13468  CG1  ILE G 683      43.550  56.133  36.717  1.00 59.54           G
ATOM  13469  CD   ILE G 683      42.934  57.366  36.061  1.00 59.54           G
ATOM  13470  C    ILE G 683      40.665  54.180  38.253  1.00 38.32           G
ATOM  13471  O    ILE G 683      40.248  55.070  38.993  1.00 38.32           G
ATOM  13472  N    LYS G 684      40.246  52.928  38.354  1.00 43.89           G
ATOM  13473  CA   LYS G 684      39.251  52.618  39.364  1.00 43.89           G
ATOM  13474  CB   LYS G 684      38.720  51.190  39.205  1.00 78.47           G
ATOM  13475  CG   LYS G 684      37.257  51.070  39.599  1.00 78.47           G
ATOM  13476  CD   LYS G 684      36.910  49.691  40.121  1.00 78.47           G
ATOM  13477  CE   LYS G 684      35.516  49.689  40.748  1.00 78.47           G
ATOM  13478  NZ   LYS G 684      35.209  48.429  41.497  1.00 78.47           G
ATOM  13479  C    LYS G 684      39.867  52.807  40.745  1.00 43.89           G
ATOM  13480  O    LYS G 684      41.096  52.845  40.887  1.00 43.89           G
ATOM  13481  N    ASP G 685      39.008  52.931  41.755  1.00100.07           G
ATOM  13482  CA   ASP G 685      39.452  53.136  43.132  1.00100.07           G
ATOM  13483  CB   ASP G 685      38.262  53.085  44.111  1.00 87.93           G
ATOM  13484  CG   ASP G 685      37.108  52.229  43.610  1.00 87.93           G
ATOM  13485  OD1  ASP G 685      36.414  52.649  42.654  1.00 87.93           G
ATOM  13486  OD2  ASP G 685      36.893  51.140  44.183  1.00 87.93           G
```

| ATOM | 13487 | C | ASP G 685 | 40.533 | 52.173 | 43.595 | 1.00100.07 | G |
|---|---|---|---|---|---|---|---|---|
| ATOM | 13488 | O | ASP G 685 | 41.146 | 52.378 | 44.639 | 1.00100.07 | G |
| ATOM | 13489 | N | GLU G 686 | 40.772 | 51.129 | 42.813 | 1.00100.07 | G |
| ATOM | 13490 | CA | GLU G 686 | 41.784 | 50.147 | 43.165 | 1.00100.07 | G |
| ATOM | 13491 | CB | GLU G 686 | 41.770 | 49.002 | 42.164 | 1.00 84.76 | G |
| ATOM | 13492 | CG | GLU G 686 | 40.408 | 48.380 | 42.036 | 1.00 84.76 | G |
| ATOM | 13493 | CD | GLU G 686 | 40.394 | 47.204 | 41.103 | 1.00 84.76 | G |
| ATOM | 13494 | OE1 | GLU G 686 | 40.990 | 46.161 | 41.452 | 1.00 84.76 | G |
| ATOM | 13495 | OE2 | GLU G 686 | 39.786 | 47.329 | 40.018 | 1.00 84.76 | G |
| ATOM | 13496 | C | GLU G 686 | 43.146 | 50.805 | 43.190 | 1.00100.07 | G |
| ATOM | 13497 | O | GLU G 686 | 44.085 | 50.279 | 43.795 | 1.00100.07 | G |
| ATOM | 13498 | N | VAL G 687 | 43.250 | 51.958 | 42.533 | 1.00 46.49 | G |
| ATOM | 13499 | CA | VAL G 687 | 44.514 | 52.682 | 42.508 | 1.00 46.49 | G |
| ATOM | 13500 | CB | VAL G 687 | 44.814 | 53.289 | 41.138 | 1.00 35.04 | G |
| ATOM | 13501 | CG1 | VAL G 687 | 46.045 | 54.179 | 41.242 | 1.00 35.04 | G |
| ATOM | 13502 | CG2 | VAL G 687 | 45.052 | 52.188 | 40.118 | 1.00 35.04 | G |
| ATOM | 13503 | C | VAL G 687 | 44.544 | 53.797 | 43.547 | 1.00 46.49 | G |
| ATOM | 13504 | O | VAL G 687 | 45.270 | 53.686 | 44.526 | 1.00 46.49 | G |
| ATOM | 13505 | N | TRP G 688 | 43.772 | 54.863 | 43.333 | 1.00 20.87 | G |
| ATOM | 13506 | CA | TRP G 688 | 43.720 | 55.965 | 44.281 | 1.00 20.87 | G |
| ATOM | 13507 | CB | TRP G 688 | 42.305 | 56.476 | 44.383 | 1.00 49.62 | G |
| ATOM | 13508 | CG | TRP G 688 | 41.901 | 57.091 | 43.144 | 1.00 49.62 | G |
| ATOM | 13509 | CD2 | TRP G 688 | 42.654 | 58.040 | 42.391 | 1.00 49.62 | G |
| ATOM | 13510 | CE2 | TRP G 688 | 41.899 | 58.355 | 41.247 | 1.00 49.62 | G |
| ATOM | 13511 | CE3 | TRP G 688 | 43.897 | 58.658 | 42.574 | 1.00 49.62 | G |
| ATOM | 13512 | CD1 | TRP G 688 | 40.754 | 56.869 | 42.459 | 1.00 49.62 | G |
| ATOM | 13513 | NE1 | TRP G 688 | 40.740 | 57.622 | 41.313 | 1.00 49.62 | G |
| ATOM | 13514 | CZ2 | TRP G 688 | 42.341 | 59.262 | 40.278 | 1.00 49.62 | G |
| ATOM | 13515 | CZ3 | TRP G 688 | 44.338 | 59.555 | 41.615 | 1.00 49.62 | G |
| ATOM | 13516 | CH2 | TRP G 688 | 43.560 | 59.849 | 40.480 | 1.00 49.62 | G |
| ATOM | 13517 | C | TRP G 688 | 44.188 | 55.531 | 45.645 | 1.00 20.87 | G |
| ATOM | 13518 | O | TRP G 688 | 45.009 | 56.198 | 46.269 | 1.00 20.87 | G |
| ATOM | 13519 | N | ASP G 689 | 43.660 | 54.408 | 46.113 | 1.00 42.52 | G |
| ATOM | 13520 | CA | ASP G 689 | 44.078 | 53.882 | 47.394 | 1.00 42.52 | G |
| ATOM | 13521 | CB | ASP G 689 | 43.327 | 52.580 | 47.721 | 1.00100.07 | G |
| ATOM | 13522 | CG | ASP G 689 | 41.810 | 52.717 | 47.599 | 1.00100.07 | G |
| ATOM | 13523 | OD1 | ASP G 689 | 41.310 | 53.862 | 47.662 | 1.00100.07 | G |
| ATOM | 13524 | OD2 | ASP G 689 | 41.117 | 51.678 | 47.456 | 1.00100.07 | G |
| ATOM | 13525 | C | ASP G 689 | 45.577 | 53.600 | 47.241 | 1.00 42.52 | G |
| ATOM | 13526 | O | ASP G 689 | 46.134 | 52.746 | 47.921 | 1.00 42.52 | G |
| ATOM | 13527 | N | ALA G 690 | 46.222 | 54.327 | 46.333 | 1.00 47.89 | G |
| ATOM | 13528 | CA | ALA G 690 | 47.643 | 54.188 | 46.058 | 1.00 47.89 | G |
| ATOM | 13529 | CB | ALA G 690 | 47.882 | 54.194 | 44.566 | 1.00 36.87 | G |
| ATOM | 13530 | C | ALA G 690 | 48.389 | 55.344 | 46.698 | 1.00 47.89 | G |
| ATOM | 13531 | O | ALA G 690 | 49.052 | 55.180 | 47.727 | 1.00 47.89 | G |
| ATOM | 13532 | N | LEU G 691 | 48.280 | 56.518 | 46.087 | 1.00 40.84 | G |
| ATOM | 13533 | CA | LEU G 691 | 48.955 | 57.678 | 46.623 | 1.00 40.84 | G |
| ATOM | 13534 | CB | LEU G 691 | 48.634 | 58.920 | 45.804 | 1.00 23.09 | G |
| ATOM | 13535 | CG | LEU G 691 | 47.944 | 58.688 | 44.465 | 1.00 23.09 | G |
| ATOM | 13536 | CD1 | LEU G 691 | 46.503 | 58.272 | 44.744 | 1.00 23.09 | G |
| ATOM | 13537 | CD2 | LEU G 691 | 47.974 | 59.951 | 43.599 | 1.00 23.09 | G |
| ATOM | 13538 | C | LEU G 691 | 48.513 | 57.876 | 48.069 | 1.00 40.84 | G |
| ATOM | 13539 | O | LEU G 691 | 49.340 | 58.165 | 48.942 | 1.00 40.84 | G |
| ATOM | 13540 | N | GLU G 692 | 47.219 | 57.705 | 48.342 | 1.00 64.10 | G |
| ATOM | 13541 | CA | GLU G 692 | 46.733 | 57.880 | 49.710 | 1.00 64.10 | G |
| ATOM | 13542 | CB | GLU G 692 | 45.261 | 57.489 | 49.842 | 1.00 49.74 | G |
| ATOM | 13543 | CG | GLU G 692 | 44.271 | 58.463 | 49.215 | 1.00 49.74 | G |
| ATOM | 13544 | CD | GLU G 692 | 42.837 | 58.188 | 49.660 | 1.00 49.74 | G |
| ATOM | 13545 | OE1 | GLU G 692 | 42.624 | 58.220 | 50.892 | 1.00 49.74 | G |
| ATOM | 13546 | OE2 | GLU G 692 | 41.940 | 57.943 | 48.801 | 1.00 49.74 | G |
| ATOM | 13547 | C | GLU G 692 | 47.559 | 57.062 | 50.689 | 1.00 64.10 | G |
| ATOM | 13548 | O | GLU G 692 | 47.240 | 57.006 | 51.874 | 1.00 64.10 | G |
| ATOM | 13549 | N | GLU G 693 | 48.598 | 56.405 | 50.179 | 1.00 49.95 | G |
| ATOM | 13550 | CA | GLU G 693 | 49.506 | 55.633 | 51.011 | 1.00 49.95 | G |
| ATOM | 13551 | CB | GLU G 693 | 49.291 | 54.126 | 50.825 | 1.00100.07 | G |
| ATOM | 13552 | CG | GLU G 693 | 49.785 | 53.255 | 52.009 | 1.00100.07 | G |
| ATOM | 13553 | CD | GLU G 693 | 49.297 | 53.739 | 53.391 | 1.00100.07 | G |
| ATOM | 13554 | OE1 | GLU G 693 | 48.170 | 54.273 | 53.492 | 1.00100.07 | G |
| ATOM | 13555 | OE2 | GLU G 693 | 50.036 | 53.569 | 54.387 | 1.00100.07 | G |
| ATOM | 13556 | C | GLU G 693 | 50.951 | 56.039 | 50.683 | 1.00 49.95 | G |
| ATOM | 13557 | O | GLU G 693 | 51.817 | 56.065 | 51.566 | 1.00 49.95 | G |
| ATOM | 13558 | N | VAL G 694 | 51.227 | 56.366 | 49.426 | 1.00 39.51 | G |
| ATOM | 13559 | CA | VAL G 694 | 52.577 | 56.814 | 49.076 | 1.00 39.51 | G |
| ATOM | 13560 | CB | VAL G 694 | 52.730 | 56.982 | 47.569 | 1.00 40.15 | G |
| ATOM | 13561 | CG1 | VAL G 694 | 54.179 | 56.794 | 47.165 | 1.00 40.15 | G |
| ATOM | 13562 | CG2 | VAL G 694 | 51.826 | 56.012 | 46.863 | 1.00 40.15 | G |
| ATOM | 13563 | C | VAL G 694 | 52.721 | 58.198 | 49.727 | 1.00 39.51 | G |
| ATOM | 13564 | O | VAL G 694 | 53.490 | 58.395 | 50.672 | 1.00 39.51 | G |
| ATOM | 13565 | N | ILE G 395 | 51.952 | 59.145 | 49.197 | 1.00 36.94 | G |
| ATOM | 13566 | CA | ILE G 695 | 51.902 | 60.512 | 49.683 | 1.00 36.94 | G |
| ATOM | 13567 | CB | ILE G 695 | 50.572 | 61.185 | 49.226 | 1.00 24.82 | G |
| ATOM | 13568 | CG2 | ILE G 695 | 49.718 | 61.592 | 50.406 | 1.00 24.82 | G |
| ATOM | 13569 | CG1 | ILE G 695 | 50.886 | 62.396 | 48.368 | 1.00 24.82 | G |
| ATOM | 13570 | CD | ILE G 695 | 51.757 | 62.063 | 47.194 | 1.00 24.82 | G |

```
ATOM  13571  C    ILE G 695      51.979  60.492  51.195  1.00 36.94      G
ATOM  13572  O    ILE G 695      52.712  61.270  51.796  1.00 36.94      G
ATOM  13573  N    HIS G 696      51.211  59.584  51.789  1.00 38.08      G
ATOM  13574  CA   HIS G 696      51.133  59.403  53.238  1.00 38.08      G
ATOM  13575  CB   HIS G 696      50.525  58.035  53.536  1.00 99.89      G
ATOM  13576  CG   HIS G 696      50.622  57.623  54.969  1.00 99.89      G
ATOM  13577  CD2  HIS G 696      50.832  58.342  56.095  1.00 99.89      G
ATOM  13578  ND1  HIS G 696      50.485  56.312  55.371  1.00 99.89      G
ATOM  13579  CE1  HIS G 696      50.610  56.241  56.683  1.00 99.89      G
ATOM  13580  NE2  HIS G 696      50.820  57.460  57.147  1.00 99.89      G
ATOM  13581  C    HIS G 696      52.484  59.523  53.936  1.00 38.08      G
ATOM  13582  O    HIS G 696      53.291  58.600  53.901  1.00 38.08      G
ATOM  13583  N    GLY G 697      52.714  60.661  54.583  1.00 56.00      G
ATOM  13584  CA   GLY G 697      53.966  60.884  55.281  1.00 56.00      G
ATOM  13585  C    GLY G 697      54.874  61.798  54.490  1.00 56.00      G
ATOM  13586  O    GLY G 697      55.994  62.093  54.896  1.00 56.00      G
ATOM  13587  N    ALA G 698      54.381  62.256  53.349  1.00 37.91      G
ATOM  13588  CA   ALA G 698      55.161  63.125  52.487  1.00 37.91      G
ATOM  13589  CB   ALA G 698      55.250  62.534  51.078  1.00 39.23      G
ATOM  13590  C    ALA G 698      54.565  64.515  52.427  1.00 37.91      G
ATOM  13591  O    ALA G 698      53.345  64.676  52.308  1.00 37.91      G
ATOM  13592  N    VAL G 699      55.446  65.510  52.518  1.00 52.30      G
ATOM  13593  CA   VAL G 699      55.066  66.916  52.462  1.00 52.30      G
ATOM  13594  CB   VAL G 699      55.817  67.763  53.482  1.00 20.29      G
ATOM  13595  CG1  VAL G 699      55.163  67.671  54.842  1.00 20.29      G
ATOM  13596  CG2  VAL G 699      57.244  67.301  53.546  1.00 20.29      G
ATOM  13597  C    VAL G 699      55.454  67.436  51.111  1.00 52.30      G
ATOM  13598  O    VAL G 699      56.109  66.744  50.348  1.00 52.30      G
ATOM  13599  N    VAL G 700      55.078  68.674  50.837  1.00 20.52      G
ATOM  13600  CA   VAL G 700      55.373  69.297  49.558  1.00 20.52      G
ATOM  13601  CB   VAL G 700      54.227  69.080  48.593  1.00  5.07      G
ATOM  13602  CG1  VAL G 700      54.421  69.949  47.418  1.00  5.07      G
ATOM  13603  CG2  VAL G 700      54.162  67.637  48.170  1.00  5.07      G
ATOM  13604  C    VAL G 700      55.652  70.805  49.580  1.00 20.52      G
ATOM  13605  O    VAL G 700      54.876  71.586  50.116  1.00 20.52      G
ATOM  13606  N    LEU G 701      56.750  71.224  48.975  1.00 23.60      G
ATOM  13607  CA   LEU G 701      57.036  72.642  48.938  1.00 23.60      G
ATOM  13608  CB   LEU G 701      58.326  72.913  48.163  1.00 29.05      G
ATOM  13609  CG   LEU G 701      59.569  72.325  48.830  1.00 29.05      G
ATOM  13610  CD1  LEU G 701      59.495  72.639  50.302  1.00 29.05      G
ATOM  13611  CD2  LEU G 701      59.639  70.814  48.647  1.00 29.05      G
ATOM  13612  C    LEU G 701      55.878  73.293  48.218  1.00 23.60      G
ATOM  13613  O    LEU G 701      55.483  72.837  47.147  1.00 23.60      G
ATOM  13614  N    LEU G 702      55.307  74.332  48.810  1.00 11.36      G
ATOM  13615  CA   LEU G 702      54.215  75.033  48.153  1.00 11.36      G
ATOM  13616  CB   LEU G 702      53.049  75.191  49.126  1.00  9.14      G
ATOM  13617  CG   LEU G 702      51.658  75.494  48.568  1.00  9.14      G
ATOM  13618  CD1  LEU G 702      51.857  76.287  47.304  1.00  9.14      G
ATOM  13619  CD2  LEU G 702      50.855  74.233  48.287  1.00  9.14      G
ATOM  13620  C    LEU G 702      54.823  76.392  47.771  1.00 11.36      G
ATOM  13621  O    LEU G 702      55.236  77.161  48.636  1.00 11.36      G
ATOM  13622  N    ASN G 703      54.895  76.671  46.471  1.00 17.78      G
ATOM  13623  CA   ASN G 703      55.508  77.904  45.927  1.00 17.78      G
ATOM  13624  CB   ASN G 703      55.575  77.826  44.406  1.00100.07      G
ATOM  13625  CG   ASN G 703      56.980  77.643  43.880  1.00100.07      G
ATOM  13626  OD1  ASN G 703      57.845  78.512  44.042  1.00100.07      G
ATOM  13627  ND2  ASN G 703      57.215  76.508  43.230  1.00100.07      G
ATOM  13628  C    ASN G 703      54.821  79.195  46.251  1.00 17.78      G
ATOM  13629  O    ASN G 703      54.011  79.266  47.154  1.00 17.78      G
ATOM  13630  N    ARG G 704      55.165  80.212  45.475  1.00 55.34      G
ATOM  13631  CA   ARG G 704      54.579  81.538  45.572  1.00 55.34      G
ATOM  13632  CB   ARG G 704      54.661  82.120  46.964  1.00 43.55      G
ATOM  13633  CG   ARG G 704      54.072  83.507  46.979  1.00 43.55      G
ATOM  13634  CD   ARG G 704      52.663  83.513  46.360  1.00 43.55      G
ATOM  13635  NE   ARG G 704      52.338  84.820  45.790  1.00 43.55      G
ATOM  13636  CZ   ARG G 704      51.119  85.214  45.436  1.00 43.55      G
ATOM  13637  NH1  ARG G 704      50.087  84.404  45.594  1.00 43.55      G
ATOM  13638  NH2  ARG G 704      50.936  86.422  44.919  1.00 43.55      G
ATOM  13639  C    ARG G 704      55.320  82.460  44.640  1.00 55.34      G
ATOM  13640  O    ARG G 704      56.522  82.297  44.438  1.00 55.34      G
ATOM  13641  N    ALA G 705      54.609  83.437  44.085  1.00100.07      G
ATOM  13642  CA   ALA G 705      55.216  84.364  43.143  1.00100.07      G
ATOM  13643  CB   ALA G 705      54.160  85.316  42.575  1.00  5.07      G
ATOM  13644  C    ALA G 705      56.422  85.129  43.694  1.00100.07      G
ATOM  13645  O    ALA G 705      57.431  84.508  44.027  1.00100.07      G
ATOM  13646  N    PRO G 706      56.345  86.467  43.831  1.00 36.82      G
ATOM  13647  CD   PRO G 706      55.233  87.410  44.038  1.00 13.47      G
ATOM  13648  CA   PRO G 706      57.583  87.045  44.348  1.00 36.82      G
ATOM  13649  CB   PRO G 706      57.236  88.514  44.473  1.00 13.47      G
ATOM  13650  CG   PRO G 706      55.845  88.438  44.951  1.00 13.47      G
ATOM  13651  C    PRO G 706      57.929  86.410  45.669  1.00 36.82      G
ATOM  13652  O    PRO G 706      57.302  86.696  46.683  1.00 36.82      G
ATOM  13653  N    THR G 707      58.911  85.520  45.660  1.00 41.13      G
ATOM  13654  CA   THR G 707      59.288  84.870  46.897  1.00 41.13      G
```

```
ATOM  13655  CB   THR G 707      59.990  83.528  46.652  1.00 42.58      G
ATOM  13656  OG1  THR G 707      59.029  82.579  46.188  1.00 42.58      G
ATOM  13657  CG2  THR G 707      60.601  83.001  47.925  1.00 42.58      G
ATOM  13658  C    THR G 707      60.203  85.783  47.667  1.00 41.13      G
ATOM  13659  O    THR G 707      61.409  85.781  47.460  1.00 41.13      G
ATOM  13660  N    LEU G 708      59.615  86.598  48.528  1.00 13.85      G
ATOM  13661  CA   LEU G 708      60.391  87.493  49.351  1.00 13.85      G
ATOM  13662  CB   LEU G 708      59.617  88.782  49.559  1.00 53.00      G
ATOM  13663  CG   LEU G 708      59.283  89.477  48.244  1.00 53.00      G
ATOM  13664  CD1  LEU G 708      58.119  90.445  48.412  1.00 53.00      G
ATOM  13665  CD2  LEU G 708      60.539  90.181  47.751  1.00 53.00      G
ATOM  13666  C    LEU G 708      60.474  86.702  50.642  1.00 13.85      G
ATOM  13667  O    LEU G 708      59.524  86.023  50.983  1.00 13.85      G
ATOM  13668  N    HIS G 709      61.599  86.753  51.341  1.00 34.04      G
ATOM  13669  CA   HIS G 709      61.773  86.024  52.602  1.00 34.04      G
ATOM  13670  CB   HIS G 709      61.260  86.887  53.769  1.00 21.97      G
ATOM  13671  CG   HIS G 709      59.773  86.850  53.971  1.00 21.97      G
ATOM  13672  CD2  HIS G 709      59.035  86.635  55.087  1.00 21.97      G
ATOM  13673  ND1  HIS G 709      58.870  87.119  52.965  1.00 21.97      G
ATOM  13674  CE1  HIS G 709      57.641  87.072  53.449  1.00 21.97      G
ATOM  13675  NE2  HIS G 709      57.714  86.781  54.735  1.00 21.97      G
ATOM  13676  C    HIS G 709      61.200  84.587  52.724  1.00 34.04      G
ATOM  13677  O    HIS G 709      60.108  84.277  52.255  1.00 34.04      G
ATOM  13678  N    ALA G 710      61.972  83.725  53.378  1.00 37.34      G
ATOM  13679  CA   ALA G 710      61.637  82.321  53.617  1.00 37.34      G
ATOM  13680  CB   ALA G 710      61.887  81.998  55.087  1.00 39.67      G
ATOM  13681  C    ALA G 710      60.267  81.776  53.225  1.00 37.34      G
ATOM  13682  O    ALA G 710      60.165  80.749  52.556  1.00 37.34      G
ATOM  13683  N    LEU G 711      59.213  82.459  53.644  1.00 37.53      G
ATOM  13684  CA   LEU G 711      57.845  82.000  53.406  1.00 37.53      G
ATOM  13685  CB   LEU G 711      56.930  82.763  54.368  1.00 68.00      G
ATOM  13686  CG   LEU G 711      57.603  82.864  55.753  1.00 68.00      G
ATOM  13687  CD1  LEU G 711      56.779  83.729  56.671  1.00 68.00      G
ATOM  13688  CD2  LEU G 711      57.801  81.484  56.361  1.00 68.00      G
ATOM  13689  C    LEU G 711      57.247  81.966  51.984  1.00 37.53      G
ATOM  13690  O    LEU G 711      56.051  81.728  51.803  1.00 37.53      G
ATOM  13691  N    GLY G 712      58.065  82.192  50.970  1.00 55.55      G
ATOM  13692  CA   GLY G 712      57.543  82.115  49.620  1.00 55.55      G
ATOM  13693  C    GLY G 712      57.451  80.630  49.296  1.00 55.55      G
ATOM  13694  O    GLY G 712      56.982  80.221  48.219  1.00 55.55      G
ATOM  13695  N    ILE G 713      57.925  79.811  50.235  1.00 19.96      G
ATOM  13696  CA   ILE G 713      57.883  78.372  50.050  1.00 19.96      G
ATOM  13697  CB   ILE G 713      59.309  77.764  49.902  1.00 24.03      G
ATOM  13698  CG2  ILE G 713      59.247  76.251  49.930  1.00 24.03      G
ATOM  13699  CG1  ILE G 713      59.905  78.125  48.542  1.00 24.03      G
ATOM  13700  CD   ILE G 713      60.331  79.531  48.420  1.00 24.03      G
ATOM  13701  C    ILE G 713      57.107  77.672  51.166  1.00 19.96      G
ATOM  13702  O    ILE G 713      55.919  77.423  51.004  1.00 19.96      G
ATOM  13703  N    ALA G 714      57.740  77.364  52.291  1.00 25.28      G
ATOM  13704  CA   ALA G 714      57.035  76.662  53.376  1.00 25.28      G
ATOM  13705  CB   ALA G 714      56.110  77.619  54.090  1.00 16.21      G
ATOM  13706  C    ALA G 714      56.257  75.409  52.884  1.00 25.28      G
ATOM  13707  O    ALA G 714      55.477  75.464  51.920  1.00 25.28      G
ATOM  13708  N    ALA G 715      56.449  74.282  53.569  1.00 15.03      G
ATOM  13709  CA   ALA G 715      55.838  73.023  53.135  1.00 15.03      G
ATOM  13710  CB   ALA G 715      56.881  71.902  53.217  1.00 20.14      G
ATOM  13711  C    ALA G 715      54.547  72.552  53.777  1.00 15.03      G
ATOM  13712  O    ALA G 715      54.178  72.982  54.861  1.00 15.03      G
ATOM  13713  N    PHE G 716      53.901  71.612  53.093  1.00 36.91      G
ATOM  13714  CA   PHE G 716      52.633  71.038  53.521  1.00 36.91      G
ATOM  13715  CB   PHE G 716      51.507  71.756  52.797  1.00 16.08      G
ATOM  13716  CG   PHE G 716      51.349  73.198  53.180  1.00 16.08      G
ATOM  13717  CD1  PHE G 716      51.264  74.179  52.200  1.00 16.08      G
ATOM  13718  CD2  PHE G 716      51.178  73.567  54.513  1.00 16.08      G
ATOM  13719  CE1  PHE G 716      51.001  75.494  52.541  1.00 16.08      G
ATOM  13720  CE2  PHE G 716      50.913  74.884  54.862  1.00 16.08      G
ATOM  13721  CZ   PHE G 716      50.822  75.846  53.878  1.00 16.08      G
ATOM  13722  C    PHE G 716      52.492  69.534  53.242  1.00 36.91      G
ATOM  13723  O    PHE G 716      53.312  68.930  52.554  1.00 36.91      G
ATOM  13724  N    GLN G 717      51.434  68.938  53.781  1.00 43.02      G
ATOM  13725  CA   GLN G 717      51.159  67.529  53.543  1.00 43.02      G
ATOM  13726  CB   GLN G 717      50.658  66.868  54.810  1.00 62.12      G
ATOM  13727  CG   GLN G 717      51.700  66.046  55.496  1.00 62.12      G
ATOM  13728  CD   GLN G 717      51.127  65.260  56.646  1.00 62.12      G
ATOM  13729  OE1  GLN G 717      50.101  64.590  56.500  1.00 62.12      G
ATOM  13730  NE2  GLN G 717      51.785  65.327  57.800  1.00 62.12      G
ATOM  13731  C    GLN G 717      50.063  67.482  52.489  1.00 43.02      G
ATOM  13732  O    GLN G 717      48.958  67.942  52.739  1.00 43.02      G
ATOM  13733  N    PRO G 718      50.348  66.937  51.293  1.00 40.24      G
ATOM  13734  CD   PRO G 718      51.639  66.529  50.716  1.00 66.21      G
ATOM  13735  CA   PRO G 718      49.297  66.895  50.270  1.00 40.24      G
ATOM  13736  CB   PRO G 718      49.978  66.213  49.092  1.00 66.21      G
ATOM  13737  CG   PRO G 718      51.370  66.680  49.216  1.00 66.21      G
ATOM  13738  C    PRO G 718      48.074  66.147  50.728  1.00 40.24      G
```

| ATOM | 13739 | O   | PRO G 718 | 48.171 | 65.153 | 51.433 | 1.00 | 40.24 | G |
| ATOM | 13740 | N   | VAL G 719 | 46.919 | 66.642 | 50.320 | 1.00 | 18.41 | G |
| ATOM | 13741 | CA  | VAL G 719 | 45.669 | 66.019 | 50.677 | 1.00 | 18.41 | G |
| ATOM | 13742 | CB  | VAL G 719 | 45.034 | 66.762 | 51.806 | 1.00 |  5.76 | G |
| ATOM | 13743 | CG1 | VAL G 719 | 43.514 | 66.781 | 51.638 | 1.00 |  5.76 | G |
| ATOM | 13744 | CG2 | VAL G 719 | 45.416 | 66.081 | 53.096 | 1.00 |  5.76 | G |
| ATOM | 13745 | C   | VAL G 719 | 44.723 | 65.994 | 49.499 | 1.00 | 18.41 | G |
| ATOM | 13746 | O   | VAL G 719 | 44.280 | 67.042 | 49.026 | 1.00 | 18.41 | G |
| ATOM | 13747 | N   | LEU G 720 | 44.396 | 64.794 | 49.038 | 1.00 | 24.94 | G |
| ATOM | 13748 | CA  | LEU G 720 | 43.524 | 64.659 | 47.889 | 1.00 | 24.94 | G |
| ATOM | 13749 | CB  | LEU G 720 | 43.204 | 63.191 | 47.676 | 1.00 | 29.73 | G |
| ATOM | 13750 | CG  | LEU G 720 | 44.252 | 62.527 | 46.770 | 1.00 | 29.73 | G |
| ATOM | 13751 | CD1 | LEU G 720 | 45.679 | 62.911 | 47.124 | 1.00 | 29.73 | G |
| ATOM | 13752 | CD2 | LEU G 720 | 44.075 | 61.048 | 46.887 | 1.00 | 29.73 | G |
| ATOM | 13753 | C   | LEU G 720 | 42.274 | 65.517 | 47.979 | 1.00 | 24.94 | G |
| ATOM | 13754 | O   | LEU G 720 | 41.368 | 65.268 | 48.767 | 1.00 | 24.94 | G |
| ATOM | 13755 | N   | VAL G 721 | 42.279 | 66.557 | 47.158 | 1.00 | 18.32 | G |
| ATOM | 13756 | CA  | VAL G 721 | 41.215 | 67.542 | 47.073 | 1.00 | 18.32 | G |
| ATOM | 13757 | CB  | VAL G 721 | 41.810 | 68.968 | 47.145 | 1.00 | 80.67 | G |
| ATOM | 13758 | CG1 | VAL G 721 | 40.800 | 70.004 | 46.649 | 1.00 | 80.67 | G |
| ATOM | 13759 | CG2 | VAL G 721 | 42.255 | 69.267 | 48.574 | 1.00 | 80.67 | G |
| ATOM | 13760 | C   | VAL G 721 | 40.505 | 67.357 | 45.739 | 1.00 | 18.32 | G |
| ATOM | 13761 | O   | VAL G 721 | 41.067 | 66.781 | 44.820 | 1.00 | 18.32 | G |
| ATOM | 13762 | N   | GLU G 722 | 39.288 | 67.876 | 45.629 | 1.00 | 45.32 | G |
| ATOM | 13763 | CA  | GLU G 722 | 38.489 | 67.734 | 44.426 | 1.00 | 45.32 | G |
| ATOM | 13764 | CB  | GLU G 722 | 37.206 | 68.544 | 44.550 | 1.00 | 44.29 | G |
| ATOM | 13765 | CG  | GLU G 722 | 36.123 | 68.015 | 43.653 | 1.00 | 44.29 | G |
| ATOM | 13766 | CD  | GLU G 722 | 36.437 | 66.609 | 43.166 | 1.00 | 44.29 | G |
| ATOM | 13767 | OE1 | GLU G 722 | 36.622 | 65.704 | 44.023 | 1.00 | 44.29 | G |
| ATOM | 13768 | OE2 | GLU G 722 | 36.507 | 66.423 | 41.925 | 1.00 | 44.29 | G |
| ATOM | 13769 | C   | GLU G 722 | 39.136 | 68.012 | 43.077 | 1.00 | 45.32 | G |
| ATOM | 13770 | O   | GLU G 722 | 40.215 | 67.496 | 42.795 | 1.00 | 45.32 | G |
| ATOM | 13771 | N   | GLY G 723 | 38.491 | 68.829 | 42.243 | 1.00 | 34.23 | G |
| ATOM | 13772 | CA  | GLY G 723 | 39.013 | 69.064 | 40.899 | 1.00 | 34.23 | G |
| ATOM | 13773 | C   | GLY G 723 | 39.745 | 70.316 | 40.433 | 1.00 | 34.23 | G |
| ATOM | 13774 | O   | GLY G 723 | 39.124 | 71.321 | 40.077 | 1.00 | 34.23 | G |
| ATOM | 13775 | N   | GLN G 724 | 41.071 | 70.223 | 40.375 | 1.00 | 56.41 | G |
| ATOM | 13776 | CA  | GLN G 724 | 41.933 | 71.320 | 39.938 | 1.00 | 56.41 | G |
| ATOM | 13777 | CB  | GLN G 724 | 41.507 | 71.809 | 38.546 | 1.00 | 59.60 | G |
| ATOM | 13778 | CG  | GLN G 724 | 41.979 | 70.867 | 37.425 | 1.00 | 59.60 | G |
| ATOM | 13779 | CD  | GLN G 724 | 41.227 | 71.027 | 36.111 | 1.00 | 59.60 | G |
| ATOM | 13780 | OE1 | GLN G 724 | 41.635 | 70.488 | 35.088 | 1.00 | 59.60 | G |
| ATOM | 13781 | NE2 | GLN G 724 | 40.117 | 71.753 | 36.140 | 1.00 | 59.60 | G |
| ATOM | 13782 | C   | GLN G 724 | 41.984 | 72.458 | 40.944 | 1.00 | 56.41 | G |
| ATOM | 13783 | O   | GLN G 724 | 41.268 | 72.440 | 41.941 | 1.00 | 56.41 | G |
| ATOM | 13784 | N   | SER G 725 | 42.845 | 73.435 | 40.684 | 1.00 | 20.83 | G |
| ATOM | 13785 | CA  | SER G 725 | 43.041 | 74.579 | 41.580 | 1.00 | 20.83 | G |
| ATOM | 13786 | CB  | SER G 725 | 41.783 | 75.448 | 41.637 | 1.00 | 24.46 | G |
| ATOM | 13787 | OG  | SER G 725 | 40.720 | 74.781 | 42.274 | 1.00 | 24.46 | G |
| ATOM | 13788 | C   | SER G 725 | 43.439 | 74.083 | 42.979 | 1.00 | 20.83 | G |
| ATOM | 13789 | O   | SER G 725 | 42.712 | 73.341 | 43.624 | 1.00 | 20.83 | G |
| ATOM | 13790 | N   | ILE G 726 | 44.620 | 74.489 | 43.427 | 1.00 | 28.03 | G |
| ATOM | 13791 | CA  | ILE G 726 | 45.144 | 74.063 | 44.718 | 1.00 | 28.03 | G |
| ATOM | 13792 | CB  | ILE G 726 | 46.613 | 74.423 | 44.891 | 1.00 |  7.17 | G |
| ATOM | 13793 | CG2 | ILE G 726 | 47.140 | 73.705 | 46.094 | 1.00 |  7.17 | G |
| ATOM | 13794 | CG1 | ILE G 726 | 47.415 | 74.071 | 43.636 | 1.00 |  7.17 | G |
| ATOM | 13795 | CD  | ILE G 726 | 48.900 | 74.259 | 43.804 | 1.00 |  7.17 | G |
| ATOM | 13796 | C   | ILE G 726 | 44.433 | 74.717 | 45.871 | 1.00 | 28.03 | G |
| ATOM | 13797 | O   | ILE G 726 | 44.211 | 75.929 | 45.865 | 1.00 | 28.03 | G |
| ATOM | 13798 | N   | GLN G 727 | 44.117 | 73.913 | 46.879 | 1.00 | 22.73 | G |
| ATOM | 13799 | CA  | GLN G 727 | 43.425 | 74.398 | 48.060 | 1.00 | 22.73 | G |
| ATOM | 13800 | CB  | GLN G 727 | 42.509 | 73.310 | 48.592 | 1.00 | 21.00 | G |
| ATOM | 13801 | CG  | GLN G 727 | 41.204 | 73.203 | 47.843 | 1.00 | 21.00 | G |
| ATOM | 13802 | CD  | GLN G 727 | 40.183 | 72.386 | 48.609 | 1.00 | 21.00 | G |
| ATOM | 13803 | OE1 | GLN G 727 | 38.996 | 72.355 | 48.258 | 1.00 | 21.00 | G |
| ATOM | 13804 | NE2 | GLN G 727 | 40.636 | 71.714 | 49.670 | 1.00 | 21.00 | G |
| ATOM | 13805 | C   | GLN G 727 | 44.409 | 74.809 | 49.139 | 1.00 | 22.73 | G |
| ATOM | 13806 | O   | GLN G 727 | 45.249 | 74.014 | 49.536 | 1.00 | 22.73 | G |
| ATOM | 13807 | N   | LEU G 728 | 44.298 | 76.041 | 49.626 | 1.00 | 60.72 | G |
| ATOM | 13808 | CA  | LEU G 728 | 45.216 | 76.533 | 50.653 | 1.00 | 60.72 | G |
| ATOM | 13809 | CB  | LEU G 728 | 45.834 | 77.845 | 50.207 | 1.00 |  5.43 | G |
| ATOM | 13810 | CG  | LEU G 728 | 47.128 | 78.382 | 50.791 | 1.00 |  5.43 | G |
| ATOM | 13811 | CD1 | LEU G 728 | 48.307 | 77.922 | 49.982 | 1.00 |  5.43 | G |
| ATOM | 13812 | CD2 | LEU G 728 | 47.062 | 79.868 | 50.705 | 1.00 |  5.43 | G |
| ATOM | 13813 | C   | LEU G 728 | 44.501 | 76.752 | 51.972 | 1.00 | 60.72 | G |
| ATOM | 13814 | O   | LEU G 728 | 43.278 | 76.611 | 52.050 | 1.00 | 60.72 | G |
| ATOM | 13815 | N   | HIS G 729 | 45.270 | 77.132 | 52.993 | 1.00 | 39.07 | G |
| ATOM | 13816 | CA  | HIS G 729 | 44.740 | 77.352 | 54.346 | 1.00 | 39.07 | G |
| ATOM | 13817 | CB  | HIS G 729 | 45.521 | 76.462 | 55.321 | 1.00 | 20.64 | G |
| ATOM | 13818 | CG  | HIS G 729 | 45.291 | 76.786 | 56.759 | 1.00 | 20.64 | G |
| ATOM | 13819 | CD2 | HIS G 729 | 46.134 | 76.772 | 57.814 | 1.00 | 20.64 | G |
| ATOM | 13820 | ND1 | HIS G 729 | 44.064 | 77.171 | 57.254 | 1.00 | 20.64 | G |
| ATOM | 13821 | CE1 | HIS G 729 | 44.162 | 77.381 | 58.554 | 1.00 | 20.64 | G |
| ATOM | 13822 | NE2 | HIS G 729 | 45.409 | 77.144 | 58.919 | 1.00 | 20.64 | G |

```
ATOM  13823  C    HIS G 729    44.767  78.826  54.792  1.00 39.07      G
ATOM  13824  O    HIS G 729    45.839  79.420  54.937  1.00 39.07      G
ATOM  13825  N    PRO G 730    43.581  79.412  55.063  1.00 24.89      G
ATOM  13826  CD   PRO G 730    42.423  78.677  55.568  1.00  6.55      G
ATOM  13827  CA   PRO G 730    43.439  80.799  55.477  1.00 24.89      G
ATOM  13828  CB   PRO G 730    42.062  80.829  56.102  1.00  6.55      G
ATOM  13829  CG   PRO G 730    42.020  79.545  56.748  1.00  6.55      G
ATOM  13830  C    PRO G 730    44.507  81.276  56.420  1.00 24.89      G
ATOM  13831  O    PRO G 730    44.875  82.443  56.366  1.00 24.89      G
ATOM  13832  N    LEU G 731    45.026  80.420  57.288  1.00 27.73      G
ATOM  13833  CA   LEU G 731    46.059  80.943  58.162  1.00 27.73      G
ATOM  13834  CB   LEU G 731    46.388  79.987  59.301  1.00  6.67      G
ATOM  13835  CG   LEU G 731    45.513  80.570  60.407  1.00  6.67      G
ATOM  13836  CD1  LEU G 731    45.547  79.790  61.728  1.00  6.67      G
ATOM  13837  CD2  LEU G 731    45.989  82.000  60.599  1.00  6.67      G
ATOM  13838  C    LEU G 731    47.306  81.323  57.408  1.00 27.73      G
ATOM  13839  O    LEU G 731    47.825  82.424  57.575  1.00 27.73      G
ATOM  13840  N    VAL G 732    47.777  80.448  56.536  1.00 25.75      G
ATOM  13841  CA   VAL G 732    48.981  80.787  55.812  1.00 25.75      G
ATOM  13842  CB   VAL G 732    49.443  79.641  54.877  1.00 22.98      G
ATOM  13843  CG1  VAL G 732    50.201  80.201  53.696  1.00 22.98      G
ATOM  13844  CG2  VAL G 732    50.369  78.698  55.640  1.00 22.98      G
ATOM  13845  C    VAL G 732    48.911  82.095  55.035  1.00 25.75      G
ATOM  13846  O    VAL G 732    49.847  82.869  55.146  1.00 25.75      G
ATOM  13847  N    CYS G 733    47.836  82.369  54.287  1.00 25.89      G
ATOM  13848  CA   CYS G 733    47.777  83.617  53.510  1.00 25.89      G
ATOM  13849  CB   CYS G 733    46.400  84.289  53.614  1.00 40.39      G
ATOM  13850  SG   CYS G 733    46.388  86.066  53.027  1.00 40.39      G
ATOM  13851  C    CYS G 733    48.870  84.626  53.936  1.00 25.89      G
ATOM  13852  O    CYS G 733    49.939  84.687  53.318  1.00 25.89      G
ATOM  13853  N    GLU G 734    48.600  85.395  54.995  1.00 26.35      G
ATOM  13854  CA   GLU G 734    49.537  86.388  55.541  1.00 26.35      G
ATOM  13855  CB   GLU G 734    49.660  86.214  57.060  1.00 95.88      G
ATOM  13856  CG   GLU G 734    48.382  86.468  57.808  1.00 95.88      G
ATOM  13857  CD   GLU G 734    47.743  87.754  57.360  1.00 95.88      G
ATOM  13858  OE1  GLU G 734    48.461  88.777  57.327  1.00 95.88      G
ATOM  13859  OE2  GLU G 734    46.534  87.741  57.033  1.00 95.88      G
ATOM  13860  C    GLU G 734    50.930  86.333  54.938  1.00 26.35      G
ATOM  13861  O    GLU G 734    51.175  86.902  53.895  1.00 26.35      G
ATOM  13862  N    ALA G 735    51.835  85.633  55.611  1.00 10.09      G
ATOM  13863  CA   ALA G 735    53.206  85.498  55.160  1.00 10.09      G
ATOM  13864  CB   ALA G 735    53.868  84.376  55.869  1.00  5.07      G
ATOM  13865  C    ALA G 735    53.339  85.291  53.672  1.00 10.09      G
ATOM  13866  O    ALA G 735    53.891  86.148  52.982  1.00 10.09      G
ATOM  13867  N    PHE G 736    52.839  84.161  53.172  1.00 22.54      G
ATOM  13868  CA   PHE G 736    52.941  83.842  51.737  1.00 22.54      G
ATOM  13869  CB   PHE G 736    52.390  82.425  51.451  1.00 26.85      G
ATOM  13870  CG   PHE G 736    52.978  81.341  52.358  1.00 26.85      G
ATOM  13871  CD1  PHE G 736    53.090  81.545  53.758  1.00 26.85      G
ATOM  13872  CD2  PHE G 736    53.337  80.093  51.848  1.00 26.85      G
ATOM  13873  CE1  PHE G 736    53.549  80.521  54.637  1.00 26.85      G
ATOM  13874  CE2  PHE G 736    53.798  79.067  52.732  1.00 26.85      G
ATOM  13875  CZ   PHE G 736    53.891  79.296  54.129  1.00 26.85      G
ATOM  13876  C    PHE G 736    52.233  84.899  50.893  1.00 22.54      G
ATOM  13877  O    PHE G 736    52.726  85.314  49.848  1.00 22.54      G
ATOM  13878  N    ASN G 737    51.085  85.354  51.366  1.00 43.47      G
ATOM  13879  CA   ASN G 737    50.345  86.381  50.661  1.00 43.47      G
ATOM  13880  CB   ASN G 737    51.310  87.464  50.175  1.00 31.04      G
ATOM  13881  CG   ASN G 737    50.610  88.555  49.396  1.00 31.04      G
ATOM  13882  OD1  ASN G 737    49.995  88.291  48.360  1.00 31.04      G
ATOM  13883  ND2  ASN G 737    50.693  89.796  49.893  1.00 31.04      G
ATOM  13884  C    ASN G 737    49.575  85.827  49.477  1.00 43.47      G
ATOM  13885  O    ASN G 737    50.190  85.327  48.533  1.00 43.47      G
ATOM  13886  N    ALA G 738    48.241  85.920  49.510  1.00 23.77      G
ATOM  13887  CA   ALA G 738    47.450  85.416  48.388  1.00 23.77      G
ATOM  13888  CB   ALA G 738    47.645  83.901  48.276  1.00 72.85      G
ATOM  13889  C    ALA G 738    45.955  85.744  48.327  1.00 23.77      G
ATOM  13890  O    ALA G 738    45.138  84.845  48.319  1.00 23.77      G
ATOM  13891  N    ASP G 739    45.568  87.008  48.256  1.00 84.88      G
ATOM  13892  CA   ASP G 739    44.137  87.278  48.165  1.00 84.88      G
ATOM  13893  CB   ASP G 739    43.879  88.785  48.016  1.00100.07      G
ATOM  13894  CG   ASP G 739    44.843  89.460  47.056  1.00100.07      G
ATOM  13895  OD1  ASP G 739    46.057  89.500  47.354  1.00100.07      G
ATOM  13896  OD2  ASP G 739    44.381  89.958  46.006  1.00100.07      G
ATOM  13897  C    ASP G 739    43.553  86.501  46.971  1.00 84.88      G
ATOM  13898  O    ASP G 739    43.701  86.918  45.821  1.00 84.88      G
ATOM  13899  N    PHE G 740    42.905  85.369  47.253  1.00  5.65      G
ATOM  13900  CA   PHE G 740    42.317  84.520  46.217  1.00  5.65      G
ATOM  13901  CB   PHE G 740    41.488  83.404  46.839  1.00 13.82      G
ATOM  13902  CG   PHE G 740    42.123  82.754  48.021  1.00 13.82      G
ATOM  13903  CD1  PHE G 740    42.274  83.436  49.207  1.00 13.82      G
ATOM  13904  CD2  PHE G 740    42.572  81.449  47.954  1.00 13.82      G
ATOM  13905  CE1  PHE G 740    42.868  82.826  50.308  1.00 13.82      G
ATOM  13906  CE2  PHE G 740    43.168  80.839  49.058  1.00 13.82      G
```

| ATOM | 13907 | CZ | PHE | G | 740 | 43.313 | 81.529 | 50.223 | 1.00 | 13.82 | G |
|------|-------|----|-----|---|-----|--------|--------|--------|------|-------|---|
| ATOM | 13908 | C | PHE | G | 740 | 41.393 | 85.278 | 45.284 | 1.00 | 5.65 | G |
| ATOM | 13909 | O | PHE | G | 740 | 40.206 | 85.392 | 45.574 | 1.00 | 5.65 | G |
| ATOM | 13910 | N | ASP | G | 741 | 41.912 | 85.780 | 44.168 | 1.00 | 14.73 | G |
| ATOM | 13911 | CA | ASP | G | 741 | 41.091 | 86.510 | 43.187 | 1.00 | 14.73 | G |
| ATOM | 13912 | CB | ASP | G | 741 | 41.012 | 88.015 | 43.511 | 1.00 | 68.42 | G |
| ATOM | 13913 | CG | ASP | G | 741 | 42.381 | 88.672 | 43.653 | 1.00 | 68.42 | G |
| ATOM | 13914 | OD1 | ASP | G | 741 | 43.400 | 87.991 | 43.428 | 1.00 | 68.42 | G |
| ATOM | 13915 | OD2 | ASP | G | 741 | 42.434 | 89.875 | 43.995 | 1.00 | 68.42 | G |
| ATOM | 13916 | C | ASP | G | 741 | 41.694 | 86.305 | 41.807 | 1.00 | 14.73 | G |
| ATOM | 13917 | O | ASP | G | 741 | 41.600 | 87.163 | 40.914 | 1.00 | 14.73 | G |
| ATOM | 13918 | N | GLY | G | 742 | 42.314 | 85.136 | 41.661 | 1.00 | 35.12 | G |
| ATOM | 13919 | CA | GLY | G | 742 | 42.963 | 84.760 | 40.425 | 1.00 | 35.12 | G |
| ATOM | 13920 | C | GLY | G | 742 | 44.412 | 84.397 | 40.683 | 1.00 | 35.12 | G |
| ATOM | 13921 | O | GLY | G | 742 | 45.136 | 84.056 | 39.756 | 1.00 | 35.12 | G |
| ATOM | 13922 | N | ASP | G | 743 | 44.839 | 84.448 | 41.942 | 1.00 | 31.29 | G |
| ATOM | 13923 | CA | ASP | G | 743 | 46.231 | 84.156 | 42.286 | 1.00 | 31.29 | G |
| ATOM | 13924 | CB | ASP | G | 743 | 46.521 | 84.495 | 43.767 | 1.00 | 71.46 | G |
| ATOM | 13925 | CG | ASP | G | 743 | 46.512 | 86.019 | 44.050 | 1.00 | 71.46 | G |
| ATOM | 13926 | OD1 | ASP | G | 743 | 47.067 | 86.790 | 43.231 | 1.00 | 71.46 | G |
| ATOM | 13927 | OD2 | ASP | G | 743 | 45.965 | 86.449 | 45.094 | 1.00 | 71.46 | G |
| ATOM | 13928 | C | ASP | G | 743 | 46.613 | 82.721 | 41.983 | 1.00 | 31.29 | G |
| ATOM | 13929 | O | ASP | G | 743 | 45.757 | 81.844 | 41.929 | 1.00 | 31.29 | G |
| ATOM | 13930 | N | GLN | G | 744 | 47.911 | 82.506 | 41.776 | 1.00 | 17.67 | G |
| ATOM | 13931 | CA | GLN | G | 744 | 48.479 | 81.190 | 41.446 | 1.00 | 17.67 | G |
| ATOM | 13932 | CB | GLN | G | 744 | 48.826 | 81.135 | 39.957 | 1.00 | 50.63 | G |
| ATOM | 13933 | CG | GLN | G | 744 | 47.652 | 81.262 | 39.027 | 1.00 | 50.63 | G |
| ATOM | 13934 | CD | GLN | G | 744 | 48.052 | 81.012 | 37.591 | 1.00 | 50.63 | G |
| ATOM | 13935 | OE1 | GLN | G | 744 | 48.747 | 80.045 | 37.298 | 1.00 | 50.63 | G |
| ATOM | 13936 | NE2 | GLN | G | 744 | 47.611 | 81.877 | 36.687 | 1.00 | 50.63 | G |
| ATOM | 13937 | C | GLN | G | 744 | 49.740 | 80.795 | 42.237 | 1.00 | 17.67 | G |
| ATOM | 13938 | O | GLN | G | 744 | 50.767 | 81.473 | 42.178 | 1.00 | 17.67 | G |
| ATOM | 13939 | N | MET | G | 745 | 49.661 | 79.693 | 42.972 | 1.00 | 9.28 | G |
| ATOM | 13940 | CA | MET | G | 745 | 50.808 | 79.220 | 43.727 | 1.00 | 9.28 | G |
| ATOM | 13941 | CB | MET | G | 745 | 50.420 | 78.855 | 45.153 | 1.00 | 35.53 | G |
| ATOM | 13942 | CG | MET | G | 745 | 50.362 | 80.045 | 46.064 | 1.00 | 35.53 | G |
| ATOM | 13943 | SD | MET | G | 745 | 49.823 | 79.622 | 47.713 | 1.00 | 35.53 | G |
| ATOM | 13944 | CE | MET | G | 745 | 48.263 | 80.588 | 47.859 | 1.00 | 35.53 | G |
| ATOM | 13945 | C | MET | G | 745 | 51.302 | 78.001 | 42.994 | 1.00 | 9.28 | G |
| ATOM | 13946 | O | MET | G | 745 | 50.521 | 77.355 | 42.300 | 1.00 | 9.28 | G |
| ATOM | 13947 | N | ALA | G | 746 | 52.596 | 77.708 | 43.114 | 1.00 | 20.56 | G |
| ATOM | 13948 | CA | ALA | G | 746 | 53.182 | 76.554 | 42.449 | 1.00 | 20.56 | G |
| ATOM | 13949 | CB | ALA | G | 746 | 54.471 | 76.927 | 41.790 | 1.00 | 16.51 | G |
| ATOM | 13950 | C | ALA | G | 746 | 53.436 | 75.513 | 43.490 | 1.00 | 20.56 | G |
| ATOM | 13951 | O | ALA | G | 746 | 53.366 | 75.807 | 44.680 | 1.00 | 20.56 | G |
| ATOM | 13952 | N | VAL | G | 747 | 53.735 | 74.295 | 43.061 | 1.00 | 15.01 | G |
| ATOM | 13953 | CA | VAL | G | 747 | 53.989 | 73.231 | 44.025 | 1.00 | 15.01 | G |
| ATOM | 13954 | CB | VAL | G | 747 | 52.772 | 72.326 | 44.180 | 1.00 | 9.72 | G |
| ATOM | 13955 | CG1 | VAL | G | 747 | 52.477 | 71.618 | 42.883 | 1.00 | 9.72 | G |
| ATOM | 13956 | CG2 | VAL | G | 747 | 53.031 | 71.333 | 45.226 | 1.00 | 9.72 | G |
| ATOM | 13957 | C | VAL | G | 747 | 55.153 | 72.383 | 43.581 | 1.00 | 15.01 | G |
| ATOM | 13958 | O | VAL | G | 747 | 55.249 | 72.059 | 42.413 | 1.00 | 15.01 | G |
| ATOM | 13959 | N | HIS | G | 748 | 56.046 | 72.031 | 44.497 | 1.00 | 20.53 | G |
| ATOM | 13960 | CA | HIS | G | 748 | 57.183 | 71.189 | 44.131 | 1.00 | 20.53 | G |
| ATOM | 13961 | CB | HIS | G | 748 | 58.520 | 71.864 | 44.438 | 1.00 | 11.94 | G |
| ATOM | 13962 | CG | HIS | G | 748 | 58.761 | 73.093 | 43.637 | 1.00 | 11.94 | G |
| ATOM | 13963 | CD2 | HIS | G | 748 | 58.955 | 74.379 | 44.012 | 1.00 | 11.94 | G |
| ATOM | 13964 | ND1 | HIS | G | 748 | 58.776 | 73.083 | 42.263 | 1.00 | 11.94 | G |
| ATOM | 13965 | CE1 | HIS | G | 748 | 58.955 | 74.314 | 41.823 | 1.00 | 11.94 | G |
| ATOM | 13966 | NE2 | HIS | G | 748 | 59.078 | 75.120 | 42.863 | 1.00 | 11.94 | G |
| ATOM | 13967 | C | HIS | G | 748 | 57.105 | 69.905 | 44.910 | 1.00 | 20.53 | G |
| ATOM | 13968 | O | HIS | G | 748 | 56.125 | 69.654 | 45.603 | 1.00 | 20.53 | G |
| ATOM | 13969 | N | VAL | G | 749 | 58.150 | 69.097 | 44.804 | 1.00 | 41.37 | G |
| ATOM | 13970 | CA | VAL | G | 749 | 58.160 | 67.843 | 45.514 | 1.00 | 41.37 | G |
| ATOM | 13971 | CB | VAL | G | 749 | 57.857 | 66.680 | 44.591 | 1.00 | 30.63 | G |
| ATOM | 13972 | CG1 | VAL | G | 749 | 57.342 | 65.512 | 45.417 | 1.00 | 30.63 | G |
| ATOM | 13973 | CG2 | VAL | G | 749 | 56.874 | 67.099 | 43.528 | 1.00 | 30.63 | G |
| ATOM | 13974 | C | VAL | G | 749 | 59.482 | 67.538 | 46.156 | 1.00 | 41.37 | G |
| ATOM | 13975 | O | VAL | G | 749 | 60.484 | 67.397 | 45.469 | 1.00 | 41.37 | G |
| ATOM | 13976 | N | PRO | G | 750 | 59.516 | 67.453 | 47.486 | 1.00 | 36.25 | G |
| ATOM | 13977 | CD | PRO | G | 750 | 58.461 | 67.485 | 48.506 | 1.00 | 66.28 | G |
| ATOM | 13978 | CA | PRO | G | 750 | 60.807 | 67.136 | 48.083 | 1.00 | 36.25 | G |
| ATOM | 13979 | CB | PRO | G | 750 | 60.511 | 67.173 | 49.572 | 1.00 | 66.28 | G |
| ATOM | 13980 | CG | PRO | G | 750 | 59.093 | 66.709 | 49.628 | 1.00 | 66.28 | G |
| ATOM | 13981 | C | PRO | G | 750 | 61.079 | 65.731 | 47.565 | 1.00 | 36.25 | G |
| ATOM | 13982 | O | PRO | G | 750 | 60.444 | 64.759 | 47.991 | 1.00 | 36.25 | G |
| ATOM | 13983 | N | LEU | G | 751 | 61.996 | 65.647 | 46.609 | 1.00 | 56.44 | G |
| ATOM | 13984 | CA | LEU | G | 751 | 62.352 | 64.392 | 45.974 | 1.00 | 56.44 | G |
| ATOM | 13985 | CB | LEU | G | 751 | 62.192 | 64.533 | 44.463 | 1.00 | 99.95 | G |
| ATOM | 13986 | CG | LEU | G | 751 | 62.585 | 63.350 | 43.581 | 1.00 | 99.95 | G |
| ATOM | 13987 | CD1 | LEU | G | 751 | 61.344 | 62.546 | 43.254 | 1.00 | 99.95 | G |
| ATOM | 13988 | CD2 | LEU | G | 751 | 63.241 | 63.851 | 42.303 | 1.00 | 99.95 | G |
| ATOM | 13989 | C | LEU | G | 751 | 63.791 | 64.025 | 46.279 | 1.00 | 56.44 | G |
| ATOM | 13990 | O | LEU | G | 751 | 64.614 | 63.996 | 45.365 | 1.00 | 56.44 | G |

| ATOM | 13991 | N | SER G 752 | 64.105 | 63.747 | 47.544 | 1.00 34.49 | G |
|---|---|---|---|---|---|---|---|---|
| ATOM | 13992 | CA | SER G 752 | 65.478 | 63.387 | 47.919 | 1.00 34.49 | G |
| ATOM | 13993 | CB | SER G 752 | 66.422 | 64.606 | 47.802 | 1.00 22.59 | G |
| ATOM | 13994 | OG | SER G 752 | 66.071 | 65.525 | 46.770 | 1.00 22.59 | G |
| ATOM | 13995 | C | SER G 752 | 65.532 | 62.886 | 49.357 | 1.00 34.49 | G |
| ATOM | 13996 | O | SER G 752 | 66.478 | 63.201 | 50.074 | 1.00 34.49 | G |
| ATOM | 13997 | N | SER G 753 | 64.542 | 62.092 | 49.764 | 1.00 28.54 | G |
| ATOM | 13998 | CA | SER G 753 | 64.461 | 61.602 | 51.149 | 1.00 28.54 | G |
| ATOM | 13999 | CB | SER G 753 | 65.237 | 60.297 | 51.378 | 1.00 15.37 | G |
| ATOM | 14000 | OG | SER G 753 | 65.300 | 60.000 | 52.775 | 1.00 15.37 | G |
| ATOM | 14001 | C | SER G 753 | 65.033 | 62.659 | 52.062 | 1.00 28.54 | G |
| ATOM | 14002 | O | SER G 753 | 64.301 | 63.472 | 52.604 | 1.00 28.54 | G |
| ATOM | 14003 | N | PHE G 754 | 66.347 | 62.643 | 52.223 | 1.00 39.13 | G |
| ATOM | 14004 | CA | PHE G 754 | 67.004 | 63.626 | 53.049 | 1.00 39.13 | G |
| ATOM | 14005 | CB | PHE G 754 | 68.463 | 63.757 | 52.646 | 1.00 77.81 | G |
| ATOM | 14006 | CG | PHE G 754 | 69.311 | 64.402 | 53.689 | 1.00 77.81 | G |
| ATOM | 14007 | CD1 | PHE G 754 | 70.101 | 63.629 | 54.531 | 1.00 77.81 | G |
| ATOM | 14008 | CD2 | PHE G 754 | 69.291 | 65.772 | 53.862 | 1.00 77.81 | G |
| ATOM | 14009 | CE1 | PHE G 754 | 70.858 | 64.212 | 55.528 | 1.00 77.81 | G |
| ATOM | 14010 | CE2 | PHE G 754 | 70.041 | 66.361 | 54.854 | 1.00 77.81 | G |
| ATOM | 14011 | CZ | PHE G 754 | 70.827 | 65.579 | 55.692 | 1.00 77.81 | G |
| ATOM | 14012 | C | PHE G 754 | 66.318 | 64.977 | 52.875 | 1.00 39.13 | G |
| ATOM | 14013 | O | PHE G 754 | 66.154 | 65.713 | 53.849 | 1.00 39.13 | G |
| ATOM | 14014 | N | ALA G 755 | 65.907 | 65.295 | 51.643 | 1.00 38.20 | G |
| ATOM | 14015 | CA | ALA G 755 | 65.231 | 66.570 | 51.347 | 1.00 38.20 | G |
| ATOM | 14016 | CB | ALA G 755 | 65.105 | 66.761 | 49.844 | 1.00100.07 | G |
| ATOM | 14017 | C | ALA G 755 | 63.851 | 66.699 | 52.001 | 1.00 38.20 | G |
| ATOM | 14018 | O | ALA G 755 | 63.132 | 67.675 | 51.800 | 1.00 38.20 | G |
| ATOM | 14019 | N | GLN G 756 | 63.494 | 65.693 | 52.779 | 1.00 45.28 | G |
| ATOM | 14020 | CA | GLN G 756 | 62.237 | 65.669 | 53.487 | 1.00 45.28 | G |
| ATOM | 14021 | CB | GLN G 756 | 61.710 | 64.241 | 53.534 | 1.00 49.70 | G |
| ATOM | 14022 | CG | GLN G 756 | 60.226 | 64.101 | 53.381 | 1.00 49.70 | G |
| ATOM | 14023 | CD | GLN G 756 | 59.795 | 64.491 | 52.010 | 1.00 49.70 | G |
| ATOM | 14024 | OE1 | GLN G 756 | 60.614 | 64.532 | 51.095 | 1.00 49.70 | G |
| ATOM | 14025 | NE2 | GLN G 756 | 58.503 | 64.771 | 51.841 | 1.00 49.70 | G |
| ATOM | 14026 | C | GLN G 756 | 62.609 | 66.115 | 54.892 | 1.00 45.28 | G |
| ATOM | 14027 | O | GLN G 756 | 62.048 | 67.067 | 55.432 | 1.00 45.28 | G |
| ATOM | 14028 | N | ALA G 757 | 63.577 | 65.410 | 55.467 | 1.00 99.84 | G |
| ATOM | 14029 | CA | ALA G 757 | 64.059 | 65.686 | 56.810 | 1.00 99.84 | G |
| ATOM | 14030 | CB | ALA G 757 | 65.377 | 64.992 | 57.031 | 1.00100.07 | G |
| ATOM | 14031 | C | ALA G 757 | 64.210 | 67.174 | 57.063 | 1.00 99.84 | G |
| ATOM | 14032 | O | ALA G 757 | 64.363 | 67.604 | 58.204 | 1.00 99.84 | G |
| ATOM | 14033 | N | GLU G 758 | 64.186 | 67.959 | 55.993 | 1.00 26.91 | G |
| ATOM | 14034 | CA | GLU G 758 | 64.295 | 69.403 | 56.117 | 1.00 26.91 | G |
| ATOM | 14035 | CB | GLU G 758 | 65.573 | 69.898 | 55.440 | 1.00 83.00 | G |
| ATOM | 14036 | CG | GLU G 758 | 65.950 | 69.148 | 54.180 | 1.00 83.00 | G |
| ATOM | 14037 | CD | GLU G 758 | 67.354 | 69.483 | 53.715 | 1.00 83.00 | G |
| ATOM | 14038 | OE1 | GLU G 758 | 68.296 | 69.353 | 54.524 | 1.00 83.00 | G |
| ATOM | 14039 | OE2 | GLU G 758 | 67.520 | 69.871 | 52.543 | 1.00 83.00 | G |
| ATOM | 14040 | C | GLU G 758 | 63.060 | 70.060 | 55.516 | 1.00 26.91 | G |
| ATOM | 14041 | O | GLU G 758 | 62.695 | 71.177 | 55.881 | 1.00 26.91 | G |
| ATOM | 14042 | N | ALA G 759 | 62.416 | 69.353 | 54.595 | 1.00 27.38 | G |
| ATOM | 14043 | CA | ALA G 759 | 61.210 | 69.857 | 53.968 | 1.00 27.38 | G |
| ATOM | 14044 | CB | ALA G 759 | 60.796 | 68.940 | 52.854 | 1.00 83.74 | G |
| ATOM | 14045 | C | ALA G 759 | 60.134 | 69.903 | 55.044 | 1.00 27.38 | G |
| ATOM | 14046 | O | ALA G 759 | 59.373 | 70.864 | 55.131 | 1.00 27.38 | G |
| ATOM | 14047 | N | ARG G 760 | 60.079 | 68.857 | 55.865 | 1.00 54.39 | G |
| ATOM | 14048 | CA | ARG G 760 | 59.104 | 68.784 | 56.952 | 1.00 54.39 | G |
| ATOM | 14049 | CB | ARG G 760 | 58.176 | 67.563 | 56.787 | 1.00 87.50 | G |
| ATOM | 14050 | CG | ARG G 760 | 58.863 | 66.196 | 56.844 | 1.00 87.50 | G |
| ATOM | 14051 | CD | ARG G 760 | 57.868 | 65.039 | 57.050 | 1.00 87.50 | G |
| ATOM | 14052 | NE | ARG G 760 | 57.108 | 65.177 | 58.293 | 1.00 87.50 | G |
| ATOM | 14053 | CZ | ARG G 760 | 56.325 | 64.235 | 58.808 | 1.00 87.50 | G |
| ATOM | 14054 | NH1 | ARG G 760 | 56.194 | 63.068 | 58.191 | 1.00 87.50 | G |
| ATOM | 14055 | NH2 | ARG G 760 | 55.669 | 64.465 | 59.939 | 1.00 87.50 | G |
| ATOM | 14056 | C | ARG G 760 | 59.818 | 68.723 | 58.307 | 1.00 54.39 | G |
| ATOM | 14057 | O | ARG G 760 | 60.204 | 67.655 | 58.778 | 1.00 54.39 | G |
| ATOM | 14058 | N | ILE G 761 | 59.977 | 69.892 | 58.920 | 1.00 83.15 | G |
| ATOM | 14059 | CA | ILE G 761 | 60.655 | 70.069 | 60.205 | 1.00 83.15 | G |
| ATOM | 14060 | CB | ILE G 761 | 62.057 | 69.383 | 60.248 | 1.00 23.93 | G |
| ATOM | 14061 | CG2 | ILE G 761 | 63.066 | 70.245 | 61.019 | 1.00 23.93 | G |
| ATOM | 14062 | CG1 | ILE G 761 | 61.957 | 67.994 | 60.872 | 1.00 23.93 | G |
| ATOM | 14063 | CD | ILE G 761 | 63.283 | 67.234 | 60.868 | 1.00 23.93 | G |
| ATOM | 14064 | C | ILE G 761 | 60.909 | 71.552 | 60.253 | 1.00 83.15 | G |
| ATOM | 14065 | O | ILE G 761 | 60.311 | 72.280 | 61.035 | 1.00 83.15 | G |
| ATOM | 14066 | N | GLN G 762 | 61.801 | 71.980 | 59.369 | 1.00 50.63 | G |
| ATOM | 14067 | CA | GLN G 762 | 62.194 | 73.361 | 59.283 | 1.00 50.63 | G |
| ATOM | 14068 | CB | GLN G 762 | 63.702 | 73.446 | 59.035 | 1.00 33.97 | G |
| ATOM | 14069 | CG | GLN G 762 | 64.280 | 72.394 | 58.087 | 1.00 33.97 | G |
| ATOM | 14070 | CD | GLN G 762 | 65.804 | 72.305 | 58.165 | 1.00 33.97 | G |
| ATOM | 14071 | OE1 | GLN G 762 | 66.514 | 73.233 | 57.780 | 1.00 33.97 | G |
| ATOM | 14072 | NE2 | GLN G 762 | 66.304 | 71.187 | 58.679 | 1.00 33.97 | G |
| ATOM | 14073 | C | GLN G 762 | 61.433 | 74.236 | 58.289 | 1.00 50.63 | G |
| ATOM | 14074 | O | GLN G 762 | 61.644 | 75.444 | 58.278 | 1.00 50.63 | G |

```
ATOM  14075  N    MET G 763      60.574  73.669  57.442  1.00 75.54      G
ATOM  14076  CA   MET G 763      59.792  74.528  56.542  1.00 75.54      G
ATOM  14077  CB   MET G 763      60.440  74.702  55.156  1.00 42.15      G
ATOM  14078  CG   MET G 763      61.334  73.611  54.621  1.00 42.15      G
ATOM  14079  SD   MET G 763      62.296  74.380  53.277  1.00 42.15      G
ATOM  14080  CE   MET G 763      61.831  73.444  51.911  1.00 42.15      G
ATOM  14081  C    MET G 763      58.327  74.152  56.387  1.00 75.54      G
ATOM  14082  O    MET G 763      57.639  74.623  55.489  1.00 75.54      G
ATOM  14083  N    LEU G 764      57.859  73.309  57.293  1.00 19.27      G
ATOM  14084  CA   LEU G 764      56.462  72.879  57.324  1.00 19.27      G
ATOM  14085  CB   LEU G 764      56.300  71.674  58.242  1.00  7.79      G
ATOM  14086  CG   LEU G 764      54.852  71.393  58.543  1.00  7.79      G
ATOM  14087  CD1  LEU G 764      54.225  70.721  57.366  1.00  7.79      G
ATOM  14088  CD2  LEU G 764      54.802  70.523  59.727  1.00  7.79      G
ATOM  14089  C    LEU G 764      55.745  74.048  57.946  1.00 19.27      G
ATOM  14090  O    LEU G 764      56.239  74.631  58.891  1.00 19.27      G
ATOM  14091  N    SER G 765      54.578  74.391  57.459  1.00 20.09      G
ATOM  14092  CA   SER G 765      53.952  75.537  58.048  1.00 20.09      G
ATOM  14093  CB   SER G 765      52.547  75.737  57.499  1.00 41.15      G
ATOM  14094  OG   SER G 765      51.797  74.553  57.602  1.00 41.15      G
ATOM  14095  C    SER G 765      53.928  75.456  59.561  1.00 20.09      G
ATOM  14096  O    SER G 765      54.512  76.305  60.218  1.00 20.09      G
ATOM  14097  N    ALA G 766      53.318  74.422  60.131  1.00  8.14      G
ATOM  14098  CA   ALA G 766      53.192  74.341  61.593  1.00  8.14      G
ATOM  14099  CB   ALA G 766      52.370  73.110  61.989  1.00 27.34      G
ATOM  14100  C    ALA G 766      54.440  74.416  62.467  1.00  8.14      G
ATOM  14101  O    ALA G 766      54.320  74.354  63.687  1.00  8.14      G
ATOM  14102  N    HIS G 767      55.631  74.541  61.893  1.00 56.35      G
ATOM  14103  CA   HIS G 767      56.827  74.644  62.740  1.00 56.35      G
ATOM  14104  CB   HIS G 767      57.864  73.552  62.418  1.00 60.80      G
ATOM  14105  CG   HIS G 767      57.333  72.153  62.488  1.00 60.80      G
ATOM  14106  CD2  HIS G 767      57.573  71.072  61.709  1.00 60.80      G
ATOM  14107  ND1  HIS G 767      56.457  71.736  63.466  1.00 60.80      G
ATOM  14108  CE1  HIS G 767      56.177  70.458  63.285  1.00 60.80      G
ATOM  14109  NE2  HIS G 767      56.842  70.031  62.227  1.00 60.80      G
ATOM  14110  C    HIS G 767      57.495  76.001  62.560  1.00 56.35      G
ATOM  14111  O    HIS G 767      57.615  76.789  63.504  1.00 56.35      G
ATOM  14112  N    ASN G 768      57.920  76.266  61.331  1.00 57.30      G
ATOM  14113  CA   ASN G 768      58.612  77.497  61.013  1.00 57.30      G
ATOM  14114  CB   ASN G 768      59.683  77.236  59.950  1.00100.07      G
ATOM  14115  CG   ASN G 768      60.693  78.371  59.838  1.00100.07      G
ATOM  14116  OD1  ASN G 768      60.412  79.416  59.248  1.00100.07      G
ATOM  14117  ND2  ASN G 768      61.878  78.168  60.416  1.00100.07      G
ATOM  14118  C    ASN G 768      57.704  78.608  60.555  1.00 57.30      G
ATOM  14119  O    ASN G 768      58.066  79.373  59.668  1.00 57.30      G
ATOM  14120  N    LEU G 769      56.520  78.701  61.142  1.00 57.03      G
ATOM  14121  CA   LEU G 769      55.618  79.780  60.769  1.00 57.03      G
ATOM  14122  CB   LEU G 769      54.343  79.244  60.091  1.00100.07      G
ATOM  14123  CG   LEU G 769      54.305  79.352  58.553  1.00100.07      G
ATOM  14124  CD1  LEU G 769      53.026  78.778  57.965  1.00100.07      G
ATOM  14125  CD2  LEU G 769      54.424  80.815  58.179  1.00100.07      G
ATOM  14126  C    LEU G 769      55.270  80.552  62.023  1.00 57.03      G
ATOM  14127  O    LEU G 769      55.384  81.781  62.077  1.00 57.03      G
ATOM  14128  N    LEU G 770      54.868  79.816  63.043  1.00 76.29      G
ATOM  14129  CA   LEU G 770      54.500  80.419  64.304  1.00 76.29      G
ATOM  14130  CB   LEU G 770      54.107  79.308  65.277  1.00 85.89      G
ATOM  14131  CG   LEU G 770      53.001  78.347  64.805  1.00 85.89      G
ATOM  14132  CD1  LEU G 770      52.638  78.556  63.339  1.00 85.89      G
ATOM  14133  CD2  LEU G 770      53.476  76.927  65.023  1.00 85.89      G
ATOM  14134  C    LEU G 770      55.709  81.214  64.803  1.00 76.29      G
ATOM  14135  O    LEU G 770      56.746  80.632  65.153  1.00 76.29      G
ATOM  14136  N    SER G 771      55.567  82.540  64.824  1.00 79.21      G
ATOM  14137  CA   SER G 771      56.645  83.434  65.241  1.00 79.21      G
ATOM  14138  CB   SER G 771      57.364  82.892  66.490  1.00  8.81      G
ATOM  14139  OG   SER G 771      56.532  82.849  67.636  1.00  8.81      G
ATOM  14140  C    SER G 771      57.626  83.483  64.066  1.00 79.21      G
ATOM  14141  O    SER G 771      58.483  82.614  63.933  1.00 79.21      G
ATOM  14142  N    PRO G 772      57.514  84.501  63.197  1.00 69.42      G
ATOM  14143  CD   PRO G 772      56.537  85.600  63.224  1.00100.07      G
ATOM  14144  CA   PRO G 772      58.390  84.648  62.032  1.00 69.42      G
ATOM  14145  CB   PRO G 772      57.597  85.572  61.133  1.00100.07      G
ATOM  14146  CG   PRO G 772      57.065  86.533  62.117  1.00100.07      G
ATOM  14147  C    PRO G 772      59.758  85.232  62.317  1.00 69.42      G
ATOM  14148  O    PRO G 772      60.314  85.080  63.404  1.00 69.42      G
ATOM  14149  N    ALA G 773      60.273  85.936  61.317  1.00 37.24      G
ATOM  14150  CA   ALA G 773      61.582  86.536  61.413  1.00 37.24      G
ATOM  14151  CB   ALA G 773      62.305  86.331  60.113  1.00  5.07      G
ATOM  14152  C    ALA G 773      61.520  88.018  61.793  1.00 37.24      G
ATOM  14153  O    ALA G 773      61.762  88.907  60.982  1.00 37.24      G
ATOM  14154  N    SER G 774      61.165  88.246  63.057  1.00 52.69      G
ATOM  14155  CA   SER G 774      61.052  89.566  63.696  1.00 52.69      G
ATOM  14156  CB   SER G 774      60.253  90.550  62.852  1.00 39.48      G
ATOM  14157  OG   SER G 774      61.139  91.185  61.940  1.00 39.48      G
ATOM  14158  C    SER G 774      60.426  89.423  65.068  1.00 52.69      G
```

```
ATOM  14159  O   SER G 774      59.937  90.391  65.643  1.00 52.69           G
ATOM  14160  N   GLY G 775      60.437  88.178  65.549  1.00 44.33           G
ATOM  14161  CA  GLY G 775      59.961  87.832  66.873  1.00 44.33           G
ATOM  14162  C   GLY G 775      58.526  87.526  67.238  1.00 44.33           G
ATOM  14163  O   GLY G 775      58.315  86.602  68.023  1.00 44.33           G
ATOM  14164  N   GLU G 776      57.554  88.276  66.710  1.00 27.43           G
ATOM  14165  CA  GLU G 776      56.147  88.065  67.082  1.00 27.43           G
ATOM  14166  CB  GLU G 776      55.523  89.395  67.498  1.00 93.34           G
ATOM  14167  CG  GLU G 776      55.346  90.388  66.386  1.00 93.34           G
ATOM  14168  CD  GLU G 776      54.658  91.635  66.877  1.00 93.34           G
ATOM  14169  OE1 GLU G 776      53.521  91.526  67.376  1.00 93.34           G
ATOM  14170  OE2 GLU G 776      55.255  92.723  66.777  1.00 93.34           G
ATOM  14171  C   GLU G 776      55.239  87.373  66.065  1.00 27.43           G
ATOM  14172  O   GLU G 776      55.429  87.505  64.881  1.00 27.43           G
ATOM  14173  N   PRO G 777      54.203  86.659  66.536  1.00 27.40           G
ATOM  14174  CD  PRO G 777      53.578  86.842  67.855  1.00 16.98           G
ATOM  14175  CA  PRO G 777      53.277  85.943  65.658  1.00 27.40           G
ATOM  14176  CB  PRO G 777      51.962  85.949  66.450  1.00 16.98           G
ATOM  14177  CG  PRO G 777      52.139  87.022  67.470  1.00 16.98           G
ATOM  14178  C   PRO G 777      53.088  86.456  64.240  1.00 27.40           G
ATOM  14179  O   PRO G 777      52.856  87.634  64.032  1.00 27.40           G
ATOM  14180  N   LEU G 778      53.205  85.555  63.267  1.00 23.68           G
ATOM  14181  CA  LEU G 778      52.998  85.886  61.863  1.00 23.68           G
ATOM  14182  CB  LEU G 778      54.217  85.521  61.027  1.00  5.44           G
ATOM  14183  CG  LEU G 778      54.227  85.722  59.508  1.00  5.44           G
ATOM  14184  CD1 LEU G 778      52.972  86.414  59.067  1.00  5.44           G
ATOM  14185  CD2 LEU G 778      55.450  86.545  59.083  1.00  5.44           G
ATOM  14186  C   LEU G 778      51.817  85.017  61.480  1.00 23.68           G
ATOM  14187  O   LEU G 778      51.045  85.367  60.601  1.00 23.68           G
ATOM  14188  N   ALA G 779      51.673  83.880  62.163  1.00 27.77           G
ATOM  14189  CA  ALA G 779      50.549  82.972  61.921  1.00 27.77           G
ATOM  14190  CB  ALA G 779      50.931  81.548  62.305  1.00 41.16           G
ATOM  14191  C   ALA G 779      49.364  83.443  62.772  1.00 27.77           G
ATOM  14192  O   ALA G 779      48.674  82.643  63.404  1.00 27.77           G
ATOM  14193  N   LYS G 780      49.140  84.753  62.797  1.00  5.38           G
ATOM  14194  CA  LYS G 780      48.051  85.290  63.594  1.00  5.38           G
ATOM  14195  CB  LYS G 780      48.168  86.816  63.816  1.00 69.97           G
ATOM  14196  CG  LYS G 780      49.285  87.553  63.080  1.00 69.97           G
ATOM  14197  CD  LYS G 780      49.016  87.666  61.589  1.00 69.97           G
ATOM  14198  CE  LYS G 780      50.089  88.495  60.888  1.00 69.97           G
ATOM  14199  NZ  LYS G 780      49.909  88.533  59.404  1.00 69.97           G
ATOM  14200  C   LYS G 780      46.760  84.994  62.894  1.00  5.38           G
ATOM  14201  O   LYS G 780      46.738  84.773  61.675  1.00  5.38           G
ATOM  14202  N   PRO G 781      45.671  84.945  63.664  1.00 12.75           G
ATOM  14203  CD  PRO G 781      45.693  84.795  65.129  1.00 21.48           G
ATOM  14204  CA  PRO G 781      44.338  84.678  63.134  1.00 12.75           G
ATOM  14205  CB  PRO G 781      43.561  84.248  64.383  1.00 21.48           G
ATOM  14206  CG  PRO G 781      44.251  84.947  65.496  1.00 21.48           G
ATOM  14207  C   PRO G 781      43.794  85.954  62.482  1.00 12.75           G
ATOM  14208  O   PRO G 781      43.331  86.868  63.171  1.00 12.75           G
ATOM  14209  N   SER G 782      43.846  86.005  61.153  1.00 11.11           G
ATOM  14210  CA  SER G 782      43.402  87.188  60.423  1.00 11.11           G
ATOM  14211  CB  SER G 782      43.968  87.192  59.005  1.00100.07           G
ATOM  14212  OG  SER G 782      43.216  86.339  58.165  1.00100.07           G
ATOM  14213  C   SER G 782      41.905  87.380  60.340  1.00 11.11           G
ATOM  14214  O   SER G 782      41.138  86.734  61.056  1.00 11.11           G
ATOM  14215  N   ALA G 783      41.523  88.300  59.458  1.00 51.63           G
ATOM  14216  CA  ALA G 783      40.143  88.694  59.193  1.00 51.63           G
ATOM  14217  CB  ALA G 783      40.061  89.331  57.802  1.00 58.44           G
ATOM  14218  C   ALA G 783      39.150  87.550  59.294  1.00 51.63           G
ATOM  14219  O   ALA G 783      39.518  86.429  59.615  1.00 51.63           G
ATOM  14220  N   ASP G 784      37.882  87.849  59.037  1.00 50.55           G
ATOM  14221  CA  ASP G 784      36.825  86.843  59.044  1.00 50.55           G
ATOM  14222  CB  ASP G 784      36.885  86.065  57.713  1.00 57.04           G
ATOM  14223  CG  ASP G 784      35.519  85.896  57.042  1.00 57.04           G
ATOM  14224  OD1 ASP G 784      34.718  85.065  57.512  1.00 57.04           G
ATOM  14225  OD2 ASP G 784      35.248  86.586  56.031  1.00 57.04           G
ATOM  14226  C   ASP G 784      36.942  85.870  60.219  1.00 50.55           G
ATOM  14227  O   ASP G 784      36.324  84.813  60.198  1.00 50.55           G
ATOM  14228  N   ILE G 785      37.724  86.210  61.239  1.00 32.32           G
ATOM  14229  CA  ILE G 785      37.899  85.312  62.382  1.00 32.32           G
ATOM  14230  CB  ILE G 785      39.216  84.523  62.272  1.00 18.63           G
ATOM  14231  CG2 ILE G 785      39.408  83.596  63.472  1.00 18.63           G
ATOM  14232  CG1 ILE G 785      39.175  83.700  60.989  1.00 18.63           G
ATOM  14233  CD  ILE G 785      40.440  82.951  60.689  1.00 18.63           G
ATOM  14234  C   ILE G 785      37.940  86.166  63.619  1.00 32.32           G
ATOM  14235  O   ILE G 785      37.302  85.880  64.653  1.00 32.32           G
ATOM  14236  N   ILE G 786      38.722  87.224  63.524  1.00 16.56           G
ATOM  14237  CA  ILE G 786      38.784  88.121  64.635  1.00 16.56           G
ATOM  14238  CB  ILE G 786      39.721  89.272  64.332  1.00 16.24           G
ATOM  14239  CG2 ILE G 786      39.651  90.296  65.456  1.00 16.24           G
ATOM  14240  CG1 ILE G 786      41.144  88.720  64.118  1.00 16.24           G
ATOM  14241  CD  ILE G 786      41.856  89.321  62.903  1.00 16.24           G
ATOM  14242  C   ILE G 786      37.336  88.560  64.681  1.00 16.56           G
```

```
ATOM  14243  O    ILE G 786      36.772  88.712  65.752  1.00 16.56      G
ATOM  14244  N    LEU G 787      36.714  88.678  63.504  1.00 29.58      G
ATOM  14245  CA   LEU G 787      35.304  89.086  63.422  1.00 29.58      G
ATOM  14246  CB   LEU G 787      34.827  89.178  61.976  1.00 21.67      G
ATOM  14247  CG   LEU G 787      33.699  90.214  61.913  1.00 21.67      G
ATOM  14248  CD1  LEU G 787      33.549  90.786  60.513  1.00 21.67      G
ATOM  14249  CD2  LEU G 787      32.427  89.577  62.384  1.00 21.67      G
ATOM  14250  C    LEU G 787      34.413  88.109  64.175  1.00 29.58      G
ATOM  14251  O    LEU G 787      33.492  88.493  64.914  1.00 29.58      G
ATOM  14252  N    GLY G 788      34.690  86.833  63.974  1.00 35.27      G
ATOM  14253  CA   GLY G 788      33.924  85.829  64.669  1.00 35.27      G
ATOM  14254  C    GLY G 788      34.175  86.014  66.142  1.00 35.27      G
ATOM  14255  O    GLY G 788      33.361  86.603  66.838  1.00 35.27      G
ATOM  14256  N    LEU G 789      35.327  85.548  66.600  1.00 31.55      G
ATOM  14257  CA   LEU G 789      35.681  85.621  68.008  1.00 31.55      G
ATOM  14258  CB   LEU G 789      37.169  85.334  68.159  1.00 14.08      G
ATOM  14259  CG   LEU G 789      37.534  83.938  67.655  1.00 14.08      G
ATOM  14260  CD1  LEU G 789      39.001  83.644  67.897  1.00 14.08      G
ATOM  14261  CD2  LEU G 789      36.686  82.918  68.366  1.00 14.08      G
ATOM  14262  C    LEU G 789      35.303  86.912  68.744  1.00 31.55      G
ATOM  14263  O    LEU G 789      35.149  86.915  69.976  1.00 31.55      G
ATOM  14264  N    TYR G 790      35.146  88.008  68.003  1.00 24.55      G
ATOM  14265  CA   TYR G 790      34.769  89.272  68.625  1.00 24.55      G
ATOM  14266  CB   TYR G 790      34.790  90.401  67.606  1.00 16.62      G
ATOM  14267  CG   TYR G 790      34.931  91.765  68.214  1.00 16.62      G
ATOM  14268  CD1  TYR G 790      34.658  92.901  67.478  1.00 16.62      G
ATOM  14269  CE1  TYR G 790      34.828  94.155  68.016  1.00 16.62      G
ATOM  14270  CD2  TYR G 790      35.371  91.916  69.516  1.00 16.62      G
ATOM  14271  CE2  TYR G 790      35.549  93.161  70.074  1.00 16.62      G
ATOM  14272  CZ   TYR G 790      35.273  94.284  69.322  1.00 16.62      G
ATOM  14273  OH   TYR G 790      35.457  95.541  69.878  1.00 16.62      G
ATOM  14274  C    TYR G 790      33.350  89.074  69.112  1.00 24.55      G
ATOM  14275  O    TYR G 790      33.121  88.743  70.273  1.00 24.55      G
ATOM  14276  N    TYR G 791      32.409  89.262  68.192  1.00 26.86      G
ATOM  14277  CA   TYR G 791      30.979  89.096  68.444  1.00 26.86      G
ATOM  14278  CB   TYR G 791      30.298  88.618  67.166  1.00 36.91      G
ATOM  14279  CG   TYR G 791      29.405  89.611  66.493  1.00 36.91      G
ATOM  14280  CD1  TYR G 791      29.922  90.593  65.666  1.00 36.91      G
ATOM  14281  CE1  TYR G 791      29.080  91.494  65.007  1.00 36.91      G
ATOM  14282  CD2  TYR G 791      28.028  89.546  66.659  1.00 36.91      G
ATOM  14283  CE2  TYR G 791      27.173  90.440  66.012  1.00 36.91      G
ATOM  14284  CZ   TYR G 791      27.700  91.416  65.184  1.00 36.91      G
ATOM  14285  OH   TYR G 791      26.853  92.313  64.542  1.00 36.91      G
ATOM  14286  C    TYR G 791      30.660  88.091  69.562  1.00 26.86      G
ATOM  14287  O    TYR G 791      29.657  88.229  70.256  1.00 26.86      G
ATOM  14288  N    ILE G 792      31.501  87.070  69.710  1.00 27.61      G
ATOM  14289  CA   ILE G 792      31.312  86.037  70.717  1.00 27.61      G
ATOM  14290  CB   ILE G 792      32.137  84.780  70.365  1.00 95.47      G
ATOM  14291  CG2  ILE G 792      31.735  83.605  71.237  1.00 95.47      G
ATOM  14292  CG1  ILE G 792      31.895  84.407  68.911  1.00 95.47      G
ATOM  14293  CD   ILE G 792      30.433  84.282  68.576  1.00 95.47      G
ATOM  14294  C    ILE G 792      31.783  86.557  72.059  1.00 27.61      G
ATOM  14295  O    ILE G 792      31.990  85.792  72.997  1.00 27.61      G
ATOM  14296  N    THR G 793      31.956  87.864  72.166  1.00 29.38      G
ATOM  14297  CA   THR G 793      32.438  88.415  73.419  1.00 29.38      G
ATOM  14298  CB   THR G 793      33.967  88.257  73.523  1.00 26.93      G
ATOM  14299  OG1  THR G 793      34.437  87.284  72.570  1.00 26.93      G
ATOM  14300  CG2  THR G 793      34.340  87.825  74.924  1.00 26.93      G
ATOM  14301  C    THR G 793      32.118  89.888  73.595  1.00 29.38      G
ATOM  14302  O    THR G 793      32.703  90.727  72.939  1.00 29.38      G
ATOM  14303  N    GLN G 794      31.194  90.218  74.477  1.00 34.55      G
ATOM  14304  CA   GLN G 794      30.890  91.621  74.685  1.00 34.55      G
ATOM  14305  CB   GLN G 794      30.151  92.188  73.469  1.00 41.57      G
ATOM  14306  CG   GLN G 794      31.074  92.784  72.417  1.00 41.57      G
ATOM  14307  CD   GLN G 794      31.762  94.075  72.880  1.00 41.57      G
ATOM  14308  OE1  GLN G 794      32.257  94.173  74.012  1.00 41.57      G
ATOM  14309  NE2  GLN G 794      31.808  95.069  71.989  1.00 41.57      G
ATOM  14310  C    GLN G 794      30.095  91.910  75.949  1.00 34.55      G
ATOM  14311  O    GLN G 794      30.647  92.188  77.021  1.00 34.55      G
ATOM  14312  N    VAL G 795      28.790  91.812  75.785  1.00 69.62      G
ATOM  14313  CA   VAL G 795      27.780  92.065  76.791  1.00 69.62      G
ATOM  14314  CB   VAL G 795      28.338  92.647  78.104  1.00 60.61      G
ATOM  14315  CG1  VAL G 795      27.197  93.133  78.987  1.00 60.61      G
ATOM  14316  CG2  VAL G 795      29.097  91.565  78.863  1.00 60.61      G
ATOM  14317  C    VAL G 795      27.038  93.105  75.999  1.00 69.62      G
ATOM  14318  O    VAL G 795      27.174  93.143  74.776  1.00 69.62      G
ATOM  14319  N    ARG G 796      26.280  93.975  76.634  1.00 47.34      G
ATOM  14320  CA   ARG G 796      25.558  94.902  75.806  1.00 47.34      G
ATOM  14321  CB   ARG G 796      24.277  94.237  75.307  1.00 79.01      G
ATOM  14322  CG   ARG G 796      24.422  92.894  74.644  1.00 79.01      G
ATOM  14323  CD   ARG G 796      23.335  92.822  73.633  1.00 79.01      G
ATOM  14324  NE   ARG G 796      23.152  91.514  73.040  1.00 79.01      G
ATOM  14325  CZ   ARG G 796      22.372  91.311  71.986  1.00 79.01      G
ATOM  14326  NH1  ARG G 796      21.735  92.339  71.441  1.00 79.01      G
```

```
ATOM  14327  NH2  ARG G 796      22.216  90.093  71.485  1.00 79.01         G
ATOM  14328  C    ARG G 796      25.181  96.245  76.383  1.00 47.34         G
ATOM  14329  O    ARG G 796      25.818  96.790  77.286  1.00 47.34         G
ATOM  14330  N    ALA G 797      24.097  96.743  75.802  1.00 99.50         G
ATOM  14331  CA   ALA G 797      23.480  98.002  76.121  1.00 99.50         G
ATOM  14332  CB   ALA G 797      24.266  99.138  75.489  1.00100.07         G
ATOM  14333  C    ALA G 797      22.105  97.880  75.478  1.00 99.50         G
ATOM  14334  O    ALA G 797      21.772  98.619  74.549  1.00 99.50         G
ATOM  14335  N    ALA G 798      21.327  96.903  75.937  1.00 95.05         G
ATOM  14336  CA   ALA G 798      19.981  96.720  75.410  1.00 95.05         G
ATOM  14337  CB   ALA G 798      19.300  95.529  76.088  1.00 12.09         G
ATOM  14338  C    ALA G 798      19.280  98.029  75.769  1.00 95.05         G
ATOM  14339  O    ALA G 798      18.342  98.474  75.095  1.00 95.05         G
ATOM  14340  N    ALA G 799      19.785  98.635  76.845  1.00100.07         G
ATOM  14341  CA   ALA G 799      19.321  99.911  77.383  1.00100.07         G
ATOM  14342  CB   ALA G 799      19.820 101.055  76.495  1.00 87.62         G
ATOM  14343  C    ALA G 799      17.819 100.069  77.628  1.00100.07         G
ATOM  14344  O    ALA G 799      16.985  99.772  76.762  1.00100.07         G
ATOM  14345  N    ALA G 800      17.498 100.543  78.831  1.00 99.90         G
ATOM  14346  CA   ALA G 800      16.128 100.814  79.244  1.00 99.90         G
ATOM  14347  CB   ALA G 800      15.501  99.598  79.861  1.00 61.20         G
ATOM  14348  C    ALA G 800      16.229 101.932  80.266  1.00 99.90         G
ATOM  14349  O    ALA G 800      15.510 102.930  80.181  1.00 99.90         G
ATOM  14350  N    GLY G 801      17.140 101.770  81.224  1.00 82.64         G
ATOM  14351  CA   GLY G 801      17.329 102.799  82.235  1.00 82.64         G
ATOM  14352  C    GLY G 801      17.659 102.317  83.631  1.00 82.64         G
ATOM  14353  O    GLY G 801      16.895 101.563  84.221  1.00 82.64         G
ATOM  14354  N    ALA G 802      18.787 102.764  84.172  1.00 81.10         G
ATOM  14355  CA   ALA G 802      19.189 102.352  85.511  1.00 81.10         G
ATOM  14356  CB   ALA G 802      20.520 103.002  85.881  1.00 95.74         G
ATOM  14357  C    ALA G 802      18.131 102.673  86.575  1.00 81.10         G
ATOM  14358  O    ALA G 802      17.716 103.823  86.743  1.00 81.10         G
ATOM  14359  N    GLY G 803      17.695 101.635  87.283  1.00 90.76         G
ATOM  14360  CA   GLY G 803      16.710 101.797  88.335  1.00 90.76         G
ATOM  14361  C    GLY G 803      17.317 101.362  89.660  1.00 90.76         G
ATOM  14362  O    GLY G 803      18.458 100.899  89.707  1.00 90.76         G
ATOM  14363  N    ALA G 804      16.555 101.508  90.741  1.00100.07         G
ATOM  14364  CA   ALA G 804      17.027 101.128  92.075  1.00100.07         G
ATOM  14365  CB   ALA G 804      16.739 102.251  93.079  1.00100.07         G
ATOM  14366  C    ALA G 804      16.424  99.814  92.579  1.00100.07         G
ATOM  14367  O    ALA G 804      15.292  99.441  92.241  1.00100.07         G
ATOM  14368  N    ALA G 805      17.199  99.122  93.403  1.00100.07         G
ATOM  14369  CA   ALA G 805      16.786  97.853  93.966  1.00100.07         G
ATOM  14370  CB   ALA G 805      17.143  96.723  93.017  1.00100.07         G
ATOM  14371  C    ALA G 805      17.550  97.702  95.257  1.00100.07         G
ATOM  14372  O    ALA G 805      17.021  97.208  96.251  1.00100.07         G
ATOM  14373  N    ALA G 806      18.804  98.147  95.220  1.00 89.04         G
ATOM  14374  CA   ALA G 806      19.717  98.081  96.362  1.00 89.04         G
ATOM  14375  CB   ALA G 806      19.110  98.779  97.578  1.00100.07         G
ATOM  14376  C    ALA G 806      19.995  96.622  96.676  1.00 89.04         G
ATOM  14377  O    ALA G 806      20.928  96.298  97.417  1.00 89.04         G
ATOM  14378  N    ALA G 807      19.172  95.758  96.085  1.00100.07         G
ATOM  14379  CA   ALA G 807      19.266  94.314  96.266  1.00100.07         G
ATOM  14380  CB   ALA G 807      19.533  93.989  97.738  1.00100.07         G
ATOM  14381  C    ALA G 807      18.015  93.553  95.780  1.00100.07         G
ATOM  14382  O    ALA G 807      16.881  93.842  96.188  1.00100.07         G
ATOM  14383  N    ALA G 808      18.256  92.575  94.908  1.00100.07         G
ATOM  14384  CA   ALA G 808      17.234  91.712  94.324  1.00100.07         G
ATOM  14385  CB   ALA G 808      17.155  90.424  95.117  1.00 18.34         G
ATOM  14386  C    ALA G 808      15.836  92.291  94.139  1.00100.07         G
ATOM  14387  O    ALA G 308      15.530  92.860  93.089  1.00100.07         G
ATOM  14388  N    ALA G 809      14.987  92.141  95.150  1.00 92.40         G
ATOM  14389  CA   ALA G 809      13.612  92.618  95.060  1.00 92.40         G
ATOM  14390  CB   ALA G 809      13.579  94.135  94.867  1.00 85.72         G
ATOM  14391  C    ALA G 809      12.973  91.905  93.862  1.00 92.40         G
ATOM  14392  O    ALA G 809      13.635  91.126  93.165  1.00 92.40         G
ATOM  14393  N    ALA G 810      11.692  92.156  93.621  1.00 99.97         G
ATOM  14394  CA   ALA G 810      11.010  91.508  92.507  1.00 99.97         G
ATOM  14395  CB   ALA G 810       9.553  91.232  92.867  1.00100.07         G
ATOM  14396  C    ALA G 810      11.090  92.336  91.236  1.00 99.97         G
ATOM  14397  O    ALA G 810      10.547  91.943  90.208  1.00 99.97         G
ATOM  14398  N    ALA G 811      11.769  93.480  91.310  1.00 87.38         G
ATOM  14399  CA   ALA G 811      11.933  94.353  90.151  1.00 87.38         G
ATOM  14400  CB   ALA G 811      12.874  95.495  90.475  1.00 86.01         G
ATOM  14401  C    ALA G 811      12.492  93.531  89.000  1.00 87.38         G
ATOM  14402  O    ALA G 811      12.590  94.010  87.868  1.00 87.38         G
ATOM  14403  N    ALA G 812      12.880  92.294  89.312  1.00100.07         G
ATOM  14404  CA   ALA G 812      13.397  91.377  88.309  1.00100.07         G
ATOM  14405  CB   ALA G 812      13.622  89.971  88.921  1.00 22.09         G
ATOM  14406  C    ALA G 812      12.292  91.343  87.257  1.00100.07         G
ATOM  14407  O    ALA G 812      12.359  92.051  86.249  1.00100.07         G
ATOM  14408  N    ALA G 813      11.259  90.549  87.516  1.00 77.38         G
ATOM  14409  CA   ALA G 813      10.137  90.454  86.593  1.00 77.38         G
ATOM  14410  CB   ALA G 813       9.417  89.119  86.760  1.00100.07         G
```

```
ATOM  14411  C   ALA G 813    9.174  91.602  86.837  1.00 77.38      G
ATOM  14412  O   ALA G 813    8.318  91.879  85.999  1.00 77.38      G
ATOM  14413  N   ALA G 814    9.308  92.263  87.988  1.00 98.94      G
ATOM  14414  CA  ALA G 814    8.441  93.394  88.314  1.00 98.94      G
ATOM  14415  CB  ALA G 814    8.872  94.060  89.609  1.00 60.22      G
ATOM  14416  C   ALA G 814    8.634  94.349  87.170  1.00 98.94      G
ATOM  14417  O   ALA G 814    7.774  95.176  86.868  1.00 98.94      G
ATOM  14418  N   ALA G 815    9.795  94.213  86.543  1.00100.07      G
ATOM  14419  CA  ALA G 815   10.169  95.025  85.405  1.00100.07      G
ATOM  14420  CB  ALA G 815   11.559  95.595  85.616  1.00100.07      G
ATOM  14421  C   ALA G 815   10.151  94.110  84.194  1.00100.07      G
ATOM  14422  O   ALA G 815    9.588  94.445  83.148  1.00100.07      G
ATOM  14423  N   ALA G 816   10.782  92.951  84.345  1.00 69.38      G
ATOM  14424  CA  ALA G 816   10.810  91.985  83.268  1.00 69.38      G
ATOM  14425  CB  ALA G 816   11.576  90.745  83.684  1.00100.07      G
ATOM  14426  C   ALA G 816    9.352  91.653  83.034  1.00 69.38      G
ATOM  14427  O   ALA G 816    8.793  90.752  83.668  1.00 69.38      G
ATOM  14428  N   ALA G 817    8.740  92.416  82.137  1.00100.07      G
ATOM  14429  CA  ALA G 817    7.335  92.256  81.788  1.00100.07      G
ATOM  14430  CB  ALA G 817    6.468  92.273  83.047  1.00100.07      G
ATOM  14431  C   ALA G 817    6.952  93.413  80.874  1.00100.07      G
ATOM  14432  O   ALA G 817    5.852  93.436  80.317  1.00100.07      G
ATOM  14433  N   ALA G 818    7.877  94.365  80.744  1.00 83.84      G
ATOM  14434  CA  ALA G 818    7.718  95.560  79.913  1.00 83.84      G
ATOM  14435  CB  ALA G 818    6.302  96.119  80.026  1.00100.07      G
ATOM  14436  C   ALA G 818    8.723  96.608  80.375  1.00 83.84      G
ATOM  14437  O   ALA G 818    8.722  97.012  81.541  1.00 83.84      G
ATOM  14438  N   GLY G 819    9.585  97.038  79.459  1.00 92.75      G
ATOM  14439  CA  GLY G 819   10.585  98.037  79.794  1.00 92.75      G
ATOM  14440  C   GLY G 819   11.473  97.667  80.972  1.00 92.75      G
ATOM  14441  O   GLY G 819   11.377  96.567  81.517  1.00 92.75      G
ATOM  14442  N   ALA G 820   12.345  98.594  81.358  1.00 71.25      G
ATOM  14443  CA  ALA G 820   13.262  98.387  82.475  1.00 71.25      G
ATOM  14444  CB  ALA G 820   12.479  98.234  83.759  1.00 78.61      G
ATOM  14445  C   ALA G 820   14.178  97.183  82.286  1.00 71.25      G
ATOM  14446  O   ALA G 820   14.258  96.322  83.164  1.00 71.25      G
ATOM  14447  N   ALA G 821   14.881  97.149  81.150  1.00100.07      G
ATOM  14448  CA  ALA G 821   15.809  96.063  80.788  1.00100.07      G
ATOM  14449  CB  ALA G 821   16.166  96.157  79.296  1.00100.07      G
ATOM  14450  C   ALA G 821   17.099  95.975  81.618  1.00100.07      G
ATOM  14451  O   ALA G 821   17.278  96.694  82.605  1.00100.07      G
ATOM  14452  N   ALA G 822   17.999  95.089  81.196  1.00100.07      G
ATOM  14453  CA  ALA G 822   19.264  94.872  81.899  1.00100.07      G
ATOM  14454  CB  ALA G 822   19.765  93.457  81.611  1.00100.07      G
ATOM  14455  C   ALA G 822   20.361  95.897  81.574  1.00100.07      G
ATOM  14456  O   ALA G 822   21.342  95.577  80.890  1.00100.07      G
ATOM  14457  N   ALA G 823   20.206  97.118  82.082  1.00 99.87      G
ATOM  14458  CA  ALA G 823   21.179  98.177  81.831  1.00 99.87      G
ATOM  14459  CB  ALA G 823   20.653  99.114  80.741  1.00100.07      G
ATOM  14460  C   ALA G 823   21.493  98.973  83.094  1.00 99.87      G
ATOM  14461  O   ALA G 823   21.013 100.096  83.251  1.00 99.87      G
ATOM  14462  N   ALA G 824   22.302  98.387  83.978  1.00100.07      G
ATOM  14463  CA  ALA G 824   22.710  98.998  85.251  1.00100.07      G
ATOM  14464  CB  ALA G 824   22.729 100.523  85.143  1.00 59.03      G
ATOM  14465  C   ALA G 824   21.851  98.569  86.449  1.00100.07      G
ATOM  14466  O   ALA G 824   22.259  97.685  87.200  1.00100.07      G
ATOM  14467  N   ALA G 825   20.676  99.184  86.622  1.00 78.72      G
ATOM  14468  CA  ALA G 825   19.775  98.866  87.742  1.00 78.72      G
ATOM  14469  CB  ALA G 825   18.897  97.659  87.411  1.00  5.07      G
ATOM  14470  C   ALA G 825   20.590  98.589  89.001  1.00 78.72      G
ATOM  14471  O   ALA G 825   21.112  97.487  89.189  1.00 78.72      G
ATOM  14472  N   ALA G 826   20.673  99.594  89.866  1.00100.07      G
ATOM  14473  CA  ALA G 826   21.458  99.524  91.096  1.00100.07      G
ATOM  14474  CB  ALA G 826   21.509 100.907  91.732  1.00100.07      G
ATOM  14475  C   ALA G 826   21.106  98.491  92.165  1.00100.07      G
ATOM  14476  O   ALA G 826   20.024  97.899  92.183  1.00100.07      G
ATOM  14477  N   ALA G 827   22.073  98.302  93.058  1.00100.00      G
ATOM  14478  CA  ALA G 827   21.997  97.393  94.199  1.00100.00      G
ATOM  14479  CB  ALA G 827   21.977  95.938  93.736  1.00 59.82      G
ATOM  14480  C   ALA G 827   23.269  97.697  94.995  1.00100.00      G
ATOM  14481  O   ALA G 827   23.587  98.868  95.211  1.00100.00      G
ATOM  14482  N   ALA G 828   23.996  96.667  95.426  1.00100.07      G
ATOM  14483  CA  ALA G 828   25.246  96.877  96.172  1.00100.07      G
ATOM  14484  CB  ALA G 828   25.485  95.734  97.170  1.00100.07      G
ATOM  14485  C   ALA G 828   26.393  96.951  95.161  1.00100.07      G
ATOM  14486  O   ALA G 828   27.516  97.357  95.491  1.00100.07      G
ATOM  14487  N   ALA G 829   26.072  96.543  93.930  1.00100.07      G
ATOM  14488  CA  ALA G 829   26.980  96.545  92.782  1.00100.07      G
ATOM  14489  CB  ALA G 829   27.730  95.209  92.674  1.00 46.71      G
ATOM  14490  C   ALA G 829   26.099  96.757  91.548  1.00100.07      G
ATOM  14491  O   ALA G 829   26.581  97.145  90.484  1.00100.07      G
ATOM  14492  N   ALA G 830   24.801  96.502  91.726  1.00 98.89      G
ATOM  14493  CA  ALA G 830   23.780  96.640  90.683  1.00 98.89      G
ATOM  14494  CB  ALA G 830   24.032  97.918  89.862  1.00 32.06      G
```

```
ATOM  14495  C   ALA G 830    23.721  95.410  89.767  1.00 98.89      G
ATOM  14496  O   ALA G 830    24.370  94.395  90.037  1.00 98.89      G
ATOM  14497  N   GLY G 831    22.918  95.489  88.707  1.00 99.91      G
ATOM  14498  CA  GLY G 831    22.836  94.380  87.769  1.00 99.91      G
ATOM  14499  C   GLY G 831    21.501  93.698  87.547  1.00 99.91      G
ATOM  14500  O   GLY G 831    20.659  93.637  88.437  1.00 99.91      G
ATOM  14501  N   ALA G 832    21.316  93.177  86.339  1.00100.01      G
ATOM  14502  CA  ALA G 832    20.098  92.467  85.977  1.00100.01      G
ATOM  14503  CB  ALA G 832    19.354  93.219  84.891  1.00 84.40      G
ATOM  14504  C   ALA G 832    20.487  91.072  85.490  1.00100.01      G
ATOM  14505  O   ALA G 832    19.935  90.551  84.517  1.00100.01      G
ATOM  14506  N   ALA G 833    21.476  90.495  86.165  1.00 78.13      G
ATOM  14507  CA  ALA G 833    21.956  89.155  85.865  1.00 78.13      G
ATOM  14508  CB  ALA G 833    23.428  89.170  85.624  1.00 20.38      G
ATOM  14509  C   ALA G 833    21.642  88.378  87.127  1.00 78.13      G
ATOM  14510  O   ALA G 833    22.520  87.767  87.744  1.00 78.13      G
ATOM  14511  N   ALA G 934    20.370  88.444  87.512  1.00100.07      G
ATOM  14512  CA  ALA G 834    19.857  87.781  88.701  1.00100.07      G
ATOM  14513  CB  ALA G 834    18.708  88.588  89.276  1.00 59.74      G
ATOM  14514  C   ALA G 834    19.395  86.365  88.372  1.00100.07      G
ATOM  14515  O   ALA G 834    19.479  85.469  89.213  1.00100.07      G
ATOM  14516  N   ALA G 835    18.898  86.175  87.151  1.00 61.36      G
ATOM  14517  CA  ALA G 835    18.444  84.865  86.685  1.00 61.36      G
ATOM  14518  CB  ALA G 835    17.337  85.047  85.653  1.00 96.27      G
ATOM  14519  C   ALA G 835    19.635  84.101  86.071  1.00 61.36      G
ATOM  14520  O   ALA G 835    19.711  83.913  84.846  1.00 61.36      G
ATOM  14521  N   ALA G 836    20.565  83.679  86.932  1.00 43.72      G
ATOM  14522  CA  ALA G 836    21.767  82.962  86.507  1.00 43.72      G
ATOM  14523  CB  ALA G 836    22.849  83.953  86.087  1.00 50.53      G
ATOM  14524  C   ALA G 836    22.327  82.013  87.571  1.00 43.72      G
ATOM  14525  O   ALA G 836    22.268  82.277  88.777  1.00 43.72      G
ATOM  14526  N   GLY G 837    22.879  80.904  87.087  1.00 85.16      G
ATOM  14527  CA  GLY G 837    23.466  79.883  87.938  1.00 85.16      G
ATOM  14528  C   GLY G 837    24.560  79.178  87.153  1.00 85.16      G
ATOM  14529  O   GLY G 837    24.566  79.228  85.918  1.00 85.16      G
ATOM  14530  N   ALA G 838    25.478  78.517  87.852  1.00 66.54      G
ATOM  14531  CA  ALA G 838    26.583  77.838  87.185  1.00 66.54      G
ATOM  14532  CB  ALA G 838    27.829  78.693  87.277  1.00100.07      G
ATOM  14533  C   ALA G 838    26.873  76.444  87.727  1.00 66.54      G
ATOM  14534  O   ALA G 838    26.427  76.094  88.814  1.00 66.54      G
ATOM  14535  N   ALA G 839    27.644  75.669  86.959  1.00 89.68      G
ATOM  14536  CA  ALA G 839    28.014  74.294  87.314  1.00 89.68      G
ATOM  14537  CB  ALA G 839    28.158  73.456  86.031  1.00 45.77      G
ATOM  14538  C   ALA G 839    29.294  74.186  88.163  1.00 89.68      G
ATOM  14539  O   ALA G 839    30.054  75.154  88.293  1.00 89.68      G
ATOM  14540  N   ALA G 840    29.522  73.000  88.737  1.00100.07      G
ATOM  14541  CA  ALA G 840    30.698  72.747  89.584  1.00100.07      G
ATOM  14542  CB  ALA G 840    30.292  71.879  90.831  1.00  5.07      G
ATOM  14543  C   ALA G 840    31.842  72.075  88.806  1.00100.07      G
ATOM  14544  O   ALA G 840    31.603  71.170  87.998  1.00100.07      G
ATOM  14545  N   ALA G 841    33.077  72.523  89.053  1.00100.07      G
ATOM  14546  CA  ALA G 841    34.269  71.987  88.379  1.00100.07      G
ATOM  14547  CB  ALA G 841    35.514  72.775  88.805  1.00100.07      G
ATOM  14548  C   ALA G 841    34.481  70.489  88.635  1.00100.07      G
ATOM  14549  O   ALA G 841    34.902  70.078  89.722  1.00100.07      G
ATOM  14550  N   ALA G 842    34.200  69.683  87.613  1.00100.07      G
ATOM  14551  CA  ALA G 842    34.329  68.235  87.714  1.00100.07      G
ATOM  14552  CB  ALA G 842    33.067  67.663  88.354  1.00 47.21      G
ATOM  14553  C   ALA G 842    34.579  67.558  86.358  1.00100.07      G
ATOM  14554  O   ALA G 842    34.214  66.389  86.176  1.00100.07      G
ATOM  14555  N   ALA G 843    35.200  68.296  85.429  1.00 83.68      G
ATOM  14556  CA  ALA G 843    35.535  67.842  84.063  1.00 83.68      G
ATOM  14557  CB  ALA G 843    34.731  66.594  83.679  1.00100.07      G
ATOM  14558  C   ALA G 843    35.219  68.971  83.088  1.00 83.68      G
ATOM  14559  O   ALA G 843    36.070  69.804  82.775  1.00 83.68      G
ATOM  14560  N   ALA G 844    33.983  68.976  82.605  1.00100.07      G
ATOM  14561  CA  ALA G 844    33.514  70.012  81.700  1.00100.07      G
ATOM  14562  CB  ALA G 844    32.724  69.386  80.534  1.00 34.11      G
ATOM  14563  C   ALA G 844    32.613  70.903  82.568  1.00100.07      G
ATOM  14564  O   ALA G 844    31.675  70.409  83.211  1.00100.07      G
ATOM  14565  N   ALA G 845    32.912  72.204  82.602  1.00100.07      G
ATOM  14566  CA  ALA G 845    32.148  73.160  83.413  1.00100.07      G
ATOM  14567  CB  ALA G 845    33.097  73.915  84.335  1.00 85.18      G
ATOM  14568  C   ALA G 845    31.288  74.162  82.626  1.00100.07      G
ATOM  14569  O   ALA G 845    31.410  74.279  81.403  1.00100.07      G
ATOM  14570  N   ALA G 846    30.421  74.881  83.344  1.00 76.95      G
ATOM  14571  CA  ALA G 846    29.536  75.871  82.737  1.00 76.95      G
ATOM  14572  CB  ALA G 846    30.352  77.027  82.201  1.00 22.44      G
ATOM  14573  C   ALA G 846    28.745  75.244  81.602  1.00 76.95      G
ATOM  14574  O   ALA G 846    28.201  75.953  80.754  1.00 76.95      G
ATOM  14575  N   ALA G 847    28.689  73.914  81.592  1.00 82.66      G
ATOM  14576  CA  ALA G 847    27.996  73.167  80.545  1.00 82.66      G
ATOM  14577  CB  ALA G 847    28.336  71.669  80.659  1.00  5.07      G
ATOM  14578  C   ALA G 947    26.483  73.376  80.541  1.00 82.66      G
```

```
ATOM  14579  O   ALA G 847    25.814  73.082  79.550  1.00 82.66      G
ATOM  14580  N   ALA G 848    25.950  73.897  81.641  1.00 72.60      G
ATOM  14581  CA  ALA G 848    24.516  74.144  81.748  1.00 72.60      G
ATOM  14582  CB  ALA G 848    24.069  73.945  83.187  1.00 94.69      G
ATOM  14583  C   ALA G 848    24.142  75.551  81.272  1.00 72.60      G
ATOM  14584  O   ALA G 848    22.965  75.870  81.111  1.00 72.60      G
ATOM  14585  N   ALA G 849    25.150  76.385  81.044  1.00 34.26      G
ATOM  14586  CA  ALA G 849    24.931  77.754  80.602  1.00 34.26      G
ATOM  14587  CB  ALA G 849    25.918  78.677  81.287  1.00 39.16      G
ATOM  14588  C   ALA G 849    25.065  77.877  79.092  1.00 34.26      G
ATOM  14589  O   ALA G 849    24.208  78.451  78.427  1.00 34.26      G
ATOM  14590  N   ALA G 850    26.153  77.355  78.544  1.00 60.24      G
ATOM  14591  CA  ALA G 850    26.334  77.430  77.106  1.00 60.24      G
ATOM  14592  CB  ALA G 850    27.637  76.722  76.697  1.00 20.96      G
ATOM  14593  C   ALA G 850    25.103  76.739  76.510  1.00 60.24      G
ATOM  14594  O   ALA G 850    24.624  77.099  75.430  1.00 60.24      G
ATOM  14595  N   ALA G 851    24.586  75.757  77.250  1.00 53.83      G
ATOM  14596  CA  ALA G 851    23.400  75.007  76.849  1.00 53.83      G
ATOM  14597  CB  ALA G 851    23.416  73.625  77.481  1.00 62.17      G
ATOM  14598  C   ALA G 851    22.191  75.799  77.338  1.00 53.83      G
ATOM  14599  O   ALA G 851    21.104  75.748  76.754  1.00 53.83      G
ATOM  14600  N   ALA G 852    22.378  76.524  78.435  1.00 66.34      G
ATOM  14601  CA  ALA G 852    21.299  77.348  78.939  1.00 66.34      G
ATOM  14602  CB  ALA G 852    21.785  78.206  80.088  1.00 52.64      G
ATOM  14603  C   ALA G 852    20.964  78.213  77.730  1.00 66.34      G
ATOM  14604  O   ALA G 852    19.809  78.303  77.310  1.00 66.34      G
ATOM  14605  N   ALA G 853    22.012  78.815  77.162  1.00 33.20      G
ATOM  14606  CA  ALA G 853    21.914  79.670  75.982  1.00 33.20      G
ATOM  14607  CB  ALA G 853    23.315  80.047  75.502  1.00  5.07      G
ATOM  14608  C   ALA G 853    21.168  78.938  74.873  1.00 33.20      G
ATOM  14609  O   ALA G 853    20.368  79.535  74.153  1.00 33.20      G
ATOM  14610  N   ALA G 854    21.436  77.637  74.755  1.00 64.50      G
ATOM  14611  CA  ALA G 854    20.827  76.804  73.724  1.00 64.50      G
ATOM  14612  CB  ALA G 854    21.117  75.344  73.977  1.00 18.45      G
ATOM  14613  C   ALA G 854    19.339  77.016  73.610  1.00 64.50      G
ATOM  14614  O   ALA G 854    18.900  77.858  72.835  1.00 64.50      G
ATOM  14615  N   ALA G 855    18.560  76.255  74.373  1.00 66.03      G
ATOM  14616  CA  ALA G 855    17.107  76.387  74.317  1.00 66.03      G
ATOM  14617  CB  ALA G 855    16.448  75.572  75.456  1.00  8.00      G
ATOM  14618  C   ALA G 855    16.730  77.874  74.392  1.00 66.03      G
ATOM  14619  O   ALA G 855    16.534  78.434  75.464  1.00 66.03      G
ATOM  14620  N   GLY G 856    16.668  78.496  73.219  1.00 76.46      G
ATOM  14621  CA  GLY G 856    16.337  79.904  73.077  1.00 76.46      G
ATOM  14622  C   GLY G 856    16.235  80.810  74.290  1.00 76.46      G
ATOM  14623  O   GLY G 856    15.143  81.240  74.654  1.00 76.46      G
ATOM  14624  N   ALA G 857    17.363  81.121  74.913  1.00100.07      G
ATOM  14625  CA  ALA G 857    17.369  82.008  76.073  1.00100.07      G
ATOM  14626  CB  ALA G 857    16.901  81.254  77.322  1.00 16.13      G
ATOM  14627  C   ALA G 857    18.788  82.543  76.259  1.00100.07      G
ATOM  14628  O   ALA G 857    19.762  81.815  76.042  1.00100.07      G
ATOM  14629  N   ALA G 858    18.911  83.811  76.652  1.00 77.23      G
ATOM  14630  CA  ALA G 858    20.231  84.419  76.830  1.00 77.23      G
ATOM  14631  CB  ALA G 858    20.993  83.713  77.982  1.00  5.07      G
ATOM  14632  C   ALA G 858    20.977  84.263  75.496  1.00 77.23      G
ATOM  14633  O   ALA G 858    21.750  83.327  75.316  1.00 77.23      G
ATOM  14634  N   ALA G 859    20.726  85.187  74.571  1.00 84.29      G
ATOM  14635  CA  ALA G 859    21.319  85.160  73.235  1.00 84.29      G
ATOM  14636  CB  ALA G 859    20.999  86.453  72.491  1.00 13.60      G
ATOM  14637  C   ALA G 859    22.813  84.883  73.157  1.00 84.29      G
ATOM  14638  O   ALA G 859    23.388  84.937  72.068  1.00 84.29      G
ATOM  14639  N   ALA G 860    23.442  84.605  74.298  1.00 66.13      G
ATOM  14640  CA  ALA G 860    24.870  84.275  74.354  1.00 66.13      G
ATOM  14641  CB  ALA G 860    25.172  83.070  73.458  1.00100.07      G
ATOM  14642  C   ALA G 860    25.853  85.380  74.031  1.00 66.13      G
ATOM  14643  O   ALA G 860    26.915  85.420  74.647  1.00 66.13      G
ATOM  14644  N   ALA G 861    25.523  86.241  73.057  1.00 46.95      G
ATOM  14645  CA  ALA G 861    26.394  87.354  72.645  1.00 46.95      G
ATOM  14646  CB  ALA G 861    25.728  88.222  71.566  1.00  5.07      G
ATOM  14647  C   ALA G 861    26.658  88.185  73.864  1.00 46.95      G
ATOM  14648  O   ALA G 861    26.401  89.387  73.880  1.00 46.95      G
ATOM  14649  N   ALA G 862    27.172  87.512  74.885  1.00100.07      G
ATOM  14650  CA  ALA G 862    27.483  88.115  76.155  1.00100.07      G
ATOM  14651  CB  ALA G 862    28.612  89.105  75.984  1.00100.07      G
ATOM  14652  C   ALA G 862    26.234  88.793  76.698  1.00100.07      G
ATOM  14653  O   ALA G 862    25.741  89.773  76.136  1.00100.07      G
ATOM  14654  N   ALA G 863    25.704  88.242  77.779  1.00 51.13      G
ATOM  14655  CA  ALA G 863    24.522  88.806  78.391  1.00 51.13      G
ATOM  14656  CB  ALA G 863    23.486  87.729  78.589  1.00 40.03      G
ATOM  14657  C   ALA G 863    24.986  89.361  79.728  1.00 51.13      G
ATOM  14658  O   ALA G 863    24.372  90.273  80.312  1.00 51.13      G
ATOM  14659  N   ALA G 864    26.107  88.803  80.176  1.00 59.26      G
ATOM  14660  CA  ALA G 864    26.738  89.155  81.440  1.00 59.26      G
ATOM  14661  CB  ALA G 864    26.681  90.666  81.667  1.00 11.63      G
ATOM  14662  C   ALA G 864    26.025  88.403  82.559  1.00 59.26      G
```

```
ATOM  14663  O    ALA G 864      25.530  88.997  83.506  1.00 59.26           G
ATOM  14664  N    ALA G 865      25.973  87.082  82.422  1.00 87.91           G
ATOM  14665  CA   ALA G 865      25.331  86.219  83.406  1.00 87.91           G
ATOM  14666  CB   ALA G 865      24.974  84.889  82.768  1.00100.07           G
ATOM  14667  C    ALA G 865      26.264  85.991  84.584  1.00 87.91           G
ATOM  14668  O    ALA G 865      27.304  86.632  84.686  1.00 87.91           G
ATOM  14669  N    ALA G 866      25.894  85.076  85.474  1.00 34.71           G
ATOM  14670  CA   ALA G 866      26.731  84.788  86.632  1.00 34.71           G
ATOM  14671  CB   ALA G 866      26.005  85.176  87.923  1.00 55.51           G
ATOM  14672  C    ALA G 866      27.116  83.311  86.666  1.00 34.71           G
ATOM  14673  O    ALA G 866      26.460  82.511  87.317  1.00 34.71           G
ATOM  14674  N    ALA G 867      28.185  82.949  85.965  1.00 39.82           G
ATOM  14675  CA   ALA G 867      28.634  81.561  85.932  1.00 39.82           G
ATOM  14676  CB   ALA G 867      29.203  81.239  84.556  1.00 62.28           G
ATOM  14677  C    ALA G 867      29.664  81.244  87.019  1.00 39.82           G
ATOM  14678  O    ALA G 867      29.844  82.018  87.956  1.00 39.82           G
ATOM  14679  N    ALA G 868      30.340  80.104  86.873  1.00 64.20           G
ATOM  14680  CA   ALA G 868      31.349  79.655  87.835  1.00 64.20           G
ATOM  14681  CB   ALA G 868      30.685  78.785  88.897  1.00 84.35           G
ATOM  14682  C    ALA G 868      32.527  78.889  87.206  1.00 64.20           G
ATOM  14683  O    ALA G 868      32.466  78.469  86.047  1.00 64.20           G
ATOM  14684  N    ALA G 869      33.594  78.718  87.988  1.00 41.77           G
ATOM  14685  CA   ALA G 869      34.805  78.000  87.569  1.00 41.77           G
ATOM  14686  CB   ALA G 869      35.367  78.600  86.283  1.00 90.23           G
ATOM  14687  C    ALA G 869      35.849  78.076  88.692  1.00 41.77           G
ATOM  14688  O    ALA G 869      37.059  78.037  88.460  1.00 41.77           G
ATOM  14689  N    GLY G 870      35.357  78.165  89.919  1.00 56.34           G
ATOM  14690  CA   GLY G 870      36.231  78.268  91.065  1.00 56.34           G
ATOM  14691  C    GLY G 870      35.805  79.529  91.785  1.00 56.34           G
ATOM  14692  O    GLY G 870      36.219  79.789  92.918  1.00 56.34           G
ATOM  14693  N    ALA G 871      34.957  80.309  91.114  1.00 42.45           G
ATOM  14694  CA   ALA G 871      34.452  81.567  91.656  1.00 42.45           G
ATOM  14695  CB   ALA G 871      35.491  82.675  91.471  1.00 45.12           G
ATOM  14696  C    ALA G 871      33.166  81.952  90.947  1.00 42.45           G
ATOM  14697  O    ALA G 871      32.849  81.396  89.901  1.00 42.45           G
ATOM  14698  N    ARG G 872      32.423  82.894  91.523  1.00 72.53           G
ATOM  14699  CA   ARG G 872      31.186  83.356  90.907  1.00 72.53           G
ATOM  14700  CB   ARG G 872      30.175  83.831  91.951  1.00 99.90           G
ATOM  14701  CG   ARG G 872      29.530  82.738  92.771  1.00 99.90           G
ATOM  14702  CD   ARG G 872      28.335  83.297  93.520  1.00 99.90           G
ATOM  14703  NE   ARG G 872      27.867  82.393  94.564  1.00 99.90           G
ATOM  14704  CZ   ARG G 872      26.840  82.654  95.365  1.00 99.90           G
ATOM  14705  NH1  ARG G 872      26.174  83.790  95.237  1.00 99.90           G
ATOM  14706  NH2  ARG G 872      26.484  81.787  96.300  1.00 99.90           G
ATOM  14707  C    ARG G 872      31.537  84.523  90.013  1.00 72.53           G
ATOM  14708  O    ARG G 872      31.968  85.567  90.486  1.00 72.53           G
ATOM  14709  N    LEU G 873      31.359  84.354  88.716  1.00 73.46           G
ATOM  14710  CA   LEU G 873      31.680  85.439  87.819  1.00 73.46           G
ATOM  14711  CB   LEU G 873      32.598  84.952  86.700  1.00 57.59           G
ATOM  14712  CG   LEU G 873      34.004  84.542  87.138  1.00 57.59           G
ATOM  14713  CD1  LEU G 873      34.852  84.271  85.905  1.00 57.59           G
ATOM  14714  CD2  LEU G 873      34.630  85.650  87.992  1.00 57.59           G
ATOM  14715  C    LEU G 873      30.432  86.051  87.228  1.00 73.46           G
ATOM  14716  O    LEU G 873      29.363  85.435  87.225  1.00 73.46           G
ATOM  14717  N    ALA G 874      30.575  87.282  86.751  1.00 62.33           G
ATOM  14718  CA   ALA G 874      29.479  87.987  86.123  1.00 62.33           G
ATOM  14719  CB   ALA G 874      29.407  89.417  86.637  1.00 62.14           G
ATOM  14720  C    ALA G 874      29.782  87.953  84.628  1.00 62.33           G
ATOM  14721  O    ALA G 874      29.227  88.717  83.849  1.00 62.33           G
ATOM  14722  N    THR G 875      30.680  87.045  84.253  1.00 40.57           G
ATOM  14723  CA   THR G 875      31.112  86.818  82.868  1.00 40.57           G
ATOM  14724  CB   THR G 875      31.813  85.428  82.741  1.00 78.23           G
ATOM  14725  OG1  THR G 875      32.990  85.409  83.556  1.00 78.23           G
ATOM  14726  CG2  THR G 875      32.212  85.131  81.315  1.00 78.23           G
ATOM  14727  C    THR G 875      29.948  86.861  81.886  1.00 40.57           G
ATOM  14728  O    THR G 875      28.846  87.262  82.222  1.00 40.57           G
ATOM  14729  N    ASN G 876      30.205  86.438  80.661  1.00 47.09           G
ATOM  14730  CA   ASN G 876      29.192  86.416  79.624  1.00 47.09           G
ATOM  14731  CB   ASN G 876      29.488  87.478  78.578  1.00100.07           G
ATOM  14732  CG   ASN G 876      30.792  87.228  77.851  1.00100.07           G
ATOM  14733  OD1  ASN G 876      31.873  87.593  78.325  1.00100.07           G
ATOM  14734  ND2  ASN G 876      30.697  86.590  76.694  1.00100.07           G
ATOM  14735  C    ASN G 876      29.251  85.051  78.976  1.00 47.09           G
ATOM  14736  O    ASN G 876      30.336  84.540  78.681  1.00 47.09           G
ATOM  14737  N    PRO G 877      28.083  84.452  78.712  1.00 53.32           G
ATOM  14738  CD   PRO G 877      26.804  85.134  78.457  1.00 94.03           G
ATOM  14739  CA   PRO G 877      28.090  83.125  78.092  1.00 53.32           G
ATOM  14740  CB   PRO G 877      26.705  83.034  77.453  1.00 94.03           G
ATOM  14741  CG   PRO G 877      26.351  84.459  77.194  1.00 94.03           G
ATOM  14742  C    PRO G 877      29.217  83.031  77.086  1.00 53.32           G
ATOM  14743  O    PRO G 877      30.053  82.135  77.154  1.00 53.32           G
ATOM  14744  N    GLY G 878      29.258  84.000  76.183  1.00 84.36           G
ATOM  14745  CA   GLY G 878      30.290  84.016  75.166  1.00 84.36           G
ATOM  14746  C    GLY G 878      31.708  83.835  75.671  1.00 84.36           G
```

```
ATOM  14747  O    GLY G 878      32.363  82.839  75.376  1.00 84.36           G
ATOM  14748  N    ALA G 879      32.194  84.804  76.428  1.00 60.99           G
ATOM  14749  CA   ALA G 879      33.540  84.726  76.942  1.00 60.99           G
ATOM  14750  CB   ALA G 879      33.767  85.822  77.995  1.00  5.07           G
ATOM  14751  C    ALA G 879      33.769  83.337  77.528  1.00 60.99           G
ATOM  14752  O    ALA G 879      34.891  82.833  77.516  1.00 60.99           G
ATOM  14753  N    ILE G 880      32.707  82.704  78.021  1.00 46.99           G
ATOM  14754  CA   ILE G 880      32.842  81.369  78.595  1.00 46.99           G
ATOM  14755  CB   ILE G 880      31.533  80.893  79.247  1.00 55.49           G
ATOM  14756  CG2  ILE G 880      31.479  79.380  79.279  1.00 55.49           G
ATOM  14757  CG1  ILE G 880      31.437  81.435  80.673  1.00 55.49           G
ATOM  14758  CD   ILE G 880      32.559  80.961  81.591  1.00 55.49           G
ATOM  14759  C    ILE G 880      33.247  80.381  77.518  1.00 46.99           G
ATOM  14760  O    ILE G 880      34.223  79.652  77.664  1.00 46.99           G
ATOM  14761  N    LEU G 881      32.483  80.356  76.435  1.00 31.65           G
ATOM  14762  CA   LEU G 881      32.761  79.473  75.307  1.00 31.65           G
ATOM  14763  CB   LEU G 881      31.857  79.866  74.146  1.00 22.42           G
ATOM  14764  CG   LEU G 881      31.993  79.225  72.783  1.00 22.42           G
ATOM  14765  CD1  LEU G 881      31.799  77.728  72.847  1.00 22.42           G
ATOM  14766  CD2  LEU G 881      30.940  79.863  71.912  1.00 22.42           G
ATOM  14767  C    LEU G 881      34.230  79.591  74.895  1.00 31.65           G
ATOM  14768  O    LEU G 881      34.956  78.591  74.847  1.00 31.65           G
ATOM  14769  N    PHE G 882      34.659  80.821  74.605  1.00 53.70           G
ATOM  14770  CA   PHE G 882      36.039  81.093  74.220  1.00 53.70           G
ATOM  14771  CB   PHE G 882      36.350  82.585  74.397  1.00 30.67           G
ATOM  14772  CG   PHE G 882      37.700  83.006  73.861  1.00 30.67           G
ATOM  14773  CD1  PHE G 882      37.843  84.216  73.194  1.00 30.67           G
ATOM  14774  CD2  PHE G 882      38.829  82.209  74.025  1.00 30.67           G
ATOM  14775  CE1  PHE G 882      39.095  84.622  72.694  1.00 30.67           G
ATOM  14776  CE2  PHE G 882      40.080  82.612  73.526  1.00 30.67           G
ATOM  14777  CZ   PHE G 882      40.209  83.816  72.862  1.00 30.67           G
ATOM  14778  C    PHE G 882      36.969  80.249  75.086  1.00 53.70           G
ATOM  14779  O    PHE G 882      37.839  79.553  74.568  1.00 53.70           G
ATOM  14780  N    ALA G 883      36.781  80.308  76.401  1.00 51.90           G
ATOM  14781  CA   ALA G 883      37.604  79.522  77.316  1.00 51.90           G
ATOM  14782  CB   ALA G 883      36.893  79.343  78.654  1.00 44.21           G
ATOM  14783  C    ALA G 883      37.882  78.158  76.694  1.00 51.90           G
ATOM  14784  O    ALA G 883      38.882  77.991  75.987  1.00 51.90           G
ATOM  14785  N    ARG G 884      36.999  77.192  76.960  1.00 28.10           G
ATOM  14786  CA   ARG G 884      37.129  75.841  76.412  1.00 28.10           G
ATOM  14787  CB   ARG G 884      35.761  75.270  76.046  1.00 80.63           G
ATOM  14788  CG   ARG G 884      34.859  74.789  77.156  1.00 80.63           G
ATOM  14789  CD   ARG G 884      33.455  74.718  76.573  1.00 80.63           G
ATOM  14790  NE   ARG G 884      32.598  73.723  77.194  1.00 80.63           G
ATOM  14791  CZ   ARG G 884      31.421  73.358  76.697  1.00 80.63           G
ATOM  14792  NH1  ARG G 884      30.962  73.910  75.580  1.00 80.63           G
ATOM  14793  NH2  ARG G 884      30.709  72.422  77.304  1.00 80.63           G
ATOM  14794  C    ARG G 884      37.928  75.926  75.120  1.00 28.10           G
ATOM  14795  O    ARG G 884      39.054  75.426  75.015  1.00 28.10           G
ATOM  14796  N    ILE G 885      37.314  76.583  74.140  1.00 22.47           G
ATOM  14797  CA   ILE G 885      37.914  76.737  72.835  1.00 22.47           G
ATOM  14798  CB   ILE G 885      37.448  78.014  72.183  1.00 17.59           G
ATOM  14799  CG2  ILE G 885      37.937  78.056  70.755  1.00 17.59           G
ATOM  14800  CG1  ILE G 885      35.918  78.051  72.215  1.00 17.59           G
ATOM  14801  CD   ILE G 885      35.296  79.288  71.628  1.00 17.59           G
ATOM  14802  C    ILE G 885      39.407  76.744  73.015  1.00 22.47           G
ATOM  14803  O    ILE G 885      40.105  75.903  72.453  1.00 22.47           G
ATOM  14804  N    VAL G 886      39.882  77.674  73.834  1.00 15.70           G
ATOM  14805  CA   VAL G 886      41.296  77.763  74.142  1.00 15.70           G
ATOM  14806  CB   VAL G 886      41.651  79.115  74.750  1.00 52.29           G
ATOM  14807  CG1  VAL G 886      42.900  78.989  75.600  1.00 52.29           G
ATOM  14808  CG2  VAL G 886      41.883  80.114  73.651  1.00 52.29           G
ATOM  14809  C    VAL G 886      41.627  76.677  75.149  1.00 15.70           G
ATOM  14810  O    VAL G 886      42.557  75.902  74.959  1.00 15.70           G
ATOM  14811  N    GLY G 887      40.862  76.627  76.227  1.00 50.56           G
ATOM  14812  CA   GLY G 887      41.106  75.620  77.235  1.00 50.56           G
ATOM  14813  C    GLY G 887      41.294  74.256  76.605  1.00 50.56           G
ATOM  14814  O    GLY G 887      42.392  73.700  76.629  1.00 50.56           G
ATOM  14815  N    GLU G 888      40.220  73.725  76.028  1.00 72.31           G
ATOM  14816  CA   GLU G 888      40.242  72.414  75.393  1.00 72.31           G
ATOM  14817  CB   GLU G 888      38.875  72.096  74.783  1.00 38.95           G
ATOM  14818  CG   GLU G 888      37.821  71.769  75.829  1.00 38.95           G
ATOM  14819  CD   GLU G 888      36.410  71.852  75.288  1.00 38.95           G
ATOM  14820  OE1  GLU G 888      36.030  72.928  74.791  1.00 38.95           G
ATOM  14821  OE2  GLU G 888      35.680  70.844  75.365  1.00 38.95           G
ATOM  14822  C    GLU G 888      41.319  72.295  74.338  1.00 72.31           G
ATOM  14823  O    GLU G 888      42.016  71.284  74.288  1.00 72.31           G
ATOM  14824  N    ALA G 889      41.464  73.312  73.495  1.00 27.72           G
ATOM  14825  CA   ALA G 889      42.493  73.242  72.468  1.00 27.72           G
ATOM  14826  CB   ALA G 889      42.761  74.616  71.864  1.00  5.07           G
ATOM  14827  C    ALA G 889      43.764  72.698  73.106  1.00 27.72           G
ATOM  14828  O    ALA G 889      44.357  71.743  72.610  1.00 27.72           G
ATOM  14829  N    VAL G 890      44.169  73.298  74.218  1.00 41.79           G
ATOM  14830  CA   VAL G 890      45.371  72.871  74.922  1.00 41.79           G
```

| ATOM | 14831 | CB | VAL | G | 890 | 46.208 | 74.090 | 75.344 | 1.00 | 99.98 | G |
|------|-------|-----|-----|---|-----|--------|--------|--------|------|-------|---|
| ATOM | 14832 | CG1 | VAL | G | 890 | 47.509 | 73.640 | 75.965 | 1.00 | 99.98 | G |
| ATOM | 14833 | CG2 | VAL | G | 890 | 46.466 | 74.975 | 74.142 | 1.00 | 99.98 | G |
| ATOM | 14834 | C | VAL | G | 890 | 44.974 | 72.088 | 76.164 | 1.00 | 41.79 | G |
| ATOM | 14835 | O | VAL | G | 890 | 43.809 | 71.749 | 76.335 | 1.00 | 41.79 | G |
| ATOM | 14836 | N | GLY | G | 891 | 45.940 | 71.795 | 77.026 | 1.00 | 34.83 | G |
| ATOM | 14837 | CA | GLY | G | 891 | 45.633 | 71.076 | 78.246 | 1.00 | 34.83 | G |
| ATOM | 14838 | C | GLY | G | 891 | 44.673 | 71.865 | 79.128 | 1.00 | 34.83 | G |
| ATOM | 14839 | O | GLY | G | 891 | 45.069 | 72.408 | 80.172 | 1.00 | 34.83 | G |
| ATOM | 14840 | N | ASP | G | 892 | 43.411 | 71.910 | 78.696 | 1.00 | 63.47 | G |
| ATOM | 14841 | CA | ASP | G | 892 | 42.307 | 72.611 | 79.365 | 1.00 | 63.47 | G |
| ATOM | 14842 | CB | ASP | G | 892 | 41.343 | 71.594 | 80.013 | 1.00 | 100.07 | G |
| ATOM | 14843 | CG | ASP | G | 892 | 42.058 | 70.395 | 80.615 | 1.00 | 100.07 | G |
| ATOM | 14844 | OD1 | ASP | G | 892 | 42.715 | 69.651 | 79.857 | 1.00 | 100.07 | G |
| ATOM | 14845 | OD2 | ASP | G | 892 | 41.958 | 70.189 | 81.843 | 1.00 | 100.07 | G |
| ATOM | 14846 | C | ASP | G | 892 | 42.598 | 73.752 | 80.360 | 1.00 | 63.47 | G |
| ATOM | 14847 | O | ASP | G | 892 | 43.747 | 73.990 | 80.763 | 1.00 | 63.47 | G |
| ATOM | 14848 | N | GLU | G | 893 | 41.528 | 74.460 | 80.730 | 1.00 | 56.06 | G |
| ATOM | 14849 | CA | GLU | G | 893 | 41.584 | 75.595 | 81.645 | 1.00 | 56.06 | G |
| ATOM | 14850 | CB | GLU | G | 893 | 40.166 | 75.893 | 82.163 | 1.00 | 100.07 | G |
| ATOM | 14851 | CG | GLU | G | 893 | 39.183 | 76.338 | 81.054 | 1.00 | 100.07 | G |
| ATOM | 14852 | CD | GLU | G | 893 | 37.749 | 76.600 | 81.547 | 1.00 | 100.07 | G |
| ATOM | 14853 | OE1 | GLU | G | 893 | 37.527 | 77.525 | 82.367 | 1.00 | 100.07 | G |
| ATOM | 14854 | OE2 | GLU | G | 893 | 36.834 | 75.874 | 81.097 | 1.00 | 100.07 | G |
| ATOM | 14855 | C | GLU | G | 893 | 42.571 | 75.401 | 82.803 | 1.00 | 56.06 | G |
| ATOM | 14856 | O | GLU | G | 893 | 43.278 | 74.401 | 82.861 | 1.00 | 56.06 | G |
| ATOM | 14857 | N | LYS | G | 894 | 42.622 | 76.368 | 83.715 | 1.00 | 100.07 | G |
| ATOM | 14858 | CA | LYS | G | 894 | 43.530 | 76.331 | 84.866 | 1.00 | 100.07 | G |
| ATOM | 14859 | CB | LYS | G | 894 | 43.449 | 74.976 | 85.611 | 1.00 | 99.75 | G |
| ATOM | 14860 | CG | LYS | G | 894 | 44.554 | 73.940 | 85.291 | 1.00 | 99.75 | G |
| ATOM | 14861 | CD | LYS | G | 894 | 44.432 | 72.659 | 86.159 | 1.00 | 99.75 | G |
| ATOM | 14862 | CE | LYS | G | 894 | 45.514 | 71.610 | 85.830 | 1.00 | 99.75 | G |
| ATOM | 14863 | NZ | LYS | G | 894 | 45.452 | 70.399 | 86.710 | 1.00 | 99.75 | G |
| ATOM | 14864 | C | LYS | G | 894 | 44.957 | 76.591 | 84.392 | 1.00 | 100.07 | G |
| ATOM | 14865 | O | LYS | G | 894 | 45.714 | 77.327 | 85.027 | 1.00 | 100.07 | G |
| ATOM | 14866 | N | VAL | G | 895 | 45.311 | 75.980 | 83.268 | 1.00 | 49.89 | G |
| ATOM | 14867 | CA | VAL | G | 895 | 46.635 | 76.145 | 82.684 | 1.00 | 49.89 | G |
| ATOM | 14868 | CB | VAL | G | 895 | 47.090 | 74.855 | 81.939 | 1.00 | 99.66 | G |
| ATOM | 14869 | CG1 | VAL | G | 895 | 48.600 | 74.852 | 81.779 | 1.00 | 99.66 | G |
| ATOM | 14870 | CG2 | VAL | G | 895 | 46.629 | 73.609 | 82.693 | 1.00 | 99.66 | G |
| ATOM | 14871 | C | VAL | G | 895 | 46.459 | 77.274 | 81.677 | 1.00 | 49.89 | G |
| ATOM | 14872 | O | VAL | G | 895 | 47.292 | 78.165 | 81.553 | 1.00 | 49.89 | G |
| ATOM | 14873 | N | ALA | G | 896 | 45.343 | 77.213 | 80.962 | 1.00 | 65.22 | G |
| ATOM | 14874 | CA | ALA | G | 896 | 45.012 | 78.216 | 79.970 | 1.00 | 65.22 | G |
| ATOM | 14875 | CB | ALA | G | 896 | 43.830 | 77.760 | 79.123 | 1.00 | 34.75 | G |
| ATOM | 14876 | C | ALA | G | 896 | 44.650 | 79.481 | 80.708 | 1.00 | 65.22 | G |
| ATOM | 14877 | O | ALA | G | 896 | 45.286 | 80.508 | 80.525 | 1.00 | 65.22 | G |
| ATOM | 14878 | N | GLN | G | 897 | 43.621 | 79.386 | 81.545 | 1.00 | 97.43 | G |
| ATOM | 14879 | CA | GLN | G | 897 | 43.126 | 80.514 | 82.324 | 1.00 | 97.43 | G |
| ATOM | 14880 | CB | GLN | G | 897 | 42.975 | 80.110 | 83.792 | 1.00 | 100.07 | G |
| ATOM | 14881 | CG | GLN | G | 897 | 42.576 | 81.253 | 84.727 | 1.00 | 100.07 | G |
| ATOM | 14882 | CD | GLN | G | 897 | 41.293 | 81.973 | 84.314 | 1.00 | 100.07 | G |
| ATOM | 14883 | OE1 | GLN | G | 897 | 40.782 | 82.815 | 85.052 | 1.00 | 100.07 | G |
| ATOM | 14884 | NE2 | GLN | G | 897 | 40.776 | 81.652 | 83.134 | 1.00 | 100.07 | G |
| ATOM | 14885 | C | GLN | G | 897 | 43.989 | 81.767 | 82.213 | 1.00 | 97.43 | G |
| ATOM | 14886 | O | GLN | G | 897 | 43.545 | 82.794 | 81.691 | 1.00 | 97.43 | G |
| ATOM | 14887 | N | GLU | G | 898 | 45.222 | 81.676 | 82.699 | 1.00 | 100.07 | G |
| ATOM | 14888 | CA | GLU | G | 898 | 46.160 | 82.795 | 82.648 | 1.00 | 100.07 | G |
| ATOM | 14889 | CB | GLU | G | 898 | 47.529 | 82.338 | 83.156 | 1.00 | 100.07 | G |
| ATOM | 14890 | CG | GLU | G | 898 | 47.533 | 81.817 | 84.580 | 1.00 | 100.07 | G |
| ATOM | 14891 | CD | GLU | G | 898 | 48.633 | 80.791 | 84.818 | 1.00 | 100.07 | G |
| ATOM | 14892 | OE1 | GLU | G | 898 | 48.391 | 79.587 | 84.580 | 1.00 | 100.07 | G |
| ATOM | 14893 | OE2 | GLU | G | 998 | 49.744 | 81.187 | 85.230 | 1.00 | 100.07 | G |
| ATOM | 14894 | C | GLU | G | 898 | 46.305 | 83.364 | 81.225 | 1.00 | 100.07 | G |
| ATOM | 14895 | O | GLU | G | 898 | 45.985 | 84.532 | 80.978 | 1.00 | 100.07 | G |
| ATOM | 14896 | N | LEU | G | 899 | 46.800 | 82.529 | 80.307 | 1.00 | 54.36 | G |
| ATOM | 14897 | CA | LEU | G | 899 | 47.007 | 82.907 | 78.909 | 1.00 | 54.36 | G |
| ATOM | 14898 | CB | LEU | G | 899 | 47.535 | 81.734 | 78.077 | 1.00 | 94.45 | G |
| ATOM | 14899 | CG | LEU | G | 899 | 48.893 | 81.078 | 78.303 | 1.00 | 94.45 | G |
| ATOM | 14900 | CD1 | LEU | G | 899 | 48.948 | 80.411 | 79.669 | 1.00 | 94.45 | G |
| ATOM | 14901 | CD2 | LEU | G | 899 | 49.110 | 80.048 | 77.201 | 1.00 | 94.45 | G |
| ATOM | 14902 | C | LEU | G | 899 | 45.689 | 83.299 | 78.313 | 1.00 | 54.36 | G |
| ATOM | 14903 | O | LEU | G | 899 | 45.262 | 82.698 | 77.335 | 1.00 | 54.36 | G |
| ATOM | 14904 | N | ILE | G | 900 | 45.040 | 84.292 | 78.892 | 1.00 | 29.34 | G |
| ATOM | 14905 | CA | ILE | G | 900 | 43.753 | 84.731 | 78.391 | 1.00 | 29.34 | G |
| ATOM | 14906 | CB | ILE | G | 900 | 42.609 | 83.719 | 78.772 | 1.00 | 38.38 | G |
| ATOM | 14907 | CG2 | ILE | G | 900 | 41.239 | 84.318 | 78.475 | 1.00 | 38.38 | G |
| ATOM | 14908 | CG1 | ILE | G | 900 | 42.735 | 82.428 | 77.961 | 1.00 | 38.38 | G |
| ATOM | 14909 | CD | ILE | G | 900 | 42.908 | 81.177 | 78.789 | 1.00 | 38.38 | G |
| ATOM | 14910 | C | ILE | G | 900 | 43.429 | 86.076 | 79.009 | 1.00 | 29.34 | G |
| ATOM | 14911 | O | ILE | G | 900 | 43.752 | 86.317 | 80.180 | 1.00 | 29.34 | G |
| ATOM | 14912 | N | GLN | G | 901 | 42.822 | 86.959 | 78.220 | 1.00 | 41.82 | G |
| ATOM | 14913 | CA | GLN | G | 901 | 42.398 | 88.252 | 78.738 | 1.00 | 41.82 | G |
| ATOM | 14914 | CB | GLN | G | 901 | 42.550 | 89.357 | 77.685 | 1.00 | 100.07 | G |

```
ATOM  14915  CG   GLN G 901      43.910  90.058  77.731  1.00100.07      G
ATOM  14916  CD   GLN G 901      43.896  91.438  77.088  1.00100.07      G
ATOM  14917  OE1  GLN G 901      43.106  92.307  77.464  1.00100.07      G
ATOM  14918  NE2  GLN G 901      44.779  91.645  76.122  1.00100.07      G
ATOM  14919  C    GLN G 901      40.933  88.037  79.093  1.00 41.82      G
ATOM  14920  O    GLN G 901      40.034  88.584  78.449  1.00 41.82      G
ATOM  14921  N    MET G 902      40.726  87.225  80.132  1.00 36.52      G
ATOM  14922  CA   MET G 902      39.404  86.840  80.608  1.00 36.52      G
ATOM  14923  CB   MET G 902      39.459  86.357  82.058  1.00 73.44      G
ATOM  14924  CG   MET G 902      39.471  84.823  82.184  1.00 73.44      G
ATOM  14925  SD   MET G 902      38.474  83.969  80.908  1.00 73.44      G
ATOM  14926  CE   MET G 902      36.839  84.599  81.236  1.00 73.44      G
ATOM  14927  C    MET G 902      38.321  87.869  80.451  1.00 36.52      G
ATOM  14928  O    MET G 902      38.546  89.069  80.611  1.00 36.52      G
ATOM  14929  N    ASP G 903      37.127  87.369  80.152  1.00100.07      G
ATOM  14930  CA   ASP G 903      35.982  88.222  79.906  1.00100.07      G
ATOM  14931  CB   ASP G 903      35.318  88.688  81.202  1.00100.07      G
ATOM  14932  CG   ASP G 903      34.097  87.852  81.555  1.00100.07      G
ATOM  14933  OD1  ASP G 903      34.287  86.680  81.942  1.00100.07      G
ATOM  14934  OD2  ASP G 903      32.958  88.363  81.431  1.00100.07      G
ATOM  14935  C    ASP G 903      36.476  89.397  79.099  1.00100.07      G
ATOM  14936  O    ASP G 903      36.743  89.223  77.907  1.00100.07      G
ATOM  14937  N    VAL G 904      36.632  90.573  79.722  1.00 35.44      G
ATOM  14938  CA   VAL G 904      37.081  91.740  78.965  1.00 35.44      G
ATOM  14939  CB   VAL G 904      38.610  91.748  78.870  1.00 99.60      G
ATOM  14940  CG1  VAL G 904      39.085  92.918  78.023  1.00 99.60      G
ATOM  14941  CG2  VAL G 904      39.197  91.808  80.259  1.00 99.60      G
ATOM  14942  C    VAL G 904      36.495  91.513  77.563  1.00 35.44      G
ATOM  14943  O    VAL G 904      37.179  91.723  76.542  1.00 35.44      G
ATOM  14944  N    PRO G 905      35.213  91.068  77.508  1.00100.07      G
ATOM  14945  CD   PRO G 905      34.267  91.101  78.645  1.00 35.40      G
ATOM  14946  CA   PRO G 905      34.472  90.763  76.283  1.00100.07      G
ATOM  14947  CB   PRO G 905      33.028  90.680  76.781  1.00 35.40      G
ATOM  14948  CG   PRO G 905      33.183  90.179  78.179  1.00 35.40      G
ATOM  14949  C    PRO G 905      34.661  91.686  75.072  1.00100.07      G
ATOM  14950  O    PRO G 905      33.722  92.331  74.600  1.00100.07      G
ATOM  14951  N    GLN G 906      35.897  91.709  74.578  1.00 48.66      G
ATOM  14952  CA   GLN G 906      36.326  92.483  73.424  1.00 48.66      G
ATOM  14953  CB   GLN G 906      36.430  93.970  73.781  1.00100.07      G
ATOM  14954  CG   GLN G 906      35.082  94.657  74.078  1.00100.07      G
ATOM  14955  CD   GLN G 906      34.858  94.969  75.562  1.00100.07      G
ATOM  14956  OE1  GLN G 906      34.928  94.084  76.418  1.00100.07      G
ATOM  14957  NE2  GLN G 906      34.580  96.237  75.865  1.00100.07      G
ATOM  14958  C    GLN G 906      37.705  91.884  73.169  1.00 48.66      G
ATOM  14959  O    GLN G 906      38.565  91.921  74.053  1.00 48.66      G
ATOM  14960  N    GLU G 907      37.898  91.309  71.981  1.00 57.50      G
ATOM  14961  CA   GLU G 907      39.157  90.654  71.615  1.00 57.50      G
ATOM  14962  CB   GLU G 907      38.996  89.158  71.819  1.00 15.90      G
ATOM  14963  CG   GLU G 907      40.233  88.440  72.240  1.00 15.90      G
ATOM  14964  CD   GLU G 907      40.084  87.869  73.630  1.00 15.90      G
ATOM  14965  OE1  GLU G 907      38.939  87.498  73.974  1.00 15.90      G
ATOM  14966  OE2  GLU G 907      41.093  87.784  74.381  1.00 15.90      G
ATOM  14967  C    GLU G 907      39.488  90.917  70.145  1.00 57.50      G
ATOM  14968  O    GLU G 907      38.589  90.863  69.304  1.00 57.50      G
ATOM  14969  N    LYS G 908      40.757  91.186  69.824  1.00 31.57      G
ATOM  14970  CA   LYS G 908      41.142  91.442  68.428  1.00 31.57      G
ATOM  14971  CB   LYS G 908      40.448  92.710  67.929  1.00100.07      G
ATOM  14972  CG   LYS G 908      41.120  93.364  66.743  1.00100.07      G
ATOM  14973  CD   LYS G 908      42.219  94.317  67.196  1.00100.07      G
ATOM  14974  CE   LYS G 908      42.775  95.148  66.039  1.00100.07      G
ATOM  14975  NZ   LYS G 908      43.752  96.207  66.481  1.00100.07      G
ATOM  14976  C    LYS G 908      42.651  91.537  68.153  1.00 31.57      G
ATOM  14977  O    LYS G 908      43.131  91.330  67.026  1.00 31.57      G
ATOM  14978  N    ASN G 909      43.409  91.867  69.179  1.00 45.38      G
ATOM  14979  CA   ASN G 909      44.844  91.978  69.011  1.00 45.38      G
ATOM  14980  CB   ASN G 909      45.292  93.348  69.506  1.00 50.76      G
ATOM  14981  CG   ASN G 909      46.711  93.669  69.132  1.00 50.76      G
ATOM  14982  OD1  ASN G 909      47.637  92.953  69.505  1.00 50.76      G
ATOM  14983  ND2  ASN G 909      46.896  94.759  68.394  1.00 50.76      G
ATOM  14984  C    ASN G 909      45.408  90.871  69.879  1.00 45.38      G
ATOM  14985  O    ASN G 909      46.264  90.103  69.450  1.00 45.38      G
ATOM  14986  N    SER G 910      44.883  90.809  71.101  1.00 35.05      G
ATOM  14987  CA   SER G 910      45.249  89.815  72.090  1.00 35.05      G
ATOM  14988  CB   SER G 910      44.181  89.739  73.167  1.00 16.04      G
ATOM  14989  OG   SER G 910      42.943  89.345  72.603  1.00 16.04      G
ATOM  14990  C    SER G 910      45.378  88.435  71.467  1.00 35.05      G
ATOM  14991  O    SER G 910      46.270  87.671  71.840  1.00 35.05      G
ATOM  14992  N    LEU G 911      44.471  88.094  70.548  1.00 32.43      G
ATOM  14993  CA   LEU G 911      44.541  86.787  69.899  1.00 32.43      G
ATOM  14994  CB   LEU G 911      43.677  86.741  68.636  1.00 41.34      G
ATOM  14995  CG   LEU G 911      42.151  86.821  68.771  1.00 41.34      G
ATOM  14996  CD1  LEU G 911      41.600  85.619  69.528  1.00 41.34      G
ATOM  14997  CD2  LEU G 911      41.794  88.114  69.473  1.00 41.34      G
ATOM  14998  C    LEU G 911      46.001  86.671  69.535  1.00 32.43      G
```

```
ATOM  14999  O    LEU G 911      46.691  85.741  69.960  1.00 32.43           G
ATOM  15000  N    LYS G 912      46.465  87.663  68.782  1.00 26.24           G
ATOM  15001  CA   LYS G 912      47.854  87.734  68.371  1.00 26.24           G
ATOM  15002  CB   LYS G 912      48.134  89.075  67.710  1.00 42.77           G
ATOM  15003  CG   LYS G 912      49.594  89.346  67.439  1.00 42.77           G
ATOM  15004  CD   LYS G 912      49.675  90.480  66.438  1.00 42.77           G
ATOM  15005  CE   LYS G 912      51.095  90.931  66.124  1.00 42.77           G
ATOM  15006  NZ   LYS G 912      51.108  91.949  65.018  1.00 42.77           G
ATOM  15007  C    LYS G 912      48.753  87.574  69.589  1.00 26.24           G
ATOM  15008  O    LYS G 912      49.753  86.851  69.542  1.00 26.24           G
ATOM  15009  N    ASP G 913      48.399  88.245  70.683  1.00 37.60           G
ATOM  15010  CA   ASP G 913      49.207  88.148  71.888  1.00 37.60           G
ATOM  15011  CB   ASP G 913      48.731  89.125  72.966  1.00100.07           G
ATOM  15012  CG   ASP G 913      49.732  89.257  74.109  1.00100.07           G
ATOM  15013  OD1  ASP G 913      50.918  89.530  73.819  1.00100.07           G
ATOM  15014  OD2  ASP G 913      49.343  89.091  75.289  1.00100.07           G
ATOM  15015  C    ASP G 913      49.153  86.725  72.410  1.00 37.60           G
ATOM  15016  O    ASP G 913      50.153  86.018  72.344  1.00 37.60           G
ATOM  15017  N    LEU G 914      47.991  86.309  72.912  1.00 68.78           G
ATOM  15018  CA   LEU G 914      47.812  84.958  73.440  1.00 68.78           G
ATOM  15019  CB   LEU G 914      46.397  84.424  73.144  1.00 21.88           G
ATOM  15020  CG   LEU G 914      45.847  83.327  74.081  1.00 21.88           G
ATOM  15021  CD1  LEU G 914      44.512  82.819  73.558  1.00 21.88           G
ATOM  15022  CD2  LEU G 914      46.828  82.182  74.220  1.00 21.88           G
ATOM  15023  C    LEU G 914      48.820  84.053  72.758  1.00 68.78           G
ATOM  15024  O    LEU G 914      49.779  83.595  73.383  1.00 68.78           G
ATOM  15025  N    VAL G 915      48.602  83.838  71.460  1.00 25.52           G
ATOM  15026  CA   VAL G 915      49.455  82.986  70.652  1.00 25.52           G
ATOM  15027  CB   VAL G 915      49.341  83.348  69.215  1.00  5.07           G
ATOM  15028  CG1  VAL G 915      50.200  82.442  68.399  1.00  5.07           G
ATOM  15029  CG2  VAL G 915      47.910  83.243  68.808  1.00  5.07           G
ATOM  15030  C    VAL G 915      50.916  83.009  71.033  1.00 25.52           G
ATOM  15031  O    VAL G 915      51.476  81.961  71.340  1.00 25.52           G
ATOM  15032  N    TYR G 916      51.542  84.184  70.996  1.00 41.66           G
ATOM  15033  CA   TYR G 916      52.948  84.275  71.378  1.00 41.66           G
ATOM  15034  CB   TYR G 916      53.486  85.711  71.262  1.00 18.15           G
ATOM  15035  CG   TYR G 916      54.914  85.896  71.781  1.00 18.15           G
ATOM  15036  CD1  TYR G 916      55.974  86.157  70.913  1.00 18.15           G
ATOM  15037  CE1  TYR G 916      57.285  86.297  71.395  1.00 18.15           G
ATOM  15038  CD2  TYR G 916      55.200  85.786  73.140  1.00 18.15           G
ATOM  15039  CE2  TYR G 916      56.496  85.919  73.630  1.00 18.15           G
ATOM  15040  CZ   TYR G 916      57.538  86.171  72.763  1.00 18.15           G
ATOM  15041  OH   TYR G 916      58.823  86.266  73.280  1.00 18.15           G
ATOM  15042  C    TYR G 916      53.050  83.806  72.821  1.00 41.66           G
ATOM  15043  O    TYR G 916      53.426  82.667  73.069  1.00 41.66           G
ATOM  15044  N    GLN G 917      52.703  84.676  73.771  1.00 94.98           G
ATOM  15045  CA   GLN G 917      52.781  84.323  75.190  1.00 94.98           G
ATOM  15046  CB   GLN G 917      52.465  85.554  76.079  1.00 67.42           G
ATOM  15047  CG   GLN G 917      53.678  86.529  76.295  1.00 67.42           G
ATOM  15048  CD   GLN G 917      53.314  88.045  76.339  1.00 67.42           G
ATOM  15049  OE1  GLN G 917      52.847  88.618  75.348  1.00 67.42           G
ATOM  15050  NE2  GLN G 917      53.550  88.686  77.488  1.00 67.42           G
ATOM  15051  C    GLN G 917      51.868  83.138  75.512  1.00 94.98           G
ATOM  15052  O    GLN G 917      51.292  83.059  76.591  1.00 94.98           G
ATOM  15053  N    ALA G 918      51.762  82.230  74.539  1.00 30.48           G
ATOM  15054  CA   ALA G 918      50.991  80.982  74.599  1.00 30.48           G
ATOM  15055  CB   ALA G 918      49.742  81.064  73.747  1.00 23.16           G
ATOM  15056  C    ALA G 918      51.932  79.961  73.990  1.00 30.48           G
ATOM  15057  O    ALA G 918      52.021  78.815  74.432  1.00 30.48           G
ATOM  15058  N    PHE G 919      52.609  80.417  72.941  1.00 37.87           G
ATOM  15059  CA   PHE G 919      53.592  79.652  72.190  1.00 37.87           G
ATOM  15060  CB   PHE G 919      54.153  80.561  71.071  1.00 25.21           G
ATOM  15061  CG   PHE G 919      55.256  79.952  70.220  1.00 25.21           G
ATOM  15062  CD1  PHE G 919      55.259  80.153  68.837  1.00 25.21           G
ATOM  15063  CD2  PHE G 919      56.339  79.281  70.789  1.00 25.21           G
ATOM  15064  CE1  PHE G 919      56.315  79.708  68.042  1.00 25.21           G
ATOM  15065  CE2  PHE G 919      57.398  78.835  69.996  1.00 25.21           G
ATOM  15066  CZ   PHE G 919      57.378  79.053  68.621  1.00 25.21           G
ATOM  15067  C    PHE G 919      54.651  79.222  73.205  1.00 37.87           G
ATOM  15068  O    PHE G 919      54.606  78.097  73.685  1.00 37.87           G
ATOM  15069  N    LEU G 920      55.574  80.101  73.573  1.00 31.15           G
ATOM  15070  CA   LEU G 920      56.598  79.696  74.525  1.00 31.15           G
ATOM  15071  CB   LEU G 920      57.518  80.859  74.885  1.00 50.94           G
ATOM  15072  CG   LEU G 920      56.924  82.240  75.111  1.00 50.94           G
ATOM  15073  CD1  LEU G 920      57.982  83.180  75.653  1.00 50.94           G
ATOM  15074  CD2  LEU G 920      56.404  82.757  73.793  1.00 50.94           G
ATOM  15075  C    LEU G 920      56.000  79.114  75.794  1.00 31.15           G
ATOM  15076  O    LEU G 920      56.715  78.559  76.637  1.00 31.15           G
ATOM  15077  N    ARG G 921      54.685  79.234  75.929  1.00 42.43           G
ATOM  15078  CA   ARG G 921      54.004  78.695  77.096  1.00 42.43           G
ATOM  15079  CB   ARG G 921      52.665  79.392  77.284  1.00100.07           G
ATOM  15080  CG   ARG G 921      52.771  80.890  77.390  1.00100.07           G
ATOM  15081  CD   ARG G 921      52.866  81.362  78.826  1.00100.07           G
ATOM  15082  NE   ARG G 921      52.538  82.782  78.913  1.00100.07           G
```

```
ATOM  15083  CZ   ARG G 921      52.284  83.419  80.048  1.00100.07      G
ATOM  15084  NH1  ARG G 921      52.324  82.764  81.201  1.00100.07      G
ATOM  15085  NH2  ARG G 921      51.970  84.705  80.027  1.00100.07      G
ATOM  15086  C    ARG G 921      53.766  77.206  76.911  1.00 42.43      G
ATOM  15087  O    ARG G 921      53.982  76.419  77.827  1.00 42.43      G
ATOM  15088  N    LEU G 922      53.327  76.838  75.710  1.00 44.04      G
ATOM  15089  CA   LEU G 922      53.030  75.451  75.361  1.00 44.04      G
ATOM  15090  CB   LEU G 922      51.512  75.287  75.270  1.00  7.34      G
ATOM  15091  CG   LEU G 922      50.720  76.050  76.343  1.00  7.34      G
ATOM  15092  CD1  LEU G 922      49.227  76.146  76.025  1.00  7.34      G
ATOM  15093  CD2  LEU G 922      50.944  75.348  77.636  1.00  7.34      G
ATOM  15094  C    LEU G 922      53.686  75.135  74.010  1.00 44.04      G
ATOM  15095  O    LEU G 922      53.556  75.902  73.063  1.00 44.04      G
ATOM  15096  N    GLY G 923      54.387  74.010  73.922  1.00 72.53      G
ATOM  15097  CA   GLY G 923      55.075  73.648  72.687  1.00 72.53      G
ATOM  15098  C    GLY G 923      54.411  73.979  71.358  1.00 72.53      G
ATOM  15099  O    GLY G 923      53.186  74.029  71.275  1.00 72.53      G
ATOM  15100  N    MET G 924      55.218  74.200  70.317  1.00 43.18      G
ATOM  15101  CA   MET G 924      54.697  74.513  68.986  1.00 43.18      G
ATOM  15102  CB   MET G 924      55.687  74.157  67.886  1.00 30.36      G
ATOM  15103  CG   MET G 924      56.921  74.996  67.850  1.00 30.36      G
ATOM  15104  SD   MET G 924      57.814  74.652  66.340  1.00 30.36      G
ATOM  15105  CE   MET G 924      58.292  72.974  66.643  1.00 30.36      G
ATOM  15106  C    MET G 924      53.456  73.710  68.722  1.00 43.18      G
ATOM  15107  O    MET G 924      52.382  74.271  68.488  1.00 43.18      G
ATOM  15108  N    GLU G 925      53.618  72.387  68.755  1.00 32.52      G
ATOM  15109  CA   GLU G 925      52.511  71.489  68.506  1.00 32.52      G
ATOM  15110  CB   GLU G 925      52.806  70.096  69.053  1.00100.07      G
ATOM  15111  CG   GLU G 925      53.470  70.084  70.392  1.00100.07      G
ATOM  15112  CD   GLU G 925      54.402  68.905  70.528  1.00100.07      G
ATOM  15113  OE1  GLU G 925      55.204  68.695  69.595  1.00100.07      G
ATOM  15114  OE2  GLU G 925      54.346  68.197  71.556  1.00100.07      G
ATOM  15115  C    GLU G 925      51.262  72.061  69.131  1.00 32.52      G
ATOM  15116  O    GLU G 925      50.353  72.475  68.417  1.00 32.52      G
ATOM  15117  N    LYS G 926      51.215  72.129  70.453  1.00 40.61      G
ATOM  15118  CA   LYS G 926      50.027  72.672  71.076  1.00 40.61      G
ATOM  15119  CB   LYS G 926      50.277  72.984  72.542  1.00 81.62      G
ATOM  15120  CG   LYS G 926      50.375  71.727  73.363  1.00 81.62      G
ATOM  15121  CD   LYS G 926      50.031  71.990  74.803  1.00 81.62      G
ATOM  15122  CE   LYS G 926      49.978  70.696  75.601  1.00 81.62      G
ATOM  15123  NZ   LYS G 926      49.600  70.913  77.033  1.00 81.62      G
ATOM  15124  C    LYS G 926      49.543  73.898  70.320  1.00 40.61      G
ATOM  15125  O    LYS G 926      48.554  73.813  69.606  1.00 40.61      G
ATOM  15126  N    THR G 927      50.244  75.017  70.428  1.00 44.70      G
ATOM  15127  CA   THR G 927      49.823  76.226  69.733  1.00 44.70      G
ATOM  15128  CB   THR G 927      50.993  77.101  69.374  1.00 25.61      G
ATOM  15129  OG1  THR G 927      51.706  77.460  70.559  1.00 25.61      G
ATOM  15130  CG2  THR G 927      50.491  78.360  68.687  1.00 25.61      G
ATOM  15131  C    THR G 927      49.076  75.949  68.435  1.00 44.70      G
ATOM  15132  O    THR G 927      47.968  76.455  68.237  1.00 44.70      G
ATOM  15133  N    ALA G 928      49.688  75.160  67.548  1.00 38.44      G
ATOM  15134  CA   ALA G 928      49.064  74.817  66.265  1.00 38.44      G
ATOM  15135  CB   ALA G 928      49.713  73.564  65.653  1.00 10.51      G
ATOM  15136  C    ALA G 928      47.605  74.551  66.551  1.00 38.44      G
ATOM  15137  O    ALA G 928      46.722  75.151  65.946  1.00 38.44      G
ATOM  15138  N    ARG G 929      47.358  73.650  67.491  1.00 18.89      G
ATOM  15139  CA   ARG G 929      45.999  73.341  67.846  1.00 18.89      G
ATOM  15140  CB   ARG G 929      45.953  72.464  69.094  1.00 93.16      G
ATOM  15141  CG   ARG G 929      46.502  71.090  68.814  1.00 93.16      G
ATOM  15142  CD   ARG G 929      46.388  70.151  69.983  1.00 93.16      G
ATOM  15143  NE   ARG G 929      46.770  68.804  69.571  1.00 93.16      G
ATOM  15144  CZ   ARG G 929      46.714  67.734  70.355  1.00 93.16      G
ATOM  15145  NH1  ARG G 929      46.293  67.855  71.608  1.00 93.16      G
ATOM  15146  NH2  ARG G 929      47.059  66.541  69.880  1.00 93.16      G
ATOM  15147  C    ARG G 929      45.277  74.659  68.051  1.00 18.89      G
ATOM  15148  O    ARG G 929      44.634  75.137  67.134  1.00 18.89      G
ATOM  15149  N    LEU G 930      45.393  75.259  69.230  1.00 27.41      G
ATOM  15150  CA   LEU G 930      44.728  76.529  69.493  1.00 27.41      G
ATOM  15151  CB   LEU G 930      45.461  77.304  70.597  1.00 41.94      G
ATOM  15152  CG   LEU G 930      44.855  78.623  71.112  1.00 41.94      G
ATOM  15153  CD1  LEU G 930      45.141  79.778  70.179  1.00 41.94      G
ATOM  15154  CD2  LEU G 930      43.364  78.440  71.280  1.00 41.94      G
ATOM  15155  C    LEU G 930      44.676  77.370  68.220  1.00 27.41      G
ATOM  15156  O    LEU G 930      43.660  78.003  67.937  1.00 27.41      G
ATOM  15157  N    LEU G 931      45.764  77.369  67.453  1.00 19.20      G
ATOM  15158  CA   LEU G 931      45.830  78.134  66.204  1.00 19.20      G
ATOM  15159  CB   LEU G 931      47.185  77.897  65.530  1.00 16.34      G
ATOM  15160  CG   LEU G 931      48.025  79.122  65.193  1.00 16.34      G
ATOM  15161  CD1  LEU G 931      47.242  80.021  64.251  1.00 16.34      G
ATOM  15162  CD2  LEU G 931      48.402  79.843  66.472  1.00 16.34      G
ATOM  15163  C    LEU G 931      44.707  77.660  65.281  1.00 19.20      G
ATOM  15164  O    LEU G 931      44.128  78.420  64.503  1.00 19.20      G
ATOM  15165  N    ASP G 932      44.433  76.371  65.383  1.00 53.43      G
ATOM  15166  CA   ASP G 932      43.397  75.713  64.619  1.00 53.43      G
```

```
ATOM  15167  CB   ASP G 932      43.775  74.250  64.423  1.00 40.48           G
ATOM  15168  CG   ASP G 932      44.188  73.955  63.011  1.00 40.48           G
ATOM  15169  OD1  ASP G 932      43.355  74.213  62.112  1.00 40.48           G
ATOM  15170  OD2  ASP G 932      45.327  73.476  62.793  1.00 40.48           G
ATOM  15171  C    ASP G 932      42.072  75.819  65.369  1.00 53.43           G
ATOM  15172  O    ASP G 932      41.074  76.311  64.831  1.00 53.43           G
ATOM  15173  N    ALA G 933      42.073  75.349  66.614  1.00 22.75           G
ATOM  15174  CA   ALA G 933      40.893  75.395  67.454  1.00 22.75           G
ATOM  15175  CB   ALA G 933      41.297  75.350  68.898  1.00 12.60           G
ATOM  15176  C    ALA G 933      40.165  76.684  67.171  1.00 22.75           G
ATOM  15177  O    ALA G 933      38.956  76.676  66.996  1.00 22.75           G
ATOM  15178  N    LEU G 934      40.927  77.780  67.100  1.00 45.10           G
ATOM  15179  CA   LEU G 934      40.403  79.126  66.848  1.00 45.10           G
ATOM  15180  CB   LEU G 934      41.485  80.172  67.078  1.00 14.64           G
ATOM  15181  CG   LEU G 934      41.968  80.342  68.516  1.00 14.64           G
ATOM  15182  CD1  LEU G 934      43.095  81.362  68.574  1.00 14.64           G
ATOM  15183  CD2  LEU G 934      40.816  80.784  69.368  1.00 14.64           G
ATOM  15184  C    LEU G 934      39.798  79.375  65.477  1.00 45.10           G
ATOM  15185  O    LEU G 934      38.682  79.871  65.375  1.00 45.10           G
ATOM  15186  N    LYS G 935      40.522  79.059  64.416  1.00 40.13           G
ATOM  15187  CA   LYS G 935      39.971  79.296  63.092  1.00 40.13           G
ATOM  15188  CB   LYS G 935      40.876  78.716  62.011  1.00 64.39           G
ATOM  15189  CG   LYS G 935      40.839  77.215  61.933  1.00 64.39           G
ATOM  15190  CD   LYS G 935      40.838  76.780  60.499  1.00 64.39           G
ATOM  15191  CE   LYS G 935      40.732  75.284  60.400  1.00 64.39           G
ATOM  15192  NZ   LYS G 935      40.455  74.896  58.997  1.00 64.39           G
ATOM  15193  C    LYS G 935      38.576  78.692  62.951  1.00 40.13           G
ATOM  15194  O    LYS G 935      37.656  79.356  62.482  1.00 40.13           G
ATOM  15195  N    TYR G 936      38.409  77.439  63.360  1.00 53.66           G
ATOM  15196  CA   TYR G 936      37.106  76.798  63.246  1.00 53.66           G
ATOM  15197  CB   TYR G 936      37.117  75.442  63.948  1.00 52.88           G
ATOM  15198  CG   TYR G 936      35.804  74.667  63.921  1.00 52.88           G
ATOM  15199  CD1  TYR G 936      35.735  73.373  64.450  1.00 52.88           G
ATOM  15200  CE1  TYR G 936      34.535  72.653  64.468  1.00 52.88           G
ATOM  15201  CD2  TYR G 936      34.634  75.220  63.408  1.00 52.88           G
ATOM  15202  CE2  TYR G 936      33.432  74.509  63.426  1.00 52.88           G
ATOM  15203  CZ   TYR G 936      33.391  73.231  63.955  1.00 52.88           G
ATOM  15204  OH   TYR G 936      32.210  72.528  63.975  1.00 52.88           G
ATOM  15205  C    TYR G 936      36.028  77.684  63.846  1.00 53.66           G
ATOM  15206  O    TYR G 936      35.275  78.339  63.114  1.00 53.66           G
ATOM  15207  N    TYR G 937      35.952  77.704  65.175  1.00 79.97           G
ATOM  15208  CA   TYR G 937      34.948  78.511  65.855  1.00 79.97           G
ATOM  15209  CB   TYR G 937      35.297  78.656  67.337  1.00 58.88           G
ATOM  15210  CG   TYR G 937      35.137  77.356  68.078  1.00 58.88           G
ATOM  15211  CD1  TYR G 937      35.983  76.282  67.812  1.00 58.88           G
ATOM  15212  CE1  TYR G 937      35.814  75.042  68.444  1.00 58.88           G
ATOM  15213  CD2  TYR G 937      34.110  77.171  68.999  1.00 58.88           G
ATOM  15214  CE2  TYR G 937      33.927  75.936  69.640  1.00 58.88           G
ATOM  15215  CZ   TYR G 937      34.787  74.875  69.354  1.00 58.88           G
ATOM  15216  OH   TYR G 937      34.642  73.650  69.968  1.00 58.88           G
ATOM  15217  C    TYR G 937      34.828  79.871  65.187  1.00 79.97           G
ATOM  15218  O    TYR G 937      33.725  80.382  64.967  1.00 79.97           G
ATOM  15219  N    GLY G 938      35.973  80.443  64.839  1.00 60.21           G
ATOM  15220  CA   GLY G 938      35.968  81.729  64.177  1.00 60.21           G
ATOM  15221  C    GLY G 938      35.047  81.722  62.974  1.00 60.21           G
ATOM  15222  O    GLY G 938      34.048  82.439  62.948  1.00 60.21           G
ATOM  15223  N    PHE G 939      35.355  80.896  61.981  1.00 22.71           G
ATOM  15224  CA   PHE G 939      34.525  80.871  60.785  1.00 22.71           G
ATOM  15225  CB   PHE G 939      35.062  79.868  59.746  1.00 18.06           G
ATOM  15226  CG   PHE G 939      36.390  80.246  59.161  1.00 18.06           G
ATOM  15227  CD1  PHE G 939      37.567  79.921  59.810  1.00 18.06           G
ATOM  15228  CD2  PHE G 939      36.458  80.922  57.963  1.00 18.06           G
ATOM  15229  CE1  PHE G 939      38.784  80.272  59.281  1.00 18.06           G
ATOM  15230  CE2  PHE G 939      37.664  81.276  57.430  1.00 18.06           G
ATOM  15231  CZ   PHE G 939      38.832  80.947  58.086  1.00 18.06           G
ATOM  15232  C    PHE G 939      33.061  80.556  61.075  1.00 22.71           G
ATOM  15233  O    PHE G 939      32.180  81.354  60.726  1.00 22.71           G
ATOM  15234  N    THR G 940      32.811  79.403  61.705  1.00 35.31           G
ATOM  15235  CA   THR G 940      31.452  78.956  62.031  1.00 35.31           G
ATOM  15236  CB   THR G 940      31.456  77.814  63.039  1.00 78.82           G
ATOM  15237  OG1  THR G 940      32.338  76.790  62.585  1.00 78.82           G
ATOM  15238  CG2  THR G 940      30.050  77.241  63.201  1.00 78.82           G
ATOM  15239  C    THR G 940      30.625  80.062  62.652  1.00 35.31           G
ATOM  15240  O    THR G 940      29.586  80.471  62.107  1.00 35.31           G
ATOM  15241  N    LEU G 941      31.090  80.505  63.820  1.00 73.58           G
ATOM  15242  CA   LEU G 941      30.459  81.576  64.574  1.00 73.58           G
ATOM  15243  CB   LEU G 941      31.392  82.061  65.672  1.00 25.16           G
ATOM  15244  CG   LEU G 941      31.250  81.452  67.062  1.00 25.16           G
ATOM  15245  CD1  LEU G 941      29.776  81.350  67.372  1.00 25.16           G
ATOM  15246  CD2  LEU G 941      31.904  80.101  67.142  1.00 25.16           G
ATOM  15247  C    LEU G 941      30.190  82.725  63.631  1.00 73.58           G
ATOM  15248  O    LEU G 941      29.045  83.129  63.422  1.00 73.58           G
ATOM  15249  N    SER G 942      31.274  83.254  63.082  1.00 23.90           G
ATOM  15250  CA   SER G 942      31.213  84.341  62.137  1.00 23.90           G
```

| | | | | | | | | | |
|---|---|---|---|---|---|---|---|---|---|
| ATOM | 15251 | CB | SER G 942 | 32.423 | 84.280 | 61.226 | 1.00 | 9.16 | G |
| ATOM | 15252 | OG | SER G 942 | 32.145 | 85.004 | 60.053 | 1.00 | 9.16 | G |
| ATOM | 15253 | C | SER G 942 | 29.957 | 84.256 | 61.286 | 1.00 | 23.90 | G |
| ATOM | 15254 | O | SER G 942 | 29.270 | 85.257 | 61.076 | 1.00 | 23.90 | G |
| ATOM | 15255 | N | THR G 943 | 29.669 | 83.049 | 60.799 | 1.00 | 44.02 | G |
| ATOM | 15256 | CA | THR G 943 | 28.506 | 82.791 | 59.942 | 1.00 | 44.02 | G |
| ATOM | 15257 | CB | THR G 943 | 28.489 | 81.341 | 59.420 | 1.00 | 26.04 | G |
| ATOM | 15258 | OG1 | THR G 943 | 29.828 | 80.886 | 59.195 | 1.00 | 26.04 | G |
| ATOM | 15259 | CG2 | THR G 943 | 27.722 | 81.270 | 58.120 | 1.00 | 26.04 | G |
| ATOM | 15260 | C | THR G 943 | 27.185 | 83.001 | 60.665 | 1.00 | 44.02 | G |
| ATOM | 15261 | O | THR G 943 | 26.441 | 83.932 | 60.358 | 1.00 | 44.02 | G |
| ATOM | 15262 | N | THR G 944 | 26.913 | 82.103 | 61.612 | 1.00 | 36.28 | G |
| ATOM | 15263 | CA | THR G 944 | 25.700 | 82.094 | 62.430 | 1.00 | 36.28 | G |
| ATOM | 15264 | CB | THR G 944 | 25.942 | 81.356 | 63.735 | 1.00 | 19.29 | G |
| ATOM | 15265 | OG1 | THR G 944 | 27.162 | 80.621 | 63.625 | 1.00 | 19.29 | G |
| ATOM | 15266 | CG2 | THR G 944 | 24.817 | 80.386 | 64.017 | 1.00 | 19.29 | G |
| ATOM | 15267 | C | THR G 944 | 25.205 | 83.475 | 62.788 | 1.00 | 36.28 | G |
| ATOM | 15268 | O | THR G 944 | 24.009 | 83.763 | 62.693 | 1.00 | 36.28 | G |
| ATOM | 15269 | N | SER G 945 | 26.124 | 84.328 | 63.216 | 1.00 | 25.97 | G |
| ATOM | 15270 | CA | SER G 945 | 25.752 | 85.682 | 63.592 | 1.00 | 25.97 | G |
| ATOM | 15271 | CB | SER G 945 | 26.934 | 86.379 | 64.278 | 1.00 | 73.26 | G |
| ATOM | 15272 | OG | SER G 945 | 27.170 | 85.825 | 65.565 | 1.00 | 73.26 | G |
| ATOM | 15273 | C | SER G 945 | 25.240 | 86.510 | 62.409 | 1.00 | 25.97 | G |
| ATOM | 15274 | O | SER G 945 | 24.060 | 86.843 | 62.345 | 1.00 | 25.97 | G |
| ATOM | 15275 | N | GLY G 946 | 26.112 | 86.828 | 61.462 | 1.00 | 46.19 | G |
| ATOM | 15276 | CA | GLY G 946 | 25.679 | 87.625 | 60.330 | 1.00 | 46.19 | G |
| ATOM | 15277 | C | GLY G 946 | 26.517 | 88.879 | 60.201 | 1.00 | 46.19 | G |
| ATOM | 15278 | O | GLY G 946 | 27.158 | 89.339 | 61.145 | 1.00 | 46.19 | G |
| ATOM | 15279 | N | ILE G 947 | 26.519 | 89.431 | 59.006 | 1.00 | 21.23 | G |
| ATOM | 15280 | CA | ILE G 947 | 27.273 | 90.632 | 58.712 | 1.00 | 21.23 | G |
| ATOM | 15281 | CB | ILE G 947 | 28.714 | 90.268 | 58.350 | 1.00 | 100.07 | G |
| ATOM | 15282 | CG2 | ILE G 947 | 29.392 | 91.440 | 57.678 | 1.00 | 100.07 | G |
| ATOM | 15283 | CG1 | ILE G 947 | 29.451 | 89.773 | 59.604 | 1.00 | 100.07 | G |
| ATOM | 15284 | CD | ILE G 947 | 29.439 | 90.735 | 60.789 | 1.00 | 100.07 | G |
| ATOM | 15285 | C | ILE G 947 | 26.529 | 91.158 | 57.501 | 1.00 | 21.23 | G |
| ATOM | 15286 | O | ILE G 947 | 25.935 | 90.364 | 56.797 | 1.00 | 21.23 | G |
| ATOM | 15287 | N | ILE G 948 | 26.520 | 92.456 | 57.228 | 1.00 | 20.15 | G |
| ATOM | 15288 | CA | ILE G 948 | 25.756 | 92.875 | 56.059 | 1.00 | 20.15 | G |
| ATOM | 15289 | CB | ILE G 948 | 24.259 | 92.923 | 56.375 | 1.00 | 82.40 | G |
| ATOM | 15290 | CG2 | ILE G 948 | 23.604 | 91.690 | 55.848 | 1.00 | 82.40 | G |
| ATOM | 15291 | CG1 | ILE G 948 | 24.045 | 93.126 | 57.881 | 1.00 | 82.40 | G |
| ATOM | 15292 | CD | ILE G 948 | 22.604 | 93.418 | 58.294 | 1.00 | 82.40 | G |
| ATOM | 15293 | C | ILE G 948 | 26.082 | 94.186 | 55.377 | 1.00 | 20.15 | G |
| ATOM | 15294 | O | ILE G 948 | 25.354 | 94.588 | 54.465 | 1.00 | 20.15 | G |
| ATOM | 15295 | N | THR G 949 | 27.154 | 94.851 | 55.790 | 1.00 | 17.57 | G |
| ATOM | 15296 | CA | THR G 949 | 27.483 | 96.137 | 55.199 | 1.00 | 17.57 | G |
| ATOM | 15297 | CB | THR G 949 | 28.791 | 96.048 | 54.445 | 1.00 | 22.46 | G |
| ATOM | 15298 | OG1 | THR G 949 | 29.784 | 95.482 | 55.309 | 1.00 | 22.46 | G |
| ATOM | 15299 | CG2 | THR G 949 | 29.243 | 97.433 | 54.029 | 1.00 | 22.46 | G |
| ATOM | 15300 | C | THR G 949 | 26.335 | 96.588 | 54.283 | 1.00 | 17.57 | G |
| ATOM | 15301 | O | THR G 949 | 26.424 | 96.542 | 53.048 | 1.00 | 17.57 | G |
| ATOM | 15302 | N | ILE G 950 | 25.238 | 96.984 | 54.930 | 1.00 | 37.62 | G |
| ATOM | 15303 | CA | ILE G 950 | 24.018 | 97.425 | 54.257 | 1.00 | 37.62 | G |
| ATOM | 15304 | CB | ILE G 950 | 22.784 | 97.348 | 55.217 | 1.00 | 100.07 | G |
| ATOM | 15305 | CG2 | ILE G 950 | 21.613 | 98.122 | 54.644 | 1.00 | 100.07 | G |
| ATOM | 15306 | CG1 | ILE G 950 | 22.406 | 95.891 | 55.496 | 1.00 | 100.07 | G |
| ATOM | 15307 | CD | ILE G 950 | 21.014 | 95.699 | 56.090 | 1.00 | 100.07 | G |
| ATOM | 15308 | C | ILE G 950 | 24.083 | 98.854 | 53.726 | 1.00 | 37.62 | G |
| ATOM | 15309 | O | ILE G 950 | 24.836 | 99.681 | 54.240 | 1.00 | 37.62 | G |
| ATOM | 15310 | N | GLY G 951 | 23.271 | 99.142 | 52.709 | 1.00 | 29.39 | G |
| ATOM | 15311 | CA | GLY G 951 | 23.231 | 100.478 | 52.154 | 1.00 | 29.39 | G |
| ATOM | 15312 | C | GLY G 951 | 23.311 | 101.364 | 53.356 | 1.00 | 29.39 | G |
| ATOM | 15313 | O | GLY G 951 | 23.989 | 102.388 | 53.329 | 1.00 | 29.39 | G |
| ATOM | 15314 | N | ILE G 952 | 22.644 | 100.914 | 54.423 | 1.00 | 55.50 | G |
| ATOM | 15315 | CA | ILE G 952 | 22.588 | 101.618 | 55.701 | 1.00 | 55.50 | G |
| ATOM | 15316 | CB | ILE G 952 | 21.127 | 101.746 | 56.244 | 1.00 | 70.06 | G |
| ATOM | 15317 | CG2 | ILE G 952 | 21.077 | 102.844 | 57.304 | 1.00 | 70.06 | G |
| ATOM | 15318 | CG1 | ILE G 952 | 20.147 | 102.061 | 55.101 | 1.00 | 70.06 | G |
| ATOM | 15319 | CD | ILE G 952 | 18.874 | 102.811 | 55.523 | 1.00 | 70.06 | G |
| ATOM | 15320 | C | ILE G 952 | 23.429 | 100.957 | 56.793 | 1.00 | 55.50 | G |
| ATOM | 15321 | O | ILE G 952 | 24.374 | 101.575 | 57.269 | 1.00 | 55.50 | G |
| ATOM | 15322 | N | ASP G 953 | 23.068 | 99.726 | 57.191 | 1.00 | 66.00 | G |
| ATOM | 15323 | CA | ASP G 953 | 23.776 | 98.959 | 58.240 | 1.00 | 66.00 | G |
| ATOM | 15324 | CB | ASP G 953 | 23.793 | 97.467 | 57.915 | 1.00 | 60.15 | G |
| ATOM | 15325 | CG | ASP G 953 | 22.908 | 96.648 | 58.834 | 1.00 | 60.15 | G |
| ATOM | 15326 | OD1 | ASP G 953 | 23.361 | 96.269 | 59.940 | 1.00 | 60.15 | G |
| ATOM | 15327 | OD2 | ASP G 953 | 21.750 | 96.384 | 58.445 | 1.00 | 60.15 | G |
| ATOM | 15328 | C | ASP G 953 | 25.209 | 99.404 | 58.378 | 1.00 | 66.00 | G |
| ATOM | 15329 | O | ASP G 953 | 26.112 | 98.706 | 57.932 | 1.00 | 66.00 | G |
| ATOM | 15330 | N | ALA G 954 | 25.398 | 100.549 | 59.026 | 1.00 | 33.02 | G |
| ATOM | 15331 | CA | ALA G 954 | 26.700 | 101.176 | 59.215 | 1.00 | 33.02 | G |
| ATOM | 15332 | CB | ALA G 954 | 27.814 | 100.142 | 59.248 | 1.00 | 100.07 | G |
| ATOM | 15333 | C | ALA G 954 | 26.866 | 102.120 | 58.026 | 1.00 | 33.02 | G |
| ATOM | 15334 | O | ALA G 954 | 26.660 | 101.750 | 56.874 | 1.00 | 33.02 | G |

```
ATOM  15335  N    ALA G 955      27.229 103.351  58.343  1.00 66.89           G
ATOM  15336  CA   ALA G 955      27.407 104.457  57.404  1.00 66.89           G
ATOM  15337  CB   ALA G 955      26.561 104.266  56.149  1.00 48.39           G
ATOM  15338  C    ALA G 955      26.764 105.468  58.318  1.00 66.89           G
ATOM  15339  O    ALA G 955      27.113 106.647  58.349  1.00 66.89           G
ATOM  15340  N    VAL G 956      25.828 104.919  59.088  1.00 44.92           G
ATOM  15341  CA   VAL G 956      25.065 105.620  60.087  1.00 44.92           G
ATOM  15342  CB   VAL G 956      25.136 104.886  61.409  1.00 88.16           G
ATOM  15343  CG1  VAL G 956      24.219 105.546  62.398  1.00 88.16           G
ATOM  15344  CG2  VAL G 956      24.790 103.431  61.208  1.00 88.16           G
ATOM  15345  C    VAL G 956      25.650 106.989  60.283  1.00 44.92           G
ATOM  15346  O    VAL G 956      26.437 107.217  61.209  1.00 44.92           G
ATOM  15347  N    ILE G 957      25.274 107.899  59.398  1.00100.07           G
ATOM  15348  CA   ILE G 957      25.772 109.255  59.473  1.00100.07           G
ATOM  15349  CB   ILE G 957      25.656 109.961  58.116  1.00 72.26           G
ATOM  15350  CG2  ILE G 957      25.611 111.463  58.304  1.00 72.26           G
ATOM  15351  CG1  ILE G 957      26.847 109.573  57.246  1.00 72.26           G
ATOM  15352  CD   ILE G 957      28.179 109.852  57.901  1.00 72.26           G
ATOM  15353  C    ILE G 957      25.058 110.073  60.534  1.00100.07           G
ATOM  15354  O    ILE G 957      23.835 109.997  60.692  1.00100.07           G
ATOM  15355  N    PRO G 958      25.827 110.865  61.287  1.00 30.76           G
ATOM  15356  CD   PRO G 958      27.301 110.863  61.294  1.00 41.33           G
ATOM  15357  CA   PRO G 958      25.291 111.719  62.352  1.00 30.76           G
ATOM  15358  CB   PRO G 958      26.502 111.949  63.237  1.00 41.33           G
ATOM  15359  CG   PRO G 958      27.620 112.022  62.204  1.00 41.33           G
ATOM  15360  C    PRO G 958      24.739 113.028  61.802  1.00 30.76           G
ATOM  15361  O    PRO G 958      25.352 113.644  60.925  1.00 30.76           G
ATOM  15362  N    GLU G 959      23.583 113.452  62.310  1.00 66.33           G
ATOM  15363  CA   GLU G 959      22.996 114.710  61.865  1.00 66.33           G
ATOM  15364  CB   GLU G 959      21.893 115.172  62.824  1.00 83.69           G
ATOM  15365  CG   GLU G 959      20.767 114.172  63.094  1.00 83.69           G
ATOM  15366  CD   GLU G 959      19.574 114.326  62.159  1.00 83.69           G
ATOM  15367  OE1  GLU G 959      19.132 115.470  61.907  1.00 83.69           G
ATOM  15368  OE2  GLU G 959      19.062 113.290  61.691  1.00 83.69           G
ATOM  15369  C    GLU G 959      24.165 115.682  61.950  1.00 66.33           G
ATOM  15370  O    GLU G 959      24.290 116.612  61.147  1.00 66.33           G
ATOM  15371  N    GLU G 960      25.030 115.418  62.932  1.00 44.62           G
ATOM  15372  CA   GLU G 960      26.213 116.225  63.206  1.00 44.62           G
ATOM  15373  CB   GLU G 960      27.166 115.471  64.120  1.00 41.47           G
ATOM  15374  CG   GLU G 960      26.551 115.152  65.456  1.00 41.47           G
ATOM  15375  CD   GLU G 960      27.587 114.720  66.454  1.00 41.47           G
ATOM  15376  OE1  GLU G 960      28.651 115.366  66.468  1.00 41.47           G
ATOM  15377  OE2  GLU G 960      27.348 113.756  67.224  1.00 41.47           G
ATOM  15378  C    GLU G 960      26.964 116.706  61.989  1.00 44.62           G
ATOM  15379  O    GLU G 960      27.533 117.794  62.014  1.00 44.62           G
ATOM  15380  N    LYS G 961      26.981 115.913  60.922  1.00 61.28           G
ATOM  15381  CA   LYS G 961      27.679 116.365  59.730  1.00 61.28           G
ATOM  15382  CB   LYS G 961      27.333 115.517  58.505  1.00100.07           G
ATOM  15383  CG   LYS G 961      28.207 115.854  57.298  1.00100.07           G
ATOM  15384  CD   LYS G 961      27.824 115.079  56.045  1.00100.07           G
ATOM  15385  CE   LYS G 961      28.768 115.401  54.889  1.00100.07           G
ATOM  15386  NZ   LYS G 961      28.351 114.749  53.617  1.00100.07           G
ATOM  15387  C    LYS G 961      27.187 117.787  59.524  1.00 61.28           G
ATOM  15388  O    LYS G 961      27.934 118.661  59.104  1.00 61.28           G
ATOM  15389  N    GLN G 962      25.923 118.015  59.857  1.00 40.61           G
ATOM  15390  CA   GLN G 962      25.352 119.334  59.726  1.00 40.61           G
ATOM  15391  CB   GLN G 962      23.860 119.289  60.019  1.00 82.10           G
ATOM  15392  CG   GLN G 962      23.047 118.931  58.791  1.00 82.10           G
ATOM  15393  CD   GLN G 962      21.593 118.692  59.117  1.00 82.10           G
ATOM  15394  OE1  GLN G 962      21.023 119.360  59.981  1.00 82.10           G
ATOM  15395  NE2  GLN G 962      20.976 117.743  58.422  1.00 82.10           G
ATOM  15396  C    GLN G 962      26.066 120.324  60.636  1.00 40.61           G
ATOM  15397  O    GLN G 962      26.977 121.001  60.181  1.00 40.61           G
ATOM  15398  N    ARG G 963      25.672 120.414  61.907  1.00 99.81           G
ATOM  15399  CA   ARG G 963      26.314 121.351  62.845  1.00 99.81           G
ATOM  15400  CB   ARG G 963      26.111 120.869  64.311  1.00 54.04           G
ATOM  15401  CG   ARG G 963      27.109 121.385  65.386  1.00 54.04           G
ATOM  15402  CD   ARG G 963      27.015 120.551  66.704  1.00 54.04           G
ATOM  15403  NE   ARG G 963      28.264 120.514  67.491  1.00 54.04           G
ATOM  15404  CZ   ARG G 963      28.413 119.893  68.669  1.00 54.04           G
ATOM  15405  NH1  ARG G 963      27.388 119.254  69.209  1.00 54.04           G
ATOM  15406  NH2  ARG G 963      29.586 119.902  69.307  1.00 54.04           G
ATOM  15407  C    ARG G 963      27.806 121.557  62.514  1.00 99.81           G
ATOM  15408  O    ARG G 963      28.276 122.695  62.493  1.00 99.81           G
ATOM  15409  N    TYR G 964      28.536 120.474  62.223  1.00 59.83           G
ATOM  15410  CA   TYR G 964      29.965 120.576  61.895  1.00 59.83           G
ATOM  15411  CB   TYR G 964      30.638 119.204  61.920  1.00 96.05           G
ATOM  15412  CG   TYR G 964      30.789 118.613  63.306  1.00 96.05           G
ATOM  15413  CD1  TYR G 964      29.684 118.133  64.006  1.00 96.05           G
ATOM  15414  CE1  TYR G 964      29.822 117.572  65.261  1.00 96.05           G
ATOM  15415  CD2  TYR G 964      32.042 118.517  63.908  1.00 96.05           G
ATOM  15416  CE2  TYR G 964      32.190 117.957  65.164  1.00 96.05           G
ATOM  15417  CZ   TYR G 964      31.077 117.483  65.836  1.00 96.05           G
ATOM  15418  OH   TYR G 964      31.223 116.901  67.077  1.00 96.05           G
```

```
ATOM  15419  C   TYR G 964      30.135 121.210  60.527  1.00 59.83           G
ATOM  15420  O   TYR G 964      31.088 121.950  60.277  1.00 59.83           G
ATOM  15421  N   LEU G 965      29.219 120.877  59.629  1.00 67.15           G
ATOM  15422  CA  LEU G 965      29.207 121.483  58.314  1.00 67.15           G
ATOM  15423  CB  LEU G 965      28.290 120.715  57.366  1.00 37.73           G
ATOM  15424  CG  LEU G 965      28.954 119.741  56.395  1.00 37.73           G
ATOM  15425  CD1 LEU G 965      29.579 120.523  55.269  1.00 37.73           G
ATOM  15426  CD2 LEU G 965      30.002 118.901  57.109  1.00 37.73           G
ATOM  15427  C   LEU G 965      28.565 122.800  58.691  1.00 67.15           G
ATOM  15428  O   LEU G 965      28.130 122.960  59.833  1.00 67.15           G
ATOM  15429  N   GLU G 966      28.482 123.738  57.762  1.00 60.94           G
ATOM  15430  CA  GLU G 966      27.886 125.020  58.090  1.00 60.94           G
ATOM  15431  CB  GLU G 966      26.510 124.837  58.729  1.00 84.32           G
ATOM  15432  CG  GLU G 966      25.885 126.154  59.055  1.00 84.32           G
ATOM  15433  CD  GLU G 966      26.086 127.143  57.928  1.00 84.32           G
ATOM  15434  OE1 GLU G 966      25.421 126.998  56.884  1.00 84.32           G
ATOM  15435  OE2 GLU G 966      26.925 128.052  58.076  1.00 84.32           G
ATOM  15436  C   GLU G 966      28.812 125.758  59.045  1.00 60.94           G
ATOM  15437  O   GLU G 966      29.256 126.850  58.734  1.00 60.94           G
ATOM  15438  N   GLU G 967      29.091 125.188  60.217  1.00 53.77           G
ATOM  15439  CA  GLU G 967      30.026 125.844  61.123  1.00 53.77           G
ATOM  15440  CB  GLU G 967      30.360 124.982  62.338  1.00 91.99           G
ATOM  15441  CG  GLU G 967      29.328 125.037  63.442  1.00 91.99           G
ATOM  15442  CD  GLU G 967      29.883 124.556  64.764  1.00 91.99           G
ATOM  15443  OE1 GLU G 967      30.588 123.528  64.768  1.00 91.99           G
ATOM  15444  OE2 GLU G 967      29.613 125.200  65.800  1.00 91.99           G
ATOM  15445  C   GLU G 967      31.234 125.937  60.226  1.00 53.77           G
ATOM  15446  O   GLU G 967      31.886 126.975  60.116  1.00 53.77           G
ATOM  15447  N   ALA G 968      31.518 124.829  59.564  1.00 42.86           G
ATOM  15448  CA  ALA G 968      32.615 124.819  58.634  1.00 42.86           G
ATOM  15449  CB  ALA G 968      32.560 123.564  57.780  1.00100.07           G
ATOM  15450  C   ALA G 968      32.319 126.061  57.796  1.00 42.86           G
ATOM  15451  O   ALA G 968      33.150 126.964  57.691  1.00 42.86           G
ATOM  15452  N   ASP G 969      31.111 126.108  57.238  1.00 60.16           G
ATOM  15453  CA  ASP G 969      30.682 127.242  56.426  1.00 60.16           G
ATOM  15454  CB  ASP G 969      29.268 127.017  55.886  1.00100.07           G
ATOM  15455  CG  ASP G 969      29.192 125.866  54.908  1.00100.07           G
ATOM  15456  OD1 ASP G 969      29.842 125.939  53.841  1.00100.07           G
ATOM  15457  OD2 ASP G 969      28.476 124.888  55.206  1.00100.07           G
ATOM  15458  C   ASP G 969      30.703 128.524  57.253  1.00 60.16           G
ATOM  15459  O   ASP G 969      31.718 128.838  57.867  1.00 60.16           G
ATOM  15460  N   ARG G 970      29.565 129.229  57.281  1.00 66.13           G
ATOM  15461  CA  ARG G 970      29.389 130.505  57.998  1.00 66.13           G
ATOM  15462  CB  ARG G 970      28.495 130.340  59.247  1.00100.07           G
ATOM  15463  CG  ARG G 970      29.156 129.686  60.461  1.00100.07           G
ATOM  15464  CD  ARG G 970      28.290 129.738  61.734  1.00100.07           G
ATOM  15465  NE  ARG G 970      29.079 129.408  62.924  1.00100.07           G
ATOM  15466  CZ  ARG G 970      28.574 129.218  64.136  1.00100.07           G
ATOM  15467  NH1 ARG G 970      27.269 129.319  64.336  1.00100.07           G
ATOM  15468  NH2 ARG G 970      29.377 128.928  65.151  1.00100.07           G
ATOM  15469  C   ARG G 970      30.716 131.138  58.374  1.00 66.13           G
ATOM  15470  O   ARG G 970      31.054 132.200  57.855  1.00 66.13           G
ATOM  15471  N   LYS G 971      31.466 130.488  59.263  1.00 35.90           G
ATOM  15472  CA  LYS G 971      32.777 130.973  59.666  1.00 35.90           G
ATOM  15473  CB  LYS G 971      33.341 130.134  60.812  1.00 88.31           G
ATOM  15474  CG  LYS G 971      32.571 130.325  62.110  1.00 88.31           G
ATOM  15475  CD  LYS G 971      33.108 129.475  63.253  1.00 88.31           G
ATOM  15476  CE  LYS G 971      32.252 129.658  64.495  1.00 88.31           G
ATOM  15477  NZ  LYS G 971      32.805 128.925  65.659  1.00 88.31           G
ATOM  15478  C   LYS G 971      33.671 130.866  58.438  1.00 35.90           G
ATOM  15479  O   LYS G 971      34.901 130.803  58.554  1.00 35.90           G
ATOM  15480  N   LEU G 972      33.015 130.839  57.269  1.00 52.38           G
ATOM  15481  CA  LEU G 972      33.636 130.763  55.944  1.00 52.38           G
ATOM  15482  CB  LEU G 972      32.990 129.654  55.100  1.00 78.81           G
ATOM  15483  CG  LEU G 972      33.806 128.378  54.844  1.00 78.81           G
ATOM  15484  CD1 LEU G 972      32.920 127.316  54.222  1.00 78.81           G
ATOM  15485  CD2 LEU G 972      34.992 128.688  53.930  1.00 78.81           G
ATOM  15486  C   LEU G 972      33.397 132.108  55.281  1.00 52.38           G
ATOM  15487  O   LEU G 972      34.309 132.710  54.727  1.00 52.38           G
ATOM  15488  N   ARG G 973      32.151 132.565  55.331  1.00 30.63           G
ATOM  15489  CA  ARG G 973      31.800 133.863  54.776  1.00 30.63           G
ATOM  15490  CB  ARG G 973      30.288 134.083  54.794  1.00100.07           G
ATOM  15491  CG  ARG G 973      29.478 133.043  54.042  1.00100.07           G
ATOM  15492  CD  ARG G 973      28.040 133.524  53.852  1.00100.07           G
ATOM  15493  NE  ARG G 973      27.192 132.529  53.194  1.00100.07           G
ATOM  15494  CZ  ARG G 973      26.032 132.802  52.598  1.00100.07           G
ATOM  15495  NH1 ARG G 973      25.574 134.047  52.567  1.00100.07           G
ATOM  15496  NH2 ARG G 973      25.322 131.827  52.039  1.00100.07           G
ATOM  15497  C   ARG G 973      32.464 134.843  55.728  1.00 30.63           G
ATOM  15498  O   ARG G 973      32.840 135.946  55.343  1.00 30.63           G
ATOM  15499  N   GLN G 974      32.599 134.431  56.987  1.00 51.16           G
ATOM  15500  CA  GLN G 974      33.260 135.268  57.985  1.00 51.16           G
ATOM  15501  CB  GLN G 974      33.129 134.678  59.408  1.00 99.53           G
ATOM  15502  CG  GLN G 974      31.688 134.496  59.927  1.00 99.53           G
```

```
ATOM  15503  CD   GLN G 974      31.607 134.163 61.424  1.00 99.53      G
ATOM  15504  OE1  GLN G 974      32.313 133.287 61.928  1.00 99.53      G
ATOM  15505  NE2  GLN G 974      30.727 134.859 62.129  1.00 99.53      G
ATOM  15506  C    GLN G 974      34.735 135.321 57.580  1.00 51.16      G
ATOM  15507  O    GLN G 974      35.537 136.038 58.188  1.00 51.16      G
ATOM  15508  N    ILE G 975      35.076 134.532 56.559  1.00 73.80      G
ATOM  15509  CA   ILE G 975      36.431 134.480 56.018  1.00 73.80      G
ATOM  15510  CB   ILE G 975      36.876 133.048 55.639  1.00 69.60      G
ATOM  15511  CG2  ILE G 975      38.374 133.046 55.334  1.00 69.60      G
ATOM  15512  CG1  ILE G 975      36.519 132.062 56.750  1.00 69.60      G
ATOM  15513  CD   ILE G 975      37.703 131.415 57.428  1.00 69.60      G
ATOM  15514  C    ILE G 975      36.376 135.271 54.723  1.00 73.80      G
ATOM  15515  O    ILE G 975      37.146 136.202 54.515  1.00 73.80      G
ATOM  15516  N    GLU G 976      35.450 134.879 53.855  1.00100.07      G
ATOM  15517  CA   GLU G 976      35.260 135.533 52.564  1.00100.07      G
ATOM  15518  CB   GLU G 976      34.044 134.926 51.846  1.00100.07      G
ATOM  15519  CG   GLU G 976      34.101 133.401 51.687  1.00100.07      G
ATOM  15520  CD   GLU G 976      34.875 132.942 50.454  1.00100.07      G
ATOM  15521  OE1  GLU G 976      34.250 132.805 49.378  1.00100.07      G
ATOM  15522  OE2  GLU G 976      36.103 132.723 50.561  1.00100.07      G
ATOM  15523  C    GLU G 976      35.046 137.032 52.777  1.00100.07      G
ATOM  15524  O    GLU G 976      35.492 137.856 51.973  1.00100.07      G
ATOM  15525  N    GLN G 977      34.358 137.374 53.865  1.00 83.23      G
ATOM  15526  CA   GLN G 977      34.090 138.767 54.187  1.00 83.23      G
ATOM  15527  CB   GLN G 977      32.725 138.920 54.863  1.00100.07      G
ATOM  15528  CG   GLN G 977      31.546 138.556 53.958  1.00100.07      G
ATOM  15529  CD   GLN G 977      30.210 139.054 54.490  1.00100.07      G
ATOM  15530  OE1  GLN G 977      29.901 140.247 54.414  1.00100.07      G
ATOM  15531  NE2  GLN G 977      29.415 138.141 55.041  1.00100.07      G
ATOM  15532  C    GLN G 977      35.190 139.304 55.084  1.00 83.23      G
ATOM  15533  O    GLN G 977      35.227 140.495 55.389  1.00 83.23      G
ATOM  15534  N    ALA G 978      36.081 138.412 55.509  1.00 32.65      G
ATOM  15535  CA   ALA G 978      37.218 138.798 56.343  1.00 32.65      G
ATOM  15536  CB   ALA G 978      37.604 137.656 57.273  1.00100.07      G
ATOM  15537  C    ALA G 978      38.377 139.129 55.390  1.00 32.65      G
ATOM  15538  O    ALA G 978      39.435 139.601 55.807  1.00 32.65      G
ATOM  15539  N    ALA G 979      38.170 138.850 54.107  1.00 95.90      G
ATOM  15540  CA   ALA G 979      39.175 139.143 53.099  1.00 95.90      G
ATOM  15541  CB   ALA G 979      39.123 138.128 51.968  1.00100.07      G
ATOM  15542  C    ALA G 979      38.827 140.526 52.586  1.00 95.90      G
ATOM  15543  O    ALA G 979      39.700 141.376 52.422  1.00 95.90      G
ATOM  15544  N    GLU G 980      37.538 140.741 52.333  1.00100.05      G
ATOM  15545  CA   GLU G 980      37.050 142.033 51.870  1.00100.05      G
ATOM  15546  CB   GLU G 980      35.573 141.924 51.468  1.00 99.45      G
ATOM  15547  CG   GLU G 980      35.306 140.904 50.353  1.00 99.45      G
ATOM  15548  CD   GLU G 980      33.822 140.758 49.996  1.00 99.45      G
ATOM  15549  OE1  GLU G 980      33.045 140.253 50.839  1.00 99.45      G
ATOM  15550  OE2  GLU G 980      33.433 141.149 48.868  1.00 99.45      G
ATOM  15551  C    GLU G 980      37.225 142.964 53.071  1.00100.05      G
ATOM  15552  O    GLU G 980      36.253 143.369 53.712  1.00100.05      G
ATOM  15553  N    MET G 981      38.489 143.270 53.365  1.00 71.76      G
ATOM  15554  CA   MET G 981      38.909 144.114 54.484  1.00 71.76      G
ATOM  15555  CB   MET G 981      38.143 143.754 55.758  1.00 45.47      G
ATOM  15556  CG   MET G 981      37.002 144.675 56.121  1.00 45.47      G
ATOM  15557  SD   MET G 981      35.923 143.864 57.316  1.00 45.47      G
ATOM  15558  CE   MET G 981      34.615 143.305 56.204  1.00 45.47      G
ATOM  15559  C    MET G 981      40.383 143.803 54.710  1.00 71.76      G
ATOM  15560  O    MET G 981      41.166 143.726 53.762  1.00 71.76      G
ATOM  15561  N    GLY G 982      40.746 143.606 55.971  1.00 75.90      G
ATOM  15562  CA   GLY G 982      42.119 143.287 56.306  1.00 75.90      G
ATOM  15563  C    GLY G 982      42.354 141.798 56.158  1.00 75.90      G
ATOM  15564  O    GLY G 982      42.964 141.167 57.029  1.00 75.90      G
ATOM  15565  N    ALA G 983      41.855 141.252 55.046  1.00100.07      G
ATOM  15566  CA   ALA G 983      41.964 139.830 54.702  1.00100.07      G
ATOM  15567  CB   ALA G 983      42.307 139.665 53.204  1.00 32.44      G
ATOM  15568  C    ALA G 983      43.003 139.113 55.533  1.00100.07      G
ATOM  15569  O    ALA G 983      42.671 138.387 56.470  1.00100.07      G
ATOM  15570  N    LEU G 984      44.256 139.343 55.152  1.00 83.75      G
ATOM  15571  CA   LEU G 984      45.453 138.777 55.764  1.00 83.75      G
ATOM  15572  CB   LEU G 984      45.126 137.645 56.745  1.00100.07      G
ATOM  15573  CG   LEU G 984      44.647 138.015 58.151  1.00100.07      G
ATOM  15574  CD1  LEU G 984      44.551 136.742 58.987  1.00100.07      G
ATOM  15575  CD2  LEU G 984      45.608 139.012 58.796  1.00100.07      G
ATOM  15576  C    LEU G 984      46.338 138.225 54.654  1.00 83.75      G
ATOM  15577  O    LEU G 984      47.294 137.492 54.923  1.00 83.75      G
ATOM  15578  N    THR G 985      46.010 138.586 53.413  1.00 74.79      G
ATOM  15579  CA   THR G 985      46.743 138.135 52.231  1.00 74.79      G
ATOM  15580  CB   THR G 985      48.236 137.839 52.512  1.00 50.42      G
ATOM  15581  OG1  THR G 985      48.754 138.751 53.489  1.00 50.42      G
ATOM  15582  CG2  THR G 985      49.043 137.944 51.211  1.00 50.42      G
ATOM  15583  C    THR G 985      46.154 136.822 51.741  1.00 74.79      G
ATOM  15584  O    THR G 985      45.797 135.953 52.542  1.00 74.79      G
ATOM  15585  N    ASP G 986      46.073 136.663 50.427  1.00 99.98      G
ATOM  15586  CA   ASP G 986      45.546 135.429 49.860  1.00 99.98      G
```

```
ATOM  15587  CB   ASP G 986      45.780 135.417  48.340  1.00 70.09           G
ATOM  15588  CG   ASP G 986      44.960 134.362  47.623  1.00 70.09           G
ATOM  15589  OD1  ASP G 986      43.716 134.381  47.743  1.00 70.09           G
ATOM  15590  OD2  ASP G 986      45.564 133.518  46.928  1.00 70.09           G
ATOM  15591  C    ASP G 986      46.287 134.273  50.551  1.00 99.98           G
ATOM  15592  O    ASP G 986      45.659 133.376  51.113  1.00 99.98           G
ATOM  15593  N    ARG G 987      47.620 134.333  50.533  1.00 78.96           G
ATOM  15594  CA   ARG G 987      48.476 133.318  51.150  1.00 78.96           G
ATOM  15595  CB   ARG G 987      49.862 133.885  51.463  1.00100.07           G
ATOM  15596  CG   ARG G 987      50.903 133.739  50.375  1.00100.07           G
ATOM  15597  CD   ARG G 987      52.304 133.890  50.976  1.00100.07           G
ATOM  15598  NE   ARG G 987      53.366 133.604  50.014  1.00100.07           G
ATOM  15599  CZ   ARG G 987      54.645 133.435  50.339  1.00100.07           G
ATOM  15600  NH1  ARG G 987      55.033 133.522  51.604  1.00100.07           G
ATOM  15601  NH2  ARG G 987      55.541 133.173  49.398  1.00100.07           G
ATOM  15602  C    ARG G 987      47.929 132.757  52.445  1.00 78.96           G
ATOM  15603  O    ARG G 987      47.896 131.542  52.639  1.00 78.96           G
ATOM  15604  N    GLU G 988      47.520 133.652  53.339  1.00 41.85           G
ATOM  15605  CA   GLU G 988      47.013 133.241  54.639  1.00 41.85           G
ATOM  15606  CB   GLU G 988      47.095 134.407  55.617  1.00100.07           G
ATOM  15607  CG   GLU G 988      48.452 135.095  55.588  1.00100.07           G
ATOM  15608  CD   GLU G 988      49.597 134.125  55.316  1.00100.07           G
ATOM  15609  OE1  GLU G 988      49.717 133.122  56.055  1.00100.07           G
ATOM  15610  OE2  GLU G 988      50.375 134.368  54.364  1.00100.07           G
ATOM  15611  C    GLU G 988      45.598 132.724  54.541  1.00 41.85           G
ATOM  15612  O    GLU G 988      45.237 131.746  55.198  1.00 41.85           G
ATOM  15613  N    ARG G 989      44.803 133.374  53.700  1.00 56.58           G
ATOM  15614  CA   ARG G 989      43.423 132.964  53.505  1.00 56.58           G
ATOM  15615  CB   ARG G 989      42.772 133.839  52.442  1.00 52.10           G
ATOM  15616  CG   ARG G 989      41.293 134.030  52.648  1.00 52.10           G
ATOM  15617  CD   ARG G 989      40.804 135.169  51.789  1.00 52.10           G
ATOM  15618  NE   ARG G 989      39.617 134.794  51.032  1.00 52.10           G
ATOM  15619  CZ   ARG G 989      39.570 133.783  50.172  1.00 52.10           G
ATOM  15620  NH1  ARG G 989      40.650 133.033  49.954  1.00 52.10           G
ATOM  15621  NH2  ARG G 989      38.437 133.523  49.531  1.00 52.10           G
ATOM  15622  C    ARG G 989      43.408 131.489  53.090  1.00 56.58           G
ATOM  15623  O    ARG G 989      42.542 130.730  53.521  1.00 56.58           G
ATOM  15624  N    TYR G 990      44.366 131.094  52.248  1.00100.07           G
ATOM  15625  CA   TYR G 990      44.479 129.692  51.838  1.00100.07           G
ATOM  15626  CB   TYR G 990      45.761 129.407  51.030  1.00 89.18           G
ATOM  15627  CG   TYR G 990      45.707 129.578  49.527  1.00 89.18           G
ATOM  15628  CD1  TYR G 990      46.894 129.680  48.791  1.00 89.18           G
ATOM  15629  CE1  TYR G 990      46.877 129.881  47.420  1.00 89.18           G
ATOM  15630  CD2  TYR G 990      44.493 129.671  48.842  1.00 89.18           G
ATOM  15631  CE2  TYR G 990      44.464 129.872  47.461  1.00 89.18           G
ATOM  15632  CZ   TYR G 990      45.661 129.981  46.762  1.00 89.18           G
ATOM  15633  OH   TYR G 990      45.651 130.229  45.412  1.00 89.18           G
ATOM  15634  C    TYR G 990      44.660 128.993  53.167  1.00100.07           G
ATOM  15635  O    TYR G 990      43.753 128.339  53.685  1.00100.07           G
ATOM  15636  N    ASP G 991      45.858 129.177  53.715  1.00 45.67           G
ATOM  15637  CA   ASP G 991      46.252 128.578  54.969  1.00 45.67           G
ATOM  15638  CB   ASP G 991      47.458 129.321  55.530  1.00 54.88           G
ATOM  15639  CG   ASP G 991      48.608 129.375  54.544  1.00 54.88           G
ATOM  15640  OD1  ASP G 991      48.575 128.625  53.546  1.00 54.88           G
ATOM  15641  OD2  ASP G 991      49.549 130.158  54.768  1.00 54.88           G
ATOM  15642  C    ASP G 991      45.120 128.557  55.971  1.00 45.67           G
ATOM  15643  O    ASP G 991      45.107 127.732  56.872  1.00 45.67           G
ATOM  15644  N    GLN G 992      44.161 129.459  55.801  1.00 54.42           G
ATOM  15645  CA   GLN G 992      43.008 129.534  56.695  1.00 54.42           G
ATOM  15646  CB   GLN G 992      42.394 130.937  56.637  1.00 66.37           G
ATOM  15647  CG   GLN G 992      41.570 131.321  57.846  1.00 66.37           G
ATOM  15648  CD   GLN G 992      42.399 131.350  59.116  1.00 66.37           G
ATOM  15649  OE1  GLN G 992      43.593 131.674  59.090  1.00 66.37           G
ATOM  15650  NE2  GLN G 992      41.767 131.025  60.241  1.00 66.37           G
ATOM  15651  C    GLN G 992      41.978 128.511  56.234  1.00 54.42           G
ATOM  15652  O    GLN G 992      41.833 127.442  56.825  1.00 54.42           G
ATOM  15653  N    VAL G 993      41.280 128.861  55.156  1.00 72.53           G
ATOM  15654  CA   VAL G 993      40.253 128.016  54.564  1.00 72.53           G
ATOM  15655  CB   VAL G 993      39.999 128.415  53.097  1.00 58.92           G
ATOM  15656  CG1  VAL G 993      38.613 127.939  52.664  1.00 58.92           G
ATOM  15657  CG2  VAL G 993      40.129 129.928  52.932  1.00 58.92           G
ATOM  15658  C    VAL G 993      40.681 126.552  54.619  1.00 72.53           G
ATOM  15659  O    VAL G 993      39.864 125.653  54.823  1.00 72.53           G
ATOM  15660  N    ILE G 994      41.972 126.321  54.432  1.00 34.12           G
ATOM  15661  CA   ILE G 994      42.505 124.975  54.484  1.00 34.12           G
ATOM  15662  CB   ILE G 994      43.914 124.909  53.875  1.00 45.82           G
ATOM  15663  CG2  ILE G 994      44.679 123.732  54.441  1.00 45.82           G
ATOM  15664  CG1  ILE G 994      43.792 124.803  52.352  1.00 45.82           G
ATOM  15665  CD   ILE G 994      45.011 125.269  51.567  1.00 45.82           G
ATOM  15666  C    ILE G 994      42.555 124.555  55.931  1.00 34.12           G
ATOM  15667  O    ILE G 994      41.850 123.640  56.346  1.00 34.12           G
ATOM  15668  N    GLN G 995      43.375 125.241  56.710  1.00 43.22           G
ATOM  15669  CA   GLN G 995      43.482 124.900  58.114  1.00 43.22           G
ATOM  15670  CB   GLN G 995      44.263 125.970  58.874  1.00100.07           G
```

```
ATOM  15671  CG   GLN G  995      44.708 125.547  60.264  1.00100.07      G
ATOM  15672  CD   GLN G  995      45.751 126.484  60.847  1.00100.07      G
ATOM  15673  OE1  GLN G  995      45.488 127.669  61.077  1.00100.07      G
ATOM  15674  NE2  GLN G  995      46.949 125.958  61.083  1.00100.07      G
ATOM  15675  C    GLN G  995      42.071 124.791  58.657  1.00 43.22      G
ATOM  15676  O    GLN G  995      41.827 124.107  59.646  1.00 43.22      G
ATOM  15677  N    LEU G  996      41.134 125.471  58.010  1.00 48.66      G
ATOM  15678  CA   LEU G  996      39.754 125.395  58.447  1.00 48.66      G
ATOM  15679  CB   LEU G  996      38.888 126.424  57.714  1.00 24.68      G
ATOM  15680  CG   LEU G  996      37.379 126.150  57.639  1.00 24.68      G
ATOM  15681  CD1  LEU G  996      36.837 125.913  59.035  1.00 24.68      G
ATOM  15682  CD2  LEU G  996      36.665 127.306  56.951  1.00 24.68      G
ATOM  15683  C    LEU G  996      39.283 123.994  58.119  1.00 48.66      G
ATOM  15684  O    LEU G  996      39.166 123.147  58.999  1.00 48.66      G
ATOM  15685  N    TRP G  997      39.044 123.751  56.835  1.00 24.05      G
ATOM  15686  CA   TRP G  997      38.561 122.458  56.387  1.00 24.05      G
ATOM  15687  CB   TRP G  997      38.665 122.366  54.875  1.00 29.82      G
ATOM  15688  CG   TRP G  997      37.605 123.170  54.247  1.00 29.82      G
ATOM  15689  CD2  TRP G  997      36.191 123.017  54.431  1.00 29.82      G
ATOM  15690  CE2  TRP G  997      35.557 124.006  53.649  1.00 29.82      G
ATOM  15691  CE3  TRP G  997      35.398 122.136  55.179  1.00 29.82      G
ATOM  15692  CD1  TRP G  997      37.769 124.212  53.395  1.00 29.82      G
ATOM  15693  NE1  TRP G  997      36.545 124.724  53.026  1.00 29.82      G
ATOM  15694  CZ2  TRP G  997      34.158 124.143  53.591  1.00 29.82      G
ATOM  15695  CZ3  TRP G  997      34.009 122.270  55.122  1.00 29.82      G
ATOM  15696  CH2  TRP G  997      33.405 123.268  54.331  1.00 29.82      G
ATOM  15697  C    TRP G  997      39.293 121.329  57.060  1.00 24.05      G
ATOM  15698  O    TRP G  997      38.693 120.333  57.460  1.00 24.05      G
ATOM  15699  N    THR G  998      40.596 121.495  57.206  1.00 38.79      G
ATOM  15700  CA   THR G  998      41.382 120.478  57.861  1.00 38.79      G
ATOM  15701  CB   THR G  998      42.862 120.874  57.908  1.00 75.07      G
ATOM  15702  OG1  THR G  998      43.425 120.758  56.595  1.00 75.07      G
ATOM  15703  CG2  THR G  998      43.622 119.982  58.875  1.00 75.07      G
ATOM  15704  C    THR G  998      40.837 120.343  59.270  1.00 38.79      G
ATOM  15705  O    THR G  998      40.408 119.270  59.682  1.00 38.79      G
ATOM  15706  N    GLU G  999      40.831 121.453  59.996  1.00 73.09      G
ATOM  15707  CA   GLU G  999      40.344 121.486  61.367  1.00 73.09      G
ATOM  15708  CB   GLU G  999      40.299 122.943  61.845  1.00 99.81      G
ATOM  15709  CG   GLU G  999      39.789 123.164  63.261  1.00 99.81      G
ATOM  15710  CD   GLU G  999      40.741 124.002  64.107  1.00 99.81      G
ATOM  15711  OE1  GLU G  999      41.475 124.844  63.541  1.00 99.81      G
ATOM  15712  OE2  GLU G  999      40.742 123.822  65.346  1.00 99.81      G
ATOM  15713  C    GLU G  999      38.975 120.813  61.531  1.00 73.09      G
ATOM  15714  O    GLU G  999      38.788 120.018  62.447  1.00 73.09      G
ATOM  15715  N    THR G1000      38.027 121.108  60.646  1.00 65.50      G
ATOM  15716  CA   THR G1000      36.699 120.503  60.761  1.00 65.50      G
ATOM  15717  CB   THR G1000      35.631 121.226  59.885  1.00 71.39      G
ATOM  15718  OG1  THR G1000      34.366 120.555  60.007  1.00 71.39      G
ATOM  15719  CG2  THR G1000      36.047 121.235  58.425  1.00 71.39      G
ATOM  15720  C    THR G1000      36.703 119.037  60.381  1.00 65.50      G
ATOM  15721  O    THR G1000      36.282 118.195  61.166  1.00 65.50      G
ATOM  15722  N    THR G1001      37.182 118.736  59.179  1.00 66.70      G
ATOM  15723  CA   THR G1001      37.227 117.363  58.693  1.00 66.70      G
ATOM  15724  CB   THR G1001      38.076 117.269  57.394  1.00 47.40      G
ATOM  15725  OG1  THR G1001      37.222 116.909  56.299  1.00 47.40      G
ATOM  15726  CG2  THR G1001      39.197 116.237  57.530  1.00 47.40      G
ATOM  15727  C    THR G1001      37.749 116.380  59.745  1.00 66.70      G
ATOM  15728  O    THR G1001      37.316 115.231  59.791  1.00 66.70      G
ATOM  15729  N    GLU G1002      38.669 116.829  60.593  1.00 46.81      G
ATOM  15730  CA   GLU G1002      39.207 115.959  61.633  1.00 46.81      G
ATOM  15731  CB   GLU G1002      40.405 116.615  62.348  1.00100.07      G
ATOM  15732  CG   GLU G1002      41.697 116.709  61.514  1.00100.07      G
ATOM  15733  CD   GLU G1002      42.922 117.150  62.328  1.00100.07      G
ATOM  15734  OE1  GLU G1002      42.865 118.224  62.969  1.00100.07      G
ATOM  15735  OE2  GLU G1002      43.946 116.426  62.319  1.00100.07      G
ATOM  15736  C    GLU G1002      38.134 115.611  62.662  1.00 46.81      G
ATOM  15737  O    GLU G1002      38.270 114.632  63.394  1.00 46.81      G
ATOM  15738  N    LYS G1003      37.067 116.408  62.713  1.00 54.21      G
ATOM  15739  CA   LYS G1003      35.989 116.182  63.672  1.00 54.21      G
ATOM  15740  CB   LYS G1003      35.452 117.510  64.199  1.00 99.60      G
ATOM  15741  CG   LYS G1003      36.027 117.896  65.557  1.00 99.60      G
ATOM  15742  CD   LYS G1003      35.454 119.220  66.032  1.00 99.60      G
ATOM  15743  CE   LYS G1003      36.013 119.631  67.379  1.00 99.60      G
ATOM  15744  NZ   LYS G1003      35.569 121.010  67.719  1.00 99.60      G
ATOM  15745  C    LYS G1003      34.828 115.324  63.195  1.00 54.21      G
ATOM  15746  O    LYS G1003      34.446 114.388  63.880  1.00 54.21      G
ATOM  15747  N    VAL G1004      34.247 115.623  62.040  1.00 13.25      G
ATOM  15748  CA   VAL G1004      33.147 114.798  61.574  1.00 13.25      G
ATOM  15749  CB   VAL G1004      32.758 115.080  60.144  1.00  5.22      G
ATOM  15750  CG1  VAL G1004      31.309 114.716  59.982  1.00  5.22      G
ATOM  15751  CG2  VAL G1004      33.007 116.540  59.778  1.00  5.22      G
ATOM  15752  C    VAL G1004      33.640 113.369  61.628  1.00 13.25      G
ATOM  15753  O    VAL G1004      32.847 112.434  61.689  1.00 13.25      G
ATOM  15754  N    THR G1005      34.964 113.216  61.593  1.00 29.83      G
```

```
ATOM  15755  CA  THR G1005      35.617 111.912  61.692  1.00 29.83           G
ATOM  15756  CB  THR G1005      37.144 112.039  61.555  1.00100.07           G
ATOM  15757  OG1 THR G1005      37.474 112.585  60.273  1.00100.07           G
ATOM  15758  CG2 THR G1005      37.803 110.682  61.717  1.00100.07           G
ATOM  15759  C   THR G1005      35.328 111.397  63.102  1.00 29.83           G
ATOM  15760  O   THR G1005      34.555 110.461  63.302  1.00 29.83           G
ATOM  15761  N   GLN G1006      35.968 112.032  64.078  1.00 20.60           G
ATOM  15762  CA  GLN G1006      35.802 111.716  65.494  1.00 20.60           G
ATOM  15763  CB  GLN G1006      36.556 112.772  66.307  1.00 99.92           G
ATOM  15764  CG  GLN G1006      36.337 112.758  67.796  1.00 99.92           G
ATOM  15765  CD  GLN G1006      36.748 114.077  68.425  1.00 99.92           G
ATOM  15766  OE1 GLN G1006      36.080 115.100  68.253  1.00 99.92           G
ATOM  15767  NE2 GLN G1006      37.862 114.065  69.142  1.00 99.92           G
ATOM  15768  C   GLN G1006      34.307 111.732  65.841  1.00 20.60           G
ATOM  15769  O   GLN G1006      33.881 111.172  66.841  1.00 20.60           G
ATOM  15770  N   ALA G1007      33.515 112.382  64.995  1.00 31.60           G
ATOM  15771  CA  ALA G1007      32.076 112.492  65.198  1.00 31.60           G
ATOM  15772  CB  ALA G1007      31.524 113.653  64.391  1.00 95.22           G
ATOM  15773  C   ALA G1007      31.433 111.210  64.750  1.00 31.60           G
ATOM  15774  O   ALA G1007      31.092 110.357  65.563  1.00 31.60           G
ATOM  15775  N   VAL G1008      31.276 111.090  63.438  1.00 32.17           G
ATOM  15776  CA  VAL G1008      30.690 109.907  62.830  1.00 32.17           G
ATOM  15777  CB  VAL G1008      30.996 109.855  61.349  1.00100.07           G
ATOM  15778  CG1 VAL G1008      30.366 108.621  60.752  1.00100.07           G
ATOM  15779  CG2 VAL G1008      30.492 111.112  60.679  1.00100.07           G
ATOM  15780  C   VAL G1008      31.239 108.630  63.446  1.00 32.17           G
ATOM  15781  O   VAL G1008      30.519 107.653  63.636  1.00 32.17           G
ATOM  15782  N   PHE G1009      32.524 108.650  63.762  1.00 59.69           G
ATOM  15783  CA  PHE G1009      33.172 107.490  64.340  1.00 59.69           G
ATOM  15784  CB  PHE G1009      34.681 107.590  64.169  1.00 53.76           G
ATOM  15785  CG  PHE G1009      35.331 106.286  63.850  1.00 53.76           G
ATOM  15786  CD1 PHE G1009      35.590 105.935  62.538  1.00 53.76           G
ATOM  15787  CD2 PHE G1009      35.663 105.399  64.860  1.00 53.76           G
ATOM  15788  CE1 PHE G1009      36.169 104.727  62.234  1.00 53.76           G
ATOM  15789  CE2 PHE G1009      36.242 104.186  64.567  1.00 53.76           G
ATOM  15790  CZ  PHE G1009      36.497 103.849  63.250  1.00 53.76           G
ATOM  15791  C   PHE G1009      32.866 107.332  65.815  1.00 59.69           G
ATOM  15792  O   PHE G1009      33.252 106.342  66.432  1.00 59.69           G
ATOM  15793  N   ASN G1010      32.175 108.307  66.385  1.00 80.37           G
ATOM  15794  CA  ASN G1010      31.854 108.250  67.804  1.00 80.37           G
ATOM  15795  CB  ASN G1010      32.055 109.625  68.434  1.00100.07           G
ATOM  15796  CG  ASN G1010      32.197 109.554  69.929  1.00100.07           G
ATOM  15797  OD1 ASN G1010      31.345 108.984  70.613  1.00100.07           G
ATOM  15798  ND2 ASN G1010      33.280 110.130  70.453  1.00100.07           G
ATOM  15799  C   ASN G1010      30.425 107.789  68.035  1.00 80.37           G
ATOM  15800  O   ASN G1010      30.128 107.112  69.026  1.00 80.37           G
ATOM  15801  N   ASN G1011      29.553 108.163  67.100  1.00 51.35           G
ATOM  15802  CA  ASN G1011      28.143 107.822  67.167  1.00 51.35           G
ATOM  15803  CB  ASN G1011      27.463 108.003  65.807  1.00 24.43           G
ATOM  15804  CG  ASN G1011      25.942 107.939  65.909  1.00 24.43           G
ATOM  15805  OD1 ASN G1011      25.399 107.794  67.008  1.00 24.43           G
ATOM  15806  ND2 ASN G1011      25.249 108.052  64.771  1.00 24.43           G
ATOM  15807  C   ASN G1011      27.937 106.395  67.611  1.00 51.35           G
ATOM  15808  O   ASN G1011      27.208 106.137  68.574  1.00 51.35           G
ATOM  15809  N   PHE G1012      28.581 105.459  66.916  1.00 30.82           G
ATOM  15810  CA  PHE G1012      28.387 104.069  67.276  1.00 30.82           G
ATOM  15811  CB  PHE G1012      28.832 103.118  66.144  1.00 83.90           G
ATOM  15812  CG  PHE G1012      30.308 102.907  66.051  1.00 83.90           G
ATOM  15813  CD1 PHE G1012      31.076 103.653  65.171  1.00 83.90           G
ATOM  15814  CD2 PHE G1012      30.931 101.937  66.830  1.00 83.90           G
ATOM  15815  CE1 PHE G1012      32.449 103.435  65.067  1.00 83.90           G
ATOM  15816  CE2 PHE G1012      32.297 101.712  66.737  1.00 83.90           G
ATOM  15817  CZ  PHE G1012      33.060 102.460  65.854  1.00 83.90           G
ATOM  15818  C   PHE G1012      29.030 103.703  68.600  1.00 30.82           G
ATOM  15819  O   PHE G1012      28.472 102.904  69.364  1.00 30.82           G
ATOM  15820  N   GLU G1013      30.165 104.312  68.918  1.00 19.23           G
ATOM  15821  CA  GLU G1013      30.805 103.951  70.170  1.00 19.23           G
ATOM  15822  CB  GLU G1013      31.945 104.902  70.523  1.00100.07           G
ATOM  15823  CG  GLU G1013      32.981 104.239  71.434  1.00100.07           G
ATOM  15824  CD  GLU G1013      33.979 105.221  72.032  1.00100.07           G
ATOM  15825  OE1 GLU G1013      33.603 105.950  72.980  1.00100.07           G
ATOM  15826  OE2 GLU G1013      35.138 105.269  71.552  1.00100.07           G
ATOM  15827  C   GLU G1013      29.790 103.928  71.303  1.00 19.23           G
ATOM  15828  O   GLU G1013      29.998 103.259  72.307  1.00 19.23           G
ATOM  15829  N   GLU G1014      28.682 104.639  71.136  1.00 57.43           G
ATOM  15830  CA  GLU G1014      27.668 104.674  72.177  1.00 57.43           G
ATOM  15831  CB  GLU G1014      27.414 106.110  72.616  1.00 99.43           G
ATOM  15832  CG  GLU G1014      28.679 106.924  72.770  1.00 99.43           G
ATOM  15833  CD  GLU G1014      28.407 108.312  73.290  1.00 99.43           G
ATOM  15834  OE1 GLU G1014      27.410 108.931  72.857  1.00 99.43           G
ATOM  15835  OE2 GLU G1014      29.200 108.785  74.126  1.00 99.43           G
ATOM  15836  C   GLU G1014      26.376 104.054  71.696  1.00 57.43           G
ATOM  15837  O   GLU G1014      25.816 103.206  72.372  1.00 57.43           G
ATOM  15838  N   ASN G1015      25.888 104.493  70.543  1.00 74.08
```

```
ATOM  15839  CA   ASN G1015    24.665 103.926 69.985  1.00 74.08      G
ATOM  15840  CB   ASN G1015    23.743 105.018 69.456  1.00 87.88      G
ATOM  15841  CG   ASN G1015    23.795 106.260 70.290  1.00 87.88      G
ATOM  15842  OD1  ASN G1015    23.993 106.189 71.502  1.00 87.88      G
ATOM  15843  ND2  ASN G1015    23.608 107.414 69.654  1.00 87.88      G
ATOM  15844  C    ASN G1015    25.113 103.053 68.827  1.00 74.08      G
ATOM  15845  O    ASN G1015    25.681 103.565 67.870  1.00 74.08      G
ATOM  15846  N    TYR G1016    24.847 101.750 68.912  1.00 31.52      G
ATOM  15847  CA   TYR G1016    25.236 100.771 67.891  1.00 31.52      G
ATOM  15848  CB   TYR G1016    25.433 101.441 66.529  1.00 23.52      G
ATOM  15849  CG   TYR G1016    24.223 102.177 66.003  1.00 23.52      G
ATOM  15850  CD1  TYR G1016    23.125 102.433 66.818  1.00 23.52      G
ATOM  15851  CE1  TYR G1016    22.003 103.103 66.327  1.00 23.52      G
ATOM  15852  CD2  TYR G1016    24.173 102.608 64.683  1.00 23.52      G
ATOM  15853  CE2  TYR G1016    23.063 103.269 64.179  1.00 23.52      G
ATOM  15854  CZ   TYR G1016    21.976 103.518 65.000  1.00 23.52      G
ATOM  15855  OH   TYR G1016    20.863 104.173 64.503  1.00 23.52      G
ATOM  15856  C    TYR G1016    26.548 100.093 68.293  1.00 31.52      G
ATOM  15857  O    TYR G1016    27.556 100.254 67.606  1.00 31.52      G
ATOM  15858  N    PRO G1017    26.554  99.332 69.408  1.00 48.22      G
ATOM  15859  CD   PRO G1017    25.356  98.835 70.111  1.00 99.89      G
ATOM  15860  CA   PRO G1017    27.760  98.634 69.880  1.00 48.22      G
ATOM  15861  CB   PRO G1017    27.244  97.832 71.071  1.00 99.89      G
ATOM  15862  CG   PRO G1017    25.831  97.513 70.665  1.00 99.89      G
ATOM  15863  C    PRO G1017    28.266  97.746 68.735  1.00 48.22      G
ATOM  15864  O    PRO G1017    29.338  97.988 68.177  1.00 48.22      G
ATOM  15865  N    PHE G1018    27.506  96.702 68.411  1.00 40.21      G
ATOM  15866  CA   PHE G1018    27.837  95.866 67.273  1.00 40.21      G
ATOM  15867  CB   PHE G1018    27.365  94.428 67.429  1.00 30.87      G
ATOM  15868  CG   PHE G1018    27.435  93.907 68.820  1.00 30.87      G
ATOM  15869  CD1  PHE G1018    26.489  94.276 69.760  1.00 30.87      G
ATOM  15870  CD2  PHE G1018    28.441  93.030 69.191  1.00 30.87      G
ATOM  15871  CE1  PHE G1018    26.546  93.774 71.055  1.00 30.87      G
ATOM  15872  CE2  PHE G1018    28.512  92.519 70.477  1.00 30.87      G
ATOM  15873  CZ   PHE G1018    27.565  92.889 71.414  1.00 30.87      G
ATOM  15874  C    PHE G1018    26.887  96.562 66.328  1.00 40.21      G
ATOM  15875  O    PHE G1018    26.684  97.771 66.440  1.00 40.21      G
ATOM  15876  N    ALA G1019    26.286  95.827 65.404  1.00100.07      G
ATOM  15877  CA   ALA G1019    25.342  96.447 64.478  1.00100.07      G
ATOM  15878  CB   ALA G1019    24.063  96.871 65.237  1.00 49.74      G
ATOM  15879  C    ALA G1019    25.917  97.653 63.720  1.00100.07      G
ATOM  15880  O    ALA G1019    25.164  98.505 63.231  1.00100.07      G
ATOM  15881  N    PRO G1020    27.252  97.748 63.611  1.00 48.11      G
ATOM  15882  CD   PRO G1020    28.352  97.111 64.340  1.00 64.34      G
ATOM  15883  CA   PRO G1020    27.798  98.884 62.892  1.00 48.11      G
ATOM  15884  CB   PRO G1020    28.628  99.559 63.958  1.00 64.34      G
ATOM  15885  CG   PRO G1020    29.118  98.335 64.838  1.00 64.34      G
ATOM  15886  C    PRO G1020    28.666  98.222 61.851  1.00 48.11      G
ATOM  15887  O    PRO G1020    29.502  98.871 61.232  1.00 48.11      G
ATOM  15888  N    LEU G1021    28.472  96.905 61.742  1.00 28.79      G
ATOM  15889  CA   LEU G1021    29.150  96.027 60.812  1.00 28.79      G
ATOM  15890  CB   LEU G1021    28.198  95.688 59.693  1.00 48.08      G
ATOM  15891  CG   LEU G1021    26.833  95.531 60.362  1.00 48.08      G
ATOM  15892  CD1  LEU G1021    25.774  95.376 59.305  1.00 48.08      G
ATOM  15893  CD2  LEU G1021    26.844  94.337 61.335  1.00 48.08      G
ATOM  15894  C    LEU G1021    30.398  96.664 60.275  1.00 28.79      G
ATOM  15895  O    LEU G1021    31.485  96.133 60.472  1.00 28.79      G
ATOM  15896  N    ALA G1022    30.264  97.795 59.590  1.00 39.56      G
ATOM  15897  CA   ALA G1022    31.438  98.492 59.096  1.00 39.56      G
ATOM  15898  CB   ALA G1022    31.044  99.728 58.261  1.00  5.07      G
ATOM  15899  C    ALA G1022    32.241  98.914 60.325  1.00 39.56      G
ATOM  15900  O    ALA G1022    32.987  99.873 60.258  1.00 39.56      G
ATOM  15901  N    VAL G1023    32.085  98.198 61.442  1.00 32.21      G
ATOM  15902  CA   VAL G1023    32.814  98.505 62.670  1.00 32.21      G
ATOM  15903  CB   VAL G1023    31.943  99.213 63.682  1.00 13.83      G
ATOM  15904  CG1  VAL G1023    32.649  99.262 65.025  1.00 13.83      G
ATOM  15905  CG2  VAL G1023    31.641 100.596 63.200  1.00 13.83      G
ATOM  15906  C    VAL G1023    33.504  97.369 63.418  1.00 32.21      G
ATOM  15907  O    VAL G1023    34.717  97.412 63.538  1.00 32.21      G
ATOM  15908  N    MET G1024    32.764  96.394 63.961  1.00 21.83      G
ATOM  15909  CA   MET G1024    33.400  95.278 64.693  1.00 21.83      G
ATOM  15910  CB   MET G1024    32.548  94.013 64.659  1.00 99.86      G
ATOM  15911  CG   MET G1024    31.085  94.257 64.504  1.00 99.86      G
ATOM  15912  SD   MET G1024    30.585  95.555 65.592  1.00 99.86      G
ATOM  15913  CE   MET G1024    31.225  94.952 67.155  1.00 99.86      G
ATOM  15914  C    MET G1024    34.699  94.970 63.952  1.00 21.83      G
ATOM  15915  O    MET G1024    35.757  94.702 64.555  1.00 21.83      G
ATOM  15916  N    ALA G1025    34.579  94.985 62.624  1.00 20.04      G
ATOM  15917  CA   ALA G1025    35.705  94.771 61.756  1.00 20.04      G
ATOM  15918  CB   ALA G1025    35.296  95.002 60.320  1.00 11.81      G
ATOM  15919  C    ALA G1025    36.632  95.874 62.231  1.00 20.04      G
ATOM  15920  O    ALA G1025    37.493  95.651 63.088  1.00 20.04      G
ATOM  15921  N    ALA G1026    36.401  97.076 61.703  1.00 19.14      G
ATOM  15922  CA   ALA G1026    37.177  98.274 62.046  1.00 19.14      G
```

```
ATOM  15923  CB  ALA G1026      36.339  99.514  61.777  1.00 65.03      G
ATOM  15924  C   ALA G1026      37.678  98.301  63.490  1.00 19.14      G
ATOM  15925  O   ALA G1026      38.877  98.334  63.737  1.00 19.14      G
ATOM  15926  N   SER G1027      36.754  98.305  64.437  1.00 48.99      G
ATOM  15927  CA  SER G1027      37.101  98.315  65.851  1.00 48.99      G
ATOM  15928  CB  SER G1027      35.852  98.000  66.671  1.00100.07      G
ATOM  15929  OG  SER G1027      35.212  96.830  66.183  1.00100.07      G
ATOM  15930  C   SER G1027      38.205  97.293  66.163  1.00 48.99      G
ATOM  15931  O   SER G1027      38.736  97.237  67.277  1.00 48.99      G
ATOM  15932  N   GLY G1028      38.548  96.487  65.168  1.00 18.82      G
ATOM  15933  CA  GLY G1028      39.569  95.486  65.359  1.00 18.82      G
ATOM  15934  C   GLY G1028      39.142  94.220  64.658  1.00 18.82      G
ATOM  15935  O   GLY G1028      38.309  93.468  65.168  1.00 18.82      G
ATOM  15936  N   ALA G1029      39.711  94.003  63.474  1.00 26.00      G
ATOM  15937  CA  ALA G1029      39.420  92.835  62.643  1.00 26.00      G
ATOM  15938  CB  ALA G1029      37.917  92.568  62.619  1.00100.07      G
ATOM  15939  C   ALA G1029      39.939  93.033  61.211  1.00 26.00      G
ATOM  15940  O   ALA G1029      41.006  92.528  60.850  1.00 26.00      G
ATOM  15941  N   ALA G1030      39.178  93.771  60.407  1.00 21.88      G
ATOM  15942  CA  ALA G1030      39.565  94.026  59.033  1.00 21.88      G
ATOM  15943  CB  ALA G1030      39.231  92.793  58.194  1.00  5.07      G
ATOM  15944  C   ALA G1030      38.962  95.321  58.409  1.00 21.88      G
ATOM  15945  O   ALA G1030      38.502  95.326  57.254  1.00 21.88      G
ATOM  15946  N   GLY G1031      39.006  96.416  59.174  1.00 38.70      G
ATOM  15947  CA  GLY G1031      38.482  97.698  58.716  1.00 38.70      G
ATOM  15948  C   GLY G1031      39.555  98.728  58.388  1.00 38.70      G
ATOM  15949  O   GLY G1031      40.404  98.443  57.559  1.00 38.70      G
ATOM  15950  N   ASN G1032      39.501  99.902  59.032  1.00 39.45      G
ATOM  15951  CA  ASN G1032      40.433 101.045  58.869  1.00 39.45      G
ATOM  15952  CB  ASN G1032      41.222 100.955  57.546  1.00 58.33      G
ATOM  15953  CG  ASN G1032      40.573 101.731  56.385  1.00 58.33      G
ATOM  15954  OD1 ASN G1032      40.478 102.953  56.426  1.00 58.33      G
ATOM  15955  ND2 ASN G1032      40.153 101.016  55.339  1.00 58.33      G
ATOM  15956  C   ASN G1032      39.613 102.341  58.892  1.00 39.45      G
ATOM  15957  O   ASN G1032      38.833 102.579  57.971  1.00 39.45      G
ATOM  15958  N   PRO G1033      39.766 103.192  59.940  1.00 70.33      G
ATOM  15959  CD  PRO G1033      40.675 103.006  61.077  1.00 19.66      G
ATOM  15960  CA  PRO G1033      39.041 104.467  60.100  1.00 70.33      G
ATOM  15961  CB  PRO G1033      39.534 104.995  61.442  1.00 19.66      G
ATOM  15962  CG  PRO G1033      40.869 104.437  61.542  1.00 19.66      G
ATOM  15963  C   PRO G1033      39.193 105.499  59.005  1.00 70.33      G
ATOM  15964  O   PRO G1033      38.264 106.260  58.754  1.00 70.33      G
ATOM  15965  N   GLN G1034      40.363 105.552  58.377  1.00 55.87      G
ATOM  15966  CA  GLN G1034      40.563 106.481  57.275  1.00 55.87      G
ATOM  15967  CB  GLN G1034      41.847 106.155  56.540  1.00 99.58      G
ATOM  15968  CG  GLN G1034      43.027 105.991  57.436  1.00 99.58      G
ATOM  15969  CD  GLN G1034      44.202 105.435  56.684  1.00 99.58      G
ATOM  15970  OE1 GLN G1034      44.547 105.924  55.607  1.00 99.58      G
ATOM  15971  NE2 GLN G1034      44.829 104.404  57.240  1.00 99.58      G
ATOM  15972  C   GLN G1034      39.387 106.224  56.336  1.00 55.87      G
ATOM  15973  O   GLN G1034      38.699 107.148  55.894  1.00 55.87      G
ATOM  15974  N   ALA G1035      39.168 104.950  56.033  1.00 39.34      G
ATOM  15975  CA  ALA G1035      38.067 104.562  55.177  1.00 39.34      G
ATOM  15976  CB  ALA G1035      37.945 103.052  55.127  1.00 74.13      G
ATOM  15977  C   ALA G1035      36.797 105.182  55.752  1.00 39.34      G
ATOM  15978  O   ALA G1035      36.286 106.138  55.180  1.00 39.34      G
ATOM  15979  N   ILE G1036      36.312 104.663  56.886  1.00 24.89      G
ATOM  15980  CA  ILE G1036      35.095 105.176  57.530  1.00 24.89      G
ATOM  15981  CB  ILE G1036      34.932 104.625  58.966  1.00 18.32      G
ATOM  15982  CG2 ILE G1036      33.647 105.118  59.556  1.00 18.32      G
ATOM  15983  CG1 ILE G1036      34.815 103.107  58.964  1.00 18.32      G
ATOM  15984  CD  ILE G1036      36.084 102.410  58.683  1.00 18.32      G
ATOM  15985  C   ILE G1036      35.060 106.715  57.592  1.00 24.89      G
ATOM  15986  O   ILE G1036      34.034 107.340  57.269  1.00 24.89      G
ATOM  15987  N   ARG G1037      36.179 107.314  58.011  1.00 42.24      G
ATOM  15988  CA  ARG G1037      36.328 108.776  58.089  1.00 42.24      G
ATOM  15989  CB  ARG G1037      37.740 109.148  58.567  1.00100.07      G
ATOM  15990  CG  ARG G1037      38.227 110.531  58.112  1.00100.07      G
ATOM  15991  CD  ARG G1037      39.709 110.730  58.357  1.00100.07      G
ATOM  15992  NE  ARG G1037      40.302 111.669  57.405  1.00100.07      G
ATOM  15993  CZ  ARG G1037      41.591 112.008  57.391  1.00100.07      G
ATOM  15994  NH1 ARG G1037      42.426 111.487  58.282  1.00100.07      G
ATOM  15995  NH2 ARG G1037      42.053 112.865  56.487  1.00100.07      G
ATOM  15996  C   ARG G1037      36.115 109.347  56.694  1.00 42.24      G
ATOM  15997  O   ARG G1037      36.341 110.533  56.443  1.00 42.24      G
ATOM  15998  N   GLN G1038      35.692 108.471  55.791  1.00 20.38      G
ATOM  15999  CA  GLN G1038      35.439 108.809  54.409  1.00 20.38      G
ATOM  16000  CB  GLN G1038      36.716 108.553  53.591  1.00100.07      G
ATOM  16001  CG  GLN G1038      36.659 107.425  52.584  1.00100.07      G
ATOM  16002  CD  GLN G1038      37.971 107.252  51.831  1.00100.07      G
ATOM  16003  OE1 GLN G1038      38.454 108.172  51.168  1.00100.07      G
ATOM  16004  NE2 GLN G1038      38.552 106.064  51.933  1.00100.07      G
ATOM  16005  C   GLN G1038      34.262 107.949  53.942  1.00 20.38      G
ATOM  16006  O   GLN G1038      33.441 108.367  53.124  1.00 20.38      G
```

```
ATOM  16007  N    LEU G1039      34.172 106.747  54.499  1.00 37.90       G
ATOM  16008  CA   LEU G1039      33.092 105.834  54.165  1.00 37.90       G
ATOM  16009  CB   LEU G1039      33.329 104.457  54.802  1.00 33.12       G
ATOM  16010  CG   LEU G1039      33.478 103.330  53.774  1.00 33.12       G
ATOM  16011  CD1  LEU G1039      33.916 102.022  54.422  1.00 33.12       G
ATOM  16012  CD2  LEU G1039      32.153 103.161  53.080  1.00 33.12       G
ATOM  16013  C    LEU G1039      31.801 106.448  54.688  1.00 37.90       G
ATOM  16014  O    LEU G1039      30.810 106.518  53.965  1.00 37.90       G
ATOM  16015  N    CYS G1040      31.822 106.918  55.934  1.00100.07       G
ATOM  16016  CA   CYS G1040      30.639 107.534  56.540  1.00100.07       G
ATOM  16017  CB   CYS G1040      30.544 107.153  58.013  1.00 57.75       G
ATOM  16018  SG   CYS G1040      30.616 105.388  58.317  1.00 57.75       G
ATOM  16019  C    CYS G1040      30.659 109.056  56.407  1.00100.07       G
ATOM  16020  O    CYS G1040      30.244 109.602  55.385  1.00100.07       G
ATOM  16021  N    GLY G1041      31.112 109.741  57.452  1.00 33.05       G
ATOM  16022  CA   GLY G1041      31.185 111.189  57.394  1.00 33.05       G
ATOM  16023  C    GLY G1041      32.155 111.521  56.283  1.00 33.05       G
ATOM  16024  O    GLY G1041      32.978 110.677  55.914  1.00 33.05       G
ATOM  16025  N    MET G1042      32.087 112.745  55.771  1.00 19.67       G
ATOM  16026  CA   MET G1042      32.929 113.176  54.652  1.00 19.67       G
ATOM  16027  CB   MET G1042      32.460 114.571  54.203  1.00 29.12       G
ATOM  16028  CG   MET G1042      33.565 115.649  54.105  1.00 29.12       G
ATOM  16029  SD   MET G1042      34.228 116.401  55.664  1.00 29.12       G
ATOM  16030  CE   MET G1042      33.334 117.960  55.672  1.00 29.12       G
ATOM  16031  C    MET G1042      34.466 113.176  54.717  1.00 19.67       G
ATOM  16032  O    MET G1042      35.063 113.676  55.670  1.00 19.67       G
ATOM  16033  N    ARG G1043      35.100 112.580  53.707  1.00 53.72       G
ATOM  16034  CA   ARG G1043      36.561 112.640  53.571  1.00 53.72       G
ATOM  16035  CB   ARG G1043      37.107 111.547  52.655  1.00 80.54       G
ATOM  16036  CG   ARG G1043      36.553 111.586  51.215  1.00 80.54       G
ATOM  16037  CD   ARG G1043      37.381 110.721  50.255  1.00 80.54       G
ATOM  16038  NE   ARG G1043      36.770 110.562  48.933  1.00 80.54       G
ATOM  16039  CZ   ARG G1043      37.404 110.060  47.874  1.00 80.54       G
ATOM  16040  NH1  ARG G1043      38.666 109.673  47.977  1.00 80.54       G
ATOM  16041  NH2  ARG G1043      36.778 109.936  46.713  1.00 80.54       G
ATOM  16042  C    ARG G1043      36.386 113.885  52.746  1.00 53.72       G
ATOM  16043  O    ARG G1043      35.242 114.187  52.405  1.00 53.72       G
ATOM  16044  N    GLY G1044      37.421 114.630  52.385  1.00 61.65       G
ATOM  16045  CA   GLY G1044      37.064 115.795  51.591  1.00 61.65       G
ATOM  16046  C    GLY G1044      38.052 116.803  51.083  1.00 61.65       G
ATOM  16047  O    GLY G1044      37.652 117.719  50.380  1.00 61.65       G
ATOM  16048  N    LEU G1045      39.324 116.659  51.415  1.00 53.85       G
ATOM  16049  CA   LEU G1045      40.289 117.627  50.931  1.00 53.85       G
ATOM  16050  CB   LEU G1045      40.910 118.361  52.118  1.00 31.35       G
ATOM  16051  CG   LEU G1045      41.210 119.843  51.879  1.00 31.35       G
ATOM  16052  CD1  LEU G1045      40.043 120.485  51.123  1.00 31.35       G
ATOM  16053  CD2  LEU G1045      41.458 120.543  53.221  1.00 31.35       G
ATOM  16054  C    LEU G1045      41.366 117.001  50.051  1.00 53.85       G
ATOM  16055  O    LEU G1045      42.457 116.677  50.509  1.00 53.85       G
ATOM  16056  N    MET G1046      41.055 116.821  48.778  1.00 45.06       G
ATOM  16057  CA   MET G1046      42.028 116.240  47.876  1.00 45.06       G
ATOM  16058  CB   MET G1046      41.372 115.766  46.578  1.00 66.51       G
ATOM  16059  CG   MET G1046      40.903 114.339  46.615  1.00 66.51       G
ATOM  16060  SD   MET G1046      39.661 114.124  47.862  1.00 66.51       G
ATOM  16061  CE   MET G1046      40.689 113.667  49.271  1.00 66.51       G
ATOM  16062  C    MET G1046      43.099 117.241  47.532  1.00 45.06       G
ATOM  16063  O    MET G1046      42.923 118.452  47.684  1.00 45.06       G
ATOM  16064  N    ALA G1047      44.216 116.716  47.055  1.00100.03       G
ATOM  16065  CA   ALA G1047      45.328 117.544  46.656  1.00100.03       G
ATOM  16066  CB   ALA G1047      46.605 117.070  47.332  1.00 53.50       G
ATOM  16067  C    ALA G1047      45.457 117.427  45.150  1.00100.03       G
ATOM  16068  O    ALA G1047      45.187 116.376  44.567  1.00100.03       G
ATOM  16069  N    ALA G1048      45.844 118.524  44.519  1.00100.07       G
ATOM  16070  CA   ALA G1048      46.047 118.542  43.083  1.00100.07       G
ATOM  16071  CB   ALA G1048      46.364 119.973  42.633  1.00 19.35       G
ATOM  16072  C    ALA G1048      47.245 117.632  42.840  1.00100.07       G
ATOM  16073  O    ALA G1048      47.790 117.057  43.779  1.00100.07       G
ATOM  16074  N    PRO G1049      47.648 117.451  41.580  1.00 55.87       G
ATOM  16075  CD   PRO G1049      46.985 117.756  40.306  1.00 30.75       G
ATOM  16076  CA   PRO G1049      48.810 116.591  41.359  1.00 55.87       G
ATOM  16077  CB   PRO G1049      48.784 116.360  39.858  1.00 30.75       G
ATOM  16078  CG   PRO G1049      48.109 117.590  39.345  1.00 30.75       G
ATOM  16079  C    PRO G1049      50.065 117.340  41.798  1.00 55.87       G
ATOM  16080  O    PRO G1049      51.047 116.737  42.241  1.00 55.87       G
ATOM  16081  N    SER G1050      50.008 118.666  41.684  1.00 90.84       G
ATOM  16082  CA   SER G1050      51.122 119.544  42.050  1.00 90.84       G
ATOM  16083  CB   SER G1050      51.060 120.835  41.228  1.00 93.57       G
ATOM  16084  OG   SER G1050      49.903 121.593  41.549  1.00 93.57       G
ATOM  16085  C    SER G1050      51.137 119.912  43.532  1.00 90.84       G
ATOM  16086  O    SER G1050      51.320 121.080  43.877  1.00 90.84       G
ATOM  16087  N    GLY G1051      50.942 118.918  44.397  1.00 68.75       G
ATOM  16088  CA   GLY G1051      50.937 119.151  45.836  1.00 68.75       G
ATOM  16089  C    GLY G1051      49.827 120.045  46.371  1.00 68.75       G
ATOM  16090  O    GLY G1051      49.215 119.749  47.395  1.00 68.75       G
```

```
ATOM  16091  N    ALA G1052      49.575 121.148  45.678  1.00 37.38       G
ATOM  16092  CA   ALA G1052      48.552 122.099  46.076  1.00 37.38       G
ATOM  16093  CB   ALA G1052      48.304 123.098  44.930  1.00 36.85       G
ATOM  16094  C    ALA G1052      47.249 121.401  46.476  1.00 37.38       G
ATOM  16095  O    ALA G1052      46.880 120.372  45.904  1.00 37.38       G
ATOM  16096  N    THR G1053      46.567 121.963  47.472  1.00 47.47       G
ATOM  16097  CA   THR G1053      45.294 121.424  47.956  1.00 47.47       G
ATOM  16098  CB   THR G1053      45.148 121.581  49.483  1.00100.07       G
ATOM  16099  OG1  THR G1053      46.060 120.700  50.149  1.00100.07       G
ATOM  16100  CG2  THR G1053      43.722 121.266  49.916  1.00100.07       G
ATOM  16101  C    THR G1053      44.132 122.165  47.317  1.00 47.47       G
ATOM  16102  O    THR G1053      44.203 123.376  47.079  1.00 47.47       G
ATOM  16103  N    PHE G1054      43.054 121.444  47.046  1.00 54.78       G
ATOM  16104  CA   PHE G1054      41.905 122.089  46.448  1.00 54.78       G
ATOM  16105  CB   PHE G1054      41.107 121.090  45.616  1.00 38.67       G
ATOM  16106  CG   PHE G1054      41.775 120.722  44.312  1.00 38.67       G
ATOM  16107  CD1  PHE G1054      42.420 119.499  44.158  1.00 38.67       G
ATOM  16108  CD2  PHE G1054      41.748 121.597  43.232  1.00 38.67       G
ATOM  16109  CE1  PHE G1054      43.014 119.159  42.951  1.00 38.67       G
ATOM  16110  CE2  PHE G1054      42.346 121.260  42.024  1.00 38.67       G
ATOM  16111  CZ   PHE G1054      42.974 120.045  41.884  1.00 38.67       G
ATOM  16112  C    PHE G1054      41.031 122.751  47.504  1.00 54.78       G
ATOM  16113  O    PHE G1054      40.428 122.082  48.346  1.00 54.78       G
ATOM  16114  N    GLU G1055      40.993 124.079  47.435  1.00 58.79       G
ATOM  16115  CA   GLU G1055      40.240 124.926  48.341  1.00 58.79       G
ATOM  16116  CB   GLU G1055      40.417 126.379  47.892  1.00 98.67       G
ATOM  16117  CG   GLU G1055      39.668 127.417  48.708  1.00 98.67       G
ATOM  16118  CD   GLU G1055      40.077 128.838  48.360  1.00 98.67       G
ATOM  16119  OE1  GLU G1055      40.192 129.150  47.156  1.00 98.67       G
ATOM  16120  OE2  GLU G1055      40.276 129.649  49.289  1.00 98.67       G
ATOM  16121  C    GLU G1055      38.749 124.583  48.490  1.00 58.79       G
ATOM  16122  O    GLU G1055      37.997 125.343  49.100  1.00 58.79       G
ATOM  16123  N    VAL G1056      38.313 123.445  47.945  1.00 36.77       G
ATOM  16124  CA   VAL G1056      36.906 123.026  48.059  1.00 36.77       G
ATOM  16125  CB   VAL G1056      36.123 123.284  46.760  1.00 35.12       G
ATOM  16126  CG1  VAL G1056      34.649 122.929  46.958  1.00 35.12       G
ATOM  16127  CG2  VAL G1056      36.287 124.741  46.337  1.00 35.12       G
ATOM  16128  C    VAL G1056      36.788 121.542  48.391  1.00 36.77       G
ATOM  16129  O    VAL G1056      37.109 120.691  47.576  1.00 36.77       G
ATOM  16130  N    PRO G1057      36.327 121.220  49.605  1.00 45.23       G
ATOM  16131  CD   PRO G1057      35.995 122.170  50.679  1.00100.07       G
ATOM  16132  CA   PRO G1057      36.159 119.844  50.071  1.00 45.23       G
ATOM  16133  CB   PRO G1057      35.880 120.014  51.559  1.00100.07       G
ATOM  16134  CG   PRO G1057      35.181 121.313  51.618  1.00100.07       G
ATOM  16135  C    PRO G1057      35.064 119.081  49.340  1.00 45.23       G
ATOM  16136  O    PRO G1057      34.674 119.474  48.230  1.00 45.23       G
ATOM  16137  N    VAL G1058      34.554 118.011  49.958  1.00 49.19       G
ATOM  16138  CA   VAL G1058      33.544 117.197  49.287  1.00 49.19       G
ATOM  16139  CB   VAL G1058      34.187 115.907  48.756  1.00 67.57       G
ATOM  16140  CG1  VAL G1058      33.615 115.586  47.374  1.00 67.57       G
ATOM  16141  CG2  VAL G1058      35.707 116.046  48.730  1.00 67.57       G
ATOM  16142  C    VAL G1058      32.235 116.773  49.971  1.00 49.19       G
ATOM  16143  O    VAL G1058      32.082 116.845  51.190  1.00 49.19       G
ATOM  16144  N    ALA G1059      31.299 116.318  49.133  1.00 56.79       G
ATOM  16145  CA   ALA G1059      29.991 115.810  49.566  1.00 56.79       G
ATOM  16146  CB   ALA G1059      28.936 116.016  48.480  1.00 53.14       G
ATOM  16147  C    ALA G1059      30.278 114.346  49.699  1.00 56.79       G
ATOM  16148  O    ALA G1059      29.563 113.504  49.168  1.00 56.79       G
ATOM  16149  N    SER G1060      31.344 114.065  50.423  1.00 44.75       G
ATOM  16150  CA   SER G1060      31.822 112.715  50.583  1.00 44.75       G
ATOM  16151  CB   SER G1060      33.166 112.735  51.307  1.00100.07       G
ATOM  16152  OG   SER G1060      34.187 113.222  50.453  1.00100.07       G
ATOM  16153  C    SER G1060      30.948 111.665  51.213  1.00 44.75       G
ATOM  16154  O    SER G1060      31.382 110.525  51.330  1.00 44.75       G
ATOM  16155  N    SER G1061      29.735 112.002  51.620  1.00 91.29       G
ATOM  16156  CA   SER G1061      28.906 110.978  52.234  1.00 91.29       G
ATOM  16157  CB   SER G1061      27.421 111.250  51.961  1.00 31.24       G
ATOM  16158  OG   SER G1061      26.868 112.171  52.893  1.00 31.24       G
ATOM  16159  C    SER G1061      29.302 109.574  51.729  1.00 91.29       G
ATOM  16160  O    SER G1061      29.409 108.642  52.528  1.00 91.29       G
ATOM  16161  N    PHE G1062      29.577 109.451  50.422  1.00 60.01       G
ATOM  16162  CA   PHE G1062      29.941 108.173  49.774  1.00 60.01       G
ATOM  16163  CB   PHE G1062      31.177 107.531  50.426  1.00 59.48       G
ATOM  16164  CG   PHE G1062      32.367 107.356  49.481  1.00 59.48       G
ATOM  16165  CD1  PHE G1062      32.912 108.438  48.793  1.00 59.48       G
ATOM  16166  CD2  PHE G1062      32.977 106.117  49.330  1.00 59.48       G
ATOM  16167  CE1  PHE G1062      34.048 108.281  47.977  1.00 59.48       G
ATOM  16168  CE2  PHE G1062      34.107 105.961  48.518  1.00 59.48       G
ATOM  16169  CZ   PHE G1062      34.638 107.044  47.846  1.00 59.48       G
ATOM  16170  C    PHE G1062      28.721 107.280  49.934  1.00 60.01       G
ATOM  16171  O    PHE G1062      28.233 106.696  48.976  1.00 60.01       G
ATOM  16172  N    ARG G1063      28.231 107.197  51.164  1.00 63.31       G
ATOM  16173  CA   ARG G1063      27.027 106.458  51.483  1.00 63.31       G
ATOM  16174  CB   ARG G1063      26.768 106.528  52.997  1.00 46.23       G
```

```
ATOM  16175  CG   ARG G1063    25.404 106.010 53.448  1.00 46.23      G
ATOM  16176  CD   ARG G1063    24.309 107.032 53.187  1.00 46.23      G
ATOM  16177  NE   ARG G1063    22.956 106.509 53.358  1.00 46.23      G
ATOM  16178  CZ   ARG G1063    22.492 105.972 54.482  1.00 46.23      G
ATOM  16179  NH1  ARG G1063    23.272 105.872 55.552  1.00 46.23      G
ATOM  16180  NH2  ARG G1063    21.236 105.549 54.539  1.00 46.23      G
ATOM  16181  C    ARG G1063    25.935 107.206 50.713  1.00 63.31      G
ATOM  16182  O    ARG G1063    24.848 106.689 50.461  1.00 63.31      G
ATOM  16183  N    ALA G1064    26.243 108.442 50.342  1.00 53.81      G
ATOM  16184  CA   ALA G1064    25.304 109.266 49.605  1.00 53.81      G
ATOM  16185  CB   ALA G1064    24.887 110.466 50.430  1.00100.07      G
ATOM  16186  C    ALA G1064    25.934 109.722 48.310  1.00 53.81      G
ATOM  16187  O    ALA G1064    27.155 109.797 48.186  1.00 53.81      G
ATOM  16188  N    GLY G1065    25.077 110.027 47.346  1.00100.07      G
ATOM  16189  CA   GLY G1065    25.538 110.451 46.045  1.00100.07      G
ATOM  16190  C    GLY G1065    26.752 111.350 46.040  1.00100.07      G
ATOM  16191  O    GLY G1065    26.602 112.568 46.109  1.00100.07      G
ATOM  16192  N    LEU G1066    27.951 110.768 45.976  1.00 30.93      G
ATOM  16193  CA   LEU G1066    29.171 111.570 45.902  1.00 30.93      G
ATOM  16194  CB   LEU G1066    30.423 110.692 46.014  1.00 17.99      G
ATOM  16195  CG   LEU G1066    31.718 111.425 45.639  1.00 17.99      G
ATOM  16196  CD1  LEU G1066    31.775 112.698 46.437  1.00 17.99      G
ATOM  16197  CD2  LEU G1066    32.948 110.593 45.892  1.00 17.99      G
ATOM  16198  C    LEU G1066    29.144 112.252 44.531  1.00 30.93      G
ATOM  16199  O    LEU G1066    30.179 112.636 43.988  1.00 30.93      G
ATOM  16200  N    THR G1067    27.934 112.371 43.983  1.00 51.81      G
ATOM  16201  CA   THR G1067    27.670 112.995 42.685  1.00 51.81      G
ATOM  16202  CB   THR G1067    26.306 113.748 42.693  1.00100.07      G
ATOM  16203  OG1  THR G1067    25.237 112.820 42.936  1.00100.07      G
ATOM  16204  CG2  THR G1067    26.075 114.456 41.360  1.00100.07      G
ATOM  16205  C    THR G1067    28.769 113.987 42.348  1.00 51.81      G
ATOM  16206  O    THR G1067    29.286 114.008 41.231  1.00 51.81      G
ATOM  16207  N    VAL G1068    29.110 114.807 43.333  1.00 57.77      G
ATOM  16208  CA   VAL G1068    30.157 115.796 43.191  1.00 57.77      G
ATOM  16209  CB   VAL G1068    30.963 115.937 44.503  1.00100.07      G
ATOM  16210  CG1  VAL G1068    31.207 117.387 44.802  1.00100.07      G
ATOM  16211  CG2  VAL G1068    30.221 115.286 45.654  1.00100.07      G
ATOM  16212  C    VAL G1068    31.115 115.356 42.093  1.00 57.77      G
ATOM  16213  O    VAL G1068    32.024 114.560 42.335  1.00 57.77      G
ATOM  16214  N    LEU G1069    30.887 115.842 40.876  1.00 44.05      G
ATOM  16215  CA   LEU G1069    31.772 115.516 39.773  1.00 44.05      G
ATOM  16216  CB   LEU G1069    31.363 116.236 38.497  1.00 86.00      G
ATOM  16217  CG   LEU G1069    30.122 115.665 37.831  1.00 86.00      G
ATOM  16218  CD1  LEU G1069    29.777 116.516 36.629  1.00 86.00      G
ATOM  16219  CD2  LEU G1069    30.373 114.226 37.430  1.00 86.00      G
ATOM  16220  C    LEU G1069    33.111 116.014 40.242  1.00 44.05      G
ATOM  16221  O    LEU G1069    34.131 115.720 39.638  1.00 44.05      G
ATOM  16222  N    GLU G1070    33.094 116.788 41.326  1.00 52.77      G
ATOM  16223  CA   GLU G1070    34.321 117.258 41.931  1.00 52.77      G
ATOM  16224  CB   GLU G1070    34.043 117.909 43.301  1.00100.07      G
ATOM  16225  CG   GLU G1070    33.432 119.344 43.223  1.00100.07      G
ATOM  16226  CD   GLU G1070    33.019 119.962 44.597  1.00100.07      G
ATOM  16227  OE1  GLU G1070    33.891 120.176 45.478  1.00100.07      G
ATOM  16228  OE2  GLU G1070    31.809 120.248 44.790  1.00100.07      G
ATOM  16229  C    GLU G1070    35.064 115.924 42.079  1.00 52.77      G
ATOM  16230  O    GLU G1070    36.260 115.867 42.355  1.00 52.77      G
ATOM  16231  N    TYR G1071    34.314 114.842 41.880  1.00 53.29      G
ATOM  16232  CA   TYR G1071    34.838 113.481 41.892  1.00 53.29      G
ATOM  16233  CB   TYR G1071    33.873 112.579 41.110  1.00 40.83      G
ATOM  16234  CG   TYR G1071    34.220 111.100 41.044  1.00 40.83      G
ATOM  16235  CD1  TYR G1071    34.974 110.573 39.995  1.00 40.83      G
ATOM  16236  CE1  TYR G1071    35.224 109.207 39.915  1.00 40.83      G
ATOM  16237  CD2  TYR G1071    33.737 110.220 42.007  1.00 40.83      G
ATOM  16238  CE2  TYR G1071    33.985 108.863 41.934  1.00 40.83      G
ATOM  16239  CZ   TYR G1071    34.722 108.361 40.894  1.00 40.83      G
ATOM  16240  OH   TYR G1071    34.941 107.004 40.859  1.00 40.83      G
ATOM  16241  C    TYR G1071    36.176 113.576 41.168  1.00 53.29      G
ATOM  16242  O    TYR G1071    37.179 112.987 41.570  1.00 53.29      G
ATOM  16243  N    PHE G1072    36.172 114.355 40.097  1.00 31.70      G
ATOM  16244  CA   PHE G1072    37.365 114.550 39.320  1.00 31.70      G
ATOM  16245  CB   PHE G1072    37.131 115.554 38.195  1.00 31.59      G
ATOM  16246  CG   PHE G1072    38.379 115.921 37.467  1.00 31.59      G
ATOM  16247  CD1  PHE G1072    38.887 115.092 36.490  1.00 31.59      G
ATOM  16248  CD2  PHE G1072    39.103 117.047 37.837  1.00 31.59      G
ATOM  16249  CE1  PHE G1072    40.109 115.373 35.896  1.00 31.59      G
ATOM  16250  CE2  PHE G1072    40.321 117.337 37.253  1.00 31.59      G
ATOM  16251  CZ   PHE G1072    40.830 116.495 36.278  1.00 31.59      G
ATOM  16252  C    PHE G1072    38.470 115.059 40.213  1.00 31.70      G
ATOM  16253  O    PHE G1072    39.542 114.465 40.250  1.00 31.70      G
ATOM  16254  N    ILE G1073    38.231 116.147 40.939  1.00 20.50      G
ATOM  16255  CA   ILE G1073    39.303 116.667 41.783  1.00 20.50      G
ATOM  16256  CB   ILE G1073    38.845 117.787 42.817  1.00 28.53      G
ATOM  16257  CG2  ILE G1073    39.667 119.028 42.604  1.00 28.53      G
ATOM  16258  CG1  ILE G1073    37.385 118.195 42.646  1.00 28.53      G
```

```
ATOM  16259  CD   ILE G1073     37.044 118.837 41.302  1.00 28.53      G
ATOM  16260  C    ILE G1073     39.975 115.516 42.556  1.00 20.50      G
ATOM  16261  O    ILE G1073     41.208 115.458 42.667  1.00 20.50      G
ATOM  16262  N    SER G1074     39.177 114.583 43.063  1.00 48.50      G
ATOM  16263  CA   SER G1074     39.747 113.474 43.815  1.00 48.50      G
ATOM  16264  CB   SER G1074     38.648 112.735 44.576  1.00 72.43      G
ATOM  16265  OG   SER G1074     37.802 112.045 43.684  1.00 72.43      G
ATOM  16266  C    SER G1074     40.505 112.488 42.924  1.00 48.50      G
ATOM  16267  O    SER G1074     41.507 111.896 43.346  1.00 48.50      G
ATOM  16268  N    SER G1075     40.034 112.332 41.688  1.00 35.08      G
ATOM  16269  CA   SER G1075     40.633 111.400 40.732  1.00 35.08      G
ATOM  16270  CB   SER G1075     39.968 111.554 39.354  1.00 34.50      G
ATOM  16271  OG   SER G1075     40.301 112.777 38.717  1.00 34.50      G
ATOM  16272  C    SER G1075     42.147 111.497 40.573  1.00 35.08      G
ATOM  16273  O    SER G1075     42.787 110.565 40.087  1.00 35.08      G
ATOM  16274  N    HIS G1076     42.719 112.616 40.997  1.00 36.55      G
ATOM  16275  CA   HIS G1076     44.153 112.832 40.863  1.00 36.55      G
ATOM  16276  CB   HIS G1076     44.486 114.286 41.179  1.00 57.34      G
ATOM  16277  CG   HIS G1076     43.813 115.252 40.263  1.00 57.34      G
ATOM  16278  CD2  HIS G1076     42.499 115.488 40.030  1.00 57.34      G
ATOM  16279  ND1  HIS G1076     44.511 116.060 39.393  1.00 57.34      G
ATOM  16280  CE1  HIS G1076     43.654 116.751 38.662  1.00 57.34      G
ATOM  16281  NE2  HIS G1076     42.428 116.421 39.028  1.00 57.34      G
ATOM  16282  C    HIS G1076     44.996 111.917 41.715  1.00 36.55      G
ATOM  16283  O    HIS G1076     45.540 110.930 41.228  1.00 36.55      G
ATOM  16284  N    GLY G1077     45.118 112.262 42.987  1.00 47.07      G
ATOM  16285  CA   GLY G1077     45.910 111.443 43.878  1.00 47.07      G
ATOM  16286  C    GLY G1077     45.578 109.996 43.624  1.00 47.07      G
ATOM  16287  O    GLY G1077     46.477 109.174 43.428  1.00 47.07      G
ATOM  16288  N    ALA G1078     44.276 109.708 43.607  1.00 44.33      G
ATOM  16289  CA   ALA G1078     43.766 108.365 43.378  1.00 44.33      G
ATOM  16290  CB   ALA G1078     42.358 108.439 42.848  1.00 81.23      G
ATOM  16291  C    ALA G1078     44.670 107.648 42.386  1.00 44.33      G
ATOM  16292  O    ALA G1078     45.080 106.507 42.614  1.00 44.33      G
ATOM  16293  N    ARG G1079     44.974 108.324 41.282  1.00 30.21      G
ATOM  16294  CA   ARG G1079     45.866 107.762 40.278  1.00 30.21      G
ATOM  16295  CB   ARG G1079     45.807 108.557 38.978  1.00 26.71      G
ATOM  16296  CG   ARG G1079     44.652 108.157 38.068  1.00 26.71      G
ATOM  16297  CD   ARG G1079     45.009 106.964 37.178  1.00 26.71      G
ATOM  16298  NE   ARG G1079     44.777 107.315 35.784  1.00 26.71      G
ATOM  16299  CZ   ARG G1079     45.529 108.166 35.108  1.00 26.71      G
ATOM  16300  NH1  ARG G1079     46.569 108.739 35.681  1.00 26.71      G
ATOM  16301  NH2  ARG G1079     45.213 108.479 33.875  1.00 26.71      G
ATOM  16302  C    ARG G1079     47.251 107.856 40.858  1.00 30.21      G
ATOM  16303  O    ARG G1079     47.695 106.941 41.527  1.00 30.21      G
ATOM  16304  N    LYS G1080     47.914 108.982 40.623  1.00 43.68      G
ATOM  16305  CA   LYS G1080     49.268 109.212 41.125  1.00 43.68      G
ATOM  16306  CB   LYS G1080     49.406 110.674 41.583  1.00 99.72      G
ATOM  16307  CG   LYS G1080     50.839 111.208 41.550  1.00 99.72      G
ATOM  16308  CD   LYS G1080     50.942 112.633 42.092  1.00 99.72      G
ATOM  16309  CE   LYS G1080     52.395 113.128 42.089  1.00 99.72      G
ATOM  16310  NZ   LYS G1080     52.579 114.480 42.710  1.00 99.72      G
ATOM  16311  C    LYS G1080     49.674 108.251 42.265  1.00 43.68      G
ATOM  16312  O    LYS G1080     50.712 107.585 42.199  1.00 43.68      G
ATOM  16313  N    GLY G1081     48.856 108.172 43.308  1.00 73.58      G
ATOM  16314  CA   GLY G1081     49.183 107.275 44.401  1.00 73.58      G
ATOM  16315  C    GLY G1081     49.310 105.844 43.908  1.00 73.58      G
ATOM  16316  O    GLY G1081     49.663 104.936 44.664  1.00 73.58      G
ATOM  16317  N    GLY G1082     49.019 105.657 42.625  1.00 20.82      G
ATOM  16318  CA   GLY G1082     49.080 104.348 41.997  1.00 20.82      G
ATOM  16319  C    GLY G1082     50.159 104.328 40.936  1.00 20.82      G
ATOM  16320  O    GLY G1082     50.289 103.380 40.146  1.00 20.82      G
ATOM  16321  N    ALA G1083     50.911 105.422 40.903  1.00 56.23      G
ATOM  16322  CA   ALA G1083     52.033 105.555 40.001  1.00 56.23      G
ATOM  16323  CB   ALA G1083     52.226 107.007 39.608  1.00 41.31      G
ATOM  16324  C    ALA G1083     53.201 105.034 40.859  1.00 56.23      G
ATOM  16325  O    ALA G1083     54.294 104.761 40.363  1.00 56.23      G
ATOM  16326  N    ASP G1084     52.951 104.911 42.163  1.00 49.26      G
ATOM  16327  CA   ASP G1084     53.929 104.345 43.086  1.00 49.26      G
ATOM  16328  CB   ASP G1084     53.510 104.542 44.548  1.00 99.92      G
ATOM  16329  CG   ASP G1084     54.124 105.771 45.178  1.00 99.92      G
ATOM  16330  OD1  ASP G1084     55.339 105.990 44.995  1.00 99.92      G
ATOM  16331  OD2  ASP G1084     53.393 106.508 45.875  1.00 99.92      G
ATOM  16332  C    ASP G1084     53.811 102.864 42.750  1.00 49.26      G
ATOM  16333  O    ASP G1084     54.794 102.124 42.732  1.00 49.26      G
ATOM  16334  N    THR G1085     52.572 102.452 42.486  1.00 93.32      G
ATOM  16335  CA   THR G1085     52.234 101.081 42.118  1.00 93.32      G
ATOM  16336  CB   THR G1085     50.767 101.017 41.631  1.00 71.01      G
ATOM  16337  OG1  THR G1085     49.894 101.317 42.728  1.00 71.01      G
ATOM  16338  CG2  THR G1085     50.429  99.648 41.075  1.00 71.01      G
ATOM  16339  C    THR G1085     53.179 100.589 41.019  1.00 93.32      G
ATOM  16340  O    THR G1085     53.247  99.397 40.723  1.00 93.32      G
ATOM  16341  N    ALA G1086     53.905 101.522 40.412  1.00100.07      G
ATOM  16342  CA   ALA G1086     54.872 101.184 39.378  1.00100.07      G
```

```
ATOM  16343  CB  ALA G1086    55.547 102.450 38.846  1.00 80.76      G
ATOM  16344  C   ALA G1086    55.900 100.296 40.057  1.00100.07      G
ATOM  16345  O   ALA G1086    56.518  99.441 39.425  1.00100.07      G
ATOM  16346  N   LEU G1087    56.067 100.515 41.358  1.00 86.97      G
ATOM  16347  CA  LEU G1087    57.003  99.756 42.172  1.00 86.97      G
ATOM  16348  CB  LEU G1087    57.264 100.492 43.480  1.00 84.06      G
ATOM  16349  CG  LEU G1087    58.265  99.852 44.440  1.00 84.06      G
ATOM  16350  CD1 LEU G1087    59.645  99.895 43.834  1.00 84.06      G
ATOM  16351  CD2 LEU G1087    58.251 100.594 45.775  1.00 84.06      G
ATOM  16352  C   LEU G1087    56.485  98.345 42.471  1.00 86.97      G
ATOM  16353  O   LEU G1087    56.336  97.958 43.628  1.00 86.97      G
ATOM  16354  N   ARG G1088    56.193  97.591 41.414  1.00 99.83      G
ATOM  16355  CA  ARG G1088    55.729  96.212 41.532  1.00 99.83      G
ATOM  16356  CB  ARG G1088    54.553  95.942 40.591  1.00100.07      G
ATOM  16357  CG  ARG G1088    54.402  94.462 40.249  1.00100.07      G
ATOM  16358  CD  ARG G1088    53.293  94.194 39.250  1.00100.07      G
ATOM  16359  NE  ARG G1088    53.239  92.777 38.890  1.00100.07      G
ATOM  16360  CZ  ARG G1088    52.197  92.187 38.306  1.00100.07      G
ATOM  16361  NH1 ARG G1088    51.108  92.887 38.012  1.00100.07      G
ATOM  16362  NH2 ARG G1088    52.241  90.892 38.015  1.00100.07      G
ATOM  16363  C   ARG G1088    56.897  95.327 41.123  1.00 99.83      G
ATOM  16364  O   ARG G1088    57.164  94.300 41.750  1.00 99.83      G
ATOM  16365  N   THR G1089    57.578  95.735 40.052  1.00 47.42      G
ATOM  16366  CA  THR G1089    58.729  95.007 39.540  1.00 47.42      G
ATOM  16367  CB  THR G1089    58.886  95.212 38.020  1.00100.07      G
ATOM  16368  OG1 THR G1089    58.031  94.290 37.329  1.00100.07      G
ATOM  16369  CG2 THR G1089    60.332  94.993 37.586  1.00100.07      G
ATOM  16370  C   THR G1089    59.979  95.492 40.263  1.00 47.42      G
ATOM  16371  O   THR G1089    60.905  94.718 40.533  1.00 47.42      G
ATOM  16372  N   ALA G1090    60.005  96.777 40.580  1.00100.07      G
ATOM  16373  CA  ALA G1090    61.137  97.317 41.305  1.00100.07      G
ATOM  16374  CB  ALA G1090    61.026  98.838 41.383  1.00100.07      G
ATOM  16375  C   ALA G1090    61.176  96.675 42.716  1.00100.07      G
ATOM  16376  O   ALA G1090    60.951  97.328 43.749  1.00100.07      G
ATOM  16377  N   ASP G1091    61.443  95.369 42.717  1.00 53.59      G
ATOM  16378  CA  ASP G1091    61.560  94.536 43.913  1.00 53.59      G
ATOM  16379  CB  ASP G1091    60.204  93.931 44.289  1.00100.07      G
ATOM  16380  CG  ASP G1091    59.757  92.837 43.327  1.00100.07      G
ATOM  16381  OD1 ASP G1091    59.722  93.080 42.101  1.00100.07      G
ATOM  16382  OD2 ASP G1091    59.431  91.731 43.805  1.00100.07      G
ATOM  16383  C   ASP G1091    62.490  93.453 43.399  1.00 53.59      G
ATOM  16384  O   ASP G1091    63.373  92.947 44.112  1.00 53.59      G
ATOM  16385  N   SER G1092    62.251  93.128 42.128  1.00 95.38      G
ATOM  16386  CA  SER G1092    63.023  92.157 41.372  1.00 95.38      G
ATOM  16387  CB  SER G1092    62.170  91.484 40.281  1.00100.07      G
ATOM  16388  OG  SER G1092    61.129  90.683 40.817  1.00100.07      G
ATOM  16389  C   SER G1092    64.095  93.014 40.716  1.00 95.38      G
ATOM  16390  O   SER G1092    63.918  93.524 39.609  1.00 95.38      G
ATOM  16391  N   GLY G1093    65.199  93.192 41.425  1.00 99.90      G
ATOM  16392  CA  GLY G1093    66.277  93.997 40.895  1.00 99.90      G
ATOM  16393  C   GLY G1093    66.861  94.877 41.975  1.00 99.90      G
ATOM  16394  O   GLY G1093    68.077  95.077 42.039  1.00 99.90      G
ATOM  16395  N   TYR G1094    66.003  95.412 42.835  1.00 44.83      G
ATOM  16396  CA  TYR G1094    66.505  96.256 43.888  1.00 44.83      G
ATOM  16397  CB  TYR G1094    65.902  97.670 43.798  1.00 67.32      G
ATOM  16398  CG  TYR G1094    66.882  98.719 43.284  1.00 67.32      G
ATOM  16399  CD1 TYR G1094    66.626  99.438 42.111  1.00 67.32      G
ATOM  16400  CE1 TYR G1094    67.558 100.382 41.609  1.00 67.32      G
ATOM  16401  CD2 TYR G1094    68.087  98.968 43.955  1.00 67.32      G
ATOM  16402  CE2 TYR G1094    69.018  99.906 43.469  1.00 67.32      G
ATOM  16403  CZ  TYR G1094    68.753 100.608 42.295  1.00 67.32      G
ATOM  16404  OH  TYR G1094    69.682 101.515 41.807  1.00 67.32      G
ATOM  16405  C   TYR G1094    66.284  95.663 45.265  1.00 44.83      G
ATOM  16406  O   TYR G1094    65.579  94.658 45.441  1.00 44.83      G
ATOM  16407  N   LEU G1095    66.937  96.318 46.222  1.00 70.38      G
ATOM  16408  CA  LEU G1095    66.938  96.001 47.638  1.00 70.38      G
ATOM  16409  CB  LEU G1095    65.576  96.293 48.257  1.00 79.21      G
ATOM  16410  CG  LEU G1095    65.724  96.563 49.760  1.00 79.21      G
ATOM  16411  CD1 LEU G1095    66.901  97.484 50.019  1.00 79.21      G
ATOM  16412  CD2 LEU G1095    64.447  97.176 50.309  1.00 79.21      G
ATOM  16413  C   LEU G1095    67.396  94.602 47.999  1.00 70.38      G
ATOM  16414  O   LEU G1095    68.594  94.380 48.143  1.00 70.38      G
ATOM  16415  N   THR G1096    66.469  93.659 48.143  1.00 20.62      G
ATOM  16416  CA  THR G1096    66.862  92.304 48.522  1.00 20.62      G
ATOM  16417  CB  THR G1096    65.821  91.266 48.176  1.00 21.56      G
ATOM  16418  OG1 THR G1096    64.554  91.671 48.677  1.00 21.56      G
ATOM  16419  CG2 THR G1096    66.188  89.957 48.803  1.00 21.56      G
ATOM  16420  C   THR G1096    68.118  91.885 47.790  1.00 20.62      G
ATOM  16421  O   THR G1096    69.128  91.523 48.410  1.00 20.62      G
ATOM  16422  N   ARG G1097    68.039  91.931 46.461  1.00 41.74      G
ATOM  16423  CA  ARG G1097    69.154  91.554 45.607  1.00 41.74      G
ATOM  16424  CB  ARG G1097    68.906  92.026 44.169  1.00 30.60      G
ATOM  16425  CG  ARG G1097    69.768  91.316 43.116  1.00 30.60      G
ATOM  16426  CD  ARG G1097    69.448  91.724 41.656  1.00 30.60      G
```

```
ATOM  16427  NE   ARG G1097      68.074  91.432  41.234  1.00 30.60           G
ATOM  16428  CZ   ARG G1097      67.467  90.257  41.381  1.00 30.60           G
ATOM  16429  NH1  ARG G1097      68.095  89.239  41.949  1.00 30.60           G
ATOM  16430  NH2  ARG G1097      66.228  90.093  40.944  1.00 30.60           G
ATOM  16431  C    ARG G1097      70.388  92.219  46.181  1.00 41.74           G
ATOM  16432  O    ARG G1097      71.259  91.552  46.750  1.00 41.74           G
ATOM  16433  N    LYS G1098      70.437  93.541  46.077  1.00 42.11           G
ATOM  16434  CA   LYS G1098      71.577  94.290  46.587  1.00 42.11           G
ATOM  16435  CB   LYS G1098      71.287  95.794  46.517  1.00 64.01           G
ATOM  16436  CG   LYS G1098      70.912  96.233  45.104  1.00 64.01           G
ATOM  16437  CD   LYS G1098      71.387  97.629  44.751  1.00 64.01           G
ATOM  16438  CE   LYS G1098      71.324  97.817  43.238  1.00 64.01           G
ATOM  16439  NZ   LYS G1098      71.881  99.118  42.752  1.00 64.01           G
ATOM  16440  C    LYS G1098      71.990  93.866  48.000  1.00 42.11           G
ATOM  16441  O    LYS G1098      73.178  93.832  48.317  1.00 42.11           G
ATOM  16442  N    LEU G1099      71.029  93.514  48.844  1.00 27.56           G
ATOM  16443  CA   LEU G1099      71.385  93.095  50.187  1.00 27.56           G
ATOM  16444  CB   LEU G1099      70.205  93.224  51.146  1.00 19.19           G
ATOM  16445  CG   LEU G1099      69.967  94.623  51.696  1.00 19.19           G
ATOM  16446  CD1  LEU G1099      69.308  95.475  50.634  1.00 19.19           G
ATOM  16447  CD2  LEU G1099      69.098  94.539  52.928  1.00 19.19           G
ATOM  16448  C    LEU G1099      71.906  91.678  50.254  1.00 27.56           G
ATOM  16449  O    LEU G1099      72.923  91.427  50.896  1.00 27.56           G
ATOM  16450  N    VAL G1100      71.217  90.748  49.603  1.00 50.00           G
ATOM  16451  CA   VAL G1100      71.642  89.356  49.656  1.00 50.00           G
ATOM  16452  CB   VAL G1100      70.719  88.428  48.849  1.00 23.71           G
ATOM  16453  CG1  VAL G1100      70.939  86.991  49.293  1.00 23.71           G
ATOM  16454  CG2  VAL G1100      69.277  88.826  49.024  1.00 23.71           G
ATOM  16455  C    VAL G1100      73.056  89.170  49.132  1.00 50.00           G
ATOM  16456  O    VAL G1100      73.817  88.355  49.674  1.00 50.00           G
ATOM  16457  N    ASP G1101      73.392  89.918  48.076  1.00 90.08           G
ATOM  16458  CA   ASP G1101      74.715  89.856  47.456  1.00 90.08           G
ATOM  16459  CB   ASP G1101      74.790  90.774  46.235  1.00 70.60           G
ATOM  16460  CG   ASP G1101      74.333  90.090  44.954  1.00 70.60           G
ATOM  16461  OD1  ASP G1101      74.641  88.888  44.775  1.00 70.60           G
ATOM  16462  OD2  ASP G1101      73.684  90.761  44.116  1.00 70.60           G
ATOM  16463  C    ASP G1101      75.794  90.261  48.447  1.00 90.08           G
ATOM  16464  O    ASP G1101      76.888  89.698  48.454  1.00 90.08           G
ATOM  16465  N    VAL G1102      75.479  91.258  49.269  1.00 37.65           G
ATOM  16466  CA   VAL G1102      76.386  91.753  50.302  1.00 37.65           G
ATOM  16467  CB   VAL G1102      76.268  93.275  50.477  1.00 32.78           G
ATOM  16468  CG1  VAL G1102      77.236  93.745  51.511  1.00 32.78           G
ATOM  16469  CG2  VAL G1102      76.509  93.977  49.175  1.00 32.78           G
ATOM  16470  C    VAL G1102      75.850  91.151  51.577  1.00 37.65           G
ATOM  16471  O    VAL G1102      75.069  91.812  52.245  1.00 37.65           G
ATOM  16472  N    ALA G1103      76.238  89.919  51.907  1.00 19.95           G
ATOM  16473  CA   ALA G1103      75.753  89.236  53.127  1.00 19.95           G
ATOM  16474  CB   ALA G1103      74.347  89.710  53.502  1.00  5.07           G
ATOM  16475  C    ALA G1103      75.725  87.723  52.933  1.00 19.95           G
ATOM  16476  O    ALA G1103      75.953  86.963  53.892  1.00 19.95           G
ATOM  16477  N    HIS G1104      75.411  87.308  51.697  1.00 33.27           G
ATOM  16478  CA   HIS G1104      75.359  85.902  51.293  1.00 33.27           G
ATOM  16479  CB   HIS G1104      76.207  85.700  50.035  1.00 99.06           G
ATOM  16480  CG   HIS G1104      76.412  84.263  49.668  1.00 99.06           G
ATOM  16481  CD2  HIS G1104      76.629  83.665  48.475  1.00 99.06           G
ATOM  16482  ND1  HIS G1104      76.390  83.246  50.605  1.00 99.06           G
ATOM  16483  CE1  HIS G1104      76.577  82.088  50.001  1.00 99.06           G
ATOM  16484  NE2  HIS G1104      76.726  82.310  48.706  1.00 99.06           G
ATOM  16485  C    HIS G1104      75.913  84.995  52.389  1.00 33.27           G
ATOM  16486  O    HIS G1104      75.187  84.238  53.032  1.00 33.27           G
ATOM  16487  N    GLU G1105      77.227  85.120  52.572  1.00 33.95           G
ATOM  16488  CA   GLU G1105      78.044  84.359  53.511  1.00 33.95           G
ATOM  16489  CB   GLU G1105      79.492  84.738  53.298  1.00 61.18           G
ATOM  16490  CG   GLU G1105      79.756  86.201  53.453  1.00 61.18           G
ATOM  16491  CD   GLU G1105      80.925  86.639  52.608  1.00 61.18           G
ATOM  16492  OE1  GLU G1105      81.857  85.824  52.433  1.00 61.18           G
ATOM  16493  OE2  GLU G1105      80.919  87.792  52.119  1.00 61.18           G
ATOM  16494  C    GLU G1105      77.765  84.389  55.000  1.00 33.95           G
ATOM  16495  O    GLU G1105      77.658  83.333  55.609  1.00 33.95           G
ATOM  16496  N    ILE G1106      77.675  85.576  55.599  1.00 37.01           G
ATOM  16497  CA   ILE G1106      77.442  85.675  57.045  1.00 37.01           G
ATOM  16498  CB   ILE G1106      76.808  87.012  57.458  1.00  9.16           G
ATOM  16499  CG2  ILE G1106      76.363  86.939  58.890  1.00  9.16           G
ATOM  16500  CG1  ILE G1106      77.794  88.155  57.262  1.00  9.16           G
ATOM  16501  CD   ILE G1106      78.118  88.385  55.822  1.00  9.16           G
ATOM  16502  C    ILE G1106      76.531  84.581  57.550  1.00 37.01           G
ATOM  16503  O    ILE G1106      75.422  84.428  57.055  1.00 37.01           G
ATOM  16504  N    VAL G1107      76.998  83.832  58.544  1.00 34.39           G
ATOM  16505  CA   VAL G1107      76.225  82.734  59.120  1.00 34.39           G
ATOM  16506  CB   VAL G1107      76.448  81.418  58.322  1.00 10.86           G
ATOM  16507  CG1  VAL G1107      75.886  80.234  59.079  1.00 10.86           G
ATOM  16508  CG2  VAL G1107      75.808  81.511  56.951  1.00 10.86           G
ATOM  16509  C    VAL G1107      76.630  82.481  60.571  1.00 34.39           G
ATOM  16510  O    VAL G1107      77.575  83.078  61.088  1.00 34.39           G
```

```
ATOM   16511  N    VAL G1108      75.883  81.616  61.241  1.00 74.13           G
ATOM   16512  CA   VAL G1108      76.202  81.253  62.603  1.00 74.13           G
ATOM   16513  CB   VAL G1108      74.998  80.588  63.307  1.00 94.80           G
ATOM   16514  CG1  VAL G1108      75.430  80.009  64.642  1.00 94.80           G
ATOM   16515  CG2  VAL G1108      73.877  81.607  63.503  1.00 94.80           G
ATOM   16516  C    VAL G1108      77.326  80.243  62.446  1.00 74.13           G
ATOM   16517  O    VAL G1108      77.209  79.280  61.686  1.00 74.13           G
ATOM   16518  N    ALA G1109      78.428  80.484  63.139  1.00 80.78           G
ATOM   16519  CA   ALA G1109      79.571  79.588  63.079  1.00 80.78           G
ATOM   16520  CB   ALA G1109      80.559  80.078  62.031  1.00100.07           G
ATOM   16521  C    ALA G1109      80.225  79.542  64.458  1.00 80.78           G
ATOM   16522  O    ALA G1109      80.878  80.505  64.880  1.00 80.78           G
ATOM   16523  N    ALA G1110      80.036  78.421  65.154  1.00 75.91           G
ATOM   16524  CA   ALA G1110      80.580  78.219  66.497  1.00 75.91           G
ATOM   16525  CB   ALA G1110      81.997  78.799  66.604  1.00100.07           G
ATOM   16526  C    ALA G1110      79.674  78.871  67.530  1.00 75.91           G
ATOM   16527  O    ALA G1110      78.789  79.653  67.189  1.00 75.91           G
ATOM   16528  N    ALA G1111      79.891  78.543  68.797  1.00100.07           G
ATOM   16529  CA   ALA G1111      79.082  79.118  69.857  1.00100.07           G
ATOM   16530  CB   ALA G1111      79.348  78.405  71.165  1.00 58.97           G
ATOM   16531  C    ALA G1111      79.401  80.600  69.989  1.00100.07           G
ATOM   16532  O    ALA G1111      79.284  81.357  69.025  1.00100.07           G
ATOM   16533  N    ALA G1112      79.808  81.014  71.183  1.00100.07           G
ATOM   16534  CA   ALA G1112      80.125  82.415  71.429  1.00100.07           G
ATOM   16535  CB   ALA G1112      79.212  82.969  72.532  1.00100.07           G
ATOM   16536  C    ALA G1112      81.589  82.631  71.803  1.00100.07           G
ATOM   16537  O    ALA G1112      82.048  82.185  72.855  1.00100.07           G
ATOM   16538  N    CYS G1113      82.314  83.325  70.933  1.00 79.58           G
ATOM   16539  CA   CYS G1113      83.720  83.617  71.169  1.00 79.58           G
ATOM   16540  CB   CYS G1113      84.318  84.306  69.948  1.00 54.65           G
ATOM   16541  SG   CYS G1113      83.687  85.968  69.714  1.00 54.65           G
ATOM   16542  C    CYS G1113      83.868  84.527  72.392  1.00 79.58           G
ATOM   16543  O    CYS G1113      83.153  84.370  73.387  1.00 79.58           G
ATOM   16544  N    ALA G1114      84.786  85.487  72.305  1.00 85.23           G
ATOM   16545  CA   ALA G1114      85.042  86.414  73.404  1.00 85.23           G
ATOM   16546  CB   ALA G1114      86.548  86.629  73.563  1.00 77.65           G
ATOM   16547  C    ALA G1114      84.341  87.762  73.266  1.00 85.23           G
ATOM   16548  O    ALA G1114      84.315  88.365  72.188  1.00 85.23           G
ATOM   16549  N    ALA G1115      83.777  88.224  74.380  1.00 93.16           G
ATOM   16550  CA   ALA G1115      83.086  89.504  74.429  1.00 93.16           G
ATOM   16551  CB   ALA G1115      82.504  89.738  75.814  1.00100.07           G
ATOM   16552  C    ALA G1115      84.094  90.586  74.107  1.00 93.16           G
ATOM   16553  O    ALA G1115      84.446  90.781  72.944  1.00 93.16           G
ATOM   16554  N    ALA G1116      84.573  91.271  75.142  1.00 99.71           G
ATOM   16555  CA   ALA G1116      85.545  92.336  74.955  1.00 99.71           G
ATOM   16556  CB   ALA G1116      86.885  91.753  74.517  1.00 84.39           G
ATOM   16557  C    ALA G1116      85.010  93.296  73.895  1.00 99.71           G
ATOM   16558  O    ALA G1116      85.774  93.905  73.136  1.00 99.71           G
ATOM   16559  N    ALA G1117      83.683  93.405  73.849  1.00 39.32           G
ATOM   16560  CA   ALA G1117      82.980  94.277  72.907  1.00 39.32           G
ATOM   16561  CB   ALA G1117      83.255  93.855  71.468  1.00100.07           G
ATOM   16562  C    ALA G1117      81.505  94.118  73.239  1.00 39.32           G
ATOM   16563  O    ALA G1117      81.058  93.027  73.593  1.00 39.32           G
ATOM   16564  N    ALA G1118      80.755  95.206  73.137  1.00 41.85           G
ATOM   16565  CA   ALA G1118      79.343  95.176  73.470  1.00 41.85           G
ATOM   16566  CB   ALA G1118      79.179  95.149  74.976  1.00  5.07           G
ATOM   16567  C    ALA G1118      78.684  96.414  72.912  1.00 41.85           G
ATOM   16568  O    ALA G1118      79.298  97.476  72.868  1.00 41.85           G
ATOM   16569  N    ILE G1119      77.439  96.277  72.474  1.00 43.82           G
ATOM   16570  CA   ILE G1119      76.706  97.411  71.942  1.00 43.82           G
ATOM   16571  CB   ILE G1119      75.699  96.996  70.858  1.00 99.50           G
ATOM   16572  CG2  ILE G1119      75.003  98.223  70.311  1.00 99.50           G
ATOM   16573  CG1  ILE G1119      76.407  96.255  69.726  1.00 99.50           G
ATOM   16574  CD   ILE G1119      77.419  97.094  68.983  1.00 99.50           G
ATOM   16575  C    ILE G1119      75.919  97.912  73.130  1.00 43.82           G
ATOM   16576  O    ILE G1119      75.474  97.108  73.944  1.00 43.82           G
ATOM   16577  N    SER G1120      75.768  99.228  73.253  1.00 48.70           G
ATOM   16578  CA   SER G1120      74.994  99.797  74.351  1.00 48.70           G
ATOM   16579  CB   SER G1120      75.824 100.830  75.113  1.00 93.21           G
ATOM   16580  OG   SER G1120      75.494 100.821  76.492  1.00 93.21           G
ATOM   16581  C    SER G1120      73.784 100.452  73.692  1.00 48.70           G
ATOM   16582  O    SER G1120      73.873 101.574  73.190  1.00 48.70           G
ATOM   16583  N    VAL G1121      72.665  99.728  73.681  1.00 20.14           G
ATOM   16584  CA   VAL G1121      71.415 100.184  73.059  1.00 20.14           G
ATOM   16585  CB   VAL G1121      70.455  99.024  72.848  1.00 44.00           G
ATOM   16586  CG1  VAL G1121      69.144  99.555  72.313  1.00 44.00           G
ATOM   16587  CG2  VAL G1121      71.069  98.004  71.893  1.00 44.00           G
ATOM   16588  C    VAL G1121      70.641 101.253  73.813  1.00 20.14           G
ATOM   16589  O    VAL G1121      69.948 100.956  74.782  1.00 20.14           G
ATOM   16590  N    PRO G1122      70.711 102.505  73.342  1.00 43.02           G
ATOM   16591  CD   PRO G1122      71.225 102.887  72.022  1.00 45.30           G
ATOM   16592  CA   PRO G1122      70.026 103.641  73.961  1.00 43.02           G
ATOM   16593  CB   PRO G1122      70.218 104.751  72.938  1.00 45.30           G
ATOM   16594  CG   PRO G1122      70.307 104.015  71.658  1.00 45.30           G
```

| | | | | | | | | |
|---|---|---|---|---|---|---|---|---|
| ATOM | 16595 | C | PRO G1122 | 68.565 | 103.386 | 74.275 | 1.00 43.02 | G |
| ATOM | 16596 | O | PRO G1122 | 67.815 | 102.888 | 73.439 | 1.00 43.02 | G |
| ATOM | 16597 | N | LEU G1123 | 68.177 | 103.736 | 75.492 | 1.00 52.94 | G |
| ATOM | 16598 | CA | LEU G1123 | 66.813 | 103.550 | 75.943 | 1.00 52.94 | G |
| ATOM | 16599 | CB | LEU G1123 | 66.805 | 103.003 | 77.360 | 1.00 81.45 | G |
| ATOM | 16600 | CG | LEU G1123 | 65.866 | 101.820 | 77.516 | 1.00 81.45 | G |
| ATOM | 16601 | CD1 | LEU G1123 | 66.243 | 100.763 | 76.500 | 1.00 81.45 | G |
| ATOM | 16602 | CD2 | LEU G1123 | 65.957 | 101.266 | 78.924 | 1.00 81.45 | G |
| ATOM | 16603 | C | LEU G1123 | 66.083 | 104.877 | 75.907 | 1.00 52.94 | G |
| ATOM | 16604 | O | LEU G1123 | 64.925 | 104.965 | 76.312 | 1.00 52.94 | G |
| ATOM | 16605 | N | PHE G1124 | 66.780 | 105.911 | 75.445 | 1.00 31.39 | G |
| ATOM | 16606 | CA | PHE G1124 | 66.234 | 107.261 | 75.327 | 1.00 31.39 | G |
| ATOM | 16607 | CB | PHE G1124 | 66.658 | 108.175 | 76.491 | 1.00 34.97 | G |
| ATOM | 16608 | CG | PHE G1124 | 66.067 | 107.835 | 77.839 | 1.00 34.97 | G |
| ATOM | 16609 | CD1 | PHE G1124 | 65.305 | 108.774 | 78.516 | 1.00 34.97 | G |
| ATOM | 16610 | CD2 | PHE G1124 | 66.364 | 106.642 | 78.481 | 1.00 34.97 | G |
| ATOM | 16611 | CE1 | PHE G1124 | 64.854 | 108.540 | 79.813 | 1.00 34.97 | G |
| ATOM | 16612 | CE2 | PHE G1124 | 65.916 | 106.397 | 79.783 | 1.00 34.97 | G |
| ATOM | 16613 | CZ | PHE G1124 | 65.162 | 107.349 | 80.450 | 1.00 34.97 | G |
| ATOM | 16614 | C | PHE G1124 | 66.995 | 107.749 | 74.118 | 1.00 31.39 | G |
| ATOM | 16615 | O | PHE G1124 | 68.151 | 107.376 | 73.955 | 1.00 31.39 | G |
| ATOM | 16616 | N | GLN G1125 | 66.370 | 108.564 | 73.273 | 1.00 51.71 | G |
| ATOM | 16617 | CA | GLN G1125 | 67.057 | 109.131 | 72.113 | 1.00 51.71 | G |
| ATOM | 16618 | CB | GLN G1125 | 66.763 | 108.333 | 70.841 | 1.00100.07 | G |
| ATOM | 16619 | CG | GLN G1125 | 67.457 | 106.961 | 70.849 | 1.00100.07 | G |
| ATOM | 16620 | CD | GLN G1125 | 67.872 | 106.461 | 69.464 | 1.00100.07 | G |
| ATOM | 16621 | OE1 | GLN G1125 | 67.030 | 106.164 | 68.611 | 1.00100.07 | G |
| ATOM | 16622 | NE2 | GLN G1125 | 69.181 | 106.365 | 69.241 | 1.00100.07 | G |
| ATOM | 16623 | C | GLN G1125 | 66.636 | 110.586 | 71.985 | 1.00 51.71 | G |
| ATOM | 16624 | O | GLN G1125 | 65.596 | 110.978 | 72.513 | 1.00 51.71 | G |
| ATOM | 16625 | N | MET G1126 | 67.441 | 111.392 | 71.299 | 1.00 69.05 | G |
| ATOM | 16626 | CA | MET G1126 | 67.138 | 112.817 | 71.198 | 1.00 69.05 | G |
| ATOM | 16627 | CB | MET G1126 | 68.420 | 113.637 | 71.401 | 1.00 64.82 | G |
| ATOM | 16628 | CG | MET G1126 | 68.161 | 115.065 | 71.863 | 1.00 64.82 | G |
| ATOM | 16629 | SD | MET G1126 | 69.607 | 115.912 | 72.471 | 1.00 64.82 | G |
| ATOM | 16630 | CE | MET G1126 | 69.514 | 115.592 | 74.183 | 1.00 64.82 | G |
| ATOM | 16631 | C | MET G1126 | 66.369 | 113.370 | 69.995 | 1.00 69.05 | G |
| ATOM | 16632 | O | MET G1126 | 65.937 | 112.639 | 69.099 | 1.00 69.05 | G |
| ATOM | 16633 | N | ASP G1127 | 66.222 | 114.694 | 70.028 | 1.00 63.88 | G |
| ATOM | 16634 | CA | ASP G1127 | 65.480 | 115.491 | 69.064 | 1.00 63.88 | G |
| ATOM | 16635 | CB | ASP G1127 | 64.310 | 116.128 | 69.820 | 1.00 67.63 | G |
| ATOM | 16636 | CG | ASP G1127 | 63.379 | 116.887 | 68.930 | 1.00 67.63 | G |
| ATOM | 16637 | OD1 | ASP G1127 | 63.857 | 117.778 | 68.209 | 1.00 67.63 | G |
| ATOM | 16638 | OD2 | ASP G1127 | 62.164 | 116.602 | 68.960 | 1.00 67.63 | G |
| ATOM | 16639 | C | ASP G1127 | 66.373 | 116.578 | 68.443 | 1.00 63.88 | G |
| ATOM | 16640 | O | ASP G1127 | 66.435 | 117.699 | 68.956 | 1.00 63.88 | G |
| ATOM | 16641 | N | GLU G1128 | 67.044 | 116.237 | 67.337 | 1.00 39.80 | G |
| ATOM | 16642 | CA | GLU G1128 | 67.954 | 117.148 | 66.625 | 1.00 39.80 | G |
| ATOM | 16643 | CB | GLU G1128 | 68.030 | 116.778 | 65.137 | 1.00100.07 | G |
| ATOM | 16644 | CG | GLU G1128 | 68.983 | 115.627 | 64.801 | 1.00100.07 | G |
| ATOM | 16645 | CD | GLU G1128 | 69.123 | 115.382 | 63.296 | 1.00100.07 | G |
| ATOM | 16646 | OE1 | GLU G1128 | 68.162 | 114.877 | 62.675 | 1.00100.07 | G |
| ATOM | 16647 | OE2 | GLU G1128 | 70.195 | 115.700 | 62.731 | 1.00100.07 | G |
| ATOM | 16648 | C | GLU G1128 | 67.516 | 118.593 | 66.754 | 1.00 39.80 | G |
| ATOM | 16649 | O | GLU G1128 | 68.311 | 119.480 | 67.055 | 1.00 39.80 | G |
| ATOM | 16650 | N | VAL G1129 | 66.223 | 118.791 | 66.529 | 1.00 21.61 | G |
| ATOM | 16651 | CA | VAL G1129 | 65.545 | 120.086 | 66.572 | 1.00 21.61 | G |
| ATOM | 16652 | CB | VAL G1129 | 64.079 | 119.931 | 66.094 | 1.00100.07 | G |
| ATOM | 16653 | CG1 | VAL G1129 | 63.352 | 121.273 | 66.167 | 1.00100.07 | G |
| ATOM | 16654 | CG2 | VAL G1129 | 64.050 | 119.352 | 64.679 | 1.00100.07 | G |
| ATOM | 16655 | C | VAL G1129 | 65.505 | 120.796 | 67.919 | 1.00 21.61 | G |
| ATOM | 16656 | O | VAL G1129 | 66.322 | 121.657 | 68.196 | 1.00 21.61 | G |
| ATOM | 16657 | N | THR G1130 | 64.528 | 120.436 | 68.738 | 1.00 22.57 | G |
| ATOM | 16658 | CA | THR G1130 | 64.345 | 121.059 | 70.035 | 1.00 22.57 | G |
| ATOM | 16659 | CB | THR G1130 | 62.871 | 120.994 | 70.437 | 1.00100.07 | G |
| ATOM | 16660 | OG1 | THR G1130 | 62.417 | 119.637 | 70.352 | 1.00100.07 | G |
| ATOM | 16661 | CG2 | THR G1130 | 62.036 | 121.860 | 69.510 | 1.00100.07 | G |
| ATOM | 16662 | C | THR G1130 | 65.201 | 120.495 | 71.176 | 1.00 22.57 | G |
| ATOM | 16663 | O | THR G1130 | 64.840 | 120.616 | 72.349 | 1.00 22.57 | G |
| ATOM | 16664 | N | ARG G1131 | 66.336 | 119.893 | 70.829 | 1.00 39.84 | G |
| ATOM | 16665 | CA | ARG G1131 | 67.255 | 119.330 | 71.818 | 1.00 39.84 | G |
| ATOM | 16666 | CB | ARG G1131 | 68.319 | 120.350 | 72.175 | 1.00 61.97 | G |
| ATOM | 16667 | CG | ARG G1131 | 69.260 | 120.667 | 71.053 | 1.00 61.97 | G |
| ATOM | 16668 | CD | ARG G1131 | 69.558 | 122.135 | 71.079 | 1.00 61.97 | G |
| ATOM | 16669 | NE | ARG G1131 | 70.770 | 122.468 | 70.350 | 1.00 61.97 | G |
| ATOM | 16670 | CZ | ARG G1131 | 71.282 | 123.692 | 70.319 | 1.00 61.97 | G |
| ATOM | 16671 | NH1 | ARG G1131 | 70.670 | 124.672 | 70.970 | 1.00 61.97 | G |
| ATOM | 16672 | NH2 | ARG G1131 | 72.410 | 123.933 | 69.667 | 1.00 61.97 | G |
| ATOM | 16673 | C | ARG G1131 | 66.564 | 118.898 | 73.091 | 1.00 39.84 | G |
| ATOM | 16674 | O | ARG G1131 | 66.430 | 119.694 | 74.016 | 1.00 39.84 | G |
| ATOM | 16675 | N | THR G1132 | 66.127 | 117.641 | 73.133 | 1.00 77.69 | G |
| ATOM | 16676 | CA | THR G1132 | 65.455 | 117.084 | 74.306 | 1.00 77.69 | G |
| ATOM | 16677 | CB | THR G1132 | 64.019 | 117.612 | 74.428 | 1.00 62.99 | G |
| ATOM | 16678 | OG1 | THR G1132 | 63.972 | 118.963 | 73.965 | 1.00 62.99 | G |

```
ATOM  16679  CG2 THR G1132     63.562 117.589 75.879  1.00 62.99      G
ATOM  16680  C   THR G1132     65.417 115.559 74.190  1.00 77.69      G
ATOM  16681  O   THR G1132     65.805 115.001 73.165  1.00 77.69      G
ATOM  16682  N   LEU G1133     64.943 114.883 75.231  1.00 64.19      G
ATOM  16683  CA  LEU G1133     64.892 113.428 75.208  1.00 64.19      G
ATOM  16684  CB  LEU G1133     65.770 112.891 76.326  1.00 56.52      G
ATOM  16685  CG  LEU G1133     67.187 113.433 76.167  1.00 56.52      G
ATOM  16686  CD1 LEU G1133     68.121 112.787 77.179  1.00 56.52      G
ATOM  16687  CD2 LEU G1133     67.658 113.148 74.735  1.00 56.52      G
ATOM  16688  C   LEU G1133     63.499 112.829 75.300  1.00 64.19      G
ATOM  16689  O   LEU G1133     62.511 113.541 75.442  1.00 64.19      G
ATOM  16690  N   ARG G1134     63.419 111.508 75.209  1.00 56.37      G
ATOM  16691  CA  ARG G1134     62.131 110.831 75.282  1.00 56.37      G
ATOM  16692  CB  ARG G1134     61.496 110.742 73.901  1.00100.07      G
ATOM  16693  CG  ARG G1134     61.361 112.070 73.188  1.00100.07      G
ATOM  16694  CD  ARG G1134     60.659 111.872 71.869  1.00100.07      G
ATOM  16695  NE  ARG G1134     61.392 112.486 70.773  1.00100.07      G
ATOM  16696  CZ  ARG G1134     61.219 112.165 69.497  1.00100.07      G
ATOM  16697  NH1 ARG G1134     60.334 111.230 69.162  1.00100.07      G
ATOM  16698  NH2 ARG G1134     61.931 112.776 68.557  1.00100.07      G
ATOM  16699  C   ARG G1134     62.297 109.434 75.834  1.00 56.37      G
ATOM  16700  O   ARG G1134     63.387 108.856 75.773  1.00 56.37      G
ATOM  16701  N   LEU G1135     61.208 108.880 76.352  1.00 56.74      G
ATOM  16702  CA  LEU G1135     61.266 107.549 76.931  1.00 56.74      G
ATOM  16703  CB  LEU G1135     59.902 107.127 77.451  1.00100.07      G
ATOM  16704  CG  LEU G1135     59.335 108.146 78.430  1.00100.07      G
ATOM  16705  CD1 LEU G1135     58.639 109.261 77.650  1.00100.07      G
ATOM  16706  CD2 LEU G1135     58.370 107.459 79.375  1.00100.07      G
ATOM  16707  C   LEU G1135     61.749 106.549 75.916  1.00 56.74      G
ATOM  16708  O   LEU G1135     62.032 105.405 76.269  1.00 56.74      G
ATOM  16709  N   ARG G1136     61.838 106.995 74.663  1.00 30.68      G
ATOM  16710  CA  ARG G1136     62.292 106.168 73.551  1.00 30.68      G
ATOM  16711  CB  ARG G1136     63.505 105.339 73.965  1.00 81.83      G
ATOM  16712  CG  ARG G1136     64.701 105.467 73.055  1.00 81.83      G
ATOM  16713  CD  ARG G1136     64.372 105.021 71.654  1.00 81.83      G
ATOM  16714  NE  ARG G1136     65.323 104.031 71.169  1.00 81.83      G
ATOM  16715  CZ  ARG G1136     65.356 103.594 69.919  1.00 81.83      G
ATOM  16716  NH1 ARG G1136     64.493 104.064 69.030  1.00 81.83      G
ATOM  16717  NH2 ARG G1136     66.246 102.682 69.561  1.00 81.83      G
ATOM  16718  C   ARG G1136     61.165 105.251 73.121  1.00 30.68      G
ATOM  16719  O   ARG G1136     60.949 104.200 73.706  1.00 30.68      G
ATOM  16720  N   LYS G1137     60.447 105.669 72.088  1.00 22.80      G
ATOM  16721  CA  LYS G1137     59.311 104.920 71.538  1.00 22.80      G
ATOM  16722  CB  LYS G1137     59.265 105.138 70.013  1.00 99.87      G
ATOM  16723  CG  LYS G1137     59.594 106.600 69.626  1.00 99.87      G
ATOM  16724  CD  LYS G1137     59.069 107.043 68.256  1.00 99.87      G
ATOM  16725  CE  LYS G1137     59.315 108.550 68.041  1.00 99.87      G
ATOM  16726  NZ  LYS G1137     58.580 109.157 66.878  1.00 99.87      G
ATOM  16727  C   LYS G1137     59.344 103.431 71.916  1.00 22.80      G
ATOM  16728  O   LYS G1137     60.252 102.682 71.543  1.00 22.80      G
ATOM  16729  N   ARG G1138     58.348 103.023 72.692  1.00 44.39      G
ATOM  16730  CA  ARG G1138     58.238 101.649 73.181  1.00 44.39      G
ATOM  16731  CB  ARG G1138     56.771 101.330 73.508  1.00 97.36      G
ATOM  16732  CG  ARG G1138     56.065 102.387 74.382  1.00 97.36      G
ATOM  16733  CD  ARG G1138     55.571 103.580 73.560  1.00 97.36      G
ATOM  16734  NE  ARG G1138     54.929 104.606 74.380  1.00 97.36      G
ATOM  16735  CZ  ARG G1138     54.204 105.606 73.886  1.00 97.36      G
ATOM  16736  NH1 ARG G1138     54.029 105.706 72.574  1.00 97.36      G
ATOM  16737  NH2 ARG G1138     53.657 106.508 74.697  1.00 97.36      G
ATOM  16738  C   ARG G1138     58.804 100.605 72.220  1.00 44.39      G
ATOM  16739  O   ARG G1138     59.983 100.250 72.307  1.00 44.39      G
ATOM  16740  N   SER G1139     57.952 100.127 71.315  1.00 55.38      G
ATOM  16741  CA  SER G1139     58.316  99.126 70.309  1.00 55.38      G
ATOM  16742  CB  SER G1139     57.523  99.367 69.025  1.00 27.51      G
ATOM  16743  OG  SER G1139     58.324  99.073 67.891  1.00 27.51      G
ATOM  16744  C   SER G1139     59.800  99.052 69.957  1.00 55.38      G
ATOM  16745  O   SER G1139     60.428  98.005 70.112  1.00 55.38      G
ATOM  16746  N   ASP G1140     60.346 100.163 69.472  1.00 55.18      G
ATOM  16747  CA  ASP G1140     61.748 100.222 69.082  1.00 55.18      G
ATOM  16748  CB  ASP G1140     62.195 101.677 68.934  1.00 86.85      G
ATOM  16749  CG  ASP G1140     61.370 102.436 67.919  1.00 86.85      G
ATOM  16750  OD1 ASP G1140     61.202 101.929 66.790  1.00 86.85      G
ATOM  16751  OD2 ASP G1140     60.891 103.541 68.242  1.00 86.85      G
ATOM  16752  C   ASP G1140     62.650  99.504 70.081  1.00 55.18      G
ATOM  16753  O   ASP G1140     63.573  98.778 69.694  1.00 55.18      G
ATOM  16754  N   ILE G1141     62.384  99.704 71.369  1.00 46.74      G
ATOM  16755  CA  ILE G1141     63.188  99.059 72.387  1.00 46.74      G
ATOM  16756  CB  ILE G1141     62.717  99.387 73.783  1.00 41.94      G
ATOM  16757  CG2 ILE G1141     63.697  98.799 74.780  1.00 41.94      G
ATOM  16758  CG1 ILE G1141     62.568 100.898 73.944  1.00 41.94      G
ATOM  16759  CD  ILE G1141     63.840 101.648 73.721  1.00 41.94      G
ATOM  16760  C   ILE G1141     63.036  97.571 72.206  1.00 46.74      G
ATOM  16761  O   ILE G1141     64.032  96.849 72.163  1.00 46.74      G
ATOM  16762  N   GLU G1142     61.781  97.118 72.122  1.00 37.83      G
```

```
ATOM  16763  CA   GLU G1142    61.492  95.702  71.923  1.00 37.83      G
ATOM  16764  CB   GLU G1142    60.011  95.478  71.655  1.00 84.79      G
ATOM  16765  CG   GLU G1142    59.179  95.563  72.902  1.00 84.79      G
ATOM  16766  CD   GLU G1142    57.702  95.469  72.620  1.00 84.79      G
ATOM  16767  OE1  GLU G1142    57.308  94.546  71.875  1.00 84.79      G
ATOM  16768  OE2  GLU G1142    56.939  96.313  73.150  1.00 84.79      G
ATOM  16769  C    GLU G1142    62.288  95.319  70.711  1.00 37.83      G
ATOM  16770  O    GLU G1142    63.045  94.348  70.719  1.00 37.83      G
ATOM  16771  N    SER G1143    62.144  96.131  69.674  1.00 32.09      G
ATOM  16772  CA   SER G1143    62.853  95.888  68.437  1.00 32.09      G
ATOM  16773  CB   SER G1143    62.258  96.705  67.292  1.00 33.11      G
ATOM  16774  OG   SER G1143    62.681  96.176  66.047  1.00 33.11      G
ATOM  16775  C    SER G1143    64.289  96.280  68.632  1.00 32.09      G
ATOM  16776  O    SER G1143    64.974  96.588  67.674  1.00 32.09      G
ATOM  16777  N    GLY G1144    64.742  96.281  69.875  1.00 43.72      G
ATOM  16778  CA   GLY G1144    66.120  96.640  70.137  1.00 43.72      G
ATOM  16779  C    GLY G1144    66.783  95.668  71.090  1.00 43.72      G
ATOM  16780  O    GLY G1144    67.979  95.370  70.991  1.00 43.72      G
ATOM  16781  N    LEU G1145    65.994  95.153  72.016  1.00 49.01      G
ATOM  16782  CA   LEU G1145    66.532  94.239  72.987  1.00 49.01      G
ATOM  16783  CB   LEU G1145    66.350  94.832  74.388  1.00 15.13      G
ATOM  16784  CG   LEU G1145    66.730  96.310  74.565  1.00 15.13      G
ATOM  16785  CD1  LEU G1145    66.907  96.601  76.053  1.00 15.13      G
ATOM  16786  CD2  LEU G1145    68.017  96.627  73.831  1.00 15.13      G
ATOM  16787  C    LEU G1145    65.926  92.838  72.904  1.00 49.01      G
ATOM  16788  O    LEU G1145    66.552  91.863  73.323  1.00 49.01      G
ATOM  16789  N    TYR G1146    64.720  92.709  72.365  1.00 32.08      G
ATOM  16790  CA   TYR G1146    64.140  91.376  72.286  1.00 32.08      G
ATOM  16791  CB   TYR G1146    62.919  91.340  71.371  1.00 33.82      G
ATOM  16792  CG   TYR G1146    62.241  89.993  71.364  1.00 33.82      G
ATOM  16793  CD1  TYR G1146    61.129  89.744  72.158  1.00 33.82      G
ATOM  16794  CE1  TYR G1146    60.534  88.477  72.198  1.00 33.82      G
ATOM  16795  CD2  TYR G1146    62.743  88.951  70.607  1.00 33.82      G
ATOM  16796  CE2  TYR G1146    62.160  87.686  70.640  1.00 33.82      G
ATOM  16797  CZ   TYR G1146    61.057  87.453  71.433  1.00 33.82      G
ATOM  16798  OH   TYR G1146    60.472  86.207  71.442  1.00 33.82      G
ATOM  16799  C    TYR G1146    65.194  90.463  71.711  1.00 32.08      G
ATOM  16800  O    TYR G1146    65.957  90.849  70.844  1.00 32.08      G
ATOM  16801  N    GLY G1147    65.260  89.249  72.204  1.00 27.57      G
ATOM  16802  CA   GLY G1147    66.242  88.351  71.647  1.00 27.57      G
ATOM  16803  C    GLY G1147    67.683  88.776  71.838  1.00 27.57      G
ATOM  16804  O    GLY G1147    68.588  87.944  71.712  1.00 27.57      G
ATOM  16805  N    ARG G1148    67.929  90.054  72.110  1.00 42.97      G
ATOM  16806  CA   ARG G1148    69.308  90.464  72.351  1.00 42.97      G
ATOM  16807  CB   ARG G1148    69.391  91.866  72.936  1.00 33.74      G
ATOM  16808  CG   ARG G1148    69.345  92.974  71.905  1.00 33.74      G
ATOM  16809  CD   ARG G1148    70.411  92.792  70.840  1.00 33.74      G
ATOM  16810  NE   ARG G1148    70.520  93.984  70.016  1.00 33.74      G
ATOM  16811  CZ   ARG G1148    71.387  94.115  69.021  1.00 33.74      G
ATOM  16812  NH1  ARG G1148    72.215  93.113  68.731  1.00 33.74      G
ATOM  16813  NH2  ARG G1148    71.443  95.255  68.333  1.00 33.74      G
ATOM  16814  C    ARG G1148    69.691  89.454  73.394  1.00 42.97      G
ATOM  16815  O    ARG G1148    68.860  89.057  74.210  1.00 42.97      G
ATOM  16816  N    VAL G1149    70.931  89.022  73.404  1.00 43.77      G
ATOM  16817  CA   VAL G1149    71.227  87.994  74.359  1.00 43.77      G
ATOM  16818  CB   VAL G1149    71.396  86.686  73.635  1.00 86.90      G
ATOM  16819  CG1  VAL G1149    72.230  85.727  74.446  1.00 86.90      G
ATOM  16820  CG2  VAL G1149    70.029  86.138  73.344  1.00 86.90      G
ATOM  16821  C    VAL G1149    72.371  88.192  75.265  1.00 43.77      G
ATOM  16822  O    VAL G1149    72.391  87.659  76.363  1.00 43.77      G
ATOM  16823  N    LEU G1150    73.336  88.967  74.831  1.00 82.22      G
ATOM  16824  CA   LEU G1150    74.471  89.149  75.686  1.00 82.22      G
ATOM  16825  CB   LEU G1150    75.730  88.858  74.881  1.00100.07      G
ATOM  16826  CG   LEU G1150    75.502  87.468  74.268  1.00100.07      G
ATOM  16827  CD1  LEU G1150    76.664  87.058  73.425  1.00100.07      G
ATOM  16828  CD2  LEU G1150    75.275  86.452  75.382  1.00100.07      G
ATOM  16829  C    LEU G1150    74.482  90.504  76.346  1.00 82.22      G
ATOM  16830  O    LEU G1150    74.981  91.488  75.806  1.00 82.22      G
ATOM  16831  N    ALA G1151    73.879  90.540  77.526  1.00 48.88      G
ATOM  16832  CA   ALA G1151    73.823  91.760  78.299  1.00 48.88      G
ATOM  16833  CB   ALA G1151    72.754  91.621  79.419  1.00 15.58      G
ATOM  16834  C    ALA G1151    75.238  91.849  78.875  1.00 48.88      G
ATOM  16835  O    ALA G1151    76.195  91.355  78.264  1.00 48.88      G
ATOM  16836  N    ARG G1152    75.373  92.496  80.027  1.00 66.05      G
ATOM  16837  CA   ARG G1152    76.654  92.578  80.719  1.00 66.05      G
ATOM  16838  CB   ARG G1152    77.607  93.523  80.010  1.00 81.76      G
ATOM  16839  CG   ARG G1152    79.010  93.350  80.498  1.00 81.76      G
ATOM  16840  CD   ARG G1152    79.987  93.874  79.505  1.00 81.76      G
ATOM  16841  NE   ARG G1152    81.342  93.772  80.016  1.00 81.76      G
ATOM  16842  CZ   ARG G1152    82.402  94.296  79.415  1.00 81.76      G
ATOM  16843  NH1  ARG G1152    82.256  94.960  78.273  1.00 81.76      G
ATOM  16844  NH2  ARG G1152    83.606  94.168  79.961  1.00 81.76      G
ATOM  16845  C    ARG G1152    76.398  93.026  82.156  1.00 66.05      G
ATOM  16846  O    ARG G1152    76.886  94.062  82.608  1.00 66.05      G
```

-201-

```
ATOM  16847  N    GLU G1153     75.615  92.207  82.857  1.00 47.40      G
ATOM  16848  CA   GLU G1153     75.210  92.434  84.237  1.00 47.40      G
ATOM  16849  CB   GLU G1153     76.431  92.717  85.111  1.00100.07      G
ATOM  16850  CG   GLU G1153     76.099  92.878  86.579  1.00100.07      G
ATOM  16851  CD   GLU G1153     77.334  93.045  87.435  1.00100.07      G
ATOM  16852  OE1  GLU G1153     78.173  93.913  87.104  1.00100.07      G
ATOM  16853  OE2  GLU G1153     77.460  92.312  88.441  1.00100.07      G
ATOM  16854  C    GLU G1153     74.231  93.601  84.288  1.00 47.40      G
ATOM  16855  O    GLU G1153     74.627  94.741  84.508  1.00 47.40      G
ATOM  16856  N    VAL G1154     72.951  93.316  84.058  1.00 76.39      G
ATOM  16857  CA   VAL G1154     71.943  94.365  84.086  1.00 76.39      G
ATOM  16858  CB   VAL G1154     70.617  93.919  83.475  1.00 94.04      G
ATOM  16859  CG1  VAL G1154     69.573  95.013  83.675  1.00 94.04      G
ATOM  16860  CG2  VAL G1154     70.805  93.624  81.989  1.00 94.04      G
ATOM  16861  C    VAL G1154     71.714  94.766  85.518  1.00 76.39      G
ATOM  16862  O    VAL G1154     71.189  94.004  86.325  1.00 76.39      G
ATOM  16863  N    GLU G1155     72.108  95.999  85.792  1.00 65.33      G
ATOM  16864  CA   GLU G1155     72.064  96.627  87.109  1.00 65.33      G
ATOM  16865  CB   GLU G1155     72.732  98.017  87.000  1.00100.07      G
ATOM  16866  CG   GLU G1155     74.201  98.018  86.523  1.00100.07      G
ATOM  16867  CD   GLU G1155     74.411  98.755  85.192  1.00100.07      G
ATOM  16868  OE1  GLU G1155     73.921  99.899  85.051  1.00100.07      G
ATOM  16869  OE2  GLU G1155     75.077  98.198  84.287  1.00100.07      G
ATOM  16870  C    GLU G1155     70.764  96.768  87.937  1.00 65.33      G
ATOM  16871  O    GLU G1155     70.044  95.808  88.223  1.00 65.33      G
ATOM  16872  N    ALA G1156     70.516  98.010  88.329  1.00100.07      G
ATOM  16873  CA   ALA G1156     69.407  98.409  89.173  1.00100.07      G
ATOM  16874  CB   ALA G1156     69.353  99.923  89.204  1.00100.07      G
ATOM  16875  C    ALA G1156     68.000  97.842  88.994  1.00100.07      G
ATOM  16876  O    ALA G1156     67.735  96.999  88.147  1.00100.07      G
ATOM  16877  N    LEU G1157     67.122  98.361  89.849  1.00 65.69      G
ATOM  16878  CA   LEU G1157     65.705  98.028  89.996  1.00 65.69      G
ATOM  16879  CB   LEU G1157     64.878  98.417  88.769  1.00 45.45      G
ATOM  16880  CG   LEU G1157     63.460  98.784  89.262  1.00 45.45      G
ATOM  16881  CD1  LEU G1157     62.627  99.370  88.153  1.00 45.45      G
ATOM  16882  CD2  LEU G1157     62.767  97.565  89.831  1.00 45.45      G
ATOM  16883  C    LEU G1157     65.431  96.580  90.360  1.00 65.69      G
ATOM  16884  O    LEU G1157     65.752  95.666  89.604  1.00 65.69      G
ATOM  16885  N    GLY G1158     64.826  96.399  91.534  1.00 49.67      G
ATOM  16886  CA   GLY G1158     64.491  95.082  92.034  1.00 49.67      G
ATOM  16887  C    GLY G1158     65.450  93.980  91.623  1.00 49.67      G
ATOM  16888  O    GLY G1158     66.497  93.798  92.237  1.00 49.67      G
ATOM  16889  N    ARG G1159     65.080  93.257  90.567  1.00 51.44      G
ATOM  16890  CA   ARG G1159     65.840  92.127  90.016  1.00 51.44      G
ATOM  16891  CB   ARG G1159     65.062  91.531  88.826  1.00100.06      G
ATOM  16892  CG   ARG G1159     65.528  90.152  88.339  1.00100.06      G
ATOM  16893  CD   ARG G1159     64.511  89.516  87.360  1.00100.06      G
ATOM  16894  NE   ARG G1159     64.552  88.047  87.390  1.00100.06      G
ATOM  16895  CZ   ARG G1159     63.644  87.249  86.829  1.00100.06      G
ATOM  16896  NH1  ARG G1159     62.609  87.767  86.178  1.00100.06      G
ATOM  16897  NH2  ARG G1159     63.760  85.931  86.934  1.00100.06      G
ATOM  16898  C    ARG G1159     67.264  92.444  89.581  1.00 51.44      G
ATOM  16899  O    ARG G1159     67.652  93.599  89.454  1.00 51.44      G
ATOM  16900  N    ARG G1160     68.038  91.391  89.370  1.00 47.80      G
ATOM  16901  CA   ARG G1160     69.413  91.516  88.920  1.00 47.80      G
ATOM  16902  CB   ARG G1160     70.370  91.077  90.018  1.00 92.45      G
ATOM  16903  CG   ARG G1160     70.382  92.040  91.188  1.00 92.45      G
ATOM  16904  CD   ARG G1160     70.929  93.394  90.765  1.00 92.45      G
ATOM  16905  NE   ARG G1160     72.249  93.632  91.336  1.00 92.45      G
ATOM  16906  CZ   ARG G1160     73.139  94.476  90.832  1.00 92.45      G
ATOM  16907  NH1  ARG G1160     72.857  95.169  89.740  1.00 92.45      G
ATOM  16908  NH2  ARG G1160     74.314  94.628  91.425  1.00 92.45      G
ATOM  16909  C    ARG G1160     69.526  90.605  87.718  1.00 47.80      G
ATOM  16910  O    ARG G1160     69.137  89.447  87.790  1.00 47.80      G
ATOM  16911  N    LEU G1161     70.047  91.121  86.610  1.00 61.41      G
ATOM  16912  CA   LEU G1161     70.156  90.322  85.396  1.00 61.41      G
ATOM  16913  CB   LEU G1161     69.456  91.072  84.262  1.00 25.98      G
ATOM  16914  CG   LEU G1161     68.131  91.766  84.658  1.00 25.98      G
ATOM  16915  CD1  LEU G1161     67.520  92.441  83.447  1.00 25.98      G
ATOM  16916  CD2  LEU G1161     67.135  90.760  85.234  1.00 25.98      G
ATOM  16917  C    LEU G1161     71.612  89.994  85.036  1.00 61.41      G
ATOM  16918  O    LEU G1161     72.358  90.861  84.571  1.00 61.41      G
ATOM  16919  N    GLU G1162     71.994  88.734  85.263  1.00 63.09      G
ATOM  16920  CA   GLU G1162     73.346  88.215  85.012  1.00 63.09      G
ATOM  16921  CB   GLU G1162     73.326  86.689  85.099  1.00100.07      G
ATOM  16922  CG   GLU G1162     73.055  86.145  86.489  1.00100.07      G
ATOM  16923  CD   GLU G1162     72.207  84.878  86.477  1.00100.07      G
ATOM  16924  OE1  GLU G1162     72.550  83.911  85.758  1.00100.07      G
ATOM  16925  OE2  GLU G1162     71.190  84.851  87.203  1.00100.07      G
ATOM  16926  C    GLU G1162     73.974  88.622  83.679  1.00 63.09      G
ATOM  16927  O    GLU G1162     73.356  89.316  82.880  1.00 63.09      G
ATOM  16928  N    GLU G1163     75.207  88.180  83.445  1.00 62.55      G
ATOM  16929  CA   GLU G1163     75.917  88.487  82.206  1.00 62.55      G
ATOM  16930  CB   GLU G1163     77.359  87.994  82.309  1.00 99.38      G
```

```
ATOM  16931  CG   GLU G1163      78.385  88.834  81.571  1.00 99.38           G
ATOM  16932  CD   GLU G1163      79.802  88.616  82.102  1.00 99.38           G
ATOM  16933  OE1  GLU G1163      80.300  87.470  82.050  1.00 99.38           G
ATOM  16934  OE2  GLU G1163      80.421  89.591  82.581  1.00 99.38           G
ATOM  16935  C    GLU G1163      75.169  87.735  81.113  1.00 62.55           G
ATOM  16936  O    GLU G1163      74.521  86.734  81.407  1.00 62.55           G
ATOM  16937  N    GLY G1164      75.239  88.220  79.869  1.00 52.57           G
ATOM  16938  CA   GLY G1164      74.546  87.575  78.756  1.00 52.57           G
ATOM  16939  C    GLY G1164      73.403  86.696  79.226  1.00 52.57           G
ATOM  16940  O    GLY G1164      73.563  85.490  79.413  1.00 52.57           G
ATOM  16941  N    ARG G1165      72.232  87.287  79.395  1.00 86.83           G
ATOM  16942  CA   ARG G1165      71.127  86.513  79.912  1.00 86.83           G
ATOM  16943  CB   ARG G1165      70.579  87.227  81.140  1.00100.07           G
ATOM  16944  CG   ARG G1165      69.778  86.335  82.050  1.00100.07           G
ATOM  16945  CD   ARG G1165      68.672  87.101  82.724  1.00100.07           G
ATOM  16946  NE   ARG G1165      67.837  86.206  83.507  1.00100.07           G
ATOM  16947  CZ   ARG G1165      66.639  86.530  83.972  1.00100.07           G
ATOM  16948  NH1  ARG G1165      66.140  87.734  83.723  1.00100.07           G
ATOM  16949  NH2  ARG G1165      65.945  85.652  84.685  1.00100.07           G
ATOM  16950  C    ARG G1165      69.965  86.141  78.989  1.00 86.83           G
ATOM  16951  O    ARG G1165      69.036  85.464  79.428  1.00 86.83           G
ATOM  16952  N    TYR G1166      69.995  86.552  77.725  1.00 19.61           G
ATOM  16953  CA   TYR G1166      68.880  86.230  76.824  1.00 19.61           G
ATOM  16954  CB   TYR G1166      68.670  84.713  76.691  1.00 70.81           G
ATOM  16955  CG   TYR G1166      69.613  83.973  75.776  1.00 70.81           G
ATOM  16956  CD1  TYR G1166      70.882  83.596  76.198  1.00 70.81           G
ATOM  16957  CE1  TYR G1166      71.745  82.900  75.343  1.00 70.81           G
ATOM  16958  CD2  TYR G1166      69.230  83.644  74.483  1.00 70.81           G
ATOM  16959  CE2  TYR G1166      70.084  82.955  73.623  1.00 70.81           G
ATOM  16960  CZ   TYR G1166      71.336  82.590  74.055  1.00 70.81           G
ATOM  16961  OH   TYR G1166      72.172  81.915  73.199  1.00 70.81           G
ATOM  16962  C    TYR G1166      67.622  86.805  77.463  1.00 19.61           G
ATOM  16963  O    TYR G1166      66.918  86.102  78.209  1.00 19.61           G
ATOM  16964  N    LEU G1167      67.336  88.073  77.192  1.00 24.43           G
ATOM  16965  CA   LEU G1167      66.153  88.678  77.778  1.00 24.43           G
ATOM  16966  CB   LEU G1167      66.435  90.108  78.245  1.00 56.14           G
ATOM  16967  CG   LEU G1167      67.088  91.099  77.298  1.00 56.14           G
ATOM  16968  CD1  LEU G1167      67.298  92.407  78.030  1.00 56.14           G
ATOM  16969  CD2  LEU G1167      68.415  90.556  76.825  1.00 56.14           G
ATOM  16970  C    LEU G1167      64.985  88.651  76.821  1.00 24.43           G
ATOM  16971  O    LEU G1167      64.956  89.370  75.819  1.00 24.43           G
ATOM  16972  N    SER G1168      64.028  87.787  77.144  1.00 34.32           G
ATOM  16973  CA   SER G1168      62.835  87.622  76.338  1.00 34.32           G
ATOM  16974  CB   SER G1168      62.125  86.311  76.690  1.00100.07           G
ATOM  16975  OG   SER G1168      62.836  85.186  76.190  1.00100.07           G
ATOM  16976  C    SER G1168      61.910  88.785  76.576  1.00 34.32           G
ATOM  16977  O    SER G1168      61.981  89.418  77.619  1.00 34.32           G
ATOM  16978  N    LEU G1169      61.059  89.055  75.588  1.00 40.61           G
ATOM  16979  CA   LEU G1169      60.080  90.130  75.627  1.00 40.61           G
ATOM  16980  CB   LEU G1169      58.836  89.736  74.836  1.00 38.23           G
ATOM  16981  CG   LEU G1169      57.893  90.879  74.477  1.00 38.23           G
ATOM  16982  CD1  LEU G1169      58.626  91.825  73.560  1.00 38.23           G
ATOM  16983  CD2  LEU G1169      56.640  90.358  73.796  1.00 38.23           G
ATOM  16984  C    LEU G1169      59.699  90.403  77.063  1.00 40.61           G
ATOM  16985  O    LEU G1169      59.405  91.541  77.425  1.00 40.61           G
ATOM  16986  N    GLU G1170      59.693  89.353  77.880  1.00 44.99           G
ATOM  16987  CA   GLU G1170      59.387  89.498  79.302  1.00 44.99           G
ATOM  16988  CB   GLU G1170      59.480  88.142  80.000  1.00100.07           G
ATOM  16989  CG   GLU G1170      58.645  87.033  79.370  1.00100.07           G
ATOM  16990  CD   GLU G1170      58.836  85.700  80.086  1.00100.07           G
ATOM  16991  OE1  GLU G1170      58.823  85.700  81.338  1.00100.07           G
ATOM  16992  OE2  GLU G1170      58.992  84.660  79.407  1.00100.07           G
ATOM  16993  C    GLU G1170      60.424  90.449  79.917  1.00 44.99           G
ATOM  16994  O    GLU G1170      60.119  91.596  80.262  1.00 44.99           G
ATOM  16995  N    ASP G1171      61.655  89.956  80.039  1.00 28.12           G
ATOM  16996  CA   ASP G1171      62.747  90.742  80.586  1.00 28.12           G
ATOM  16997  CB   ASP G1171      64.047  89.940  80.524  1.00 78.44           G
ATOM  16998  CG   ASP G1171      64.073  88.805  81.525  1.00 78.44           G
ATOM  16999  OD1  ASP G1171      63.769  89.059  82.708  1.00 78.44           G
ATOM  17000  OD2  ASP G1171      64.406  87.667  81.137  1.00 78.44           G
ATOM  17001  C    ASP G1171      62.929  92.104  79.899  1.00 28.12           G
ATOM  17002  O    ASP G1171      63.263  93.087  80.564  1.00 28.12           G
ATOM  17003  N    VAL G1172      62.726  92.177  78.585  1.00 39.36           G
ATOM  17004  CA   VAL G1172      62.865  93.465  77.901  1.00 39.36           G
ATOM  17005  CB   VAL G1172      62.264  93.480  76.459  1.00 54.74           G
ATOM  17006  CG1  VAL G1172      62.490  94.856  75.805  1.00 54.74           G
ATOM  17007  CG2  VAL G1172      62.880  92.376  75.613  1.00 54.74           G
ATOM  17008  C    VAL G1172      62.062  94.446  78.731  1.00 39.36           G
ATOM  17009  O    VAL G1172      62.626  95.193  79.534  1.00 39.36           G
ATOM  17010  N    HIS G1173      60.743  94.422  78.552  1.00 29.78           G
ATOM  17011  CA   HIS G1173      59.869  95.311  79.290  1.00 29.78           G
ATOM  17012  CB   HIS G1173      58.508  94.674  79.446  1.00 76.01           G
ATOM  17013  CG   HIS G1173      57.806  94.489  78.146  1.00 76.01           G
ATOM  17014  CD2  HIS G1173      58.243  94.648  76.877  1.00 76.01           G
```

```
ATOM  17015  ND1 HIS G1173     56.483  94.118  78.056  1.00 76.01      G
ATOM  17016  CE1 HIS G1173     56.135  94.059  76.784  1.00 76.01      G
ATOM  17017  NE2 HIS G1173     57.182  94.376  76.048  1.00 76.01      G
ATOM  17018  C   HIS G1173     60.456  95.661  80.645  1.00 29.78      G
ATOM  17019  O   HIS G1173     60.603  96.836  80.976  1.00 29.78      G
ATOM  17020  N   PHE G1174     60.809  94.652  81.431  1.00 27.56      G
ATOM  17021  CA  PHE G1174     61.406  94.934  82.721  1.00 27.56      G
ATOM  17022  CB  PHE G1174     62.202  93.751  83.215  1.00 26.64      G
ATOM  17023  CG  PHE G1174     63.008  94.047  84.435  1.00 26.64      G
ATOM  17024  CD1 PHE G1174     62.387  94.302  85.646  1.00 26.64      G
ATOM  17025  CD2 PHE G1174     64.396  94.055  84.381  1.00 26.64      G
ATOM  17026  CE1 PHE G1174     63.140  94.557  86.791  1.00 26.64      G
ATOM  17027  CE2 PHE G1174     65.151  94.308  85.517  1.00 26.64      G
ATOM  17028  CZ  PHE G1174     64.519  94.559  86.726  1.00 26.64      G
ATOM  17029  C   PHE G1174     62.343  96.118  82.559  1.00 27.56      G
ATOM  17030  O   PHE G1174     62.168  97.142  83.206  1.00 27.56      G
ATOM  17031  N   LEU G1175     63.332  95.990  81.687  1.00 24.01      G
ATOM  17032  CA  LEU G1175     64.246  97.098  81.485  1.00 24.01      G
ATOM  17033  CB  LEU G1175     65.152  96.852  80.275  1.00  9.68      G
ATOM  17034  CG  LEU G1175     65.990  95.571  80.233  1.00  9.68      G
ATOM  17035  CD1 LEU G1175     67.348  95.872  79.692  1.00  9.68      G
ATOM  17036  CD2 LEU G1175     66.153  95.011  81.596  1.00  9.68      G
ATOM  17037  C   LEU G1175     63.439  98.385  81.293  1.00 24.01      G
ATOM  17038  O   LEU G1175     63.660  99.365  82.013  1.00 24.01      G
ATOM  17039  N   ILE G1176     62.495  98.371  80.346  1.00 15.29      G
ATOM  17040  CA  ILE G1176     61.637  99.532  80.059  1.00 15.29      G
ATOM  17041  CB  ILE G1176     60.324  99.113  79.376  1.00 55.80      G
ATOM  17042  CG2 ILE G1176     59.366 100.304  79.324  1.00 55.80      G
ATOM  17043  CG1 ILE G1176     60.603  98.575  77.979  1.00 55.80      G
ATOM  17044  CD  ILE G1176     60.994  99.639  77.012  1.00 55.80      G
ATOM  17045  C   ILE G1176     61.239 100.362  81.287  1.00 15.29      G
ATOM  17046  O   ILE G1176     61.729 101.470  81.473  1.00 15.29      G
ATOM  17047  N   LYS G1177     60.339  99.839  82.110  1.00 68.82      G
ATOM  17048  CA  LYS G1177     59.896 100.568  83.293  1.00 68.82      G
ATOM  17049  CB  LYS G1177     58.764  99.800  83.986  1.00 98.64      G
ATOM  17050  CG  LYS G1177     57.506  99.709  83.122  1.00 98.64      G
ATOM  17051  CD  LYS G1177     56.423  98.810  83.711  1.00 98.64      G
ATOM  17052  CE  LYS G1177     55.287  98.607  82.706  1.00 98.64      G
ATOM  17053  NZ  LYS G1177     54.223  97.689  83.200  1.00 98.64      G
ATOM  17054  C   LYS G1177     61.055 100.824  84.254  1.00 68.82      G
ATOM  17055  O   LYS G1177     61.152 101.890  84.870  1.00 68.82      G
ATOM  17056  N   ALA G1178     61.946  99.850  84.371  1.00 35.80      G
ATOM  17057  CA  ALA G1178     63.100 100.001  85.236  1.00 35.80      G
ATOM  17058  CB  ALA G1178     63.830  98.683  85.362  1.00 37.16      G
ATOM  17059  C   ALA G1178     64.005 101.038  84.601  1.00 35.80      G
ATOM  17060  O   ALA G1178     65.221 100.990  84.750  1.00 35.80      G
ATOM  17061  N   ALA G1179     63.403 101.962  83.866  1.00 28.53      G
ATOM  17062  CA  ALA G1179     64.135 103.026  83.194  1.00 28.53      G
ATOM  17063  CB  ALA G1179     64.597 102.579  81.833  1.00  5.07      G
ATOM  17064  C   ALA G1179     63.151 104.166  83.071  1.00 28.53      G
ATOM  17065  O   ALA G1179     63.502 105.267  82.643  1.00 28.53      G
ATOM  17066  N   GLU G1180     61.901 103.861  83.415  1.00 40.04      G
ATOM  17067  CA  GLU G1180     60.829 104.844  83.448  1.00 40.04      G
ATOM  17068  CB  GLU G1180     59.479 104.203  83.148  1.00 69.59      G
ATOM  17069  CG  GLU G1180     58.989 104.418  81.745  1.00 69.59      G
ATOM  17070  CD  GLU G1180     57.832 103.500  81.393  1.00 69.59      G
ATOM  17071  OE1 GLU G1180     57.982 102.269  81.563  1.00 69.59      G
ATOM  17072  OE2 GLU G1180     56.779 104.001  80.939  1.00 69.59      G
ATOM  17073  C   GLU G1180     60.907 105.188  84.924  1.00 40.04      G
ATOM  17074  O   GLU G1180     60.314 106.154  85.403  1.00 40.04      G
ATOM  17075  N   ALA G1181     61.664 104.359  85.633  1.00 55.50      G
ATOM  17076  CA  ALA G1181     61.866 104.517  87.058  1.00 55.50      G
ATOM  17077  CB  ALA G1181     62.027 103.149  87.706  1.00100.07      G
ATOM  17078  C   ALA G1181     63.103 105.372  87.314  1.00 55.50      G
ATOM  17079  O   ALA G1181     63.156 106.141  88.270  1.00 55.50      G
ATOM  17080  N   GLY G1182     64.103 105.232  86.456  1.00 69.70      G
ATOM  17081  CA  GLY G1182     65.307 106.015  86.624  1.00 69.70      G
ATOM  17082  C   GLY G1182     66.529 105.166  86.867  1.00 69.70      G
ATOM  17083  O   GLY G1182     67.614 105.698  87.078  1.00 69.70      G
ATOM  17084  N   GLU G1183     66.364 103.847  86.816  1.00 20.92      G
ATOM  17085  CA  GLU G1183     67.469 102.922  87.053  1.00 20.92      G
ATOM  17086  CB  GLU G1183     66.960 101.607  87.635  1.00 50.24      G
ATOM  17087  CG  GLU G1183     66.914 101.580  89.145  1.00 50.24      G
ATOM  17088  CD  GLU G1183     65.621 102.091  89.702  1.00 50.24      G
ATOM  17089  OE1 GLU G1183     65.247 103.239  89.385  1.00 50.24      G
ATOM  17090  OE2 GLU G1183     64.980 101.338  90.461  1.00 50.24      G
ATOM  17091  C   GLU G1183     68.389 102.611  85.888  1.00 20.92      G
ATOM  17092  O   GLU G1183     69.552 102.317  86.115  1.00 20.92      G
ATOM  17093  N   VAL G1184     67.905 102.639  84.653  1.00 56.21      G
ATOM  17094  CA  VAL G1184     68.808 102.366  83.541  1.00 56.21      G
ATOM  17095  CB  VAL G1184     68.861 100.872  83.213  1.00 68.55      G
ATOM  17096  CG1 VAL G1184     69.831 100.638  82.075  1.00 68.55      G
ATOM  17097  CG2 VAL G1184     69.317 100.091  84.425  1.00 68.55      G
ATOM  17098  C   VAL G1184     68.489 103.149  82.268  1.00 56.21      G
```

```
ATOM  17099  O    VAL G1184      67.322 103.373  81.941  1.00 56.21      G
ATOM  17100  N    ARG G1185      69.545 103.563  81.564  1.00 48.00      G
ATOM  17101  CA   ARG G1185      69.423 104.345  80.332  1.00 48.00      G
ATOM  17102  CB   ARG G1185      69.996 105.748  80.550  1.00 45.21      G
ATOM  17103  CG   ARG G1185      68.957 106.865  80.575  1.00 45.21      G
ATOM  17104  CD   ARG G1185      69.547 108.174  81.096  1.00 45.21      G
ATOM  17105  NE   ARG G1185      68.556 109.242  81.161  1.00 45.21      G
ATOM  17106  CZ   ARG G1185      68.153 109.947  80.109  1.00 45.21      G
ATOM  17107  NH1  ARG G1185      68.664 109.697  78.911  1.00 45.21      G
ATOM  17108  NH2  ARG G1185      67.230 110.893  80.248  1.00 45.21      G
ATOM  17109  C    ARG G1185      70.108 103.718  79.113  1.00 48.00      G
ATOM  17110  O    ARG G1185      69.780 104.048  77.976  1.00 48.00      G
ATOM  17111  N    GLU G1186      71.064 102.827  79.338  1.00 50.67      G
ATOM  17112  CA   GLU G1186      71.766 102.185  78.233  1.00 50.67      G
ATOM  17113  CB   GLU G1186      73.130 102.832  78.019  1.00 89.37      G
ATOM  17114  CG   GLU G1186      73.123 104.074  77.175  1.00 89.37      G
ATOM  17115  CD   GLU G1186      74.504 104.701  77.079  1.00 89.37      G
ATOM  17116  OE1  GLU G1186      75.486 103.962  76.838  1.00 89.37      G
ATOM  17117  OE2  GLU G1186      74.606 105.937  77.239  1.00 89.37      G
ATOM  17118  C    GLU G1186      71.974 100.699  78.472  1.00 50.67      G
ATOM  17119  O    GLU G1186      72.868 100.298  79.214  1.00 50.67      G
ATOM  17120  N    VAL G1187      71.147  99.872  77.852  1.00 38.99      G
ATOM  17121  CA   VAL G1187      71.308  98.436  77.997  1.00 38.99      G
ATOM  17122  CB   VAL G1187      70.029  97.708  77.659  1.00 15.33      G
ATOM  17123  CG1  VAL G1187      70.200  96.235  77.928  1.00 15.33      G
ATOM  17124  CG2  VAL G1187      68.883  98.309  78.448  1.00 15.33      G
ATOM  17125  C    VAL G1187      72.388  98.009  77.010  1.00 38.99      G
ATOM  17126  O    VAL G1187      72.384  98.415  75.850  1.00 38.99      G
ATOM  17127  N    PRO G1188      73.334  97.190  77.463  1.00 71.13      G
ATOM  17128  CD   PRO G1188      73.697  97.111  78.883  1.00 15.83      G
ATOM  17129  CA   PRO G1188      74.436  96.705  76.633  1.00 71.13      G
ATOM  17130  CB   PRO G1188      75.618  96.939  77.528  1.00 15.83      G
ATOM  17131  CG   PRO G1188      75.057  96.451  78.826  1.00 15.83      G
ATOM  17132  C    PRO G1188      74.363  95.242  76.181  1.00 71.13      G
ATOM  17133  O    PRO G1188      74.762  94.337  76.918  1.00 71.13      G
ATOM  17134  N    VAL G1189      73.870  95.027  74.963  1.00 23.32      G
ATOM  17135  CA   VAL G1189      73.765  93.699  74.395  1.00 23.32      G
ATOM  17136  CB   VAL G1189      72.527  93.548  73.555  1.00 81.27      G
ATOM  17137  CG1  VAL G1189      72.410  92.112  73.107  1.00 81.27      G
ATOM  17138  CG2  VAL G1189      71.324  93.970  74.349  1.00 81.27      G
ATOM  17139  C    VAL G1189      74.966  93.487  73.501  1.00 23.32      G
ATOM  17140  O    VAL G1189      75.502  94.436  72.929  1.00 23.32      G
ATOM  17141  N    ARG G1190      75.374  92.231  73.374  1.00 45.05      G
ATOM  17142  CA   ARG G1190      76.535  91.857  72.581  1.00 45.05      G
ATOM  17143  CB   ARG G1190      77.498  91.102  73.496  1.00 62.67      G
ATOM  17144  CG   ARG G1190      78.270  89.948  72.903  1.00 62.67      G
ATOM  17145  CD   ARG G1190      78.814  89.102  74.045  1.00 62.67      G
ATOM  17146  NE   ARG G1190      79.662  88.006  73.598  1.00 62.67      G
ATOM  17147  CZ   ARG G1190      79.654  86.794  74.143  1.00 62.67      G
ATOM  17148  NH1  ARG G1190      78.826  86.533  75.147  1.00 62.67      G
ATOM  17149  NH2  ARG G1190      80.484  85.851  73.704  1.00 62.67      G
ATOM  17150  C    ARG G1190      76.149  91.022  71.367  1.00 45.05      G
ATOM  17151  O    ARG G1190      75.758  89.859  71.499  1.00 45.05      G
ATOM  17152  N    ALA G1191      76.264  91.621  70.183  1.00100.07      G
ATOM  17153  CA   ALA G1191      75.911  90.927  68.948  1.00100.07      G
ATOM  17154  CB   ALA G1191      74.449  90.510  69.000  1.00100.07      G
ATOM  17155  C    ALA G1191      76.150  91.757  67.688  1.00100.07      G
ATOM  17156  O    ALA G1191      75.895  92.968  67.682  1.00100.07      G
ATOM  17157  N    ALA G1192      76.612  91.071  66.635  1.00 43.55      G
ATOM  17158  CA   ALA G1192      76.896  91.644  65.318  1.00 43.55      G
ATOM  17159  CB   ALA G1192      75.636  91.593  64.450  1.00  5.07      G
ATOM  17160  C    ALA G1192      77.455  93.062  65.352  1.00 43.55      G
ATOM  17161  O    ALA G1192      77.163  93.845  66.259  1.00 43.55      G
ATOM  17162  N    ALA G1193      78.257  93.401  64.351  1.00 95.36      G
ATOM  17163  CA   ALA G1193      78.858  94.726  64.291  1.00 95.36      G
ATOM  17164  CB   ALA G1193      77.795  95.813  64.554  1.00  5.07      G
ATOM  17165  C    ALA G1193      79.939  94.780  65.359  1.00 95.36      G
ATOM  17166  O    ALA G1193      80.786  95.677  65.360  1.00 95.36      G
ATOM  17167  N    ALA G1194      79.907  93.808  66.268  1.00 73.58      G
ATOM  17168  CA   ALA G1194      80.887  93.763  67.337  1.00 73.58      G
ATOM  17169  CB   ALA G1194      80.297  94.386  68.611  1.00  5.07      G
ATOM  17170  C    ALA G1194      81.492  92.390  67.648  1.00 73.58      G
ATOM  17171  O    ALA G1194      81.993  92.189  68.749  1.00 73.58      G
ATOM  17172  N    CYS G1195      81.448  91.444  66.709  1.00 77.32      G
ATOM  17173  CA   CYS G1195      82.079  90.153  66.978  1.00 77.32      G
ATOM  17174  C    CYS G1195      82.814  89.456  65.860  1.00 77.32      G
ATOM  17175  O    CYS G1195      82.503  89.621  64.679  1.00 77.32      G
ATOM  17176  CB   CYS G1195      81.118  89.158  67.609  1.00100.07      G
ATOM  17177  SG   CYS G1195      79.662  88.543  66.715  1.00100.07      G
ATOM  17178  N    ALA G1196      83.799  88.661  66.273  1.00100.07      G
ATOM  17179  CA   ALA G1196      84.662  87.909  65.378  1.00100.07      G
ATOM  17180  CB   ALA G1196      85.790  87.287  66.173  1.00 56.39      G
ATOM  17181  C    ALA G1196      83.948  86.843  64.550  1.00100.07      G
ATOM  17182  O    ALA G1196      82.908  87.117  63.955  1.00100.07      G
```

```
ATOM  17183  N   ALA G1197      84.506  85.631  64.515  1.00100.07      G
ATOM  17184  CA  ALA G1197      83.942  84.544  63.710  1.00100.07      G
ATOM  17185  CB  ALA G1197      82.576  84.085  64.287  1.00  5.07      G
ATOM  17186  C   ALA G1197      83.779  85.196  62.333  1.00100.07      G
ATOM  17187  O   ALA G1197      82.956  84.796  61.511  1.00100.07      G
ATOM  17188  N   ALA G1198      84.620  86.205  62.114  1.00100.07      G
ATOM  17189  CA  ALA G1198      84.643  87.043  60.918  1.00100.07      G
ATOM  17190  CB  ALA G1198      85.793  88.041  61.028  1.00100.07      G
ATOM  17191  C   ALA G1198      84.648  86.424  59.524  1.00100.07      G
ATOM  17192  O   ALA G1198      84.342  87.129  58.557  1.00100.07      G
ATOM  17193  N   ALA G1199      85.013  85.149  59.392  1.00100.05      G
ATOM  17194  CA  ALA G1199      85.010  84.531  58.067  1.00100.05      G
ATOM  17195  CB  ALA G1199      85.527  83.093  58.129  1.00 85.87      G
ATOM  17196  C   ALA G1199      83.555  84.562  57.647  1.00100.05      G
ATOM  17197  O   ALA G1199      82.846  83.557  57.685  1.00100.05      G
ATOM  17198  N   ALA G1200      83.109  85.753  57.280  1.00 99.72      G
ATOM  17199  CA  ALA G1200      81.739  85.959  56.876  1.00 99.72      G
ATOM  17200  CB  ALA G1200      81.369  84.957  55.805  1.00100.07      G
ATOM  17201  C   ALA G1200      80.784  85.820  58.055  1.00 99.72      G
ATOM  17202  O   ALA G1200      79.763  86.503  58.117  1.00 99.72      G
ATOM  17203  N   ALA G1201      81.127  84.970  59.014  1.00 94.81      G
ATOM  17204  CA  ALA G1201      80.228  84.721  60.135  1.00 94.81      G
ATOM  17205  CB  ALA G1201      80.185  83.207  60.376  1.00100.07      G
ATOM  17206  C   ALA G1201      80.401  85.447  61.478  1.00 94.81      G
ATOM  17207  O   ALA G1201      81.044  86.490  61.592  1.00 94.81      G
ATOM  17208  N   CYS G1202      79.752  84.840  62.467  1.00 43.61      G
ATOM  17209  CA  CYS G1202      79.690  85.173  63.896  1.00 43.61      G
ATOM  17210  C   CYS G1202      78.257  85.077  64.386  1.00 43.61      G
ATOM  17211  O   CYS G1202      77.336  85.679  63.811  1.00 43.61      G
ATOM  17212  CB  CYS G1202      80.265  86.549  64.310  1.00 98.43      G
ATOM  17213  SG  CYS G1202      80.095  86.631  66.147  1.00 98.43      G
ATOM  17214  N   ALA G1203      78.100  84.307  65.464  1.00 74.39      G
ATOM  17215  CA  ALA G1203      76.806  84.073  66.074  1.00 74.39      G
ATOM  17216  CB  ALA G1203      76.015  83.139  65.207  1.00100.07      G
ATOM  17217  C   ALA G1203      76.842  83.533  67.500  1.00 74.39      G
ATOM  17218  O   ALA G1203      77.865  83.626  68.192  1.00 74.39      G
ATOM  17219  N   ALA G1204      75.702  82.960  67.904  1.00 74.28      G
ATOM  17220  CA  ALA G1204      75.476  82.407  69.242  1.00 74.28      G
ATOM  17221  CB  ALA G1204      76.571  81.440  69.612  1.00100.07      G
ATOM  17222  C   ALA G1204      75.446  83.581  70.213  1.00 74.28      G
ATOM  17223  O   ALA G1204      75.119  83.452  71.386  1.00 74.28      G
ATOM  17224  N   CYS G1205      75.806  84.735  69.680  1.00 32.55      G
ATOM  17225  CA  CYS G1205      75.829  85.996  70.391  1.00 32.55      G
ATOM  17226  CB  CYS G1205      77.289  86.494  70.583  1.00 77.38      G
ATOM  17227  SG  CYS G1205      78.090  87.613  69.354  1.00 77.38      G
ATOM  17228  C   CYS G1205      75.058  86.853  69.399  1.00 32.55      G
ATOM  17229  O   CYS G1205      74.957  88.064  69.554  1.00 32.55      G
ATOM  17230  N   ALA G1206      74.541  86.185  68.360  1.00 69.64      G
ATOM  17231  CA  ALA G1206      73.750  86.840  67.320  1.00 69.64      G
ATOM  17232  CB  ALA G1206      73.210  85.832  66.295  1.00 17.15      G
ATOM  17233  C   ALA G1206      72.615  87.354  68.127  1.00 69.64      G
ATOM  17234  O   ALA G1206      72.057  88.416  67.863  1.00 69.64      G
ATOM  17235  N   GLY G1207      72.283  86.560  69.129  1.00 44.17      G
ATOM  17236  CA  GLY G1207      71.205  86.923  70.006  1.00 44.17      G
ATOM  17237  C   GLY G1207      70.179  85.826  70.087  1.00 44.17      G
ATOM  17238  O   GLY G1207      70.220  84.992  70.983  1.00 44.17      G
ATOM  17239  N   ALA G1208      69.273  85.779  69.127  1.00 28.47      G
ATOM  17240  CA  ALA G1208      68.241  84.781  69.232  1.00 28.47      G
ATOM  17241  CB  ALA G1208      67.232  85.245  70.211  1.00 26.62      G
ATOM  17242  C   ALA G1208      67.575  84.526  67.930  1.00 28.47      G
ATOM  17243  O   ALA G1208      67.469  85.428  67.100  1.00 28.47      G
ATOM  17244  N   ASP G1209      67.115  83.290  67.770  1.00 33.74      G
ATOM  17245  CA  ASP G1209      66.413  82.851  66.569  1.00 33.74      G
ATOM  17246  CB  ASP G1209      66.281  81.337  66.589  1.00 36.06      G
ATOM  17247  CG  ASP G1209      65.528  80.813  65.407  1.00 36.06      G
ATOM  17248  OD1 ASP G1209      64.535  81.450  64.995  1.00 36.06      G
ATOM  17249  OD2 ASP G1209      65.925  79.752  64.893  1.00 36.06      G
ATOM  17250  C   ASP G1209      65.025  83.489  66.564  1.00 33.74      G
ATOM  17251  O   ASP G1209      64.034  82.849  66.908  1.00 33.74      G
ATOM  17252  N   LEU G1210      64.957  84.749  66.166  1.00 27.97      G
ATOM  17253  CA  LEU G1210      63.698  85.456  66.166  1.00 27.97      G
ATOM  17254  CB  LEU G1210      63.733  86.593  65.148  1.00 71.63      G
ATOM  17255  CG  LEU G1210      63.725  88.014  65.726  1.00 71.63      G
ATOM  17256  CD1 LEU G1210      63.341  87.974  67.189  1.00 71.63      G
ATOM  17257  CD2 LEU G1210      65.087  88.650  65.568  1.00 71.63      G
ATOM  17258  C   LEU G1210      62.467  84.589  65.924  1.00 27.97      G
ATOM  17259  O   LEU G1210      61.428  84.804  66.553  1.00 27.97      G
ATOM  17260  N   SER G1211      62.587  83.600  65.038  1.00 50.15      G
ATOM  17261  CA  SER G1211      61.463  82.729  64.687  1.00 50.15      G
ATOM  17262  CB  SER G1211      61.739  81.997  63.371  1.00 85.49      G
ATOM  17263  OG  SER G1211      62.585  80.879  63.572  1.00 85.49      G
ATOM  17264  C   SER G1211      61.081  81.704  65.740  1.00 50.15      G
ATOM  17265  O   SER G1211      59.975  81.159  65.708  1.00 50.15      G
ATOM  17266  N   MET G1212      61.992  81.419  66.659  1.00 44.94      G
```

```
ATOM  17267  CA   MET G1212      61.694  80.455  67.709  1.00 44.94      G
ATOM  17268  CB   MET G1212      62.605  79.207  67.571  1.00 49.59      G
ATOM  17269  CG   MET G1212      62.768  78.667  66.107  1.00 49.59      G
ATOM  17270  SD   MET G1212      63.348  76.920  65.840  1.00 49.59      G
ATOM  17271  CE   MET G1212      65.118  77.050  65.956  1.00 49.59      G
ATOM  17272  C    MET G1212      61.868  81.154  69.071  1.00 44.94      G
ATOM  17273  O    MET G1212      61.413  82.286  69.270  1.00 44.94      G
ATOM  17274  N    ALA G1213      62.518  80.501  70.018  1.00 18.63      G
ATOM  17275  CA   ALA G1213      62.704  81.123  71.319  1.00 18.63      G
ATOM  17276  CB   ALA G1213      62.159  80.215  72.419  1.00100.07      G
ATOM  17277  C    ALA G1213      64.175  81.410  71.561  1.00 18.63      G
ATOM  17278  O    ALA G1213      64.952  80.516  71.905  1.00 18.63      G
ATOM  17279  N    ARG G1214      64.532  82.676  71.387  1.00100.07      G
ATOM  17280  CA   ARG G1214      65.886  83.174  71.571  1.00100.07      G
ATOM  17281  CB   ARG G1214      65.874  84.245  72.689  1.00 96.83      G
ATOM  17282  CG   ARG G1214      64.918  83.980  73.836  1.00 96.83      G
ATOM  17283  CD   ARG G1214      65.669  83.616  75.107  1.00 96.83      G
ATOM  17284  NE   ARG G1214      64.794  83.045  76.135  1.00 96.83      G
ATOM  17285  CZ   ARG G1214      65.209  82.606  77.326  1.00 96.83      G
ATOM  17286  NH1  ARG G1214      66.493  82.670  77.657  1.00 96.83      G
ATOM  17287  NH2  ARG G1214      64.340  82.095  78.193  1.00 96.83      G
ATOM  17288  C    ARG G1214      67.050  82.177  71.779  1.00100.07      G
ATOM  17289  O    ARG G1214      67.524  81.989  72.895  1.00100.07      G
ATOM  17290  N    PRO G1215      67.487  81.485  70.711  1.00 95.14      G
ATOM  17291  CD   PRO G1215      66.496  80.743  69.922  1.00 39.96      G
ATOM  17292  CA   PRO G1215      68.597  80.571  70.969  1.00 95.14      G
ATOM  17293  CB   PRO G1215      67.873  79.368  71.490  1.00 39.96      G
ATOM  17294  CG   PRO G1215      66.709  79.289  70.452  1.00 39.96      G
ATOM  17295  C    PRO G1215      69.412  80.224  69.702  1.00 95.14      G
ATOM  17296  O    PRO G1215      70.292  79.373  69.759  1.00 95.14      G
ATOM  17297  N    VAL G1216      69.106  80.867  68.571  1.00 37.25      G
ATOM  17298  CA   VAL G1216      69.788  80.637  67.280  1.00 37.25      G
ATOM  17299  CB   VAL G1216      70.776  81.754  66.959  1.00 17.32      G
ATOM  17300  CG1  VAL G1216      71.369  81.542  65.578  1.00 17.32      G
ATOM  17301  CG2  VAL G1216      70.090  83.084  67.070  1.00 17.32      G
ATOM  17302  C    VAL G1216      70.570  79.336  67.125  1.00 37.25      G
ATOM  17303  O    VAL G1216      71.705  79.236  67.583  1.00 37.25      G
ATOM  17304  N    SER G1217      69.979  78.352  66.457  1.00 18.54      G
ATOM  17305  CA   SER G1217      70.653  77.080  66.250  1.00 18.54      G
ATOM  17306  CB   SER G1217      69.674  76.083  65.644  1.00 69.81      G
ATOM  17307  OG   SER G1217      68.445  76.108  66.354  1.00 69.81      G
ATOM  17308  C    SER G1217      71.772  77.398  65.282  1.00 18.54      G
ATOM  17309  O    SER G1217      71.649  78.341  64.515  1.00 18.54      G
ATOM  17310  N    ILE G1218      72.862  76.636  65.314  1.00 37.65      G
ATOM  17311  CA   ILE G1218      73.990  76.900  64.416  1.00 37.65      G
ATOM  17312  CB   ILE G1218      75.201  75.985  64.718  1.00 63.18      G
ATOM  17313  CG2  ILE G1218      76.057  75.829  63.478  1.00 63.18      G
ATOM  17314  CG1  ILE G1218      76.055  76.583  65.838  1.00 63.18      G
ATOM  17315  CD   ILE G1218      75.343  76.684  67.168  1.00 63.18      G
ATOM  17316  C    ILE G1218      73.625  76.725  62.956  1.00 37.65      G
ATOM  17317  O    ILE G1218      72.914  75.795  62.609  1.00 37.65      G
ATOM  17318  N    GLY G1219      74.131  77.621  62.111  1.00 63.41      G
ATOM  17319  CA   GLY G1219      73.859  77.568  60.684  1.00 63.41      G
ATOM  17320  C    GLY G1219      72.536  78.196  60.266  1.00 63.41      G
ATOM  17321  O    GLY G1219      71.599  77.480  59.911  1.00 63.41      G
ATOM  17322  N    GLU G1220      72.443  79.525  60.303  1.00 35.37      G
ATOM  17323  CA   GLU G1220      71.211  80.209  59.910  1.00 35.37      G
ATOM  17324  CB   GLU G1220      70.725  81.141  61.018  1.00 58.78      G
ATOM  17325  CG   GLU G1220      69.742  80.465  61.973  1.00 58.78      G
ATOM  17326  CD   GLU G1220      68.498  79.912  61.272  1.00 58.78      G
ATOM  17327  OE1  GLU G1220      67.714  80.705  60.707  1.00 58.78      G
ATOM  17328  OE2  GLU G1220      68.300  78.678  61.287  1.00 58.78      G
ATOM  17329  C    GLU G1220      71.314  80.972  58.592  1.00 35.37      G
ATOM  17330  O    GLU G1220      70.566  80.678  57.659  1.00 35.37      G
ATOM  17331  N    ALA G1221      72.201  81.959  58.516  1.00 26.20      G
ATOM  17332  CA   ALA G1221      72.396  82.709  57.275  1.00 26.20      G
ATOM  17333  CB   ALA G1221      71.853  81.915  56.084  1.00 14.55      G
ATOM  17334  C    ALA G1221      71.872  84.142  57.212  1.00 26.20      G
ATOM  17335  O    ALA G1221      71.300  84.665  58.172  1.00 26.20      G
ATOM  17336  N    VAL G1222      72.096  84.766  56.055  1.00 39.01      G
ATOM  17337  CA   VAL G1222      71.698  86.142  55.805  1.00 39.01      G
ATOM  17338  CB   VAL G1222      72.755  86.907  55.047  1.00 34.69      G
ATOM  17339  CG1  VAL G1222      72.341  88.364  54.953  1.00 34.69      G
ATOM  17340  CG2  VAL G1222      74.092  86.738  55.724  1.00 34.69      G
ATOM  17341  C    VAL G1222      70.439  86.264  54.995  1.00 39.01      G
ATOM  17342  O    VAL G1222      69.733  87.258  55.112  1.00 39.01      G
ATOM  17343  N    GLY G1223      70.178  85.295  54.125  1.00 54.48      G
ATOM  17344  CA   GLY G1223      68.943  85.363  53.379  1.00 54.48      G
ATOM  17345  C    GLY G1223      67.868  85.614  54.434  1.00 54.48      G
ATOM  17346  O    GLY G1223      66.905  86.344  54.184  1.00 54.48      G
ATOM  17347  N    VAL G1224      68.069  85.022  55.623  1.00 15.36      G
ATOM  17348  CA   VAL G1224      67.169  85.133  56.772  1.00 15.36      G
ATOM  17349  CB   VAL G1224      67.580  84.247  57.928  1.00 38.19      G
ATOM  17350  CG1  VAL G1224      66.351  83.797  58.693  1.00 38.19      G
```

| ATOM | 17351 | CG2 | VAL G1224 | 68.410 | 83.096 | 57.431 | 1.00 | 38.19 | G |
|------|-------|-----|-----------|--------|--------|--------|------|-------|---|
| ATOM | 17352 | C | VAL G1224 | 67.262 | 86.516 | 57.318 | 1.00 | 15.36 | G |
| ATOM | 17353 | O | VAL G1224 | 66.484 | 86.890 | 58.180 | 1.00 | 15.36 | G |
| ATOM | 17354 | N | VAL G1225 | 68.247 | 87.264 | 56.840 | 1.00 | 34.12 | G |
| ATOM | 17355 | CA | VAL G1225 | 68.457 | 88.632 | 57.278 | 1.00 | 34.12 | G |
| ATOM | 17356 | CB | VAL G1225 | 69.909 | 88.853 | 57.643 | 1.00 | 100.07 | G |
| ATOM | 17357 | CG1 | VAL G1225 | 70.062 | 90.207 | 58.312 | 1.00 | 100.07 | G |
| ATOM | 17358 | CG2 | VAL G1225 | 70.385 | 87.720 | 58.544 | 1.00 | 100.07 | G |
| ATOM | 17359 | C | VAL G1225 | 68.073 | 89.602 | 56.170 | 1.00 | 34.12 | G |
| ATOM | 17360 | O | VAL G1225 | 67.147 | 90.392 | 56.319 | 1.00 | 34.12 | G |
| ATOM | 17361 | N | ALA G1226 | 68.788 | 89.533 | 55.056 | 1.00 | 21.86 | G |
| ATOM | 17362 | CA | ALA G1226 | 68.513 | 90.393 | 53.898 | 1.00 | 21.86 | G |
| ATOM | 17363 | CB | ALA G1226 | 69.207 | 89.839 | 52.647 | 1.00 | 51.53 | G |
| ATOM | 17364 | C | ALA G1226 | 67.014 | 90.438 | 53.673 | 1.00 | 21.86 | G |
| ATOM | 17365 | O | ALA G1226 | 66.357 | 91.439 | 53.983 | 1.00 | 21.86 | G |
| ATOM | 17366 | N | ALA G1227 | 66.492 | 89.337 | 53.128 | 1.00 | 6.73 | G |
| ATOM | 17367 | CA | ALA G1227 | 65.069 | 89.200 | 52.879 | 1.00 | 6.73 | G |
| ATOM | 17368 | CB | ALA G1227 | 64.699 | 87.706 | 52.757 | 1.00 | 15.36 | G |
| ATOM | 17369 | C | ALA G1227 | 64.278 | 89.870 | 54.018 | 1.00 | 6.73 | G |
| ATOM | 17370 | O | ALA G1227 | 63.359 | 90.644 | 53.741 | 1.00 | 6.73 | G |
| ATOM | 17371 | N | GLU G1228 | 64.646 | 89.602 | 55.284 | 1.00 | 7.96 | G |
| ATOM | 17372 | CA | GLU G1228 | 63.941 | 90.199 | 56.425 | 1.00 | 7.96 | G |
| ATOM | 17373 | CB | GLU G1228 | 64.671 | 89.933 | 57.752 | 1.00 | 76.95 | G |
| ATOM | 17374 | CG | GLU G1228 | 64.113 | 88.725 | 58.509 | 1.00 | 76.95 | G |
| ATOM | 17375 | CD | GLU G1228 | 64.152 | 88.859 | 60.043 | 1.00 | 76.95 | G |
| ATOM | 17376 | OE1 | GLU G1228 | 63.736 | 89.910 | 60.578 | 1.00 | 76.95 | G |
| ATOM | 17377 | OE2 | GLU G1228 | 64.581 | 87.900 | 60.729 | 1.00 | 76.95 | G |
| ATOM | 17378 | C | GLU G1228 | 63.805 | 91.694 | 56.192 | 1.00 | 7.96 | G |
| ATOM | 17379 | O | GLU G1228 | 62.724 | 92.273 | 56.268 | 1.00 | 7.96 | G |
| ATOM | 17380 | N | SER G1229 | 64.912 | 92.314 | 55.854 | 1.00 | 13.86 | G |
| ATOM | 17381 | CA | SER G1229 | 64.916 | 93.732 | 55.605 | 1.00 | 13.86 | G |
| ATOM | 17382 | CB | SER G1229 | 66.375 | 94.206 | 55.562 | 1.00 | 32.16 | G |
| ATOM | 17383 | OG | SER G1229 | 66.474 | 95.612 | 55.640 | 1.00 | 32.16 | G |
| ATOM | 17384 | C | SER G1229 | 64.181 | 94.090 | 54.299 | 1.00 | 13.86 | G |
| ATOM | 17385 | O | SER G1229 | 64.258 | 95.223 | 53.846 | 1.00 | 13.86 | G |
| ATOM | 17386 | N | ILE G1230 | 63.470 | 93.147 | 53.685 | 1.00 | 35.41 | G |
| ATOM | 17387 | CA | ILE G1230 | 62.774 | 93.469 | 52.428 | 1.00 | 35.41 | G |
| ATOM | 17388 | CB | ILE G1230 | 63.600 | 93.054 | 51.185 | 1.00 | 100.07 | G |
| ATOM | 17389 | CG2 | ILE G1230 | 62.867 | 93.448 | 49.900 | 1.00 | 100.07 | G |
| ATOM | 17390 | CG1 | ILE G1230 | 64.957 | 93.758 | 51.190 | 1.00 | 100.07 | G |
| ATOM | 17391 | CD | ILE G1230 | 65.988 | 93.158 | 52.121 | 1.00 | 100.07 | G |
| ATOM | 17392 | C | ILE G1230 | 61.366 | 92.900 | 52.243 | 1.00 | 35.41 | G |
| ATOM | 17393 | O | ILE G1230 | 60.671 | 93.252 | 51.288 | 1.00 | 35.41 | G |
| ATOM | 17394 | N | GLY G1231 | 60.941 | 92.013 | 53.133 | 1.00 | 97.53 | G |
| ATOM | 17395 | CA | GLY G1231 | 59.596 | 91.481 | 53.013 | 1.00 | 97.53 | G |
| ATOM | 17396 | C | GLY G1231 | 58.707 | 92.624 | 53.440 | 1.00 | 97.53 | G |
| ATOM | 17397 | O | GLY G1231 | 57.552 | 92.439 | 53.812 | 1.00 | 97.53 | G |
| ATOM | 17398 | N | GLU G1232 | 59.286 | 93.821 | 53.377 | 1.00 | 99.15 | G |
| ATOM | 17399 | CA | GLU G1232 | 58.629 | 95.052 | 53.770 | 1.00 | 99.15 | G |
| ATOM | 17400 | CB | GLU G1232 | 59.482 | 95.765 | 54.815 | 1.00 | 100.07 | G |
| ATOM | 17401 | CG | GLU G1232 | 60.367 | 94.816 | 55.604 | 1.00 | 100.07 | G |
| ATOM | 17402 | CD | GLU G1232 | 59.580 | 93.732 | 56.335 | 1.00 | 100.07 | G |
| ATOM | 17403 | OE1 | GLU G1232 | 58.825 | 94.071 | 57.272 | 1.00 | 100.07 | G |
| ATOM | 17404 | OE2 | GLU G1232 | 59.716 | 92.540 | 55.977 | 1.00 | 100.07 | G |
| ATOM | 17405 | C | GLU G1232 | 58.371 | 95.983 | 52.589 | 1.00 | 99.15 | G |
| ATOM | 17406 | O | GLU G1232 | 57.226 | 96.159 | 52.192 | 1.00 | 99.15 | G |
| ATOM | 17407 | N | PRO G1233 | 59.431 | 96.572 | 51.996 | 1.00 | 26.64 | G |
| ATOM | 17408 | CD | PRO G1233 | 60.812 | 96.082 | 52.065 | 1.00 | 66.81 | G |
| ATOM | 17409 | CA | PRO G1233 | 59.291 | 97.494 | 50.853 | 1.00 | 26.64 | G |
| ATOM | 17410 | CB | PRO G1233 | 60.517 | 97.184 | 49.985 | 1.00 | 66.81 | G |
| ATOM | 17411 | CG | PRO G1233 | 61.128 | 95.942 | 50.615 | 1.00 | 66.81 | G |
| ATOM | 17412 | C | PRO G1233 | 57.980 | 97.437 | 50.061 | 1.00 | 26.64 | G |
| ATOM | 17413 | O | PRO G1233 | 57.178 | 98.380 | 50.128 | 1.00 | 26.64 | G |
| ATOM | 17414 | N | GLY G1234 | 57.760 | 96.345 | 49.323 | 1.00 | 55.33 | G |
| ATOM | 17415 | CA | GLY G1234 | 56.533 | 96.211 | 48.552 | 1.00 | 55.33 | G |
| ATOM | 17416 | C | GLY G1234 | 55.376 | 96.838 | 49.308 | 1.00 | 55.33 | G |
| ATOM | 17417 | O | GLY G1234 | 54.522 | 97.516 | 48.734 | 1.00 | 55.33 | G |
| ATOM | 17418 | N | THR G1235 | 55.383 | 96.616 | 50.618 | 1.00 | 100.07 | G |
| ATOM | 17419 | CA | THR G1235 | 54.375 | 97.136 | 51.537 | 1.00 | 100.07 | G |
| ATOM | 17420 | CB | THR G1235 | 54.246 | 96.218 | 52.789 | 1.00 | 100.06 | G |
| ATOM | 17421 | OG1 | THR G1235 | 53.285 | 95.185 | 52.525 | 1.00 | 100.06 | G |
| ATOM | 17422 | CG2 | THR G1235 | 53.837 | 97.023 | 54.035 | 1.00 | 100.06 | G |
| ATOM | 17423 | C | THR G1235 | 54.677 | 98.559 | 52.013 | 1.00 | 100.07 | G |
| ATOM | 17424 | O | THR G1235 | 53.766 | 99.289 | 52.418 | 1.00 | 100.07 | G |
| ATOM | 17425 | N | GLN G1236 | 55.945 | 98.955 | 51.975 | 1.00 | 41.97 | G |
| ATOM | 17426 | CA | GLN G1236 | 56.308 | 100.293 | 52.429 | 1.00 | 41.97 | G |
| ATOM | 17427 | CB | GLN G1236 | 56.933 | 100.234 | 53.839 | 1.00 | 100.07 | G |
| ATOM | 17428 | CG | GLN G1236 | 58.011 | 99.165 | 54.049 | 1.00 | 100.07 | G |
| ATOM | 17429 | CD | GLN G1236 | 58.036 | 98.615 | 55.484 | 1.00 | 100.07 | G |
| ATOM | 17430 | OE1 | GLN G1236 | 57.008 | 98.169 | 56.007 | 1.00 | 100.07 | G |
| ATOM | 17431 | NE2 | GLN G1236 | 59.214 | 98.633 | 56.113 | 1.00 | 100.07 | G |
| ATOM | 17432 | C | GLN G1236 | 57.208 | 101.058 | 51.480 | 1.00 | 41.97 | G |
| ATOM | 17433 | O | GLN G1236 | 57.212 | 100.811 | 50.278 | 1.00 | 41.97 | G |
| ATOM | 17434 | N | LEU G1237 | 57.964 | 101.997 | 52.031 | 1.00 | 17.85 | G |

```
ATOM  17435  CA  LEU G1237      58.849 102.822  51.226  1.00 17.85      G
ATOM  17436  CB  LEU G1237      59.867 101.930  50.529  1.00 99.96      G
ATOM  17437  CG  LEU G1237      60.299 100.787  51.460  1.00 99.96      G
ATOM  17438  CD1 LEU G1237      61.594 100.212  50.958  1.00 99.96      G
ATOM  17439  CD2 LEU G1237      60.472 101.275  52.893  1.00 99.96      G
ATOM  17440  C   LEU G1237      57.934 103.546  50.244  1.00 17.85      G
ATOM  17441  O   LEU G1237      56.821 103.916  50.622  1.00 17.85      G
ATOM  17442  N   THR G1238      58.369 103.761  49.006  1.00 64.90      G
ATOM  17443  CA  THR G1238      57.507 104.442  48.039  1.00 64.90      G
ATOM  17444  CB  THR G1238      57.055 105.837  48.546  1.00 81.69      G
ATOM  17445  OG1 THR G1238      56.173 106.437  47.589  1.00 81.69      G
ATOM  17446  CG2 THR G1238      58.250 106.745  48.735  1.00 81.69      G
ATOM  17447  C   THR G1238      58.154 104.648  46.687  1.00 64.90      G
ATOM  17448  O   THR G1238      57.511 105.143  45.764  1.00 64.90      G
ATOM  17449  N   MET G1239      59.423 104.271  46.572  1.00 46.39      G
ATOM  17450  CA  MET G1239      60.174 104.442  45.331  1.00 46.39      G
ATOM  17451  CB  MET G1239      60.000 103.224  44.431  1.00 94.23      G
ATOM  17452  CG  MET G1239      61.314 102.590  44.056  1.00 94.23      G
ATOM  17453  SD  MET G1239      62.513 103.849  43.594  1.00 94.23      G
ATOM  17454  CE  MET G1239      64.055 102.871  43.654  1.00 94.23      G
ATOM  17455  C   MET G1239      59.759 105.712  44.581  1.00 46.39      G
ATOM  17456  O   MET G1239      59.935 105.819  43.363  1.00 46.39      G
ATOM  17457  N   ALA G1240      59.226 106.670  45.340  1.00100.07      G
ATOM  17458  CA  ALA G1240      58.749 107.950  44.827  1.00100.07      G
ATOM  17459  CB  ALA G1240      57.806 108.591  45.839  1.00 51.43      G
ATOM  17460  C   ALA G1240      59.900 108.896  44.516  1.00100.07      G
ATOM  17461  O   ALA G1240      61.044 108.634  44.891  1.00100.07      G
ATOM  17462  N   ALA G1241      59.581 110.003  43.847  1.00100.07      G
ATOM  17463  CA  ALA G1241      60.572 111.004  43.444  1.00100.07      G
ATOM  17464  CB  ALA G1241      60.096 111.710  42.164  1.00 84.37      G
ATOM  17465  C   ALA G1241      60.905 112.044  44.518  1.00100.07      G
ATOM  17466  O   ALA G1241      61.393 111.708  45.600  1.00100.07      G
ATOM  17467  N   ALA G1242      60.656 113.310  44.193  1.00100.07      G
ATOM  17468  CA  ALA G1242      60.913 114.422  45.106  1.00100.07      G
ATOM  17469  CB  ALA G1242      62.200 115.149  44.698  1.00100.07      G
ATOM  17470  C   ALA G1242      59.732 115.403  45.120  1.00100.07      G
ATOM  17471  O   ALA G1242      59.062 115.600  44.103  1.00100.07      G
ATOM  17472  N   ALA G1243      59.483 116.010  46.278  0.00 58.09      G
ATOM  17473  CA  ALA G1243      58.386 116.964  46.421  0.00 58.09      G
ATOM  17474  CB  ALA G1243      57.051 116.249  46.249  0.00 58.09      G
ATOM  17475  C   ALA G1243      58.424 117.676  47.771  0.00 58.09      G
ATOM  17476  O   ALA G1243      58.994 117.169  48.737  0.00 58.09      G
ATOM  17477  N   ALA G1244      57.809 118.853  47.828  0.00 58.09      G
ATOM  17478  CA  ALA G1244      57.763 119.644  49.053  0.00 58.09      G
ATOM  17479  CB  ALA G1244      59.136 120.238  49.343  0.00 58.09      G
ATOM  17480  C   ALA G1244      56.725 120.757  48.934  0.00 58.09      G
ATOM  17481  O   ALA G1244      56.089 120.915  47.892  0.00 58.09      G
ATOM  17482  N   ALA G1245      56.558 121.526  50.006  0.00 58.09      G
ATOM  17483  CA  ALA G1245      55.596 122.622  50.020  0.00 58.09      G
ATOM  17484  CB  ALA G1245      54.442 122.289  50.959  0.00 58.09      G
ATOM  17485  C   ALA G1245      56.257 123.930  50.444  0.00 58.09      G
ATOM  17486  O   ALA G1245      57.454 124.128  50.237  0.00 58.09      G
ATOM  17487  N   ALA G1246      55.469 124.822  51.038  0.00 58.09      G
ATOM  17488  CA  ALA G1246      55.974 126.112  51.492  0.00 58.09      G
ATOM  17489  CB  ALA G1246      55.280 127.238  50.736  0.00 58.09      G
ATOM  17490  C   ALA G1246      55.760 126.280  52.993  0.00 58.09      G
ATOM  17491  O   ALA G1246      54.899 125.625  53.582  0.00 58.09      G
ATOM  17492  N   ALA G1247      56.548 127.161  53.602  0.00 58.09      G
ATOM  17493  CA  ALA G1247      56.458 127.428  55.034  0.00 58.09      G
ATOM  17494  CB  ALA G1247      55.059 127.922  55.388  0.00 58.09      G
ATOM  17495  C   ALA G1247      56.800 126.188  55.854  0.00 58.09      G
ATOM  17496  O   ALA G1247      56.069 125.198  55.833  0.00 58.09      G
ATOM  17497  N   ALA G1248      57.914 126.254  56.577  0.00 58.09      G
ATOM  17498  CA  ALA G1248      58.362 125.141  57.407  0.00 58.09      G
ATOM  17499  CB  ALA G1248      57.382 124.918  58.555  0.00 58.09      G
ATOM  17500  C   ALA G1248      58.501 123.868  56.579  0.00 58.09      G
ATOM  17501  O   ALA G1248      57.582 123.049  56.523  0.00 58.09      G
ATOM  17502  N   ALA G1249      59.654 123.707  55.938  0.00 58.09      G
ATOM  17503  CA  ALA G1249      59.916 122.535  55.110  0.00 58.09      G
ATOM  17504  CB  ALA G1249      59.988 122.942  53.643  0.00 58.09      G
ATOM  17505  C   ALA G1249      61.213 121.847  55.527  0.00 58.09      G
ATOM  17506  O   ALA G1249      61.757 122.124  56.596  0.00 58.09      G
ATOM  17507  N   GLY G1250      61.701 120.948  54.677  1.00100.07      G
ATOM  17508  CA  GLY G1250      62.928 120.232  54.976  1.00100.07      G
ATOM  17509  C   GLY G1250      63.488 119.435  53.807  1.00100.07      G
ATOM  17510  O   GLY G1250      63.011 119.534  52.672  1.00100.07      G
ATOM  17511  N   THR G1251      64.511 118.637  54.091  1.00100.07      G
ATOM  17512  CA  THR G1251      65.156 117.815  53.073  1.00100.07      G
ATOM  17513  CB  THR G1251      66.564 117.366  53.544  1.00100.00      G
ATOM  17514  OG1 THR G1251      67.407 118.518  53.675  1.00100.00      G
ATOM  17515  CG2 THR G1251      67.194 116.387  52.551  1.00100.00      G
ATOM  17516  C   THR G1251      64.316 116.581  52.735  1.00100.07      G
ATOM  17517  O   THR G1251      63.649 116.013  53.609  1.00100.07      G
ATOM  17518  N   ASP G1252      64.359 116.180  51.461  1.00100.07      G
```

```
ATOM  17519  CA   ASP G1252      63.614 115.020  50.972  1.00100.07      G
ATOM  17520  CB   ASP G1252      63.187 115.232  49.511  1.00 98.49      G
ATOM  17521  CG   ASP G1252      61.773 115.784  49.391  1.00 98.49      G
ATOM  17522  OD1  ASP G1252      60.841 115.135  49.907  1.00 98.49      G
ATOM  17523  OD2  ASP G1252      61.587 116.858  48.781  1.00 98.49      G
ATOM  17524  C    ASP G1252      64.328 113.668  51.118  1.00100.07      G
ATOM  17525  O    ASP G1252      65.199 113.502  51.988  1.00100.07      G
ATOM  17526  N    ILE G1253      63.951 112.715  50.260  1.00 63.35      G
ATOM  17527  CA   ILE G1253      64.471 111.342  50.302  1.00 63.35      G
ATOM  17528  CB   ILE G1253      66.015 111.296  50.414  1.00 69.32      G
ATOM  17529  CG2  ILE G1253      66.506 109.894  50.108  1.00 69.32      G
ATOM  17530  CG1  ILE G1253      66.657 112.260  49.415  1.00 69.32      G
ATOM  17531  CD   ILE G1253      68.161 112.447  49.629  1.00 69.32      G
ATOM  17532  C    ILE G1253      63.843 110.745  51.577  1.00 63.35      G
ATOM  17533  O    ILE G1253      63.841 109.531  51.804  1.00 63.35      G
ATOM  17534  N    THR G1254      63.308 111.656  52.392  1.00100.07      G
ATOM  17535  CA   THR G1254      62.623 111.370  53.652  1.00100.07      G
ATOM  17536  CB   THR G1254      61.901 112.668  54.176  1.00100.07      G
ATOM  17537  OG1  THR G1254      61.475 112.489  55.534  1.00100.07      G
ATOM  17538  CG2  THR G1254      60.677 113.003  53.303  1.00100.07      G
ATOM  17539  C    THR G1254      61.589 110.305  53.314  1.00100.07      G
ATOM  17540  O    THR G1254      61.221 109.464  54.137  1.00100.07      G
ATOM  17541  N    GLN G1255      61.144 110.369  52.067  1.00100.07      G
ATOM  17542  CA   GLN G1255      60.159 109.464  51.514  1.00100.07      G
ATOM  17543  CB   GLN G1255      60.160 109.624  49.983  1.00100.07      G
ATOM  17544  CG   GLN G1255      61.541 109.483  49.328  1.00100.07      G
ATOM  17545  CD   GLN G1255      61.559 109.915  47.868  1.00100.07      G
ATOM  17546  OE1  GLN G1255      60.690 109.536  47.084  1.00100.07      G
ATOM  17547  NE2  GLN G1255      62.561 110.703  47.498  1.00100.07      G
ATOM  17548  C    GLN G1255      60.344 107.991  51.914  1.00100.07      G
ATOM  17549  O    GLN G1255      59.661 107.495  52.822  1.00100.07      G
ATOM  17550  N    GLY G1256      61.263 107.294  51.248  1.00 57.81      G
ATOM  17551  CA   GLY G1256      61.461 105.893  51.559  1.00 57.81      G
ATOM  17552  C    GLY G1256      62.640 105.213  50.897  1.00 57.81      G
ATOM  17553  O    GLY G1256      63.728 105.781  50.821  1.00 57.81      G
ATOM  17554  N    LEU G1257      62.413 103.994  50.409  1.00 53.49      G
ATOM  17555  CA   LEU G1257      63.470 103.203  49.787  1.00 53.49      G
ATOM  17556  CB   LEU G1257      62.925 102.355  48.623  1.00 27.44      G
ATOM  17557  CG   LEU G1257      63.865 101.244  48.117  1.00 27.44      G
ATOM  17558  CD1  LEU G1257      64.133 100.245  49.226  1.00 27.44      G
ATOM  17559  CD2  LEU G1257      63.249 100.531  46.936  1.00 27.44      G
ATOM  17560  C    LEU G1257      64.623 104.076  49.304  1.00 53.49      G
ATOM  17561  O    LEU G1257      65.759 103.926  49.776  1.00 53.49      G
ATOM  17562  N    PRO G1258      64.342 105.020  48.381  1.00 35.93      G
ATOM  17563  CD   PRO G1258      63.039 105.468  47.851  1.00 27.16      G
ATOM  17564  CA   PRO G1258      65.415 105.880  47.884  1.00 35.93      G
ATOM  17565  CB   PRO G1258      64.659 107.094  47.366  1.00 27.16      G
ATOM  17566  CG   PRO G1258      63.456 106.447  46.740  1.00 27.16      G
ATOM  17567  C    PRO G1258      66.397 106.203  48.992  1.00 35.93      G
ATOM  17568  O    PRO G1258      67.605 106.172  48.783  1.00 35.93      G
ATOM  17569  N    ARG G1259      65.882 106.487  50.178  1.00 22.20      G
ATOM  17570  CA   ARG G1259      66.773 106.770  51.283  1.00 22.20      G
ATOM  17571  CB   ARG G1259      66.076 107.525  52.418  1.00 50.93      G
ATOM  17572  CG   ARG G1259      66.960 107.595  53.657  1.00 50.93      G
ATOM  17573  CD   ARG G1259      66.802 108.878  54.434  1.00 50.93      G
ATOM  17574  NE   ARG G1259      68.032 109.186  55.160  1.00 50.93      G
ATOM  17575  CZ   ARG G1259      69.208 109.397  54.572  1.00 50.93      G
ATOM  17576  NH1  ARG G1259      69.310 109.334  53.253  1.00 50.93      G
ATOM  17577  NH2  ARG G1259      70.287 109.660  55.300  1.00 50.93      G
ATOM  17578  C    ARG G1259      67.281 105.459  51.814  1.00 22.20      G
ATOM  17579  O    ARG G1259      68.488 105.269  51.965  1.00 22.20      G
ATOM  17580  N    VAL G1260      66.356 104.556  52.105  1.00 30.03      G
ATOM  17581  CA   VAL G1260      66.739 103.261  52.621  1.00 30.03      G
ATOM  17582  CB   VAL G1260      65.552 102.308  52.626  1.00 22.14      G
ATOM  17583  CG1  VAL G1260      65.972 100.939  53.160  1.00 22.14      G
ATOM  17584  CG2  VAL G1260      64.449 102.902  53.473  1.00 22.14      G
ATOM  17585  C    VAL G1260      67.867 102.696  51.770  1.00 30.03      G
ATOM  17586  O    VAL G1260      68.567 101.781  52.199  1.00 30.03      G
ATOM  17587  N    ILE G1261      68.035 103.248  50.568  1.00 59.61      G
ATOM  17588  CA   ILE G1261      69.109 102.847  49.658  1.00 59.61      G
ATOM  17589  CB   ILE G1261      68.641 102.823  48.206  1.00 37.45      G
ATOM  17590  CG2  ILE G1261      69.824 102.957  47.260  1.00 37.45      G
ATOM  17591  CG1  ILE G1261      67.889 101.534  47.946  1.00 37.45      G
ATOM  17592  CD   ILE G1261      67.453 101.408  46.518  1.00 37.45      G
ATOM  17593  C    ILE G1261      70.271 103.835  49.771  1.00 59.61      G
ATOM  17594  O    ILE G1261      71.405 103.436  50.060  1.00 59.61      G
ATOM  17595  N    GLU G1262      69.981 105.119  49.531  1.00 24.23      G
ATOM  17596  CA   GLU G1262      70.979 106.187  49.630  1.00 24.23      G
ATOM  17597  CB   GLU G1262      70.273 107.548  49.727  1.00 18.19      G
ATOM  17598  CG   GLU G1262      71.110 108.733  50.207  1.00 18.19      G
ATOM  17599  CD   GLU G1262      70.370 110.076  50.099  1.00 18.19      G
ATOM  17600  OE1  GLU G1262      70.249 110.591  48.973  1.00 18.19      G
ATOM  17601  OE2  GLU G1262      69.909 110.624  51.123  1.00 18.19      G
ATOM  17602  C    GLU G1262      71.745 105.861  50.896  1.00 24.23      G
```

```
ATOM  17603  O    GLU G1262     72.924 106.178 51.041  1.00 24.23      G
ATOM  17604  N    LEU G1263     71.051 105.199 51.810  1.00 51.86      G
ATOM  17605  CA   LEU G1263     71.656 104.762 53.043  1.00 51.86      G
ATOM  17606  CB   LEU G1263     70.586 104.248 53.993  1.00 43.95      G
ATOM  17607  CG   LEU G1263     70.120 105.160 55.121  1.00 43.95      G
ATOM  17608  CD1  LEU G1263     70.081 106.597 54.653  1.00 43.95      G
ATOM  17609  CD2  LEU G1263     68.751 104.700 55.588  1.00 43.95      G
ATOM  17610  C    LEU G1263     72.581 103.627 52.647  1.00 51.86      G
ATOM  17611  O    LEU G1263     73.733 103.853 52.301  1.00 51.86      G
ATOM  17612  N    PHE G1264     72.051 102.412 52.669  1.00 30.94      G
ATOM  17613  CA   PHE G1264     72.799 101.212 52.328  1.00 30.94      G
ATOM  17614  CB   PHE G1264     71.857 100.202 51.682  1.00 22.91      G
ATOM  17615  CG   PHE G1264     71.003  99.453 52.673  1.00 22.91      G
ATOM  17616  CD1  PHE G1264     69.687  99.104 52.355  1.00 22.91      G
ATOM  17617  CD2  PHE G1264     71.533  99.043 53.907  1.00 22.91      G
ATOM  17618  CE1  PHE G1264     68.911  98.359 53.238  1.00 22.91      G
ATOM  17619  CE2  PHE G1264     70.771  98.295 54.800  1.00 22.91      G
ATOM  17620  CZ   PHE G1264     69.457  97.951 54.464  1.00 22.91      G
ATOM  17621  C    PHE G1264     74.023 101.427 51.447  1.00 30.94      G
ATOM  17622  O    PHE G1264     75.155 101.350 51.929  1.00 30.94      G
ATOM  17623  N    GLU G1265     73.806 101.701 50.161  1.00 56.36      G
ATOM  17624  CA   GLU G1265     74.914 101.911 49.227  1.00 56.36      G
ATOM  17625  CB   GLU G1265     74.377 102.148 47.823  1.00100.07      G
ATOM  17626  CG   GLU G1265     74.336 100.898 46.984  1.00100.07      G
ATOM  17627  CD   GLU G1265     73.406 101.032 45.798  1.00100.07      G
ATOM  17628  OE1  GLU G1265     73.260 102.161 45.280  1.00100.07      G
ATOM  17629  OE2  GLU G1265     72.827 100.009 45.377  1.00100.07      G
ATOM  17630  C    GLU G1265     75.846 103.044 49.631  1.00 56.36      G
ATOM  17631  O    GLU G1265     76.828 103.322 48.954  1.00 56.36      G
ATOM  17632  N    ALA G1266     75.524 103.696 50.739  1.00 76.49      G
ATOM  17633  CA   ALA G1266     76.345 104.768 51.275  1.00 76.49      G
ATOM  17634  CB   ALA G1266     77.629 104.191 51.827  1.00  8.17      G
ATOM  17635  C    ALA G1266     76.677 105.852 50.285  1.00 76.49      G
ATOM  17636  O    ALA G1266     77.758 105.862 49.712  1.00 76.49      G
ATOM  17637  N    ARG G1267     75.758 106.776 50.088  1.00 83.66      G
ATOM  17638  CA   ARG G1267     76.008 107.865 49.166  1.00 83.66      G
ATOM  17639  CB   ARG G1267     75.024 107.815 47.998  1.00100.07      G
ATOM  17640  CG   ARG G1267     75.647 107.294 46.728  1.00100.07      G
ATOM  17641  CD   ARG G1267     76.892 108.105 46.433  1.00100.07      G
ATOM  17642  NE   ARG G1267     77.691 107.543 45.356  1.00100.07      G
ATOM  17643  CZ   ARG G1267     78.834 108.072 44.943  1.00100.07      G
ATOM  17644  NH1  ARG G1267     79.298 109.170 45.528  1.00100.07      G
ATOM  17645  NH2  ARG G1267     79.504 107.512 43.942  1.00100.07      G
ATOM  17646  C    ARG G1267     75.852 109.166 49.912  1.00 83.66      G
ATOM  17647  O    ARG G1267     75.187 109.203 50.944  1.00 83.66      G
ATOM  17648  N    ARG G1268     76.480 110.230 49.424  1.00 24.69      G
ATOM  17649  CA   ARG G1268     76.322 111.503 50.098  1.00 24.69      G
ATOM  17650  CB   ARG G1268     77.654 112.262 50.246  1.00100.07      G
ATOM  17651  CG   ARG G1268     78.353 112.751 48.990  1.00100.07      G
ATOM  17652  CD   ARG G1268     79.276 113.917 49.370  1.00100.07      G
ATOM  17653  NE   ARG G1268     80.157 114.349 48.283  1.00100.07      G
ATOM  17654  CZ   ARG G1268     80.827 115.502 48.264  1.00100.07      G
ATOM  17655  NH1  ARG G1268     80.719 116.356 49.278  1.00100.07      G
ATOM  17656  NH2  ARG G1268     81.611 115.804 47.232  1.00100.07      G
ATOM  17657  C    ARG G1268     75.326 112.281 49.281  1.00 24.69      G
ATOM  17658  O    ARG G1268     75.683 112.949 48.315  1.00 24.69      G
ATOM  17659  N    PRO G1269     74.050 112.190 49.665  1.00 49.29      G
ATOM  17660  CD   PRO G1269     73.791 111.657 51.006  1.00 23.60      G
ATOM  17661  CA   PRO G1269     72.830 112.789 49.112  1.00 49.29      G
ATOM  17662  CB   PRO G1269     71.790 112.506 50.184  1.00 23.60      G
ATOM  17663  CG   PRO G1269     72.606 112.447 51.425  1.00 23.60      G
ATOM  17664  C    PRO G1269     72.866 114.260 48.759  1.00 49.29      G
ATOM  17665  O    PRO G1269     73.908 114.817 48.429  1.00 49.29      G
ATOM  17666  N    LYS G1270     71.697 114.883 48.827  1.00100.07      G
ATOM  17667  CA   LYS G1270     71.582 116.295 48.522  1.00100.07      G
ATOM  17668  CB   LYS G1270     70.185 116.602 47.967  1.00100.07      G
ATOM  17669  CG   LYS G1270     69.039 116.478 48.976  1.00100.07      G
ATOM  17670  CD   LYS G1270     67.815 117.256 48.498  1.00100.07      G
ATOM  17671  CE   LYS G1270     66.819 117.490 49.627  1.00100.07      G
ATOM  17672  NZ   LYS G1270     65.675 118.364 49.234  1.00100.07      G
ATOM  17673  C    LYS G1270     71.826 117.108 49.791  1.00100.07      G
ATOM  17674  O    LYS G1270     72.729 117.952 49.849  1.00100.07      G
ATOM  17675  N    ALA G1271     71.012 116.829 50.803  1.00 43.78      G
ATOM  17676  CA   ALA G1271     71.089 117.511 52.080  1.00 43.78      G
ATOM  17677  CB   ALA G1271     70.400 116.671 53.140  1.00 83.00      G
ATOM  17678  C    ALA G1271     72.513 117.834 52.523  1.00 43.78      G
ATOM  17679  O    ALA G1271     72.932 118.991 52.493  1.00 43.78      G
ATOM  17680  N    LYS G1272     73.242 116.795 52.921  1.00 68.73      G
ATOM  17681  CA   LYS G1272     74.609 116.905 53.427  1.00 68.73      G
ATOM  17682  CB   LYS G1272     75.471 117.842 52.567  1.00 68.65      G
ATOM  17683  CG   LYS G1272     76.845 118.114 53.189  1.00 68.65      G
ATOM  17684  CD   LYS G1272     77.969 118.305 52.168  1.00 68.65      G
ATOM  17685  CE   LYS G1272     79.301 118.551 52.880  1.00 68.65      G
ATOM  17686  NZ   LYS G1272     80.464 118.598 51.962  1.00 68.65      G
```

```
ATOM  17687  C    LYS G1272    74.538 117.412 54.866  1.00 68.73      G
ATOM  17688  O    LYS G1272    75.182 116.878 55.766  1.00 68.73      G
ATOM  17689  N    ALA G1273    73.743 118.446 55.084  1.00 53.93      G
ATOM  17690  CA   ALA G1273    73.567 118.988 56.421  1.00 53.93      G
ATOM  17691  CB   ALA G1273    72.907 117.937 57.313  1.00 55.89      G
ATOM  17692  C    ALA G1273    74.839 119.498 57.080  1.00 53.93      G
ATOM  17693  O    ALA G1273    74.796 120.023 58.191  1.00 53.93      G
ATOM  17694  N    VAL G1274    75.971 119.351 56.406  1.00 48.02      G
ATOM  17695  CA   VAL G1274    77.231 119.811 56.971  1.00 48.02      G
ATOM  17696  CB   VAL G1274    77.241 121.332 57.210  1.00 44.30      G
ATOM  17697  CG1  VAL G1274    78.657 121.790 57.466  1.00 44.30      G
ATOM  17698  CG2  VAL G1274    76.642 122.067 56.034  1.00 44.30      G
ATOM  17699  C    VAL G1274    77.483 119.161 58.325  1.00 48.02      G
ATOM  17700  O    VAL G1274    76.626 119.167 59.201  1.00 48.02      G
ATOM  17701  N    ILE G1275    78.668 118.598 58.491  1.00 41.38      G
ATOM  17702  CA   ILE G1275    79.037 117.968 59.740  1.00 41.38      G
ATOM  17703  CB   ILE G1275    79.524 116.539 59.502  1.00 81.15      G
ATOM  17704  CG2  ILE G1275    79.986 115.940 60.799  1.00 81.15      G
ATOM  17705  CG1  ILE G1275    78.410 115.696 58.889  1.00 81.15      G
ATOM  17706  CD   ILE G1275    77.225 115.484 59.807  1.00 81.15      G
ATOM  17707  C    ILE G1275    80.212 118.799 60.209  1.00 41.38      G
ATOM  17708  O    ILE G1275    81.298 118.664 59.655  1.00 41.38      G
ATOM  17709  N    SER G1276    80.011 119.677 61.187  1.00 34.20      G
ATOM  17710  CA   SER G1276    81.112 120.507 61.688  1.00 34.20      G
ATOM  17711  CB   SER G1276    80.617 121.471 62.774  1.00 55.01      G
ATOM  17712  OG   SER G1276    81.651 121.812 63.696  1.00 55.01      G
ATOM  17713  C    SER G1276    82.234 119.660 62.262  1.00 34.20      G
ATOM  17714  O    SER G1276    82.028 118.913 63.214  1.00 34.20      G
ATOM  17715  N    GLU G1277    83.420 119.770 61.679  1.00 75.63      G
ATOM  17716  CA   GLU G1277    84.563 119.020 62.171  1.00 75.63      G
ATOM  17717  CB   GLU G1277    85.671 119.009 61.112  1.00100.07      G
ATOM  17718  CG   GLU G1277    86.050 120.391 60.585  1.00100.07      G
ATOM  17719  CD   GLU G1277    86.366 120.401 59.092  1.00100.07      G
ATOM  17720  OE1  GLU G1277    87.192 119.580 58.640  1.00100.07      G
ATOM  17721  OE2  GLU G1277    85.787 121.240 58.368  1.00100.07      G
ATOM  17722  C    GLU G1277    85.004 119.756 63.428  1.00 75.63      G
ATOM  17723  O    GLU G1277    84.208 120.490 64.010  1.00 75.63      G
ATOM  17724  N    ILE G1278    86.248 119.555 63.852  1.00 80.74      G
ATOM  17725  CA   ILE G1278    86.799 120.233 65.029  1.00 80.74      G
ATOM  17726  CB   ILE G1278    87.774 121.374 64.593  1.00100.07      G
ATOM  17727  CG2  ILE G1278    87.691 122.567 65.531  1.00100.07      G
ATOM  17728  CG1  ILE G1278    89.207 120.840 64.563  1.00100.07      G
ATOM  17729  CD   ILE G1278    89.737 120.376 65.917  1.00100.07      G
ATOM  17730  C    ILE G1278    85.789 120.801 66.027  1.00 80.74      G
ATOM  17731  O    ILE G1278    85.222 121.879 65.821  1.00 80.74      G
ATOM  17732  N    ASP G1279    85.566 120.063 67.111  1.00 50.25      G
ATOM  17733  CA   ASP G1279    84.661 120.500 68.161  1.00 50.25      G
ATOM  17734  CB   ASP G1279    84.793 119.589 69.393  1.00100.07      G
ATOM  17735  CG   ASP G1279    86.244 119.201 69.706  1.00100.07      G
ATOM  17736  OD1  ASP G1279    86.902 118.563 68.857  1.00100.07      G
ATOM  17737  OD2  ASP G1279    86.727 119.521 70.814  1.00100.07      G
ATOM  17738  C    ASP G1279    85.070 121.921 68.504  1.00 50.25      G
ATOM  17739  O    ASP G1279    86.254 122.248 68.481  1.00 50.25      G
ATOM  17740  N    GLY G1280    84.095 122.768 68.809  1.00 29.41      G
ATOM  17741  CA   GLY G1280    84.411 124.150 69.124  1.00 29.41      G
ATOM  17742  C    GLY G1280    83.245 125.071 69.430  1.00 29.41      G
ATOM  17743  O    GLY G1280    82.083 124.664 69.495  1.00 29.41      G
ATOM  17744  N    VAL G1281    83.565 126.348 69.558  1.00 28.20      G
ATOM  17745  CA   VAL G1281    82.578 127.347 69.940  1.00 28.20      G
ATOM  17746  CB   VAL G1281    83.286 128.529 70.655  1.00100.07      G
ATOM  17747  CG1  VAL G1281    82.279 129.348 71.464  1.00100.07      G
ATOM  17748  CG2  VAL G1281    84.398 127.998 71.559  1.00100.07      G
ATOM  17749  C    VAL G1281    81.600 127.946 68.937  1.00 28.20      G
ATOM  17750  O    VAL G1281    81.725 127.792 67.721  1.00 28.20      G
ATOM  17751  N    VAL G1282    80.623 128.637 69.519  1.00 99.55      G
ATOM  17752  CA   VAL G1282    79.558 129.357 68.837  1.00 99.55      G
ATOM  17753  CB   VAL G1282    78.833 130.306 69.823  1.00100.07      G
ATOM  17754  CG1  VAL G1282    77.705 131.022 69.126  1.00100.07      G
ATOM  17755  CG2  VAL G1282    78.352 129.552 71.042  1.00100.07      G
ATOM  17756  C    VAL G1282    80.169 130.251 67.773  1.00 99.55      G
ATOM  17757  O    VAL G1282    81.364 130.548 67.821  1.00 99.55      G
ATOM  17758  N    ARG G1283    79.336 130.697 66.834  1.00 95.80      G
ATOM  17759  CA   ARG G1283    79.772 131.602 65.776  1.00 95.80      G
ATOM  17760  CB   ARG G1283    81.100 131.146 65.181  1.00100.07      G
ATOM  17761  CG   ARG G1283    81.705 132.158 64.223  1.00100.07      G
ATOM  17762  CD   ARG G1283    82.261 133.375 64.952  1.00100.07      G
ATOM  17763  NE   ARG G1283    82.248 134.560 64.099  1.00100.07      G
ATOM  17764  CZ   ARG G1283    82.765 135.735 64.437  1.00100.07      G
ATOM  17765  NH1  ARG G1283    83.350 135.887 65.615  1.00100.07      G
ATOM  17766  NH2  ARG G1283    82.674 136.766 63.607  1.00100.07      G
ATOM  17767  C    ARG G1283    78.761 131.737 64.650  1.00 95.80      G
ATOM  17768  O    ARG G1283    78.414 130.758 64.001  1.00 95.80      G
ATOM  17769  N    ILE G1284    78.294 132.956 64.416  1.00 75.14      G
ATOM  17770  CA   ILE G1284    77.341 133.201 63.350  1.00 75.14      G
```

```
ATOM  17771  CB   ILE G1284      75.881 133.046  63.820  1.00100.07           G
ATOM  17772  CG2  ILE G1284      74.950 133.883  62.950  1.00100.07           G
ATOM  17773  CG1  ILE G1284      75.469 131.578  63.743  1.00100.07           G
ATOM  17774  CD   ILE G1284      75.536 130.996  62.347  1.00100.07           G
ATOM  17775  C    ILE G1284      77.502 134.586  62.779  1.00 75.14           G
ATOM  17776  O    ILE G1284      77.191 135.579  63.431  1.00 75.14           G
ATOM  17777  N    GLU G1285      78.001 134.644  61.553  1.00 40.73           G
ATOM  17778  CA   GLU G1285      78.181 135.906  60.854  1.00 40.73           G
ATOM  17779  CB   GLU G1285      79.617 136.012  60.315  1.00100.07           G
ATOM  17780  CG   GLU G1285      80.662 136.183  61.431  1.00100.07           G
ATOM  17781  CD   GLU G1285      82.099 135.879  60.996  1.00100.07           G
ATOM  17782  OE1  GLU G1285      82.378 134.724  60.594  1.00100.07           G
ATOM  17783  OE2  GLU G1285      82.956 136.792  61.068  1.00100.07           G
ATOM  17784  C    GLU G1285      77.142 135.912  59.732  1.00 40.73           G
ATOM  17785  O    GLU G1285      77.423 135.565  58.582  1.00 40.73           G
ATOM  17786  N    GLU G1286      75.918 136.268  60.111  1.00 72.48           G
ATOM  17787  CA   GLU G1286      74.801 136.337  59.183  1.00 72.48           G
ATOM  17788  CB   GLU G1286      73.624 137.068  59.855  1.00100.07           G
ATOM  17789  CG   GLU G1286      74.021 138.284  60.723  1.00100.07           G
ATOM  17790  CD   GLU G1286      72.921 138.731  61.706  1.00100.07           G
ATOM  17791  OE1  GLU G1286      72.594 137.961  62.643  1.00100.07           G
ATOM  17792  OE2  GLU G1286      72.389 139.856  61.546  1.00100.07           G
ATOM  17793  C    GLU G1286      75.221 137.033  57.887  1.00 72.48           G
ATOM  17794  O    GLU G1286      75.229 138.260  57.801  1.00 72.48           G
ATOM  17795  N    GLY G1287      75.572 136.234  56.882  1.00100.07           G
ATOM  17796  CA   GLY G1287      76.005 136.782  55.607  1.00100.07           G
ATOM  17797  C    GLY G1287      74.900 137.130  54.623  1.00100.07           G
ATOM  17798  O    GLY G1287      73.990 136.331  54.371  1.00100.07           G
ATOM  17799  N    GLU G1288      74.988 138.339  54.070  1.00 62.85           G
ATOM  17800  CA   GLU G1288      74.024 138.833  53.091  1.00 62.85           G
ATOM  17801  CB   GLU G1288      74.597 140.071  52.387  1.00100.07           G
ATOM  17802  CG   GLU G1288      73.572 140.978  51.716  1.00100.07           G
ATOM  17803  CD   GLU G1288      74.208 142.196  51.044  1.00100.07           G
ATOM  17804  OE1  GLU G1288      74.930 142.957  51.730  1.00100.07           G
ATOM  17805  OE2  GLU G1288      73.981 142.398  49.828  1.00100.07           G
ATOM  17806  C    GLU G1288      73.854 137.689  52.104  1.00 62.85           G
ATOM  17807  O    GLU G1288      72.745 137.364  51.680  1.00 62.85           G
ATOM  17808  N    ASP G1289      74.983 137.079  51.762  1.00100.07           G
ATOM  17809  CA   ASP G1289      75.033 135.943  50.856  1.00100.07           G
ATOM  17810  CB   ASP G1289      75.128 136.405  49.393  1.00 99.99           G
ATOM  17811  CG   ASP G1289      73.829 136.182  48.615  1.00 99.99           G
ATOM  17812  OD1  ASP G1289      73.307 135.045  48.625  1.00 99.99           G
ATOM  17813  OD2  ASP G1289      73.337 137.143  47.982  1.00 99.99           G
ATOM  17814  C    ASP G1289      76.261 135.110  51.229  1.00100.07           G
ATOM  17815  O    ASP G1289      76.970 134.598  50.361  1.00100.07           G
ATOM  17816  N    ARG G1290      76.507 134.997  52.533  1.00100.07           G
ATOM  17817  CA   ARG G1290      77.631 134.224  53.071  1.00100.07           G
ATOM  17818  CB   ARG G1290      78.925 135.049  53.080  1.00 81.73           G
ATOM  17819  CG   ARG G1290      79.630 135.222  51.734  1.00 81.73           G
ATOM  17820  CD   ARG G1290      80.884 136.076  51.923  1.00 81.73           G
ATOM  17821  NE   ARG G1290      81.784 136.084  50.773  1.00 81.73           G
ATOM  17822  CZ   ARG G1290      83.000 136.628  50.786  1.00 81.73           G
ATOM  17823  NH1  ARG G1290      83.461 137.207  51.892  1.00 81.73           G
ATOM  17824  NH2  ARG G1290      83.759 136.592  49.698  1.00 81.73           G
ATOM  17825  C    ARG G1290      77.317 133.820  54.505  1.00100.07           G
ATOM  17826  O    ARG G1290      78.072 134.164  55.415  1.00100.07           G
ATOM  17827  N    LEU G1291      76.214 133.097  54.708  1.00 44.00           G
ATOM  17828  CA   LEU G1291      75.819 132.677  56.054  1.00 44.00           G
ATOM  17829  CB   LEU G1291      74.773 131.572  55.974  1.00 99.56           G
ATOM  17830  CG   LEU G1291      73.511 132.008  55.239  1.00 99.56           G
ATOM  17831  CD1  LEU G1291      72.437 130.962  55.448  1.00 99.56           G
ATOM  17832  CD2  LEU G1291      73.038 133.365  55.757  1.00 99.56           G
ATOM  17833  C    LEU G1291      77.018 132.194  56.851  1.00 44.00           G
ATOM  17834  O    LEU G1291      77.280 132.651  57.972  1.00 44.00           G
ATOM  17835  N    SER G1292      77.746 131.271  56.235  1.00 86.01           G
ATOM  17836  CA   SER G1292      78.943 130.689  56.814  1.00 86.01           G
ATOM  17837  CB   SER G1292      80.190 131.428  56.300  1.00 96.71           G
ATOM  17838  OG   SER G1292      80.112 132.828  56.516  1.00 96.71           G
ATOM  17839  C    SER G1292      78.963 130.641  58.334  1.00 86.01           G
ATOM  17840  O    SER G1292      79.161 131.654  59.003  1.00 86.01           G
ATOM  17841  N    VAL G1293      78.732 129.447  58.864  1.00 46.26           G
ATOM  17842  CA   VAL G1293      78.768 129.198  60.297  1.00 46.26           G
ATOM  17843  CB   VAL G1293      77.926 127.963  60.647  1.00  8.45           G
ATOM  17844  CG1  VAL G1293      78.108 127.592  62.077  1.00  8.45           G
ATOM  17845  CG2  VAL G1293      76.487 128.252  60.385  1.00  8.45           G
ATOM  17846  C    VAL G1293      80.248 128.921  60.566  1.00 46.26           G
ATOM  17847  O    VAL G1293      80.801 127.941  60.060  1.00 46.26           G
ATOM  17848  N    ALA G1294      80.890 129.788  61.344  1.00 96.50           G
ATOM  17849  CA   ALA G1294      82.315 129.644  61.616  1.00 96.50           G
ATOM  17850  CB   ALA G1294      82.996 131.020  61.459  1.00 25.75           G
ATOM  17851  C    ALA G1294      82.700 129.008  62.959  1.00 96.50           G
ATOM  17852  O    ALA G1294      83.024 129.713  63.905  1.00 96.50           G
ATOM  17853  N    VAL G1295      82.688 127.677  63.034  1.00 37.72           G
ATOM  17854  CA   VAL G1295      83.057 126.954  64.262  1.00 37.72           G
```

```
ATOM  17855  CB   VAL G1295    82.836 125.433 64.081  1.00 41.33      G
ATOM  17856  CG1  VAL G1295    83.420 124.667 65.253  1.00 41.33      G
ATOM  17857  CG2  VAL G1295    81.358 125.143 63.956  1.00 41.33      G
ATOM  17858  C    VAL G1295    84.531 127.209 64.647  1.00 37.72      G
ATOM  17859  O    VAL G1295    85.448 126.602 64.067  1.00 37.72      G
ATOM  17860  N    GLU G1296    84.737 128.085 65.643  1.00 49.18      G
ATOM  17861  CA   GLU G1296    86.076 128.495 66.115  1.00 49.18      G
ATOM  17862  CB   GLU G1296    86.276 129.989 65.855  1.00 63.88      G
ATOM  17863  CG   GLU G1296    85.400 130.888 66.711  1.00 63.88      G
ATOM  17864  CD   GLU G1296    85.045 132.207 66.030  1.00 63.88      G
ATOM  17865  OE1  GLU G1296    84.447 133.067 66.707  1.00 63.88      G
ATOM  17866  OE2  GLU G1296    85.347 132.387 64.827  1.00 63.88      G
ATOM  17867  C    GLU G1296    86.374 128.225 67.584  1.00 49.18      G
ATOM  17868  O    GLU G1296    85.471 128.179 68.418  1.00 49.18      G
ATOM  17869  N    SER G1297    87.660 128.092 67.894  1.00 53.13      G
ATOM  17870  CA   SER G1297    88.092 127.801 69.256  1.00 53.13      G
ATOM  17871  CB   SER G1297    87.462 126.497 69.689  1.00 52.77      G
ATOM  17872  OG   SER G1297    87.895 125.482 68.807  1.00 52.77      G
ATOM  17873  C    SER G1297    89.612 127.648 69.349  1.00 53.13      G
ATOM  17874  O    SER G1297    90.095 126.668 69.927  1.00 53.13      G
ATOM  17875  N    GLU G1298    90.340 128.615 68.783  1.00 98.77      G
ATOM  17876  CA   GLU G1298    91.816 128.659 68.721  1.00 98.77      G
ATOM  17877  CB   GLU G1298    92.467 127.888 69.873  1.00 80.31      G
ATOM  17878  CG   GLU G1298    92.001 128.378 71.207  1.00 80.31      G
ATOM  17879  CD   GLU G1298    91.548 129.803 71.111  1.00 80.31      G
ATOM  17880  OE1  GLU G1298    92.422 130.687 71.023  1.00 80.31      G
ATOM  17881  OE2  GLU G1298    90.321 130.034 71.088  1.00 80.31      G
ATOM  17882  C    GLU G1298    92.278 128.086 67.394  1.00 98.77      G
ATOM  17883  O    GLU G1298    93.395 127.597 67.258  1.00 98.77      G
ATOM  17884  N    GLY G1299    91.386 128.170 66.417  1.00 97.09      G
ATOM  17885  CA   GLY G1299    91.653 127.670 65.088  1.00 97.09      G
ATOM  17886  C    GLY G1299    90.317 127.568 64.389  1.00 97.09      G
ATOM  17887  O    GLY G1299    89.890 126.475 64.037  1.00 97.09      G
ATOM  17888  N    PHE G1300    89.657 128.709 64.195  1.00 45.94      G
ATOM  17889  CA   PHE G1300    88.348 128.744 63.552  1.00 45.94      G
ATOM  17890  CB   PHE G1300    87.924 130.189 63.242  1.00 99.80      G
ATOM  17891  CG   PHE G1300    88.885 130.944 62.365  1.00 99.80      G
ATOM  17892  CD1  PHE G1300    89.239 130.464 61.105  1.00 99.80      G
ATOM  17893  CD2  PHE G1300    89.420 132.159 62.791  1.00 99.80      G
ATOM  17894  CE1  PHE G1300    90.119 131.179 60.278  1.00 99.80      G
ATOM  17895  CE2  PHE G1300    90.300 132.887 61.976  1.00 99.80      G
ATOM  17896  CZ   PHE G1300    90.648 132.394 60.714  1.00 99.80      G
ATOM  17897  C    PHE G1300    88.224 127.909 62.285  1.00 45.94      G
ATOM  17898  O    PHE G1300    89.221 127.527 61.668  1.00 45.94      G
ATOM  17899  N    SER G1301    86.977 127.620 61.920  1.00 37.90      G
ATOM  17900  CA   SER G1301    86.653 126.855 60.721  1.00 37.90      G
ATOM  17901  CB   SER G1301    86.269 125.406 61.075  1.00 80.12      G
ATOM  17902  OG   SER G1301    85.985 124.629 59.915  1.00 80.12      G
ATOM  17903  C    SER G1301    85.464 127.566 60.084  1.00 37.90      G
ATOM  17904  O    SER G1301    84.600 128.093 60.790  1.00 37.90      G
ATOM  17905  N    LYS G1302    85.425 127.594 58.758  1.00 32.96      G
ATOM  17906  CA   LYS G1302    84.330 128.244 58.066  1.00 32.96      G
ATOM  17907  CB   LYS G1302    84.867 129.259 57.062  1.00 75.05      G
ATOM  17908  CG   LYS G1302    85.137 130.617 57.638  1.00 75.05      G
ATOM  17909  CD   LYS G1302    85.512 131.560 56.532  1.00 75.05      G
ATOM  17910  CE   LYS G1302    85.825 132.926 57.079  1.00 75.05      G
ATOM  17911  NZ   LYS G1302    86.428 133.771 56.020  1.00 75.05      G
ATOM  17912  C    LYS G1302    83.395 127.290 57.332  1.00 32.96      G
ATOM  17913  O    LYS G1302    83.839 126.318 56.707  1.00 32.96      G
ATOM  17914  N    GLU G1303    82.097 127.580 57.410  1.00 66.97      G
ATOM  17915  CA   GLU G1303    81.099 126.791 56.707  1.00 66.97      G
ATOM  17916  CB   GLU G1303    80.131 126.152 57.686  1.00 21.69      G
ATOM  17917  CG   GLU G1303    80.404 124.661 57.863  1.00 21.69      G
ATOM  17918  CD   GLU G1303    81.685 124.364 58.620  1.00 21.69      G
ATOM  17919  OE1  GLU G1303    81.706 124.584 59.845  1.00 21.69      G
ATOM  17920  OE2  GLU G1303    82.671 123.910 58.000  1.00 21.69      G
ATOM  17921  C    GLU G1303    80.391 127.677 55.678  1.00 66.97      G
ATOM  17922  O    GLU G1303    80.929 128.715 55.310  1.00 66.97      G
ATOM  17923  N    TYR G1304    79.199 127.328 55.207  1.00 57.42      G
ATOM  17924  CA   TYR G1304    78.636 128.169 54.156  1.00 57.42      G
ATOM  17925  CB   TYR G1304    79.428 127.865 52.885  1.00 86.52      G
ATOM  17926  CG   TYR G1304    80.090 126.485 52.917  1.00 86.52      G
ATOM  17927  CD1  TYR G1304    79.335 125.314 52.766  1.00 86.52      G
ATOM  17928  CE1  TYR G1304    79.937 124.039 52.849  1.00 86.52      G
ATOM  17929  CD2  TYR G1304    81.470 126.350 53.150  1.00 86.52      G
ATOM  17930  CE2  TYR G1304    82.078 125.083 53.236  1.00 86.52      G
ATOM  17931  CZ   TYR G1304    81.306 123.933 53.085  1.00 86.52      G
ATOM  17932  OH   TYR G1304    81.893 122.686 53.173  1.00 86.52      G
ATOM  17933  C    TYR G1304    77.138 128.093 53.871  1.00 57.42      G
ATOM  17934  O    TYR G1304    76.321 128.045 54.795  1.00 57.42      G
ATOM  17935  N    LYS G1305    76.806 128.113 52.575  1.00 88.70      G
ATOM  17936  CA   LYS G1305    75.437 128.035 52.028  1.00 88.70      G
ATOM  17937  CB   LYS G1305    74.862 126.625 52.221  1.00100.07      G
ATOM  17938  CG   LYS G1305    74.935 125.736 50.985  1.00100.07      G
```

```
ATOM  17939  CD  LYS G1305      74.446 124.332  51.300  1.00100.07      G
ATOM  17940  CE  LYS G1305      74.634 123.403  50.115  1.00100.07      G
ATOM  17941  NZ  LYS G1305      74.421 121.972  50.491  1.00100.07      G
ATOM  17942  C   LYS G1305      74.390 129.052  52.478  1.00 88.70      G
ATOM  17943  O   LYS G1305      74.702 130.028  53.165  1.00 88.70      G
ATOM  17944  N   LEU G1306      73.144 128.799  52.070  1.00 71.40      G
ATOM  17945  CA  LEU G1306      72.002 129.660  52.385  1.00 71.40      G
ATOM  17946  CB  LEU G1306      71.846 130.700  51.274  1.00100.07      G
ATOM  17947  CG  LEU G1306      73.118 131.329  50.695  1.00100.07      G
ATOM  17948  CD1 LEU G1306      72.781 132.108  49.430  1.00100.07      G
ATOM  17949  CD2 LEU G1306      73.759 132.236  51.731  1.00100.07      G
ATOM  17950  C   LEU G1306      70.671 128.876  52.518  1.00 71.40      G
ATOM  17951  O   LEU G1306      69.653 129.273  51.942  1.00 71.40      G
ATOM  17952  N   PRO G1307      70.653 127.765  53.283  1.00100.07      G
ATOM  17953  CD  PRO G1307      71.790 126.974  53.801  1.00100.07      G
ATOM  17954  CA  PRO G1307      69.406 127.000  53.417  1.00100.07      G
ATOM  17955  CB  PRO G1307      69.895 125.571  53.308  1.00100.07      G
ATOM  17956  CG  PRO G1307      71.129 125.632  54.193  1.00100.07      G
ATOM  17957  C   PRO G1307      68.675 127.215  54.735  1.00100.07      G
ATOM  17958  O   PRO G1307      68.482 128.344  55.189  1.00100.07      G
ATOM  17959  N   LYS G1308      68.270 126.096  55.332  1.00 79.79      G
ATOM  17960  CA  LYS G1308      67.577 126.087  56.611  1.00 79.79      G
ATOM  17961  CB  LYS G1308      66.357 125.146  56.563  1.00 87.61      G
ATOM  17962  CG  LYS G1308      65.670 124.884  57.910  1.00 87.61      G
ATOM  17963  CD  LYS G1308      65.625 126.119  58.798  1.00 87.61      G
ATOM  17964  CE  LYS G1308      64.911 127.281  58.129  1.00 87.61      G
ATOM  17965  NZ  LYS G1308      65.018 128.530  58.936  1.00 87.61      G
ATOM  17966  C   LYS G1308      68.576 125.635  57.664  1.00 79.79      G
ATOM  17967  O   LYS G1308      69.071 124.512  57.645  1.00 79.79      G
ATOM  17968  N   ASP G1309      68.886 126.541  58.575  1.00 67.57      G
ATOM  17969  CA  ASP G1309      69.833 126.251  59.632  1.00 67.57      G
ATOM  17970  CB  ASP G1309      70.265 127.548  60.306  1.00 71.72      G
ATOM  17971  CG  ASP G1309      71.671 127.478  60.839  1.00 71.72      G
ATOM  17972  OD1 ASP G1309      71.908 126.716  61.802  1.00 71.72      G
ATOM  17973  OD2 ASP G1309      72.539 128.182  60.284  1.00 71.72      G
ATOM  17974  C   ASP G1309      69.151 125.349  60.633  1.00 67.57      G
ATOM  17975  O   ASP G1309      68.019 124.930  60.409  1.00 67.57      G
ATOM  17976  N   ALA G1310      69.833 125.064  61.737  1.00 74.93      G
ATOM  17977  CA  ALA G1310      69.282 124.200  62.771  1.00 74.93      G
ATOM  17978  CB  ALA G1310      69.829 122.785  62.619  1.00100.07      G
ATOM  17979  C   ALA G1310      69.582 124.717  64.166  1.00 74.93      G
ATOM  17980  O   ALA G1310      70.421 124.141  64.870  1.00 74.93      G
ATOM  17981  N   ARG G1311      68.896 125.798  64.550  1.00100.07      G
ATOM  17982  CA  ARG G1311      69.040 126.417  65.874  1.00100.07      G
ATOM  17983  CB  ARG G1311      68.272 125.566  66.900  1.00100.07      G
ATOM  17984  CG  ARG G1311      67.973 126.219  68.247  1.00100.07      G
ATOM  17985  CD  ARG G1311      67.027 125.318  69.052  1.00100.07      G
ATOM  17986  NE  ARG G1311      66.638 125.873  70.350  1.00100.07      G
ATOM  17987  CZ  ARG G1311      65.720 125.333  71.150  1.00100.07      G
ATOM  17988  NH1 ARG G1311      65.089 124.221  70.793  1.00100.07      G
ATOM  17989  NH2 ARG G1311      65.424 125.906  72.309  1.00100.07      G
ATOM  17990  C   ARG G1311      70.525 126.523  66.250  1.00100.07      G
ATOM  17991  O   ARG G1311      71.102 125.579  66.792  1.00100.07      G
ATOM  17992  N   LEU G1312      71.140 127.671  65.979  1.00 83.13      G
ATOM  17993  CA  LEU G1312      72.562 127.824  66.262  1.00 83.13      G
ATOM  17994  CB  LEU G1312      73.303 127.937  64.923  1.00 99.53      G
ATOM  17995  CG  LEU G1312      74.821 128.130  64.824  1.00 99.53      G
ATOM  17996  CD1 LEU G1312      75.574 127.346  65.896  1.00 99.53      G
ATOM  17997  CD2 LEU G1312      75.250 127.721  63.436  1.00 99.53      G
ATOM  17998  C   LEU G1312      72.996 128.937  67.234  1.00 83.13      G
ATOM  17999  O   LEU G1312      72.326 129.201  68.236  1.00 83.13      G
ATOM  18000  N   LEU G1313      74.135 129.561  66.926  1.00 74.79      G
ATOM  18001  CA  LEU G1313      74.761 130.622  67.721  1.00 74.79      G
ATOM  18002  CB  LEU G1313      73.894 131.888  67.714  1.00100.07      G
ATOM  18003  CG  LEU G1313      74.629 133.238  67.621  1.00100.07      G
ATOM  18004  CD1 LEU G1313      76.021 133.077  67.027  1.00100.07      G
ATOM  18005  CD2 LEU G1313      73.801 134.196  66.771  1.00100.07      G
ATOM  18006  C   LEU G1313      74.966 130.065  69.126  1.00 74.79      G
ATOM  18007  O   LEU G1313      75.198 130.792  70.107  1.00 74.79      G
ATOM  18008  N   VAL G1314      74.913 128.736  69.164  1.00100.07      G
ATOM  18009  CA  VAL G1314      75.064 127.921  70.359  1.00100.07      G
ATOM  18010  CB  VAL G1314      74.066 126.725  70.308  1.00 35.69      G
ATOM  18011  CG1 VAL G1314      74.460 125.633  71.313  1.00 35.69      G
ATOM  18012  CG2 VAL G1314      72.656 127.234  70.578  1.00 35.69      G
ATOM  18013  C   VAL G1314      76.490 127.387  70.465  1.00100.07      G
ATOM  18014  O   VAL G1314      77.216 127.331  69.469  1.00100.07      G
ATOM  18015  N   LYS G1315      76.889 127.028  71.684  1.00 33.32      G
ATOM  18016  CA  LYS G1315      78.211 126.472  71.936  1.00 33.32      G
ATOM  18017  CB  LYS G1315      78.537 126.507  73.437  1.00 38.58      G
ATOM  18018  CG  LYS G1315      79.852 127.213  73.844  1.00 38.58      G
ATOM  18019  CD  LYS G1315      79.984 127.252  75.392  1.00 38.58      G
ATOM  18020  CE  LYS G1315      81.052 128.218  75.884  1.00 38.58      G
ATOM  18021  NZ  LYS G1315      82.391 127.808  75.412  1.00 38.58      G
ATOM  18022  C   LYS G1315      78.103 125.030  71.461  1.00 33.32      G
```

```
ATOM  18023  O    LYS G1315    77.932 124.109 72.260  1.00 33.32       G
ATOM  18024  N    ALA G1316    78.173 124.852 70.146  1.00 73.20       G
ATOM  18025  CA   ALA G1316    78.090 123.532 69.542  1.00 73.20       G
ATOM  18026  CB   ALA G1316    77.795 123.643 68.045  1.00 52.73       G
ATOM  18027  C    ALA G1316    79.404 122.817 69.752  1.00 73.20       G
ATOM  18028  O    ALA G1316    80.012 122.357 68.787  1.00 73.20       G
ATOM  18029  N    GLY G1317    79.846 122.747 71.009  1.00 51.24       G
ATOM  18030  CA   GLY G1317    81.085 122.063 71.309  1.00 51.24       G
ATOM  18031  C    GLY G1317    81.131 120.911 70.332  1.00 51.24       G
ATOM  18032  O    GLY G1317    82.045 120.810 69.511  1.00 51.24       G
ATOM  18033  N    ALA G1318    80.098 120.074 70.397  1.00 73.77       G
ATOM  18034  CA   ALA G1318    79.958 118.920 69.521  1.00 73.77       G
ATOM  18035  CB   ALA G1318    78.974 119.239 68.427  1.00 96.53       G
ATOM  18036  C    ALA G1318    81.277 118.476 68.913  1.00 73.77       G
ATOM  18037  O    ALA G1318    82.324 118.576 69.531  1.00 73.77       G
ATOM  18038  N    TYR G1319    81.213 117.980 67.688  1.00 71.56       G
ATOM  18039  CA   TYR G1319    82.381 117.496 66.965  1.00 71.56       G
ATOM  18040  CB   TYR G1319    83.007 116.304 67.700  1.00100.07       G
ATOM  18041  CG   TYR G1319    82.040 115.608 68.634  1.00100.07       G
ATOM  18042  CD1  TYR G1319    80.958 114.883 68.142  1.00100.07       G
ATOM  18043  CE1  TYR G1319    80.014 114.318 69.006  1.00100.07       G
ATOM  18044  CD2  TYR G1319    82.160 115.747 70.016  1.00100.07       G
ATOM  18045  CE2  TYR G1319    81.225 115.193 70.884  1.00100.07       G
ATOM  18046  CZ   TYR G1319    80.156 114.483 70.375  1.00100.07       G
ATOM  18047  OH   TYR G1319    79.226 113.951 71.239  1.00100.07       G
ATOM  18048  C    TYR G1319    81.820 117.049 65.634  1.00 71.56       G
ATOM  18049  O    TYR G1319    82.557 116.701 64.716  1.00 71.56       G
ATOM  18050  N    VAL G1320    80.490 117.080 65.560  1.00 13.09       G
ATOM  18051  CA   VAL G1320    79.735 116.682 64.381  1.00 13.09       G
ATOM  18052  CB   VAL G1320    79.529 115.155 64.358  1.00 52.26       G
ATOM  18053  CG1  VAL G1320    78.414 114.791 63.391  1.00 52.26       G
ATOM  18054  CG2  VAL G1320    80.829 114.461 63.965  1.00 52.26       G
ATOM  18055  C    VAL G1320    78.362 117.343 64.385  1.00 13.09       G
ATOM  18056  O    VAL G1320    77.978 118.014 63.430  1.00 13.09       G
ATOM  18057  N    GLU G1321    77.634 117.132 65.475  1.00 17.84       G
ATOM  18058  CA   GLU G1321    76.283 117.666 65.655  1.00 17.84       G
ATOM  18059  CB   GLU G1321    76.241 118.670 66.809  1.00 99.95       G
ATOM  18060  CG   GLU G1321    75.968 118.063 68.170  1.00 99.95       G
ATOM  18061  CD   GLU G1321    75.555 119.110 69.192  1.00 99.95       G
ATOM  18062  OE1  GLU G1321    75.370 118.751 70.376  1.00 99.95       G
ATOM  18063  OE2  GLU G1321    75.410 120.292 68.805  1.00 99.95       G
ATOM  18064  C    GLU G1321    75.647 118.317 64.443  1.00 17.84       G
ATOM  18065  O    GLU G1321    75.143 119.426 64.542  1.00 17.84       G
ATOM  18066  N    ALA G1322    75.647 117.627 63.314  1.00 15.61       G
ATOM  18067  CA   ALA G1322    75.050 118.196 62.121  1.00 15.61       G
ATOM  18068  CB   ALA G1322    73.527 118.012 62.167  1.00 41.99       G
ATOM  18069  C    ALA G1322    75.394 119.685 62.050  1.00 15.61       G
ATOM  18070  O    ALA G1322    74.731 120.492 62.698  1.00 15.61       G
ATOM  18071  N    GLY G1323    76.430 120.026 61.274  1.00 62.42       G
ATOM  18072  CA   GLY G1323    76.886 121.408 61.100  1.00 62.42       G
ATOM  18073  C    GLY G1323    75.957 122.450 61.687  1.00 62.42       G
ATOM  18074  O    GLY G1323    76.387 123.412 62.326  1.00 62.42       G
ATOM  18075  N    GLN G1324    74.677 122.232 61.414  1.00 62.08       G
ATOM  18076  CA   GLN G1324    73.539 123.004 61.884  1.00 62.08       G
ATOM  18077  CB   GLN G1324    73.959 124.132 62.837  1.00 56.92       G
ATOM  18078  CG   GLN G1324    73.590 123.779 64.298  1.00 56.92       G
ATOM  18079  CD   GLN G1324    74.378 124.546 65.347  1.00 56.92       G
ATOM  18080  OE1  GLN G1324    75.604 124.417 65.454  1.00 56.92       G
ATOM  18081  NE2  GLN G1324    73.674 125.341 66.136  1.00 56.92       G
ATOM  18082  C    GLN G1324    72.522 123.486 60.859  1.00 62.08       G
ATOM  18083  O    GLN G1324    72.041 124.613 60.912  1.00 62.08       G
ATOM  18084  N    PRO G1325    72.228 122.631 59.869  1.00 41.29       G
ATOM  18085  CD   PRO G1325    73.319 121.846 59.279  1.00 22.02       G
ATOM  18086  CA   PRO G1325    71.245 122.911 58.823  1.00 41.29       G
ATOM  18087  CB   PRO G1325    72.033 122.688 57.520  1.00 22.02       G
ATOM  18088  CG   PRO G1325    73.475 122.538 57.956  1.00 22.02       G
ATOM  18089  C    PRO G1325    70.180 121.816 59.078  1.00 41.29       G
ATOM  18090  O    PRO G1325    70.499 120.613 59.113  1.00 41.29       G
ATOM  18091  N    LEU G1326    68.936 122.232 59.310  1.00 78.13       G
ATOM  18092  CA   LEU G1326    67.842 121.290 59.574  1.00 78.13       G
ATOM  18093  CB   LEU G1326    66.485 122.012 59.529  1.00100.07       G
ATOM  18094  CG   LEU G1326    65.155 121.240 59.567  1.00100.07       G
ATOM  18095  CD1  LEU G1326    65.144 120.207 60.682  1.00100.07       G
ATOM  18096  CD2  LEU G1326    64.021 122.239 59.758  1.00100.07       G
ATOM  18097  C    LEU G1326    67.892 120.199 58.527  1.00 78.13       G
ATOM  18098  O    LEU G1326    67.145 119.225 58.585  1.00 78.13       G
ATOM  18099  N    THR G1327    68.785 120.400 57.564  1.00 68.34       G
ATOM  18100  CA   THR G1327    69.028 119.476 56.472  1.00 68.34       G
ATOM  18101  CB   THR G1327    70.271 119.898 55.704  1.00100.07       G
ATOM  18102  OG1  THR G1327    71.297 120.218 56.648  1.00100.07       G
ATOM  18103  CG2  THR G1327    69.984 121.123 54.833  1.00100.07       G
ATOM  18104  C    THR G1327    69.262 118.099 57.071  1.00 68.34       G
ATOM  18105  O    THR G1327    68.832 117.087 56.523  1.00 68.34       G
ATOM  18106  N    ARG G1328    69.957 118.069 58.199  1.00 70.92       G
```

| | | | | | | | | |
|---|---|---|---|---|---|---|---|---|
| ATOM | 18107 | CA | ARG | G1328 | 70.220 | 116.820 | 58.898 | 1.00 70.92 | G |
| ATOM | 18108 | CB | ARG | G1328 | 69.021 | 116.482 | 59.808 | 1.00 84.36 | G |
| ATOM | 18109 | CG | ARG | G1328 | 67.786 | 115.908 | 59.081 | 1.00 84.36 | G |
| ATOM | 18110 | CD | ARG | G1328 | 66.631 | 115.629 | 60.051 | 1.00 84.36 | G |
| ATOM | 18111 | NE | ARG | G1328 | 65.625 | 114.726 | 59.489 | 1.00 84.36 | G |
| ATOM | 18112 | CZ | ARG | G1328 | 64.893 | 114.987 | 58.411 | 1.00 84.36 | G |
| ATOM | 18113 | NH1 | ARG | G1328 | 65.042 | 116.131 | 57.759 | 1.00 84.36 | G |
| ATOM | 18114 | NH2 | ARG | G1328 | 64.008 | 114.100 | 57.984 | 1.00 84.36 | G |
| ATOM | 18115 | C | ARG | G1328 | 70.547 | 115.602 | 58.012 | 1.00 70.92 | G |
| ATOM | 18116 | O | ARG | G1328 | 70.637 | 114.482 | 58.515 | 1.00 70.92 | G |
| ATOM | 18117 | N | GLY | G1329 | 70.730 | 115.801 | 56.710 | 1.00 33.72 | G |
| ATOM | 18118 | CA | GLY | G1329 | 71.043 | 114.671 | 55.854 | 1.00 33.72 | G |
| ATOM | 18119 | C | GLY | G1329 | 72.463 | 114.175 | 56.087 | 1.00 33.72 | G |
| ATOM | 18120 | O | GLY | G1329 | 73.117 | 113.727 | 55.139 | 1.00 33.72 | G |
| ATOM | 18121 | N | ALA | G1330 | 72.924 | 114.236 | 57.346 | 1.00 27.80 | G |
| ATOM | 18122 | CA | ALA | G1330 | 74.284 | 113.842 | 57.736 | 1.00 27.80 | G |
| ATOM | 18123 | CB | ALA | G1330 | 74.262 | 112.929 | 58.944 | 1.00 5.07 | G |
| ATOM | 18124 | C | ALA | G1330 | 75.018 | 113.183 | 56.597 | 1.00 27.80 | G |
| ATOM | 18125 | O | ALA | G1330 | 74.900 | 111.988 | 56.377 | 1.00 27.80 | G |
| ATOM | 18126 | N | ILE | G1331 | 75.750 | 114.008 | 55.861 | 1.00 29.75 | G |
| ATOM | 18127 | CA | ILE | G1331 | 76.541 | 113.598 | 54.703 | 1.00 29.75 | G |
| ATOM | 18128 | CB | ILE | G1331 | 77.830 | 114.501 | 54.562 | 1.00 54.85 | G |
| ATOM | 18129 | CG2 | ILE | G1331 | 78.054 | 114.894 | 53.093 | 1.00 54.85 | G |
| ATOM | 18130 | CG1 | ILE | G1331 | 77.698 | 115.755 | 55.450 | 1.00 54.85 | G |
| ATOM | 18131 | CD | ILE | G1331 | 78.843 | 116.748 | 55.367 | 1.00 54.85 | G |
| ATOM | 18132 | C | ILE | G1331 | 76.952 | 112.146 | 54.862 | 1.00 29.75 | G |
| ATOM | 18133 | O | ILE | G1331 | 76.834 | 111.347 | 53.947 | 1.00 29.75 | G |
| ATOM | 18134 | N | ASP | G1332 | 77.456 | 111.827 | 56.045 | 1.00 18.86 | G |
| ATOM | 18135 | CA | ASP | G1332 | 77.909 | 110.488 | 56.389 | 1.00 18.86 | G |
| ATOM | 18136 | CB | ASP | G1332 | 76.732 | 109.563 | 56.673 | 1.00100.07 | G |
| ATOM | 18137 | CG | ASP | G1332 | 75.896 | 109.281 | 55.436 | 1.00100.07 | G |
| ATOM | 18138 | OD1 | ASP | G1332 | 74.849 | 109.937 | 55.259 | 1.00100.07 | G |
| ATOM | 18139 | OD2 | ASP | G1332 | 76.287 | 108.409 | 54.634 | 1.00100.07 | G |
| ATOM | 18140 | C | ASP | G1332 | 78.727 | 109.835 | 55.327 | 1.00 18.86 | G |
| ATOM | 18141 | O | ASP | G1332 | 78.968 | 108.637 | 55.409 | 1.00 18.86 | G |
| ATOM | 18142 | N | PRO | G1333 | 79.192 | 110.603 | 54.331 | 1.00100.02 | G |
| ATOM | 18143 | CD | PRO | G1333 | 79.535 | 112.031 | 54.328 | 1.00 54.66 | G |
| ATOM | 18144 | CA | PRO | G1333 | 79.972 | 109.937 | 53.304 | 1.00100.02 | G |
| ATOM | 18145 | CB | PRO | G1333 | 79.972 | 110.952 | 52.163 | 1.00 54.66 | G |
| ATOM | 18146 | CG | PRO | G1333 | 79.686 | 112.319 | 52.852 | 1.00 54.66 | G |
| ATOM | 18147 | C | PRO | G1333 | 81.349 | 109.708 | 53.858 | 1.00100.02 | G |
| ATOM | 18148 | O | PRO | G1333 | 82.298 | 110.383 | 53.465 | 1.00100.02 | G |
| ATOM | 18149 | N | HIS | G1334 | 81.462 | 108.766 | 54.786 | 1.00100.07 | G |
| ATOM | 18150 | CA | HIS | G1334 | 82.756 | 108.469 | 55.382 | 1.00100.07 | G |
| ATOM | 18151 | CB | HIS | G1334 | 83.735 | 108.016 | 54.280 | 1.00 88.38 | G |
| ATOM | 18152 | CG | HIS | G1334 | 83.054 | 107.668 | 52.993 | 1.00 88.38 | G |
| ATOM | 18153 | CD2 | HIS | G1334 | 83.085 | 108.267 | 51.779 | 1.00 88.38 | G |
| ATOM | 18154 | ND1 | HIS | G1334 | 82.100 | 106.678 | 52.907 | 1.00 88.38 | G |
| ATOM | 18155 | CE1 | HIS | G1334 | 81.566 | 106.689 | 51.699 | 1.00 88.38 | G |
| ATOM | 18156 | NE2 | HIS | G1334 | 82.145 | 107.646 | 50.996 | 1.00 88.38 | G |
| ATOM | 18157 | C | HIS | G1334 | 83.238 | 109.754 | 56.057 | 1.00100.07 | G |
| ATOM | 18158 | O | HIS | G1334 | 84.326 | 109.803 | 56.632 | 1.00100.07 | G |
| ATOM | 18159 | N | GLN | G1335 | 82.410 | 110.792 | 55.976 | 1.00 94.89 | G |
| ATOM | 18160 | CA | GLN | G1335 | 82.735 | 112.069 | 56.582 | 1.00 94.89 | G |
| ATOM | 18161 | CB | GLN | G1335 | 81.830 | 113.168 | 56.046 | 1.00 38.51 | G |
| ATOM | 18162 | CG | GLN | G1335 | 82.347 | 113.853 | 54.805 | 1.00 38.51 | G |
| ATOM | 18163 | CD | GLN | G1335 | 81.519 | 115.069 | 54.443 | 1.00 38.51 | G |
| ATOM | 18164 | OE1 | GLN | G1335 | 81.284 | 115.944 | 55.278 | 1.00 38.51 | G |
| ATOM | 18165 | NE2 | GLN | G1335 | 81.077 | 115.135 | 53.196 | 1.00 38.51 | G |
| ATOM | 18166 | C | GLN | G1335 | 82.550 | 111.941 | 58.078 | 1.00 94.89 | G |
| ATOM | 18167 | O | GLN | G1335 | 83.516 | 112.026 | 58.839 | 1.00 94.89 | G |
| ATOM | 18168 | N | LEU | G1336 | 81.309 | 111.738 | 58.510 | 1.00 31.83 | G |
| ATOM | 18169 | CA | LEU | G1336 | 81.062 | 111.573 | 59.925 | 1.00 31.83 | G |
| ATOM | 18170 | CB | LEU | G1336 | 79.563 | 111.514 | 60.204 | 1.00 6.48 | G |
| ATOM | 18171 | CG | LEU | G1336 | 79.237 | 111.053 | 61.629 | 1.00 6.48 | G |
| ATOM | 18172 | CD1 | LEU | G1336 | 78.075 | 111.854 | 62.214 | 1.00 6.48 | G |
| ATOM | 18173 | CD2 | LEU | G1336 | 78.948 | 109.526 | 61.601 | 1.00 6.48 | G |
| ATOM | 18174 | C | LEU | G1336 | 81.771 | 110.273 | 60.321 | 1.00 31.83 | G |
| ATOM | 18175 | O | LEU | G1336 | 81.522 | 109.695 | 61.373 | 1.00 31.83 | G |
| ATOM | 18176 | N | LEU | G1337 | 82.665 | 109.822 | 59.445 | 1.00 35.22 | G |
| ATOM | 18177 | CA | LEU | G1337 | 83.460 | 108.627 | 59.677 | 1.00 35.22 | G |
| ATOM | 18178 | CB | LEU | G1337 | 83.601 | 107.814 | 58.409 | 1.00 11.19 | G |
| ATOM | 18179 | CG | LEU | G1337 | 84.570 | 106.692 | 58.718 | 1.00 11.19 | G |
| ATOM | 18180 | CD1 | LEU | G1337 | 83.873 | 105.701 | 59.621 | 1.00 11.19 | G |
| ATOM | 18181 | CD2 | LEU | G1337 | 85.031 | 106.027 | 57.457 | 1.00 11.19 | G |
| ATOM | 18182 | C | LEU | G1337 | 84.846 | 109.070 | 60.120 | 1.00 35.22 | G |
| ATOM | 18183 | O | LEU | G1337 | 85.357 | 108.630 | 61.150 | 1.00 35.22 | G |
| ATOM | 18184 | N | GLU | G1338 | 85.453 | 109.939 | 59.315 | 1.00 68.84 | G |
| ATOM | 18185 | CA | GLU | G1338 | 86.773 | 110.482 | 59.612 | 1.00 68.84 | G |
| ATOM | 18186 | CB | GLU | G1338 | 87.366 | 111.160 | 58.386 | 1.00100.07 | G |
| ATOM | 18187 | CG | GLU | G1338 | 88.812 | 111.519 | 58.561 | 1.00100.07 | G |
| ATOM | 18188 | CD | GLU | G1338 | 89.637 | 111.076 | 57.383 | 1.00100.07 | G |
| ATOM | 18189 | OE1 | GLU | G1338 | 89.474 | 111.671 | 56.296 | 1.00100.07 | G |
| ATOM | 18190 | OE2 | GLU | G1338 | 90.438 | 110.126 | 57.541 | 1.00100.07 | G |

```
ATOM  18191  C    GLU G1338      86.552 111.515 60.689  1.00 68.84      G
ATOM  18192  O    GLU G1338      87.437 111.821 61.489  1.00 68.84      G
ATOM  18193  N    ALA G1339      85.349 112.065 60.682  1.00 52.81      G
ATOM  18194  CA   ALA G1339      84.979 113.042 61.670  1.00 52.81      G
ATOM  18195  CB   ALA G1339      83.552 113.482 61.461  1.00 32.57      G
ATOM  18196  C    ALA G1339      85.119 112.305 62.985  1.00 52.81      G
ATOM  18197  O    ALA G1339      85.980 112.646 63.795  1.00 52.81      G
ATOM  18198  N    LYS G1340      84.292 111.274 63.183  1.00 38.81      G
ATOM  18199  CA   LYS G1340      84.341 110.493 64.417  1.00 38.81      G
ATOM  18200  CB   LYS G1340      83.207 110.902 65.377  1.00 72.23      G
ATOM  18201  CG   LYS G1340      83.432 110.371 66.805  1.00 72.23      G
ATOM  18202  CD   LYS G1340      82.182 110.409 67.694  1.00 72.23      G
ATOM  18203  CE   LYS G1340      82.413 109.667 69.033  1.00 72.23      G
ATOM  18204  NZ   LYS G1340      81.175 109.524 69.877  1.00 72.23      G
ATOM  18205  C    LYS G1340      84.299 108.983 64.217  1.00 38.81      G
ATOM  18206  O    LYS G1340      83.276 108.353 64.461  1.00 38.81      G
ATOM  18207  N    GLY G1341      85.422 108.413 63.786  1.00 79.81      G
ATOM  18208  CA   GLY G1341      85.521 106.973 63.583  1.00 79.81      G
ATOM  18209  C    GLY G1341      84.392 106.261 62.849  1.00 79.81      G
ATOM  18210  O    GLY G1341      83.558 106.912 62.224  1.00 79.81      G
ATOM  18211  N    PRO G1342      84.352 104.912 62.897  1.00 38.38      G
ATOM  18212  CD   PRO G1342      85.452 104.049 63.363  1.00 33.97      G
ATOM  18213  CA   PRO G1342      83.336 104.084 62.247  1.00 38.38      G
ATOM  18214  CB   PRO G1342      84.122 102.850 61.857  1.00 33.97      G
ATOM  18215  CG   PRO G1342      84.922 102.633 63.071  1.00 33.97      G
ATOM  18216  C    PRO G1342      82.204 103.720 63.187  1.00 38.38      G
ATOM  18217  O    PRO G1342      81.063 103.549 62.759  1.00 38.38      G
ATOM  18218  N    GLU G1343      82.533 103.587 64.465  1.00 57.73      G
ATOM  18219  CA   GLU G1343      81.549 103.216 65.465  1.00 57.73      G
ATOM  18220  CB   GLU G1343      82.238 103.041 66.813  1.00100.07      G
ATOM  18221  CG   GLU G1343      83.347 102.012 66.762  1.00100.07      G
ATOM  18222  CD   GLU G1343      83.958 101.736 68.116  1.00100.07      G
ATOM  18223  OE1  GLU G1343      84.495 102.683 68.732  1.00100.07      G
ATOM  18224  OE2  GLU G1343      83.901 100.569 68.560  1.00100.07      G
ATOM  18225  C    GLU G1343      80.400 104.214 65.569  1.00 57.73      G
ATOM  18226  O    GLU G1343      79.259 103.834 65.858  1.00 57.73      G
ATOM  18227  N    ALA G1344      80.690 105.492 65.346  1.00 46.13      G
ATOM  18228  CA   ALA G1344      79.637 106.492 65.400  1.00 46.13      G
ATOM  18229  CB   ALA G1344      80.232 107.890 65.395  1.00 98.70      G
ATOM  18230  C    ALA G1344      78.836 106.244 64.131  1.00 46.13      G
ATOM  18231  O    ALA G1344      77.611 106.166 64.150  1.00 46.13      G
ATOM  18232  N    VAL G1345      79.554 106.098 63.025  1.00 36.62      G
ATOM  18233  CA   VAL G1345      78.944 105.838 61.735  1.00 36.62      G
ATOM  18234  CB   VAL G1345      80.033 105.569 60.693  1.00 22.29      G
ATOM  18235  CG1  VAL G1345      79.437 104.903 59.460  1.00 22.29      G
ATOM  18236  CG2  VAL G1345      80.707 106.878 60.337  1.00 22.29      G
ATOM  18237  C    VAL G1345      77.977 104.652 61.782  1.00 36.62      G
ATOM  18238  O    VAL G1345      76.774 104.825 61.573  1.00 36.62      G
ATOM  18239  N    GLU G1346      78.510 103.455 62.051  1.00 42.14      G
ATOM  18240  CA   GLU G1346      77.696 102.238 62.116  1.00 42.14      G
ATOM  18241  CB   GLU G1346      78.356 101.176 62.997  1.00 67.01      G
ATOM  18242  CG   GLU G1346      79.682 100.662 62.471  1.00 67.01      G
ATOM  18243  CD   GLU G1346      80.155  99.425 63.209  1.00 67.01      G
ATOM  18244  OE1  GLU G1346      79.422  98.413 63.187  1.00 67.01      G
ATOM  18245  OE2  GLU G1346      81.255  99.460 63.807  1.00 67.01      G
ATOM  18246  C    GLU G1346      76.362 102.616 62.705  1.00 42.14      G
ATOM  18247  O    GLU G1346      75.305 102.283 62.171  1.00 42.14      G
ATOM  18248  N    ARG G1347      76.435 103.338 63.811  1.00 33.71      G
ATOM  18249  CA   ARG G1347      75.248 103.803 64.487  1.00 33.71      G
ATOM  18250  CB   ARG G1347      75.622 104.706 65.664  1.00100.07      G
ATOM  18251  CG   ARG G1347      75.473 104.099 67.055  1.00100.07      G
ATOM  18252  CD   ARG G1347      75.469 105.213 68.109  1.00100.07      G
ATOM  18253  NE   ARG G1347      75.255 104.720 69.467  1.00100.07      G
ATOM  18254  CZ   ARG G1347      74.939 105.503 70.492  1.00100.07      G
ATOM  18255  NH1  ARG G1347      74.803 106.807 70.299  1.00100.07      G
ATOM  18256  NH2  ARG G1347      74.760 104.990 71.706  1.00100.07      G
ATOM  18257  C    ARG G1347      74.401 104.605 63.518  1.00 33.71      G
ATOM  18258  O    ARG G1347      73.193 104.419 63.444  1.00 33.71      G
ATOM  18259  N    TYR G1348      75.032 105.498 62.769  1.00 27.52      G
ATOM  18260  CA   TYR G1348      74.277 106.336 61.855  1.00 27.52      G
ATOM  18261  CB   TYR G1348      75.176 107.349 61.188  1.00 19.59      G
ATOM  18262  CG   TYR G1348      74.356 108.319 60.404  1.00 19.59      G
ATOM  18263  CD1  TYR G1348      73.309 108.984 61.000  1.00 19.59      G
ATOM  18264  CE1  TYR G1348      72.551 109.893 60.298  1.00 19.59      G
ATOM  18265  CD2  TYR G1348      74.630 108.582 59.085  1.00 19.59      G
ATOM  18266  CE2  TYR G1348      73.885 109.493 58.368  1.00 19.59      G
ATOM  18267  CZ   TYR G1348      72.849 110.156 58.981  1.00 19.59      G
ATOM  18268  OH   TYR G1348      72.142 111.127 58.294  1.00 19.59      G
ATOM  18269  C    TYR G1348      73.437 105.647 60.776  1.00 27.52      G
ATOM  18270  O    TYR G1348      72.526 106.267 60.199  1.00 27.52      G
ATOM  18271  N    LEU G1349      73.755 104.388 60.476  1.00 24.73      G
ATOM  18272  CA   LEU G1349      72.977 103.636 59.499  1.00 24.73      G
ATOM  18273  CB   LEU G1349      73.855 102.627 58.748  1.00 12.05      G
ATOM  18274  CG   LEU G1349      74.913 103.183 57.782  1.00 12.05      G
```

```
ATOM  18275  CD1 LEU G1349      74.361 104.390  57.032  1.00 12.05      G
ATOM  18276  CD2 LEU G1349      76.160 103.574  58.558  1.00 12.05      G
ATOM  18277  C   LEU G1349      71.875 102.910  60.274  1.00 24.73      G
ATOM  18278  O   LEU G1349      70.742 103.392  60.340  1.00 24.73      G
ATOM  18279  N   VAL G1350      72.225 101.773  60.881  1.00 18.94      G
ATOM  18280  CA  VAL G1350      71.276 100.972  61.657  1.00 18.94      G
ATOM  18281  CB  VAL G1350      71.919 100.359  62.914  1.00 31.45      G
ATOM  18282  CG1 VAL G1350      70.840  99.943  63.899  1.00 31.45      G
ATOM  18283  CG2 VAL G1350      72.757  99.158  62.537  1.00 31.45      G
ATOM  18284  C   VAL G1350      70.114 101.807  62.117  1.00 18.94      G
ATOM  18285  O   VAL G1350      68.969 101.435  61.922  1.00 18.94      G
ATOM  18286  N   ASP G1351      70.410 102.935  62.744  1.00 46.85      G
ATOM  18287  CA  ASP G1351      69.352 103.792  63.209  1.00 46.85      G
ATOM  18288  CB  ASP G1351      69.904 104.895  64.101  1.00 63.80      G
ATOM  18289  CG  ASP G1351      70.402 104.370  65.431  1.00 63.80      G
ATOM  18290  OD1 ASP G1351      69.677 103.580  66.081  1.00 63.80      G
ATOM  18291  OD2 ASP G1351      71.516 104.758  65.836  1.00 63.80      G
ATOM  18292  C   ASP G1351      68.649 104.393  62.013  1.00 46.85      G
ATOM  18293  O   ASP G1351      67.459 104.166  61.811  1.00 46.85      G
ATOM  18294  N   GLU G1352      69.396 105.133  61.201  1.00 22.79      G
ATOM  18295  CA  GLU G1352      68.835 105.804  60.022  1.00 22.79      G
ATOM  18296  CB  GLU G1352      69.959 106.592  59.338  1.00 53.67      G
ATOM  18297  CG  GLU G1352      69.509 107.768  58.491  1.00 53.67      G
ATOM  18298  CD  GLU G1352      68.800 108.829  59.292  1.00 53.67      G
ATOM  18299  OE1 GLU G1352      69.364 109.288  60.304  1.00 53.67      G
ATOM  18300  OE2 GLU G1352      67.680 109.209  58.900  1.00 53.67      G
ATOM  18301  C   GLU G1352      68.130 104.842  59.021  1.00 22.79      G
ATOM  18302  O   GLU G1352      67.014 105.116  58.521  1.00 22.79      G
ATOM  18303  N   ILE G1353      68.798 103.727  58.732  1.00 33.46      G
ATOM  18304  CA  ILE G1353      68.276 102.701  57.842  1.00 33.46      G
ATOM  18305  CB  ILE G1353      69.126 101.433  57.937  1.00 60.92      G
ATOM  18306  CG2 ILE G1353      68.356 100.229  57.416  1.00 60.92      G
ATOM  18307  CG1 ILE G1353      70.415 101.631  57.164  1.00 60.92      G
ATOM  18308  CD  ILE G1353      70.206 101.639  55.690  1.00 60.92      G
ATOM  18309  C   ILE G1353      66.868 102.340  58.265  1.00 33.46      G
ATOM  18310  O   ILE G1353      66.075 101.867  57.459  1.00 33.46      G
ATOM  18311  N   GLN G1354      66.568 102.563  59.542  1.00 24.60      G
ATOM  18312  CA  GLN G1354      65.273 102.222  60.107  1.00 24.60      G
ATOM  18313  CB  GLN G1354      65.442 101.855  61.572  1.00 23.11      G
ATOM  18314  CG  GLN G1354      64.459 100.817  62.050  1.00 23.11      G
ATOM  18315  CD  GLN G1354      65.027  99.412  62.053  1.00 23.11      G
ATOM  18316  OE1 GLN G1354      64.280  98.440  62.083  1.00 23.11      G
ATOM  18317  NE2 GLN G1354      66.344  99.299  62.041  1.00 23.11      G
ATOM  18318  C   GLN G1354      64.257 103.339  59.986  1.00 24.60      G
ATOM  18319  O   GLN G1354      63.275 103.217  59.263  1.00 24.60      G
ATOM  18320  N   LYS G1355      64.496 104.414  60.726  1.00 25.11      G
ATOM  18321  CA  LYS G1355      63.634 105.588  60.725  1.00 25.11      G
ATOM  18322  CB  LYS G1355      64.502 106.843  60.590  1.00100.07      G
ATOM  18323  CG  LYS G1355      63.754 108.163  60.563  1.00100.07      G
ATOM  18324  CD  LYS G1355      64.744 109.322  60.448  1.00100.07      G
ATOM  18325  CE  LYS G1355      64.051 110.643  60.114  1.00100.07      G
ATOM  18326  NZ  LYS G1355      65.018 111.756  59.835  1.00100.07      G
ATOM  18327  C   LYS G1355      62.624 105.508  59.587  1.00 25.11      G
ATOM  18328  O   LYS G1355      61.411 105.500  59.821  1.00 25.11      G
ATOM  18329  N   VAL G1356      63.137 105.413  58.359  1.00 32.35      G
ATOM  18330  CA  VAL G1356      62.287 105.335  57.174  1.00 32.35      G
ATOM  18331  CB  VAL G1356      63.083 105.088  55.905  1.00 71.55      G
ATOM  18332  CG1 VAL G1356      62.130 104.972  54.731  1.00 71.55      G
ATOM  18333  CG2 VAL G1356      64.059 106.227  55.685  1.00 71.55      G
ATOM  18334  C   VAL G1356      61.291 104.219  57.301  1.00 32.35      G
ATOM  18335  O   VAL G1356      60.092 104.441  57.164  1.00 32.35      G
ATOM  18336  N   TYR G1357      61.784 103.009  57.527  1.00 12.31      G
ATOM  18337  CA  TYR G1357      60.867 101.904  57.706  1.00 12.31      G
ATOM  18338  CB  TYR G1357      61.572 100.572  57.976  1.00 32.25      G
ATOM  18339  CG  TYR G1357      62.207  99.884  56.798  1.00 32.25      G
ATOM  18340  CD1 TYR G1357      62.957  98.735  56.986  1.00 32.25      G
ATOM  18341  CE1 TYR G1357      63.607  98.135  55.950  1.00 32.25      G
ATOM  18342  CD2 TYR G1357      62.114 100.408  55.520  1.00 32.25      G
ATOM  18343  CE2 TYR G1357      62.760  99.814  54.470  1.00 32.25      G
ATOM  18344  CZ  TYR G1357      63.514  98.676  54.693  1.00 32.25      G
ATOM  18345  OH  TYR G1357      64.217  98.100  53.653  1.00 32.25      G
ATOM  18346  C   TYR G1357      60.102 102.251  58.957  1.00 12.31      G
ATOM  18347  O   TYR G1357      58.884 102.316  58.950  1.00 12.31      G
ATOM  18348  N   ARG G1358      60.837 102.493  60.034  1.00 28.55      G
ATOM  18349  CA  ARG G1358      60.218 102.783  61.310  1.00 28.55      G
ATOM  18350  CB  ARG G1358      61.219 103.447  62.241  1.00 61.23      G
ATOM  18351  CG  ARG G1358      61.461 102.594  63.469  1.00 61.23      G
ATOM  18352  CD  ARG G1358      62.801 102.869  64.089  1.00 61.23      G
ATOM  18353  NE  ARG G1358      63.224 101.749  64.918  1.00 61.23      G
ATOM  18354  CZ  ARG G1358      64.392 101.694  65.544  1.00 61.23      G
ATOM  18355  NH1 ARG G1358      65.249 102.702  65.434  1.00 61.23      G
ATOM  18356  NH2 ARG G1358      64.704 100.635  66.279  1.00 61.23      G
ATOM  18357  C   ARG G1358      58.933 103.581  61.248  1.00 28.55      G
ATOM  18358  O   ARG G1358      58.092 103.453  62.134  1.00 28.55      G
```

```
ATOM  18359  N    ALA G1359   58.768 104.385  60.201  1.00 35.35      G
ATOM  18360  CA   ALA G1359   57.548 105.168  60.039  1.00 35.35      G
ATOM  18361  CB   ALA G1359   57.857 106.449  59.290  1.00  5.07      G
ATOM  18362  C    ALA G1359   56.421 104.376  59.325  1.00 35.35      G
ATOM  18363  O    ALA G1359   55.670 104.931  58.517  1.00 35.35      G
ATOM  18364  N    GLN G1360   56.324 103.079  59.642  1.00 55.78      G
ATOM  18365  CA   GLN G1360   55.306 102.153  59.111  1.00 55.78      G
ATOM  18366  CB   GLN G1360   55.011 102.459  57.634  1.00 60.86      G
ATOM  18367  CG   GLN G1360   56.242 102.658  56.767  1.00 60.86      G
ATOM  18368  CD   GLN G1360   56.293 104.028  56.095  1.00 60.86      G
ATOM  18369  OE1  GLN G1360   55.413 104.388  55.311  1.00 60.86      G
ATOM  18370  NE2  GLN G1360   57.335 104.794  56.398  1.00 60.86      G
ATOM  18371  C    GLN G1360   55.646 100.649  59.312  1.00 55.78      G
ATOM  18372  O    GLN G1360   54.895  99.928  59.982  1.00 55.78      G
ATOM  18373  N    GLY G1361   56.775 100.191  58.755  1.00 66.25      G
ATOM  18374  CA   GLY G1361   57.200  98.794  58.878  1.00 66.25      G
ATOM  18375  C    GLY G1361   57.644  98.405  60.278  1.00 66.25      G
ATOM  18376  O    GLY G1361   57.312  99.102  61.233  1.00 66.25      G
ATOM  18377  N    VAL G1362   58.378  97.301  60.421  1.00 26.34      G
ATOM  18378  CA   VAL G1362   58.847  96.852  61.748  1.00 26.34      G
ATOM  18379  CB   VAL G1362   57.765  96.082  62.514  1.00 51.84      G
ATOM  18380  CG1  VAL G1362   58.077  96.098  64.005  1.00 51.84      G
ATOM  18381  CG2  VAL G1362   56.398  96.652  62.219  1.00 51.84      G
ATOM  18382  C    VAL G1362   60.037  95.893  61.699  1.00 26.34      G
ATOM  18383  O    VAL G1362   60.156  95.026  62.563  1.00 26.34      G
ATOM  18384  N    ALA G1363   60.906  96.041  60.695  1.00 53.76      G
ATOM  18385  CA   ALA G1363   62.072  95.165  60.529  1.00 53.76      G
ATOM  18386  CB   ALA G1363   63.171  95.862  59.705  1.00  5.07      G
ATOM  18387  C    ALA G1363   62.608  94.753  61.883  1.00 53.76      G
ATOM  18388  O    ALA G1363   62.649  95.549  62.817  1.00 53.76      G
ATOM  18389  N    ALA G1364   62.989  93.492  61.995  1.00 67.41      G
ATOM  18390  CA   ALA G1364   63.515  92.986  63.249  1.00 67.41      G
ATOM  18391  CB   ALA G1364   63.611  91.458  63.205  1.00 70.33      G
ATOM  18392  C    ALA G1364   64.880  93.596  63.522  1.00 67.41      G
ATOM  18393  O    ALA G1364   65.844  92.876  63.782  1.00 67.41      G
ATOM  18394  N    HIS G1365   64.954  94.925  63.462  1.00 37.62      G
ATOM  18395  CA   HIS G1365   66.203  95.646  63.714  1.00 37.62      G
ATOM  18396  CB   HIS G1365   65.906  97.094  64.152  1.00100.05      G
ATOM  18397  CG   HIS G1365   66.887  97.662  65.136  1.00100.05      G
ATOM  18398  CD2  HIS G1365   66.706  98.485  66.196  1.00100.05      G
ATOM  18399  ND1  HIS G1365   68.242  97.419  65.071  1.00100.05      G
ATOM  18400  CE1  HIS G1365   68.852  98.066  66.049  1.00100.05      G
ATOM  18401  NE2  HIS G1365   67.942  98.721  66.747  1.00100.05      G
ATOM  18402  C    HIS G1365   66.923  94.885  64.797  1.00 37.62      G
ATOM  18403  O    HIS G1365   68.153  94.931  64.891  1.00 37.62      G
ATOM  18404  N    ASP G1366   66.114  94.179  65.587  1.00 68.63      G
ATOM  18405  CA   ASP G1366   66.550  93.330  66.679  1.00 68.63      G
ATOM  18406  CB   ASP G1366   65.642  92.110  66.760  1.00100.00      G
ATOM  18407  CG   ASP G1366   65.844  91.322  68.029  1.00100.00      G
ATOM  18408  OD1  ASP G1366   66.944  90.764  68.220  1.00100.00      G
ATOM  18409  OD2  ASP G1366   64.899  91.264  68.842  1.00100.00      G
ATOM  18410  C    ASP G1366   67.979  92.895  66.430  1.00 68.63      G
ATOM  18411  O    ASP G1366   68.777  92.823  67.365  1.00 68.63      G
ATOM  18412  N    LYS G1367   68.283  92.594  65.166  1.00 32.64      G
ATOM  18413  CA   LYS G1367   69.626  92.209  64.722  1.00 32.64      G
ATOM  18414  CB   LYS G1367   69.756  90.673  64.632  1.00 35.04      G
ATOM  18415  CG   LYS G1367   69.185  89.877  65.835  1.00 35.04      G
ATOM  18416  CD   LYS G1367   69.665  88.389  65.896  1.00 35.04      G
ATOM  18417  CE   LYS G1367   69.180  87.487  64.716  1.00 35.04      G
ATOM  18418  NZ   LYS G1367   70.118  86.350  64.363  1.00 35.04      G
ATOM  18419  C    LYS G1367   69.732  92.856  63.329  1.00 32.64      G
ATOM  18420  O    LYS G1367   69.912  94.074  63.208  1.00 32.64      G
ATOM  18421  N    HIS G1368   69.595  92.013  62.306  1.00 45.78      G
ATOM  18422  CA   HIS G1368   69.598  92.354  60.880  1.00 45.78      G
ATOM  18423  CB   HIS G1368   68.161  92.585  60.463  1.00 12.69      G
ATOM  18424  CG   HIS G1368   67.303  91.413  60.772  1.00 12.69      G
ATOM  18425  CD2  HIS G1368   66.231  91.276  61.583  1.00 12.69      G
ATOM  18426  ND1  HIS G1368   67.634  90.140  60.358  1.00 12.69      G
ATOM  18427  CE1  HIS G1368   66.813  89.266  60.912  1.00 12.69      G
ATOM  18428  NE2  HIS G1368   65.951  89.930  61.661  1.00 12.69      G
ATOM  18429  C    HIS G1368   70.478  93.436  60.308  1.00 45.78      G
ATOM  18430  O    HIS G1368   71.632  93.180  59.962  1.00 45.78      G
ATOM  18431  N    ILE G1369   69.917  94.629  60.148  1.00 36.62      G
ATOM  18432  CA   ILE G1369   70.668  95.765  59.620  1.00 36.62      G
ATOM  18433  CB   ILE G1369   70.032  97.074  60.110  1.00 27.62      G
ATOM  18434  CG2  ILE G1369   70.974  98.223  59.926  1.00 27.62      G
ATOM  18435  CG1  ILE G1369   68.739  97.311  59.345  1.00 27.62      G
ATOM  18436  CD   ILE G1369   67.775  98.166  60.078  1.00 27.62      G
ATOM  18437  C    ILE G1369   72.134  95.668  60.063  1.00 36.62      G
ATOM  18438  O    ILE G1369   73.054  95.797  59.248  1.00 36.62      G
ATOM  18439  N    GLU G1370   72.335  95.413  61.355  1.00 45.01      G
ATOM  18440  CA   GLU G1370   73.672  95.260  61.906  1.00 45.01      G
ATOM  18441  CB   GLU G1370   73.607  94.569  63.276  1.00 51.14      G
ATOM  18442  CG   GLU G1370   72.456  95.052  64.190  1.00 51.14      G
```

```
ATOM  18443  CD   GLU G1370     72.916  95.729  65.497  1.00 51.14      G
ATOM  18444  OE1  GLU G1370     73.561  95.073  66.364  1.00 51.14      G
ATOM  18445  OE2  GLU G1370     72.613  96.933  65.655  1.00 51.14      G
ATOM  18446  C    GLU G1370     74.425  94.391  60.901  1.00 45.01      G
ATOM  18447  O    GLU G1370     75.259  94.896  60.156  1.00 45.01      G
ATOM  18448  N    ILE G1371     74.100  93.098  60.858  1.00 36.41      G
ATOM  18449  CA   ILE G1371     74.739  92.163  59.926  1.00 36.41      G
ATOM  18450  CB   ILE G1371     73.794  91.043  59.462  1.00  5.07      G
ATOM  18451  CG2  ILE G1371     74.418  90.314  58.318  1.00  5.07      G
ATOM  18452  CG1  ILE G1371     73.544  90.037  60.577  1.00  5.07      G
ATOM  18453  CD   ILE G1371     74.794  89.299  61.011  1.00  5.07      G
ATOM  18454  C    ILE G1371     75.213  92.848  58.657  1.00 36.41      G
ATOM  18455  O    ILE G1371     76.397  92.783  58.306  1.00 36.41      G
ATOM  18456  N    VAL G1372     74.284  93.486  57.953  1.00 30.35      G
ATOM  18457  CA   VAL G1372     74.668  94.157  56.727  1.00 30.35      G
ATOM  18458  CB   VAL G1372     73.435  94.722  55.970  1.00 18.98      G
ATOM  18459  CG1  VAL G1372     73.838  95.850  55.018  1.00 18.98      G
ATOM  18460  CG2  VAL G1372     72.807  93.615  55.154  1.00 18.98      G
ATOM  18461  C    VAL G1372     75.686  95.256  56.998  1.00 30.35      G
ATOM  18462  O    VAL G1372     76.726  95.297  56.348  1.00 30.35      G
ATOM  18463  N    VAL G1373     75.406  96.132  57.962  1.00 32.36      G
ATOM  18464  CA   VAL G1373     76.337  97.219  58.274  1.00 32.36      G
ATOM  18465  CB   VAL G1373     75.956  97.973  59.582  1.00 19.30      G
ATOM  18466  CG1  VAL G1373     77.206  98.580  60.230  1.00 19.30      G
ATOM  18467  CG2  VAL G1373     74.955  99.090  59.264  1.00 19.30      G
ATOM  18468  C    VAL G1373     77.754  96.690  58.404  1.00 32.36      G
ATOM  18469  O    VAL G1373     78.674  97.215  57.779  1.00 32.36      G
ATOM  18470  N    ARG G1374     77.940  95.646  59.203  1.00 30.31      G
ATOM  18471  CA   ARG G1374     79.278  95.100  59.353  1.00 30.31      G
ATOM  18472  CB   ARG G1374     79.265  93.805  60.157  1.00 35.80      G
ATOM  18473  CG   ARG G1374     80.651  93.390  60.552  1.00 35.80      G
ATOM  18474  CD   ARG G1374     80.758  91.913  60.635  1.00 35.80      G
ATOM  18475  NE   ARG G1374     80.234  91.405  61.886  1.00 35.80      G
ATOM  18476  CZ   ARG G1374     80.157  90.112  62.183  1.00 35.80      G
ATOM  18477  NH1  ARG G1374     80.565  89.191  61.315  1.00 35.80      G
ATOM  18478  NH2  ARG G1374     79.685  89.734  63.363  1.00 35.80      G
ATOM  18479  C    ARG G1374     79.813  94.830  57.951  1.00 30.31      G
ATOM  18480  O    ARG G1374     80.875  95.324  57.563  1.00 30.31      G
ATOM  18481  N    GLN G1375     79.060  94.052  57.188  1.00 37.70      G
ATOM  18482  CA   GLN G1375     79.445  93.747  55.825  1.00 37.70      G
ATOM  18483  CB   GLN G1375     78.274  93.096  55.107  1.00 49.34      G
ATOM  18484  CG   GLN G1375     78.090  91.735  55.624  1.00 49.34      G
ATOM  18485  CD   GLN G1375     79.426  91.058  55.691  1.00 49.34      G
ATOM  18486  OE1  GLN G1375     80.017  90.747  54.654  1.00 49.34      G
ATOM  18487  NE2  GLN G1375     79.937  90.856  56.906  1.00 49.34      G
ATOM  18488  C    GLN G1375     79.888  94.991  55.073  1.00 37.70      G
ATOM  18489  O    GLN G1375     80.903  94.990  54.366  1.00 37.70      G
ATOM  18490  N    MET G1376     79.114  96.054  55.240  1.00 42.35      G
ATOM  18491  CA   MET G1376     79.404  97.303  54.582  1.00 42.35      G
ATOM  18492  CB   MET G1376     78.471  98.383  55.107  1.00 42.60      G
ATOM  18493  CG   MET G1376     78.217  99.512  54.141  1.00 42.60      G
ATOM  18494  SD   MET G1376     76.525 100.131  54.332  1.00 42.60      G
ATOM  18495  CE   MET G1376     75.668  99.034  53.204  1.00 42.60      G
ATOM  18496  C    MET G1376     80.853  97.649  54.854  1.00 42.35      G
ATOM  18497  O    MET G1376     81.663  97.650  53.929  1.00 42.35      G
ATOM  18498  N    LEU G1377     81.190  97.900  56.120  1.00 52.66      G
ATOM  18499  CA   LEU G1377     82.564  98.254  56.480  1.00 52.66      G
ATOM  18500  CB   LEU G1377     82.575  99.349  57.567  1.00 40.09      G
ATOM  18501  CG   LEU G1377     81.825  99.253  58.902  1.00 40.09      G
ATOM  18502  CD1  LEU G1377     80.354  99.285  58.638  1.00 40.09      G
ATOM  18503  CD2  LEU G1377     82.207  97.995  59.671  1.00 40.09      G
ATOM  18504  C    LEU G1377     83.451  97.072  56.889  1.00 52.66      G
ATOM  18505  O    LEU G1377     84.036  97.035  57.972  1.00 52.66      G
ATOM  18506  N    ALA G1378     83.554  96.105  55.994  1.00 61.12      G
ATOM  18507  CA   ALA G1378     84.375  94.943  56.247  1.00 61.12      G
ATOM  18508  CB   ALA G1378     83.674  93.697  55.747  1.00 30.08      G
ATOM  18509  C    ALA G1378     85.667  95.146  55.482  1.00 61.12      G
ATOM  18510  O    ALA G1378     86.165  94.212  54.861  1.00 61.12      G
ATOM  18511  N    TYR G1379     86.208  96.361  55.500  1.00 99.86      G
ATOM  18512  CA   TYR G1379     87.434  96.619  54.753  1.00 99.86      G
ATOM  18513  CB   TYR G1379     87.083  97.128  53.361  1.00 58.85      G
ATOM  18514  CG   TYR G1379     86.157  96.194  52.654  1.00 58.85      G
ATOM  18515  CD1  TYR G1379     84.795  96.184  52.944  1.00 58.85      G
ATOM  18516  CE1  TYR G1379     83.949  95.230  52.387  1.00 58.85      G
ATOM  18517  CD2  TYR G1379     86.650  95.235  51.782  1.00 58.85      G
ATOM  18518  CE2  TYR G1379     85.817  94.279  51.217  1.00 58.85      G
ATOM  18519  CZ   TYR G1379     84.470  94.272  51.524  1.00 58.85      G
ATOM  18520  OH   TYR G1379     83.655  93.296  50.985  1.00 58.85      G
ATOM  18521  C    TYR G1379     88.428  97.567  55.392  1.00 99.86      G
ATOM  18522  O    TYR G1379     88.097  98.312  56.314  1.00 99.86      G
ATOM  18523  N    VAL G1380     89.651  97.536  54.867  1.00 45.10      G
ATOM  18524  CA   VAL G1380     90.745  98.372  55.354  1.00 45.10      G
ATOM  18525  CB   VAL G1380     91.377  97.733  56.597  1.00 36.73      G
ATOM  18526  CG1  VAL G1380     90.598  98.113  57.834  1.00 36.73      G
```

| ATOM | 18527 | CG2 | VAL | G1380 | 91.381 | 96.222 | 56.441 | 1.00 | 36.73 | G |
|---|---|---|---|---|---|---|---|---|---|---|
| ATOM | 18528 | C | VAL | G1380 | 91.835 | 98.562 | 54.289 | 1.00 | 45.10 | G |
| ATOM | 18529 | O | VAL | G1380 | 92.171 | 97.615 | 53.571 | 1.00 | 45.10 | G |
| ATOM | 18530 | N | GLU | G1381 | 92.374 | 99.781 | 54.187 | 1.00 | 91.74 | G |
| ATOM | 18531 | CA | GLU | G1381 | 93.443 | 100.077 | 53.228 | 1.00 | 91.74 | G |
| ATOM | 18532 | CB | GLU | G1381 | 93.213 | 101.427 | 52.534 | 1.00 | 66.02 | G |
| ATOM | 18533 | CG | GLU | G1381 | 93.954 | 102.588 | 53.160 | 1.00 | 66.02 | G |
| ATOM | 18534 | CD | GLU | G1381 | 93.599 | 102.772 | 54.619 | 1.00 | 66.02 | G |
| ATOM | 18535 | OE1 | GLU | G1381 | 92.435 | 103.120 | 54.902 | 1.00 | 66.02 | G |
| ATOM | 18536 | OE2 | GLU | G1381 | 94.484 | 102.561 | 55.478 | 1.00 | 66.02 | G |
| ATOM | 18537 | C | GLU | G1381 | 94.786 | 100.091 | 53.964 | 1.00 | 91.74 | G |
| ATOM | 18538 | O | GLU | G1381 | 94.826 | 99.969 | 55.189 | 1.00 | 91.74 | G |
| ATOM | 18539 | N | VAL | G1382 | 95.882 | 100.266 | 53.233 | 1.00 | 66.97 | G |
| ATOM | 18540 | CA | VAL | G1382 | 97.197 | 100.239 | 53.868 | 1.00 | 66.97 | G |
| ATOM | 18541 | CB | VAL | G1382 | 98.120 | 99.227 | 53.151 | 1.00 | 75.18 | G |
| ATOM | 18542 | CG1 | VAL | G1382 | 99.539 | 99.336 | 53.688 | 1.00 | 75.18 | G |
| ATOM | 18543 | CG2 | VAL | G1382 | 97.593 | 97.815 | 53.346 | 1.00 | 75.18 | G |
| ATOM | 18544 | C | VAL | G1382 | 97.981 | 101.538 | 54.016 | 1.00 | 66.97 | G |
| ATOM | 18545 | O | VAL | G1382 | 97.973 | 102.402 | 53.139 | 1.00 | 66.97 | G |
| ATOM | 18546 | N | THR | G1383 | 98.662 | 101.645 | 55.153 | 1.00 | 60.93 | G |
| ATOM | 18547 | CA | THR | G1383 | 99.532 | 102.769 | 55.464 | 1.00 | 60.93 | G |
| ATOM | 18548 | CB | THR | G1383 | 98.827 | 103.849 | 56.307 | 1.00 | 37.91 | G |
| ATOM | 18549 | OG1 | THR | G1383 | 98.010 | 103.222 | 57.298 | 1.00 | 37.91 | G |
| ATOM | 18550 | CG2 | THR | G1383 | 97.980 | 104.760 | 55.412 | 1.00 | 37.91 | G |
| ATOM | 18551 | C | THR | G1383 | 100.693 | 102.150 | 56.240 | 1.00 | 60.93 | G |
| ATOM | 18552 | O | THR | G1383 | 100.523 | 101.678 | 57.370 | 1.00 | 60.93 | G |
| ATOM | 18553 | N | ASP | G1384 | 101.863 | 102.152 | 55.593 | 1.00 | 100.07 | G |
| ATOM | 18554 | CA | ASP | G1384 | 103.124 | 101.574 | 56.086 | 1.00 | 100.07 | G |
| ATOM | 18555 | CB | ASP | G1384 | 103.362 | 101.854 | 57.576 | 1.00 | 100.07 | G |
| ATOM | 18556 | CG | ASP | G1384 | 104.814 | 101.597 | 57.993 | 1.00 | 100.07 | G |
| ATOM | 18557 | OD1 | ASP | G1384 | 105.416 | 100.616 | 57.494 | 1.00 | 100.07 | G |
| ATOM | 18558 | OD2 | ASP | G1384 | 105.348 | 102.373 | 58.825 | 1.00 | 100.07 | G |
| ATOM | 18559 | C | ASP | G1384 | 103.025 | 100.068 | 55.861 | 1.00 | 100.07 | G |
| ATOM | 18560 | O | ASP | G1384 | 102.878 | 99.288 | 56.805 | 1.00 | 100.07 | G |
| ATOM | 18561 | N | PRO | G1385 | 103.091 | 99.646 | 54.590 | 1.00 | 100.07 | G |
| ATOM | 18562 | CD | PRO | G1385 | 103.195 | 100.529 | 53.416 | 1.00 | 100.07 | G |
| ATOM | 18563 | CA | PRO | G1385 | 103.008 | 98.242 | 54.175 | 1.00 | 100.07 | G |
| ATOM | 18564 | CB | PRO | G1385 | 103.099 | 98.329 | 52.647 | 1.00 | 100.07 | G |
| ATOM | 18565 | CG | PRO | G1385 | 103.813 | 99.621 | 52.404 | 1.00 | 100.07 | G |
| ATOM | 18566 | C | PRO | G1385 | 103.994 | 97.227 | 54.770 | 1.00 | 100.07 | G |
| ATOM | 18567 | O | PRO | G1385 | 105.114 | 97.558 | 55.159 | 1.00 | 100.07 | G |
| ATOM | 18568 | N | GLY | G1386 | 103.528 | 95.984 | 54.833 | 1.00 | 100.07 | G |
| ATOM | 18569 | CA | GLY | G1386 | 104.295 | 94.863 | 55.345 | 1.00 | 100.07 | G |
| ATOM | 18570 | C | GLY | G1386 | 103.585 | 93.655 | 54.758 | 1.00 | 100.07 | G |
| ATOM | 18571 | O | GLY | G1386 | 102.357 | 93.654 | 54.692 | 1.00 | 100.07 | G |
| ATOM | 18572 | N | ASP | G1387 | 104.334 | 92.644 | 54.322 | 1.00 | 55.63 | G |
| ATOM | 18573 | CA | ASP | G1387 | 103.762 | 91.437 | 53.709 | 1.00 | 55.63 | G |
| ATOM | 18574 | CB | ASP | G1387 | 102.444 | 91.034 | 54.383 | 1.00 | 100.07 | G |
| ATOM | 18575 | CG | ASP | G1387 | 102.617 | 89.888 | 55.365 | 1.00 | 100.07 | G |
| ATOM | 18576 | OD1 | ASP | G1387 | 102.951 | 88.770 | 54.912 | 1.00 | 100.07 | G |
| ATOM | 18577 | OD2 | ASP | G1387 | 102.424 | 90.101 | 56.585 | 1.00 | 100.07 | G |
| ATOM | 18578 | C | ASP | G1387 | 103.533 | 91.637 | 52.217 | 1.00 | 55.63 | G |
| ATOM | 18579 | O | ASP | G1387 | 102.592 | 91.092 | 51.640 | 1.00 | 55.63 | G |
| ATOM | 18580 | N | SER | G1388 | 104.412 | 92.432 | 51.613 | 1.00 | 100.07 | G |
| ATOM | 18581 | CA | SER | G1388 | 104.387 | 92.747 | 50.186 | 1.00 | 100.07 | G |
| ATOM | 18582 | CB | SER | G1388 | 104.661 | 91.469 | 49.374 | 1.00 | 79.02 | G |
| ATOM | 18583 | OG | SER | G1388 | 103.852 | 90.379 | 49.791 | 1.00 | 79.02 | G |
| ATOM | 18584 | C | SER | G1388 | 103.138 | 93.461 | 49.643 | 1.00 | 100.07 | G |
| ATOM | 18585 | O | SER | G1388 | 102.782 | 93.290 | 48.471 | 1.00 | 100.07 | G |
| ATOM | 18586 | N | PRO | G1389 | 102.475 | 94.293 | 50.471 | 1.00 | 100.07 | G |
| ATOM | 18587 | CD | PRO | G1389 | 102.770 | 94.635 | 51.876 | 1.00 | 80.29 | G |
| ATOM | 18588 | CA | PRO | G1389 | 101.275 | 95.003 | 50.013 | 1.00 | 100.07 | G |
| ATOM | 18589 | CB | PRO | G1389 | 100.554 | 95.307 | 51.312 | 1.00 | 80.29 | G |
| ATOM | 18590 | CG | PRO | G1389 | 101.697 | 95.666 | 52.206 | 1.00 | 80.29 | G |
| ATOM | 18591 | C | PRO | G1389 | 101.622 | 96.274 | 49.236 | 1.00 | 100.07 | G |
| ATOM | 18592 | O | PRO | G1389 | 102.374 | 96.226 | 48.258 | 1.00 | 100.07 | G |
| ATOM | 18593 | N | LEU | G1390 | 101.071 | 97.406 | 49.673 | 1.00 | 99.84 | G |
| ATOM | 18594 | CA | LEU | G1390 | 101.319 | 98.689 | 49.014 | 1.00 | 99.84 | G |
| ATOM | 18595 | CB | LEU | G1390 | 100.497 | 98.787 | 47.717 | 1.00 | 100.07 | G |
| ATOM | 18596 | CG | LEU | G1390 | 100.561 | 97.706 | 46.624 | 1.00 | 100.07 | G |
| ATOM | 18597 | CD1 | LEU | G1390 | 99.685 | 96.511 | 47.007 | 1.00 | 100.07 | G |
| ATOM | 18598 | CD2 | LEU | G1390 | 100.076 | 98.299 | 45.299 | 1.00 | 100.07 | G |
| ATOM | 18599 | C | LEU | G1390 | 100.973 | 99.883 | 49.918 | 1.00 | 99.84 | G |
| ATOM | 18600 | O | LEU | G1390 | 101.035 | 99.794 | 51.146 | 1.00 | 99.84 | G |
| ATOM | 18601 | N | LEU | G1391 | 100.625 | 101.003 | 49.288 | 1.00 | 98.88 | G |
| ATOM | 18602 | CA | LEU | G1391 | 100.234 | 102.217 | 49.998 | 1.00 | 98.88 | G |
| ATOM | 18603 | CB | LEU | G1391 | 101.279 | 103.322 | 49.799 | 1.00 | 96.72 | G |
| ATOM | 18604 | CG | LEU | G1391 | 101.204 | 104.616 | 50.633 | 1.00 | 96.72 | G |
| ATOM | 18605 | CD1 | LEU | G1391 | 100.336 | 105.658 | 49.950 | 1.00 | 96.72 | G |
| ATOM | 18606 | CD2 | LEU | G1391 | 100.690 | 104.296 | 52.029 | 1.00 | 96.72 | G |
| ATOM | 18607 | C | LEU | G1391 | 98.881 | 102.643 | 49.430 | 1.00 | 98.88 | G |
| ATOM | 18608 | O | LEU | G1391 | 98.733 | 103.732 | 48.874 | 1.00 | 98.88 | G |
| ATOM | 18609 | N | GLU | G1392 | 97.908 | 101.744 | 49.567 | 1.00 | 99.92 | G |
| ATOM | 18610 | CA | GLU | G1392 | 96.532 | 101.934 | 49.101 | 1.00 | 99.92 | G |

```
ATOM  18611  CB   GLU G1392      96.509 102.443  47.649  1.00100.07      G
ATOM  18612  CG   GLU G1392      95.188 103.112  47.227  1.00100.07      G
ATOM  18613  CD   GLU G1392      95.229 103.708  45.811  1.00100.07      G
ATOM  18614  OE1  GLU G1392      95.264 102.933  44.827  1.00100.07      G
ATOM  18615  OE2  GLU G1392      95.228 104.956  45.682  1.00100.07      G
ATOM  18616  C    GLU G1392      95.866 100.559  49.188  1.00 99.92      G
ATOM  18617  O    GLU G1392      95.494  99.963  48.172  1.00 99.92      G
ATOM  18618  N    GLY G1393      95.735 100.056  50.412  1.00100.07      G
ATOM  18619  CA   GLY G1393      95.135  98.751  50.615  1.00100.07      G
ATOM  18620  C    GLY G1393      93.640  98.707  50.356  1.00100.07      G
ATOM  18621  O    GLY G1393      92.967  99.738  50.351  1.00100.07      G
ATOM  18622  N    GLN G1394      93.128  97.498  50.142  1.00 99.85      G
ATOM  18623  CA   GLN G1394      91.710  97.244  49.880  1.00 99.85      G
ATOM  18624  CB   GLN G1394      91.356  97.647  48.438  1.00100.07      G
ATOM  18625  CG   GLN G1394      91.198  99.164  48.208  1.00100.07      G
ATOM  18626  CD   GLN G1394      91.396  99.594  46.744  1.00100.07      G
ATOM  18627  OE1  GLN G1394      92.519  99.563  46.214  1.00100.07      G
ATOM  18628  NE2  GLN G1394      90.305  99.997  46.088  1.00100.07      G
ATOM  18629  C    GLN G1394      91.526  95.736  50.077  1.00 99.85      G
ATOM  18630  O    GLN G1394      91.261  95.002  49.122  1.00 99.85      G
ATOM  18631  N    VAL G1395      91.671  95.288  51.326  1.00100.07      G
ATOM  18632  CA   VAL G1395      91.581  93.866  51.674  1.00100.07      G
ATOM  18633  CB   VAL G1395      92.961  93.344  52.170  1.00 56.37      G
ATOM  18634  CG1  VAL G1395      93.057  91.836  51.988  1.00 56.37      G
ATOM  18635  CG2  VAL G1395      94.083  94.054  51.435  1.00 56.37      G
ATOM  18636  C    VAL G1395      90.558  93.539  52.766  1.00100.07      G
ATOM  18637  O    VAL G1395      90.046  94.434  53.446  1.00100.07      G
ATOM  18638  N    LEU G1396      90.269  92.247  52.924  1.00 76.34      G
ATOM  18639  CA   LEU G1396      89.342  91.792  53.956  1.00 76.34      G
ATOM  18640  CB   LEU G1396      89.113  90.277  53.886  1.00100.07      G
ATOM  18641  CG   LEU G1396      88.165  89.672  52.844  1.00100.07      G
ATOM  18642  CD1  LEU G1396      87.936  88.194  53.177  1.00100.07      G
ATOM  18643  CD2  LEU G1396      86.834  90.416  52.850  1.00100.07      G
ATOM  18644  C    LEU G1396      89.984  92.127  55.290  1.00 76.34      G
ATOM  18645  O    LEU G1396      91.069  91.637  55.604  1.00 76.34      G
ATOM  18646  N    GLU G1397      89.309  92.955  56.075  1.00 50.50      G
ATOM  18647  CA   GLU G1397      89.846  93.369  57.360  1.00 50.50      G
ATOM  18648  CB   GLU G1397      88.792  94.104  58.167  1.00100.07      G
ATOM  18649  CG   GLU G1397      89.295  94.541  59.513  1.00100.07      G
ATOM  18650  CD   GLU G1397      88.190  95.096  60.359  1.00100.07      G
ATOM  18651  OE1  GLU G1397      87.659  96.169  60.005  1.00100.07      G
ATOM  18652  OE2  GLU G1397      87.840  94.453  61.370  1.00100.07      G
ATOM  18653  C    GLU G1397      90.428  92.247  58.203  1.00 50.50      G
ATOM  18654  O    GLU G1397      91.633  92.219  58.427  1.00 50.50      G
ATOM  18655  N    LYS G1398      89.603  91.327  58.685  1.00 99.69      G
ATOM  18656  CA   LYS G1398      90.178  90.269  59.496  1.00 99.69      G
ATOM  18657  CB   LYS G1398      89.199  89.127  59.756  1.00 99.84      G
ATOM  18658  CG   LYS G1398      89.868  88.002  60.546  1.00 99.84      G
ATOM  18659  CD   LYS G1398      88.905  87.262  61.434  1.00 99.84      G
ATOM  18660  CE   LYS G1398      89.654  86.360  62.387  1.00 99.84      G
ATOM  18661  NZ   LYS G1398      88.727  85.782  63.393  1.00 99.84      G
ATOM  18662  C    LYS G1398      91.391  89.717  58.781  1.00 99.69      G
ATOM  18663  O    LYS G1398      92.478  89.658  59.354  1.00 99.69      G
ATOM  18664  N    TRP G1399      91.207  89.321  57.524  1.00 72.86      G
ATOM  18665  CA   TRP G1399      92.312  88.779  56.752  1.00 72.86      G
ATOM  18666  CB   TRP G1399      91.967  88.775  55.262  1.00100.07      G
ATOM  18667  CG   TRP G1399      92.603  87.647  54.505  1.00100.07      G
ATOM  18668  CD2  TRP G1399      93.498  87.744  53.380  1.00100.07      G
ATOM  18669  CE2  TRP G1399      93.831  86.425  52.993  1.00100.07      G
ATOM  18670  CE3  TRP G1399      94.052  88.821  52.667  1.00100.07      G
ATOM  18671  CD1  TRP G1399      92.437  86.309  54.740  1.00100.07      G
ATOM  18672  NE1  TRP G1399      93.170  85.569  53.836  1.00100.07      G
ATOM  18673  CZ2  TRP G1399      94.691  86.149  51.915  1.00100.07      G
ATOM  18674  CZ3  TRP G1399      94.910  88.545  51.593  1.00100.07      G
ATOM  18675  CH2  TRP G1399      95.220  87.219  51.234  1.00100.07      G
ATOM  18676  C    TRP G1399      93.501  89.697  57.014  1.00 72.86      G
ATOM  18677  O    TRP G1399      94.616  89.247  57.273  1.00 72.86      G
ATOM  18678  N    ASP G1400      93.226  90.995  56.997  1.00 58.87      G
ATOM  18679  CA   ASP G1400      94.242  92.010  57.205  1.00 58.87      G
ATOM  18680  CB   ASP G1400      93.758  93.341  56.627  1.00100.07      G
ATOM  18681  CG   ASP G1400      94.900  94.267  56.268  1.00100.07      G
ATOM  18682  OD1  ASP G1400      95.565  94.777  57.192  1.00100.07      G
ATOM  18683  OD2  ASP G1400      95.139  94.474  55.057  1.00100.07      G
ATOM  18684  C    ASP G1400      94.635  92.189  58.666  1.00 58.87      G
ATOM  18685  O    ASP G1400      95.691  92.736  58.962  1.00 58.87      G
ATOM  18686  N    VAL G1401      93.789  91.747  59.585  1.00 81.85      G
ATOM  18687  CA   VAL G1401      94.119  91.873  60.999  1.00 81.85      G
ATOM  18688  CB   VAL G1401      92.889  91.615  61.910  1.00100.07      G
ATOM  18689  CG1  VAL G1401      93.260  91.875  63.370  1.00100.07      G
ATOM  18690  CG2  VAL G1401      91.722  92.499  61.489  1.00100.07      G
ATOM  18691  C    VAL G1401      95.176  90.817  61.291  1.00 81.85      G
ATOM  18692  O    VAL G1401      96.022  90.977  62.169  1.00 81.85      G
ATOM  18693  N    GLU G1402      95.121  89.733  60.530  1.00100.07      G
ATOM  18694  CA   GLU G1402      96.055  88.638  60.697  1.00100.07      G
```

| | | | | | | | | |
|---|---|---|---|---|---|---|---|---|
| ATOM | 18695 | CB | GLU G1402 | 95.680 | 87.508 | 59.738 | 1.00 | 100.07 | G |
| ATOM | 18696 | CG | GLU G1402 | 95.712 | 86.145 | 60.391 | 1.00 | 100.07 | G |
| ATOM | 18697 | CD | GLU G1402 | 95.416 | 86.209 | 61.886 | 1.00 | 100.07 | G |
| ATOM | 18698 | OE1 | GLU G1402 | 94.333 | 86.710 | 62.273 | 1.00 | 100.07 | G |
| ATOM | 18699 | OE2 | GLU G1402 | 96.277 | 85.757 | 62.674 | 1.00 | 100.07 | G |
| ATOM | 18700 | C | GLU G1402 | 97.486 | 89.113 | 60.464 | 1.00 | 100.07 | G |
| ATOM | 18701 | O | GLU G1402 | 98.439 | 88.522 | 60.974 | 1.00 | 100.07 | G |
| ATOM | 18702 | N | ALA G1403 | 97.626 | 90.193 | 59.699 | 1.00 | 100.07 | G |
| ATOM | 18703 | CA | ALA G1403 | 98.935 | 90.767 | 59.406 | 1.00 | 100.07 | G |
| ATOM | 18704 | CB | ALA G1403 | 98.841 | 91.732 | 58.222 | 1.00 | 61.84 | G |
| ATOM | 18705 | C | ALA G1403 | 99.451 | 91.497 | 60.644 | 1.00 | 100.07 | G |
| ATOM | 18706 | O | ALA G1403 | 100.153 | 92.505 | 60.537 | 1.00 | 100.07 | G |
| ATOM | 18707 | N | LEU G1404 | 99.073 | 90.981 | 61.812 | 1.00 | 81.53 | G |
| ATOM | 18708 | CA | LEU G1404 | 99.478 | 91.516 | 63.112 | 1.00 | 81.53 | G |
| ATOM | 18709 | CB | LEU G1404 | 98.525 | 92.615 | 63.587 | 1.00 | 100.07 | G |
| ATOM | 18710 | CG | LEU G1404 | 98.370 | 93.892 | 62.762 | 1.00 | 100.07 | G |
| ATOM | 18711 | CD1 | LEU G1404 | 97.426 | 94.837 | 63.485 | 1.00 | 100.07 | G |
| ATOM | 18712 | CD2 | LEU G1404 | 99.714 | 94.554 | 62.563 | 1.00 | 100.07 | G |
| ATOM | 18713 | C | LEU G1404 | 99.377 | 90.337 | 64.060 | 1.00 | 81.53 | G |
| ATOM | 18714 | O | LEU G1404 | 100.104 | 90.231 | 65.053 | 1.00 | 81.53 | G |
| ATOM | 18715 | N | ASN G1405 | 98.447 | 89.450 | 63.725 | 1.00 | 100.07 | G |
| ATOM | 18716 | CA | ASN G1405 | 98.210 | 88.250 | 64.504 | 1.00 | 100.07 | G |
| ATOM | 18717 | CB | ASN G1405 | 96.745 | 87.802 | 64.376 | 1.00 | 100.07 | G |
| ATOM | 18718 | CG | ASN G1405 | 95.755 | 88.970 | 64.372 | 1.00 | 100.07 | G |
| ATOM | 18719 | OD1 | ASN G1405 | 95.742 | 89.807 | 65.284 | 1.00 | 100.07 | G |
| ATOM | 18720 | ND2 | ASN G1405 | 94.909 | 89.017 | 63.345 | 1.00 | 100.07 | G |
| ATOM | 18721 | C | ASN G1405 | 99.135 | 87.167 | 63.944 | 1.00 | 100.07 | G |
| ATOM | 18722 | O | ASN G1405 | 99.217 | 86.060 | 64.484 | 1.00 | 100.07 | G |
| ATOM | 18723 | N | GLU G1406 | 99.827 | 87.497 | 62.854 | 1.00 | 92.09 | G |
| ATOM | 18724 | CA | GLU G1406 | 100.748 | 86.555 | 62.227 | 1.00 | 92.09 | G |
| ATOM | 18725 | CB | GLU G1406 | 100.271 | 86.195 | 60.820 | 1.00 | 100.07 | G |
| ATOM | 18726 | CG | GLU G1406 | 101.105 | 85.099 | 60.160 | 1.00 | 100.07 | G |
| ATOM | 18727 | CD | GLU G1406 | 101.235 | 83.848 | 61.025 | 1.00 | 100.07 | G |
| ATOM | 18728 | OE1 | GLU G1406 | 101.940 | 83.895 | 62.062 | 1.00 | 100.07 | G |
| ATOM | 18729 | OE2 | GLU G1406 | 100.624 | 82.818 | 60.662 | 1.00 | 100.07 | G |
| ATOM | 18730 | C | GLU G1406 | 102.181 | 87.079 | 62.161 | 1.00 | 92.09 | G |
| ATOM | 18731 | O | GLU G1406 | 103.112 | 86.330 | 61.859 | 1.00 | 92.09 | G |
| ATOM | 18732 | N | ARG G1407 | 102.354 | 88.364 | 62.445 | 1.00 | 100.07 | G |
| ATOM | 18733 | CA | ARG G1407 | 103.681 | 88.964 | 62.429 | 1.00 | 100.07 | G |
| ATOM | 18734 | CB | ARG G1407 | 103.708 | 90.155 | 61.473 | 1.00 | 100.07 | G |
| ATOM | 18735 | CG | ARG G1407 | 103.663 | 89.731 | 60.004 | 1.00 | 100.07 | G |
| ATOM | 18736 | CD | ARG G1407 | 104.863 | 88.842 | 59.659 | 1.00 | 100.07 | G |
| ATOM | 18737 | NE | ARG G1407 | 104.914 | 88.470 | 58.246 | 1.00 | 100.07 | G |
| ATOM | 18738 | CZ | ARG G1407 | 105.932 | 87.822 | 57.685 | 1.00 | 100.07 | G |
| ATOM | 18739 | NH1 | ARG G1407 | 106.982 | 87.476 | 58.424 | 1.00 | 100.07 | G |
| ATOM | 18740 | NH2 | ARG G1407 | 105.901 | 87.520 | 56.391 | 1.00 | 100.07 | G |
| ATOM | 18741 | C | ARG G1407 | 104.138 | 89.369 | 63.830 | 1.00 | 100.07 | G |
| ATOM | 18742 | O | ARG G1407 | 105.221 | 88.967 | 64.264 | 1.00 | 100.07 | G |
| ATOM | 18743 | N | LEU G1408 | 103.330 | 90.159 | 64.539 | 1.00 | 100.07 | G |
| ATOM | 18744 | CA | LEU G1408 | 103.696 | 90.543 | 65.900 | 1.00 | 100.07 | G |
| ATOM | 18745 | CB | LEU G1408 | 102.678 | 91.505 | 66.517 | 1.00 | 100.07 | G |
| ATOM | 18746 | CG | LEU G1408 | 102.811 | 91.709 | 68.037 | 1.00 | 100.07 | G |
| ATOM | 18747 | CD1 | LEU G1408 | 104.259 | 91.990 | 68.421 | 1.00 | 100.07 | G |
| ATOM | 18748 | CD2 | LEU G1408 | 101.918 | 92.855 | 68.468 | 1.00 | 100.07 | G |
| ATOM | 18749 | C | LEU G1408 | 103.688 | 89.243 | 66.674 | 1.00 | 100.07 | G |
| ATOM | 18750 | O | LEU G1408 | 104.516 | 89.020 | 67.560 | 1.00 | 100.07 | G |
| ATOM | 18751 | N | ILE G1409 | 102.733 | 88.388 | 66.317 | 1.00 | 99.96 | G |
| ATOM | 18752 | CA | ILE G1409 | 102.589 | 87.079 | 66.933 | 1.00 | 99.96 | G |
| ATOM | 18753 | CB | ILE G1409 | 101.302 | 86.381 | 66.454 | 1.00 | 100.07 | G |
| ATOM | 18754 | CG2 | ILE G1409 | 101.324 | 84.911 | 66.839 | 1.00 | 100.07 | G |
| ATOM | 18755 | CG1 | ILE G1409 | 100.083 | 87.074 | 67.063 | 1.00 | 100.07 | G |
| ATOM | 18756 | CD | ILE G1409 | 99.986 | 86.946 | 68.579 | 1.00 | 100.07 | G |
| ATOM | 18757 | C | ILE G1409 | 103.792 | 86.228 | 66.551 | 1.00 | 99.96 | G |
| ATOM | 18758 | O | ILE G1409 | 104.308 | 85.471 | 67.375 | 1.00 | 99.96 | G |
| ATOM | 18759 | N | ALA G1410 | 104.233 | 86.356 | 65.300 | 1.00 | 95.47 | G |
| ATOM | 18760 | CA | ALA G1410 | 105.389 | 85.607 | 64.818 | 1.00 | 95.47 | G |
| ATOM | 18761 | CB | ALA G1410 | 105.555 | 85.781 | 63.315 | 1.00 | 72.23 | G |
| ATOM | 18762 | C | ALA G1410 | 106.612 | 86.131 | 65.546 | 1.00 | 95.47 | G |
| ATOM | 18763 | O | ALA G1410 | 107.321 | 87.007 | 65.050 | 1.00 | 95.47 | G |
| ATOM | 18764 | N | ALA G1411 | 106.832 | 85.588 | 66.739 | 1.00 | 100.07 | G |
| ATOM | 18765 | CA | ALA G1411 | 107.951 | 85.961 | 67.595 | 1.00 | 100.07 | G |
| ATOM | 18766 | CB | ALA G1411 | 109.260 | 85.417 | 67.018 | 1.00 | 100.07 | G |
| ATOM | 18767 | C | ALA G1411 | 108.053 | 87.467 | 67.804 | 1.00 | 100.07 | G |
| ATOM | 18768 | O | ALA G1411 | 107.634 | 87.982 | 68.841 | 1.00 | 100.07 | G |
| ATOM | 18769 | N | GLY G1412 | 108.600 | 88.169 | 66.814 | 1.00 | 100.07 | G |
| ATOM | 18770 | CA | GLY G1412 | 108.769 | 89.604 | 66.928 | 1.00 | 100.07 | G |
| ATOM | 18771 | C | GLY G1412 | 107.683 | 90.486 | 66.344 | 1.00 | 100.07 | G |
| ATOM | 18772 | O | GLY G1412 | 106.761 | 90.022 | 65.678 | 1.00 | 100.07 | G |
| ATOM | 18773 | N | LYS G1413 | 107.819 | 91.780 | 66.620 | 1.00 | 100.07 | G |
| ATOM | 18774 | CA | LYS G1413 | 106.907 | 92.820 | 66.158 | 1.00 | 100.07 | G |
| ATOM | 18775 | CB | LYS G1413 | 106.920 | 93.977 | 67.166 | 1.00 | 100.07 | G |
| ATOM | 18776 | CG | LYS G1413 | 106.032 | 95.144 | 66.795 | 1.00 | 100.07 | G |
| ATOM | 18777 | CD | LYS G1413 | 106.488 | 96.445 | 67.447 | 1.00 | 100.07 | G |
| ATOM | 18778 | CE | LYS G1413 | 105.713 | 97.634 | 66.865 | 1.00 | 100.07 | G |

| ATOM | 18779 | NZ | LYS | G1413 | 106.197 | 98.960 | 67.353 | 1.00 | 100.07 | G |
|------|-------|-----|-----|-------|---------|---------|--------|------|--------|---|
| ATOM | 18780 | C | LYS | G1413 | 107.393 | 93.308 | 64.785 | 1.00 | 100.07 | G |
| ATOM | 18781 | O | LYS | G1413 | 108.461 | 92.901 | 64.328 | 1.00 | 100.07 | G |
| ATOM | 18782 | N | VAL | G1414 | 106.611 | 94.180 | 64.144 | 1.00 | 100.07 | G |
| ATOM | 18783 | CA | VAL | G1414 | 106.930 | 94.748 | 62.822 | 1.00 | 100.07 | G |
| ATOM | 18784 | CB | VAL | G1414 | 106.851 | 93.644 | 61.688 | 1.00 | 100.07 | G |
| ATOM | 18785 | CG1 | VAL | G1414 | 106.821 | 94.293 | 60.295 | 1.00 | 100.07 | G |
| ATOM | 18786 | CG2 | VAL | G1414 | 108.051 | 92.693 | 61.774 | 1.00 | 100.07 | G |
| ATOM | 18787 | C | VAL | G1414 | 105.959 | 95.906 | 62.473 | 1.00 | 100.07 | G |
| ATOM | 18788 | O | VAL | G1414 | 104.793 | 95.908 | 62.893 | 1.00 | 100.07 | G |
| ATOM | 18789 | N | PRO | G1415 | 106.432 | 96.908 | 61.704 | 1.00 | 100.07 | G |
| ATOM | 18790 | CD | PRO | G1415 | 107.828 | 97.136 | 61.284 | 1.00 | 100.07 | G |
| ATOM | 18791 | CA | PRO | G1415 | 105.589 | 98.048 | 61.317 | 1.00 | 100.07 | G |
| ATOM | 18792 | CB | PRO | G1415 | 106.608 | 99.064 | 60.790 | 1.00 | 100.07 | G |
| ATOM | 18793 | CG | PRO | G1415 | 107.672 | 98.200 | 60.211 | 1.00 | 100.07 | G |
| ATOM | 18794 | C | PRO | G1415 | 104.488 | 97.740 | 60.286 | 1.00 | 100.07 | G |
| ATOM | 18795 | O | PRO | G1415 | 104.772 | 97.522 | 59.102 | 1.00 | 100.07 | G |
| ATOM | 18796 | N | VAL | G1416 | 103.236 | 97.733 | 60.748 | 1.00 | 100.07 | G |
| ATOM | 18797 | CA | VAL | G1416 | 102.068 | 97.473 | 59.896 | 1.00 | 100.07 | G |
| ATOM | 18798 | CB | VAL | G1416 | 101.742 | 95.950 | 59.817 | 1.00 | 100.07 | G |
| ATOM | 18799 | CG1 | VAL | G1416 | 100.493 | 95.722 | 58.953 | 1.00 | 100.07 | G |
| ATOM | 18800 | CG2 | VAL | G1416 | 102.941 | 95.178 | 59.255 | 1.00 | 100.07 | G |
| ATOM | 18801 | C | VAL | G1416 | 100.846 | 98.201 | 60.480 | 1.00 | 100.07 | G |
| ATOM | 18802 | O | VAL | G1416 | 100.812 | 98.480 | 61.683 | 1.00 | 100.07 | G |
| ATOM | 18803 | N | ALA | G1417 | 99.854 | 98.510 | 59.641 | 1.00 | 100.07 | G |
| ATOM | 18804 | CA | ALA | G1417 | 98.642 | 99.196 | 60.107 | 1.00 | 100.07 | G |
| ATOM | 18805 | CB | ALA | G1417 | 99.009 | 100.489 | 60.848 | 1.00 | 100.07 | G |
| ATOM | 18806 | C | ALA | G1417 | 97.679 | 99.506 | 58.964 | 1.00 | 100.07 | G |
| ATOM | 18807 | O | ALA | G1417 | 97.903 | 99.080 | 57.829 | 1.00 | 100.07 | G |
| ATOM | 18808 | N | TRP | G1418 | 96.617 | 100.261 | 59.265 | 1.00 | 99.08 | G |
| ATOM | 18809 | CA | TRP | G1418 | 95.603 | 100.612 | 58.265 | 1.00 | 99.08 | G |
| ATOM | 18810 | CB | TRP | G1418 | 94.711 | 99.396 | 58.000 | 1.00 | 99.71 | G |
| ATOM | 18811 | CG | TRP | G1418 | 94.138 | 98.796 | 59.259 | 1.00 | 99.71 | G |
| ATOM | 18812 | CD2 | TRP | G1418 | 94.313 | 97.454 | 59.725 | 1.00 | 99.71 | G |
| ATOM | 18813 | CE2 | TRP | G1418 | 93.648 | 97.348 | 60.965 | 1.00 | 99.71 | G |
| ATOM | 18814 | CE3 | TRP | G1418 | 94.973 | 96.327 | 59.214 | 1.00 | 99.71 | G |
| ATOM | 18815 | CD1 | TRP | G1418 | 93.385 | 99.432 | 60.208 | 1.00 | 99.71 | G |
| ATOM | 18816 | NE1 | TRP | G1418 | 93.089 | 98.572 | 61.237 | 1.00 | 99.71 | G |
| ATOM | 18817 | CZ2 | TRP | G1418 | 93.621 | 96.160 | 61.704 | 1.00 | 99.71 | G |
| ATOM | 18818 | CZ3 | TRP | G1418 | 94.946 | 95.147 | 59.947 | 1.00 | 99.71 | G |
| ATOM | 18819 | CH2 | TRP | G1418 | 94.276 | 95.074 | 61.178 | 1.00 | 99.71 | G |
| ATOM | 18820 | C | TRP | G1418 | 94.704 | 101.803 | 58.632 | 1.00 | 99.08 | G |
| ATOM | 18821 | O | TRP | G1418 | 95.119 | 102.744 | 59.313 | 1.00 | 99.08 | G |
| ATOM | 18822 | N | LYS | G1419 | 93.461 | 101.725 | 58.158 | 1.00 | 79.53 | G |
| ATOM | 18823 | CA | LYS | G1419 | 92.419 | 102.729 | 58.375 | 1.00 | 79.53 | G |
| ATOM | 18824 | CB | LYS | G1419 | 92.688 | 103.965 | 57.517 | 1.00 | 100.07 | G |
| ATOM | 18825 | CG | LYS | G1419 | 91.460 | 104.813 | 57.246 | 1.00 | 100.07 | G |
| ATOM | 18826 | CD | LYS | G1419 | 91.655 | 105.664 | 56.007 | 1.00 | 100.07 | G |
| ATOM | 18827 | CE | LYS | G1419 | 90.355 | 106.315 | 55.574 | 1.00 | 100.07 | G |
| ATOM | 18828 | NZ | LYS | G1419 | 90.509 | 106.958 | 54.242 | 1.00 | 100.07 | G |
| ATOM | 18829 | C | LYS | G1419 | 91.081 | 102.105 | 57.972 | 1.00 | 79.53 | G |
| ATOM | 18830 | O | LYS | G1419 | 91.040 | 101.144 | 57.207 | 1.00 | 79.53 | G |
| ATOM | 18831 | N | PRO | G1420 | 89.966 | 102.637 | 58.483 | 1.00 | 51.68 | G |
| ATOM | 18832 | CD | PRO | G1420 | 89.782 | 103.568 | 59.610 | 1.00 | 100.07 | G |
| ATOM | 18833 | CA | PRO | G1420 | 88.690 | 102.037 | 58.097 | 1.00 | 51.68 | G |
| ATOM | 18834 | CB | PRO | G1420 | 87.812 | 102.317 | 59.307 | 1.00 | 100.07 | G |
| ATOM | 18835 | CG | PRO | G1420 | 88.265 | 103.685 | 59.696 | 1.00 | 100.07 | G |
| ATOM | 18836 | C | PRO | G1420 | 88.108 | 102.629 | 56.820 | 1.00 | 51.68 | G |
| ATOM | 18837 | O | PRO | G1420 | 87.845 | 103.834 | 56.743 | 1.00 | 51.68 | G |
| ATOM | 18838 | N | LEU | G1421 | 87.915 | 101.773 | 55.820 | 1.00 | 45.79 | G |
| ATOM | 18839 | CA | LEU | G1421 | 87.339 | 102.202 | 54.552 | 1.00 | 45.79 | G |
| ATOM | 18840 | CB | LEU | G1421 | 88.038 | 101.506 | 53.379 | 1.00 | 100.07 | G |
| ATOM | 18841 | CG | LEU | G1421 | 87.504 | 101.791 | 51.965 | 1.00 | 100.07 | G |
| ATOM | 18842 | CD1 | LEU | G1421 | 87.371 | 103.295 | 51.712 | 1.00 | 100.07 | G |
| ATOM | 18843 | CD2 | LEU | G1421 | 88.443 | 101.150 | 50.945 | 1.00 | 100.07 | G |
| ATOM | 18844 | C | LEU | G1421 | 85.846 | 101.871 | 54.554 | 1.00 | 45.79 | G |
| ATOM | 18845 | O | LEU | G1421 | 85.435 | 100.815 | 55.041 | 1.00 | 45.79 | G |
| ATOM | 18846 | N | LEU | G1422 | 85.035 | 102.775 | 54.009 | 1.00 | 91.08 | G |
| ATOM | 18847 | CA | LEU | G1422 | 83.591 | 102.575 | 53.979 | 1.00 | 91.08 | G |
| ATOM | 18848 | CB | LEU | G1422 | 82.875 | 103.802 | 54.526 | 1.00 | 37.74 | G |
| ATOM | 18849 | CG | LEU | G1422 | 81.391 | 103.543 | 54.736 | 1.00 | 37.74 | G |
| ATOM | 18850 | CD1 | LEU | G1422 | 81.260 | 102.460 | 55.809 | 1.00 | 37.74 | G |
| ATOM | 18851 | CD2 | LEU | G1422 | 80.673 | 104.826 | 55.141 | 1.00 | 37.74 | G |
| ATOM | 18852 | C | LEU | G1422 | 83.015 | 102.266 | 52.607 | 1.00 | 91.08 | G |
| ATOM | 18853 | O | LEU | G1422 | 83.001 | 103.119 | 51.720 | 1.00 | 91.08 | G |
| ATOM | 18854 | N | MET | G1423 | 82.522 | 101.043 | 52.449 | 1.00 | 99.96 | G |
| ATOM | 18855 | CA | MET | G1423 | 81.919 | 100.607 | 51.200 | 1.00 | 99.96 | G |
| ATOM | 18856 | CB | MET | G1423 | 82.058 | 99.090 | 51.047 | 1.00 | 55.09 | G |
| ATOM | 18857 | CG | MET | G1423 | 83.494 | 98.584 | 50.990 | 1.00 | 55.09 | G |
| ATOM | 18858 | SD | MET | G1423 | 84.322 | 98.791 | 49.384 | 1.00 | 55.09 | G |
| ATOM | 18859 | CE | MET | G1423 | 85.184 | 97.230 | 49.250 | 1.00 | 55.09 | G |
| ATOM | 18860 | C | MET | G1423 | 80.443 | 100.982 | 51.254 | 1.00 | 99.96 | G |
| ATOM | 18861 | O | MET | G1423 | 79.980 | 101.554 | 52.240 | 1.00 | 99.96 | G |
| ATOM | 18862 | N | GLY | G1424 | 79.714 | 100.664 | 50.189 | 1.00 | 40.36 | G |

```
ATOM  18863  CA   GLY G1424      78.292 100.949  50.133  1.00 40.36      G
ATOM  18864  C    GLY G1424      77.622  99.681  49.653  1.00 40.36      G
ATOM  18865  O    GLY G1424      77.361  99.531  48.450  1.00 40.36      G
ATOM  18866  N    VAL G1425      77.348  98.778  50.602  1.00 27.66      G
ATOM  18867  CA   VAL G1425      76.746  97.474  50.319  1.00 27.66      G
ATOM  18868  CB   VAL G1425      75.197  97.536  50.408  1.00 71.14      G
ATOM  18869  CG1  VAL G1425      74.645  98.546  49.438  1.00 71.14      G
ATOM  18870  CG2  VAL G1425      74.611  96.176  50.163  1.00 71.14      G
ATOM  18871  C    VAL G1425      77.234  97.015  48.934  1.00 27.66      G
ATOM  18872  O    VAL G1425      78.266  96.347  48.836  1.00 27.66      G
ATOM  18873  N    THR G1426      76.513  97.393  47.880  1.00 31.35      G
ATOM  18874  CA   THR G1426      76.883  97.063  46.508  1.00 31.35      G
ATOM  18875  CB   THR G1426      76.714  98.278  45.601  1.00 50.61      G
ATOM  18876  OG1  THR G1426      75.341  98.663  45.566  1.00 50.61      G
ATOM  18877  CG2  THR G1426      77.170  97.963  44.214  1.00 50.61      G
ATOM  18878  C    THR G1426      78.336  96.629  46.408  1.00 31.35      G
ATOM  18879  O    THR G1426      78.653  95.442  46.511  1.00 31.35      G
ATOM  18880  N    LYS G1427      79.214  97.610  46.221  1.00 37.37      G
ATOM  18881  CA   LYS G1427      80.647  97.375  46.102  1.00 37.37      G
ATOM  18882  CB   LYS G1427      81.409  98.661  46.416  1.00100.07      G
ATOM  18883  CG   LYS G1427      80.968  99.807  45.530  1.00100.07      G
ATOM  18884  CD   LYS G1427      81.729 101.100  45.772  1.00100.07      G
ATOM  18885  CE   LYS G1427      81.308 102.155  44.737  1.00100.07      G
ATOM  18886  NZ   LYS G1427      82.068 103.436  44.836  1.00100.07      G
ATOM  18887  C    LYS G1427      81.156  96.247  46.981  1.00 37.37      G
ATOM  18888  O    LYS G1427      81.533  95.200  46.475  1.00 37.37      G
ATOM  18889  N    SER G1428      81.157  96.444  48.293  1.00 32.56      G
ATOM  18890  CA   SER G1428      81.650  95.412  49.200  1.00 32.56      G
ATOM  18891  CB   SER G1428      81.004  95.545  50.575  1.00 43.88      G
ATOM  18892  OG   SER G1428      81.457  94.518  51.442  1.00 43.88      G
ATOM  18893  C    SER G1428      81.405  94.009  48.662  1.00 32.56      G
ATOM  18894  O    SER G1428      82.312  93.176  48.634  1.00 32.56      G
ATOM  18895  N    ALA G1429      80.178  93.744  48.237  1.00 41.87      G
ATOM  18896  CA   ALA G1429      79.863  92.439  47.694  1.00 41.87      G
ATOM  18897  CB   ALA G1429      78.408  92.349  47.390  1.00 16.83      G
ATOM  18898  C    ALA G1429      80.653  92.299  46.416  1.00 41.87      G
ATOM  18899  O    ALA G1429      81.434  91.367  46.254  1.00 41.87      G
ATOM  18900  N    LEU G1430      80.435  93.256  45.521  1.00 64.11      G
ATOM  18901  CA   LEU G1430      81.071  93.310  44.209  1.00 64.11      G
ATOM  18902  CB   LEU G1430      80.535  94.516  43.432  1.00 69.44      G
ATOM  18903  CG   LEU G1430      81.144  94.800  42.061  1.00 69.44      G
ATOM  18904  CD1  LEU G1430      81.321  93.507  41.300  1.00 69.44      G
ATOM  18905  CD2  LEU G1430      80.249  95.754  41.290  1.00 69.44      G
ATOM  18906  C    LEU G1430      82.593  93.353  44.214  1.00 64.11      G
ATOM  18907  O    LEU G1430      83.240  92.671  43.421  1.00 64.11      G
ATOM  18908  N    SER G1431      83.169  94.162  45.091  1.00 61.48      G
ATOM  18909  CA   SER G1431      84.615  94.263  45.159  1.00 61.48      G
ATOM  18910  CB   SER G1431      85.025  95.349  46.145  1.00 46.46      G
ATOM  18911  OG   SER G1431      84.714  94.949  47.464  1.00 46.46      G
ATOM  18912  C    SER G1431      85.186  92.927  45.608  1.00 61.48      G
ATOM  18913  O    SER G1431      85.274  91.980  44.821  1.00 61.48      G
ATOM  18914  N    THR G1432      85.566  92.851  46.879  1.00 74.93      G
ATOM  18915  CA   THR G1432      86.136  91.632  47.432  1.00 74.93      G
ATOM  18916  CB   THR G1432      86.409  91.766  48.930  1.00100.07      G
ATOM  18917  OG1  THR G1432      85.213  92.184  49.596  1.00100.07      G
ATOM  18918  CG2  THR G1432      87.520  92.765  49.175  1.00100.07      G
ATOM  18919  C    THR G1432      85.200  90.468  47.243  1.00 74.93      G
ATOM  18920  O    THR G1432      84.019  90.651  46.956  1.00 74.93      G
ATOM  18921  N    LYS G1433      85.736  89.270  47.421  1.00 63.33      G
ATOM  18922  CA   LYS G1433      84.944  88.065  47.272  1.00 63.33      G
ATOM  18923  CB   LYS G1433      83.938  88.250  46.131  1.00 72.24      G
ATOM  18924  CG   LYS G1433      82.521  87.823  46.451  1.00 72.24      G
ATOM  18925  CD   LYS G1433      81.964  88.505  47.679  1.00 72.24      G
ATOM  18926  CE   LYS G1433      80.549  88.024  47.929  1.00 72.24      G
ATOM  18927  NZ   LYS G1433      80.035  88.445  49.254  1.00 72.24      G
ATOM  18928  C    LYS G1433      85.861  86.871  46.982  1.00 63.33      G
ATOM  18929  O    LYS G1433      87.076  86.910  47.269  1.00 63.33      G
ATOM  18930  N    SER G1434      85.278  85.817  46.406  1.00 61.50      G
ATOM  18931  CA   SER G1434      86.028  84.615  46.097  1.00 61.50      G
ATOM  18932  CB   SER G1434      85.542  83.445  46.960  1.00 32.04      G
ATOM  18933  OG   SER G1434      84.715  82.550  46.233  1.00 32.04      G
ATOM  18934  C    SER G1434      85.928  84.237  44.638  1.00 61.50      G
ATOM  18935  O    SER G1434      85.243  83.284  44.290  1.00 61.50      G
ATOM  18936  N    TRP G1435      86.619  84.997  43.794  1.00 64.00      G
ATOM  18937  CA   TRP G1435      86.670  84.757  42.351  1.00 64.00      G
ATOM  18938  CB   TRP G1435      87.920  83.885  42.053  1.00 26.78      G
ATOM  18939  CG   TRP G1435      87.749  82.713  41.139  1.00 26.78      G
ATOM  18940  CD2  TRP G1435      88.137  81.366  41.401  1.00 26.78      G
ATOM  18941  CE2  TRP G1435      87.761  80.594  40.277  1.00 26.78      G
ATOM  18942  CE3  TRP G1435      88.762  80.733  42.474  1.00 26.78      G
ATOM  18943  CD1  TRP G1435      87.177  82.710  39.895  1.00 26.78      G
ATOM  18944  NE1  TRP G1435      87.178  81.438  39.373  1.00 26.78      G
ATOM  18945  CZ2  TRP G1435      87.987  79.221  40.202  1.00 26.78      G
ATOM  18946  CZ3  TRP G1435      88.986  79.365  42.395  1.00 26.78      G
```

```
ATOM  18947  CH2 TRP G1435      88.597  78.626  41.265  1.00 26.78      G
ATOM  18948  C   TRP G1435      85.379  84.163  41.757  1.00 64.00      G
ATOM  18949  O   TRP G1435      84.683  84.813  40.963  1.00 64.00      G
ATOM  18950  N   LEU G1436      85.069  82.936  42.162  1.00 51.15      G
ATOM  18951  CA  LEU G1436      83.896  82.208  41.715  1.00 51.15      G
ATOM  18952  CB  LEU G1436      83.832  80.888  42.468  1.00 25.14      G
ATOM  18953  CG  LEU G1436      83.669  79.712  41.509  1.00 25.14      G
ATOM  18954  CD1 LEU G1436      84.624  79.867  40.321  1.00 25.14      G
ATOM  18955  CD2 LEU G1436      83.908  78.399  42.262  1.00 25.14      G
ATOM  18956  C   LEU G1436      82.551  82.924  41.840  1.00 51.15      G
ATOM  18957  O   LEU G1436      81.558  82.475  41.273  1.00 51.15      G
ATOM  18958  N   SER G1437      82.501  84.026  42.578  1.00 51.83      G
ATOM  18959  CA  SER G1437      81.246  84.744  42.744  1.00 51.83      G
ATOM  18960  CB  SER G1437      80.902  84.910  44.232  1.00100.07      G
ATOM  18961  OG  SER G1437      81.993  85.414  44.975  1.00100.07      G
ATOM  18962  C   SER G1437      81.276  86.084  42.052  1.00 51.83      G
ATOM  18963  O   SER G1437      80.369  86.402  41.299  1.00 51.83      G
ATOM  18964  N   ALA G1438      82.319  86.868  42.292  1.00 19.91      G
ATOM  18965  CA  ALA G1438      82.440  88.175  41.646  1.00 19.91      G
ATOM  18966  CB  ALA G1438      83.667  88.908  42.144  1.00 57.16      G
ATOM  18967  C   ALA G1438      82.578  87.895  40.167  1.00 19.91      G
ATOM  18968  O   ALA G1438      82.561  88.809  39.335  1.00 19.91      G
ATOM  18969  N   ALA G1439      82.721  86.603  39.878  1.00 35.11      G
ATOM  18970  CA  ALA G1439      82.866  86.066  38.530  1.00 35.11      G
ATOM  18971  CB  ALA G1439      83.073  84.558  38.602  1.00 23.40      G
ATOM  18972  C   ALA G1439      81.658  86.357  37.663  1.00 35.11      G
ATOM  18973  O   ALA G1439      81.775  86.473  36.448  1.00 35.11      G
ATOM  18974  N   SER G1440      80.495  86.454  38.297  1.00 31.18      G
ATOM  18975  CA  SER G1440      79.255  86.709  37.586  1.00 31.18      G
ATOM  18976  CB  SER G1440      78.080  86.224  38.403  1.00 29.41      G
ATOM  18977  OG  SER G1440      78.181  86.738  39.708  1.00 29.41      G
ATOM  18978  C   SER G1440      79.100  88.175  37.315  1.00 31.18      G
ATOM  18979  O   SER G1440      78.817  88.573  36.187  1.00 31.18      G
ATOM  18980  N   PHE G1441      79.292  88.981  38.349  1.00 51.22      G
ATOM  18981  CA  PHE G1441      79.176  90.421  38.203  1.00 51.22      G
ATOM  18982  CB  PHE G1441      79.901  91.130  39.342  1.00 81.19      G
ATOM  18983  CG  PHE G1441      79.230  90.968  40.670  1.00 81.19      G
ATOM  18984  CD1 PHE G1441      79.455  89.838  41.444  1.00 81.19      G
ATOM  18985  CD2 PHE G1441      78.345  91.933  41.132  1.00 81.19      G
ATOM  18986  CE1 PHE G1441      78.807  89.671  42.657  1.00 81.19      G
ATOM  18987  CE2 PHE G1441      77.694  91.774  42.339  1.00 81.19      G
ATOM  18988  CZ  PHE G1441      77.925  90.640  43.105  1.00 81.19      G
ATOM  18989  C   PHE G1441      79.745  90.873  36.866  1.00 51.22      G
ATOM  18990  O   PHE G1441      80.919  90.660  36.579  1.00 51.22      G
ATOM  18991  N   GLN G1442      78.895  91.498  36.061  1.00100.07      G
ATOM  18992  CA  GLN G1442      79.258  91.975  34.736  1.00100.07      G
ATOM  18993  CB  GLN G1442      78.912  93.461  34.606  1.00 69.01      G
ATOM  18994  CG  GLN G1442      78.746  93.923  33.155  1.00 69.01      G
ATOM  18995  CD  GLN G1442      77.521  93.315  32.462  1.00 69.01      G
ATOM  18996  OE1 GLN G1442      76.392  93.749  32.685  1.00 69.01      G
ATOM  18997  NE2 GLN G1442      77.744  92.304  31.624  1.00 69.01      G
ATOM  18998  C   GLN G1442      80.719  91.722  34.322  1.00100.07      G
ATOM  18999  O   GLN G1442      80.970  90.883  33.456  1.00100.07      G
ATOM  19000  N   ASN G1443      81.676  92.421  34.934  1.00 58.50      G
ATOM  19001  CA  ASN G1443      83.095  92.253  34.591  1.00 58.50      G
ATOM  19002  CB  ASN G1443      83.961  93.192  35.421  1.00 95.80      G
ATOM  19003  CG  ASN G1443      83.577  94.631  35.251  1.00 95.80      G
ATOM  19004  OD1 ASN G1443      83.478  95.136  34.133  1.00 95.80      G
ATOM  19005  ND2 ASN G1443      83.362  95.311  36.366  1.00 95.80      G
ATOM  19006  C   ASN G1443      83.616  90.837  34.793  1.00 58.50      G
ATOM  19007  O   ASN G1443      84.624  90.635  35.468  1.00 58.50      G
ATOM  19008  N   THR G1444      82.955  89.866  34.179  1.00 45.05      G
ATOM  19009  CA  THR G1444      83.326  88.471  34.326  1.00 45.05      G
ATOM  19010  CB  THR G1444      82.243  87.595  33.712  1.00 31.53      G
ATOM  19011  OG1 THR G1444      81.005  87.843  34.397  1.00 31.53      G
ATOM  19012  CG2 THR G1444      82.621  86.118  33.820  1.00 31.53      G
ATOM  19013  C   THR G1444      84.700  88.053  33.795  1.00 45.05      G
ATOM  19014  O   THR G1444      85.396  87.265  34.440  1.00 45.05      G
ATOM  19015  N   THR G1445      85.098  88.572  32.637  1.00 59.45      G
ATOM  19016  CA  THR G1445      86.405  88.233  32.057  1.00 59.45      G
ATOM  19017  CB  THR G1445      86.538  88.782  30.647  1.00 36.61      G
ATOM  19018  OG1 THR G1445      85.316  88.554  29.935  1.00 36.61      G
ATOM  19019  CG2 THR G1445      87.683  88.098  29.932  1.00 36.61      G
ATOM  19020  C   THR G1445      87.580  88.776  32.880  1.00 59.45      G
ATOM  19021  O   THR G1445      88.631  88.132  32.980  1.00 59.45      G
ATOM  19022  N   HIS G1446      87.402  89.974  33.440  1.00 47.46      G
ATOM  19023  CA  HIS G1446      88.423  90.586  34.278  1.00 47.46      G
ATOM  19024  CB  HIS G1446      88.144  92.065  34.519  1.00 70.63      G
ATOM  19025  CG  HIS G1446      89.023  92.664  35.572  1.00 70.63      G
ATOM  19026  CD2 HIS G1446      88.735  93.408  36.666  1.00 70.63      G
ATOM  19027  ND1 HIS G1446      90.390  92.497  35.575  1.00 70.63      G
ATOM  19028  CE1 HIS G1446      90.907  93.110  36.624  1.00 70.63      G
ATOM  19029  NE2 HIS G1446      89.924  93.671  37.303  1.00 70.63      G
ATOM  19030  C   HIS G1446      88.444  89.876  35.616  1.00 47.46      G
```

| ATOM | 19031 | O | HIS G1446 | 89.501 | 89.475 | 36.090 | 1.00 | 47.46 | G |
|------|-------|-----|----------|--------|--------|--------|------|-------|---|
| ATOM | 19032 | N | VAL G1447 | 87.277 | 89.722 | 36.232 | 1.00 | 63.52 | G |
| ATOM | 19033 | CA | VAL G1447 | 87.209 | 89.030 | 37.514 | 1.00 | 63.52 | G |
| ATOM | 19034 | CB | VAL G1447 | 85.756 | 88.898 | 38.038 | 1.00 | 99.79 | G |
| ATOM | 19035 | CG1 | VAL G1447 | 85.749 | 88.167 | 39.379 | 1.00 | 99.79 | G |
| ATOM | 19036 | CG2 | VAL G1447 | 85.126 | 90.271 | 38.196 | 1.00 | 99.79 | G |
| ATOM | 19037 | C | VAL G1447 | 87.764 | 87.630 | 37.299 | 1.00 | 63.52 | G |
| ATOM | 19038 | O | VAL G1447 | 88.009 | 86.887 | 38.251 | 1.00 | 63.52 | G |
| ATOM | 19039 | N | LEU G1448 | 87.964 | 87.281 | 36.033 | 1.00 | 89.61 | G |
| ATOM | 19040 | CA | LEU G1448 | 88.479 | 85.973 | 35.678 | 1.00 | 89.61 | G |
| ATOM | 19041 | CB | LEU G1448 | 87.777 | 85.475 | 34.412 | 1.00 | 45.68 | G |
| ATOM | 19042 | CG | LEU G1448 | 87.073 | 84.122 | 34.585 | 1.00 | 45.68 | G |
| ATOM | 19043 | CD1 | LEU G1448 | 86.575 | 83.988 | 36.023 | 1.00 | 45.68 | G |
| ATOM | 19044 | CD2 | LEU G1448 | 85.922 | 83.980 | 33.593 | 1.00 | 45.68 | G |
| ATOM | 19045 | C | LEU G1448 | 89.987 | 85.982 | 35.483 | 1.00 | 89.61 | G |
| ATOM | 19046 | O | LEU G1448 | 90.714 | 85.288 | 36.195 | 1.00 | 89.61 | G |
| ATOM | 19047 | N | THR G1449 | 90.450 | 86.771 | 34.519 | 1.00 | 52.05 | G |
| ATOM | 19048 | CA | THR G1449 | 91.877 | 86.877 | 34.223 | 1.00 | 52.05 | G |
| ATOM | 19049 | CB | THR G1449 | 92.137 | 88.050 | 33.277 | 1.00 | 22.15 | G |
| ATOM | 19050 | OG1 | THR G1449 | 91.815 | 87.649 | 31.941 | 1.00 | 22.15 | G |
| ATOM | 19051 | CG2 | THR G1449 | 93.585 | 88.500 | 33.351 | 1.00 | 22.15 | G |
| ATOM | 19052 | C | THR G1449 | 92.741 | 87.048 | 35.466 | 1.00 | 52.05 | G |
| ATOM | 19053 | O | THR G1449 | 93.483 | 86.146 | 35.853 | 1.00 | 52.05 | G |
| ATOM | 19054 | N | GLU G1450 | 92.640 | 88.221 | 36.075 | 1.00 | 92.41 | G |
| ATOM | 19055 | CA | GLU G1450 | 93.392 | 88.549 | 37.271 | 1.00 | 92.41 | G |
| ATOM | 19056 | CB | GLU G1450 | 92.710 | 89.717 | 37.973 | 1.00 | 100.07 | G |
| ATOM | 19057 | CG | GLU G1450 | 93.553 | 90.443 | 38.987 | 1.00 | 100.07 | G |
| ATOM | 19058 | CD | GLU G1450 | 92.817 | 91.635 | 39.566 | 1.00 | 100.07 | G |
| ATOM | 19059 | OE1 | GLU G1450 | 92.317 | 92.457 | 38.770 | 1.00 | 100.07 | G |
| ATOM | 19060 | OE2 | GLU G1450 | 92.739 | 91.755 | 40.809 | 1.00 | 100.07 | G |
| ATOM | 19061 | C | GLU G1450 | 93.446 | 87.333 | 38.192 | 1.00 | 92.41 | G |
| ATOM | 19062 | O | GLU G1450 | 94.466 | 87.068 | 38.827 | 1.00 | 92.41 | G |
| ATOM | 19063 | N | ALA G1451 | 92.344 | 86.590 | 38.248 | 1.00 | 52.37 | G |
| ATOM | 19064 | CA | ALA G1451 | 92.264 | 85.400 | 39.090 | 1.00 | 52.37 | G |
| ATOM | 19065 | CB | ALA G1451 | 90.887 | 84.775 | 38.981 | 1.00 | 52.68 | G |
| ATOM | 19066 | C | ALA G1451 | 93.311 | 84.404 | 38.649 | 1.00 | 52.37 | G |
| ATOM | 19067 | O | ALA G1451 | 94.072 | 83.887 | 39.462 | 1.00 | 52.37 | G |
| ATOM | 19068 | N | ALA G1452 | 93.334 | 84.141 | 37.347 | 1.00 | 100.07 | G |
| ATOM | 19069 | CA | ALA G1452 | 94.281 | 83.209 | 36.756 | 1.00 | 100.07 | G |
| ATOM | 19070 | CB | ALA G1452 | 94.072 | 83.152 | 35.257 | 1.00 | 98.47 | G |
| ATOM | 19071 | C | ALA G1452 | 95.722 | 83.604 | 37.069 | 1.00 | 100.07 | G |
| ATOM | 19072 | O | ALA G1452 | 96.505 | 82.778 | 37.539 | 1.00 | 100.07 | G |
| ATOM | 19073 | N | ILE G1453 | 96.067 | 84.862 | 36.800 | 1.00 | 68.55 | G |
| ATOM | 19074 | CA | ILE G1453 | 97.412 | 85.360 | 37.065 | 1.00 | 68.55 | G |
| ATOM | 19075 | CB | ILE G1453 | 97.456 | 86.915 | 37.067 | 1.00 | 60.83 | G |
| ATOM | 19076 | CG2 | ILE G1453 | 98.052 | 87.445 | 38.369 | 1.00 | 60.83 | G |
| ATOM | 19077 | CG1 | ILE G1453 | 98.288 | 87.416 | 35.889 | 1.00 | 60.83 | G |
| ATOM | 19078 | CD | ILE G1453 | 97.474 | 87.776 | 34.683 | 1.00 | 60.83 | G |
| ATOM | 19079 | C | ILE G1453 | 97.930 | 84.839 | 38.407 | 1.00 | 68.55 | G |
| ATOM | 19080 | O | ILE G1453 | 98.951 | 84.159 | 38.454 | 1.00 | 68.55 | G |
| ATOM | 19081 | N | ALA G1454 | 97.236 | 85.146 | 39.499 | 1.00 | 38.49 | G |
| ATOM | 19082 | CA | ALA G1454 | 97.692 | 84.673 | 40.797 | 1.00 | 38.49 | G |
| ATOM | 19083 | CB | ALA G1454 | 97.155 | 85.567 | 41.907 | 1.00 | 65.03 | G |
| ATOM | 19084 | C | ALA G1454 | 97.256 | 83.224 | 41.018 | 1.00 | 38.49 | G |
| ATOM | 19085 | O | ALA G1454 | 96.528 | 82.648 | 40.192 | 1.00 | 38.49 | G |
| ATOM | 19086 | N | GLY G1455 | 97.719 | 82.635 | 42.122 | 1.00 | 58.71 | G |
| ATOM | 19087 | CA | GLY G1455 | 97.364 | 81.262 | 42.437 | 1.00 | 58.71 | G |
| ATOM | 19088 | C | GLY G1455 | 95.856 | 81.160 | 42.416 | 1.00 | 58.71 | G |
| ATOM | 19089 | O | GLY G1455 | 95.300 | 80.124 | 42.053 | 1.00 | 58.71 | G |
| ATOM | 19090 | N | ALA G1456 | 95.211 | 82.264 | 42.800 | 1.00 | 33.60 | G |
| ATOM | 19091 | CA | ALA G1456 | 93.757 | 82.388 | 42.841 | 1.00 | 33.60 | G |
| ATOM | 19092 | CB | ALA G1456 | 93.142 | 81.836 | 41.554 | 1.00 | 100.07 | G |
| ATOM | 19093 | C | ALA G1456 | 93.187 | 81.669 | 44.054 | 1.00 | 33.60 | G |
| ATOM | 19094 | O | ALA G1456 | 92.983 | 80.453 | 44.036 | 1.00 | 33.60 | G |
| ATOM | 19095 | N | ALA G1457 | 92.927 | 82.443 | 45.103 | 1.00 | 100.07 | G |
| ATOM | 19096 | CA | ALA G1457 | 92.394 | 81.929 | 46.363 | 1.00 | 100.07 | G |
| ATOM | 19097 | CB | ALA G1457 | 92.020 | 83.099 | 47.273 | 1.00 | 100.07 | G |
| ATOM | 19098 | C | ALA G1457 | 91.207 | 80.977 | 46.226 | 1.00 | 100.07 | G |
| ATOM | 19099 | O | ALA G1457 | 90.171 | 81.176 | 46.862 | 1.00 | 100.07 | G |
| ATOM | 19100 | N | ALA G1458 | 91.384 | 79.946 | 45.406 | 1.00 | 63.71 | G |
| ATOM | 19101 | CA | ALA G1458 | 90.390 | 78.911 | 45.143 | 1.00 | 63.71 | G |
| ATOM | 19102 | CB | ALA G1458 | 90.823 | 77.625 | 45.831 | 1.00 | 100.07 | G |
| ATOM | 19103 | C | ALA G1458 | 88.930 | 79.201 | 45.495 | 1.00 | 63.71 | G |
| ATOM | 19104 | O | ALA G1458 | 88.146 | 78.269 | 45.705 | 1.00 | 63.71 | G |
| ATOM | 19105 | N | ALA G1459 | 88.547 | 80.473 | 45.536 | 1.00 | 100.06 | G |
| ATOM | 19106 | CA | ALA G1459 | 87.183 | 80.833 | 45.908 | 1.00 | 100.06 | G |
| ATOM | 19107 | CB | ALA G1459 | 86.186 | 80.331 | 44.871 | 1.00 | 88.02 | G |
| ATOM | 19108 | C | ALA G1459 | 86.914 | 80.171 | 47.247 | 1.00 | 100.06 | G |
| ATOM | 19109 | O | ALA G1459 | 85.842 | 80.340 | 47.831 | 1.00 | 100.06 | G |
| ATOM | 19110 | N | ALA G1460 | 87.907 | 79.414 | 47.714 | 1.00 | 36.14 | G |
| ATOM | 19111 | CA | ALA G1460 | 87.846 | 78.676 | 48.972 | 1.00 | 36.14 | G |
| ATOM | 19112 | CB | ALA G1460 | 88.012 | 79.636 | 50.167 | 1.00 | 20.99 | G |
| ATOM | 19113 | C | ALA G1460 | 86.509 | 77.974 | 49.056 | 1.00 | 36.14 | G |
| ATOM | 19114 | O | ALA G1460 | 86.173 | 77.381 | 50.087 | 1.00 | 36.14 | G |

```
ATOM  19115  N   ALA G1461   85.768  78.036  47.949  1.00 36.70      G
ATOM  19116  CA  ALA G1461   84.437  77.480  47.876  1.00 36.70      G
ATOM  19117  CB  ALA G1461   84.492  76.018  47.512  1.00  5.07      G
ATOM  19118  C   ALA G1461   83.897  77.683  49.282  1.00 36.70      G
ATOM  19119  O   ALA G1461   83.163  76.853  49.810  1.00 36.70      G
ATOM  19120  N   ALA G1462   84.295  78.805  49.881  1.00 56.37      G
ATOM  19121  CA  ALA G1462   83.898  79.158  51.232  1.00 56.37      G
ATOM  19122  CB  ALA G1462   84.701  80.357  51.716  1.00 77.87      G
ATOM  19123  C   ALA G1462   82.417  79.475  51.273  1.00 56.37      G
ATOM  19124  O   ALA G1462   81.581  78.590  51.416  1.00 56.37      G
ATOM  19125  N   ALA G1463   82.083  80.745  51.148  1.00 62.00      G
ATOM  19126  CA  ALA G1463   80.688  81.114  51.170  1.00 62.00      G
ATOM  19127  CB  ALA G1463   80.483  82.267  52.104  1.00100.07      G
ATOM  19128  C   ALA G1463   80.222  81.474  49.768  1.00 62.00      G
ATOM  19129  O   ALA G1463   79.056  81.234  49.435  1.00 62.00      G
ATOM  19130  N   ALA G1464   81.143  82.018  48.954  1.00 54.01      G
ATOM  19131  CA  ALA G1464   80.875  82.449  47.564  1.00 54.01      G
ATOM  19132  CB  ALA G1464   82.170  82.688  46.839  1.00 35.57      G
ATOM  19133  C   ALA G1464   79.992  81.514  46.732  1.00 54.01      G
ATOM  19134  O   ALA G1464   80.483  80.658  45.988  1.00 54.01      G
ATOM  19135  N   ALA G1465   78.682  81.721  46.875  1.00 55.92      G
ATOM  19136  CA  ALA G1465   77.657  80.959  46.197  1.00 55.92      G
ATOM  19137  CB  ALA G1465   76.993  81.823  45.142  1.00  5.07      G
ATOM  19138  C   ALA G1465   78.212  79.690  45.579  1.00 55.92      G
ATOM  19139  O   ALA G1465   78.513  79.643  44.388  1.00 55.92      G
ATOM  19140  N   ALA G1466   78.372  78.669  46.415  1.00 48.53      G
ATOM  19141  CA  ALA G1466   78.849  77.370  45.961  1.00 48.53      G
ATOM  19142  CB  ALA G1466   78.959  76.398  47.132  1.00 17.91      G
ATOM  19143  C   ALA G1466   77.763  76.916  45.008  1.00 48.53      G
ATOM  19144  O   ALA G1466   77.871  75.884  44.357  1.00 48.53      G
ATOM  19145  N   ALA G1467   76.691  77.701  44.969  1.00 49.21      G
ATOM  19146  CA  ALA G1467   75.576  77.437  44.082  1.00 49.21      G
ATOM  19147  CB  ALA G1467   74.387  78.403  44.388  1.00  5.07      G
ATOM  19148  C   ALA G1467   76.154  77.697  42.696  1.00 49.21      G
ATOM  19149  O   ALA G1467   75.820  77.011  41.733  1.00 49.21      G
ATOM  19150  N   ALA G1468   77.047  78.678  42.609  1.00 39.31      G
ATOM  19151  CA  ALA G1468   77.659  79.000  41.333  1.00 39.31      G
ATOM  19152  CB  ALA G1468   78.860  79.932  41.523  1.00  5.07      G
ATOM  19153  C   ALA G1468   78.098  77.672  40.736  1.00 39.31      G
ATOM  19154  O   ALA G1468   77.861  77.400  39.559  1.00 39.31      G
ATOM  19155  N   ALA G1469   78.710  76.832  41.567  1.00 33.40      G
ATOM  19156  CA  ALA G1469   79.182  75.519  41.129  1.00 33.40      G
ATOM  19157  CB  ALA G1469   80.513  75.159  41.855  1.00  5.07      G
ATOM  19158  C   ALA G1469   78.102  74.482  41.429  1.00 33.40      G
ATOM  19159  O   ALA G1469   78.143  73.350  40.958  1.00 33.40      G
ATOM  19160  N   ALA G1470   77.128  74.895  42.224  1.00 22.80      G
ATOM  19161  CA  ALA G1470   76.030  74.030  42.610  1.00 22.80      G
ATOM  19162  CB  ALA G1470   75.425  73.382  41.369  1.00 27.52      G
ATOM  19163  C   ALA G1470   76.426  72.962  43.631  1.00 22.80      G
ATOM  19164  O   ALA G1470   76.241  71.773  43.397  1.00 22.80      G
ATOM  19165  N   ALA G1471   76.969  73.383  44.764  1.00 50.20      G
ATOM  19166  CA  ALA G1471   77.356  72.430  45.796  1.00 50.20      G
ATOM  19167  CB  ALA G1471   78.750  72.764  46.318  1.00 14.43      G
ATOM  19168  C   ALA G1471   76.313  72.508  46.918  1.00 50.20      G
ATOM  19169  O   ALA G1471   75.236  73.069  46.705  1.00 50.20      G
ATOM  19170  N   ALA G1472   76.609  71.935  48.089  1.00 57.44      G
ATOM  19171  CA  ALA G1472   75.677  71.972  49.224  1.00 57.44      G
ATOM  19172  CB  ALA G1472   75.747  70.655  50.043  1.00  5.07      G
ATOM  19173  C   ALA G1472   76.024  73.170  50.110  1.00 57.44      G
ATOM  19174  O   ALA G1472   77.106  73.231  50.689  1.00 57.44      G
ATOM  19175  N   ALA G1473   75.094  74.118  50.203  1.00 69.19      G
ATOM  19176  CA  ALA G1473   75.257  75.347  50.985  1.00 69.19      G
ATOM  19177  CB  ALA G1473   73.945  76.131  50.946  1.00  5.07      G
ATOM  19178  C   ALA G1473   75.726  75.158  52.443  1.00 69.19      G
ATOM  19179  O   ALA G1473   76.029  74.042  52.868  1.00 69.19      G
ATOM  19180  N   ALA G1474   75.787  76.260  53.197  1.00 43.69      G
ATOM  19181  CA  ALA G1474   76.214  76.250  54.604  1.00 43.69      G
ATOM  19182  CB  ALA G1474   76.291  77.664  55.144  1.00  6.14      G
ATOM  19183  C   ALA G1474   75.376  75.403  55.566  1.00 43.69      G
ATOM  19184  O   ALA G1474   74.280  75.801  55.998  1.00 43.69      G
ATOM  19185  N   ALA G1475   75.949  74.243  55.896  1.00 99.97      G
ATOM  19186  CA  ALA G1475   75.429  73.222  56.817  1.00 99.97      G
ATOM  19187  CB  ALA G1475   74.459  72.253  56.074  1.00 14.46      G
ATOM  19188  C   ALA G1475   76.734  72.496  57.176  1.00 99.97      G
ATOM  19189  O   ALA G1475   77.151  71.618  56.432  1.00 99.97      G
ATOM  19190  N   ALA G1476   77.387  72.845  58.289  1.00 23.44      G
ATOM  19191  CA  ALA G1476   78.680  72.205  58.602  1.00 23.44      G
ATOM  19192  CB  ALA G1476   79.812  73.117  58.124  1.00100.07      G
ATOM  19193  C   ALA G1476   79.039  71.665  60.006  1.00 23.44      G
ATOM  19194  O   ALA G1476   79.881  70.760  60.123  1.00 23.44      G
ATOM  19195  N   ALA G1477   78.477  72.217  61.076  1.00 57.41      G
ATOM  19196  CA  ALA G1477   78.820  71.648  62.372  1.00 57.41      G
ATOM  19197  CB  ALA G1477   78.141  72.403  63.520  1.00 12.23      G
ATOM  19198  C   ALA G1477   78.257  70.244  62.253  1.00 57.41      G
```

```
ATOM  19199  O   ALA G1477      78.959  69.259  62.467  1.00 57.41           G
ATOM  19200  N   ALA G1478      76.991  70.173  61.853  1.00 34.33           G
ATOM  19201  CA  ALA G1478      76.284  68.910  61.684  1.00 34.33           G
ATOM  19202  CB  ALA G1478      74.827  69.193  61.363  1.00 11.12           G
ATOM  19203  C   ALA G1478      76.906  68.019  60.602  1.00 34.33           G
ATOM  19204  O   ALA G1478      76.888  68.345  59.414  1.00 34.33           G
ATOM  19205  N   ALA G1479      77.453  66.884  61.023  1.00 67.27           G
ATOM  19206  CA  ALA G1479      78.089  65.960  60.088  1.00 67.27           G
ATOM  19207  CB  ALA G1479      79.569  66.308  59.935  1.00100.07           G
ATOM  19208  C   ALA G1479      77.939  64.498  60.510  1.00 67.27           G
ATOM  19209  O   ALA G1479      78.704  63.978  61.328  1.00 67.27           G
ATOM  19210  N   ALA G1480      76.940  63.849  59.926  1.00 78.48           G
ATOM  19211  CA  ALA G1480      76.628  62.451  60.186  1.00 78.48           G
ATOM  19212  CB  ALA G1480      77.094  61.594  59.006  1.00 72.49           G
ATOM  19213  C   ALA G1480      77.147  61.859  61.502  1.00 78.48           G
ATOM  19214  O   ALA G1480      77.068  62.486  62.567  1.00 78.48           G
ATOM  19215  N   ALA G1481      77.675  60.639  61.401  1.00 99.54           G
ATOM  19216  CA  ALA G1481      78.175  59.891  62.548  1.00 99.54           G
ATOM  19217  CB  ALA G1481      79.232  60.691  63.284  1.00100.07           G
ATOM  19218  C   ALA G1481      76.946  59.658  63.423  1.00 99.54           G
ATOM  19219  O   ALA G1481      77.030  59.519  64.637  1.00 99.54           G
ATOM  19220  N   ALA G1482      75.805  59.609  62.746  1.00 33.83           G
ATOM  19221  CA  ALA G1482      74.488  59.414  63.327  1.00 33.83           G
ATOM  19222  CB  ALA G1482      73.551  58.812  62.304  1.00100.07           G
ATOM  19223  C   ALA G1482      74.484  58.558  64.541  1.00 33.83           G
ATOM  19224  O   ALA G1482      74.412  59.070  65.659  1.00 33.83           G
ATOM  19225  N   ALA G1483      74.540  57.245  64.327  1.00 86.95           G
ATOM  19226  CA  ALA G1483      74.527  56.313  65.446  1.00 86.95           G
ATOM  19227  CB  ALA G1483      73.295  56.560  66.288  1.00 85.90           G
ATOM  19228  C   ALA G1483      74.582  54.840  65.075  1.00 86.95           G
ATOM  19229  O   ALA G1483      75.328  54.411  64.192  1.00 86.95           G
ATOM  19230  N   ALA G1484      73.761  54.082  65.791  1.00 81.05           G
ATOM  19231  CA  ALA G1484      73.644  52.652  65.624  1.00 81.05           G
ATOM  19232  CB  ALA G1484      74.998  52.004  65.826  1.00 72.34           G
ATOM  19233  C   ALA G1484      72.680  52.195  66.705  1.00 81.05           G
ATOM  19234  O   ALA G1484      72.668  52.769  67.790  1.00 81.05           G
ATOM  19235  N   ALA G1485      71.858  51.188  66.417  1.00 88.89           G
ATOM  19236  CA  ALA G1485      70.935  50.680  67.430  1.00 88.89           G
ATOM  19237  CB  ALA G1485      70.103  49.518  66.871  1.00 26.45           G
ATOM  19238  C   ALA G1485      71.826  50.196  68.569  1.00 88.89           G
ATOM  19239  O   ALA G1485      73.020  49.993  68.371  1.00 88.89           G
ATOM  19240  N   ALA G1486      71.267  50.017  69.758  1.00 95.48           G
ATOM  19241  CA  ALA G1486      72.075  49.561  70.885  1.00 95.48           G
ATOM  19242  CB  ALA G1486      71.175  49.207  72.061  1.00100.07           G
ATOM  19243  C   ALA G1486      72.937  48.355  70.497  1.00 95.48           G
ATOM  19244  O   ALA G1486      73.989  48.107  71.099  1.00 95.48           G
ATOM  19245  N   ALA G1487      72.482  47.617  69.484  1.00100.07           G
ATOM  19246  CA  ALA G1487      73.187  46.435  68.988  1.00100.07           G
ATOM  19247  CB  ALA G1487      72.193  45.452  68.372  1.00100.07           G
ATOM  19248  C   ALA G1487      74.244  46.825  67.957  1.00100.07           G
ATOM  19249  O   ALA G1487      75.422  46.495  68.111  1.00100.07           G
ATOM  19250  N   ALA G1488      73.818  47.509  66.897  1.00 59.31           G
ATOM  19251  CA  ALA G1488      74.750  47.955  65.869  1.00 59.31           G
ATOM  19252  CB  ALA G1488      74.006  48.742  64.770  1.00 34.78           G
ATOM  19253  C   ALA G1488      75.765  48.844  66.594  1.00 59.31           G
ATOM  19254  O   ALA G1488      76.906  49.005  66.158  1.00 59.31           G
ATOM  19255  N   ALA G1489      75.338  49.405  67.722  1.00100.07           G
ATOM  19256  CA  ALA G1489      76.201  50.256  68.532  1.00100.07           G
ATOM  19257  CB  ALA G1489      75.360  51.105  69.489  1.00 97.34           G
ATOM  19258  C   ALA G1489      77.161  49.362  69.320  1.00100.07           G
ATOM  19259  O   ALA G1489      78.147  49.838  69.902  1.00100.07           G
ATOM  19260  N   ALA G1490      76.863  48.063  69.325  1.00100.07           G
ATOM  19261  CA  ALA G1490      77.676  47.075  70.026  1.00100.07           G
ATOM  19262  CB  ALA G1490      76.770  46.071  70.741  1.00 82.08           G
ATOM  19263  C   ALA G1490      78.635  46.341  69.080  1.00100.07           G
ATOM  19264  O   ALA G1490      79.021  45.198  69.340  1.00100.07           G
ATOM  19265  N   ALA G1491      79.012  46.997  67.984  1.00 98.76           G
ATOM  19266  CA  ALA G1491      79.936  46.408  67.018  1.00 98.76           G
ATOM  19267  CB  ALA G1491      79.519  46.760  65.593  1.00 65.95           G
ATOM  19268  C   ALA G1491      81.340  46.928  67.290  1.00 98.76           G
ATOM  19269  O   ALA G1491      82.324  46.330  66.856  1.00 98.76           G
ATOM  19270  N   ALA G1492      81.422  48.043  68.013  1.00100.07           G
ATOM  19271  CA  ALA G1492      82.703  48.659  68.357  1.00100.07           G
ATOM  19272  CB  ALA G1492      82.473  49.969  69.133  1.00 15.18           G
ATOM  19273  C   ALA G1492      83.563  47.708  69.184  1.00100.07           G
ATOM  19274  O   ALA G1492      84.652  48.081  69.625  1.00100.07           G
ATOM  19275  N   ALA G1493      83.063  46.486  69.390  1.00100.07           G
ATOM  19276  CA  ALA G1493      83.756  45.448  70.164  1.00100.07           G
ATOM  19277  CB  ALA G1493      83.460  45.612  71.671  1.00 68.43           G
ATOM  19278  C   ALA G1493      83.351  44.041  69.699  1.00100.07           G
ATOM  19279  O   ALA G1493      82.824  43.917  68.568  1.00100.07           G
ATOM  19280  OT  ALA G1493      83.576  43.074  70.465  1.00 68.43           G
ATOM  19281  CB  ALA H    1     52.522  69.829  62.812  1.00 39.71           H
ATOM  19282  C   ALA H    1     53.795  68.566  64.520  1.00 51.03           H
```

```
ATOM  19283  O    ALA H   1      54.759  68.983  65.150  1.00 51.03      H
ATOM  19284  N    ALA H   1      52.654  70.697  65.083  1.00 51.03      H
ATOM  19285  CA   ALA H   1      52.586  69.458  64.262  1.00 51.03      H
ATOM  19286  N    ALA H   2      53.742  67.334  64.028  1.00 56.19      H
ATOM  19287  CA   ALA H   2      54.835  66.385  64.210  1.00 56.19      H
ATOM  19288  CB   ALA H   2      56.165  66.998  63.720  1.00 43.59      H
ATOM  19289  C    ALA H   2      54.943  65.977  65.674  1.00 56.19      H
ATOM  19290  O    ALA H   2      55.549  66.680  66.480  1.00 56.19      H
ATOM  19291  N    PRO H   3      54.386  64.799  66.014  1.00100.07      H
ATOM  19292  CD   PRO H   3      54.440  63.706  65.037  1.00 54.58      H
ATOM  19293  CA   PRO H   3      54.355  64.231  67.358  1.00100.07      H
ATOM  19294  CB   PRO H   3      55.377  63.111  67.233  1.00 54.58      H
ATOM  19295  CG   PRO H   3      54.985  62.513  65.889  1.00 54.58      H
ATOM  19296  C    PRO H   3      54.674  65.209  68.465  1.00100.07      H
ATOM  19297  O    PRO H   3      53.788  65.921  68.955  1.00100.07      H
ATOM  19298  N    GLY H   4      55.940  65.235  68.857  1.00100.07      H
ATOM  19299  CA   GLY H   4      56.388  66.134  69.901  1.00100.07      H
ATOM  19300  C    GLY H   4      57.618  66.842  69.385  1.00100.07      H
ATOM  19301  O    GLY H   4      58.566  67.084  70.128  1.00100.07      H
ATOM  19302  N    ILE H   5      57.595  67.166  68.097  1.00 58.01      H
ATOM  19303  CA   ILE H   5      58.712  67.833  67.456  1.00 58.01      H
ATOM  19304  CB   ILE H   5      58.255  68.596  66.238  1.00 38.87      H
ATOM  19305  CG2  ILE H   5      57.357  69.716  66.666  1.00 38.87      H
ATOM  19306  CG1  ILE H   5      59.476  69.104  65.473  1.00 38.87      H
ATOM  19307  CD   ILE H   5      59.156  69.849  64.191  1.00 38.87      H
ATOM  19308  C    ILE H   5      59.415  68.401  68.691  1.00 58.01      H
ATOM  19309  O    ILE H   5      60.648  68.842  68.454  1.00 58.01      H
ATOM  19310  N    ASP H   6      58.639  69.583  69.142  1.00 43.17      H
ATOM  19311  CA   ASP H   6      59.235  70.510  70.093  1.00 43.17      H
ATOM  19312  CB   ASP H   6      58.179  71.014  71.072  1.00 72.64      H
ATOM  19313  CG   ASP H   6      57.055  71.745  70.377  1.00 72.64      H
ATOM  19314  OD1  ASP H   6      57.316  72.816  69.795  1.00 72.64      H
ATOM  19315  OD2  ASP H   6      55.913  71.249  70.400  1.00 72.64      H
ATOM  19316  C    ASP H   6      60.282  69.699  70.833  1.00 43.17      H
ATOM  19317  O    ASP H   6      61.473  69.988  70.780  1.00 43.17      H
ATOM  19318  N    ALA H   7      59.818  68.647  71.488  1.00 42.82      H
ATOM  19319  CA   ALA H   7      60.694  67.775  72.245  1.00 42.82      H
ATOM  19320  CB   ALA H   7      59.940  66.537  72.694  1.00100.07      H
ATOM  19321  C    ALA H   7      61.904  67.371  71.439  1.00 42.82      H
ATOM  19322  O    ALA H   7      62.998  67.258  71.982  1.00 42.82      H
ATOM  19323  N    LEU H   8      61.715  67.144  70.147  1.00 59.62      H
ATOM  19324  CA   LEU H   8      62.841  66.745  69.321  1.00 59.62      H
ATOM  19325  CB   LEU H   8      62.414  66.570  67.865  1.00 61.05      H
ATOM  19326  CG   LEU H   8      61.357  65.501  67.607  1.00 61.05      H
ATOM  19327  CD1  LEU H   8      61.234  65.303  66.115  1.00 61.05      H
ATOM  19328  CD2  LEU H   8      61.738  64.194  68.278  1.00 61.05      H
ATOM  19329  C    LEU H   8      63.972  67.767  69.419  1.00 59.62      H
ATOM  19330  O    LEU H   8      65.135  67.406  69.634  1.00 59.62      H
ATOM  19331  N    PHE H   9      63.648  69.046  69.262  1.00 30.31      H
ATOM  19332  CA   PHE H   9      64.691  70.053  69.369  1.00 30.31      H
ATOM  19333  CB   PHE H   9      64.151  71.430  68.962  1.00 27.21      H
ATOM  19334  CG   PHE H   9      63.535  71.453  67.590  1.00 27.21      H
ATOM  19335  CD1  PHE H   9      62.165  71.315  67.423  1.00 27.21      H
ATOM  19336  CD2  PHE H   9      64.334  71.577  66.456  1.00 27.21      H
ATOM  19337  CE1  PHE H   9      61.596  71.299  66.145  1.00 27.21      H
ATOM  19338  CE2  PHE H   9      63.771  71.558  65.165  1.00 27.21      H
ATOM  19339  CZ   PHE H   9      62.395  71.418  65.016  1.00 27.21      H
ATOM  19340  C    PHE H   9      65.149  70.013  70.832  1.00 30.31      H
ATOM  19341  O    PHE H   9      66.134  70.643  71.229  1.00 30.31      H
ATOM  19342  N    GLY H  10      64.414  69.257  71.637  1.00 44.07      H
ATOM  19343  CA   GLY H  10      64.799  69.114  73.018  1.00 44.07      H
ATOM  19344  C    GLY H  10      66.137  68.430  72.907  1.00 44.07      H
ATOM  19345  O    GLY H  10      67.159  68.988  73.274  1.00 44.07      H
ATOM  19346  N    ALA H  11      66.130  67.229  72.343  1.00 67.78      H
ATOM  19347  CA   ALA H  11      67.351  66.448  72.171  1.00 67.78      H
ATOM  19348  CB   ALA H  11      67.039  65.161  71.384  1.00 84.24      H
ATOM  19349  C    ALA H  11      68.497  67.220  71.498  1.00 67.78      H
ATOM  19350  O    ALA H  11      69.288  67.877  72.177  1.00 67.78      H
ATOM  19351  N    ALA H  12      68.575  67.138  70.170  1.00 73.74      H
ATOM  19352  CA   ALA H  12      69.628  67.792  69.388  1.00 73.74      H
ATOM  19353  CB   ALA H  12      69.314  67.653  67.913  1.00 70.65      H
ATOM  19354  C    ALA H  12      69.913  69.262  69.713  1.00 73.74      H
ATOM  19355  O    ALA H  12      69.068  69.965  70.265  1.00 73.74      H
ATOM  19356  N    ALA H  13      71.115  69.717  69.362  1.00 68.23      H
ATOM  19357  CA   ALA H  13      71.519  71.102  69.594  1.00 68.23      H
ATOM  19358  CB   ALA H  13      73.045  71.224  69.589  1.00  5.07      H
ATOM  19359  C    ALA H  13      70.931  71.972  68.493  1.00 68.23      H
ATOM  19360  O    ALA H  13      69.835  72.522  68.637  1.00 68.23      H
ATOM  19361  N    ALA H  14      71.666  72.079  67.389  1.00 67.76      H
ATOM  19362  CA   ALA H  14      71.243  72.877  66.245  1.00 67.76      H
ATOM  19363  CB   ALA H  14      72.353  72.913  65.208  1.00 33.84      H
ATOM  19364  C    ALA H  14      69.964  72.336  65.615  1.00 67.76      H
ATOM  19365  O    ALA H  14      69.936  71.203  65.147  1.00 67.76      H
ATOM  19366  N    ALA H  15      68.905  73.143  65.615  1.00 28.35      H
```

```
ATOM  19367  CA   ALA H  15      67.640  72.738  65.010  1.00 28.35           H
ATOM  19368  CB   ALA H  15      66.719  73.938  64.818  1.00 45.45           H
ATOM  19369  C    ALA H  15      68.041  72.202  63.668  1.00 28.35           H
ATOM  19370  O    ALA H  15      67.796  71.038  63.352  1.00 28.35           H
ATOM  19371  N    ALA H  16      68.684  73.076  62.891  1.00100.07           H
ATOM  19372  CA   ALA H  16      69.156  72.754  61.548  1.00100.07           H
ATOM  19373  CB   ALA H  16      70.136  73.856  61.037  1.00  5.07           H
ATOM  19374  C    ALA H  16      69.827  71.386  61.567  1.00100.07           H
ATOM  19375  O    ALA H  16      69.650  70.584  60.661  1.00100.07           H
ATOM  19376  N    ALA H  17      70.578  71.105  62.620  1.00 67.26           H
ATOM  19377  CA   ALA H  17      71.244  69.818  62.723  1.00 67.26           H
ATOM  19378  CB   ALA H  17      72.139  69.791  63.955  1.00100.07           H
ATOM  19379  C    ALA H  17      70.231  68.669  62.776  1.00 67.26           H
ATOM  19380  O    ALA H  17      70.162  67.869  61.846  1.00 67.26           H
ATOM  19381  N    ALA H  18      69.449  68.598  63.855  1.00 92.49           H
ATOM  19382  CA   ALA H  18      68.444  67.543  64.034  1.00 92.49           H
ATOM  19383  CB   ALA H  18      67.193  68.094  64.718  1.00 34.88           H
ATOM  19384  C    ALA H  18      68.050  66.915  62.719  1.00 92.49           H
ATOM  19385  O    ALA H  18      68.233  65.717  62.519  1.00 92.49           H
ATOM  19386  N    ALA H  19      67.511  67.734  61.823  1.00 50.11           H
ATOM  19387  CA   ALA H  19      67.085  67.250  60.525  1.00 50.11           H
ATOM  19388  CB   ALA H  19      66.963  68.409  59.544  1.00 21.38           H
ATOM  19389  C    ALA H  19      68.078  66.203  60.029  1.00 50.11           H
ATOM  19390  O    ALA H  19      67.683  65.163  59.518  1.00 50.11           H
ATOM  19391  N    ALA H  20      69.366  66.459  60.203  1.00 34.22           H
ATOM  19392  CA   ALA H  20      70.369  65.489  59.783  1.00 34.22           H
ATOM  19393  CB   ALA H  20      71.770  65.983  60.147  1.00 54.33           H
ATOM  19394  C    ALA H  20      70.096  64.108  60.425  1.00 34.22           H
ATOM  19395  O    ALA H  20      69.563  63.217  59.763  1.00 34.22           H
ATOM  19396  N    ALA H  21      70.441  63.927  61.702  1.00 23.83           H
ATOM  19397  CA   ALA H  21      70.219  62.640  62.373  1.00 23.83           H
ATOM  19398  CB   ALA H  21      70.144  62.823  63.885  1.00 21.97           H
ATOM  19399  C    ALA H  21      68.958  61.933  61.873  1.00 23.83           H
ATOM  19400  O    ALA H  21      69.024  60.778  61.456  1.00 23.83           H
ATOM  19401  N    ALA H  22      67.818  62.620  61.897  1.00 41.15           H
ATOM  19402  CA   ALA H  22      66.572  62.007  61.438  1.00 41.15           H
ATOM  19403  CB   ALA H  22      65.391  62.947  61.666  1.00  5.07           H
ATOM  19404  C    ALA H  22      66.674  61.650  59.963  1.00 41.15           H
ATOM  19405  O    ALA H  22      66.083  60.678  59.500  1.00 41.15           H
ATOM  19406  N    ALA H  23      67.429  62.436  59.217  1.00 29.93           H
ATOM  19407  CA   ALA H  23      67.577  62.169  57.803  1.00 29.93           H
ATOM  19408  CB   ALA H  23      68.173  63.370  57.107  1.00 91.10           H
ATOM  19409  C    ALA H  23      68.458  60.954  57.593  1.00 29.93           H
ATOM  19410  O    ALA H  23      68.223  60.166  56.683  1.00 29.93           H
ATOM  19411  N    ALA H  24      69.475  60.805  58.439  1.00 62.52           H
ATOM  19412  CA   ALA H  24      70.398  59.678  58.335  1.00 62.52           H
ATOM  19413  CB   ALA H  24      71.643  59.941  59.164  1.00 67.26           H
ATOM  19414  C    ALA H  24      69.744  58.362  58.759  1.00 62.52           H
ATOM  19415  O    ALA H  24      69.883  57.358  58.069  1.00 62.52           H
ATOM  19416  N    ALA H  25      69.033  58.359  59.886  1.00 37.92           H
ATOM  19417  CA   ALA H  25      68.360  57.134  60.337  1.00 37.92           H
ATOM  19418  CB   ALA H  25      67.632  57.366  61.694  1.00  5.07           H
ATOM  19419  C    ALA H  25      67.367  56.662  59.259  1.00 37.92           H
ATOM  19420  O    ALA H  25      67.464  55.536  58.764  1.00 37.92           H
ATOM  19421  N    ALA H  26      66.415  57.515  58.891  1.00 59.67           H
ATOM  19422  CA   ALA H  26      65.459  57.132  57.864  1.00 59.67           H
ATOM  19423  CB   ALA H  26      64.643  58.327  57.408  1.00 32.00           H
ATOM  19424  C    ALA H  26      66.332  56.627  56.739  1.00 59.67           H
ATOM  19425  O    ALA H  26      65.960  55.704  56.015  1.00 59.67           H
ATOM  19426  N    ALA H  27      67.509  57.238  56.616  1.00 67.09           H
ATOM  19427  CA   ALA H  27      68.477  56.850  55.599  1.00 67.09           H
ATOM  19428  CB   ALA H  27      69.372  58.038  55.218  1.00 25.22           H
ATOM  19429  C    ALA H  27      69.316  55.721  56.185  1.00 67.09           H
ATOM  19430  O    ALA H  27      70.543  55.811  56.247  1.00 67.09           H
ATOM  19431  N    ALA H  28      68.629  54.670  56.635  1.00 80.50           H
ATOM  19432  CA   ALA H  28      69.256  53.486  57.227  1.00 80.50           H
ATOM  19433  CB   ALA H  28      69.983  53.853  58.523  1.00 66.64           H
ATOM  19434  C    ALA H  28      68.169  52.462  57.518  1.00 80.50           H
ATOM  19435  O    ALA H  28      68.428  51.264  57.602  1.00 80.50           H
ATOM  19436  N    ALA H  29      66.947  52.955  57.672  1.00 63.90           H
ATOM  19437  CA   ALA H  29      65.804  52.103  57.959  1.00 63.90           H
ATOM  19438  CB   ALA H  29      64.956  52.734  59.078  1.00 65.39           H
ATOM  19439  C    ALA H  29      64.960  51.897  56.699  1.00 63.90           H
ATOM  19440  O    ALA H  29      64.171  50.953  56.606  1.00 63.90           H
ATOM  19441  N    ALA H  30      65.135  52.784  55.727  1.00100.07           H
ATOM  19442  CA   ALA H  30      64.377  52.699  54.489  1.00100.07           H
ATOM  19443  CB   ALA H  30      64.407  54.042  53.767  1.00 55.40           H
ATOM  19444  C    ALA H  30      64.899  51.601  53.569  1.00100.07           H
ATOM  19445  O    ALA H  30      64.514  51.537  52.400  1.00100.07           H
ATOM  19446  N    ALA H  31      65.766  50.737  54.092  1.00100.07           H
ATOM  19447  CA   ALA H  31      66.330  49.651  53.286  1.00100.07           H
ATOM  19448  CB   ALA H  31      67.609  50.132  52.591  1.00100.07           H
ATOM  19449  C    ALA H  31      66.619  48.385  54.098  1.00100.07           H
ATOM  19450  O    ALA H  31      67.592  47.675  53.834  1.00100.07           H
```

```
ATOM  19451  N   ALA H  32    65.760  48.101  55.072  1.00 46.43      H
ATOM  19452  CA  ALA H  32    65.922  46.933  55.929  1.00 46.43      H
ATOM  19453  CB  ALA H  32    67.351  46.893  56.512  1.00 27.57      H
ATOM  19454  C   ALA H  32    64.908  46.999  57.060  1.00 46.43      H
ATOM  19455  O   ALA H  32    65.258  47.360  58.181  1.00 46.43      H
ATOM  19456  N   ALA H  33    63.655  46.665  56.773  1.00100.07      H
ATOM  19457  CA  ALA H  33    62.630  46.693  57.810  1.00100.07      H
ATOM  19458  CB  ALA H  33    61.387  45.943  57.342  1.00 41.38      H
ATOM  19459  C   ALA H  33    63.181  46.042  59.079  1.00100.07      H
ATOM  19460  O   ALA H  33    63.018  46.567  60.186  1.00100.07      H
ATOM  19461  N   ALA H  34    63.849  44.903  58.891  1.00 55.51      H
ATOM  19462  CA  ALA H  34    64.431  44.123  59.979  1.00 55.51      H
ATOM  19463  CB  ALA H  34    65.037  42.835  59.414  1.00 53.39      H
ATOM  19464  C   ALA H  34    65.468  44.852  60.836  1.00 55.51      H
ATOM  19465  O   ALA H  34    66.579  44.349  61.025  1.00 55.51      H
ATOM  19466  N   ALA H  35    65.098  46.029  61.348  1.00 95.30      H
ATOM  19467  CA  ALA H  35    65.960  46.837  62.222  1.00 95.30      H
ATOM  19468  CB  ALA H  35    66.767  47.856  61.413  1.00 52.87      H
ATOM  19469  C   ALA H  35    65.088  47.558  63.248  1.00 95.30      H
ATOM  19470  O   ALA H  35    64.663  46.962  64.237  1.00 95.30      H
ATOM  19471  N   ALA H  36    64.818  48.837  63.010  1.00 99.95      H
ATOM  19472  CA  ALA H  36    63.989  49.631  63.914  1.00 99.95      H
ATOM  19473  CB  ALA H  36    62.532  49.184  63.809  1.00 40.22      H
ATOM  19474  C   ALA H  36    64.454  49.525  65.364  1.00 99.95      H
ATOM  19475  O   ALA H  36    65.555  49.043  65.643  1.00 99.95      H
ATOM  19476  N   ALA H  37    63.601  49.994  66.275  1.00 51.63      H
ATOM  19477  CA  ALA H  37    63.843  49.964  67.726  1.00 51.63      H
ATOM  19478  CB  ALA H  37    64.909  50.984  68.136  1.00  9.23      H
ATOM  19479  C   ALA H  37    62.512  50.310  68.368  1.00 51.63      H
ATOM  19480  O   ALA H  37    62.411  50.490  69.580  1.00 51.63      H
ATOM  19481  N   ALA H  38    61.498  50.420  67.514  1.00100.07      H
ATOM  19482  CA  ALA H  38    60.141  50.717  67.937  1.00100.07      H
ATOM  19483  CB  ALA H  38    59.458  51.636  66.912  1.00 19.88      H
ATOM  19484  C   ALA H  38    59.430  49.365  68.017  1.00100.07      H
ATOM  19485  O   ALA H  38    58.434  49.122  67.329  1.00100.07      H
ATOM  19486  N   ALA H  39    59.976  48.485  68.859  1.00 99.59      H
ATOM  19487  CA  ALA H  39    59.450  47.136  69.066  1.00 99.59      H
ATOM  19488  CB  ALA H  39    60.207  46.452  70.199  1.00100.07      H
ATOM  19489  C   ALA H  39    57.964  47.136  69.372  1.00 99.59      H
ATOM  19490  O   ALA H  39    57.538  47.648  70.404  1.00 99.59      H
ATOM  19491  N   ALA H  40    57.188  46.553  68.464  1.00100.07      H
ATOM  19492  CA  ALA H  40    55.741  46.468  68.604  1.00100.07      H
ATOM  19493  CB  ALA H  40    55.374  46.201  70.059  1.00 35.94      H
ATOM  19494  C   ALA H  40    55.027  47.722  68.096  1.00100.07      H
ATOM  19495  O   ALA H  40    54.747  47.842  66.901  1.00100.07      H
ATOM  19496  N   ALA H  41    54.735  48.650  69.006  1.00 84.13      H
ATOM  19497  CA  ALA H  41    54.039  49.892  68.663  1.00 84.13      H
ATOM  19498  CB  ALA H  41    53.613  50.614  69.949  1.00 50.94      H
ATOM  19499  C   ALA H  41    54.893  50.816  67.786  1.00 84.13      H
ATOM  19500  O   ALA H  41    56.018  51.167  68.166  1.00 84.13      H
ATOM  19501  N   ALA H  42    54.353  51.212  66.624  1.00 49.03      H
ATOM  19502  CA  ALA H  42    55.091  52.085  65.699  1.00 49.03      H
ATOM  19503  CB  ALA H  42    56.233  51.292  65.061  1.00 71.52      H
ATOM  19504  C   ALA H  42    54.326  52.850  64.596  1.00 49.03      H
ATOM  19505  O   ALA H  42    54.745  53.948  64.208  1.00 49.03      H
ATOM  19506  N   ALA H  43    53.229  52.297  64.080  1.00 68.08      H
ATOM  19507  CA  ALA H  43    52.498  53.003  63.021  1.00 68.08      H
ATOM  19508  CB  ALA H  43    53.404  53.132  61.793  1.00 52.55      H
ATOM  19509  C   ALA H  43    51.128  52.421  62.609  1.00 68.08      H
ATOM  19510  O   ALA H  43    50.731  51.353  63.076  1.00 68.08      H
ATOM  19511  N   ALA H  44    50.418  53.133  61.730  1.00 52.56      H
ATOM  19512  CA  ALA H  44    49.100  52.706  61.255  1.00 52.56      H
ATOM  19513  CB  ALA H  44    48.051  53.052  62.295  1.00 71.87      H
ATOM  19514  C   ALA H  44    48.718  53.328  59.901  1.00 52.56      H
ATOM  19515  O   ALA H  44    49.588  53.779  59.157  1.00 52.56      H
ATOM  19516  N   ALA H  45    47.420  53.336  59.585  1.00 84.52      H
ATOM  19517  CA  ALA H  45    46.900  53.905  58.331  1.00 84.52      H
ATOM  19518  CB  ALA H  45    47.653  53.301  57.120  1.00 45.12      H
ATOM  19519  C   ALA H  45    45.370  53.702  58.184  1.00 84.52      H
ATOM  19520  O   ALA H  45    44.638  53.805  59.165  1.00 84.52      H
ATOM  19521  N   ALA H  46    44.886  53.429  56.970  1.00 70.00      H
ATOM  19522  CA  ALA H  46    43.448  53.227  56.752  1.00 70.00      H
ATOM  19523  CB  ALA H  46    42.694  54.532  57.010  1.00 86.58      H
ATOM  19524  C   ALA H  46    43.074  52.670  55.363  1.00 70.00      H
ATOM  19525  O   ALA H  46    43.944  52.185  54.627  1.00 70.00      H
ATOM  19526  N   ALA H  47    41.776  52.747  55.032  1.00 63.06      H
ATOM  19527  CA  ALA H  47    41.202  52.255  53.766  1.00 63.06      H
ATOM  19528  CB  ALA H  47    42.101  52.641  52.585  1.00 66.74      H
ATOM  19529  C   ALA H  47    41.017  50.730  53.825  1.00 63.06      H
ATOM  19530  O   ALA H  47    40.392  50.114  52.953  1.00 63.06      H
ATOM  19531  N   ALA H  48    41.568  50.158  54.890  1.00 96.53      H
ATOM  19532  CA  ALA H  48    41.557  48.733  55.200  1.00 96.53      H
ATOM  19533  CB  ALA H  48    41.864  47.909  53.958  1.00 15.80      H
ATOM  19534  C   ALA H  48    42.695  48.626  56.215  1.00 96.53      H
```

```
ATOM  19535  O    ALA H  48      43.243  47.555  56.457  1.00 96.53           H
ATOM  19536  N    ALA H  49      43.023  49.786  56.787  1.00100.07           H
ATOM  19537  CA   ALA H  49      44.075  50.006  57.784  1.00100.07           H
ATOM  19538  CB   ALA H  49      43.541  50.893  58.906  1.00 61.55           H
ATOM  19539  C    ALA H  49      44.781  48.812  58.398  1.00100.07           H
ATOM  19540  O    ALA H  49      44.331  48.258  59.402  1.00100.07           H
ATOM  19541  N    ALA H  50      45.908  48.442  57.802  1.00 80.00           H
ATOM  19542  CA   ALA H  50      46.717  47.341  58.297  1.00 80.00           H
ATOM  19543  CB   ALA H  50      47.029  46.358  57.169  1.00 67.81           H
ATOM  19544  C    ALA H  50      47.990  47.993  58.809  1.00 80.00           H
ATOM  19545  O    ALA H  50      47.961  49.126  59.282  1.00 80.00           H
ATOM  19546  N    ALA H  51      49.106  47.285  58.706  1.00 78.65           H
ATOM  19547  CA   ALA H  51      50.387  47.819  59.157  1.00 78.65           H
ATOM  19548  CB   ALA H  51      51.431  46.692  59.217  1.00 72.47           H
ATOM  19549  C    ALA H  51      50.857  48.926  58.213  1.00 78.65           H
ATOM  19550  O    ALA H  51      50.054  49.469  57.449  1.00 78.65           H
ATOM  19551  N    ALA H  52      52.148  49.260  58.303  1.00 93.82           H
ATOM  19552  CA   ALA H  52      52.808  50.266  57.464  1.00 93.82           H
ATOM  19553  CB   ALA H  52      52.040  50.451  56.148  1.00 75.48           H
ATOM  19554  C    ALA H  52      53.123  51.638  58.068  1.00 93.82           H
ATOM  19555  O    ALA H  52      53.219  51.798  59.284  1.00 93.82           H
ATOM  19556  N    GLU H  53      53.291  52.601  57.160  1.00 81.65           H
ATOM  19557  CA   GLU H  53      53.640  54.004  57.405  1.00 81.65           H
ATOM  19558  CB   GLU H  53      53.868  54.317  58.887  1.00 97.30           H
ATOM  19559  CG   GLU H  53      54.489  55.703  59.149  1.00 97.30           H
ATOM  19560  CD   GLU H  53      53.718  56.848  58.496  1.00 97.30           H
ATOM  19561  OE1  GLU H  53      52.522  57.009  58.810  1.00 97.30           H
ATOM  19562  OE2  GLU H  53      54.306  57.588  57.675  1.00 97.30           H
ATOM  19563  C    GLU H  53      54.945  54.192  56.656  1.00 81.65           H
ATOM  19564  O    GLU H  53      55.997  54.404  57.259  1.00 81.65           H
ATOM  19565  N    ALA H  54      54.871  54.079  55.337  1.00 61.43           H
ATOM  19566  CA   ALA H  54      56.047  54.226  54.500  1.00 61.43           H
ATOM  19567  CB   ALA H  54      55.625  54.505  53.064  1.00 73.24           H
ATOM  19568  C    ALA H  54      57.006  55.317  55.001  1.00 61.43           H
ATOM  19569  O    ALA H  54      58.009  55.002  55.635  1.00 61.43           H
ATOM  19570  N    ALA H  55      56.699  56.586  54.727  1.00100.07           H
ATOM  19571  CA   ALA H  55      57.539  57.724  55.136  1.00100.07           H
ATOM  19572  CB   ALA H  55      56.648  58.897  55.558  1.00 42.52           H
ATOM  19573  C    ALA H  55      58.573  57.431  56.240  1.00100.07           H
ATOM  19574  O    ALA H  55      58.264  57.504  57.431  1.00100.07           H
ATOM  19575  N    ALA H  56      59.804  57.111  55.832  1.00100.07           H
ATOM  19576  CA   ALA H  56      60.886  56.806  56.774  1.00100.07           H
ATOM  19577  CB   ALA H  56      62.155  56.409  56.023  1.00 81.19           H
ATOM  19578  C    ALA H  56      61.180  57.984  57.690  1.00100.07           H
ATOM  19579  O    ALA H  56      61.298  57.810  58.901  1.00100.07           H
ATOM  19580  N    ALA H  57      61.308  59.178  57.113  1.00 82.00           H
ATOM  19581  CA   ALA H  57      61.568  60.369  57.905  1.00 82.00           H
ATOM  19582  CB   ALA H  57      61.273  61.615  57.110  1.00 29.17           H
ATOM  19583  C    ALA H  57      60.637  60.282  59.090  1.00 82.00           H
ATOM  19584  O    ALA H  57      60.962  60.761  60.174  1.00 82.00           H
ATOM  19585  N    ALA H  58      59.477  59.658  58.882  1.00 38.70           H
ATOM  19586  CA   ALA H  58      58.515  59.499  59.964  1.00 38.70           H
ATOM  19587  CB   ALA H  58      57.211  58.890  59.435  1.00 26.84           H
ATOM  19588  C    ALA H  58      59.109  58.632  61.090  1.00 38.70           H
ATOM  19589  O    ALA H  58      59.487  59.145  62.141  1.00 38.70           H
ATOM  19590  N    ALA H  59      59.212  57.327  60.862  1.00 42.23           H
ATOM  19591  CA   ALA H  59      59.756  56.416  61.867  1.00 42.23           H
ATOM  19592  CB   ALA H  59      60.318  55.165  61.202  1.00 58.86           H
ATOM  19593  C    ALA H  59      60.831  57.074  62.707  1.00 42.23           H
ATOM  19594  O    ALA H  59      60.717  57.133  63.923  1.00 42.23           H
ATOM  19595  N    ALA H  60      61.865  57.583  62.050  1.00 32.32           H
ATOM  19596  CA   ALA H  60      62.984  58.224  62.741  1.00 32.32           H
ATOM  19597  CB   ALA H  60      63.756  59.105  61.761  1.00 54.01           H
ATOM  19598  C    ALA H  60      62.634  59.034  64.007  1.00 32.32           H
ATOM  19599  O    ALA H  60      62.929  58.616  65.136  1.00 32.32           H
ATOM  19600  N    ALA H  61      62.020  60.197  63.818  1.00 74.09           H
ATOM  19601  CA   ALA H  61      61.658  61.054  64.942  1.00 74.09           H
ATOM  19602  CB   ALA H  61      60.778  62.216  64.445  1.00 65.70           H
ATOM  19603  C    ALA H  61      60.958  60.288  66.077  1.00 74.09           H
ATOM  19604  O    ALA H  61      61.105  60.630  67.252  1.00 74.09           H
ATOM  19605  N    ALA H  62      60.214  59.242  65.726  1.00 66.99           H
ATOM  19606  CA   ALA H  62      59.494  58.451  66.722  1.00 66.99           H
ATOM  19607  CB   ALA H  62      58.345  57.697  66.066  1.00 58.00           H
ATOM  19608  C    ALA H  62      60.404  57.475  67.451  1.00 66.99           H
ATOM  19609  O    ALA H  62      60.036  56.919  68.488  1.00 66.99           H
ATOM  19610  N    ALA H  63      61.588  57.250  66.899  1.00 48.98           H
ATOM  19611  CA   ALA H  63      62.537  56.354  67.535  1.00 48.98           H
ATOM  19612  CB   ALA H  63      63.274  55.506  66.480  1.00 41.12           H
ATOM  19613  C    ALA H  63      63.517  57.229  68.315  1.00 48.98           H
ATOM  19614  O    ALA H  63      63.776  56.973  69.492  1.00 48.98           H
ATOM  19615  N    ALA H  64      64.026  58.275  67.659  1.00 50.52           H
ATOM  19616  CA   ALA H  64      64.989  59.203  68.263  1.00 50.52           H
ATOM  19617  CB   ALA H  64      65.249  60.387  67.317  1.00 59.99           H
ATOM  19618  C    ALA H  64      64.485  59.703  69.610  1.00 50.52           H
```

| ATOM | 19619 | O | ALA H | 64 | 64.292 | 58.912 | 70.533 | 1.00 | 50.52 | H |
|------|-------|----|-------|----|--------|--------|--------|------|-------|---|
| ATOM | 19620 | N | ALA H | 65 | 64.295 | 61.016 | 69.733 | 1.00 | 83.44 | H |
| ATOM | 19621 | CA | ALA H | 65 | 63.781 | 61.577 | 70.977 | 1.00 | 83.44 | H |
| ATOM | 19622 | CB | ALA H | 65 | 63.433 | 63.049 | 70.803 | 1.00 | 100.07 | H |
| ATOM | 19623 | C | ALA H | 65 | 62.533 | 60.750 | 71.228 | 1.00 | 83.44 | H |
| ATOM | 19624 | O | ALA H | 65 | 61.431 | 61.076 | 70.774 | 1.00 | 83.44 | H |
| ATOM | 19625 | N | ALA H | 66 | 62.751 | 59.651 | 71.935 | 1.00 | 86.00 | H |
| ATOM | 19626 | CA | ALA H | 66 | 61.715 | 58.693 | 72.253 | 1.00 | 86.00 | H |
| ATOM | 19627 | CB | ALA H | 66 | 60.901 | 58.374 | 71.005 | 1.00 | 100.07 | H |
| ATOM | 19628 | C | ALA H | 66 | 62.445 | 57.445 | 72.734 | 1.00 | 86.00 | H |
| ATOM | 19629 | O | ALA H | 66 | 62.942 | 57.403 | 73.866 | 1.00 | 86.00 | H |
| ATOM | 19630 | N | ALA H | 67 | 62.520 | 56.438 | 71.865 | 1.00 | 82.79 | H |
| ATOM | 19631 | CA | ALA H | 67 | 63.205 | 55.201 | 72.202 | 1.00 | 82.79 | H |
| ATOM | 19632 | CB | ALA H | 67 | 63.423 | 54.379 | 70.958 | 1.00 | 39.56 | H |
| ATOM | 19633 | C | ALA H | 67 | 64.540 | 55.552 | 72.857 | 1.00 | 82.79 | H |
| ATOM | 19634 | O | ALA H | 67 | 65.126 | 54.742 | 73.569 | 1.00 | 82.79 | H |
| ATOM | 19635 | N | ALA H | 68 | 65.006 | 56.771 | 72.600 | 1.00 | 64.69 | H |
| ATOM | 19636 | CA | ALA H | 68 | 66.236 | 57.296 | 73.183 | 1.00 | 64.69 | H |
| ATOM | 19637 | CB | ALA H | 68 | 66.078 | 57.392 | 74.701 | 1.00 | 5.07 | H |
| ATOM | 19638 | C | ALA H | 68 | 67.518 | 56.544 | 72.838 | 1.00 | 64.69 | H |
| ATOM | 19639 | O | ALA H | 68 | 68.553 | 56.726 | 73.491 | 1.00 | 64.69 | H |
| ATOM | 19640 | N | ALA H | 69 | 67.459 | 55.703 | 71.816 | 1.00 | 71.17 | H |
| ATOM | 19641 | CA | ALA H | 69 | 68.642 | 54.960 | 71.415 | 1.00 | 71.17 | H |
| ATOM | 19642 | CB | ALA H | 69 | 68.243 | 53.644 | 70.763 | 1.00 | 73.03 | H |
| ATOM | 19643 | C | ALA H | 69 | 69.430 | 55.821 | 70.440 | 1.00 | 71.17 | H |
| ATOM | 19644 | O | ALA H | 69 | 69.299 | 57.047 | 70.439 | 1.00 | 71.17 | H |
| ATOM | 19645 | N | ALA H | 70 | 70.240 | 55.173 | 69.609 | 1.00 | 59.62 | H |
| ATOM | 19646 | CA | ALA H | 70 | 71.061 | 55.867 | 68.625 | 1.00 | 59.62 | H |
| ATOM | 19647 | CB | ALA H | 70 | 70.199 | 56.829 | 67.821 | 1.00 | 60.85 | H |
| ATOM | 19648 | C | ALA H | 70 | 72.193 | 56.611 | 69.332 | 1.00 | 59.62 | H |
| ATOM | 19649 | O | ALA H | 70 | 72.417 | 56.414 | 70.525 | 1.00 | 59.62 | H |
| ATOM | 19650 | N | ALA H | 71 | 72.899 | 57.468 | 68.606 | 1.00 | 65.27 | H |
| ATOM | 19651 | CA | ALA H | 71 | 74.010 | 58.207 | 69.185 | 1.00 | 65.27 | H |
| ATOM | 19652 | CB | ALA H | 71 | 75.305 | 57.465 | 68.937 | 1.00 | 100.07 | H |
| ATOM | 19653 | C | ALA H | 71 | 74.125 | 59.628 | 68.657 | 1.00 | 65.27 | H |
| ATOM | 19654 | O | ALA H | 71 | 73.112 | 60.281 | 68.398 | 1.00 | 65.27 | H |
| ATOM | 19655 | N | ALA H | 72 | 75.365 | 60.098 | 68.493 | 1.00 | 55.71 | H |
| ATOM | 19656 | CA | ALA H | 72 | 75.622 | 61.460 | 68.022 | 1.00 | 55.71 | H |
| ATOM | 19657 | CB | ALA H | 72 | 76.227 | 62.296 | 69.154 | 1.00 | 73.67 | H |
| ATOM | 19658 | C | ALA H | 72 | 76.492 | 61.582 | 66.778 | 1.00 | 55.71 | H |
| ATOM | 19659 | O | ALA H | 72 | 76.034 | 61.327 | 65.658 | 1.00 | 55.71 | H |
| ATOM | 19660 | N | ALA H | 73 | 77.739 | 62.008 | 66.975 | 1.00 | 40.72 | H |
| ATOM | 19661 | CA | ALA H | 73 | 78.672 | 62.189 | 65.864 | 1.00 | 40.72 | H |
| ATOM | 19662 | CB | ALA H | 73 | 78.452 | 63.541 | 65.212 | 1.00 | 79.62 | H |
| ATOM | 19663 | C | ALA H | 73 | 80.116 | 62.065 | 66.324 | 1.00 | 40.72 | H |
| ATOM | 19664 | O | ALA H | 73 | 80.528 | 62.754 | 67.256 | 1.00 | 40.72 | H |
| ATOM | 19665 | N | ALA H | 74 | 80.868 | 61.198 | 65.639 | 1.00 | 95.89 | H |
| ATOM | 19666 | CA | ALA H | 74 | 82.272 | 60.867 | 65.924 | 1.00 | 95.89 | H |
| ATOM | 19667 | CB | ALA H | 74 | 82.966 | 61.962 | 66.744 | 1.00 | 15.50 | H |
| ATOM | 19668 | C | ALA H | 74 | 82.245 | 59.564 | 66.719 | 1.00 | 95.89 | H |
| ATOM | 19669 | O | ALA H | 74 | 83.108 | 59.311 | 67.558 | 1.00 | 95.89 | H |
| ATOM | 19670 | N | ALA H | 75 | 81.226 | 58.751 | 66.446 | 1.00 | 100.07 | H |
| ATOM | 19671 | CA | ALA H | 75 | 81.038 | 57.466 | 67.111 | 1.00 | 100.07 | H |
| ATOM | 19672 | CB | ALA H | 75 | 79.548 | 57.116 | 67.165 | 1.00 | 44.27 | H |
| ATOM | 19673 | C | ALA H | 75 | 81.807 | 56.382 | 66.365 | 1.00 | 100.07 | H |
| ATOM | 19674 | O | ALA H | 75 | 82.995 | 56.186 | 66.613 | 1.00 | 100.07 | H |
| ATOM | 19675 | N | ALA H | 76 | 81.128 | 55.685 | 65.453 | 1.00 | 41.38 | H |
| ATOM | 19676 | CA | ALA H | 76 | 81.744 | 54.626 | 64.657 | 1.00 | 41.38 | H |
| ATOM | 19677 | CB | ALA H | 76 | 80.833 | 54.277 | 63.498 | 1.00 | 45.25 | H |
| ATOM | 19678 | C | ALA H | 76 | 83.119 | 55.050 | 64.127 | 1.00 | 41.38 | H |
| ATOM | 19679 | O | ALA H | 76 | 83.894 | 54.221 | 63.631 | 1.00 | 41.38 | H |
| ATOM | 19680 | N | ALA H | 77 | 83.399 | 56.350 | 64.237 | 1.00 | 99.89 | H |
| ATOM | 19681 | CA | ALA H | 77 | 84.654 | 56.951 | 63.790 | 1.00 | 99.89 | H |
| ATOM | 19682 | CB | ALA H | 77 | 85.851 | 56.182 | 64.363 | 1.00 | 75.98 | H |
| ATOM | 19683 | C | ALA H | 77 | 84.698 | 56.947 | 62.268 | 1.00 | 99.89 | H |
| ATOM | 19684 | O | ALA H | 77 | 84.543 | 57.988 | 61.622 | 1.00 | 99.89 | H |
| ATOM | 19685 | N | ALA H | 78 | 84.908 | 55.765 | 61.703 | 1.00 | 99.61 | H |
| ATOM | 19686 | CA | ALA H | 78 | 84.956 | 55.616 | 60.260 | 1.00 | 99.61 | H |
| ATOM | 19687 | CB | ALA H | 78 | 86.239 | 54.888 | 59.836 | 1.00 | 60.65 | H |
| ATOM | 19688 | C | ALA H | 78 | 83.735 | 54.831 | 59.809 | 1.00 | 99.61 | H |
| ATOM | 19689 | O | ALA H | 78 | 83.415 | 53.774 | 60.368 | 1.00 | 99.61 | H |
| ATOM | 19690 | N | ALA H | 79 | 83.040 | 55.369 | 58.811 | 1.00 | 78.33 | H |
| ATOM | 19691 | CA | ALA H | 79 | 81.877 | 54.695 | 58.264 | 1.00 | 78.33 | H |
| ATOM | 19692 | CB | ALA H | 79 | 81.225 | 55.554 | 57.189 | 1.00 | 66.29 | H |
| ATOM | 19693 | C | ALA H | 79 | 82.466 | 53.427 | 57.665 | 1.00 | 78.33 | H |
| ATOM | 19694 | O | ALA H | 79 | 81.750 | 52.492 | 57.294 | 1.00 | 78.33 | H |
| ATOM | 19695 | N | ALA H | 80 | 83.795 | 53.427 | 57.577 | 1.00 | 92.64 | H |
| ATOM | 19696 | CA | ALA H | 80 | 84.566 | 52.306 | 57.065 | 1.00 | 92.64 | H |
| ATOM | 19697 | CB | ALA H | 80 | 86.038 | 52.504 | 57.404 | 1.00 | 47.94 | H |
| ATOM | 19698 | C | ALA H | 80 | 84.022 | 51.080 | 57.775 | 1.00 | 92.64 | H |
| ATOM | 19699 | O | ALA H | 80 | 83.921 | 49.995 | 57.205 | 1.00 | 92.64 | H |
| ATOM | 19700 | N | ALA H | 81 | 83.663 | 51.283 | 59.035 | 1.00 | 78.72 | H |
| ATOM | 19701 | CA | ALA H | 81 | 83.107 | 50.229 | 59.862 | 1.00 | 78.72 | H |
| ATOM | 19702 | CB | ALA H | 81 | 83.515 | 50.441 | 61.303 | 1.00 | 100.07 | H |

```
ATOM  19703  C    ALA H  81     81.590  50.251  59.743  1.00 78.72      H
ATOM  19704  O    ALA H  81     80.924  49.253  60.012  1.00 78.72      H
ATOM  19705  N    ALA H  82     81.046  51.399  59.347  1.00 99.31      H
ATOM  19706  CA   ALA H  82     79.603  51.533  59.198  1.00 99.31      H
ATOM  19707  CB   ALA H  82     79.244  52.909  58.635  1.00 38.43      H
ATOM  19708  C    ALA H  82     79.056  50.433  58.295  1.00 99.31      H
ATOM  19709  O    ALA H  82     78.000  49.872  58.574  1.00 99.31      H
ATOM  19710  N    ALA H  83     79.767  50.108  57.221  1.00 83.69      H
ATOM  19711  CA   ALA H  83     79.297  49.054  56.323  1.00 83.69      H
ATOM  19712  CB   ALA H  83     80.126  49.050  55.038  1.00 88.80      H
ATOM  19713  C    ALA H  83     79.347  47.669  56.997  1.00 83.69      H
ATOM  19714  O    ALA H  83     79.092  46.637  56.359  1.00 83.69      H
ATOM  19715  N    ALA H  84     79.668  47.663  58.291  1.00 95.62      H
ATOM  19716  CA   ALA H  84     79.761  46.431  59.074  1.00 95.62      H
ATOM  19717  CB   ALA H  84     79.966  46.763  60.554  1.00 46.16      H
ATOM  19718  C    ALA H  84     78.504  45.590  58.910  1.00 95.62      H
ATOM  19719  O    ALA H  84     78.329  44.889  57.905  1.00 95.62      H
ATOM  19720  N    ALA H  85     77.636  45.673  59.917  1.00100.07      H
ATOM  19721  CA   ALA H  85     76.373  44.946  59.925  1.00100.07      H
ATOM  19722  CB   ALA H  85     75.660  45.146  61.260  1.00 54.80      H
ATOM  19723  C    ALA H  85     75.505  45.440  58.770  1.00100.07      H
ATOM  19724  O    ALA H  85     74.314  45.115  58.672  1.00100.07      H
ATOM  19725  N    ALA H  86     76.114  46.244  57.904  1.00100.07      H
ATOM  19726  CA   ALA H  86     75.429  46.754  56.732  1.00100.07      H
ATOM  19727  CB   ALA H  86     76.161  47.972  56.170  1.00 82.24      H
ATOM  19728  C    ALA H  86     75.487  45.590  55.752  1.00100.07      H
ATOM  19729  O    ALA H  86     75.436  45.769  54.534  1.00100.07      H
ATOM  19730  N    ALA H  87     75.612  44.393  56.316  1.00100.07      H
ATOM  19731  CA   ALA H  87     75.673  43.158  55.552  1.00100.07      H
ATOM  19732  CB   ALA H  87     77.055  42.521  55.699  1.00100.07      H
ATOM  19733  C    ALA H  87     74.592  42.221  56.088  1.00100.07      H
ATOM  19734  O    ALA H  87     73.701  41.804  55.341  1.00100.07      H
ATOM  19735  N    ALA H  88     74.678  41.911  57.386  1.00100.07      H
ATOM  19736  CA   ALA H  88     73.722  41.031  58.066  1.00100.07      H
ATOM  19737  CB   ALA H  88     73.884  41.151  59.585  1.00 88.45      H
ATOM  19738  C    ALA H  88     72.297  41.396  57.657  1.00100.07      H
ATOM  19739  O    ALA H  88     71.702  42.328  58.210  1.00100.07      H
ATOM  19740  N    ALA H  89     71.767  40.638  56.696  1.00 84.93      H
ATOM  19741  CA   ALA H  89     70.434  40.850  56.142  1.00 84.93      H
ATOM  19742  CB   ALA H  89     69.360  40.611  57.198  1.00100.07      H
ATOM  19743  C    ALA H  89     70.353  42.276  55.613  1.00 84.93      H
ATOM  19744  O    ALA H  89     70.494  42.503  54.414  1.00 84.93      H
ATOM  19745  N    ALA H  90     70.153  43.229  56.519  1.00100.07      H
ATOM  19746  CA   ALA H  90     70.042  44.648  56.177  1.00100.07      H
ATOM  19747  CB   ALA H  90     70.386  45.510  57.406  1.00 38.54      H
ATOM  19748  C    ALA H  90     70.904  45.071  54.986  1.00100.07      H
ATOM  19749  O    ALA H  90     72.040  45.507  55.167  1.00100.07      H
ATOM  19750  N    ALA H  91     70.339  44.944  53.781  1.00100.07      H
ATOM  19751  CA   ALA H  91     70.989  45.301  52.511  1.00100.07      H
ATOM  19752  CB   ALA H  91     72.501  45.116  52.596  1.00100.07      H
ATOM  19753  C    ALA H  91     70.439  44.473  51.346  1.00100.07      H
ATOM  19754  O    ALA H  91     70.869  43.307  51.205  1.00100.07      H
ATOM  19755  OT   ALA H  91     69.584  44.991  50.592  1.00100.07      H
ATOM  19756  MG+2 MG  I   1     45.365  88.876  44.194  1.00 58.09      I
ATOM  19757  ZN+2 ZN  J   1     80.834  86.397  68.754  1.00 58.09      J
END
```

What is claimed is:

1. A method of identifying an agent for use as an inhibitor of bacterial RNA polymerase comprising:
   (a) obtaining a set of atomic coordinates defining the three-dimensional structure of the core RNA polymerase (RNAP) from *T. aquaticus* consisting essentially of the β', β, α and ω subunits of RNAP from *T. aquaticus* and using a crystal having the space group of $P4_12_12$ and unit cell dimensions of a=b=201 and c=294 Å;
   (b) selecting a potential agent by performing rational drug design with the atomic coordinates obtained in step (a), wherein said selecting is performed in conjunction with computer modeling;
   (c) contacting the potential agent with a bacterial RNA polymerase; and
   (d) measuring the activity of the bacterial RNA polymerase; wherein a potential agent is identified as an agent that inhibits bacterial RNA polymerase when there is a decrease in the activity of the bacterial RNA polymerase in the presence of the agent relative to in its absence.

2. The method of claim 1, further comprising:
   (e) contacting the agent with a eukaryotic RNA polymerase; and
   (f) measuring the activity of the eukaryotic RNA polymerase; wherein an agent is identified as an agent for use as an inhibitor of bacterial RNA polymerase when there is no change in the activity of the eukaryotic RNA polymerase in the presence of the agent relative to in its absence; and wherein the agent identified inhibits bacterial but not eukaryotic RNA polymerase.

3. A method of identifying an agent that inhibits bacterial growth comprising:
   (a) obtaining a set of atomic coordinates defining the three-dimensional structure of the core RNA polymerase (RNAP) from *T. aquaticus* consisting essentially of the β', β, α and ω subunits of RNAP from *T. aquaticus* and using a crystal having the space group of $P4_12_12$ and unit cell dimensions of a=b=201 and c=294 Å;
   (b) selecting a potential agent by performing rational drug design with the atomic coordinates obtained in step (a), wherein said selecting is performed in conjunction with computer modeling;
   (c) contacting the potential agent with a bacterial culture; and
   (d) measuring the growth of the bacterial culture under conditions in which the bacterial culture grows in the absence of the agent; wherein a potential agent is identified as an agent that inhibits bacterial growth when there is a decrease in the growth of the bacterial culture in the presence of the agent relative to in its absence.

4. The method of claim 3, further comprising:
   (e) contacting the agent with a eukaryotic cell; and
   (f) measuring the amount of proliferation of the eukaryotic cell under conditions in which the eukaryotic cell proliferates in the absence of the agent; wherein an agent is identified as an agent for inhibiting bacterial growth when there is no change in the proliferation of the eukaryotic cell in the presence of the agent relative to in its absence; and wherein the agent identified inhibits bacterial growth but not eukaryotic proliferation.

5. A method of identifying an agent for use as an inhibitor of bacterial RNA polymerase comprising:
   (a) selecting a potential agent by performing rational drug design with the set of atomic coordinates in Table 3, wherein said selecting is performed in conjunction with computer modeling;
   (b) contacting the potential agent with a bacterial RNA polymerase; and
   (c) measuring the activity of the bacterial RNA polymerase; wherein a potential agent is identified as an agent that inhibits bacterial RNA polymerase when there is a decrease in the activity of the bacterial RNA polymerase in the presence of the agent relative to in its absence.

6. The method of claim 5, further comprising:
   (d) contacting the agent with a eukaryotic RNA polymerase; and
   (e) measuring the activity of the eukaryotic RNA polymerase; wherein an agent is identified as an agent for use as an inhibitor of bacterial RNA polymerase when there is no change in the activity of the eukaryotic RNA polymerase in the presence of the agent relative to in its absence; and wherein the agent identified inhibits bacterial but not eukaryotic RNA polymerase.

7. A method of identifying an agent that inhibits bacterial growth comprising:
   (a) selecting a potential agent by performing rational drug design with the set of atomic coordinates in Table 3, wherein said selecting is performed in conjunction with computer modeling;
   (b) contacting the potential agent with a bacterial culture; and
   (c) measuring the growth of the bacterial culture under conditions in which the bacterial culture grows in the absence of the agent; wherein a potential agent is identified as an agent that inhibits bacterial growth when there is a decrease in the growth of the bacterial culture in the presence of the agent relative to in its absence.

8. The method of claim 7, further comprising:
   (d) contacting the agent with a eukaryotic cell; and
   (e) measuring the amount of proliferation of the eukaryotic cell under conditions in which the eukaryotic cell proliferates in the absence of the agent; wherein an agent is identified as an agent for inhibiting bacterial growth when there is no change in the proliferation of the eukaryotic cell in the presence of the agent relative to in its absence; and wherein the agent identified inhibits bacterial growth but not eukaryotic proliferation.

9. A method of identifying a compound that is predicted to inhibit bacterial RNA polymerase comprising:
   (a) defining the structure of the core bacterial RNA polymerase (RNAP) or a portion of the core bacterial RNAP by the atomic coordinates in Table 3; wherein the portion of the core bacterial RNAP comprises sufficient structural information to perform step (b); and
   (b) identifying a compound that is predicted to inhibit bacterial RNA polymerase; wherein said identifying is performed using the structure defined in step (a).

10. The method of claim 9, further comprising:
    (c) contacting the compound with a bacterial RNA polymerase; and
    (d) measuring the activity of the bacterial RNA polymerase; wherein the compound is identified as an agent that inhibits bacterial RNA polymerase when there is a decrease in the activity of the bacterial RNA polymerase in the presence of the compound relative to in its absence.

11. The method of claim 10, further comprising:
(e) contacting the compound with a eukaryotic RNA polymerase; and
(f) measuring the activity of the eukaryotic RNA polymerase; wherein the compound is identified as an agent for use as an inhibitor of bacterial RNA polymerase when there is no change in the activity of the eukaryotic RNA polymerase in the presence of the compound relative to in its absence; and wherein the compound identified inhibits bacterial but not eukaryotic RNA polymerase.

12. A method of identifying a compound that is predicted to inhibit bacterial growth comprising:
(a) defining the structure of the core bacterial RNA polymerase (RNAP) or a portion of the core bacterial RNAP by the atomic coordinates in Table 3; wherein the portion of the core bacterial RNAP comprises sufficient structural information to perform step (b); and
(b) identifying a compound that is predicted to inhibit bacterial growth; wherein said identifying is performed using the structure defined in step (a).

13. The method of claim 12, further comprising:
(c) contacting the compound with a bacterial culture; and
(d) measuring the growth of the bacterial culture under conditions in which the bacterial culture grows in the absence of the compound; wherein the compound is identified as an agent that inhibits bacterial growth when there is a decrease in the growth of the bacterial culture in the presence of the compound relative to in its absence.

14. The method of claim 13, further comprising:
(e) contacting the compound with a eukaryotic cell; and
(f) measuring the amount of proliferation of the eukaryotic cell under conditions in which the eukaryotic cell proliferates in the absence of the compound; wherein the compound is identified as an agent for inhibiting bacterial growth when there is no change in the proliferation of the eukaryotic cell in the presence of the compound relative to in its absence; and wherein the compound identified inhibits bacterial growth but not eukaryotic proliferation.

* * * * *